(12) United States Patent
Bair et al.

(10) Patent No.: US 10,995,078 B2
(45) Date of Patent: *May 4, 2021

(54) COMPOUNDS AND COMPOSITIONS FOR INHIBITION OF FASN

(71) Applicant: FORMA Therapeutics, Inc., Watertown, MA (US)

(72) Inventors: Kenneth W. Bair, Wellesley, MA (US); David R. Lancia, Jr., Boston, MA (US); Hongbin Li, Watertown, MA (US); James Loch, Watertown, MA (US); Wei Lu, Newton, MA (US); Matthew W. Martin, Arlington, MA (US); David S. Millan, Watertown, MA (US); Shawn E. R. Schiller, Watertown, MA (US); Mark J. Tebbe, Arlington, MA (US)

(73) Assignee: Forma Therapeutics, Inc., Watertown, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/929,751

(22) Filed: May 20, 2020

(65) Prior Publication Data
US 2020/0347025 A1 Nov. 5, 2020

Related U.S. Application Data

(60) Continuation of application No. 16/566,119, filed on Sep. 10, 2019, which is a continuation of application
(Continued)

(51) Int. Cl.
| | |
|---|---|
| *C07D 295/192* | (2006.01) |
| *C07D 401/04* | (2006.01) |
| *C07D 403/04* | (2006.01) |
| *C07D 405/12* | (2006.01) |
| *C07D 413/12* | (2006.01) |
| *A61K 31/4965* | (2006.01) |
| *A61P 35/00* | (2006.01) |

(Continued)

(52) U.S. Cl.
CPC ........ *C07D 295/192* (2013.01); *A61K 31/495* (2013.01); *A61K 31/496* (2013.01); *A61K 31/497* (2013.01); *A61K 31/4965* (2013.01); *A61K 31/4985* (2013.01); *A61K 31/506* (2013.01); *A61K 31/5025* (2013.01); *A61K 45/06* (2013.01); *A61P 35/00* (2018.01); *C07D 209/08* (2013.01); *C07D 209/18* (2013.01); *C07D 213/56* (2013.01); *C07D 213/65* (2013.01); *C07D 213/69* (2013.01); *C07D 215/14* (2013.01); *C07D 217/16* (2013.01); *C07D 231/12* (2013.01); *C07D 231/56* (2013.01); *C07D 235/08* (2013.01); *C07D 257/04* (2013.01); *C07D 263/57* (2013.01); *C07D 271/12* (2013.01); *C07D 277/62* (2013.01); *C07D 277/66* (2013.01); *C07D 305/08* (2013.01); *C07D 401/04* (2013.01); *C07D 403/04* (2013.01); *C07D 405/12* (2013.01); *C07D 413/12* (2013.01); *C07D 417/04* (2013.01); *C07D 417/12* (2013.01); *C07D 471/04* (2013.01); *C07D 487/04* (2013.01); *C07D 491/048* (2013.01); *C07D 495/04* (2013.01); *C07D 513/04* (2013.01)

(58) Field of Classification Search
CPC .. C07D 295/03; C07D 401/10; C07D 403/10; A61K 31/496; A61K 31/495
USPC ........ 544/359, 357, 387; 514/252.02, 252.03
See application file for complete search history.

(56) References Cited

U.S. PATENT DOCUMENTS

| | | | |
|---|---|---|---|
| 5,011,928 A | 4/1991 | Venero et al. | |
| 5,510,345 A | 4/1996 | Tuba et al. | |

(Continued)

FOREIGN PATENT DOCUMENTS

| | | | |
|---|---|---|---|
| CA | 2260767 A1 | 1/1998 | |
| CA | 2391534 A1 | 5/2001 | |

(Continued)

OTHER PUBLICATIONS

Aicher, T.D., et al., Secondary Amides of ®-3,3,3-Trifluoro-2-hydroxy-2-methylpropionic Acid as Inhibitors of Pyruvate Dehydrogenase Kinase, J. Med. Chem., 43: 236-249 (2000).

(Continued)

*Primary Examiner* — Venkataraman Balasubramanian
(74) *Attorney, Agent, or Firm* — Barnes & Thornburg LLP

(57) ABSTRACT

The present invention relates to compounds and composition for inhibition of FASN, their synthesis, applications, and antidotes. An illustrative compound of the invention is shown below:

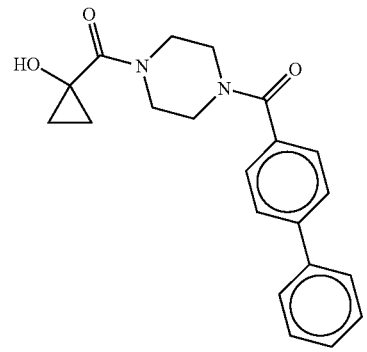

2 Claims, No Drawings

Related U.S. Application Data

No. 15/786,539, filed on Oct. 17, 2017, now Pat. No. 10,457,655, which is a division of application No. 14/775,877, filed as application No. PCT/US2014/023388 on Mar. 11, 2014, now abandoned.

(60) Provisional application No. 61/779,908, filed on Mar. 13, 2013, provisional application No. 61/779,962, filed on Mar. 13, 2013.

(51) Int. Cl.

| | | |
|---|---|---|
| *A61K 45/06* | (2006.01) |
| *C07D 215/14* | (2006.01) |
| *C07D 231/56* | (2006.01) |
| *C07D 417/12* | (2006.01) |
| *C07D 471/04* | (2006.01) |
| *C07D 257/04* | (2006.01) |
| *C07D 487/04* | (2006.01) |
| *C07D 263/57* | (2006.01) |
| *C07D 491/048* | (2006.01) |
| *C07D 271/12* | (2006.01) |
| *C07D 495/04* | (2006.01) |
| *C07D 209/18* | (2006.01) |
| *C07D 277/62* | (2006.01) |
| *C07D 277/66* | (2006.01) |
| *C07D 513/04* | (2006.01) |
| *C07D 213/56* | (2006.01) |
| *C07D 305/08* | (2006.01) |
| *A61K 31/495* | (2006.01) |
| *A61K 31/496* | (2006.01) |
| *A61K 31/497* | (2006.01) |
| *A61K 31/4985* | (2006.01) |
| *A61K 31/5025* | (2006.01) |
| *A61K 31/506* | (2006.01) |
| *C07D 209/08* | (2006.01) |
| *C07D 213/65* | (2006.01) |
| *C07D 213/69* | (2006.01) |
| *C07D 217/16* | (2006.01) |
| *C07D 231/12* | (2006.01) |
| *C07D 235/08* | (2006.01) |
| *C07D 417/04* | (2006.01) |

(56) References Cited

U.S. PATENT DOCUMENTS

| | | | |
|---|---|---|---|
| 5,759,837 A | 6/1998 | Kuhajda et al. |
| 5,856,326 A | 1/1999 | Anthony et al. |
| 6,080,860 A | 6/2000 | Karimian et al. |
| 6,410,540 B1 | 6/2002 | Goehring et al. |
| 6,469,046 B1 | 10/2002 | Daines et al. |
| 6,486,192 B1 | 11/2002 | Daines et al. |
| 6,486,211 B1 | 11/2002 | Daines et al. |
| 6,492,368 B1 | 12/2002 | Dorsch et al. |
| 6,498,187 B1 | 12/2002 | Christensen, IV et al. |
| 6,559,179 B1 | 5/2003 | Gaitanopoulos et al. |
| 6,608,059 B1 | 8/2003 | Daines et al. |
| 6,617,317 B1 | 9/2003 | Adams et al. |
| 6,670,388 B1 | 12/2003 | Daines et al. |
| 6,723,749 B2 | 4/2004 | Christensen et al. |
| 6,897,207 B2 | 5/2005 | Cox et al. |
| 7,309,714 B2 | 12/2007 | Duffy et al. |
| 7,375,134 B2 | 5/2008 | Bayly et al. |
| 7,459,448 B2 | 12/2008 | Blackburn et al. |
| 7,473,688 B2 | 1/2009 | Bergstrom et al. |
| 7,501,407 B2 | 3/2009 | Castelhano et al. |
| 7,504,400 B2 | 3/2009 | Meerpoel et al. |
| 7,511,062 B2 | 3/2009 | Kuang et al. |
| 7,601,716 B2 | 10/2009 | Dorsey et al. |
| 7,649,012 B2 | 1/2010 | Kuhajda et al. |
| 7,662,826 B2 | 2/2010 | Seno et al. |
| 7,671,219 B2 | 3/2010 | Shigemitsu et al. |
| 7,682,857 B2 | 3/2010 | Hanamaki et al. |
| 7,728,153 B2 | 6/2010 | Smith et al. |
| 7,763,623 B2 | 7/2010 | Palani et al. |
| 7,795,284 B2 | 9/2010 | Galcera-Contour et al. |
| 7,799,826 B2 | 9/2010 | Smith et al. |
| 7,807,676 B2 | 10/2010 | Wang et al. |
| 7,816,360 B2 | 10/2010 | Meerpoel et al. |
| 7,834,015 B2 | 11/2010 | Jones et al. |
| 7,919,502 B2 | 4/2011 | Dorsey et al. |
| 7,935,694 B2 | 5/2011 | Blackburn et al. |
| 7,943,616 B2 | 5/2011 | Cox et al. |
| 7,943,620 B2 | 5/2011 | Harbeson et al. |
| 7,973,037 B2 | 7/2011 | Bayly et al. |
| 7,977,374 B2 | 7/2011 | Ferrigno et al. |
| 7,998,995 B2 | 8/2011 | Boren et al. |
| 8,008,301 B2 | 8/2011 | Beavers et al. |
| 8,017,637 B2 | 9/2011 | Galcera-Contour et al. |
| 8,080,561 B2 | 12/2011 | Dorsey et al. |
| 8,088,923 B2 | 1/2012 | Romo et al. |
| 8,114,880 B2 | 2/2012 | Meerpoel et al. |
| 8,129,398 B2 | 3/2012 | Beaulieu et al. |
| 8,173,629 B2 | 5/2012 | Singh et al. |
| 8,188,084 B2 | 5/2012 | Jones et al. |
| 8,242,129 B2 | 8/2012 | Tsuhako et al. |
| 8,263,633 B2 | 9/2012 | Blaquiere et al. |
| 9,428,464 B2 | 8/2016 | Courtney et al. |
| 9,809,552 B2 | 11/2017 | Staehle et al. |
| 10,399,951 B2 * | 9/2019 | Bair .................... C07D 417/12 |
| 10,450,286 B2 * | 10/2019 | Bair .................... C07D 231/12 |
| 10,457,655 B2 * | 10/2019 | Bair .................... A61K 31/495 |
| 10,472,342 B2 * | 11/2019 | Bair .................... A61K 31/4985 |
| 2002/0115671 A1 | 8/2002 | Goehring et al. |
| 2003/0138432 A1 | 7/2003 | Glazier |
| 2003/0170244 A1 | 9/2003 | Pluenneke et al. |
| 2003/0220392 A1 | 11/2003 | Leber et al. |
| 2004/0001801 A1 | 1/2004 | Madison et al. |
| 2004/0022779 A1 | 2/2004 | Rudel et al. |
| 2004/0024050 A1 | 2/2004 | Smith et al. |
| 2004/0053931 A1 | 3/2004 | Cox et al. |
| 2004/0058988 A1 | 3/2004 | Christensen, IV et al. |
| 2004/0082786 A1 | 4/2004 | Zhu et al. |
| 2004/0122033 A1 | 6/2004 | Nargund et al. |
| 2005/0043300 A1 | 2/2005 | Middleton et al. |
| 2005/0240023 A1 | 10/2005 | Bayly et al. |
| 2005/0261292 A1 | 11/2005 | Antel et al. |
| 2005/0267304 A1 | 12/2005 | Cox et al. |
| 2005/0288213 A1 | 12/2005 | MacNeil et al. |
| 2006/0040906 A1 | 2/2006 | Bakshi et al. |
| 2006/0100194 A1 | 5/2006 | Blackburn et al. |
| 2006/0106062 A1 | 5/2006 | Kuang et al. |
| 2006/0128963 A1 | 6/2006 | Sings et al. |
| 2006/0148721 A1 | 7/2006 | Erondu |
| 2006/0160834 A1 | 7/2006 | Fong et al. |
| 2006/0270650 A1 | 11/2006 | MacNeil et al. |
| 2007/0010513 A1 | 1/2007 | Aslanian et al. |
| 2007/0032529 A1 | 2/2007 | Takagi et al. |
| 2007/0099884 A1 | 5/2007 | Erondu et al. |
| 2007/0112000 A1 | 5/2007 | Barton et al. |
| 2007/0142394 A1 | 6/2007 | Solomon et al. |
| 2007/0161615 A1 | 7/2007 | Andrews et al. |
| 2007/0167435 A1 | 7/2007 | Mutahi et al. |
| 2007/0173495 A1 | 7/2007 | Palani et al. |
| 2007/0191383 A1 | 8/2007 | Meerpoel et al. |
| 2007/0203236 A1 | 8/2007 | Smith et al. |
| 2007/0208087 A1 | 9/2007 | Sanders et al. |
| 2007/0244186 A1 | 10/2007 | Galcera-Contour et al. |
| 2007/0249579 A1 | 10/2007 | Wang et al. |
| 2008/0032972 A1 | 2/2008 | Dorsey et al. |
| 2008/0064632 A1 | 3/2008 | Amatruda et al. |
| 2008/0139572 A1 | 6/2008 | Wang et al. |
| 2008/0166378 A1 | 7/2008 | Schimmer et al. |
| 2008/0188529 A1 | 8/2008 | Bayly et al. |
| 2008/0200376 A1 | 8/2008 | MacCoss et al. |
| 2008/0207569 A1 | 8/2008 | Spada |
| 2008/0207605 A1 | 8/2008 | Spada |
| 2008/0242677 A1 | 10/2008 | Dehmlow et al. |
| 2008/0269234 A1 | 10/2008 | Gandhi et al. |

(56) References Cited

U.S. PATENT DOCUMENTS

| | | |
|---|---|---|
| 2008/0312247 A1 | 12/2008 | Gant et al. |
| 2008/0318969 A1 | 12/2008 | Harbeson et al. |
| 2009/0048276 A1 | 2/2009 | Goulet et al. |
| 2009/0082560 A1 | 3/2009 | Kobayashi et al. |
| 2009/0105213 A1 | 4/2009 | Blackburn et al. |
| 2009/0105305 A1 | 4/2009 | Butlin et al. |
| 2009/0111789 A1 | 4/2009 | Bartkovitz et al. |
| 2009/0118332 A1 | 5/2009 | Butlin et al. |
| 2009/0156591 A1 | 6/2009 | Ferrigno et al. |
| 2009/0163545 A1 | 6/2009 | Goldfarb |
| 2009/0176765 A1 | 7/2009 | Jones et al. |
| 2009/0197863 A1 | 8/2009 | Chu et al. |
| 2009/0197894 A1 | 8/2009 | Fu et al. |
| 2009/0209523 A1 | 8/2009 | Jones et al. |
| 2009/0253677 A1 | 10/2009 | Beaulieu et al. |
| 2009/0264402 A1 | 10/2009 | Jaehne et al. |
| 2009/0264416 A1 | 10/2009 | Ho et al. |
| 2009/0275624 A1 | 11/2009 | Galcera-Contour et al. |
| 2009/0286778 A1 | 11/2009 | Combs et al. |
| 2009/0325877 A1 | 12/2009 | Grunt et al. |
| 2009/0325980 A1 | 12/2009 | Meerpoel et al. |
| 2010/0029621 A1 | 2/2010 | Cooke et al. |
| 2010/0048576 A1 | 2/2010 | Dorsey et al. |
| 2010/0069367 A1 | 3/2010 | Boren et al. |
| 2010/0125075 A1 | 5/2010 | Pratt et al. |
| 2010/0135954 A1 | 6/2010 | Tsuhako et al. |
| 2010/0160290 A1 | 6/2010 | Kobayashi et al. |
| 2010/0190856 A1 | 7/2010 | Colomer Bosch et al. |
| 2010/0305121 A1 | 12/2010 | Smith et al. |
| 2010/0317658 A1 | 12/2010 | Galcera-Contour et al. |
| 2011/0039820 A1 | 2/2011 | Blackburn et al. |
| 2011/0076291 A1 | 3/2011 | Blaquiere et al. |
| 2011/0105389 A1 | 5/2011 | Hoveyda et al. |
| 2011/0124021 A1 | 5/2011 | Medghalchi |
| 2011/0160204 A1 | 6/2011 | Dorsey et al. |
| 2011/0172230 A1 | 7/2011 | Ishii et al. |
| 2011/0230446 A1 | 9/2011 | Bayly et al. |
| 2011/0274654 A1 | 11/2011 | Bahadoor et al. |
| 2011/0274655 A1 | 11/2011 | Bahadoor et al. |
| 2012/0004260 A1 | 1/2012 | Ossovskaya et al. |
| 2012/0015958 A1 | 1/2012 | Cooke et al. |
| 2012/0021976 A1 | 1/2012 | Boyle et al. |
| 2012/0122842 A1 | 5/2012 | Curtin et al. |
| 2012/0149683 A1 | 6/2012 | Cox et al. |
| 2012/0156138 A1 | 6/2012 | Smith |
| 2012/0178739 A1 | 7/2012 | Blackburn et al. |
| 2012/0195961 A1 | 8/2012 | Kritikou et al. |
| 2012/0196851 A1 | 8/2012 | Varrone et al. |
| 2012/0208827 A1 | 8/2012 | Dock et al. |
| 2012/0264737 A1 | 10/2012 | Oslob et al. |
| 2014/0329795 A1 | 11/2014 | Courtney et al. |
| 2015/0051211 A1 | 2/2015 | Ji et al. |
| 2016/0002188 A1 | 1/2016 | Bair et al. |
| 2017/0312273 A1 | 11/2017 | Millan et al. |
| 2018/0050997 A1 | 2/2018 | Bair et al. |
| 2018/0370933 A1 | 12/2018 | Bair et al. |

FOREIGN PATENT DOCUMENTS

| | | |
|---|---|---|
| CA | 2447023 A1 | 11/2002 |
| CA | 2492225 A1 | 1/2004 |
| CA | 2609957 A1 | 1/2007 |
| CA | 2634250 A1 | 7/2007 |
| CA | 2634847 A1 | 7/2007 |
| CA | 2637717 A1 | 8/2007 |
| CA | 2668094 A1 | 5/2008 |
| CA | 2696053 A1 | 9/2008 |
| CA | 2759098 A1 | 10/2010 |
| CA | 2764526 A1 | 12/2010 |
| CA | 2778990 A1 | 5/2011 |
| CN | 1272107 A | 3/2000 |
| CN | 101203510 A | 6/2008 |
| CN | 101384553 A | 3/2009 |
| CN | 101400682 A | 4/2009 |
| CN | 101426777 A | 5/2009 |
| CN | 101668520 A | 3/2010 |
| CN | 102372698 A | 3/2012 |
| CN | 102627610 A | 8/2012 |
| CN | 103420890 A | 12/2013 |
| EP | 0922099 A1 | 6/1999 |
| EP | 1073891 A2 | 2/2001 |
| EP | 1164374 A1 | 12/2001 |
| EP | 1255567 A1 | 11/2002 |
| EP | 1290446 A2 | 3/2003 |
| EP | 1397360 A1 | 3/2004 |
| EP | 1401469 A2 | 3/2004 |
| EP | 1465631 A2 | 10/2004 |
| EP | 1482924 A2 | 12/2004 |
| EP | 1534074 A2 | 6/2005 |
| EP | 1545572 A2 | 6/2005 |
| EP | 1751131 A1 | 2/2007 |
| EP | 1764616 A2 | 3/2007 |
| EP | 1807102 A2 | 7/2007 |
| EP | 1814879 A1 | 8/2007 |
| EP | 1831209 A2 | 9/2007 |
| EP | 1884513 A1 | 2/2008 |
| EP | 1896453 A1 | 3/2008 |
| EP | 1926721 A2 | 6/2008 |
| EP | 1966143 A2 | 9/2008 |
| EP | 1976848 A2 | 10/2008 |
| EP | 1976854 A2 | 10/2008 |
| EP | 1981341 A2 | 10/2008 |
| EP | 2019091 A1 | 1/2009 |
| EP | 2074103 A1 | 7/2009 |
| EP | 2076494 A1 | 7/2009 |
| EP | 2091951 A2 | 8/2009 |
| EP | 2139877 A1 | 1/2010 |
| EP | 2142533 A1 | 1/2010 |
| EP | 2144604 A2 | 1/2010 |
| EP | 2170802 A1 | 4/2010 |
| EP | 2233486 A1 | 9/2010 |
| EP | 2274288 A2 | 1/2011 |
| EP | 2445506 A1 | 5/2012 |
| EP | 2483277 A1 | 8/2012 |
| EP | 2485728 A1 | 8/2012 |
| EP | 2493310 A1 | 9/2012 |
| EP | 2493910 A1 | 9/2012 |
| EP | 2503890 A1 | 10/2012 |
| FR | 2829766 A1 | 3/2003 |
| KR | 100637955 A1 | 10/2006 |
| KR | 20080080201 A | 9/2008 |
| KR | 20080087833 A | 10/2008 |
| KR | 20080091814 A | 10/2008 |
| RU | 2194044 C2 | 12/2002 |
| RU | 2011/108493 A | 3/2011 |
| WO | WO 1994002466 A1 | 2/1994 |
| WO | WO 1996030343 A1 | 10/1996 |
| WO | WO 1998003648 A1 | 1/1998 |
| WO | WO 1999016751 A1 | 4/1999 |
| WO | WO 1999054728 A2 | 10/1999 |
| WO | WO 1999064446 A1 | 12/1999 |
| WO | WO 2000022909 A2 | 4/2000 |
| WO | WO 2000078309 A1 | 12/2000 |
| WO | WO 2000078310 A1 | 12/2000 |
| WO | WO 2001014362 A1 | 3/2001 |
| WO | WO 2001014363 A1 | 3/2001 |
| WO | WO 2001014364 A1 | 3/2001 |
| WO | WO 2001017942 A1 | 3/2001 |
| WO | WO 2001030752 A2 | 5/2001 |
| WO | WO 2001030775 A1 | 5/2001 |
| WO | WO 2001036003 A2 | 5/2001 |
| WO | WO 2001090099 A1 | 11/2001 |
| WO | WO 2001096873 A2 | 12/2001 |
| WO | WO 2002000620 A1 | 1/2002 |
| WO | WO 2002000646 A1 | 1/2002 |
| WO | WO 2002002119 A1 | 1/2002 |
| WO | WO 2002009651 A2 | 2/2002 |
| WO | WO 2002009688 A1 | 2/2002 |
| WO | WO 2002024197 A1 | 3/2002 |
| WO | WO 2002026745 A1 | 4/2002 |
| WO | WO 2002055661 A2 | 7/2002 |
| WO | WO 2002080952 A2 | 10/2002 |
| WO | WO 2002095007 A2 | 11/2002 |
| WO | WO 2003000688 A1 | 1/2003 |

(56) References Cited

FOREIGN PATENT DOCUMENTS

| | | |
|---|---|---|
| WO | WO 2003024956 A1 | 3/2003 |
| WO | WO 2004009015 A2 | 1/2004 |
| WO | WO 2004014370 A2 | 2/2004 |
| WO | WO 2004030637 A2 | 4/2004 |
| WO | WO 2004037800 A1 | 5/2004 |
| WO | WO 2004050022 A2 | 6/2004 |
| WO | WO 2004110368 A2 | 12/2004 |
| WO | WO 2004110375 A2 | 12/2004 |
| WO | WO 2005000217 A2 | 1/2005 |
| WO | WO 2005009950 A2 | 2/2005 |
| WO | WO 2005016344 A1 | 2/2005 |
| WO | WO 2005035534 A1 | 4/2005 |
| WO | WO 2005046685 A1 | 5/2005 |
| WO | WO 2005073186 A1 | 8/2005 |
| WO | WO 2005085226 A1 | 9/2005 |
| WO | WO 2005097740 A1 | 10/2005 |
| WO | WO 2005097746 A2 | 10/2005 |
| WO | WO 2005097750 A1 | 10/2005 |
| WO | WO 2005110413 A2 | 11/2005 |
| WO | WO 2005116006 A1 | 12/2005 |
| WO | WO 2005116009 A1 | 12/2005 |
| WO | WO 2006021801 A1 | 3/2006 |
| WO | WO 2006032322 A1 | 3/2006 |
| WO | WO 2006034341 A2 | 3/2006 |
| WO | WO 2006049933 A2 | 5/2006 |
| WO | WO 2006051202 A1 | 5/2006 |
| WO | WO 2006060461 A1 | 6/2006 |
| WO | WO 2006067311 A2 | 6/2006 |
| WO | WO 2007002057 A1 | 1/2007 |
| WO | WO 2007029035 A2 | 3/2007 |
| WO | WO 2007033175 A1 | 3/2007 |
| WO | WO 2007038669 A2 | 4/2007 |
| WO | WO 2007049532 A1 | 5/2007 |
| WO | WO 2007068620 A1 | 6/2007 |
| WO | WO 2007068641 A1 | 6/2007 |
| WO | WO 2007075629 A2 | 7/2007 |
| WO | WO 2007075688 A2 | 7/2007 |
| WO | WO 2007080140 A1 | 7/2007 |
| WO | WO 2007082840 A1 | 7/2007 |
| WO | WO 2007087204 A2 | 8/2007 |
| WO | WO 2007089634 A2 | 8/2007 |
| WO | WO 2007092065 A2 | 8/2007 |
| WO | WO 2007130468 A2 | 11/2007 |
| WO | WO 2007137955 A1 | 12/2007 |
| WO | WO 2007138351 A2 | 12/2007 |
| WO | WO 2007138355 A1 | 12/2007 |
| WO | WO 2008011453 A2 | 1/2008 |
| WO | WO 2008030891 A2 | 3/2008 |
| WO | WO 2008052658 A1 | 5/2008 |
| WO | WO 2008059214 A1 | 5/2008 |
| WO | WO 2008061399 A1 | 5/2008 |
| WO | WO 2008066789 A2 | 6/2008 |
| WO | WO 2008073825 A1 | 6/2008 |
| WO | WO 2008075064 A1 | 6/2008 |
| WO | WO 2008075070 A1 | 6/2008 |
| WO | WO 2008075077 A1 | 6/2008 |
| WO | WO 2008099000 A2 | 8/2008 |
| WO | WO 2008106166 A2 | 9/2008 |
| WO | WO 2008106167 A1 | 9/2008 |
| WO | WO 2008109175 A1 | 9/2008 |
| WO | WO 2008133273 A1 | 11/2008 |
| WO | WO 2008133955 A1 | 11/2008 |
| WO | WO 2008157751 A2 | 12/2008 |
| WO | WO 2009000864 A1 | 12/2008 |
| WO | WO 2009004356 A1 | 1/2009 |
| WO | WO 2009064927 A2 | 5/2009 |
| WO | WO 2009098282 A1 | 8/2009 |
| WO | WO 2009099736 A1 | 8/2009 |
| WO | WO 2009132202 A2 | 10/2009 |
| WO | WO 2009143404 A1 | 11/2009 |
| WO | WO 2009151910 A2 | 12/2009 |
| WO | WO 2010017055 A2 | 2/2010 |
| WO | WO 2010056309 A2 | 5/2010 |
| WO | WO 2010120262 A1 | 10/2010 |
| WO | WO 2010138589 A1 | 12/2010 |
| WO | WO 2010150100 A1 | 12/2010 |
| WO | WO 2011035018 A2 | 3/2011 |
| WO | WO 2011036284 A1 | 3/2011 |
| WO | WO 2011042145 A1 | 4/2011 |
| WO | WO 2011053821 A1 | 5/2011 |
| WO | WO 2011056635 A1 | 5/2011 |
| WO | WO 2011066211 A1 | 6/2011 |
| WO | WO 2011103546 A1 | 8/2011 |
| WO | WO 2011140190 A1 | 11/2011 |
| WO | WO 2011140296 A1 | 11/2011 |
| WO | WO 2011163612 A1 | 12/2011 |
| WO | WO 2011163619 A1 | 12/2011 |
| WO | WO 2012016217 A1 | 2/2012 |
| WO | WO 2012019430 A1 | 2/2012 |
| WO | WO 2012037298 A1 | 3/2012 |
| WO | WO 2012037299 A2 | 3/2012 |
| WO | WO 2012064632 A1 | 5/2012 |
| WO | WO 2012064642 A1 | 5/2012 |
| WO | WO 2012071562 A2 | 5/2012 |
| WO | WO 2012092442 A1 | 7/2012 |
| WO | WO 2012096928 A2 | 7/2012 |
| WO | WO 2012101013 A1 | 8/2012 |
| WO | WO 2012122391 A1 | 9/2012 |
| WO | WO 2012125521 A1 | 9/2012 |
| WO | WO 2012130166 A1 | 10/2012 |
| WO | WO 2012151451 A1 | 11/2012 |
| WO | WO 2012151452 A1 | 11/2012 |
| WO | WO 2013028445 A1 | 2/2013 |
| WO | WO 2013028495 A1 | 2/2013 |
| WO | WO 2013033068 A1 | 3/2013 |
| WO | WO 2013045413 A1 | 4/2013 |
| WO | WO 2013060636 A1 | 5/2013 |
| WO | WO 2013064083 A1 | 5/2013 |
| WO | WO 2013078771 A1 | 6/2013 |
| WO | WO 2013156608 A1 | 10/2013 |
| WO | WO 2014044356 A1 | 3/2014 |
| WO | WO 2014146747 A1 | 9/2014 |
| WO | WO 2014164749 A1 | 10/2014 |
| WO | WO 2014164767 A1 | 10/2014 |
| WO | WO 2015014446 A1 | 2/2015 |
| WO | WO 2016205590 A1 | 12/2016 |
| WO | WO 2016205633 A1 | 12/2016 |
| WO | WO 2017189613 A1 | 11/2017 |

OTHER PUBLICATIONS

Berod, Luciana, et al., "De novo fatty acid synthesis controls the fate between regulatory T and T helper 17 cells," Nature Medicine, vol. 20, No. 11, Nov. 2014. 1327-1335.

Clayden, Greeves, Warren and Wothers, Summary: The Three Major Approaches to the Synthesis of Aromatic Heterocycles, Aromatic heterocycles 2: synthesis, Organic Chemistry, Oxford University Press, 44: 1214-1215 (2001).

Database Registry [Online] Chemical Abstracts Service, Columbus, Ohio, US; Database accession No. 1387900-07-3 (Aug. 8, 2012); Database accession No. 1014245-05-6 (Apr. 13, 2008); and, Database accession No. 927570-20-5 (Mar. 20, 2007). 1 page.

Database Registry [Online] Chemical Abstracts Service, Columbus, Ohio, US; Database accession No. 1630806-71-1 (Oct. 29, 2014); Database accession No. 1630806-69-7 (Oct. 29, 2014); Database accession No. 1630806-63-1 (Oct. 29, 2014); Database accession No. 1630806-59-5 (Oct. 29, 2014); Database accession No. 1630806-56-2 (Oct. 29, 2014); Database accession No. 1630806-55-1 (Oct. 29, 2014); Database accession No. 1630806-49-3 (Oct. 29, 2014); Database accession No. 1630806-44-8 (Oct. 29, 2014); Database accession No. 1630806-41-5 (Oct. 29, 2014); Database accession No. 871002-005-0 (Jan. 3, 2006).

De Schrijver, et al., RNA Interference-mediated Silencing of the Fatty Acid Synthase Gene Attenuates Growth and induces Morphological Changes and Apoptosis of LNCaP Prostate Cancer Cells, Cancer Res (2003) 63:3799-3804.

Endo, Yusuke, et al., "Obesity Drives Th17 Cell Differentiation by Inducing the lipid Metabolic Kinase, ACC1," Cell Reports, 12, Aug. 11, 2015, 1042-1055.

Fako, V.E., et al., Mechanism of Orlistat Hydrolysis by the Thioesterase of Human Fatty Acid Synthase, ACS Catal, 4: 3444-3453 (2014).

(56) References Cited

OTHER PUBLICATIONS

Fatima, S., et al., Molecular docking and 3D-QSAR studies on inhibitors of DNA damage signaling enzyme human PARP-1, Journal of Receptors and Signal Transduction, 32(4): 214-224 (2012).
Ferrigno, F., et al., Development of substituted 6-[4-fluoro-3-(piperazin-1-ylcarbonyl)benzyl]-4,5-dimethylpyridazin-3(2H)-ones as potent poly(ADP-ribose) polymerase-1 (PARP-1) inhibitors active in BRCA deficient cells, Bioorganic & Medicinal Chemistry Letters, 20(3): 1100-1105 (2010).
First Formal Official Action: Colombian Patent Application No. 15-242.983, dated Dec. 17, 2015.
First Formal Official Action: Cuban Patent Application No. 2015-0120, dated Dec. 3, 2015.
Flavin, R., et al., Fatty acid synthase as a potential therapeutic target in cancer, Future Oncol, 6(4): 551-562 (2010).
Gansler TS, et al., Increased expression of fatty acid synthase {OA-519} in ovarian neoplasms predicts shorter survival. Hum. Pathol. (1997) 28 (6): 686-92.
Heaton, et al., Dengue virus nonstructural protein 3 redistributes fatty acid synthase to sites of viral replication and increases cellular fatty acid synthesis. Proc. Natl. Acad. Sci., (210) 107(40): 17345-17350.
Harriman, Geraldine, et al., "Acetyl-CoA carboxylase inhibition by ND-630 reduces hepatic steatosis, improves insulin sensitivity, and modulates dyslipidemia in rats," PNAS Early Edition, 1-10.
Harrison, Stephen A., et al., "Orlistat in the Treatment of NASH: A Case Series," The American Journal of Gastroenterology, vol. 98, No. 4, 2003, 926-930.
Harrison, S.A., et al., "A pilot study of orlistat treatment in obese, non-alchoholic steatohepatitis patients," Aliment Pharmacol Ther, 2004, 20, 623-628.
Hunt DA, et al., MRNA stability and overexpression of fatty acid synthase inhuman breast cancer cell lines. Anticancer Res. (2007) 27{1A): 27-34.
International Search Report for PCT/US2014/023388, 4 pages (dated Aug. 18, 2014).
International Search Report for PCT/US2017/029469, 4 pages (dated Jun. 24, 2017).
Jones, S.F. and Infante, J.R., Molecular Pathways: Fatty Acid Synthase, Clin Cancer Res; 21(24): 5434-5438 (2015).
Kant, Shiva, et al., "Myelopoietic Efficacy of Orlistat in Murine Hosts Bearing T Cell Lymphoma: Implication in Macrophage Differentiation and Activation," PLoS One, Dec. 2013, vol. 8, Issue 12, e82396, 1-14.
Kridel, et al., Orlistat Is a Novel Inhibitor of Fatty Acid Synthase with Antitumor Activity, Cancer Res (2004) 54:2070-2075.
Kuhajda FP, Fatty acid synthase an dcancer: New application of an old pathway. Cancer Research, (2006) 66(12):5977-5980.
Li, et al., Fatty acid synthase expression is induced by the Epstein-Barr virus immediate-early protein BRLF1 and is required for lytic viral gene expression. Journal of Virology, (2004) 78(8):4197-4206.
Martin, Matthew W., et al., "Discovery and optimization of novel piperazines as potent inhibitors of fatty acid synthase (FASN)," Bioorganic & Medicinal Chemistry Letters, 29, 2019, 1001-1006.
Menear, K.A., et al., 4-[3-(4-Cyclopropanecarbonylpiperazine-1-carbonyl)-4-fluorobenzyl]-2H-phthalazin-1-one: A Novel Bioavailable Inhibitor of Poly(ADP-ribose) Polymerase-1, Journal of Medicinal Chemistry, 51(20), 6581-6591 (2008).
Menendez JA and Lupu R, Fatty acid synthase and the lipogenic phenotype in cancer pathogenesis, Nature Review Cancer, (2007) 7: 763-777.
Montgomery, J.I., et al., Discovery and SAR of benzyl phenyl ethers as inhibitors of bacterial phenylalanyl-tRNA synthetase, Bioorganic & Medicinal Chemistry Letters, 19(3): 665-669 (2009).
Munger, et al., Systems-level metabolic flux profiling identifies fatty acid synthesis as a target for antiviral therapy. Nature Biotechnology, (2008) 26: 1179-1186.
Notice of First Formal Official Action: Panama Patent Application No. PI/2015/90868-01, dated Dec. 21, 2015.
Oliveras, et al., Novel anti-fatty acid synthase compounds with anti-cancer activity in HER2+breast cancer, Ann. N. Acad. Sci. (2010) 1210: 86-93.
Rassmann, et al., The human fatty acid synthase: a new therapeutic target for coxsackievirus B3-induced diseases? Antiviral Research, (2007) 76: 150-158.
Rhee, H.-K., et al., Synthesis and cytotoxicity of 2-phenylquinazolin-4(3)-one derivatives, European Journal of Medicinal Chemistry, 46(9): 3900-3908 (2011).
Samsa, et al., Dengue virus capsid protein usurps lipid droplets for viral particle formation. PLoS Pathegens, (2009) 5 10):e1000632.
Smagris, Eriks, "Pnpla3I148M Knockin Mice Accumulate PNPLA3 on Lipid Droplets and Develp Hepatic Steatosis," Hepatology, vol. 61, No. 1, 2015, 108-118.
Vazquez, et al., Discovery of GSK837149A, an inhibitor of human fatty acid synthase targeting the b-ketoacyl reductase reaction, FEBS Journal (20008) 275:1556-1567.
Written Opinion for PCT/US17/29469 from the International Searching Authority dated Oct. 2, 2017.
Xenical_Orlistat_Prescribing_Infomation insert. Genentech, 2015, Reference ID: 3803457.
Yang, W., et al, Fatty acid synthase is up-regulated during hepatitis C virus infection and regulates hepatitis C virus entry and production. Hepatology (2008) 48, 13967-1403.
Zhang, et al., b-Lactam congeners of orlistat as inhibitors of fatty acid synthase, Bioorg. Med. Chem. Let. 18 491-2494 (2008).
Chemical Abstracts Services, [4-[[6-(3-bromophenyl)-2-methyl-3-pyridinyl]carbonyl]-1-piperazinyl]cyclobutyl-methanone, CAS Registry No. 1318984-78-9 (Aug. 17, 2011).

* cited by examiner

COMPOUNDS AND COMPOSITIONS FOR INHIBITION OF FASN

CROSS REFERENCE TO RELATED APPLICATIONS

This application is a continuation of U.S. patent application Ser. No. 16/566,119, filed Sep. 10, 2019, which is a continuation of U.S. patent application Ser. No. 15/786,539, filed Oct. 17, 2017, which is a divisional of U.S. patent application Ser. No. 14/775,877, filed Sep. 14, 2015, which is the U.S. national phase of International Application No. PCT/US2014/023388, filed Mar. 11, 2014, which claims the benefit of U.S. Provisional Application No. 61/779,908, filed Mar. 13, 2013, and U.S. Provisional Application No. 61/779,962, filed Mar. 13, 2013, all of which are incorporated by reference in their entirety.

FIELD OF THE INVENTION

The present invention relates to compounds and compositions for inhibition of fatty acid synthase ("FASN"), their synthesis, applications and antidote.

BACKGROUND OF THE INVENTION

Fatty acid synthase (hereinafter "FASN;" also known as "FAS") plays fundamental roles in both cellular metabolism and cellular signaling. FASN catalyzes the formation of long-chain fatty acids from acetyl-CoA, malonyl-CoA and nicotinamide adenine dinucleotide phosphate (NADPH), thus getting involved in energy production and storage, cellular structure and formation of intermediates in the biosynthesis of hormones and other biologically important molecules.

Extensive research has been conducted to study the expression, function, and regulation of both FASN encoding genes and the various forms of FASN proteins. Several studies indicate that FASN is involved in the oncogenesis and tumor progression of various cancers. For example, FASN gene amplification and protein overexpression was observed in human breast cancer cell lines. (Hunt D A, Lane H M, Zygmont M E, Dervan P A, Hennigar R A (2007), *MRNA stability and overexpression of fatty acid synthase in human breast cancer cell lines*. Anticancer Res. 27 (1A): 27-34; Kuhaja F P, (2006) *Fatty acid synthase and cancer: New application of an old pathway*. Cancer Research, 66(12) 5977-5980; Menendez J A, Lupu R (2007) *Fatty acid synthase and the lipogenic phenotype in cancer pathogenesis*. Nature Review Cancer, 7, 763-777.) In addition, a study focusing on ovarian neoplasms revealed that elevated levels of FASN serve as an indicator for shorter survival of the subject. (Gansler T S, Hardman W, Hunt D A, Schaffel S, Hennigar R A (June 1997). *Increased expression of fatty acid synthase (OA-519) in ovarian neoplasms predicts shorter survival*. Hum. Pathol. 28 (6): 686-92). In summary, correlation of elevated FASN expression or activity with high tumor grade and advanced stage in primary breast, prostate, and colorectal cancers has drawn attention to the enzyme as a possible drug target and marker of poor prognosis.

In addition to the involvement in oncogenesis, FASN has also been identified as a factor that may influence the progression of diseases such as diabetes and uterine leiomyomata. In particular, one study found that a FASN inhibitor, platensimycin, reduced ambient glucose levels in mouse models of diabetes. Furthermore, FASN inhibitors have been shown to be potentially effective in inducing weight loss (e.g EP0869784-A). Similarly, a genome-wide study suggests that FASN may contribute to the predisposition to uterine leiomyomata.

Furthermore, FASN has been identified as a target for treatment of microbial infections. In particular, fatty acid synthesis or the level of fatty acid has been reported to be critical in viral pathogenesis. In addition, FASN has been implicated in pathogeneiss of human cytomegalo virus (HCMV), influenza A viruses and Hepatitis C (See, e.g., Munger et al., Nature Biotechnology, 26: 1179-1186 (2008)). It has also been reported that the FASN expression is increased in the cells infected by coxsackievirus B3 (CVB3), a picornavirus, and the replication of CVB3 is blocked by FASN inhibitors. (See Rassmann et al., Antiviral Research, 76: 150-158 (2007)). In addition, FASN has been reported to be important in lytic viral replication of Epstein-Barr virus (EBV). (Li et al., Journal of Virology, 78(8): 4197-4206 (2004)). FASN has also been implicated to have a role in the replication of dengue virus (See, e.g., Heaton et al., Proc. Natl. Acad. Sci., 107(40): 17345-17350 (2010); and Samsa et al., PLoS Pathegens, 5(10): e1000632 (2009)). Moreover, FASN plays important role in HCV infection by controlling viral entry and production (Yang W, Hood B L, Chadwick S L, Watkins, Luo G, Conrads T P, Wang T (2008), *Fatty acid synthase is up-regulated during hepatitis C virus infection and regulates hepatitis C virus entry and production*. Hepatology, 48, 13967-1403)

Significant efforts have been focusing on generating FASN inhibitors that may help to provide a treatment for cancer and other related diseases. A number of inhibitor families have been identified and published, such as the azabenzimidazoles series (WO 2011/066211 and related publications) and the sulfonamide derivatives series (WO 2008/075070 and related publications) from AstraZeneca UK Ltd. However, due to FASN's importance and the shortcomings in the published compounds, there is still an unmet need for potent and highly specific FASN inhibitors.

The current invention introduces a new set of compounds that selectively inhibits FASN activities and modulates the growth and proliferation of cancer cell lines. The synthetic processes of the new compounds are also included. These compounds may have significant pharmaceutical implications in the treatment of cancer, as well as other diseases such as viral infections, obesity, and diabetes.

SUMMARY OF THE INVENTION

One aspect of this invention is the provision of compounds, compositions, and kits for FASN inhibition comprising a compound of formula I

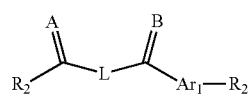

I wherein
$R_1$ is a $C_1$-$C_3$ hydroxyl-alkyl either unsubstituted or substituted with —$CH_3$ or —$CH_zF_{3-z}$, 5 membered cycloalkyl either unsubstituted or substituted with substituents selected from the group consisting of deuterium, —$R_p$, —$OR_p$, —$NHR_p$, and —$NR_pR_{p1}$,
or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —$R_a$, —$OR_a$, —$NHR_a$, and —$NR_aR_{a1}$;

L is a 5-10 membered monocyclic or bicyclic alkyl or heteroalkyl wherein (i) the heteroatom ring members of the 5-10 membered monocyclic or bicyclic heteroalkyl are independently selected from O, S, or N, and (ii) each of the 5-10 membered monocyclic or bicyclic alkyl or heteroalkyl is either unsubstituted or optionally substituted with substituents selected from the group consisting of deuterium and —$R_b$;

A and B are independently O or S;

$Ar_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —$CH_zF_{3-z}$, cyano, hydroxyl, hydroxylalkyl, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$OCH_zF_{3-z}$, -alkyl, -alkenyl, -alkynyl, -alkoxy or (alkoxyalkyl)amino-, —N($R_c$)—C(O)-alkyl, —N(Re)—C(O)-aryl, -cycloalkyl, -heterocycloalkyl, -aryl, and -heteroaryl, with the proviso that no two adjacent ring heteroatoms are both S or both O;

$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), $ONH_2$, —C(O)NH(alkyl), —C(O)N(aryl)$_2$, —C(O)NH(cycloalkyl), —NH(CO)cycloalkyl, —NH($SO_2$), —NH($SO_2$)alkyl, —NH($SO_2$)aryl, —NH($SO_2$)heteroaryl, —N($SO_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocloalkyl-$R_d$, —NH—C(O)—$R_d$—(O)alkyl, —NH—C(O)-aryl, —NH—C(O)—NH-alkyl, NH—C(O)—NH-cycloalkyl, $NH_2$(CO)cycloalkyl-, NH—C(O)—NH-aryl, —NH—C(O)—O—alkyl, NH—C(O)—NH-cycloalkyl, —NH—C(O)—O-cycloalkyl, —NH($R_a$)—C(O)-alkyl, —NH($R_a$)—C(O)-aryl, —NH($R_a$)—S(O)$_2$cycloalkyl, —S($O_2$)$NH_2$, —S($O_2$)NH(alkyl), —S($O_2$)N($R_a$)cycloalkyl, —S($O_2$)N(alkyl)$_2$, —C(O)N(H)(alkyl), —C(O)N(Rd)(cycloalkyl), methylenedioxy, —$CH_zF_{3-z}$, —$OCH_zF_{3-z}$, and -alkoxy;

$R_p$ and $R_{p1}$ are independently H, halo, $C_1$-$C_4$ alkyl, or $C_3$-$C_4$ cycloalkyl;

$R_a$ and $R_{a1}$ are independently H, halo, $C_1$-$C_4$ alkyl, or $C_3$-$C_4$ cycloalkyl;

$R_b$ is H, halo, $C_1$-$C_4$ alkyl, $C_1$-$C_3$ hydroxyl-alkyl, or $C_3$-$C_4$ cycloalkyl;

$R_c$ is H, halo, $C_1$-$C_4$ alkyl, or $C_3$-$C_4$ cycloalkyl;

$R_d$ is H, halo, $C_1$-$C_4$ alkyl, or $C_3$-$C_4$ cycloalkyl;

and z is 0, 1 or 2;

and pharmaceutically acceptable salts, solvates, esters, prodrugs and isomers thereof.

Another aspect of this invention is the provision of compounds, compositions, and kits for FASN inhibition comprising a compound of formula I-A:

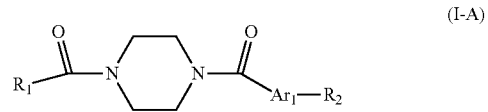

(I-A)

wherein:

$R_1$ is a $C_1$-$C_3$ hydroxyl-alkyl either unsubstituted or substituted with —$CH_3$ or —$CH_zF_{3-z}$, 5-membered cycloalkyl either unsubstituted or substituted with substituents selected from the group consisting of deuterium, —$R_p$, —$OR_p$, —$NHR_p$, and —$NR_pR_{p1}$, or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —$R_a$, —$OR_a$, —$NHR_a$, and —$NR_aR_{a1}$;

$Ar_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —$CH_zF_{3-z}$, cyano, hydroxyl, hydroxylalkyl, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$OCH_zF_{3-z}$, -alkyl, -alkenyl, -alkynyl, -alkoxy or (alkoxyalkyl)amino-, —N($R_c$)—C(O)-alkyl, —N(Re)—C(O)-aryl, -cycloalkyl, -heterocycloalkyl, -aryl, and -heteroaryl, with the proviso that no two adjacent ring heteroatoms are both S or both O;

$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_a$)(cycloalkyl), methylenedioxy, —CH$_z$F$_{3-z}$, —OCH$_z$F$_{3-z}$, and -alkoxy;

R$_p$ and R$_{p1}$ are independently H, halo, C$_1$-C$_4$ alkyl, or C$_3$-C$_4$ cycloalkyl;

R$_a$ and R$_{a1}$ are independently H, halo, C$_1$-C$_4$ alkyl, or C$_3$-C$_4$ cycloalkyl;

R$_c$ is H, halo, C$_1$-C$_4$ alkyl, or C$_3$-C$_4$ cycloalkyl;

R$_d$ is H, halo, C$_1$-C$_4$ alkyl, or C$_3$-C$_4$ cycloalkyl;

and z is 0, 1 or 2;

and pharmaceutically acceptable salts, solvates, esters, prodrugs and isomers thereof.

Another aspect of this invention is the provision of compounds, compositions, and kits for FASN inhibition comprising a compound of formula I-B:

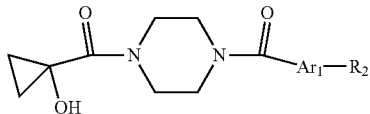

(I-B)

wherein:

Ar$_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —CH$_z$F$_{3-z}$, cyano, hydroxyl, hydroxylalkyl, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —OCH$_z$F$_{3-z}$, -alkyl, -alkenyl, -alkynyl, -alkoxy or (alkoxyalkyl)amino-, —N(R$_c$)—C(O)-alkyl, —N(Re)—C(O)-aryl, -cycloalkyl, -heterocycloalkyl, -aryl, and -heteroaryl, with the proviso that no two adjacent ring heteroatoms are both S or both O;

R$_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_d$)(cycloalkyl), methylenedioxy, —CH$_z$F$_{3-z}$, —OCH$_z$F$_{3-z}$, and -alkoxy;

R$_c$ is H, halo, C$_1$-C$_4$ alkyl, or C$_3$-C$_4$ cycloalkyl;

R$_d$ is H, halo, C$_1$-C$_4$ alkyl, or C$_3$-C$_4$ cycloalkyl;

and z is 0, 1 or 2;

and pharmaceutically acceptable salts, solvates, esters, prodrugs and isomers thereof.

Another aspect of this invention is the provision of compounds, compositions, and kits for FASN inhibition comprising a compound of formula I-C:

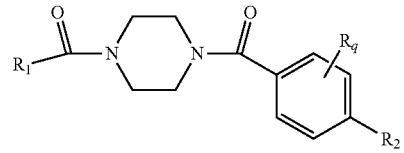

(I-C)

wherein:

R$_1$ is a C$_1$-C$_3$ hydroxyl-alkyl either unsubstituted or substituted with —CH$_3$ or —CH$_z$F$_{3-z}$, 5 membered cycloalkyl either unsubstituted or substituted with substituents selected from the group consisting of deuterium, —R$_p$, —OR$_p$, —NHR$_p$, and —NR$_p$R$_{p1}$, or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —R$_a$, —OR$_a$, —NHR$_a$, and —NR$_a$R$_{a1}$;

R$_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_d$)(cycloalkyl), methylenedioxy, —CH$_z$F$_{3-z}$, —OCH$_z$F$_{3-z}$, and -alkoxy;

R$_p$ and R$_{p1}$ are independently H, halo, C$_1$-C$_4$ alkyl, or C$_3$-C$_4$ cycloalkyl;

R$_a$ and R$_{a1}$ are independently H, halo, C$_1$-C$_4$ alkyl, or C$_3$-C$_4$ cycloalkyl;

R$_d$ is H, halo, C$_1$-C$_4$ alkyl, or C$_3$-C$_4$ cycloalkyl;

R$_q$ is H, halo, C$_1$-C$_4$ alkyl, or C$_3$-C$_4$ cycloalkyl;

and z is 0, 1 or 2;

and pharmaceutically acceptable salts, solvates, esters, prodrugs and isomers thereof.

Another aspect of this invention is the provision of compounds, compositions, and kits for FASN inhibition comprising a compound of formula I-D:

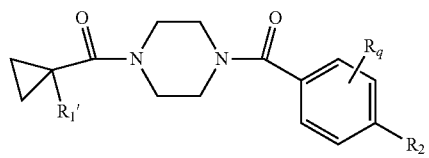

(I-D)

wherein:
R$_1$' is OH or NH$_2$;
R$_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_d$)(cycloalkyl), methylenedioxy, —CH$_z$F$_{3-z}$, —OCH$_z$F$_{3-z}$, and -alkoxy;

R$_d$ is H, halo, C$_1$-C$_4$ alkyl, or C$_3$-C$_4$ cycloalkyl;

and z is 0, 1 or 2;

and pharmaceutically acceptable salts, solvates, esters, prodrugs and isomers thereof.

Another aspect of this invention is the provision of methods of treating a disease via the inhibition of FASN in a subject (e.g., a human) in need thereof by administering to the subject an effective amount of the compound or the pharmaceutical formulation of the present invention.

Another preferred embodiment is a pharmaceutical formulation comprising a pharmaceutically acceptable compound of the present invention, which provides, upon administration to a human, a decrease in tumor burden and/or metastases. The pharmaceutical formulation can be administered by oral means or other suitable means. e.g., intravenously or by injection.

Yet another embodiment is a method of treating ovarian cancer in a subject (e.g., a human) in need thereof by administering to the subject a therapeutically effective amount of the compound or the pharmaceutical formulation of the present invention.

Yet another embodiment is a method of treating colon cancer in a subject (e.g., a human) in need thereof by administering to the subject an effective amount of the compound or the pharmaceutical formulation of the present invention.

Yet another embodiment is a method of treating breast cancer in a subject (e.g., a human) in need thereof by administering to the subject an effective amount of the pharmaceutical formulation of the present invention.

Yet another embodiment is a method of treating leukemia in a subject (e.g., a human) in need thereof by administering to the subject an effective amount of the compound or the pharmaceutical formulation of the present invention.

Yet another embodiment is a method of treating colon cancer, before or after surgical resection and/or radiation therapy, in a subject (e.g., a human) in need thereof by administering to the subject an effective amount of the compound or the pharmaceutical formulation of the present invention.

Yet another embodiment is a method of treating cancer, before or after surgical resection and/or radiation therapy, in a subject (e.g., a human) in need thereof by administering to the subject an effective amount of the compound or the pharmaceutical formulation of the present invention, including adjunctive therapy to treat nausea, with or without dexamethasone.

Yet another embodiment is a method of treating cancer, before or after surgical resection and or radiation therapy, in a subject (e.g., a human) in need thereof by administering to the subject an effective amount of the compound or the pharmaceutical formulation of the present invention, including adjunctive therapy with one or more additional therapeutic agents, or their pharmaceutically acceptable salts thereof. Non-limiting examples of such additional therapeutic agents include cytotoxic agents (such as for example, but not limited to, DNA interactive agents (such as cisplatin or doxorubicin)); taxanes (e.g. taxotere, taxol); topoisomerase II inhibitors (such as etoposide); topoisomerase I inhibitors (such as irinotecan (or CPT-11), camptostar, or topotecan); tubulin interacting agents (such as paclitaxel, docetaxel or the epothilones); hormonal agents (such as tamoxifen); thymidilate synthase inhibitors (such as 5-fluorouracil or 5-FU); anti-metabolites (such as methoxtrexate); alkylating agents (such as temozolomide, cyclophosphamide); Farnesyl protein transferase inhibitors (such as, SARASAR™. (4-[2-[4-[(11R)-3,10-dibromo-8-chloro-6,11-dihydro-5H-benzo[5,-6]cyclohepta[1,2-b]pyridin-11-yl-]-1-piperidinyl]-2-oxoethyl]-1-piperidine-carboxamide, or SCH 66336), tipifarnib (Zarnestra® or R115777 from Janssen Pharmaceuticals), L778,123 (a farnesyl protein transferase inhibitor from Merck & Company, Whitehouse Station, N.J.), BMS 214662 (a farnesyl protein transferase inhibitor from Bristol-Myers Squibb Pharmaceuticals, Princeton, N.J.); signal transduction inhibitors (such as, Iressa® (from Astra Zeneca Pharmaceuticals, England), Tarceva® (EGFR kinase inhibitors), antibodies to EGFR (e.g., C225), GLEEVEC® (C-abl kinase inhibitor from Novartis Pharmaceuticals, East Hanover, N.J.); interferons such as, for example, Intron® (from Merck & Company), Peg-Intron® (from Merck & Company); hormonal therapy combinations; aromatase combinations; ara-C, adriamycin, cytoxan, and gemcitabine.

Other anti-cancer (also known as anti-neoplastic) agents include but are not limited to Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, oxaliplatin, leucovirin, oxaliplatin (ELOXATIN®. from Sanofi-Synthelabo Pharmaceuticals, France), Pentostatine, Vinblastine, Vincristine, Vindesine, Bleomycin, Dactinomycin, Daunorubicin, Doxorubicin, Epirubicin, Idarubicin, Mithramycin, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, Herceptin, Bexxar, Velcade®, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Ifosfomide, Rituximab, C225, and Campath, 5-fluorouracil and leucovorin, with or without a 5-HT$_3$ receptor inhibitor (e.g., dolansetron, granisetron, ondansetron) with or without dexamethasone.

Yet another embodiment is a method of treating diabetes in a subject (e.g., a human) in need thereof by administering to the subject an effective amount of the compound or the pharmaceutical formulation of the present invention.

Yet another embodiment is a method of treating obesity or over weight in a subject (e.g., a human) in need thereof by administering to the subject an effective amount of the compound or the pharmaceutical formulation of the present invention.

Yet another embodiment is a method of treating uterine leiomyomata in a subject (e.g., a human) in need thereof by administering to the subject an effective amount of the compound or the pharmaceutical formulation of the present invention.

Yet another embodiment is a method of treating microbial infections in a subject (e.g., a human) in need thereof by administering to the subject an effective amount of the compound or the pharmaceutical formulation of the present invention.

Yet another embodiment is a method of treating viral infections, including but not limited to infections caused by HCMV, influenza A-virus, HepatisC-virus, CVB3, picorna virus, EBC and dengue virus in a subject (e.g., a human) in need thereof by administering to the subject an effective amount of the compound or the pharmaceutical formulation of the present invention.

If formulated as a fixed dose, such combination products employ the compounds of this invention within the dosage range described herein (or as known to those skilled in the art) and the other pharmaceutically active agent or treatment within its dosage range. For example, the CDCl$_2$ inhibitor olomucine has been found to act synergistically with known cytotoxic agents in inducing apoptosis (J. Cell Sci., (1995) 108, 2897). The compounds of the invention may also be administered sequentially with known anticancer or cytotoxic agents when a combination formulation is inappropriate. In any combination treatment, the invention is not limited in the sequence of administration; compounds of the Formulas may be administered either prior to or after administration of the known anticancer or cytotoxic agent. For example, the cytotoxic activity of the cyclin-dependent kinase inhibitor flavopiridol is affected by the sequence of administration with anticancer agents. Cancer Research, (1997) 57, 3375. Such techniques are within the skills of persons skilled in the art as well as attending physicians.

Any of the aforementioned methods may be augmented by administration of fluids (such as water), loop diuretics, one or more of a chemotherapeutic or antineoplastic agent, such as leucovorin and fluorouracil, and an adjunctive chemotherapeutic agent (such as filgrastim and erythropoietin), or any combination of the foregoing.

Yet another embodiment is a method for administering a compound of the instant invention to a subject (e.g., a human) in need thereof by administering to the subject the pharmaceutical formulation of the present invention.

Yet another embodiment is a method of preparing a pharmaceutical formulation of the present invention by mixing at least one pharmaceutically acceptable compound of the present invention, and, optionally, one or more pharmaceutically acceptable additives or excipients.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compounds of this invention may also be delivered subcutaneously.

Preferably the compound is administered orally or intravenously.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 1000 mg, preferably from about 1 mg to about 500 mg, more preferably from about 1 mg to about 250 mg, still more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 500 mg/day, preferably 1 mg/day to 200 mg/day, in two to four divided doses.

Definitions

As used above, and throughout this disclosure, the following terms, unless otherwise indicated, shall be understood to have the following meanings. If a definition is missing, convention definition as known to one skilled in the art controls.

"Patient" includes both human and animals.

"Mammal" means humans and other mammalian animals.

The term "FASN" refers all classes, types, subtypes, isotypes, segments, variants, and mutant forms of fatty acid synthase.

The term "inhibitor" refers to a molecule such as a compound, a drug, an enzyme activator or a hormone that blocks or otherwise interferes with a particular biological activity.

The terms "effective amount" or "therapeutically effective amount" refer to a sufficient amount of the agent to provide the desired biological result. That result can be reduction and/or alleviation of the signs, symptoms, or causes of a disease, or any other desired alteration of a biological system. For example, an "effective amount" for therapeutic use is the amount of the composition comprising a compound as disclosed herein required to provide a clinically significant decrease in a disease. An appropriate "effective" amount in any individual case may be determined by one of ordinary skill in the art using routine experimentation. Thus, the expression "effective amount" generally refers to the quantity for which the active substance has therapeutic effects. In the present case the active substance is the inhibitor of the fatty acid synthase (FASN).

As used herein, the terms "treat" or "treatment" are synonymous with the term "prevent" and are meant to indicate a postponement of development of diseases, preventing the development of diseases, and/or reducing severity of such symptoms that will or are expected to develop. Thus, these terms include ameliorating existing disease symptoms, preventing additional symptoms, ameliorating or preventing the underlying metabolic causes of symptoms, inhibiting the disorder or disease, e.g., arresting the development of the disorder or disease, relieving the disorder or disease, causing regression of the disorder or disease, relieving a condition caused by the disease or disorder, or stopping or alleviating the symptoms of the disease or disorder.

By "pharmaceutically acceptable" or "pharmacologically acceptable" is meant a material which is not biologically or otherwise undesirable—the material may be administered to an individual without causing any undesirable biological effects or interacting in a deleterious manner with any of the components of the composition in which it is contained.

"Carrier materials" or what are also referred to as "excipients" include any commonly used excipients in pharmaceutics and should be selected on the basis of compatibility and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" may comprise, e.g., acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, and the like. See, e.g., Hoover, John E., *Remington's Pharmaceutical Sciences*, Mack Publishing Co., Easton, Pa. 1975.

As used herein, the term "subject" encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the present invention, the mammal is a human.

As used herein, "alkyl" means a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight, branched or cyclized. As used herein, "lower alkyl" means an alkyl having from 1 to 6 carbon atoms.

As used herein, an "alkenyl" includes an unbranched or branched hydrocarbon chain having one or more double bonds therein. The double bond of an alkenyl group can be unconjugated or conjugated to another unsaturated group. Illustrative alkenyl groups include, but are not limited to, ($C_2$-$C_8$) alkenyl groups, such as ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted.

As used herein, "alkynyl" includes an unbranched or branched hydrocarbon chain having one or more triple bonds therein. The triple bond of an alkynyl group can be unconjugated or conjugated to another unsaturated group. Suitable alkynyl groups include, but are not limited to, ($C_2$-$C_6$) alkynyl groups, such as ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The terms "trifluoromethyl," "sulfonyl," and "carboxyl" include $CF_3$, $SO_2$, and $CO_2H$, respectively.

The term "hydroxyl" means an OH group;

The term alkyl hydroxyl or hydroxyalkyl means an alkyl group as defined above, where the alkyl group has an OH group disposed thereon.

The term "alkoxy" as used herein includes O-(alkyl), wherein alkyl is defined above.

The term "aminoalkyl" as used herein means a group having one or more nitrogen atoms and one or more alkyl groups as defined above on the nitrogen.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Heteroarylalkyl" means a heteroaryl moiety as defined herein linked via an alkyl moiety (defined above) to a parent core. Non-limiting examples of suitable heteroaryls include 2-pyridinylmethyl, quinolinylmethyl and the like.

"Heterocyclylalkyl" means a heterocyclyl moiety as defined herein linked via an alkyl moiety (defined above) to a parent core. Non-limiting examples of suitable heterocyclylalkyls include piperidinylmethyl, piperazinylmethyl and the like.

It should also be noted that any carbon as well as heteroatom with unsatisfied valences in the text, schemes, examples and Tables herein is assumed to have the sufficient number of hydrogen atom(s) to satisfy the valences.

When any variable (e.g., aryl, heterocycle, $R^2$, etc.) occurs more than one time in any constituent or in the Formulas, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

The term "deuterium" as used herein means a stable isotope of hydrogen having odd numbers of protons and neutrons.

The term "halo" as used herein means a substituent having at least one halogen selected from fluorine, chlorine, bromine, and iodine.

The term "cyano" as used herein means a substituent having a carbon atom joined to a nitrogen atom by a triple bond.

The term "amino" as used herein means a substituent containing at least one nitrogen atom.

The term "(amino)alkoxy" as used herein means a substituent having at least one amino group and at least one alkoxy group.

The term "aryloxy" as used herein means a substituent of the form Ar—O— where Ar is an aryl group as defined herein.

The term "methylenedioxy" as used herein means a functional group with the structural formula —O—$CH_2$— which is connected to the molecule by two chemical bonds via the oxygens.

As used herein, "alkoxyalkyl" means -(alkyl)-O-(alkyl), wherein each "alkyl" is independently an alkyl group defined above.

The term "(alkoxyalkyl)amino" as used herein means a substituent having at least one alkoxyalkyl group as defined above and at least one amino group as defined above.

As used herein, the term "aryl" refers to a monocyclic, or fused polycyclic, aromatic carbocycle (ring structure having ring atoms that are all carbon) having from 3 to 24 ring atoms per ring. Illustrative examples of aryl groups include, but are not limited to, the following moieties:

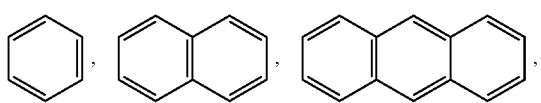

-continued
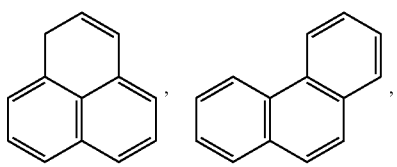
and the like.
Illustrative substituted aryls include:
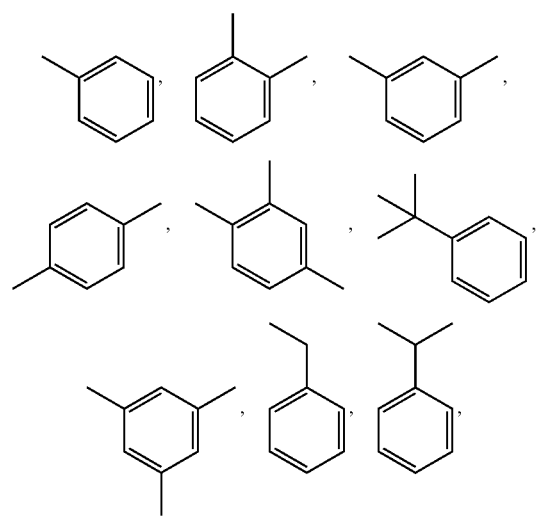
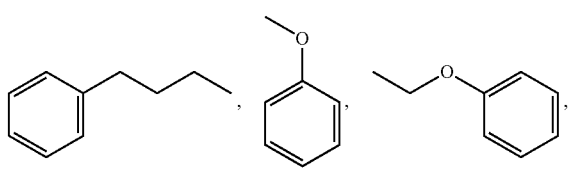
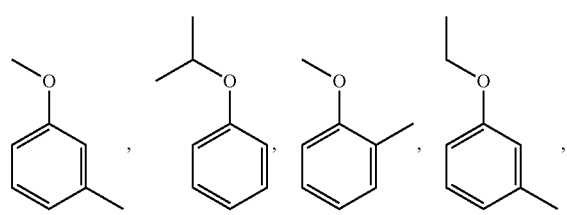
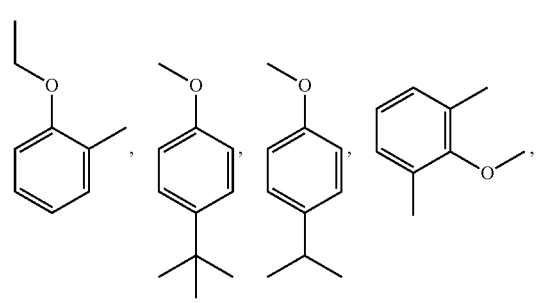
-continued
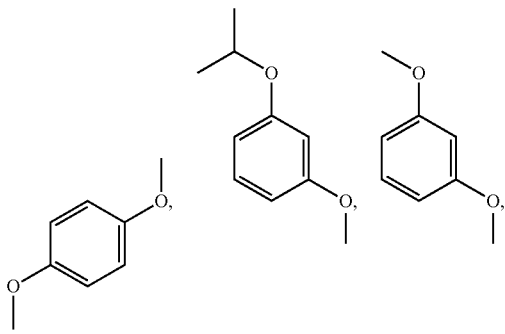
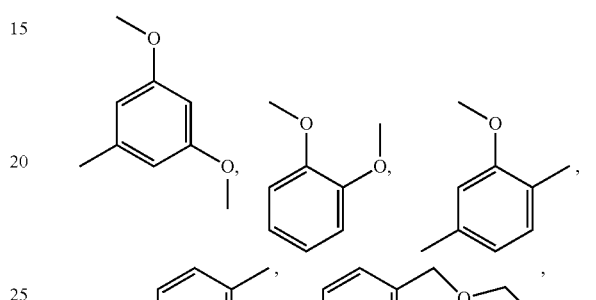
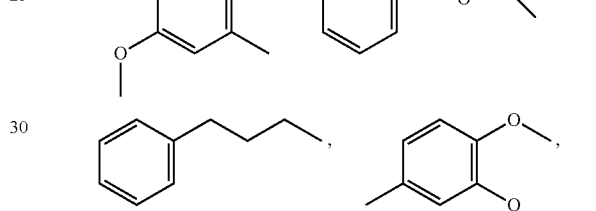
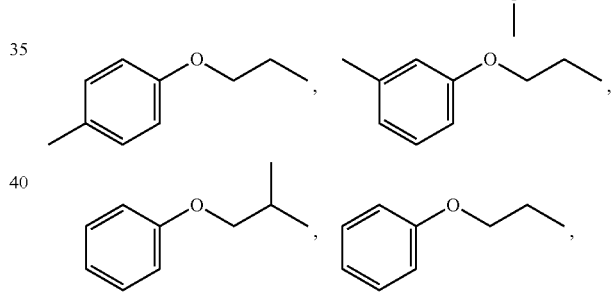
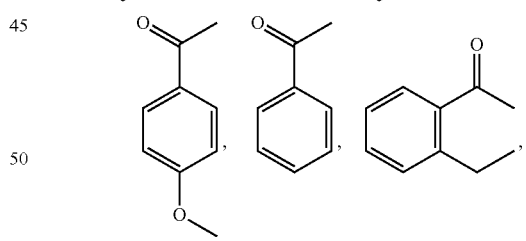
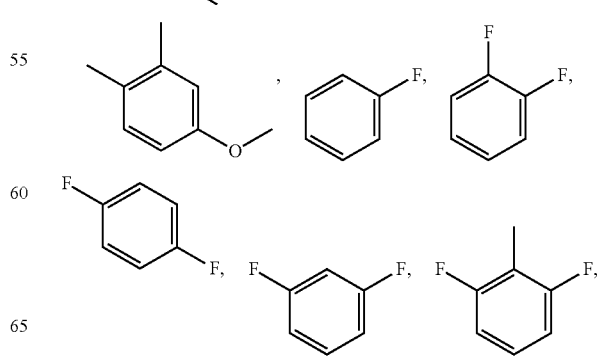

-continued
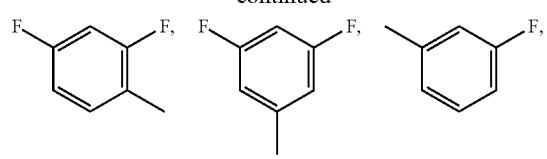
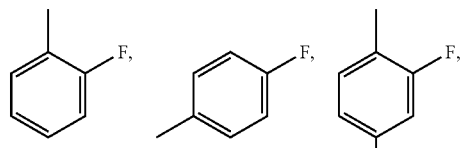
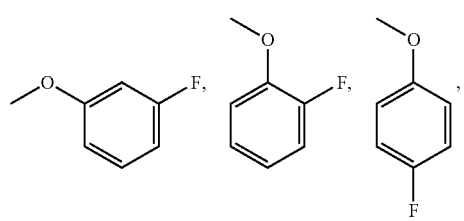
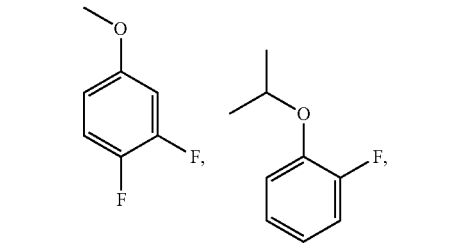
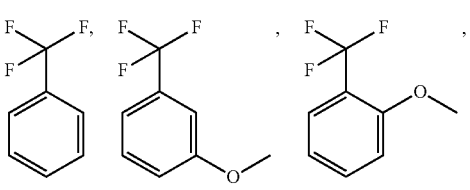
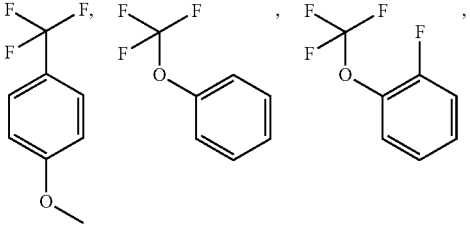
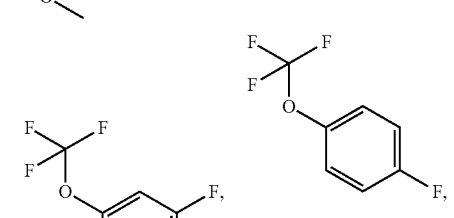

-continued
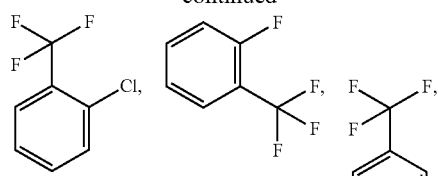
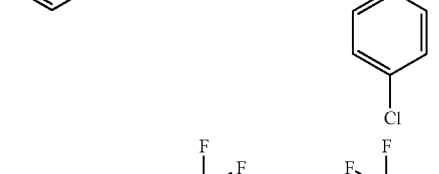
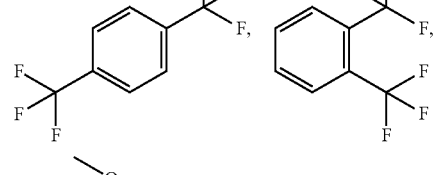
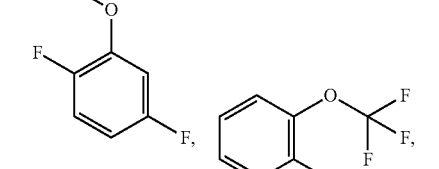
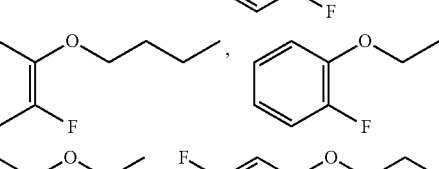
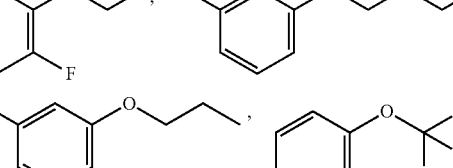
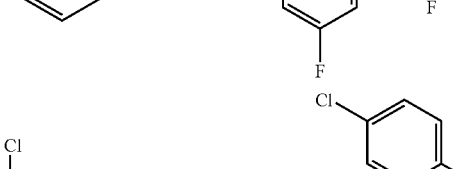
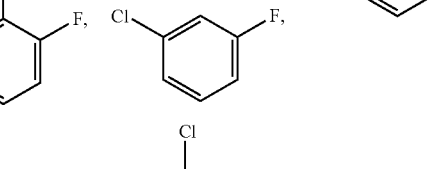
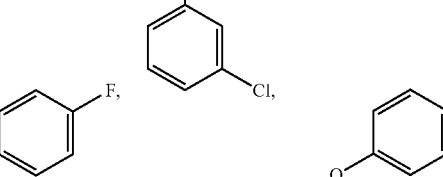
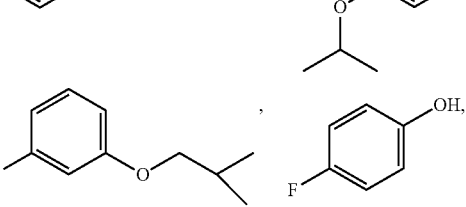

-continued
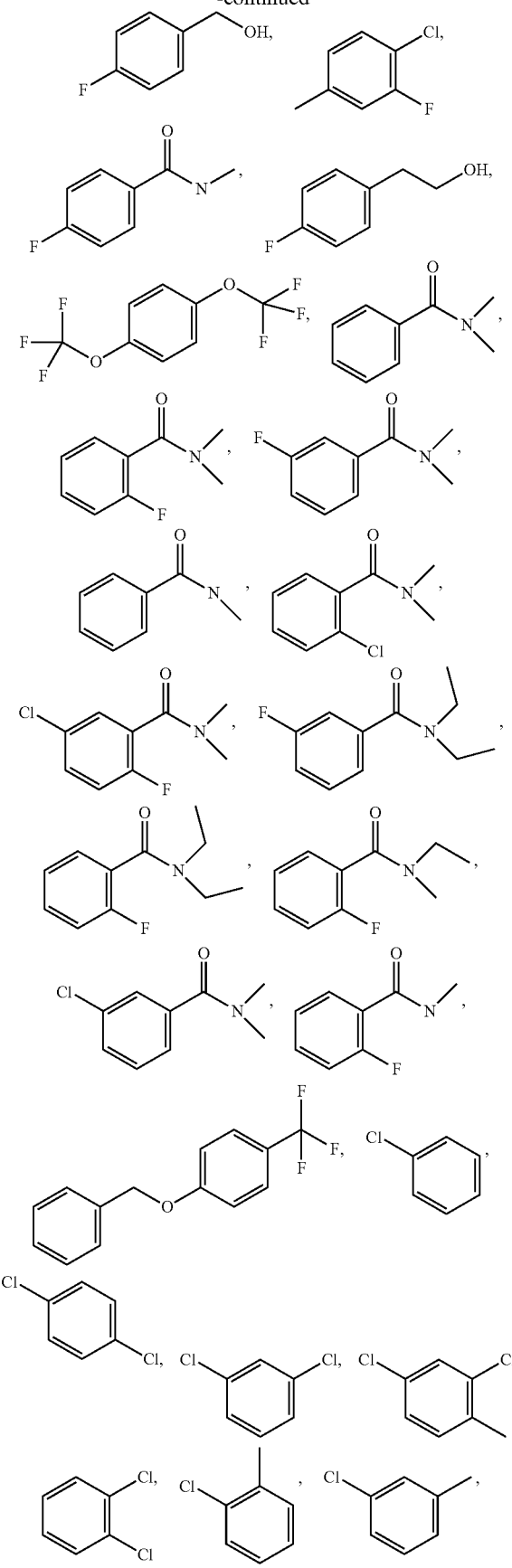
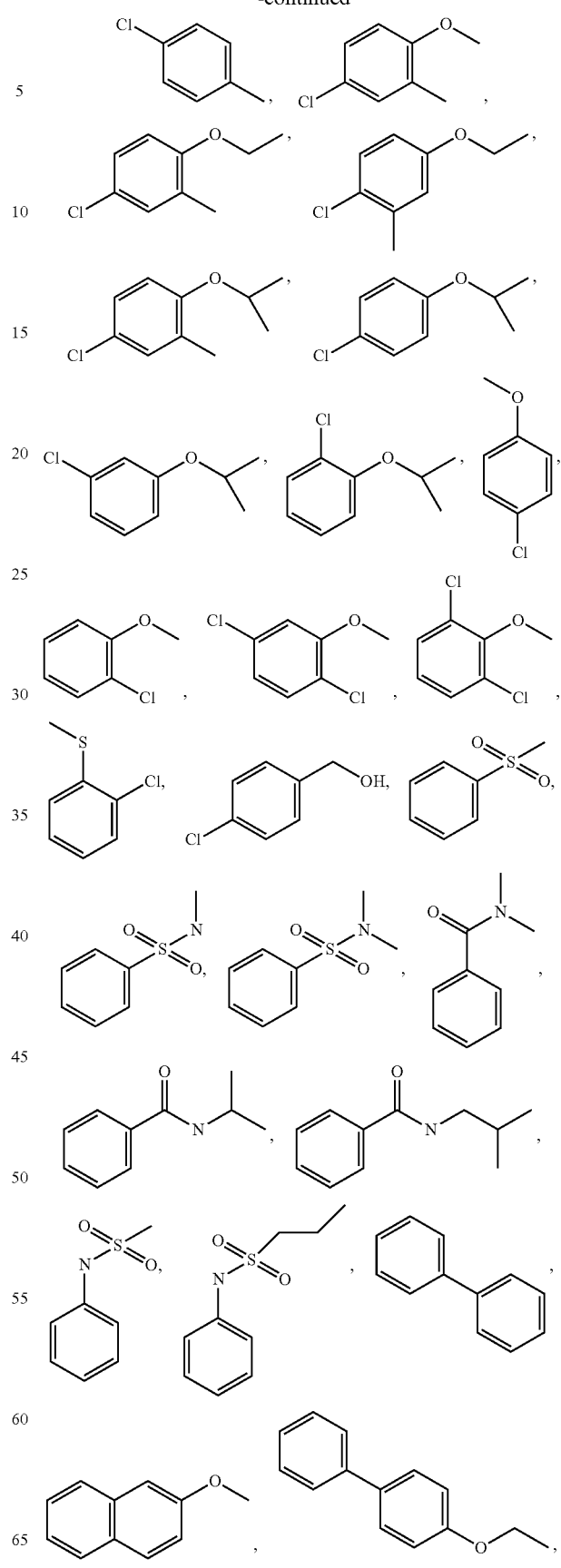

-continued
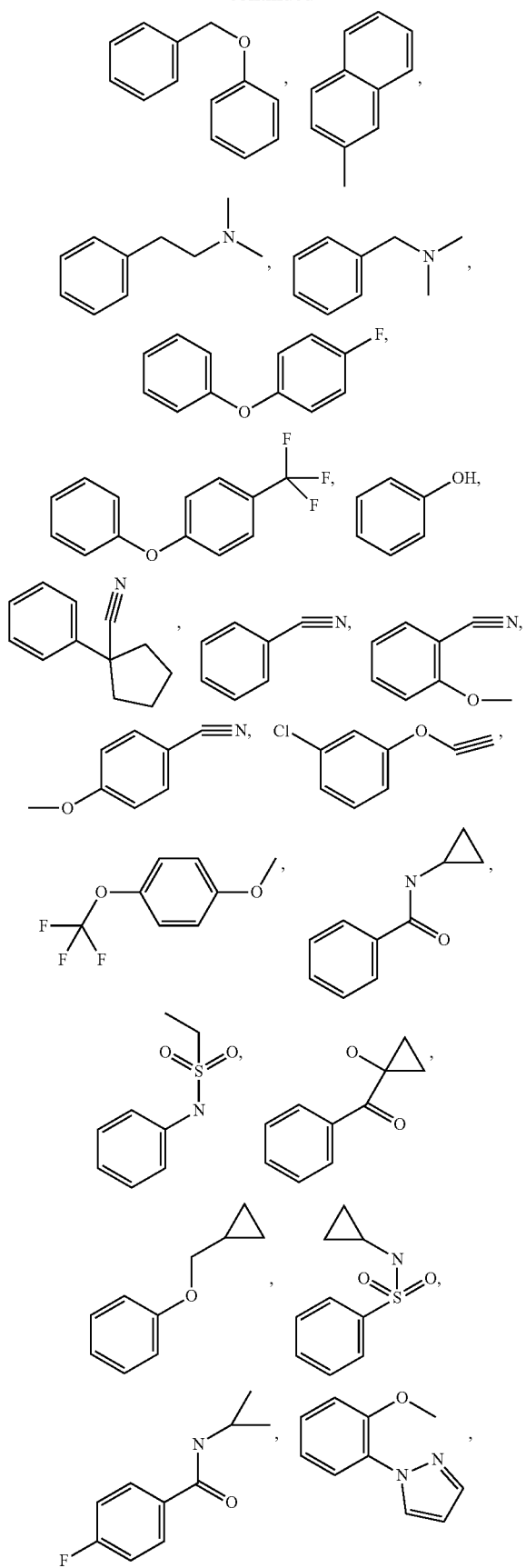
-continued
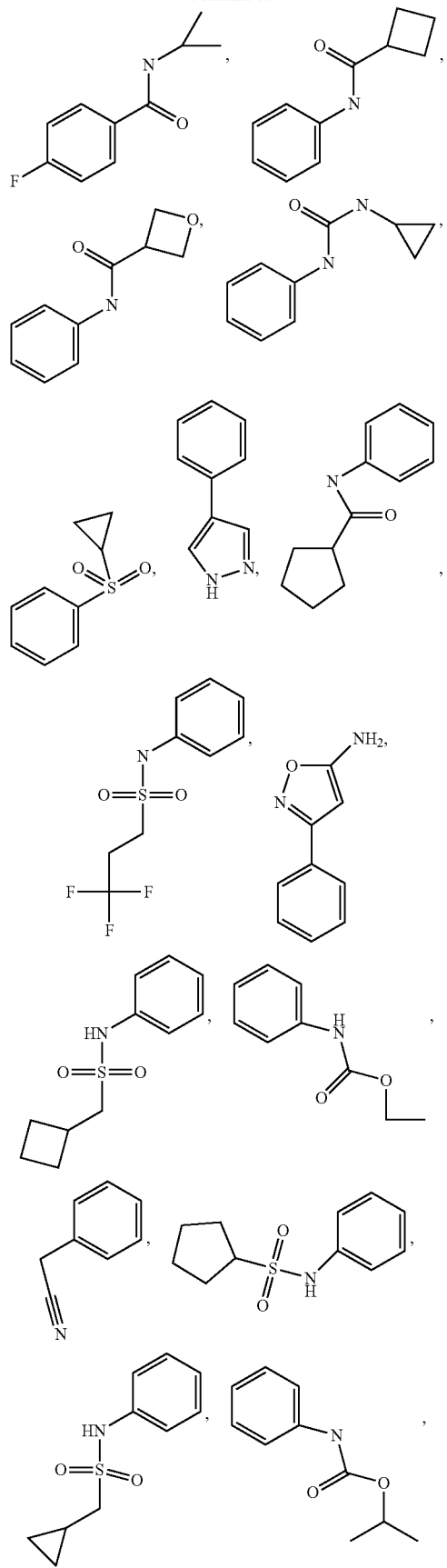

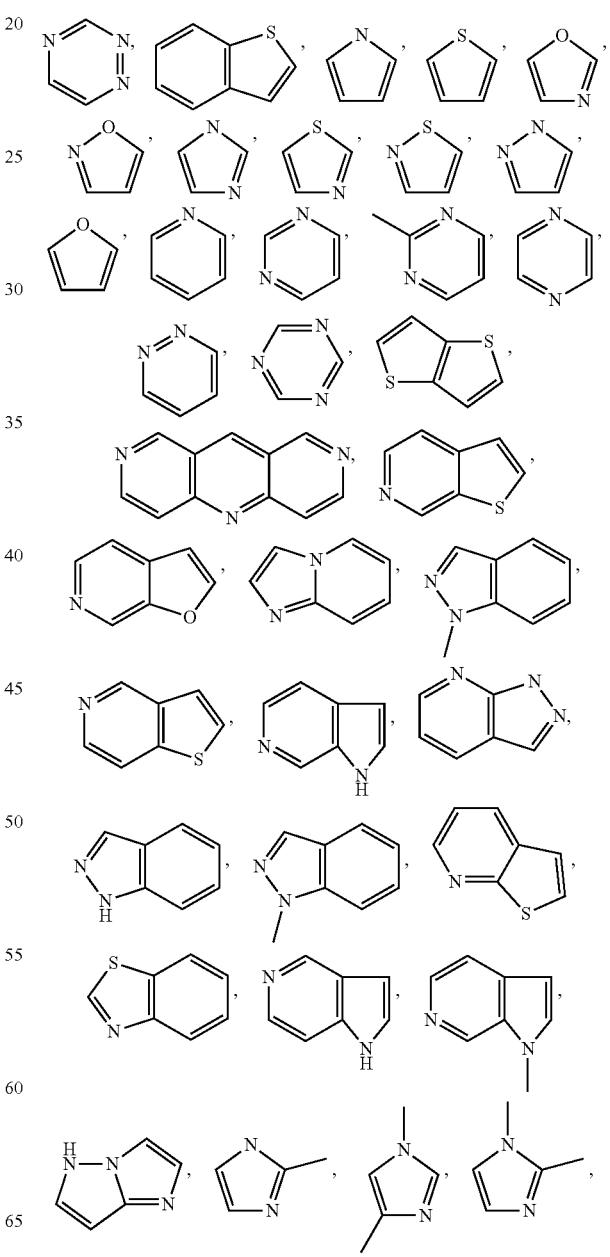

and the like.

As used herein, the term "heteroaryl" refers to a monocyclic, or fused polycyclic, aromatic heterocycle (ring structure having ring atoms selected from carbon atoms as well as nitrogen, oxygen, and sulfur heteroatoms) having from 3 to 24 ring atoms per ring. Illustrative examples of heteroaryl and substituted heteroaryl groups include, but are not limited to the following moieties:

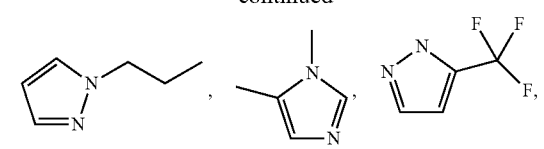
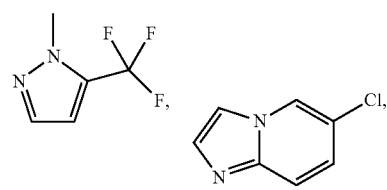
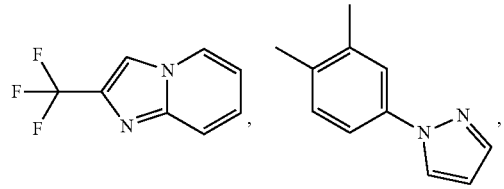
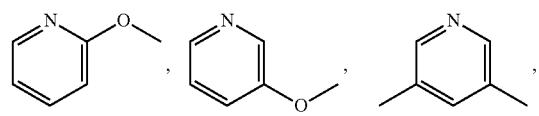
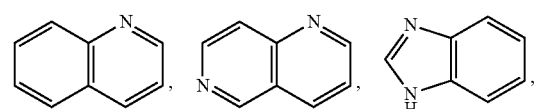
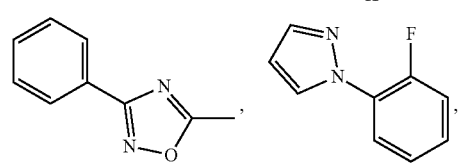
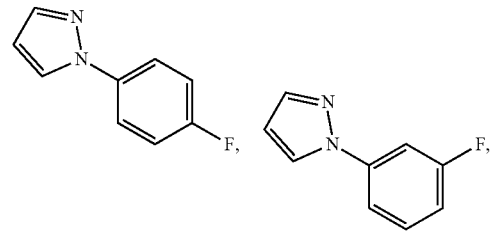
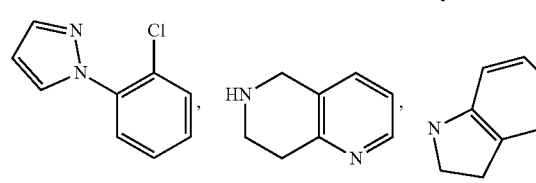
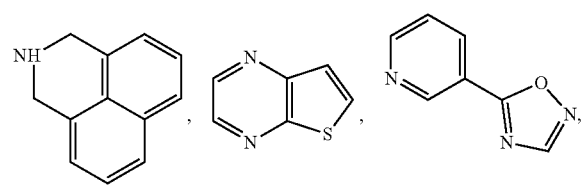

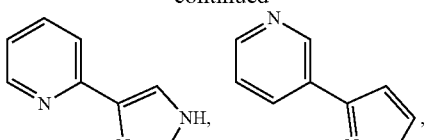
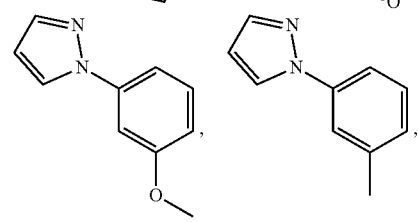
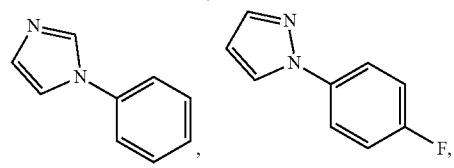
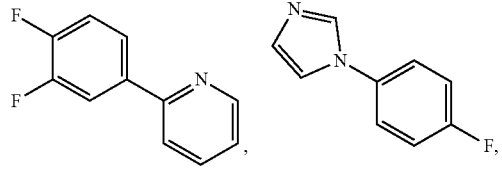
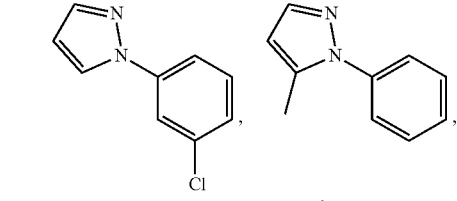
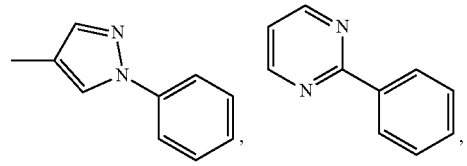
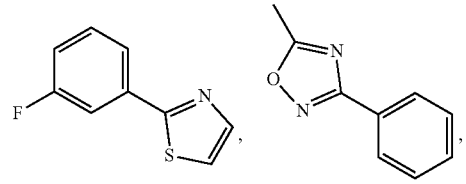
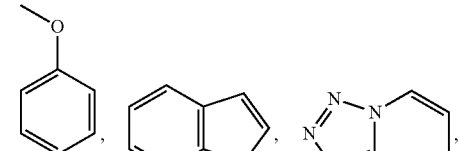
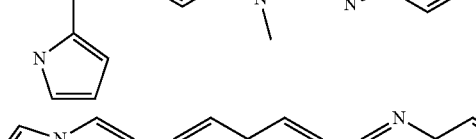
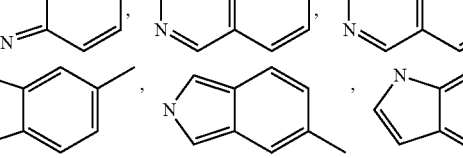

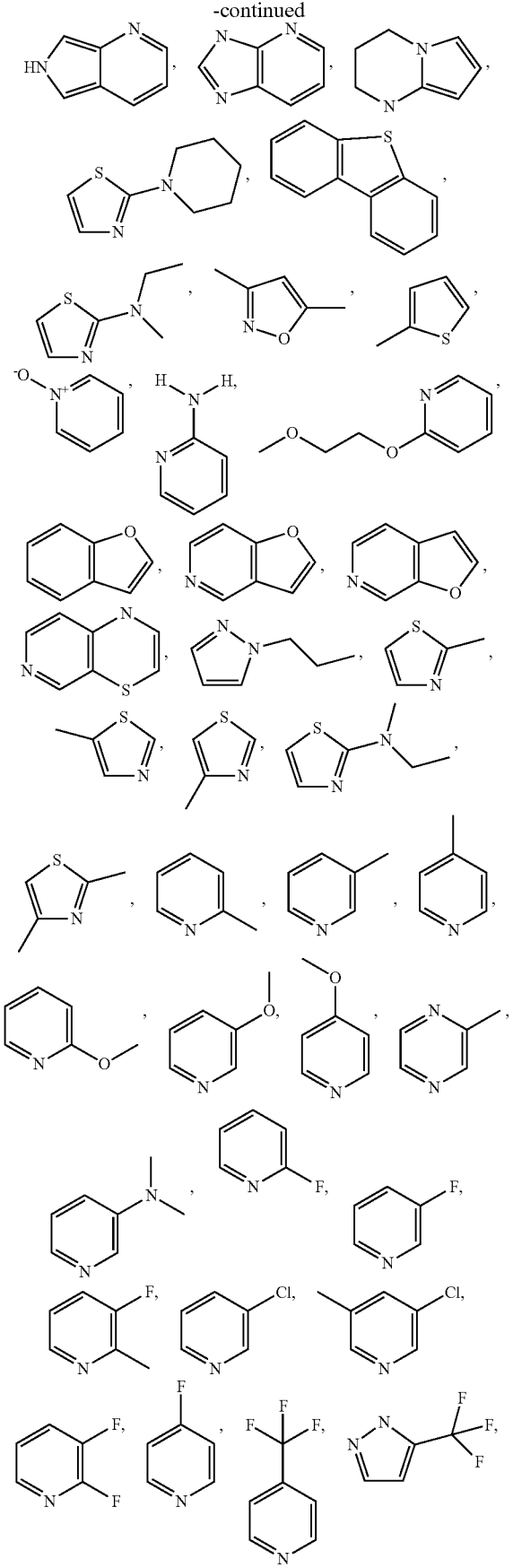
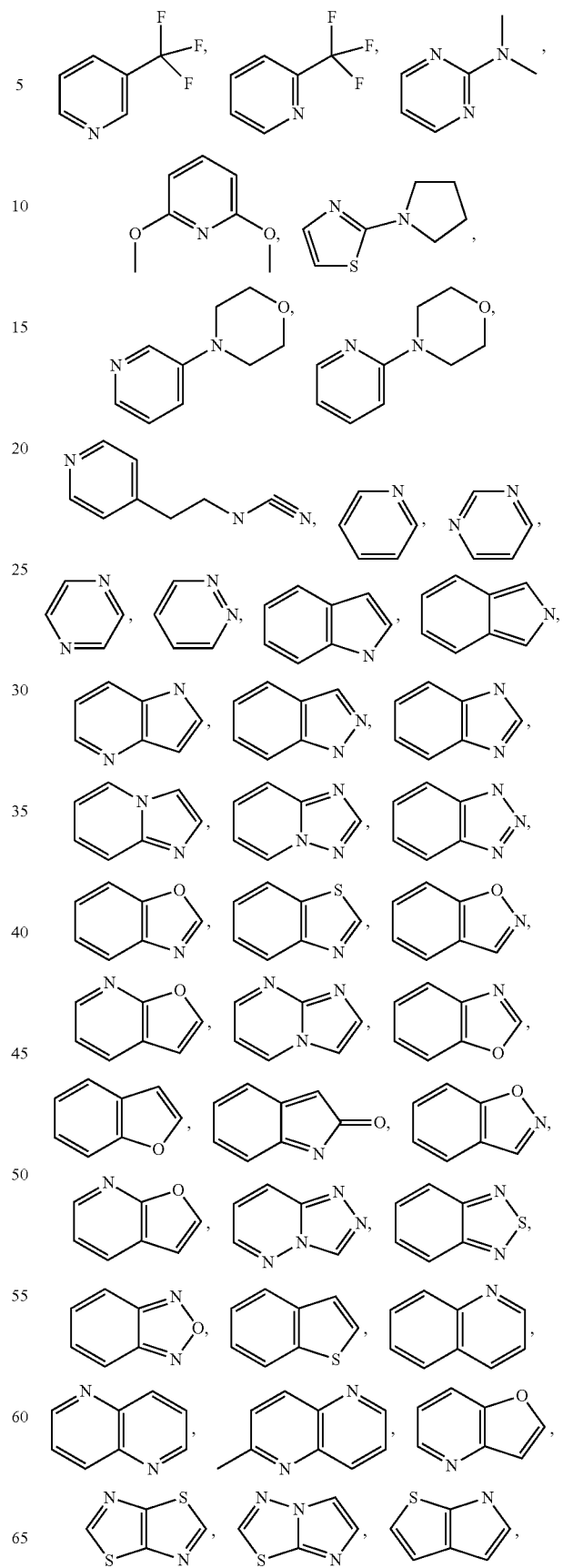

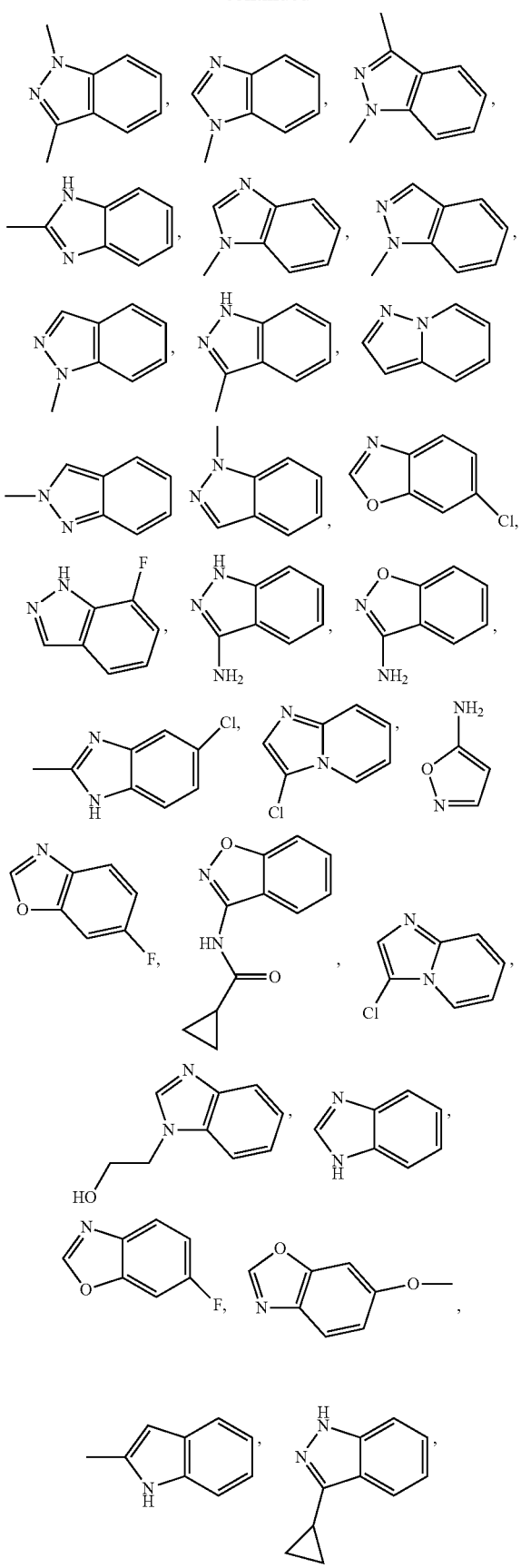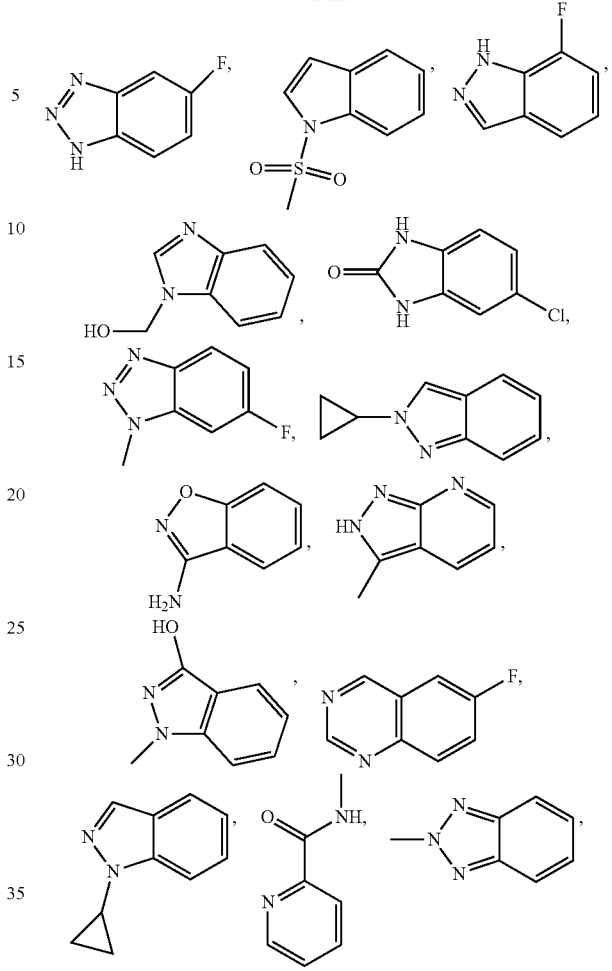
and the like.
As used herein, the term "cycloalkyl" refers to a saturated or partially saturated, monocyclic or fused or spiro polycyclic, carbocycle having from 3 to 24 ring atoms per ring. Illustrative examples of cycloalkyl groups include, but are not limited to, the following moieties:
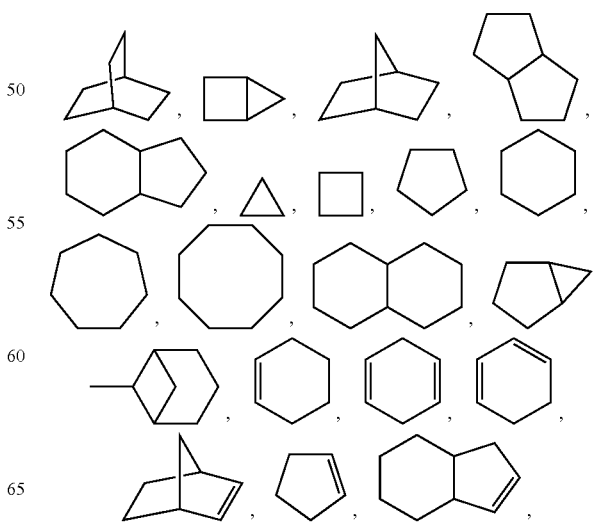

-continued

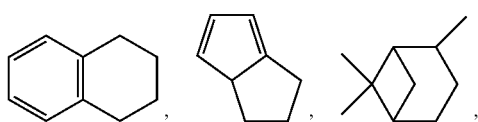

and the like.

As used herein, the term "heterocycloalkyl" refers to a monocyclic, or fused or spiro, polycyclic, ring structure that is saturated or partially saturated and has from 3 to 24 ring atoms per ring selected from C atoms and N, O, and S heteroatoms. Illustrative examples of heterocycloalkyl and substituted heterocycloalkyl groups include, but are not limited to:

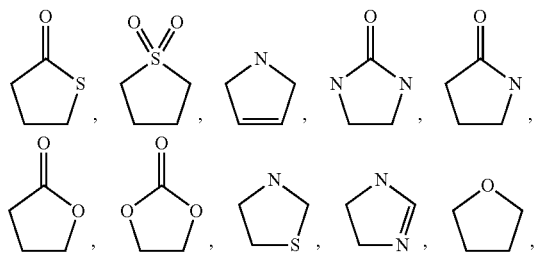

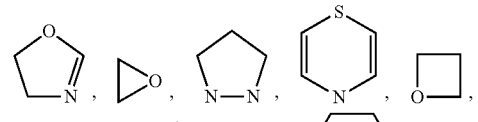

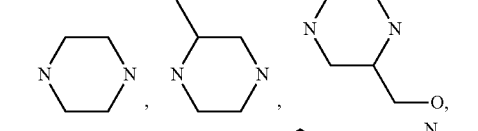

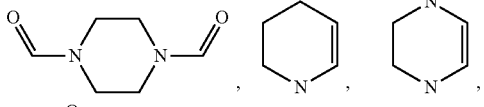

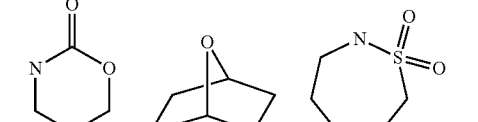

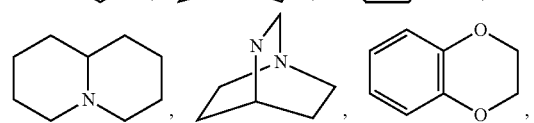

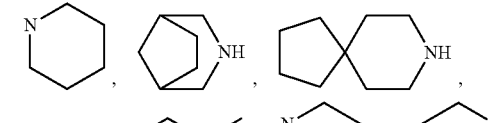

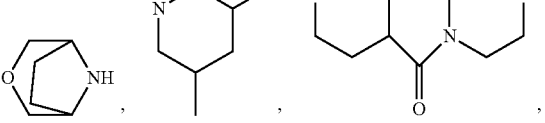

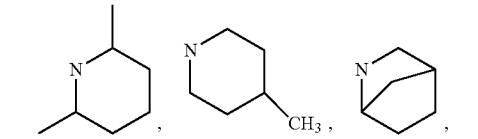

-continued

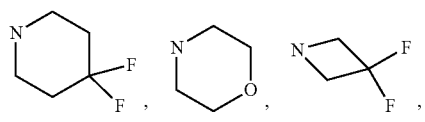

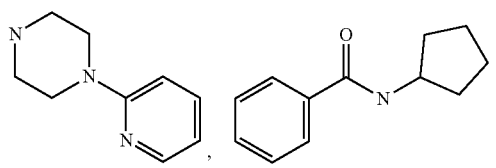

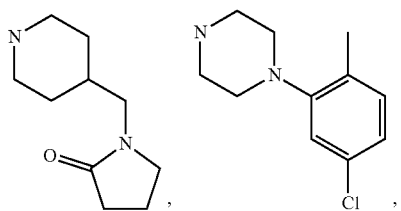

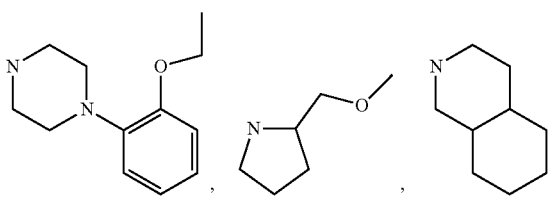

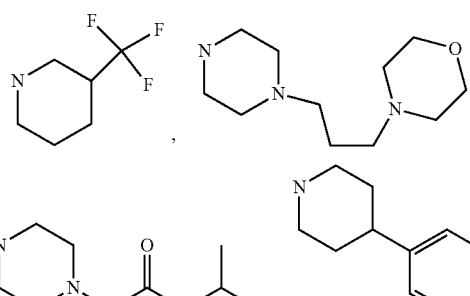

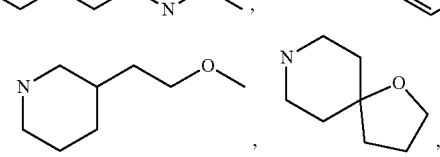

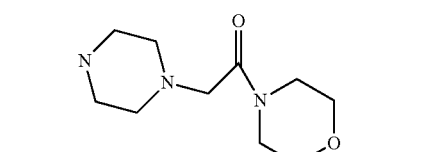

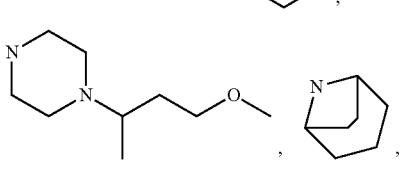

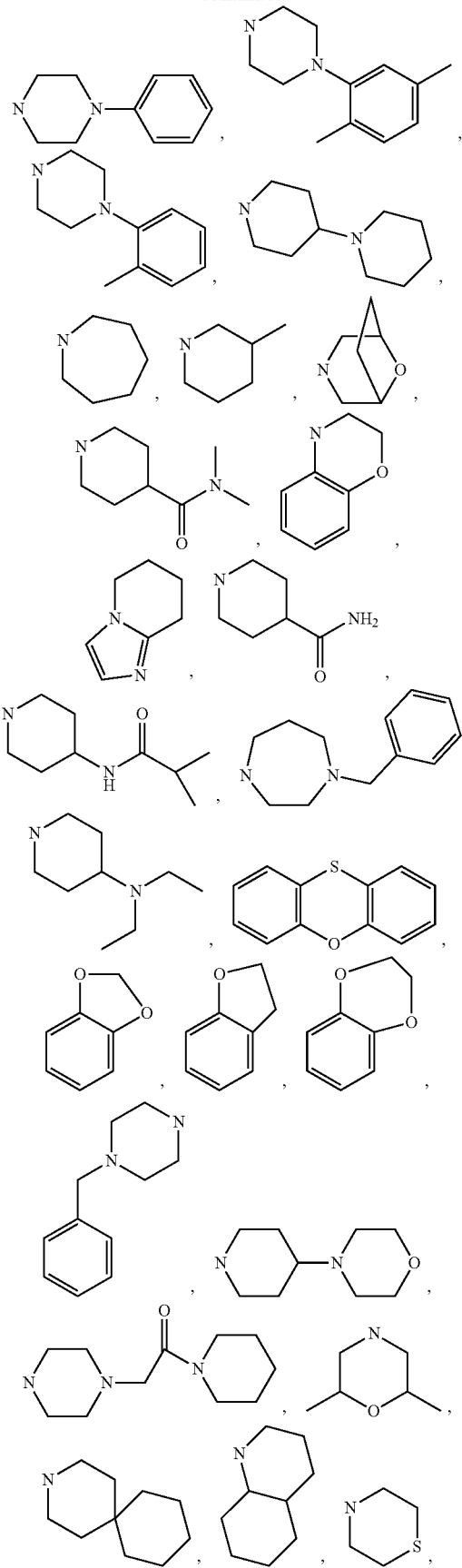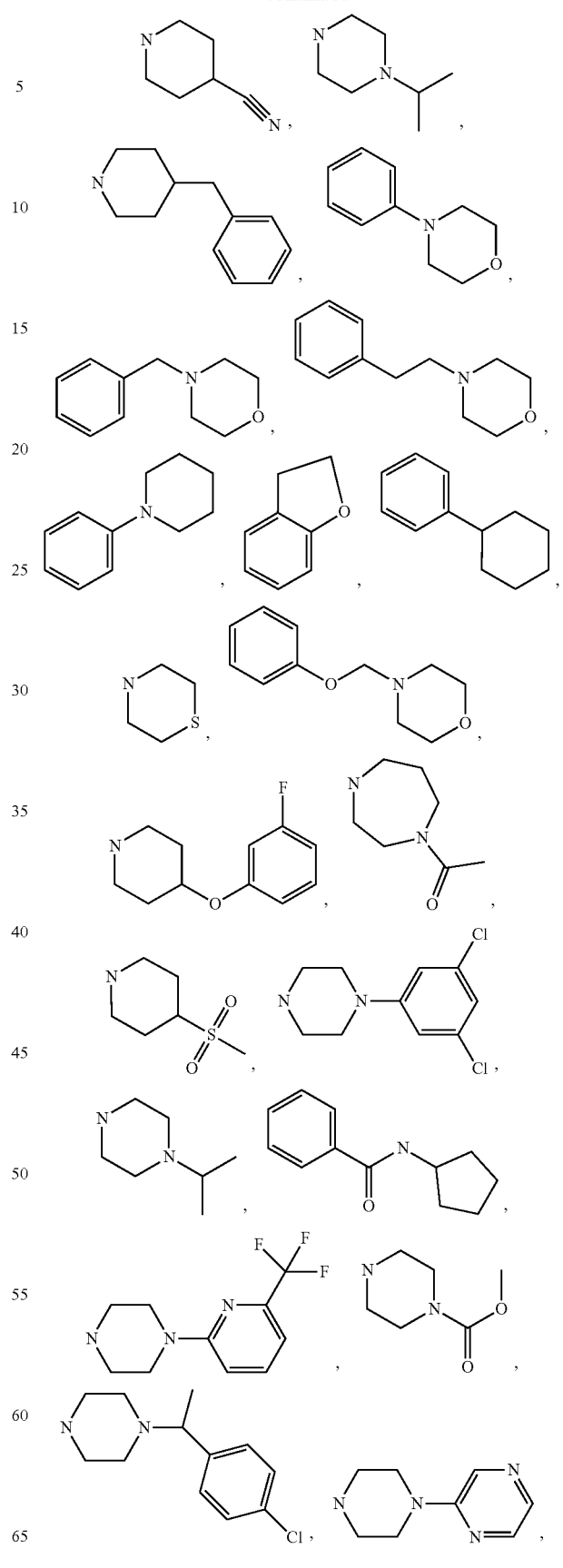

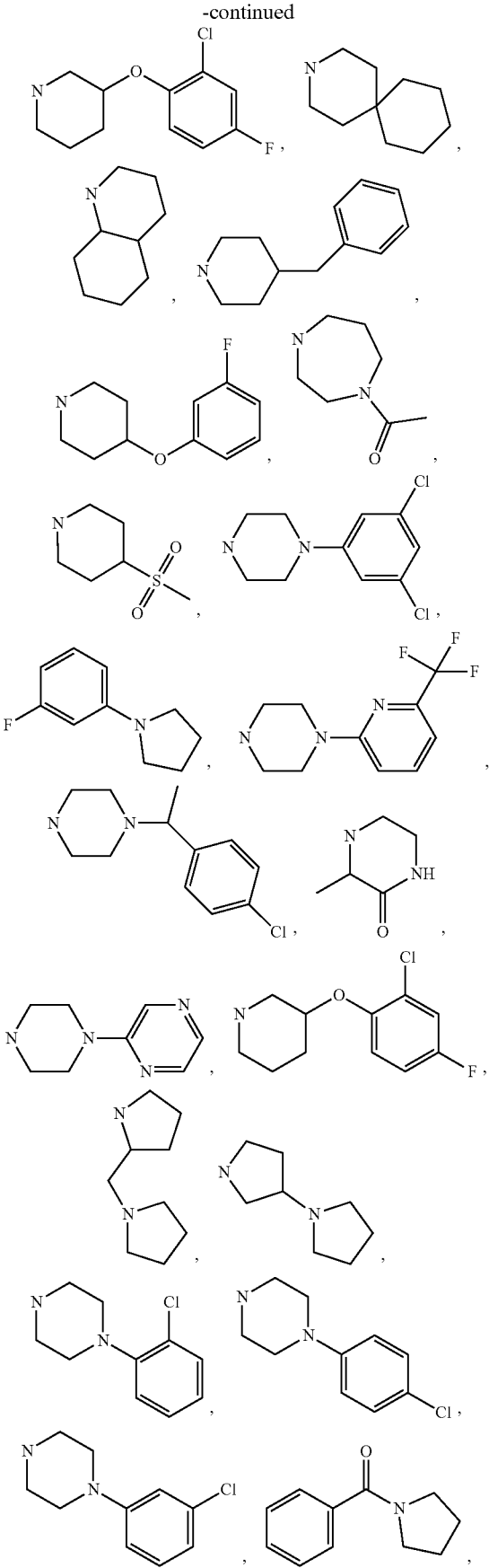
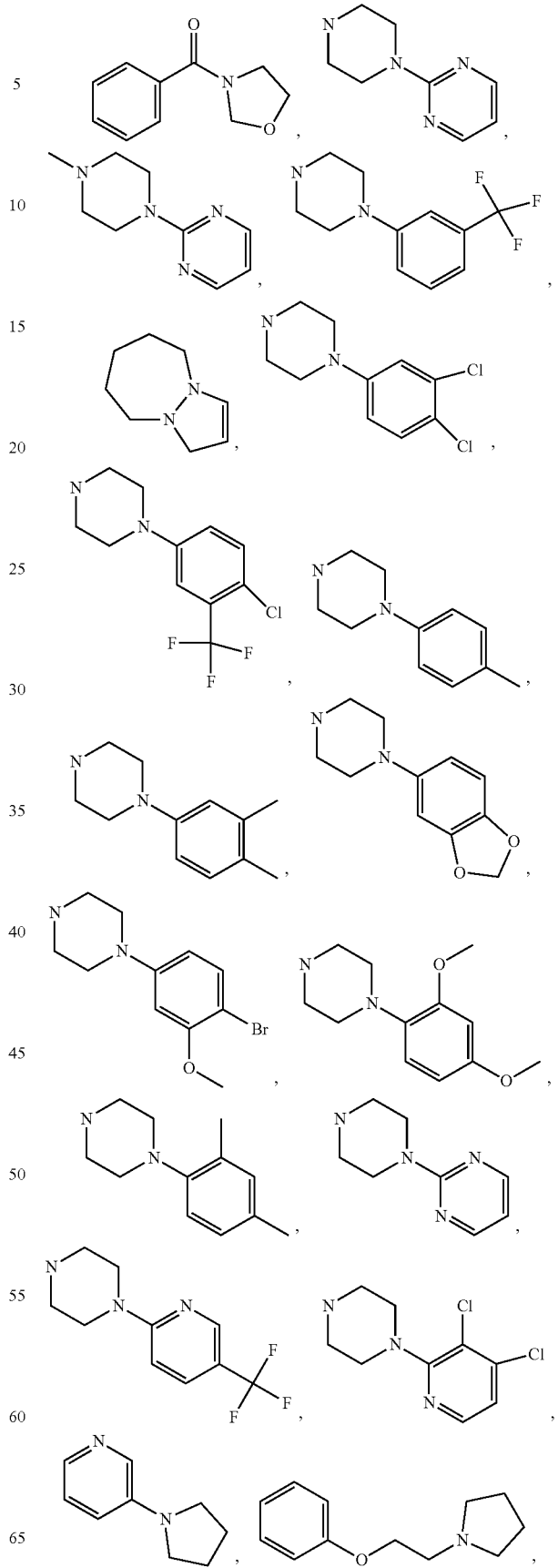

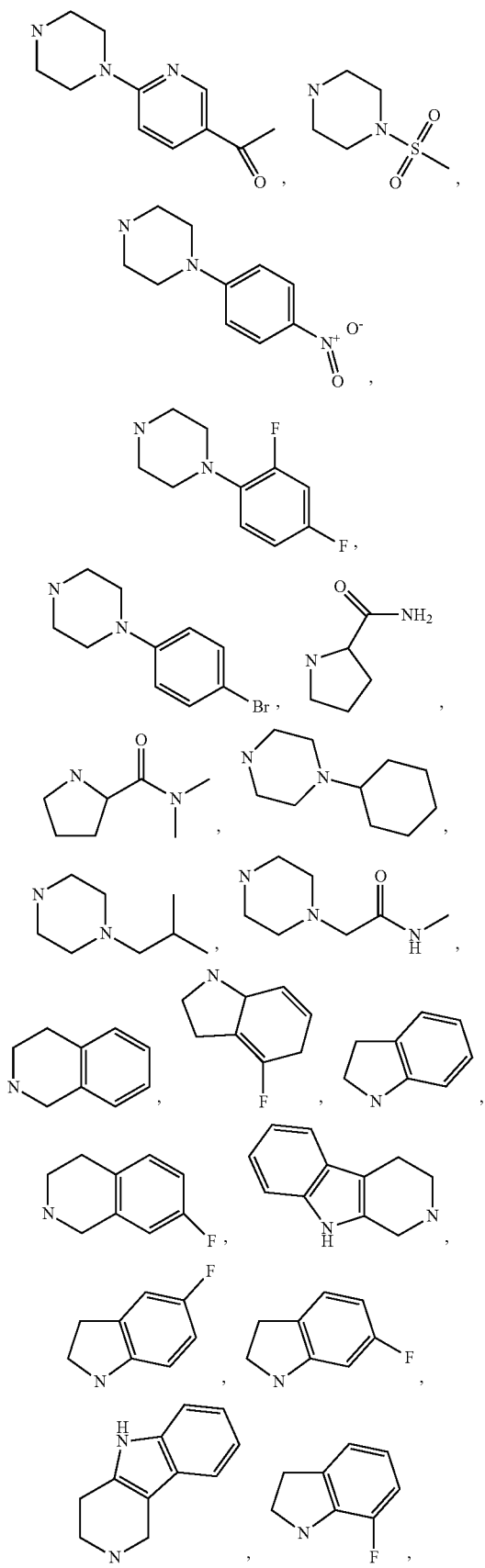
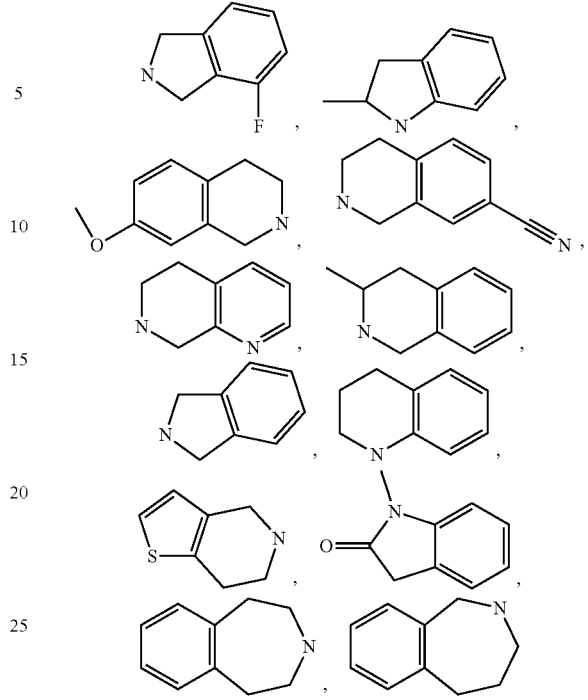

and the like.

Numerical ranges, as used herein, are intended to include sequential integers. For example, a range expressed as "from 0 to 4" would include 0, 1, 2, 3 and 4.

As used herein, the terms "monocyclic, bicyclic, or tricyclic aryl, heteroaryl, cycloalkyl, or heterocycloalkyl," mean any ring of a bicyclic or tricyclic structure may independently be aryl, heteroaryl, cycloalkyl, or heterocycloalkyl in an ortho or ortho and peri fused system.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

As used herein, the term "optionally substituted" means that the specified group is unsubstituted or substituted by one or more substituents.

When a multifunctional moiety is shown, the point of attachment to the core may be identified by a line. For e.g. (cycloalkyloxy)alkyl- refers to alkyl being the point of attachment to the core while cycloalkyl is attached to alkyl via the oxy group. In the absence of a line, attachment at any position may be assumed.

The expression "adjunctive chemotherapeutic agent" generally refers to agents which treat, alleviate, relieve, or ameliorate the side effects of chemotherapeutic agents. Such agents include those which modify blood cell growth and maturation. Examples of adjunctive chemotherapeutic agents include, but are not limited to, filgrastim and erythropoietin. Other such adjunctive chemotherapeutic agents include those which inhibit nausea associated with administration of the chemotherapeutic agents, such as a 5-HT$_3$ receptor inhibitor (e.g., dolansetron, granisetron, or ondansetron), with or without dexamethasone.

The terms "chemotherapeutic agent" and "antineoplastic agent" generally refer to agents which treat, prevent, cure, heal, alleviate, relieve, alter, remedy, ameliorate, improve, or affect malignancies and their metastasis. Examples of such agents (also known as "antineoplastic agents") include, but are not limited to, prednisone, fluorouracil (e.g., 5-fluorouracil (5-FU)), anastrozole, bicalutamide, carboplatin, cisplatin, chlorambucil, cisplatin, carboplatin, docetaxel, doxorubicin, flutamide, interferon-alpha, letrozole, leuprolide, megestrol, mitomycin, oxaliplatin, paclitaxel, plicamycin (Mithracin™), tamoxifen, thiotepa, topotecan, valrubicin, vinblastine, vincristine, and any combination of any of the foregoing. Additional such agents are described later.

It must be noted that, as used in the specification and the appended claims, the singular forms "a," "an" and "the" include plural referents unless the context clearly dictates otherwise.

When used as a therapeutic agent the inhibitors of the FASN (FASN) described herein may be administered with one or more physiologically acceptable excipients. A physiologically acceptable carrier or excipient is a formulation to which the compound can be added to dissolve it or otherwise facilitate its administration.

The dosage forms of the present invention, may contain a mixture of one or more compounds of this invention, and may include additional materials known to those skilled in the art as pharmaceutical excipients. Stabilizing additives may be incorporated into the delivery agent solution. With some drugs, the presence of such additives promotes the stability and dispersibility of the agent in solution. The stabilizing additives may be employed at a concentration ranging from about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

Acidifying agents (acetic acid, glacial acetic acid, citric acid, fumaric acid, hydrochloric acid, diluted hydrochloric acid, malic acid, nitric acid, phosphoric acid, diluted phosphoric acid, sulfuric acid, tartaric acid); Aerosol propellants (butane, dichlorodifluoro-methane, dichlorotetrafluoroethane, isobutane, propane, trichloromonofluoromethane); Air displacements (carbon dioxide, nitrogen); Alcohol denaturants (denatonium benzoate, methyl isobutyl ketone, sucrose octacetate); Alkalizing agents (strong ammonia solution, ammonium carbonate, diethanolamine, diisopropanolamine, potassium hydroxide, sodium bicarbonate, sodium borate, sodium carbonate, sodium hydroxide, trolamine); Anticaking agents (see glidant); Antifoaming agents (dimethicone, simethicone); Antimicrobial preservatives (benzalkonium chloride, benzalkonium chloride solution, benzelthonium chloride, benzoic acid, benzyl alcohol, butylparaben, cetylpyridinium chloride, chlorobutanol, chlorocresol, cresol, dehydroacetic acid, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, thymol); Antioxidants (ascorbic acid, acorbyl palmitate, butylated hydroxyanisole, butylated hydroxytoluene, hypophosphorous acid, monothioglycerol, propyl gallate, sodium formaldehyde sulfoxylate, sodium metabisulfite, sodium thiosulfate, sulfur dioxide, tocopherol, tocopherols excipient); Buffering agents (acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate); Capsule lubricants (see tablet and capsule lubricant); Chelating agents (edetate disodium, ethylenediaminetetraacetic acid and salts, edetic acid); Coating agents (sodium carboxymethylcellulose, cellulose acetate, cellulose acetate phthalate, ethylcellulose, gelatin, pharmaceutical glaze, hydroxypropyl cellulose, hydroxypropyl methylcellulose, hydroxypropyl methylcellulose phthalate, methacrylic acid copolymer, methylcellulose, polyethylene glycol, polyvinyl acetate phthalate, shellac, sucrose, titanium dioxide, carnauba wax, microcrystalline wax, zein); Colorants (caramel, red, yellow, black or blends, ferric oxide); Complexing agents (ethylenediaminetetraacetic acid and salts (EDTA), edetic acid, gentisic acid ethanolmaide, oxyquinoline sulfate); Desiccants (calcium chloride, calcium sulfate, silicon dioxide); Emulsifying and/or solubilizing agents (acacia, cholesterol, diethanolamine (adjunct), glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 caster oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, trolamine, emulsifying wax); Filtering aids (powdered cellulose, purified siliceous earth); Flavors and perfumes (anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, vanillin); Glidants and/or anticaking agents (calcium silicate, magnesium silicate, colloidal silicon dioxide, talc); Humectants (glycerin, hexylene glycol, propylene glycol, sorbitol); Plasticizers (castor oil, diacetylated monoglycerides, diethyl phthalate, glycerin, mono- and di-acetylated monoglycerides, polyethylene glycol, propylene glycol, triacetin, triethyl citrate); Polymers (e.g., cellulose acetate, alkyl celluloses, hydroxyalkylcelloloses, acrylic polymers and copolymers); Solvents (acetone, alcohol, diluted alcohol, amylene hydrate, benzyl benzoate, butyl alcohol, carbon tetrachloride, chloroform, corn oil, cottonseed oil, ethyl acetate, glycerin, hexylene glycol, isopropyl alcohol, methyl alcohol, methylene chloride, methyl isobutyl ketone, mineral oil, peanut oil, polyethylene glycol, propylene carbonate, propylene glycol, sesame oil, water for injection, sterile water for injection, sterile water for irrigation, purified water); Sorbents (powdered cellulose, charcoal, purified siliceous earth); Carbon dioxide sorbents (barium hydroxide lime, soda lime); Stiffening agents (hydrogenated castor oil, cetostearyl alcohol, cetyl alcohol, cetyl esters wax, hard fat, paraffin, polyethylene excipient, stearyl alcohol, emulsifying wax, white wax, yellow wax); Suspending and/or viscosity-increasing agents (acacia, agar, alginic acid, aluminum monostearate, bentonite, purified bentonite, magma bentonite, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, xanthan gum); Sweetening agents (aspartame, dextrates, dextrose, excipient dextrose, fructose, mannitol, saccharin, calcium saccharin, sodium saccharin, sorbitol, solution sorbitol, sucrose, compressible sugar, confectioner's sugar, syrup); Tablet binders (acacia, alginic acid, sodium carboxymethylcellulose, microcrystalline cellulose, dextrin, ethylcellulose, gelatin, liquid glucose, guar gum, hydroxypropyl methylcellulose, methycellulose, polyethylene oxide, povidone, pregelatinized starch, syrup); Tablet and/or capsule diluents (calcium carbonate, dibasic calcium phosphate, tribasic calcium phosphate, calcium sulfate, microcrystalline cellulose, powdered cellulose, dextrates, dextrin, dextrose excipient, fructose, kaolin, lactose, mannitol, sorbitol, starch, pregelatinized starch, sucrose, compressible sugar, confectioner's sugar); Tablet disintegrants (alginic acid, microcrystalline cellulose, croscarmellose sodium, corspovidone, polacrilin potassium, sodium starch glycolate, starch, pregelatinized starch); Tablet and/or capsule lubricants (calcium stearate, glyceryl behenate, magnesium stearate, light mineral oil, polyethylene glycol, sodium stearyl fumarate, stearic acid, purified stearic acid, talc, hydrogenated vegetable oil, zinc stearate); Tonicity agent (dextrose, glycerin, mannitol, potassium chloride, sodium chloride); Vehicle: flavored and/or sweetened (aromatic elixir, compound benzaldehyde elixir, iso-alcoholic elixir, peppermint water, sorbitol solution, syrup, tolu balsam syrup); Vehicle: oleaginous (almond oil, corn oil, cottonseed oil, ethyl oleate, isopropyl myristate, isopropyl palmitate, mineral oil, light mineral oil, myristyl alcohol, octyldodecanol, olive oil, peanut oil, persic oil, seame oil, soybean oil, squalane); Vehicle: solid carrier (sugar spheres); Vehicle: sterile (bacteriostatic water for injection, bacteriostatic sodium chloride injection); Viscosity-increasing (see suspending agent); Water repelling agent (cyclomethicone, dimethicone, simethicone); and Wetting and/or solubilizing agent (benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol) may be used as excipients. This list is not meant to be exclusive, but instead merely representative of the classes of excipients and the particular excipients which may be used in dosage forms of the present invention.

The compounds of Formulas I, I-A, I-B, I-C and I-D can form salts which are also within the scope of this invention. Reference to a compound of the Formula herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of the Formula contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula may be formed, for example, by reacting a compound of Formula with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates) and the like. Additionally, acids which are generally considered suitable for the formation of pharmaceutically useful salts from basic pharmaceutical compounds are discussed, for example, by P. Stahl et al, Camille G. (eds.) Handbook of Pharmaceutical Salts. Properties, Selection and Use. (2002) Zurich: Wiley-VCH; S. Berge et al, Journal of Pharmaceutical Sciences (1977) 66(1) 1-19; P. Gould, International J. of Pharmaceutics (1986) 33 201-217; Anderson et al, The Practice of Medicinal Chemistry (1996), Academic Press, New York; and in The Orange Book (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of the various Formulas, and salts, solvates, esters and prodrugs thereof, may exist in their tautomeric form (for example, as an amide or imino ether). All such tautomeric forms are contemplated herein as part of the present invention.

The compounds of the various Formulas may contain asymmetric or chiral centers, and, therefore, exist in different stereoisomeric forms. It is intended that all stereoisomeric forms of the compounds of the various Formulas as well as mixtures thereof, including racemic mixtures, form part of the present invention. In addition, the present invention embraces all geometric and positional isomers. For example, if a compound of the various Formulas incorporates a double bond or a fused ring, both the cis- and trans-forms, as well as mixtures, are embraced within the scope of the invention.

Each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the various Formulas may be atropisomers (e.g., substituted biaryls) and are considered as part of this invention. Enantiomers can also be separated by use of chiral HPLC column.

It is also possible that the compounds of the various Formulas may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of the various Formulas incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of the various Formulas (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of the various Formulas can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of the various Formulas, and of the salts, solvates, esters and prodrugs of the compounds of the various Formulas, are intended to be included in the present invention.

Benefits of the present invention include oral administration of an optimal amount of a FASN inhibitor.

Benefits of the present invention include intravenous administration of an optimal amount of a FASN inhibitor.

Benefits of the present invention include intraperitoneal administration of an optimal amount of a FASN inhibitor.

Benefits of the present invention include intramural administration of an optimal amount of a FASN inhibitor.

Benefits of the present invention include intramuscular administration of an optimal amount of a FASN inhibitor.

Benefits of the present invention include subcutaneous administration of an optimal amount of a FASN inhibitor.

Benefits of the present invention include intra-tumor administration of an optimal amount of a FASN inhibitor.

Benefits of the present invention include intrathecal administration of an optimal amount of a FASN inhibitor.

Benefits of the present invention include subdural administration of an optimal amount of a FASN inhibitor.

Benefits of the present invention include periorbital administration of an optimal amount of a FASN inhibitor.

Based on these results, the present invention has important implications for the design of novel treatment strategies for patients with cancer, including leukemias and solid tumors, inflammatory diseases, viral infections, osteoporosis, atherosclerosis; irritable or inflammatory bowel syndrome; diabetes, obesity and other conditions disclosed herein or that are known to those skilled in the art.

DESCRIPTION OF THE PREFERRED EMBODIMENTS

An aspect of the present invention concerns compounds disclosed herein.

An aspect of the present invention concerns compounds which are or can be inhibitors of FASN.

An aspect of the present invention concerns the use of an inhibitor of FASN for the preparation of a medicament used in the treatment, prevention, inhibition or elimination of tumors.

An aspect of the present invention concerns the use of an inhibitor of FASN for the preparation of a medicament used in the treatment, prevention, inhibition or elimination of cancer.

An aspect of the present invention concerns the use of an inhibitor of FASN for the preparation of a medicament used in the treatment, prevention, inhibition or elimination of cancer, where the cancer is selected from leukemia, lymphoma, ovarian cancer, breast cancer, uterine cancer, colon cancer, cervical cancer, lung cancer, prostate cancer, skin cancer, CNS cancer, bladder cancer, pancreatic cancer and Hodgkin's disease.

An aspect of the present invention concerns the use of an inhibitor of FASN for the preparation of a medicament used in the treatment, prevention, inhibition or elimination of diabetes.

An aspect of the present invention concerns the use of an inhibitor of FASN for the preparation of a medicament used in the treatment, prevention, inhibition or elimination of viral infectious diseases.

An aspect of the present invention concerns the use of an inhibitor of FASN for the preparation of a medicament used in the treatment, prevention, inhibition or elimination of overweight or obesity.

An aspect of the present invention concerns the use of an inhibitor of FASN for the preparation of a medicament used in the treatment, prevention, inhibition or elimination of uterine leiomyomata.

The present invention also describes one or more methods of synthesizing the compounds of the present invention.

The invention also describes one or more uses of the compounds of the present invention.

The invention also describes one or more uses of the compounds of the present invention with an adjunctive agent such as use with TNF, GCSF, or other chemotherapeutic agents The invention also describes one or more uses of the pharmaceutical compositions of the present invention.

An aspect of the present invention concerns the use as an inhibitor of FASN for the preparation of a medicament used in the treatment of inflammatory diseases.

An aspect of the present invention concerns the use as an inhibitor of FASN for the preparation of a medicament used in the treatment of inflammatory diseases, such as Irritable Bowel Syndrome or Inflammatory Bowel Disease.

An aspect of the present invention concerns the use as an inhibitor of FASN for the preparation of a medicament used in the treatment of disease of the bone such as osteoporosis.

An aspect of the present invention concerns the use as an inhibitor of FASN for the preparation of a medicament used in the treatment of disease of the cardiovascular system, such as atherosclerosis.

An aspect of the present invention concerns the use as an inhibitor of FASN for the preparation of a medicament used in the treatment of disease or a condition caused by an elevated level of FASN.

Such disease or condition is one or more selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spondylitis, graft-versus-host disease, cerebrovascular accident, atherosclerosis, diabetes, glomerulonephiritis, metabolic syndrome, non-small cell lung cancer, small cell lung cancer, multiple myeloma, lymphomas, squamous cell cancers, kidney cancer, urethral and bladder cancers, cancers of head and neck, cancers of the brain and central nervous system (CNS).

The inventive compounds of can be useful in the therapy of proliferative diseases such as cancer, autoimmune diseases, viral diseases, fungal diseases, neurological/neurodegenerative disorders, arthritis, inflammation, anti-proliferative (e.g., ocular retinopathy), neuronal, alopecia and cardiovascular disease. Many of these diseases and disorders are listed in U.S. Pat. No. 6,413,974, incorporated by reference herein.

More specifically, the compounds can be useful in the treatment of a variety of cancers, including (but not limited to) the following: carcinoma, including that of the bladder, breast, colon, kidney, liver, lung, including small cell lung cancer, non-small cell lung cancer, head and neck, esophagus, gall bladder, ovary, pancreas, stomach, cervix, thyroid, prostate, and skin, including squamous cell carcinoma; hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, mantle cell lymphoma, myeloma, and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

The compounds of the invention may induce or inhibit apoptosis.

The compounds of the invention may also be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

A further aspect of the invention is a method of inhibiting FASN in an animal, said method comprising administering to said animal a pharmaceutically acceptable amount of a compound of the invention to an animal in need thereof.

A further aspect of the invention is a pharmaceutical formulation comprising a compound of the invention.

Another embodiment of the invention comprises a pharmaceutical formulation of the invention, wherein the pharmaceutical formulation, upon administration to a human, results in a decrease in tumor burden.

Still another embodiment of the invention is a pharmaceutical formulation, further comprising one or more of an antineoplastic agent, a chemotherapeutic agent, or an adjunctive chemotherapeutic agent.

The pharmaceutical formulations of the invention may further comprise a therapeutic effective amount of an adjunctive chemotherapeutic agent.

The adjunctive chemotherapeutic agent may be an agent which modifies blood cell growth and maturation. Non-limiting examples of adjunctive chemotherapeutic agent are filgrastim, pegfilgrastim and erythropoietin.

The invention is also directed to a method of treating or preventing a disorder associated with excessive rate of growth of cells in a mammal comprising administering to the mammal an effective amount of the pharmaceutical formulation of the invention. Non-limiting examples of disorder include cancer or metastasis from malignant tumors.

Another aspect of the invention is a method of inhibiting tumor cell growth and rate of division in a mammal with cancer, or other disorder associated with abnormally dividing cells comprising administering to the mammal an effective amount of the pharmaceutical formulation of this invention.

Another embodiment of the invention is a method of treating bone pain due to excessive growth of a tumor or metastasis to bone in a mammal in need thereof comprising administering to the mammal an effective amount of the pharmaceutical formulation of this invention.

Still another embodiment of the invention is a method for administering an FASN-inhibitor-containing compound to a mammal in need thereof comprising administering to the mammal the pharmaceutical formulation of the invention. In one embodiment, the mammal is a human.

A further embodiment of the invention is a method of preparing a pharmaceutical formulation comprising mixing at least one pharmaceutically acceptable compound of the present invention, and, optionally, one or more pharmaceutically acceptable excipients or additives.

The invention is also directed to methods of synthesizing compounds of the present invention.

Compounds of the Invention

The present invention relates to particular molecules and pharmaceutically acceptable salts or isomers thereof. The invention further relates to molecules which are useful in inhibiting the enzyme fatty acid synthase (FASN) and pharmaceutically acceptable salts or isomers thereof.

The invention is directed to compounds as described herein and pharmaceutically acceptable salts or isomers thereof, and pharmaceutical compositions comprising one or more compounds as described herein and pharmaceutically acceptable salts or isomers thereof. One aspect of this invention is the provision of compounds, compositions, and kits for FASN inhibition comprising a compound of formula I

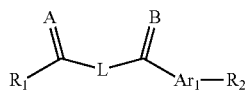

I wherein
$R_1$ is a $C_1$-$C_3$ hydroxyl-alkyl either unsubstituted or substituted with —$CH_3$ or —$CH_zF_{3-z}$, 5 membered cycloalkyl either unsubstituted or substituted with substituents selected from the group consisting of deuterium, —$R_p$, —$OR_p$, —$NHR_p$, and —$NR_pR_{p1}$,
or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —$R_a$, —$OR_a$, —$NHR_a$, and —$NR_aR_{a1}$;
L is a 5-10 membered monocyclic or bicyclic alkyl or heteroalkyl wherein (i) the heteroatom ring members of the 5-10 membered monocyclic or bicyclic heteroalkyl are independently selected from O, S, or N, and (ii) each of the 5-10 membered monocyclic or bicyclic alkyl or heteroalkyl is either unsubstituted or optionally substituted with substituents selected from the group consisting of deuterium and —$R_b$;
A and B are independently O or S;
$Ar_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —$CH_zF_{3-z}$, cyano, hydroxyl, hydroxylalkyl, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$OCH_zF_{3-z}$, -alkyl, -alkenyl, -alkynyl, -alkoxy or (alkoxyalkyl)amino-, —N($R_c$)—C(O)-alkyl, —N(Re)—C(O)-aryl, -cycloalkyl, -heterocycloalkyl, -aryl, and -heteroaryl, with the proviso that no two adjacent ring heteroatoms are both S or both O;

$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), $ONH_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-$R_d$, —NH—C(O)—$R_d$—(O)alkyl, —NH—C(O)-aryl, —NH—C(O)—NH-alkyl, NH—C(O)—NH-cycloalkyl, NH$_2$(CO)cycloalkyl-, —NH—C(O)—NH-aryl, —NH—C(O)—O-alkyl, NH—C(O)—NH-cycloalkyl, —NH—C(O)—O-cycloalkyl, —NH($R_a$)—C(O)-alkyl, —NH($R_a$)—C(O)-aryl, —NH($R_a$)—S(O$_2$)cycloalkyl, —S(O$_2$)NH$_2$, —S(O$_2$)NH(alkyl), —S(O$_2$)N($R_a$)cycloalkyl, —S(O$_2$)N(alkyl)$_2$, —C(O)N(H)(alkyl), —C(O)N($R_d$) (cycloalkyl), methylenedioxy, —$CH_zF_{3-z}$, —$OCH_zF_{3-z}$, and -alkoxy;
$R_p$ and $R_{p1}$ are independently H, halo, $C_1$-$C_4$ alkyl, or $C_3$-$C_4$ cycloalkyl;
$R_a$ and $R_{a1}$ are independently H, halo, $C_1$-$C_4$ alkyl, or $C_3$-$C_4$ cycloalkyl;
$R_b$ is H, halo, $C_1$-$C_4$ alkyl, $C_1$-$C_3$ hydroxyl-alkyl, or $C_3$-$C_4$ cycloalkyl;
$R_c$ is H, halo, $C_1$-$C_4$ alkyl, or $C_3$-$C_4$ cycloalkyl;
$R_d$ is H, halo, $C_1$-$C_4$ alkyl, or $C_3$-$C_4$ cycloalkyl;
and z is 0, 1 or 2;
and pharmaceutically acceptable salts, solvates, esters, prodrugs and isomers thereof.

In another embodiment, the compound of Formula I is represented by the compound of Formula I-A:

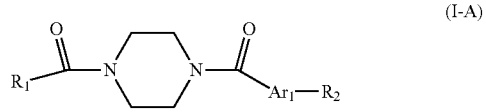

(I-A)

wherein:
$R_1$ is a $C_1$-$C_3$ hydroxyl-alkyl either unsubstituted or substituted with —$CH_3$ or —$CH_zF_{3-z}$, 5 membered cycloalkyl either unsubstituted or substituted with substituents selected from the group consisting of deuterium, —$R_p$, —$OR_p$, —$NHR_p$, and —$NR_pR_{p1}$,
  or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —$R_a$, —$OR_a$, —$NHR_a$, and —$NR_aR_{a1}$;
$Ar_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —$CH_zF_{3-z}$, cyano, hydroxyl, hydroxylalkyl, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$OCH_zF_{3-z}$, -alkyl, -alkenyl, -alkynyl, -alkoxy or (alkoxyalkyl)amino-, —N($R_c$)—C(O)-alkyl, —N(Re)—C(O)-aryl, -cycloalkyl, -heterocycloalkyl, -aryl, and -heteroaryl, with the proviso that no two adjacent ring heteroatoms are both S or both O;
$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), $ONH_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-$R_d$, —NH—C(O)—$R_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH($R_a$)—C(O)-alkyl, —NH($R_a$)—C(O)-aryl, —NH($R_a$)—S(O)$_2$cycloalkyl, —S(O)$_2$NH$_2$, —S(O)$_2$NH(alkyl), —S(O)$_2$N($R_a$)cycloalkyl, —S(O)$_2$N(alkyl)$_2$, —C(O)N(H)(alkyl), —C(O)N($R_d$) (cycloalkyl), methylenedioxy, —$CH_zF_{3-z}$, —$OCH_zF_{3-z}$, and -alkoxy;
$R_p$ and $R_{p1}$ are independently H, halo, $C_1$-$C_4$ alkyl, or $C_3$-$C_4$ cycloalkyl;
$R_a$ and $R_{a1}$ are independently H, halo, $C_1$-$C_4$ alkyl, or $C_3$-$C_4$ cycloalkyl;
$R_c$ is H, halo, $C_1$-$C_4$ alkyl, or $C_3$-$C_4$ cycloalkyl;
$R_d$ is H, halo, $C_1$-$C_4$ alkyl, or $C_3$-$C_4$ cycloalkyl;
and z is 0, 1 or 2;
and pharmaceutically acceptable salts, solvates, esters, prodrugs and isomers thereof.

In another embodiment, the compound of Formula I is represented by the compound of Formula I-B:

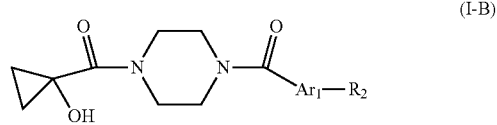

(I-B)

Wherein:
$Ar_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —$CH_zF_{3-z}$, cyano, hydroxyl, hydroxylalkyl, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, -alkenyl, -alkynyl, -alkoxy or (alkoxyalkyl)amino-, —N($R_c$)—C(O)-alkyl, —N(Re)—C(O)-aryl, -cycloalkyl, -heterocycloalkyl, -aryl, and -heteroaryl, with the proviso that no two adjacent ring heteroatoms are both S or both O;
$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —$CONH_2$, —C(O)NH(alkyl), —C(O)N(alkyl)$_2$, —C(O)NH(aryl), —C(O)N(aryl)$_2$, —$CH_zF_{3-z}$, —$OCH_zF_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), $ONH_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_d$) (cycloalkyl), methylenedioxy, —CH$_z$F$_{3-z}$, —OCH$_z$F$_{3-z}$, and -alkoxy;

R$_c$ is H, halo, C$_1$-C$_4$ alkyl, or C$_3$-C$_4$ cycloalkyl;
R$_d$ is H, halo, C$_1$-C$_4$ alkyl, or C$_3$-C$_4$ cycloalkyl;
and z is 0, 1 or 2;
and pharmaceutically acceptable salts, solvates, esters, prodrugs and isomers thereof.

In another embodiment, the compound of Formula I is represented by the compound of Formula I-C:

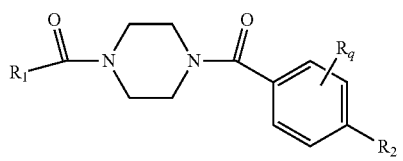

(I-C)

wherein:
R$_1$ is a C$_1$-C$_3$ hydroxyl-alkyl either unsubstituted or substituted with —CH$_3$ or —CH$_z$F$_{3-z}$, 5 membered cycloalkyl either unsubstituted or substituted with substituents selected from the group consisting of deuterium, —R$_p$, —OR$_p$, —NHR$_p$, and —NR$_p$R$_{p1}$,
or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —R$_a$, —OR$_a$, —NHR$_a$, and —NR$_a$R$_{a1}$;
R$_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_d$) (cycloalkyl), methylenedioxy, —CH$_z$F$_{3-z}$, —OCH$_z$F$_{3-z}$, and -alkoxy;

R$_p$ and R$_{p1}$ are independently H, halo, C$_1$-C$_4$ alkyl, or C$_3$-C$_4$ cycloalkyl;
R$_a$ and R$_{a1}$ are independently H, halo, C$_1$-C$_4$ alkyl, or C$_3$-C$_4$ cycloalkyl;
R$_d$ is H, halo, C$_1$-C$_4$ alkyl, or C$_3$-C$_4$ cycloalkyl;
R$_q$ is H, halo, C$_1$-C$_4$ alkyl, or C$_3$-C$_4$ cycloalkyl;
and z is 0, 1 or 2;
and pharmaceutically acceptable salts, solvates, esters, prodrugs and isomers thereof.

In another embodiment, the compound of Formula I is represented by the compound of Formula I-D:

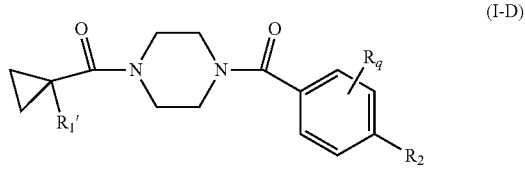

(I-D)

wherein:
R$_1$' is OH or NH$_2$;
R$_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycoalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycolalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH($R_a$)—C(O)-alkyl, —NH($R_a$)—C(O)-aryl, —NH($R_a$)—S($O_2$)cycloalkyl, —S($O_2$)N$H_2$, —S($O_2$)NH(alkyl), —S($O_2$)N($R_a$)cycloalkyl, —S($O_2$)N(alkyl)$_2$, —C(O)N(H)(alkyl), —C(O)N($R_d$)(cycloalkyl), methylenedioxy, —C$H_z$$F_{3-z}$, —OC$H_z$$F_{3-z}$, and -alkoxy;

$R_d$ is H, halo, $C_1$-$C_4$ alkyl, or $C_3$-$C_4$ cycloalkyl;
and z is 0, 1 or 2;
and pharmaceutically acceptable salts, solvates, esters, prodrugs and isomers thereof.

In the compounds of Formulas I, I-A, I-B, I-C and I-D, the various moieties are independently selected.

The following embodiments are directed to Formulas I, I-A, I-B, I-C and I-D, as applicable. For any moieties that are not specifically defined, the previous definitions control. Further, the moieties aryl, heteroaryl, and heterocycloalkyl in these embodiments can be independently unsubstituted or optionally substituted or optionally fused as described earlier.

An embodiment of the invention is the provision of a compound, where the various moieties are independently selected, $R_1$ is $C_1$-$C_3$ hydroxyl-alkyl either unsubstituted or substituted with —C$H_3$ or —C$H_z$$F_{3-z}$, and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_1$ is a 5 membered cycloalkyl either unsubstituted or substituted with hydroxyl, and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_1$ is a 3 or 4 membered cycloalkyl, and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_1$ is a 3 or 4 membered heterocycloalkyl, and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_1$ is

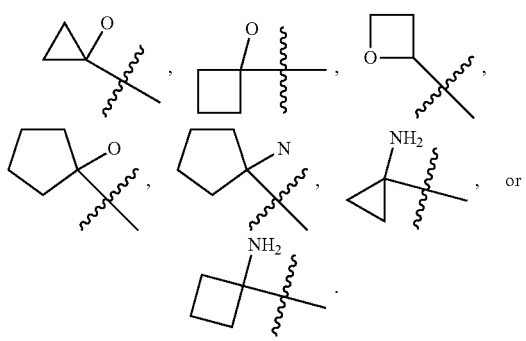

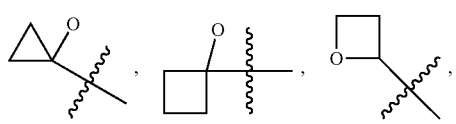

and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_1$ is

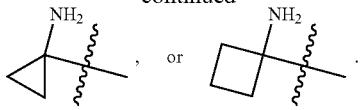

and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_1$ is

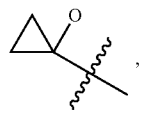 [SMILES: *C1(O)CC1]

and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_1$ is

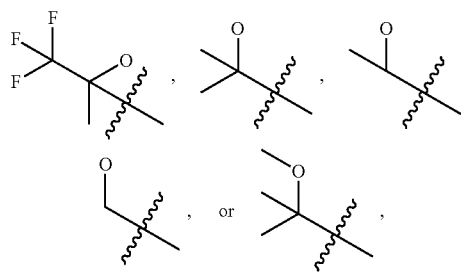

and A, B, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, A and B are O, and $R_1$, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, A and B are S, and $R_1$, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, either A or B is O, the other is S, and $R_1$, L, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, L is a 5-10 membered monocyclic alkyl, and A, B, $R_1$, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, L is a 5-10 membered bicyclic alkyl, and A, B, $R_1$, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, L is a 5-10 membered monocyclic heteroalkyl, and A, B, $R_1$, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, L is a 5-10 membered bicyclic hetroalkyl, and A, B, $R_1$, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, L is

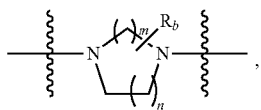

m is 1, 2, or 3, n is 0, 1, 2, or 3, and A, B, $R_1$, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, L is

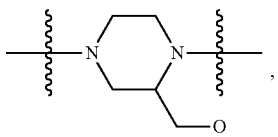

and A, B, $R_1$, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, L is

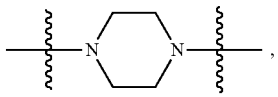 [SMILES: *N1CCN(*)CC1]

and A, B, $R_1$, $Ar_1$, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is an aryl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a heteroaryl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a 5-10 membered monocyclic aryl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a 5-10 membered monocyclic heteroaryl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a 5-10 membered bicyclic aryl, and A, $B_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a 5-10 membered bicyclic heteroaryl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted 5 membered monocyclic aryl or heteroaryl and said heteroaryl has 1 or 2 heteroatoms which are independently S or N, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted form of

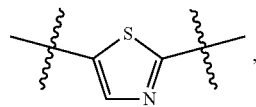 [SMILES: *c1cnc(*)s1]

and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted 6 membered monocyclic aryl or heteroaryl and said heteroaryl has 1 or 2 heteroatoms which are N, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted form of

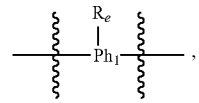

$Ph_1$ is phenyl, pyridinyl, pyrazinyl, or pyrimidinyl, $R_c$ is H, halo, or $C_1$-$C_3$ alkyl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted form of

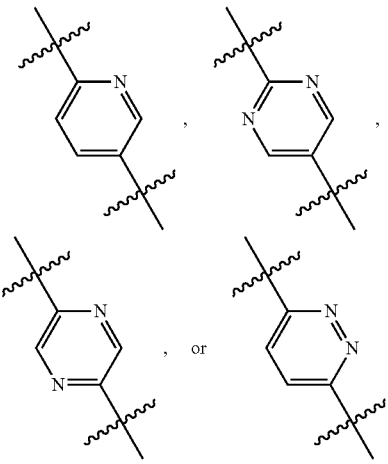

and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted 6 membered monocyclic aryl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is

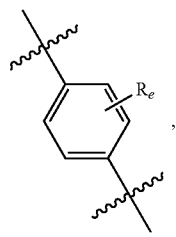

$R_e$ is H, halo, or $C_1$-$C_3$ alkyl, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is

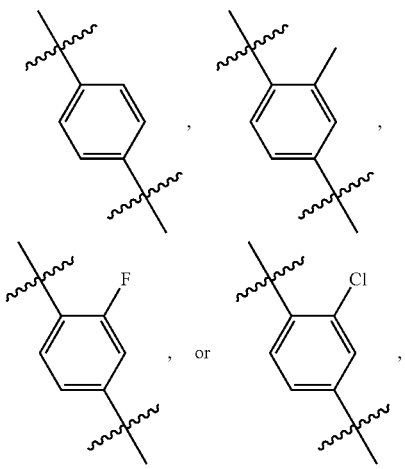

and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted 9 membered 6,5-bicyclic heteroaryl and and said heteroaryl has 1, 2, or 3 heteroatoms which are independently O, S or N, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $Ar_1$ is a substituted or unsubstituted form of

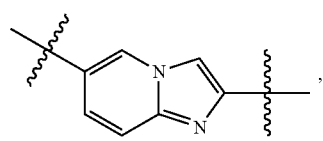

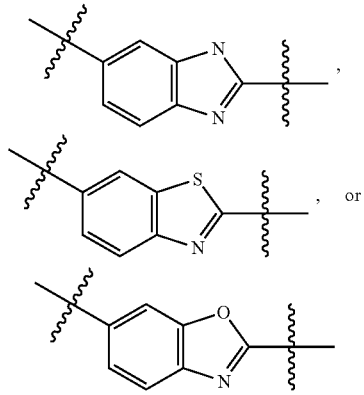

and said heteroaryl has 1, 2, or 3 heteroatoms which are independently S or N, and A, B, $R_1$, L, $R_2$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted aryl, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted heteroaryl, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted cycloalkyl, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted heterocycloalkyl, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted monocyclic or bicyclic 5-10 membered aryl or heteroaryl, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a unsubstituted or substituted monocyclic 6 membered aryl, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is

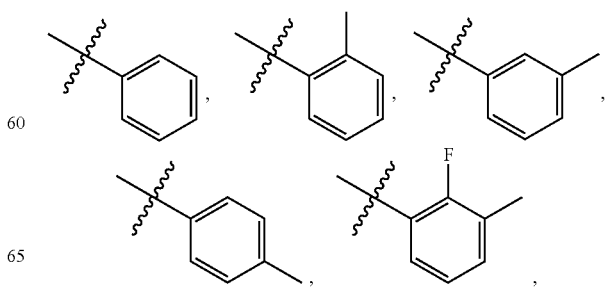

-continued

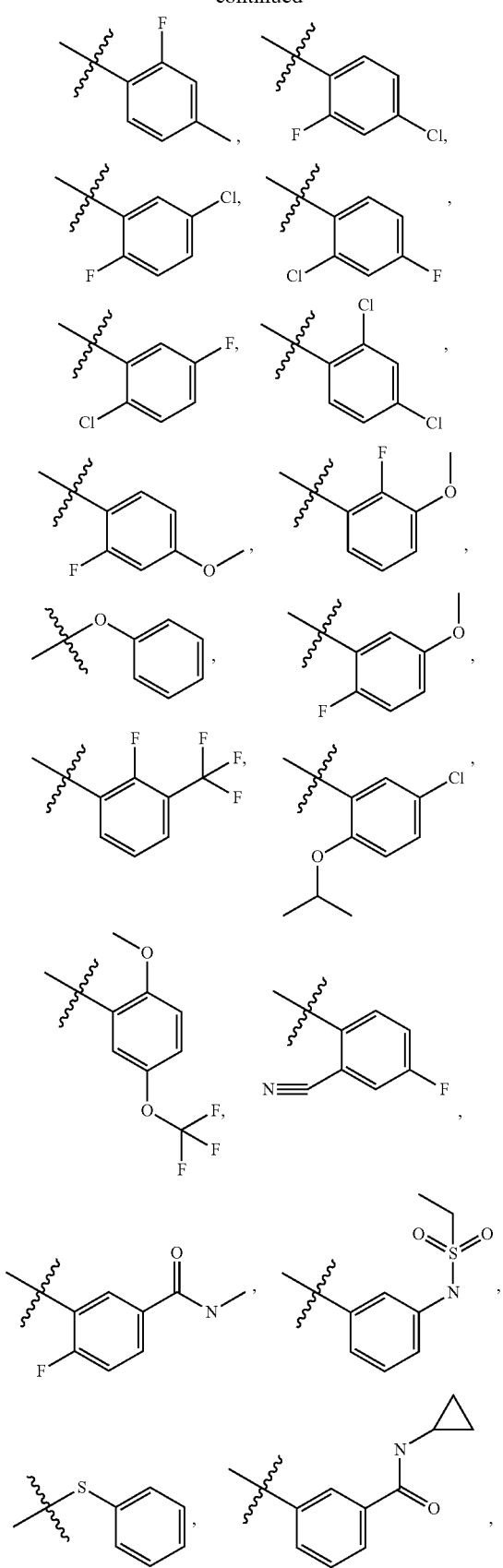

-continued

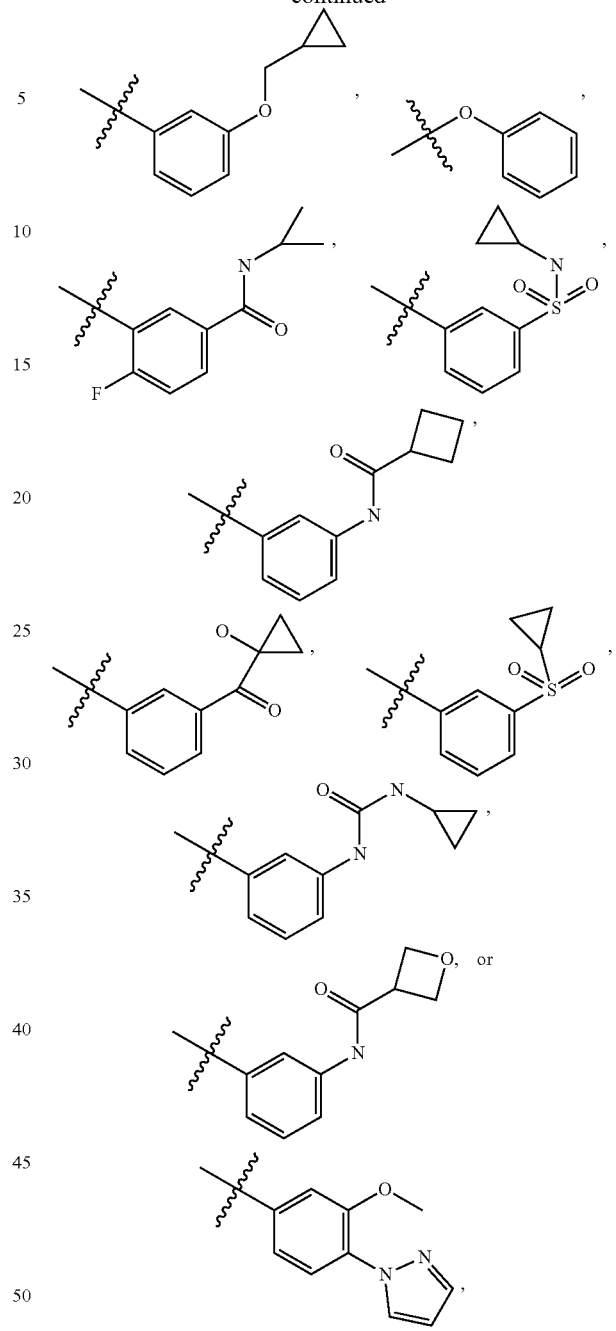

$R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted bicyclic 8-10 membered aryl or 8-10 membered heteroaryl, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted 8 membered 5,5 bicyclic heteroaryl and said heteroaryl has 1, 2, 3, or 4 heteroatoms and said heteroatoms are independently O, S, or N, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted form of

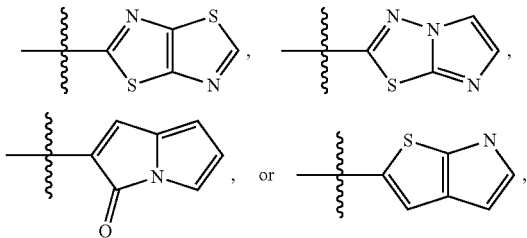

and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted 9 membered 6,5 bicyclic heteroaryl and said heteroaryl has 1, 2, 3, or 4 heteroatoms and said heteroatoms are independently O, S, or N, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted form

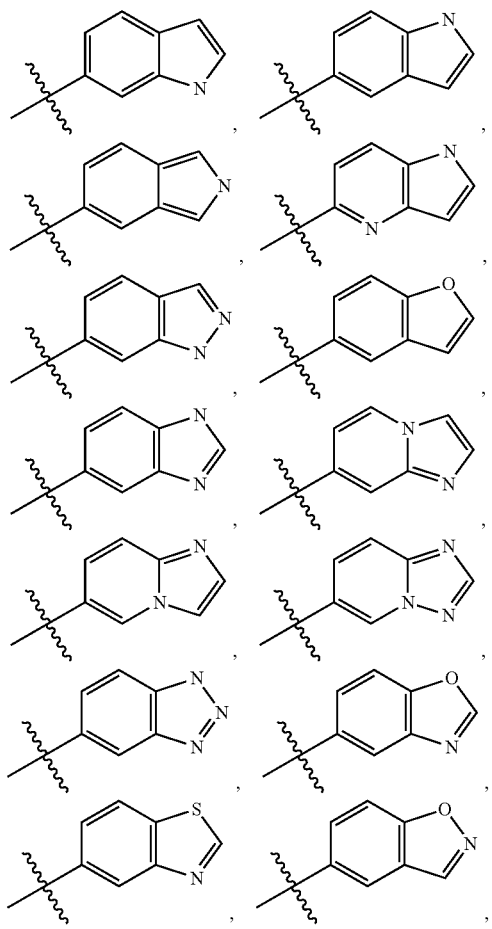

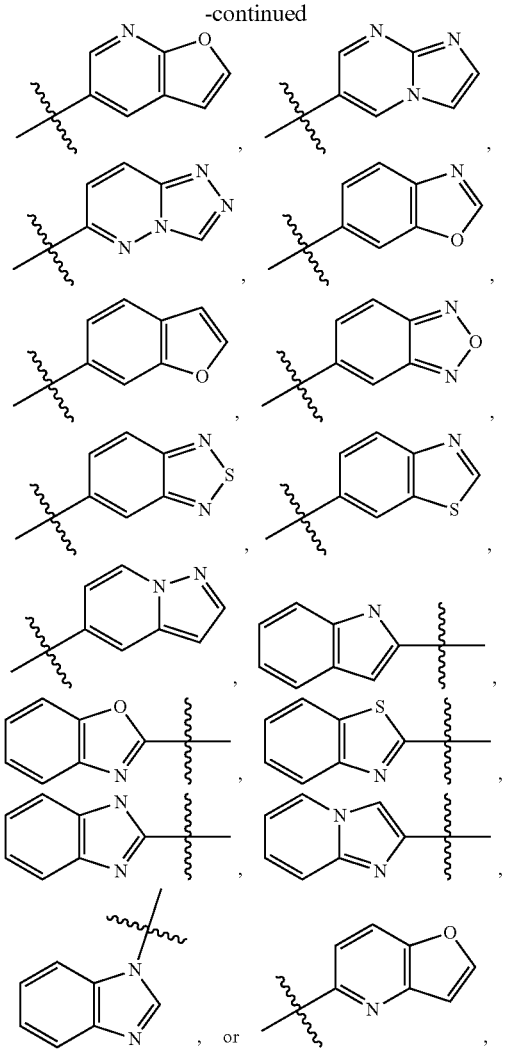

and A, B, $R_1$, L, $Ar_1$, $R_p$, $R_{p1}$, $R_a$, $R_{a1}$, $R_b$, $R_c$, $R_d$ and z are as defined.

An embodiment of the invention is the provision of a compound, where the various moieties are independently selected, $R_2$ is a substituted or unsubstituted 10 membered 6,6 bicyclic aryl or heteroaryl and said heteroaryl has 1, 2, 3, or 4 heteroatoms and said heteroatoms are O, S, or N, and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_2$ is a substituted or unsubstituted form of

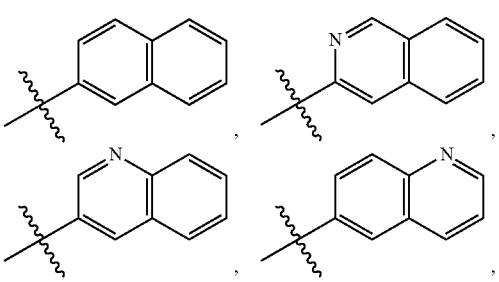

and A, B, $R_1$, L, $Ar_1$, $R_p$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_p$ is H, and A, B, $R_1$, L, $Ar_1$, $R_2$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_p$ is halo, and A, B, $R_1$, L, $Ar_1$, $R_2$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_p$ is $C_1$-$C_4$ alkyl, and A, B, $R_1$, L, $Ar_1$, $R_2$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_p$ is $C_3$-$C_4$ cycloalkyl, and A, B, $R_1$, L, $Ar_1$, $R_2$, $R_{p1}$, $R_a$, $R_{a1}$, $R_b$, $R_c$, $R_d$, $R_q$ and z are as defined.

An embodiment of the invention is the provision of a compound, where the various moieties are independently selected, $R_{p1}$ is H, and A, B, $R_1$, L, $Ar_1$, $R_2$, $R_p$, $R_a$, $R_{a1}$, $R_b$, $R_c$, $R_d$, $R_q$ and z are as defined.

An embodiment of the invention is the provision of a compound, where the various moieties are independently selected, $R_{p1}$ is halo, and A, B, $R_1$, L, $Ar_1$, $R_2$, $R_p$, $R_a$, $R_{a1}$, $R_b$, $R_c$, $R_d$, $R_q$ and z are as defined.

An embodiment of the invention is the provision of a compound, where the various moieties are independently selected, $R_{p1}$ is $C_1$-$C_4$ alkyl, and A, B, $R_1$, L, $Ar_1$, $R_2$, $R_p$, $R_a$, $R_{a1}$, $R_b$, $R_c$, $R_d$, $R_q$ and z are as defined.

An embodiment of the invention is the provision of a compound, where the various moieties are independently selected, $R_{p1}$ is $C_3$-$C_4$ cycloalkyl, and A, B, $R_1$, L, $Ar_1$, $R_2$, $R_p$, $R_a$, $R_{a1}$, $R_b$, $R_c$, $R_d$, $R_q$ and z are as defined.

An embodiment of the invention is the provision of a compound, where the various moieties are independently selected, $R_a$ is H, and A, B, $R_1$, L, $Ar_1$, $R_2$, $R_p$, $R_{p1}$, $R_{a1}$, $R_b$, $R_c$, $R_d$, $R_q$ and z are as defined.

An embodiment of the invention is the provision of a compound, where the various moieties are independently selected, $R_a$ is halo, and A, B, $R_1$, L, $Ar_1$, $R_2$, $R_p$, $R_{p1}$, $R_{a1}$, $R_b$, $R_c$, $R_d$, $R_q$ and z are as defined.

An embodiment of the invention is the provision of a compound, where the various moieties are independently selected, $R_a$ is $C_1$-$C_4$ alkyl, and A, B, $R_1$, L, $Ar_1$, $R_2$, $R_p$, $R_{p1}$, $R_{a1}$, $R_b$, $R_c$, $R_d$, $R_q$ and z are as defined.

An embodiment of the invention is the provision of a compound, where the various moieties are independently selected, $R_a$ is $C_3$-$C_4$ cycloalkyl, and A, B, $R_1$, L, $Ar_1$, $R_2$, $R_p$, $R_{p1}$, $R_{a1}$, $R_b$, $R_c$, $R_d$, $R_q$ and z are as defined.

An embodiment of the invention is the provision of a compound, where the various moieties are independently selected, $R_{a1}$ is H, and A, B, $R_1$, L, $Ar_1$, $R_2$, $R_p$, $R_{p1}$, $R_a$, $R_b$, $R_c$, $R_d$, $R_q$ and z are as defined.

An embodiment of the invention is the provision of a compound, where the various moieties are independently selected, $R_{a1}$ is halo, and A, B, $R_1$, L, $Ar_1$, $R_2$, $R_p$, $R_{p1}$, $R_a$, $R_b$, $R_c$, $R_d$, $R_q$ and z are as defined.

An embodiment of the invention is the provision of a compound, where the various moieties are independently selected, $R_{a1}$ is $C_1$-$C_4$ alkyl, and A, B, $R_1$, L, $Ar_1$, $R_2$, $R_p$, $R_{p1}$, $R_a$, $R_b$, $R_c$, $R_d$, $R_q$ and z are as defined.

An embodiment of the invention is the provision of a compound, where the various moieties are independently selected, $R_{a1}$ is $C_3$-$C_4$ cycloalkyl, and A, B, $R_1$, L, $Ar_1$, $R_2$, $R_p$, $R_{p1}$, $R_a$, $R_b$, $R_c$, $R_d$, $R_q$ and z are as defined.

An embodiment of the invention is the provision of a compound, where the various moieties are independently selected, $R_b$ is H, and A, B, $R_1$, L, $Ar_1$, $R_2$, $R_p$, $R_{p1}$, $R_a$, $R_{a1}$, $R_c$, $R_d$, $R_q$ and z are as defined.

An embodiment of the invention is the provision of a compound, where the various moieties are independently selected, $R_b$ is halo, and A, B, $R_1$, L, $Ar_1$, $R_2$, $R_p$, $R_{p1}$, $R_a$, $R_{a1}$, $R_c$, $R_d$, $R_q$ and z are as defined.

An embodiment of the invention is the provision of a compound, where the various moieties are independently selected, $R_b$ is $C_1$-$C_4$ alkyl, and A, B, $R_1$, L, $Ar_1$, $R_2$, $R_p$, $R_{p1}$, $R_a$, $R_{a1}$, $R_c$, $R_d$, $R_q$ and z are as defined.

An embodiment of the invention is the provision of a compound, where the various moieties are independently selected, $R_b$ is $C_1$-$C_3$ hydroxyl-alkyl, and A, B, $R_1$, L, $Ar_1$, $R_2$, $R_p$, $R_{p1}$, $R_a$, $R_{a1}$, $R_c$, $R_d$, $R_q$ and z are as defined.

An embodiment of the invention is the provision of a compound, where the various moieties are independently selected, $R_b$ is $C_3$-$C_4$ cycloalkyl, and A, B, $R_1$, L, $Ar_1$, $R_2$, $R_p$, $R_{p1}$, $R_a$, $R_{a1}$, $R_c$, $R_d$, $R_q$ and z are as defined.

An embodiment of the invention is the provision of a compound, where the various moieties are independently selected, $R_c$ is H, and A, B, $R_1$, L, $Ar_1$, $R_2$, $R_p$, $R_{p1}$, $R_a$, $R_{a1}$, $R_b$, $R_d$, $R_q$ and z are as defined.

An embodiment of the invention is the provision of a compound, where the various moieties are independently selected, Re is halo, and A, B, $R_1$, L, $Ar_1$, $R_2$, $R_p$, $R_{p1}$, $R_a$, $R_{a1}$, $R_b$, $R_d$, $R_q$ and z are as defined.

An embodiment of the invention is the provision of a compound, where the various moieties are independently selected, Re is $C_1$-$C_4$ alkyl, and A, B, $R_1$, L, $Ar_1$, $R_2$, $R_p$, $R_{p1}$, $R_a$, $R_{a1}$, $R_b$, $R_d$, $R_q$ and z are as defined.

An embodiment of the invention is the provision of a compound, where the various moieties are independently selected, Re is $C_3$-$C_4$ cycloalkyl, and A, B, $R_1$, L, $Ar_1$, $R_2$, $R_p$, $R_{p1}$, $R_a$, $R_{a1}$, $R_b$, $R_d$, $R_q$ and z are as defined.

An embodiment of the invention is the provision of a compound, where the various moieties are independently selected, R is H, and A, B, $R_1$, L, $Ar_1$, $R_2$, $R_p$, $R_{p1}$, $R_a$, $R_{a1}$, $R_b$, $R_c$, $R_q$ and z are as defined.

An embodiment of the invention is the provision of a compound, where the various moieties are independently selected, R is halo, and A, B, $R_1$, L, $Ar_1$, $R_2$, $R_p$, $R_{p1}$, $R_a$, $R_{a1}$, $R_b$, $R_c$, $R_q$ and z are as defined.

An embodiment of the invention is the provision of a compound, where the various moieties are independently selected, R is $C_1$-$C_4$ alkyl, and A, B, $R_1$, L, $Ar_1$, $R_2$, $R_p$, $R_{p1}$, $R_a$, $R_{a1}$, $R_b$, $R_c$, $R_q$ and z are as defined.

An embodiment of the invention is the provision of a compound, where the various moieties are independently selected, $R_d$ is $C_3$-$C_4$ cycloalkyl, and A, B, $R_1$, L, $Ar_1$, $R_2$, $R_p$, $R_{p1}$, $R_a$, $R_{a1}$, $R_b$, $R_c$, $R_q$ and z are as defined.

An embodiment of the invention is the provision of a compound, where the various moieties are independently selected, $R_q$ is H, and A, B, $R_1$, L, $Ar_1$, $R_2$, $R_p$, $R_{p1}$, $R_a$, $R_{a1}$, $R_b$, $R_c$, $R_d$ and z are as defined.

An embodiment of the invention is the provision of a compound, where the various moieties are independently selected, $R_q$ is halo, and A, B, $R_1$, L, $Ar_1$, $R_2$, $R_p$, $R_{p1}$, $R_a$, $R_{a1}$, $R_b$, $R_c$, $R_d$ and z are as defined.

An embodiment of the invention is the provision of a compound, where the various moieties are independently selected, $R_q$ is $C_1$-$C_4$ alkyl, and A, B, $R_1$, L, $Ar_1$, $R_2$, $R_p$, $R_{p1}$, $R_a$, $R_{a1}$, $R_b$, $R_c$, $R_d$ and z are as defined.

An embodiment of the invention is the provision of a compound, where the various moieties are independently selected, $R_q$ is $C_3$-$C_4$ cycloalkyl, and A, B, $R_1$, L, $Ar_1$, $R_2$, $R_p$, $R_{p1}$, $R_a$, $R_{a1}$, $R_b$, $R_c$, $R_d$ and z are as defined.

An embodiment of the invention is the provision of a compound, where the various moieties are independently selected, z is 0, and A, B, $R_1$, L, $Ar_1$, $R_2$, $R_p$, $R_{p1}$, $R_a$, $R_{a1}$, $R_b$, $R_c$, $R_d$ and $R_q$ are as defined.

An embodiment of the invention is the provision of a compound, where the various moieties are independently selected, z is 1 and A, B, $R_1$, L, $Ar_1$, $R_2$, $R_p$, $R_{p1}$, $R_a$, $R_{a1}$, $R_b$, $R_c$, $R_d$ and $R_q$ are as defined.

An embodiment of the invention is the provision of a compound, where the various moieties are independently selected, z is 2 and A, B, $R_1$, L, $Ar_1$, $R_2$, $R_p$, $R_{p1}$, $R_a$, $R_{a1}$, $R_b$, $R_c$, $R_d$ and $R_q$ are as defined.

An embodiment of the invention is the provision of a compound as described in Formulas I, I-A, I-B, I-C or I-D wherein $R_2$ is not a substituted or unsubstituted form of

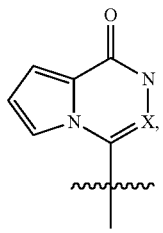

where X is N or CH.

An embodiment of the invention is the provision of a compound as described in Formulas I, I-A, I-B, I-C or I-D wherein when $Ar_1$ is

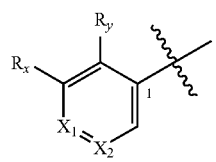

connected to

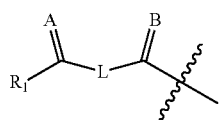

at position 1, and $X_1$ and $X_2$ are independently N or C—$R_z$, and $R_y$ and $R_z$ are any substituent, then Rx does not include alkynyl, alkenyl, aryl, 5-14 membered heterocyclic, 5-14 membered heteroaromatic, or 4-9 membered carbocyclic.

An embodiment of the invention is the provision of a compound as described in Formulas I, I-A, I-B, I-C, or I-D wherein when $R_2$ is

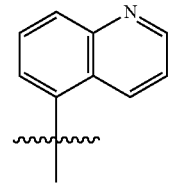

$Ar_1$ is not a substituted or unsubstituted form of

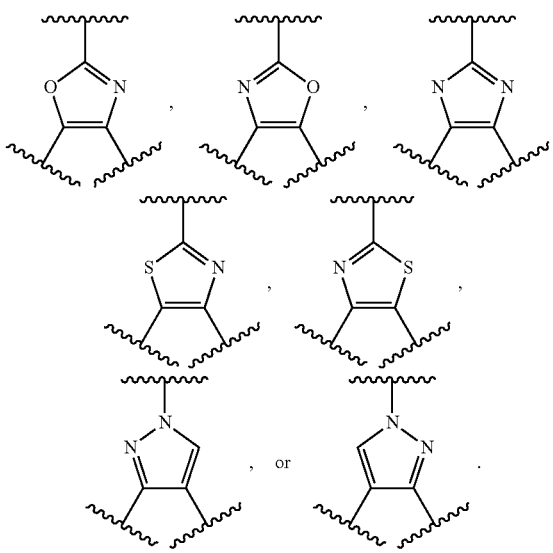

An embodiment of the invention is the provision of a compound as described in Formulas I, I-A, I-B, I-C, or I-D wherein when $Ar_1$ is a substituted or unsubstituted form of a 5 membered heteroaryl, $Ar_1$ is

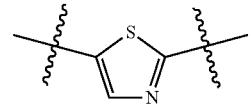 [SMILES: *c1cnc(*)s1]

In another embodiment, the invention is further illustrated by the compounds shown in Table 1, which lists the IUPAC names and the structures of the compounds.

TABLE 1

| IUPAC Name | Compound Structure |
| --- | --- |
| 1-({4-[(4-phenylphenyl)carbonyl]piperazin-1-yl}carbonyl)cyclopropan-1-ol | 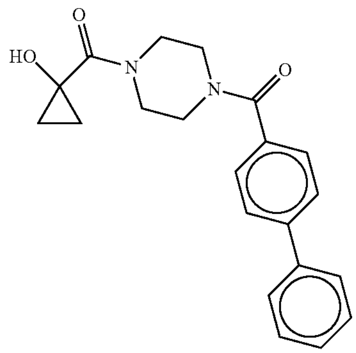 |
| 2-hydroxy-2-methyl-1-{4-[(4-phenylphenyl)carbonyl]piperazin-1-yl}carbonyl)propan-1-one | 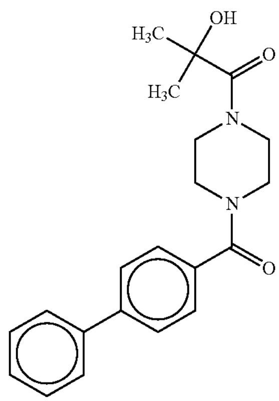 |
| 2-hydroxy-1-{4-[(4-phenylphenyl)carbonyl]piperazin-1-yl}ethan-1-ol | 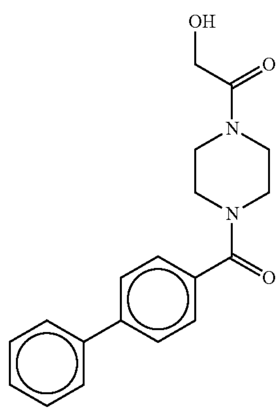 |
| 1-({4-[(4-phenylphenyl)carbonyl]piperazin-1-yl}carbonyl)cycloprentan-1-ol | 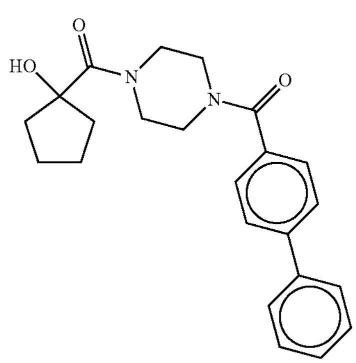 |

TABLE 1-continued

| IUPAC Name | Compound Structure |
|---|---|
| 3,3,3-trifluoro-2-hydroxy-2-methyl-1-{4-[(4-phenylphenyl)carbonyl]piperazin-1-yl}propan-1-one | |
| 1-[(4-{[4-(3-methylphenyl)phenyl]carbonyl}piperazin-1-yl)carbonyl]cyclopropan-1-ol | 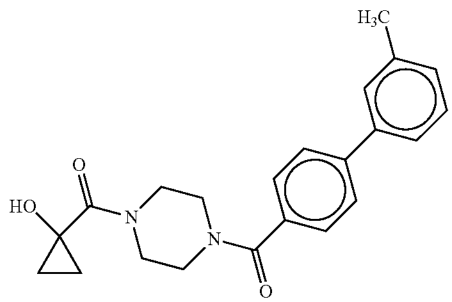 |
| 1-[(4-{[4-(4-methylphenyl)phenyl]carbonyl}piperazin-1-yl)carbonyl]cyclopropan-1-ol | 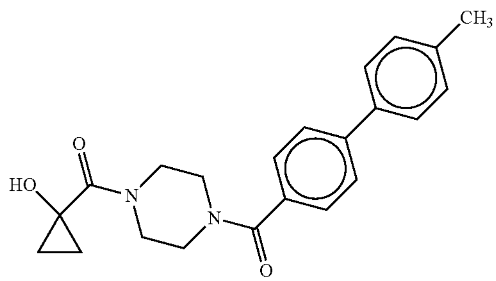 |
| 1-[(4-{[4-(2-fluoro-3-methoxyphenyl)phenyl]carbonyl}piperazin-1-yl)carbonyl]cyclopropan-1-ol | 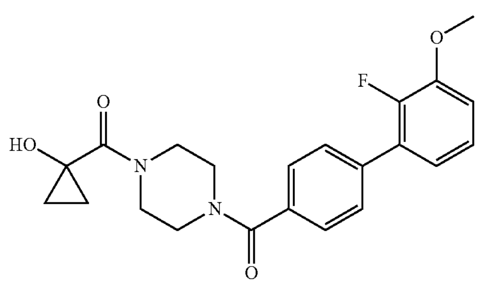 [SMILES: COc1cccc(-c2ccc(C(=O)N3CCN(C(=O)C4(O)CC4)CC3)cc2)c1F] |
| 1-[(4-{[4-(2-fluoro-4-methylphenyl)phenyl]carbonyl}piperazin-1-yl)carbonyl]cyclopropan-1-ol | 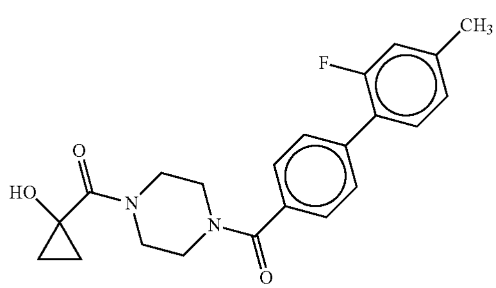 |

TABLE 1-continued

| IUPAC Name | Compound Structure |
|---|---|
| 1-[(4-{[4-(2-fluoro-4-methoxyphenyl)phenyl]carbonyl}piperazin-1-yl)carbonyl]cyclopropan-1-ol | 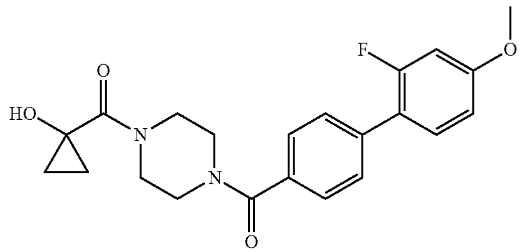 [SMILES: COc1ccc(-c2ccc(C(=O)N3CCN(C(=O)C4(O)CC4)CC3)cc2)c(F)c1] |
| 1-[(4-{[4-(2-chloro-4-fluorophenyl)phenyl]carbonyl}piperazin-1-yl)carbonyl]cyclopropan-1-ol | 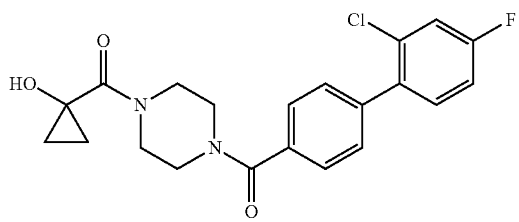 [SMILES: O=C(c1ccc(-c2ccc(F)cc2Cl)cc1)N1CCN(C(=O)C2(O)CC2)CC1] |
| 1-[(4-{[4-(3-chloro-4-fluorophenyl)phenyl]carbonyl}piperazin-1-yl)carbonyl]cyclopropan-1-ol | 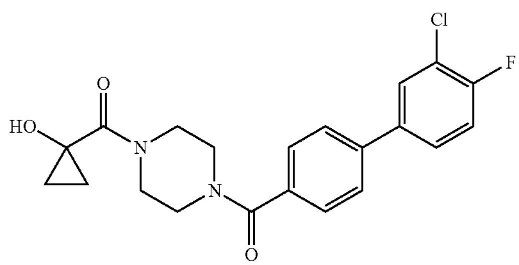 [SMILES: O=C(c1ccc(-c2ccc(F)c(Cl)c2)cc1)N1CCN(C(=O)C2(O)CC2)CC1] |
| 1-[(4-{[4-(4-chloro-2-fluorophenyl)phenyl]carbonyl}piperazin-1-yl)carbonyl]cyclopropan-1-ol | 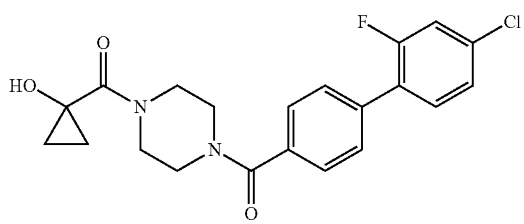 [SMILES: O=C(c1ccc(-c2ccc(Cl)cc2F)cc1)N1CCN(C(=O)C2(O)CC2)CC1] |
| 1-[(4-{[4-(2,4-dichlorophenyl)phenyl]carbonyl}piperazin-1-yl)carbonyl]cyclopropan-1-ol | 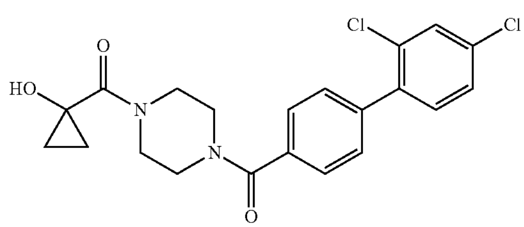 [SMILES: O=C(c1ccc(-c2ccc(Cl)cc2Cl)cc1)N1CCN(C(=O)C2(O)CC2)CC1] |
| 1-[(4-{[4-(5-fluoro-2-methylphenyl)phenyl]carbonyl}piperazin-1-yl)carbonyl]cyclopropan-1-ol | 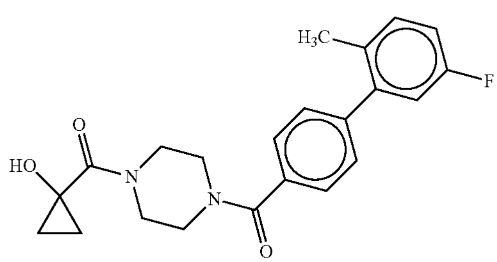 |

TABLE 1-continued

| IUPAC Name | Compound Structure |
|---|---|
| 1-[(4-{[4-(3-fluoro-4-methylphenyl)phenyl]carbonyl}piperazin-1-yl)carbonyl]cyclopropan-1-ol | 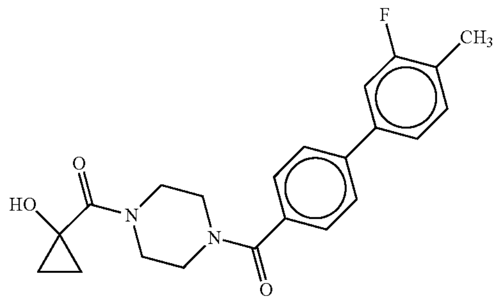 |
| 1-[(4-{[4-(2,3-dichlorophenyl)phenyl]carbonyl}piperazin-1-yl)carbonyl]cyclopropan-1-ol | 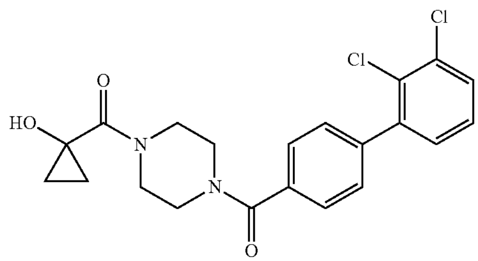 [SMILES: O=C(c1ccc(-c2cccc(Cl)c2Cl)cc1)N1CCN(C(=O)C2(O)CC2)CC1] |
| 1-[(4-{[4-(2,5-dichlorophenyl)phenyl]carbonyl}piperazin-1-yl)carbonyl]cyclopropan-1-ol | 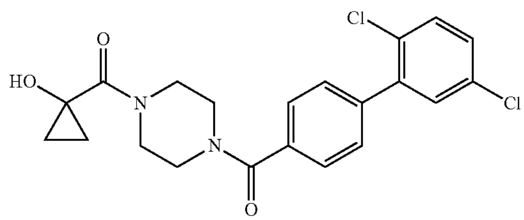 [SMILES: O=C(c1ccc(-c2cc(Cl)ccc2Cl)cc1)N1CCN(C(=O)C2(O)CC2)CC1] |
| 1-[(4-{[4-(4-chloro-3-fluorophenyl)phenyl]carbonyl}piperazin-1-yl)carbonyl]cyclopropan-1-ol | 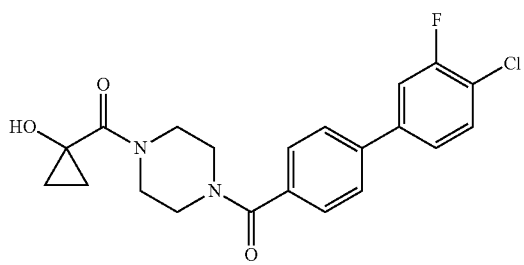 [SMILES: O=C(c1ccc(-c2ccc(Cl)c(F)c2)cc1)N1CCN(C(=O)C2(O)CC2)CC1] |
| 1-[(4-{[4-(2,5-difluorophenyl)phenyl]carbonyl}piperazin-1-yl)carbonyl]cyclopropan-1-ol | 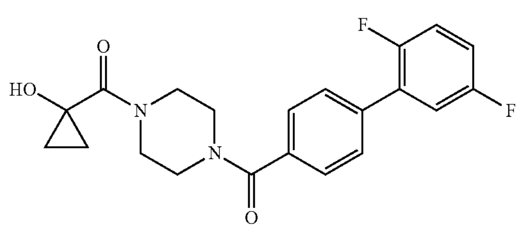 [SMILES: O=C(c1ccc(-c2cc(F)ccc2F)cc1)N1CCN(C(=O)C2(O)CC2)CC1] |
| 1-[(4-{[4-(3,4-dichlorophenyl)phenyl]carbonyl}piperazin-1-yl)carbonyl]cyclopropan-1-ol | 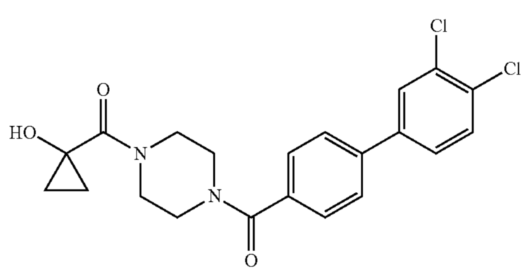 |

TABLE 1-continued

| IUPAC Name | Compound Structure |
|---|---|
| 1-[(4-{[4-(2,3-difluorophenyl)phenyl]carbonyl}piperazin-1-yl)carbonyl]cyclopropan-1-ol | 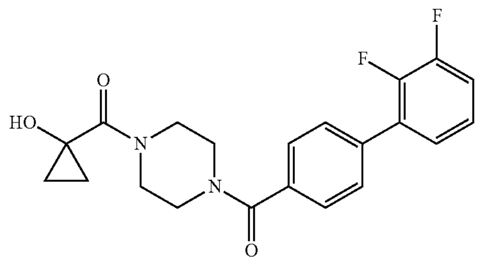 [SMILES: O=C(c1ccc(-c2cccc(F)c2F)cc1)N1CCN(C(=O)C2(O)CC2)CC1] |
| 1-[(4-{[4-(1-methyl-1H-indol-5-yl)phenyl]carbonyl}piperazin-1-yl)carbonyl]cyclopropan-1-ol | 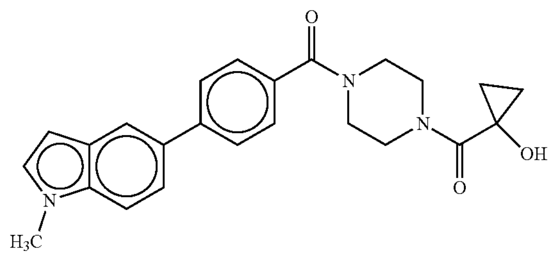 |
| 1-{[4-({4-[2-methoxy-4-(1H-pyrazol-1-yl)phenyl]phenyl}carbonyl)piperazin-1-yl]carbonyl}cyclopropan-1-ol | 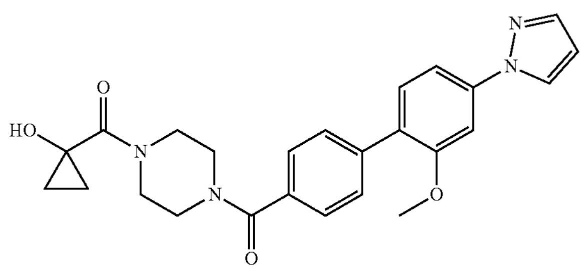 [SMILES: COc1cc(-n2cccn2)ccc1-c1ccc(C(=O)N2CCN(C(=O)C3(O)CC3)CC2)cc1] |
| 1-[(4-{[4-(2-fluoro-5-methylphenyl)phenyl]carbonyl}piperazin-1-yl)carbonyl]cyclopropan-1-ol | 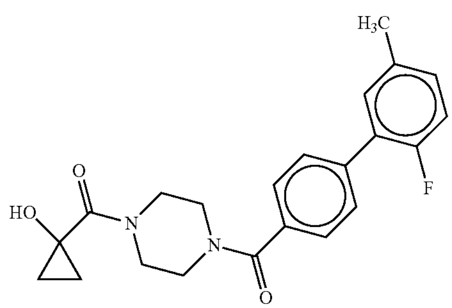 |
| 1-{[4-({4-[2-chloro-5-(trifluoromethyl)phenyl]phenyl}carbonyl)piperazin-1-yl]carbonyl}cyclopropan-1-ol | 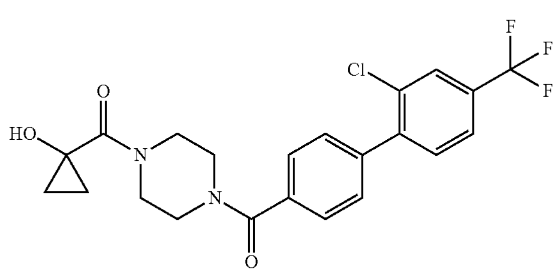 [SMILES: O=C(c1ccc(-c2ccc(C(F)(F)F)cc2Cl)cc1)N1CCN(C(=O)C2(O)CC2)CC1] |

TABLE 1-continued

| IUPAC Name | Compound Structure |
|---|---|
| 1-[(4-{[4-(4-chloro-2-methoxyphenyl)phenyl]carbonyl}piperazin-1-yl)carbonyl]cyclopropan-1-ol | 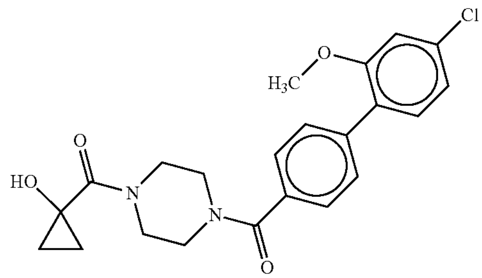 |
| 1-[(4-{[4-(3-chloro-2-methoxyphenyl)phenyl]carbonyl}piperazin-1-yl)carbonyl]cyclopropan-1-ol | 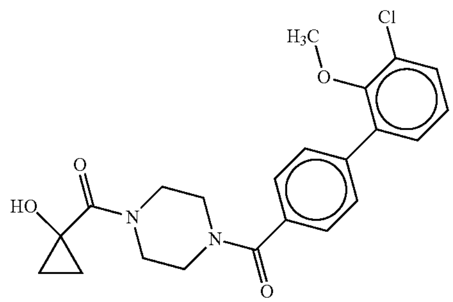 |
| 1-[(4-{[4-(4,5-difluoro-2-methoxyphenyl)phenyl]carbonyl}piperazin-1-yl)carbonyl]cyclopropan-1-ol | 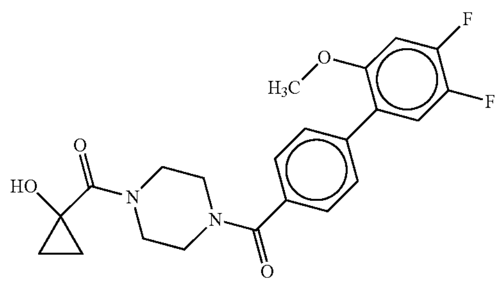 |
| 1-{[4-({4-[2-fluoro-3-(trifluoromethyl)phenyl]phenyl}carbonyl)piperazin-1-yl]carbonyl}cyclopropan-1-ol | 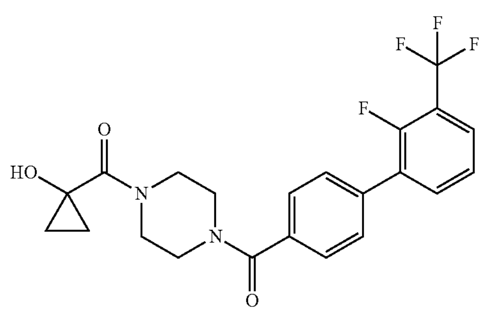 [SMILES: O=C(c1ccc(-c2cccc(C(F)(F)F)c2F)cc1)N1CCN(C(=O)C2(O)CC2)CC1] |
| 1-{[4-({4-[4-chloro-2-(trifluoromethyl)phenyl]phenyl}carbonyl)piperazin-1-yl]carbonyl}cyclopropan-1-ol | 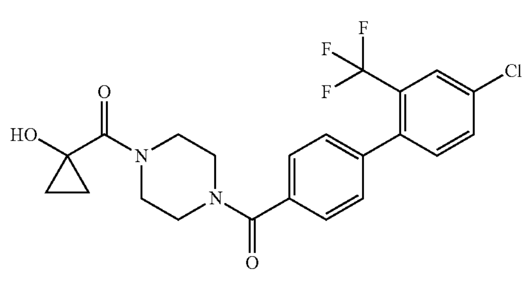 [SMILES: O=C(c1ccc(-c2ccc(Cl)cc2C(F)(F)F)cc1)N1CCN(C(=O)C2(O)CC2)CC1] |

TABLE 1-continued

| IUPAC Name | Compound Structure |
| --- | --- |
| 1-[(4-{[4-(2-chloro-4-methoxyphenyl)phenyl]carbonyl}piperazin-1-yl)carbonyl]cyclopropan-1-ol | 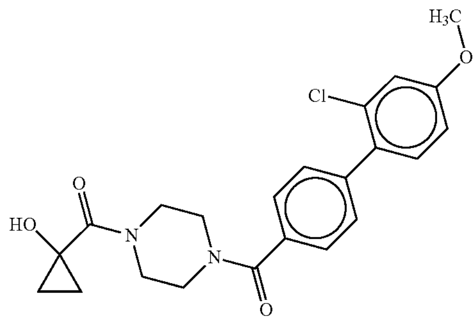 |
| 1-{[4-({4-[5-chloro-2-(propan-2-yloxy)phenyl]phenyl}carbonyl)piperazin-1-yl]carbonyl}cyclopropan-1-ol | 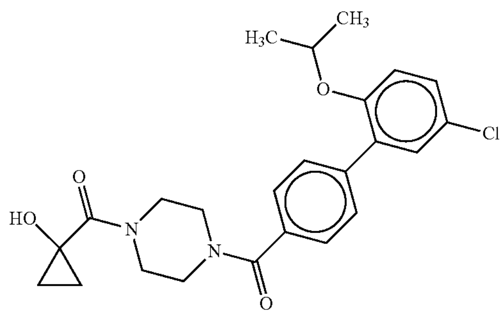 |
| 1-{[4-({4-[3-fluoro-5-(trifluoromethyl)phenyl]phenyl}carbonyl)piperazin-1-yl]carbonyl}cyclopropan-1-ol | 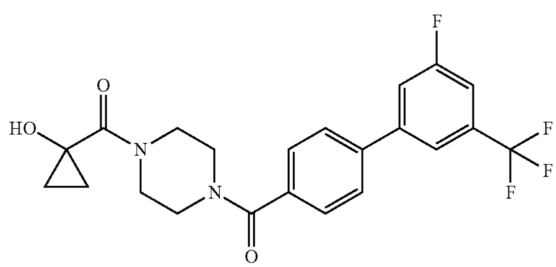 [SMILES: O=C(c1ccc(-c2cc(F)cc(C(F)(F)F)c2)cc1)N1CCN(C(=O)C2(O)CC2)CC1] |
| 1-{[4-({4-[2-methoxy-5-(trifluoromethoxy)phenyl]phenyl}carbonyl)piperazin-1-yl]carbonyl}cyclopropan-1-ol | 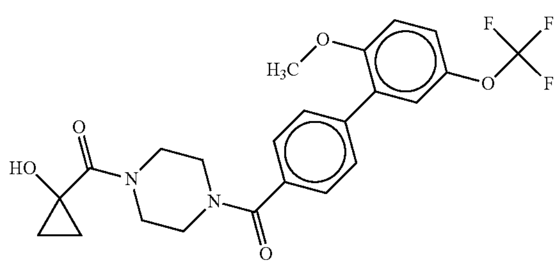 |
| 1-[(4-{[4-(3-fluoro-2-methoxyphenyl)phenyl]carbonyl}piperazin-1-yl)carbonyl]cyclopropan-1-ol | 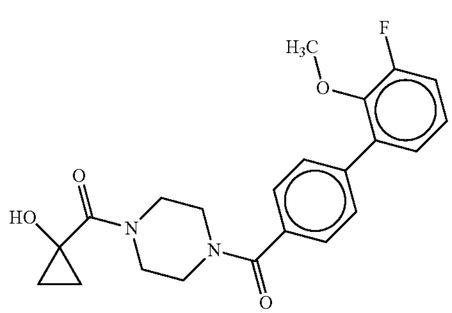 |

TABLE 1-continued

| IUPAC Name | Compound Structure |
|---|---|
| 1-[(4-{[4-(3-methoxypyridin-4-yl)phenyl]carbonyl}piperazin-1-yl)carbonyl]cyclopropan-1-ol | 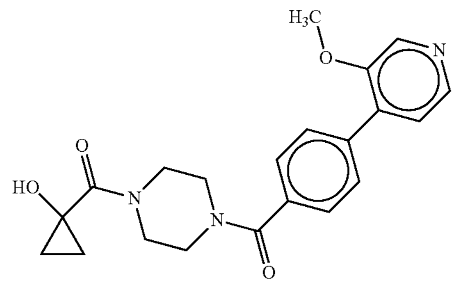 |
| 1-[(4-{[4-(quinolin-3-yl)phenyl]carbonyl}piperazin-1-yl)carbonyl]cyclopropan-1-ol | 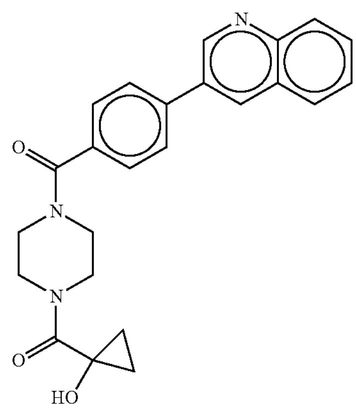 |
| 1-[(4-{[4-(isoquinolin-6-yl)phenyl]carbonyl}piperazin-1-yl)carbonyl]cyclopropan-1-ol | 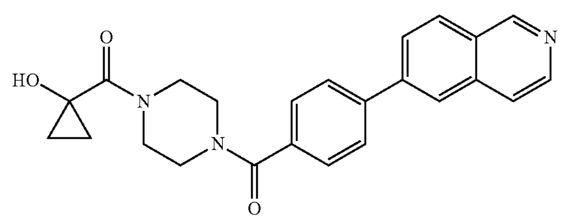 [SMILES: O=C(c1ccc(-c2ccc3cnccc3c2)cc1)N1CCN(C(=O)C2(O)CC2)CC1] |
| 1-({4-[(4-{imidazo[1,2-a]pyridin-6-yl}phenyl)carbonyl]piperazin-1-yl}carbonyl)cyclopropan-1-ol | 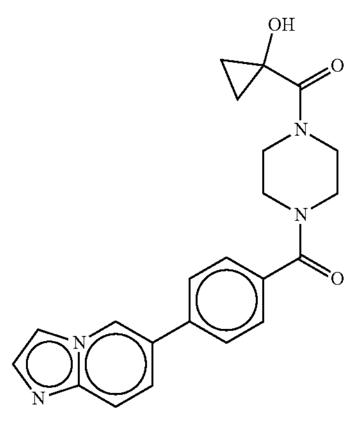 |
| 1-[(4-{[4-(1,3-benzothiazol-5-yl)phenyl]carbonyl}piperazin-1-yl)carbonyl]cyclopropan-1-ol | 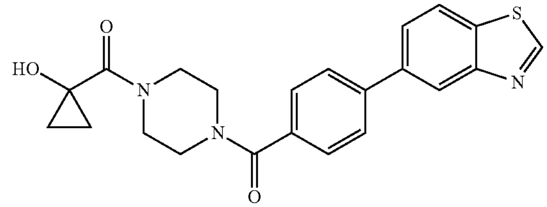 [SMILES: O=C(c1ccc(-c2ccc3scnc3c2)cc1)N1CCN(C(=O)C2(O)CC2)CC1] |

TABLE 1-continued

| IUPAC Name | Compound Structure |
|---|---|
| 1-{[4-({4-[6-(trifluoromethyl)pyridin-3-yl]phenyl}carbonyl)piperazin-1-yl]carbonyl}cyclopropan-1-ol | 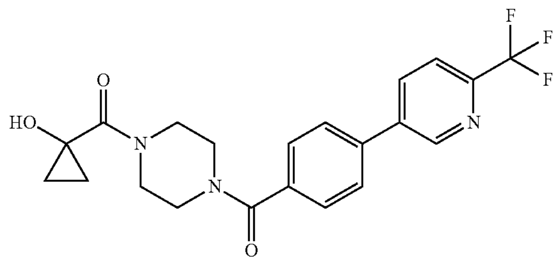 [SMILES: O=C(c1ccc(-c2ccc(C(F)(F)F)nc2)cc1)N1CCN(C(=O)C2(O)CC2)CC1] |
| 1-[(4-{[4-(5-chloro-2-fluorophenyl)phenyl]carbonyl}piperazin-1-yl)carbonyl]cyclopropan-1-ol | 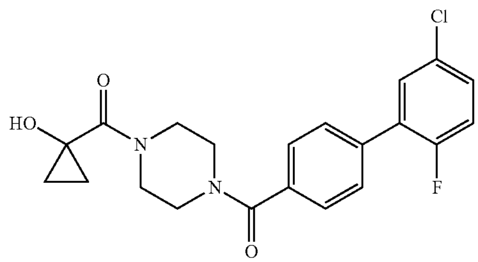 [SMILES: O=C(c1ccc(-c2cc(Cl)ccc2F)cc1)N1CCN(C(=O)C2(O)CC2)CC1] |
| 1-[(4-{[4-(6-methylpyridin-3-yl)phenyl]carbonyl}piperazin-1-yl)carbonyl]cyclopropan-1-ol | 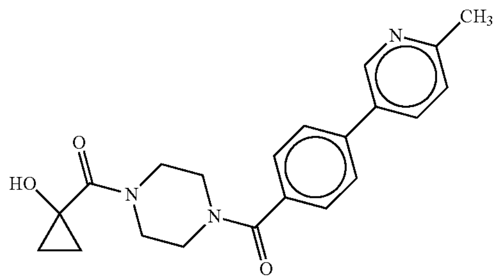 |
| 1-[(4-{[4-(2,6-dimethoxypyridin-3-yl)phenyl]carbonyl}piperazin-1-yl)carbonyl]cyclopropan-1-ol | 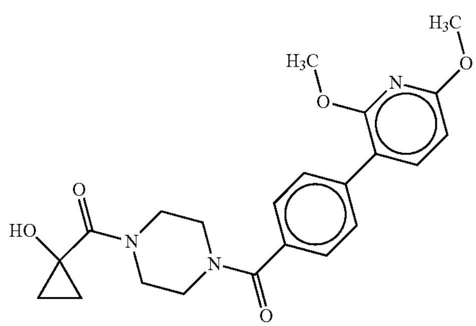 |
| 1-[(4-{[4-(5-fluoropyridin-3-yl)phenyl]carbonyl}piperazin-1-yl)carbonyl]cyclopropan-1-ol | 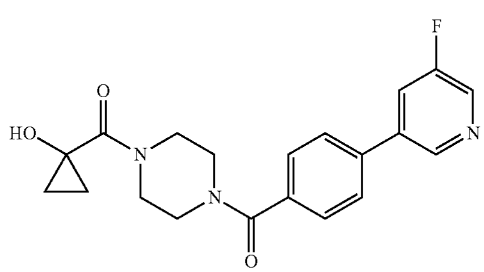 [SMILES: O=C(c1ccc(-c2cncc(F)c2)cc1)N1CCN(C(=O)C2(O)CC2)CC1] |

TABLE 1-continued

| IUPAC Name | Compound Structure |
| --- | --- |
| 1-[(4-{[4-(1-methyl-1H-indol-2-yl)phenyl]carbonyl}piperazin-1-yl)carbonyl]cyclopropan-1-ol | 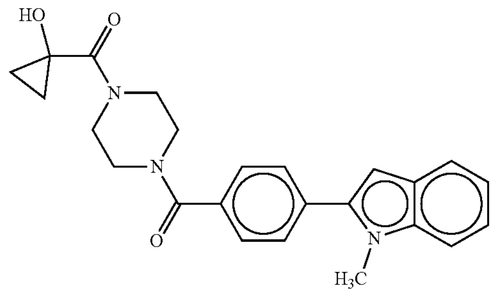 |
| 1-[(4-{[4-(2-chloro-5-fluorophenyl)phenyl]carbonyl}piperazin-1-yl)carbonyl]cyclopropan-1-ol | 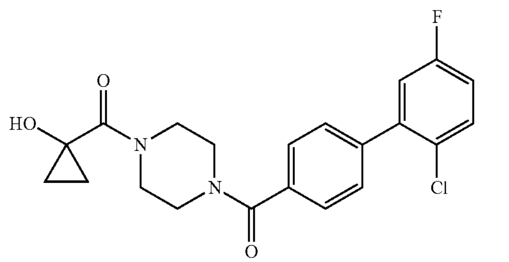 [SMILES: O=C(c1ccc(-c2cc(F)ccc2Cl)cc1)N1CCN(C(=O)C2(O)CC2)CC1] |
| 1-[(4-{[4-(2-fluoro-5-methoxyphenyl)phenyl]carbonyl}piperazin-1-yl)carbonyl]cyclopropan-1-ol | 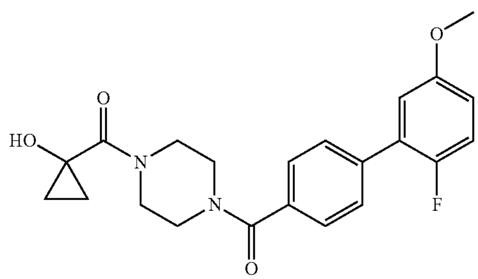 [SMILES: COc1ccc(F)c(-c2ccc(C(=O)N3CCN(C(=O)C4(O)CC4)CC3)cc2)c1] |
| 1-[(4-{[4-(2-fluoro-3-methylphenyl)phenyl]carbonyl}piperazin-1-yl)carbonyl]cyclopropan-1-ol | 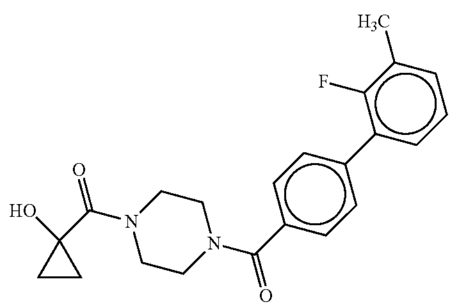 |
| 1-{[4-({4-[4-fluoro-2-(trifluoromethyl)phenyl]phenyl}carbonyl)piperazin-1-yl]carbonyl}cyclopropan-1-ol | 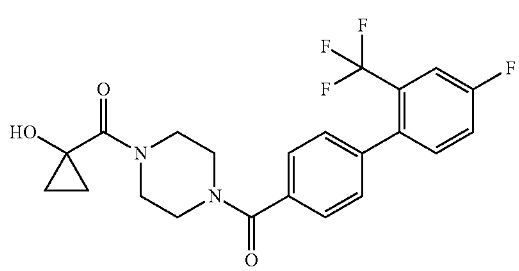 [SMILES: O=C(c1ccc(-c2ccc(F)cc2C(F)(F)F)cc1)N1CCN(C(=O)C2(O)CC2)CC1] |

TABLE 1-continued

| IUPAC Name | Compound Structure |
|---|---|
| 1-{[4-({4-[2-chloro-5-(hydroxymethyl)phenyl]phenyl}carbonyl)piperazin-1-yl]carbonyl}cyclopropan-1-ol | 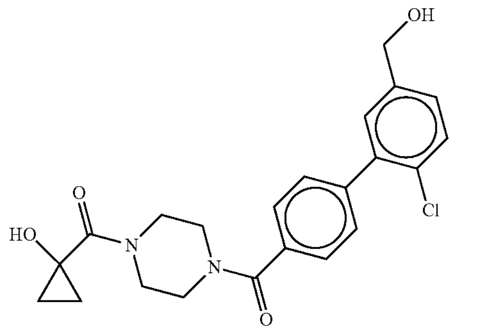 |
| 1-[(4-{[4-(2-methyl-2H-indazol-6-yl)phenyl]carbonyl}piperazin-1-yl)carbonyl]cyclopropan-1-ol | 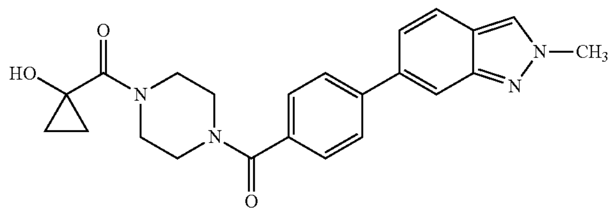 [SMILES: Cn1cc2ccc(-c3ccc(C(=O)N4CCN(C(=O)C5(O)CC5)CC4)cc3)cc2n1] |
| 1-[(4-{[4-(1-methyl-1H-indazol-7-yl)phenyl]carbonyl}piperazin-1-yl)carbonyl]cyclopropan-1-ol | 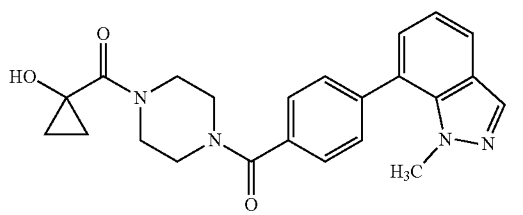 [SMILES: Cn1ncc2cccc(-c3ccc(C(=O)N4CCN(C(=O)C5(O)CC5)CC4)cc3)c21] |
| 1-[(4-{[4-(1H-indol-4-yl)phenyl]carbonyl}piperazin-1-yl)carbonyl]cyclopropan-1-ol | 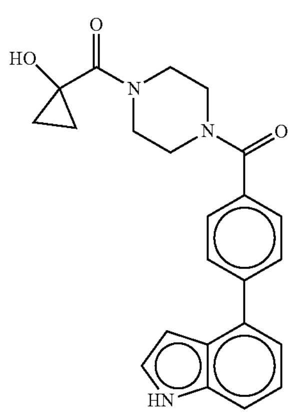 |

TABLE 1-continued

| IUPAC Name | Compound Structure |
|---|---|
| N-cyclcopropyl-3-[4-({4-[(1-hydroxycyclopropyl)carbonyl]piperazin-1-yl}carbonyl)phenyl]benzamide | 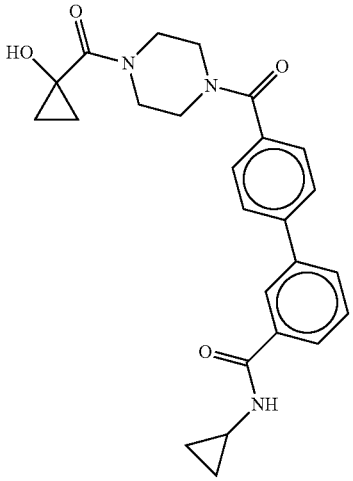 |
| N-{3-[4-({4-[(1-hydroxycyclopropyl)carbonyl]piperazin-1-yl}carbonyl)phenyl]phenyl}ethane-1-sulfonamide | 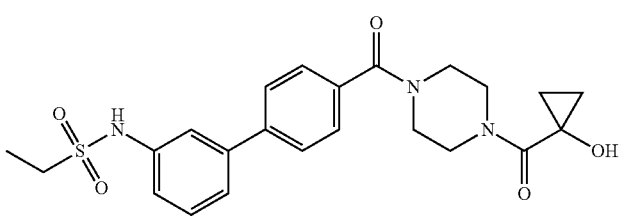 [SMILES: CCS(=O)(=O)Nc1cccc(-c2ccc(C(=O)N3CCN(C(=O)C4(O)CC4)CC3)cc2)c1] |
| 4-fluoro-3-[4-({4-[(1-hydroxycyclopropyl)carbonyl]piperazin-1-yl}carbonyl)phenyl]-N-methylbenzamide | 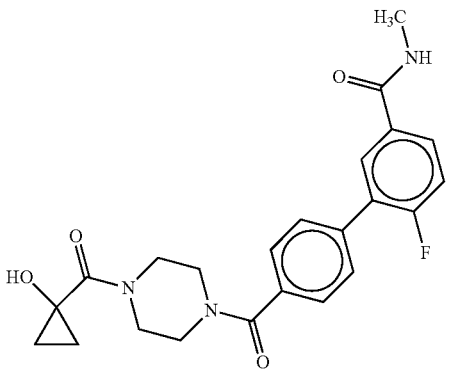 |
| 4-fluoro-3-[4-({4-[(1-hydroxycyclopropyl)carbonyl]piperazin-1-yl}carbonyl)phenyl]-N-(propan-2-yl)benzamide | 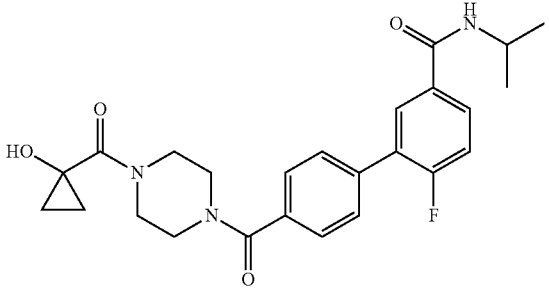 [SMILES: CC(C)NC(=O)c1ccc(F)c(-c2ccc(C(=O)N3CCN(C(=O)C4(O)CC4)CC3)cc2)c1] |

TABLE 1-continued

| IUPAC Name | Compound Structure |
|---|---|
| 1-[(4-{[4-(2,4-dichloro-3-methoxyphenyl)phenyl]carbonyl}piperazin-1-yl)carbonyl]cyclopropan-1-ol | 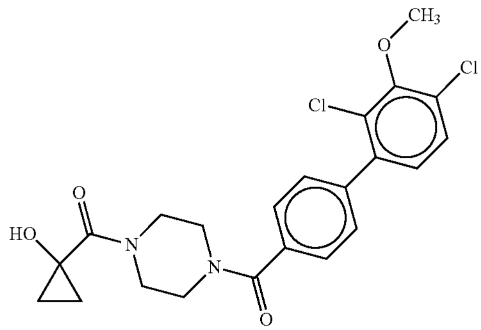 |
| 1-{[4-({4-[2-fluoro-3-(propan-2-yloxy)phenyl]phenyl}carbonyl)pipenizin-1-yl]carbonyl}cyclopropan-1-ol | 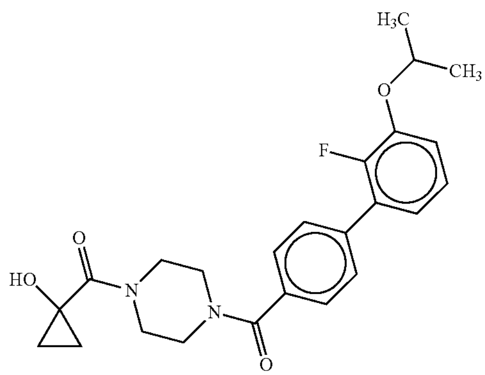 |
| 1-{[-4-({4-[2-fluoro-3-(trifluoromethoxy)phenyl]phenyl}carbonyl)piperazin-1-yl]carbonyl}cyclopropan-1-ol | 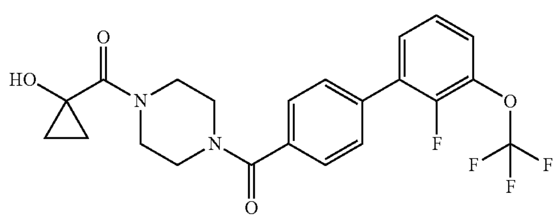 [SMILES: O=C(c1ccc(-c2cccc(OC(F)(F)F)c2F)cc1)N1CCN(C(=O)C2(O)CC2)CC1] |
| 1-{[-4-({4-[3-(cyclopropylmethoxy)phenyl]phenyl}carbonyl)piperazin-1-yl]carbonyl}cyclopropan-1-ol | 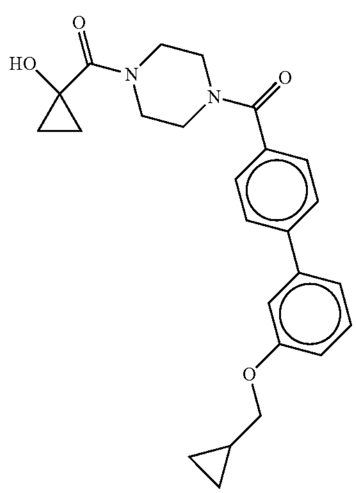 |

TABLE 1-continued

| IUPAC Name | Compound Structure |
|---|---|
| 5-fluoro-2-[4-({4-[(1-hydroxycyclopropyl)carbonyl]piperazin-1-yl}carbonyl)phenyl]benzonitrile | 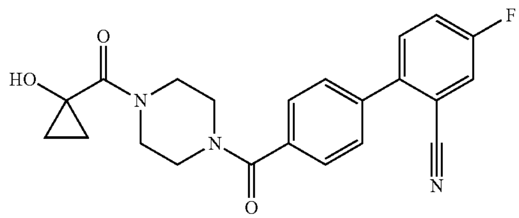 [SMILES: N#Cc1cc(F)ccc1-c1ccc(C(=O)N2CCN(C(=O)C3(O)CC3)CC2)cc1] |
| 1-[(4-{[4-(1-methyl-1H-indazol-6-yl)phenyl]carbonyl}piperazin-1-yl)carbonyl]cyclcopropan-1-ol | 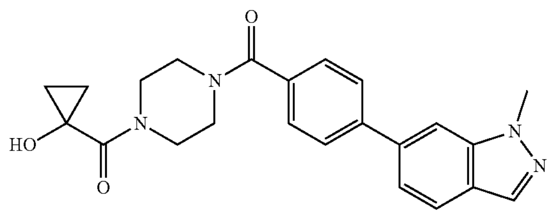 [SMILES: Cn1ncc2ccc(-c3ccc(C(=O)N4CCN(C(=O)C5(O)CC5)CC4)cc3)cc21] |
| 1-[(4-{[4-(1-methyl-1H-indazol-5-yl)phenyl]carbonyl}piperazin-1-yl)carbonyl]cyclopropan-1-ol | 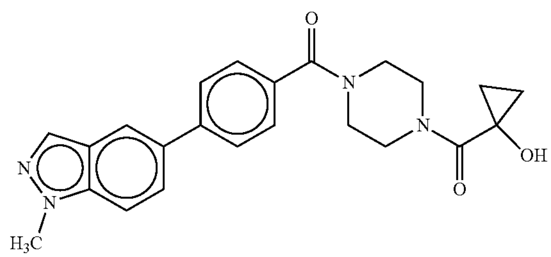 |
| 1-[(4-{[6-(1-methyl-1H-indol-5-yl)pyridin-3-yl]carbonyl}piperazin-1-yl)carbonyl]cyclopropan-1-ol | 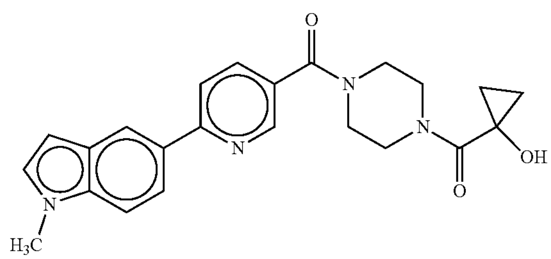 |
| 1-[(4-{[5-(1-methyl-1H-indol-5-yl)pyridin-2-yl]carbonyl}piperazin-1-yl)carbonyl]cyclopropan-1-ol | 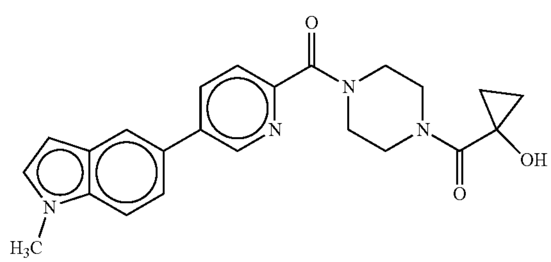 |
| 1-[(4-{[2-fluoro-4-(1-methyl-1H-indol-5-yl)phenyl]carbonyl}piperazin-1-yl)carbonyl]cyclopropan-1-ol | 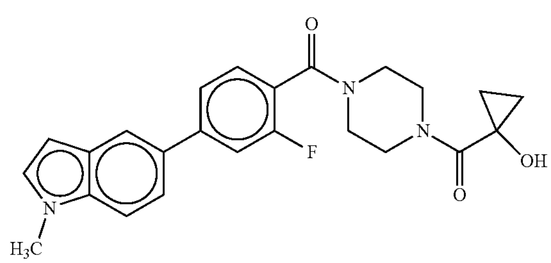 |

TABLE 1-continued

| IUPAC Name | Compound Structure |
|---|---|
| 1-[(4-{[2-fluoro-4-(quinolin-6-yl)phenyl]carbonyl}piperazin-1-yl)carbonyl]cyclopropan-1-ol | 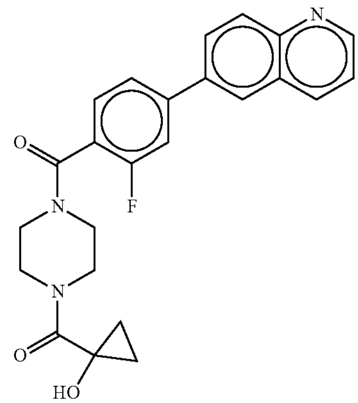 |
| 2-methoxy-2-methyl-1-{4-[(4-phenylphenyl)carbonyl]piperazin-1-yl}propan-1-one | 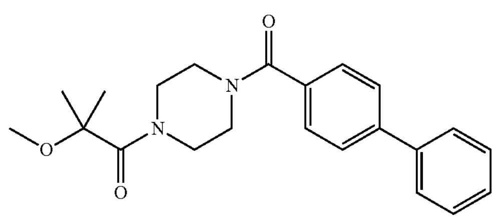 [SMILES: COC(C)(C)C(=O)N1CCN(C(=O)c2ccc(-c3ccccc3)cc2)CC1] |
| (2S)-2-hydroxy-1-{4-[(4-phenylphenyl)carbonyl]piperazin-1-yl}propan-1-one | 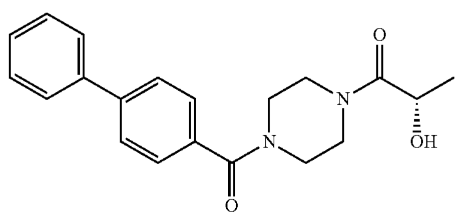 [SMILES: C[C@H](O)C(=O)N1CCN(C(=O)c2ccc(-c3ccccc3)cc2)CC1] |
| 1-[(4-{[4-(quinolin-3-yl)phenyl]carbonyl}piperazin-1-yl)carbonyl]cyclobutan-1-ol | 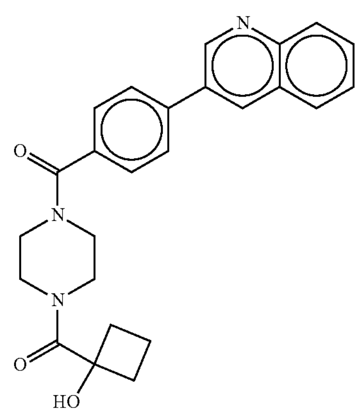 |

TABLE 1-continued

| IUPAC Name | Compound Structure |
| --- | --- |
| 1-[(4-{[2-chloro-4-(quinolin-6-yl)phenyl]carbonyl}piperazin-1-yl)carbonyl]cyclopropan-1-ol | 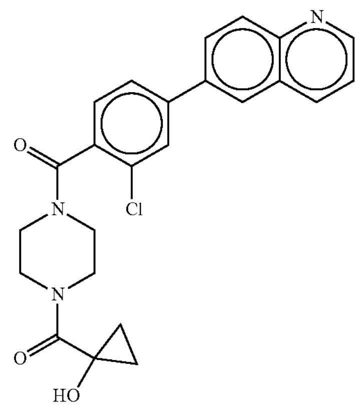 |
| 1-[(4-{[2-chloro-4-(1-methyl-1H-indol-5-yl)phenyl]carbonyl}piperazin-1-yl)carbonyl]cyclopropan-1-ol | 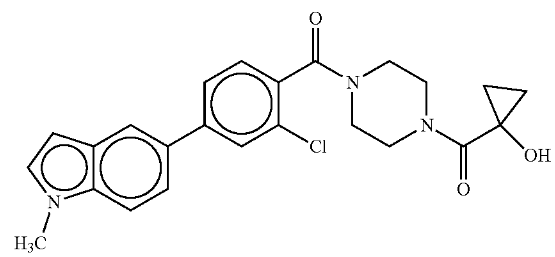 |
| 1-[(4-{[6-(quinolin-6-yl)pyridin-3-yl]carbonyl}piperazin-1-yl)carbonyl]cyclopropan-1-ol | 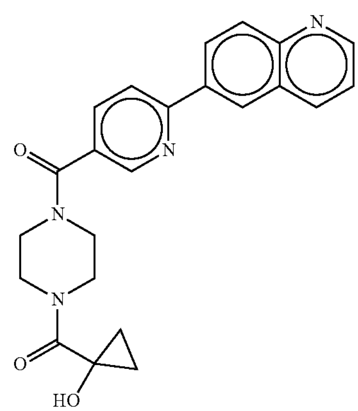 |
| 1-[(4-{[4-methyl-2-(1-methyl-1H-indol-5-yl)-1,3-thiazol-5-yl]carbonyl}piperazin-1-yl)carbonyl]cyclopropan-1-ol | 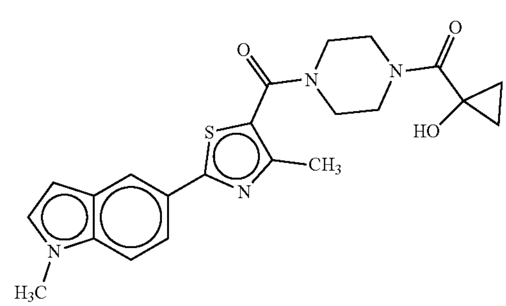 |

TABLE 1-continued

| IUPAC Name | Compound Structure |
|---|---|
| 1-[(4-{[4-methyl-2-(quinolin-3-yl)-1,3-thiazol-5-yl]carbonyl}piperazin-1-yl)carbonyl]cyclopropan-1-ol | 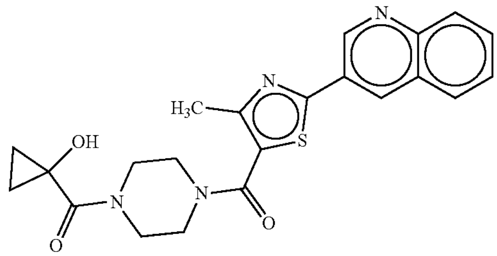 |
| 1-[(4-{[2-(1,3-benzothiazol-5-yl)-4-methyl-1,3-thiazol-5-yl]carbonyl}piperazin-1-yl)carbonyl]cyclopropan-1-ol | 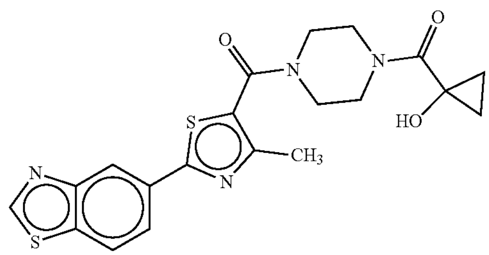 |
| 1-[(4-{[3-fluoro-4-(quinolin-3-yl)phenyl]carbonyl}piperazin-1-yl)carbonyl]cyclopropan-1-ol | 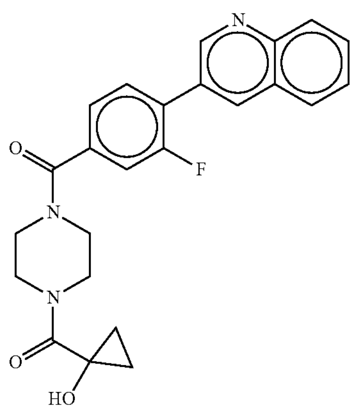 |
| 1-[(4-{[3-fluoro-4-(quinolin-6-yl)phenyl]carbonyl}piperazin-1-yl)carbonyl]cyclopropan-1-ol | 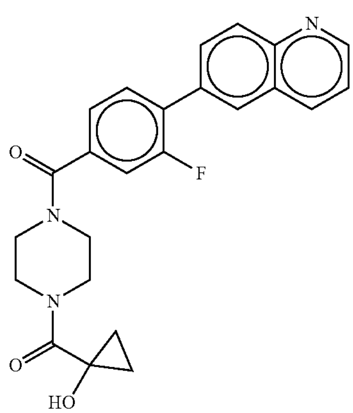 |
| 1-[(4-{[4-(1,3-benzothiazol-5-yl)-3-fluorophenyl]carbonyl}piperazin-1-yl)carbonyl]cyclopropan-1-ol | 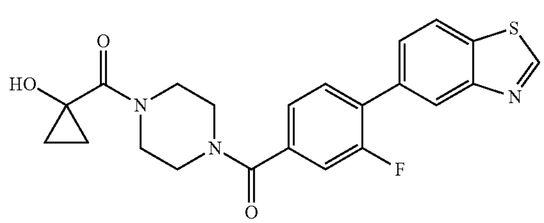 [SMILES: O=C(c1ccc(-c2ccc3scnc3c2)c(F)c1)N1CCN(C(=O)C2(O)CC2)CC1] |

TABLE 1-continued

| IUPAC Name | Compound Structure |
|---|---|
| 1-[(4-{[3-methyl-4-(1-methyl-1H-indol-5-yl)phenyl]carbonyl}piperazin-1-yl)carbonyl]cyclopropan-1-ol | 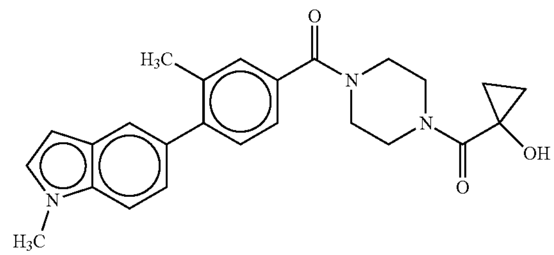 |
| 1-[(4-{[3-methyl-4-(quinolin-3-yl)phenyl]carbonyl}piperazin-1-yl)carbonyl]cyclopropan-1-ol | 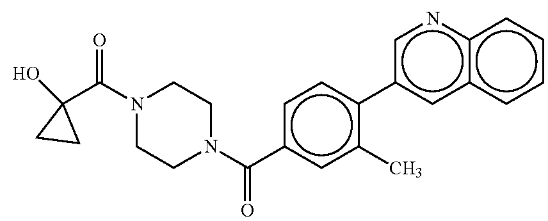 |
| 1-[(4-{[3-methyl-4-(quinolin-6-yl)phenyl]carbonyl}piperazin-1-yl)carbonyl]cyclopropan-1-ol | 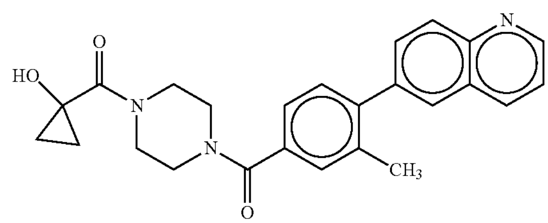 |
| 1-[(4-{[4-(1,3-benzothiazol-5-yl)-3-methylphenyl]carbonyl}piperazin-1-yl)carbonyl]cyclopropan-1-ol | 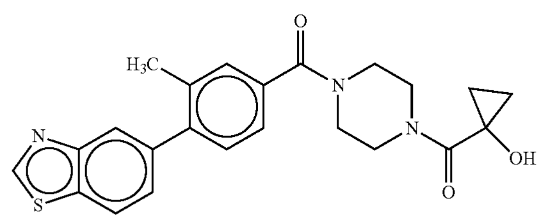 |
| 1-[(4-{[2-chloro-4-(quinolin-3-yl)phenyl]carbonyl}piperazin-1-yl)carbonyl]cyclopropan-1-ol | 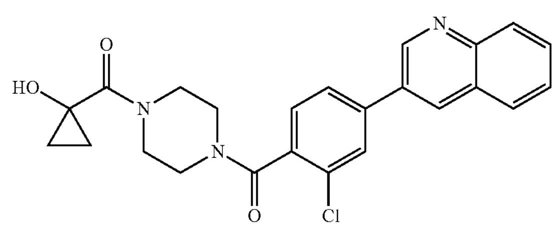 [SMILES: O=C(c1ccc(-c2cnc3ccccc3c2)cc1Cl)N1CCN(C(=O)C2(O)CC2)CC1] |
| 1-[(4-{[4-(1,3-benzothiazol-5-yl)-2-chlorophenyl]carbonyl}piperazin-1-yl)carbonyl]cyclopropan-1-ol | 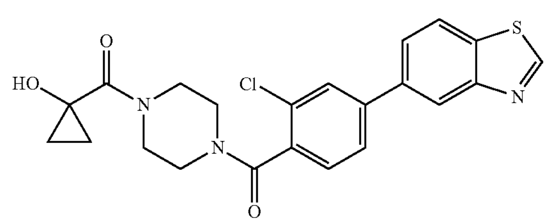 [SMILES: O=C(c1ccc(-c2ccc3scnc3c2)cc1Cl)N1CCN(C(=O)C2(O)CC2)CC1] |

TABLE 1-continued

| IUPAC Name | Compound Structure |
|---|---|
| 1-[(4-{[3-chloro-4-(1-methyl-1H-indol-5-yl)phenyl]carbonyl}piperazin-1-yl)carbonyl]cyclopropan-1-ol | 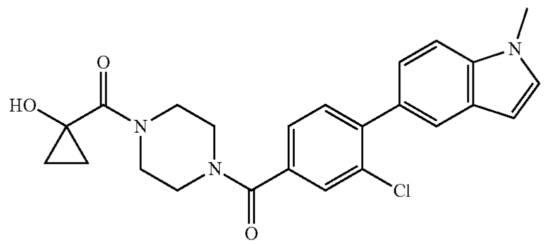 [SMILES: Cn1ccc2cc(-c3ccc(C(=O)N4CCN(C(=O)C5(O)CC5)CC4)cc3Cl)ccc21] |
| 1-[(4-{[3-chloro-4-(quinolin-3-yl)phenyl]carbonyl}piperazin-1-yl)carbonyl]cyclopropan-1-ol | 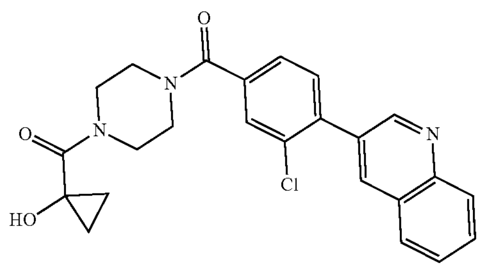 [SMILES: O=C(c1ccc(-c2cnc3ccccc3c2)c(Cl)c1)N1CCN(C(=O)C2(O)CC2)CC1] |
| 1-[(4-{[3-chloro-4-(quinolin-6-yl)phenyl]carbonyl}pjperazin-1-yl)carbonyl]cyclopropan-1-ol | 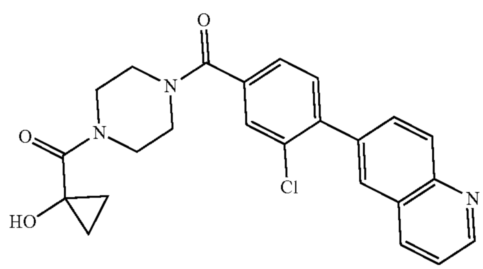 [SMILES: O=C(c1ccc(-c2ccc3ncccc3c2)c(Cl)c1)N1CCN(C(=O)C2(O)CC2)CC1] |
| 1-[(4-{[4-(1,3-benzothiazol-5-yl)-3-chlorophenyl]carbonyl}piperazin-1-yl)carbonyl]cyclopropan-1-ol | 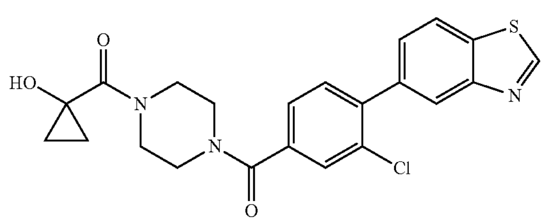 |
| 1-[(4-{[4-(1-methyl-1H-indol-5-yl)-2-(trifluoromethyl)phenyl]carbonyl}piperazin-1-yl)carbonyl]cyclopropan-1-ol | 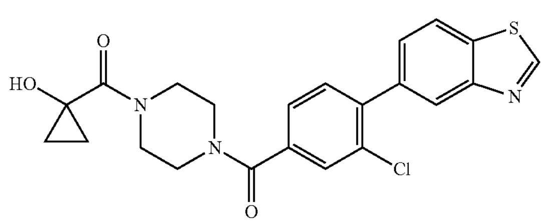 |
| 1-[(4-{[4-(quinolin-6-yl)-2-(trifluoromethyl)phenyl]carbonyl}piperazin-1-yl)carbonyl]cyclopropan-1-ol | 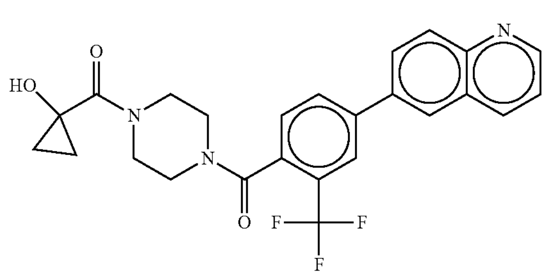 |

TABLE 1-continued

| IUPAC Name | Compound Structure |
|---|---|
| 1-[(4-{[3-methoxy-4-(quinolin-6-yl)phenyl]carbonyl}piperazin-1-yl)carbonyl]cyclopropan-1-ol | 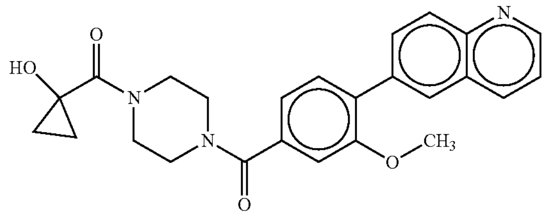 |
| 1-[(4-{[2-methoxy-4-(quinolin-3-yl)phenyl]carbonyl}piperazin-1-yl)carbonyl]cyclopropan-1-ol | 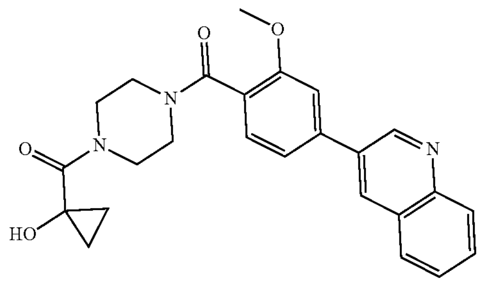 [SMILES: COc1cc(-c2cnc3ccccc3c2)ccc1C(=O)N1CCN(C(=O)C2(O)CC2)CC1] |
| 1-[(4-{[2-methoxy-4-(quinolin-6-yl)phenyl]carbonyl}piperazin-1-yl)carbonyl]cyclopropan-1-ol | 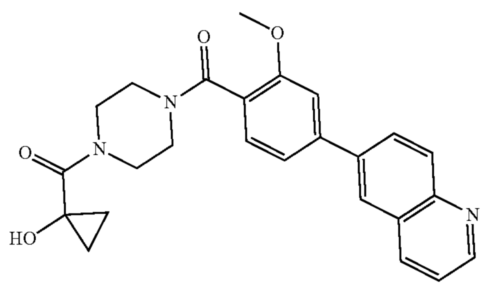 [SMILES: COc1cc(-c2ccc3ncccc3c2)ccc1C(=O)N1CCN(C(=O)C2(O)CC2)CC1] |
| 1-[(4-{[4-(1,3-benzothiazol-5-yl)-2-methoxyphenyl]carbonyl}piperazin-1-yl)carbonyl]cyclopropan-1-ol | 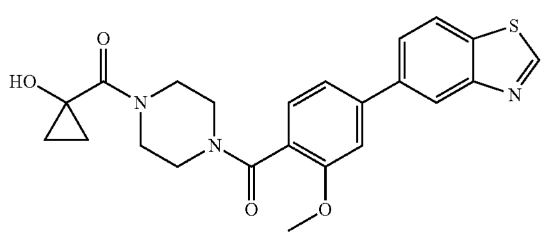 [SMILES: COc1cc(-c2ccc3scnc3c2)ccc1C(=O)N1CCN(C(=O)C2(O)CC2)CC1] |
| 1-[(4-{[5-(quinolin-6-yl)pyrimidin-2-yl]carbonyl}piperazin-1-yl)carbonyl]cyclopropan-1-ol | 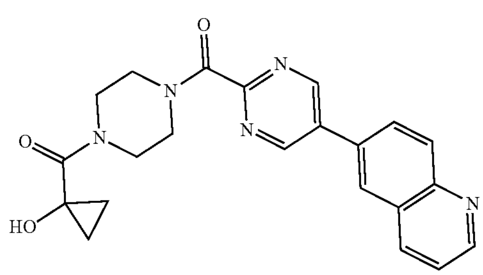 [SMILES: O=C(c1ncc(-c2ccc3ncccc3c2)cn1)N1CCN(C(=O)C2(O)CC2)CC1] |
| 1-[(4-{[5-(1-methyl-1H-indol-5-yl)pyrazin-2-yl]carbonyl}piperazin-1-yl)carbonyl]cyclopropan-1-ol | 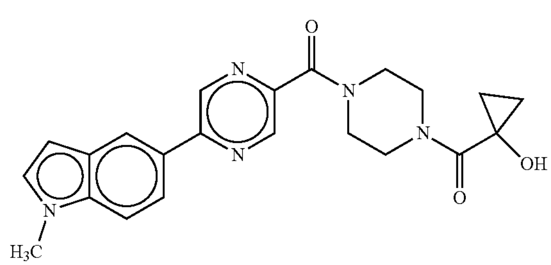 |

TABLE 1-continued
| IUPAC Name | Compound Structure |
|---|---|
| 1-[(4-{[5-(quinolin-3-yl)pyrazin-2-yl]carbonyl}piperazin-1-yl)carbonyl]cyclopropan-1-ol | 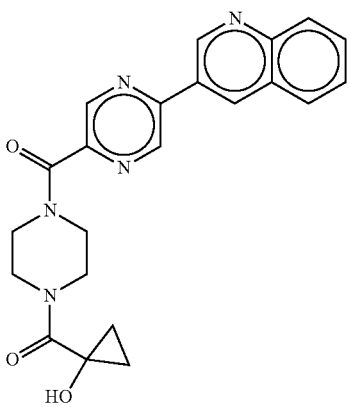 |
| 1-[(4-{[5-(quinolin-6-yl)pyrazin-2-yl]carbonyl}piperazin-1-yl)carbonyl]cyclopropan-1-ol | 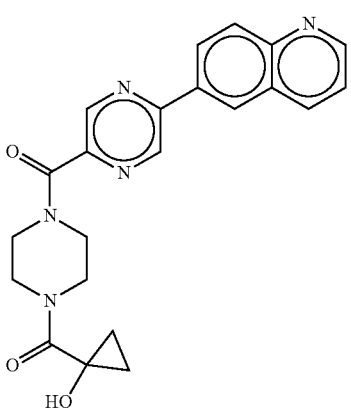 |
| 1-({4-[(4-phenylphenyl)carbonyl]piperazin-1-yl}carbonyl)cyclobutan-1-ol | 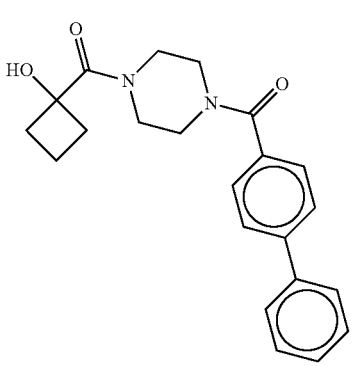 |
| 1-[(4-{[4-(isoquinolin-6-yl)phenyl]carbonyl}piperazin-1-yl)carbonyl]cyclobutan-1-ol | 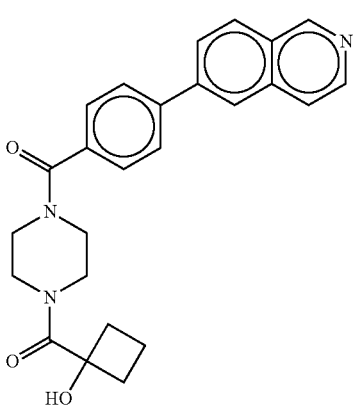 |

TABLE 1-continued

| IUPAC Name | Compound Structure |
|---|---|
| 1-{[(2S,5R)-4-{[4-(isoquinolin-6-yl)phenyl]carbonyl}-2,5-dimethylpiperazin-1-yl]carbonyl}cyclopropan-1-ol | 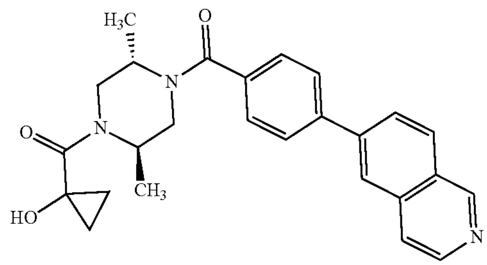 [SMILES: C[C@@H]1CN(C(=O)c2ccc(-c3ccc4cnccc4c3)cc2)[C@@H](C)CN1C(=O)C1(O)CC1] |
| 1-[(4-{[4-(1H-indol-5-yl)phenyl]carbonyl}piperazin-1-yl)carbonyl]cyclopropan-1-ol | 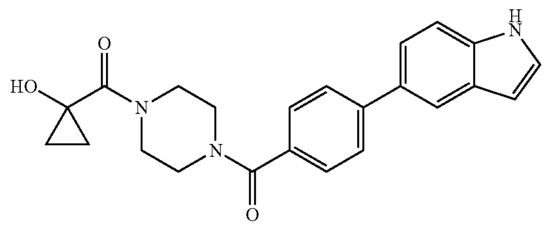 [SMILES: O=C(c1ccc(-c2ccc3[nH]ccc3c2)cc1)N1CCN(C(=O)C2(O)CC2)CC1] |
| 3-[4-({4-[(oxetan-2-yl)carbonyl]piperazin-1-yl}carbonyl)phenyl]quinoline | 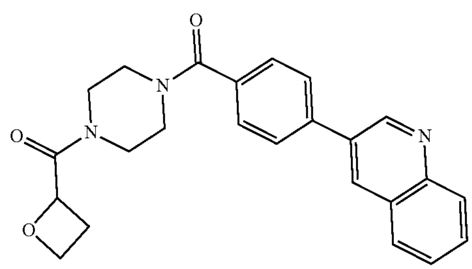 [SMILES: O=C(c1ccc(-c2cnc3ccccc3c2)cc1)N1CCN(C(=O)C2CCO2)CC1] |
| 5-[4-({4-[(oxetan-2-yl)carbonyl]piperazin-1-yl}carbonyl)phenyl]-1H-indole | 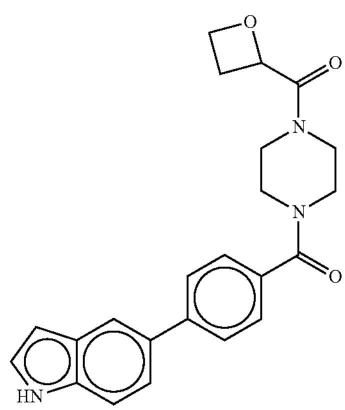 |
| 1-[(4-{[2-fluoro-4-(quinolin-3-yl)phenyl]carbonyl}piperazin-1-yl)carbonyl]cyclopropan-1-ol | 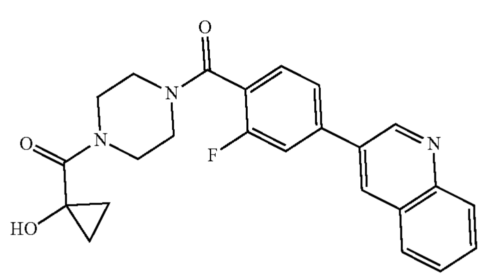 [SMILES: O=C(c1ccc(-c2cnc3ccccc3c2)cc1F)N1CCN(C(=O)C2(O)CC2)CC1] |

TABLE 1-continued

| IUPAC Name | Compound Structure |
|---|---|
| 6-[4-({4-[(oxetan-2-yl)carbonyl]pipenizin-1-yl}carbonyl)phenyl]isoquinoline | 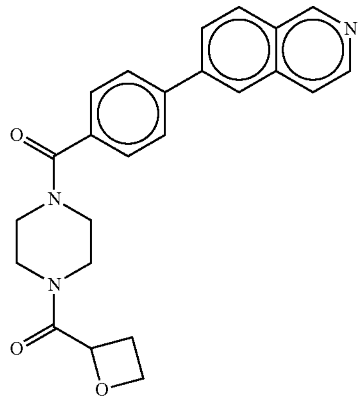 |
| 1-[(4-{[4-(1,5-naphthyridin-3-yl)phenyl]carbonyl}piperazin-1-yl)carbonyl]cyclopropan-1-ol | 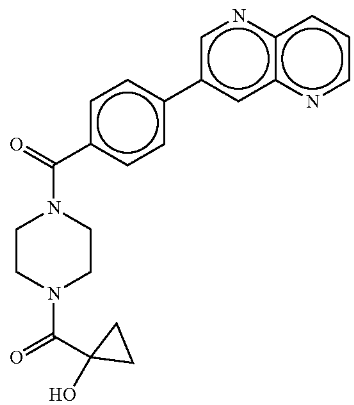 |
| 1-[(4-{[4-(1-benzofuran-5-yl)phenyl]carbonyl}piperazin-1-yl)carbonyl]cyclopropan-1-ol | 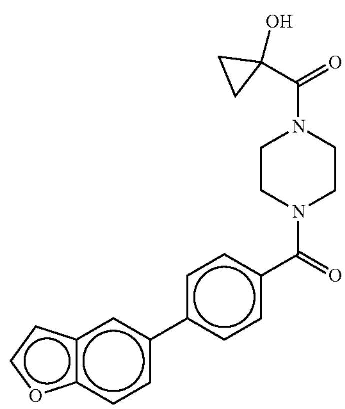 |
| 1-({4-[(4-phenoxyphenyl)carbonyl]piperazin-1-yl}carbonyl)cyclopropan-1-ol | 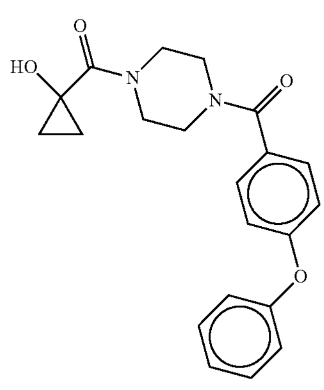 |

TABLE 1-continued

| IUPAC Name | Compound Structure |
|---|---|
| 1-[(4-{[2-fluoro-4-(7-fluoro-1H-indol-5-yl)phenyl]carbonyl}piperazin-1-yl)carbonyl]cyclopropan-1-ol | 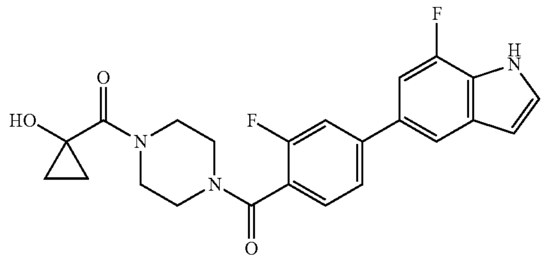 [SMILES: O=C(c1ccc(-c2cc(F)c3[nH]ccc3c2)cc1F)N1CCN(C(=O)C2(O)CC2)CC1] |
| 1-{[4-({3-chloro-4-[1-(trifluoromethyl)-1H-indol-5-yl]phenyl}carbonyl)piperazin-1-yl]carbonyl}cyclopropan-1-ol | 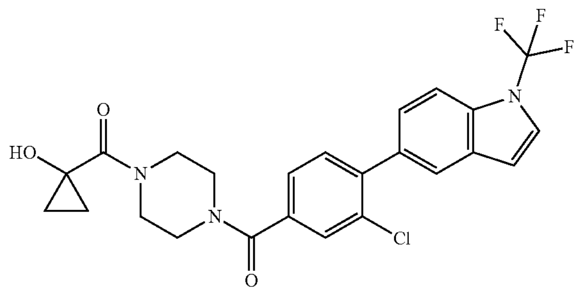 [SMILES: O=C(c1ccc(-c2ccc3c(ccn3C(F)(F)F)c2)c(Cl)c1)N1CCN(C(=O)C2(O)CC2)CC1] |
| 1-[(4-{[4-(1,3-benzoxazol-5-yl)phenyl]carbonyl}piperazin-1-yl)carbonyl]cyclopropan-1-ol | 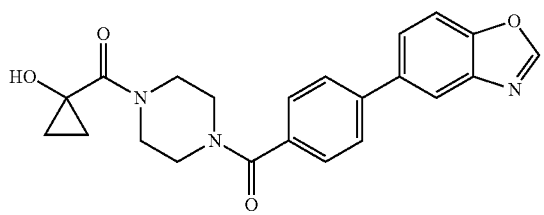 [SMILES: O=C(c1ccc(-c2ccc3ocnc3c2)cc1)N1CCN(C(=O)C2(O)CC2)CC1] |
| 1-[(4-{[4-(1,3-benzothiazol-6-yl)phenyl]carbonyl}piperazin-1-yl)carbonyl]cyclopropan-1-ol | 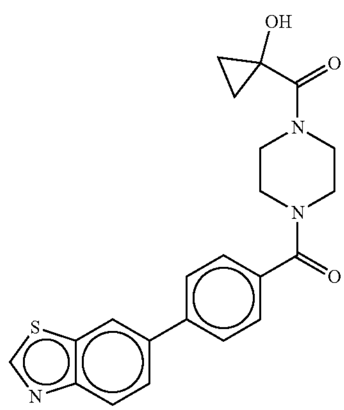 |
| 1-{[4-({3-chloro-4-[1-(propan-2-yl)-1H-indol-5-yl]phenyl}carbonyl)piperazin-1-yl]carbonyl}cyclopropan-1-ol | 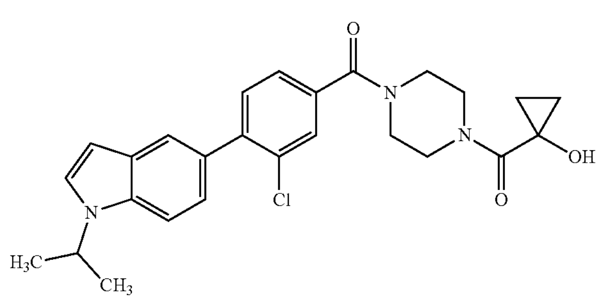 [SMILES: CC(C)n1ccc2cc(-c3ccc(C(=O)N4CCN(C(=O)C5(O)CC5)CC4)cc3Cl)ccc21] |

TABLE 1-continued

| IUPAC Name | Compound Structure |
|---|---|
| 1-[(4-{[4-(1H-1,3-benzodiazol-5-yl)phenyl]carbonyl}piperazin-1-yl)carbonyl]cyclopropan-1-ol | 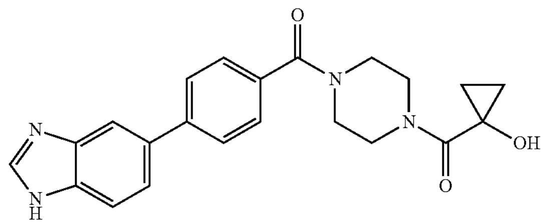 [SMILES: O=C(c1ccc(-c2ccc3[nH]cnc3c2)cc1)N1CCN(C(=O)C2(O)CC2)CC1] |
| 5-[4-({4-[(1-hydroxycyclopropyl)carbonyl]piperazin-1-yl}carbonyl)phenyl]-1H-indole-3-carbonitrile | 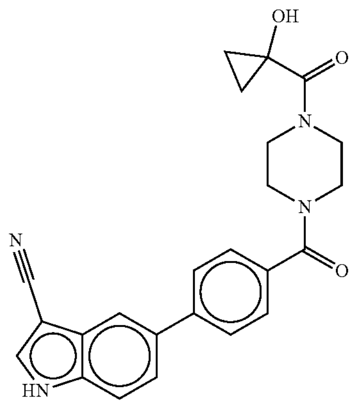 |
| 3-[3-fluoro-4-({4-[(1-hydroxycyclopropyl)carbonyl]piperazin-1-yl}carbonyl)phenyl]quinolin-2-ol | 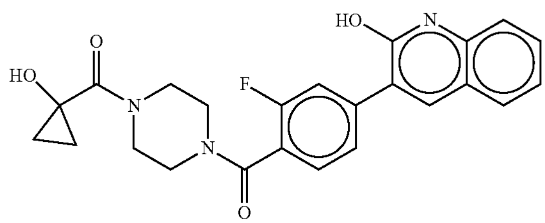 |
| 1-[(4-{[4-(1,3-benzoxazol-2-yl)phenyl]carbonyl}piperazin-1-yl)carbonyl]cyclopropan-1-ol | 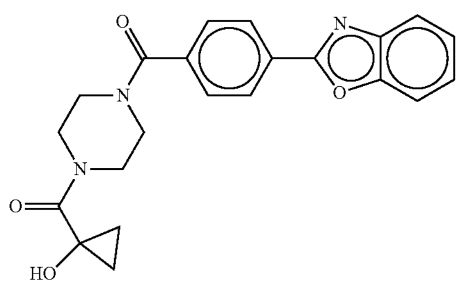 |
| 1-[(4-{[2-fluoro-4-(2-methoxyquinolin-3-yl)phenyl]carbonyl}piperazin-1-yl)carbonyl]cyclopropan-1-ol | 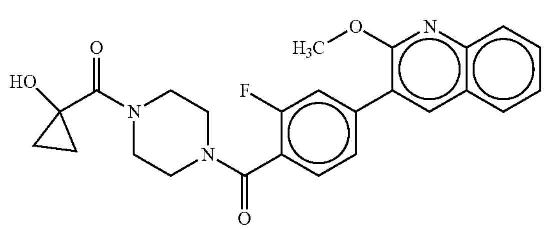 |
| 1-[(4-{[4-(4-chloroquinolin-3-yl)phenyl]carbonyl}piperazin-1-yl)carbonyl]cyclopropan-1-ol | 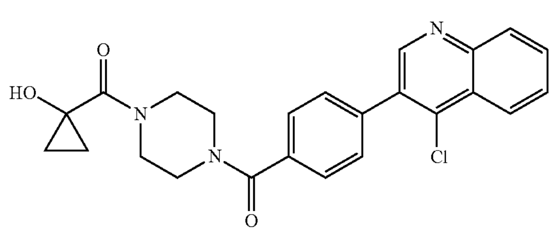 [SMILES: O=C(c1ccc(-c2cnc3ccccc3c2Cl)cc1)N1CCN(C(=O)C2(O)CC2)CC1] |

TABLE 1-continued

| IUPAC Name | Compound Structure |
|---|---|
| 1-[(4-{[4-(7-fluoro-1H-indol-5-yl)phenyl]carbonyl}piperazin-1-yl)carbonyl]cyclopropan-1-ol | 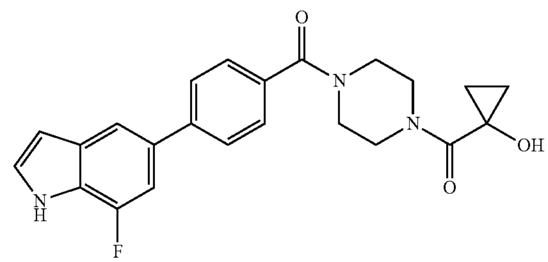 [SMILES: O=C(c1ccc(-c2cc(F)c3[nH]ccc3c2)cc1)N1CCN(C(=O)C2(O)CC2)CC1] |
| 1-[(4-{[4-(quinolin-2-yl)phenyl]carbonyl}piperazin-1-yl)carbonyl]cyclopropan-1-ol | 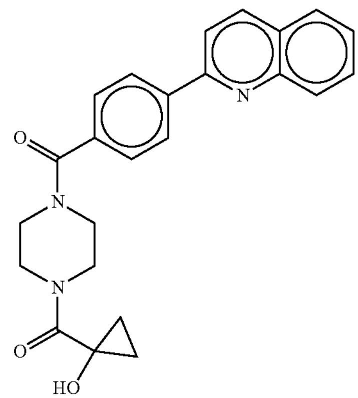 |
| 1-[(4-{[4-(1,3-benzothiazol-2-yl)phenyl]carbonyl}piperazin-1-yl)carbonyl]cyclopropan-1-ol | 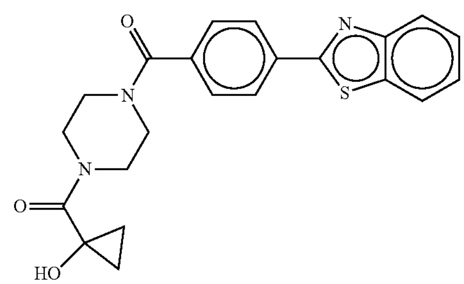 |
| 1-[(4-{[4-(2-methoxyquinolin-6-yl)phenyl]carbonyl}piperazin-1-yl)carbonyl]cyclopropan-1-ol | 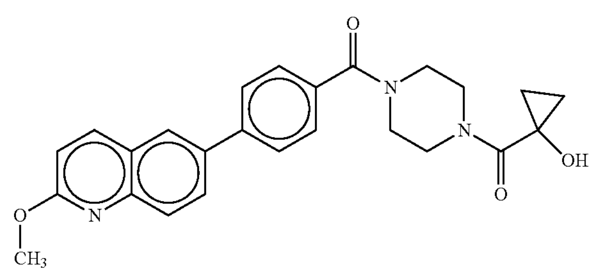 |
| 1-{[4-({4-[1-(trifluoromethyl)-1H-indol-5-yl]phenyl}carbonyl)piperazin-1-yl]carbonyl}cyclopropan-1-ol | 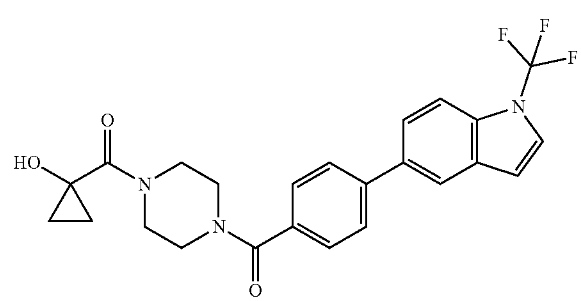 [SMILES: O=C(c1ccc(-c2ccc3c(ccn3C(F)(F)F)c2)cc1)N1CCN(C(=O)C2(O)CC2)CC1] |

TABLE 1-continued

| IUPAC Name | Compound Structure |
|---|---|
| 1-[(4-{[4-(6-methoxynaphthalen-2-yl)phenyl]carbonyl}piperazin-1-yl)carbonyl]cyclopropan-1-ol | 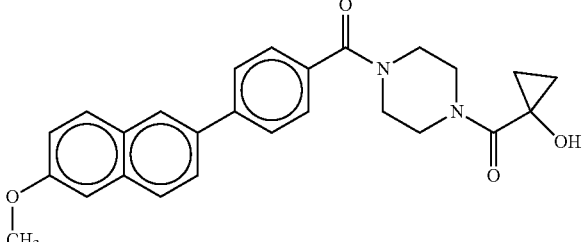 |
| 1-[(4-{[4-(5-chloro-1,3-benzoxazol-2-yl)phenyl]carbonyl}piperazin-1-yl)carbonyl]cyclopropan-1-ol | 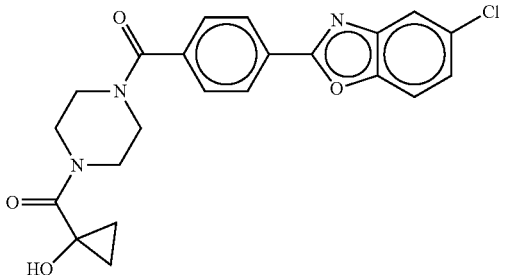 |
| 1-[(4-{[4-(6-chloro-1,3-benzoxazol-2-yl)phenyl]carbonyl}piperazin-1-yl)carbonyl]cyclopropan-1-ol | 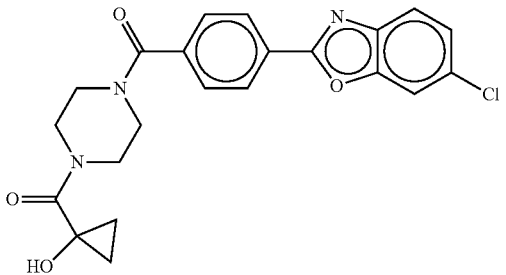 |
| 1-[(4-{[4-(5-fluoro-1,3-benzoxazol-2-yl)phenyl]carbonyl}piperazin-1-yl)carbonyl]cyclopropan-1-ol | 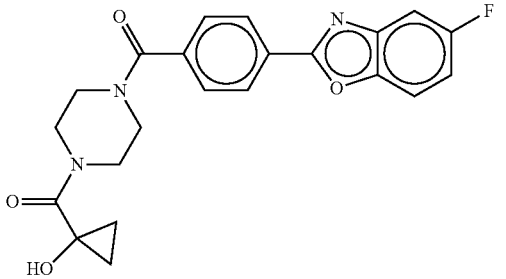 |
| 1-[(4-{[4-(6-fluoro-1,3-benzoxazol-2-yl)phenyl]carbonyl}piperazin-1-yl)carbonyl]cyclopropan-1-ol | 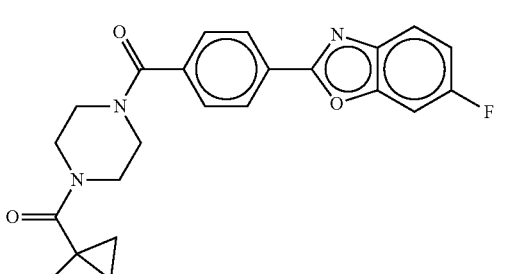 |

TABLE 1-continued

| IUPAC Name | Compound Structure |
|---|---|
| 1-[(4-{[4-(6-methoxynaphthalen-2-yl)phenyl]carbonyl}piperazin-1-yl)carbonyl]cyclopropan-1-ol | 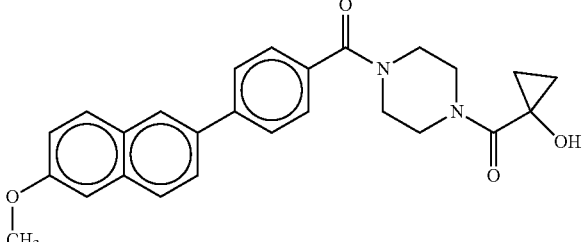 |
| 1-[(4-{[4-(5-chloro-1,3-benzoxazol-2-yl)phenyl]carbonyl}piperazin-1-yl)carbonyl]cyclopropan-1-ol | 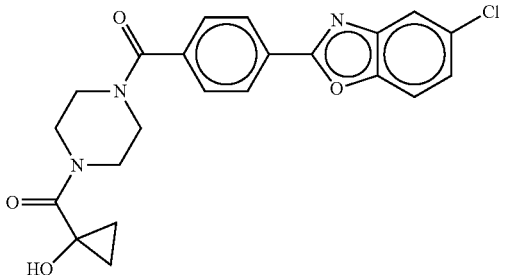 |
| 1-[(4-{[4-(6-chloro-1,3-benzoxazol-2-yl)phenyl]carbonyl}piperazin-1-yl)carbonyl]cyclopropan-1-ol | 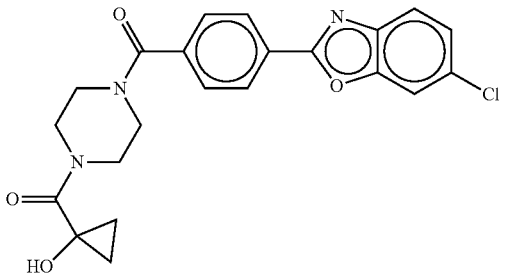 |
| 1-[(4-{[4-(5-fluoro-1,3-benzoxazol-2-yl)phenyl]carbonyl}piperazin-1-yl)carbonyl]cyclopropan-1-ol | 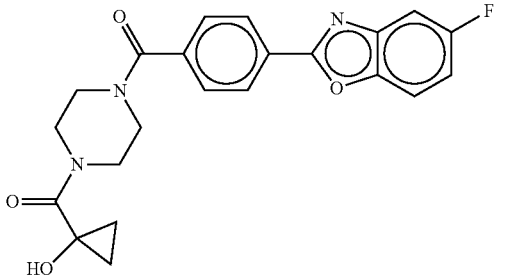 |
| 1-[(4-{[4-(6-fluoro-1,3-benzoxazol-2-yl)phenyl]carbonyl}piperazin-1-yl)carbonyl]cyclopropan-1-ol | 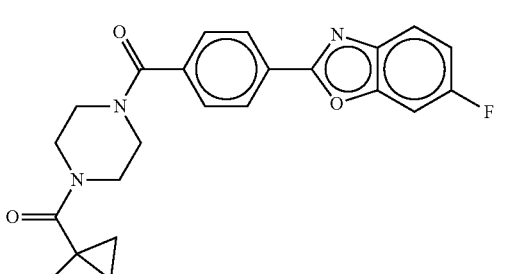 |

TABLE 1-continued

| IUPAC Name | Compound Structure |
| --- | --- |
| 1-({4-[(4-{pyrazolo[1,5-a]pyridin-2-yl}phenyl)carbonyl]piperazin-1-yl}carbonyl)cyclopropan-1-ol | 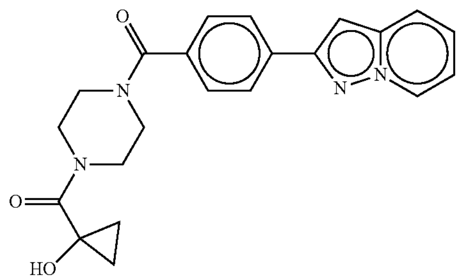 |
| 1-{[4-({4-[1-(propan-2-yl)-1H-indazol-5-yl]phenyl}carbonyl)piperazin-1-yl]carbonyl}cyclopropan-1-ol | 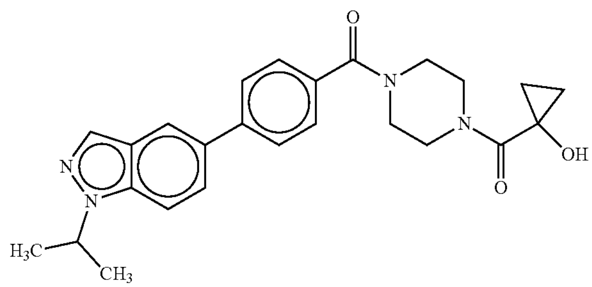 |
| 1-[(4-{[6-(2-methoxyquinolin-6-yl)pyridin-3-yl]carbonyl}piperazin-1-yl)carbonyl]cyclopropan-1-ol | 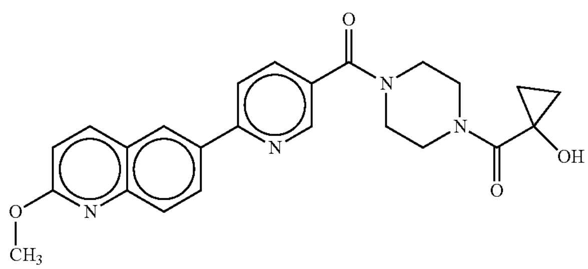 |
| 1-[(4-{[5-(2-methoxyquinolin-6-yl)pyridin-2-yl]carbonyl}piperazin-1-yl)carbonyl]cyclopropan-1-ol | 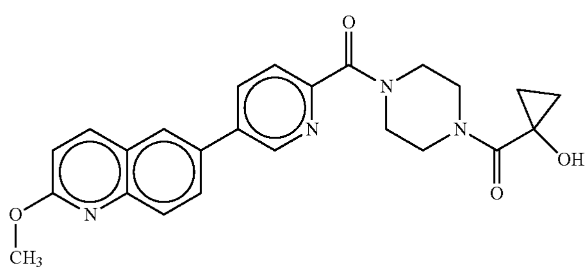 |
| 1-{[4-({6-phenylimidazo[1,2-a]pyridin-2-yl}carbonyl)piperazin-1-yl]carbonyl}cyclopropan-1-ol | 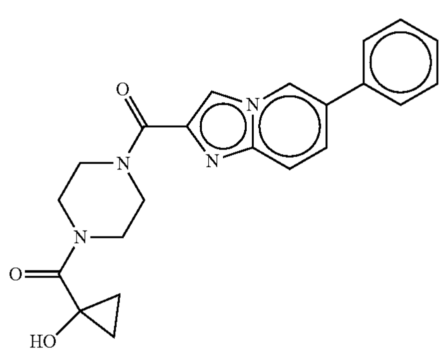 |

TABLE 1-continued

| IUPAC Name | Compound Structure |
|---|---|
| 1-[(4-{[6-(4-fluorophenyl)imidazo[1,2-a]pyridin-2-yl]carbonyl}piperazin-1-yl)carbonyl]cyclopropan-1-ol | 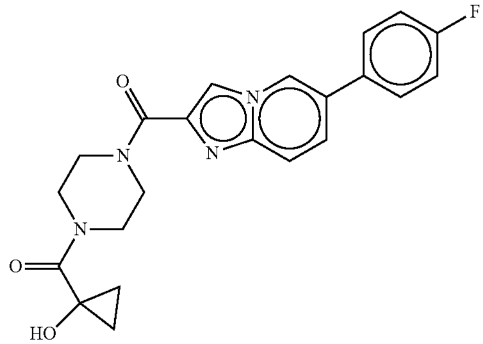 |
| 1-[(4-{[5-(4-chloro-2-fluorophenyl)pyridin-2-yl]carbonyl}piperazin-1-yl)carbonyl]cyclopropan-1-ol | 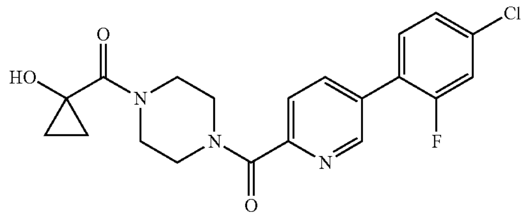 [SMILES: O=C(c1ccc(-c2ccc(Cl)cc2F)cn1)N1CCN(C(=O)C2(O)CC2)CC1] |
| 1-[(4-{[6-(4-chloro-2-fluorophenyl)pyridin-3-yl]carbonyl}piperazin-1-yl)carbonyl]cyclopropan-1-ol | 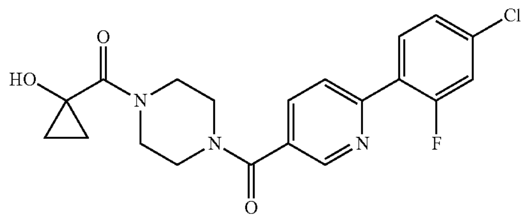 [SMILES: O=C(c1ccc(-c2ccc(Cl)cc2F)nc1)N1CCN(C(=O)C2(O)CC2)CC1] |
| 1-[(4-{[5-(4-chloro-2-fluorophenyl)pyrimidin-2-yl]carbonyl}piperazin-1-yl)carbonyl]cyclopropan-1-ol | 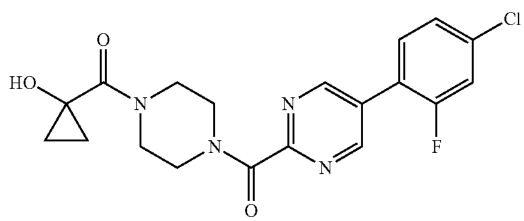 [SMILES: O=C(c1ncc(-c2ccc(Cl)cc2F)cn1)N1CCN(C(=O)C2(O)CC2)CC1] |
| 1-[(4-{[2-fluoro-4-(6-fluoroquinolin-2-yl)phenyl]carbonyl}piperazin-1-yl)carbonyl]cyclopropan-1-ol | 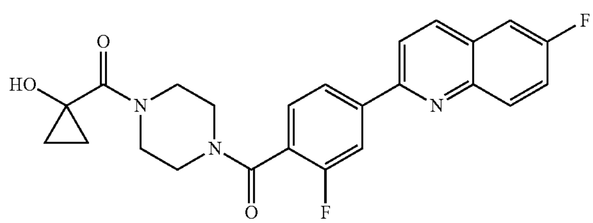 |
| 1-[(4-{[2-fluoro-4-(6-methoxyquinolin-2-yl)phenyl]carbonyl}piperazin-1-yl)carbonyl]cyclopropan-1-ol | 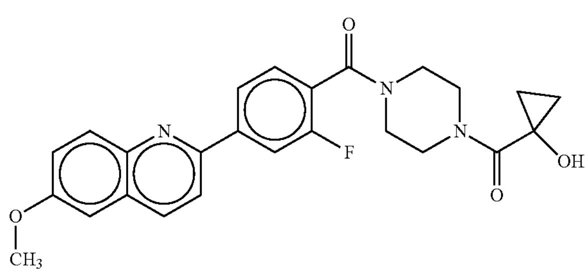 |

TABLE 1-continued

| IUPAC Name | Compound Structure |
|---|---|
| 1-[(4-{[2,3-difluoro-4-(quinolin-2-yl)phenyl]carbonyl}piperazin-1-yl)carbonyl]cyclopropan-1-ol | 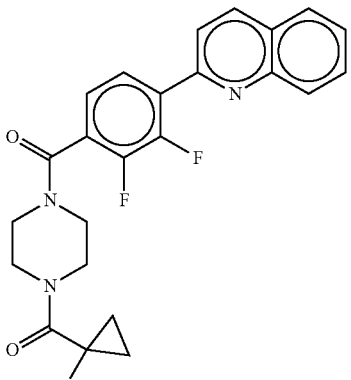 |
| 1-[(4-{[2,3-difluoro-4-(6-fluoroquinolin-2-yl)phenyl]carbonyl}piperazin-1-yl)carbonyl]cyclopropan-1-ol | 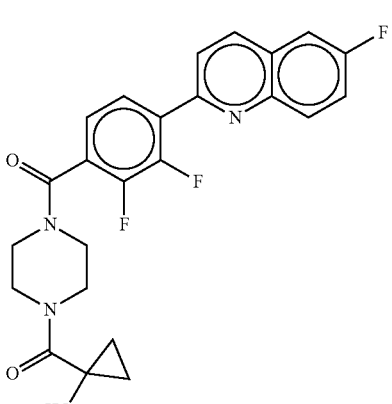 |
| 1-[(4-{[2,3-difluoro-4-(6-methoxyquinolin-2-yl)phenyl]carbonyl}piperazin-1-yl)carbonyl]cyclopropan-1-ol | 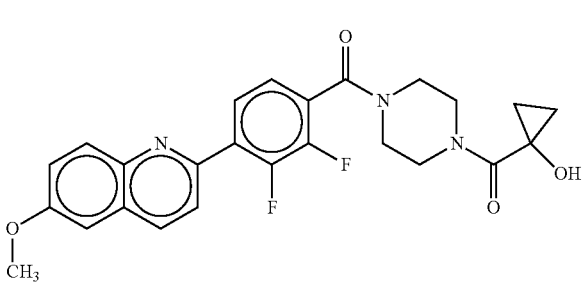 |
| 1-[(4-{[4-(6-fluoroquinolin-2-yl)phenyl]carbonyl}piperazin-1-yl)carbonyl]cyclopropan-1-ol | 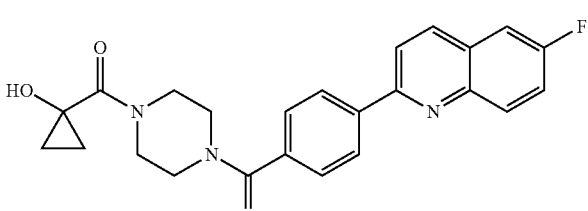 |
| 1-[(4-{[4-(6-methoxyquinolin-2-yl)phenyl]carbonyl}piperazin-1-yl)carbonyl]cyclopropan-1-ol | 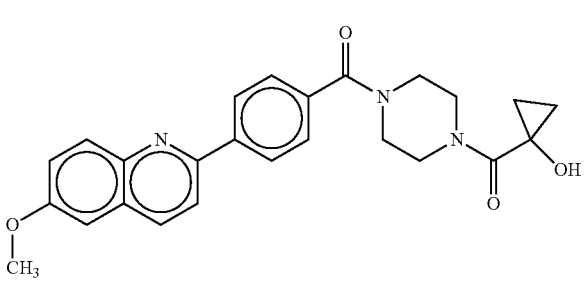 |

TABLE 1-continued

| IUPAC Name | Compound Structure |
| --- | --- |
| 1-({4-[(4-{imidazo[1,2-a]pyridin-2-yl}phenyl)carbonyl]piperazin-1-yl}carbonyl)cyclopropan-1-ol | 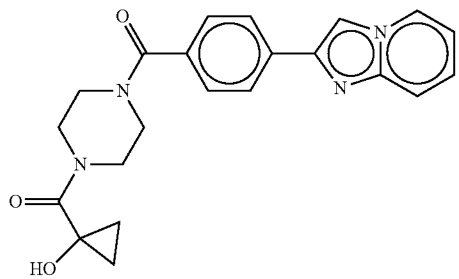 |
| 1-[(4-{[4-(2,1,3-benzoxadiazol-5-yl)phenyl]carbonyl}piperazin-1-yl)carbonyl]cyclopropan-1-ol | 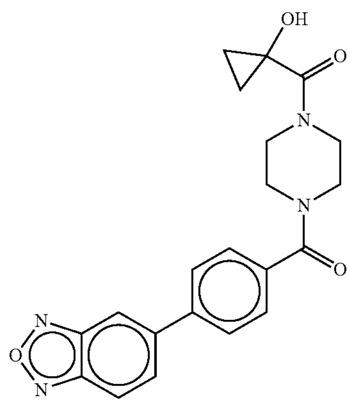 |
| N-{3-[4-({4-[(1-hydroxycyclopropyl)carbonyl]piperazin-1-yl}carbonyl)phenyl]phenyl}benzenesulfonamide | 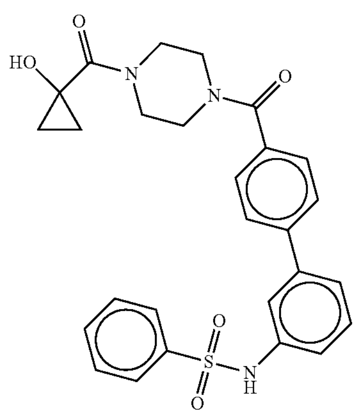 |
| N-{3-[4-({4-[(1-hydroxycyclopropyl)carbonyl]piperazin-1-yl}carbonyl)phenyl]phenyl}methanesulfonamide | 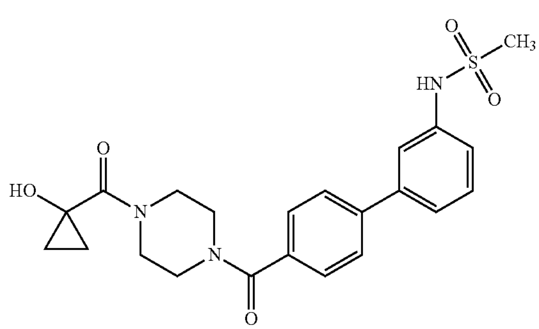 [SMILES: CS(=O)(=O)Nc1cccc(-c2ccc(C(=O)N3CCN(C(=O)C4(O)CC4)CC3)cc2)c1] |

TABLE 1-continued

| IUPAC Name | Compound Structure |
|---|---|
| N-{3-[4-({4-[(1-hydroxycyclopropyl)carbonyl]piperzin-1-yl}carbonyl)phenyl]phenyl}propane-2-sulfonamide | 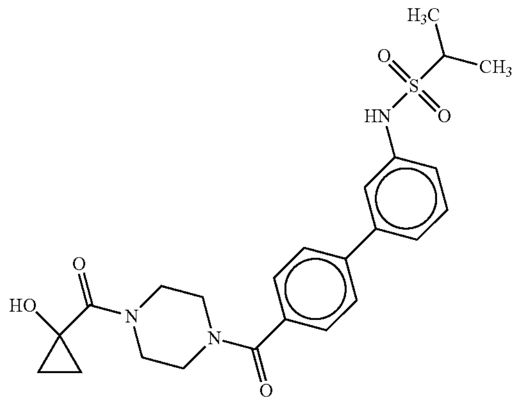 |
| N-{3-[4-({4-[(1-hydroxycyclopropyl)carbonyl]piperazin-1-yl}carbonyl)phenyl]phenyl}cyclopropanesulfonamide | 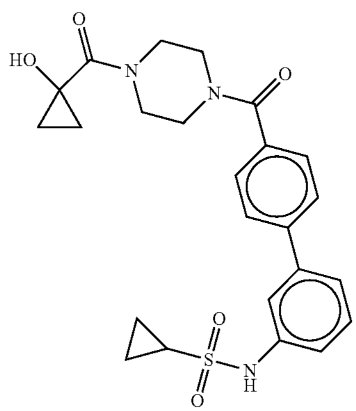 |
| 1-[(4-{[4-(isoquinolin-1-yl)phenyl]carbonyl}piperazin-1-yl)carbonyl]cyclopropan-1-ol | 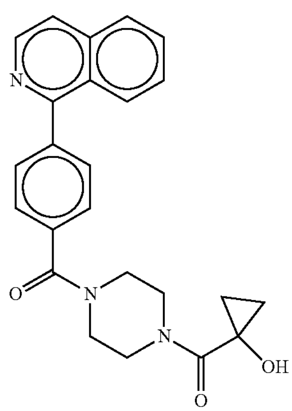 |

TABLE 1-continued

| IUPAC Name | Compound Structure |
|---|---|
| 1-{[4-({4-[7-(trifluoromethyl)quinolin-4-yl]phenyl}carbonyl)piperazin-1-yl]carbonyl}cyclopropan-1-ol | 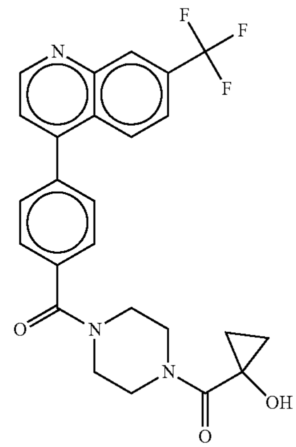 |
| 1-[(4-{[4-(6-methoxy-4-methylquinolin-2-yl)phenyl]carbonyl}piperazin-1-yl)carbonyl]cyclopropan-1-ol | 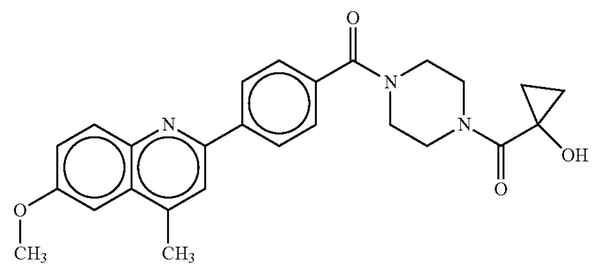 |
| 1-[(4-{[4-(5-chloro-1H-1,3-benzodiazol-2-yl)phenyl]carbonyl}piperazin-1-yl)carbonyl]cyclopropan-1-ol | 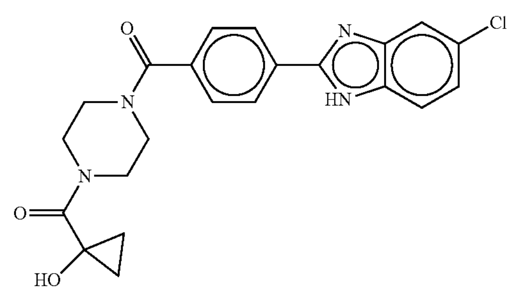 |
| 1-[(4-{[4-(4-chloro-1H-1,3-benzodiazol-2-yl)phenyl]carbonyl}piperazin-1-yl)carbonyl]cyclopropan-1-ol | 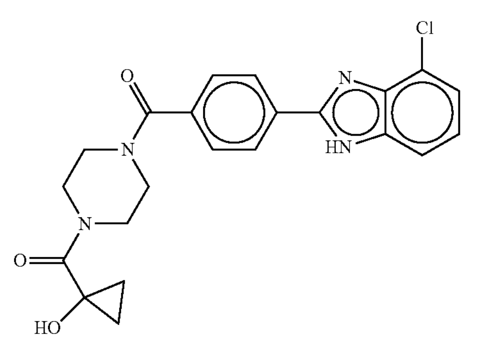 |

TABLE 1-continued

| IUPAC Name | Compound Structure |
|---|---|
| 1-[(4-{[4-(5,6-difluoro-1H-1,3-benzodiazol-2-yl)phenyl]carbonyl}piperazin-1-yl)carbonyl]cyclopropan-1-ol | 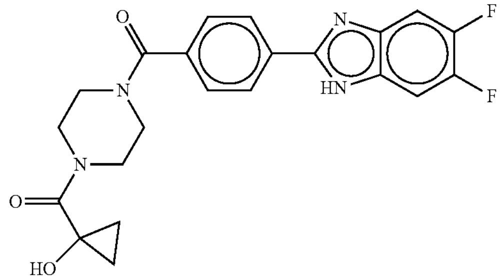 |
| 1-[(4-{[4-(5-methoxy-1H-1,3-benzodiazol-2-yl)phenyl]carbonyl}piperazin-1-yl)carbonyl]cyclopropan-1-ol | 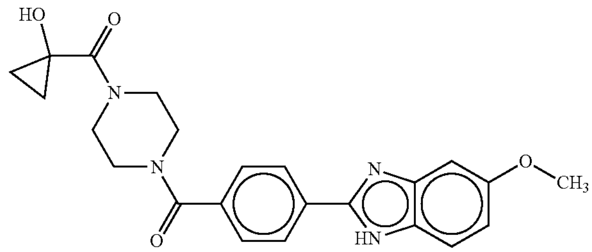 |
| 1-[(4-{[4-(5-fluoro-1H-1,3-benzodiazol-2-yl)phenyl]carbonyl}piperazin-1-yl)carbonyl]cyclopropan-1-ol | 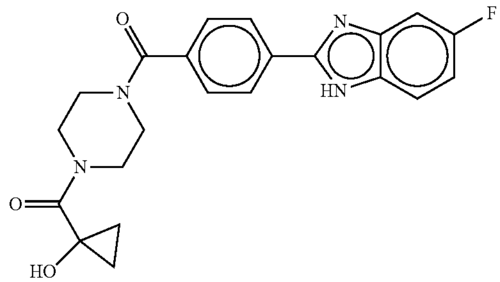 |
| 1-[(4-{[4-(1,3-dimethyl-1H-indazol-5-yl)phenyl]carbonyl}piperazin-1-yl)carbonyl]cyclopropan-1-ol | 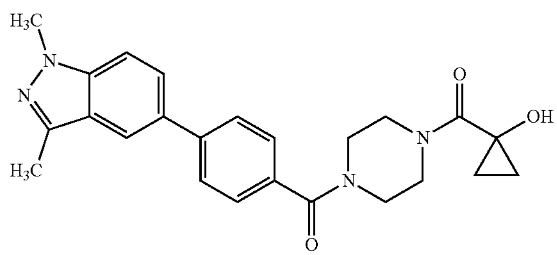 [SMILES: Cc1nn(C)c2ccc(-c3ccc(C(=O)N4CCN(C(=O)C5(O)CC5)CC4)cc3)cc12] |
| 6-[4-({4-[(1-hydroxycyclopropyl)carbonyl]piperazin-1-yl}carbonyl)phenyl]-2,3-dihydro-1,3-benzoxazol-2-one | 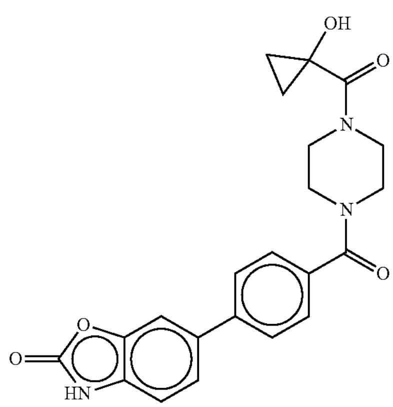 |

TABLE 1-continued

| IUPAC Name | Compound Structure |
|---|---|
| 5-[4-({4-[(1-hydroxycyclopropyl)carbonyl]piperazin-1-yl}carbonyl)phenyl]-2,3-dihydro-1,3-benzoxazol-2-one | 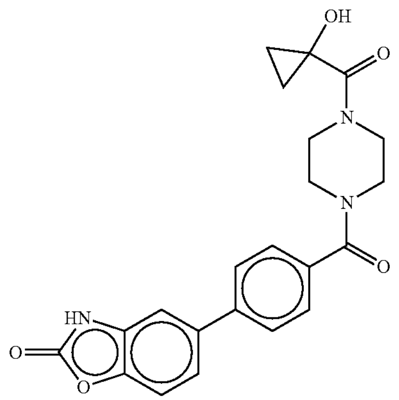 |
| 1-[(4-{[4-(3-methyl-1,2-benzoxazol-6-yl)phenyl]carbonyl}piperazin-1-yl)carbonyl]cyclopropan-1-ol | 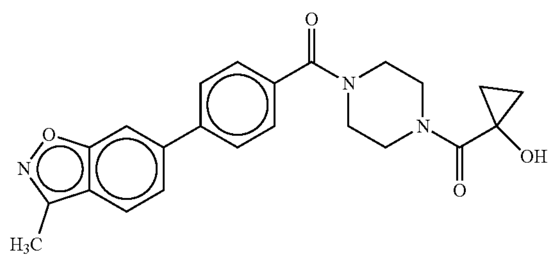 |
| 1-[(4-{[4-(1H-1,3-benzodiazol-4-yl)phenyl]carbonyl}piperazin-1-yl)carbonyl]cyclopropan-1-ol | 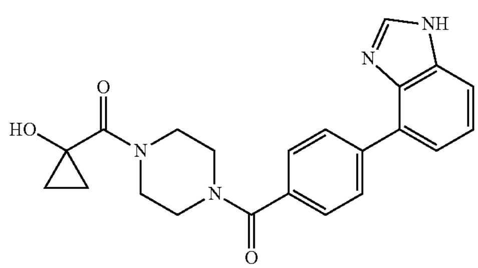 [SMILES: O=C(c1ccc(-c2cccc3[nH]cnc23)cc1)N1CCN(C(=O)C2(O)CC2)CC1] |
| 1-[(4-{[4-(1,3-benzoxazol]-4-yl)phenyl]carbonyl}piperazin-1-yl)carbonyl]cyclopropan-1-ol | 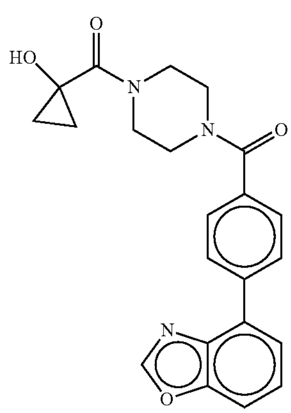 |

TABLE 1-continued
| IUPAC Name | Compound Structure |
|---|---|
| 1-[(4-{[4-(quinolin-5-yl)phenyl]carbonyl}piperazin-1-yl)carbonyl]cyclopropan-1-ol | 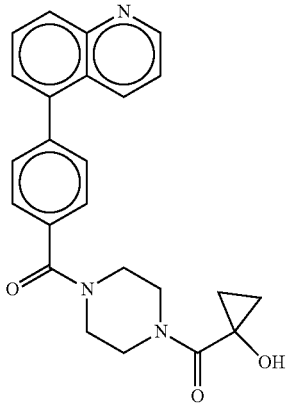 |
| 1-[(4-{[4-(1H-indazol-3-yl)phenyl]carbonyl}piperazin-1-yl)carbonyl]cyclopropan-1-ol | 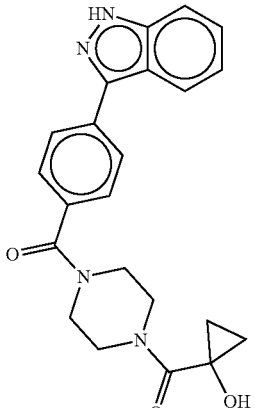 |
| 1-({4-[(4-{furo[3,2-b]pyridin-5-yl}phenyl)carbonyl]piperazin-1-yl}carbonyl)cyclopropan-1-ol | 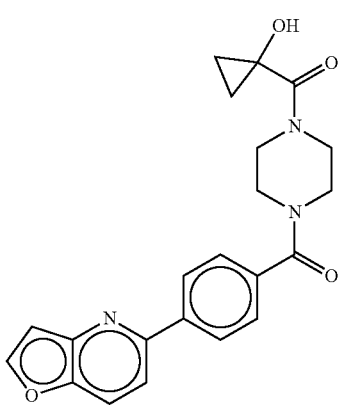 |

TABLE 1-continued

| IUPAC Name | Compound Structure |
|---|---|
| 1-({4-[(4-{furo[3,2-c]pyridin-4-yl}phenyl)carbonyl]piperazin-1-yl}carbonyl)cyclopropan-1-ol | 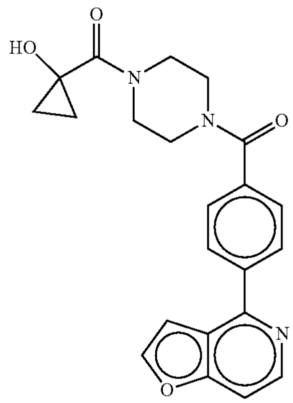 |
| 1-({4-[(4-{[1,2,4]triazolo[4,3-b]pyridazin-6-yl}phenyl)carbonyl]piperazin-1-yl}carbonyl)cyclopropan-1-ol | 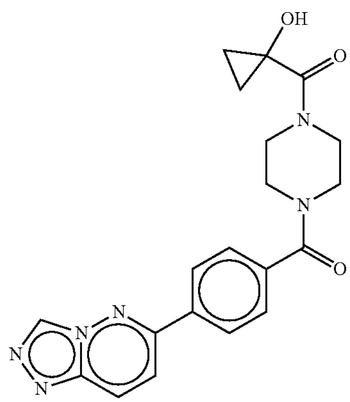 |
| 1-({4-[(4-{imidazo[1,2-a]pyrazin-6-yl}phenyl)carbonyl]piperazin-1-yl}carbonyl)cyclopropan-1-ol | 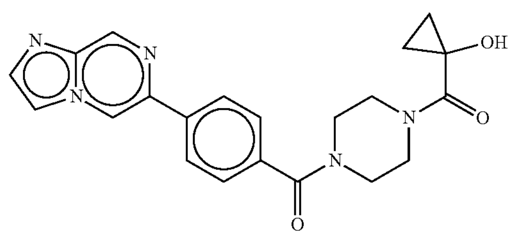 |
| 1-({4-[(4-{1H-pyrrolo[3,2-b]pyridin-5-yl}phenyl)carbonyl]piperazin-1-yl}carbonyl)cyclopropan-1-ol | 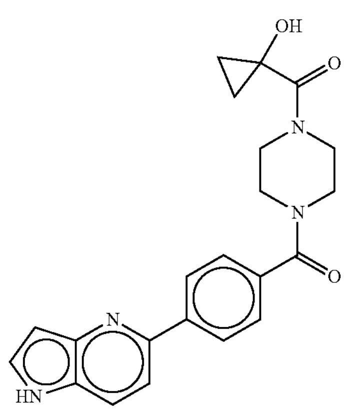 |

TABLE 1-continued

| IUPAC Name | Compound Structure |
| --- | --- |
| 1-({4-[(4-{imidazo[1,2-b]pyridazin-6-yl}phenyl)carbonyl]piperazin-1-yl}carbonyl)cyclopropan-1-ol | 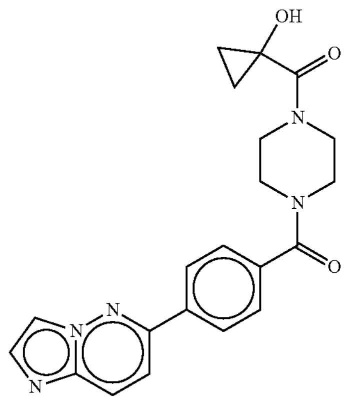 |
| 1-[(4-{[4-(1-methyl-1H-1,3-benzodiazol-5-yl)phenyl]carbonyl}piperazin-1-yl)carbonyl]cyclopropan-1-ol | 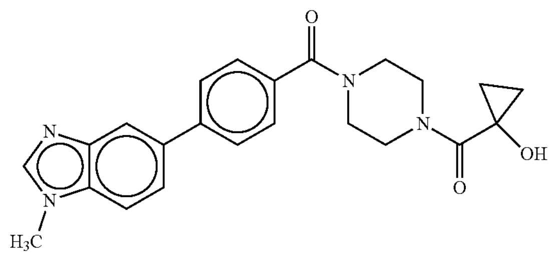 |
| 1-[(4-{[4-(2,1,3-benzothiadiazol-4-yl)phenyl]carbonyl}piperazin-1-yl)carbonyl]cyclopropan-1-ol | 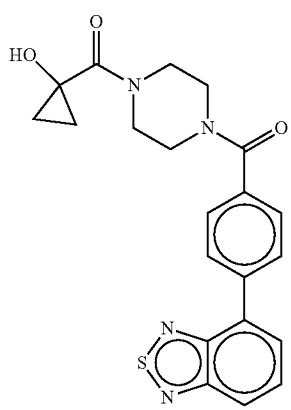 |
| 1-{[4-({4-[2-(trifluoromethyl)imidazo[1,2-a]pyridin-6-yl]phenyl}carbonyl)piperazin-1-yl]carbonyl}cyclopropan-1-ol | 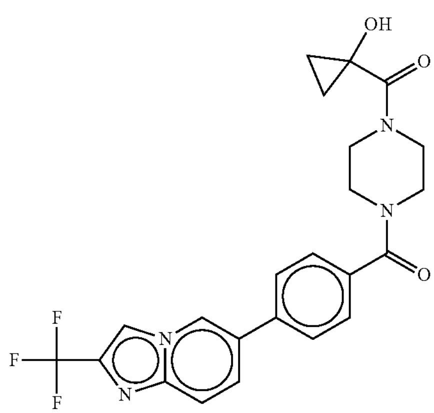 |

TABLE 1-continued

| IUPAC Name | Compound Structure |
| --- | --- |
| 1-({4-[(4-{6-chloroimidazo[1,2-a]pyridin-3-yl}phenyl)carbonyl]piperazin-1-yl}carbonyl)cyclopropan-1-ol | 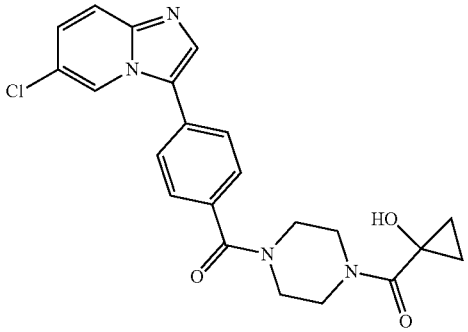 [SMILES: O=C(c1ccc(-c2cnc3ccc(Cl)cn23)cc1)N1CCN(C(=O)C2(O)CC2)CC1] |
| 1-[(4-{[4-(2-methyl-2H-indazol-5-yl)phenyl]carbonyl}piperazin-1-yl)carbonyl]cyclopropan-1-ol | 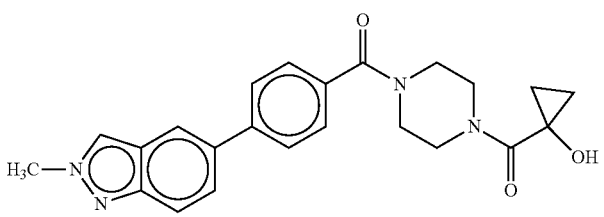 |
| 1-({4-[(4-{imidazo[1,2-a]pyrimidin-7-yl}phenyl)carbonyl]piperazin-1-yl}carbonyl)cyclopropan-1-ol | 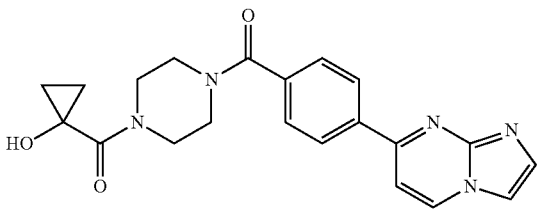 [SMILES: O=C(c1ccc(-c2ccn3ccnc3n2)cc1)N1CCN(C(=O)C2(O)CC2)CC1] |
| 5-[4-({4-[(1-hydroxycyclopropyl)carbonyl]piperazin-1-yl}carbonyl)phenyl]-1H-indole-2-carbonitrile | 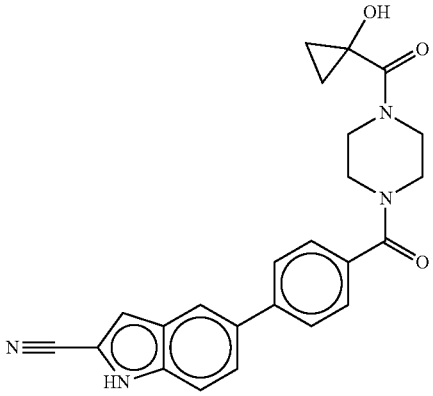 |
| 2-[4-({4-[(1-hydroxycyclopropyl)carbonyl]piperazin-1-yl}carbonyl)phenyl]-1,3-benzoxazole-6-carbonitrile | 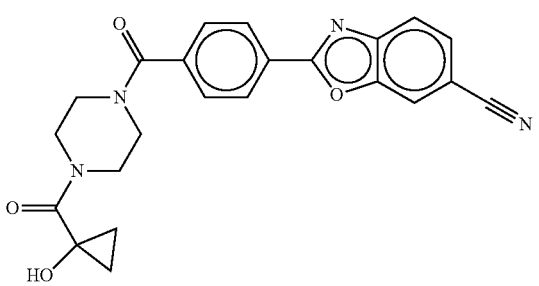 |

TABLE 1-continued

| IUPAC Name | Compound Structure |
|---|---|
| 1-[(4-{[4-(2,1,3-benzothiadiazol-5-yl)phenyl]carbonyl}piperazin-1-yl)carbonyl]cyclopropan-1-ol | 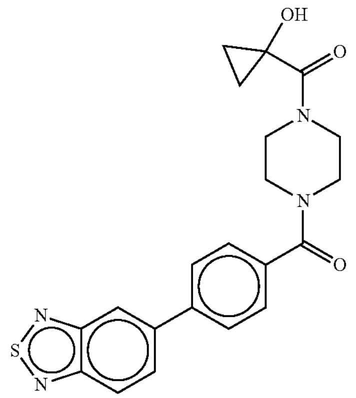 |
| 1-[(4-{[4-(2H-1,2,3-benzotriazol-5-yl)phenyl]carbonyl}piperazin-1-yl)carbonyl]cyclopropan-1-ol | 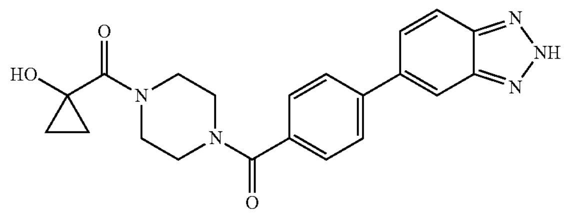 [SMILES: O=C(c1ccc(-c2ccc3n[nH]nc3c2)cc1)N1CCN(C(=O)C2(O)CC2)CC1] |
| 1-({4-[(2-phenyl-1,3-benzothiazol-6-yl)carbonyl]piperazin-1-yl}carbonyl)cyclopropan-1-ol | 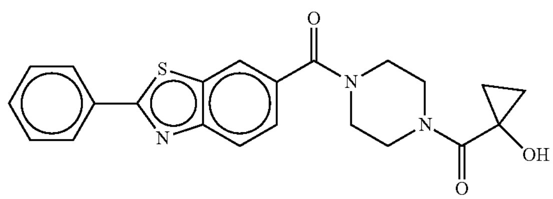 |
| 1-[(4-{[2-(4-fluorophenyl)-1,3-benzothiazol-6-yl]carbonyl}piperazin-1-yl)carbonyl]cyclopropan-1-ol | 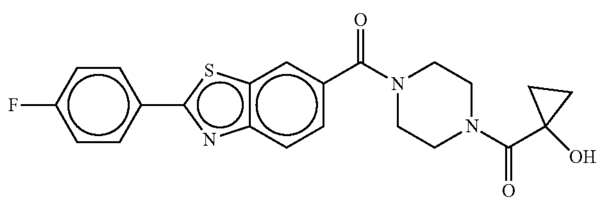 |
| 2-[4-({4-[(1-hydroxycyclopropyl)carbonyl]piperazin-1-yl}carbonyl)phenyl]-1,3-benzoxazole-5-carbonitrile | 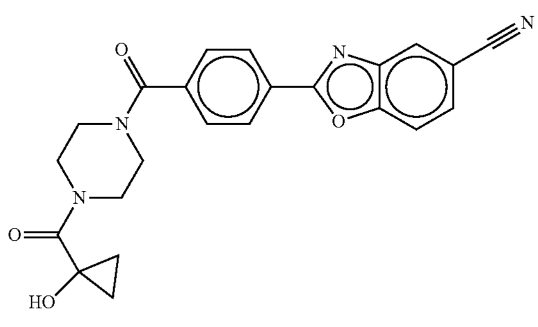 |
| 3-[4-({4-[(1-hydroxycyclopropyl)carbonyl]piperazin-1-yl}carbonyl)phenyl]-1,2-dihydroquinolin-2-one | 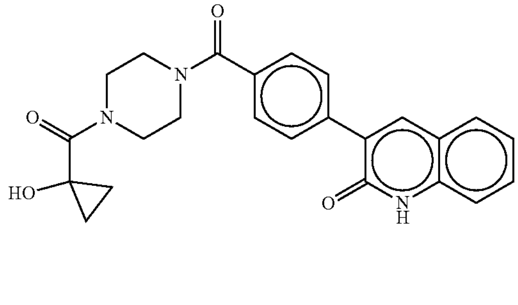 |

TABLE 1-continued

| IUPAC Name | Compound Structure |
|---|---|
| 1-({4-[(2-chloro-4-{imidazo[1,2-a]pyridin-2-yl}phenyl)carbonyl]piperazin-1-yl}carbonyl)cyclopropan-1-ol | 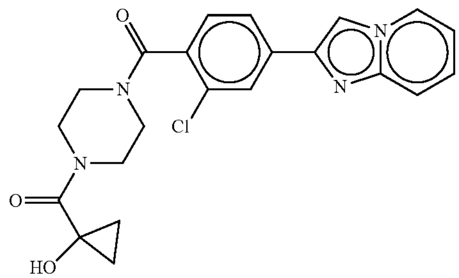 |
| 1-({4-[(3-phenoxyphenyl)carbonyl]piperazin-1-yl}carbonyl)cyclopropan-1-ol | 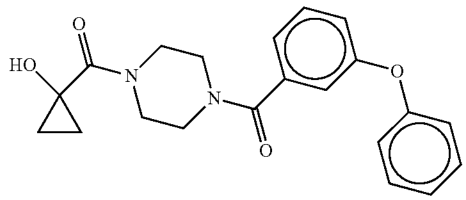 |
| 1-({4-[(4-{6-fluoroimidazo[1,2-a]pyridin-2-yl}phenyl)carbonyl]piperazin-1-yl}carbonyl)cyclopropan-1-ol | 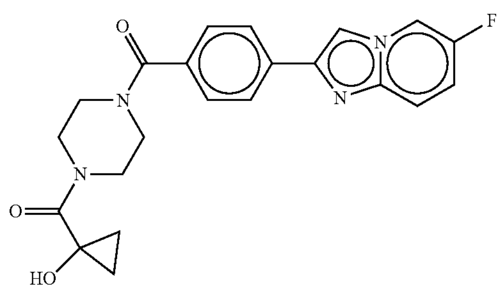 |
| 1-({4-[(4-{6-methoxyimidazo[1,2-a]pyridin-2-yl}phenyl)carbonyl]piperazin-1-yl}carbonyl)cyclopropan-1-ol | 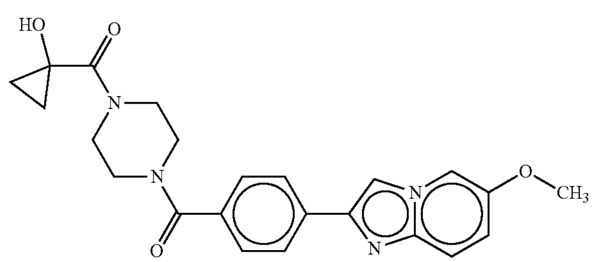 |
| N-{3-[4-({4-[(1-hydroxycyclopropyl)carbonyl]piperazin-1-yl}carbonyl)phenyl]phenyl}cyclopropanecarboxamide | 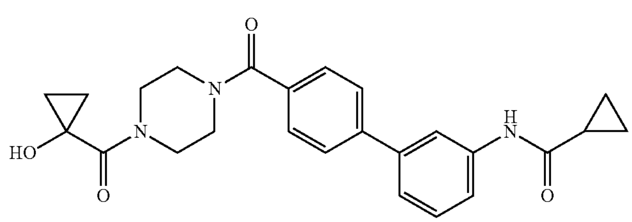 [SMILES: O=C(Nc1cccc(-c2ccc(C(=O)N3CCN(C(=O)C4(O)CC4)CC3)cc2)c1)C1CC1] |
| 1-{[(2S)-4-{[4-(4-chloro-2-fluorophenyl)phenyl]carbonyl}-2-(hydroxymethyl)piperazin-1-yl]carbonyl}cyclopropan-1-ol | 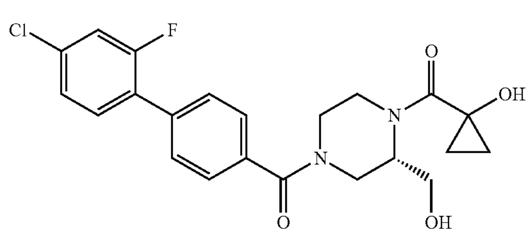 [SMILES: O=C(c1ccc(-c2ccc(Cl)cc2F)cc1)N1CCN(C(=O)C2(O)CC2)[C@H](CO)C1] |

TABLE 1-continued

| IUPAC Name | Compound Structure |
|---|---|
| 1-[(4-{[4-(3-cyclopropoxyphenyl)phenyl]carbonyl}piperazin-1-yl)carbonyl]cyclopropan-1-ol | 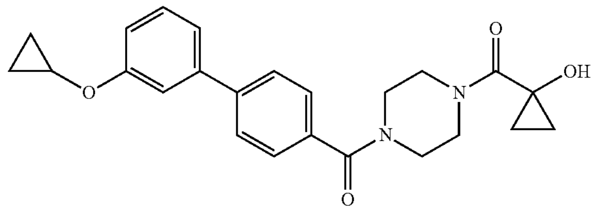 [SMILES: O=C(c1ccc(-c2cccc(OC3CC3)c2)cc1)N1CCN(C(=O)C2(O)CC2)CC1] |
| N-cyclopropyl-3-[4-({4-[(1-hydroxycyclopropyl}carbonyl]piperazin-1-yl}carbonyl)phenyl]benzene-1-sulfonamide | 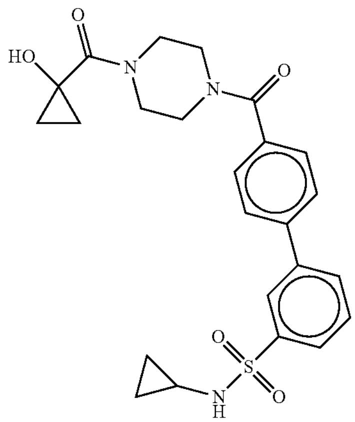 |
| 5-[4-({4-[(1-hydroxycyclopropyl)carbonyl]piperazin-1-yl}carbonyl)phenyl]-1H-indole-2-carboxamide | 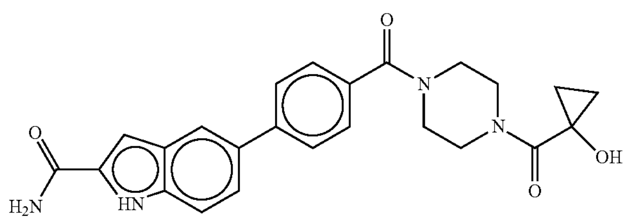 |
| 1-[(4-{[4-(3-chlorophenyl)phenyl]carbonyl}piperazin-1-yl)carbonyl]cyclopropan-1-ol | |
| 1-[(4-{[4-(3-chlorophenyl)phenyl]carbonyl}piperazin-1-yl)carbonyl]cyclopropan-1-ol | |

TABLE 1-continued

| IUPAC Name | Compound Structure |
|---|---|
| 1-{[(3S)-4-{[4-(4-chloro-2-fluorophenyl)phenyl]carbonyl}-3-(hydroxymethyl)piperazin-1-yl]carbonyl}cyclopropan-1-ol | 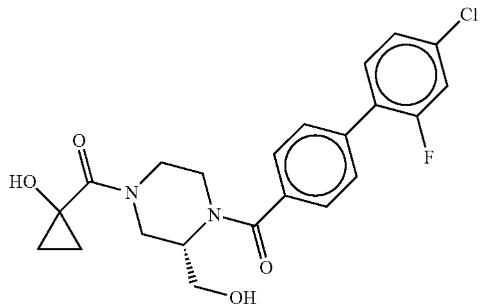 |
| 1-[(4-{[4-(1H-indol-2-yl)phenyl]carbonyl}piperazin-1-yl)carbonyl]cyclopropan-1-ol | 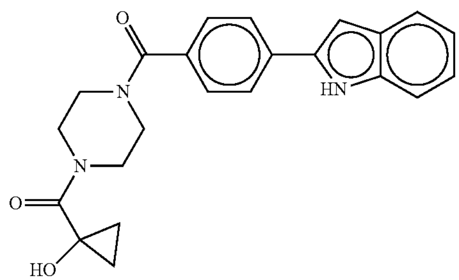 |
| 1-({4-[(4-{3-chloroimidazo[1,2-a]pyridin-2-yl}phenyl)carbonyl]piperazin-1-yl}carbonyl)cyclopropan-1-ol | 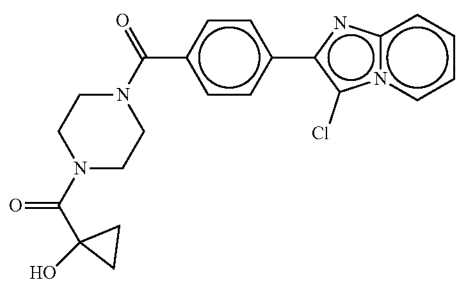 |
| 1-[(4-{[4-(1-methyl-1H-1,3-benzodiazol-2-yl)phenyl]carbonyl}piperazin-1-yl)carbonyl]cyclopropan-1-ol | 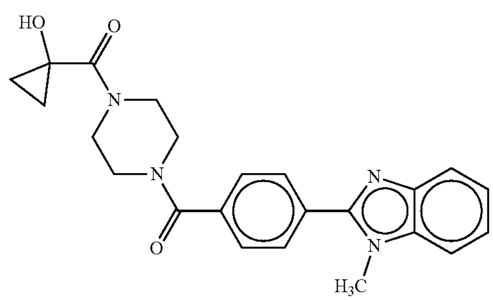 |
| 3-[3-chloro-4-({4-[(1-hydroxycyclopropyl)carbonyl]piperazin-1-yl}carbonyl)phenyl]-N-cyclopropylbenzene-1-sulfonamide | 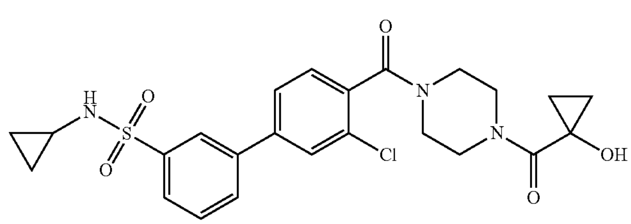 [SMILES: O=C(c1ccc(-c2cccc(S(=O)(=O)NC3CC3)c2)cc1Cl)N1CCN(C(=O)C2(O)CC2)CC1] |
| 1-({4-[(2-chloro-4-{furo[3,2-b]pyridin-5-yl}phenyl)carbonyl]piperazin-1-yl}carbonyl)cyclopropan-1-ol | 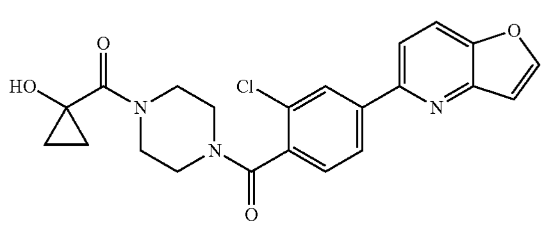 [SMILES: O=C(c1ccc(-c2ccc3occc3n2)cc1Cl)N1CCN(C(=O)C2(O)CC2)CC1] |

TABLE 1-continued

| IUPAC Name | Compound Structure |
| --- | --- |
| 1-[(4-{[2-chloro-4-(1-methyl-1H-1,3-benzodiazol-5-yl)phenyl]carbonyl}piperazin-1-yl)carbonyl]cycfopropan-1-ol | 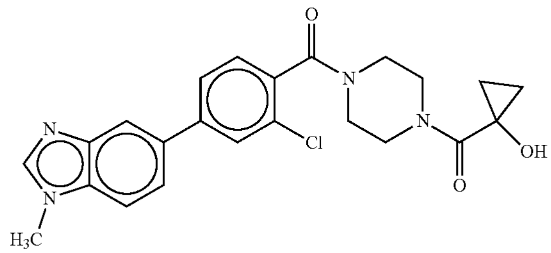 |
| N-{3-[3-chloro-4-({4-[(1-hydroxycyclopropyl)carbonyl]piperazin-1-yl}carbonyl)phenyl]phenyl}cyclopropanesulfonamide | 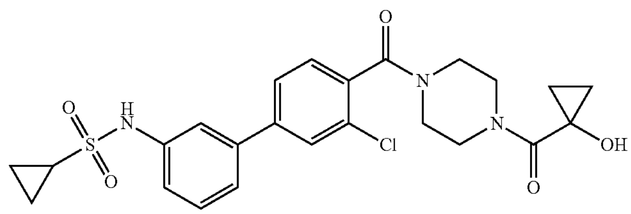 [SMILES: O=C(c1ccc(-c2cccc(NS(=O)(=O)C3CC3)c2)cc1Cl)N1CCN(C(=O)C2(O)CC2)CC1] |
| N-{3-[4-({4-[(1-hydroxycyclopropyl)carbonyl]piperazin-1-yl}carbonyl)phenyl]phenyl}cyclobutanecarboxamide | 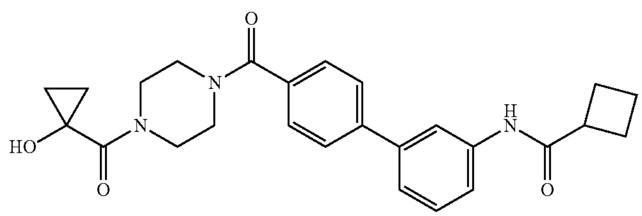 [SMILES: O=C(Nc1cccc(-c2ccc(C(=O)N3CCN(C(=O)C4(O)CC4)CC3)cc2)c1)C1CCC1] |
| 1-{[4-({4-[3-(cyclopropanesulfonyl)phenyl]phenyl}carbonyl)piperazin-1-yl]carbonyl}cyclopropan-1-ol | 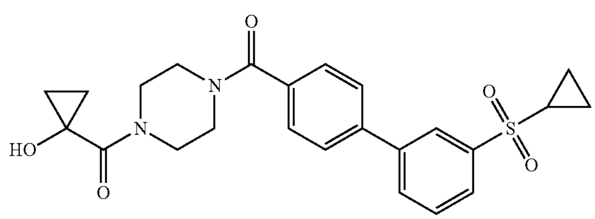 [SMILES: O=C(c1ccc(-c2cccc(S(=O)(=O)C3CC3)c2)cc1)N1CCN(C(=O)C2(O)CC2)CC1] |
| N-{5-[3-chloro-4-({4-[(1-hydroxycyclopropyl)carbonyl]piperazin-1-yl}carbonyl)phenyl]pyridin-3-yl}cyclopropanesulfonamide | 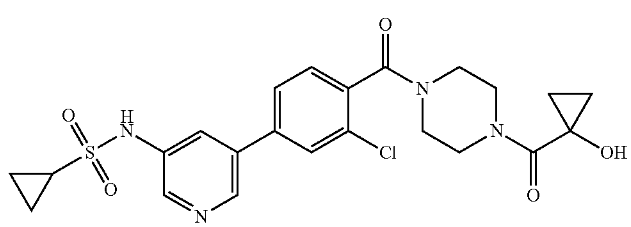 [SMILES: O=C(c1ccc(-c2cncc(NS(=O)(=O)C3CC3)c2)cc1Cl)N1CCN(C(=O)C2(O)CC2)CC1] |
| N-{5-[3-chloro-4-({4-[(1-hydroxycyclopropyl)carbonyl]piperazin-1-yl}carbonyl)phenyl]pyridin-3-yl}cyclopropanecarboxamide | 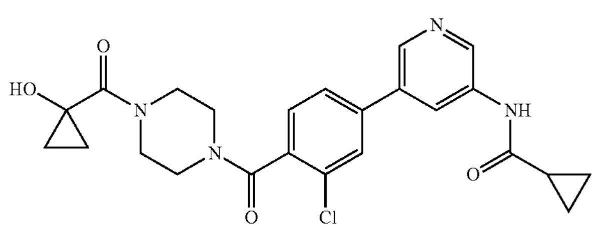 [SMILES: O=C(Nc1cncc(-c2ccc(C(=O)N3CCN(C(=O)C4(O)CC4)CC3)c(Cl)c2)c1)C1CC1] |

TABLE 1-continued

| IUPAC Name | Compound Structure |
|---|---|
| N-{3-[4-({4-[(1-hydroxycyclopropyl)carbonyl]piperazin-1-yl}carbonyl)phenyl]phenyl}oxetane-3-carboxamide | 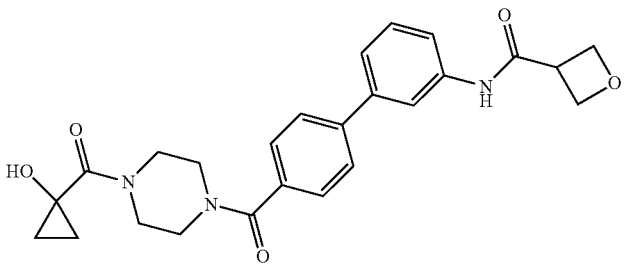 [SMILES: O=C(Nc1cccc(-c2ccc(C(=O)N3CCN(C(=O)C4(O)CC4)CC3)cc2)c1)C1COC1] |
| 1-{[4-({4-[3-(cyclopropanesulfonyl)phenyl]phenyl}carbonyl)piperazin-1-yl]carbonyl}cyclobutan-1-ol | 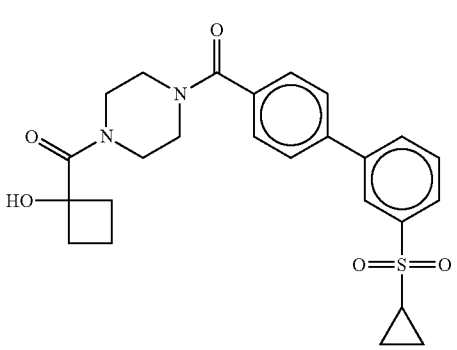 |
| 1-({4-[3-(cyclopropanesulfonyl)phenyl]phenyl}carbonyl)-4-[(oxetan-2-yl)carbonyl]piperazine | 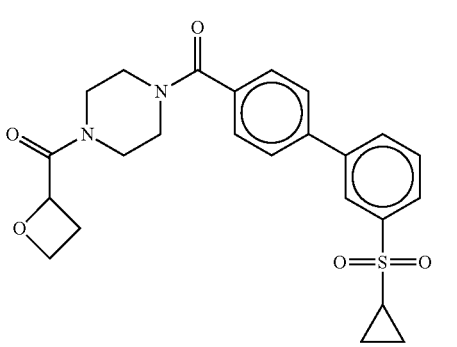 |
| 1-({4-[(4-{3-chloroimidazo[1,2-a]pyridin-2-yl}phenyl)carbonyl]piperazin-1-yl}carbonyl)cyclobutan-1-ol | 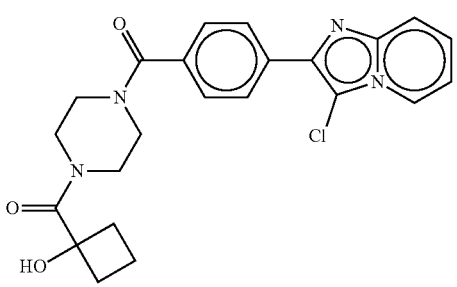 |
| 1-[(4-{3-chloroimidazo[1,2-a]pyridin-2-yl}phenyl)carbonyl]-4-[(oxetan-2-yl)carbonyl]piperazine | 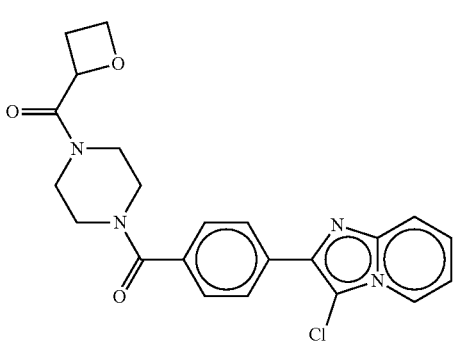 |

TABLE 1-continued

| IUPAC Name | Compound Structure |
| --- | --- |
| 1-[(4-{[4-(3-cyclopropoxyphenyl)phenyl]carbonyl}piperazin-1-yl)carbonyl]cyclobutan-1-ol | 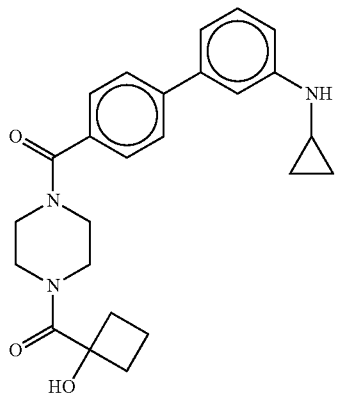 |
| 1-{[4-(3-cyclopropoxyphenyl)phenyl]carbonyl}-4-[(oxetan-2-yl)carbonyl]piperazine | 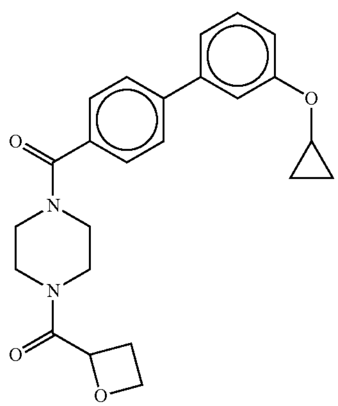 |
| N-{3-[4-({4-[(1-hydroxycyclobutyl)carbonyl]piperazin-1-yl}carbonyl)phenyl]phenyl}cyclopropanecarboxamide | 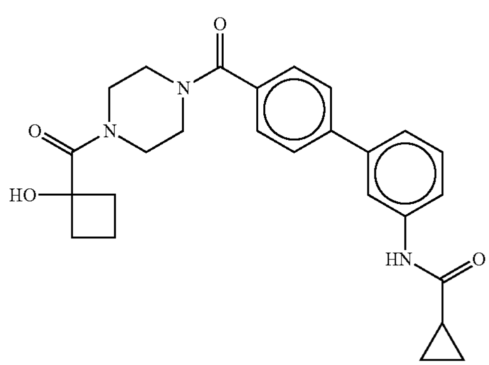 |
| N-{3-[4-({4-[(oxetan-2-yl)carbonyl]piperazin-1-yl}carbonyl)phenyl]phenyl}cyclopropanecarboxamide | 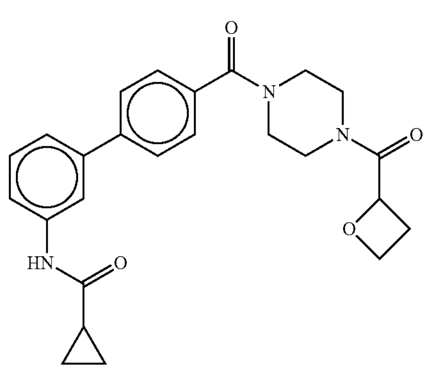 |

TABLE 1-continued

| IUPAC Name | Compound Structure |
|---|---|
| 3-[4-({4-[(1-hydroxycyclobutyl)carbonyl]piperazin-1-yl}carbonyl)phenyl]-1,2-dihydroquinolin-2-one | 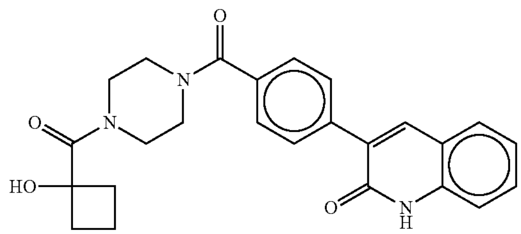 |
| 3-[4-({4-[(oxetan-2-yl)carbonyl]piperazin-1-yl}carbonyl)phenyl]-1,2-dihydroquinolin-2-one | 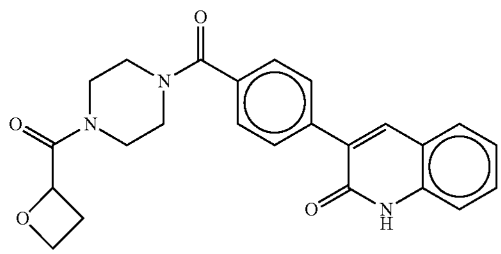 |
| 5-[4-({4-[(1-hydroxycyclobutyl)carbonyl]piperazin-1-yl}carbonyl)phenyl]-1H-indole-2-carbonitrile | 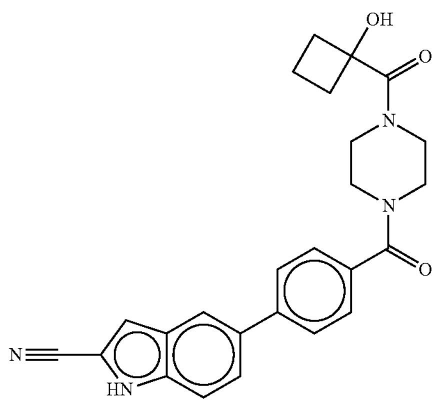 |
| 5-[4-({4-[(oxetan-2-yl)carbonyl]piperazin-1-yl}carbonyl)phenyl]-1H-indole-2-carbonitrile | 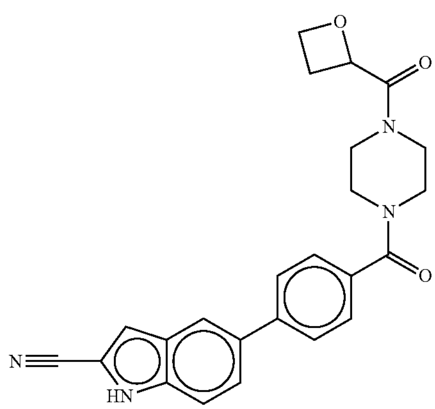 |
| 1-[(4-{[4-(1-methyl-1H-1,3-benzodiazol-5-yl)phenyl]carbonyl}piperazin-1-yl)carbonyl]cyclobutan-1-ol | 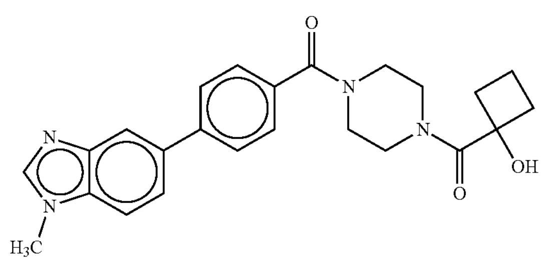 |

TABLE 1-continued

| IUPAC Name | Compound Structure |
| --- | --- |
| 1-methyl-5-[4-({4-[(oxetan-2-yl)carbonyl]piperazin-1-yl}carbonyl)phenyl]-1H-1,3-benzodiazole | 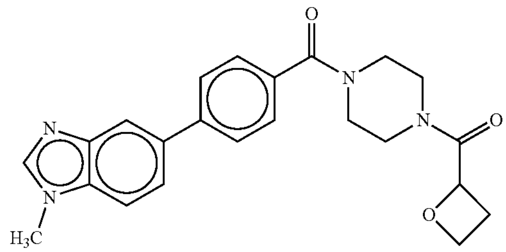 |
| 1-({4-[(4-{imidazo[1,2-b]pyridazin-6-yl}phenyl)carbonyl]piperazin-1-yl}carbonyl)cyclobutan-1-ol | 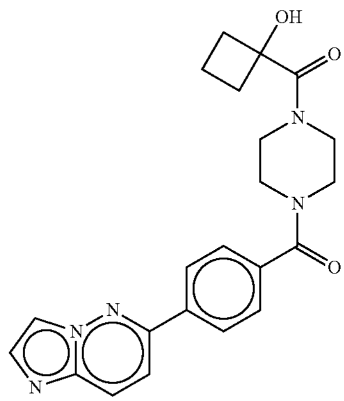 |
| 1-[(4-{imidazo[1,2-b]pyridazin-6-yl}phenyl)carbonyl]-4-(oxetan-2-yl)carbonyl]piperazine | 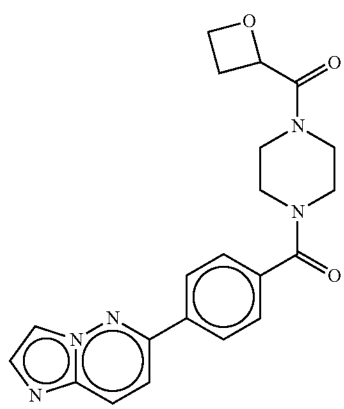 |
| 1-({4-[(4-{furo[3,2-b]pyridin-5-yl}phenyl)carbonyl]piperazin-1-yl}carbonyl)cyclobutan-1-ol | 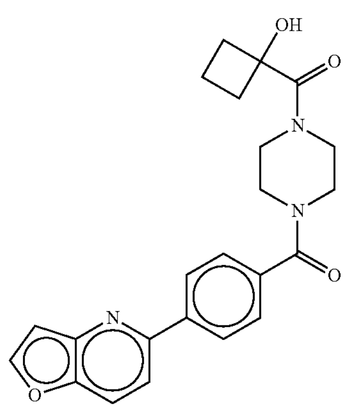 |

TABLE 1-continued

| IUPAC Name | Compound Structure |
|---|---|
| 1-[(4-{furo[3,2-b]pyridin-5-yl}phenyl)carbonyl]-4-[(oxetan-2-yl)carbonyl]piperazine | 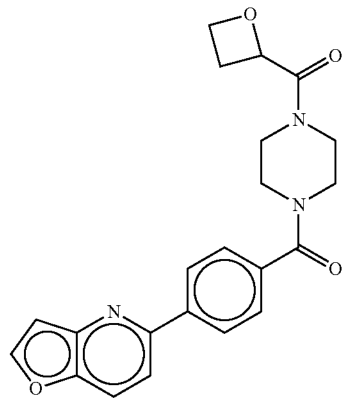 |
| 1-[(4-{[4-(1H-indazol-3-yl)phenyl]carbonyl}piperazin-1-yl)carbonyl]cyclobutan-1-ol | 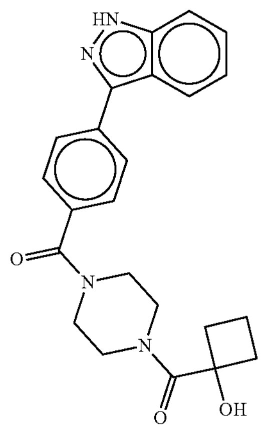 |
| 3-[4-({4-[(oxetan-2-yl)carbonyl]piperazin-1-yl}carbonyl)phenyl]-1H-indazole | 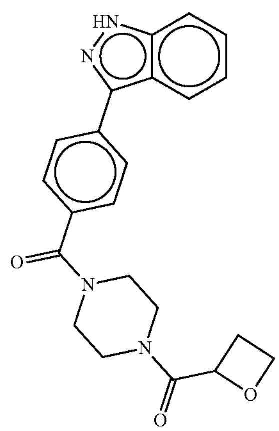 |
| 1-[(4-{[4-(1,3-dimethyl-1H-indazol-5-yl)phenyl]carbonyl}piperazin-1-yl)carbonyl]cyclobutan-1-ol | 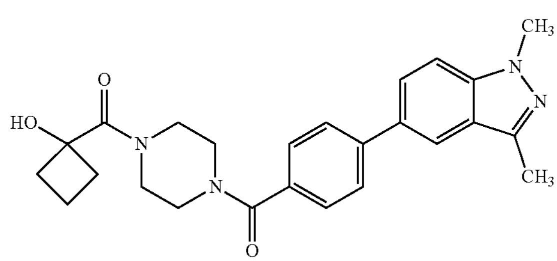 |

TABLE 1-continued

| IUPAC Name | Compound Structure |
|---|---|
| 1,3-dimethyl-5-[4-({4-[(oxetan-2-yl)carbonyl]piperazin-1-yl}carbonyl)phenyl]-1H-indazole | 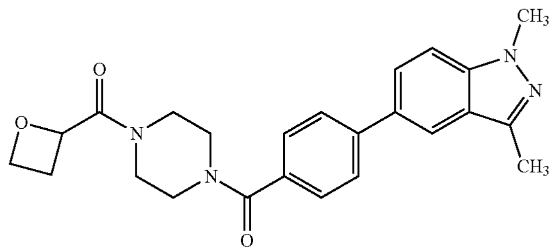 [SMILES: Cc1nn(C)c2ccc(-c3ccc(C(=O)N4CCN(C(=O)C5CCO5)CC4)cc3)cc12] |
| N-{3-[4-({4-[(1-hydroxycyclobutyl)carbonyl]piperazin-1-yl}carbonyl)phenyl]phenyl}cyclopropanesulfonamide | 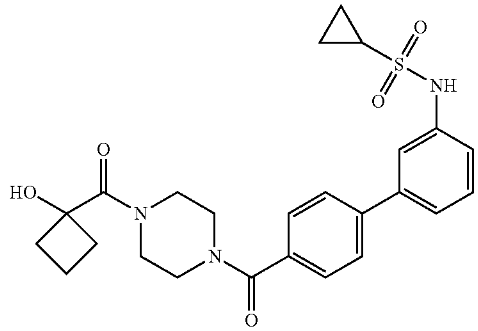 [SMILES: O=C(c1ccc(-c2cccc(NS(=O)(=O)C3CC3)c2)cc1)N1CCN(C(=O)C2(O)CCC2)CC1] |
| N-{3-[4-({4-[(oxetan-2-yl)carbonyl]piperazin-1-yl}carbonyl)phenyl]phenyl}cyclopropanesulfonamide | 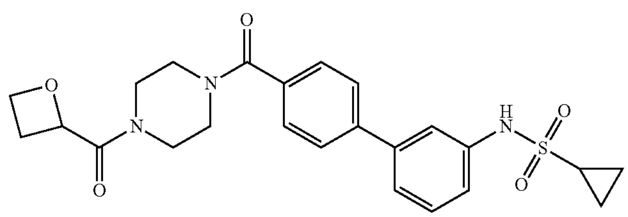 [SMILES: O=C(c1ccc(-c2cccc(NS(=O)(=O)C3CC3)c2)cc1)N1CCN(C(=O)C2CCO2)CC1] |
| 1-[(4-{[4-(6-fluoro-1,3-benzoxazole-2-yl)phenyl]carbonyl}piperazin-1-yl)carbonyl]cyclobutan-1-ol | 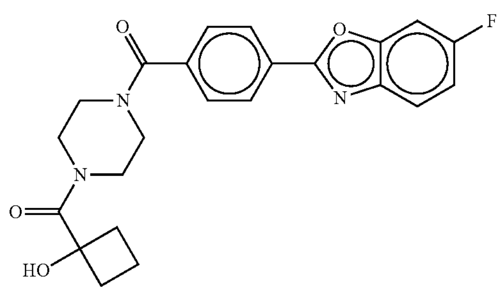 |
| 6-fluoro-2-[4-({4-[(oxetan-2-yl)carbonyl]piperazin-1-yl}carbonyl)phenyl]-1,3-benzoxazole | 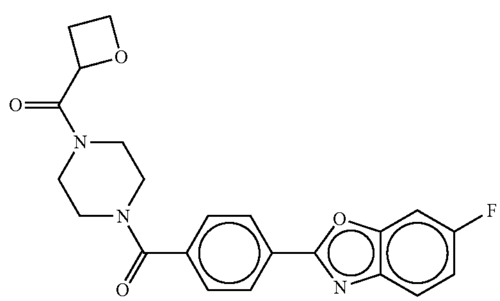 |

TABLE 1-continued

| IUPAC Name | Compound Structure |
|---|---|
| 1-[(4-{[4-(6-chloro-1,3-benzoxazol-2-yl)phenyl]carbonyl}piperazin-1-yl)carbonyl]cyclobutan-1-ol | 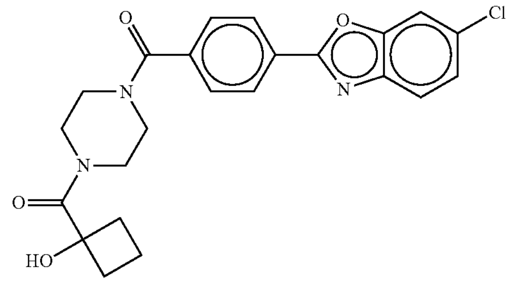 |
| 6-chloro-2-[4-({4-[(oxetan-2-yl)carbonyl]piperazin-1-yl}carbonyl)phenyl]-1,3-benzoxazole | 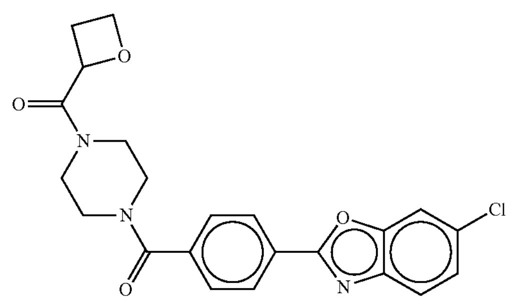 |
| 5-[4-({4-[(1-hydroxycyclobutyl)carbonyl]piperazin-1-yl}carbonyl)phenyl]-1H-indole-3-carbonitrile | 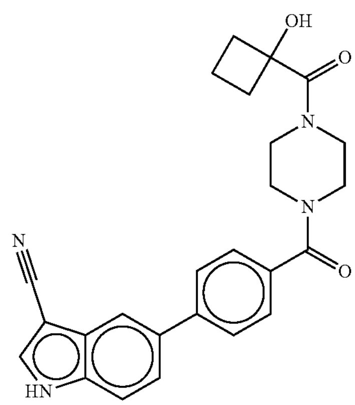 |
| 5-[4-({4-[(oxetan-2-yl)carbonyl]piperazin-1-yl}carbonyl)phenyl]-1H-indole-3-carbonitrile | 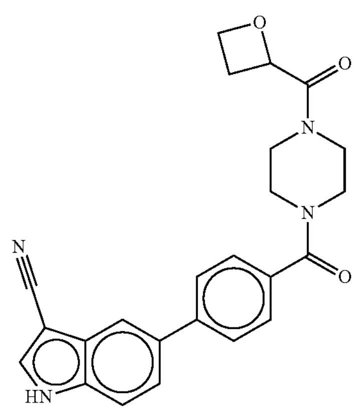 |

TABLE 1-continued

| IUPAC Name | Compound Structure |
| --- | --- |
| 1-[(4-{[4-(1,3-benzothiazol-2-yl)phenyl]carbonyl}piperazin-1-yl)carbonyl]cyclobutan-1-ol | 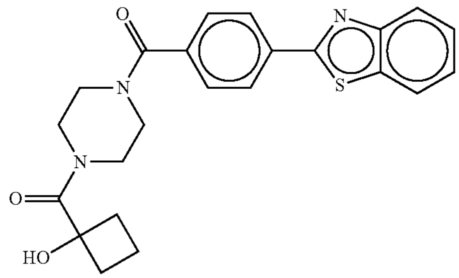 |
| 2-[4-({4-[(oxetan-2-yl)carbonyl]piperazin-1-yl}carbonyl)phenyl]-1,3-benzothiazole | 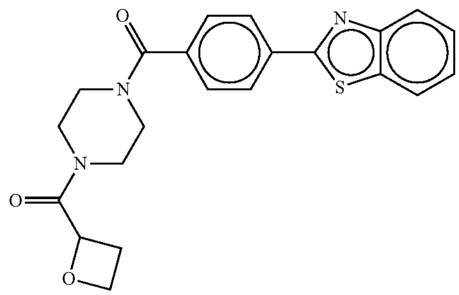 |
| 1-[(4-{[4-(quinolin-2-yl)phenyl]carbonyl}piperazin-1-yl)carbonyl]cyclobutan-1-ol | 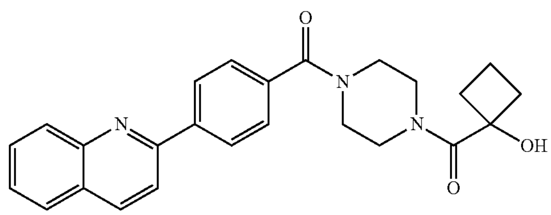 [SMILES: O=C(c1ccc(-c2ccc3ccccc3n2)cc1)N1CCN(C(=O)C2(O)CCC2)CC1] |
| 2-[4-({4-[(oxetan-2-yl)carbonyl]piperazin-1-yl}carbonyl)phenyl]quinoline | 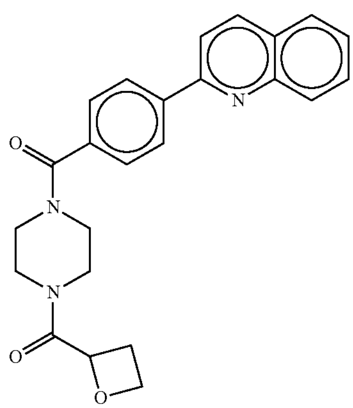 |
| 1-[(4-{[4-(1H-1,3-benzodiazol-5-yl)phenyl]carbonyl}piperazin-1-yl)carbonyl]cyclobutan-1-ol | 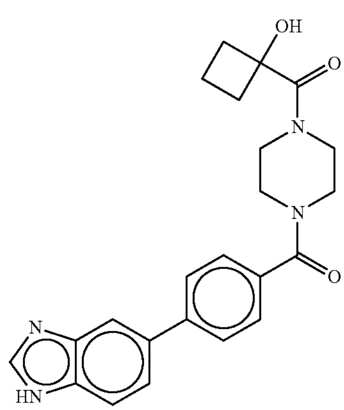 |

TABLE 1-continued

| IUPAC Name | Compound Structure |
|---|---|
| 5-[4-({4-[(oxetan-2-yl)carbonyl]piperazin-1-yl}carbonyl)phenyl]-1H-1,3-benzodiazole | 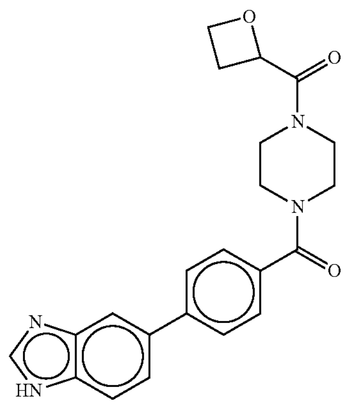 |
| 1-[(4-{[4-(1,3-benzothiazol-6-yl)phenyl]carbonyl}piperazin-1-yl)carbonyl]cyclobutan-1-ol | 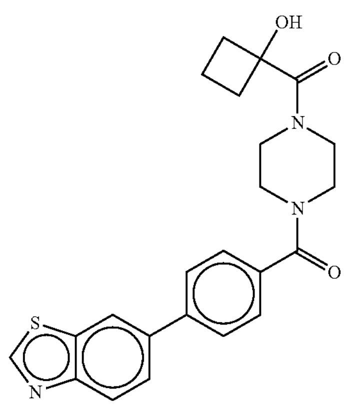 |
| 6-[4-({4-[(oxetan-2-yl)carbonyl]piperazin-1-yl}carbonyl)phenyl]-1,3-benzodiazole | 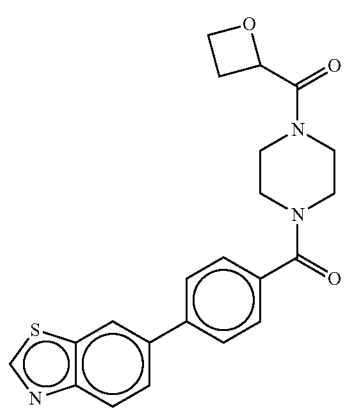 |
| 1-[(4-{[4-(1,3-benzoxazol-5-yl)phenyl]carbonyl}piperazin-1-yl)carbonyl]cyclobutan-1-ol | 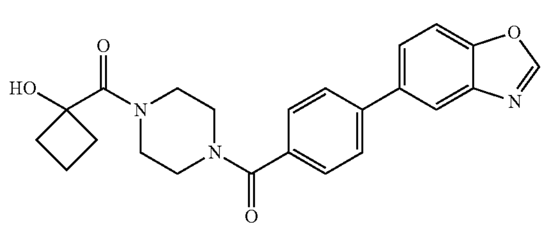 [SMILES: O=C(c1ccc(-c2ccc3ocnc3c2)cc1)N1CCN(C(=O)C2(O)CCC2)CC1] |

TABLE 1-continued

| IUPAC Name | Compound Structure |
|---|---|
| 5-[4({4-[(oxetan-2-yl)carbonyl]piperazin-1-yl}carbonyl)phenyl]-1,3-benzoxazole | 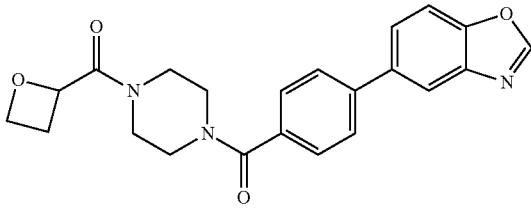 [SMILES: O=C(c1ccc(-c2ccc3ocnc3c2)cc1)N1CCN(C(=O)C2CCO2)CC1] |
| 1-[(4-{[4-(1,3-benzothiazol-5-yl)phenyl]carbonyl}piperazin-1-yl)carbonyl]cyclobutan-1-ol | 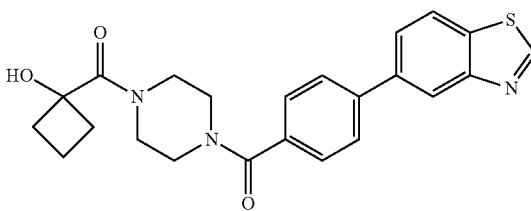 |
| 5-[4-({4-[{oxetan-2-yl)carbonyl]piperazin-1-yl}carbonyl)phenyl]-1,3-benzothiazole | 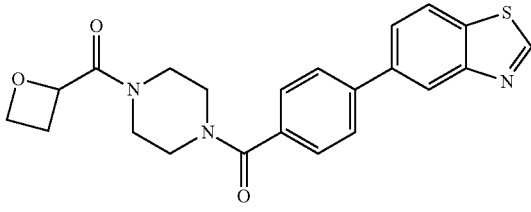 |
| 1-[(4-{[4-(1-methyl-1H-indazol-6-yl)phenyl]carbonyl}piperazin-1-yl)carbonyl]cyclobutan-1-ol | 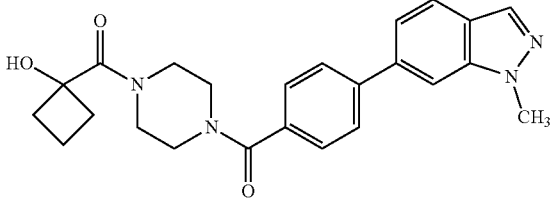 [SMILES: Cn1ncc2ccc(-c3ccc(C(=O)N4CCN(C(=O)C5(O)CCC5)CC4)cc3)cc21] |
| 1-methyl-6-[4-({4-[(oxetan-2-yl)carbonyl]piperazin-1-yl}carbonyl)phenyl]-1H-indazole | 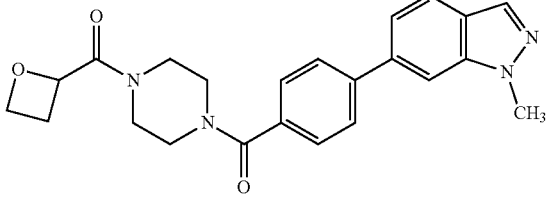 |
| N-cyclopropyl-3-[4-({4-[(1-hydroxycyclobutyl)carbonyl]piperazin-1-yl}carbonyl)phenyl]benzamide | 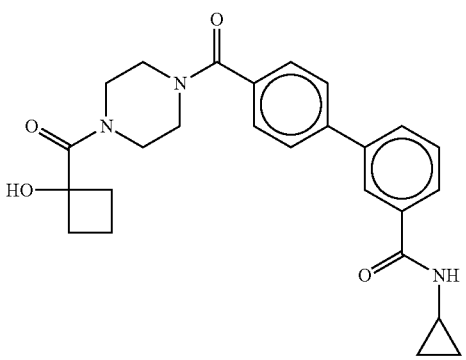 |

TABLE 1-continued

| IUPAC Name | Compound Structure |
|---|---|
| N-cyclopropyl-3-[4-({4-[(oxetan-2-yl)carbonyl]piperazin-1-yl}carbonyl)phenyl]benzamide | 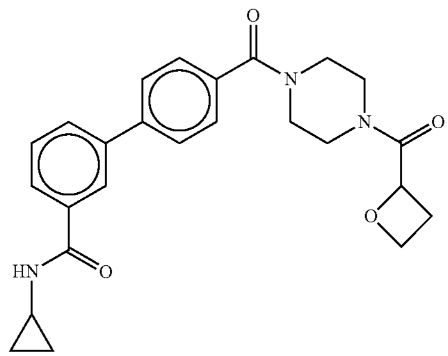 |
| 1-[(4-{[4-(2-methyl-2H-indazol-6-yl)phenyl]carbonyl}piperazin-1-yl)carbonyl]cyclobutan-1-ol | 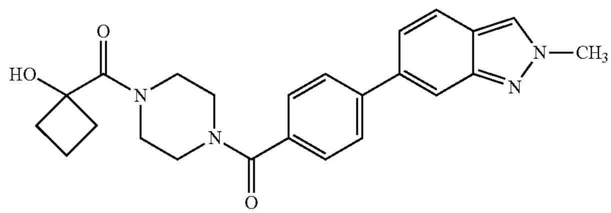 [SMILES: Cn1cc2ccc(-c3ccc(C(=O)N4CCN(C(=O)C5(O)CCC5)CC4)cc3)cc2n1] |
| 2-methyl-6-[4-({4-[(oxetan-2-yl)carbonyl]piperazin-1-yl}carbonyl)phenyl]-2H-indazole | 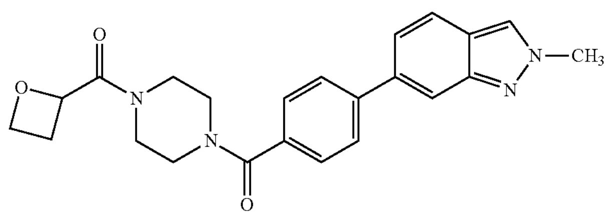 [SMILES: Cn1cc2ccc(-c3ccc(C(=O)N4CCN(C(=O)C5CCO5)CC4)cc3)cc2n1] |
| 1-[(4-{[4-(4-chloro-2-fluorophenyl)phenyl]carbonyl}piperazin-1-yl)carbonyl]cyclobutan-1-ol | 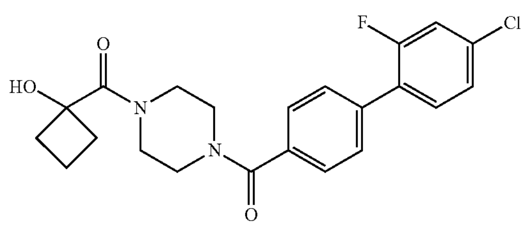 [SMILES: O=C(c1ccc(-c2ccc(Cl)cc2F)cc1)N1CCN(C(=O)C2(O)CCC2)CC1] |
| 1-{[4-(4-chloro-2-fluorophenyl)phenyl]carbonyl}-4-[(oxetan-2-yl)carbonyl]piperazine | 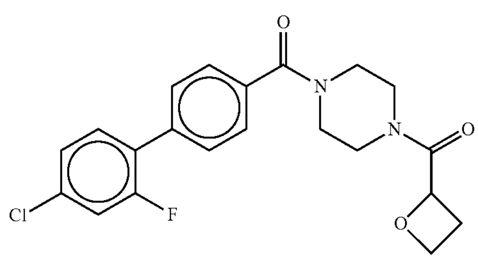 |
| 1-[(4-{[4-(5-chloro-2-fluorophenyl)phenyl]carbonyl}piperazin-1-yl)carbonyl]cyclobutan-1-ol | 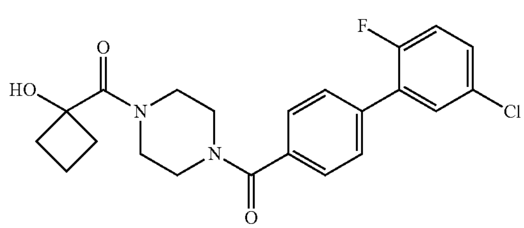 [SMILES: O=C(c1ccc(-c2cc(Cl)ccc2F)cc1)N1CCN(C(=O)C2(O)CCC2)CC1] |

TABLE 1-continued

| IUPAC Name | Compound Structure |
|---|---|
| 1-{[4-(5-chloro-2-fluorophenyl)phenyl]carbonyl}-4-[(oxetan-2-yl)carbonyl]piperazine | 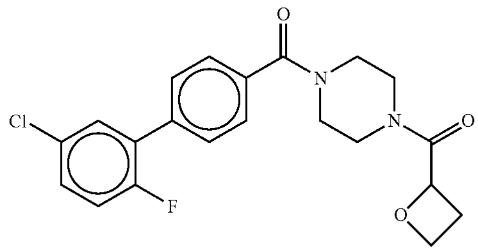 |
| 1-{[4-({4-[3-(cyclopropanesulfonyl)phenyl]phenyl}carbonyl)piperazin-1-yl]carbonyl}cyclobutan-1-amine | 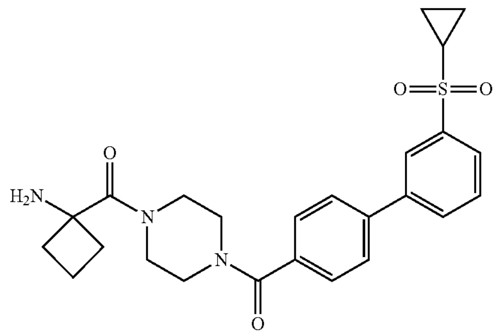 [SMILES: NC1(C(=O)N2CCN(C(=O)c3ccc(-c4cccc(S(=O)(=O)C5CC5)c4)cc3)CC2)CCC1] |
| 1-{[4-({4-[3-(cyclopropanesulfonyl]phenyl]phenyl}carbonyl)pipearazin-1-yl]carbonyl}cyclopropan-1-amine | 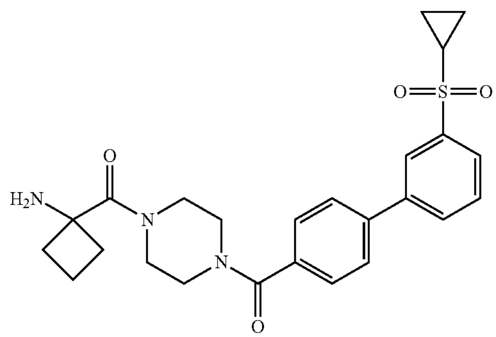 [SMILES: NC1(C(=O)N2CCN(C(=O)c3ccc(-c4cccc(S(=O)(=O)C5CC5)c4)cc3)CC2)CCC1] |
| 1-({4-[(4-[3-chloroimidazo[1,2-a]pyridin-2-yl}phenyl)carbonyl]piperazin-1-yl}carbonyl)cyclobutan-1-amine | 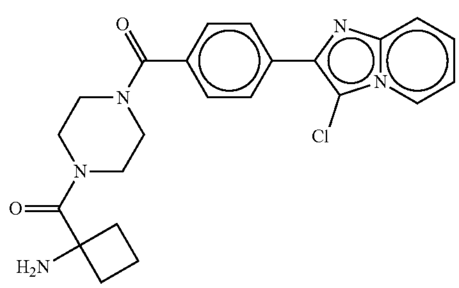 |
| 1-({4-[(4-{3-chloroimidazo[1,2-a]pyridin-2-yl}phenyl)carbonyl]piperazin-1-yl}carbonyl)cyclopropan-1-amine | 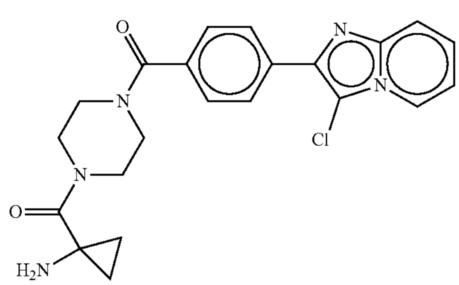 |

TABLE 1-continued

| IUPAC Name | Compound Structure |
|---|---|
| 1-[(4-{[4-(3-cyclopropoxyphenyl)phenyl]carbonyl}piperazin-1-yl)carbonyl]cyclobutan-1-amine | 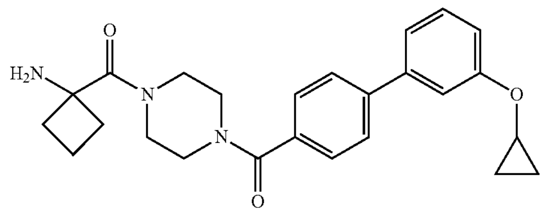 [SMILES: NC1(C(=O)N2CCN(C(=O)c3ccc(-c4cccc(OC5CC5)c4)cc3)CC2)CCC1] |
| 1-[(4-{[4-(3-cyclopropoxyphenyl)phenyl]carbonyl}piperazin-1-yl)carbonyl]cyclopropan-1-amine | 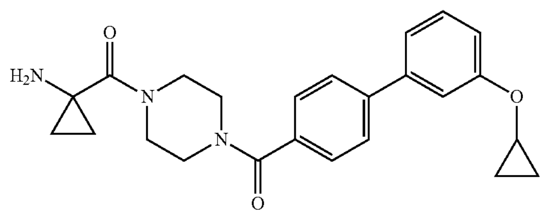 [SMILES: NC1(C(=O)N2CCN(C(=O)c3ccc(-c4cccc(OC5CC5)c4)cc3)CC2)CC1] |
| N-{3-[4-({4-[(1-aminocyclobutyl)carbonyl]piperazin-1-yl}carbonyl)phenyl]phenyl}cyclopropanecarboxamide | 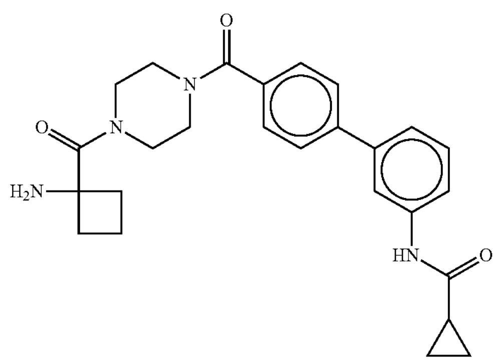 |
| N-{3-[4-({4-[(1-aminocyclopropyl)carbonyl]piperazin-1-yl}carbonyl)phenyl]phenyl}cyclopropanecarboxamide | 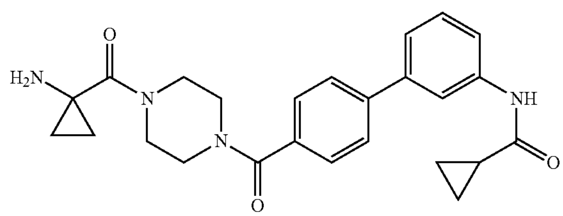 [SMILES: NC1(C(=O)N2CCN(C(=O)c3ccc(-c4cccc(NC(=O)C5CC5)c4)cc3)CC2)CC1] |
| 3-[4-({4-[(1-aminocyclobutyl)carbonyl]piperazin-1-yl}carbonyl)phenyl]-1,2-dihydroquinolin-2-one | 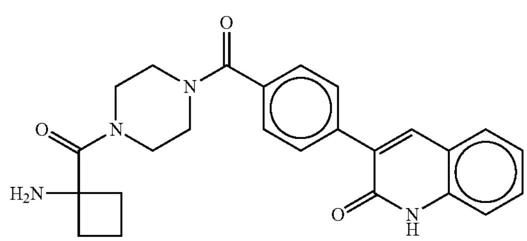 |
| 3-[4-({4-[(1-aminocyclopropyl)carbonyl]piperazin-1-yl}carbonyl)phenyl]-1,2-dihydroquinolin-2-one | 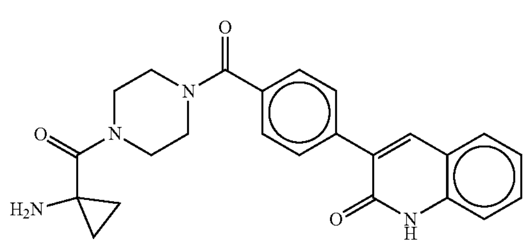 |

TABLE 1-continued

| IUPAC Name | Compound Structure |
|---|---|
| 5-[4-({4-[(1-aminocyclobutyl)carbonyl]piperazin-1-yl}carbonyl)phenyl]-1H-indole-2-carbonitrile | 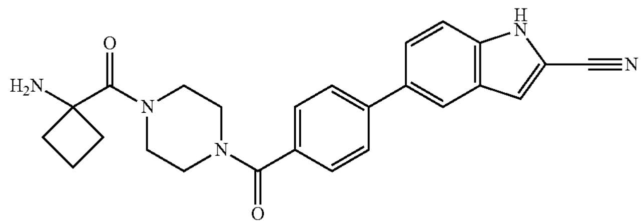 [SMILES: N#Cc1cc2cc(-c3ccc(C(=O)N4CCN(C(=O)C5(N)CCC5)CC4)cc3)ccc2[nH]1] |
| 5-[4-({4-[(1-aminocyclopropyl)carbonyl]piperazin-1-yl}carbonyl)phenyl]-1H-indole-2-carbonitrile | 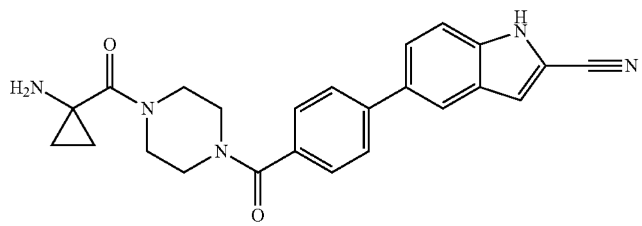 [SMILES: N#Cc1cc2cc(-c3ccc(C(=O)N4CCN(C(=O)C5(N)CC5)CC4)cc3)ccc2[nH]1] |
| 1-[(4-{[4-(1-methyl-1H-1,3-benzodiazol-5-yl)phenyl]carbonyl}piperazin-1-yl)carbonyl]cyclobutan-1-amine | 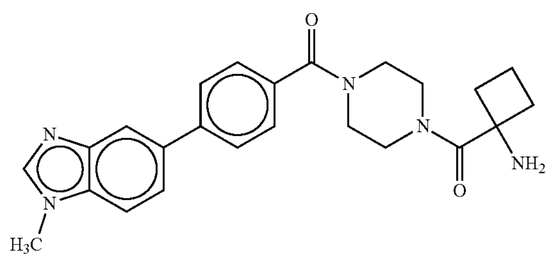 |
| 1-[(4-{[4-(1-methyl-1H-1,3-benzodiazol-5-yl)phenyl]carbonyl}piperazin-1-yl)carbonyl]cyclopropan-1-amine | 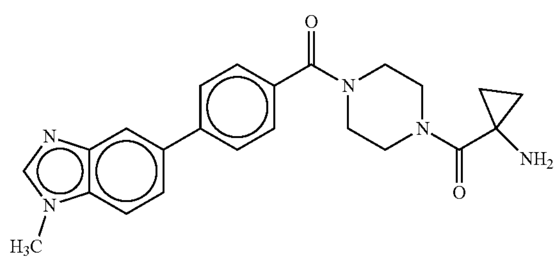 |
| 1-({4-[(4-{imidazo[1,2-b]pyridazin-6-yl}phenyl)carbonyl]piperazin-1-yl}carbonyl)cyclobutan-1-amine | 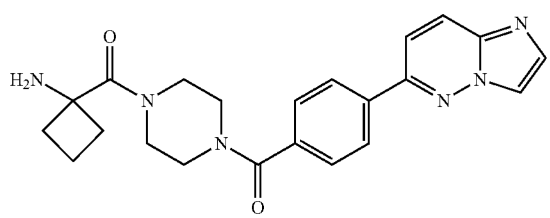 [SMILES: NC1(C(=O)N2CCN(C(=O)c3ccc(-c4ccc5nccn5n4)cc3)CC2)CCC1] |
| 1-({4-[(4-{imidazo[1,2-b]pyridazin-6-yl}phenyl)carbonyl]piperazin-1-yl}carbonyl)cyclopropan-1-amine | 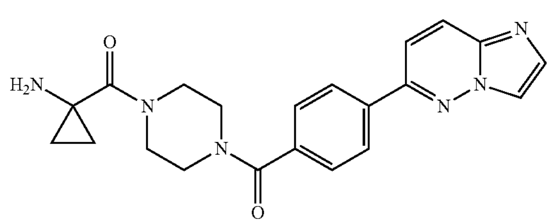 [SMILES: NC1(C(=O)N2CCN(C(=O)c3ccc(-c4ccc5nccn5n4)cc3)CC2)CC1] |

TABLE 1-continued

| IUPAC Name | Compound Structure |
|---|---|
| 1-({4-[(4-{furo[3,2-b]pyridin-5-yl}phenyl)carbonyl]piperazin-1-yl}carbonyl)cyclopropan-1-amine | |
| 1-({4-[(4-{furo[3,2-b]pyridin-5-yl}phenyl)carbonyl]piperazin-1-yl}carbonyl)cyclopropan-1-amine | |
| 1-[(4-{[4-(1H-indazol-3-yl)phenyl]carbonyl}piperazin-1-yl)carbonyl]cyclobutan-1-amine | 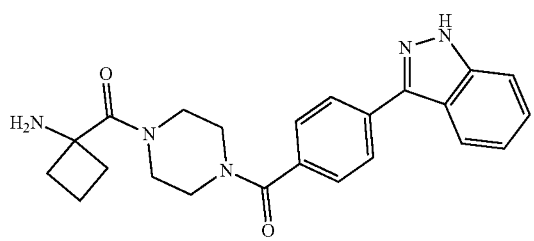 [SMILES: NC1(C(=O)N2CCN(C(=O)c3ccc(-c4n[nH]c5ccccc45)cc3)CC2)CCC1] |
| 1-[(4-{[4-(1H-indazol-3-yl)phenyl]carbonyl}piperazin-1-yl)carbonyl]cyclopropan-1-amine | 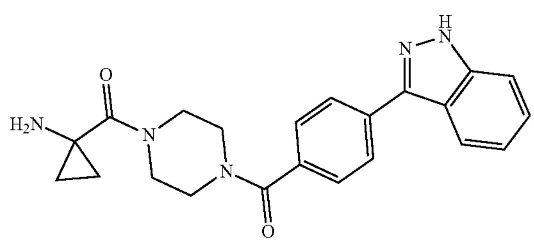 [SMILES: NC1(C(=O)N2CCN(C(=O)c3ccc(-c4n[nH]c5ccccc45)cc3)CC2)CC1] |
| 1-[(4-{[4-(1,3-dimethyl-1H-indazol-5-yl)phenyl]carbonyl}piperazin-1-yl)carbonyl]cyclobutan-1-amine | 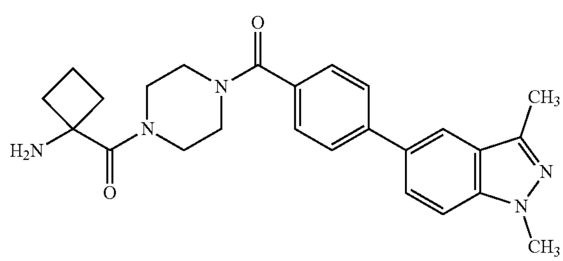 [SMILES: Cc1nn(C)c2ccc(-c3ccc(C(=O)N4CCN(C(=O)C5(N)CCC5)CC4)cc3)cc12] |
| 1-[(4-{[4-(1,3-dimethyl-1H-indazol-5-yl)phenyl]carbonyl}piperazin-1-yl)carbonyl]cyclopropan-1-amine | 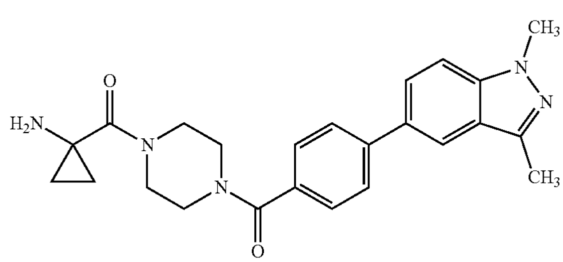 [SMILES: Cc1nn(C)c2ccc(-c3ccc(C(=O)N4CCN(C(=O)C5(N)CC5)CC4)cc3)cc12] |

TABLE 1-continued

| IUPAC Name | Compound Structure |
|---|---|
| N-{3-[4-([4-[(1-aminocyclobutyl)carbonyl]piperazin-1-yl}carbonyl)phenyl]phenyl}cyclopropanesulfonamide | 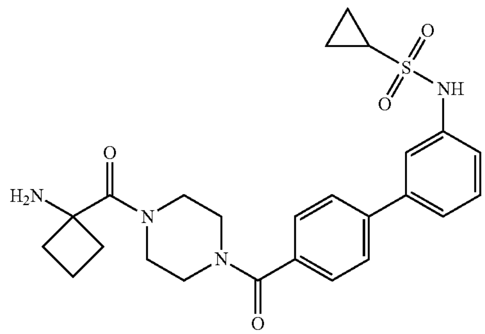 |
| N-{3-[4-({4-[(1-aminocyclopropyl)carbonyl]piperazin-1-yl}carbonyl)phenyl]phenyl}cyclopropanesulfonamide | 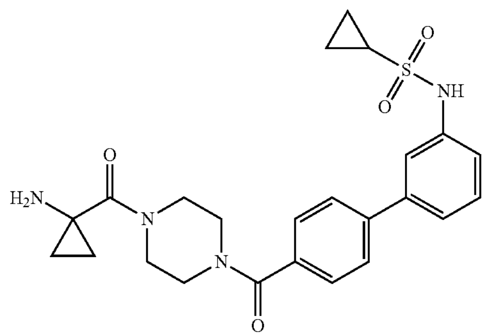 [SMILES: NC1(C(=O)N2CCN(C(=O)c3ccc(-c4cccc(NS(=O)(=O)C5CC5)c4)cc3)CC2)CC1] |
| 1-[(4-{[4-(6-fluoro-1,3-benzoxazol-2-yl)phenyl]carbonyl}piperazin-1-yl)carbonyl]cyclobutan-1-amine | 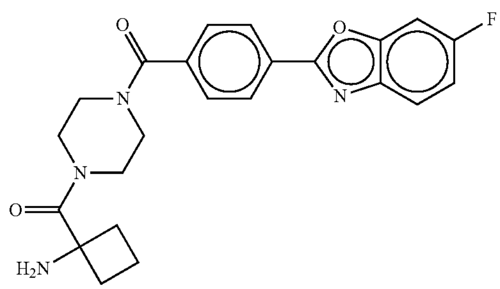 |
| 1-[(4-{[4-(6-fluoro-1,3-benzoxazol-2-yl)phenyl]carbonyl}piperazin-1-yl)carbonyl]cyclopropan-1-amine | 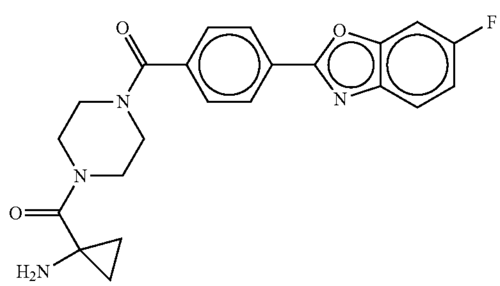 |
| 1-[(4-{[4-(6-chloro-1,3-benzoxazol-2-yl)phenyl]carbonyl}piperazin-1-yl)carbonyl]cyclobutan-1-amine | 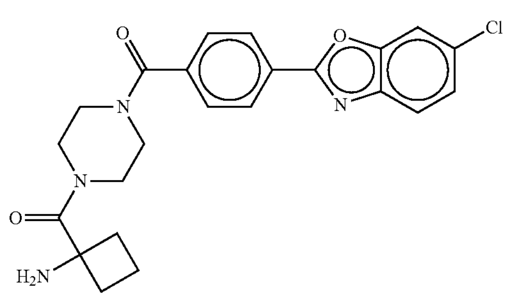 |

TABLE 1-continued

| IUPAC Name | Compound Structure |
|---|---|
| 1-[(4-{[4-(6-chloro-1,3-benzoxazol-2-yl)phenyl]carbonyl}piperazin-1-yl)carbonyl]cyclopropan-1-amine | 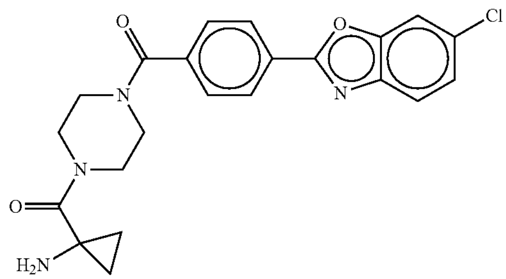 |
| 5-[4-({4-[(1-aminocyclobutyl)carbonyl]piperazin-1-yl}carbonyl)phenyl]-1H-indole-3-carbonitrile | 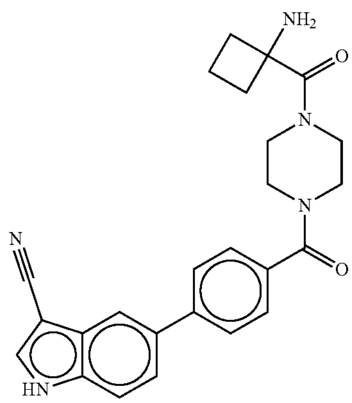 |
| 5-[4-({4-[(1-aminocyclopropyl)carbonyl]piperazin-1-yl}carbonyl)phenyl]-1H-indole-3-carbonitrile | 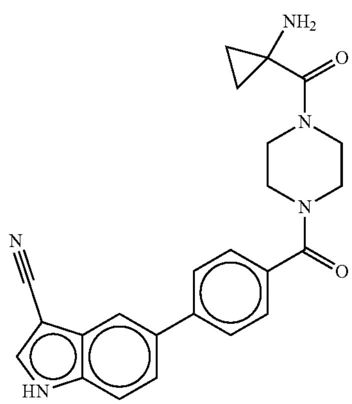 |
| 1-[(4-{[4-(1,3-benzothiazol-2-yl)phenyl]carbonyl}piperazin-1-yl)carbonyl]cyclobutan-1-amine | 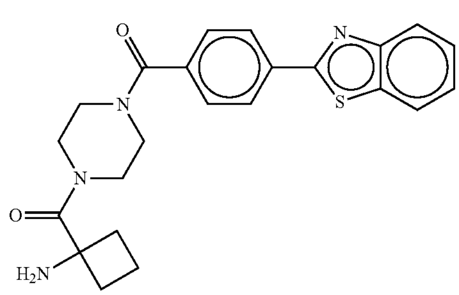 |

TABLE 1-continued

| IUPAC Name | Compound Structure |
|---|---|
| 1-[(4-{[4-(1,3-benzothiazol-2-yl)phenyl]carbonyl}piperazin-1-yl)carbonyl]cyclopropan-1-amine | 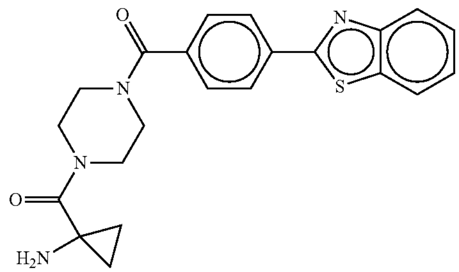 |
| 1-[(4-{[4-(qninolin-2-yl)phenyl]carbonyl}piperazin-1-yl)carbonyl]cyclobutan-1-amine | 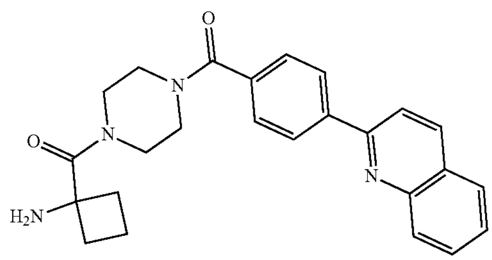 [SMILES: NC1(C(=O)N2CCN(C(=O)c3ccc(-c4ccc5ccccc5n4)cc3)CC2)CCC1] |
| 1-[(4-{[4-(qninolin-2-yl)phenyl]carbonyl}piperazin-1-yl)carbonyl]cyclopropan-1-amine | 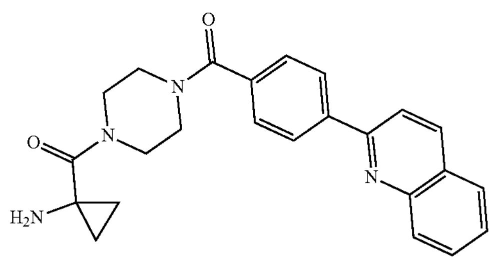 [SMILES: NC1(C(=O)N2CCN(C(=O)c3ccc(-c4ccc5ccccc5n4)cc3)CC2)CC1] |
| 1-[(4-{[4-(1H-1,3-benzodiazol-5-yl)phenyl]carbonyl}piperazin-1-yl)carbonyl]cyclobutan-1-amine | 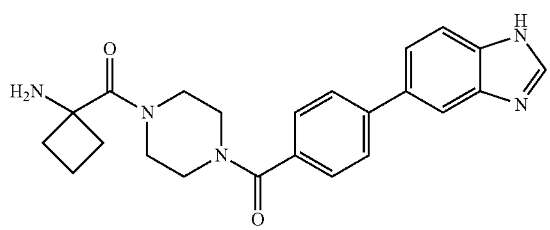 [SMILES: NC1(C(=O)N2CCN(C(=O)c3ccc(-c4ccc5[nH]cnc5c4)cc3)CC2)CCC1] |
| 1-[(4-{[4-(1H-1,3-benzodiazol-5-yl)phenyl]carbonyl}piperazin-1-yl)carbonyl]cyclopropan-1-amine | 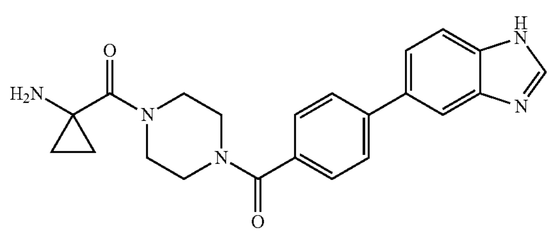 [SMILES: NC1(C(=O)N2CCN(C(=O)c3ccc(-c4ccc5[nH]cnc5c4)cc3)CC2)CC1] |
| 1-[(4-{[4-(1,3-benzothiazol-6-yl)phenyl]carbonyl}piperazin-1-yl)carbonyl]cyclobutan-1-amine | 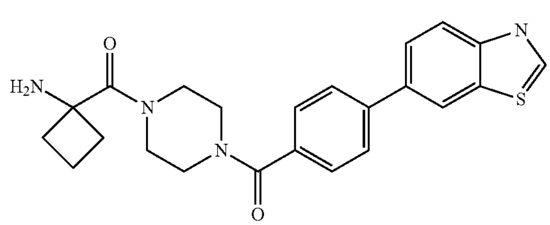 |

TABLE 1-continued

| IUPAC Name | Compound Structure |
|---|---|
| 1-[(4-{[4-(1,3-benzothiazol-6-yl)phenyl]carbonyl}piperazin-1-yl)carbonyl]cyclopropan-1-amine | 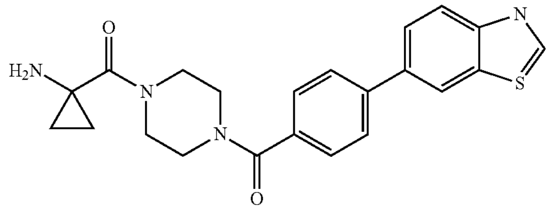 |
| 1-[(4-{[4-(1,3-benzoxazol-5-yl)phenyl]carbonyl}piperazin-1-yl)carbonyl]cyclobutan-1-amine | 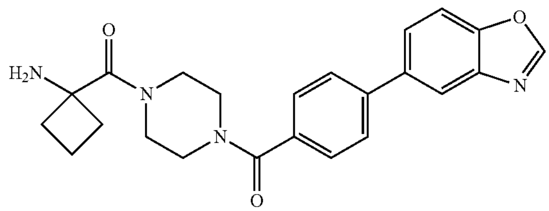 |
| 1-[(4-{[4-(1,3-benzoxazol-5-yl)phenyl]carbonyl}piperazin-1-yl)carbonyl]cyclopropan-1-amine | 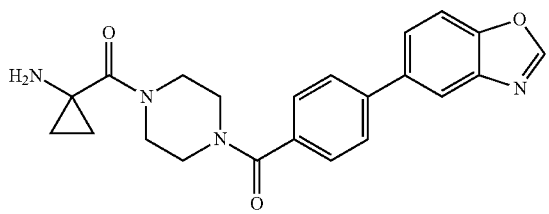 [SMILES: NC1(C(=O)N2CCN(C(=O)c3ccc(-c4ccc5ocnc5c4)cc3)CC2)CC1] |
| 1-[(4-{[4-(1,3-benzothiazol-5-yl)phenyl]carbonyl}piperazin-1-yl)carbonyl]cyclobutan-1-amine | 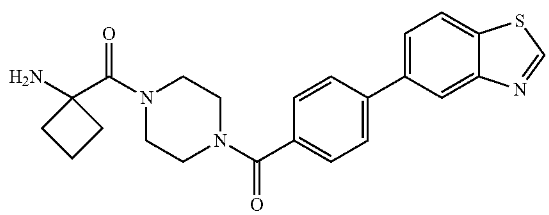 |
| 1-[(4-{[4-(1,3-benzothiazol-5-yl)phenyl]carbonyl}piperazin-1-yl)carbonyl]cyclopropan-1-amine | 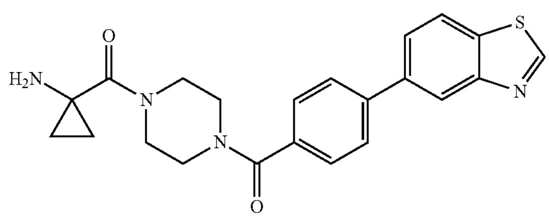 [SMILES: NC1(C(=O)N2CCN(C(=O)c3ccc(-c4ccc5scnc5c4)cc3)CC2)CC1] |
| 1-[(4-{[4-(1-methyl-1H-indazol-6-yl)phenyl]carbonyl}piperazin-1-yl)carbonyl]cyclobutan-1-amine | 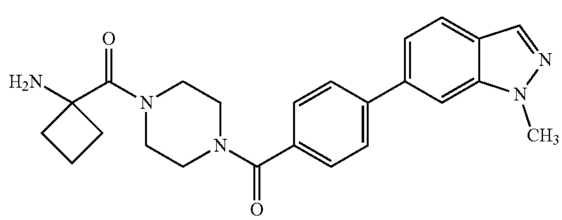 [SMILES: Cn1ncc2ccc(-c3ccc(C(=O)N4CCN(C(=O)C5(N)CCC5)CC4)cc3)cc21] |
| 1-[(4-{[4-(1-methyl-1H-indazol-6-yl)phenyl]carbonyl}piperazin-1-yl)carbonyl]cyclopropan-1-amine | 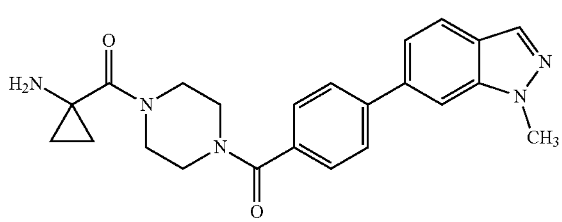 [SMILES: Cn1ncc2ccc(-c3ccc(C(=O)N4CCN(C(=O)C5(N)CC5)CC4)cc3)cc21] |

TABLE 1-continued

| IUPAC Name | Compound Structure |
|---|---|
| 3-[4-({4-[(1-aminocyclobutyl)carbonyl]piperazin-1-yl}carbonyl)phenyl]-N-cyclopropylbenzamide | 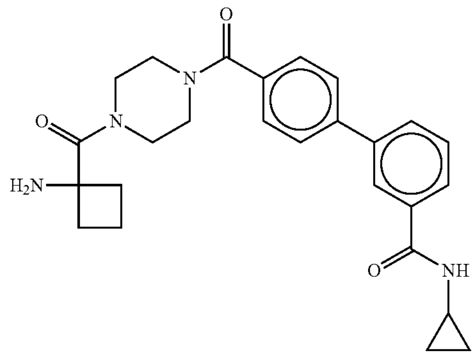 |
| 3-[4-({4-[(1-aminocyclopropyl)carbonyl]piperazin-1-yl}carbonyl)phenyl]-N-cyclopropylbenzamide | 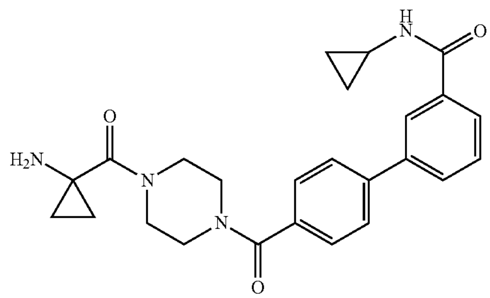 [SMILES: NC1(C(=O)N2CCN(C(=O)c3ccc(-c4cccc(C(=O)NC5CC5)c4)cc3)CC2)CC1] |
| 1-[(4-{[4-(2-methyl-2H-indazol-6-yl)phenyl]carbonyl}piperazin-1-yl)carbonyl]cyclobutan-1-amine | 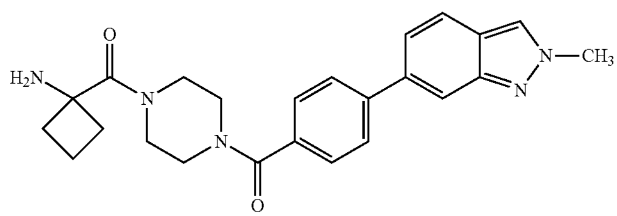 [SMILES: Cn1cc2ccc(-c3ccc(C(=O)N4CCN(C(=O)C5(N)CCC5)CC4)cc3)cc2n1] |
| 1-[(4-{[4-(2-methyl-2H-indazol-6-yl)phenyl]carbonyl}piperazin-1-yl)carbonyl]cyclopropan-1-amine | 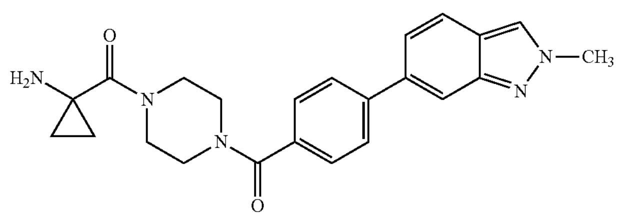 [SMILES: Cn1cc2ccc(-c3ccc(C(=O)N4CCN(C(=O)C5(N)CC5)CC4)cc3)cc2n1] |
| 1-[(4-{[4-(4-chloro-2-fluorophenyl)phenyl]carbonyl}piperazin-1-yl)carbonyl]cyclobutan-1-amine | 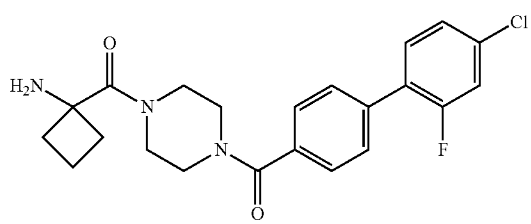 [SMILES: NC1(C(=O)N2CCN(C(=O)c3ccc(-c4ccc(Cl)cc4F)cc3)CC2)CCC1] |
| 1-[(4-{[4-(4-chloro-2-fluorophenyl)phenyl]carbonyl}piperazin-1-yl)carbonyl]cyclopropan-1-amine | 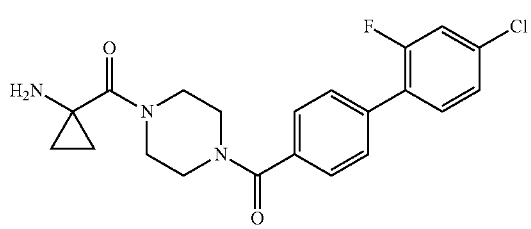 [SMILES: NC1(C(=O)N2CCN(C(=O)c3ccc(-c4ccc(Cl)cc4F)cc3)CC2)CC1] |

TABLE 1-continued

| IUPAC Name | Compound Structure |
| --- | --- |
| 1-[(4-{[4-(5-chloro-2-fluorophenyl)phenyl]carbonyl}piperazin-1-yl)carbonyl]cyclobutan-1-amine | 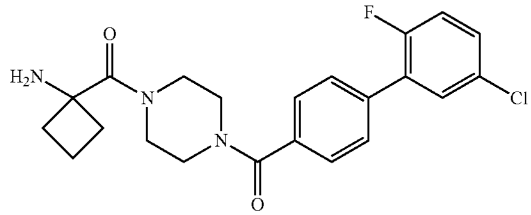 [SMILES: NC1(C(=O)N2CCN(C(=O)c3ccc(-c4cc(Cl)ccc4F)cc3)CC2)CCC1] |
| 1-[(4-{[4-(5-chloro-2-fluorophenyl)phenyl]carbonyl}piperazin-1-yl)carbonyl]cyclopropan-1-amine | 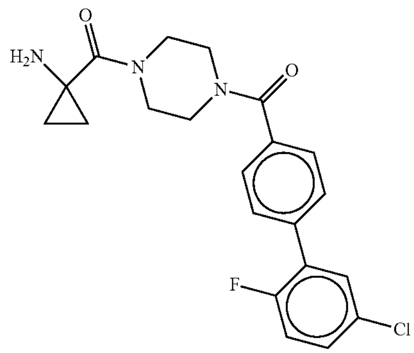 |
| 3-{[4-({4-[3-(cyclopropanesulfonyl)phenyl]phenyl}carbonyl)piperazin-1-yl]carbonyl}oxetan-3-ol | 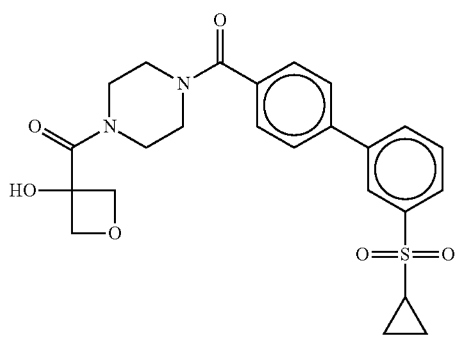 |
| 3-{[4-({4-[3-(cyclopropanesulfonyl)phenyl]phenyl}carbonyl)piperazin-1-yl]carbonyl}oxetan-3-amine | 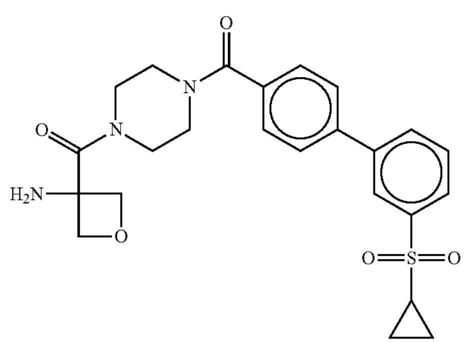 |
| 3-({4-[(4-{3-chloroimidazo[1,2-a]pyridin-2-yl}phenyl)carbonyl]piperazin-1-yl}carbonyl)oxetan-3-ol | 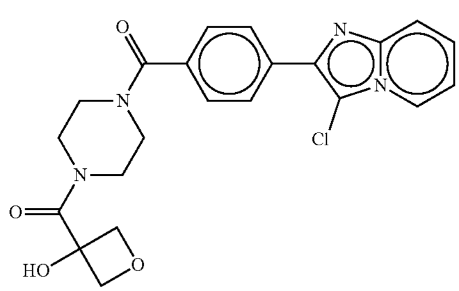 |

TABLE 1-continued

| IUPAC Name | Compound Structure |
|---|---|
| 3-({4-[(4-{3-chloroimidazo[1,2-a]pyridin-2-yl}phenyl)carbonyl]piperazin-1-yl}carbonyl)oxetan-3-amine | 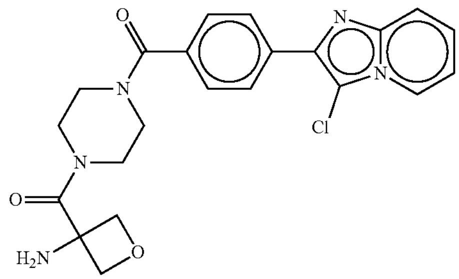 |
| 3-[(4-{[4-(3-cyclopropoxyphenyl)phenyl]carbonyl}piperazin-1-yl)carbonyl]oxetan-3-ol | 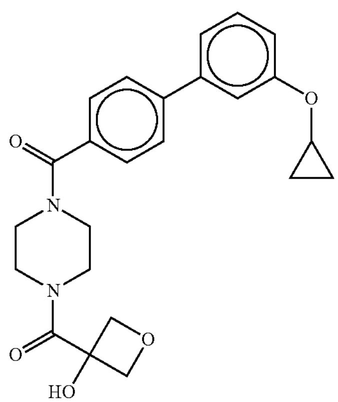 |
| 3-[(4-{[4-(3-cyclopropoxyphenyl)phenyl]carbonyl}piperazin-1-yl)carbonyl]oxetan-3-amine | 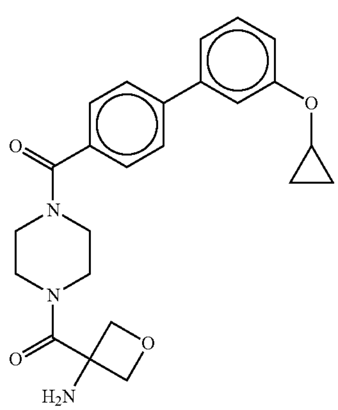 |
| N-{3-[4-({4-[(3-hydroxyoxetan-3-yl)carbonyl]piperazin-1-yl}carbonyl)phenyl]phenyl}cyclopropanecarboxamide | 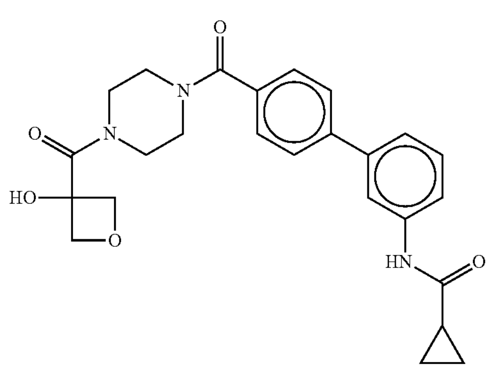 |

TABLE 1-continued

| IUPAC Name | Compound Structure |
|---|---|
| N-{3-[4-({4-[(3-aminooxetan-3-yl)carbonyl]piperazin-1-yl}carbonyl)phenyl]phenyl}cyclopropanecarboxamide | 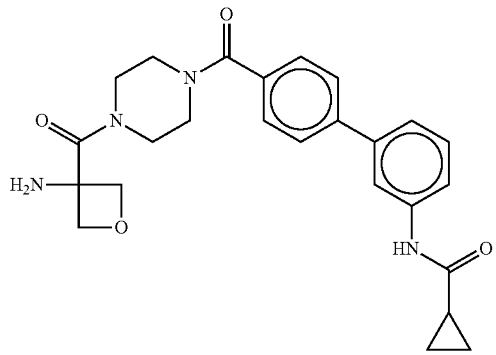 |
| 3-[4-({4-[(3-hydroxyoxetan-3-yl)carbonyl]piperazin-1-yl}carbonyl)phenyl]-1,2-dihydroquinolin-2-one | 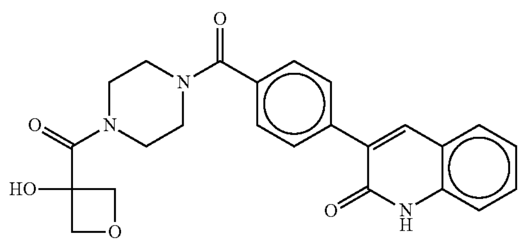 |
| 3-[4-({4-[(3-aminooxetan-3-yl)carbonyl]piperazin-1-yl}carbonyl)phenyl]-1,2-dihyroquinolin-2-one | 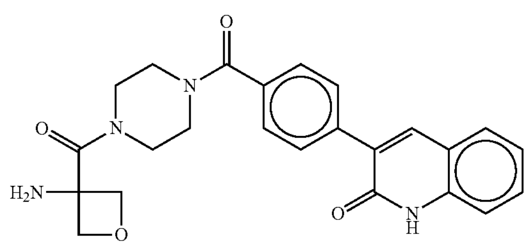 |
| 5-[4-({4-[(3-hydroxyoxetan-3-yl)carbonyl]piperazin-1-yl}carbonyl)phenyl]-1H-indole-2-carbonitrile | 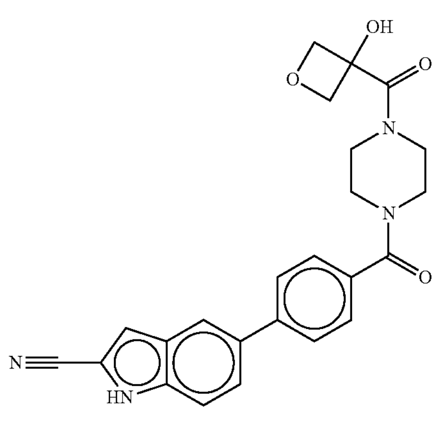 |

TABLE 1-continued
| IUPAC Name | Compound Structure |
|---|---|
| 5-[4-({4-[(3-aminooxetan-3-yl)carbonyl]piperazin-1-yl}carbonyl)phenyl]-1H-indole-2-carbonitrile | 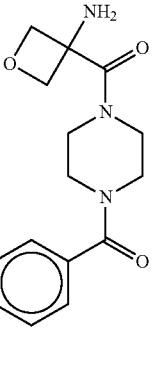 |
| 3-[(4-{[4-(1-methyl-1H-1,3-benzodiazol-5-yl)phenyl]carbonyl}piperazin-1-yl)carbonyl]oxetan-3-ol | 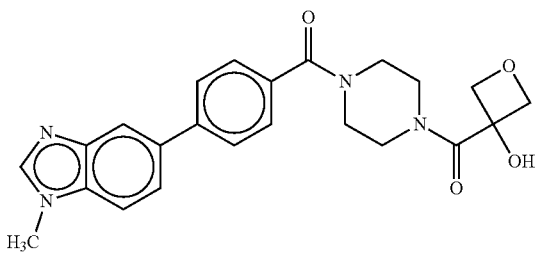 |
| 3-[(4-{[4-(1-methyl-1H-1,3-benzodiazol-5-yl)phenyl]carbonyl}piperazin-1-yl)carbonyl]oxetan-3-amine | 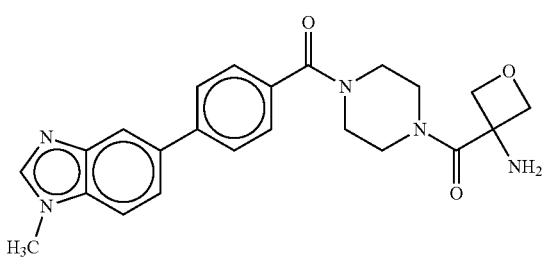 |
| 3-({4-[(4-{imidazo[1,2-b]pyridazin-6-yl}phenyl)carbonyl]piperazin-1-yl}carbonyl)oxetan-3-ol | 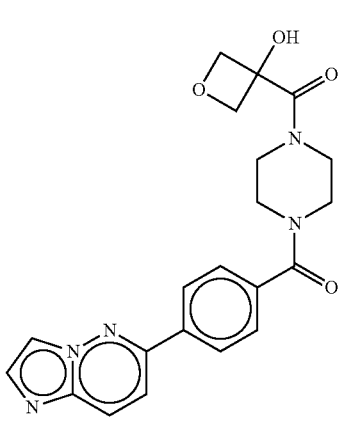 |

TABLE 1-continued

| IUPAC Name | Compound Structure |
|---|---|
| 3-({4-[(4-{imidazo[1,2-b]pyridazin-6-yl}phenyl)carbonyl]piperazin-1-yl}carbonyl)oxetan-3-amine | |
| 3-({4-[(4-{furo[3,2-b]pyridin-5-yl}phenyl)carbonyl]piperazin-1-yl}carbonyl)oxetan-3-ol | 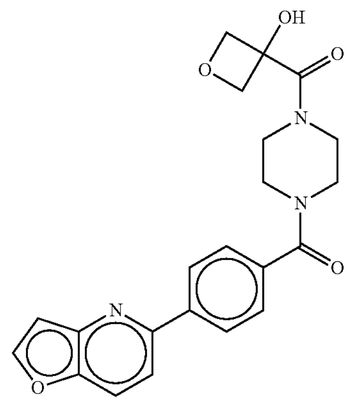 |
| 3-({4-[(4-{furo[3,2-b]pyridin-5-yl}phenyl)carbonyl]piperazin-1-yl}carbonyl)oxetan-3-amine | 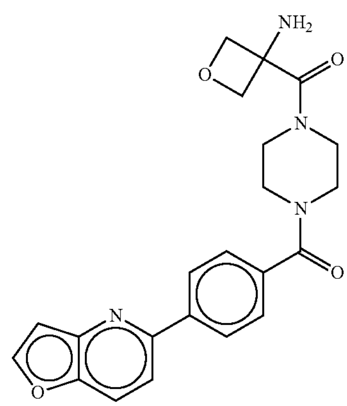 |
| 3-[(4-{[4-(1H-indazol-3-yl)phenyl]carbonyl}piperazin-1-yl)carbonyl]oxetan-3-ol | 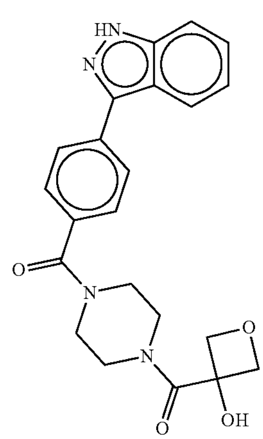 |

TABLE 1-continued

| IUPAC Name | Compound Structure |
|---|---|
| 3-[(4-{[4-(1H-indazol-3-yl)phenyl]carbonyl}piperazin-1-yl)carbonyl]oxetan-3-amine | 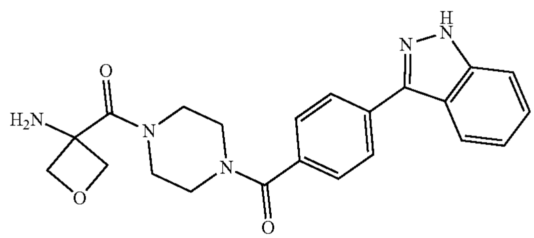 [SMILES: NC1(C(=O)N2CCN(C(=O)c3ccc(-c4n[nH]c5ccccc45)cc3)CC2)COC1] |
| 3-[(4-{[4-(1,3-dimethyl-1H-indazol-5-yl)phenyl]carbonyl}piperazin-1-yl)carbonyl]oxetan-3-ol | 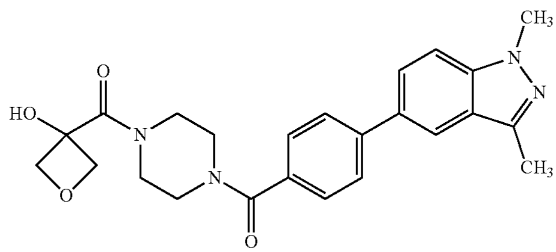 [SMILES: Cc1nn(C)c2ccc(-c3ccc(C(=O)N4CCN(C(=O)C5(O)COC5)CC4)cc3)cc12] |
| 3-[(4-{[4-(1,3-dimethyl-1H-indazol-5-yl)phenyl]carbonyl}piperazin-1-yl)caxbonyl]oxetan-3-amine | 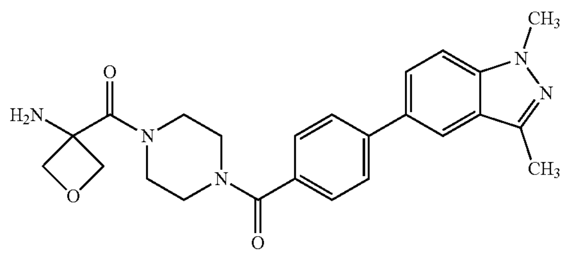 [SMILES: Cc1nn(C)c2ccc(-c3ccc(C(=O)N4CCN(C(=O)C5(N)COC5)CC4)cc3)cc12] |
| N-{3-[4-({4-[(3-hydroxyoxetan-3-yl)carbonyl]piperazin-1-yl}carbonyl)phenyl]phenyl}cyclopropanesulfonamide | 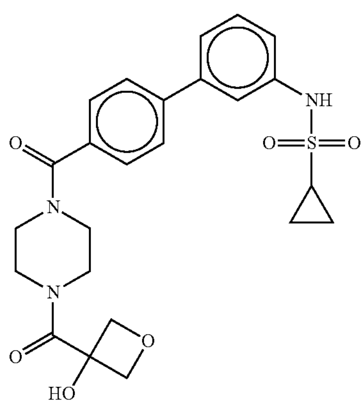 |
| N-{3-[4-({4-[{3-aminooxetan-3-yl)carbonyl]piperazin-1-yl}carbonyl)phenyl]phenyl}cyclopropanesulfonamide | 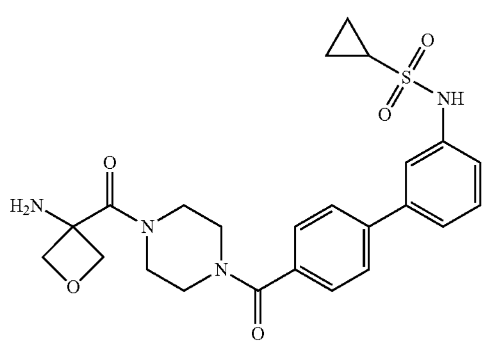 |

TABLE 1-continued

| IUPAC Name | Compound Structure |
|---|---|
| 3-[(4-{[4-(6-fluoro-1,3-benzoxazol-2-yl)phenyl]carbonyl}piperazin-1-yl)carbonyl]oxetan-3-ol | 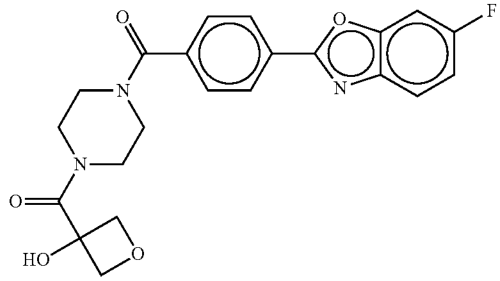 |
| 3-[(4-{[4-(6-fluoro-1,3-benzoxazol-2-yl)phenyl]carbonyl}piperazin-1-yl)carbonyl]oxetan-3-amine | 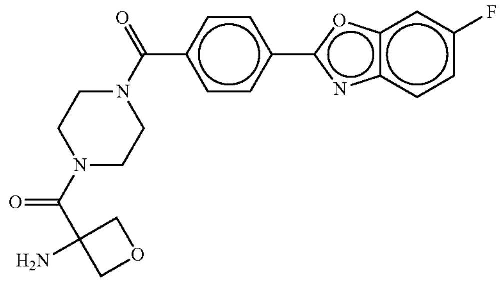 |
| 3-[(4-{[4-(6-chloro-1,3-benzoxazol-2-yl)phenyl]carbonyl}piperazin-1-yl)carbonyl]oxetan-3-ol | 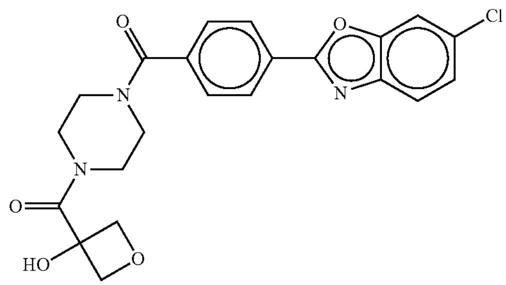 |
| 3-[(4-{[4-(6-chloro-1,3-benzoxazol-2-yl)phenyl]carbonyl}piperazin-1-yl)carbonyl]oxetan-3-amine | 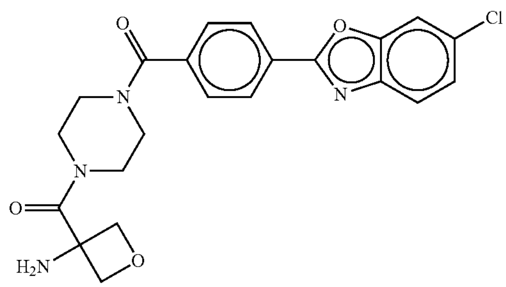 |
| 5-[4-([4-[(3-hydroxyoxetan-3-yl)carbonyl]piperazin-1-yl}carbonyl)phenyl]-1H-indole-3-carbonitrile | |

TABLE 1-continued

| IUPAC Name | Compound Structure |
|---|---|
| 5-[4-({4-[(3-aminooxetan-3-yl)carbonyl]piperazin-1-yl}carbonyl)phenyl]-1H-indole-3-carbonitrile | 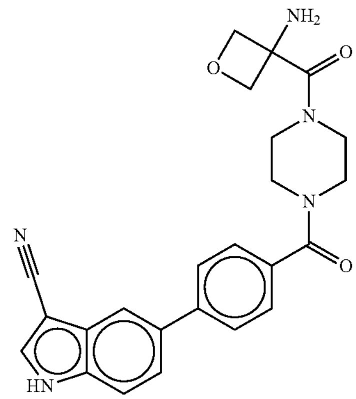 |
| 3-[(4-{[4-(1,3-benzothiazol-2-yl)phenyl]carbonyl}piperazin-1-yl)carbonyl]oxetan-3-ol | 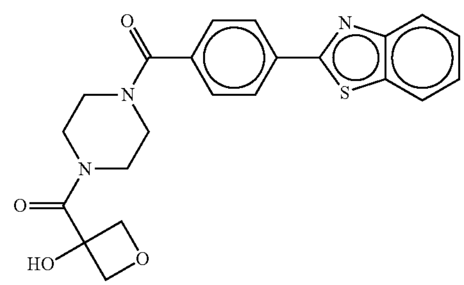 |
| 3-[(4-{[4-(1,3-benzothiazol-2-yl)phenyl]carbonyl}piperazin-1-yl)carbonyl]oxetan-3-amine | 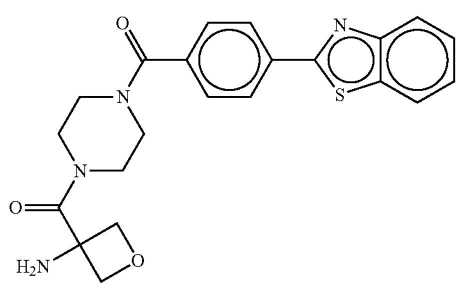 |
| 3-[(4-{[4-(quinolin-2-yl)phenyl]carbonyl}piperazin-1-yl)carbonyl]oxetan-3-ol | 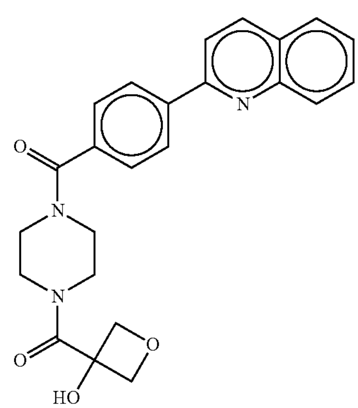 |

TABLE 1-continued

| IUPAC Name | Compound Structure |
|---|---|
| 3-[(4-{[4-{quinolin-2-yl}phenyl]carbonyl}piperazin-1-yl)carbonyl]oxetan-3-amine | |
| 3-[(4-{[4-(1H-1,3-benzodiazol-5-yl)phenyl]carbonyl}piperazin-1-yl)carbonyl]oxetan-3-ol | 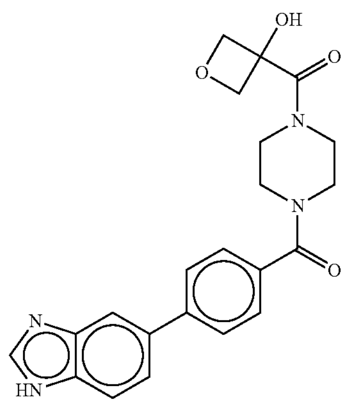 |
| 3-[(4-{[4-(1H-1,3-benzodiazol-5-yl)phenyl]carbonyl}piperazin-1-yl)carbonyl]oxetan-3-amine | 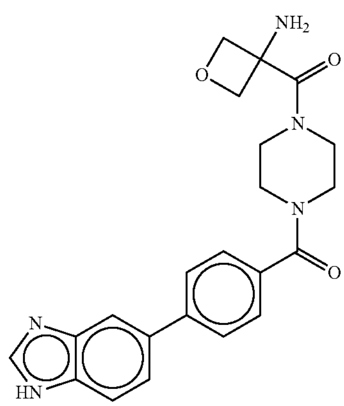 |
| 3-[(4-{[4-(1,3-benzothiazol-6-yl)phenyl]carbonyl}piperazin-1-yl)carbonyl]oxetan-3-ol | 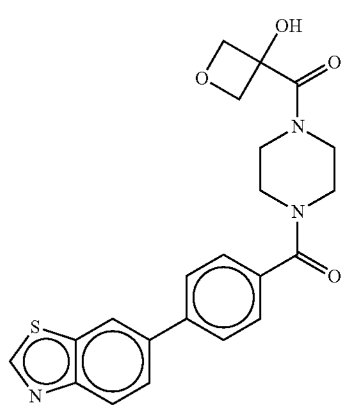 |

TABLE 1-continued
| IUPAC Name | Compound Structure |
|---|---|
| 3-[(4-{[4-(1,3-benzothiazol-6-yl)phenyl]carbonyl}piperazin-1-yl)carbonyl]oxetan-3-amine | 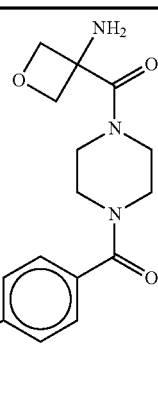 |
| 3-[(4-{[4-(1,3-benzoxazol-5-yl)phenyl]carbonyl}piperazin-1-yl)carbonyl]oxetan-3-ol | 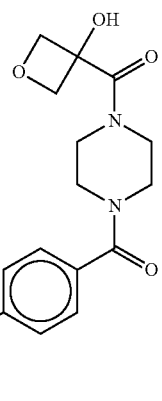 |
| 3-[(4-{[4-(1,3-benzoxazol-5-yl)phenyl]carbonyl}piperazin-1-yl)carbonyl]oxetan-3-amine | 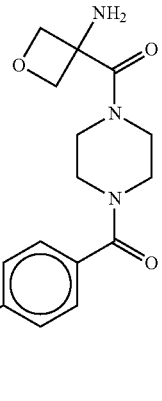 |
| 3-[(4-{[4-(1,3-benzothiazol-5-yl)phenyl]carbonyl}piperazin-1-yl)carbonyl]oxetan-3-ol | 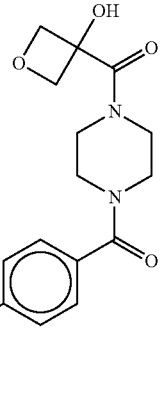 |

TABLE 1-continued

| IUPAC Name | Compound Structure |
|---|---|
| 3-[(4-{[4-(1,3-benzothiazol-5-yl)phenyl]carbonyl}piperazin-1-yl)carbonyl]oxetan-3-amine | 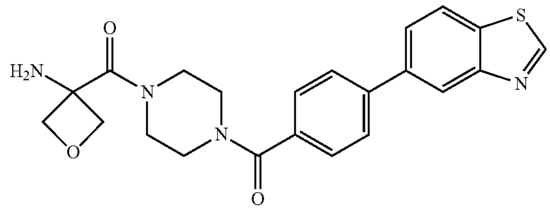 |
| 3-[(4-{[4-(1-methyl-1H-indazol-6-yl)phenyl]carbonyl}piperazin-1-yl)carbonyl]oxetan-3-ol | 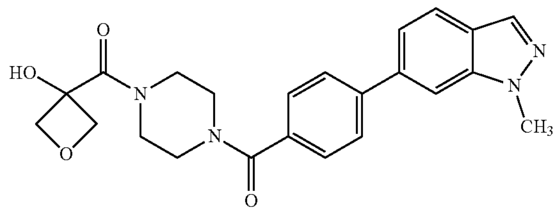 [SMILES: Cn1ncc2ccc(-c3ccc(C(=O)N4CCN(C(=O)C5(O)COC5)CC4)cc3)cc21] |
| 3-[(4-{[4-(1-methyl-1H-indazol-6-yl)phenyl]carbonyl}piperazin-1-yl)carbonyl]oxetan-3-amine | 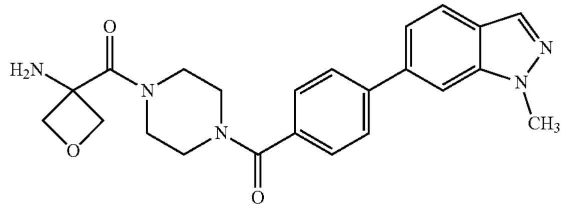 [SMILES: Cn1ncc2ccc(-c3ccc(C(=O)N4CCN(C(=O)C5(N)COC5)CC4)cc3)cc21] |
| N-cyclopropyl-3-[4-({4-[(3-hydroxyoxetan-3-yl)carbonyl]piperazin-1-yl}carbonyl)phenyl]benzamide | 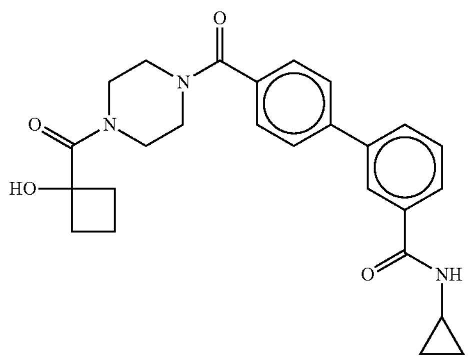 |
| 3-[4-({4-[(3-aminooxetan-3-yl)carbonyl]piperazin-1-yl}carbonyl)phenyl]-N-cyclopropylbenzamide | 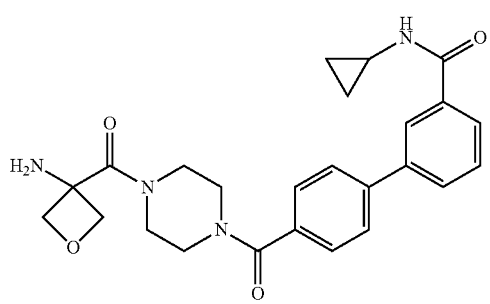 [SMILES: NC1(C(=O)N2CCN(C(=O)c3ccc(-c4cccc(C(=O)NC5CC5)c4)cc3)CC2)COC1] |
| 3-[(4-{[4-(2-methyl-2H-indazol-6-yl)phenyl]carbonyl}piperazin-1-yl)carbonyl]oxetan-3-ol | 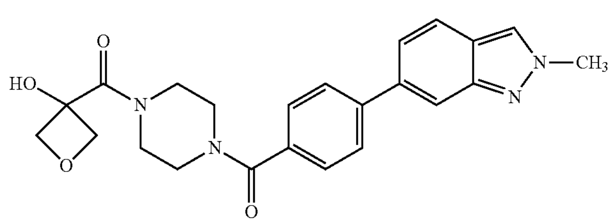 [SMILES: Cn1cc2ccc(-c3ccc(C(=O)N4CCN(C(=O)C5(O)COC5)CC4)cc3)cc2n1] |

TABLE 1-continued

| IUPAC Name | Compound Structure |
| --- | --- |
| 3-[(4-{[4-(2-methyl-2H-indazol-6-yl)phenyl]carbonyl}piperazin-1-yl)carbonyl]oxetan-3-amine | 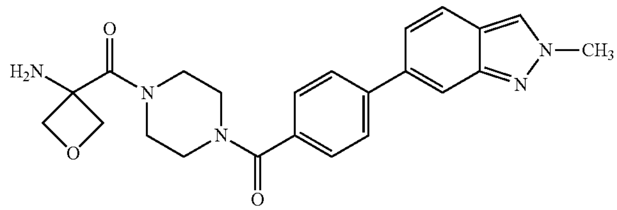 [SMILES: Cn1cc2ccc(-c3ccc(C(=O)N4CCN(C(=O)C5(N)COC5)CC4)cc3)cc2n1] |
| 3-[(4-{[4-(4-chloro-2-fluorophenyl)phenyl]carbonyl}piperazin-1-yl)carbonyl]oxetan-3-ol | 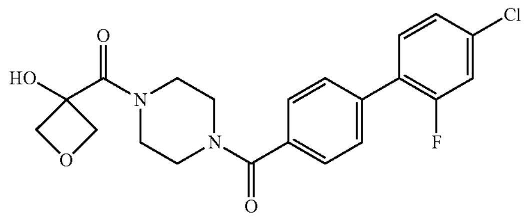 [SMILES: O=C(c1ccc(-c2ccc(Cl)cc2F)cc1)N1CCN(C(=O)C2(O)COC2)CC1] |
| 3-[(4-{[4-(4-chloro-2-fluorophenyl)phenyl]carbonyl}piperazin-1-yl)carbonyl]oxetan-3-amine | 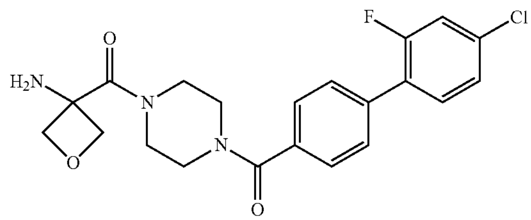 [SMILES: NC1(C(=O)N2CCN(C(=O)c3ccc(-c4ccc(Cl)cc4F)cc3)CC2)COC1] |
| 3-[(4-{[4-(5-chloro-2-fluorophenyl)phenyl]carbonyl}piperazin-1-yl)carbonyl]oxetan-3-ol | 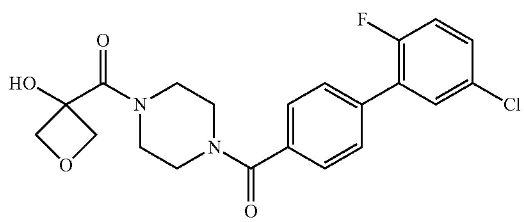 [SMILES: O=C(c1ccc(-c2cc(Cl)ccc2F)cc1)N1CCN(C(=O)C2(O)COC2)CC1] |
| 3-[(4-{[4-(5-chloro-2-fluorophenyl)phenyl]carbonyl}piperazin-1-yl)carbonyl]oxetan-3-amine | 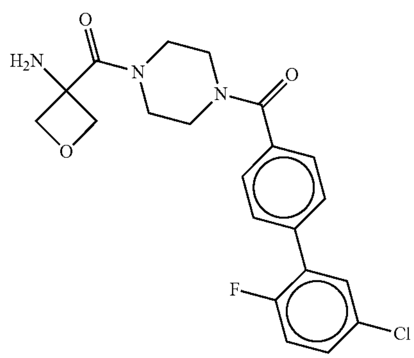 |
| 1-({4-[(4-{5-chloro-[1,3]thiazolo[5,4-d][1,3]thiazol-2-yl}phenyl)carbonyl]piperazin-1-yl}carbonyl)cyclopropan-1-ol | 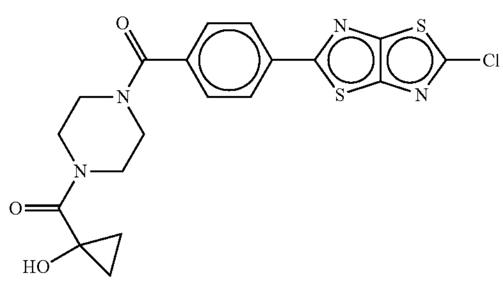 |

TABLE 1-continued

| IUPAC Name | Compound Structure |
| --- | --- |
| 1-{[4-({4-[4-(2H-1,2,3,4-tetrazol-5-yl)phenyl]phenyl}carbonyl)piperazin-1-yl]carbonyl}cyclopropan-1-ol | 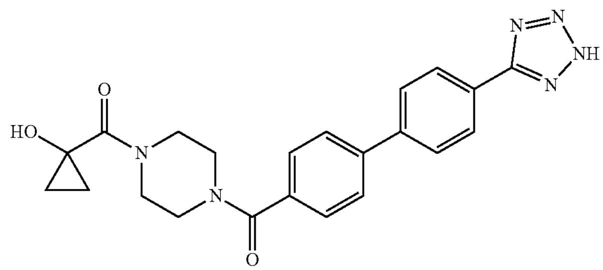 [SMILES: O=C(c1ccc(-c2ccc(-c3nn[nH]n3)cc2)cc1)N1CCN(C(=O)C2(O)CC2)CC1] |
| 1-({4-[(4-{imidazo[2,1-b][1,3,4]thiadiazol-2-yl}phenyl)carbonyl]piperazin-1-yl}carbonyl)cyclopropan-1-ol | 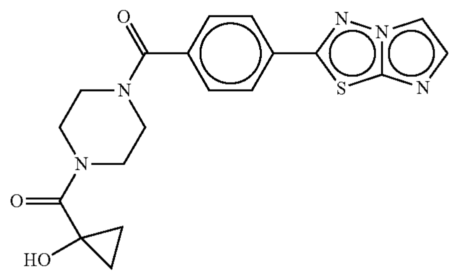 |
| 1-({4-[(4-{6H-thieno[2,3-b]pyrrol-2-yl}phenyl)carbonyl]piperazin-1-yl}carbonyl)cyclopropan-1-ol | |
| 1-({4-[(4-{4H-thieno[3,2-b]pyrrol-3-yl}phenyl)carbonyl]piperazin-1-yl}carbonyl)cyclopropan-1-ol | 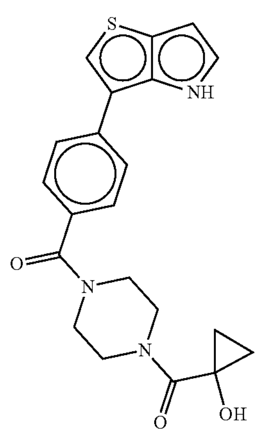 |
| 2-[4-({4-[(1-hydroxycyclopropyl)carbonyl]piperazin-1-yl}carbonyl)phenyl]-3H-pyrrolizin-3-one | 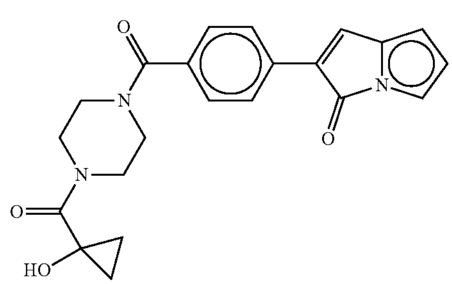 |

TABLE 1-continued

| IUPAC Name | Compound Structure |
|---|---|
| 6-[4-({4-[(1-hydroxycyclopropyl)carbonyl]piperazin-1-yl}carbonyl)phenyl]-3H-pyrrolizin-3-one | 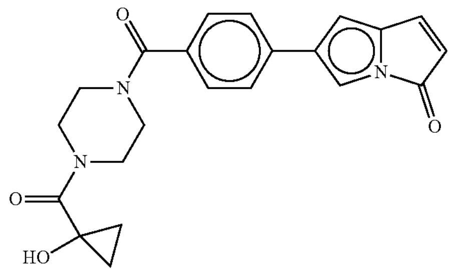 |
| 1-[(4-{[4-(1-methanesulfonyl-1H-indol-6-yl)phenyl]carbonyl}piperazin-1-yl)carbonyl]cyclopropan-1-ol | 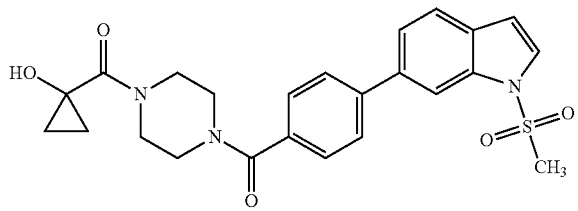 [SMILES: CS(=O)(=O)n1ccc2ccc(-c3ccc(C(=O)N4CCN(C(=O)C5(O)CC5)CC4)cc3)cc21] |
| 1-{[4-({4-[4-(1-methyl-1H-pyrazol-5-yl)phenyl]phenyl}carbonyl)piperazin-1-yl]carbonyl}cyclopropan-1-ol | 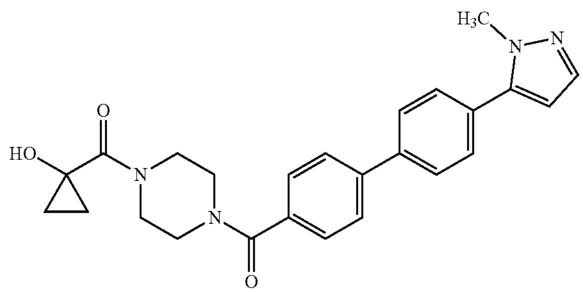 [SMILES: Cn1nccc1-c1ccc(-c2ccc(C(=O)N3CCN(C(=O)C4(O)CC4)CC3)cc2)cc1] |
| 1-{[4-({4-[4-(1-methyl-1H-pyrazol-3-yl)phenyl]phenyl}carbonyl)piperazin-1-yl]carbonyl}cyclopropan-1-ol | 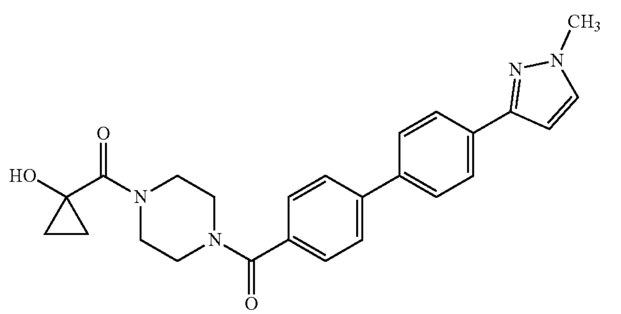 [SMILES: Cn1ccc(-c2ccc(-c3ccc(C(=O)N4CCN(C(=O)C5(O)CC5)CC4)cc3)cc2)n1] |
| 1-{[4-([4-[4-(1-methyl-1H-pyrazol-4-yl)phenyl]phenyl}carbonyl)piperazin-1-yl]carbonyl}cyclopropan-1-ol | 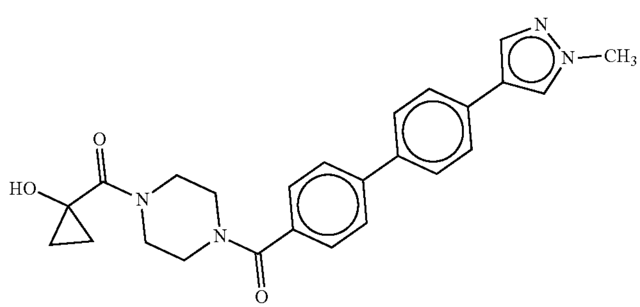 |

TABLE 1-continued

| IUPAC Name | Compound Structure |
|---|---|
| 1-[(4-{[4-(1-ethyl-1H-indazol-5-yl)phenyl]carbonyl}piperazin-1-yl)carbonyl]cyclopropan-1-ol | 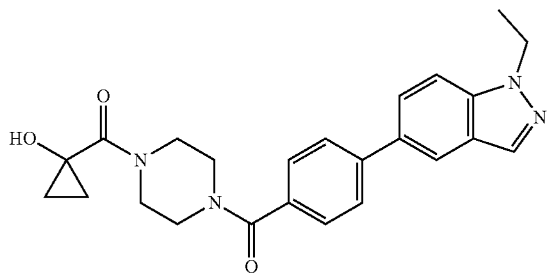 [SMILES: CCn1ncc2cc(-c3ccc(C(=O)N4CCN(C(=O)C5(O)CC5)CC4)cc3)ccc21] |
| 1-[(4-{[4-(1-cyclobutyl-1H-indazol-5-yl)phenyl]carbonyl}piperazin-1-yl)carbonyl]cyclopropan-1-ol | 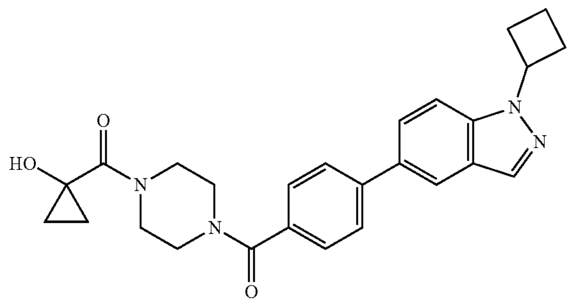 [SMILES: O=C(c1ccc(-c2ccc3c(cnn3C3CCC3)c2)cc1)N1CCN(C(=O)C2(O)CC2)CC1] |
| 1-{[4-({4-[1-(oxetan-3-yl)-1H-indazol-5-yl]phenyl}carbonyl)piperazin-1-yl]carbonyl}cyclopropan-1-ol | 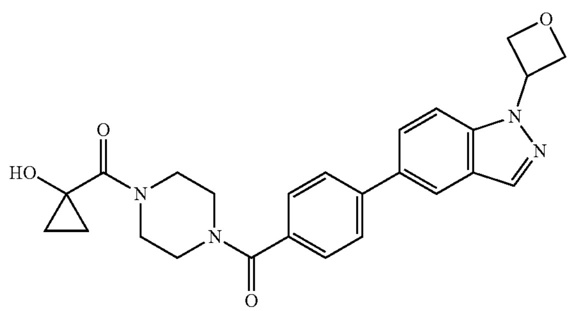 [SMILES: O=C(c1ccc(-c2ccc3c(cnn3C3COC3)c2)cc1)N1CCN(C(=O)C2(O)CC2)CC1] |
| 1-{[4-({4-[1-(propan-2-yl)-1H-indazol-5-yl]phenyl}carbonyl)piperazin-1-yl]carbonyl}cyclopropan-1-ol | 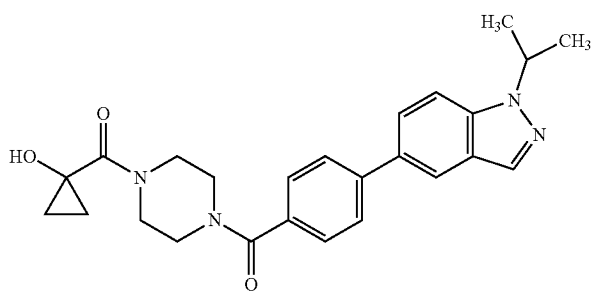 [SMILES: CC(C)n1ncc2cc(-c3ccc(C(=O)N4CCN(C(=O)C5(O)CC5)CC4)cc3)ccc21] |
| 1-{[4-({4-[1-(2-methoxyethyl)-1H-indazol-5-yl]phenyl}carbonyl)piperazin-1-yl]carbonyl}cyclopropan-1-ol | 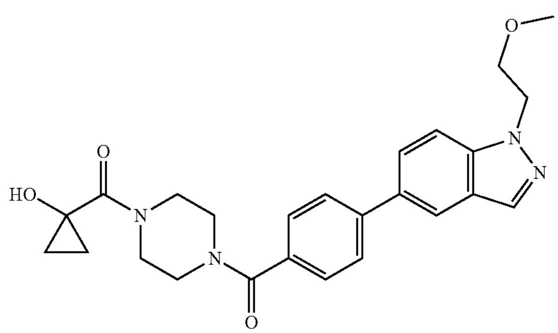 [SMILES: COCCn1ncc2cc(-c3ccc(C(=O)N4CCN(C(=O)C5(O)CC5)CC4)cc3)ccc21] |

TABLE 1-continued

| IUPAC Name | Compound Structure |
|---|---|
| 1-{[4-({4-[1-(cyclopropylmethyl)-1H-indazol-5-yl]phenyl}carbonyl)piperazin-1-yl]carbonyl}cyclopropan-1-ol | 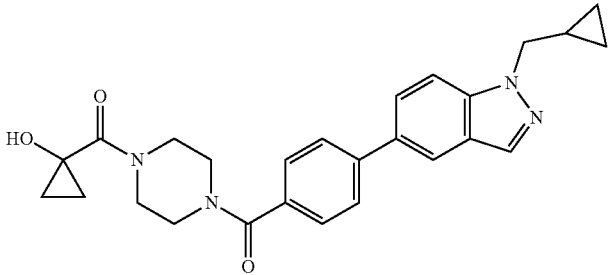 [SMILES: O=C(c1ccc(-c2ccc3c(cnn3CC3CC3)c2)cc1)N1CCN(C(=O)C2(O)CC2)CC1] |
| 1-[(4-{[4-(1-propyl-1H-indazol-5-yl)phenyl]carbonyl}piperazin-1-yl)carbonyl]cyclopropan-1-ol | 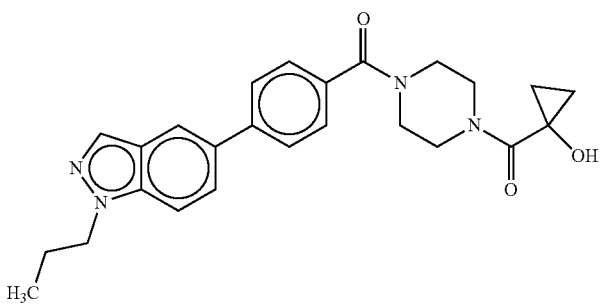 |
| 1-{[4-({4-[1-(cyclobutylmethyl)-1H-indazol-5-yl]phenyl}carbonyl)piperazin-1-yl]carbonyl}cyclopropan-1-ol | 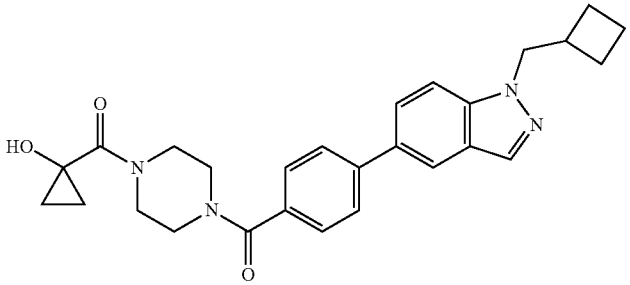 [SMILES: O=C(c1ccc(-c2ccc3c(cnn3CC3CCC3)c2)cc1)N1CCN(C(=O)C2(O)CC2)CC1] |
| 1-{[4-({4-[1-(oxetan-3-ylmethyl)-1H-indazol-5-yl]phenyl}carbonyl)piperazin-1-yl]carbonyl}cyclopropan-1-ol | 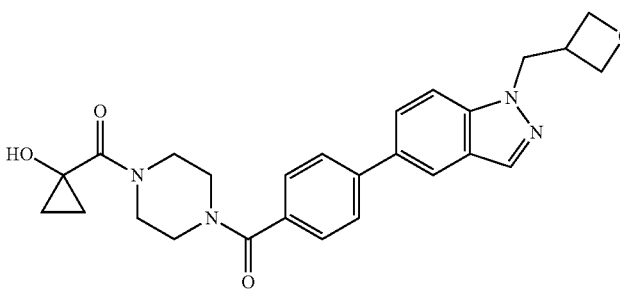 |
| 1-{[4-({4-[1-(2-hydroxyethyl)-1H-indazol-5-yl]phenyl}carbonyl)piperazin-1-yl]carbonyl}cyclopropan-1-ol | 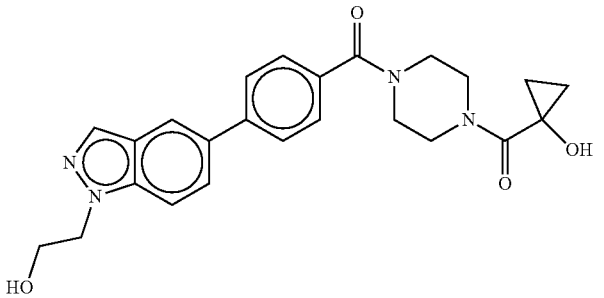 |

TABLE 1-continued

| IUPAC Name | Compound Structure |
|---|---|
| 1-{[4-({4-[4-(1H-pyrazol-5-yl)phenyl]phenyl}carbonyl)piperazin-1-yl]carbonyl}cyclopropan-1-ol | 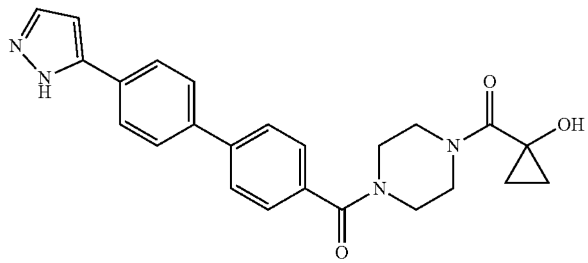 [SMILES: O=C(c1ccc(-c2ccc(-c3ccn[nH]3)cc2)cc1)N1CCN(C(=O)C2(O)CC2)CC1] |
| 1-{[4-({4-[4-(1H-pyrazol-4-yl)phenyl]phenyl}carbonyl)piperazin-1-yl]carbonyl}cyclopropan-1-ol | 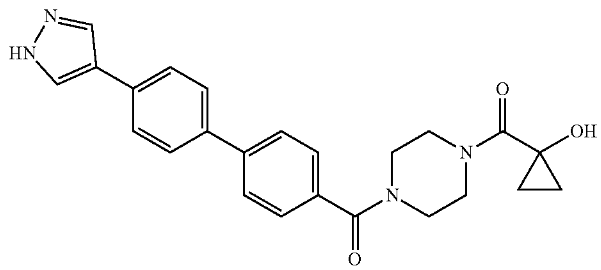 [SMILES: O=C(c1ccc(-c2ccc(-c3cn[nH]c3)cc2)cc1)N1CCN(C(=O)C2(O)CC2)CC1] |
| 1-{[4-({4-[4-(2-methyl-2H-1,2,3-triazol-4-yl)phenyl]phenyl}carbonyl)piperazin-1-yl]carbonyl}clopropan-1-ol | 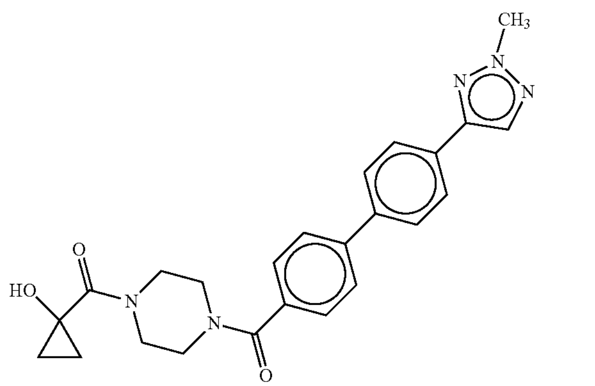 |
| 1-{[4-({4-[4-(1-methyl-1H-1,2,3-triazol-4-yl)phenyl]phenyl}carbonyl)piperazin-1-yl]carbonyl}cyclopropan-1-ol | 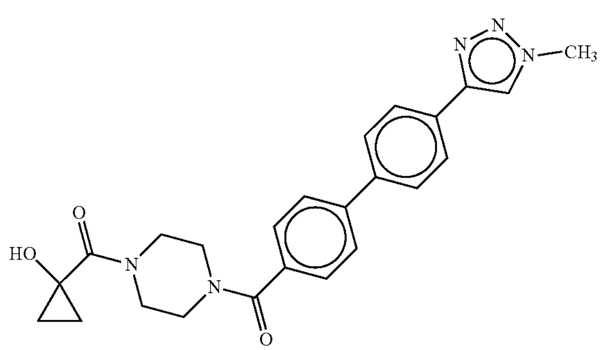 |
| 1-[(4-{[4-(1-methanesulfonyl-1H-indol-5-yl)phenyl]carbonyl}piperazin-1-yl)carbonyl]cyclopropan-1-ol | 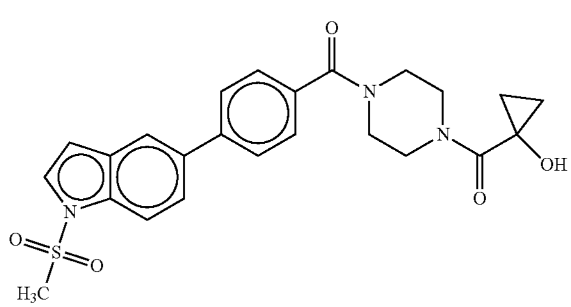 |

TABLE 1-continued

| IUPAC Name | Compound Structure |
| --- | --- |
| 1-{[4-({4-[1-(cyclopropanesulfonyl)-1H-indol-5-yl]phenyl}carbonyl)piperazin-1-yl]carbonyl}cyclopropan-1-ol | 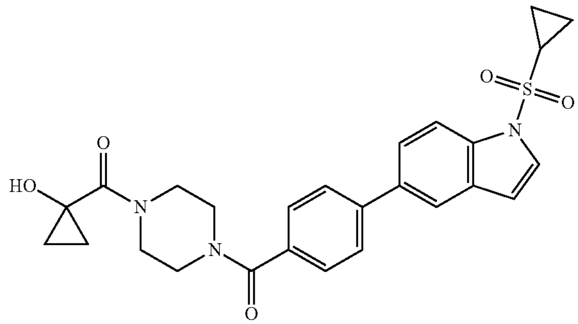 [SMILES: O=C(c1ccc(-c2ccc3c(ccn3S(=O)(=O)C3CC3)c2)cc1)N1CCN(C(=O)C2(O)CC2)CC1] |
| 1-{[4-({4-[1-(cyclopropanesulfonyl)-1H-indol-6-yl]phenyl}carbonyl)piperazin-1-yl]carbonyl}cyclopropan-1-ol | 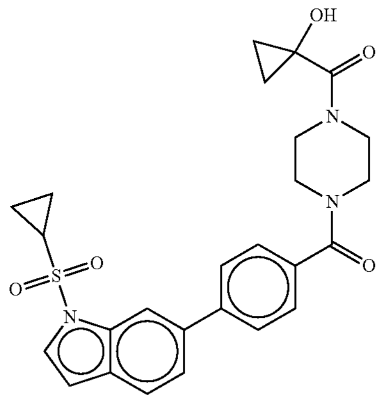 |
| 1-{[4-({4-[2-(hydroxymethyl)-1H-indol-5-yl]phenyl}carbonyl)piperazin-1-yl]carbonyl}cyclopropan-1-ol | 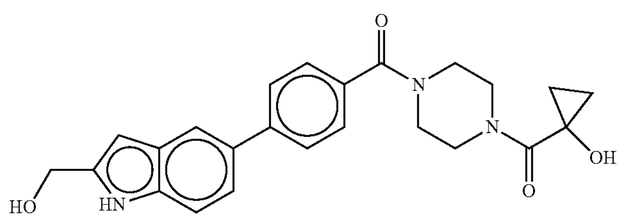 |
| 2-{5-[4-({4-[(1-hydroxycyclopropyl)carbonyl]piperazin-1-yl}carbonyl)phenyl]-1H-indol-3-yl}acetonitrile | 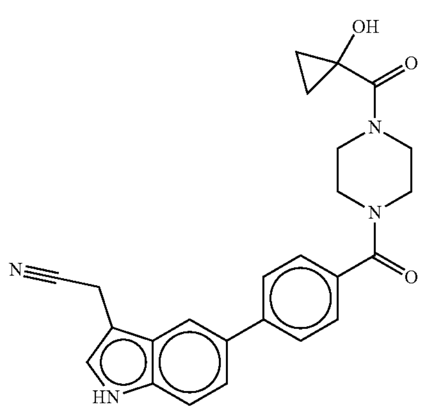 |

TABLE 1-continued

| IUPAC Name | Compound Structure |
|---|---|
| 1-{[4-({4-[3-(2-hydroxyethyl)-1H-indol-5-yl]phenyl}carbonyl)piperazin-1-yl]carbonyl}cyclopropan-1-ol | 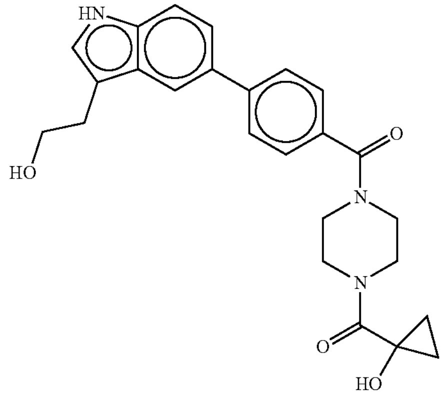 |
| 5-[4-({4-[(1-hydroxycyclopropyl)carbonyl]piperazin-1-yl}carbonyl)phenyl]-1-benzofuran-2-carbonitrile | 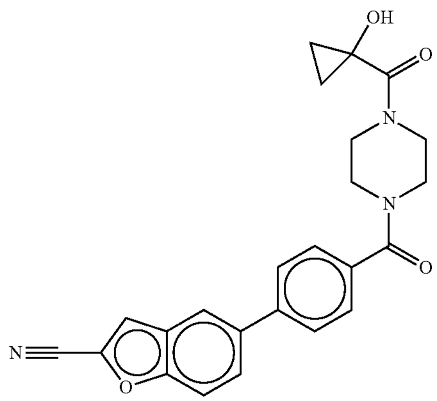 |
| 1-[(4-{[4-(3-amino-1-methyl-1H-indazol-6-yl)phenyl]carbonyl}piperazin-1-yl)carbonyl]cyclopropan-1-ol | 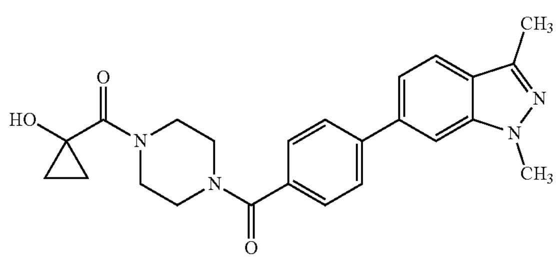 [SMILES: Cc1nn(C)c2cc(-c3ccc(C(=O)N4CCN(C(=O)C5(O)CC5)CC4)cc3)ccc12] |
| 1-[(4-{[4-(1-aminoisoquinolin-6-yl)phenyl]carbonyl}piperazin-1-yl)carbonyl]cyclopropan-1-ol | 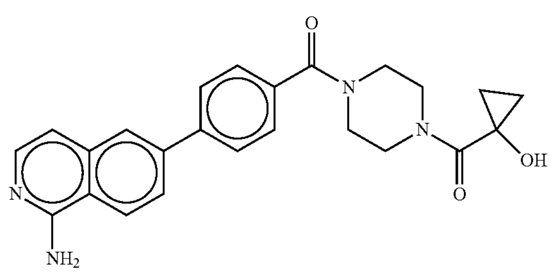 |
| 1-[(4-{[4-(3-aminoisoquinolin-6-yl)phenyl]carbonyl}piperazin-1-yl)carbonyl]cyclopropan-1-ol | 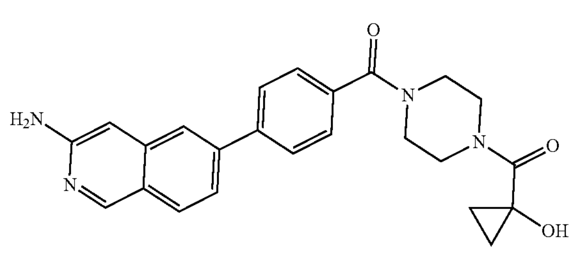 [SMILES: Nc1cc2cc(-c3ccc(C(=O)N4CCN(C(=O)C5(O)CC5)CC4)cc3)ccc2cn1] |

TABLE 1-continued

| IUPAC Name | Compound Structure |
|---|---|
| 1-[(4-{[4-{1,3-dimethylisoquinolin-6-yl)phenyl]carbonyl}piperazin-1-yl)carbonyl]cyclopropan-1-ol | 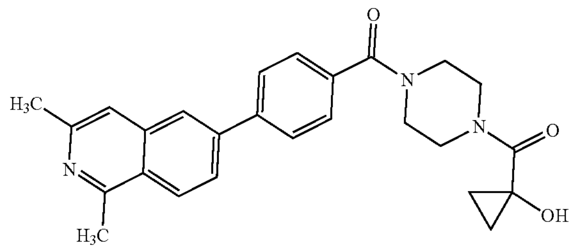 [SMILES: Cc1cc2cc(-c3ccc(C(=O)N4CCN(C(=O)C5(O)CC5)CC4)cc3)ccc2c(C)n1] |
| 1-{[4-({4-[3-(methoxymethyl)-1-methyl-1H-indazol-6-yl]phenyl}carbonyl)piperazin-1-yl]carbonyl}cyclopropan-1-ol | 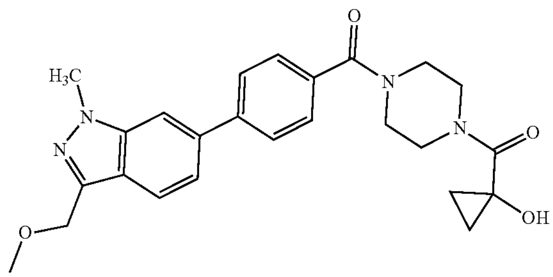 [SMILES: COCc1nn(C)c2cc(-c3ccc(C(=O)N4CCN(C(=O)C5(O)CC5)CC4)cc3)ccc12] |
| 1-{[4-({4-[3-(hydroxymethyl)-1-methyl-1H-indazol-6-yl]phenyl}carbonyl)piperazin-1-yl]carbonyl}cyclopropan-1-ol | 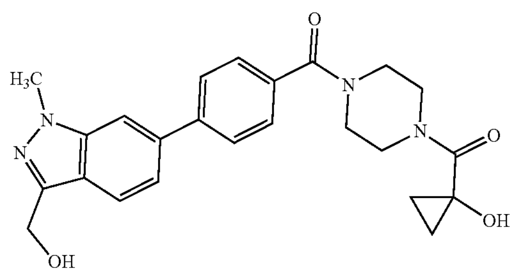 [SMILES: Cn1nc(CO)c2ccc(-c3ccc(C(=O)N4CCN(C(=O)C5(O)CC5)CC4)cc3)cc21] |
| 1-[(4-{[4-{2-methylquinolin-6-yl)phenyl]carbonyl}piperazin-1-yl)carbonyl]cyclopropan-1-ol | 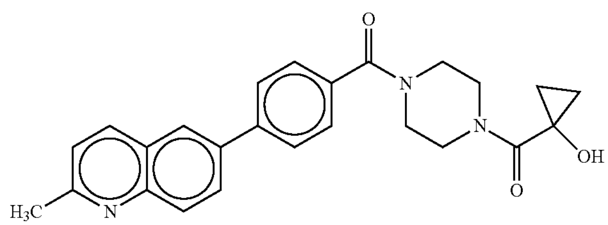 |
| 1-[(4-{[4-(2-aminoquinolin-6-yl)phenyl]carbonyl}piperazin-1-yl)carbonyl]cyclopropan-1-ol | 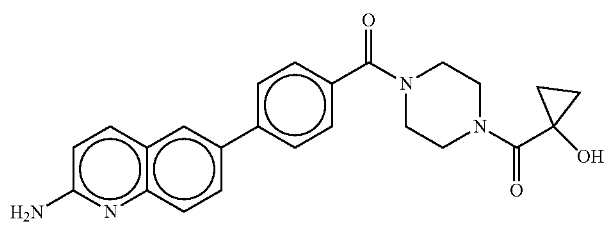 |
| 1-[(4-{[4-(1-ethyl-1H-indazol-6-yl)phenyl]carbonyl}piperazin-1-yl)carbonyl]cyclopropan-1-ol | 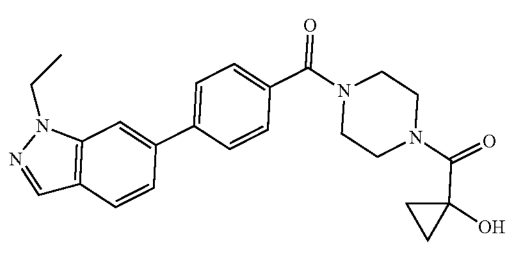 [SMILES: CCn1ncc2ccc(-c3ccc(C(=O)N4CCN(C(=O)C5(O)CC5)CC4)cc3)cc21] |

TABLE 1-continued

| IUPAC Name | Compound Structure |
|---|---|
| 1-[(4-{[4-(1-cyclobutyl-1H-indazol-6-yl)phenyl]carbonyl}piperazin-1-yl)carbonyl]cyclopropan-1-ol | 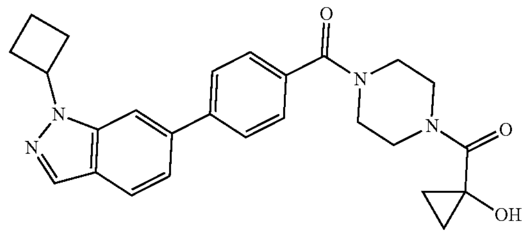 [SMILES: O=C(c1ccc(-c2ccc3cnn(C4CCC4)c3c2)cc1)N1CCN(C(=O)C2(O)CC2)CC1] |
| 1-{[4-({4-[1-(oxetan-3-yl)-1H-indazol-6-yl]phenyl}carbonyl)piperazin-1-yl]carbonyl}cyclopropan-1-ol | 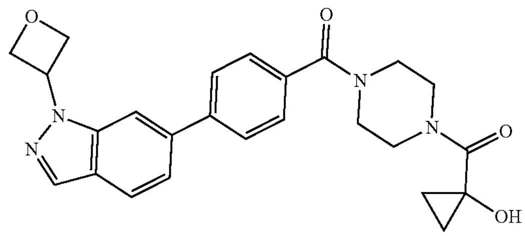 |
| 1-{[4-({4-[1-(propan-2-yl)-1H-indazol-6-yl]phenyl}carbonyl)piperazin-1-yl]carbonyl}cyclopropan-1-ol | 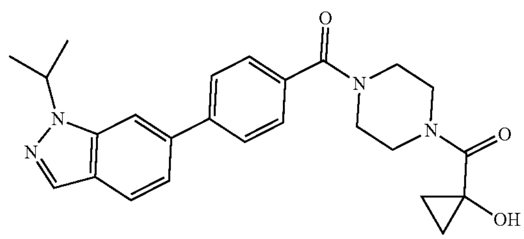 [SMILES: CC(C)n1ncc2ccc(-c3ccc(C(=O)N4CCN(C(=O)C5(O)CC5)CC4)cc3)cc21] |
| 1-{[4-({4-[1-(2-methoxyethyl)-1H-indazol-6-yl]phenyl}carbonyl)piperazin-1-yl]carbonyl}cyclopropan-1-ol | 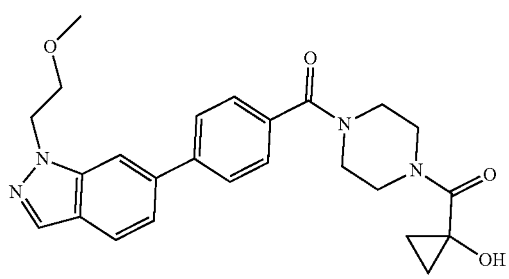 [SMILES: COCCn1ncc2ccc(-c3ccc(C(=O)N4CCN(C(=O)C5(O)CC5)CC4)cc3)cc21] |
| 1-{[4-({4-[1-(cyclopropylmethyl)-1H-indazol-6-yl]phenyl}carbonyl)piperazin-1-yl]carbonyl}cyclopropan-1-ol | 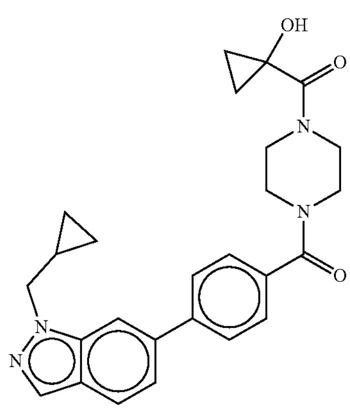 |

TABLE 1-continued

| IUPAC Name | Compound Structure |
| --- | --- |
| 1-[(4-{[4-(1-propyl-1H-indazol-6-yl)phenyl]carbonyl}piperazin-1-yl)carbonyl]cyclopropan-1-ol | 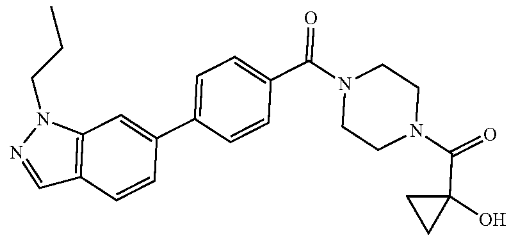 [SMILES: CCCn1ncc2ccc(-c3ccc(C(=O)N4CCN(C(=O)C5(O)CC5)CC4)cc3)cc21] |
| 1-{[4-({4-[1-(cyclobutylmethyl)-1H-indazol-6-yl]phenyl}carbonyl)piperazin-1-yl]carbonyl}cyclopropan-1-ol | 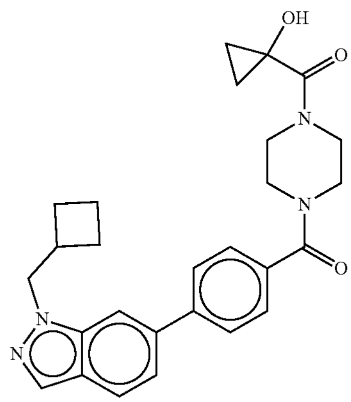 |
| 1-{[4-({4-[1-(oxetan-3-ylmethyl)-1H-indazol-6-yl]phenyl}carbonyl)piperazin-1-yl]carbonyl}cyclopropan-1-ol | 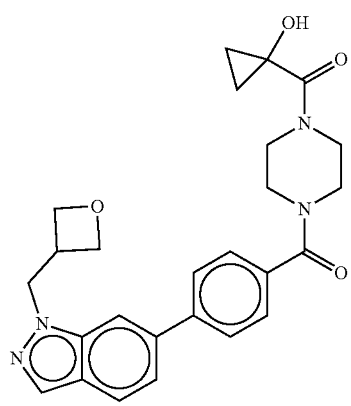 |
| 1-{[4-({4-[1-(2-hydroxyethyl)-1H-indazol-6-yl]phenyl}carbonyl)piperazin-1-yl]carbonyl}cyclopropan-1-ol | 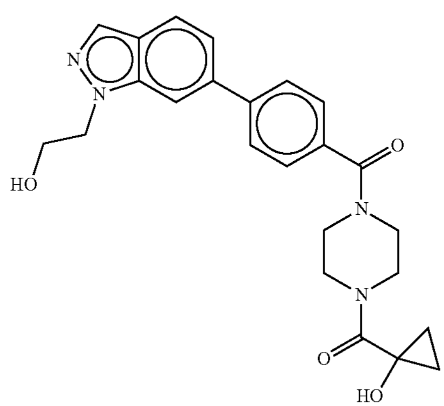 |

TABLE 1-continued

| IUPAC Name | Compound Structure |
| --- | --- |
| 1-[(4-{[4-(1-cyclopropyl-1H-indazol-6-yl)phenyl]carbonyl}piperazin-1-yl)carbonyl]cyclopropan-1-ol | |
| N-{3-[4-({4-[(1-hydroxycyclopropyl)carbonyl]piperazin-1-yl}carbonyl)phenyl]phenyl}-N-methylcyclopropanecarboxamide | 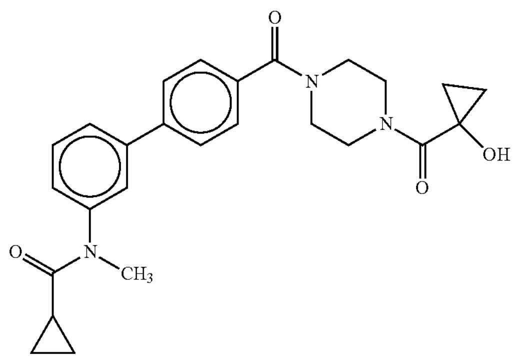 |
| N-{3-[4-({4-[(1-hydroxycyclopropyl)carbonyl]piperazin-1-yl}carbonyl)phenyl]phenyl}-N-methylcyclobutanecarboxamide | 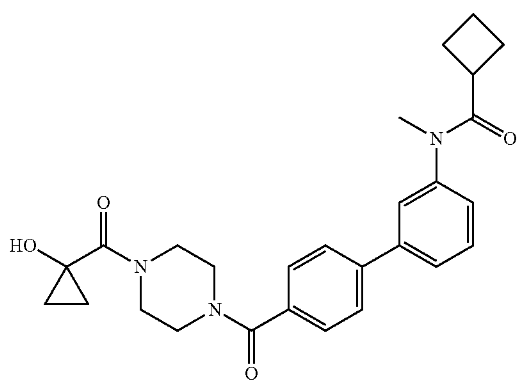 [SMILES: CN(C(=O)C1CCC1)c1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}-N-methylcyclobutanesulfonamide | 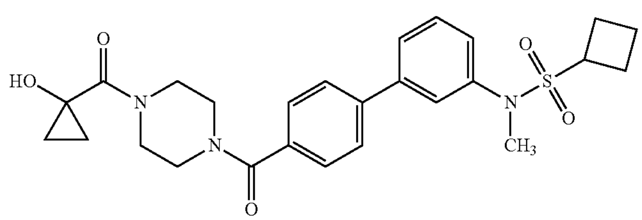 [SMILES: CN(c1cccc(-c2ccc(C(=O)N3CCN(C(=O)C4(O)CC4)CC3)cc2)c1)S(=O)(=O)C1CCC1] |

TABLE 1-continued

| IUPAC Name | Compound Structure |
|---|---|
| N-cyclopropyl-3-[4-({4-[(1-hydroxycyclopropyl)carbonyl]piperazin-1-yl}carbonyl)phenyl]-N-methylbenzene-1-sulfonamide | 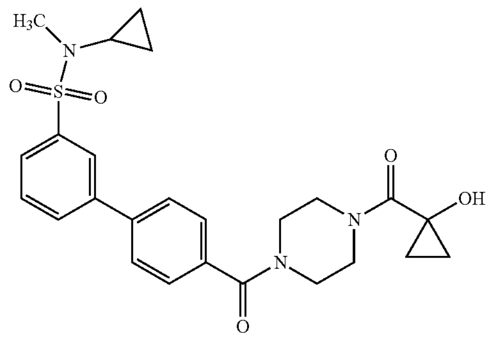 [SMILES: CN(C1CC1)S(=O)(=O)c1cccc(-c2ccc(C(=O)N3CCN(C(=O)C4(O)CC4)CC3)cc2)c1] |
| N-cyclopropyl-3-[4-({4-[(1-hydroxycyclopropyl)carbonyl]piperazin-1-yl}carbonyl)phenyl]-N-methylbenzamide | 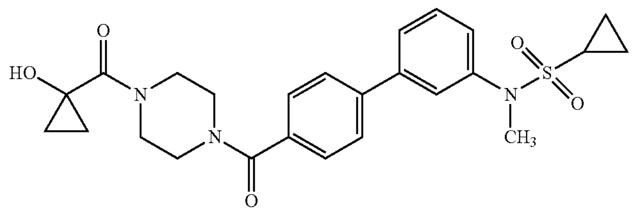 [SMILES: CN(c1cccc(-c2ccc(C(=O)N3CCN(C(=O)C4(O)CC4)CC3)cc2)c1)S(=O)(=O)C1CC1] |
| 2-cyclobutyl-N-{3-[4-({4-[(1-hydroxycyclopropyl)carbonyl]piperazin-1-yl}carbonyl)phenyl]phenyl}acetamide | 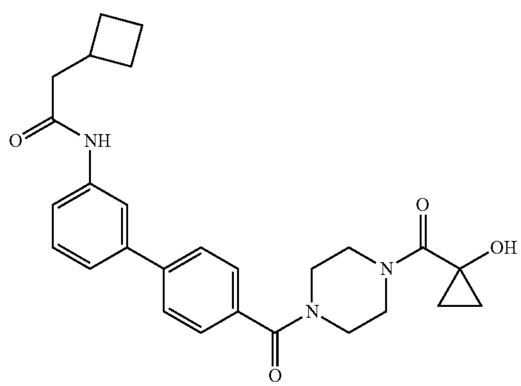 |
| N-{3-[4-({4-[(1-hydroxycyclopropyl)carbonyl]piperazin-1-yl}carbonyl)phenyl]phenyl}-1-methylazetidine-3-carboxamide | 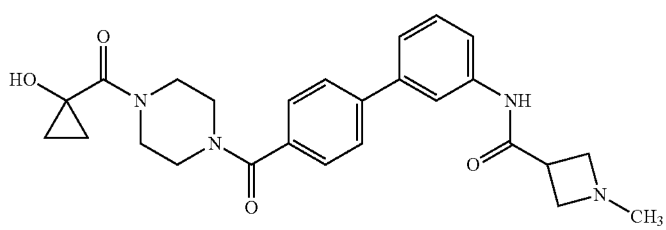 [SMILES: CN1CC(C(=O)Nc2cccc(-c3ccc(C(=O)N4CCN(C(=O)C5(O)CC5)CC4)cc3)c2)C1] |
| N-{3-[4-({4-[(1-hydroxycyclopropyl)carbonyl]piperazin-1-yl}carbonyl)phenyl]phenyl}-3-methyloxetane-3-carboxamide | 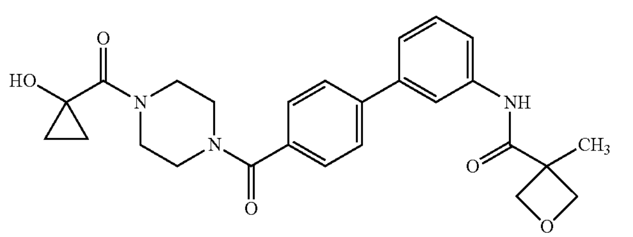 [SMILES: CC1(C(=O)Nc2cccc(-c3ccc(C(=O)N4CCN(C(=O)C5(O)CC5)CC4)cc3)c2)COC1] |

TABLE 1-continued

| IUPAC Name | Compound Structure |
|---|---|
| N-{3-[4-({4-[(1-hydroxycyclopropyl)carbonyl]piperazin-1-yl}carbonyl)phenyl]phenyl}-2-(oxetan-3-yl)acetamide | 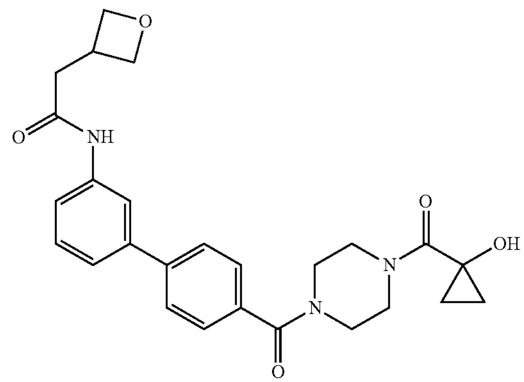 |
| 3-fluoro-N-{3-[4-({4-[(1-hydroxycyclopropyl)carbonyl]piperazin-1-yl}carbonyl)phenyl]phenyl}cyclobutane-1-carboxamide | 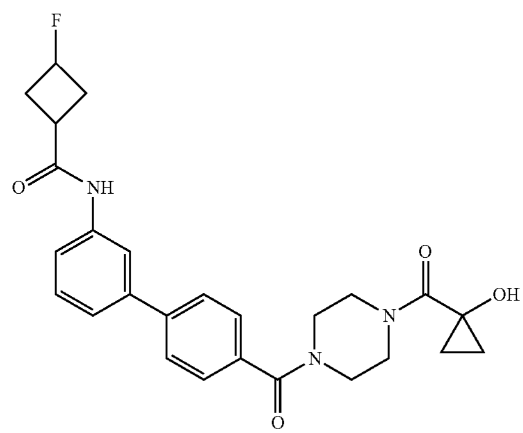 [SMILES: O=C(Nc1cccc(-c2ccc(C(=O)N3CCN(C(=O)C4(O)CC4)CC3)cc2)c1)C1CC(F)C1] |
| 3-ethyl-N-{3-[4-({4-[(1-hydroxycyclopropyl)carbonyl]piperazin-1-yl}carbonyl)phenyl]phenyl}-oxetane-3-carboxamide | 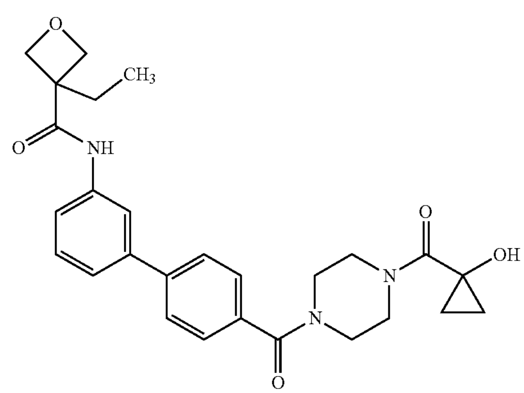 [SMILES: CCC1(C(=O)Nc2cccc(-c3ccc(C(=O)N4CCN(C(=O)C5(O)CC5)CC4)cc3)c2)COC1] |
| N-{3-[4-({4-[(1-hydroxycyclopropyl)carbonyl]piperazin-1-yl}carbonyl)phenyl]phenyl}propanamide | 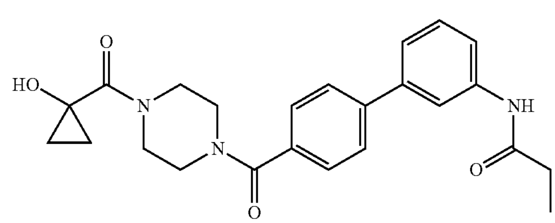 [SMILES: CCC(=O)Nc1cccc(-c2ccc(C(=O)N3CCN(C(=O)C4(O)CC4)CC3)cc2)c1] |

TABLE 1-continued

| IUPAC Name | Compound Structure |
|---|---|
| N-{3-[4-({4-[(1-hydroxycyclopropyl)carbonyl]piperazin-1-yl}carbonyl)phenyl]phenyl}-2-methylpropanamide | 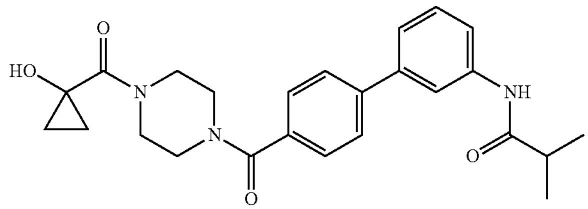 [SMILES: CC(C)C(=O)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}butanamide | 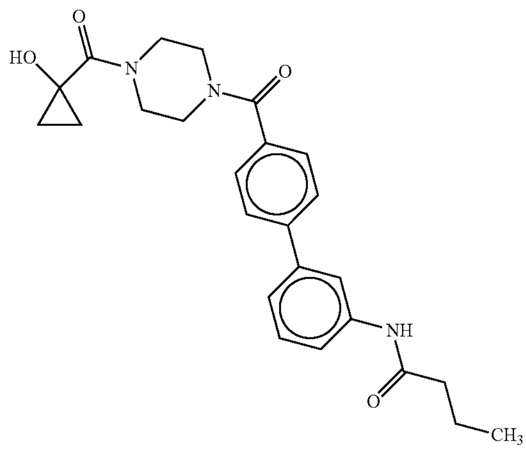 |
| N-{3-[4-({4-[(1-hydroxycyclopropyl)carbonyl]piperazin-1-yl}carbonyl)phenyl]phenyl}-2-methoxyacetamide | 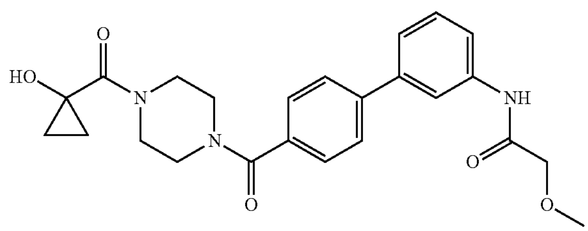 [SMILES: COCC(=O)Nc1cccc(-c2ccc(C(=O)N3CCN(C(=O)C4(O)CC4)CC3)cc2)c1] |
| 2-cyclopropyl-N-{3-[4-({4-[(1-hydroxycyclopropyl)carbonyl]piperazin-1-yl}carbonyl)phenyl]phenyl}acetamide | 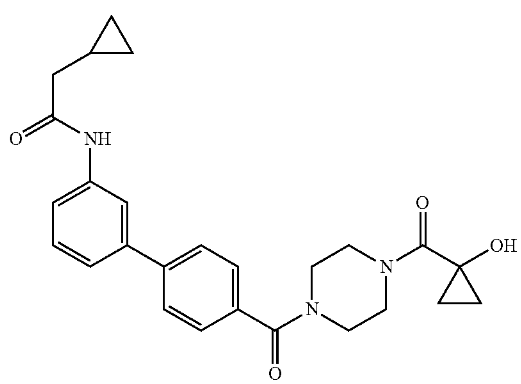 [SMILES: O=C(CC1CC1)Nc1cccc(-c2ccc(C(=O)N3CCN(C(=O)C4(O)CC4)CC3)cc2)c1] |
| 2,2-difluoro-N-{3-[4-({4-[(1-hydroxycyclopropyl)carbonyl]piperazin-1-yl}carbonyl)phenyl]phenyl}acetamide | 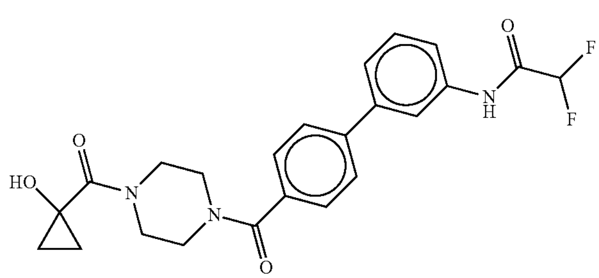 |

TABLE 1-continued

| IUPAC Name | Compound Structure |
|---|---|
| N-{3-[4-({4-[(1-hydroxycyclopropyl)carbonyl]piperazin-1-yl}carbonyl)phenyl]phenyl}-1-methylcyclopropane-1-carboxamide | 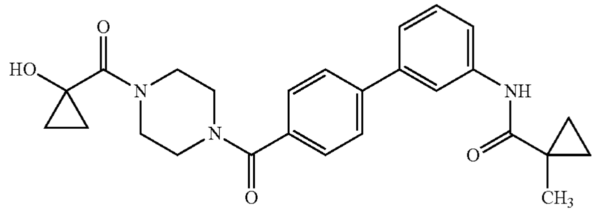 [SMILES: CC1(C(=O)Nc2cccc(-c3ccc(C(=O)N4CCN(C(=O)C5(O)CC5)CC4)cc3)c2)CC1] |
| N-{3-[4-({4-[(1-hydroxycyclopropyl)carbonyl]piperazin-1-yl}carbonyl)phenyl]phenyl}cyclopentanecarboxamide | 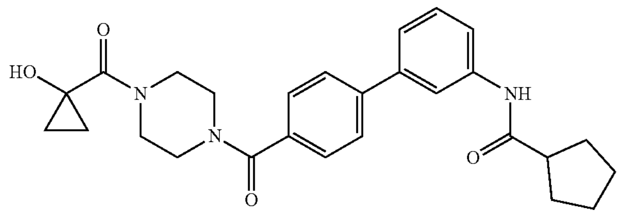 [SMILES: O=C(Nc1cccc(-c2ccc(C(=O)N3CCN(C(=O)C4(O)CC4)CC3)cc2)c1)C1CCCC1] |
| N-{3-[4-({4-[(1-hydroxycyclopropyl)carbonyl]piperazin-1-yl}carbonyl)phenyl]phenyl}cyclohexanecarboxamide | 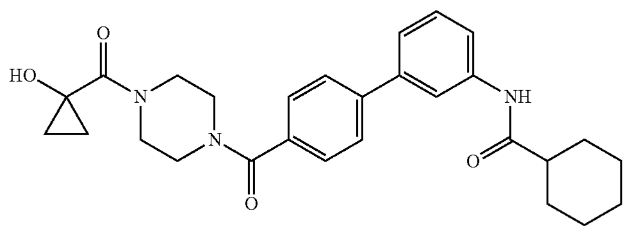 [SMILES: O=C(Nc1cccc(-c2ccc(C(=O)N3CCN(C(=O)C4(O)CC4)CC3)cc2)c1)C1CCCCC1] |
| N-{3-[4-({4-[(1-hydroxycyclopropyl)carbonyl]piperazin-1-yl}carbonyl)phenyl]phenyl}oxane-4-carboxamide | 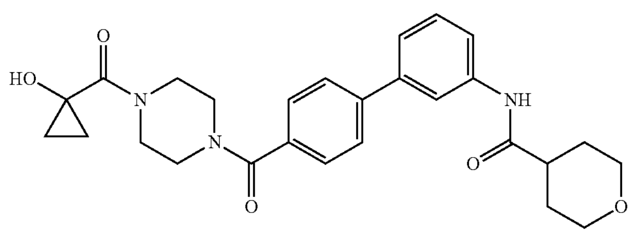 [SMILES: O=C(Nc1cccc(-c2ccc(C(=O)N3CCN(C(=O)C4(O)CC4)CC3)cc2)c1)C1CCOCC1] |
| 1-cyclopropyl-N-{3-[4-({4-[(1-hydroxycyclopropyl)carbonyl]piperazin-1-yl}carbonyl)phenyl]phenyl}methanesulfonamide | 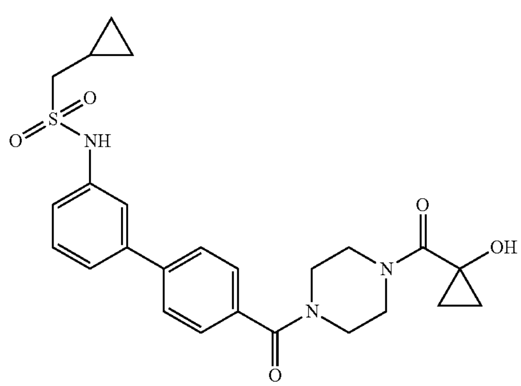 [SMILES: O=C(c1ccc(-c2cccc(NS(=O)(=O)CC3CC3)c2)cc1)N1CCN(C(=O)C2(O)CC2)CC1] |

TABLE 1-continued

| IUPAC Name | Compound Structure |
|---|---|
| N-{3-[4-({4-[(1-hydroxycyclopropyl)carbonyl]piperazin-1-yl}carbonyl)phenyl]phenyl}-2-methylpropane-1-sulfonamide | 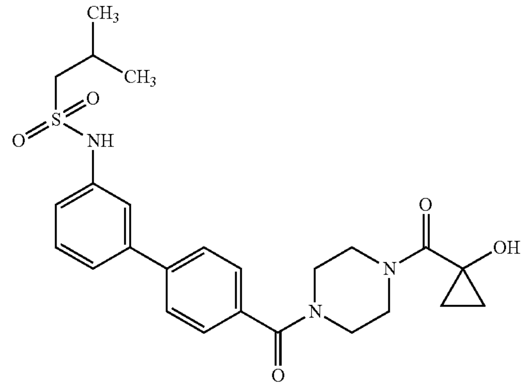 [SMILES: CC(C)CS(=O)(=O)Nc1cccc(-c2ccc(C(=O)N3CCN(C(=O)C4(O)CC4)CC3)cc2)c1] |
| 1,1-difluoro-N-{3-[4-({4-[(1-hydroxycyclopropyl)carbonyl]piperazin-1-yl}carbonyl)phenyl]phenyl}methanesulfonamide | 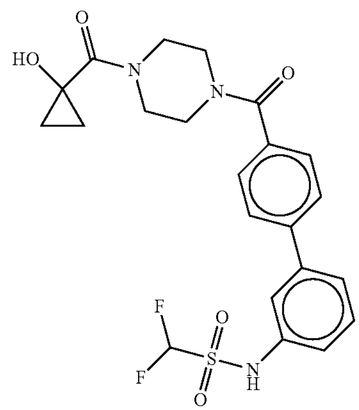 |
| 3,3,3-trifluoro-N-{3-[4-({4-[(1-hydroxycyclopropyl)carbonyl]piperazin-1-yl}carbonyl)phenyl]phenyl}propane-1-sulfonamide | 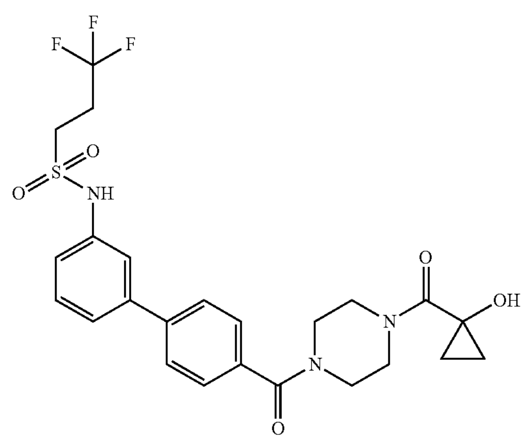 [SMILES: O=C(c1ccc(-c2cccc(NS(=O)(=O)CCC(F)(F)F)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}-1-methylcyclopropane-1-sulfonamide | 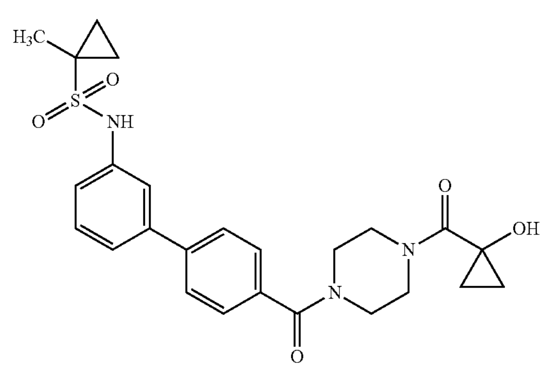 [SMILES: CC1(S(=O)(=O)Nc2cccc(-c3ccc(C(=O)N4CCN(C(=O)C5(O)CC5)CC4)cc3)c2)CC1] |

TABLE 1-continued

| IUPAC Name | Compound Structure |
|---|---|
| N-{3-[4-({4-[(1-hydroxycyclopropyl)carbonyl]piperazin-1-yl}carbonyl)phenyl]phenyl}cyclobutanesulfonamide | 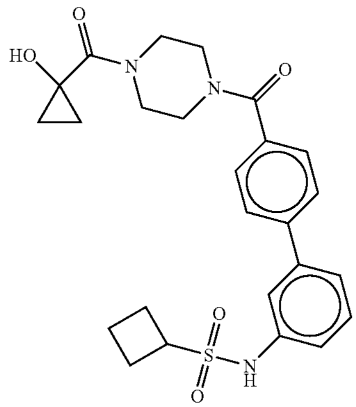 |
| N-{3-[4-({4-[(1-hydroxycyclopropyl)carbonyl]piperazin-1-yl}carbonyl)phenyl]phenyl}oxolane-3-sulfonamide | 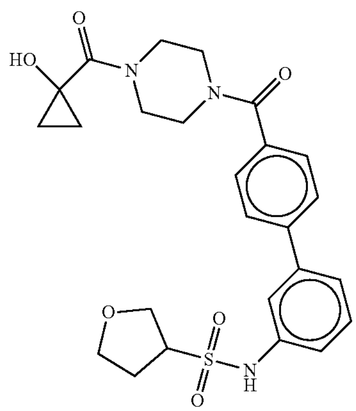 |
| N-{3-[4-({4-[(1-hydroxycyclopropyl)carbonyl]piperazin-1-yl}carbonyl)phenyl]phenyl}cyclopentanesulfonamide | 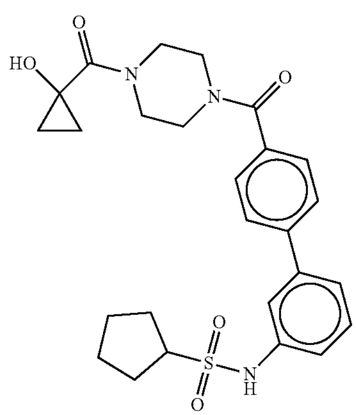 |
| 2,2-difluoro-N-{3-[4-({4-[(1-hydroxycyclopropyl)carbonyl]piperazin-1-yl}carbonyl)phenyl]phenyl}ethane-1-sulfonamide | 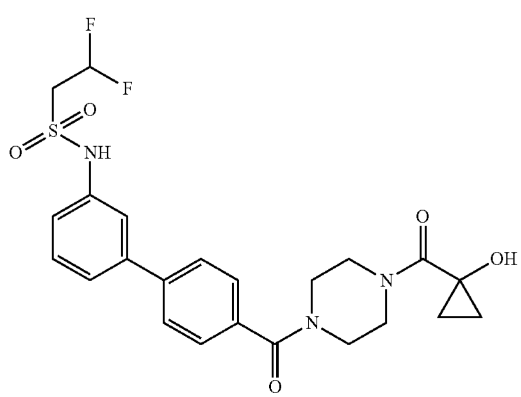 [SMILES: O=C(c1ccc(-c2cccc(NS(=O)(=O)CC(F)F)c2)cc1)N1CCN(C(=O)C2(O)CC2)CC1] |

| IUPAC Name | Compound Structure |
|---|---|
| N-{3-[4-({4-[(1-hydroxycyclopropyl)carbonyl]piperazin-1-yl}carbonyl)phenyl]phenyl}-2-methoxyethane-1-sulfonamide | 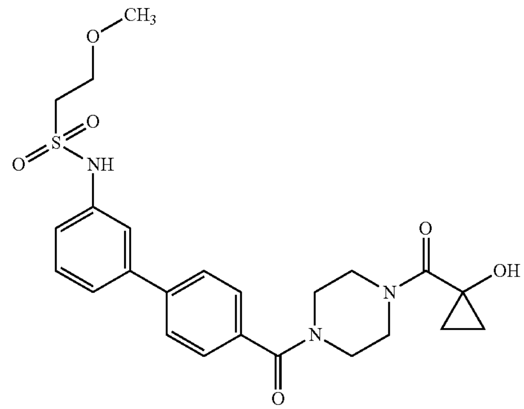 [SMILES: COCCS(=O)(=O)Nc1cccc(-c2ccc(C(=O)N3CCN(C(=O)C4(O)CC4)CC3)cc2)c1] |
| 1-cyclobutyl-N-{3-[4-({4-[(1-hydroxycyclopropyl)carbonyl]piperazin-1-yl}carbonyl)phenyl]phenyl}methanesulfonamide | 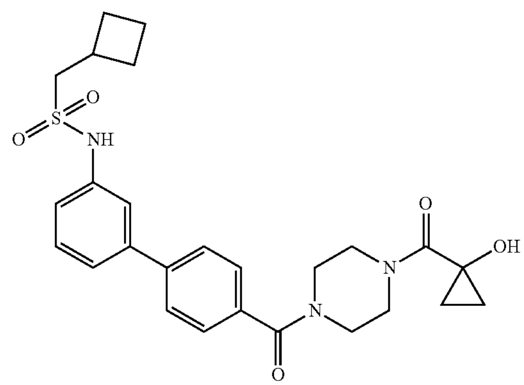 [SMILES: O=C(c1ccc(-c2cccc(NS(=O)(=O)CC3CCC3)c2)cc1)N1CCN(C(=O)C2(O)CC2)CC1] |
| 2-hydroxy-N-{3-[4-({4-[(1-hydroxycyclopropyl)carbonyl]piperazin-1-yl}carbonyl)phenyl]phenyl}ethane-1-sulfonamide | 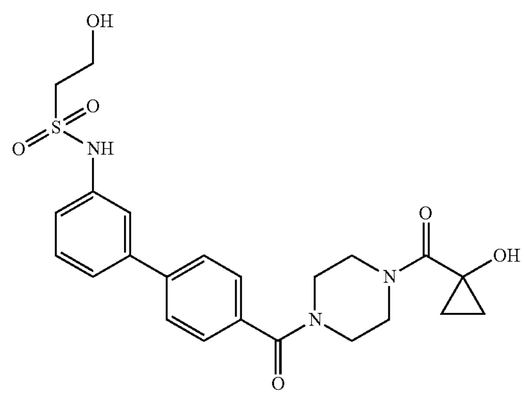 [SMILES: O=C(c1ccc(-c2cccc(NS(=O)(=O)CCO)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}oxane-4-sulfonamide | 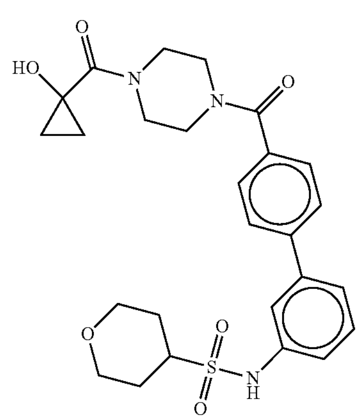 |

TABLE 1-continued

| IUPAC Name | Compound Structure |
|---|---|
| 2-cyclopropyl-N-{3-[4-({4-[(1-hydroxycyclopropyl)carbonyl]piperazin-1-yl}carbonyl)phenyl]phenyl}ethane-1-sulfonamide | 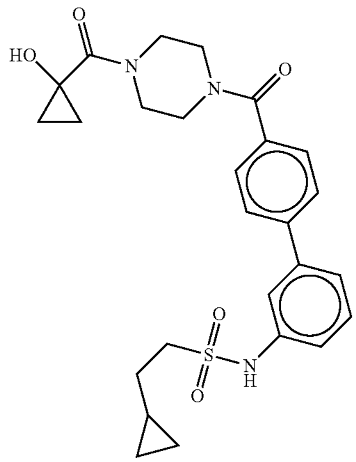 |
| 3,3-difluoro-N-{3-[4-({4-[(1-hydroxycyclopropyl)carbonyl]piperazin-1-yl}carbonyl)phenyl]phenyl}cyclobutane-1-carboxamide | 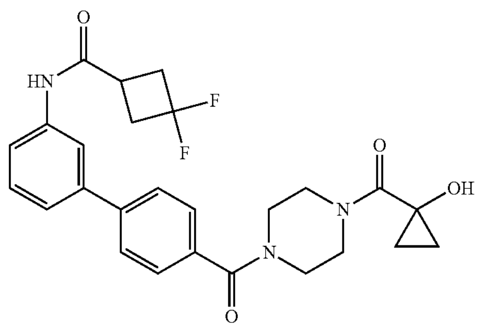 [SMILES: O=C(Nc1cccc(-c2ccc(C(=O)N3CCN(C(=O)C4(O)CC4)CC3)cc2)c1)C1CC(F)(F)C1] |
| 1-[(4-{[4-(1H-1,3-benzodiazol-4-yl)-2-chlorophenyl]carbonyl}piperazin-1-yl)carbonyl]cyclopropan-1-ol | 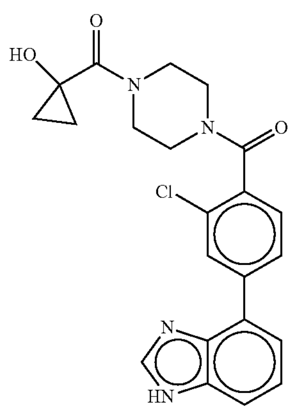 |
| 1-[(4-{[4-(2-cyclopropyl-2H-indazol]-5-yl)phenyl]carbonyl}piperazin-1-yl)carbonyl]cyclopropan-1-ol | |

TABLE 1-continued

| IUPAC Name | Compound Structure |
|---|---|
| 1-[(4-{[4-(1-cyclopropyl-1H-indazol-5-yl)phenyl]carbonyl}piperazin-1-yl)carbonyl]cyclopropan-1-ol | 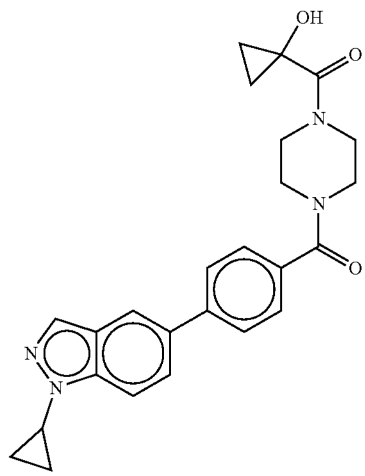 |
| N-{4-[4-({4-[(1-hydroxycyclopropyl)carbonyl]piperazin-1-yl}carbonyl)phenyl]phenyl}cyclopropanecarboxamide | 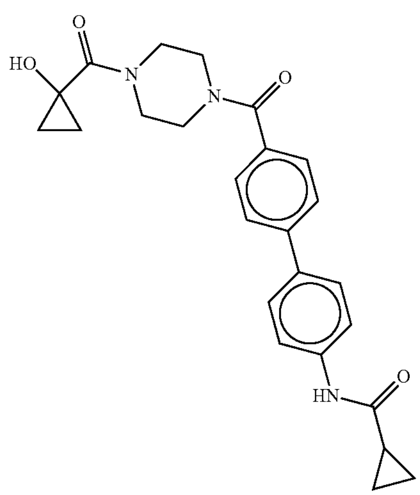 |
| N-{3-[4-({4-[(1-hydroxycyclopropyl)carbonyl]piperazin-1-yl}carbonyl)phenyl]phenyl}-N-methylcyclopropanesulfonamide | 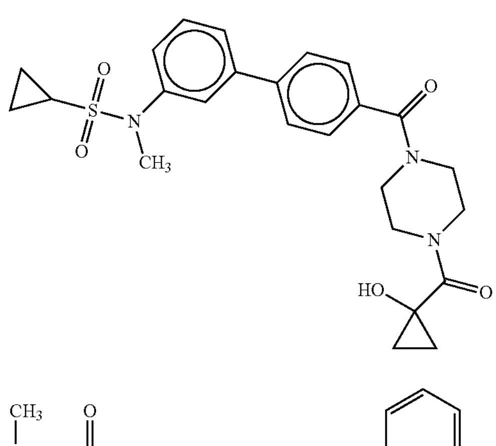 |
| N-{3-[4-({4-[(1-methoxycyclopropyl)carbonyl]piperazin-1-yl}carbonyl)phenyl]phenyl}-N-methylcyclopropanesulfonamide | 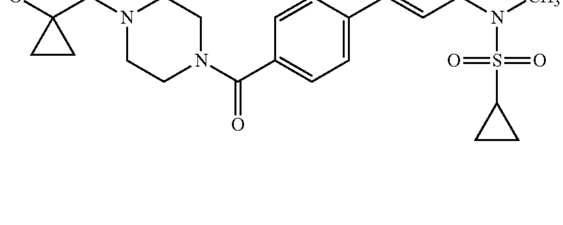 |

TABLE 1-continued

| IUPAC Name | Compound Structure |
|---|---|
| 3-cyclopropyl-1-{3-[4-({4-[(1-hydroxycyclopropyl)carbonyl]piperazin-1-yl}carbonyl)phenyl]phenyl}urea | 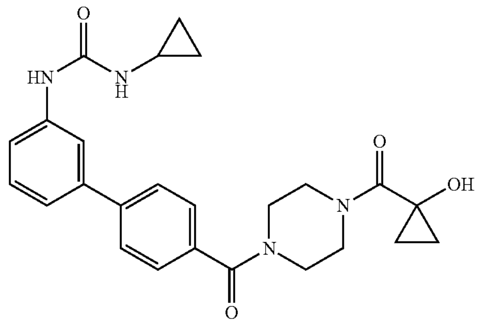 [SMILES: O=C(Nc1cccc(-c2ccc(C(=O)N3CCN(C(=O)C4(O)CC4)CC3)cc2)c1)NC1CC1] |
| 3-[4-({4-[(1-hydroxycyclopropyl)carbonyl]piperazin-1-yl}carbonyl)phenyl]phenyl N-cyclopropylcarbamate | 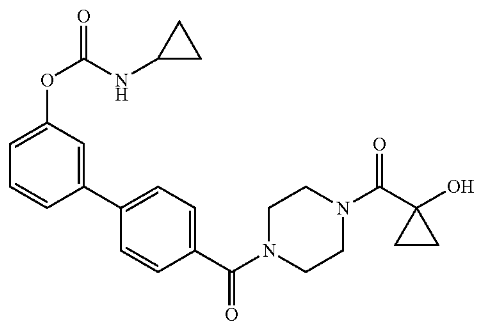 [SMILES: O=C(NC1CC1)Oc1cccc(-c2ccc(C(=O)N3CCN(C(=O)C4(O)CC4)CC3)cc2)c1] |
| N-{4-[4-({4-[(1-hydroxycyclopropyl)carbonyl]piperazin-1-yl}carbonyl)phenyl]phenyl}cyclopropanesulfonamide | 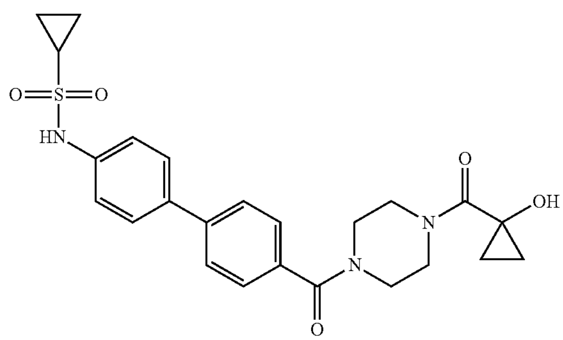 [SMILES: O=C(c1ccc(-c2ccc(NS(=O)(=O)C3CC3)cc2)cc1)N1CCN(C(=O)C2(O)CC2)CC1] |
| N-{3-[3-chloro-4-({4-[(1-hydroxycyclopropyl)carbonyl]piperazin-1-yl}carbonyl)phenyl]phenyl}cyclopropanecarboxamide | 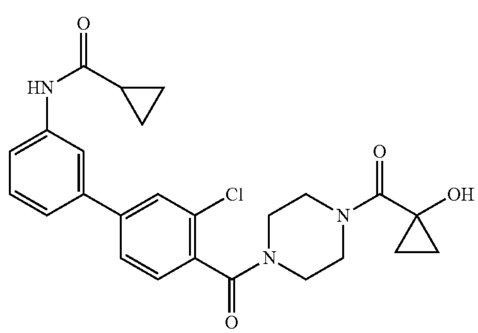 [SMILES: O=C(Nc1cccc(-c2ccc(C(=O)N3CCN(C(=O)C4(O)CC4)CC3)c(Cl)c2)c1)C1CC1] |
| N-(3-{4-[4-(1-hydroxycyclopropanecarbonyl)piperazine-1-carbonyl]phenyl}phenyl)cyclopentanecarboxamide | 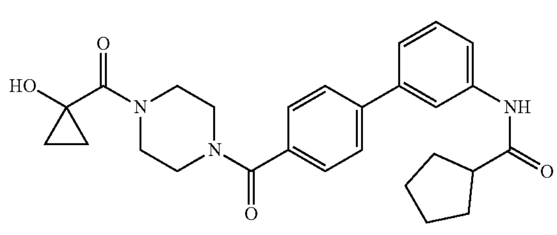 [SMILES: O=C(Nc1cccc(-c2ccc(C(=O)N3CCN(C(=O)C4(O)CC4)CC3)cc2)c1)C1CCCC1] |

TABLE 1-continued

| IUPAC Name | Compound Structure |
|---|---|
| 1-(4-{4-[4-(1H-pyrazol-4-yl)phenyl]benzoyl}piperazine-1-carbonyl)cyclopropan-1-ol | 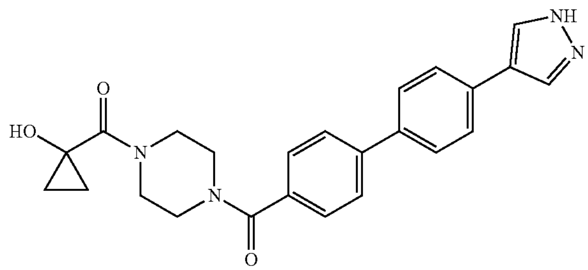 [SMILES: O=C(c1ccc(-c2ccc(-c3cn[nH]c3)cc2)cc1)N1CCN(C(=O)C2(O)CC2)CC1] |
| 1-{4-[4-(1,2,3,4-tetrahydroisoquinolin-2-yl)benzoyl]piperazine-1-carbonyl}cyclopropan-1-ol | 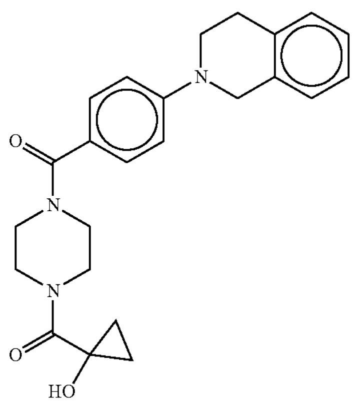 |
| 1-{4-[4-(1,3-dimethyl-1H-indazol-5-yl)-2-fluorobenzoyl]piperazine-1-carbonyl}cyclopropan-1-amine | 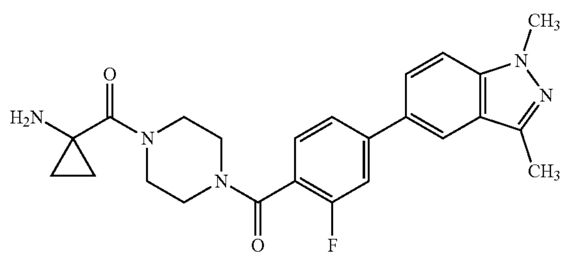 [SMILES: Cc1nn(C)c2ccc(-c3ccc(C(=O)N4CCN(C(=O)C5(N)CC5)CC4)c(F)c3)cc12] |
| 1-(4-{4-[4-(1-methyl-1H-pyrazol-4-yl)phenyl]benzoyl}piperazine-1-carbonyl)cyclopropan-1-ol | 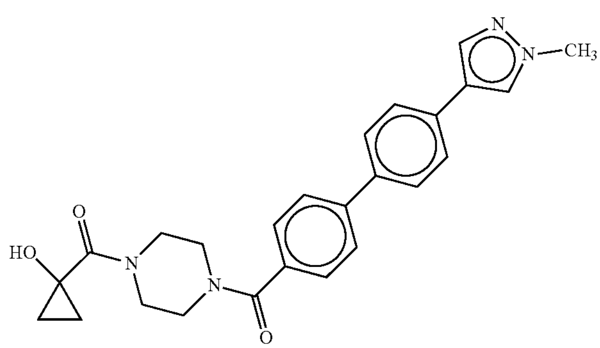 |
| 1-[(2S)-4-[2-fluoro-4-(1-methyl-1H-1,3-benzodiazol-5-yl)benzoyl]-2-methylpiperazine-1-carbonyl]cyclopropan-1-ol | 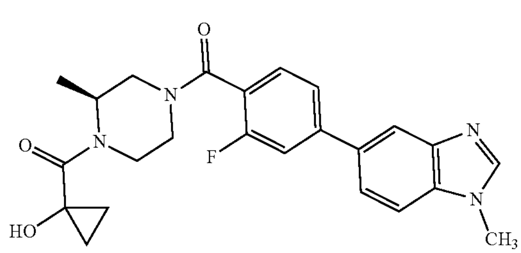 [SMILES: C[C@H]1CN(C(=O)c2ccc(-c3ccc4c(c3)ncn4C)cc2F)CCN1C(=O)C1(O)CC1] |

TABLE 1-continued

| IUPAC Name | Compound Structure |
|---|---|
| 1-{4-[3-chloro-4-(1-methyl-1H-indazol-6-yl)benzoyl]piperazine-1-carbonyl}cyclopropan-1-ol | 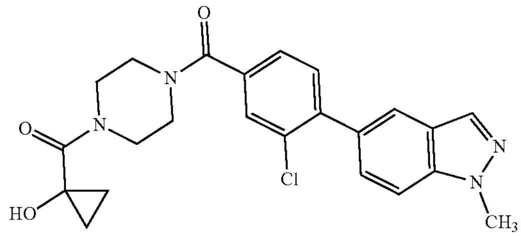 [SMILES: Cn1ncc2cc(-c3ccc(C(=O)N4CCN(C(=O)C5(O)CC5)CC4)cc3Cl)ccc21] |
| 1-{4-[2-fluoro-4-(1-methyl-1H-1,3-benzodiazol-5-yl)benzoyl]piperazine-1-carbonyl}cyclopropan-1-ol | 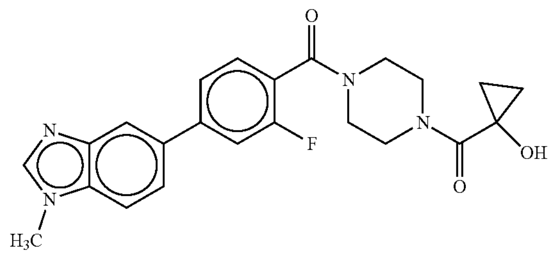 |
| 1-{4-[3-chloro-4-(1-methyl-1H-1,3-benzodiazol-5-yl)benzoyl]piperazine-1-carbonyl}cyclopropan-1-ol | 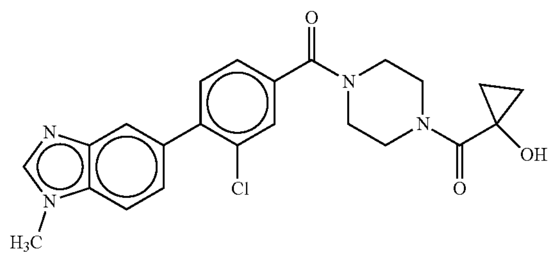 |
| 1-[4-(4-{pyrazolo[1,5-a]pyridin-6-yl}benzoyl)piperazine-1-carbonyl]cyclopropan-1-ol | 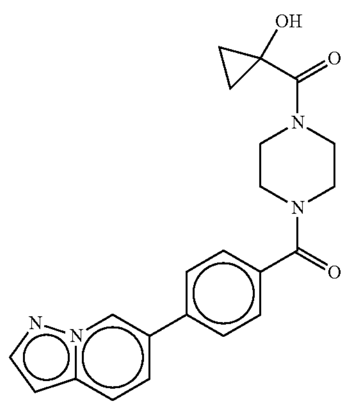 |
| 1-{4-[4-(4-fluoro-2,3-dihydro-1H-indol-1-yl)benzoyl]piperazine-1-carbonyl}cyclopropan-1-ol | 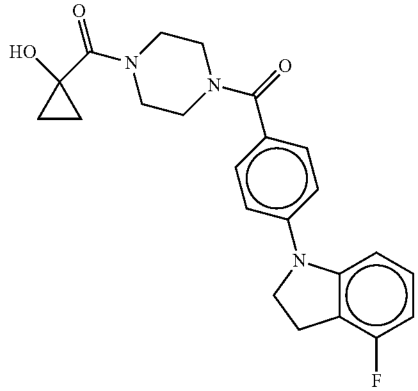 |

TABLE 1-continued

| IUPAC Name | Compound Structure |
| --- | --- |
| 1-{4-[4-(3-methyl-1H-indazol-6-yl)benzoyl]piperazine-1-carbonyl}cyclopropan-1-ol | 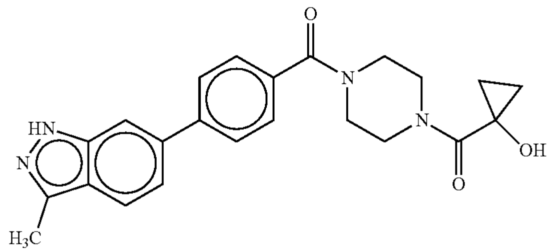 |
| 1-{4-[2-fluoro-4-(3-methyl-1H-indazol-7-yl)benzoyl]piperazine-1-carbonyl}cyclopropan-1-ol | 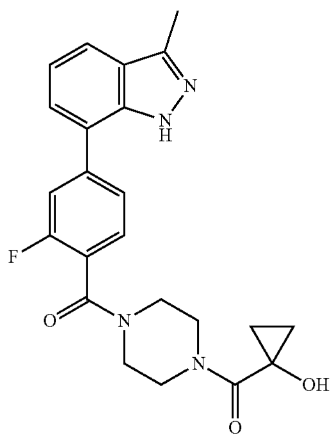 [SMILES: Cc1n[nH]c2c(-c3ccc(C(=O)N4CCN(C(=O)C5(O)CC5)CC4)c(F)c3)cccc12] |
| 1-[(2S)-2-methyl-4-[4-(1-methyl-1H-indazol-6-yl)benzoyl]piperazine-1-carbonyl]cyclopropan-1-ol | 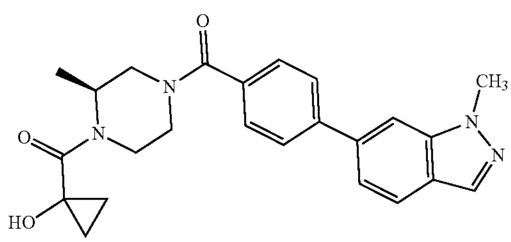 [SMILES: C[C@H]1CN(C(=O)c2ccc(-c3ccc4cnn(C)c4c3)cc2)CCN1C(=O)C1(O)CC1] |
| 1-{4-[3-chloro-4-(2-methyl-2H-indazol-6-yl)benzoyl]piperazine-1-carbonyl}cyclopropan-1-ol | 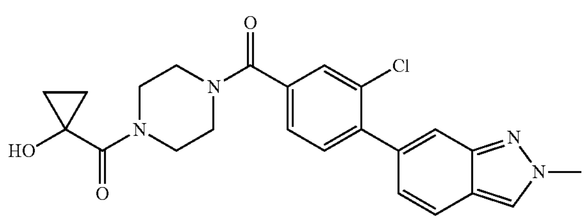 [SMILES: Cn1cc2ccc(-c3ccc(C(=O)N4CCN(C(=O)C5(O)CC5)CC4)cc3Cl)cc2n1] |
| 3,3,3-trifluoro-N-(3-{4-[4-(1-hydroxycyclopropanecarbonyl)piperazine-1-carbonyl]phenyl}phenyl)propane-1-sulfonamide | 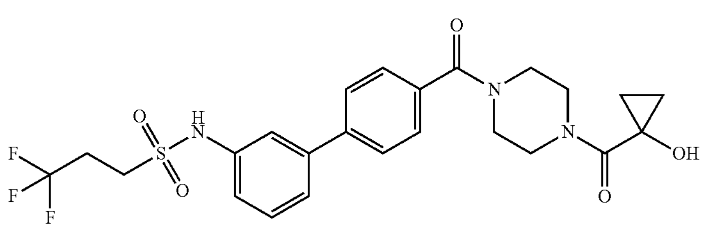 [SMILES: O=C(c1ccc(-c2cccc(NS(=O)(=O)CCC(F)(F)F)c2)cc1)N1CCN(C(=O)C2(O)CC2)CC1] |
| 1-{4-[2-fluoro-4-(1-methyl-1H-indazol-6-yl)benzoyl]piperazine-1-carbonyl}cyclopropan-1-ol | 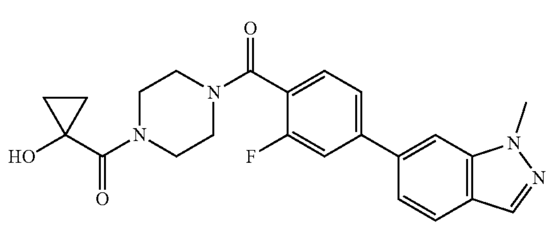 [SMILES: Cn1ncc2ccc(-c3ccc(C(=O)N4CCN(C(=O)C5(O)CC5)CC4)c(F)c3)cc21] |

TABLE 1-continued

| IUPAC Name | Compound Structure |
| --- | --- |
| 1-{3,3-dimethyl-4-[4-(1-methyl-1H-1,3-benzodiazol-5-yl)benzoyl]piperazine-1-carbonyl}cyclopropan-1-ol | 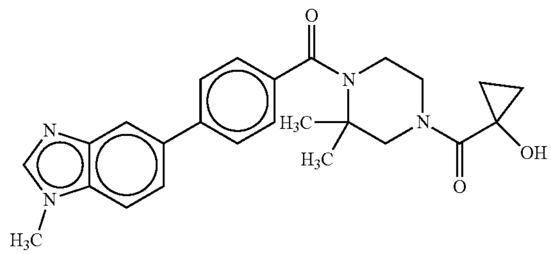 |
| 1-{4-[2,6-difluoro-4-(1-methyl-1H-1,3-benzodiazol-5-yl)benzoyl]piperazine-1-carbonyl}cyclopropan-1-ol | 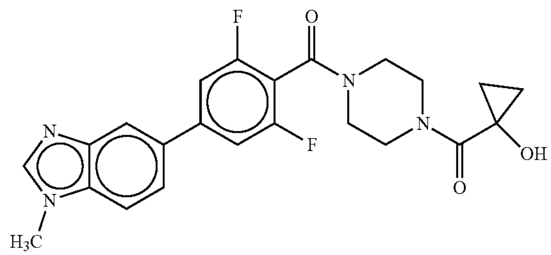 |
| 1-{4-[2-fluoro-4-(1-methyl-1H-indazol-6-yl)benzoyl]piperazine-1-carbonyl}cyclobutan-1-amine | 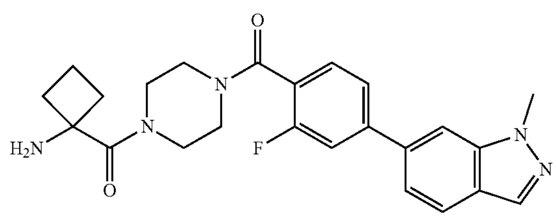 [SMILES: Cn1ncc2ccc(-c3ccc(C(=O)N4CCN(C(=O)C5(N)CCC5)CC4)c(F)c3)cc21] |
| 1-{4-[3-chloro-4-{6-chloro-1,3-benzoxazol-2-yl)benzoyl]piperazine-1-carbonyl}cyclopropan-1-ol | 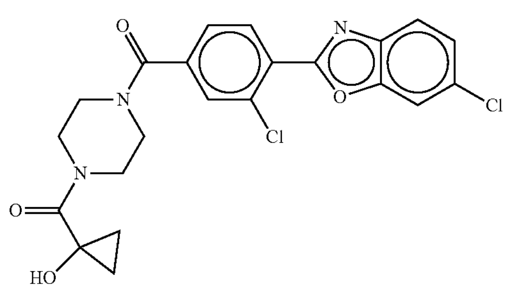 |
| 1-{4-[4-(1,3-dimethyl-1H-indazol-5-yl)-2-fluorobenzoyl]piperazine-1-carbonyl}cyclopropan-1-ol | 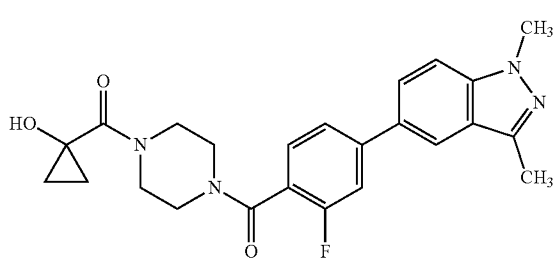 [SMILES: Cc1nn(C)c2ccc(-c3ccc(C(=O)N4CCN(C(=O)C5(O)CC5)CC4)c(F)c3)cc12] |

TABLE 1-continued

| IUPAC Name | Compound Structure |
|---|---|
| N-(3-{4-[4-(1-hydroxycyclopropanecarbonyl)piperazine-1-carbonyl]phenyl}phenyl)cyclobutanesulfonamide | |
| 1-{4-[4-(2,3-dihydro-1H-indol-1-yl)benzoyl]piperazine-1-carbonyl}cyclopropan-1-ol | 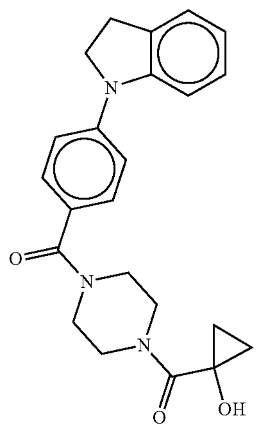 |
| 1-{4-[3-chloro-4-(1,3-dimethyl-1H-indazol-5-yl)benzoyl]piperazine-1-carbonyl}cyclopropan-1-ol | 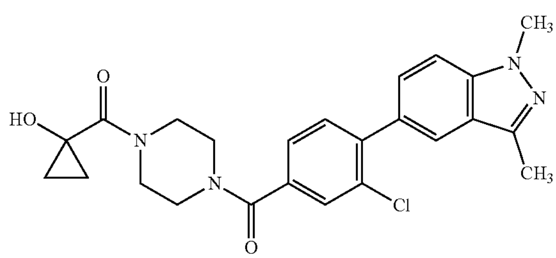 [SMILES: Cc1nn(C)c2ccc(-c3ccc(C(=O)N4CCN(C(=O)C5(O)CC5)CC4)cc3Cl)cc12] |
| 1-[(2S)-2-methyl-4-[4-(1-methyl-1H-1,3-benzodiazol-5-yl)benzoyl]piperazine-1-carbonyl]cyclopropan-1-ol | 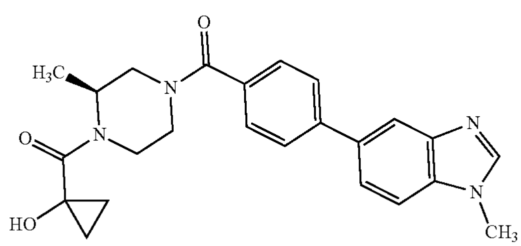 [SMILES: C[C@H]1CN(C(=O)c2ccc(-c3ccc4c(c3)ncn4C)cc2)CCN1C(=O)C1(O)CC1] |
| 1-{4-[2,6-difluoro-4-(2-methyl-2H-indazol-6-yl)benzoyl]piperazine-1-carbonyl}cyclopropan-1-ol | 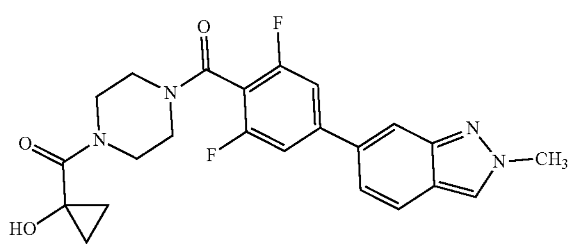 [SMILES: Cn1cc2ccc(-c3cc(F)c(C(=O)N4CCN(C(=O)C5(O)CC5)CC4)c(F)c3)cc2n1] |

TABLE 1-continued

| IUPAC Name | Compound Structure |
|---|---|
| 1-(4-{4-[3-(5-amino-1,2-oxazol-3-yl)phenyl]-2-fluorobenzoyl}piperazine-1-carbonyl)cyclopropan-1-ol | 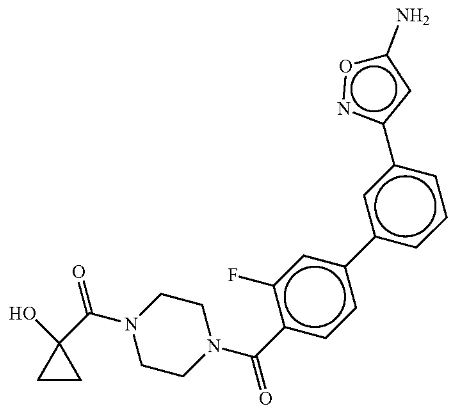 |
| 1-[(2S)-2-methyl-4-[4-(2-methyl-2H-indazol-6-yl)benzoyl]piperazine-1-carbonyl]cyclopropan-1-ol | 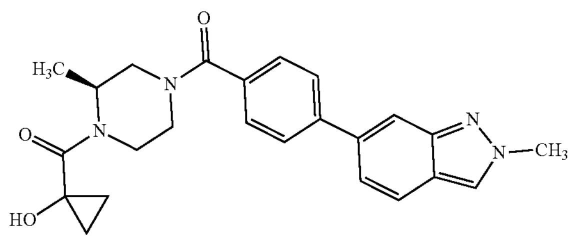 [SMILES: C[C@H]1CN(C(=O)c2ccc(-c3ccc4cn(C)nc4c3)cc2)CCN1C(=O)C1(O)CC1] |
| 1-cyclobutyl-N-(3-{4-[4-(1-hydroxycyclopropanecarbonyl)piperazine-1-carbonyl]phenyl}phenyl)methanesulfonamide | 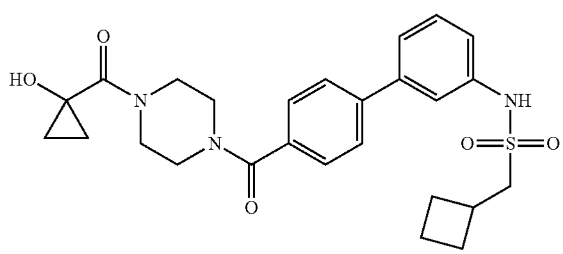 [SMILES: O=C(c1ccc(-c2cccc(NS(=O)(=O)CC3CCC3)c2)cc1)N1CCN(C(=O)C2(O)CC2)CC1] |
| 1-{4-[2-fluoro-4-(7-fluoro-1H-indazol-3-yl)benzoyl]piperazine-1-carbonyl}cyclopropan-1-ol | 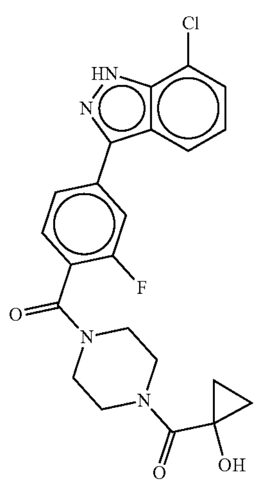 |

TABLE 1-continued

| IUPAC Name | Compound Structure |
|---|---|
| 1-[(2S)-4-[4-(6-chloro-1,3-benzoxazol-2-yl)benzoyl]-2-methylpiperazine-1-carbonyl]cyclopropan-1-ol | 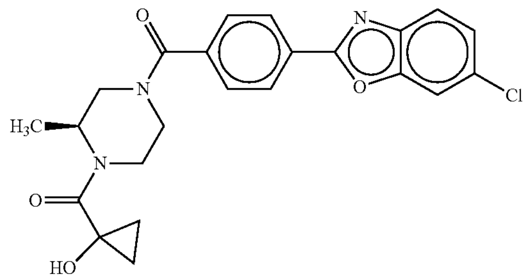 |
| 1-{4-[4-(1H-indol-1-yl)benzoyl]piperazine-1-carbonyl}cyclopropan-1-ol | 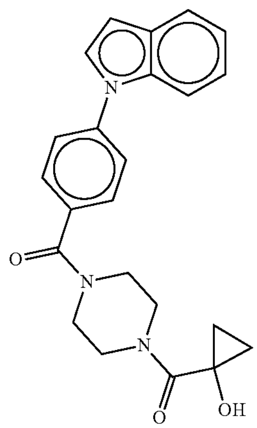 |
| 1-{4-[4-(7-fluoro-1H-indazol-3-yl)benzoyl]piperazine-1-carbonyl}cyclopropan-1-ol | 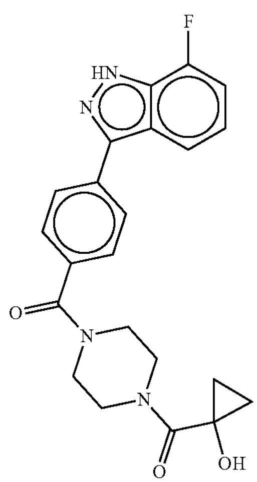 |
| 1-{4-[4-(7-fluoro-1,2,3,4-tetrahydroisoquinolin-2-yl)benzoyl]piperazine-1-carbonyl}cyclopropan-1-ol | 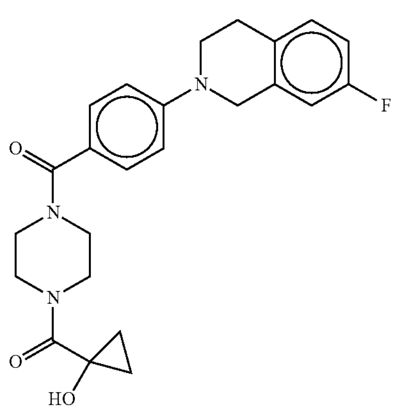 |

TABLE 1-continued

| IUPAC Name | Compound Structure |
|---|---|
| 1-{4-[2-fluoro-4-(2-methyl-2H-indazol-6-yl)benzoyl]piperazine-1-carbonyl}cyclopropan-1-ol | 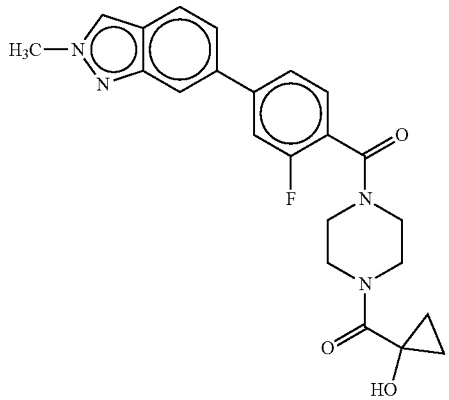 |
| 1-{4-[4-(3-amino-1H-indazol-6-yl)benzoyl]piperazine-1-carbonyl}cyclopropan-1-ol | 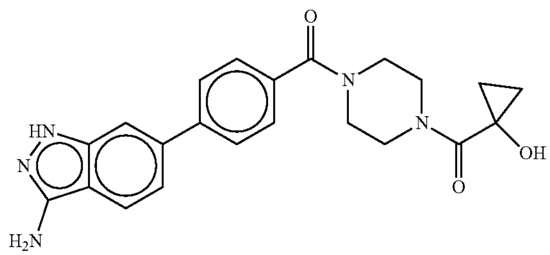 |
| 1-{4-[4-(3-amino-1,2-benzoxazol-5-yl)benzoyl]piperazine-1-carbonyl}cyclopropan-1-ol | 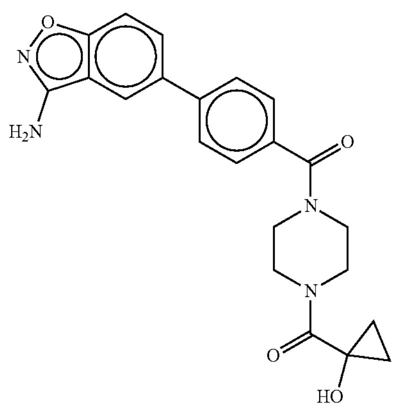 |
| 1-{4-[4-(1,3-dimethyl-1H-indazol-5-yl)-2-fluorobenzoyl]piperazine-1-carbonyl}cyclobutan-1-amine | 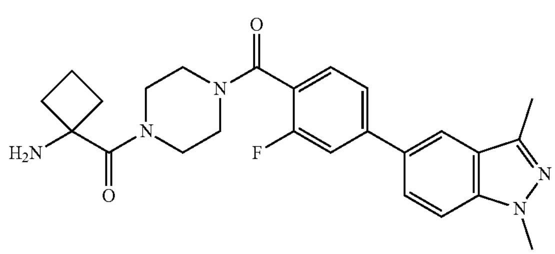 [SMILES: Cc1nn(C)c2ccc(-c3ccc(C(=O)N4CCN(C(=O)C5(N)CCC5)CC4)c(F)c3)cc12] |
| 1-{4-[2-fluoro-4-(3-methyl-1H-indazol-6-yl)benzoyl]piperazine-1-carbonyl}cyclopropan-1-ol | 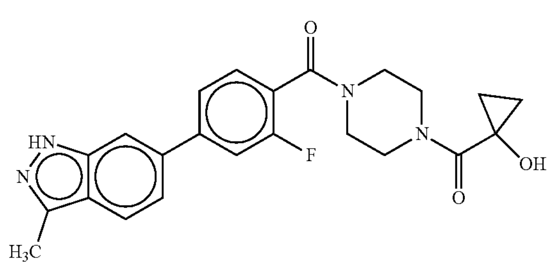 |

TABLE 1-continued

| IUPAC Name | Compound Structure |
|---|---|
| ethyl N-(3-{4-[4-(1-hydroxycyclopropanecarbonyl)piperazine-1-carbonyl]phenyl}phenyl)carbamate | 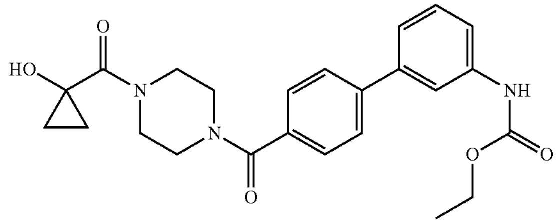 [SMILES: CCOC(=O)Nc1cccc(-c2ccc(C(=O)N3CCN(C(=O)C4(O)CC4)CC3)cc2)c1] |
| 1-{4-[4-(5-chloro-2-methyl-1H-1,3-benzodiazol-7-yl)benzoyl]piperazine-1-carbonyl}cyclopropan-1-ol | 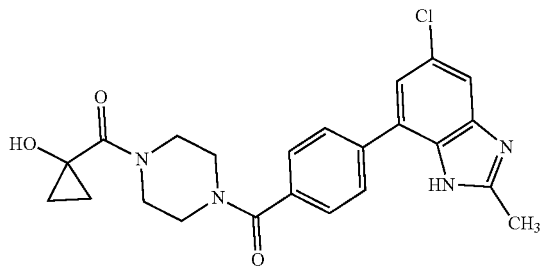 [SMILES: Cc1nc2cc(Cl)cc(-c3ccc(C(=O)N4CCN(C(=O)C5(O)CC5)CC4)cc3)c2[nH]1] |
| 1-[4-(4-{1H,2H,3H,4H,9H-pyrido[3,4-b]indol-2-yl}benzoyl)piperazine-1-carbonyl]cyclopropan-1-ol | 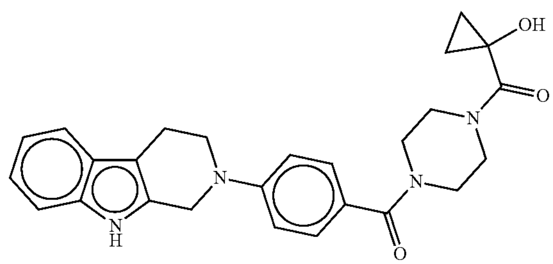 |
| 1-[(2R,6S)-2,6-dimethyl-4-[4-(1-methyl-1H-1,3-benzodiazol-5-yl)benzoyl]piperazine-1-carbonyl]cyclopropan-1-ol | 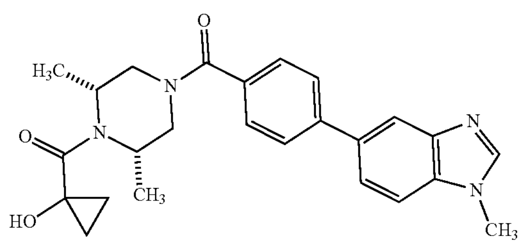 [SMILES: C[C@@H]1CN(C(=O)c2ccc(-c3ccc4c(c3)ncn4C)cc2)C[C@H](C)N1C(=O)C1(O)CC1] |
| 1-[4-(2-chloro-4-{3-chloroimidazo[1,2-a]pyridin-2-yl}benzoyl)piperazine-1-carbonyl]cyclopropan-1-ol | 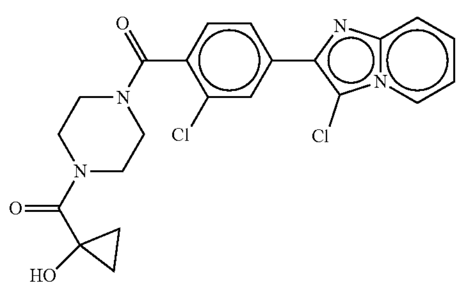 |
| 1-{4-[4-(4-chloro-2-fluorophenyl)benzoyl]-3,3-dimethylpiperazine-1-carbonyl}cyclopropan-1-ol | 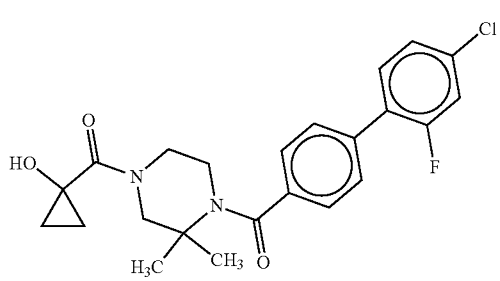 |

TABLE 1-continued

| IUPAC Name | Compound Structure |
|---|---|
| 1-{4-[2-chloro-4-(1-methyl-1H-indazol-6-yl)benzoyl]piperazine-1-carbonyl}cyclopropan-1-ol | 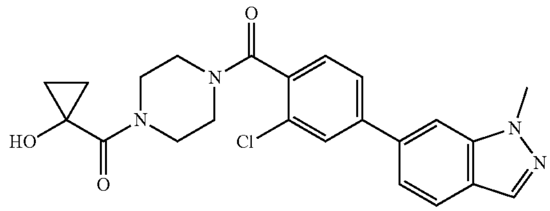 |
| 1-[(2S)-4-[4-(4-chloro-2-fluorophenyl)benzoyl]-2-methylpiperazine-1-carbonyl]cyclopropan-1-ol | 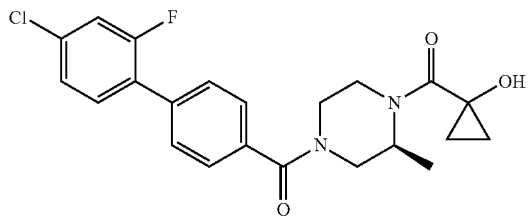 [SMILES: C[C@H]1CN(C(=O)c2ccc(-c3ccc(Cl)cc3F)cc2)CCN1C(=O)C1(O)CC1] |
| 1-[(2S)-4-[4-(1,3-dimethyl-1H-indazol-5-yl)benzoyl]-2-methylpiperazine-1-carbonyl]cyclopropan-1-ol | 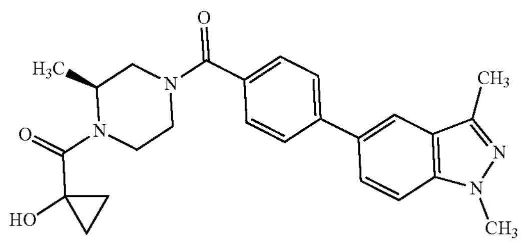 [SMILES: Cc1nn(C)c2ccc(-c3ccc(C(=O)N4CCN(C(=O)C5(O)CC5)[C@@H](C)C4)cc3)cc12] |
| 1-(4-{4-[3-(5-amino-1,2-oxazol-3-yl)phenyl]benzoyl}piperazine-1-carbonyl)cyclopropan-1-ol | 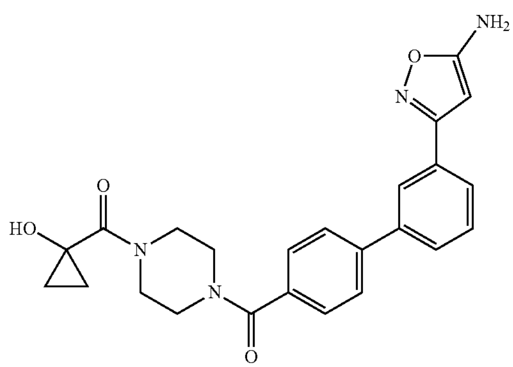 |
| 2-(3-{4-[4-(1-hydroxycyclopropanecarbonyl)piperazine-1-carbonyl]phenyl}phenyl)acetonitrile | 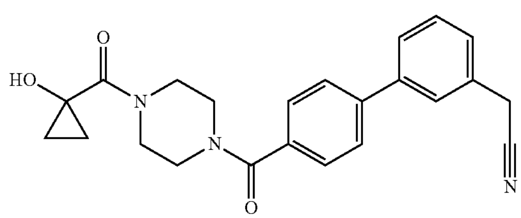 [SMILES: N#CCc1cccc(-c2ccc(C(=O)N3CCN(C(=O)C4(O)CC4)CC3)cc2)c1] |
| N-(3-{4-[4-(1-hydroxycyclopropanecarbonyl)piperazine-1-carbonyl]phenyl}phenyl)cyclopentanesulfonamide | 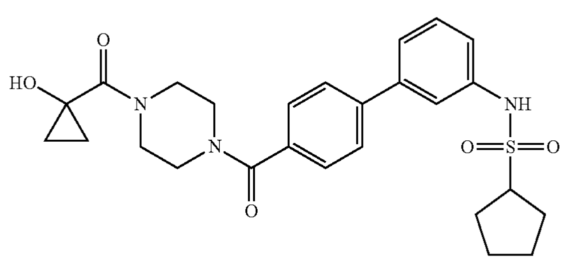 [SMILES: O=C(c1ccc(-c2cccc(NS(=O)(=O)C3CCCC3)c2)cc1)N1CCN(C(=O)C2(O)CC2)CC1] |

TABLE 1-continued

| IUPAC Name | Compound Structure |
| --- | --- |
| 1-[(3S)-3-methyl-4-[4-(1-methyl-1H-1,3-benzodiazol-5-yl)benzoyl]piperazine-1-carbonyl]cyclopropan-1-ol | 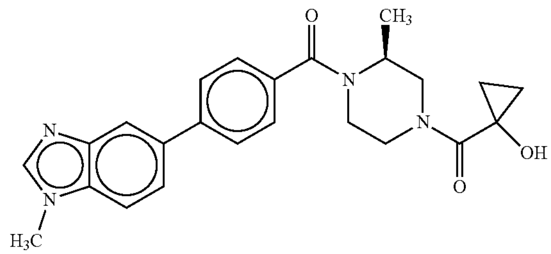 |
| 1-cyclopropyl-N-(3-{4-[4-(1-hydroxycyclopropanecarbonyl)piperazine-1-carbonyl]phenyl}phenyl)methanesulfonamide | 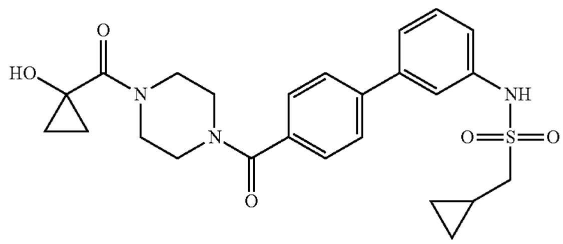 [SMILES: O=C(c1ccc(-c2cccc(NS(=O)(=O)CC3CC3)c2)cc1)N1CCN(C(=O)C2(O)CC2)CC1] |
| 1-{4-[3-chloro-4-(6-fluoro-1,3-benzoxazol-2-yl)benzoyl]piperazine-1-carbonyl}cyclopropan-1-ol | 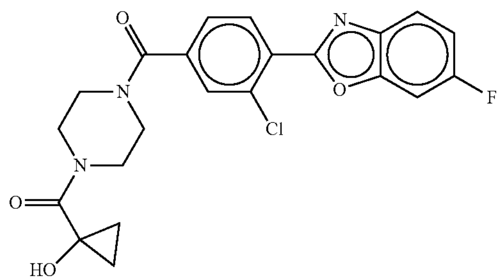 |
| 1-{4-[2-chloro-4-(2-methyl-2H-indazol-6-yl)benzoyl]piperazine-1-carbonyl}cyclopropan-1-ol | 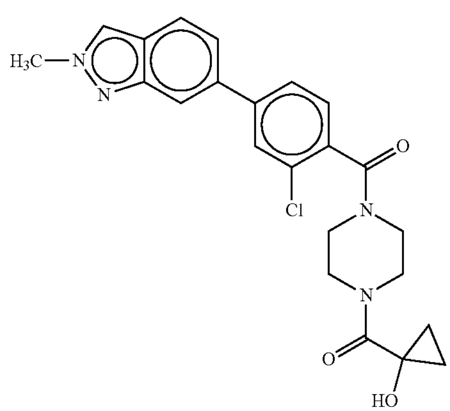 |
| 1-{4-[2,6-difluoro-4-(1-methyl-1H-indazol-6-yl)benzoyl]piperazine-1-carbonyl}cyclopropan-1-ol | 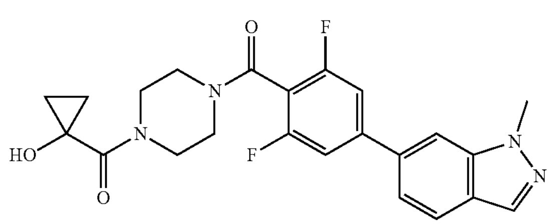 [SMILES: Cn1ncc2ccc(-c3cc(F)c(C(=O)N4CCN(C(=O)C5(O)CC5)CC4)c(F)c3)cc21] |

TABLE 1-continued

| IUPAC Name | Compound Structure |
| --- | --- |
| 1-[(3R)-3-methyl-4-[4-(1-methyl-1H-1,3-benzodiazol-5-yl)benzoyl]piperazine-1-carbonyl]cyclopropan-1-ol | 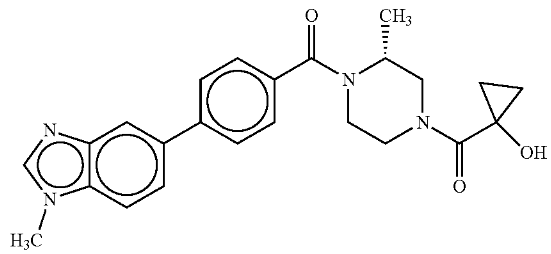 |
| N-(6-{4-[4-(1-hydroxycyclopropanecarbonyl)piperazine-1-carbonyl]phenyl}-1,2-benzoxazol-3-yl)cyclopropanecarboxamide | 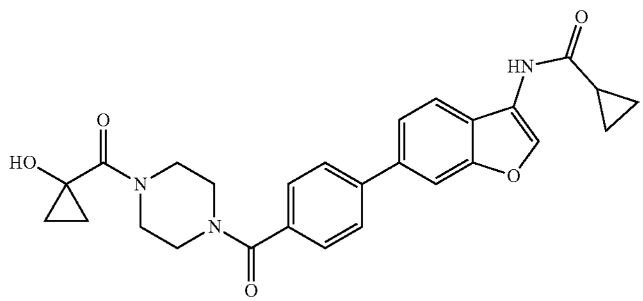 [SMILES: O=C(Nc1coc2cc(-c3ccc(C(=O)N4CCN(C(=O)C5(O)CC5)CC4)cc3)ccc12)C1CC1] |
| 1-[(3R,5S)-3,5-dimethyl-4-[4-(1-methyl-1H-1,3-benzodiazol-5-yl)benzoyl]piperazine-1-carbonyl]cyclopropan-1-ol | 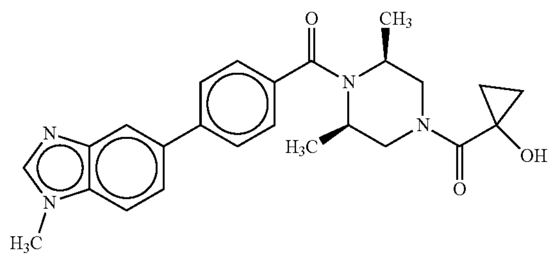 |
| propan-2-yl N-(3-{4-[4-(1-hydroxycyclopropanecarbonyl)piperazine-1-carbonyl]phenyl}phenyl)carbamate | 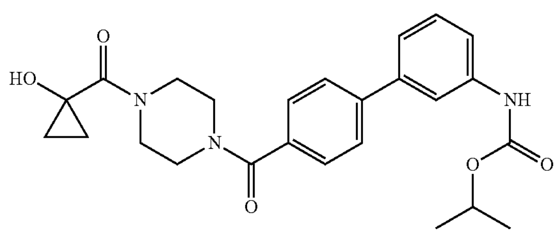 [SMILES: CC(C)OC(=O)Nc1cccc(-c2ccc(C(=O)N3CCN(C(=O)C4(O)CC4)CC3)cc2)c1] |
| 1-{4-[4-(3-amino-1H-indazol-5-yl)benzoyl]piperazine-1-carbonyl}cyclopropan-1-ol | 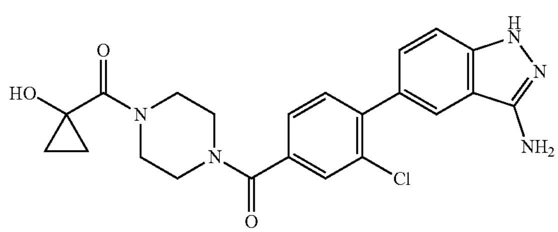 [SMILES: Nc1n[nH]c2ccc(-c3ccc(C(=O)N4CCN(C(=O)C5(O)CC5)CC4)cc3Cl)cc12] |
| 1-[(2R)-2-methyl-4-[4-(1-methyl-1H-1,3-benzodiazol-5-yl)benzoyl]piperazine-1-carbonyl]cyclopropan-1-ol | 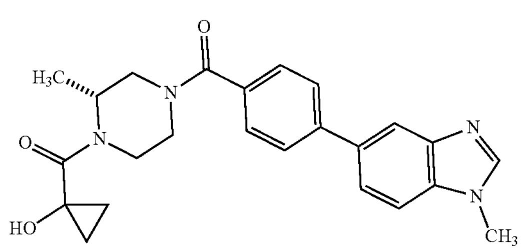 [SMILES: C[C@@H]1CN(C(=O)c2ccc(-c3ccc4c(c3)ncn4C)cc2)CCN1C(=O)C1(O)CC1] |

TABLE 1-continued

| IUPAC Name | Compound Structure |
|---|---|
| 3,3-difluoro-N-(3-{4-[4-(1-hydroxycyclopropanecarbonyl)piperazine-1-carbonyl]phenyl}phenyl)cyclobutane-1-carboxamide | 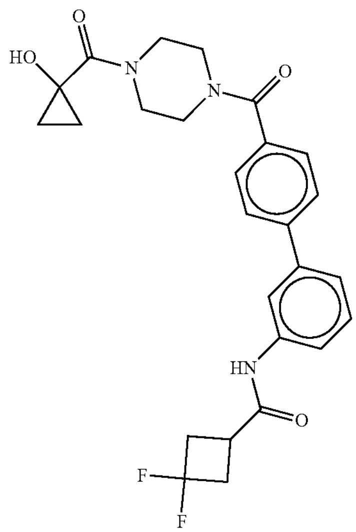 |
| 1-[(2S,6R)-4-[4-(6-fluoro-1,3-benzoxazol-2-yl)benzoyl]-2,6-dimethylpiperazine-1-carbonyl]cyclopropan-1-ol | 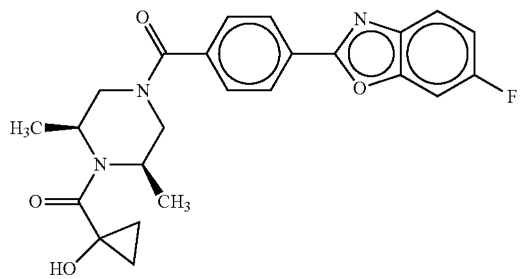 |
| 1-(4-{4-[1-(2-hydroxyethyl)-1H-1,3-benzodiazol-6-yl]benzoyl}piperazine-1-carbonyl)cyclopropan-1-ol | 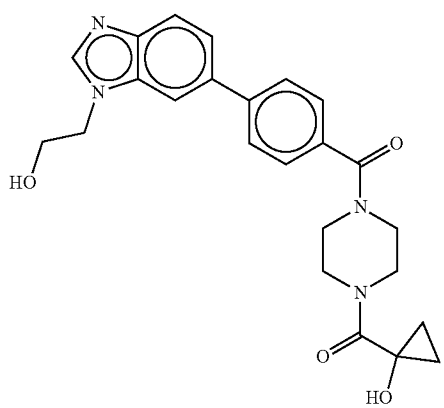 |
| 1-{4-[4-(1H-1,3-benzodiazol-4-yl)-2-chlorobenzoyl]piperazine-1-carbonyl}cyclopropan-1-ol | 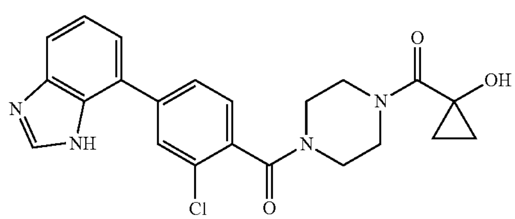 [SMILES: O=C(c1ccc(-c2cccc3nc[nH]c23)cc1Cl)N1CCN(C(=O)C2(O)CC2)CC1] |

TABLE 1-continued

| IUPAC Name | Compound Structure |
|---|---|
| 1-{4-[4-(5-fluoro-2,3-dihydro-1H-indol-1-yl)benzoyl]piperazine-1-carbonyl}cyclopropan-1-ol | 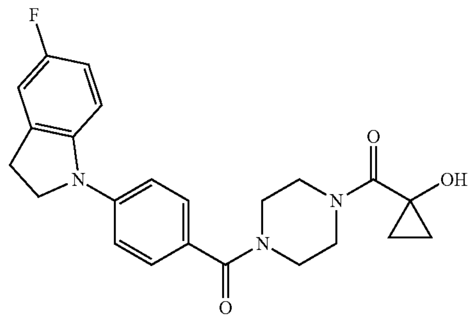 [SMILES: O=C(c1ccc(N2CCc3cc(F)ccc32)cc1)N1CCN(C(=O)C2(O)CC2)CC1] |
| 1-[4-(4-{3-chloroimidazo[1,2-a]pyridin-2-yl}-2-fluorobenzoyl)piperazine-1-carbonyl]cyclopropan-1-ol | 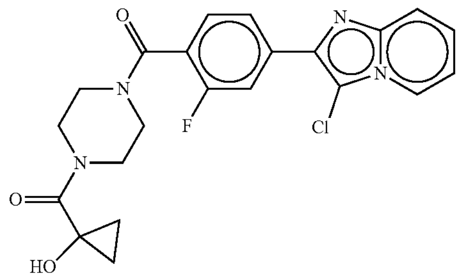 |
| 1-{4-[4-(4-chloro-2-fluorophenyl}-2-fluorobenzoyl]piperazine-1-carbonyl}cyclopropan-1-ol | 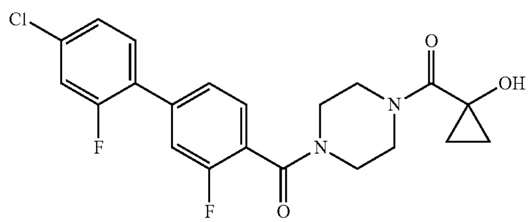 [SMILES: O=C(c1ccc(-c2ccc(Cl)cc2F)cc1F)N1CCN(C(=O)C2(O)CC2)CC1] |
| 1-{4-[3-chloro-4-(4-chloro-2-fluorophenyl)benzoyl]piperazine-1-carbonyl}cyclopropan-1-ol | 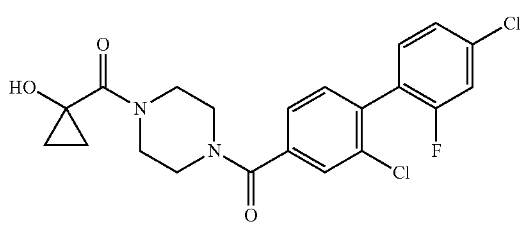 [SMILES: O=C(c1ccc(-c2ccc(Cl)cc2F)c(Cl)c1)N1CCN(C(=O)C2(O)CC2)CC1] |
| 1-{4-[2-chloro-4-(6-chloro-1,3-benzoxazol-2-yl)benzoyl]piperazine-1-carbonyl}cyclopropan-1-ol | 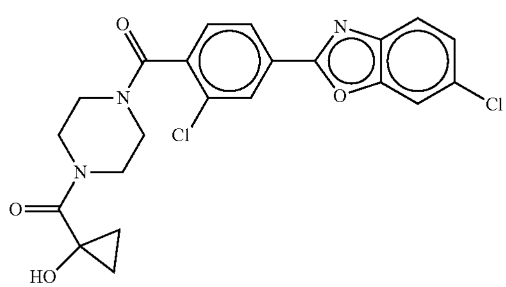 |

TABLE 1-continued

| IUPAC Name | Compound Structure |
|---|---|
| 1-{4-[4-(5-fluoro-2,3-dihydro-1H-isoindol-2-yl)benzoyl]piperazine-1-carbonyl}cyclopropan-1-ol | 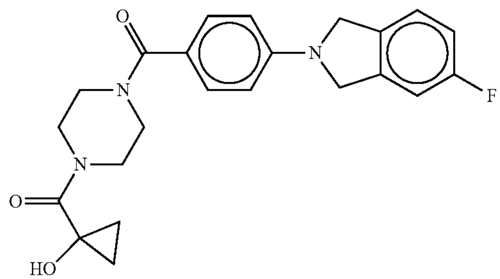 |
| 1-{4-[4-(3-methyl-1H-indazol-4-yl)benzoyl]piperazine-1-carbonyl}cyclopropan-1-ol | 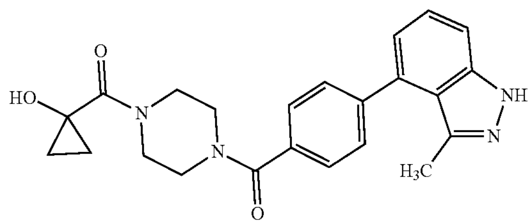 [SMILES: Cc1n[nH]c2cccc(-c3ccc(C(=O)N4CCN(C(=O)C5(O)CC5)CC4)cc3)c12] |
| 1-{4-[4-(6-methoxy-1,3-benzoxazol-2-yl)benzoyl]piperazine-1-carbonyl}cyclopropan-1-ol | 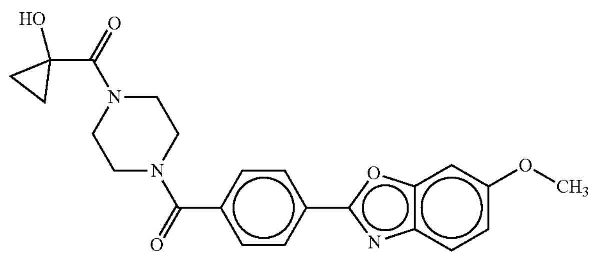 |
| 1-{4-[4-(3-methyl-1H-indazol-7-yl)benzoyl]piperazine-1-carbonyl}cyclopropan-1-ol | 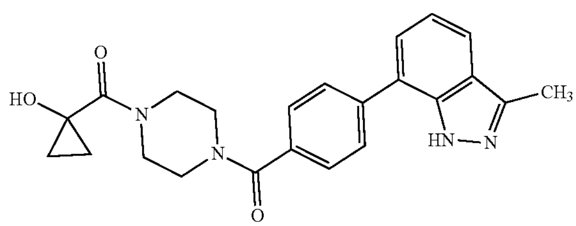 [SMILES: Cc1n[nH]c2c(-c3ccc(C(=O)N4CCN(C(=O)C5(O)CC5)CC4)cc3)cccc12] |
| 1-[(2R)-4-[4-(4-chloro-2-fluorophenyl)benzoyl]-2-methylpiperazine-1-carbonyl]cyclopropan-1-ol | 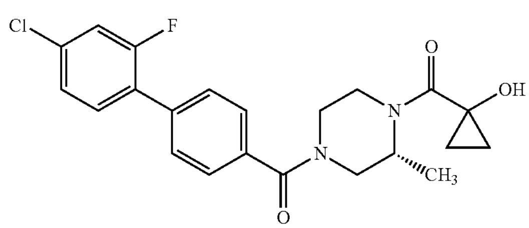 [SMILES: C[C@@H]1CN(C(=O)c2ccc(-c3ccc(Cl)cc3F)cc2)CCN1C(=O)C1(O)CC1] |
| 1-(3-{4-[4-(1-hydroxycyclopropanecarbonyl)piperazine-1-carbonyl]phenyl}phenyl)cyclobutane-1-carbonitrile | 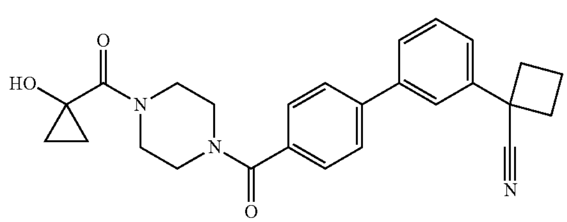 [SMILES: N#CC1(c2cccc(-c3ccc(C(=O)N4CCN(C(=O)C5(O)CC5)CC4)cc3)c2)CCC1] |

TABLE 1-continued

| IUPAC Name | Compound Structure |
|---|---|
| 1-{4-[2-fluoro-4-(6-fluoro-1,3-benzoxazol-2-yl)benzoyl]piperazine-1-carbonyl}cyclopropan-1-ol | 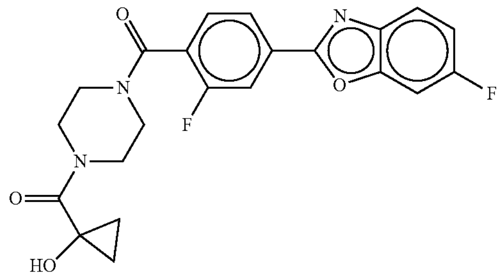 |
| 1-[4-(4-{1H,2H,3H,4H,5H-pyrido[4,3-b]indol-2-yl}benzoyl)piperazine-1-carbonyl]cyclopropan-1-ol | 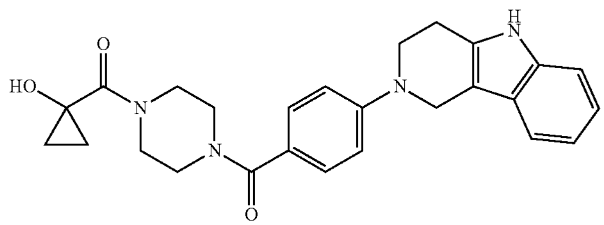 [SMILES: O=C(c1ccc(N2CCc3[nH]c4ccccc4c3C2)cc1)N1CCN(C(=O)C2(O)CC2)CC1] |
| 1-{4-[4-(2-methyl-1H-indol-1-yl)benzoyl]piperazine-1-carbonyl}cyclopropan-1-ol | 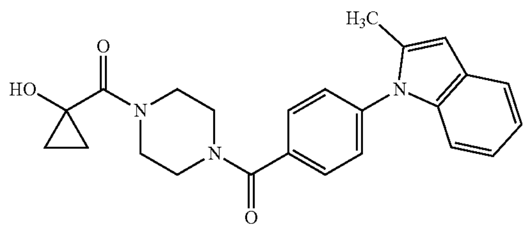 [SMILES: Cc1cc2ccccc2n1-c1ccc(C(=O)N2CCN(C(=O)C3(O)CC3)CC2)cc1] |
| 1-[(2S)-2-methyl-4-[4-(1-methyl-1H-1,3-benzodiazol-5-yl)benzoyl]piperazine-1-carbonyl]cyclopropan-1-amine | 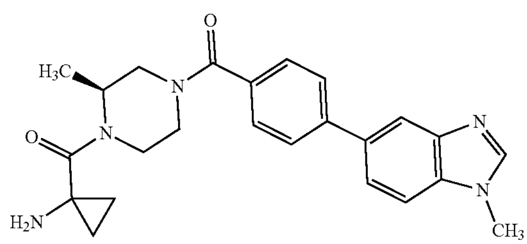 [SMILES: C[C@H]1CN(C(=O)c2ccc(-c3ccc4c(c3)ncn4C)cc2)CCN1C(=O)C1(N)CC1] |
| 1-{4-[3-fluoro-4-(1-methyl-1H-1,3-benzodiazol-5-yl)benzoyl]piperazine-1-carbonyl}cyclopropan-1-ol | 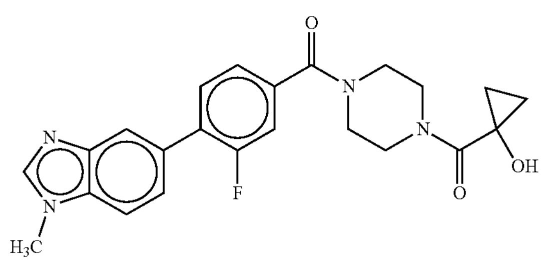 |
| 1-{4-[2-fluoro-4-(1-methyl-1H-1,3-benzodiazol-5-yl)benzoyl]piperazine-1-carbonyl}cyclobutan-1-amine | 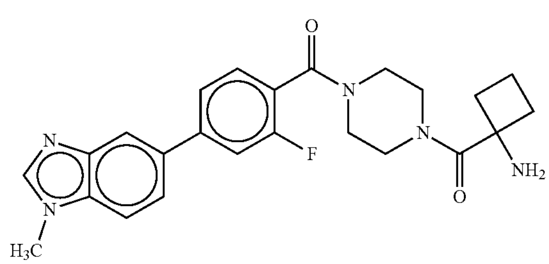 |

TABLE 1-continued

| IUPAC Name | Compound Structure |
|---|---|
| 1-{4-[3-fluoro-4-(1-methyl-1H-indazol-6-yl)benzoyl]piperazine-1-carbonyl}cyclopropan-1-ol | 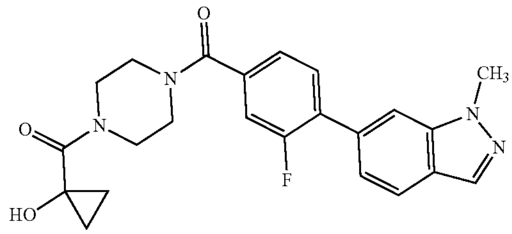 [SMILES: Cn1ncc2ccc(-c3ccc(C(=O)N4CCN(C(=O)C5(O)CC5)CC4)cc3F)cc21] |
| 1-[(2S)-4-[4-(6-fluoro-1,3-benzoxazol-2-yl)benzoyl]-2-methylpiperazine-1-carbonyl]cyclopropan-1-ol | 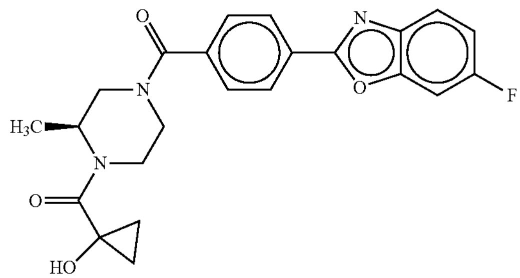 |
| 1-{4-[4-(4-fluoro-2,3-dihydro-1H-isoindol-2-yl)benzoyl]piperazine-1-carbonyl}cyclopropan-1-ol | 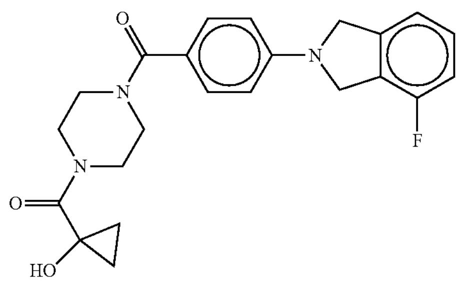 |
| 1-(4-{3-chloro-4-[3-(cyclopropanesulfonyl)phenyl]benzoyl}piperazine-1-carbonyl)cyclopropan-1-ol | 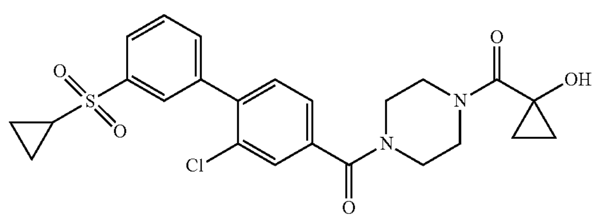 [SMILES: O=C(c1ccc(-c2cccc(S(=O)(=O)C3CC3)c2)c(Cl)c1)N1CCN(C(=O)C2(O)CC2)CC1] |
| 1-{4-[4-(7-fluoro-2,3-dihydro-1H-indol-1-yl)benzoyl]piperazine-1-carbonyl}cyclopropan-1-ol | 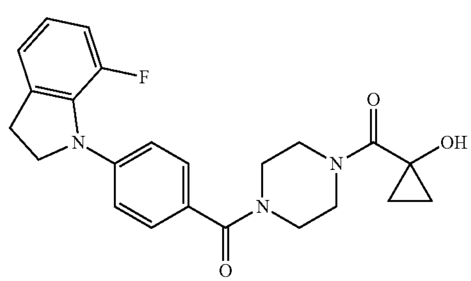 [SMILES: O=C(c1ccc(N2CCc3cccc(F)c32)cc1)N1CCN(C(=O)C2(O)CC2)CC1] |
| 1-{4-[4-(3-cyclopropyl-1H-indazol-6-yl)benzoyl]piperazine-1-carbonyl}cyclopropan-1-ol | 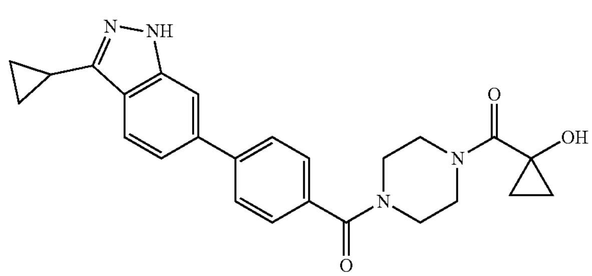 [SMILES: O=C(c1ccc(-c2ccc3c(C4CC4)n[nH]c3c2)cc1)N1CCN(C(=O)C2(O)CC2)CC1] |

TABLE 1-continued

| IUPAC Name | Compound Structure |
|---|---|
| 1-{4-[4-(6-fluoro-1,3-benzoxazol-2-yl)benzoyl]-3,3-dimethylpiperazine-1-carbonyl}cyclopropan-1-ol | 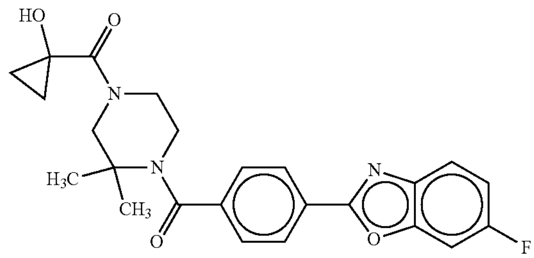 |
| 1-{4-[4-(3-methyl-1H-indazol-1-yl)benzoyl]piperazine-1-carbonyl}cyclopropan-1-ol | 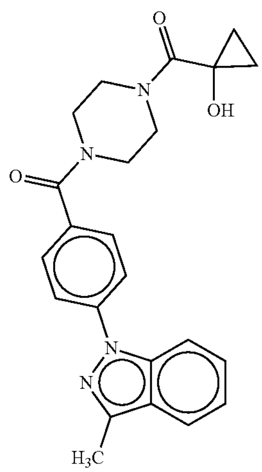 |
| 1-{4-[2-fluoro-4-(3-methyl-1H-indazol-7-yl)benzoyl]piperazine-1-carbonyl}cyclopropan-1-amine | 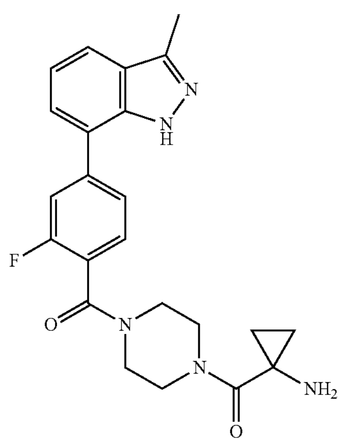 [SMILES: Cc1n[nH]c2c(-c3ccc(C(=O)N4CCN(C(=O)C5(N)CC5)CC4)c(F)c3)cccc12] |
| 1-{4-[4-(1-methanesulfonyl-1H-indol-6-yl)benzoyl]piperazine-1-carbonyl}cyclopropan-1-ol | 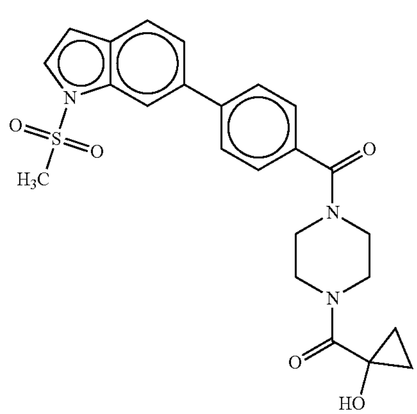 |

TABLE 1-continued

| IUPAC Name | Compound Structure |
|---|---|
| 1-{4-[4-(1-methyl-1H-1,3-benzodiazol-5-yl)benzoyl]piperazine-1-carbonyl}cyclopropan-1-amine | |
| 1-{4-[4-(2-methyl-2,3-dihydro-1H-indol-1-yl)benzoyl]piperazine-1-carbonyl}cyclopropan-1-ol | 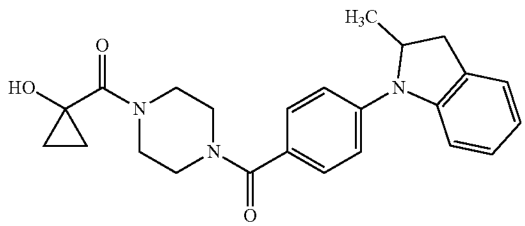 [SMILES: CC1Cc2ccccc2N1c1ccc(C(=O)N2CCN(C(=O)C3(O)CC3)CC2)cc1] |
| 1-{4-[4-(5-fluoro-1H-1,2,3-benzotriazol-6-yl)benzoyl]piperazine-1-carbonyl}cyclopropan-1-ol | 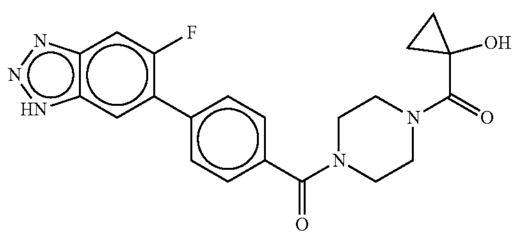 |
| 1-{4-[3-chloro-4-(5-chloro-2-fluorophenyl)benzoyl]piperazine-1-carbonyl}cyclopropan-1-ol | 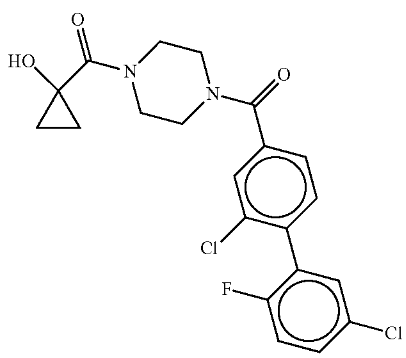 |
| 1-[(2S,6R)-4-[4-(4-chloro-2-fluorophenyl)benzoyl]-2,6-dimethylpiperazine-1-carbonyl]cyclopropan-1-ol | 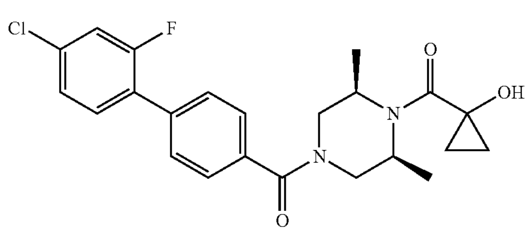 [SMILES: C[C@@H]1CN(C(=O)c2ccc(-c3ccc(Cl)cc3F)cc2)C[C@H](C)N1C(=O)C1(O)CC1] |
| N-(3-{4-[4-(1-hydroxycyclopropanecarbonyl)piperazine-1-carbonyl]phenyl}phenyl)oxane-4-sulfonamide | 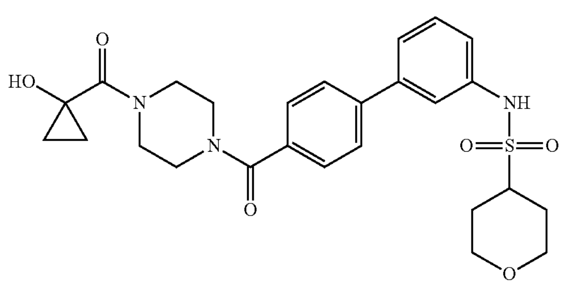 [SMILES: O=C(c1ccc(-c2cccc(NS(=O)(=O)C3CCOCC3)c2)cc1)N1CCN(C(=O)C2(O)CC2)CC1] |

TABLE 1-continued

| IUPAC Name | Compound Structure |
|---|---|
| 1-{4-[4-(1-methyl-1H-indazol-6-yl)benzoyl]piperazine-1-carbonyl}cyclopropan-1-amine | 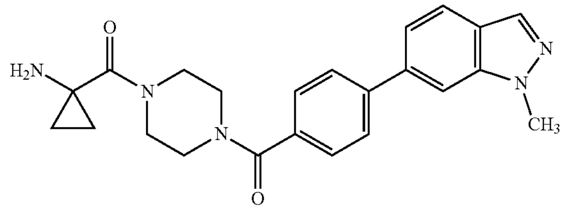 [SMILES: Cn1ncc2ccc(-c3ccc(C(=O)N4CCN(C(=O)C5(N)CC5)CC4)cc3)cc21] |
| 1-{4-[4-(7-methoxy-1,2,3,4-tetrahydroisoquinolin-2-yl)benzoyl]piperazine-1-carbonyl}cyclopropan-1-ol | 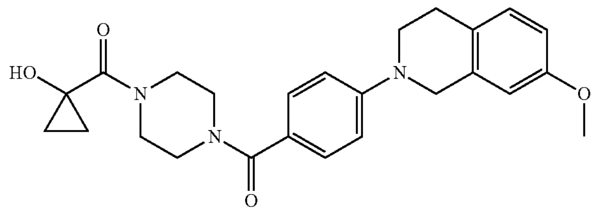 [SMILES: COc1ccc2c(c1)CN(c1ccc(C(=O)N3CCN(C(=O)C4(O)CC4)CC3)cc1)CC2] |
| 1-(3-{3-fluoro-4-[4-(1-hydroxycyclopropanecarbonyl)piperazine-1-carbonyl]phenyl}phenyl)cyclopropane-1-carbonitrile | 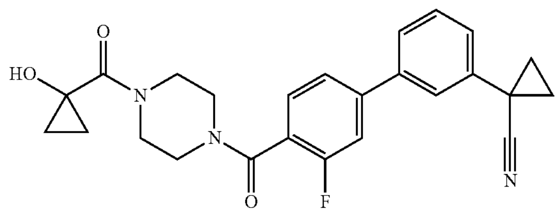 [SMILES: N#CC1(c2cccc(-c3ccc(C(=O)N4CCN(C(=O)C5(O)CC5)CC4)c(F)c3)c2)CC1] |
| 1-{4-[2-fluoro-4-(2-methyl-1H-indol-1-yl)benzoyl]piperazine-1-carbonyl}cyclopropan-1-ol | 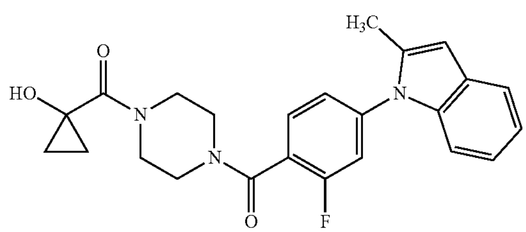 [SMILES: Cc1cc2ccccc2n1-c1ccc(C(=O)N2CCN(C(=O)C3(O)CC3)CC2)c(F)c1] |
| 1-{4-[4-(1H-1,3-benzodiazol-1-yl)benzoyl]piperazine-1-carbonyl}cyclopropan-1-ol | 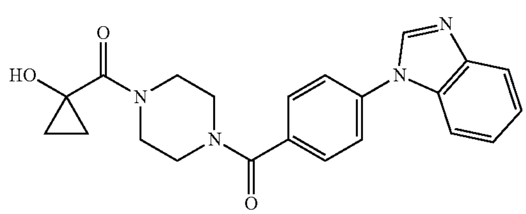 [SMILES: O=C(c1ccc(-n2cnc3ccccc32)cc1)N1CCN(C(=O)C2(O)CC2)CC1] |
| 1-(3-{4-[4-(1-hydroxycyclopropanecarbonyl)piperazine-1-carbonyl]phenyl}phenyl)cyclopropane-1-carbonitrile | 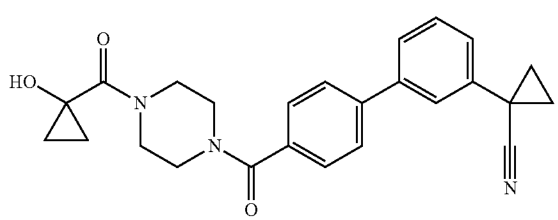 [SMILES: N#CC1(c2cccc(-c3ccc(C(=O)N4CCN(C(=O)C5(O)CC5)CC4)cc3)c2)CC1] |
| 1-{4-[2-fluoro-4-(3-methyl-1H-indazol-1-yl)benzoyl]piperazine-1-carbonyl}cyclopropan-1-ol | 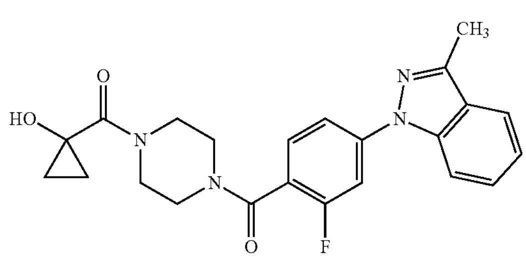 [SMILES: Cc1nn(-c2ccc(C(=O)N3CCN(C(=O)C4(O)CC4)CC3)c(F)c2)c2ccccc12] |

TABLE 1-continued

| IUPAC Name | Compound Structure |
|---|---|
| 1-{4-[2-fluoro-4-(1-methyl-1H-indazol-6-yl)benzoyl]piperazine-1-carbonyl}cyclopropan-1-amine | 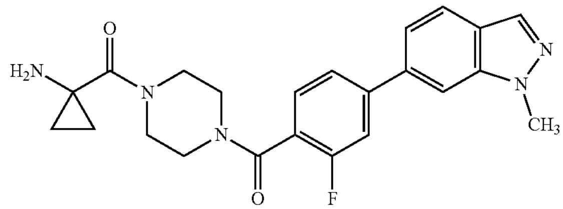 [SMILES: Cn1ncc2ccc(-c3ccc(C(=O)N4CCN(C(=O)C5(N)CC5)CC4)c(F)c3)cc21] |
| 2-{4-[4-(1-hydroxycyclopropanecarbonyl)piperazine-1-carbonyl]phenyl}-1,2,3,4-tetrahydroisoquinoline-7-carbonitrile | 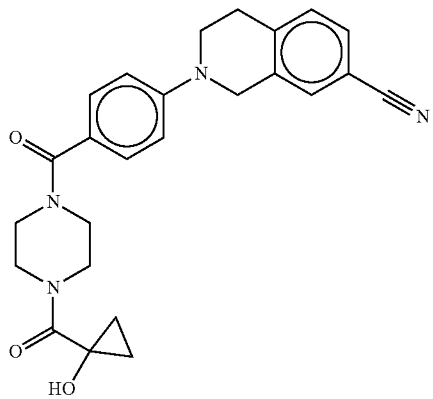 |
| 1-(4-{4-[1-(2-hydroxyethyl)-1H-1,3-benzodiazol-5-yl]benzoyl}piperazine-1-carbonyl)cyclopropan-1-ol | 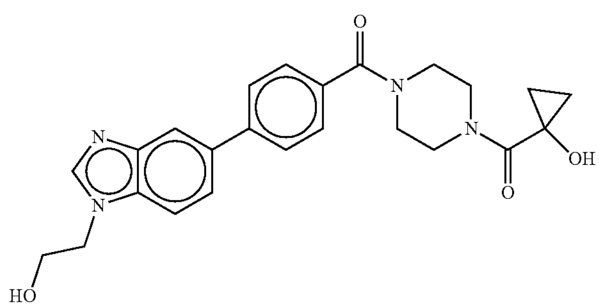 |
| 1-[(2R)-4-[4-(6-fluoro-1,3-benzoxazol-2-yl)benzoyl]-2-methylpiperazine-1-carbonyl]cyclopropan-1-ol | 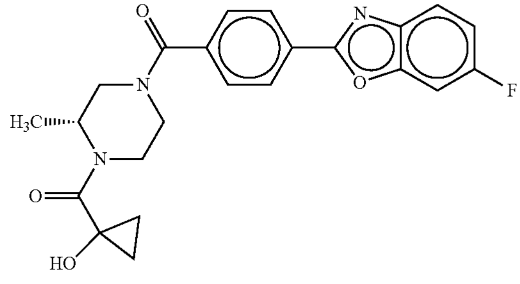 |

TABLE 1-continued

| IUPAC Name | Compound Structure |
|---|---|
| 1-{4-[4-(1H-indazol-1-yl)benzoyl]piperazine-1-carbonyl}cyclopropan-1-ol | 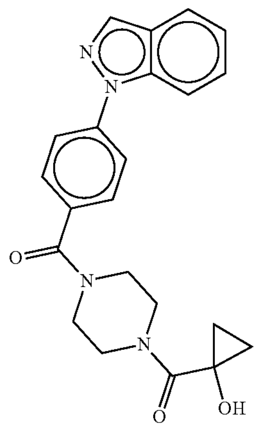 |
| 1-{4-[2-chloro-4-(5-chloro-2-fluorophenyl)benzoyl]piperazine-1-carbonyl}cyclopropan-1-ol | 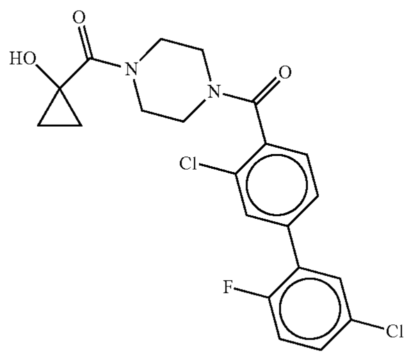 |
| 1-{4-[4-(1,3-dimethyl-1H-indazol-5-yl)-3-fluorobenzoyl]piperazine-1-carbonyl}cyclopropan-1-ol | 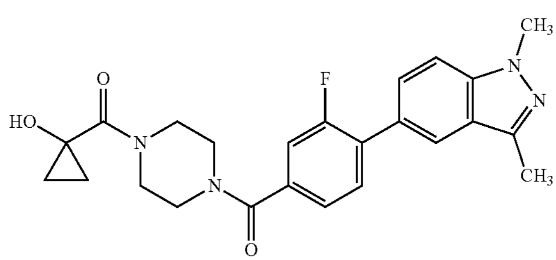 [SMILES: Cc1nn(C)c2ccc(-c3ccc(C(=O)N4CCN(C(=O)C5(O)CC5)CC4)cc3F)cc12] |
| 1-{4-[4-(4-chloro-2-fluorophenyl)benzoyl]-4,7-diazaspiro[2.5]octane-7-carbonyl}cyclopropan-1-ol | 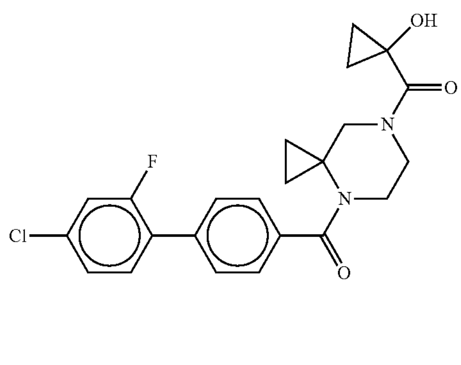 |

TABLE 1-continued

| IUPAC Name | Compound Structure |
|---|---|
| 1-{4-[2-fluoro-4-(7-fluoro-1H-indazol-3-yl)benzoyl]piperazine-1-carbonyl}cyclopropan-1-amine | 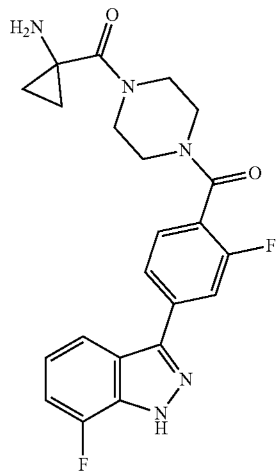 [SMILES: NC1(C(=O)N2CCN(C(=O)c3ccc(-c4n[nH]c5c(F)cccc45)cc3F)CC2)CC1] |
| 6-{1-[4-(1-hydroxycyclopropanecarbonyl)piperazine-1-carbonyl]piperidin-4-yl}naphthalene-2-carbonitrile | 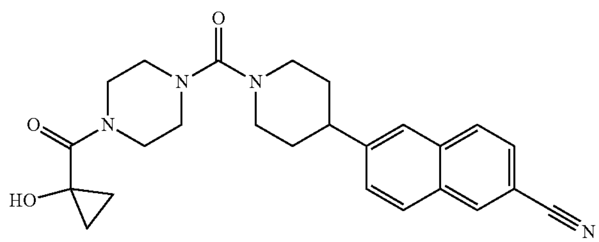 [SMILES: N#Cc1ccc2cc(C3CCN(C(=O)N4CCN(C(=O)C5(O)CC5)CC4)CC3)ccc2c1] |
| 1-(3-{4-[4-(1-hydroxycyclopropanecarbonyl)piperazine-1-carbonyl]phenyl}phenyl)imidazoidin-2-one | 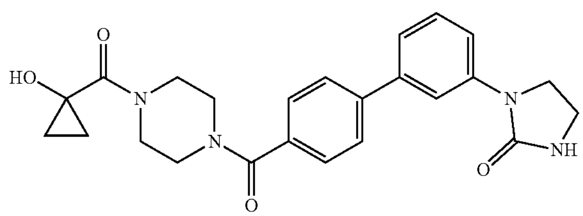 [SMILES: O=C(c1ccc(-c2cccc(N3CCNC3=O)c2)cc1)N1CCN(C(=O)C2(O)CC2)CC1] |
| 1-{4-[2,6-difluoro-4-(2-methyl-2H-indazol-6-yl)benzoyl]piperazine-1-carbonyl}cyclopropan-1-amine | 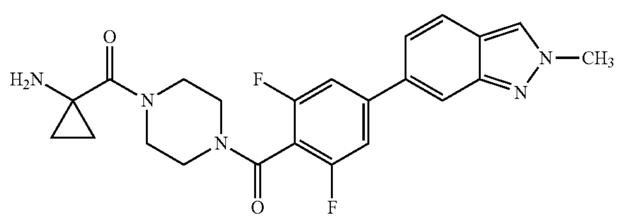 [SMILES: Cn1cc2ccc(-c3cc(F)c(C(=O)N4CCN(C(=O)C5(N)CC5)CC4)c(F)c3)cc2n1] |
| 1,3-dimethyl-5-{4-[4-(oxetane-2-carbonyl)piperazine-1-carbonyl]phenyl}-1H-indazole | 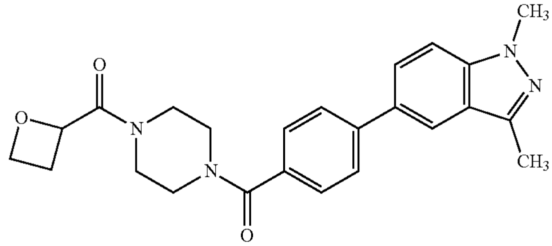 [SMILES: Cc1nn(C)c2ccc(-c3ccc(C(=O)N4CCN(C(=O)C5CCO5)CC4)cc3)cc12] |

TABLE 1-continued

| IUPAC Name | Compound Structure |
|---|---|
| 1-{4-[2-fluoro-4-(2-methyl-2H-indazol-6-yl)benzoyl]piperazine-1-carbonyl}cyclopropan-1-amine | 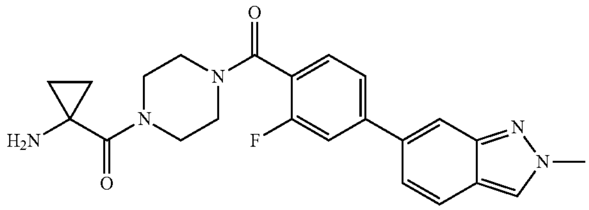 [SMILES: Cn1cc2ccc(-c3ccc(C(=O)N4CCN(C(=O)C5(N)CC5)CC4)c(F)c3)cc2n1] |
| 1-(4-{4-[3-(5-amino-1H-1,2,4-triazol-3-yl)phenyl]benzoyl}piperazine-1-carbonyl)cyclopropan-1-ol | 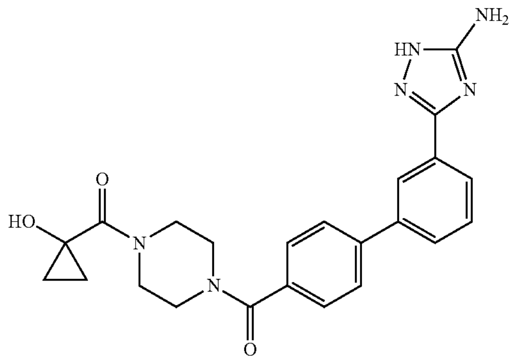 |
| 1-{4-[4-(1-methyl-1H-1,3-benzodiazol-5-yl)benzoyl]-4,7-diazaspiro[2.5]octane-7-carbonyl}cyclopropan-1-ol | 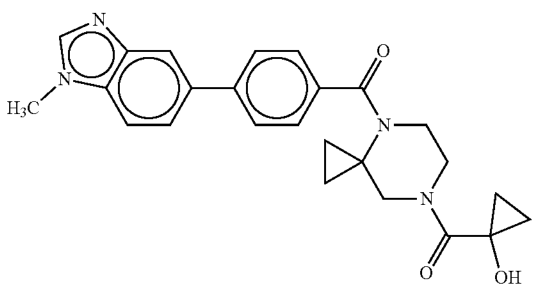 |
| 1-{4-[4-(2-methyl-1H-indol-3-yl)benzoyl]piperazine-1-carbonyl}cyclopropan-1-ol | 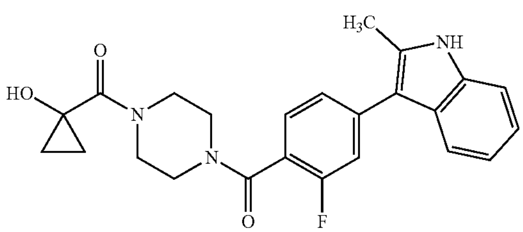 [SMILES: Cc1[nH]c2ccccc2c1-c1ccc(C(=O)N2CCN(C(=O)C3(O)CC3)CC2)c(F)c1] |
| 1-{4-[4-(2-methyl-1H-1,3-benzodiazol-5-yl)benzoyl]piperazine-1-carbonyl}cyclopropan-1-ol | 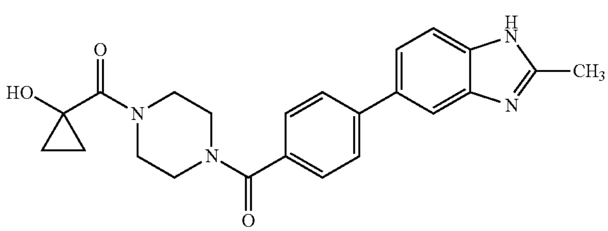 [SMILES: Cc1nc2cc(-c3ccc(C(=O)N4CCN(C(=O)C5(O)CC5)CC4)cc3)ccc2[nH]1] |
| 1-{4-[4-(6-fluoro-1,3-benzoxazol-2-yl)benzoyl]-4,7-diazaspiro[2.5]octane-7-carbonyl}cyclopropan-1-ol | 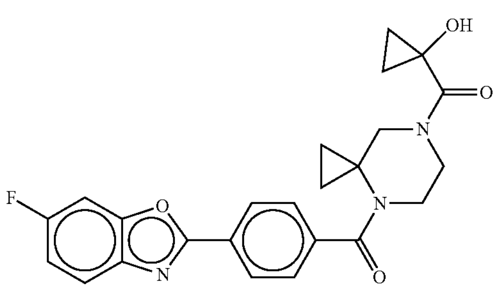 |

TABLE 1-continued

| IUPAC Name | Compound Structure |
|---|---|
| 1-{4-[4-(6-fluoro-1-methyl-1H-1,2,3-benzotriazol-5-yl)benzoyl]piperazine-1-carbonyl}cyclopropan-1-ol | 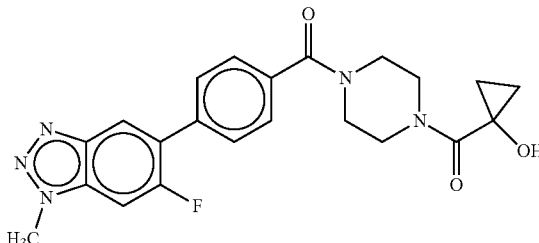 |
| 1-{4-[4-(1-methyl-1H-1,3-benzodiazol-5-yl)benzoyl]piperazine-1-carbonyl}cyclobutan-1-ol | 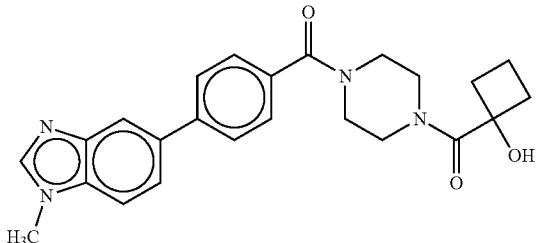 |
| 6-chloro-4-{4-[4-(1-hydroxycyclopropanecarbonyl)piperazine-1-carbonyl]phenyl}-2,3-dihydro-1H-1,3-benzodiazol-2-one | 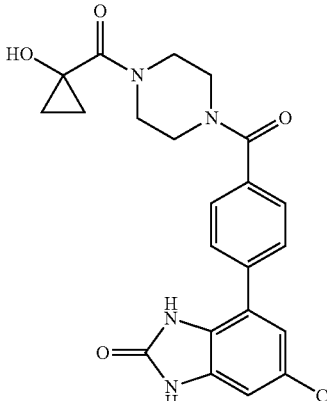 |
| 1-(4-{4-[2-(hydroxymethyl)-1H-1,3-benzodiazol-5-yl]benzoyl}piperazine-1-carbonyl)cyclopropan-1-ol | 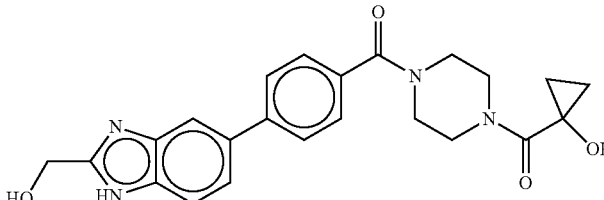 |
| 5-{4-[4-(1-aminocyclopropanecarbonyl)piperazine-1-carbonyl]phenyl}-1,2-benzoxazol-3-amine | 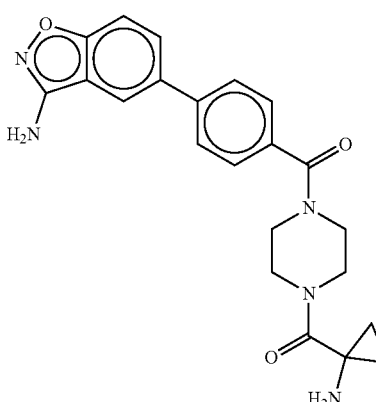 |

TABLE 1-continued

| IUPAC Name | Compound Structure |
|---|---|
| 1-{4-[4-(2-cyclopropyl-2H-indazol-5-yl)benzoyl]piperazine-1-carbonyl}cyclopropan-1-ol | 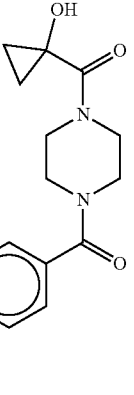 |
| 1-{4-[2-fluoro-4-(5,6,7,8-tetrahydro-1,7-naphthyridin-7-yl)benzoyl]piperazine-1-carbonyl}cyclopropan-1-ol | 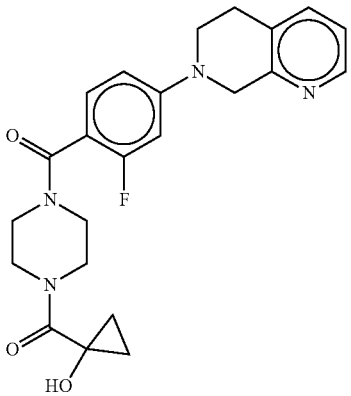 |
| 1-{4-[4-(3-methyl-1,2,3,4-tetrahydroisoquinolin-2-yl)benzoyl]piperazine-1-carbonyl}cyclopropan-1-ol | 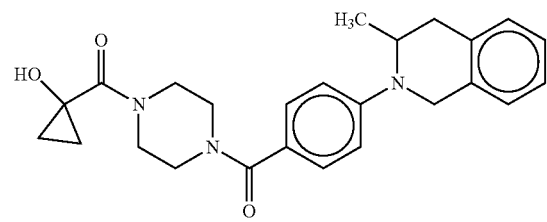 |
| 1-{4-[4-(2,3-dihydro-1H-isoindol-2-yl)benzoyl]piperazine-1-carbonyl}cyclopropan-1-ol | 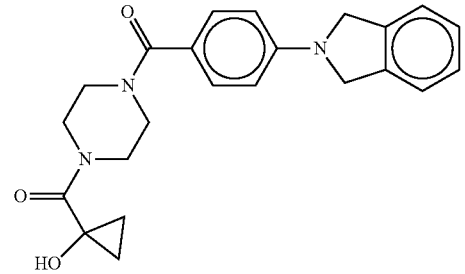 |
| 1-[(3R)-4-[4-(4-chloro-2-fluorophenyl)benzoyl]-3-methylpiperazine-1-carbonyl]cyclopropan-1-ol | 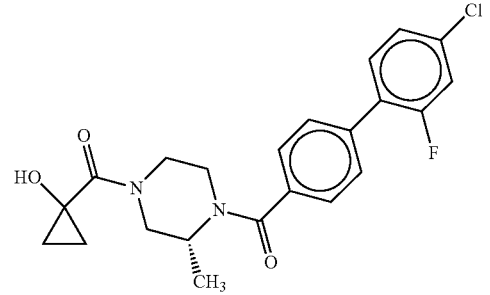 |

TABLE 1-continued

| IUPAC Name | Compound Structure |
|---|---|
| 1-[4-(4-{3-methyl-1H-pyrazolo[3,4-b]pyridin-5-yl}benzoyl)piperazine-1-carbonyl]cyclopropan-1-ol | 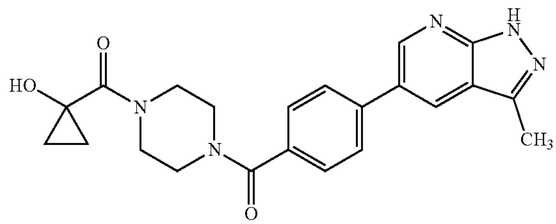 [SMILES: Cc1n[nH]c2ncc(-c3ccc(C(=O)N4CCN(C(=O)C5(O)CC5)CC4)cc3)cc12] |
| 1-{4-[4-(3-methyl-1H-indazol-6-yl)benzoyl]piperazine-1-carbonyl}cyclopropan-1-amine | 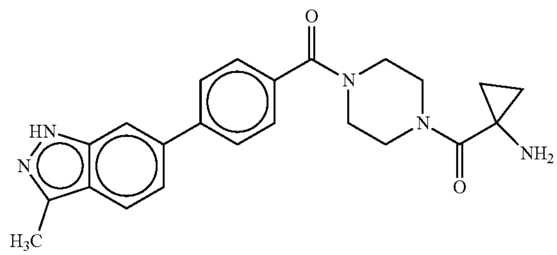 |
| 1-{4-[2-fluoro-4-(1-methyl-1H-1,3-benzodiazol-5-yl)benzoyl]piperazine-1-carbonyl}cyclopropan-1-amine | 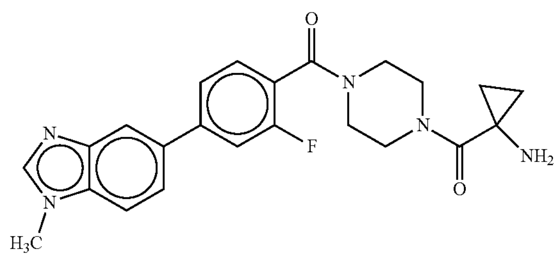 |
| 6-{4-[4-(1-hydroxycyclopropanecarbonyl)piperazine-1-carbonyl]phenyl}-1-methyl-1H-indazol-3-ol | 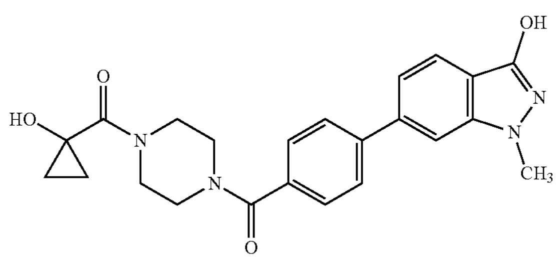 [SMILES: Cn1nc(O)c2ccc(-c3ccc(C(=O)N4CCN(C(=O)C5(O)CC5)CC4)cc3)cc21] |
| 1-{4-[4-(1,2,3,4-tetrahydroquinolin-1-yl)benzoyl]piperazine-1-carbonyl}cyclopropan-1-ol | 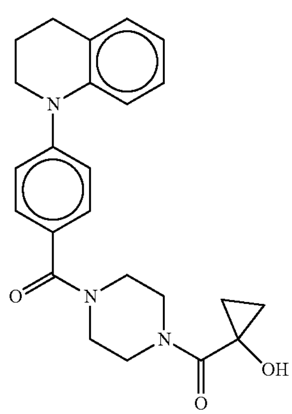 |

TABLE 1-continued

| IUPAC Name | Compound Structure |
|---|---|
| 1-{4-[4-(3-methyl-1H-indazol-7-yl)benzoyl]piperazine-1-carbonyl}cyclopropan-1-amine | 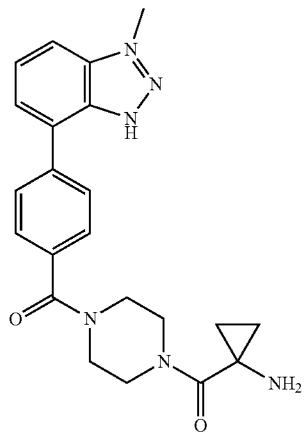 |
| 1-[4-(4-{4H,5H,6H,7H-thieno[3,2-c]pyridin-5-yl}benzoyl)piperazine-1-carbonyl]cyclopropan-1-ol | 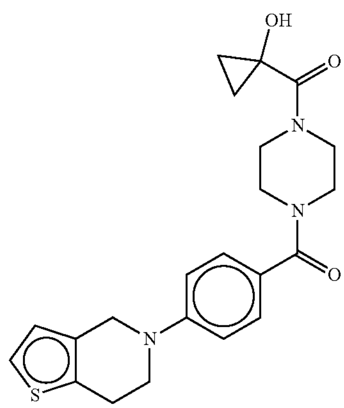 |
| 1-{4-[4-(1-methyl-1H-indazol-6-yl)benzoyl]piperazine-1-carbonyl}cyclobutan-1-amine | 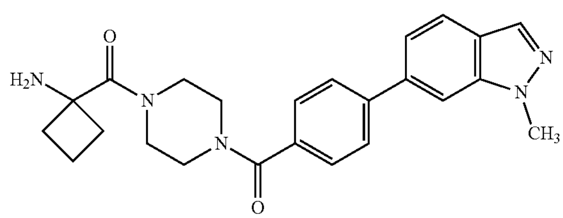 [SMILES: Cn1ncc2ccc(-c3ccc(C(=O)N4CCN(C(=O)C5(N)CCC5)CC4)cc3)cc21] |
| 1-(4-{4-[3-(2-amino-1,3-thiazol-4-yl)phenyl]benzoyl}piperazine-1-carbonyl)cyclopropan-1-ol | 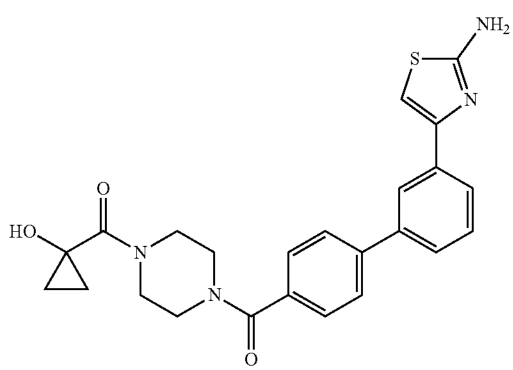 [SMILES: Nc1nc(-c2cccc(-c3ccc(C(=O)N4CCN(C(=O)C5(O)CC5)CC4)cc3)c2)cs1] |

TABLE 1-continued

| IUPAC Name | Compound Structure |
|---|---|
| 1-{4-[4-{1,3-dimethyl-1H-indazol-5-yl)benzoyl]piperazine-1-carbonyl}cyclobutan-1-amine | 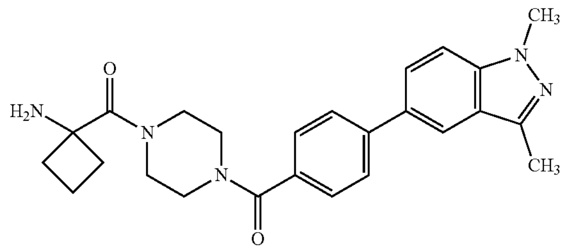 [SMILES: Cc1nn(C)c2ccc(-c3ccc(C(=O)N4CCN(C(=O)C5(N)CCC5)CC4)cc3)cc12] |
| 1-(4-{4-[3-(cyclopropanesulfonyl)phenyl]-2-fluorobenzoyl}piperazine-1-carbonyl)cyclopropan-1-ol | 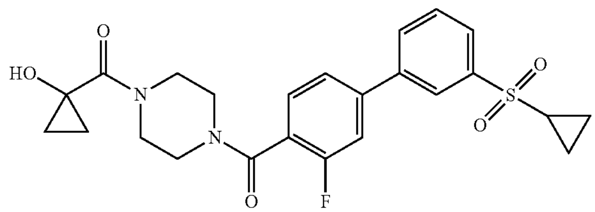 [SMILES: O=C(c1ccc(-c2cccc(S(=O)(=O)C3CC3)c2)cc1F)N1CCN(C(=O)C2(O)CC2)CC1] |
| 1-{4-[4-(6-fluoroquinazolin-2-yl)benzoyl]piperazine-1-carbonyl}cyclopropan-1-ol | 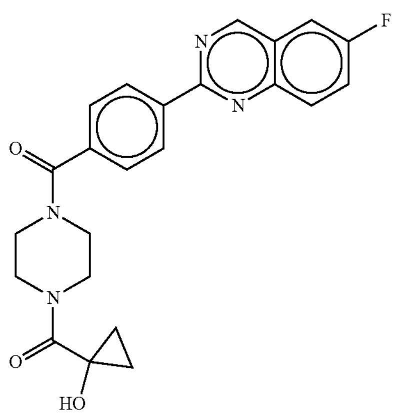 |
| N-(5-{4-[4-(1-hydroxycyclopropanecarbonyl)piperazine-1-carbonyl]phenyl}-1,2-benzoxazol-3-yl)cyclopropanecarboxamide | 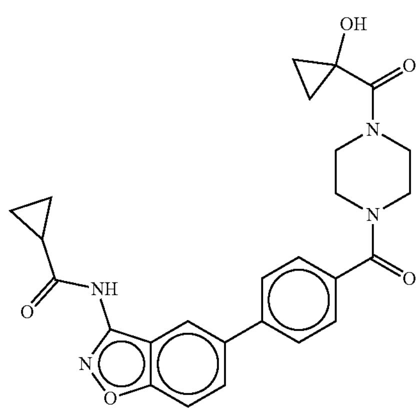 |

TABLE 1-continued

| IUPAC Name | Compound Structure |
|---|---|
| 4-{4-[4-(1-hydroxycyclopropanecarbonyl)piperazine-1-carbonyl]phenyl}-1-methyl-2,3-dihydro-1H-indol-2-one | 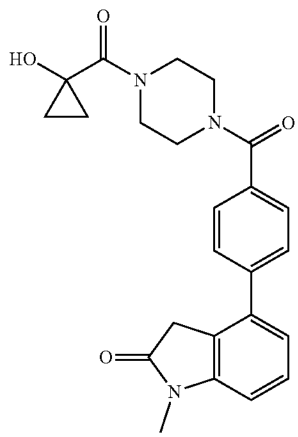 [SMILES: CN1C(=O)Cc2c(-c3ccc(C(=O)N4CCN(C(=O)C5(O)CC5)CC4)cc3)cccc21] |
| 1-[(3R)-4-[4-(6-fluoro-1,3-benzoxazol-2-yl)benzoyl]-3-methylpiperazine-1-carbonyl]cyclopropan-1-ol | 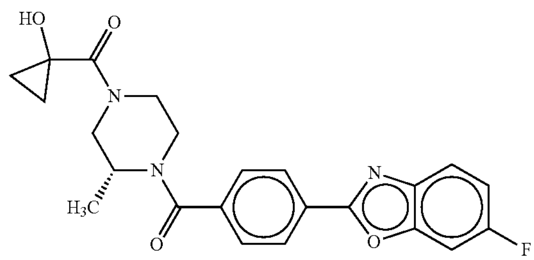 |
| 1-{4-[4-(2-methyl-1H-1,3-benzodiazol-1-yl)benzoyl]piperazine-1-carbonyl}cyclopropan-1-ol | 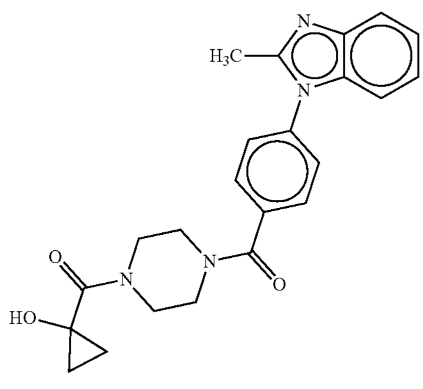 |
| 1-{4-[4-(5-chloro-2-fluorophenyl)benzoyl]piperazine-1-carbonyl}cyclopropan-1-amine | 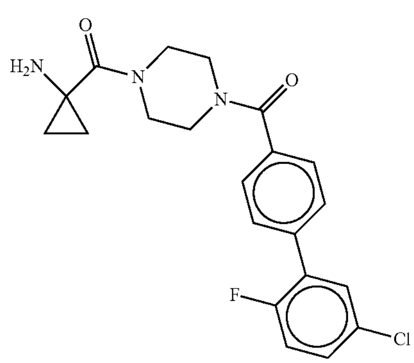 |

TABLE 1-continued

| IUPAC Name | Compound Structure |
|---|---|
| 1-{4-[3-fluoro-4-(2-methyl-2H-indazol-6-yl)benzoyl]piperazine-1-carbonyl}cyclopropan-1-ol | 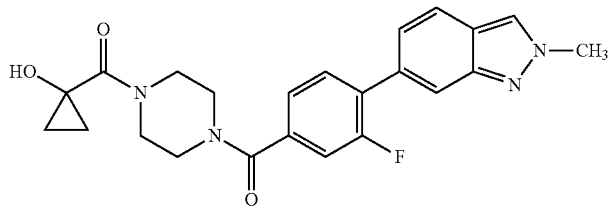 [SMILES: Cn1cc2ccc(-c3ccc(C(=O)N4CCN(C(=O)C5(O)CC5)CC4)cc3F)cc2n1] |
| 3-{4-[4-(1-hydroxycyclopropanecarbonyl)piperazine-1-carbonyl]phenyl}-N-methylbenzamide | 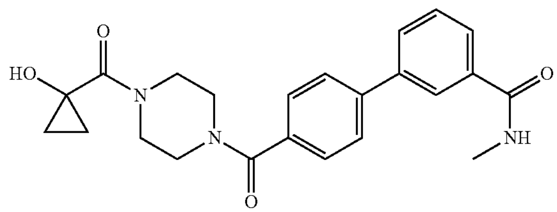 [SMILES: CNC(=O)c1cccc(-c2ccc(C(=O)N3CCN(C(=O)C4(O)CC4)CC3)cc2)c1] |
| 1-(4-{4-[3-(5-amino-1H-pyrazol-3-yl)phenyl]benzoyl}piperazine-1-carbonyl)cyclopropan-1-ol | 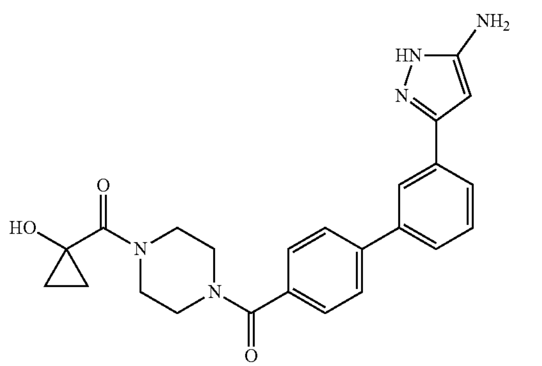 [SMILES: Nc1cc(-c2cccc(-c3ccc(C(=O)N4CCN(C(=O)C5(O)CC5)CC4)cc3)c2)n[nH]1] |
| 1-[(2S)-2-methyl-4-[4-(5,6,7,8-tetrahydro-1,7-naphthyridin-7-yl)benzoyl]piperazine-1-carbonyl]cyclopropan-1-ol | 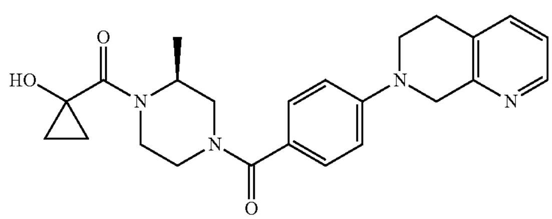 [SMILES: C[C@H]1CN(C(=O)c2ccc(N3CCc4cccnc4C3)cc2)CCN1C(=O)C1(O)CC1] |
| 1-[(3S)-4-[4-(4-chloro-2-fluorophenyl)benzoyl]-3-methylpiperazine-1-carbonyl]cyclopropan-1-ol | 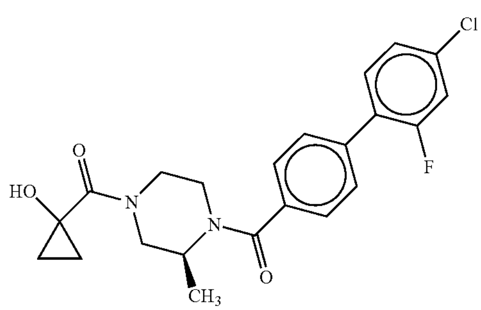 |
| 2-(3-{4-[4-(1-hydroxycyclopropanecarbonyl)piperazine-1-carbonyl]phenyl}phenoxy)-N-methylacetamide | 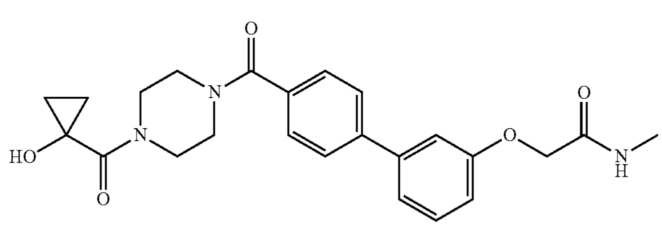 [SMILES: CNC(=O)COc1cccc(-c2ccc(C(=O)N3CCN(C(=O)C4(O)CC4)CC3)cc2)c1] |

TABLE 1-continued

| IUPAC Name | Compound Structure |
|---|---|
| 1-{4-[4-(1-cyclopropyl-1H-indazol-5-yl)benzoyl]piperazine-1-carbonyl}cyclopropan-1-ol | 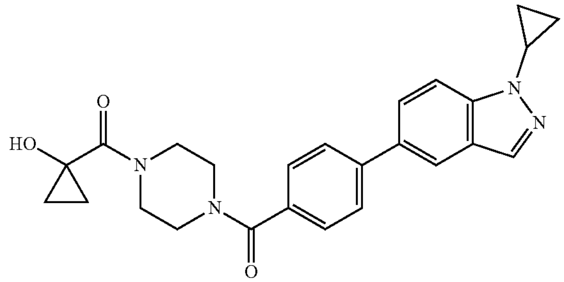 [SMILES: O=C(c1ccc(-c2ccc3c(cnn3C3CC3)c2)cc1)N1CCN(C(=O)C2(O)CC2)CC1] |
| 1-methyl-5-{4-[4-(oxetane-2-carbonyl)piperazine-1-carbonyl]phenyl}-1H-1,3-benzodiazole | 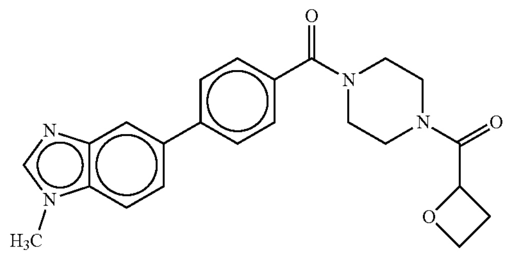 |
| (1-{4-[4-(1-methyl-1H-1,3-benzodiazol-5-yl)benzoyl]piperazine-1-carbonyl}cyclopropyl)methanol | 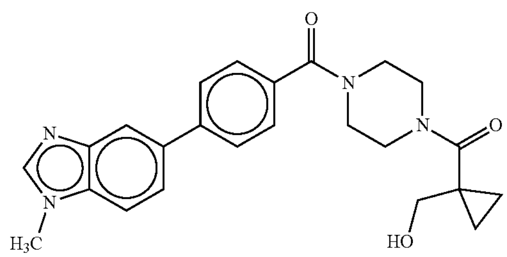 |
| 1-{4-[4-(1-methyl-1H-1,3-benzodiazol-5-yl)benzoyl]piperazine-1-carbonyl}cyclobutan-1-amine | 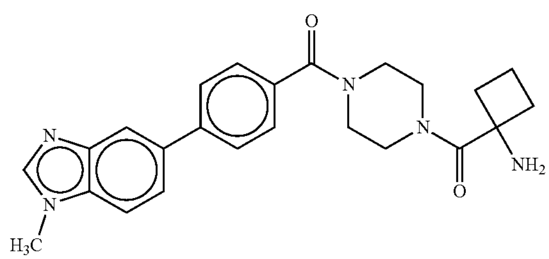 |
| 1-[4-(3-chloro-4-{3-chloroimidazo[1,2-a]pyridin-2-yl}benzoyl)piperazine-1-carbonyl]cyclopropan-1-ol | 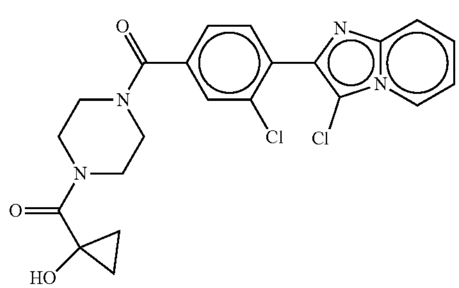 |
| 1-[(2R)-2-(hydroxymethyl)-4-[4-(1-methyl-1H-1,3-benzodiazol-5-yl)benzoyl]piperazine-1-carbonyl]cyclopropan-1-ol | 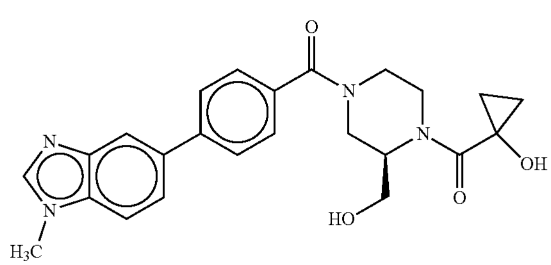 |

TABLE 1-continued

| IUPAC Name | Compound Structure |
|---|---|
| 1-{4-[4-(2,3,4,5-tetrahydro-1H-3-benzazepin-3-yl)benzoyl]piperazine-1-carbonyl}cyclopropan-1-ol | 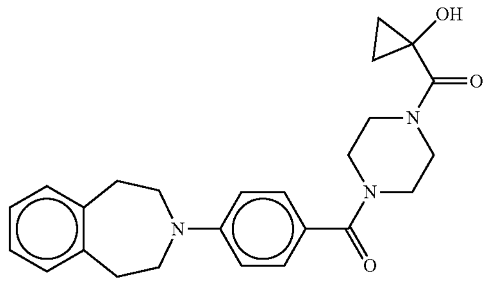 |
| 1-[(2S,6R)-4-[4-(6-fluoro-1,3-benzoxazol-2-yl)benzoyl]-2,6-dimethylpiperazine-1-carbonyl]cyclopropan-1-amine | 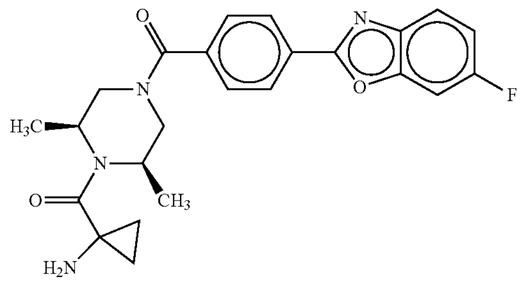 |
| 1-[(2S)-4-[4-(6-fluoro-1,3-benzoxazol-2-yl)benzoyl]-2-methylpiperazine-1-carbonyl]cyclopropan-1-amine | 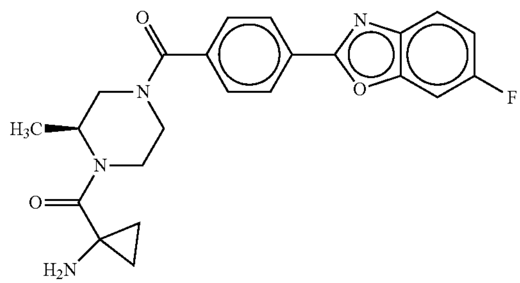 |
| 1-(4-{4-[3-(5-methyl-1,3,4-thiadiazol-2-yl)phenyl]benzoyl}piperazine-1-carbonyl)cyclopropan-1-ol | 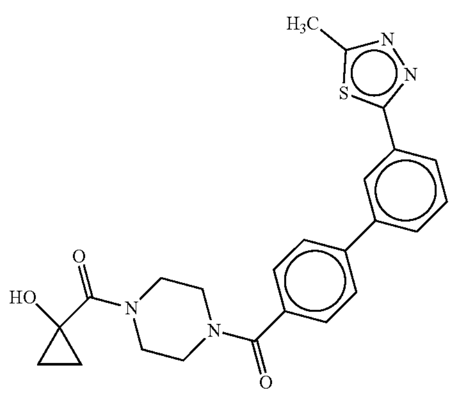 |
| 1-{4-[4-(3-methyl-2H-indazol-2-yl)benzoyl]piperazine-1-carbonyl}cyclopropan-1-ol | 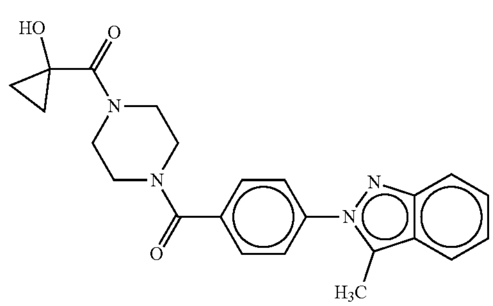 |

TABLE 1-continued

| IUPAC Name | Compound Structure |
|---|---|
| 2-(3-{4-[4-(1-hydroxycyclopropanecarbonyl)piperazine-1-carbonyl]phenyl}phenyl)-2-methylpropanenitrile | 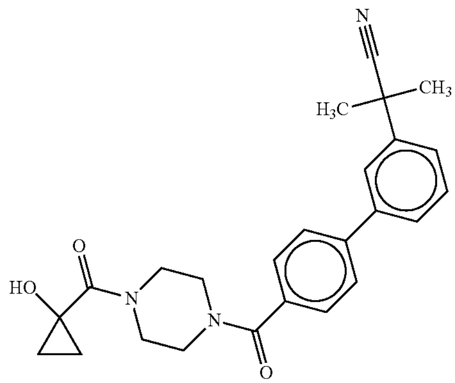 |
| 1-[(2S)-4-{4-[3-(cyclopropanesulfonyl)phenyl]benzoyl}-2-methylpiperazine-1-carbonyl]cyclopropan-1-ol | 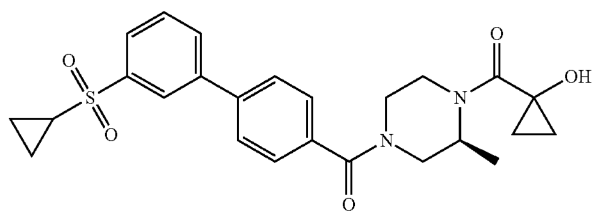 [SMILES: C[C@H]1CN(C(=O)c2ccc(-c3cccc(S(=O)(=O)C4CC4)c3)cc2)CCN1C(=O)C1(O)CC1] |
| 1-(3-{4-[4-(1-hydroxycyclopropanecarbonyl)piperazine-1-carbonyl]phenyl}phenyl)pyrrolidin-2-one | 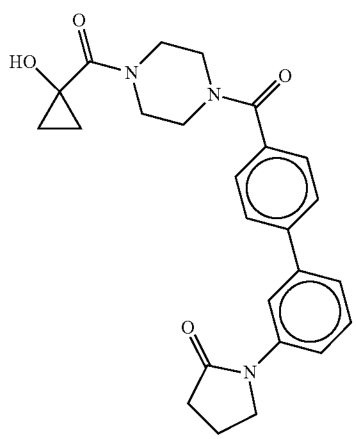 |
| 3-(3-{4-[4-(1-aminocyclopropanecarbonyl)piperazine-1-carbonyl]-3-fluorophenyl}phenyl)-1,2-oxazol-5-amine | 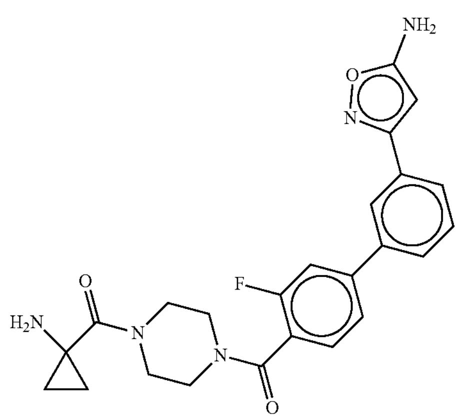 |

TABLE 1-continued

| IUPAC Name | Compound Structure |
| --- | --- |
| 6-{4-[4-(1-hydroxycyclopropanecarbonyl)piperazine-1-carbonyl]phenyl}-N-methylpyridine-2-carboxamide | 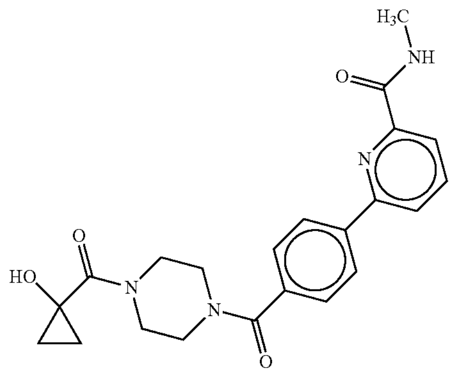 |
| 1-[(3S)-4-[4-(6-fluoro-1,3-benzoxazol-2-yl)benzoyl]-3-methylpiperazine-1-carbonyl]cyclopropan-1-ol | 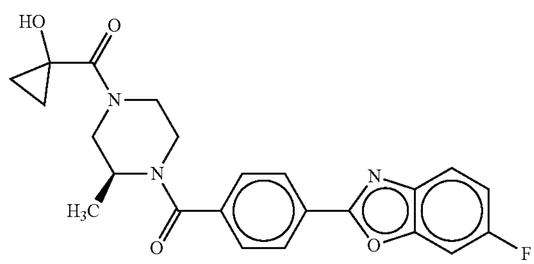 |
| 4-(3-{4-[4-{1-hydroxycyclopropanecarbonyl)piperazine-1-carbonyl]phenyl}phenyl)oxane-4-carbonitrile | 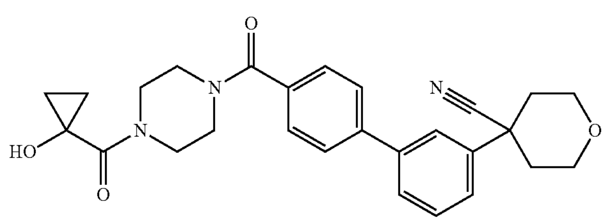 [SMILES: N#CC1(c2cccc(-c3ccc(C(=O)N4CCN(C(=O)C5(O)CC5)CC4)cc3)c2)CCOCC1] |
| 1-(4-{4-[3-(5-methyl-1,2,4-oxadiazol-3-yl)phenyl]benzoyl}piperazine-1-carbonyl)cyclopropan-1-ol | 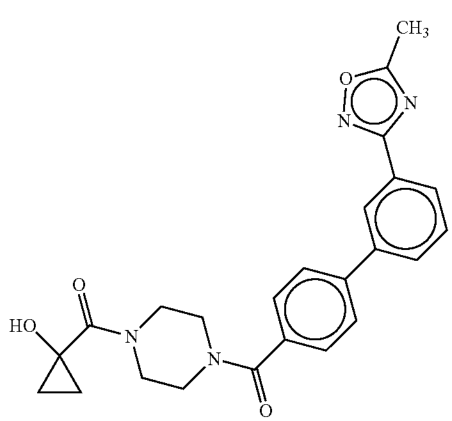 |

TABLE 1-continued

| IUPAC Name | Compound Structure |
|---|---|
| 5-(3-{4-[4-(1-hydroxycyclopropanecarbonyl)piperazine-1-carbonyl]phenyl}phenyl)-5-methylimidazoidine-2,4-dione | 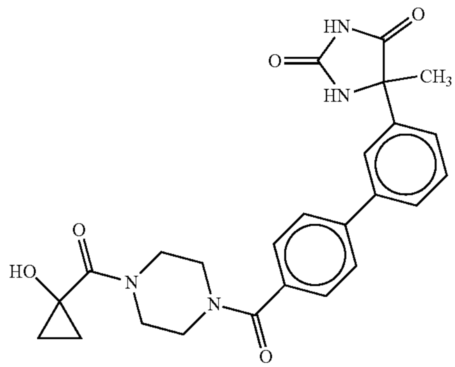 |
| 1-{4-[2-fluoro-4-(2-methyl-1H-indol-1-yl)benzoyl]piperazine-1-carbonyl}cyclopropan-1-amine | 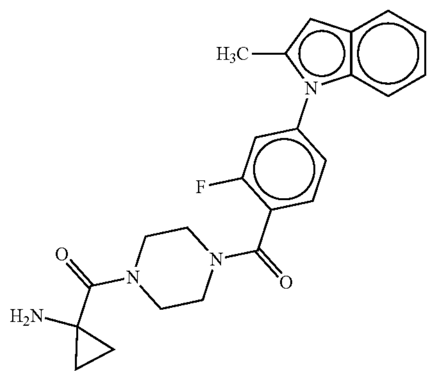 |
| 1-{4-[4-(3-amino-1,2-benzoxazol-6-yl)benzoyl]piperazine-1-carbonyl}cyclopropan-1-ol | 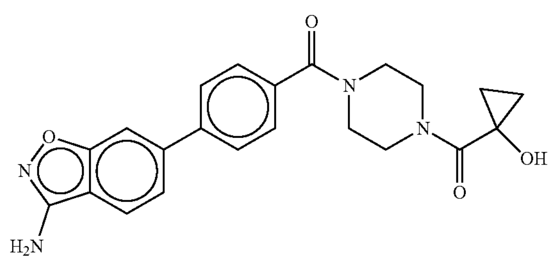 |
| 1-{4-[2-fluoro-4-(2-methyl-2H-indazol-6-yl)benzoyl]piperazine-1-carbonyl}cyclobutan-1-amine | 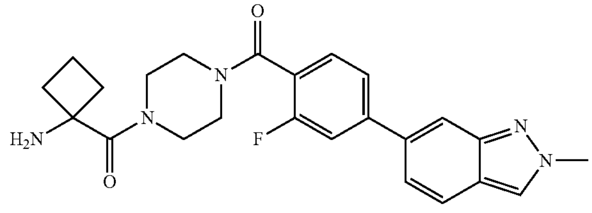 [SMILES: Cn1cc2ccc(-c3ccc(C(=O)N4CCN(C(=O)C5(N)CCC5)CC4)c(F)c3)cc2n1] |

TABLE 1-continued

| IUPAC Name | Compound Structure |
|---|---|
| 2-(3-{4-[4-(1-hydroxycyclopropanecarbonyl)piperazine-1-carbonyl]phenyl]phenyl)-1λ⁶,2-thiazolidine-1,1-dione | |
| 1-{4-[4-(6-chloro-1,3-benzoxazol-2-yl)-3-fluorobenzoyl]piperazine-1-carbonyl}cyclopropan-1-ol | 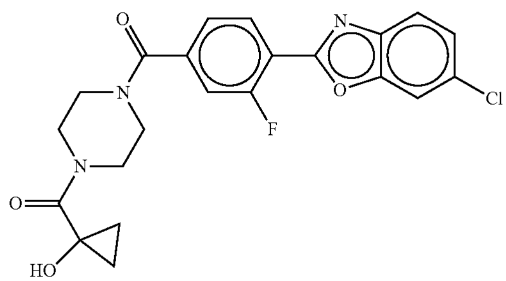 |
| 1-{4-[4-(2,3,4,5-tetrahydro-1H-2-benzazepin-2-yl)benzoyl]piperazine-1-carbonyl}cyclopropan-1-ol | 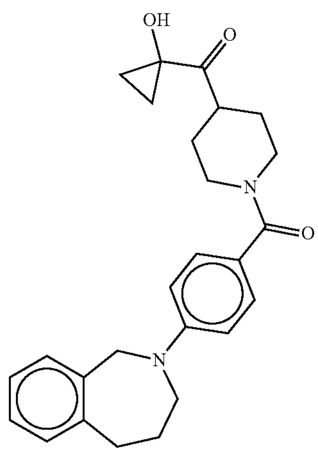 |
| 1-[4-(4-{3-chloroimidazo[1,2-a]pyridin-2-yl}-3-fluorobenzoyl)piperazine-1-carbonyl]cyclopropan-1-ol | 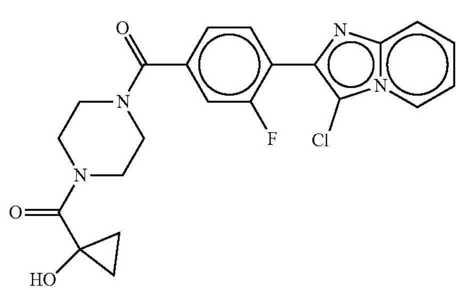 |

TABLE 1-continued

| IUPAC Name | Compound Structure |
|---|---|
| 1-(3-{4-[4-(1-aminocyclopropanecarbonyl)piperazine-1-carbonyl]phenyl}phenyl)cyclopropane-1-carbonitrile | 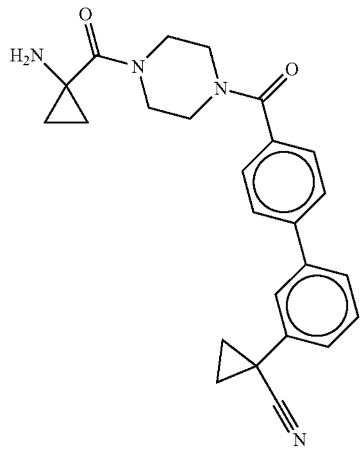 |
| 1-{4-[3-fluoro-4-(6-fluoro-1,3-benzoxazol-2-yl)benzoyl]piperazine-1-carbonyl}cyclopropan-1-ol | 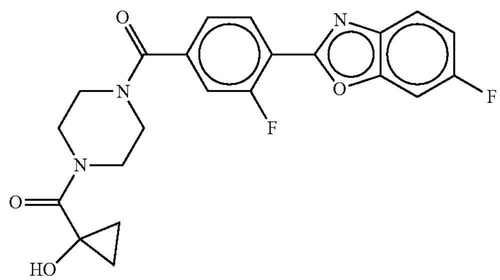 |
| 1-{4-[4-(2-methyl-2H-1,2,3-benzotriazol-5-yl)benzoyl]piperazine-1-carbonyl}cyclopropan-1-ol | 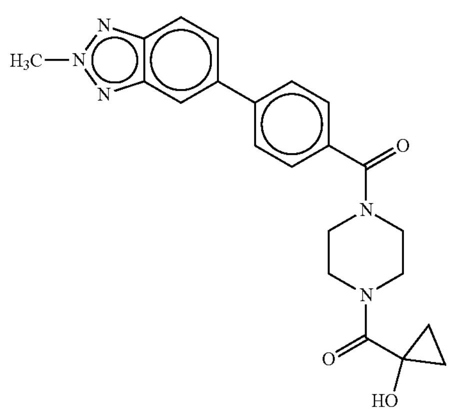 |
| 1-[(3S)-3-methyl-4-[4-(1-methyl-1H-1,3-benzodiazol-5-yl)benzoyl]piperazine-1-carbonyl]cyclopropan-1-amine | 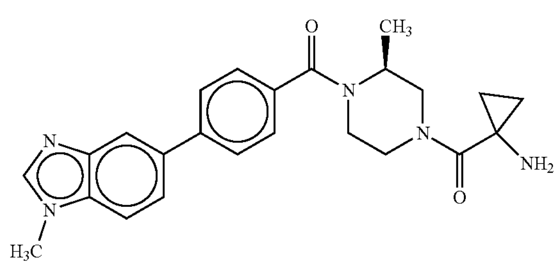 |

EXAMPLES

The following are illustrative, but non-limiting, examples of certain embodiments of the present invention. The synthetic schemes are presented for the synthesis of certain compounds herein disclosed. The process and results for the assays testing FASN inhibition and effects on cancer cell line proliferation are also described.

Definitions used in the following Schemes and elsewhere herein are:
- Ar—B(OH)$_2$ aryl boronic acid
- Ar—B(OR)$_2$ aryl boronic ester
- Ar—X aryl halide
- Atm atmosphere
- BOP ammonium 4-(3-(pyridin-3-1methyl)ureido)benzenesulfinate
- δ chemical shift (ppm)
- CbzCl benzyl chloroformate
- DCM dichloromethane or methylene chloride
- DDQ 2,3-Dichloro-5,6-dicyano-p-benzoquinone
- DIEA N,N-diisopropylethylamine
- DMA N,N-dimethylacetamide
- DMF N,N-dimethylformamide
- DMSO dimethylsulfoxide
- EDC N1-((ethylimino)methylene)-N3,N3-dimethylpropane-1,3-diamine hydrochloride
- ES electrospray
- Et$_3$N triethylamine
- EtOAc ethyl acetate
- EtOH ethanol
- EtN(i-Pr)2 diisopropylethyl amine
- equiv equivalents
- FCC flash column chromatography
- GF/F glass microfiber filter
- $^1$H NMR proton nuclear magnetic resonance
- HCl hydrogen chloride
- HOAc acetic acid
- HATU 2-(3H-[1,2,3]triazolo[4,5-b]pyridin-3-yl)-1,1,3,3-tetramethylisouronium hexafluorophosphate
- HBTU O-(benzotriazol-1-yl)-N,N,N',N'-tetramethyluronium hexafluorophosphate
- HOBt 1H-benzo[d][1,2,3]triazol-1-ol hydrate
- HPLC high pressure liquid chromatography
- i-PrOH isopropanol
- (i-Pr$_2$)NEt N,N-Diisopropylethylamine
- LC-MS liquid chromatography/mass spectrometry
- LiOH lithium hydroxide
- (M+1) mass+1
- m/z mass to charge ratio
- MS mass spectrometry or molecular sieves
- N$_2$ nitrogen
- NaH sodium hydride
- nm nanometer
- NaOH sodium hydroxide
- NaHCO$_3$ sodium bicarbonate
- MeI methyl iodide
- MeOH methanol
- MeSO$_3$H methane sulfonic acid
- MgSO$_4$ magnesium sulfate
- mmol millimoles
- μwave microwave
- Pd(PPh$_3$)$_4$ Tetrakis(triphenylphosphine)palladium
- Pd$_2$(dba)$_3$ tris(dibenzylideneacetone)dipalladium
- Pd(dppf)Cl$_2$ [1,1'-Bis(diphenylphosphino)ferrocene]dichloropalladium(II)
- PTLC preparative thin layer chromatography
- RCO$_2$H 1-hydroxycyclopropanecarboxylic acid
- r.t. or RT room temperature
- SOCl$_2$ thionyl chloride
- TEA triethylamine
- TFA trifluoroacetic acid
- THF tetrahydrofuran
- TLC thin layer chromatography
- UV ultraviolet
- X-Phos 2-dicyclohexylphosphino-2',4',6'-triisopropylbiphenyl Materials Unless otherwise noted, all materials were obtained from commercial suppliers and were used without further purification. Anhydrous solvents were obtained from Sigma-Aldrich (Milwaukee, Wis.) and used directly. All reactions involving air- or moisture-sensitive reagents were performed under a nitrogen atmosphere. Purity and low resolution mass spectral data were measured using either: (1) Waters Acquity ultra performance liquid chromatography (UPLC) system (Waters Acquity UPLC with Sample Organizer and Waters Micromass ZQ Mass Spectrometer) with UV detection at 220 nm and a low resonance electrospray positive ion mode (ESI) (Column: Acquity UPLC BEH Cis 1.7 μm 2.1×50 mm; gradient: 5-100% Solvent B (95/5/0.09%: Acetonitrile/Water/Formic Acid) in Solvent A (95/5/0.1%: 10 mM Ammonium Formate/Acetonitrile/Formic Acid) for 2.2 min then 100-5% Solvent B in Solvent A for 0.01 min then hold at 5% Solvent B in Solvent A for 0.29 min) or (2) Waters H T2790 Alliance high performance liquid chromatography (HPLC) system (Waters 996 PDA and Waters Z Q Single Quad Mass Spectrometer) with UV detection at 220 nm and 254 nm and a low resonance electrospray ionization (positive/negative) mode (ESI) (Column: XBridge Phenyl or C18, 5 μm 4.6×50 mm; gradient: 5-95% Solvent B (95% methanol/5% water with 0.1% Formic Acid) in Solvent A (95% water/5% methanol with 0.1% Formic Acid) for 2.5 min then hold at 95% Solvent B in Solvent A for 1 min).

General Methods for Compound Synthesis:

Method 1.

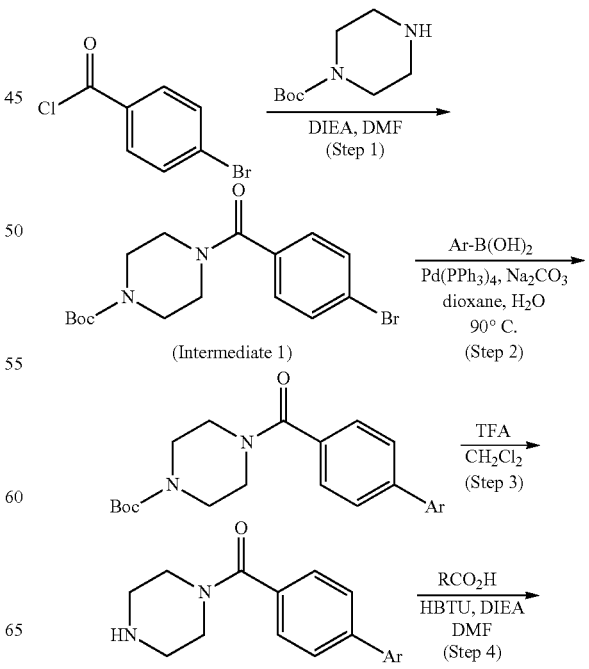

-continued

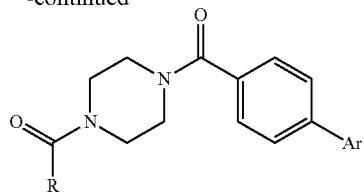

Step 1. tert-butyl 4-(4-bromobenzoyl)piperazine-1-carboxylate (Intermediate 1)

N,N-Diisopropylethylamine (28.6 mL, 164 mmol) was added to a 0° C. solution of tert-butyl piperazine-1-carboxylate (10.18 g, 54.7 mmol) and 4-bromobenzoyl chloride (12.0 g, 54.7 mmol) in DMF (80 mL), and the reaction mixture stirred at rt for 6 h. Water was added and the resulting mixture was stirred overnight and then filtered and dried to afford tert-butyl 4-(4-bromobenzoyl)piperazine-1-carboxylate (19.388 g, 52.5 mmol, 96% yield) as an off-white solid. MS (ESI, pos. ion) m/z: 369, 371 (M+1).

Step 2. tert-butyl 4-(4'-chloro-2'-fluorobiphenylcarbonyl)piperazine-1-carboxylate Tetrakis(triphenylphosphine)palladium (0) (1.565 g, 1.354 mmol) was added to a mixture of tert-butyl 4-(4-bromobenzoyl)piperazine-1-carboxylate (5.00 g, 13.54 mmol), 4-chloro-2-fluorophenylboronic acid (2.95 g, 16.93 mmol), and sodium carbonate (5.74 g, 54.2 mmol) in 1,4-dioxane (50 mL) and water (10 mL). The mixture stirred at 70° C. for 5 h. The reaction mixture was filtered through Celite and concentrated to afford an orange oil. This material was purified via column chromatography on silica gel (Biotage 100 g column, gradient elution with 0-50% ethyl acetate-hexane) to afford tert-butyl 4-(4'-chloro-2'-fluorobiphenylcarbonyl)piperazine-1-carboxylate (5.508 g, 13.15 mmol, 97% yield) as a tan solid. MS (ESI, pos. ion) m/z: 419 (M+1).

Step 3. (4'-chloro-2'-fluorobiphenyl-4-yl)(piperazin-1-yl)methanone 2,2,2-trifluoroacetate Trifluoroacetic acid (20.0 mL, 260 mmol) was added to a solution of tert-butyl 4-(4'-chloro-2'-fluorobiphenylcarbonyl)piperazine-1-carboxylate (11.35 g, 27.1 mmol) in dichloromethane (100 mL) and the solution stirred at rt for 1.5 h. The reaction mixture was concentrated and the residue was triturated with diethyl ether to afford (4'-chloro-2'-fluorobiphenyl-4-yl)(piperazin-1-yl)methanone 2,2,2-trifluoroacetate (12.02 g, 27.8 mmol, 100% yield) as a tan solid. MS (ESI, pos. ion) m/z: 319 (M+1).

Step 4. (4'-chloro-2'-fluorobiphenyl-4-yl)(4-(1-hydroxycyclopropanecarbonyl)piperazin-1-yl)methanone N,N-Diisopropylethylamine (9.12 mL, 52.2 mmol) was added to a solution of (4'-chloro-2'-fluorobiphenyl-4-yl)(piperazin-1-yl)methanone 2,2,2-trifluoroacetate (5.647 g, 13.05 mmol), 1-hydroxycyclopropanecarboxylic acid (1.332 g, 13.05 mmol), and O-(benzotriazol-1-yl)-N,N,N',N'-tetramethyluronium hexafluorophosphate (7.42 g, 19.57 mmol) in DMF (50.0 mL), and the reaction mixture stirred at rt for 18 h. The reaction mixture was partitioned between ethyl acetate and water. The organic phase was washed with water and brine, dried over anhydrous sodium sulfate, filtered, and concentrated to afford a yellow oil. This material was purified via column chromatography on silica gel (Biotage 100 g column, gradient elution with 0-5% methanol-ethyl acetate) to afford an off-white solid which was further purified via column chromatography on silica gel (Biotage 100 g column, gradient elution with 0-10% methanol-dichloromethane) to afford (4'-chloro-2'-fluorobiphenyl-4-yl)(4-(1-hydroxycyclopropanecarbonyl)piperazin-1-yl)methanone (1.554 g, 3.86 mmol, 30% yield) as a white solid. MS (ESI, pos. ion) m/z: 403 (M+1).

Method 2.

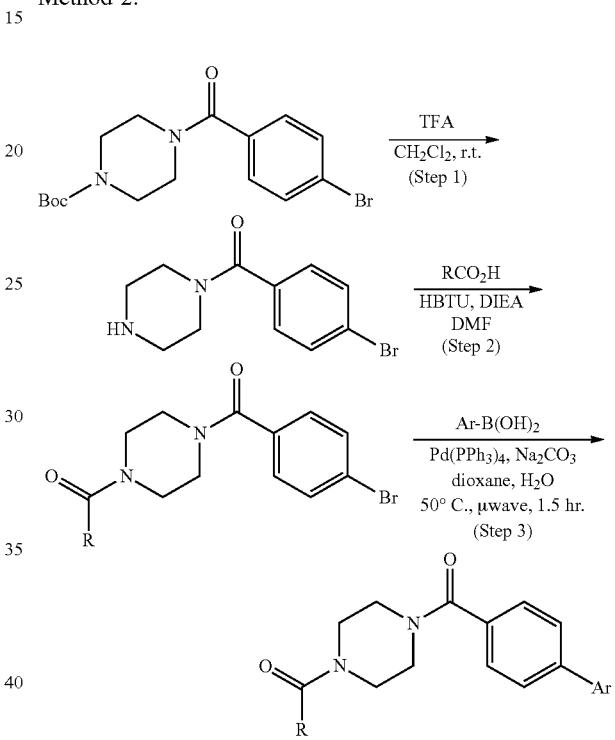

Step 1. (4-bromophenyl)(piperazin-1-yl)methanone 2,2,2-trifluoroacetate

Trifluoroacetic acid (5.0 mL, 64.9 mmol) was added to a solution of tert-butyl 4-(4-bromobenzoyl)piperazine-1-carboxylate (2.00 g, 5.42 mmol) in dichloromethane (25.0 mL), and the solution stirred at rt for 2 h. The reaction mixture was concentrated and the residue was triturated with diethyl ether to afford (4-bromophenyl)(piperazin-1-yl)methanone 2,2,2-trifluoroacetate. (1.992 g, 5.20 mmol, 96% yield) as a white solid. MS (ESI, pos. ion) m/z: 269, 271 (M+1).

Step 2. (4-(4-bromobenzoyl)piperazin-1-yl)(1-hydroxycyclopropyl)methanone

N,N-Diisopropylethylamine (0.46 mL, 2.6 mmol) was added to a solution of (4-bromophenyl)(piperazin-1-yl)methanone 2,2,2-trifluoroacetate (0.250 g, 0.652 mmol), 1-hydroxycyclopropanecarboxylic acid (0.067 g, 0.652 mmol), and O-(benzotriazol-1-yl)-N,N,N',N'-tetramethyluronium hexafluorophosphate (0.371 g, 0.979 mmol) in DMF (5.0 mL), and the reaction mixture stirred at rt for 18 h. The reaction mixture was partitioned between ethyl acetate and water. The organic phase was washed with brine, dried over anhydrous sodium sulfate, filtered, and concentrated to afford an orange oil. This material was purified via column chromatography on silica gel (Biotage 25 g column, gradient elution with 0-5% methanol-dichloromethane) to afford (4-(4-bromobenzoyl)piperazin-1-yl)(1-hydroxycyclopropyl)methanone (0.195 g, 0.552 mmol, 85% yield) as a light orange solid. MS (ESI, pos. ion) m/z: 353, 355 (M+1).

Step 3. (4-(4-(benzo[d]thiazol-5-yl)benzoyl)piperazin-1-yl)(1-hydroxycyclopropyl)methanone Tetrakis(triphenylphosphine)palladium(0) (0.016 g, 0.014 mmol) was added to a mixture of (4-(4-bromobenzoyl)piperazin-1-yl)(1-hydroxycyclopropyl)methanone (0.050 g, 0.142 mmol), 5-(4,4,5,5-tetramethyl-1,3,2-dioxaborolan-2-yl)benzo[d]thiazole (0.055 g, 0.212 mmol), and sodium carbonate (0.060 g, 0.566 mmol) in dioxane (1.5 mL) and water (0.30 mL). The mixture stirred in the microwave at 50° C. for 1 h. The reaction mixture was filtered through Celite and concentrated to afford a yellow oil. This material was purified via column chromatography on silica gel (Biotage 25 g column, gradient elution with 0-5% methanol-ethyl acetate) to afford (4-(4-(benzo[d]thiazol-5-yl)benzoyl)piperazin-1-yl)(1-hydroxycyclopropyl)methanone (0.020 g, 0.049 mmol, 35% yield) as an off-white solid. MS (ESI, pos. ion) m/z: 408 (M+1).
Method 3.

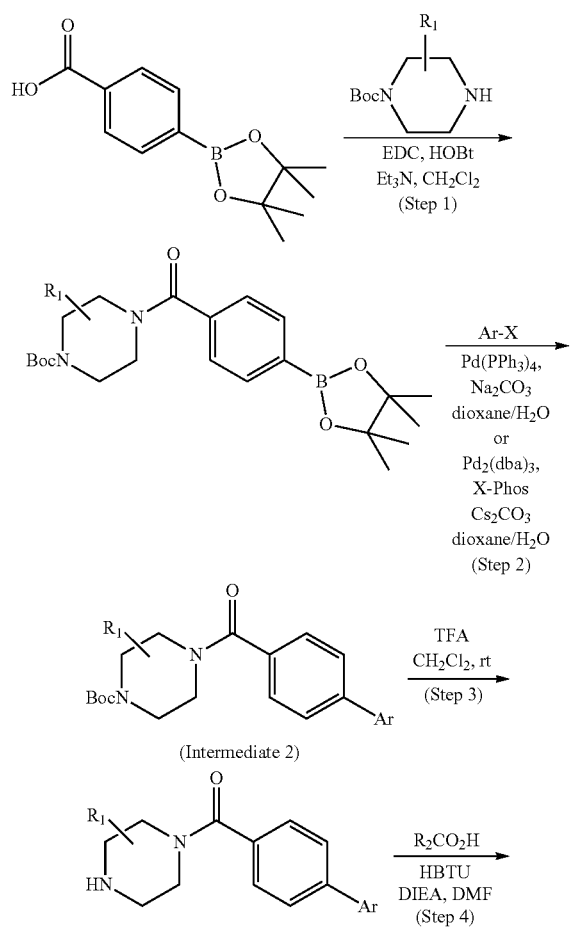

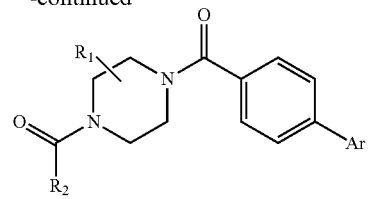

Step 1. tert-butyl 4-(4-(4,4,5,5-tetramethyl-1,3,2-dioxaborolan-2-yl)benzoyl)piperazine-1-carboxylate A mixture of 4-(4,4,5,5-tetramethyl-1,3,2-dioxaborolan-2-yl)benzoic acid (15 g, 60.5 mmol), tert-butyl piperazine-1-carboxylate (11.26 g, 60.5 mmol), 1H-benzo[d][1,2,3]triazol-1-ol hydrate (4.63 g, 30.2 mmol), N1-((ethylimino)methylene)-N3,N3-dimethylpropane-1,3-diamine hydrochloride (12.75 g, 66.5 mmol), and triethylamine (33.7 mL, 242 mmol) in dichloromethane (180 mL) was stirred at room temperature overnight. The reaction mixture was washed with saturated aqueous sodium bicarbonate solution (75 mL), 0.5 M HCl solution (75 mL), and again with saturated aqueous sodium bicarbonate solution (75 mL). The combined organic phases were concentrated and the resulting solid was slurried in a solution of 1:1 methyl tert-butyl ether/hexane (200 mL). The material was filtered and dried to afford tert-butyl 4-(4-(4,4,5,5-tetramethyl-1,3,2-dioxaborolan-2-yl)benzoyl)piperazine-1-carboxylate (20.03 g, 48.1 mmol, 80%). MS (ESI, pos. ion) m/z: 417 (M+1).

Step 2 (Pd(PPh$_3$)$_4$). tert-butyl 4-(4-(1H-benzo[d]imidazol-2-yl)benzoyl)piperazine-1-carboxylate Tetrakis(triphenylphosphine)palladium(0) (0.028 g, 0.024 mmol) was added to a mixture of tert-butyl 4-(4-(4,4,5,5-tetramethyl-1,3,2-dioxaborolan-2-yl)benzoyl)piperazine-1-carboxylate (0.050 g, 0.120 mmol), 2-bromo-1H-benzo[d]imidazole (0.035 g, 0.180 mmol), and sodium carbonate (0.051 g, 0.480 mmol) in dioxane (1.5 mL) and water (0.30 mL). The mixture stirred in the microwave at 50° C. for 3 h. The reaction mixture was filtered through Celite and concentrated. The residue was purified via column chromatography on silica gel (Biotage 10 g column, gradient elution with 0-50% ethyl acetate-hexane) to afford tert-butyl 4-(4-(1H-benzo[d]imidazol-2-yl)benzoyl)piperazine-1-carboxylate (0.027 g, 0.066 mmol, 55% yield) as an off-white solid. MS (ESI, pos. ion) m/z: 407 (M+1).

Step 2 (X-Phos). tert-butyl 4-(4-(pyrazolo[1,5-a]pyridin-2-yl)benzoyl)piperazine-1-carboxylate A mixture of tert-butyl 4-(4-(4,4,5,5-tetramethyl-1,3,2-dioxaborolan-2-yl)benzoyl)piperazine-1-carboxylate (0.100 g, 0.240 mmol), 2-chloropyrazolo[1,5-a]pyridine (0.046 g, 0.300 mmol), tris(dibenzylideneacetone)dipalladium (0.011 g, 0.012 mmol), 2-dicyclohexylphosphino-2',4',6'-triisopropylbiphenyl (X-Phos, 0.011 g, 0.024 mmol), and cesium carbonate (0.235 g, 0.721 mmol) in dioxane (2.5 mL) and water (0.50 mL) was stirred in the microwave at 80° C. for 1 h. The reaction mixture was filtered through Celite and concentrated to afford a yellow-brown oil. This material was purified via column chromatography on silica gel (Biotage 25 g column, gradient elution with 0-50-100% ethyl acetate-hexane) to afford tert-butyl 4-(4-(pyrazolo[1,5-a]pyridin-2- yl)benzoyl)piperazine-1-carboxylate (0.056 g, 0.138 mmol, 57% yield) as an off-white solid. MS (ESI, pos. ion) m/z: 407 (M+1).

Step 3. (4-(1H-benzo[d]imidazol-2-yl)phenyl)(piperazin-1-yl)methanone 2,2,2-trifluoroacetate (Intermediate 2)

Trifluoroacetic acid (1.0 mL, 12.98 mmol) was added to a solution of tert-butyl 4-(4-(1H-benzo[d]imidazol-2-yl)benzoyl)piperazine-1-carboxylate (0.027 g, 0.066 mmol) in dichloromethane (3.0 mL), and the solution stirred at rt for 1.5 h. The reaction mixture was concentrated and the residue was triturated with diethyl ether and filtered to afford (4-(1H-benzo[d]imidazol-2-yl)phenyl)(piperazin-1-yl)methanone 2,2,2-trifluoroacetate (0.028 g, 0.067 mmol, 100% yield) as a brown film. MS (ESI, pos. ion) m/z: 307 (M+1).

Step 4. (4-(4-(1H-benzo[d]imidazol-2-yl)benzoyl)piperazin-1-yl)(1-hydroxycyclopropyl)methanone DIEA (0.047 mL, 0.266 mmol) was added to a solution of (4-(1H-benzo[d]imidazol-2-yl)phenyl)(piperazin-1-yl)methanone 2,2,2-trifluoroacetate (0.028 g, 0.067 mmol), 1-hydroxycyclopropanecarboxylic acid (7.14 mg, 0.070 mmol), and O-(benzotriazol-1-yl)-N,N,N',N'-tetramethyluronium hexafluorophosphate (0.038 g, 0.100 mmol) in DMF (1.0 mL), and the reaction mixture stirred at rt for 20 h. Water was added and the mixture was partitioned between ethyl acetate and water. The aqueous phase was separated and extracted with dichloromethane. The combined organic phases were washed with brine, dried over anhydrous sodium sulfate, and filtered to afford a brown oil. This material was purified via column chromatography on silica gel (Biotage 10 g column, gradient elution with 0-5% methanol-ethyl acetate) to afford (4-(4-(1H-benzo[d]imidazol-2-yl)benzoyl)piperazin-1-yl)(1-hydroxycyclopropyl)methanone (0.004 g, 10.24 μmol, 15% yield) as a white solid. MS (ESI, pos. ion) m/z: 391 (M+1).

Method 4.

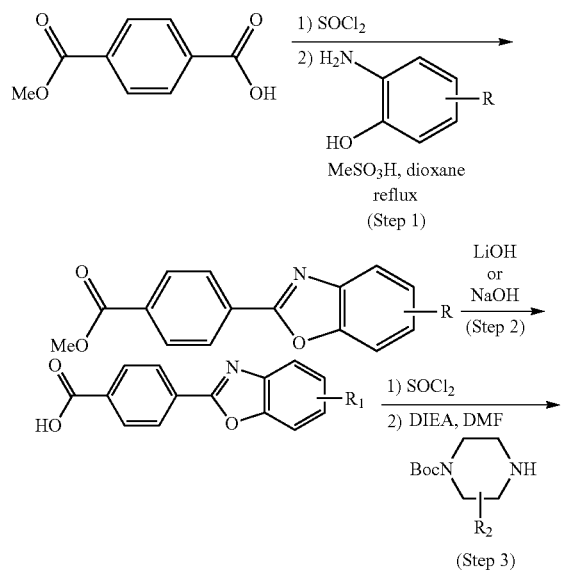

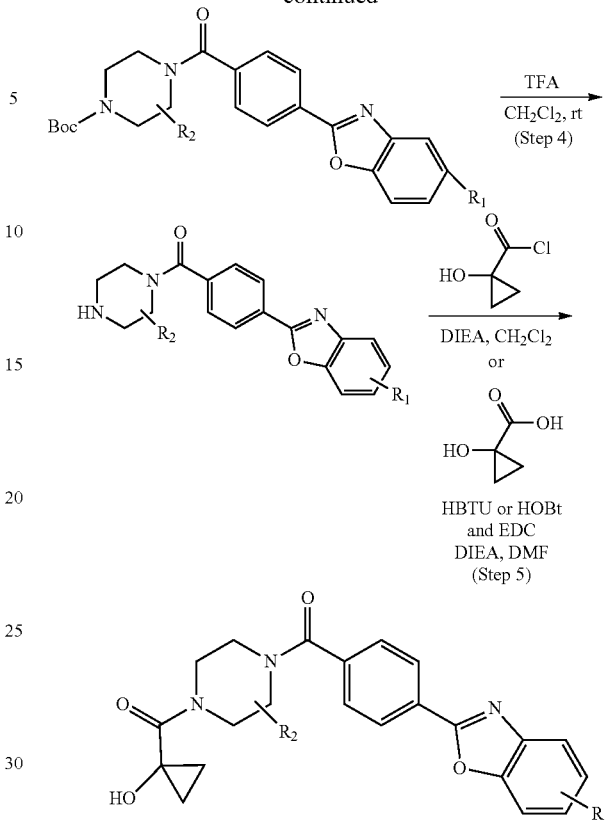

Step 1. Methyl 4-(benzo[d]oxazol-2-yl)benzoate

Thionyl chloride (10 mL, 137 mmol) was added to mono-methyl terephthalate (5.00 g, 27.8 mmol). A drop of DMF was added, and the mixture was heated at 80° C. for 2 h. The excess thionyl chloride was removed, and the residue was treated with 2-aminophenol (3.03 g, 27.8 mmol) and dioxane (60 mL). Methanesulfonic acid (5.59 mL, 86 mmol) was added and the reaction mixture was heated at reflux for 18 h. The solution was concentrated and the residue was partitioned between dichloromethane and satd. aq. sodium bicarbonate solution. The aqueous phase was separated and washed with dichloromethane and the combined organic phases were washed with brine, filtered, and concentrated to afford a brown solid. This material was triturated with methanol, filtered, and dried to afford methyl 4-(benzo[d]oxazol-2-yl)benzoate (4.827 g, 19.06 mmol, 69% yield) as an off-white solid. MS (ESI, pos. ion) m/z: 254 (M+1).

Step 2 (LiOH). 4-(Benzo[d]oxazol-2-yl)benzoic acid

Lithium hydroxide (0.894 g, 37.3 mmol) was added to a solution of methyl 4-(benzo[d]oxazol-2-yl)benzoate (4.728 g, 18.67 mmol) in THF (25 mL), Methanol (25 mL), and Water (25 mL), and the mixture stirred at rt for 18 h. The reaction mixture was concentrated and the aqueous solution was acidified to pH=5-6 with 1 N aq HCl solution. The resulting off-white precipitate was filtered and dried to afford 4-(benzo[d]oxazol-2-yl)benzoic acid (3.846 g, 16.08 mmol, 86% yield) as an off-white solid. MS (ESI, pos. ion) m/z: 240 (M+1).

Step 2 (NaOH). 4-(5-cyanobenzo[d]oxazol-2-yl)benzoic acid

Sodium hydroxide (0.067 g, 1.675 mmol) was added to a solution of methyl 4-(5-cyanobenzo[d]oxazol-2-yl)benzoate (0.233 g, 0.837 mmol) in THF (4.0 mL) and water (2.00 mL), and the mixture stirred at rt for 18 h. The reaction mixture was concentrated and the aqueous solution was acidified to pH=5-6 with 1 N aq HCl solution. The resulting off-white precipitate was filtered and dried to afford 4-(5-cyanobenzo[d]oxazol-2-yl)benzoic acid (0.176 g, 0.666 mmol, 80% yield) as an off-white solid. MS (ESI, pos. ion) m/z: 265 (M+1).

Step 3. tert-Butyl 4-(4-(benzo[d]oxazol-2-yl)benzoyl)piperazine-1-carboxylate Thionyl chloride (25.0 mL, 343 mmol) was added to 4-(benzo[d]oxazol-2-yl)benzoic acid (3.5 g, 14.63 mmol). A drop of DMF was added and the mixture was heated at 80° C. for 1 h. The excess thionyl chloride was removed and DMF (40 mL) was added. tert-Butyl piperazine-1-carboxylate (2.72 g, 14.63 mmol) and N,N-diisopropylethylamine (7.67 mL, 43.9 mmol) were added, and the reaction mixture stirred at rt for 1.5 h. Water was added and the resulting mixture was stirred and then filtered and dried to afford tert-butyl 4-(4-(benzo[d]oxazol-2-yl)benzoyl)piperazine-1-carboxylate (5.006 g, 12.29 mmol, 84% yield) as a light tan solid. MS (ESI, pos. ion) m/z: 408 (M+1).

Step 4. (4-(Benzo[d]oxazol-2-yl)phenyl)(piperazin-1-yl)methanone 2,2,2-trifluoroacetate Trifluoroacetic acid (10.0 mL, 130 mmol) was added to a solution of tert-butyl 4-(4-(benzo[d]oxazol-2-yl)benzoyl)piperazine-1-carboxylate (5.006 g, 12.29 mmol) in dichloromethane (50 mL), and the solution stirred at rt for 5 h. The reaction mixture was concentrated and the residue was triturated with diethyl ether and filtered to afford (4-(benzo[d]oxazol-2-yl)phenyl)(piperazin-1-yl)methanone 2,2,2-trifluoroacetate (5.501 g, 13.06 mmol, 100% yield) as an off-white solid. MS (ESI, pos. ion) m/z: 308 (M+1).

Step 5 (acid chloride coupling). (4-(4-(Benzo[d]oxazol-2-yl)benzoyl)piperazin-1-yl)(1-hydroxycyclopropyl)methanone Thionyl chloride (2.0 mL, 27.4 mmol) was added to 1-hydroxycyclopropanecarboxylic acid (0.115 g, 1.123 mmol). A drop of DMF was added and the mixture was heated at 80° C. for 1 h. The excess thionyl chloride was removed to afford a brown oil. This material was added to a solution of (4-(benzo[d]oxazol-2-yl)phenyl)(piperazin-1-yl)methanone 2,2,2-trifluoroacetate (0.338 g, 0.802 mmol) and N,N-diisopropylethylamine (0.70 mL, 4.01 mmol) in dichloromethane (3.0 mL). The reaction mixture stirred at rt for 2 h. The mixture was concentrated and the residue was purified via column chromatography on silica gel (Biotage 25 g column, gradient elution with 0-5% methanol-ethyl acetate) to afford (4-(4-(benzo[d]oxazol-2-yl)benzoyl)piperazin-1-yl)(1-hydroxycyclopropyl)-methanone (0.208 g, 0.531 mmol, 66% yield) as a pink solid. MS (ESI, pos. ion) m/z: 392 (M+1).

Step 5 (HBTU coupling). (4-(4-(5-Chlorobenzo[d]oxazol-2-yl)benzoyl)piperazin-1-yl)(1-hydroxycyclopropyl)methanone N,N-Diisopropylethylamine (0.376 mL, 2.150 mmol) was added to a solution of (4-(5-chlorobenzo[d]oxazol-2-yl)phenyl)(piperazin-1-yl)methanone 2,2,2-trifluoroacetate (0.245 g, 0.537 mmol), 1-hydroxycyclopropanecarboxylic acid (0.058 g, 0.564 mmol), and O-(benzotriazol-1-yl)-N,N,N',N'-tetramethyluronium hexafluorophosphate (HBTU, 0.306 g, 0.806 mmol) in DMF (5.0 mL), and the reaction mixture stirred at rt for 20 h. Water was added and the resulting precipitate was filtered and dried. This material was purified via column chromatography on silica gel (Biotage 50 g column, gradient elution with 0-5% methanol-ethyl acetate) to afford (4-(4-(5-chlorobenzo[d]oxazol-2-yl)benzoyl)piperazin-1-yl)(1-hydroxycyclopropyl)methanone (0.136 g, 0.319 mmol, 59% yield) as an off-white solid. MS (ESI, pos. ion) m/z: 426 (M+1).

Method 5.

Preparation of (4-(2-chloro-4-(quinolin-6-yl)benzoyl)piperazin-1-yl)(1-hydroxycyclopropyl)methanone 4-Bromo-2-chlorobenzoic acid (0.2 M in 1,4-dioxane, 180 μL, 0.036 mmol) was added to a solution of tert-butyl piperazine-1-carboxylate (0.2 M solution in 1,4-dioxane with 5% N,N-diisopropylethylamine, 150 μL, 0.03 mmol). (Benzotriazol-1-yloxy)tris(dimethylamino)phosphonium hexafluorophophate (BOP, 0.5 M solution in 1,2-dichloroethane, 72 μL, 0.036 mmol) was added, and the resulting mixture was put on a shaker at rt for 2 hour. Quinolin-6-ylboronic acid (0.2 M solution in 1,4-dioxane, 225 μL, 0.045 mmoL) and potassium phosphate (1 M aqueous, 150 μL, 0.15 mmol) were added. Tetrakis(triphenylphosphine)palladium (0) solution (0.02 M toluene, 75 μL, 1.5 μmol) was then added under a nitrogen atmosphere, and the resulting mixture was put on shaker in a glove box under nitrogen atmosphere and heated at 80° C. overnight. After being cooled to rt, the mixture was diluted with brine (0.30 mL) and ethyl acetate (0.5 mL). The organic layer was separated and the aqueous layer was extracted again with ethyl acetate (0.6 mL). The combined organic layers were dried down and the residue was re-dissolved in methanol (400 μL). HCl solution (4 N in 1,4-dioxane, 75 μL, 0.2 mmol) was added, and the mixture was heated on a shaker at 50° C. for 1 hour. The reaction mixture was dried down in vacuo and the residue was re-dissolved in a solution of 10% N,N-diisopropylethylamine in dimethylacetamide (200 μL). 1-Hydroxycyclopropanecarboxylic acid (0.2 M in 1,4-dioxane, 225 μL, 0.045 mmol) was added followed by BOP solution (0.5 M in 1,2-DCE, 90 μL, 0.045 mmol). The mixture was put on a shaker at rt for 2 hour. The reaction mixture was then diluted with sodium hydroxide solution (1 N in brine, 0.45 mL) and ethyl acetate (0.5 mL). The organic layer was separated and the aqueous layer was extracted with ethyl acetate (0.6 mL). The combined organic layers were concentrated and the residue was purified by high performance liquid chromatography (Waters Autopurification MS-directed HPLC prep fraction collection with the following conditions: Column: Waters XBridge OBD C18, 5 μm, 19×50 mm; flow rate 20 mL/min; mobile phase, water with 0.1% ammonium hydroxide (A) and methanol with 0.1% ammonium hydroxide (B) running the following gradient 0 to 2 mins (15% B), 2 to 6 mins (15-100% B); Detector ZQ Mass Detector in electrospray ionization mode) to afford (4-(2-chloro-4-(quinolin-6-yl)benzoyl)piperazin-1-yl)(1-hydroxycyclopropyl)methanone (5.9 mg, 14 μmol, 45% yield). MS (ESI, pos. ion) m/z: 436 (M+1).

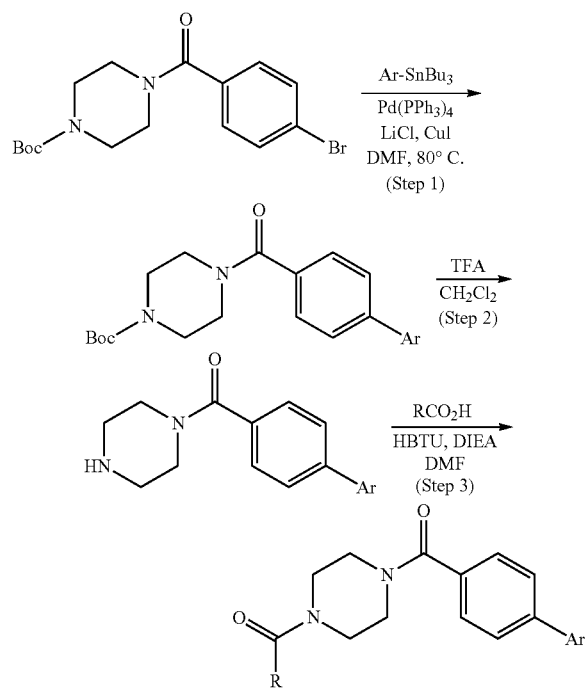

Method 6.

Step 1. tert-butyl 4-(4-(benzo[d]thiazol-2-yl)benzoyl)piperazine-1-carboxylate Tetrakis(triphenylphosphine)palladium(0) (0.313 g, 0.271 mmol) was added to a mixture of tert-butyl 4-(4-bromobenzoyl)piperazine-1-carboxylate (1.00 g, 2.71 mmol), 2-(tributylstannyl)benzo[d]thiazole (1.00 mL, 2.84 mmol), lithium chloride (0.230 g, 5.42 mmol), and copper(I) iodide (0.026 g, 0.135 mmol) in DMF (25 mL). The mixture stirred at 80° C. for 2 h and then at 90° C. for 8 h. The reaction mixture was filtered through Celite and the filtrate was partitioned between dichloromethane and water. The organic phase was separated and washed with brine, dried over anhydrous sodium sulfate, filtered, and concentrated to afford an orange oil. This material was purified via column chromatography on silica gel (Biotage 50 g column, gradient elution with 0-50% ethyl acetate-hexane) to afford tert-butyl 4-(4-(benzo[d]thiazol-2-yl)benzoyl)piperazine-1-carboxylate (0.586 g, 1.384 mmol, 51% yield) as a brown solid. MS (ESI, pos. ion) m/z: 424 (M+1).

Step 2. (4-(benzo[d]thiazol-2-yl)phenyl)(piperazin-1-yl)methanone 2,2,2-trifluoroacetate Trifluoroacetic acid (1.00 mL, 13.0 mmol) was added to a solution of tert-butyl 4-(4-(benzo[d]thiazol-2-yl)benzoyl)piperazine-1-carboxylate (0.586 g, 1.38 mmol) in dichloromethane (5.0 mL), and the solution stirred at rt for 3 h. The reaction mixture was concentrated and the residue was triturated with diethyl ether and filtered to afford (4-(benzo[d]thiazol-2-yl)phenyl)(piperazin-1-yl)methanone 2,2,2-trifluoroacetate (0.542 g, 1.239 mmol, 90% yield) as a tan solid. MS (ESI, pos. ion) m/z: 324 (M+1).

Step 3. (4-(4-(benzo[d]thiazol-2-yl)benzoyl)piperazin-1-yl)(1-hydroxycyclopropyl)methanone N,N-Diisopropylethylamine (0.87 mL, 5.0 mmol) was added to a solution of (4-(benzo[d]thiazol-2-yl)phenyl)(piperazin-1-yl)methanone 2,2,2-trifluoroacetate (0.542 g, 1.239 mmol), 1-hydroxycyclopropanecarboxylic acid (0.133 g, 1.301 mmol), and O-(benzotriazol-1-yl)-N,N,N',N'-tetramethyluronium hexafluorophosphate (0.705 g, 1.859 mmol) in DMF (5.0 mL), and the reaction mixture stirred at rt for 16 h. Water was added and the resulting precipitate was filtered and dried. This material was purified via column chromatography on silica gel (Biotage 50 g column, gradient elution with 0-5% methanol-ethyl acetate) to afford (4-(4-(benzo[d]thiazol-2-yl)benzoyl)piperazin-1-yl)(1-hydroxycyclopropyl)methanone (0.235 g, 0.577 mmol, 47% yield) as an off-white solid. MS (ESI, pos. ion) m/z: 408 (M+1).
Method 7.

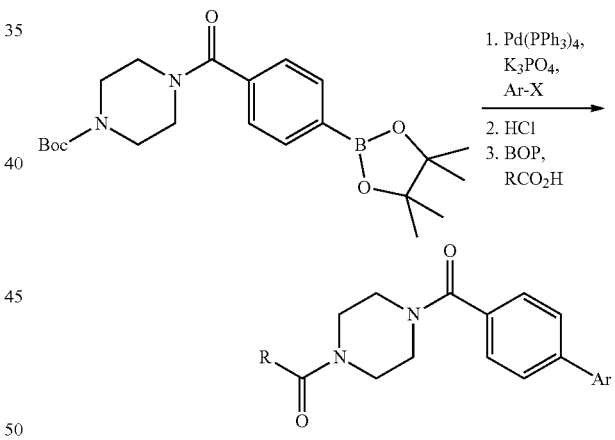

Preparation of 5-(4-(4-(1-hydroxycyclopropanecarbonyl)piperazine-1-carbonyl)phenyl)-1H-indole-3-carbonitrile To a solution of tert-butyl 4-(4-(4,4,5,5-tetramethyl-1,3,2-dioxaborolan-2-yl)benzoyl)piperazine-1-carboxylate (0.2 M in 1,4-dioxane, 100 μL, 0.02 mmol), was added 5-bromo-1H-indole-3-carbonitrile (0.2 M in 1,4-dioxane, 100 μL, 0.02 mmol) and potassium phosphate solution (1 M aqueous, 100 μL, 0.1 mmol). The mixture was bubbled with nitrogen and tetrakis(triphenylphosphine)palladium (0) (0.02 M in toluene, 50 μL, 1 μmol) was added. The resulting mixture was put on a shaker in a glove box under nitrogen atmosphere and heated at 80° C. overnight. After being cooled to rt, the mixture was diluted with 0.35 mL of brine and 0.5 mL of ethyl acetate. The organic layer was separated and the aqueous layer was extracted again with ethyl acetate (0.6 mL). The combined organic layers were concentrated and the residue was dissolved in 200 μL of methanol. HCl solution (50 μL, 4 N in 1,4-dioxane, 0.2 mmol) was added. The mixture was put on a shaker at 50° C. for 1 hour. The reaction mixture was concentrated in vacuo and the residue was dissolved in a solution of 10% N,N-diisopropylethylamine in dimethylacetamide (200 μL). 1-Hydroxycyclopropanecarboxylic acid (0.2 M in 1,4-dioxane, 120 μL, 0.024 mmol) was added, followed by BOP solution (0.5 M in 1,2-dichloroethane, 48 μL, 0.024 mmol). The mixture was put on a shaker at rt for 2 hour. The reaction mixture was then diluted with 0.45 mL of 1N NaOH in brine and 0.5 mL of ethyl acetate. The organic layer was separated and the aqueous layer was extracted again with ethyl acetate (0.6 mL). The combined organic layers were concentrated and the residue was purified by HPLC: Water Autopurification MS-directed HPLC prep fraction collection with the following conditions Column, Waters XBridge OBD C18, 5 μm, 19×50 mm; flow rate 20 ml/min; mobile phase, water with 0.1% ammonium hydroxide (A) and methanol with 0.1% ammonium hydroxide (B) running the following gradient 0 to 2 mins (15% B), 2 to 6 mins (15-100% B); Detector ZQ Mass Detector in electrospray ionization mode. 5-(4-(4-(1-Hydroxycyclopropanecarbonyl)piperazin-1-carbonyl)phenyl)-1H-indole-3-carbonitrile (3.5 mg, 8.4 μmol, 42% yield) was obtained. MS (ESI, pos. ion) m/z: 415 (M+1).

Method 8.

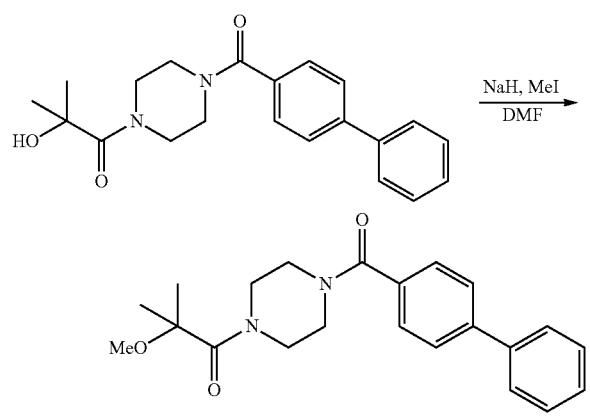

1-(4-(biphenylcarbonyl)piperazin-1-yl)-2-methoxy-2-methylpropan-1-one

Sodium hydride (9.08 mg, 0.227 mmol) was added to a solution of 1-(4-(biphenylcarbonyl)piperazin-1-yl)-2-hydroxy-2-methylpropan-1-one (32 mg, 0.091 mmol) in DMF (4 mL). After stirring at rt for 30 min, methyl iodide (0.028 mL, 0.454 mmol) was added. The mixture was stirred at rt overnight. The mixture was concentrated and the residue was purified via preparative reversed phase HPLC (20 mL/min, 10 min gradient 15%-85% CH$_3$CN, 0.01% HCO$_2$H on an XTerra Prep MS C18 OBD 5 μM, 19×100 mm column) to afford 1-(4-(biphenylcarbonyl)piperazin-1-yl)-2-methoxy-2-methylpropan-1-one (12.2 mg, 37%). MS (ESI, pos. ion) m/z: 367 (M+1).

Method 9.

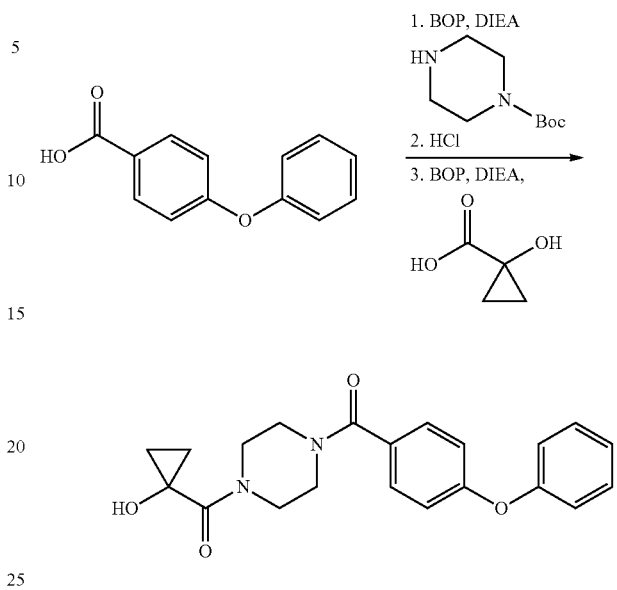

Preparation of (4-(2-chloro-4-(quinolin-6-yl)benzoyl)piperazin-1-yl)(1-hydroxycyclopropyl)methanone To a solution of tert-butyl piperazine-1-carboxylate (0.2 M 1,4-dioxane with 5% N,N-diisopropylethylamine, 150 μL, 0.03 mmol), was added 4-phenoxybenzoic acid (0.2 M 1,4-dioxane, 150 μL, 0.03 mmol), followed by (benzotriazol-1-yloxy)tris(dimethylamino)phosphonium hexafluorophophate solution (BOP, 0.5 M in 1,2-dichloroethane, 66 μL, 0.033 mmol). The resulting mixture was put on a shaker at room temperature for 2 hours. Hydrochloric acid solution (4 N in 1,4-dioxane, 75 μL) was added and the mixture was put on a shaker at 50° C. for 1 hour. After being cooled to room temperature, the mixture was concentrated, and the residue was re-dissolved in a solution of 10% diisopropylethyl amine in dimethylacetamide (200 μL). 1-Hydroxycyclopropanecarboxylic acid (0.2 M 1,4-dioxane, 180 μL, 0.036 mmol) was added to the mixture, followed by BOP solution (0.5 M in 1,2-dichloroethane, 72 μL, 0.036 mmol). The mixture was put on a shaker at room temperature for 2 hours. The reaction mixture was then diluted with sodium hydroxide solution (1 N in brine, 0.45 mL) and ethyl acetate (0.5 mL). The organic layer was separated and the aqueous layer was extracted with ethyl acetate (0.6 mL). The combined organic layers were concentrated and the residue was purified by high performance liquid chromatography (Waters Autopurification MS-directed HPLC prep fraction collection with the following conditions: Column: Waters XBridge OBD C18, 5 μm, 19×50 mm; flow rate 20 mL/min; mobile phase, water with 0.1% ammonium hydroxide (A) and methanol with 0.1% ammonium hydroxide (B) running the following gradient 0 to 2 mins (15% B), 2 to 6 mins (15-100% B); Detector ZQ Mass Detector in electrospray ionization mode) to afford (4-(2-chloro-4-(quinolin-6-yl)benzoyl)piperazin-1-yl)(1-hydroxycyclopropyl)methanone (4.1 mg, 11 μmol, 37% yield). MS (ESI, pos. ion) m/z: 367 (M+1).

Method 10.

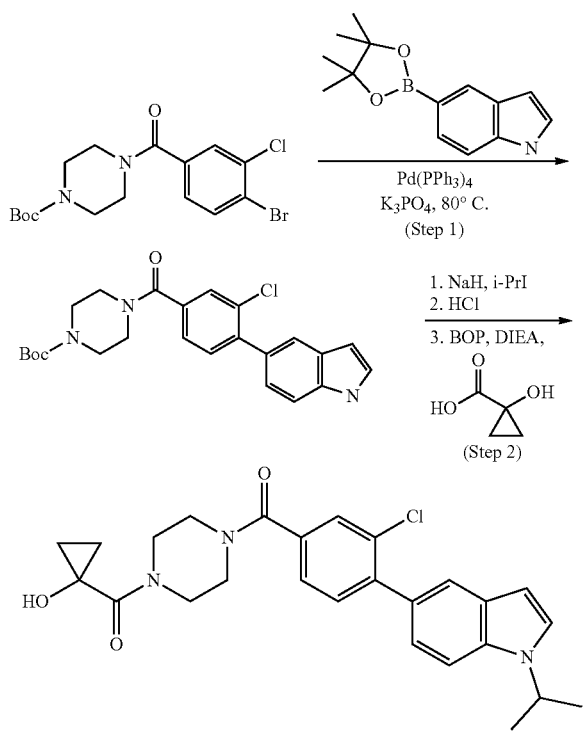

Step 1. tert-Butyl 4-(3-chloro-4-(1H-indol-5-yl)benzoyl)piperazine-1-carboxylate To a solution of tert-butyl 4-(4-bromo-3-chlorobenzoyl)piperazine-1-carboxylate (505 mg, 1.25 mmol) in 1,4-dioxane (9 mL) was added 5-(4,4,5,5-tetramethyl-1,3,2-dioxaborolan-2-yl)-1H-indole (365 mg, 1.5 mmol), potassium phosphate (1.06 g, 5 mmol) and water (3 mL). The mixture was bubbled with nitrogen and tetrakis(triphenylphosphine)palladium (0) (72.2 mg, 0.063 mmol) was added. The mixture was sealed and heated at 80° C. overnight. After being cooled to rt, the mixture was diluted with water (10 mL) and ethyl acetate (20 mL). The organic layer was separated and the aqueous layer was extracted with ethyl acetate (20 mL). The combined organic layers were concentrated to yield tert-butyl 4-(3-chloro-4-(1H-indol-5-yl)benzoyl)piperazine-1-carboxylate (578 mg, 1.31 mmol, 100% yield). The crude product was used without further purification. MS (ESI, pos. ion) m/z: 440 (M+1).

Step 2. (4-(3-chloro-4-(1-isopropyl-1H-indol-5-yl)benzoyl)piperazin-1-yl)(1-hydroxycyclopropyl)methanone To a vial charged with sodium hydride (60% in mineral oil, 1.6 mg, 0.040 mmol) and DMF (0.1 mL), was added tert-butyl 4-(3-chloro-4-(1H-indol-5-yl)benzoyl)piperazine-1-carboxylate (0.2 M in DMF, 0.1 mL, 0.02 mmol), followed by 2-iodopropane (0.2 M in DMF, 0.2 mL, 0.04 mmol). The resulting mixture was put on a shaker for 30 min. at room temperature. The mixture was then diluted with water and ethyl acetate. The organic layer was separated and the aqueous layer was extracted with ethyl acetate. The combined organic layers were concentrated in vacuo. The residue was dissolved in methanol (0.3 mL) and HCl solution (4 N 1,4-dioxane, 50 μL) was added. The mixture was put on a shaker at 50° C. for 1 hour. After being cooled to room temperature, the mixture was concentrated. The residue was dissolved in a solution of 5% N,N-diisopropylethylamine in dimethylacetamide (0.2 mL) and 1-hydroxycyclopropanecarboxylic acid (0.2 M 1,4-dioxane, 120 μL, 0.024 mmol) was added, followed by BOP solution (0.5 M in 1,2-dichloroethane, 48 μL, 0.024 mmol). The mixture was put on a shaker at room temperature for 2 hours. The reaction mixture was diluted with sodium hydroxide solution (1 N in brine, 0.45 mL) and ethyl acetate (0.5 mL). The organic layer was separated and the aqueous layer was extracted with ethyl acetate (0.6 mL). The combined organic layers were concentrated and the residue was purified by high performance liquid chromatography (Waters Autopurification MS-directed HPLC prep fraction collection with the following conditions: Column: Waters XBridge OBD C18, 5 μm, 19×50 mm; flow rate 20 mL/min; mobile phase, water with 0.1% ammonium hydroxide (A) and methanol with 0.1% ammonium hydroxide (B) running the following gradient 0 to 2 mins (15% B), 2 to 6 mins (15-100% B); Detector ZQ Mass Detector in electrospray ionization mode) to afford (4-(3-chloro-4-(1-isopropyl-1H-indol-5-yl)benzoyl)piperazin-1-yl)(1-hydroxycyclopropyl)methanone (2.2 mg, 4.7 μmol, 24% yield). MS (ESI, pos. ion) m/z: 466 (M+1).

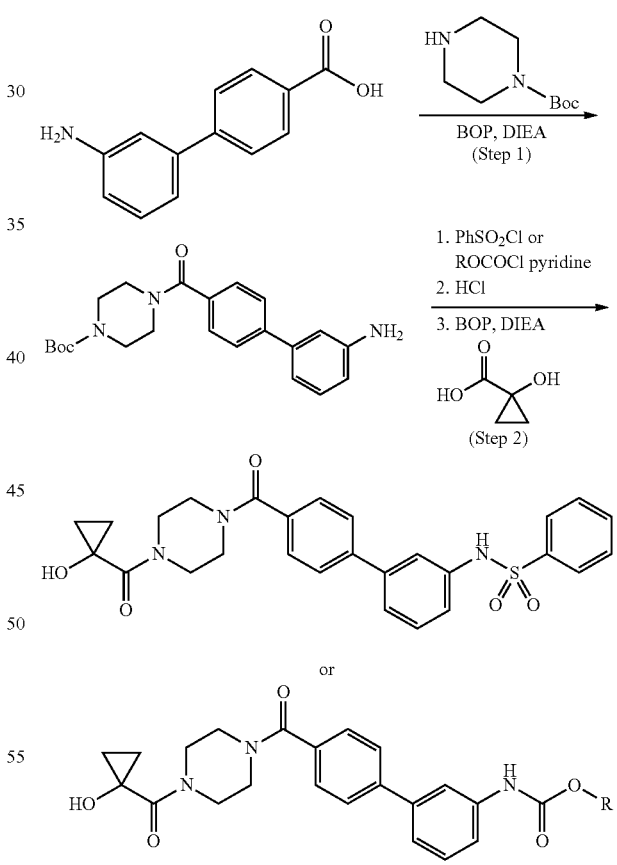

Method 11.

Step 1. tert-Butyl 4-(3'-amino-[1,1'-biphenyl]-4-carbonyl)piperazine-1-carboxylate To a solution of tert-butyl piperazine-1-carboxylate (745 mg, 4 mmol) in DMF (20 mL) was added N,N-diisopropylethylamine (1.43 mL, 8 mmol), followed by 3'-aminobiphenyl-4-carboxylic acid (853 mg, 4 mmol) and (benzotriazol-1-yloxy)tris(dimethylamino)phosphonium hexafluorophophate (BOP, 2.12 g, 4.8 mmol). The resulting mixture was stirred at room temperature for 1 hour. The mixture was then poured into ice-water (40 mL) with stirring. The precipitate was filtered off, washed with water and air-dried to afford tert-butyl 4-(3'-aminobiphenylcarbonyl)piperazine-1-carboxylate (1.2 g, 3.15 mmol, 79% yield). The product was used for next step without further purification. MS (ESI, pos. ion) m/z: 382 (M+1).

Step 2. N-(4'-(4-(1-Hydroxycyclopropanecarbonyl)piperazine-1-carbonyl)-[1,1'-biphenyl]-3-yl)benzenesulfonamide or ethyl (4'-(4-(1-hydroxycyclopropane-1-carbonyl)piperazine-1-carbonyl)-[1,1'-biphenyl]-3-yl)carbamate To a solution of tert-butyl 4-(3'-aminobiphenylcarbonyl)piperazine-1-carboxylate (0.2 M 1,4-dioxane, 150 μL, 0.03 mmol) was added pyridine (9.7 μL, 0.12 mmol) followed by benzenesulfonyl chloride (0.2 M in 1,4-dioxane, 300 μL, 0.06 mmol) or ethyl carbonochloridate (0.2 M in 1,4-dioxane, 300 μL, 0.06 mmol). The resulting mixture was put on a shaker at 80° C. overnight. The reaction mixture was diluted with sodium hydroxide solution (1 N in brine, 0.45 mL) and ethyl acetate (0.6 mL). The organic layer was separated and the aqueous layer was extracted with ethyl acetate (0.6 mL). The combined organic layers were concentrated. The residue was dissolved in methanol (200 μL) and HCl solution (4 N in 1,4-dioxane, 75 μL) was added. The mixture was put on a shaker at 50° C. for 1 hour. The reaction mixture was concentrated in vacuo and the residue was dissolved in a solution of dimethylacetamide with 10% N,N-diisopropylethylamine (200 μL). 1-Hydroxycyclopropanecarboxylic acid (0.2 M in 1,4-dioxane, 180 μL, 0.036 mmol) was added followed by BOP solution (0.5 M in 1,2-dichloroethane, 72 μL, 0.036 mmol). The mixture was put on a shaker at rt for 2 hours. The reaction mixture was then diluted with sodium hydroxide solution (1 N in brine, 0.45 mL) and ethyl acetate (0.5 mL). The organic layer was separated and the aqueous layer was extracted with ethyl acetate (0.6 mL). The combined organic layers were concentrated and the residue was purified by high performance liquid chromatography (Waters Autopurification MS-directed HPLC prep fraction collection with the following conditions: Column: Waters XBridge OBD C18, 5 μm, 19×50 mm; flow rate 20 mL/min; mobile phase, water with 0.1% ammonium hydroxide (A) and methanol with 0.1% ammonium hydroxide (B) running the following gradient 0 to 2 mins (15% B), 2 to 6 mins (15-100% B); Detector ZQ Mass Detector in electrospray ionization mode) to afford N-(4'-(4-(1-hydroxycyclopropanecarbonyl)piperazine-1-carbonyl)biphenyl-3-yl)benzenesulfonamide (7.8 mg, 15 μmol, 51% yield). MS (ESI, pos. ion) m/z: 506 (M+1).

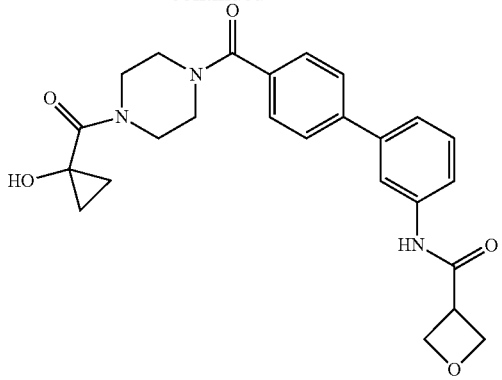

Preparation of N-(4'-(4-(1-hydroxycyclopropanecarbonyl)piperazine-1-carbonyl)biphenyl-3-yl)oxetane-3-carboxamide (3'-Aminobiphenyl-4-yl)(4-(1-hydroxycyclopropanecarbonyl)piperazin-1-yl)methanone (0.168 g, 0.460 mmol), N,N-diisopropylethylamine (0.241 mL, 1.379 mmol) and oxetane-3-carboxylic acid (0.055 g, 0.506 mmol) were combined in DMF (5 mL). 0-(benzotriazol-1-yl)-N,N,N',N'-tetramethyluronium hexafluorophosphate (0.244 g, 0.644 mmol) was added to give a light yellow solution. This was stirred for 18 h. N,N-Diisopropylethyl amine (0.120 mL, 0.687 mmol), 0-(benzotriazol-1-yl)-N,N,N',N'-tetramethyluronium hexafluorophosphate (0.18 g, 0.474 mmol), and oxetane-3-carboxylic acid (0.025 g, 0.244 mmol) were added. Stirring was continued for 5 h. The reaction was diluted with 10 mL of water and stirred. Another 15 mL of water was added and the aqueous emulsion was extracted with 50 mL of dichloromethane and then 20 mL of dichloromethane. The combined organic layers were washed with 20 mL of water and then with 20 mL of brine, dried over MgSO$_4$ and concentrated. The material was purified via column chromatography on silica gel (Biotage 25 g column, gradient elution with 0-6% methanol/dichloromethane). The material obtained was repurified on a second silica gel column (Biotage 25 g column, 4-6.5% methanol/dichloromethane). Concentration of the fractions afforded a yellow film. This material was taken up in 40 mL of dichloromethane and washed twice with 5 mL of dilute NaHCO$_3$ and once with 5 mL of brine. The solution was dried over MgSO$_4$ and concentrated to afford a yellow oil. This oil was taken up in dichloromethane and triturated with hexanes. Filtration afforded N-(4'-(4-(1-hydroxycyclopropanecarbonyl)piperazine-1-carbonyl)biphenyl-3-yl)oxetane-3-carboxamide (0.036 g, 0.076 mmol, 17%) as a yellow solid. MS (ESI, pos. ion) m/z: 450 (M+1).
Method 13.

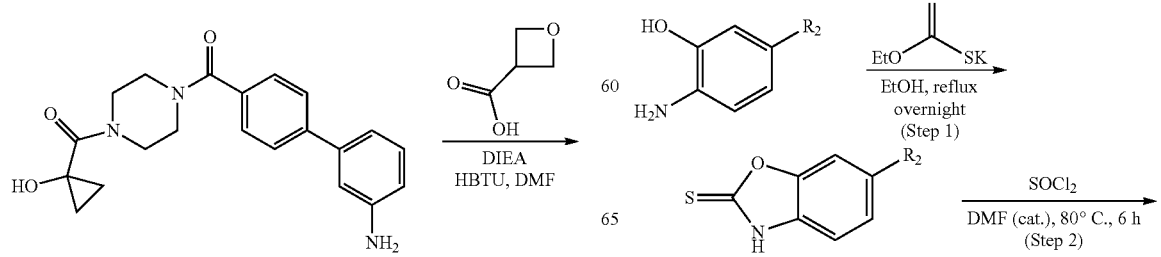

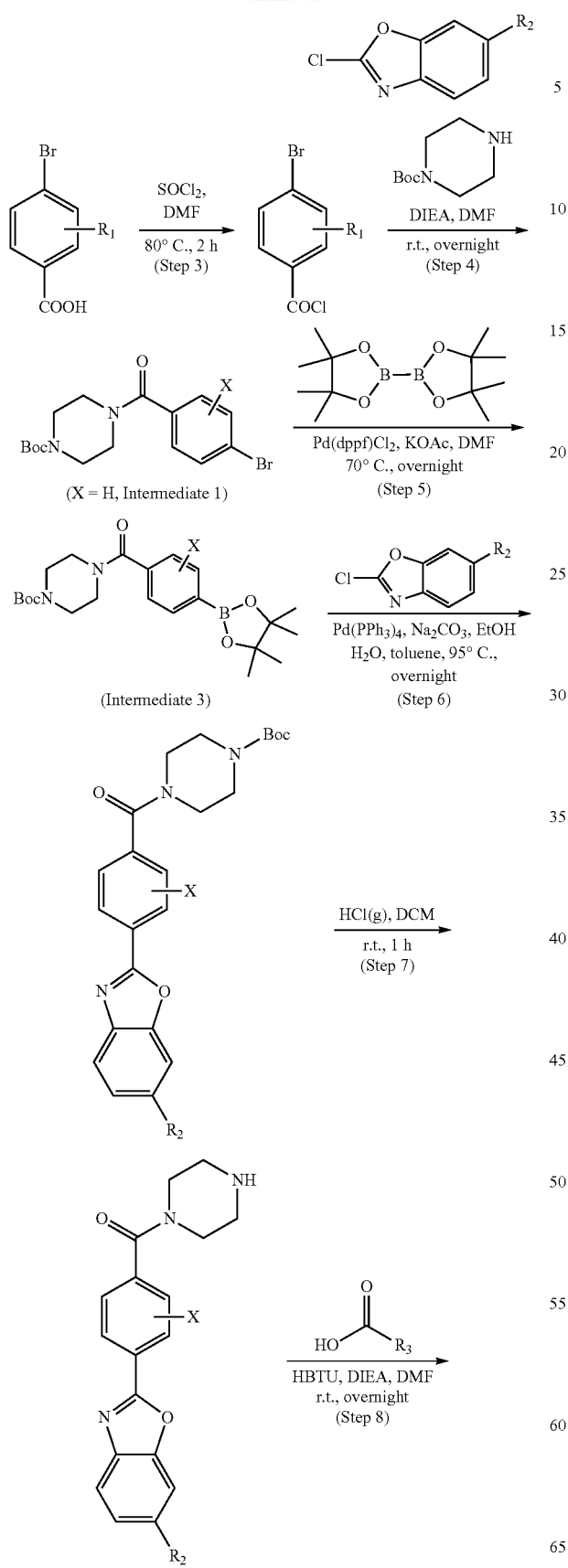

Step 1. 6-fluorobenzo[d]oxazole-2(3H)-thione

Into a 250-mL round-bottom flask, was placed 2-amino-5-fluorophenol (8 g, 62.93 mmol, 1.00 equiv), ethoxy(potassiosulfanyl)methanethione (11.1 g, 69.25 mmol, 1.10 equiv), ethanol (150 mL). The resulting solution was heated to reflux overnight in an oil bath. The reaction mixture was cooled to room temperature with a water bath and then concentrated under vacuum. The resulting slurry was diluted with 150 mL of water and its pH value was adjusted to 5 with acetic acid and precipitation formed. The solids were collected by filtration and dried in an oven. This resulted in 9.2 g (86%) of the title compound as a gray solid. LC-MS (ES, m/z) 170 [M+H]$^+$ Step 2. 2-chloro-6-fluorobenzo[d]oxazole Into a 500-mL round-bottom flask, was placed 6-fluoro-2,3-dihydro-1,3-benzoxazole-2-thione (9.2 g, 54.38 mmol, 1.00 equiv), thionyl chloride (200 mL) and DMF (0.5 mL). The resulting solution was stirred for 6 h at 80° C. in an oil bath. After reaction, the excess of SOCl$_2$ was removed under vacuum. The residue was applied onto a silica gel column with ethyl acetate/petroleum ether (0/100~7/93). The fractions were collected and concentrated under vacuum. This resulted in 3.5 g (38%) of the title compound as brown oil. LC-MS (ES, m/z) 172 [M+H]+

Step 3. 4-bromo-2-fluorobenzoyl chloride

Into a 250-mL round-bottom flask, was placed 4-bromo-2-fluorobenzoic acid (10 g, 45.66 mmol), thionyl chloride (50 mL) and N,N-dimethylformamide (0.1 mL). The resulting mixture was stirred for 2 h at 80° C. After cooling to room temperature, the solution concentrated under vacuum. This resulted in 10 g (92%) of the title compound as light yellow oil. The product was used in the next step directly without further purification.

Step 4. tert-butyl 4-(4-bromo-2-fluorobenzoyl)piperazine-1-carboxylate

Into a 250-mL round-bottom flask, was placed a solution of 4-bromo-2-fluorobenzoyl chloride (10 g, 42.11 mmol, 1.00 equiv) in N,N-dimethylformamide (100 mL). This was followed by the addition of tert-butyl piperazine-1-carboxylate (7.88 g, 42.31 mmol, 1.00 equiv) in several portions. Then DIEA (16.25 g, 125.74 mmol, 2.99 equiv) was added in. The resulting solution was stirred overnight at room temperature. The product was precipitated by the addition of 400 mL of H$_2$O. The solids were collected by filtration and dried in an oven. This resulted in 14 g (86%) of the title compound as a white solid. LC-MS (ES, m/z) 387,389 [M+H]+

Step 5. tert-butyl 4-(2-fluoro-4-(4,4,5,5-tetramethyl-1,3,2-dioxaborolan-2-yl)benzoyl)piperazine-1-carboxylate (Intermediate 3)

Into a 2000-mL round-bottom flask purged and maintained with an inert atmosphere of nitrogen, was placed a solution of tert-butyl 4-[(4-bromo-2-fluorophenyl)carbonyl]piperazine-1-carboxylate (57 g, 147.19 mmol, 1.00 equiv) in N,N-dimethylformamide (800 mL), 4,4,5,5-tetramethyl-2-(tetramethyl-1,3,2-dioxaborolan-2-yl)-1,3,2-dioxaborolane (76.2 g, 300.07 mmol, 2.01 equiv), PdCl$_2$(dppf) (11 g, 15.03 mmol, 0.10 equiv), KOAc (44.1 g, 449.36 mmol, 3.00 equiv). The resulting mixture was stirred overnight at 70° C. After cooling to room temperature, the mixture was poured into 3 L of H$_2$O. The solids were collected by filtration, further purified by a silica gel column with ethyl acetate/petroleum ether (3:7). The collected fractions were combined and concentrated under vacuum. This resulted in 30 g (47%) of the title compound as a light brown solid. LC-MS (ES, m/z) 435 [M+H]+

Step 6. tert-butyl 4-(2-fluoro-4-(6-fluorobenzo[d]oxazol-2-yl)benzoyl)piperazine-1-carboxylate Into a 100-mL round-bottom flask purged and maintained with an inert atmosphere of nitrogen, was placed a solution of tert-butyl 4-[[2-fluoro-4-(tetramethyl-1,3,2-dioxaborolan-2-yl)phenyl]carbonyl]piperazine-1-carboxylate (1.26 g, 2.90 mmol, 1.00 equiv) in toluene (24 mL), 2-chloro-6-fluoro-1,3-benzoxazole (500 mg, 2.91 mmol, 1.00 equiv), Pd(PPh$_3$)$_4$ (336 mg, 0.29 mmol, 0.10 equiv), sodium carbonate (12 mL, 2M), ethanol (3.3 mL). The resulting mixture was stirred overnight at 95° C. After cooling to room temperature, the resulting solution was diluted with 30 ml of water and extracted with 2×30 mL of ethyl acetate. The organic layers were combined and dried over anhydrous sodium sulfate and concentrated under vacuum. The residue was applied onto a silica gel column with EA/DCM (3/10). This resulted in 1.1 g (86%) of the title compound as a gray solid. LC-MS (ES, m/z) 444 [M+H]+

Step 7. (2-fluoro-4-(6-fluorobenzo[d]oxazol-2-yl) phenyl)(piperazin-1-yl)methanone Into a 250-mL round-bottom flask, was placed a solution of tert-butyl 4-[[2-fluoro-4-(6-fluoro-1,3-benzoxazol-2-yl)phenyl]carbonyl]piperazine-1-carboxylate (1.1 g, 2.48 mmol, 1.00 equiv) in dichloromethane (100 mL). To the above hydrogen chloride gas was introduced in. The resulting solution was stirred for 1 h at room temperature. The solids were collected by filtration and then dissolved in water, then adjusted to pH 6-7 with sodium bicarbonate. Then the solids were collected by filtration and dried in oven. This resulted in 700 mg (82%) of the title compound as a gray solid. LC-MS (ES, m/z) 344 [M+H]+

Step 8. (4-(2-fluoro-4-(6-fluorobenzo[d]oxazol-2-yl)benzoyl)piperazin-1-yl)(1-hydroxycyclopropyl)methanone Into a 50-mL round-bottom flask, was placed a solution of 6-fluoro-2-[3-fluoro-4-[(piperazin-1-yl)carbonyl]phenyl]-1,3-benzoxazole (538 mg, 1.57 mmol, 1.00 equiv) in N,N-dimethylformamide (15 mL), 1-hydroxycyclopropane-1-carboxylic acid (160 mg, 1.57 mmol, 1.00 equiv), HBTU (891 mg, 2.35 mmol, 1.50 equiv), DIEA (809 mg, 6.26 mmol, 4.00 equiv). The resulting solution was stirred overnight at room temperature. The reaction mixture was then diluted with 30 mL of water. The resulting solution was extracted with 2×20 mL of dichloromethane and the organic layers combined and dried over anhydrous sodium sulfate and concentrated under vacuum. The residue was applied onto a silica gel column with ethyl acetate/petroleum ether (7:1). The fraction was collected and concentrated. This product was re-crystallized from EA/PE in the ratio of 10/1. This resulted in 206.7 mg (30%) of the title compound as an off-white solid. LC-MS (ES, m/z) 428 [M+H]+

Method 14.

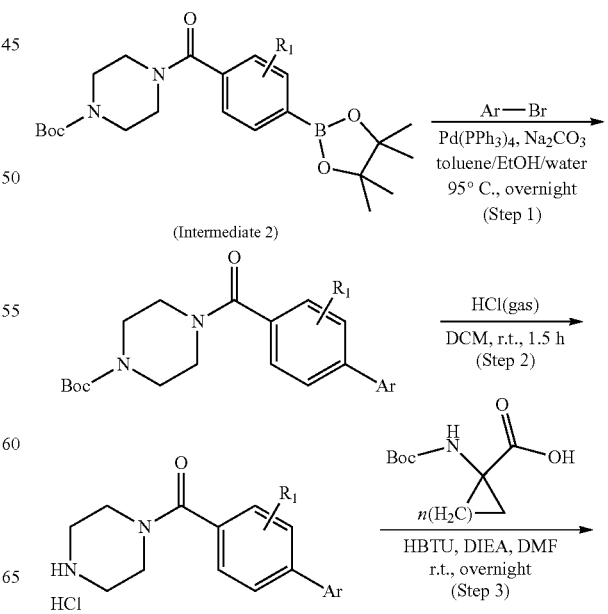

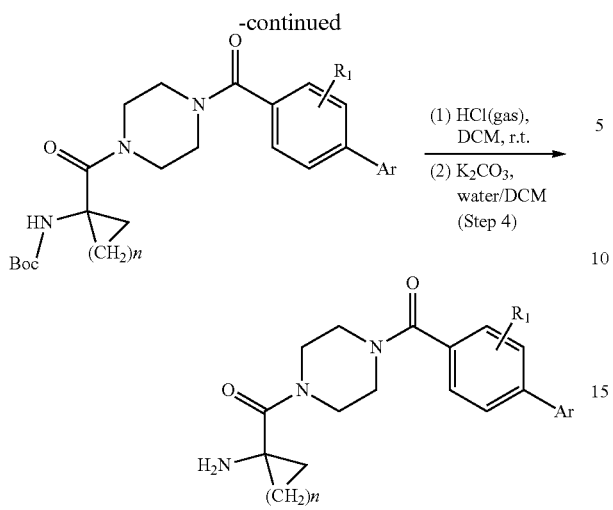

Step 1. tert-butyl 4-(4-(1-methyl-1H-benzo[d]imidazol-5-yl)benzoyl)piperazine-1-carboxylate Into a 100-mL round-bottom flask, was placed tert-butyl 4-[[4-(tetramethyl-1,3,2-dioxaborolan-2-yl)phenyl]carbonyl]piperazine-1-carboxylate (832 mg, 2.00 mmol, 1.00 equiv), 5-bromo-1-methyl-1H-1,3-benzodiazole (422 mg, 2.00 mmol, 1.00 equiv), Pd(PPh$_3$)$_4$ (232 mg, 0.20 mmol, 0.10 equiv), sodium carbonate (2N, 5 mL), toluene (10 mL), ethanol (3 mL). The resulting mixture was stirred overnight at 95° C. in an oil bath. After cooled to room temperature, the resulting solution was diluted with 10 mL of water, extracted with 3×20 mL of ethyl acetate. The organic layers were combined, dried over anhydrous sodium sulfate and concentrated under vacuum. The residue was applied onto a silica gel column with ethyl acetate/petroleum ether (0/100~100/0). The collected fractions were combined and concentrated under vacuum. This resulted in 800 mg (95%) of the title compound as a light yellow solid. LC-MS (ES, m/z): 421 [M+H]$^+$

Step 2. (4-(1-methyl-1H-benzo[d]imidazol-5-yl)phenyl)(piperazin-1-yl)methanone hydrochloride Into a 100-mL round-bottom flask, was placed tert-butyl 4-[[4-(1-methyl-1H-1,3-benzodiazol-5-yl)phenyl]carbonyl]piperazine-1-carboxylate (800 mg, 1.90 mmol, 1.00 equiv), dichloromethane (20 mL). Then HCl gas was introduced in. The resulting solution was stirred for 1.5 h at room temperature. The solids were collected by filtration and dried under vacuum. This resulted in 580 mg (95%) of the title compound as an off-white solid. LC-MS (ES, m/z): 321 [M+H]$^+$

Step 3. tert-butyl (1-(4-(4-(1-methyl-1H-benzo[d]imidazol-5-yl)benzoyl)piperazine-1-carbonyl)cyclopropyl)carbamate Into a 50-mL round-bottom flask, was placed 1-methyl-5-[4-[(piperazin-1-yl)carbonyl]phenyl]-1H-1,3-benzodiazole hydrochloride (580 mg, 1.63 mmol, 1.00 equiv), 1-[[(tert-butoxy)carbonyl]amino]cyclopropane-1-carboxylic acid (360 mg, 1.79 mmol, 1.10 equiv), HBTU (927 mg, 2.44 mmol, 1.50 equiv), DIEA (841 mg, 6.51 mmol, 4.00 equiv), N,N-dimethylformamide (10 mL). The mixture was stirred overnight at room temperature for overnight. The resulting solution was diluted with 60 mL of water, extracted with 3×60 mL of dichloromethane. The organic layers were combined, dried over anhydrous sodium sulfate and concentrated under vacuum. The residue was applied onto a silica gel column with dichloromethane/methanol (80/20). The collected fractions were combined and concentrated under vacuum. This resulted in 800 mg (quantitative) of the title compound as colorless oil. LC-MS (ES, m/z): 504 [M+H]$^+$

Step 4. (4-(1-aminocyclopropane-1-carbonyl)piperazin-1-yl)(4-(1-methyl-1H-benzo[d]imidazol-5-yl)phenyl)methanone Into a 100-mL round-bottom flask, was placed tert-butyl N-[1-[(4-[[4-(1-methyl-1H-1,3-benzodiazol-5-yl)phenyl]carbonyl]piperazin-1-yl)carbonyl]cyclopropyl]carbamate (800 mg, 1.59 mmol, 1.00 equiv), dichloromethane (50 mL). Then HCl gas was bubbled in for 1.5 h at room temperature. The solids were collected by filtration and washed with DCM (50 mL). Then the solids were dissolved in 5 mL of water. The pH value of the solution was adjusted to 8 with potassium carbonate (2M). The resulting mixture was extracted with 2×50 mL of dichloromethane and the organic layers combined and concentrated under vacuum. The crude product was purified by Prep-HPLC with the following conditions (Waters III): Column, Xbridge RP18 19*150; mobile phase, water (0.05% NH$_4$HCO$_3$) and MeCN (15% CH$_3$CN up to 75% in 10 min); Detector, UV 220&254 nm. This resulted in 93.1 mg (15%) of the title compound as a white solid. LC-MS (ES, m/z) 404[M+H]$^+$ Method 15.

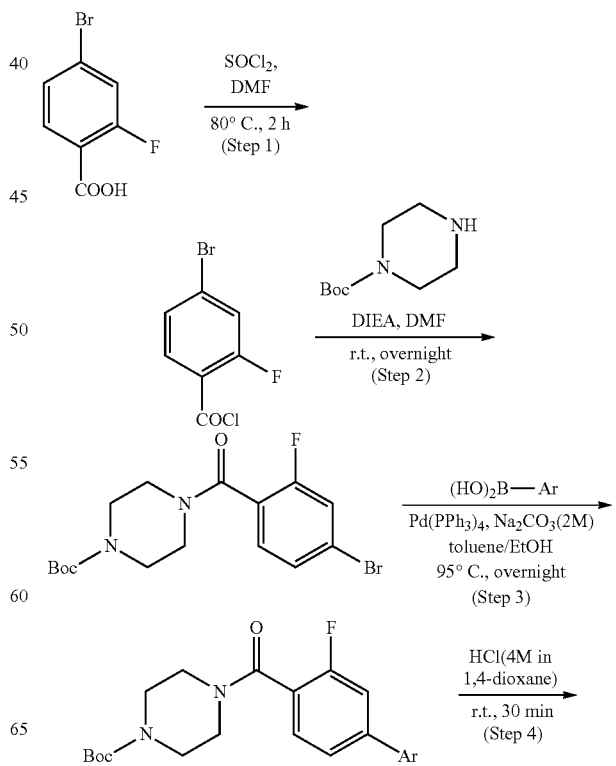

-continued

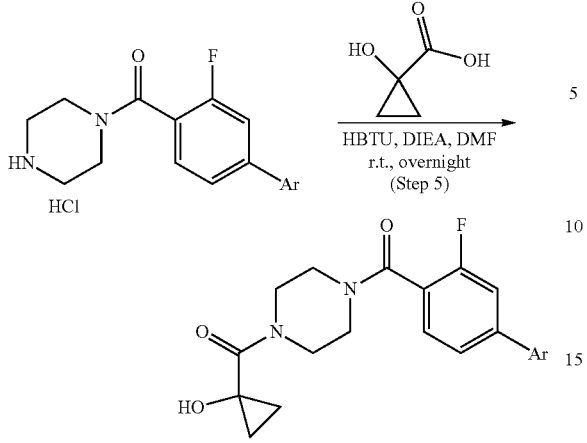

Step 1. 4-bromo-2-fluorobenzoyl chloride

Into a 250-mL round-bottom flask, was placed 4-bromo-2-fluorobenzoic acid (10 g, 45.66 mmol, 1.00 equiv), thionyl chloride (50 mL), N,N-dimethylformamide (0.1 mL). The resulting solution was stirred for 2 h at 80° C. After cooled to room temperature, the resulting mixture was concentrated under vacuum. This resulted in 10 g (92%) of the title compound as light yellow oil. The product was used in the next step directly without further purification.

Step 2. tert-butyl 4-(4-bromo-2-fluorobenzoyl)piperazine-1-carboxylate

Into a 250-mL round-bottom flask, was placed a solution of 4-bromo-2-fluorobenzoyl chloride (10 g, 42.11 mmol, 1.00 equiv) in N,N-dimethylformamide (100 mL). This was followed by the addition of tert-butyl piperazine-1-carboxylate (7.88 g, 42.31 mmol, 1.00 equiv) in several portions. Then to this was added DIEA (16.25 g, 125.74 mmol, 2.99 equiv). The resulting mixture was stirred overnight at room temperature. The mixture was poured into 300 mL water. The solids were collected by filtration and dried under vacuum. This resulted in 14 g (86%) of the title compound as a white solid. LC-MS (ES, m/z): 387, 389[M+H]$^+$

Step 3. tert-butyl 4-(4'-chloro-2',3-difluoro-[1,1'-biphenyl]-4-carbonyl)piperazine-1-carboxylate Into a 100-mL round-bottom flask purged and maintained with an inert atmosphere of nitrogen, was placed a solution of tert-butyl 4-(4-bromo-2-fluorobenzoyl)piperazine-1-carboxylate (1 g, 2.58 mmol, 1.00 equiv) in toluene (10 mL), (4-chloro-2-fluorophenyl)boronic acid (540 mg, 3.10 mmol, 1.20 equiv), Pd(PPh$_3$)$_4$ (358 mg, 0.31 mmol, 0.12 equiv), sodium carbonate (2 M in water, 5 mL), ethanol (1.4 mL). The resulting mixture was stirred overnight at 105° C. After cooled to room temperature, the resulting solution was diluted with 20 mL of H$_2$O and extracted with 3×20 mL of ethyl acetate. The organic layers were combined, washed with 3×20 mL of brine, dried over anhydrous sodium sulfate and concentrated under vacuum. The residue was applied onto a silica gel column with ethyl acetate/petroleum ether (3:7). The collected fractions were combined and concentrated under vacuum. This resulted in 1 g (89%) of the title compound as a light yellow solid. LC-MS (ES, m/z): 437 [M+H]$^+$

Step 4. (4'-chloro-2',3-difluoro-[1,1'-biphenyl]-4-yl)(piperazin-1-yl)methanone hydrochloride Into a 100-mL round-bottom flask, was placed tert-butyl 4-(4'-chloro-2',3-difluoro-[1,1'-biphenyl]-4-carbonyl)piperazine-1-carboxylate (1 g, 2.28 mmol, 1.00 equiv), hydrochloric acid in 1,4-dioxane (4 M, 30 mL). The resulting solution was stirred for 30 min at room temperature. The resulting mixture was concentrated under vacuum. This resulted in 600 mg (78%) of the title compound as an off-white solid. LC-MS (ES, m/z): 337[M+H]$^+$

Step 5. (4-(4'-chloro-2',3-difluoro-[1,1'-biphenyl]-4-carbonyl)piperazin-1-yl)(1-hydroxycyclopropyl)methanone Into a 100-mL round-bottom flask, was placed a solution of (4'-chloro-2',3-difluoro-[1,1'-biphenyl]-4-yl)(piperazin-1-yl)methanone hydrochloride (500 mg, 1.48 mmol, 1.00 equiv), N,N-dimethylformamide (20 mL), 1-hydroxycyclopropane-1-carboxylic acid (166 mg, 1.63 mmol, 1.10 equiv), HBTU (841 mg, 2.22 mmol, 1.49 equiv), DIEA (764 mg, 5.91 mmol, 3.98 equiv). The resulting solution was stirred overnight at room temperature. The mixture was poured into 80 mL of water and precipitation was formed. The solids were collected by filtration and applied onto a silica gel column with ethyl acetate/hexane (3:2). The collected fractions were combined and concentrated under vacuum. This resulted in 260 mg (42%) of the title compound as an off-white solid. LC-MS (ES, m/z): 421[M+H]$^+$ Method 16.

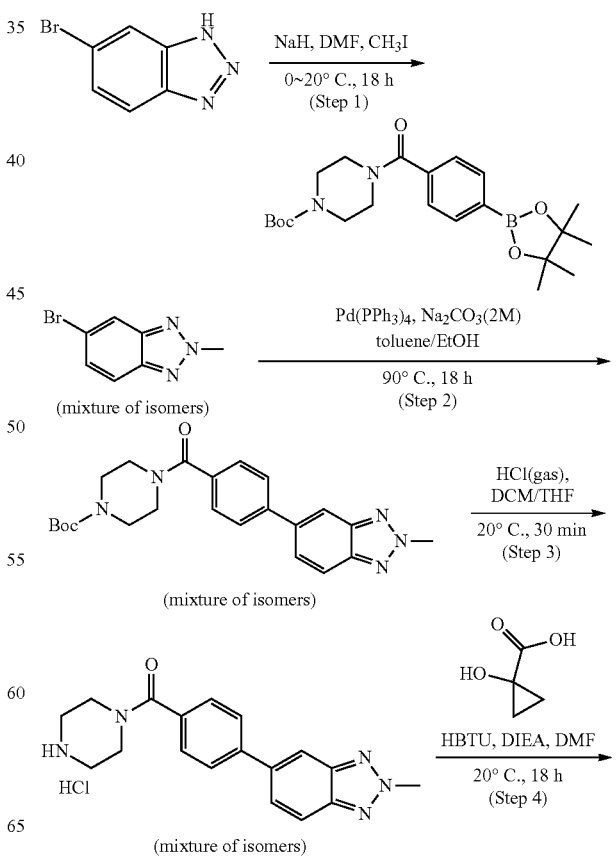

365

-continued

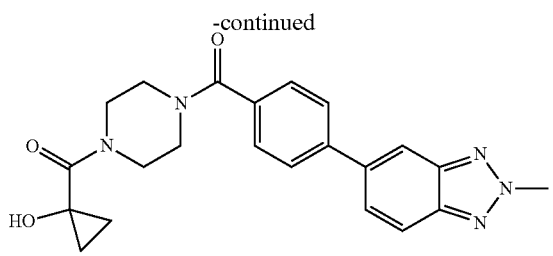

Step 1. 5-bromo-N-methyl-2H-benzo[d][1,2,3]triazole

Into a 100-mL round-bottom flask, was placed a solution of 6-bromo-H-1,2,3-benzotriazole (600 mg, 3.03 mmol, 1.00 equiv) in N,N-dimethylformamide (10 mL). This was followed by the addition of sodium hydride (60% in oil, 303 mg, 7.58 mmol, 2.50 equiv) in portions at 0° C. After stirring for 30 min at 0° C., CH₃I (650 mg, 4.58 mmol, 1.50 equiv) was added in drop wise. The resulting solution was allowed to react, with stirring, for an additional 18 h at 20° C. The reaction mixture was then diluted with 10 mL of ice/water, extracted with 3×20 mL of ethyl acetate. The organic layers were combined, dried over anhydrous sodium sulfate and concentrated under vacuum. The residue was applied onto a silica gel column with PE:EA (200:1-3:1). This resulted in 700 mg (crude) of a mixture of the title compounds as a yellow oil. LC-MS (ES, m/z): 212, 214 [M+H]⁺

Step 2. tert-butyl 4-(4-(N-methyl-2H-benzo[d][1,2,3]triazol-5-yl)benzoyl)piperazine-1-carboxylate Into a 100-mL round-bottom flask purged and maintained with an inert atmosphere of nitrogen, was placed tert-butyl 4-[[4-(tetramethyl-1,3,2-dioxaborolan-2-yl)phenyl]carbonyl]piperazine-1-carboxylate (1.51 g, 3.63 mmol, 1.10 equiv), the mixture of 5-bromo-N-methyl-2H-benzo[d][1,2,3]triazoles (700 mg, 3.30 mmol, 1.00 equiv), Pd(PPh₃)₄ (382 mg, 0.33 mmol, 0.10 equiv) and toluene/EtOH (30/4.5 mL), sodium carbonate (15 mL, 2M). The resulting mixture was stirred for 18 h at 90° C. After cooled to room temperature, the reaction mixture was diluted with 50 mL of water, extracted with 3×30 mL of ethyl acetate. The organic layers were combined, dried over anhydrous sodium sulfate and concentrated under vacuum. The residue was applied onto a silica gel column with dichloromethane/methanol (200/1~20/1). This resulted in 1.2 g (crude) of a mixture of the title compounds as a light yellow solid. LC-MS (ES, m/z): 422 [M+H]⁺

Step 3. (4-(N-methyl-2H-benzo[d][1,2,3]triazol-5-yl)phenyl)(piperazin-1-yl)methanone hydrochloride Into a 100-mL round-bottom flask, was placed the mixture of tert-butyl 4-(4-(N-methyl-2H-benzo[d][1,2,3]triazol-5-yl)benzoyl)piperazine-1-carboxylate (1.2 g, 2.85 mmol, 1.00 equiv) and dichloromethane (50 mL). Then hydrogen chloride (gas) was introduced in. The resulting solution was stirred for 30 min at 20° C. The resulting solids were collected by filtration and dried under reduced pressure. This resulted in 800 mg (79%) of a mixture of the title compounds as a light yellow solid. LC-MS (ES, m/z): 322 [M+H]⁺

366

Step 4. (4-(1-hydroxycyclopropane-1-carbonyl)piperazin-1-yl)(4-(2-methyl-2H-benzo[d][1,2,3]triazol-5-yl)phenyl)methanone Into a 100-mL round-bottom flask, was placed a solution of 1-hydroxycyclopropane-1-carboxylic acid (240 mg, 2.35 mmol, 1.10 equiv) in N,N-dimethylformamide (10 mL), the mixture of (4-(N-methyl-2H-benzo[d][1,2,3]triazol-5-yl)phenyl)(piperazin-1-yl)methanone hydrochloride (766 mg, 2.14 mmol, 1.00 equiv, 98%), HBTU (1.22 g, 3.22 mmol, 1.50 equiv), DIEA (1.11 g, 8.59 mmol, 4.00 equiv). The resulting solution was stirred for 18 h at 20° C. The reaction mixture was diluted with 20 mL of water, extracted with 3×20 mL of ethyl acetate. The organic layers were combined, dried over anhydrous sodium sulfate and concentrated under vacuum. The residue was purified by Prep-HPLC with the following conditions (Waters III): Column, XBridge Prep Cis OBD Column, 5 um, 19*150 mm; mobile phase, water with 0.03% NH₃H₂O and MeCN (16% MeCN up to 34% in 8 min); Detector, 254&220 nm. This resulted in 90 mg (10%) of the title compound as a light yellow solid. LC-MS (ES, m/z) 406[M+H]⁺

Method 17.

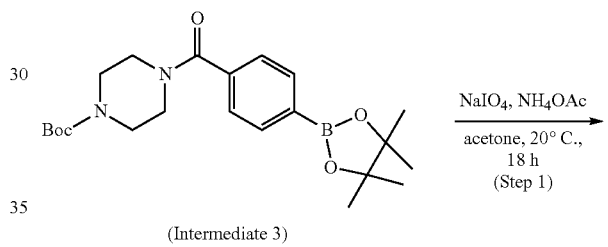

(Intermediate 3)

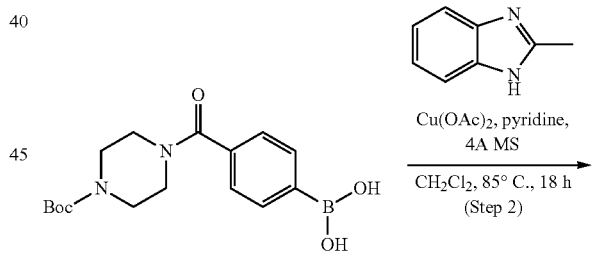

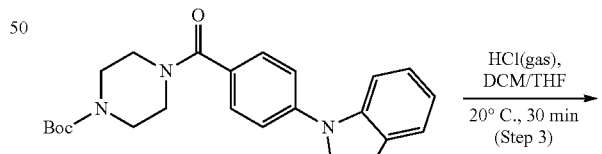

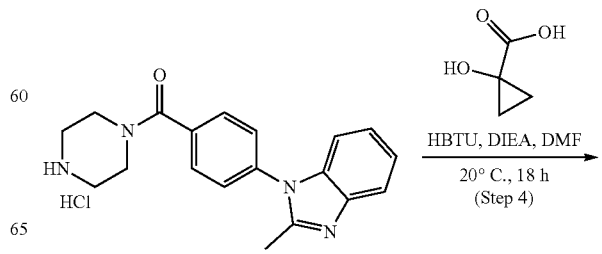

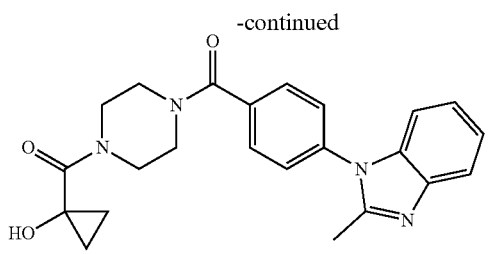

Step 1. (4-(4-(tert-butoxycarbonyl)piperazine-1-carbonyl)phenyl)boronic acid Into a 1 L round-bottom flask was placed Intermediate 3 (12.5 g, 30.03 mmol, 1.00 eqiv) a solution of sodium periodate (32.1 g, 150.00 mmol, 5.00 eqiv) in acetone (300 mL), ammonium acetate (150 mL, 5.00 eqiv, 1M). The resulting solution was stirred for 18 h at RT. The resulting solution was diluted with 300 mL of water and extracted with 3×100 mL of ethyl acetate. The organic layers were combined and dried over sodium sulfate. The solids were filtered out and the solution was concentrated in vacuo. This afforded the title compound (10.1 g, 96%) as a light yellow solid. LC-MS (ES, m/z) 335[M+H]+

Step 2. tert-butyl 4-(4-(2-methyl-1H-benzo[d]imidazol-1-yl)benzoyl)piperazine-1-carboxylate Into a 250-mL round-bottom flask, was placed a solution of (4-(4-(tert-butoxycarbonyl)piperazine-1-carbonyl)phenyl)boronic acid (3.34 g, 9.05 mmol, 2.00 equiv) in dichloromethane (50 mL), 2-methyl-1H-benzo[d]imidazole (660 mg, 4.99 mmol, 1.00 equiv), Cu(OAc)$_2$ (1.23 mg, 1.50 equiv), pyridine (790 mg, 9.99 mmol, 2.00 equiv), 4A molecular sieves (3 g). The resulting mixture was stirred for 18 h at 20° C. The solids were filtered out. The filtrate was concentrated under vacuum. The residue was applied onto a silica gel column with DCM/MeOH (200/1~20/1). This resulted in 1 g (27%) of the title compound as yellow oil. LC-MS (ES, m/z): 421[M+H]+

Step 3. (4-(2-methyl-1H-benzo[d]imidazol-1-yl)phenyl)(piperazin-1-yl)methanone hydrochloride Into a 100-mL round-bottom flask, was placed tert-butyl 4-(4-(2-methyl-1H-benzo[d]imidazol-1-yl)benzoyl)piperazine-1-carboxylate (960 mg, 2.28 mmol, 1.00 equiv), DCM (30 mL), THF (30 mL). Then hydrogen chloride (gas) was introduced in. The resulting solution was stirred for 30 min at 20° C. The solids were collected by filtration and dried under vacuum. This resulted in 600 mg of the title compound as a light yellow solid. LC-MS (ES, m/z): 321[M+H]+

Step 4. (4-(1-hydroxycyclopropane-1-carbonyl)piperazin-1-yl)(4-(2-methyl-1H-benzo[d]imidazol-1-yl)phenyl)methanone Into a 100-mL round-bottom flask, was placed 1-hydroxycyclopropane-1-carboxylic acid (190 mg, 1.86 mmol, 1.10 equiv), (4-(2-methyl-1H-benzo[d]imidazol-1-yl)phenyl)(piperazin-1-yl)methanone hydrochloride (600 mg, 1.68 mmol, 1.00 equiv), HBTU (955 mg, 2.52 mmol, 1.50 equiv), N,N-dimethylformamide (10 mL), DIEA (867 mg, 6.71 mmol, 4.00 equiv). The resulting solution was stirred for 18 h at 20° C. The reaction mixture was diluted with 20 mL of water, extracted with 3×20 mL of ethyl acetate. All the organic layers were combined, dried over anhydrous sodium sulfate and concentrated under vacuum. The residue was purified by Prep-HPLC with the following conditions (Waters I): Column, Xbridge Prep C18 OBD column, 5 um, 19*150 mm; mobile phase, Water (0.05% NH$_4$HCO$_3$) and CH$_3$CN (16% CH$_3$CN up to 34% in 10 min); Detector, UV 220&254 nm. This resulted in 130 mg (19%) of the title compound as a white solid. LC-MS (ES, m/z): 405[M+H]+
Method 18.

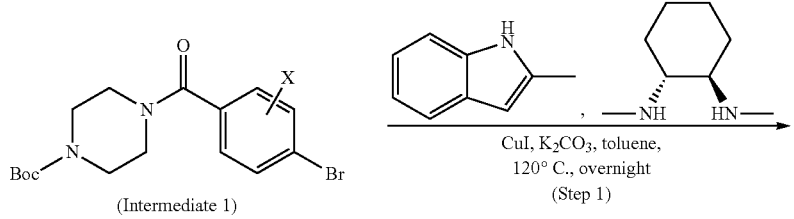

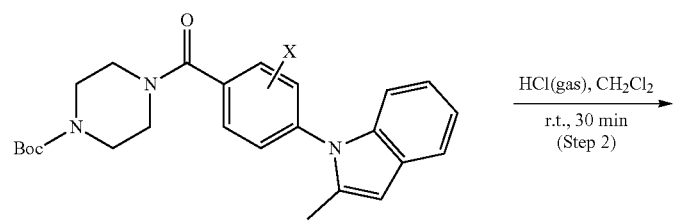

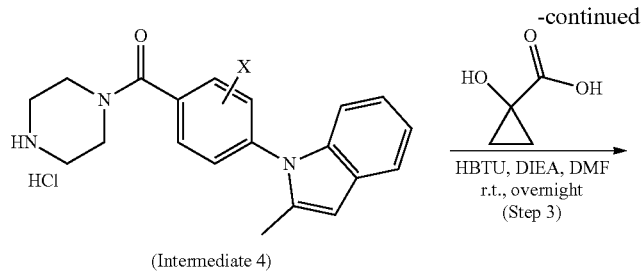
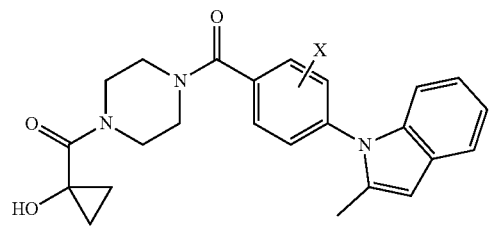

Step 1. tert-butyl 4-(4-(2-methyl-1H-indol-1-yl)benzoyl)piperazine-1-carboxylate Into a 250-mL round-bottom flask purged and maintained with an inert atmosphere of nitrogen, was placed a solution of tert-butyl 4-[(4-bromophenyl)carbonyl]piperazine-1-carboxylate (Intermediate 1 (X=H), 1.69 g, 4.58 mmol, 1.00 equiv) in toluene (50 mL), 2-methyl-1H-indole (600 mg, 4.57 mmol, 1.00 equiv), CuI (87 mg, 0.46 mmol, 0.10 equiv), potassium carbonate (1.9 g, 13.75 mmol, 3.00 equiv), (1R,2R)-1-N,2-N-dimethylcyclohexane-1,2-diamine (130 mg, 0.91 mmol, 0.20 equiv). The resulting mixture was stirred overnight at 120° C. After cooled to room temperature, the reaction mixture was diluted with 50 mL of H$_2$O, extracted with 3×50 mL of ethyl acetate. The organic layers were combined, dried over anhydrous sodium sulfate and concentrated under vacuum. The residue was applied onto a silica gel column with ethyl acetate/petroleum ether (1:1). The collected fractions were combined and concentrated under vacuum. This resulted in 1.4 g (73%) of the title compound as a red solid. LC-MS (ES, m/z): 420[M+H]$^+$

Step 2. (4-(2-methyl-1H-indol-1-yl)phenyl)(piperazin-1-yl)methanone hydrochloride (Intermediate 4)

Into a 100-mL round-bottom flask, was placed a solution of tert-butyl 4-(4-(2-methyl-1H-indol-1-yl)benzoyl)piperazine-1-carboxylate (1.4 g, 3.34 mmol) in dichloromethane (30 mL). To the above HCl gas was introduced in. The resulting solution was stirred for 30 min at room temperature. The resulting mixture was concentrated under vacuum. This resulted in 1.4 g (59%) of the title compound as a red solid. LC-MS (ES, m/z): 320[M+H]$^+$

Step 3. (4-(1-hydroxycyclopropane-1-carbonyl)piperazin-1-yl)(4-(2-methyl-1H-indol-1-yl)phenyl)methanone Into a 100-mL round-bottom flask, was placed a solution of (4-(2-methyl-1H-indol-1-yl)phenyl)(piperazin-1-yl)methanone hydrochloride (658 mg, 1.85 mmol, 1.00 equiv) in N,N-dimethylformamide (20 mL), 1-hydroxycyclopropane-1-carboxylic acid (189 mg, 1.85 mmol, 1.00 equiv), HBTU (1.05 g, 2.77 mmol, 1.50 equiv), DIEA (955 mg, 7.39 mmol, 4.00 equiv). The resulting solution was stirred overnight at room temperature. The reaction mixture was diluted with 30 mL of water and extracted with 3×30 mL of ethyl acetate. The organic layers were combined, dried over sodium sulfate anhydrous and concentrated under vacuum. The residue was applied onto a silica gel column with dichloromethane/methanol (10:1). The collected fractions were combined and concentrated under vacuum. This resulted in 112.3 mg (15%) of the title compound as a light brown solid. LC-MS (ES, m/z): 404[M+H]$^+$
Method 19.

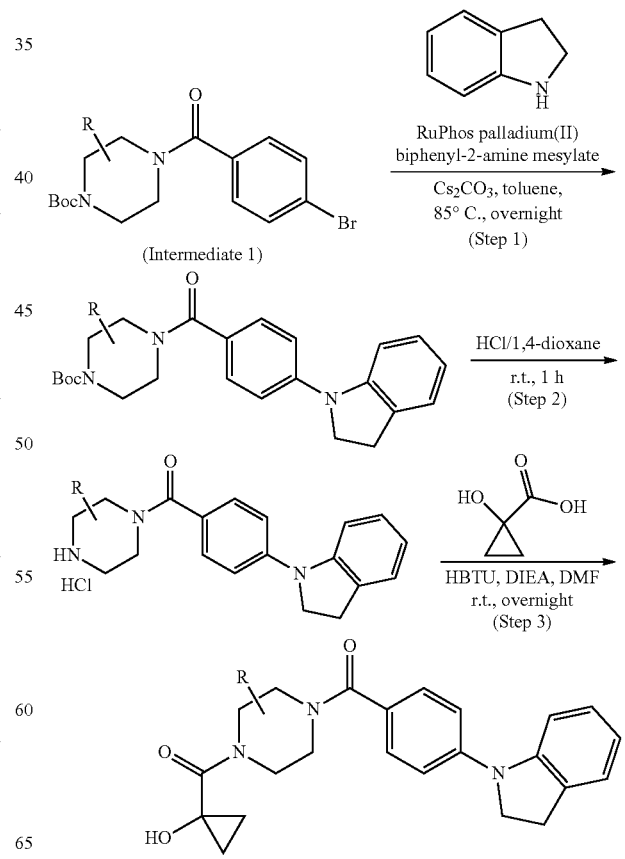

371

Step 1. tert-butyl 4-(4-(indolin-1-yl)benzoyl)piperazine-1-carboxylate

Into a 100-mL round-bottom flask purged and maintained with an inert atmosphere of nitrogen, was placed 2,3-dihydro-1H-indole (390 mg, 3.27 mmol, 1.00 equiv), tert-butyl 4-[(4-bromophenyl)carbonyl]piperazine-1-carboxylate (Intermediate 1 (R=H), 1.5 g, 3.60 mmol, 1.10 equiv), Cs$_2$CO$_3$ (3.74 g, 11.48 mmol, 3.51 equiv), toluene (50 mL), RuPhos palladium(II) biphenyl-2-amine mesylate (276 mg). The resulting mixture was stirred overnight at 85° C. After cooled to room temperature, the resulting mixture was concentrated under vacuum and re-dissolved with 200 mL of EA. The resulting mixture was washed with 3×50 mL of brine, dried over anhydrous sodium sulfate and concentrated under vacuum. The residue was applied onto a silica gel column with ethyl acetate/petroleum ether (50:50). This resulted in 1 g (75%) of the title compound as a yellow solid. LC-MS (ES, m/z): 408[M+H]$^+$

Step 2. (4-(indolin-1-yl)phenyl)(piperazin-1-yl)methanone hydrochloride

Into a 100-mL round-bottom flask, was placed tert-butyl 4-(4-(indolin-1-yl)benzoyl)piperazine-1-carboxylate (1 g, 2.45 mmol, 1.00 equiv), a solution of hydrogen chloride in 1,4-dioxane (4M, 20 mL). The resulting solution was stirred for 1 h at room temperature. The solids were collected by filtration and dried under vacuum. This resulted in 800 mg (95%) of the title compound as a yellow solid. LC-MS (ES, m/z): 308[M+H]$^+$

Step 3. (4-(1-hydroxycyclopropane-1-carbonyl)piperazin-1-yl)(4-(indolin-1-yl)phenyl)methanone Into a 100-mL round-bottom flask, was placed (4-(indolin-1-yl)phenyl)(piperazin-1-yl)methanone hydrochloride (540 mg, 1.57 mmol, 1.00 equiv), 1-hydroxycyclopropane-1-carboxylic acid (160 mg, 1.57 mmol, 1.00 equiv), N,N-dimethylformamide (20 mL), HBTU (892 mg, 2.35 mmol, 1.50 equiv), DIEA (810 mg, 6.27 mmol, 3.99 equiv). The resulting solution was stirred overnight at room temperature. The reaction mixture was diluted with 50 mL of EA, washed with 3×30 mL of brine, dried over anhydrous sodium sulfate and concentrated under vacuum. The residue was purified by Prep-HPLC with the following conditions (Waters I): Column, SunFire Prep C18, 5 um, 19*100 mm; mobile phase, Water (0.05% NH$_4$HCO$_3$) and CH$_3$CN (50% CH$_3$CN up to 100% in 10 min); Detector, UV 220&254 nm. This resulted in 63.8 mg (10%) of the title compound as an off-white solid. LC-MS (ES, m/z): 392[M+H]$^+$ Method 20.

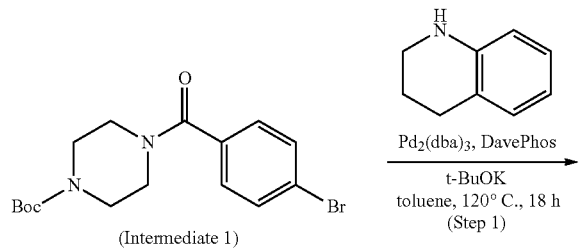

(Intermediate 1)

372

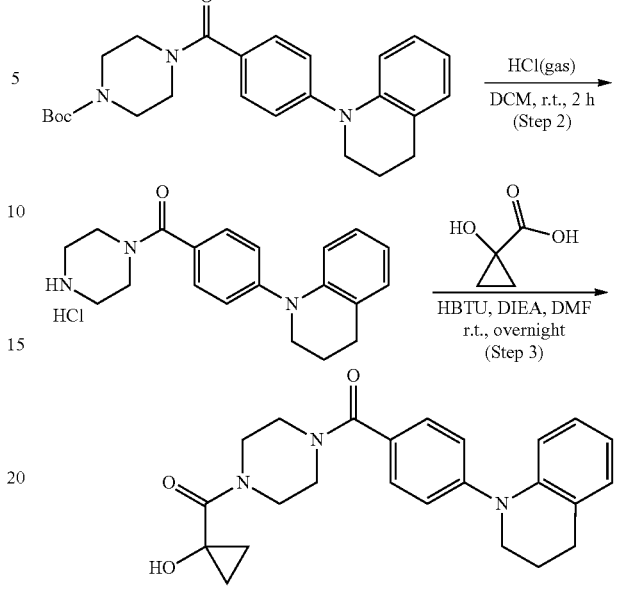

Step 1. tert-butyl 4-(4-(3,4-dihydroquinolin-1(2H)-yl)benzoyl)piperazine-1-carboxylate Into a 100-mL round-bottom flask purged and maintained with an inert atmosphere of nitrogen, was placed Pd$_2$(dba)$_4$ (305 mg), DavePhos (627 mg), toluene (50 mL). The mixture was stirred at room temperature for 30 min. Then 1,2,3,4-tetrahydroquinoline (700 mg, 5.26 mmol, 1.00 equiv), tert-butyl 4-[(4-bromophenyl)carbonyl]piperazine-1-carboxylate (Intermediate 1, 1.94 g, 5.25 mmol, 1.00 equiv), t-BuOK (1.18 g, 10.52 mmol, 2.00 equiv) were added in. The system was evacuated and back-filled with N2 for 5 times. The resulting mixture was stirred for 18 h at 120° C. in an oil bath. After cooled to room temperature, the resulting mixture was concentrated under vacuum. The residue was applied onto a silica gel column with ethyl acetate/petroleum ether (0/100~45/55). The collected fractions were combined and concentrated under vacuum. This resulted in 540 mg (24%) of the title compound as a yellow solid. LC-MS (ES, m/z): 422 [M+H]$^+$

Step 2. (4-(3,4-dihydroquinolin-1(2H)-yl)phenyl)(piperazin-1-yl)methanone hydrochloride Into a 100-mL round-bottom flask, was placed tert-butyl 4-(4-(3,4-dihydroquinolin-1(2H)-yl)benzoyl)piperazine-1-carboxylate (540 mg, 1.28 mmol, 1.00 equiv), dichloromethane (40 mL). Then hydrogen chloride gas was bubbled in. The resulting solution was stirred for 2 h at room temperature. The resulting mixture was concentrated under vacuum. This resulted in 635 mg (quantitative) of the title compound as a yellow solid. LC-MS (ES, m/z): 322 [M+H]$^+$

Step 3. (4-(4-(3,4-dihydroquinolin-1(2H)-yl)benzoyl)piperazin-1-yl)(1-hydroxycyclopropyl)methanone Into a 100-mL round-bottom flask, was placed 1-hydroxycyclopropane-1-carboxylic acid (635 mg, 6.22 mmol, 1.00 equiv), (4-(3,4-dihydroquinolin-1(2H)-yl)phenyl)(piperazin-1-yl)methanone hydrochloride (181 mg, 0.51 mmol, 0.08 equiv), HBTU (1.34 g, 3.53 mmol, 0.57 equiv), N,N-dimethylformamide (15 mL), DIEA (457 mg, 3.54 mmol, 0.57 equiv). The resulting solution was stirred overnight at room temperature. The reaction mixture was diluted with 60 mL of EA, washed with 4×20 mL of water and 1×20 mL of brine. The organic phase was dried over anhydrous sodium sulfate and concentrated under vacuum. The residue was applied onto a silica gel column with ethyl acetate/petroleum ether (0/100-100/0). The resulting crude product was further purified by Prep-HPLC with the following conditions (Waters III): Column, Xbridge RP18 19*150; mobile phase, water (0.05% $NH_4HCO_3$) and MeCN (15% $CH_3CN$ up to 75% in 10 min); Detector, UV 220&254 nm. This resulted in 66.3 mg (3%) of the title compound as a purple solid. LC-MS (ES, m/z): 406 $[M+H]^+$ Method 21.

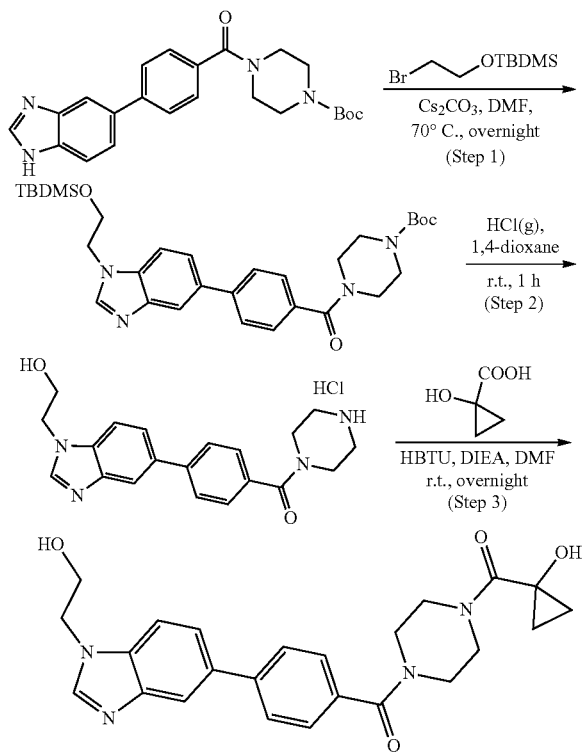

Step 1. tert-butyl 4-(4-(1-(2-((tert-butyldimethylsilyl)oxy)ethyl)-1H-benzo[d]imidazol-5 and 6-yl)benzoyl)piperazine-1-carboxylate Into a 250-mL round-bottom flask, was placed tert-butyl 4-(4-(1H-benzo[d]imidazol-5-yl)benzoyl)piperazine-1-carboxylate (1 g, 2.46 mmol, 1.00 equiv), (2-bromoethoxy)(tert-butyl)dimethylsilane (883 mg, 3.69 mmol, 1.50 equiv), N,N-dimethylformamide (50 mL), $Cs_2CO_3$ (2.41 g, 7.40 mmol, 3.01 equiv). The resulting mixture was stirred overnight at 70° C. After cooled to room temperature, the reaction mixture was diluted with 100 mL of EA, washed with 3×50 mL of water and 50 mL of brine. The organic phase was dried over anhydrous sodium sulfate and concentrated under vacuum. The residue was purified by Prep-HPLC with the following conditions (Waters I): Column, SunFire Prep C18, 5 um, 19*100 mm; mobile phase, Water (0.05% $NH_4HCO_3$) and $CH_3CN$ (55% $CH_3CN$ up to 75% in 7 min); Detector, UV 220&254 nm. This resulted in 380 mg (27%) of tert-butyl 4-(4-(1-(2-((tert-butyldimethylsilyl)oxy)ethyl)-1H-benzo[d]imidazol-5-yl)benzoyl)piperazine-1-carboxylate as a yellow solid and 390 mg (28%) tert-butyl 4-(4-(1-(2-((tert-butyldimethylsilyl)oxy)ethyl)-1H-benzo[d]imidazol-6-yl)benzoyl)piperazine-1-carboxylate as a yellow solid. LC-MS (ES, m/z): 565$[M+H]^+$ Step 2. (4-(1-(2-hydroxyethyl)-1H-benzo[d]imidazol-6-yl)phenyl)(piperazin-1-yl)methanone hydrochloride Into a 100-mL round-bottom flask, was placed tert-butyl 4-(4-(1-(2-((tert-butyldimethylsilyl)oxy)ethyl)-1H-benzo[d]imidazol-6-yl)benzoyl)piperazine-1-carboxylate (380 mg, 0.67 mmol, 1.00 equiv) and dioxane (40 mL). Then HCl gas was introduced in. The resulting solution was stirred for 1 h at room temperature. The resulting mixture was concentrated under vacuum. This resulted in 250 mg (96%) of the title compound as a yellow solid. LC-MS (ES, m/z): 351 $[M+H]^+$ Step 3. (4-(1-hydroxycyclopropane-1-carbonyl)piperazin-1-yl)(4-(1-(2-hydroxyethyl)-1H-benzo[d]imidazol-5-yl)phenyl)methanone Into a 100-mL round-bottom flask, was placed (4-(1-(2-hydroxyethyl)-1H-benzo[d]imidazol-6-yl)phenyl)(piperazin-1-yl)methanone hydrochloride (250 mg, 0.65 mmol, 1.00 equiv), 1-hydroxycyclopropane-1-carboxylic acid (66 mg, 0.65 mmol, 1.00 equiv), N,N-dimethylformamide (20 mL), HBTU (367 mg, 0.97 mmol, 1.50 equiv), DIEA (333 mg, 2.58 mmol, 3.99 equiv). The resulting solution was stirred overnight at room temperature. The reaction mixture was washed with water, dried over $Na_2SO_4$ and concentrated under vacuum. The residue was purified by Prep-HPLC with the following conditions (Waters I): Column, SunFire Prep C18, 5 um, 19*100 mm; mobile phase, Water (0.05% $NH_4HCO_3$) and $CH_3CN$ (55% $CH_3CN$ up to 75% in 7 min); Detector, UV 220&254 nm. This resulted in 75 mg (27%) of the title compound as an off-white solid. LC-MS (ES, m/z): 435$[M+H]^+$ Method 22.

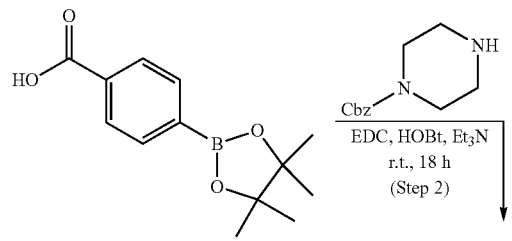

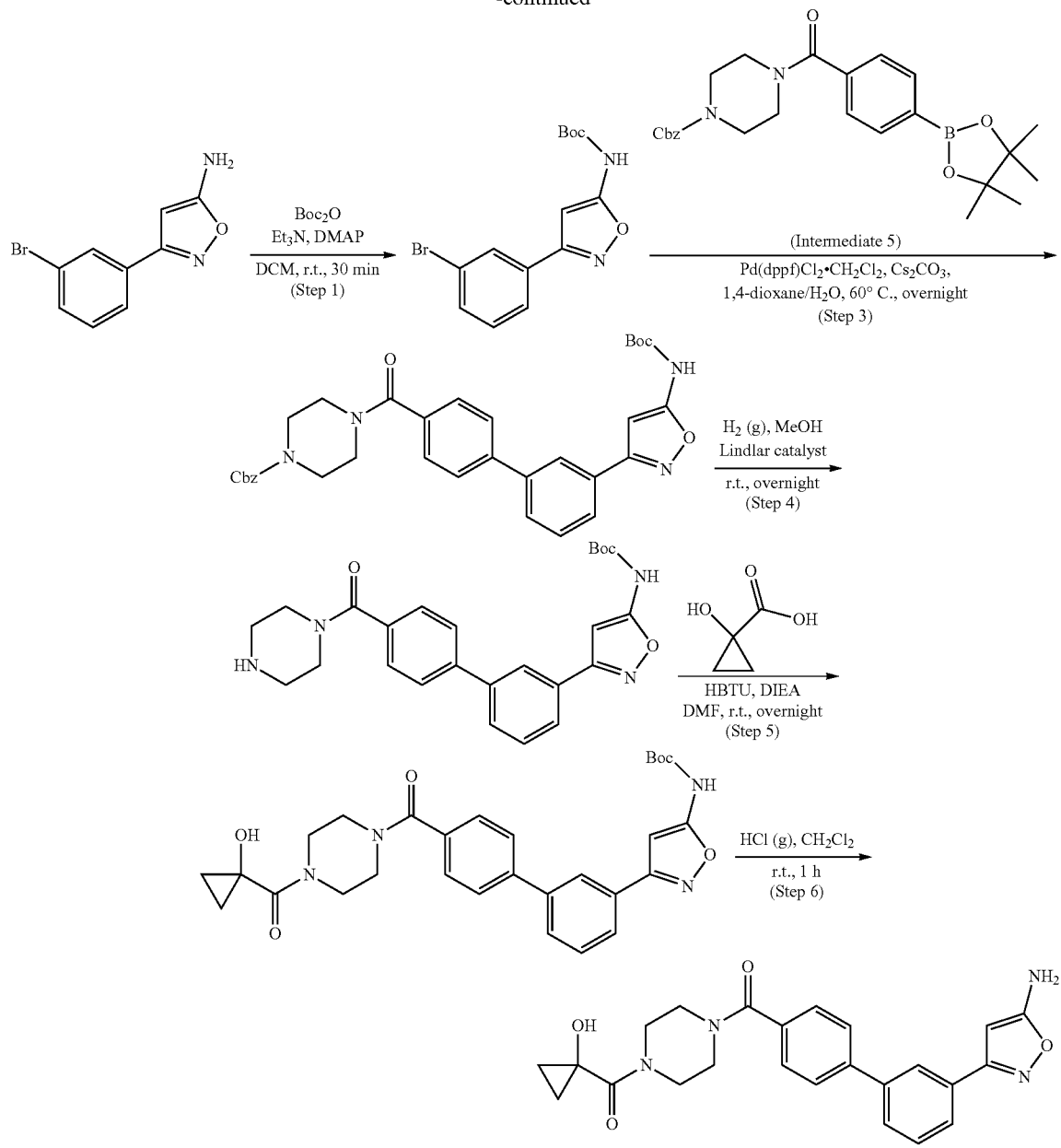

Step 1. tert-butyl (3-(3-bromophenyl)isoxazol-5-yl)carbamate

Into a 250-mL round-bottom flask, was placed a solution of 3-(3-bromophenyl)-1, 2-oxazol-5-amine (1 g, 4.18 mmol, 1.00 equiv) in dichloromethane (40 mL), Boc₂O (1.83 g, 8.38 mmol, 2.00 equiv), triethylamine (1.27 g, 12.55 mmol, 3.00 equiv), 4-dimethylaminopyridine (51.24 mg, 0.42 mmol, 0.10 equiv). The resulting solution was stirred for 1 h at room temperature. The resulting mixture was washed with 2×20 mL of hydrochloric acid (0.5M), dried over anhydrous sodium sulfate, concentrated under vacuum. This resulted in 1.42 g (crude) of the title compound as an off-white solid. LC-MS (ES, m/z): 339[M+H]⁺

Step 2. benzyl 4-(4-(4,4,5,5-tetramethyl-1,3,2-dioxaborolan-2-yl)benzoyl)piperazine-1-carboxylate (Intermediate 5)

Into a 1 L round-bottom flask was placed benzyl piperazine-1-carboxylate (15 g, 68.10 mmol, 1.00 equiv), 4-(tetramethyl-1,3,2-dioxaborolan-2-yl)benzoic acid (16.9 g, 68.12 mmol, 1.00 equiv), EDC (14.4 g, 75.12 mmol, 1.10 equiv), HOBt (5.8 g, 42.92 mmol, 0.50 equiv), and triethylamine (27.6 g 272.75 mmol, 4.00 equiv) in dichloromethane (300 mL). The resulting solution was stirred for 18 h at RT. The mixture was then washed with 0.5M sodium carbonate (aq, 75 mL). The resulting mixture was then washed with 0.5M HCl (aq, 75 mL) followed by 0.5M sodium carbonate (aq, 75 mL). The solution was concentrated in vacuo and the crude product was recrystallized from tBME/ hexane (1:1). This afforded the title compound (26 g, 84%) as a white solid. LC-MS (ES, m/z): 451[M+H]+

Step 3. benzyl 4-(3'-(5-((tert-butoxycarbonyl)amino)isoxazol-3-yl)-[1,1'-biphenyl]-4-carbonyl)piperazine-1-carboxylate Into a 250-mL round-bottom flask purged and maintained with an inert atmosphere of nitrogen, was placed a solution of tert-butyl (3-(3-bromophenyl)isoxazol-5-yl)carbamate (1.42 g, 4.19 mmol, 1.00 equiv) in 1,4-dioxane (30 mL), benzyl 4-(4-(4,4,5,5-tetramethyl-1,3,2-dioxaborolan-2-yl)benzoyl)piperazine-1-carboxylate (1.89 g, 4.20 mmol, 1.00 equiv), Pd(dppf)Cl$_2$.CH$_2$Cl$_2$ (410 mg, 0.50 mmol, 0.12 equiv), Cs$_2$CO$_3$ (4.11 g, 12.61 mmol, 3.01 equiv), water (10 mL). The resulting solution was stirred overnight at 60° C. After cooled to room temperature, the reaction mixture was diluted with 30 mL of H$_2$O, extracted with 3×30 mL of ethyl acetate. The organic layers were combined, washed with 30 mL of brine, dried over anhydrous sodium sulfate and concentrated under vacuum. The residue was applied onto a silica gel column with ethyl acetate/petroleum ether (1:1). The collected fractions were combined and concentrated under vacuum. This resulted in 780 mg (32%) of the title compound as an off-white solid. LC-MS (ES, m/z): 583[M+H]+

Step 4. tert-butyl (3-(4'-(piperazine-1-carbonyl)-[1,1'-biphenyl]-3-yl)isoxazol-5-yl)carbamate Into a 100-mL round-bottom flask, was placed benzyl 4-(3'-(5-((tert-butoxycarbonyl)amino)isoxazol-3-yl)-[1,1'-biphenyl]-4-carbonyl)piperazine-1-carboxylate (1.8 g, 3.09 mmol, 1.00 equiv), methanol (40 mL) and Lindlar catalyst (1.8 g). The flask was evacuated and back-filled with hydrogen for 6 times. The resulting solution was stirred overnight at room temperature. The solids were filtered out. The filtrate was concentrated under vacuum. The residue was applied onto a silica gel column with dichloromethane/methanol (90:10). The collected fractions were combined and concentrated under vacuum. This resulted in 850 mg (61%) of the title compound as a light yellow solid. LC-MS (ES, m/z): 449[M+H]+

Step 5. tert-butyl (3-(4'-(4-(1-hydroxycyclopropane-1-carbonyl)piperazine-1-carbonyl)-[1,1'-biphenyl]-3-yl)isoxazol-5-yl)carbamate Into a 100-mL round-bottom flask, was placed a solution of tert-butyl (3-(4'-(piperazine-1-carbonyl)-[1,1'-biphenyl]-3-yl)isoxazol-5-yl)carbamate (850 mg, 1.90 mmol, 1.00 equiv) in N,N-dimethylformamide (20 mL), 1-hydroxycyclopropane-1-carboxylic acid (194 mg, 1.90 mmol, 1.00 equiv), HBTU (1.08 g, 2.85 mmol, 1.50 equiv), DIEA (980 mg, 7.58 mmol, 4.00 equiv). The resulting solution was stirred overnight at room temperature. The reaction mixture was diluted with 30 mL of EA, washed with 3×30 mL of brine, dried over anhydrous sodium sulfate and concentrated under vacuum. The residue was applied onto a silica gel column with dichloromethane/methanol (90:10). The collected fractions were combined and concentrated under vacuum. This resulted in 600 mg (59%) of the title compound as a brown solid. LC-MS (ES, m/z): 533[M+H]+

Step 6. (4-(3'-(5-aminoisoxazol-3-yl)-[1,1'-biphenyl]-4-carbonyl)piperazin-1-yl)(1-hydroxycyclopropyl)methanone Into a 100-mL round-bottom flask, was placed tert-butyl (3-(4'-(4-(1-hydroxycyclopropane-1-carbonyl)piperazine-1-carbonyl)-[1,1'-biphenyl]-3-yl)isoxazol-5-yl)carbamate (600 mg, 1.13 mmol, 1.00 equiv), dichloromethane (30 mL). To the above HCl gas was introduced in. The resulting solution was stirred for 1 h at room temperature. The mixture was concentrated and dissolved in 5 mL methanol. The pH value of the solution was adjusted to 8 with saturated sodium bicarbonate solution. The resulting solution was extracted with 2×30 mL of dichloromethane. The organic layers were combined, dried over anhydrous sodium sulfate and concentrated under vacuum. The residue was purified by Prep-HPLC with the following conditions (Waters I): Column, Xbridge Prep C18 OBD column, 5 um, 19*150 mm; mobile phase, Water (0.05% NH$_4$HCO$_3$) and CH$_3$CN (30% CH$_3$CN up to 70% in 9 min); Detector, UV 220&254 nm. This resulted in 107.4 mg (22%) of the title compound as a white solid. LC-MS (ES, m/z): 433[M+H]+

Method 23.

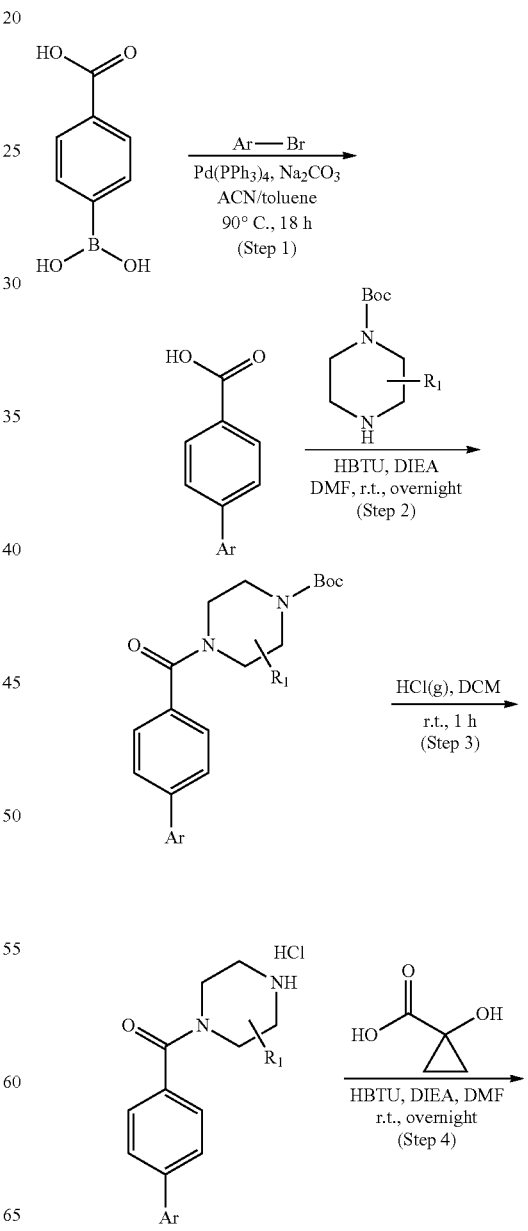

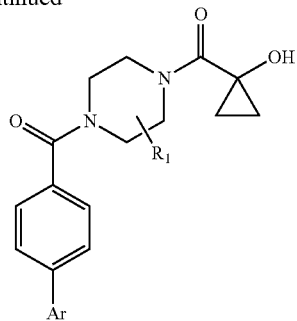

Step 1. 4-(1-methyl-1H-benzo[d]imidazol-5-yl)benzoic acid

Into a 250-mL round-bottom flask purged and maintained with an inert atmosphere of nitrogen, was placed a solution of 4-(tetramethyl-1,3,2-dioxaborolan-2-yl)benzoic acid (2.35 g, 9.47 mmol, 1.00 equiv) in CH$_3$CN/toluene (70/12 mL), 5-bromo-1-methyl-1H-benzo[d]imidazole (2 g, 9.48 mmol, 1.00 equiv), Pd(PPh$_3$)$_4$ (548 mg, 0.47 mmol, 0.05 equiv), sodium carbonate (0.4M, 50 mL, 2.00 equiv). The resulting solution was stirred for 18 h at 90° C. After cooled to room temperature, the reaction mixture was poured into 50 ml of water. The mixture was washed with 2×100 mL of ethyl acetate and the aqueous layer was collected. The pH value of the solution was adjusted to 4 with hydrochloric acid (1N). The solids were collected by filtration and dried under vacuum. This resulted in 2 g (84%) of the title compound as a white solid, which was dried under vacuum. LC-MS (ES, m/z): 253 [M+H]$^+$

Step 2. tert-butyl (R)-2-methyl-4-(4-(1-methyl-1H-benzo[d]imidazol-5-yl)benzoyl)piperazine-1-carboxylate Into a 50-mL round-bottom flask, was placed a solution of 4-(1-methyl-1H-benzo[d]imidazol-5-yl)benzoic acid (600 mg, 2.38 mmol, 1.00 equiv) in N,N-dimethylformamide (15 mL), tert-butyl (2R)-2-methylpiperazine-1-carboxylate (476 mg, 2.38 mmol, 1.00 equiv), HBTU (1.35 g, 3.56 mmol, 1.50 equiv), DIEA (1.22 g, 9.44 mmol, 4.00 equiv). The resulting solution was stirred overnight at room temperature. The reaction mixture was poured into 100 mL of water, extracted with 3×100 mL of dichloromethane. The organic layers were combined, dried over anhydrous sodium sulfate and concentrated under vacuum. The residue was applied onto a silica gel column with ethyl acetate/petroleum ether (1/15). This resulted in 650 mg (63%) of the title compound as red oil. LC-MS (ES, m/z): 435 [M+H]$^+$

Step 3. (R)-(4-(1-methyl-1H-benzo[d]imidazol-5-yl)phenyl)(3-methylpiperazin-1-yl)methanone hydrochloride Into a 50-mL round-bottom flask, was placed a solution of tert-butyl (R)-2-methyl-4-(4-(1-methyl-1H-benzo[d]imidazol-5-yl)benzoyl)piperazine-1-carboxylate (650 mg, 1.50 mmol, 1.00 equiv) in dichloromethane (20 mL). To the above hydrogen chloride (gas) was introduced in. The resulting solution was stirred for 0.5 h at room temperature. The resulting mixture was concentrated under vacuum. The residue was triturated with 2×100 mL of ether. The solids were collected by filtration and dried under vacuum. This resulted in 500 mg (90%) of the title compound as a red solid. LC-MS (ES, m/z): 335 [M+H]$^+$

Step 4. (R)-(4-(1-hydroxycyclopropane-1-carbonyl)-3-methylpiperazin-1-yl)(4-(1-methyl-1H-benzo[d]imidazol-5-yl)phenyl)methanone Into a 50-mL round-bottom flask, was placed a solution of (R)-(4-(1-methyl-1H-benzo[d]imidazol-5-yl)phenyl)(3-methylpiperazin-1-yl)methanone hydrochloride (500 mg, 1.35 mmol, 1.00 equiv) in N,N-dimethylformamide (15 mL), 1-hydroxycyclopropane-1-carboxylic acid (137 mg, 1.34 mmol, 1.00 equiv), HBTU (766 mg, 2.02 mmol, 1.50 equiv), DIEA (695 mg, 5.38 mmol, 4.00 equiv). The resulting solution was stirred for overnight at room temperature. The reaction mixture was poured into 100 mL of water, extracted with 3×50 mL of dichloromethane. The organic layers were combined, dried over anhydrous sodium sulfate and concentrated under vacuum. The residue was purified by Prep-HPLC with the following conditions (IntelFlash-1): Column, Cis silica gel; mobile phase, CH$_3$CN/water with 0.05% NH$_4$HCO$_3$=20% increasing to CH$_3$CN/water with 0.05% NH$_4$HCO$_3$=60% within 30 min; Detector, UV 254&220 nm. This resulted in 200.3 mg (36%) of the title compound as a white solid. LC-MS (ES, m/z): 419 [M+H]

Method 24.

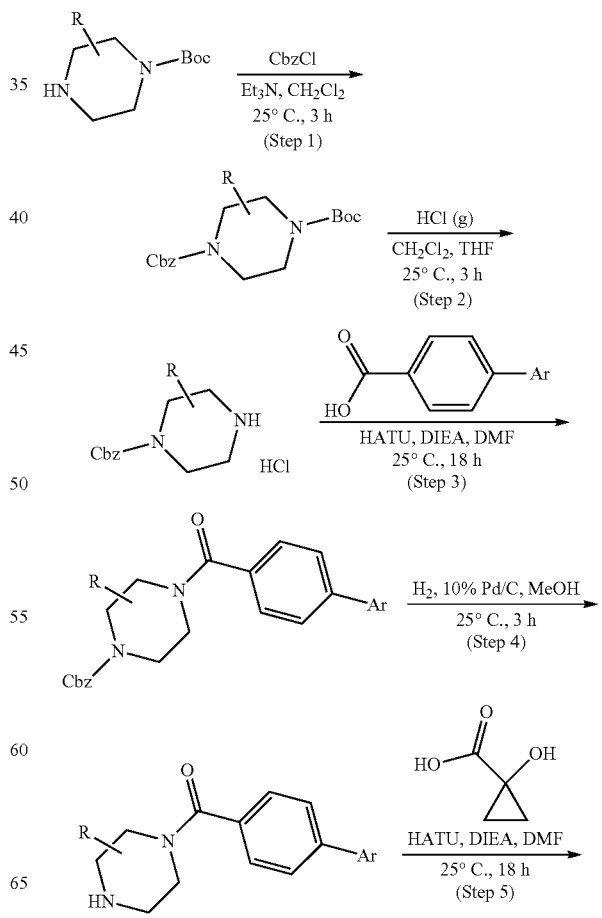

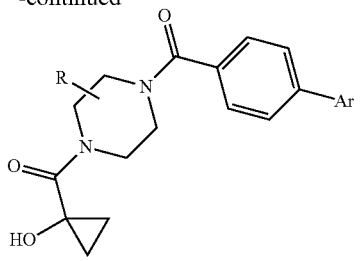

Step 1. 7-benzyl 4-(tert-butyl) 4,7-diazaspiro[2.5]octane-4,7-dicarboxylate

Into a 100-mL round-bottom flask, was placed a solution of tert-butyl 4, 7-diazaspiro[2.5]octane-4-carboxylate (3 g, 14.13 mmol, 1.00 equiv) and TEA (4.25 g, 42.00 mmol, 2.97 equiv) in dichloromethane (30 mL). This was followed by the addition of CbzCl (2.88 g, 16.88 mmol, 1.19 equiv) dropwise with stirring at 0° C. The resulting solution was stirred for 3 h at 25° C. The reaction mixture was diluted with 50 mL of water, extracted with 3×50 mL of dichloromethane. The organic layers were combined, washed with 2×100 mL of sodium carbonate solution (2M), dried over $Na_2SO_4$, and concentrated under vacuum. This resulted in 4 g (82%) of the title compound as yellow oil. LC-MS (ES, m/z) 347 [M+H]+

Step 2. benzyl 4,7-diazaspiro[2.5]octane-7-carboxylate hydrochloride

Into a 100-mL round-bottom flask, was placed a solution of 7-benzyl 4-tert-butyl 4, 7-diazaspiro[2.5]octane-4,7-dicarboxylate (4 g, 11.55 mmol, 1.00 equiv) in dichloromethane/tetrahydrofuran (20/20 mL). To the above solution, hydrogen chloride (gas) was introduced in. The resulting solution was stirred for 3 h at 25° C. The solids were collected by filtration. This resulted in 3 g (crude) of the title compound as a yellow oil. LC-MS (ES, m/z) 247 [M+H]+

Step 3. benzyl 4-(4-(6-fluorobenzo[d]oxazol-2-yl)benzoyl)-4,7-diazaspiro[2.5]octane-7-carboxylate Into a 100-mL round-bottom flask, was placed HATU (1.55 g, 4.08 mmol, 1.00 equiv), 4-(6-fluoro-1,3-benzoxazol-2-yl)benzoic acid (951 mg, 3.70 mmol, 0.91 equiv), benzyl 4,7-diazaspiro[2.5]octane-7-carboxylate hydrogen chloride salt (1 g, 4.06 mmol, 1.00 equiv), DIEA (955 mg, 7.39 mmol, 1.82 equiv) and N,N-dimethylformamide (30 mL). The resulting solution was stirred for 18 h at 25° C. The mixture was then diluted with 50 mL of EA, washed with 2×50 mL of water, dried over $Na_2SO_4$ and concentrated under vacuum. The residue was applied onto a silica gel column with ethyl acetate/petroleum ether (10%-90%). This resulted in 1.2 g (crude) of the title compound as yellow oil. LC-MS (ES, m/z): 486 [M+H]+

Step 4. (4-(6-fluorobenzo[d]oxazol-2-yl)phenyl)(4,7-diazaspiro[2.5]octan-4-yl)methanone Into a 100-mL round-bottom flask, was placed benzyl 4-[[4-(6-fluoro-1,3-benzoxazol-2-yl)phenyl]carbonyl]-4,7-diazaspiro[2.5]octane-7-carboxylate (Intermediate 2, 1.2 g, 2.47 mmol, 1.00 equiv), palladium on active carbon (1.2 g) and methanol (30 mL). Then the flask was evacuated and back-filled with hydrogen for three times. The resulting solution was stirred for 3 h at 25° C. The solids were filtered out. The filtrate was concentrated under vacuum. This resulted in 700 mg (crude) of the title compound as a light yellow solid. LC-MS (ES, m/z): 352 [M+H]+

Step 5. (4-(4-(6-fluorobenzo[d]oxazol-2-yl)benzoyl)-4,7-diazaspiro[2.5]octan-7-yl)(1-hydroxycyclopropyl)methanone Into a 100-mL round-bottom flask, was placed HATU (658 mg, 1.73 mmol, 1.00 equiv), 1-hydroxycyclopropane-1-carboxylic acid (160 mg, 1.57 mmol, 0.91 equiv), 2-[4-([4,7-diazaspiro[2.5]octan-4-yl]carbonyl)phenyl]-6-fluoro-1,3-benzoxazole (608 mg, 1.73 mmol, 1.00 equiv), DIEA (406 mg, 3.14 mmol, 1.82 equiv) and N,N-dimethylformamide (15 mL). The resulting solution was stirred for 18 h at 25° C. The resulting mixture was concentrated under vacuum. The residue was applied onto a silica gel column with ethyl acetate/petroleum ether (10%-90%). The crude product was purified by Prep-HPLC with the following conditions (Waters I): Column, Xbridge Prep C18 OBD column, 5 um, 19*150 mm; mobile phase, Water (0.05% $NH_4HCO_3$) and $CH_3CN$ (10% $CH_3CN$ up to 40% in 9 min); Detector, UV 220&254 nm. This resulted in 171.6 mg (23%) of the title compound as a white solid. LC-MS (ES, m/z): 436 [M+H]+

Method 25.

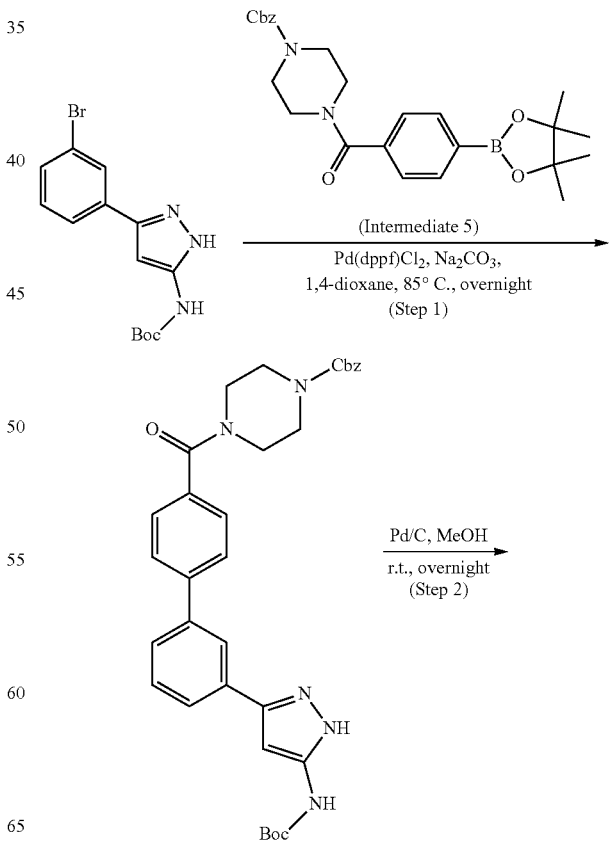

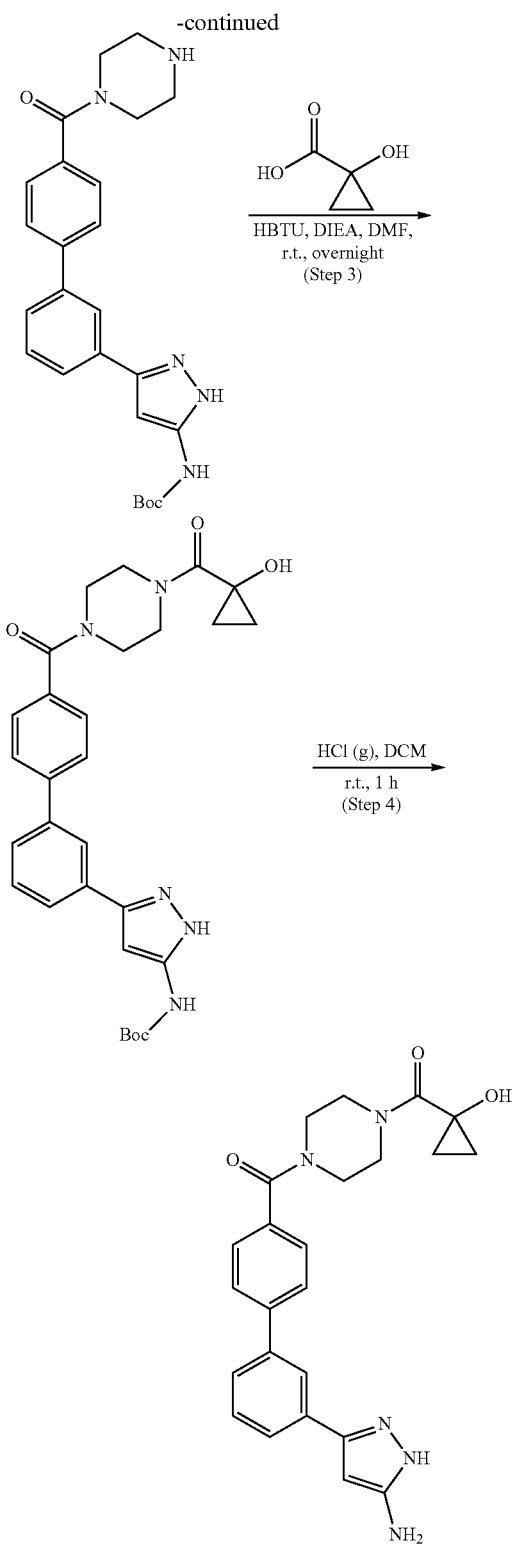

Step 1. benzyl 4-(3'-(5-((tert-butoxycarbonyl) amino)-1H-pyrazol-3-yl)-[1,1'-biphenyl]-4-carbonyl) piperazine-1-carboxylate Into a 100-mL round-bottom flask purged and maintained with an inert atmosphere of nitrogen, was placed a solution of benzyl 4-[[4-(tetramethyl-1,3,2-dioxaborolan-2-yl)phenyl]carbonyl]piperazine-1-carboxylate (Intermediate 5, 710 mg, 1.58 mmol, 1.00 equiv) in 1,4-dioxane (20 mL), tert-butyl N-[3-(3-bromophenyl)-1H-pyrazol-5-yl]carbamate (533.2 mg, 1.58 mmol, 1.00 equiv), Pd(dppf)Cl2 (115.5 mg, 0.16 mmol, 0.10 equiv), sodium carbonate (2M, 5 mL). The resulting mixture was stirred overnight at 85° C. After cooled to room temperature, the reaction mixture was diluted with 30 mL of water, extracted with 2×100 mL of ethyl acetate. The organic layers were combined, dried over anhydrous sodium sulfate and concentrated under vacuum. The residue was applied onto a silica gel column with ethyl acetate/petroleum ether (4/1). This resulted in 300 mg (33%) of the title compound as a yellow solid. LC-MS (ES, m/z): 582[M+H]$^+$ Step 2. tert-butyl (3-(4'-(piperazine-1-carbonyl)-[1, 1'-biphenyl]-3-yl)-1H-pyrazol-5-yl)carbamate Into a 50-mL round-bottom flask, was placed a solution of benzyl 4-(3'-(5-((tert-butoxycarbonyl)amino)-1H-pyrazol-3-yl)-[1,1'-biphenyl]-4-carbonyl)piperazine-1-carboxylate (670 mg, 1.15 mmol, 1.00 equiv) in methanol (20 mL). This was followed by the addition of Palladium carbon (670 mg). To the above hydrogen was introduced in. The resulting solution was stirred for 5 h at room temperature. The solids were filtered out. The filtrate was concentrated under vacuum. This resulted in 515.7 mg (100%) of the title compound as an orange solid. LC-MS (ES, m/z): 448[M+H]$^+$ Step 3. tert-butyl (3-(4'-(4-(1-hydroxycyclopropane-1-carbonyl)piperazine-1-carbonyl)-[1,1'-biphenyl]-3-yl)-1H-pyrazol-5-yl)carbamate Into a 250-mL round-bottom flask, was placed a solution of tert-butyl (3-(4'-(piperazine-1-carbonyl)-[1,1'-biphenyl]-3-yl)-1H-pyrazol-5-yl)carbamate (515.7 mg, 1.15 mmol, 1.00 equiv) in N,N-dimethylformamide (50 mL), 1-hydroxycyclopropane-1-carboxylic acid (117 mg, 1.15 mmol, 1.00 equiv), HBTU (654 mg, 1.72 mmol, 1.50 equiv), DIEA (445.5 mg, 3.45 mmol, 3.00 equiv). The resulting solution was stirred overnight at room temperature. The reaction mixture was then diluted with 50 mL of water, extracted with 2×150 mL of dichloromethane. The organic layers were combined, dried over anhydrous sodium sulfate and concentrated under vacuum. The residue was applied onto a silica gel column with ethyl acetate/petroleum ether (2/1). This resulted in 400 mg (65%) of the title compound as a brown solid. LC-MS (ES, m/z): 532[M+H]$^+$ Step 4. (4-(3'-(5-amino-1H-pyrazol-3-yl)-[1,1'-biphenyl]-4-carbonyl)piperazin-1-yl)(1-hydroxycyclopropyl)methanone Into a 100-mL round-bottom flask, was placed a solution of tert-butyl (3-(4'-(4-(1-hydroxycyclopropane-1-carbonyl)piperazine-1-carbonyl)-[1,1'-biphenyl]-3-yl)-1H-pyrazol-5-yl)carbamate (400 mg, 0.75 mmol, 1.00 equiv) in dichloromethane (30 mL). To the above HCl gas was introduced in. The resulting solution was stirred for 1 h at room temperature. The solids were collected by filtration and dissolved in 10 mL of water. The pH value was adjusted to 6-7 with saturated sodium bicarbonate solution. The solids were collected by filtration. The residue was purified by Flash-Prep-HPLC with the following conditions (IntelFlash-1): Column, Cis silica gel; mobile phase, CH$_3$CN/water with 0.1% NH$_4$HCO$_3$=1/5 increasing to CH$_3$CN/water with 0.1% NH$_4$HCO$_3$=3/2 within 20 min; Detector, UV 254&220 nm. This resulted in 102.9 mg (32%) of the title compound as a white solid. LC-MS (ES, m/z): 432[M+H]$^+$ Method 26.

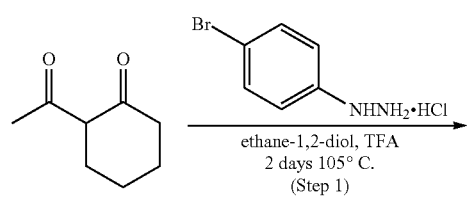

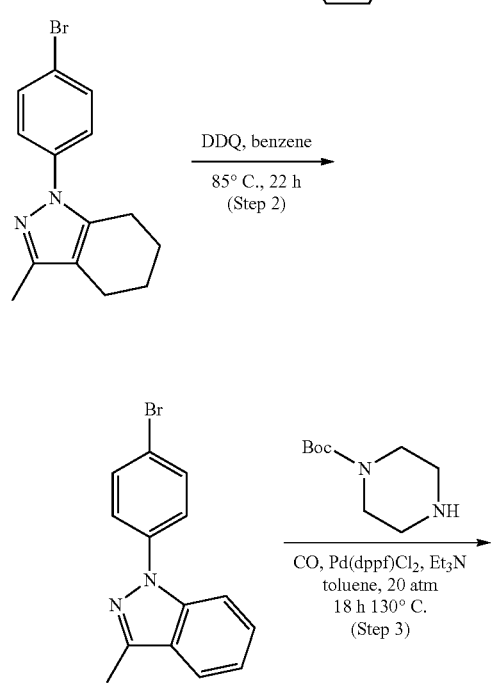

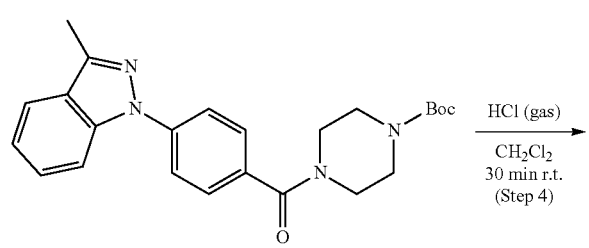

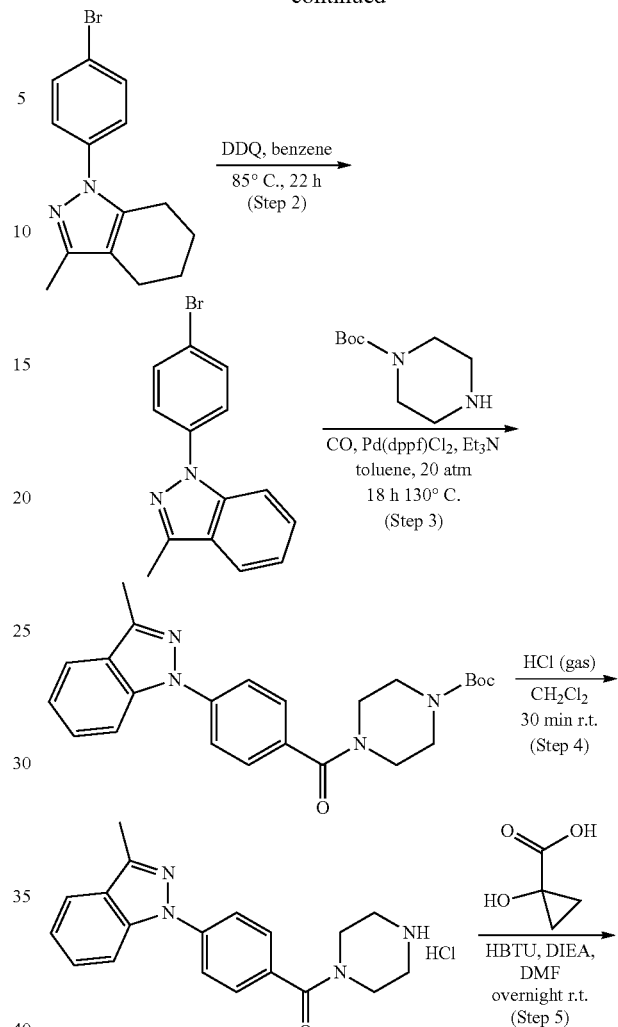

Step 1.
N-(4-bromophenyl)-3-methyl-4,5,6,7-tetrahydro-1 and 2H-indazole

Into a 250-mL round-bottom flask (1 atm) purged and maintained with an inert atmosphere of nitrogen, was placed 2-acetylcyclohexan-1-one (4.08 g, 29.11 mmol, 1.00 equiv), (4-bromophenyl)hydrazine hydrochloride (6.5 g, 29.08 mmol, 1.00 equiv), TsOH (500 mg, 2.90 mmol, 0.10 equiv), ethane-1,2-diol (100 mL). The resulting solution was stirred for 2 days at 105° C. in an oil bath. The resulting mixture was concentrated under vacuum. The crude product (4 g) was purified by Flash-Prep-HPLC with the following conditions (IntelFlash-1): Column, C18 silica gel; mobile phase, 0.05% NH$_4$HCO$_3$ solution, MeCN=95/5 increasing to 0.05% NH4HCO3 solution, MeCN=0/100 within 60 min; Detector, UV 254 nm. 1.5 g product was obtained. This resulted in 1.5 g (18%) of 2-(4-bromophenyl)-3-methyl-4,5,6,7-tetrahydro-2H-indazole as a light yellow solid and 0.8 g (9%) of 1-(4-bromophenyl)-3-methyl-4,5,6,7-tetrahydro-2H-indazole as a light yellow solid. LC-MS (ES, m/z): 292 [M+H]$^+$ Step 2. 1-(4-bromophenyl)-3-methyl-1H-indazole Into a 250-mL round-bottom flask purged and maintained with an inert atmosphere of nitrogen, was placed 1-(4-bromophenyl)-3-methyl-4,5,6,7-tetrahydro-1H-indazole (3.5 g, 12.02 mmol, 1.00 equiv), benzene (100 mL), DDQ (10.9 g, 48.02 mmol, 3.99 equiv). The resulting solution was stirred for 22 h at 85° C. in an oil bath. After cooled to room temperature, the resulting mixture was concentrated under vacuum and diluted with 200 mL of EA and washed with 1×250 mL of water and 3×100 mL of brine. The organic phase was dried over anhydrous sodium sulfate and concentrated under vacuum. The residue was applied onto a silica gel column with ethyl acetate/petroleum ether (0/100-10/90). This resulted in 800 mg (23%) of the title compound as a white solid. LC-MS (ES, m/z) 287,289 [M+H]$^+$ Step 3. tert-butyl 4-(4-(3-methyl-1H-indazol-1-yl)benzoyl)piperazine-1-carboxylate Into a 250-mL pressure tank, was placed 1-(4-bromophenyl)-3-methyl-1H-indazole (800 mg, 2.79 mmol, 1.00 equiv), tert-butyl piperazine-1-carboxylate (770 mg, 4.13 mmol, 1.48 equiv), Pd(dppf)Cl$_2$.CH$_2$Cl$_2$ (113 mg, 0.14 mmol, 0.05 equiv), toluene (120 mL), triethylamine (837 mg, 8.27 mmol, 2.97 equiv). Then the reactor was evacuated and back-filled with CO for three times. The resulting mixture was stirred for 24 h at 130° C. under CO pressure of 20 atm. After cooled to room temperature, the resulting mixture was concentrated under vacuum. The residue was applied onto a silica gel column with ethyl acetate/petroleum ether (0/100~25/75). This resulted in 1.0 g (85%) of the title compound as a light yellow solid. LC-MS (ES, m/z) 421 [M+H]$^+$ Step 4. (4-(3-methyl-1H-indazol-1-yl)phenyl)(piperazin-1-yl)methanone hydrochloride Into a 250-mL round-bottom flask, was placed tert-butyl 4-(4-(3-methyl-1H-indazol-1-yl)benzoyl)piperazine-1-carboxylate (1 g, 2.38 mmol, 1.00 equiv), dichloromethane (100 mL). Then hydrogen chloride (gas) was introduced in. The resulting solution was stirred for 2 h at room temperature. The solids were collected by filtration. This resulted in 930 mg (crude) of the title compound as a light yellow solid. LC-MS (ES, m/z) 321 [M+H]$^+$ Step 5. (4-(1-hydroxycyclopropane-1-carbonyl)piperazin-1-yl)(4-(3-methyl-1H-indazol-1-yl)phenyl)methanone Into a 100-mL round-bottom flask, was placed 1-hydroxycyclopropane-1-carboxylic acid (265 mg, 2.60 mmol, 1.00 equiv), HBTU (1.086 g, 2.86 mmol, 1.10 equiv), N,N-dimethylformamide (20 mL), (4-(3-methyl-H-indazol-1-yl)phenyl)(piperazin-1-yl)methanone hydrochloride (930 mg, 2.61 mmol, 1.00 equiv), DIEA (1.68 g, 13.00 mmol, 5.01 equiv). The resulting solution was stirred overnight at room temperature. The resulting solution was diluted with 100 mL of EA, washed with 3×20 mL of water and 1×20 mL of brine. The organic phase was dried over anhydrous sodium sulfate and concentrate under vacuum. The residue was applied onto a silica gel column with ethyl acetate/petroleum ether (0/100~100/0). The collected fractions were combined and concentrated under vacuum. The resulting solid was stirred in 2×20 mL of MeCN, collected by filtration and dried under reduced pressure. This resulted in 228.5 mg (22%) of the title compound as an off-white solid. LC-MS (ES, m/z) 405 [M+H]$^+$ Method 27.

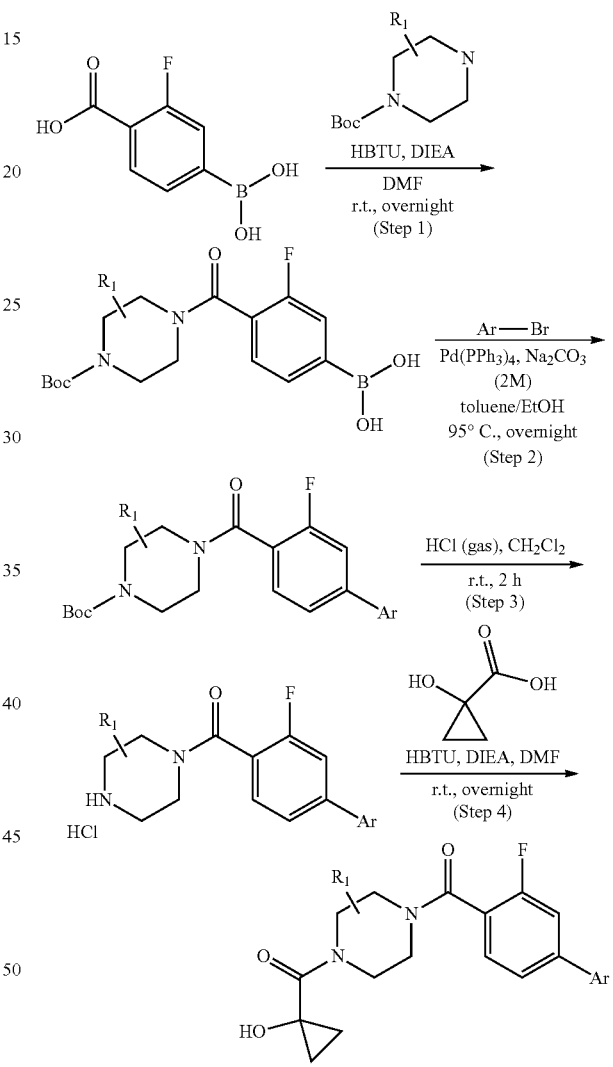

Step 1. (S)-(4-(4-(tert-butoxycarbonyl)-3-methylpiperazine-1-carbonyl)-3-fluorophenyl)boronic acid Into a 250 mL round-bottom flask was placed a solution of 4-(dihydroxyboranyl)-2-fluorobenzoic acid (1.84 g, 10.00 mmol, 1.00 equiv) in DMF (30 mL). HBTU (15.16 g, 39.97 mmol, 4.00 equiv) was added followed by DIEA (1.94 g, 15.01 mmol, 1.50 equiv). The resulting solution was stirred for 10 min. at RT, then a solution of tert-butyl (2R)-2-methylpiperazine-1-carboxylate (2 g, 9.99 mmol, 1.00 equiv) in DMF (5 mL) was added. The resulting solution was allowed to stir overnight. The solution was then diluted with EtOAc (50 mL) and washed with brine (3×50 mL). The organic layer was then dried over sodium sulfate, filtered and concentrated in vacuo. The residue was purified by FCC eluting with dichloromethane/methanol (90:10). This afforded the title compound (3.5 g, 96%) as a brown solid. LC-MS (ES, m/z) 367 [M+H]$^+$ Step 2. tert-butyl (S)-4-(2-fluoro-4-(1-methyl-1H-benzo[d]imidazol-5-yl)benzoyl)-2-methylpiperazine-1-carboxylate Into a 100-mL round-bottom flask purged and maintained with an inert atmosphere of nitrogen, was placed a solution of (S)-(4-(4-(tert-butoxycarbonyl)-3-methylpiperazine-1-carbonyl)-3-fluorophenyl)boronic acid (837 mg, 2.29 mmol, 1.00 equiv) in toluene (20 mL), 5-bromo-1-methyl-1H-1,3-benzodiazole (400 mg, 1.90 mmol, 0.83 equiv), Pd(PPh$_3$)$_4$ (264 mg, 0.23 mmol, 0.10 equiv), sodium carbonate (2M, 10 mL), ethanol (2.8 mL). The resulting mixture was stirred overnight at 95° C. After cooled to room temperature, the resulting solution was diluted with 20 mL of H$_2$O, extracted with 3×30 mL of ethyl acetate. The organic layers were combined, dried over anhydrous sodium sulfate and concentrated under vacuum. The residue was applied onto a silica gel column with dichloromethane/methanol (90:10). The collected fractions were combined and concentrated under vacuum. This resulted in 800 mg (77%) of the title compound as a brown solid. LC-MS (ES, m/z) 453 [M+H]$^+$ Step 3. (S)-(2-fluoro-4-(1-methyl-1H-benzo[d]imidazol-5-yl)phenyl)(3-methylpiperazin-1-yl)methanone hydrochloride Into a 100-mL round-bottom flask, was placed a solution of tert-butyl (S)-4-(2-fluoro-4-(1-methyl-1H-benzo[d]imidazol-5-yl)benzoyl)-2-methylpiperazine-1-carboxylate (800 mg, 1.77 mmol, 1.00 equiv) in dichloromethane (30 mL). To the above HCl (gas) was introduced in. The resulting solution was stirred for 2 h at room temperature. The solids were collected by filtration. This resulted in 650 mg (95%) of the title compound as a brown solid. LC-MS (ES, m/z) 353 [M+H]$^+$ Step 4. (S)-(4-(2-fluoro-4-(1-methyl-1H-benzo[d]imidazol-5-yl)benzoyl)-2-methylpiperazin-1-yl)(1-hydroxycyclopropyl)methanone Into a 100-mL round-bottom flask, was placed a solution of (S)-(2-fluoro-4-(1-methyl-1H-benzo[d]imidazol-5-yl)phenyl)(3-methylpiperazin-1-yl)methanone hydrochloride (650 mg, 1.67 mmol, 1.00 equiv) in N,N-dimethylformamide (20 mL), 1-hydroxycyclopropane-1-carboxylic acid (180 mg, 1.76 mmol, 1.05 equiv), HBTU (734 mg, 1.94 mmol, 1.16 equiv), DIEA (908 mg, 7.03 mmol, 4.20 equiv). The resulting solution was stirred overnight at room temperature. The reaction mixture was diluted with 30 mL of EA, washed with 3×30 mL of water and 30 mL of brine. The organic phase was dried over anhydrous sodium sulfate and concentrated under vacuum. The residue was applied onto a silica gel column with dichloromethane/methanol (90:10). The crude product was further purified by Prep-HPLC with the following conditions (Waters III): Column, Xbridge RP18 5 um, 19*150; mobile phase, water (0.05% NH$_4$HCO$_3$) and MeCN (10% CH$_3$CN up to 70% in 9 min);

Detector, UV 220&254 nm. This resulted in 203.1 mg (28%) of the title compound as a white solid. LC-MS (ES, m/z) 437 [M+H]$^+$ Method 28.

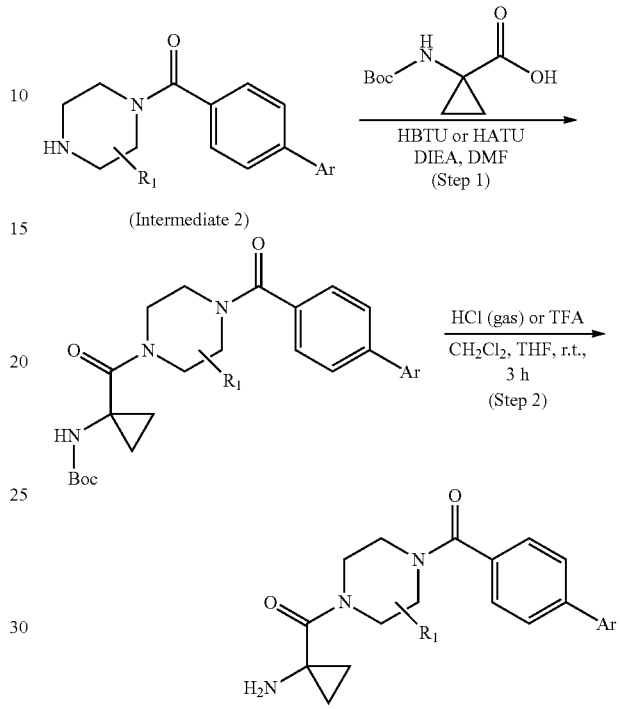

Step 1. tert-butyl (S)-(1-(4-(4-(6-fluorobenzo[d]oxazol-2-yl)benzoyl)-2-methylpiperazine-1-carbonyl)cyclopropyl)carbamate Into a 100-mL round-bottom flask, was placed 1-[(tert-butoxy)carbonyl]aminocyclopropane-1-carboxylic acid (Intermediate 2, 400 mg, 1.99 mmol, 0.90 equiv), HBTU (830 mg, 2.19 mmol, 1.0 equiv), N,N-dimethylformide (30 mL), (S)-(4-(6-fluorobenzo[d]oxazol-2-yl)phenyl)(3-methylpiperazin-1-yl)methanone hydrochloride (750 mg, 2.21 mmol, 1.00 equiv) and DIEA (514 mg, 3.98 mmol, 1.80 equiv). The resulting solution was stirred for 18 h at 25° C. The resulting solution was diluted with 50 mL of EA and washed with 2×50 mL of water. The organic layer dried over Na$_2$SO$_4$ and concentrated under vacuum. This resulted in 800 mg (crude) of the title compound as a yellow solid. LC-MS (ES, m/z): 523 [M+H]$^+$ Step 2. (S)-(4-(1-aminocyclopropane-1-carbonyl)-3-methylpiperazin-1-yl)(4-(6-fluorobenzo[d]oxazol-2-yl)phenyl)methanone Into a 100-mL round-bottom flask, was placed tert-butyl (S)-(1-(4-(4-(6-fluorobenzo[d]oxazol-2-yl)benzoyl)-2-methylpiperazine-1-carbonyl)cyclopropyl)carbamate (800 mg, 1.53 mmol, 1.00 equiv), dichloromethane (20 mL), tetrahydrofuran (20 mL). Then hydrogen chloride (gas) was bubbled into the mixture. The resulting solution was stirred for 3 h at 25° C. The resulting mixture was concentrated under vacuum and dissolved in 10 mL of water. The pH value of the solution was adjusted to 8 with saturated sodium carbonate solution. The solids were collected by filtration.

The crude product was purified by Prep-HPLC with the following conditions (Waters I): Column, Xbridge Prep C18 OBD column, 5 um, 19*150 mm; mobile phase, Water (0.05% NH₄HCO₃) and CH₃CN (7% CH₃CN up to 35% in 10 min); Detector, UV 220&254 nm. This resulted in 163.6 mg (25%) of the title compound as a white solid. LC-MS (ES, m/z): 423 [M+H]⁺

Method 29.

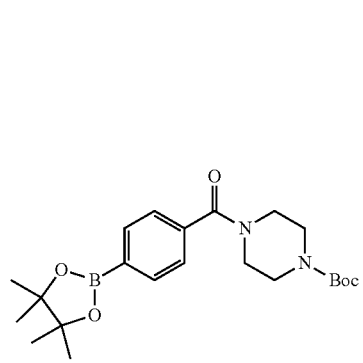

(Intermediate 3)

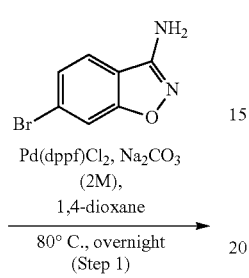

Pd(dppf)Cl₂, Na₂CO₃ (2M), 1,4-dioxane
80° C., overnight
(Step 1)

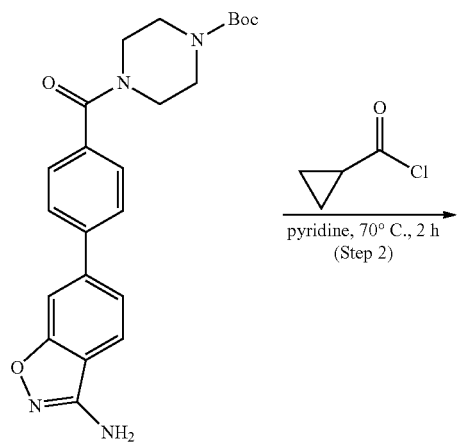

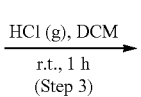

pyridine, 70° C., 2 h
(Step 2)

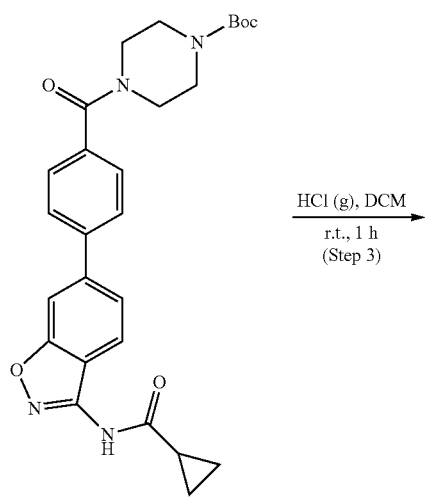

HCl (g), DCM
r.t., 1 h
(Step 3)

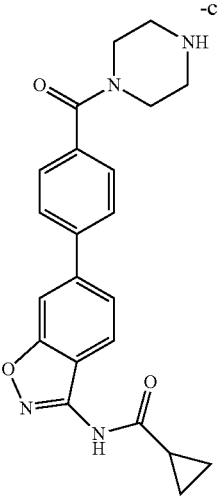

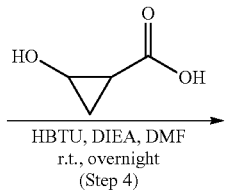

HBTU, DIEA, DMF
r.t., overnight
(Step 4)

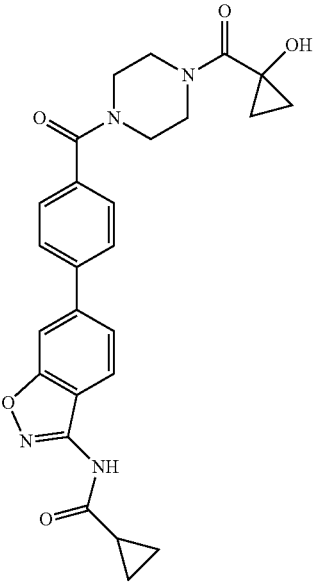

Step 1. tert-butyl 4-(4-(3-aminobenzo[d]isoxazol-6-yl)benzoyl)piperazine-1-carboxylate Into a 250-mL round-bottom flask purged and maintained with an inert atmosphere of nitrogen, was placed a solution of tert-butyl 4-[[4-(tetramethyl-1,3,2-dioxaborolan-2-yl)phenyl]carbonyl]piperazine-1-carboxylate (Intermediate 3, 1.9 g, 4.56 mmol, 1.00 equiv) in dioxane (100 mL), 6-bromo-1,2-benzoxazol-3-amine (1 g, 4.69 mmol, 1.00 equiv), Pd(dppf)Cl₂ (344 mg, 0.47 mmol, 0.10 equiv), sodium carbonate (20 mL, 2M). The resulting solution was stirred overnight at 80° C. After cooled to room temperature, the resulting mixture was diluted with DCM, washed with water and concentrated under vacuum. The residue was applied onto a silica gel column with dichloromethane/methanol (10/1). This resulted in 1.6 g (83%) of the title compound as a gray solid. LC-MS (ES, m/z) 423 [M+H]⁺

Step 2. tert-butyl 4-(4-(3-(cyclopropanecarboxamido)benzo[d]isoxazol-6-yl)benzoyl)piperazine-1-carboxylate Into a 100 mL round-bottom flask, was placed a solution of tert-butyl 4-[[4-(3-amino-1,2-benzoxazol-6-yl)phenyl]

carbonyl]piperazine-1-carboxylate (800 mg, 1.89 mmol, 1.00 equiv) in pyridine (20 mL), cyclopropanecarbonyl chloride (199 mg, 1.90 mmol, 1.00 equiv). The resulting solution was stirred for 2 h at 70° C. After cooled to room temperature, the reaction mixture was diluted with EtOAc, washed with water and concentrated under vacuum. The residue was applied onto a silica gel column with ethyl acetate/petroleum ether (1/1). This resulted in 535 mg (58%) of the title compound as a white solid. LC-MS (ES, m/z): 491[M+H]$^+$ Step 3. N-(6-(4-(piperazine-1-carbonyl)phenyl)benzo[d]isoxazol-3-yl)cyclopropanecarboxamide hydrochloride Into a 100-mL round-bottom flask, was placed a solution of tert-butyl 4-[[4-(3-cyclopropaneamido-1,2-benzoxazol-6-yl)phenyl]carbonyl]piperazine-1-carboxylate (535 mg, 1.09 mmol, 1.00 equiv) in dichloromethane (30 mL). To the above hydrogen chloride (g) was introduced in. The resulting solution was stirred for 1 h at room temperature. The resulting mixture was concentrated under vacuum. This resulted in 466 mg (quantitative) of the title compound as a white solid. LC-MS (ES, m/z): 391[M+H]$^+$ Step 4. N-(6-(4-(4-(1-hydroxycyclopropane-1-carbonyl)piperazine-1-carbonyl)phenyl)benzo[d]isoxazol-3-yl)cyclopropanecarboxamide Into a 50-mL round-bottom flask, was placed a solution of 1-hydroxycyclopropane-1-carboxylic acid (111 mg, 1.09 mmol, 1.00 equiv) in N,N-dimethylformamide (20 mL), HBTU (620 mg, 1.63 mmol, 1.50 equiv), DIEA (563 mg, 4.36 mmol, 4.00 equiv). The above mixture was stirred for 1 h at room temperature. To this was added N-(6-[4-[(piperazin-1-yl)carbonyl]phenyl]-1,2-benzoxazol-3-yl)cyclopropanecarboxamide hydrochloride (466 mg, 1.09 mmol, 1.00 equiv). The resulting mixture was stirred overnight at room temperature. The reaction mixture was diluted with DCM, washed with water and concentrated under vacuum. The residue was applied onto a silica gel column with dichloromethane/methanol (10/1), and further purified by Prep-HPLC with the following conditions (IntelFlash-1): Column, Cis silica gel; mobile phase, CH$_3$CN/water with 0.05% NH$_4$HCO$_3$=40% increasing to CH$_3$CN/water with 0.05% NH$_4$HCO$_3$=60% within 15 min; Detector, UV 254&220 nm. This resulted in 123.9 mg (24%) of the title compound as a white solid. LC-MS (ES, m/z): 475[M+H]$^+$ Method 30.

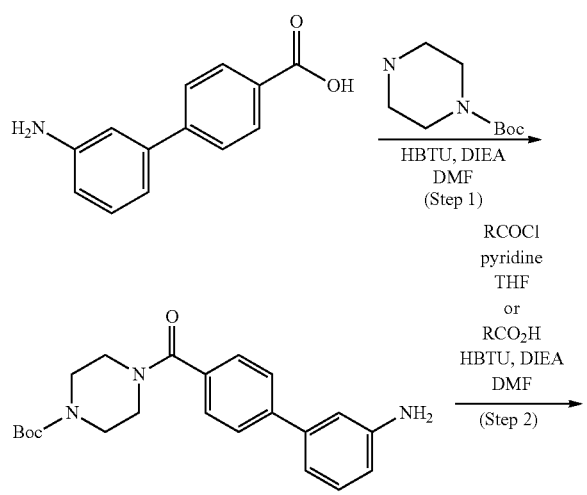

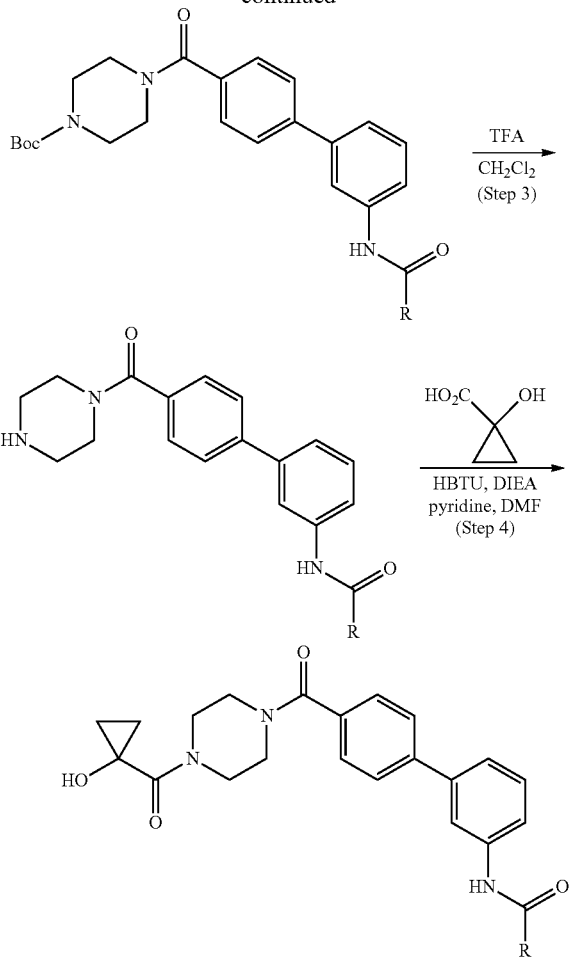

Step 1. tert-butyl 4-(3'-amino-[1,1'-biphenyl]-4-carbonyl)piperazine-1-carboxylate To a 100 mL flask was added tert-butyl piperazine-1-carboxylate (1.310 g, 7.03 mmol), 3'-aminobiphenyl-4-carboxylic acid (1.5 g, 7.03 mmol) and DIEA (2.457 ml, 14.07 mmol) in DMF (25 ml) followed by HBTU (3.20 g, 8.44 mmol) to give a brown suspension. This was stirred at RT for 8 hrs. Water (50 mL) was added and the reaction was extracted twice with methylene chloride (2×100 mL). The organic layers were combined and washed with water (25 mL) and brine (25 mL). The organic layer was then dried over magnesium sulfate, filtered and concentrated in vacuo. The crude residue was purified by FCC (04% MeOH/CH$_2$Cl$_2$) affording the title compound (1.70 g, 63%) as a yellow solid. LC-MS (ES, m/z): 382[M+H]$^+$ Step 2 (RCOCl). tert-butyl 4-(3'-(cyclopentanecarboxamido)-[1,1'-biphenyl]-4-carbonyl)piperazine-1-carboxylate In a 20 mL scintillation vial was added tert-butyl 4-(3'-aminobiphenylcarbonyl)piperazine-1-carboxylate (150 mg, 0.393 mmol), pyridine (0.095 ml, 1.180 mmol), and cyclopentanecarbonyl chloride (0.057 ml, 0.472 mmol) in THF (9 ml) to give an light yellow suspension. This was stirred at RT for 2 hours. The reaction was taken up in 75 mls of methylene chloride. The organic solution was washed twice with dilute sodium bicarbonate solution (aq, 35 mL) and once with brine (15 mL). The organic layer was then dried over magnesium sulfate, filtered and concentrated in vacuo. The crude product was purified by FCC (0-60% EtOAc/ hexanes) affording the title compound (116 mg, 62%). LC-MS (ES, m/z): 478[M+H]$^+$ Step 2 (RCO$_2$H). tert-Butyl 4-(3'-(3,3-difluorocy-clobutanecarboxamido)biphenylcarbonyl)piperazine-1-carboxylate In a 20 mL scintillation vial was added tert-butyl 4-(3'-aminobiphenylcarbonyl)piperazine-1-carboxylate (200 mg, 0.524 mmol), 3,3-difluorocyclobutanecarboxylic acid (86 mg, 0.629 mmol) and Hunig's Base (0.275 ml, 1.573 mmol) in DMF (5 ml) followed by HBTU (239 mg, 0.629 mmol) to give a brown suspension. This was stirred at RT overnight and then the reaction was diluted with water (20 mL). The reaction mixture was then extracted with methylene chloride (2×40 mL). The combined organic layers were washed with water (20 mL) and brine (20 mL). The organic layer was dried over magnesium sulfate, filtered and concentrated in vacuo. The crude product was purified by FCC (0-60% EtOAc/hexanes) affording the title compound as a foamy glass. LC-MS (ES, m/z): 500[M+H]$^+$ Step 3. N-(4'-(piperazine-1-carbonyl)-[1,1'-biphenyl]-3-yl)cyclopentanecarboxamide 2,2,2-trifluoro-acetate In a 100 mL round-bottomed flask was added tert-butyl 4-(3'-(cyclopentanecarboxamido)biphenylcarbonyl)piperazine-1-carboxylate (114 mg, 0.239 mmol) in methylene chloride (15 ml) to give a yellow suspension. Trifluoroacetic acid (0.552 mls, 7.16 mmol) was added gradually by syringe. The solution was stirred at RT for 2.5 hours. The solution was concentrate and the crude product was triturated with ether and then decanted. The resulting solid was dried in vacuo affording the title compound (117 mg, 100%) as a foamy solid. LC-MS (ES, m/z): 378[M+H]$^+$ Step 4. N-(4'-(4-(1-hydroxycyclopropane-1-carbonyl)piperazine-1-carbonyl)-[1,1'-biphenyl]-3-yl)cyclopentanecarboxamide In a 100 mL round-bottomed flask was added N-(4'-(piperazine-1-carbonyl)biphenyl-3-yl)cyclopentanecarboxamide 2,2,2-trifluoroacetate (118 mg, 0.24 mmol), 1-hydroxycyclopropanecarboxylic acid (19.60 mg, 0.192 mmol) and pyridine (0.058 ml, 0.720 mmol) in DMF (5 ml) followed by HBTU (127 mg, 0.336 mmol) to give a yellow suspension. This was stirred at RT for 4.5 hours. Hunig's base was added (0.021 mL, 0.12 mmols) and the stirring was continued. After 18 hours additional Hunig's base (0.063 mL, 0.36 mmols) was added and the reaction solution was stirred overnight. The reaction was diluted with water (20 mL) and extracted with methylene chloride (2×50 mL). The organic layers were combined and washed with water (10 mL) and brine (10 mL). The solvent was dried over magnesium sulfate, filtered and concentrated in vacuo. The crude product was purified by FCC (0-7% MeOH/CH$_2$Cl$_2$) affording the title compound (35.5 mg, 29%) as an off-white solid. LC-MS (ES, m/z): 462[M+H]$^+$ Method 31.

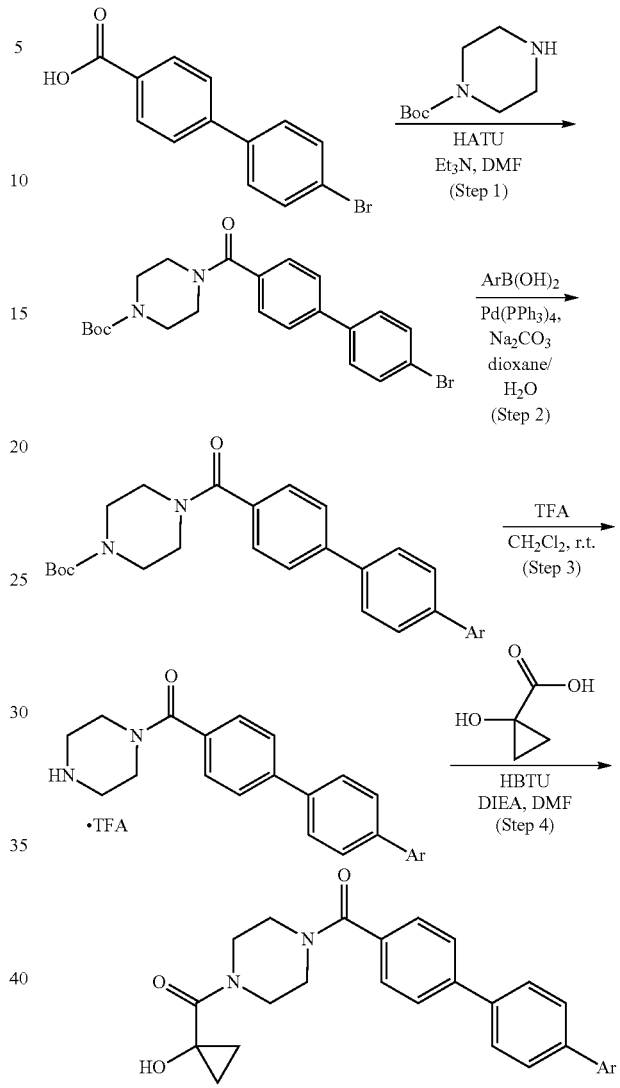

Step 1. tert-Butyl 4-(4'-bromo-[1,1'-biphenyl]-4-carbonyl)piperazine-1-carboxylate To a suspension of 4'-bromo-[1,1'-biphenyl]-4-carboxylic acid (1.5 g, 5.4 mmol) in DMF (35 mL) was added TEA (1.21 mL, 8.6 mmol), followed by tert-butyl piperazine-1-carboxylate (1.11 g, 6.0 mmol) and HATU (2.6 g, 6.8 mmol). The reaction mixture was stirred at room temperature overnight then diluted with water and extracted with EtOAc. Organic phase was washed with water, 5% acetic acid, saturated NaHCO$_3$, brine, dried over Na$_2$SO$_4$ and concentrated under reduced pressure. The crude material was chromatographed on a silica gel column eluting with a gradient of EtOAc in CH$_2$Cl$_2$ to afford 2.0 g (83% yield) of the title compound.

Step 2. tert-Butyl 4-(4'-(1H-pyrazol-4-yl)-[1,1'-biphenyl]-4-carbonyl)piperazine-1-carboxylate tert-Butyl 4-(4'-bromo-[1,1'-biphenyl]-4-carbonyl)piperazine-1-carboxylate (1.0 g, 2.3 mmol), (1H-pyrazol-4-yl) boronic acid (as HCl salt, 0.67 g, 4.5 mmol) and 2M K$_3$PO$_4$ (aq) (4.5 mL, 9.0 mmol) were mixed with 30 mL of DMF in a microwave tube. The resulting mixture was vacuumed several times and refilled with argon before adding Pd(PPh$_3$)$_4$ (0.39 g, 0.3 mmol). The reaction mixture was microwaved for 35 min at 150° C. After cooling to room temperature, the reaction mixture was diluted with water and saturated NaHCO$_3$ and extracted with MeOH/CHCl$_3$ mixture of solvents. Organic phase was dried over Na$_2$SO$_4$ and concentrated under reduced pressure. The crude was purified twice by ISCO (24 g silica gel column) eluting with a gradient of 0.7 N NH$_3$/MeOH in CHCl$_3$ to afford 160 mg (17% yield) of the desired product.

Step 3. (4'-(1H-pyrazol-4-yl)-[1,1'-biphenyl]-4-yl)(piperazin-1-yl)methanone, HCl salt tert-Butyl 4-(4'-(1H-pyrazol-4-yl)-[1,1'-biphenyl]-4-carbonyl)piperazine-1-carboxylate (160 mg, 0.37 mmol) was dissolved in 18 mL of anhydrous MeOH saturated with HCl (gas) at 0° C. and was stirred at room temperature for 3 h. The resulting solution was concentrated to dryness under reduced pressure. The residue was triturated with 2% MeOH in Et$_2$O followed by Et$_2$O and pentane to afford 150 mg (quant. yield) of the title compound as the hydrochloride salt which was used in the next step without further purification.

Step 4. (4-(4'-(1H-pyrazol-4-yl)-[1,1'-biphenyl]-4-carbonyl)piperazin-1-yl)(1-hydroxycyclopropyl)methanone To a solution of (4'-(1H-pyrazol-4-yl)-[1,1'-biphenyl]-4-yl)(piperazin-1-yl)methanone, HCl salt (150 mg, 0.37 mol) and 1-hydroxycyclopropane-1-carboxylic acid (69 mg, 0.56 mmol) in 3 mL of DMF was added HBTU (230 mg, 0.6 mmol), followed by addition of DIEA (0.33 mL, 1.8 mmol). The resulting solution was stirred overnight at room temperature. The the reaction mixture was diluted with water and saturated NaHCO$_3$ and extracted several times with with EtOAc/MeOH and MeOH/CHCl$_3$ mixture of solvents. The organic layers were combined, washed with water, brine, dried over Na$_2$SO$_4$ and concentrated under reduced pressure. The crude was purified by ISCO twice (24 g silica gel gold column) eluting with a gradient of 0.7 N NH$_3$/MeOH in EtOAc and 0.7 N NH$_3$/MeOH in CHCl$_3$. The product obtained after chromatography was triturated in Et$_2$O to afford 110 mg (71% yield) of the pure target compound. LC-MS (ES, m/z): 417[M+H]$^+$ Method 32.

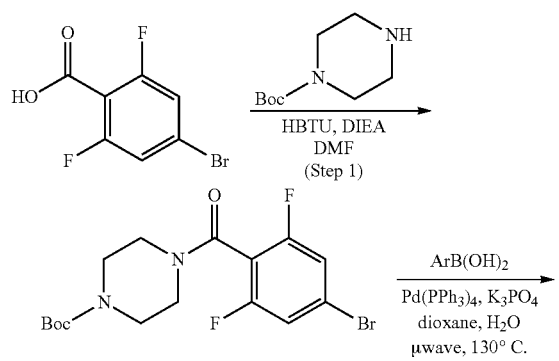

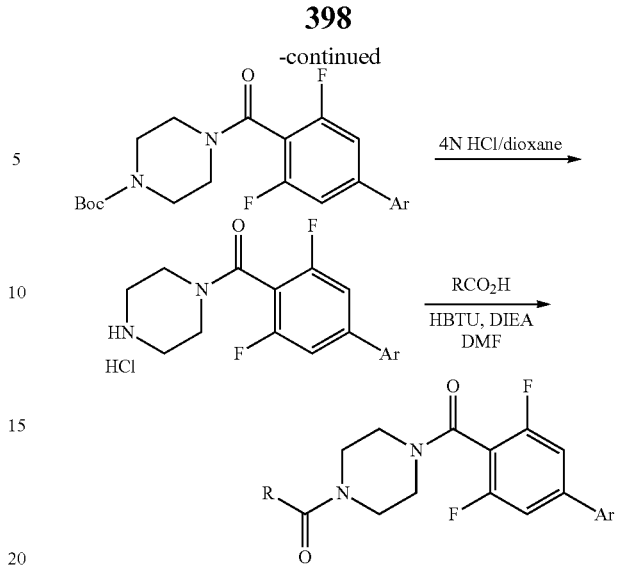

Step 1. tert-Butyl 4-(4-bromo-2,6-difluorobenzoyl)piperazine-1-carboxylate

To a solution of 4-bromo-2,6-difluorobenzoic acid (1.00 g, 4.22 mmol), tert-butyl piperazine-1-carboxylate (0.786 g, 4.22 mmol), and HBTU (1.925 g, 5.06 mmol) in DMF (10.0 ml) was added DIEA (2.95 ml, 16.88 mmol). The reaction was stirred at room temperature overnight. Saturated sodium bicarbonate (aqueous, 10 mL) was added followed by water (10 mL). The reaction solution was then extracted several times with EtOAc (3×20 mL). The organic extracts were pooled and washed with water (2×20 mL) and brine (20 mL). The organic layer was dried over sodium sulfate, filtered and concentrated in vacuo providing the crude product as an orange oil. The crude product was subjected to FCC (Biotage SNAP 25; eluent: 15%-25% EtOAc in hexanes over 10 CV). This afforded the title compound (1.44 g, 86%) as an off-white solid. LC-MS (ES, m/z): 405[M+H]$^+$ Step 2. tert-Butyl 4-(2,6-difluoro-4-(1-methyl-1H-indazol-6-yl)benzoyl)piperazine-1-carboxylate tert-Butyl 4-(4-bromo-2,6-difluorobenzoyl)piperazine-1-carboxylate (383.2 mg, 0.946 mmol), 1-methyl-1H-indazol-6-ylboronic acid (166 mg, 0.946 mmol) and potassium phosphate (1.00 g, 4.73 mmol) were suspended in a nitrogen purged solution of Dioxane (6.0 ml) and Water (1.2 ml). The reaction mixture was further purged with nitrogen for 5 minutes. Palladium Tetrakis (109 mg, 0.095 mmol) was added and the reaction solution was purged with nitrogen for 5 more minutes. The mixture was subjected to microwave irradiation at 130° C. for 30 minutes resulting in a yellow biphasic solution. The organic layer (top) was removed, filtered through celite and concentrated in vacuo to afford the crude product as a light red powder. The crude product was subjected to FCC (Biotage SNAP 25; Gradient Eluent: 0-20% MeOH in in EtOAc with 0.5% triethylamine over 15 CV). This afforded the title compound (327 mg, 76%) as a light beige powder. LC-MS (ES, m/z): 421[M+H]$^+$ Step 3. (2,6-difluoro-4-(1-methyl-1H-indazol-6-yl)phenyl)(piperazin-1-yl)methanone hydrochloride HCl (4N in 1,4-dioxane) (0.106 ml, 3.51 mmol) was added to a solution of tert-butyl 4-(2,6-difluoro-4-(1-methyl- 1H-indazol-6-yl)benzoyl)piperazine-1-carboxylate (320.0 mg, 0.701 mmol) in Dioxane (4.0 ml). The reaction solution was stirred at room temperature for 2 hours resulting in the formation of a white precipitate. Ether (10 mL) was added to the reaction and the precipitate was then collected by filtration. The precipitate was further washed with ether (10 mL), collected and dried in vacuo affording the title compound (275 mg, 100%) as a white powder. LC-MS (ES, m/z): 356[M+H]$^+$ Step 4. (4-(2,6-difluoro-4-(1-methyl-1H-indazol-6-yl)benzoyl)piperazin-1-yl)(1-hydroxycyclopropyl)methanone To a solution of (2,6-difluoro-4-(1-methyl-H-indazol-6-yl)phenyl)(piperazin-1-yl)methanone hydrochloride (218.3 mg, 0.556 mmol), 1-hydroxycyclopropanecarboxylic acid (56.7 mg, 0.556 mmol), and HBTU (254 mg, 0.667 mmol) in DMF (4.0 ml) was added DIEA (0.388 ml, 2.223 mmol). The reaction was stirred at room temperature overnight. Saturated sodium bicarbonate (aqueous, 10 mL) was added followed by water (10 mL). The reaction solution was then extracted several times with EtOAc (3×20 mL). The organic extracts were pooled and washed with water (2×20 mL) and brine (20 mL). The organic layer was dried over sodium sulfate, filtered and concentrated in vacuo providing the crude product as an orange oil. The crude product was subjected to FCC (Biotage SNAP 25; eluent: 20-10% hexanes in EtOAc over 10 CV). The product was then subjected to an additional purification via FCC (Biotage SNAP 25; gradient eluent: 5-15% MeOH in methylene chloride). This afforded the title compound (105.2 mg, 43%) as a white powder. LC-MS (ES, m/z): 441[M+H]$^+$
Method 33.

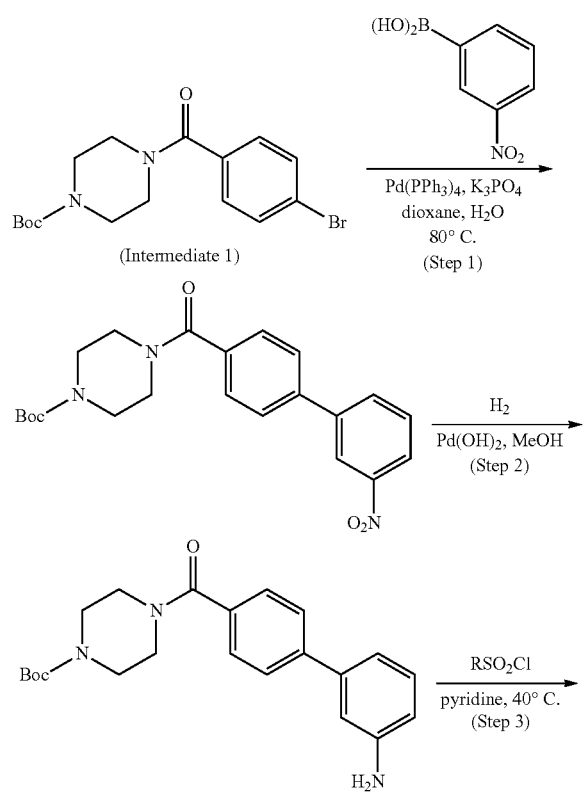

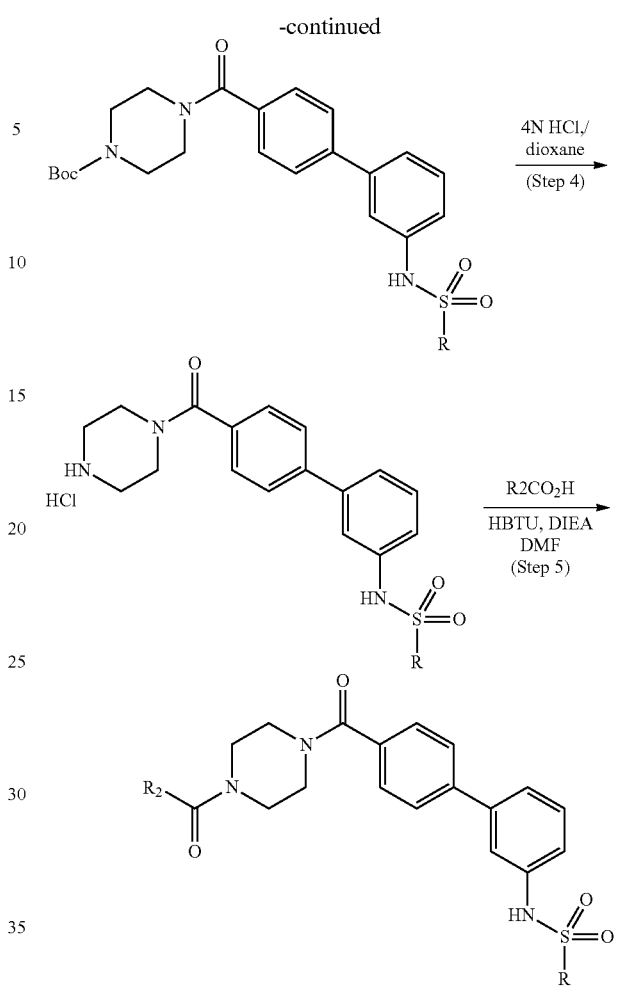

Step 1. tert-Butyl 4-(3'-nitrobiphenylcarbonyl)piperazine-1-carboxylate

To a solution of tert-butyl 4-(4-bromobenzoyl)piperazine-1-carboxylate (1.00 g, 2.71 mmol), 3-nitrophenylboronic acid (0.452 g, 2.71 mmol) and potassium phosphate (2.87 g, 13.54 mmol) in nitrogen bubbled dioxane (10.0 ml) and nitrogen bubbled Water (2.0 ml) was added palladium tetrakis (0.313 g, 0.271 mmol). The reaction solution was further bubbled with a stream of nitrogen for 15 minutes. The reaction was then run overnight at 80° C. The reaction was cooled to room temperature resulting in a yellow precipitate. The precipitate was collected via filtration. The precipitate was then washed with methanol (20 mL) and ether (10 mL). This afforded the title compound (1.0 g, 92%) as a light yellow powder. LC-MS (ES, m/z): 412[M+H]$^+$ Step 2. tert-Butyl 4-(3'-aminobiphenylcarbonyl)piperazine-1-carboxylate A mixture of tert-butyl 4-(3'-nitrobiphenylcarbonyl)piperazine-1-carboxylate (1.00 g, 2.430 mmol) and palladium hydroxide on activated carbon (0.341 g, 2.430 mmol) was suspended in MeOH (30 ml). The bomb was placed on a Parr Shaker and charged with hydrogen gas at 30 psi. The reaction was allowed to shake for 3 hours. The reaction was then vented with nitrogen, filtered through celite and concentrated in vacuo affording the title compound (924 mg, 100%) as a light brown solid. LC-MS (ES, m/z): 382[M+H]+

Step 3. tert-Butyl 4-(3'-(cyclobutanesulfonamido) biphenylcarbonyl)piperazine-1-carboxylate To a solution of tert-butyl 4-(3'-aminobiphenylcarbonyl)piperazine-1-carboxylate (500.0 mg, 1.311 mmol) in anhydrous pyridine (6.5 ml) was added cyclobutanesulfonyl chloride (203 mg, 1.311 mmol) at 40° C. The reaction solution (red color) was stirred at 40° C. for 2 days. The reaction solution was cooled to room temperature and diluted with water (10 mL). The solution was then extracted several times with EtOAc (3×20 mL). The organic extracts were pooled and washed with 1M citric acid (aqueous, 20 mL), water (20 mL) and brine (20 mL). The organic layer was dried over sodium sulfate, filtered and concentrated in vacuo. The crude product was subjected to FCC (Biotage SNAP 50; gradient eluent: 40-50% EtOAc in hexanes over 15 CV). This afforded the title compound (173 mg, 26.3%) as a white powder. LC-MS (ES, m/z): 500[M+H]+

Step 4. N-(4'-(piperazine-1-carbonyl)biphenyl-3-yl) cyclobutanesulfonamide hydrochloride Hydrogen chloride (4.0N in 1,4-dioxane) (0.438 ml, 1.751 mmol) was added to a solution of tert-butyl 4-(3'-(cyclobutanesulfonamido)biphenylcarbonyl)piperazine-1-carboxylate (175.0 mg, 0.350 mmol) in Dioxane (2.0 ml). The reaction solution was stirred at room temperature for 3 hours resulting in the formation of a off-white precipitate. Ether (10 mL) was added to the reaction and the precipitate was then collected by filtration. The precipitate was further washed with ether (10 mL), collected and dried in vacuo affording the title compound (153 mg, 100%) as an off-white powder. LC-MS (ES, m/z): 400[M+H]+

Step 5. N-(4'-(4-(1-hydroxycyclopropanecarbonyl) piperazine-1-carbonyl)biphenyl-3-yl)cyclobutanesulfonamide To a solution of N-(4'-(piperazine-1-carbonyl)biphenyl-3-yl)cyclobutanesulfonamide hydrochloride (164.5 mg, 0.377 mmol), 1-hydroxycyclopropanecarboxylic acid (38.5 mg, 0.377 mmol), and HBTU (172 mg, 0.453 mmol) in DMF (2.0 ml) was added DIEA (0.264 ml, 1.509 mmol). The reaction was stirred at room temperature overnight. Saturated sodium bicarbonate (aqueous, 10 mL) was added followed by water (10 mL). The reaction solution was then extracted several times with EtOAc (3×20 mL). The organic extracts were pooled and washed with water (2×20 mL) and brine (20 mL). The organic layer was dried over sodium sulfate, filtered and concentrated in vacuo providing the crude product as an orange oil. The crude product was subjected to FCC (Biotage SNAP 25; eluent: 100% EtOAc over 10 CV) followed by an additional FCC purification (Biotage SNAP 25; gradient eluent: 0-5% MeOH in methylene chloride). This afforded the title compound (55 mg, 30.3%) as a glassy clear solid. LC-MS (ES, m/z): 484[M+H]+

Method 34.

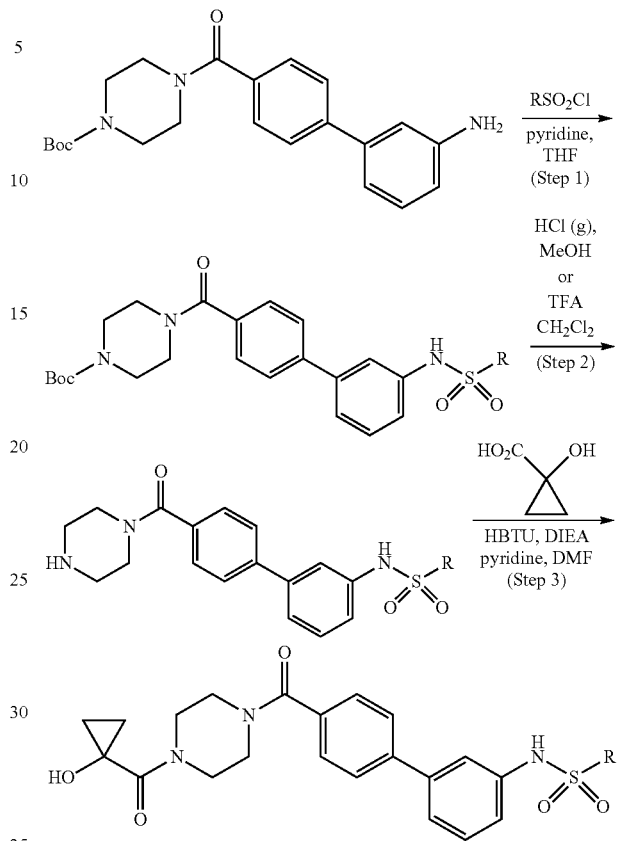

Step 1. tert-Butyl 4-(3'-(cyclobutylmethylsulfonamido)-[1,1'-biphenyl]-4-carbonyl)piperazine-1-carboxylate To an ice-cold solution of tert-butyl 4-(3'-amino-[1,1'-biphenyl]-4-carbonyl)piperazine-1-carboxylate (300 mg, 0.79 mmol) in pyridine (4 mL) cyclobutylmethanesulfonyl chloride (200 mg, 1.2 mmol) was added dropwise. The resulting mixture was allowed to warm up to room temperature over 4 h then concentrated and kept on a high vacuum line overnight. The residue was dissolved in EtOAc, washed with water, 5% acetic acid, saturated NaHCO₃, brine, dried over Na₂SO₄ and concentrated under reduced pressure. The crude material was chromatographed on a silica gel column eluting with a gradient of EtOAc in CH₂Cl₂ to obtain 295 mg (73% yield) of the title compound.

Step 2 (HCl). 1-cyclobutyl-N-(4'-(piperazine-1-carbonyl)-[1,1'-biphenyl]-3-yl)methanesulfonamide hydrogen chloride tert-Butyl 4-(3'-(cyclobutylmethylsulfonamido)-[1,1'-biphenyl]-4-carbonyl)piperazine-1-carboxylate (295 mg, 0.57 mmol) was dissolved in 18 mL of anhydrous MeOH saturated with HCl (gas) and stirred at room temperature for 3 h. The resulting solution was concentrated to dryness under reduced pressure. The residue was triturated with 2% MeOH in Et₂O followed by trituration with Et₂O and dried to afford 200 mg (78% yield) of the title compound as the hydrochloride salt which was used for the next step without further purification.

Step 2 (TFA). N-(4'-(Piperazine-1-carbonyl)-[1,1'-biphenyl]-3-yl)tetrahydro-2H-pyran-4-sulfonamide trifluoroacetate To a solution of tert-butyl 4-(3'-(tetrahydro-2H-pyran-4-sulfonamido)-[1,1'-biphenyl]-4-carbonyl)-piperazine-1-carboxylate (70 mg, 0.13 mmol) in DCM (3 mL) was added TFA (0.5 mL). The mixture was stirred at room temperature for 2 hours. After removal of solvents under reduced pressure, the crude title compound (69 mg, 100%) was used directly in the next step without further purification.

Step 3. 1-cyclobutyl-N-(4'-(4-(1-hydroxycyclopropanecarbonyl)piperazine-1-carbonyl)-[1,1'-biphenyl]-3-yl)methanesulfonamide To a solution of 1-cyclobutyl-N-(4'-(piperazine-1-carbonyl)-[1,1'-biphenyl]-3-yl)methanesulfonamide hydrogen chloride (295 mg, 0.45 mol) and 1-hydroxycyclopropane-1-carboxylic acid (77 mg, 0.76 mmol) in 3 mL of DMF was added HBTU (300 mg, 0.81 mmol) followed by an addition of DIEA (0.42 mL, 2.4 mmol). The resulting solution was stirred at room temperature overnight. The reaction mixture was diluted with water and satu. NaHCO$_3$ and extracted several times with CH$_2$Cl$_2$ and MeOH/CHCl$_3$ mixture of solvents. The organic layers were combined, washed with water, brine, dried over Na$_2$SO$_4$ and concentrated under reduced pressure. The crude material was twice purified by ISCO (40 g silica gel gold column) eluting with a gradient of MeOH in CH$_2$Cl$_2$ and then triturated in 2-3% MeOH in Et$_2$O to afford 129 mg (58% yield) of the title compound. LC-MS (ES, m/z): 498[M+H]$^+$
Method 35.

hydrochloride (Intermediate 4, 600 mg, 1.60 mmol, 1.00 equiv), 1-[[(tert-butoxy)carbonyl]amino]cyclopropane-1-carboxylic acid (322 mg, 1.60 mmol, 1.00 equiv), N,N-dimethylformamide (40 mL), HBTU (729 mg, 1.92 mmol, 1.20 equiv), DIEA (828 mg, 6.41 mmol, 3.99 equiv). The resulting solution was stirred overnight at room temperature. The reaction mixture was diluted with 50 mL of EA, washed with 3×50 mL of water and 50 mL of brine. The organic phase was concentrated under vacuum. The residue was applied onto a silica gel column with ethyl acetate/petroleum ether (70:30). This resulted in 300 mg (36%) of the title compound as a yellow solid. LC-MS (ES, m/z): 521[M+H]$^+$

Step 2. (4-(1-aminocyclopropane-1-carbonyl)piperazin-1-yl)(2-fluoro-4-(2-methyl-1H-indol-1-yl)phenyl)methanone Into a 100-mL round-bottom flask, was placed tert-butyl N-[1-[(4-[[2-fluoro-4-(2-methyl-1H-indol-1-yl)phenyl]carbonyl]piperazin-1-yl)carbonyl]cyclopropyl]carbamate (300 mg, 0.58 mmol, 1.00 equiv), dichloromethane (20 mL), trifluoroacetic acid (5 mL). The resulting solution was stirred overnight at room temperature. The resulting mixture was concentrated under vacuum. The residue was purified by Prep-HPLC with the following conditions (Waters I): Column, SunFire Prep C18, 5 um, 19*100 mm; mobile phase, Water (0.05% NH$_4$HCO$_3$) and CH$_3$CN (65% CH$_3$CN up to 85% in 7 min); Detector, UV 220&254 nm. This resulted in 73.3 mg (30%) of the title compound as a white solid. LC-MS (ES, m/z): 421[M+H]$^+$
Method 36.

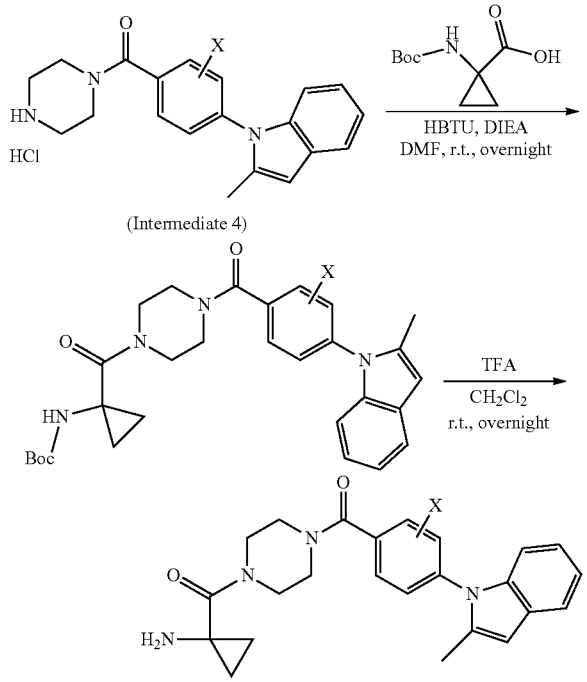

Step 1. tert-butyl (1-(4-(2-fluoro-4-(2-methyl-1H-indol-1-yl)benzoyl)piperazine-1-carbonyl)cyclopropyl)carbamate Into a 100-mL round-bottom flask was placed 1-[3-fluoro-4-[(piperazin-1-yl)carbonyl]phenyl]-2-methyl-H-indole

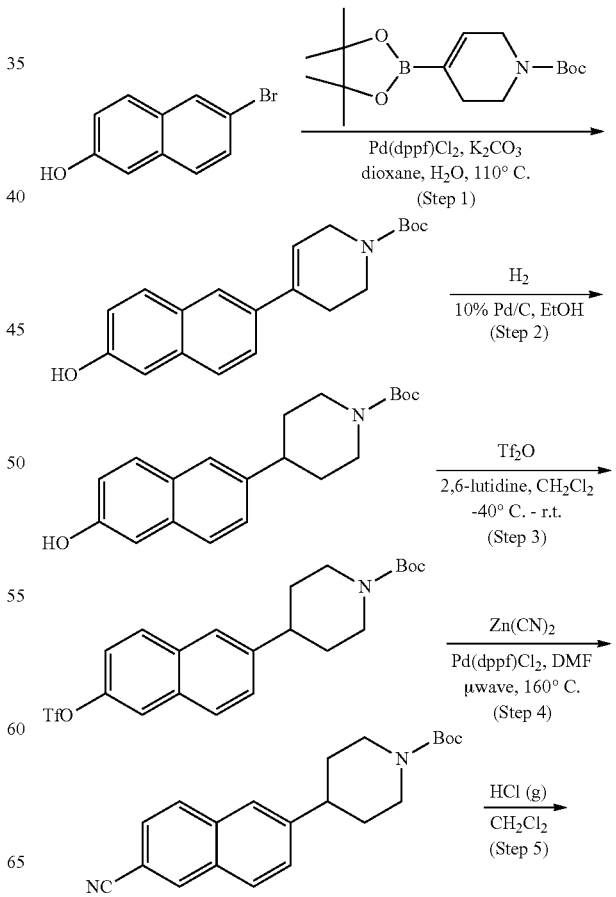

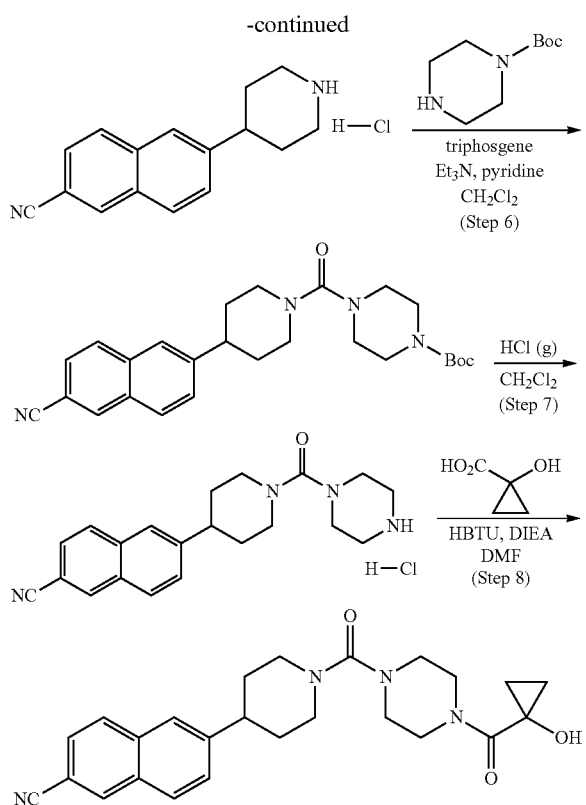

Step 1. tert-butyl 4-(6-hydroxynaphthalen-2-yl)-3,6-dihydropyridine-1(2H)-carboxylate Into a 250 mL round bottom flash was placed 6-bromonaphthalen-2-ol (2 g, 8.97 mmol, 1.00 equiv), tert-butyl 4-(4,4,5,5-tetramethyl-1,3,2-dioxaborolan-2-yl)-3,6-dihydropyridine-1(2H)-carboxylate (2.7 g, 8.70 mmol, 1.00 equiv), potassium carbonate (3.6 g, 26.05 mmol, 3.00 equiv), and Pd(dppf)Cl$_2$ (100 mg, 0.14 mmol, 0.01 equiv) in 1,4-dioxane (30 mL) and water (10 mL). The resulting solution was stirred overnight at 110° C. in an oil bath. The reaction mixture was cooled, diluted with EtOAc (120 mL) and washed with brine (2×100 mL). The organic layer was dried over sodium sulfate, filtered and concentrated in vacuo. The crude product was purified by silica gel chromatography eluting with dichloromethane/methanol (50:1). This resulted in 1.9 g (65%) of the title compound as a yellow solid. LC-MS (ES, m/z): 326[M+H]$^+$

Step 2. tert-butyl 4-(6-hydroxynaphthalen-2-yl)piperidine-1-carboxylate

Into a 250 mL round bottom flask was placed tert-butyl 4-(6-hydroxynaphthalen-2-yl)-3,6-dihydropyridine-1(2H)-carboxylate (1.9 g, 5.84 mmol, 1.00 equiv), ethanol (50 mL), and 10% palladium on carbon (0.5 g). To this suspension was charged in hydrogen gas. The resulting solution was stirred for 2 hours at r.t. The solids were filtered out and the solution was concentrated in vacuo affording the title compound (1.9 g, 99%) as a light yellow solid. LC-MS (ES, m/z): 328[M+H]$^+$

Step 3. tert-butyl 4-(6-(((trifluoromethyl)sulfonyl)oxy)naphthalen-2-yl)piperidine-1-carboxylate Into a 100 mL round bottom flask was placed tert-butyl 4-(6-hydroxynaphthalen-2-yl)piperidine-1-carboxylate (1.9 g, 5.79 mmol, 1.00 equiv), dichloromethane (20 mL), 2,6-lutidine (3.4 mL, 3.00 equiv) and triflic anhydride (1.5 mL, 1.50 equiv). The resulting solution was stirred at −40° C. for 10 minutes and then slowly warmed to r.t. over 2 hours. The reaction was quenched via the addition of water (100 mL). The organic layer was then washed with brine (2×100 mL) and 5% hydrochloric acid (2×50 mL). The organic layer was dried over sodium sulfate, filtered and concentrated in vacuo. The crude product was purified by silica gel chromatography eluting with EtOAc/petroleum ether (1:5). This resulted in 2.1 g (79%) of the title compound as a white solid. LC-MS (ES, m/z): 461[M+H]$^+$

Step 4. tert-butyl 4-(6-cyanonaphthalen-2-yl)piperidine-1-carboxylate

Into a 30 mL vial was placed tert-butyl 4-(6-(((trifluoromethyl)sulfonyl)oxy)naphthalen-2-yl)piperidine-1-carboxylate (1.5 g, 3.26 mmol, 1.00 equiv), zinc cyanide (840 mg, 7.15 mmol, 2.20 equiv), and Pd(dppf)Cl$_2$ (100 mg, 0.14 mmol, 0.04 equiv) in DMF (10 mL). The resulting solution was subjected to microwave irradiation at 160° C. for 15 minutes. The reaction was cooled, diluted with 100 mL of EtOAc and washed with water (2×100 mL) and brine (2×50 mL). The organic layer was dried over sodium sulfate, filtered and concentrated in vacuo. The crude product was purified by silica gel chromatography eluting with EtOAc/petroleum ether (1:10). This resulted in 1.0 g (91%) of the title compound as a white solid. LC-MS (ES, m/z): 337[M+H]$^+$

Step 5. 6-(piperidin-4-yl)-2-naphthonitrile hydrochloride

Into a 100 mL round bottom flask was placed tert-butyl 4-(6-cyanonaphthalen-2-yl)piperidine-1-carboxylate (1.0 g, 2.97 mmol, 1.00 equiv) in dichloromethane (20 mL). HCl (g) was bubbled into the reaction solution and stirred for 30 minutes at r.t. resulting in a precipitate. The solid was collected and dried in vacuo affording the title compound (0.7 g, 100%) as a white solid. LC-MS (ES, m/z): 237[M+H]$^+$

Step 6. tert-butyl 4-(4-(6-cyanonaphthalen-2-yl)piperidine-1-carbonyl)piperazine-1-carboxylate Into a 100 mL round bottom flask was placed 6-(piperidin-4-yl)-2-naphthonitrile hydrochloride, triphosgene (1.0 g, 3.37 mmol, 1.10 equiv), Et$_3$N (1.8 mL, 4.80 equiv) in dichloromethane (20 mL). The reaction was stirred for 2 hours and then pyridine (0.35 mL, 1.50 equiv) and tert-butyl piperazine-1-carboxylate (700 mg, 3.76 mmol, 1.20 equiv) were added. The resulting solution was stirred overnight at r.t. The reaction mixture was then washed with water (2×100 mL) and brine (2×50 mL). The organic layer was dried over sodium sulfate, filtered and concentrated in vacuo affording the title compound (0.8 g, 60%) as a yellow solid. LC-MS (ES, m/z): 449[M+H]$^+$

Step 7. 6-(1-(piperazine-1-carbonyl)piperidin-4-yl)-2-naphthonitrile hydrochloride Into a 100 mL round bottom flask was placed tert-butyl 4-(4-(6-cyanonaphthalen-2-yl)piperidine-1-carbonyl)piperazine-1-carboxylate (800 mg, 1.78 mmol, 1.00 equiv) in dichloromethane (15 mL). HCl (g) was bubbled into the reaction solution and stirred for 2 hours at r.t. The reaction solution was concentrated in vacuo affording the title compound (0.6 g, 97%) as a white solid. LC-MS (ES, m/z): 349[M+H]+

Step 8. 6-(1-(4-(1-hydroxycyclopropane-1-carbonyl)piperazine-1-carbonyl)piperidin-4-yl)-2-naphthonitrile Into a 100 mL round bottom flask was placed 1-hydroxycyclopropane-1-carboxylic acid (180 mg, 1.76 mmol, 1.00 equiv), HBTU (900 mg, 2.37 mmol, 2.30 equiv), and 6-(1-(piperazine-1-carbonyl)piperidin-4-yl)-2-naphthonitrile hydrochloride (600 mg, 1.72 mmol, 1.00 equiv) in DMF (15 mL). DIEA (0.8 mL, 5.00 equiv) was added and the resulting solution was stirred overnight at r.t. The reaction solution was then diluted with 100 mL of EtOAc and washed with water (2×100 mL) and brine (2×50 mL). The organic layer was then dried over sodium sulfate, filtered and concentrated in vacuo. The crude product was purified by silica gel chromatography eluting with dichloromethane/methanol (20:1) and then subjected to Prep-HPLC with the following conditions conditions (Waters I): Column, Xbridge Prep C18 OBD column, 5 um, 19*150 mm; mobile phase, Water (0.05% NH4HCO3) and CH3CN (33% CH3CN up to 38% in 12 min). This resulted in 106.9 mg (14%) of the title compound as a white solid. LC-MS (ES, m/z): 433 [M+H]+

Intermediates

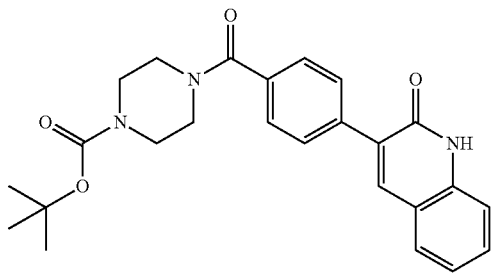 [SMILES: CC(C)(C)OC(=O)N1CCN(C(=O)c2ccc(-c3cc4ccccc4[nH]c3=O)cc2)CC1]

tert-Butyl 4-(4-(2-oxo-1,2-dihydroquinolin-3-yl)benzoyl)piperazine-1-carboxylate Tetrakis(triphenylphosphine)palladium(0) (0.078 g, 0.068 mmol) was added to a mixture of tert-butyl 4-(4-bromobenzoyl)piperazine-1-carboxylate (0.250 g, 0.677 mmol), 2-fluoroquinolin-3-ylboronic acid (0.129 g, 0.677 mmol), and sodium carbonate (0.287 g, 2.71 mmol) in dioxane (5.0 mL) and water (1.0 mL). The mixture stirred in the microwave at 60° C. for 1.5 h. The reaction mixture was filtered and concentrated to afford a yellow oil. This material was purified via column chromatography on silica gel (Biotage 25 g column, gradient elution with 50-100% ethyl acetate-hexane) to afford tert-butyl 4-(4-(2-oxo-1,2-dihydroquinolin-3-yl)benzoyl)piperazine-1-carboxylate (0.228 g, 0.526 mmol, 78% yield) as a white solid. MS (ESI, pos. ion) m/z: 434 (M+1).

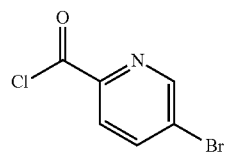

5-bromopicolinoyl chloride

Thionyl chloride (10 ml, 137 mmol) was added to 5-bromopicolinic acid (5.00 g, 24.75 mmol). A drop of DMF was added, and the mixture was heated at 80° C. for 2 h. The excess thionyl chloride was removed to afford 5-bromopicolinoyl chloride (5.413 g, 24.55 mmol, 99% yield) as a pale yellow solid. An aliquot was quenched with methanol to afford methyl 5-bromopicolinate. MS (ESI, pos. ion) m/z: 216, 218 (M+1).

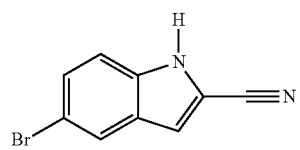 [SMILES: N#Cc1cc2cc(Br)ccc2[nH]1]

5-bromo-1H-indole-2-carbonitrile

Step 1. 5-bromo-1H-indole-2-carboxamide 5-bromo-1H-indole-2-carboxylic acid (0.75 g, 3.12 mmol) was added to dichloromethane (10 mL) to give a suspension. Thionyl chloride (0.616 mL, 8.44 mmol) was added gradually by syringe. A drop of DMF was added and the suspension was heated at reflux for 2.5 h. The mixture was cooled to rrom temperature and then poured with stirring into 5 N ammonium hydroxide (20 mL, 100 mmol) in 18 mL of ice. The precipitate was stirred for 2 h. The aqueous emulsion was diluted and then extracted twice with ethyl acetate. Drying over MgSO4 and concentrating yielded a yellow crude solid. This was triturated with hexanes, filtered, washed with hexanes, and dried to afford 5-bromo-1H-indole-2-carboxamide (0.81 g, 3.15 mmol, 93% yield) as a tan solid. MS (ESI, pos. ion) m/z: 239, 241 (M+1)

Step 2. 5-bromo-1H-indole-2-carbonitrile 5-bromo-1H-indole-2-carboxamide (0.68 mg, 2.84 mmol) was added to toluene (20 mL) to give a suspension. Phosphorus oxychloride (1.326 mL, 14.22 mmol) was added gradually by syringe. The suspension was heated at reflux for 1.5 h. The reaction was poured into saturated NaHCO3 and allowed to quench. The layers were extracted twice with 50 mL of dichloromethane. The combined layers were washed with 20 mL of brine, dried over MgSO4, and concentrated to yield the crude product. This material was purified via column chromatography on silica gel (Biotage 25 g column, gradient elution with 0-5% ethyl acetate/dichloromethane) to afford 5-bromo-1H-indole-2-carbonitrile (0.408 g, 1.85 mmol, 65%) as a tan solid. MS (ESI, neg. ion) m/z 219/221

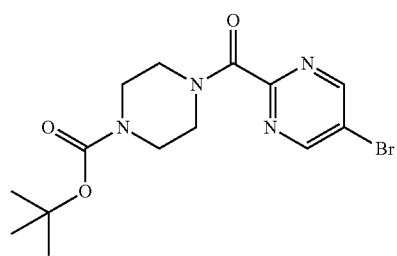 [SMILES: CC(C)(C)OC(=O)N1CCN(C(=O)c2ncc(Br)cn2)CC1]

tert-butyl 4-(5-bromopyrimidine-2-carbonyl)piperazine-1-carboxylate

Step 1. 5-bromopyrimidine-2-carbonyl chloride

Thionyl chloride (3.96 mL, 54.2 mmol) was added to 5-bromopyrimidine-2-carboxylic acid (2.0 g, 9.85 mmol). A drop of DMF was added, and the mixture was heated at 80° C. for 2 hours. The excess thionyl chloride was removed in vacuo to afford 5-bromopyrimidine-2-carbonyl chloride as a pale yellow solid. The material was used without purification in the next step.

Step 2. tert-butyl 4-(5-bromopyrimidine-2-carbonyl)piperazine-1-carboxylate

5-Bromopyrimidine-2-carbonyl chloride (2.181 g, 9.85 mmol) and N,N-diisopropylethylamine (5.16 mL, 29.6 mmol) were taken up solution in DMF (30 mL). tert-Butyl piperazine-1-carboxylate was added and the reaction mixture stirred for 1.25 h. Water (100 mL) was added and the mixture was stirred. The aqueous mixture was then extracted twice with 100 mL of ethyl acetate. The second was an emulsion but saturating with NaCl separated the phases. The combined organic phases were washed once with brine, dried over $MgSO_4$, and concentrated. The crude was purified via column chromatography on silica gel (Biotage, gradient elution with 0-10% methanol/dichloromethane) to afford tert-butyl 4-(5-bromopyrimidine-2-carbonyl)piperazine-1-carboxylate (3.1 g, 7.93 mmol, 81%) as a light tan solid. MS (ESI, pos. ion) m/z: 371/373 (M+1)

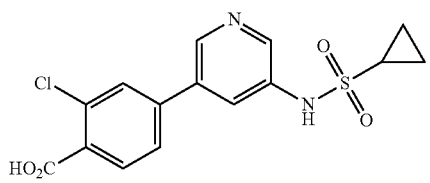 [SMILES: O=C(O)c1ccc(-c2cncc(NS(=O)(=O)C3CC3)c2)cc1Cl]

2-chloro-4-(5-(cyclopropanesulfonamido)pyridin-3-yl)benzoic acid

Step 1. N-(5-bromopyridin-3-yl)cyclopropanesulfonamide

5-Bromopyridin-3-amine (0.304 mL, 3.0 mmol) and pyridine (0.534 mL, 1.1 mmol) were combined in dichloromethane (15 ml) to give a brown solution. Cyclopropanesulfonyl chloride (0.973 mL, 9.00 mmol) was added gradually by syringe. This was stirred at rt for 1 day. Additional pyridine (3.0 mmol) and 1 equivalent of cyclopropanesulfonyl chloride (3.00 mmol) were added. After an additional 1 day the reaction was complete. The reaction was diluted with 75 mL of dichloromethane and washed with 40 mL of saturated $NaHCO_3$. The aqueous layer was extracted with 10 mL of dichloromethane and the combined organic phases were washed with 20 mL of brine. The solvent was then dried with $MgSO_4$ and concentrated. The crude product was purified via column chromatography on silica gel (Biotage 100 g column, gradient elution with 0-50% ethyl acetate/hexanes) to afford N-(5-bromopyridin-3-yl)cyclopropanesulfonamide (0.81 mgs, 2.92 mmol, 73%) as a peach colored solid. MS (ESI, pos. ion) m/z: 277, 279 (M+1).

Step 2. 2-chloro-4-(5-(cyclopropanesulfonamido)pyridin-3-yl)benzoic acid

N-(5-bromopyridin-3-yl)cyclopropanesulfonamide (0.810 g, 2.92 mmol), sodium carbonate (1.24 g, 11.69 mmol) and 2-chloro-4-(4,4,5,5-tetramethyl-1,3,2-dioxaborolan-2-yl)benzoic acid (0.991 g, 3.51 mmol) were combined in 1,4-dioxane (32 mL) and water (6.4 mL) followed by tetrakis(triphenylphosphine)palladium (0) (0.34 g, 0.292 mmol) to give a light yellow suspension. The suspension was placed under nitrogen and heated for 16 h at 80° C. The reaction was filtered through Celite and the solids washed with 1,4-dioxane followed by ethyl acetate. Concentrating the solvents obtained a pale yellow sticky solid. This was suspended in 50 mL of water and basified with 1 N NaOH solution until the pH was 12. The basic layer was washed once with 25 mL of ethyl acetate. After a back-extraction of the organic phase with 20 mL of water at pH=12, the combined basic phases were acidified with 1 N HCl until pH=5 was reached. After standing overnight the precipitate was collected and dried to afford 2-chloro-4-(5-(cyclopropanesulfon-amido)pyridin-3-yl)benzoic acid (0.438 g, 1.24 mmol, 35%) as an off-white solid. MS (ESI, pos. ion) m/z: 353, 355 (M+1).

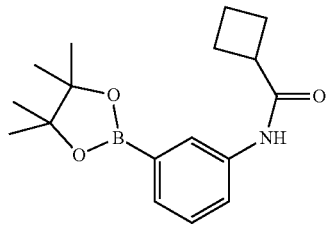 [SMILES: CC1(C)OB(c2cccc(NC(=O)C3CCC3)c2)OC1(C)C]

N-(3-(4,4,5,5-tetramethyl-1,3,2-dioxaborolan-2-yl)phenyl)cyclobutanecarboxamide 3-(4,4,5,5-Tetramethyl-1,3,2-dioxaborolan-2-yl)aniline (0.50 g, 2.28 mmol) and N,N-diisopropylethylamine (1.20 ml, 6.85 mmol), were combined in dichloromethane (5 mL) to give a light yellow solution. Cyclobutanecarbonyl chloride (0.260 mL, 2.282 mmol) was added gradually by syringe. The mixture was stirred for 2.5 h. The reaction was diluted with 70 mL of dichloromethane and then was washed twice with 20 mL of water. The organic layer was then washed with 20 mL of brine and dried over $MgSO_4$. Concentrating gave a white solid which was purified via column chromatography on silica gel (Biotage 50 g column, gradient elution with 0-40% ethyl acetate/hexanes) to afford N-(4'-(4-(1-hydroxycyclopropanecarbonyl)piperazine-1-carbonyl)biphenyl-3-yl)oxetane-3-carboxamide as a waxy white solid. MS (ESI, pos. ion) m/z 302 (M+1).

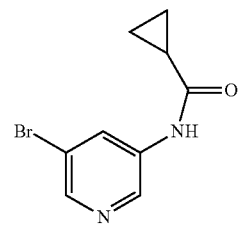

N-(5-bromopyridin-3-yl)cyclopropanecarboxamide

5-Bromopyridin-3-amine (0.292 mL, 2.89 mmol) and N,N-diisopropylethylamine (0.757 mL, 4.33 mmol) were combined in dichloromethane (15 mL) to give a light yellow solution. Cyclopropanecarbonyl chloride (0.263 mL, 2.89 mmol) was added gradually by syringe. The reaction was stirred at rt for 1.5 h. The reaction was diluted with 50 mL of dichloromethane and washed with 25 mL of saturated NaHCO₃. After extracting the aqueous layer with 20 mL of dichloromethane the combined organic layers were washed with 20 mL NaHCO₃, 20 mL of brine, and dried over MgSO₄. The solvent was concentrated leaving a brown semi-solid. The residue was purified via column chromatography on silica gel (Biotage 50 g column, gradient elution with 04% methanol/dichloromethane) to afford N-(5-bromopyridin-3-yl)cyclopropanecarboxamide (0.603 g, 2.50 mmol, 87%) as a light tan solid. MS (ESI, pos. ion) m/z: 241,243 (M+1).

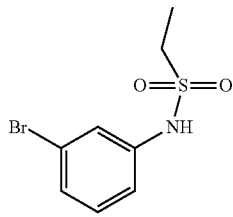

N-(3-bromophenyl)ethanesulfonamide

3-Bromoaniline (0.158 mL, 1.453 mmol), and pyridine (0.118 mL, 1.453 mmoles) were combined in water (10 mL) to give a tan solution and ethanesulfonyl chloride (0.138 mL, 1.453 mmol) was added gradually by syringe. After 1 h additional ethanesulfonyl chloride (0.138 ml, 1.453 mmol) was added and the stirring was continued another 1 h. The reaction was extracted with twice with 15 mL of ethyl acetate and the combined organic layers were washed with 10 mL of brine and dried over MgSO₄. The solvent was concentrated to afford a pale red oil. This material was purified via column chromatography on silica gel (Biotage 25 g column, gradient elution with 0-30% ethyl acetate/hexanes) to afford N-(3-bromophenyl)ethanesulfonamide (0.345 g, 1.24 mmol, 85%) as a colorless viscous film that partially solidified on standing. MS (ESI neg. ion) m/z 262,264 (M−1).

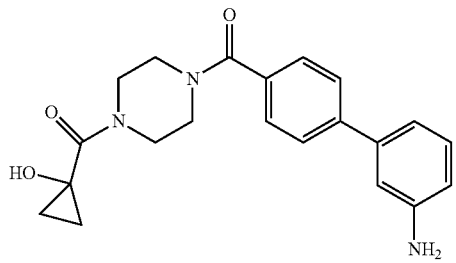 [SMILES: Nc1cccc(-c2ccc(C(=O)N3CCN(C(=O)C4(O)CC4)CC3)cc2)c1]

(3'-aminobiphenyl-4-yl)(4-(1-hydroxycyclopropanecarbonyl)piperazin-1-yl)methanone (4-(1-Hydroxycyclopropanecarbonyl)piperazin-1-yl)(3'-nitrobiphenyl-4-yl)methanone (0.263 g, 0.665 mmol, prepared according to General Method B) was suspended in ethanol (6 mL) and water (2 mL). Iron powder (0.371 g, 6.65 mmol) and ammonium chloride (8.89 mg, 0.166 mmol) were added and the suspension was heated at 80° C. for 2 h. The suspension was diluted with methanol and filtered through Celite. The filtrate was concentrated and 50 mL of chloroform was added. The solution was washed with 30 mL of saturated NaHCO₃ and the aqueous phase was separated and washed with 20 mL chloroform. The combined organic layers were washed with 20 mL of brine and dried over MgSO₄. The mixture was concentrated and the residue was purified via column chromatography on silica gel (Biotage 25 g column, gradient elution with 0-6% methanol/chloroform) to afford an amber film. This was taken up in dichloromethane and triturated with hexanes to afford (3'-aminobiphenyl-4-yl)(4-(1-hydroxycyclopropanecarbonyl)-piperazin-1-yl)methanone (0.152 g, 0.345 mmol, 52%) as a foamy solid. MS (ESI, pos. ion) m/z 366 (M+1).

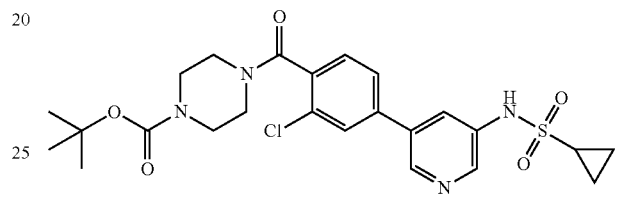

tert-butyl 4-(2-chloro-4-(5-(cyclopropanesulfonamido)pyridin-3-yl)benzoyl)piperazine-1-carboxylate tert-Butyl piperazine-1-carboxylate (0.139 g, 0.748 mmol), 2-chloro-4-(5-(cyclopropanesulfonamido)-pyridin-3-yl)benzoic acid (0.240 g, 0.680 mmol) and N,N-diisopropylethylamine (0.131 mL, 0.748 mmol) were combined in DMF (5 mL), and O-(benzotriazol-1-yl)-N,N,N',N'-tetramethyluronium hexafluorophosphate (0.387 g, 1.020 mmol) was added to give a brown solution. This was stirred for 1 d.

The reaction was diluted with 30 mL of water and stirred. The mixture was extracted with 60 mL dichloromethane and then with 15 mL of dichloromethane. The combined organic layers were washed with 20 mL of water and 20 mL of brine, and concentrated. The residue was purified via column chromatography on silica gel (Biotage 50 g column, gradient elution with 04% methanol/dichloromethane) to afford tert-butyl 4-(2-chloro-4-(5-(cyclopropanesulfonamido)pyridin-3-yl)benzoyl)piperazine-1-carboxylate (0.252 g, 71% yield) as an amber glassy film. MS (ESI, pos. ion) m/z: 521/523.

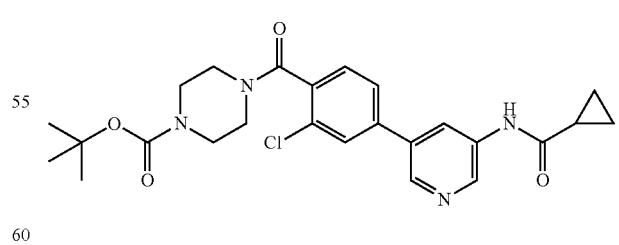

tert-butyl 4-(2-chloro-4-(5-(cyclopropanecarboxamido)pyridin-3-yl)benzoyl)piperazine-1-carboxylate tert-Butyl piperazine-1-carboxylate (0.137 g, 0.736 mmol), 2-chloro-4-(5-(cyclopropanecarboxamido)-pyridin- 3-yl)benzoic acid (0.212 g, 0.669 mmol), and N,N-diisopropylethylamine (0.129 mL, 0.736 mmol) were combined in DMF (5 mL) followed by O-(benzotriazol-1-yl)-N,N,N',N'-tetramethyluronium hexafluorophosphate (0.381 mg, 1.004 mmol) to give a brown solution. This was stirred for 1 d. Water (10 mL) was added and the reaction was stirred. The suspension was diluted with 60 mL of dichloromethane and 20 mL of water. The aqueous phase was separated and extracted with 15 mL of dichloromethane. The combined organic layers were washed with 20 mL of water and 20 mL of brine, dried over anhydrous magnesium sulfate, filtered, and concentrated. The crude product was purified via column chromatography on silica gel (Biotage 50 g column, gradient elution with 04% methanol/dichloromethane) to afford tert-butyl 4-(2-chloro-4-(5-(cyclopropanecarboxamido)-pyridin-3-yl)benzoyl)piperazine-1-carboxylate (0.454 g, 140%) as an amber glass. MS (ESI, pos. ion) m/z: 485/487.

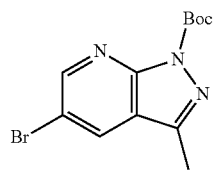

tert-butyl 5-bromo-3-methyl-1H-pyrazolo[3,4-b]pyridine-1-carboxylate

Into a 100-mL round-bottom flask, was placed 5-bromo-3-methyl-H-pyrazolo[3,4-b]pyridine (800 mg, 3.77 mmol, 1.00 equiv), Boc$_2$O (1.22 g, 5.59 mmol, 1.50 equiv), 4-dimethylaminopyridine (55 mg, 0.45 mmol, 0.12 equiv), TEA (756 mg, 7.47 mmol, 2.00 equiv) and tetrahydrofuran (20 mL). The resulting solution was stirred for 18 h at 20° C. The resulting solution was diluted with 50 mL of H$_2$O, extracted with 3×20 mL of ethyl acetate. The organic layers were combined, dried over anhydrous sodium sulfate and concentrated under vacuum. This resulted in 1.18 g (95%) of the title compound as a white solid. LC-MS (ES, m/z): 312, 314 [M+H]$^+$

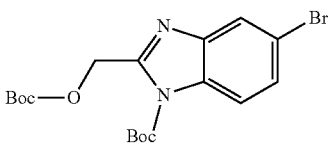 [SMILES: CC(C)(C)OC(=O)OCc1nc2cc(Br)ccc2n1C(=O)OC(C)(C)C]

tert-butyl 5-bromo-2-(((tert-butoxycarbonyl)oxy)methyl)-1H-benzo[d]imidazole-1-carboxylate Into a 50-mL round-bottom flask, was placed (5-bromo-1H-1,3-benzodiazol-2-yl)methanol (600 mg, 2.64 mmol, 1.00 equiv), dichloromethane (20 mL), Boc$_2$O (1 g, 4.58 mmol, 1.73 equiv), TEA (800 mg, 7.91 mmol, 2.99 equiv), 4-dimethylaminopyridine (32 mg, 0.26 mmol, 0.10 equiv). The resulting solution was stirred for 4 h at 25° C. The mixture was diluted with 20 mL of dichloromethane, washed with 3*30 mL of water and 30 mL of brine. The organic phase was dried over anhydrous sodium sulfate and concentrated under vacuum. This resulted in 600 mg (crude) of the title compound as yellow oil. LC-MS (ES, m/z) 429, 427[M+H]$^+$

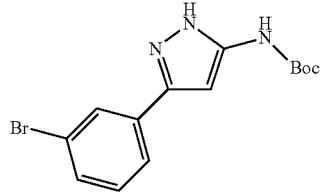 [SMILES: CC(C)(C)OC(=O)Nc1cc(-c2cccc(Br)c2)n[nH]1]

tert-butyl (3-(3-bromophenyl)-1H-pyrazol-5-yl)carbamate

Into a 50-mL round-bottom flask, was placed a solution of 3-(3-bromophenyl)-1H-pyrazol-5-amine (500 mg, 2.10 mmol, 1.00 equiv) in dichloromethane (20 mL), (Boc)$_2$O (916 mg, 4.20 mmol, 2.00 equiv), 4-dimethylaminopyridine (25.6 mg, 0.21 mmol, 0.10 equiv), TEA (636.5 mg, 6.29 mmol, 3.00 equiv). The resulting solution was stirred for 1 h at room temperature. The reaction mixture was then poured into 100 mL of water, extracted with 2×100 mL of dichloromethane. The organic layers were combined, dried over anhydrous sodium sulfate and concentrated under vacuum. This resulted in 710 mg (100%) of tert-butyl N-[3-(3-bromophenyl)-1H-pyrazol-5-yl]carbamate as brown oil. LC-MS (ES, m/z): 338[M+H]$^+$

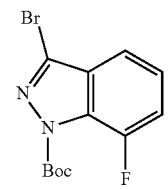 [SMILES: CC(C)(C)OC(=O)n1nc(Br)c2cccc(F)c21]

tert-butyl 3-bromo-7-fluoro-1H-indazole-1-carboxylate

Into a 50-mL round-bottom flask, was placed 3-bromo-7-fluoro-1H-indazole (700 mg, 3.26 mmol, 1.00 equiv), dichloromethane (20 mL), Boc$_2$O (1.5 g, 6.87 mmol, 2.11 equiv), TEA (1 g, 9.88 mmol, 3.04 equiv), 4-dimethylaminopyridine (40 mg, 0.33 mmol, 0.10 equiv). The resulting solution was stirred for 4 h at 25° C. The resulting mixture was poured into 50 ml of water, extracted and concentrated under vacuum. This resulted in 1 g (crude) of the title compound as red oil. LC-MS (ES, m/z): 315, 317[M+H]$^+$

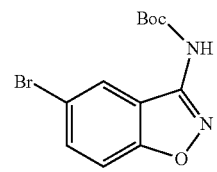

tert-butyl (5-bromobenzo[d]isoxazol-3-yl)carbamate

Into a 50-mL round-bottom flask, was placed 5-bromo-1,2-benzoxazol-3-amine (1 g, 4.69 mmol, 1.00 equiv), dichloromethane (20 mL), Boc₂O (2.1 g, 9.62 mmol, 2.05 equiv), 4-dimethylaminopyridine (57 mg, 0.47 mmol, 0.10 equiv), TEA (1.4 g, 13.84 mmol, 2.95 equiv). The reaction mixture was stirred for 3 h at 25° C. The resulting mixture was washed with 30 ml of water, 3×30 mL of brine, dried over anhydrous sodium sulfate and concentrated under vacuum. This resulted in 650 mg (crude) of the title compound as yellow oil. LC-MS (ES, m/z): 313, 315[M+H]⁺

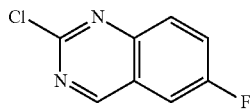 [SMILES: Fc1ccc2nc(Cl)ncc2c1]

2-chloro-6-fluoroquinazoline

Into a 100-mL round-bottom flask purged and maintained with an inert atmosphere of nitrogen, was placed 2,4-dichloro-6-fluoroquinazoline (1 g, 4.61 mmol, 1.00 equiv), brine (23 mL), dichloromethane (25 mL), ammonia hydrate (2 ml), Zn (0.9 g, 13.8 mmol, 3.0 equiv). The resulting mixture was stirred for overnight at 50° C. in an oil bath. The reaction mixture was cooled to room temperature and diluted with 50 mL of H₂O, extracted with 2×100 mL of dichloromethane. The organic layers were combined and concentrated under vacuum. The residue was purified by Combi-Flash with the following conditions (IntelFlash-1): Column, silica gel; mobile phase, EA:PE=100% increasing to EA:PE=60% within 40 min; Detector, UV 254 nm. This resulted in 0.35 g (35%) of the title compound as a yellow solid. LC-MS (ES, m/z) 183 [M+H]⁺

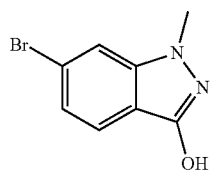

6-bromo-1-methyl-1H-indazol-3-ol

Into a 5-mL sealed tube, was placed methyl 4-bromo-2-fluorobenzoate (300 mg, 1.29 mmol, 1.00 equiv), methylhydrazine (71.4 mg, 1.55 mmol, 1.20 equiv), DMA (2 mL). The resulting solution was stirred overnight at 150° C. in a sand bath. After cooled to room temperature, the reaction mixture was diluted with 10 mL of ethyl acetate, washed with 3×10 mL of H₂O and 1×20 mL of brine. The organic phase was concentrated under vacuum. This resulted in 225 mg (77%) of 6-bromo-1-methyl-1H-indazol-3-ol as an off-white solid. LC-MS (ES, m/z): 227, 229 [M+H]⁺

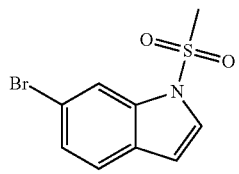

6-bromo-1-(methylsulfonyl)-1H-indole

To a solution of 6-bromoindole (2.94 g, 15 mmol, 1 eq.) in anhydrous DMF (45 mL) cooled in an ice-water bath was added NaH (0.72 g, 18 mmol, 1.2 eq.) portionwise under N2. The mixture was stirred for additional 20 min. and MeSO₂Cl (1.4 mL, 18 mmol, 1.2 eq.) was then added dropwise. The reaction mixture was allowed to warm to room temperature and stirred for 1 hour before being quenched with ice and diluted with EtOAc. The organic layer was washed with water (2×) and brine (2×), dried over Na₂SO₄ and concentrated in vacuum. The crude residue was purified by flash chromatography (silica gel) eluting with EtOAc/hexanes (0~20%) to give the title compound as a white solid (0.94 g, 23%).

Enzymatic Assay for FASN Inhibitors

Assays were performed in a 384-well black plate to measure the inhibition of FASN activities by individual compounds herein disclosed. An aliquot of 250 nL of compound was incubated with 10 L of 40 nM FASN enzyme in assay buffer (50 mM HEPES pH=7.3, 0.5 mM EDTA, 1 mM Ascorbate, 100 mM NaCl and 0.04% TritonX-100) in each well at 25° C. for 60 minutes. After the plate was centrifuged briefly, 10 μL of substrate mix (20 M Acetyl-CoA, 60 M Malonyl-CoA, and 100 M NADPH in assay buffer) was added to each well. The reaction was maintained at 25° C. for 90 minutes. The reaction was then quenched by adding 10 L of 90 M 7-Diethylamino-3-(4'-Maleimidylpheynyl)-4-Methylcoumarin in 50/50 Ethanol/H₂O solution. The assay plate was incubated at 25° C. for 15 minutes, and read on a plate reader with excitation and emission wavelength at 360 nm and 530 nm, respectively. The IC50 of a given compound was calculated by fitting the dose response curve with a four parameter logistic equation.

Results

Table 2-1 lists the compounds having an IC 50<0.5 μM.
Table 2-2 lists the compounds having an IC 50≥0.5 M and <5.0 μM.
Table 2-3 lists the compounds having an IC 50≥5.0 μM.
In addition, the Molecular Weight, Mass Ion Spectrometry Results, HPLC retention time, and the Method used to synthesize the compound are also listed.

TABLE 2-1

| IC50 (uM) < 0.5 | Mol. Weight | Mass Ion Observed | HPLC retention time (min) | Method |
|---|---|---|---|---|
| 5-[4-({4-[(1-hydroxy-cyclopropyl)carbonyl]piperazin-1-yl}carbonyl)phenyl]-1-(propan-2-yl)-1H-indole-3-carbonitrile | 456.54 | 457.16 | 1.29 | 10 |
| 1-[(4-{[4-(4-chloro-3-fluorophenyl)phenyl]carbonyl}piperazin-1-yl)carbonyl]cyclopropan-1-ol | 402.85 | 403.10 | 1.37 | 1 |
| 1-[(4-{[4-(6-methoxy-4-methylquinolin-2-yl)phenyl]carbonyl}piperazin-1-yl)carbonyl]cyclopropan-1-ol | 445.51 | 446.16 | 1.16 | 7 |
| 1-[(4-{[3-methyl-4-(quinolin-6-yl)phenyl]carbonyl}piperazin-1-yl)carbonyl]cyclopropan-1-ol | 415.48 | 416.21 | 0.92 | 5 |
| 1-[(4-{[4-(1-methyl-1H-indol-2-yl)phenyl]carbonyl}piperazin-1-yl)carbonyl]cyclopropan-1-ol | 403.47 | 404.25 | 1.56 | 5 |
| 1-[(4-{[4-(2-methoxyquinolin-6-yl)phenyl]carbonyl}piperazin-1-yl)carbonyl]cyclopropan-1-ol | 431.18 | 432.08 | 2.28 | 2 |

TABLE 2-1-continued

| IC50 (uM) < 0.5 | Mol. Weight | Mass Ion Observed | HPLC retention time (min) | Method |
|---|---|---|---|---|
| 1-({4-[(4-{imidazo[1,2-a]pyridin-2-yl}phenyl)carbonyl]piperazin-1-yl]carbonyl)cyclopropan-1-ol | 390.44 | 391.19 | 0.61 | 3 |
| 1-[(4-({3-chloro-4-[1-(trifluoromethyl)-1H-indol-5-yl]phenyl}carbonyl)piperazin-1-yl]carbonyl}cyclopropan-1-ol | 491.89 | 492.03 | 1.3 | 10 |
| 1-[(4-{[5-(1-methyl-1H-indol-5-yl)pyrazin-2-yl]carbonyl}piperazin-1-yl)carbonyl]cyclopropan-1-ol | 405.45 | 406.22 | 1.09 | 5 |
| 1-[(4-{[4-[1,3-benzothiazol-5-yl)-2-chlorophenyl]carbonyl}piperazin-1-yl)carbonyl]cyclopropan-1-ol | 441.93 | 442.11 | 1.14 | 5 |
| 3-[3-fluoro-4-({4-[(1-hydroxycyclopropyl)carbonyl]piperazin-1-yl}carbonyl)phenyl]quinolin-2-ol | 435.45 | 436.13 | 0.96 | 5 |
| 5-[4-({4-[(1-hydroxycyclopropyl)carbonyl]piperazin-1-yl}carbonyl)phenyl]-1H-indole-2-carbonitrile | 414.46 | 415.15 | 1.09 | 2 |
| 1-[(4-{[4-(5-chloro-1,3-benzoxazol-2-yl)phenyl]carbonyl}piperazin-1-yl)carbonyl]cyclopropan-1-ol | 425.87 | 426.13 | 1.31 | 4 |
| 1-[(4-{[4-(2,4-dichlorophenyl)phenyl]carbonyl}piperazin-1-yl)carbonyl]cyclopropan-1-ol | 419.30 | 419.12 | 1.47, 1.68 | 5 |
| 1-[(4-{[4-(quinolin-3-yl)phenyl]carbonyl}piperazin-1-yl)carbonyl]cyclopropan-1-ol | 401.46 | 402.14 | 0.99 | 1 |
| 3-[4-({4-[(oxetan-2-yl)carbonyl]piperazin-1-yl}carbonyl)phenyl]quinoline | 401.46 | 402.14 | 0.95 | 2 |
| 1-[(4-{[4-[1,3-benzoxazol-2-yl)phenyl]carbonyl}piperazin-1-yl)carbonyl]cyclopropan-1-ol | 391.42 | 392.16 | 1.14 | 4 |
| 1-[(4-{[2-chloro-4-(quinolin-3-yl)phenyl]carbonyl}piperazin-1-yl)carbonyl]cyclopropan-1-ol | 435.90 | 436.16 | 1.11 | 5 |
| 1-[(4-{[4-(1-methyl-1H-1,3-benzodiazol-5-yl)phenyl]carbonyl}piperazin-1-yl)carbonyl]cyclopropan-1-ol | 404.46 | 405.08 | 0.68 | 7 |
| 1-[(4-{[4-(1H-indazol-3-yl)phenyl]carbonyl}piperazin-1-yl)carbonyl]cyclopropan-1-ol | 390.44 | 391.12 | 0.98 | 7 |
| 1-[(4-{[4-(1-methyl-1H-indol-5-yl)phenyl]carbonyl}piperazin-1-yl)carbonyl]cyclopropan-1-ol | 403.47 | 404.12 | 1.26 | 2 |
| 1-[(4-{[4-(1-benzofuran-5-yl)phenyl]carbonyl}piperazin-1-yl)carbonyl]cyclopropan-1-ol | 390.16 | 391.01 | 2.43 | 2 |
| 1-[(4-{[4-(1H-1,3-benzodiazol-5-yl)phenyl]carbonyl}piperazin-1-yl)carbonyl]cyclopropan-1-ol | 390.44 | 391.20 | 0.6 | 2 |
| 1-[(4-{[4-(1,3-dimethyl-1H-indazol-5-yl)phenyl]carbonyl}piperazin-1-yl)carbonyl]cyclopropan-1-ol | 418.49 | 419.09 | 1.07 | 7 |
| 1-[(4-{[4-(2,1,3-benzothiadiazol-4-yl)phenyl]carbonyl}piperazin-1-yl)carbonyl]cyclopropan-1-ol | 408.47 | 409.11 | 1.17 | 7 |
| 1-[(4-{[4-(6-methoxyquinolin-2-yl)phenyl]carbonyl}piperazin-1-yl)carbonyl]cyclopropan-1-ol | 431.48 | 432.20 | 1.16 | 5 |
| 1-({4-[(2-phenyl-1,3-benzothiazol-6-yl)carbonyl]piperazin-1-yl}carbonyl)cyclopropan-1-ol | 407.49 | 408.09 | 1.22 | 5 |
| 1-[(4-{[4-[1,3-benzothiazol-5-yl)phenyl]carbonyl}piperazin-1-yl)carbonyl]cyclopropan-1-ol | 407.49 | 408.13 | 1.04 | 2 |
| 1-[(4-{[3-methyl-4-(quinolin-3-yl)phenyl]carbonyl}piperazin-1-yl)carbonyl]cyclopropan-1-ol | 415.48 | 416.21 | 1.07 | 5 |
| 1-[(4-{[2-fluoro-4-(quinolin-6-yl)phenyl]carbonyl}piperazin-1-yl)carbonyl]cyclopropan-1-ol | 419.45 | 420.19 | 0.91 | 5 |
| 1-[(4-{[4-(6-fluoroquinolin-2-yl)phenyl]carbonyl}piperazin-1-yl)carbonyl]cyclopropan-1-ol | 419.45 | 420.16 | 1.24 | 5 |
| 1-[(4-{[2-chloro-4-(1-methyl-1H-indol-5-yl)phenyl]carbonyl}piperazin-1-yl)carbonyl]cyclopropan-1-ol | 437.92 | 438.15 | 1.32 | 5 |
| 1-[(4-{[4-(1H-1,3-benzodiazol-4-yl)phenyl]carbonyl}piperazin-1-yl)carbonyl]cyclopropan-1-ol | 390.44 | 391.14 | 0.7 | 7 |
| 1-[(4-{[4-[1,3-benzothiazol-5-yl)-3-methylphenyl]carbonyl}piperazin-1-yl)carbonyl]cyclopropan-1-ol | 421.51 | 422.16 | 1.13 | 5 |
| 1-[(4-{[4-[1,3-benzothiazol-6-yl)phenyl]carbonyl}piperazin-1-yl)carbonyl]cyclopropan-1-ol | 407.49 | 408.14 | 1 | 2 |
| 1-[(4-{[4-(4-chlorophenyl)phenyl]carbonyl}piperazin-1-yl)carbonyl]cyclopropan-1-ol | 384.86 | 385.13 | 1.35 | 1 |
| 1-[(4-{[4-(6-chloro-1,3-benzoxazol-2-yl)phenyl]carbonyl}piperazin-1-yl)carbonyl]cyclopropan-1-ol | 425.87 | 426.11 | 1.33 | 4 |
| 1-[(4-{[4-(4-chloro-2-fluorophenyl)phenyl]carbonyl}piperazin-1-yl)carbonyl]cyclopropan-1-ol | 402.85 | 403.12 | 1.36 | 1 |
| 1-[(4-{[4-[1,3-benzothiazol-5-yl)-3-chlorophenyl]carbonyl}piperazin-1-yl)carbonyl]cyclopropan-1-ol | 441.93 | 442.12 | 1.16 | 5 |
| 1-[(4-{[2-fluoro-4-(7-fluoro-1H-indol-5-yl)phenyl]carbonyl}piperazin-1-yl)carbonyl]cyclopropan-1-ol | 425.43 | 426.04 | 1.16 | 5 |
| 1-[(4-{[4-[1,3-benzothiazol-2-yl)phenyl]carbonyl}piperazin-1-yl)carbonyl]cyclopropan-1-ol | 407.49 | 408.09 | 1.24 | 6 |
| 1-[(4-{[4-(4-chloroquinolin-3-yl)phenyl]carbonyl}piperazin-1-yl)carbonyl]cyclopropan-1-ol | 435.90 | 436.11 | 1.19 | 7 |
| 1-[(4-{[4-(isoquinolin-1-yl)phenyl]carbonyl}piperazin-1-yl)carbonyl]cyclopropan-1-ol | 401.46 | 402.20 | 0.9 | 7 |
| 1-[(4-{[4-(5-chloro-1H-1,3-benzodiazol-2-yl)phenyl]carbonyl}piperazin-1-yl)carbonyl]cyclopropan-1-ol | 424.88 | 425.08 | 1.01 | 7 |
| 1-[(4-{[4-(1,3-benzoxazol-5-yl)phenyl]carbonyl}piperazin-1-yl)carbonyl]cyclopropan-1-ol | 391.42 | 392.16 | 0.97 | 2 |
| 1-[(4-{[4-(1,3-benzoxazol-4-yl)phenyl]carbonyl}piperazin-1-yl)carbonyl]cyclopropan-1-ol | 391.42 | 392.16 | 1.1 | 7 |
| 1-[(4-{[3-fluoro-4-(quinolin-6-yl)phenyl]carbonyl}piperazin-1-yl)carbonyl]cyclopropan-1-ol | 419.45 | 420.18 | 0.91 | 5 |
| 1-[(4-{[4-(3,4-dichlorophenyl)phenyl]carbonyl}piperazin-1-yl)carbonyl]cyclopropan-1-ol | 419.30 | 419.03 | 1.45 | 2 |
| 1-[(4-{[6-(1-methyl-1H-indol-5-yl)pyridin-3-yl]carbonyl}piperazin-1-yl)carbonyl]cyclopropan-1-ol | 404.46 | 405.21 | 1.04 | 5 |

TABLE 2-1-continued

| IC50 (uM) < 0.5 | Mol. Weight | Mass Ion Observed | HPLC retention time (min) | Method |
|---|---|---|---|---|
| 1-[(4-{[4-(2,1,3-benzothiadiazol-5-yl)phenyl]carbonyl}piperazin-1-yl)carbonyl]cyclopropan-1-ol | 408.47 | 409.11 | 1.17 | 3 |
| 1-[(4-{[2-fluoro-4-(quinolin-3-yl)phenyl]carbonyl}piperazin-1-yl)carbonyl]cyclopropan-1-ol | 419.45 | 420.18 | 1.07 | 5 |
| 5-[4-({4-[(1-hydroxycyclopropyl)carbonyl]piperazin-1-yl}carbonyl)phenyl]-1H-indole-2-carboxamide | 432.47 | 433.15 | 0.81 | 3 |
| 1-[(4-{[4-(2-methyl-2H-indazol-6-yl)phenyl]carbonyl}piperazin-1-yl)carbonyl]cyclopropan-1-ol | 404.46 | 405.08 | 0.94 | 5 |
| 3-[4-({4-[(1-hydroxycyclopropyl)carbonyl]piperazin-1-yl}carbonyl)phenyl]-1,2-dihydroquinolin-2-one | 417.46 | 418.15 | 0.93 | 1 |
| 1-[(4-{[4-(3-chloro-4-fluorophenyl)phenyl]carbonyl}piperazin-1-yl)carbonyl]cyclopropan-1-ol | 402.85 | 403.11 | 1.36 | 1 |
| 1-{[4-({4-[2-methoxy-4-(1H-pyrazol-1-yl)phenyl]phenyl}carbonyl)piperazin-1-yl]carbonyl}cyclopropan-1-ol | 446.50 | 447.23 | 1.19 | 5 |
| 1-[(4-{[2-chloro-4-(quinolin-6-yl)phenyl]carbonyl}piperazin-1-yl)carbonyl]cyclopropan-1-ol | 435.90 | 436.14 | 0.96 | 5 |
| 1-[(4-{[4-(2-methyl-2H-indazol-5-yl)phenyl]carbonyl}piperazin-1-yl)carbonyl]cyclopropan-1-ol | 404.46 | 405.17 | 0.88 | 7 |
| 1-[(4-{[4-(5-chloro-2-fluorophenyl)phenyl]carbonyl}piperazin-1-yl)carbonyl]cyclopropan-1-ol | 402.85 | 403.10 | 1.33 | 1 |
| 5-[4-({4-[(1-hydroxycyclopropyl)carbonyl]piperazin-1-yl}carbonyl)phenyl]-1H-indole-3-carbonitrile | 414.46 | 415.17 | 0.97 | 1 |
| 5-[4-({4-[(oxetan-2-yl)carbonyl]piperazin-1-yl}carbonyl)phenyl]-1H-indole | 389.45 | 389.18 | 1.03 | 2 |
| 5-[2-chloro-4-({4-[(1-hydroxycyclopropyl)carbonyl]piperazin-1-yl}carbonyl)phenyl]-1H-indole-3-carbonitrile | 448.90 | 449.10 | 1.06 | 5 |
| 1-[(4-{[4-(quinolin-5-yl)phenyl]carbonyl}piperazin-1-yl)carbonyl]cyclopropan-1-ol | 401.46 | 402.17 | 0.84 | 7 |
| N-{3-[4-({4-[(1-hydroxycyclopropyl)carbonyl]piperazin-1-yl}carbonyl)phenyl]phenyl}methanesulfonamide | 443.52 | 444.17 | 0.93 | 11 |
| 1-[(4-{[5-(1-methyl-1H-indol-5-yl)pyridin-2-yl]carbonyl}piperazin-1-yl)carbonyl]cyclopropan-1-ol | 404.46 | 405.28 | 1.1 | 5 |
| 1-[(4-{[2-fluoro-4-(2-methoxyquinolin-3-yl)phenyl]carbonyl}piperazin-1-yl)carbonyl]cyclopropan-1-ol | 449.47 | 450.17 | 1.39 | 5 |
| 1-({4-[(4-phenylphenyl)carbonyl]piperazin-1-yl}carbonyl)cyclopropan-1-ol | 350.41 | 351.20 | 1.2 | 5 |
| 1-[(4-{[4-(7-fluoro-1H-indol-5-yl)phenyl]carbonyl}piperazin-1-yl)carbonyl]cyclopropan-1-ol | 407.44 | 408.12 | 1.11 | 5 |
| 1-[(4-{[2,3-difluoro-4-(6-methoxyquinolin-2-yl)phenyl]carbonyl}piperazin-1-yl)carbonyl]cyclopropan-1-ol | 467.46 | 468.16 | 1.28 | 7 |
| N-{3-[4-({4-[(1-hydroxycyclopropyl)carbonyl]piperazin-1-yl}carbonyl)phenyl]phenyl}cyclopropanesulfonamide | 469.55 | 470.08 | 1.04 | 11 |
| 1-[(4-{[3-methyl-4-(1-methyl-1H-indol-5-yl)phenyl]carbonyl}piperazin-1-yl)carbonyl]cyclopropan-1-ol | 417.50 | 418.25 | 1.3 | 5 |
| 1-[(4-{[4-(3-cyclopropoxyphenyl)phenyl]carbonyl}piperazin-1-yl)carbonyl]cyclopropan-1-ol | 406.47 | 407.08 | 1.37 | 7 |
| 1-[(4-{[4-(2,5-dichlorophenyl)phenyl]carbonyl}piperazin-1-yl)carbonyl]cyclopropan-1-ol | 419.30 | 419.13 | 1.43 | 5 |
| 1-[(4-{[3-chloro-4-(1-methyl-1H-indol-5-yl)phenyl]carbonyl}piperazin-1-yl)carbonyl]cyclopropan-1-ol | 437.92 | 438.18 | 1.33 | 5 |
| 5-[3-chloro-4-({4-[(1-hydroxycyclopropyl)carbonyl]piperazin-1-yl}carbonyl)phenyl]-1H-indole-3-carbonitrile | 448.90 | 449.10 | 1.06 | 5 |
| 1-[(4-{[4-(2H-1,2,3-benzotriazol-5-yl)phenyl]carbonyl}piperazin-1-yl)carbonyl]cyclopropan-1-ol | 391.42 | 392.14 | 0.79 | 3 |
| 1-[(4-{[4-(3-chloro-2-methoxyphenyl)phenyl]carbonyl}piperazin-1-yl)carbonyl]cyclopropan-1-ol | 414.88 | 415.15 | 1.34 | 5 |
| 1-[(4-{[2,3-difluoro-4-(quinolin-2-yl)phenyl]carbonyl}piperazin-1-yl)carbonyl]cyclopropan-1-ol | 437.44 | 438.15 | 1.27 | 7 |
| 1-[(4-{[4-(1H-indol-2-yl)phenyl]carbonyl}piperazin-1-yl)carbonyl]cyclopropan-1-ol | 389.45 | 390.12 | 1.24 | 2 |
| 3-[3-chloro-4-({4-[(1-hydroxycyclopropyl)carbonyl]piperazin-1-yl}carbonyl)phenyl]-N-cyclopropylbenzene-1-sulfonamide | 504.00 | 504.05 | 1.15 | 3 |
| 1-[(4-{[3-chloro-4-(quinolin-6-yl)phenyl]carbonyl}piperazin-1-yl)carbonyl]cyclopropan-1-ol | 435.90 | 436.16 | 0.99 | 5 |
| 1-[(4-{[4-(5-fluoro-1,3-benzoxazol-2-yl)phenyl]carbonyl}piperazin-1-yl)carbonyl]cyclopropan-1-ol | 409.41 | 410.14 | 1.18 | 4 |
| 1-[(4-{[4-(1-methyl-1H-indol-5-yl)-2-(trifluoromethyl)phenyl]carbonyl}piperazin-1-yl)carbonyl]cyclopropan-1-ol | 471.47 | 472.22 | 1.39 | 5 |
| 1-[(4-{[4-(1-methyl-1H-indazol-6-yl)phenyl]carbonyl}piperazin-1-yl)carbonyl]cyclopropan-1-ol | 404.46 | 405.09 | 1.05 | 5 |
| N-cyclopropyl-3-[4-({4-[(1-hydroxycyclopropyl)carbonyl]piperazin-1-yl}carbonyl)phenyl]benzamide | 433.50 | 434.13 | 0.95 | 7 |
| 1-[(4-{[4-(4-chloro-2-methoxyphenyl)phenyl]carbonyl}piperazin-1-yl)carbonyl]cyclopropan-1-ol | 414.88 | 415.17 | 1.37 | 5 |
| 1-[(4-{[4-(1-methyl-1H-indazol-5-yl)phenyl]carbonyl}piperazin-1-yl)carbonyl]cyclopropan-1-ol | 404.46 | 405.11 | 1.01 | 7 |
| 1-[(4-{[2-fluoro-4-(6-fluoroquinolin-2-yl)phenyl]carbonyl}piperazin-1-yl)carbonyl]cyclopropan-1-ol | 437.44 | 438.16 | 1.32 | 5 |

TABLE 2-1-continued

| IC50 (uM) < 0.5 | Mol. Weight | Mass Ion Observed | HPLC retention time (min) | Method |
|---|---|---|---|---|
| 1-[(4-{[4-(isoquinolin-6-yl)phenyl]carbonyl}piperazin-1-yl)carbonyl]cyclopropan-1-ol | 401.46 | 402.02 | 1.48 | 1 |
| 1-{[4-({3-(cyclopropyl-methoxy)phenyl]phenyl}carbonyl)piperazin-1-yl]carbonyl}cyclopropan-1-ol | 420.50 | 421.16 | 1.4 | 5 |
| 2-[4-({4-[(1-hydroxycyclopropyl)carbonyl]piperazin-1-yl}carbonyl)phenyl]-1,3-benzoxazole-5-carbonitrile | 416.43 | 417.14 | 1.07 | 4 |
| 1-({4-[(4-{imidazo[1,2-b]pyridazin-6-yl}phenyl)carbonyl]piperazin-1-yl}carbonyl)cyclopropan-1-ol | 391.42 | 392.10 | 0.69 | 7 |
| 1-({4-[(4-{1H-pyrrolo[3,2-b]pyridin-5-yl}phenyl)carbonyl]piperazin-1-yl}carbonyl)cyclopropan-1-ol | 390.44 | 391.14 | 0.58 | 3 |
| 1-[(4-{[3-fluoro-4-(quinolin-3-yl)phenyl]carbonyl}piperazin-1-yl)carbonyl]cyclopropan-1-ol | 419.45 | 420.20 | 1.08 | 5 |
| 1-[(4-{[2-fluoro-4-(6-methoxyquinolin-2-yl)phenyl]carbonyl}piperazin-1-yl)carbonyl]cyclopropan-1-ol | 449.47 | 450.15 | 1.25 | 5 |
| 1-[(4-{[4-(2,3-dichlorophenyl)phenyl]carbonyl}piperazin-1-yl)carbonyl]cyclopropan-1-ol | 419.30 | 419.08 | 1.38 | 2 |
| 1-[(4-{[2,3-difluoro-4-(6-fluoroquinolin-2-yl)phenyl]carbonyl}piperazin-1-yl)carbonyl]cyclopropan-1-ol | 455.43 | 456.14 | 1.33 | 7 |
| N-cyclopropyl-3-[4-({4-[(1-hydroxycyclopropyl)carbonyl]piperazin-1-yl}carbonyl)phenyl]benzene-1-sulfonamide | 469.55 | 470.13 | 1.05 | 11 |
| 1-({4-[(4-{furo[3,2-b]pyridin-5-yl}phenyl)carbonyl]piperazin-1-yl}carbonyl)cyclopropan-1-ol | 391.42 | 392.08 | 0.97 | 7 |
| 1-({4-[(4-{3-chloroimidazo[1,2-a]pyridin-2-yl}phenyl)carbonyl]piperazin-1-yl}carbonyl)cyclopropan-1-ol | 424.88 | 425.06 | 0.98 | 3 |
| 1-[(4-{[4-(1,3-benzothiazol-5-yl)-3-fluorophenyl]carbonyl}piperazin-1-yl)carbonyl]cyclopropan-1-ol | 425.48 | 426.12 | 1.1 | 5 |
| N-{3-[4-({4-[(1-hydroxycyclopropyl)carbonyl]piperazin-1-yl}carbonyl)phenyl]phenyl}propane-2-sulfonamide | 471.57 | 472.19 | 1.08 | 11 |
| 6-[4-({4-[(oxetan-2-yl)carbonyl]piperazin-1-yl}carbonyl)phenyl]isoquinoline | 401.17 | 402.02 | 1.46 | 2 |
| N-{3-[4-({4-[(1-hydroxycyclopropyl)carbonyl]piperazin-1-yl}carbonyl)phenyl]phenyl}benzene-sulfonamide | 505.59 | 506.10 | 1.18 | 11 |
| 1-{[4-({4-[2-methoxy-5-(trifluoromethoxy)phenyl]phenyl}carbonyl)piperazin-1-yl]carbonyl}cyclopropan-1-ol | 464.43 | 465.17 | 1.43 | 5 |
| 1-[(4-{[4-(2-chloro-4-fluorophenyl)phenyl]carbonyl}piperazin-1-yl)carbonyl]cyclopropan-1-ol | 402.85 | 403.17 | 1.33 | 5 |
| 1-[(4-{[4-(3-chlorophenyl)phenyl]carbonyl}piperazin-1-yl)carbonyl]cyclopropan-1-ol | 384.86 | 385.06 | 1.33 | 1 |
| 1-[(4-{[4-(quinolin-3-yl)phenyl]carbonyl}piperazin-1-yl)carbonyl]cyclobutan-1-ol | 415.48 | 416.04 | 2.13 | 1 |
| 1-({4-[(2-chloro-4-{imidazo[1,2-a]pyridin-2-yl}phenyl)carbonyl]piperazin-1-yl}carbonyl)cyclopropan-1-ol | 424.88 | 425.11 | 0.71 | 3 |
| 1-[(4-{[4-(1H-indol-5-yl)phenyl]carbonyl}piperazin-1-yl)carbonyl]cyclopropan-1-ol | 389.17 | 390.06 | 2.11 | 2 |
| 1-[(4-{[4-(isoquinolin-6-yl)phenyl]carbonyl}piperazin-1-yl)carbonyl]cyclobutan-1-ol | 415.48 | 416.04 | 1.61 | 1 |
| 1-[(4-{[2-fluoro-4-(1-methyl-1H-indol-5-yl)phenyl]carbonyl}piperazin-1-yl)carbonyl]cyclopropan-1-ol | 421.46 | 422.22 | 1.29 | 5 |
| 1-[(4-{[4-(6-fluoro-1,3-benzoxazol-2-yl)phenyl]carbonyl}piperazin-1-yl)carbonyl]cyclopropan-1-ol | 409.41 | 410.14 | 1.2 | 4 |
| N-{3-[4-({4-[(1-hydroxycyclopropyl)carbonyl]phenyl]phenyl}cyclopropanecarboxamide | 433.50 | 434.13 | 1.06 | 5 |
| 1-({4-[(4-{pyrazolo[1,5-a]pyridin-2-yl}phenyl)carbonyl]piperazin-1-yl}carbonyl)cyclopropan-1-ol | 390.44 | 391.15 | 0.95 | 3 |
| 1-[(4-{[3-chloro-4-(quinolin-3-yl)phenyl]carbonyl}piperazin-1-yl)carbonyl]cyclopropan-1-ol | 435.90 | 436.15 | 1.14 | 5 |
| 1-[(4-{[4-(quinolin-2-yl)phenyl]carbonyl}piperazin-1-yl)carbonyl]cyclopropan-1-ol | 401.46 | 402.16 | 1.14 | 7 |
| 1-[(4-{[4-(1H-indol-4-yl)phenyl]carbonyl}piperazin-1-yl)carbonyl]cyclopropan-1-ol | 389.45 | 390.18 | 1.06 | 7 |
| 6-[4-({4-[(1-hydroxycyclopropyl)carbonyl]piperazin-1-yl}carbonyl)phenyl]-1,2-dihydroquinolin-2-one | 417.46 | 418.13 | 0.76 | 3 |
| 2-[4-({4-[(1-hydroxycyclopropyl)carbonyl]piperazin-1-yl}carbonyl)phenyl]-1,3-benzoxazole-6-carbonitrile | 416.43 | 417.15 | 1.06 | 4 |
| 1-{[4-({3-chloro-4-[1-(propan-2-yl)-1H-indol-5-yl]phenyl}carbonyl)piperazin-1-yl]carbonyl}cyclopropan-1-ol | 465.97 | 466.05 | 1.5 | 10 |
| 1-[(4-{[4-(6-methoxynaphthalen-2-yl)phenyl]carbonyl}piperazin-1-yl)carbonyl]cyclopropan-1-ol | 430.50 | 431.12 | 1.36 | 5 |
| N-(3-{4-[4-(1-hydroxycyclopropane-carbonyl)piperazine-1-carbonyl]phenyl}phenyl)cyclopentanecarboxamide | 461.23 | 462.15 | 1.23 | 30 |
| 1-(4-{4-[4-(1H-pyrazol-4-yl)phenyl]benzoyl}piperazine-1-carbonyl)cyclopropan-1-ol | 416.18 | 417.05 | 0.93 | 31 |
| 1-{4-[4-(1,2,3,4-tetrahydroisoquinolin-2-yl)benzoyl]piperazine-1-carbonyl}cyclopropan-1-ol | 405.21 | 406.15 | 1.25 | 20 |
| 1-{4-[4-(1,3-dimethyl-1H-indazol-5-yl)-2-fluorobenzoyl]piperazine-1-carbonyl}cyclopropan-1-amine | 435.21 | 436.27 | 0.88 | 14 |
| 1-(4-{4-[4-(1-methyl-1H-pyrazol-4-yl)phenyl]benzoyl}piperazine-1-carbonyl)cyclopropan-1-ol | 430.20 | 431.06 | 1.03 | 31 |
| 1-[(2S)-4-[2-fluoro-4-(1-methyl-1H-1,3-benzodiazol-5-yl)benzoyl]-2-methylpiperazine-1-carbonyl]cyclopropan-1-ol | 436.19 | 437.20 | 0.74 | 27 |

TABLE 2-1-continued

| IC50 (uM) < 0.5 | Mol. Weight | Mass Ion Observed | HPLC retention time (min) | Method |
|---|---|---|---|---|
| 1-{4-[3-chloro-4-(1-methyl-1H-indazol-6-yl)benzoyl]piperazine-1-carbonyl}cyclopropan-1-ol | 438.15 | 439.11 | 1.11 | 13 |
| 1-{4-[2-fluoro-4-(1-methyl-1H-1,3-benzodiazol-5-yl)benzoyl]piperazine-1-carbonyl}cyclopropan-1-ol | 422.18 | 423.17 | 0.70 | 13 |
| 1-{4-[3-chloro-4-(1-methyl-1H-1,3-benzodiazol-5-yl)benzoyl]piperazine-1-carbonyl}cyclopropan-1-ol | 438.15 | 439.09 | 0.74 | 13 |
| 1-[4-(4-{pyrazolo[1,5-a]pyridin-6-yl}benzoyl)piperazine-1-carbonyl]cyclopropan-1-ol | 390.17 | 391.11 | 0.97 | 13 |
| 1-{4-[4-(4-fluoro-2,3-dihydro-1H-indol-1-yl)benzoyl]piperazine-1-carbonyl}cyclopropan-1-ol | 409.18 | 410.23 | 1.34 | 19 |
| 1-{4-[4-(3-methyl-1H-indazol-6-yl)benzoyl]piperazine-1-carbonyl}cyclopropan-1-ol | 404.18 | 405.15 | 0.95 | 13 |
| 1-{4-[2-fluoro-4-(3-methyl-1H-indazol-7-yl)benzoyl]piperazine-1-carbonyl}cyclopropan-1-ol | 422.18 | 423.16 | 1.11 | 13 |
| 1-[(2S)-2-methyl-4-[4-(1-methyl-1H-indazol-6-yl)benzoyl]piperazine-1-carbonyl]cyclopropan-1-ol | 418.20 | 419.25 | 1.06 | 3 |
| 1-{4-[3-chloro-4-(2-methyl-2H-indazol-6-yl)benzoyl]piperazine-1-carbonyl}cyclopropan-1-ol | 438.15 | 439.10 | 1.00 | 13 |
| 3,3,3-trifluoro-N-(3-{4-[4-(1-hydroxycyclopropane-carbonyl)piperazine-1-carbonyl]phenyl}phenyl)propane-1-sulfonamide | 525.15 | 526.06 | 1.20 | 11 |
| 1-{4-[2-fluoro-4-(1-methyl-1H-indazol-6-yl)benzoyl]piperazine-1-carbonyl}cyclopropan-1-ol | 422.18 | 423.11 | 1.06 | 13 |
| 1-{3,3-dimethyl-4-[4-(1-methyl-1H-1,3-benzodiazol-5-yl)benzoyl]piperazine-1-carbonyl}cyclopropan-1-ol | 432.22 | 433.20 | 0.75 | 24 |
| 1-{4-[2,6-difluoro-4-(1-methyl-1H-1,3-benzodiazol-5-yl)benzoyl]piperazine-1-carbonyl}cyclopropan-1-ol | 440.17 | 441.17 | 0.75 | 32 |
| 1-{4-[2-fluoro-4-(1-methyl-1H-indazol-6-yl)benzoyl]piperazine-1-carbonyl}cyclobutan-1-amine | 435.21 | 436.27 | 0.88 | 14 |
| 1-{4-[3-chloro-4-(6-chloro-1,3-benzoxazol-2-yl)benzoyl]piperazine-1-carbonyl}cyclopropan-1-ol | 459.08 | 460.02 | 1.40 | 13 |
| 1-{4-[4-(1,3-dimethyl-1H-indazol-5-yl)-2-fluorobenzoyl]piperazine-1-carbonyl}cyclopropan-1-ol | 436.19 | 437.16 | 1.08 | 13 |
| N-(3-{4-[4-(1-hydroxycyclopropanecarbonyl)piperazine-1-carbonyl]phenyl}phenyl)cyclobutanesulfonamide | 483.18 | 484.16 | 1.07 | 33 |
| 1-{4-[4-(2,3-dihydro-1H-indol-1-yl)benzoyl]piperazine-1-carbonyl}cyclopropan-1-ol | 391.19 | 392.18 | 1.24 | 19 |
| 1-{4-[3-chloro-4-(1,3-dimethyl-1H-indazol-5-yl)benzoyl]piperazine-1-carbonyl}cyclopropan-1-ol | 452.16 | 453.10 | 1.13 | 13 |
| 1-[(2S)-2-methyl-4-[4-(1-methyl-1H-1,3-benzodiazol-5-yl)benzoyl]piperazine-1-carbonyl]cyclopropan-1-ol | 418.20 | 419.26 | 0.70 | 23 |
| 1-{4-[2,6-difluoro-4-(2-methyl-2H-indazol-6-yl)benzoyl]piperazine-1-carbonyl}cyclopropan-1-ol | 440.17 | 441.16 | 0.97 | 32 |
| 1-(4-{4-[3-(5-amino-1,2-oxazol-3-yl)phenyl]-2-fluorobenzoyl}piperazine-1-carbonyl)cyclopropan-1-ol | 450.17 | 451.12 | 1.02 | 13 |
| 1-[(2S)-2-methyl-4-[4-(2-methyl-2H-indazol-6-yl)benzoyl]piperazine-1-carbonyl]cyclopropan-1-ol | 418.20 | 419.23 | 0.95 | 3 |
| 1-cyclobutyl-N-(3-{4-[4-(1-hydroxycyclopropane-carbonyl)piperazine-1-carbonyl]phenyl}phenyl)methane-sulfonamide | 497.20 | 498.10 | 1.21 | 34 |
| 1-{4-[2-fluoro-4-(7-fluoro-1H-indazol-3-yl)benzoyl]piperazine-1-carbonyl}cyclopropan-1-ol | 426.15 | 427.12 | 1.07 | 13 |
| 1-[(2S)-4-[4-(6-chloro-1,3-benzoxazol-2-yl)benzoyl]-2-methylpiperazine-1-carbonyl]cyclopropan-1-ol | 439.13 | 440.18 | 1.39 | 23 |
| 1-{4-[4-(1H-indol-1-yl)benzoyl]piperazine-1-carbonyl}cyclopropan-1-ol | 389.17 | 390.06 | 1.30 | 18 |
| 1-{4-[4-(7-fluoro-1H-indazol-3-yl)benzoyl]piperazine-1-carbonyl}cyclopropan-1-ol | 408.16 | 409.08 | 0.99 | 3 |
| 1-{4-[4-(7-fluoro-1,2,3,4-tetrahydroisoquinolin-2-yl)benzoyl]piperazine-1-carbonyl}cyclopropan-1-ol | 423.20 | 424.20 | 1.28 | 19 |
| 1-{4-[2-fluoro-4-(2-methyl-2H-indazol-6-yl)benzoyl]piperazine-1-carbonyl}cyclopropan-1-ol | 422.18 | 423.14 | 0.94 | 13 |
| 1-{4-[4-(3-amino-1H-indazol-6-yl)benzoyl]piperazine-1-carbonyl}cyclopropan-1-ol | 405.18 | 406.17 | 0.71 | 13 |
| 1-{4-[4-(3-amino-1,2-benzoxazol-5-yl)benzoyl]piperazine-1-carbonyl}cyclopropan-1-ol | 406.16 | 407.11 | 0.86 | 3 |
| 1-{4-[4-(1,3-dimethyl-1H-indazol-5-yl)-2-fluorobenzoyl]piperazine-1-carbonyl}cyclobutan-1-amine | 449.22 | 450.29 | 0.89 | 14 |
| 1-{4-[2-fluoro-4-(3-methyl-1H-indazol-6-yl)benzoyl]piperazine-1-carbonyl}cyclopropan-1-ol | 422.18 | 423.24 | 1.03 | 13 |
| ethyl N-(3-{4-[4-(1-hydroxycyclopropanecarbonyl)piperazine-1-carbonyl]phenyl}phenyl)carbamate | 437.20 | 438.13 | 1.12 | 11 |
| 1-{4-[4-(5-chloro-2-methyl-1H-1,3-benzodiazol-7-yl)benzoyl]piperazine-1-carbonyl}cyclopropan-1-ol | 438.15 | 439.09 | 0.83 | 13 |
| 1-[4-(4-{1H,2H,3H,4H,9H-pyrido[3,4-b]indol-2-yl}benzoyl)piperazine-1-carbonyl]cyclopropan-1-ol | 444.22 | 445.17 | 1.26 | 19 |
| 1-[(2R,6S)-2,6-dimethyl-4-[4-(1-methyl-1H-1,3-benzodiazol-5-yl)benzoyl]piperazine-1-carbonyl]cyclopropan-1-ol | 432.22 | 433.20 | 0.73 | 23 |
| 1-[4-(2-chloro-4-{3-chloroimidazo[1,2-a]pyridin-2-yl}benzoyl)piperazine-1-carbonyl]cyclopropan-1-ol | 458.09 | 459.06 | 1.07 | 13 |
| 1-{4-[4-(4-chloro-2-fluorophenyl)benzoyl]-3,3-dimethylpiperazine-1-carbonyl}cyclopropan-1-ol | 430.15 | 431.14 | 1.47 | 24 |

TABLE 2-1-continued

| IC50 (uM) < 0.5 | Mol. Weight | Mass Ion Observed | HPLC retention time (min) | Method |
|---|---|---|---|---|
| 1-{4-[2-chloro-4-(1-methyl-1H-indazol-6-yl)benzoyl]piperazine-1-carbonyl}cyclopropan-1-ol | 438.15 | 439.10 | 1.10 | 13 |
| 1-[(2S)-4-[4-(4-chloro-2-fluorophenyl)benzoyl]-2-methylpiperazine-1-carbonyl]cyclopropan-1-ol | 416.13 | 417.14 | 1.40 | 23 |
| 1-[(2S)-4-[4-(1,3-dimethyl-1H-indazol-5-yl)benzoyl]-2-methylpiperazine-1-carbonyl]cyclopropan-1-ol | 432.22 | 433.27 | 1.10 | 3 |
| 1-(4-{4-[3-(5-amino-1,2-oxazol-3-yl)phenyl]benzoyl}piperazine-1-carbonyl)cyclopropan-1-ol | 432.18 | 433.23 | 0.97 | 22 |
| 2-(3-{4-[4-(1-hydroxycyclopropanecarbonyl)piperazine-1-carbonyl]phenyl}phenyl)acetonitrile | 389.17 | 390.12 | 1.06 | 13 |
| N-(3-{4-[4-(1-hydroxycyclopropanecarbonyl)piperazine-1-carbonyl]phenyl}phenyl)cyclopentanesulfonamide | 497.20 | 498.16 | 1.14 | 33 |
| 1-[(3S)-3-methyl-4-[4-(1-methyl-1H-1,3-benzodiazol-5-yl)benzoyl]piperazine-1-carbonyl]cyclopropan-1-ol | 418.20 | 419.21 | 0.67 | 23 |
| 1-cyclopropyl-N-(3-{4-[4-(1-hydroxycyclopropanecarbonyl)piperazine-1-carbonyl]phenyl}phenyl)methanesulfonamide | 483.18 | 484.05 | 1.13 | 34 |
| 1-{4-[3-chloro-4-(6-fluoro-1,3-benzoxazol-2-yl)benzoyl]piperazine-1-carbonyl}cyclopropan-1-ol | 443.10 | 444.08 | 1.25 | 13 |
| 1-{4-[2-chloro-4-(2-methyl-2H-indazol-6-yl)benzoyl]piperazine-1-carbonyl}cyclopropan-1-ol | 438.15 | 439.09 | 0.98 | 13 |
| 1-{4-[2,6-difluoro-4-(1-methyl-1H-indazol-6-yl)benzoyl]piperazine-1-carbonyl}cyclopropan-1-ol | 440.17 | 441.14 | 1.10 | 32 |
| 1-[(3R)-3-methyl-4-[4-(1-methyl-1H-1,3-benzodiazol-5-yl)benzoyl]piperazine-1-carbonyl]cyclopropan-1-ol | 418.20 | 419.25 | 0.69 | 23 |
| N-(6-{4-[4-(1-hydroxycyclopropanecarbonyl)piperazine-1-carbonyl]phenyl}-1,2-benzoxazol-3-yl)cyclopropanecarboxamide | 474.19 | 475.15 | 1.01 | 29 |
| 1-[(3R,5S)-3,5-dimethyl-4-[4-(1-methyl-1H-1,3-benzodiazol-5-yl)benzoyl]piperazine-1-carbonyl]cyclopropan-1-ol | 432.51 | 433.16 | 0.74 | 23 |
| propan-2-yl N-(3-{4-[4-(1-hydroxycyclopropanecarbonyl)piperazine-1-carbonyl]phenyl}phenyl)carbamate | 451.21 | 452.16 | 1.24 | 11 |
| 1-{4-[4-(3-amino-1H-indazol-5-yl)benzoyl]piperazine-1-carbonyl}cyclopropan-1-ol | 405.18 | 406.17 | 0.73 | 13 |
| 1-[(2R)-2-methyl-4-[4-(1-methyl-1H-1,3-benzodiazol-5-yl)benzoyl]piperazine-1-carbonyl]cyclopropan-1-ol | 418.20 | 419.25 | 0.69 | 23 |
| 3,3-difluoro-N-(3-{4-[4-(1-hydroxycyclopropanecarbonyl)piperazine-1-carbonyl]phenyl}phenyl)cyclobutane-1-carboxamide | 483.20 | 484.14 | 1.19 | 30 |
| 1-[(2S,6R)-4-[4-(6-fluoro-1,3-benzoxazol-2-yl)benzoyl]-2,6-dimethylpiperazine-1-carbonyl]cyclopropan-1-ol | 437.18 | 438.13 | 1.28 | 4 |
| 1-(4-{4-[1-(2-hydroxyethyl)-1H-1,3-benzodiazol-6-yl]benzoyl}piperazine-1-carbonyl)cyclopropan-1-ol | 434.20 | 435.19 | 0.59 | 21 |
| 1-{4-[4-(1H-1,3-benzodiazol-4-yl)-2-chlorobenzoyl]piperazine-1-carbonyl}cyclopropan-1-ol | 424.13 | 425.04 | 0.79 | 5 |
| 1-{4-[4-(5-fluoro-2,3-dihydro-1H-indol-1-yl)benzoyl]piperazine-1-carbonyl}cyclopropan-1-ol | 409.18 | 410.17 | 1.28 | 19 |
| 1-[4-(4-{3-chloroimidazo[1,2-a]pyridin-2-yl}-2-fluorobenzoyl)piperazine-1-carbonyl]cyclopropan-1-ol | 442.12 | 443.12 | 1.00 | 13 |
| 1-{4-[4-(4-chloro-2-fluorophenyl)-2-fluorobenzoyl]piperazine-1-carbonyl}cyclopropan-1-ol | 420.11 | 421.01 | 1.39 | 15 |
| 1-{4-[3-chloro-4-(4-chloro-2-fluorophenyl)benzoyl]piperazine-1-carbonyl}cyclopropan-1-ol | 436.08 | 437.04 | 1.44 | 15 |
| 1-{4-[2-chloro-4-(6-chloro-1,3-benzoxazol-2-yl)benzoyl]piperazine-1-carbonyl}cyclopropan-1-ol | 459.08 | 460.03 | 1.43 | 13 |
| 1-{4-[4-(5-fluoro-2,3-dihydro-1H-isoindol-2-yl)benzoyl]piperazine-1-carbonyl}cyclopropan-1-ol | 409.18 | 410.23 | 1.31 | 19 |
| 1-{4-[4-(3-methyl-1H-indazol-4-yl)benzoyl]piperazine-1-carbonyl}cyclopropan-1-ol | 404.18 | 405.15 | 0.90 | 13 |
| 1-{4-[4-(6-methoxy-1,3-benzoxazol-2-yl)benzoyl]piperazine-1-carbonyl}cyclopropan-1-ol | 421.16 | 422.04 | 1.13 | 4 |
| 1-{4-[4-(3-methyl-1H-indazol-7-yl)benzoyl]piperazine-1-carbonyl}cyclopropan-1-ol | 404.18 | 405.13 | 1.05 | 13 |
| 1-[(2R)-4-[4-(4-chloro-2-fluorophenyl)benzoyl]-2-methylpiperazine-1-carbonyl]cyclopropan-1-ol | 416.13 | 417.14 | 1.40 | 23 |
| 1-(3-{4-[4-(1-hydroxycyclopropanecarbonyl)piperazine-1-carbonyl]phenyl}phenyl)cyclobutane-1-carbonitrile | 429.21 | 430.20 | 1.23 | 13 |
| 1-{4-[2-fluoro-4-(6-fluoro-1,3-benzoxazol-2-yl)benzoyl]piperazine-1-carbonyl}cyclopropan-1-ol | 427.13 | 428.09 | 1.22 | 13 |
| 1-[4-(4-{1H,2H,3H,4H,5H-pyrido[4,3-b]indol-2-yl}benzoyl)piperazine-1-carbonyl]cyclopropan-1-ol | 444.22 | 445.16 | 1.20 | 19 |
| 1-{4-[4-(2-methyl-1H-indol-1-yl)benzoyl]piperazine-1-carbonyl}cyclopropan-1-ol | 403.19 | 404.15 | 1.32 | 18 |
| 1-[(2S)-2-methyl-4-[4-(1-methyl-1H-1,3-benzodiazol-5-yl)benzoyl]piperazine-1-carbonyl]cyclopropan-1-amine | 417.22 | 418.23 | 0.54 | 28 |
| 1-{4-[3-fluoro-4-(1-methyl-1H-1,3-benzodiazol-5-yl)benzoyl]piperazine-1-carbonyl}cyclopropan-1-ol | 422.18 | 423.14 | 0.68 | 13 |
| 1-{4-[2-fluoro-4-(1-methyl-1H-1,3-benzodiazol-5-yl)benzoyl]piperazine-1-carbonyl}cyclobutan-1-amine | 435.21 | 436.27 | 0.57 | 14 |

TABLE 2-1-continued

| IC50 (uM) < 0.5 | Mol. Weight | Mass Ion Observed | HPLC retention time (min) | Method |
|---|---|---|---|---|
| 1-{4-[3-fluoro-4-(1-methyl-1H-indazol-6-yl)benzoyl]piperazine-1-carbonyl}cyclopropan-1-ol | 422.18 | 423.09 | 1.05 | 13 |
| 1-[(2S)-4-[4-(6-fluoro-1,3-benzoxazol-2-yl)benzoyl]-2-methylpiperazine-1-carbonyl]cyclopropan-1-ol | 423.16 | 424.18 | 1.21 | 4 |
| 1-{4-[4-(4-fluoro-2,3-dihydro-1H-isoindol-2-yl)benzoyl]piperazine-1-carbonyl}cyclopropan-1-ol | 409.18 | 410.21 | 1.30 | 19 |
| 1-(4-{3-chloro-4-[3-(cyclopropanesulfonyl)phenyl]benzoyl}piperazine-1-carbonyl)cyclopropan-1-ol | 488.12 | 489.07 | 1.10 | 13 |
| 1-{4-[4-(7-fluoro-2,3-dihydro-1H-indol-1-yl)benzoyl]piperazine-1-carbonyl}cyclopropan-1-ol | 409.18 | 410.23 | 1.28 | 19 |
| 1-{4-[4-(3-cyclopropyl-1H-indazol-6-yl)benzoyl]piperazine-1-carbonyl}cyclopropan-1-ol | 430.20 | 431.15 | 1.09 | 13 |
| 1-{4-[4-(6-fluoro-1,3-benzoxazol-2-yl)benzoyl]-3,3-dimethylpiperazine-1-carbonyl}cyclopropan-1-ol | 437.18 | 438.19 | 1.28 | 24 |
| 1-{4-[4-(3-methyl-1H-indazol-1-yl)benzoyl]piperazine-1-carbonyl}cyclopropan-1-ol | 404.18 | 405.11 | 1.14 | 18 |
| 1-{4-[2-fluoro-4-(3-methyl-1H-indazol-7-yl)benzoyl]piperazine-1-carbonyl}cyclopropan-1-amine | 421.19 | 422.20 | 0.91 | 14 |
| 1-{4-[4-(1-methanesulfonyl-1H-indol-6-yl)benzoyl]piperazine-1-carbonyl}cyclopropan-1-ol | 467.15 | 468.03 | 1.20 | 3 |
| 1-{4-[4-(1-methyl-1H-1,3-benzodiazol-5-yl)benzoyl]piperazine-1-carbonyl}cyclopropan-1-amine | 403.20 | 404.16 | 0.81 | 14 |
| 1-{4-[4-(2-methyl-2,3-dihydro-1H-indol-1-yl)benzoyl]piperazine-1-carbonyl}cyclopropan-1-ol | 405.21 | 406.24 | 1.37 | 19 |
| 1-{4-[4-(5-fluoro-1H-1,2,3-benzotriazol-6-yl)benzoyl]piperazine-1-carbonyl}cyclopropan-1-ol | 409.16 | 410.10 | 0.79 | 13 |
| 1-{4-[3-chloro-4-(5-chloro-2-fluorophenyl)benzoyl]piperazine-1-carbonyl}cyclopropan-1-ol | 436.08 | 436.98 | 1.40 | 13 |
| 1-[(2S,6R)-4-[4-(4-chloro-2-fluorophenyl)benzoyl]-2,6-dimethylpiperazine-1-carbonyl]cyclopropan-1-ol | 430.15 | 431.18 | 1.48 | 23 |
| N-(3-{4-[4-(1-hydroxycyclopropanecarbonyl)piperazine-1-carbonyl]phenyl}phenyl)oxane-4-sulfonamide | 513.19 | 514.05 | 0.98 | 34 |
| 1-{4-[4-(1-methyl-1H-indazol-6-yl)benzoyl]piperazine-1-carbonyl}cyclopropan-1-amine | 403.20 | 404.15 | 0.79 | 14 |
| 1-{4-[4-(7-methoxy-1,2,3,4-tetrahydroisoquinolin-2-yl)benzoyl]piperazine-1-carbonyl}cyclopropan-1-ol | 435.22 | 436.21 | 1.26 | 19 |
| 1-(3-{3-fluoro-4-[4-(1-hydroxycyclopropanecarbonyl)piperazine-1-carbonyl]phenyl}phenyl)cyclopropane-1-carbonitrile | 433.18 | 434.16 | 1.22 | 13 |
| 1-{4-[2-fluoro-4-(2-methyl-1H-indol-1-yl)benzoyl]piperazine-1-carbonyl}cyclopropan-1-ol | 421.18 | 422.12 | 1.41 | 18 |
| 1-{4-[4-(1H-1,3-benzodiazol-1-yl)benzoyl]piperazine-1-carbonyl}cyclopropan-1-ol | 390.17 | 391.14 | 0.81 | 18 |
| 1-(3-{4-[4-(1-hydroxycyclopropanecarbonyl)piperazine-1-carbonyl]phenyl}phenyl)cyclopropane-1-carbonitrile | 415.19 | 416.18 | 1.14 | 13 |
| 1-[4-[2-fluoro-4-(3-methyl-1H-indazol-1-yl)benzoyl]piperazine-1-carbonyl]cyclopropan-1-ol | 422.18 | 423.09 | 1.25 | 18 |
| 1-{4-[2-fluoro-4-(1-methyl-1H-indazol-6-yl)benzoyl]piperazine-1-carbonyl}cyclopropan-1-amine | 421.19 | 422.20 | 0.86 | 14 |
| 2-{4-[4-(1-hydroxycyclopropanecarbonyl)piperazine-1-carbonyl]phenyl}-1,2,3,4-tetrahydroisoquinoline-7-carbonitrile | 430.20 | 431.19 | 1.15 | 19 |
| 1-(4-{4-[1-(2-hydroxyethyl)-1H-1,3-benzodiazol-5-yl]benzoyl}piperazine-1-carbonyl)cyclopropan-1-ol | 434.20 | 435.23 | 0.59 | 21 |
| 1-[(2R)-4-[4-(6-fluoro-1,3-benzoxazol-2-yl)benzoyl]-2-methylpiperazine-1-carbonyl]cyclopropan-1-ol | 423.16 | 424.18 | 1.20 | 4 |
| 1-{4-[4-(1H-indazol-1-yl)benzoyl]piperazine-1-carbonyl}cyclopropan-1-ol | 390.17 | 391.10 | 1.08 | 18 |
| 1-{4-[2-chloro-4-(5-chloro-2-fluorophenyl)benzoyl]piperazine-1-carbonyl}cyclopropan-1-ol | 436.08 | 437.00 | 1.40 | 13 |
| 1-{4-[4-(1,3-dimethyl-1H-indazol-5-yl)-3-fluorobenzoyl]piperazine-1-carbonyl}cyclopropan-1-ol | 436.19 | 437.12 | 1.07 | 13 |
| 1-{4-[4-(4-chloro-2-fluorophenyl)benzoyl]-4,7-diazaspiro[2.5]octane-7-carbonyl}cyclopropan-1-ol | 428.13 | 429.15 | 1.48 | 24 |
| 1-{4-[2-fluoro-4-(7-fluoro-1H-indazol-3-yl)benzoyl]piperazine-1-carbonyl}cyclopropan-1-amine | 425.17 | 426.10 | 0.87 | 14 |
| 6-{1-[4-(1-hydroxycyclopropanecarbonyl)piperazine-1-carbonyl]piperidin-4-yl}naphthalene-2-carbonitrile | 432.22 | 433.17 | 1.25 | 36 |
| 1-(3-{4-[4-(1-hydroxycyclopropanecarbonyl)piperazine-1-carbonyl]phenyl}phenyl)imidazolidin-2-one | 434.20 | 435.24 | 0.91 | 13 |
| 1-{4-[2,6-difluoro-4-(2-methyl-2H-indazol-6-yl)benzoyl]piperazine-1-carbonyl}cyclopropan-1-amine | 439.18 | 440.19 | 0.80 | 14 |
| 1,3-dimethyl-5-{4-[4-(oxetane-2-carbonyl)piperazine-1-carbonyl]phenyl}-1H-indazole | 418.20 | 419.16 | 1.00 | 13 |
| 1-{4-[2-fluoro-4-(2-methyl-2H-indazol-6-yl)benzoyl]piperazine-1-carbonyl}cyclopropan-1-amine | 421.19 | 422.26 | 0.78 | 14 |
| 1-(4-{4-[3-(5-amino-1H-1,2,4-triazol-3-yl)phenyl]benzoyl}piperazine-1-carbonyl)cyclopropan-1-ol | 432.19 | 433.14 | 0.75 | 13 |
| 1-{4-[4-(1-methyl-1H-1,3-benzodiazol-5-yl)benzoyl]-4,7-diazaspiro[2.5]octane-7-carbonyl}cyclopropan-1-ol | 430.20 | 431.21 | 0.74 | 24 |
| 1-{4-[4-(2-methyl-1H-indol-3-yl)benzoyl]piperazine-1-carbonyl}cyclopropan-1-ol | 403.19 | 404.28 | 1.15 | 13 |

TABLE 2-1-continued

| IC50 (uM) < 0.5 | Mol. Weight | Mass Ion Observed | HPLC retention time (min) | Method |
|---|---|---|---|---|
| 1-{4-[4-(2-methyl-1H-1,3-benzodiazol-5-yl)benzoyl]piperazine-1-carbonyl}cyclopropan-1-ol | 404.18 | 405.14 | 0.59 | 13 |
| 1-{4-[4-(6-fluoro-1,3-benzoxazol-2-yl)benzoyl]-4,7-diazaspiro[2.5]octane-7-carbonyl}cyclopropan-1-ol | 435.16 | 436.17 | 1.28 | 24 |
| 1-{4-[4-(6-fluoro-1-methyl-1H-1,2,3-benzotriazol-5-yl)benzoyl]piperazine-1-carbonyl}cyclopropan-1-ol | 423.17 | 424.12 | 0.92 | 13 |
| 1-{4-[4-(1-methyl-1H-1,3-benzodiazol-5-yl)benzoyl]piperazine-1-carbonyl}cyclobutan-1-ol | 418.20 | 419.04 | 0.73 | 1 |
| 6-chloro-4-{4-[4-(1-hydroxycyclopropanecarbonyl)piperazine-1-carbonyl]phenyl}-2,3-dihydro-1H-1,3-benzodiazol-2-one | 440.13 | 441.07 | 0.92 | 13 |
| 1-(4-{4-[2-(hydroxymethyl)-1H-1,3-benzodiazol-5-yl]benzoyl}piperazine-1-carbonyl)cyclopropan-1-ol | 420.18 | 421.13 | 0.57 | 13 |
| 5-{4-[4-(1-aminocyclopropanecarbonyl)piperazine-1-carbonyl]phenyl}-1,2-benzoxazol-3-amine | 405.18 | 406.18 | 0.70 | 14 |
| 1-{4-[4-(2-cyclopropyl-2H-indazol-5-yl)benzoyl]piperazine-1-carbonyl}cyclopropan-1-ol | 430.20 | 431.12 | 1.04 | 7 |
| 1-{4-[2-fluoro-4-(5,6,7,8-tetrahydro-1,7-naphthyridin-7-yl)benzoyl]piperazine-1-carbonyl}cyclopropan-1-ol | 424.19 | 425.15 | 0.84 | 19 |
| 1-{4-[4-(3-methyl-1,2,3,4-tetrahydroisoquinolin-2-yl)benzoyl]piperazine-1-carbonyl}cyclopropan-1-ol | 419.22 | 420.21 | 1.38 | 19 |
| 1-{4-[4-(2,3-dihydro-1H-isoindol-2-yl)benzoyl]piperazine-1-carbonyl}cyclopropan-1-ol | 391.19 | 392.18 | 1.22 | 19 |
| 1-[(3R)-4-[4-(4-chloro-2-fluorophenyl)benzoyl]-3-methylpiperazine-1-carbonyl]cyclopropan-1-ol | 416.13 | 417.14 | 1.40 | 23 |
| 1-[4-(4-{3-methyl-1H-pyrazolo[3,4-b]pyridin-5-yl}benzoyl)piperazine-1-carbonyl]cyclopropan-1-ol | 405.18 | 406.13 | 0.76 | 13 |
| 1-{4-[4-(3-methyl-1H-indazol-6-yl)benzoyl]piperazine-1-carbonyl}cyclopropan-1-amine | 403.20 | 404.26 | 0.80 | 14 |
| 1-{4-[2-fluoro-4-(1-methyl-1H-1,3-benzodiazol-5-yl)benzoyl]piperazine-1-carbonyl}cyclopropan-1-amine | 421.19 | 422.20 | 0.54 | 14 |
| 6-{4-[4-(1-hydroxycyclopropanecarbonyl)piperazine-1-carbonyl]phenyl}-1-methyl-1H-indazol-3-ol | 420.18 | 421.11 | 0.78 | 13 |
| 1-{4-[4-(1,2,3,4-tetrahydroquinolin-1-yl)benzoyl]piperazine-1-carbonyl}cyclopropan-1-ol | 405.21 | 406.14 | 1.33 | 20 |
| 1-{4-[4-(3-methyl-1H-indazol-7-yl)benzoyl]piperazine-1-carbonyl}cyclopropan-1-amine | 403.20 | 404.20 | 0.88 | 14 |
| 1-[4-(4-{4H,5H,6H,7H-thieno[3,2-c]pyridin-5-yl}benzoyl)piperazine-1-carbonyl]cyclopropan-1-ol | 411.16 | 412.15 | 1.23 | 19 |
| 1-{4-[4-(1-methyl-1H-indazol-6-yl)benzoyl]piperazine-1-carbonyl}cyclobutan-1-amine | 417.22 | 418.29 | 0.84 | 14 |
| 1-(4-{4-[3-(2-amino-1,3-thiazol-4-yl)phenyl]benzoyl}piperazine-1-carbonyl)cyclopropan-1-ol | 448.16 | 449.14 | 0.97 | 13 |
| 1-{4-[4-(1,3-dimethyl-1H-indazol-5-yl)benzoyl]piperazine-1-carbonyl}cyclobutan-1-amine | 431.23 | 432.31 | 0.86 | 14 |
| 1-(4-{4-[3-(cyclopropanesulfonyl)phenyl]-2-fluorobenzoyl}piperazine-1-carbonyl)cyclopropan-1-ol | 472.15 | 473.13 | 1.05 | 13 |
| 1-{4-[4-(6-fluoroquinazolin-2-yl)benzoyl]piperazine-1-carbonyl}cyclopropan-1-ol | 420.16 | 421.10 | 1.13 | 13 |
| N-(5-{4-[4-(1-hydroxycyclopropanecarbonyl)piperazine-1-carbonyl]phenyl}-1,2-benzoxazol-3-yl)cyclopropanecarboxamide | 474.19 | 475.15 | 1.00 | 29 |
| 4-{4-[4-(1-hydroxycyclopropanecarbonyl)piperazine-1-carbonyl]phenyl}-1-methyl-2,3-dihydro-1H-indol-2-one | 419.18 | 420.13 | 0.94 | 13 |
| 1-[(3R)-4-[4-(6-fluoro-1,3-benzoxazol-2-yl)benzoyl]-3-methylpiperazine-1-carbonyl]cyclopropan-1-ol | 423.16 | 424.18 | 1.20 | 4 |
| 1-{4-[4-(2-methyl-1H-1,3-benzodiazol-1-yl)benzoyl]piperazine-1-carbonyl}cyclopropan-1-ol | 404.18 | 405.17 | 0.71 | 17 |
| 1-{4-[4-(5-chloro-2-fluorophenyl)benzoyl]piperazine-1-carbonyl}cyclopropan-1-amine | 401.13 | 402.09 | 1.06 | 14 |
| 1-{4-[3-fluoro-4-(2-methyl-2H-indazol-6-yl)benzoyl]piperazine-1-carbonyl}cyclopropan-1-ol | 422.18 | 423.10 | 0.94 | 13 |
| 3-{4-[4-(1-hydroxycyclopropanecarbonyl)piperazine-1-carbonyl]phenyl}-N-methylbenzamide | 407.18 | 408.18 | 0.80 | 13 |
| 1-(4-{4-[3-(5-amino-1H-pyrazol-3-yl)phenyl]benzoyl}piperazine-1-carbonyl)cyclopropan-1-ol | 431.20 | 432.18 | 0.79 | 25 |
| 1-[(2S)-2-methyl-4-[4-(5,6,7,8-tetrahydro-1,7-naphthyridin-7-yl)benzoyl]piperazine-1-carbonyl]cyclopropan-1-ol | 420.22 | 421.09 | 1.02 | 19 |
| 1-[(3S)-4-[4-(4-chloro-2-fluorophenyl)benzoyl]-3-methylpiperazine-1-carbonyl]cyclopropan-1-ol | 416.13 | 417.14 | 1.40 | 23 |
| 2-(3-{4-[4-(1-hydroxycyclopropanecarbonyl)piperazine-1-carbonyl]phenyl}phenoxy)-N-methylacetamide | 437.20 | 438.19 | 0.86 | 13 |
| 1-{4-[4-(1-cyclopropyl-1H-indazol-5-yl)benzoyl]piperazine-1-carbonyl}cyclopropan-1-ol | 430.20 | 431.12 | 1.15 | 7 |
| 1-methyl-5-{4-[4-(oxetane-2-carbonyl)piperazine-1-carbonyl]phenyl}-1H-1,3-benzodiazole | 404.18 | 405.13 | 0.60 | 13 |
| (1-{4-[4-(1-methyl-1H-1,3-benzodiazol-5-yl)benzoyl]piperazine-1-carbonyl}cyclopropyl)methanol | 418.20 | 419.19 | 0.60 | 1 |
| 1-{4-[4-(1-methyl-1H-1,3-benzodiazol-5-yl)benzoyl]piperazine-1-carbonyl}cyclobutan-1-amine | 417.22 | 418.23 | 0.53 | 14 |

TABLE 2-1-continued

| IC50 (uM) < 0.5 | Mol. Weight | Mass Ion Observed | HPLC retention time (min) | Method |
|---|---|---|---|---|
| 1-[4-(3-chloro-4-{3-chloroimidazo[1,2-a]pyridin-2-yl}benzoyl)piperazine-1-carbonyl]cyclopropan-1-ol | 458.09 | 459.08 | 1.00 | 13 |
| 1-[(2R)-2-(hydroxymethyl)-4-[4-(1-methyl-1H-1,3-benzodiazol-5-yl)benzoyl]piperazine-1-carbonyl]cyclopropan-1-ol | 434.20 | 435.25 | 0.60 | 23 |
| 1-{4-[4-(2,3,4,5-tetrahydro-1H-3-benzazepin-3-yl)benzoyl]piperazine-1-carbonyl}cyclopropan-1-ol | 419.22 | 420.28 | 1.35 | 19 |
| 1-[(2S,6R)-4-[4-(6-fluoro-1,3-benzoxazol-2-yl)benzoyl]-2,6-dimethylpiperazine-1-carbonyl]cyclopropan-1-amine | 436.19 | 437.23 | 1.06 | 28 |
| 1-[(2S)-4-[4-(6-fluoro-1,3-benzoxazol-2-yl)benzoyl]-2-methylpiperazine-1-carbonyl]cyclopropan-1-amine | 422.18 | 423.16 | 0.99 | 28 |
| 1-(4-{4-[3-(5-methyl-1,3,4-thiadiazol-2-yl)phenyl]benzoyl}piperazine-1-carbonyl)cyclopropan-1-ol | 448.16 | 449.14 | 1.01 | 13 |
| 1-{4-[4-(3-methyl-2H-indazol-2-yl)benzoyl]piperazine-1-carbonyl}cyclopropan-1-ol | 404.18 | 405.18 | 1.18 | 26 |
| 2-(3-{4-[4-(1-hydroxycyclopropanecarbonyl)piperazine-1-carbonyl]phenyl}phenyl)-2-methylpropanenitrile | 417.21 | 418.23 | 1.23 | 1 |
| 1-[(2S)-4-{4-[3-(cyclopropanesulfonyl)phenyl]benzoyl}-2-methylpiperazine-1-carbonyl]cyclopropan-1-ol | 468.17 | 469.23 | 1.08 | 3 |
| 1-(3-{4-[4-(1-hydroxycyclopropanecarbonyl)piperazine-1-carbonyl]phenyl}phenyl)pyrrolidin-2-one | 433.20 | 434.18 | 0.95 | 13 |
| 3-(3-{4-[4-(1-aminocyclopropanecarbonyl)piperazine-1-carbonyl]-3-fluorophenyl}phenyl)-1,2-oxazol-5-amine | 449.19 | 450.19 | 0.82 | 14 |
| 6-{4-[4-(1-hydroxycyclopropanecarbonyl)piperazine-1-carbonyl]phenyl}-N-methylpyridine-2-carboxamide | 408.18 | 409.14 | 0.80 | 3 |
| 1-[(3S)-4-[4-(6-fluoro-1,3-benzoxazol-2-yl)benzoyl]-3-methylpiperazine-1-carbonyl]cyclopropan-1-ol | 423.16 | 424.18 | 1.20 | 4 |
| 4-(3-{4-[4-(1-hydroxycyclopropanecarbonyl)piperazine-1-carbonyl]phenyl}phenyl)oxane-4-carbonitrile | 459.22 | 460.23 | 1.13 | 13 |
| 1-(4-{4-[3-(5-methyl-1,2,4-oxadiazol-3-yl)phenyl]benzoyl}piperazine-1-carbonyl)cyclopropan-1-ol | 432.18 | 433.12 | 1.13 | 13 |
| 5-(3-{4-[4-(1-hydroxycyclopropanecarbonyl)piperazine-1-carbonyl]phenyl}phenyl)-5-methylimidazolidine-2,4-dione | 462.19 | 463.22 | 0.81 | 13 |
| 1-{4-[2-fluoro-4-(2-methyl-1H-indol-1-yl)benzoyl]piperazine-1-carbonyl}cyclopropan-1-amine | 420.20 | 421.16 | 1.15 | 35 |
| 1-{4-[4-(3-amino-1,2-benzoxazol-6-yl)benzoyl]piperazine-1-carbonyl}cyclopropan-1-ol | 406.16 | 407.16 | 0.91 | 13 |
| 1-{4-[2-fluoro-4-(2-methyl-2H-indazol-6-yl)benzoyl]piperazine-1-carbonyl}cyclobutan-1-amine | 435.21 | 436.27 | 0.80 | 14 |
| 2-(3-{4-[4-(1-hydroxycyclopropanecarbonyl)piperazine-1-carbonyl]phenyl}phenyl)-1λ⁶,2-thiazolidine-1,1-dione | 469.17 | 470.13 | 0.98 | 13 |
| 1-{4-[4-(6-chloro-1,3-benzoxazol-2-yl)-3-fluorobenzoyl]piperazine-1-carbonyl}cyclopropan-1-ol | 443.10 | 444.05 | 1.30 | 13 |
| 1-{4-[4-(2,3,4,5-tetrahydro-1H-2-benzazepin-2-yl)benzoyl]piperazine-1-carbonyl}cyclopropan-1-ol | 419.22 | 420.26 | 1.29 | 19 |
| 1-[4-(4-{3-chloroimidazo[1,2-a]pyridin-2-yl}-3-fluorobenzoyl)piperazine-1-carbonyl]cyclopropan-1-ol | 442.12 | 443.07 | 0.98 | 13 |
| 1-(3-{4-[4-(1-aminocyclopropanecarbonyl)piperazine-1-carbonyl]phenyl}phenyl)cyclopropane-1-carbonitrile | 414.21 | 415.16 | 0.97 | 14 |
| 1-{4-[3-fluoro-4-(6-fluoro-1,3-benzoxazol-2-yl)benzoyl]piperazine-1-carbonyl}cyclopropan-1-ol | 427.13 | 428.08 | 1.17 | 13 |
| 1-{4-[4-(2-methyl-2H-1,2,3-benzotriazol-5-yl)benzoyl]piperazine-1-carbonyl}cyclopropan-1-ol | 405.18 | 406.13 | 0.95 | 16 |
| 1-[(3S)-3-methyl-4-[4-(1-methyl-1H-1,3-benzodiazol-5-yl)benzoyl]piperazine-1-carbonyl]cyclopropan-1-amine | 417.22 | 418.23 | 0.54 | 28 |

TABLE 2-2

| IC50 (uM) ≥0.5 and <5.0 | Mol. Weight | Mass Ion Observed | HPLC retention time (min) | Method |
|---|---|---|---|---|
| 1-[(4-{[4-(2-fluoro-3-methoxyphenyl)phenyl]carbonyl}piperazin-1-yl)carbonyl]cyclopropan-1-ol | 398.43 | 399.20 | 1.19 | 5 |
| 1-{[4-({4-[2-fluoro-3-(trifluoromethoxy)phenyl]phenyl}carbonyl)piperazin-1-yl]carbonyl}cyclopropan-1-ol | 452.40 | 453.16 | 1.43 | 5 |
| 1-({4-[4-{6-chloroimidazo[1,2-a]pyridin-3-yl}phenyl)carbonyl]piperazin-1-yl}carbonyl)cyclopropan-1-ol | 424.88 | 425.04 | 0.75 | 7 |

TABLE 2-2-continued

| IC50 (uM) ≥0.5 and <5.0 | Mol. Weight | Mass Ion Observed | HPLC retention time (min) | Method |
|---|---|---|---|---|
| 1-({4-[(4-{furo[3,2-c]pyridin-4-yl}phenyl)carbonyl]piperazin-1-yl}carbonyl)cyclopropan-1-ol | 391.42 | 392.15 | 0.77 | 7 |
| 1-[(4-{[4-methyl-2-(quinolin-3-yl)-1,3-thiazol-5-yl]carbonyl}piperazin-1-yl)carbonyl]cyclopropan-1-ol | 422.50 | 423.13 | 1.01 | 5 |
| 1-({4-[(4-{imidazo[1,2-a]pyrazin-6-yl}phenyl)carbonyl]piperazin-1-yl}carbonyl)cyclopropan-1-ol | 391.42 | 392.16 | 0.69 | 7 |
| 4-fluoro-3-[4-({4-[(1-hydroxycyclopropyl)carbonyl]piperazin-1-yl}carbonyl)phenyl]-N-(propan-2-yl)benzamide | 453.51 | 454.24 | 1.28 | 5 |
| 1-{[(3S)-4-{[4-(4-chloro-2-fluorophenyl)phenyl]carbonyl}-3-(hydroxymethyl)piperazin-1-yl]carbonyl}cyclopropan-1-ol | 432.87 | 433.13 | 1.28 | 1 |
| 1-{[4-({4-[1-(trifluoromethyl)-1H-indol-5-yl]phenyl}carbonyl)piperazin-1-yl]carbonyl}cyclopropan-1-ol | 457.45 | 458.12 | 1.22 | 10 |
| 1-{[4-({4-[2-(trifluoromethyl)imidazo[1,2-a]pyridin-6-yl]phenyl}carbonyl)piperazin-1-yl]carbonyl}cyclopropan-1-ol | 458.43 | 459.14 | 1.09 | 7 |
| 1-({4-[(4-{imidazo[1,2-a]pyrimidin-7-yl}phenyl)carbonyl]piperazin-1-yl}carbonyl)cyclopropan-1-ol | 391.42 | 392.16 | 0.55 | 7 |
| 1-[(4-{[2-methoxy-4-(quinolin-6-yl)phenyl]carbonyl}piperazin-1-yl)carbonyl]cyclopropan-1-ol | 431.48 | 432.20 | 0.86 | 5 |
| 1-[(4-{[4-(5-methoxy-1H-1,3-benzodiazol-2-yl)phenyl]carbonyl}piperazin-1-yl)carbonyl]cyclopropan-1-ol | 420.46 | 421.18 | 0.75 | 7 |
| 1-[(4-{[4-(4-chloro-1H-1,3-benzodiazol-2-yl)phenyl]carbonyl}piperazin-1-yl)carbonyl]cyclopropan-1-ol | 424.88 | 425.11 | 1 | 7 |
| 1-[(4-{[6-(2-methoxyquinolin-6-yl)pyridin-3-yl]carbonyl}piperazin-1-yl)carbonyl]cyclopropan-1-ol | 432.47 | 433.17 | 1.16 | 5 |
| 1-[(4-{[5-(2-methoxyquinolin-6-yl)pyridin-2-yl]carbonyl}piperazin-1-yl)carbonyl]cyclopropan-1-ol | 432.47 | 433.17 | 1.17 | 5 |
| 1-[(4-{[2-(4-fluorophenyl)-1,3-benzothiazol-6-yl]carbonyl}piperazin-1-yl)carbonyl]cyclopropan-1-ol | 425.48 | 426.07 | 1.26 | 5 |
| 1-[(4-{[4-(2-fluoro-5-methylphenyl)phenyl]carbonyl}piperazin-1-yl)carbonyl]cyclopropan-1-ol | 382.43 | 383.21 | 1.54 | 5 |
| 1-[(4-{[4-(1,3-benzothiazol-5-yl)-2-methoxyphenyl]carbonyl}piperazin-1-yl)carbonyl]cyclopropan-1-ol | 437.51 | 438.17 | 1.06 | 5 |
| 1-[(4-{[4-methyl-2-(1-methyl-1H-indol-5-yl)-1,3-thiazol-5-yl]carbonyl}piperazin-1-yl)carbonyl]cyclopropan-1-ol | 424.52 | 425.16 | 1.13 | 5 |
| 6-[4-({4-[(1-hydroxycyclopropyl)carbonyl]piperazin-1-yl}carbonyl)phenyl]-2,3-dihydro-1,3-benzoxazol-2-one | 407.42 | 408.14 | 0.84 | 7 |
| 1-[(4-{[5-(4-chloro-2-fluorophenyl)pyridin-2-yl]carbonyl}piperazin-1-yl)carbonyl]cyclopropan-1-ol | 403.84 | 404.16 | 1.23 | 1 |
| 1-[(4-{[4-(1H-1,3-benzodiazol-2-yl)phenyl]carbonyl}piperazin-1-yl)carbonyl]cyclopropan-1-ol | 390.44 | 391.14 | 0.73 | 3 |
| 1-{[4-({4-[2-chloro-5-(trifluoromethyl)phenyl]phenyl}carbonyl)piperazin-1-yl]carbonyl}cyclopropan-1-ol | 452.85 | 453.12 | 1.47 | 5 |
| 1-[(4-{[5-(quinolin-6-yl)pyrazin-2-yl]carbonyl}-piperazin-1yl)carbonyl]cyclopropan-1-ol | 403.43 | 404.19 | 0.79 | 5 |
| 1-[(4-{[6-(quinolin-6-yl)pyridin-3-yl]carbonyl}piperazin-1-yl)carbonyl]cyclopropan-1-ol | 402.45 | 403.17 | 0.73 | 5 |
| 1-{[4-({4-[2-fluoro-3-(trifluoromethyl)phenyl]phenyl}carbonyl)piperazin-1-yl]carbonyl}cyclopropan-1-ol | 436.40 | 437.19 | 1.38 | 5 |
| 1-[(4-{[4-(quinolin-6-yl)-2-(trifluoromethyl)phenyl]carbonyl}piperazin-1-yl)carbonyl]cyclopropan-1-ol | 469.46 | 470.19 | 1.06 | 5 |
| 1-{[4-({4-[3-fluoro-5-(trifluoromethyl)phenyl]phenyl}carbonyl)piperazin-1-yl]carbonyl}cyclopropan-1-ol | 436.40 | 437.17 | 1.43 | 5 |

TABLE 2-2-continued

| IC50 (uM) ≥0.5 and <5.0 | Mol. Weight | Mass Ion Observed | HPLC retention time (min) | Method |
|---|---|---|---|---|
| 1-[(4-{[4-(5-fluoro-1H-1,3-benzodiazol-2-yl)phenyl]carbonyl}piperazin-1-yl)carbonyl]cyclopropan-1-ol | 408.43 | 409.09 | 0.86 | 5 |
| 4-fluoro-3-[4-({4-[(1-hydroxycyclopropyl)carbonyl]piperazin-1-yl}carbonyl)phenyl]-N-methylbenzamide | 425.45 | 426.19 | 1.1 | 5 |
| 1-[(4-{{4-(3-methyl-1,2-benzoxazol-6-yl)phenyl]carbonyl}piperazin-1-yl)carbonyl]cyclopropan-1-ol | 405.45 | 406.17 | 1.01 | 7 |
| 5-[4-({4-[(1-hydroxycyclopropyl)carbonyl]piperazin-1-yl}carbonyl)phenyl]-2,3-dihydro-1,3-benzoxazol-2-one | 407.42 | 408.15 | 0.91 | 7 |
| 1-({4-[(4-{[1,2,4]triazolo[4,3-b]pyridazin-6-yl}phenyl)carbonyl]piperazin-1-yl}carbonyl)cyclopropan-1-ol | 392.41 | 393.13 | 0.65 | 7 |
| 1-{[4-({4-[7-(trifluoromethyl)quinolin-4-yl]phenyl}carbonyl)piperazin-1-yl]carbonyl}cyclopropan-1-ol | 469.46 | 470.09 | 1.28 | 7 |
| 1-{[4-({4-[4-chloro-2-(trifluoromethyl)phenyl]phenyl}carbonyl)piperazin-1-yl]carbonyl}cyclopropan-1-ol | 452.85 | 453.15 | 1.5 | 5 |
| 1-{[4-({4-[1-(propan-2-yl)-1H-indazol-5-yl]phenyl}carbonyl)piperazin-1-yl]carbonyl}cyclopropan-1-ol | 432.51 | 433.24 | 1.23 | 3 |
| 1-[(4-{[5-(quinolin-3-yl)pyrazin-2-yl]carbonyl}piperazin-1-yl)carbonyl]cyclopropan-1-ol | 403.43 | 404.22 | 0.92 | 5 |
| 1-{(4-{{3-methoxy-4-(quinolin-6-yl)phenyl]carbonyl}piperazin-1-yl)carbonyl]cyclopropan-1-ol | 431.48 | 432.20 | 0.86 | 5 |
| 1-[(4-{{4-(5,6-difluoro-1H-1,3-benzodiazol-2-yl)phenyl]carbonyl}piperazin-1-yl)carbonyl]cyclopropan-1-ol | 426.42 | 427.15 | 0.99 | 7 |
| 1-[(4-{{4-(1-methyl-1H-1,3-benzodiazol-2-yl)phenyl]carbonyl}piperazin-1-yl)carbonyl]cyclopropan-1-ol | 404.46 | 405.11 | 0.73 | 3 |
| 1-[(4-{[4-(2-fluoro-3-methylphenyl)phenyl]carbonyl}piperazin-1-yl)carbonyl]cyclopropan-1-ol | 382.43 | 383.22 | 1.54 | 5 |
| 1-({4-[(4-{6-methoxyimidazo[1,2-a]pyridin-2-yl}phenyl)carbonyl]piperazin-1-yl}carbonyl)cyclopropan-1-ol | 420.46 | 421.19 | 0.69 | 3 |
| 1-[(4-{[4-(2-fluoro-4-methoxyphenyl)phenyl]carbonyl}piperazin-1-yl)carbonyl]cyclopropan-1-ol | 398.43 | 399.20 | 1.45 | 5 |
| 1-[(4-{[5-(quinolin-6-yl)pyrimidin-2-yl]carbonyl}piperazin-1-yl)carbonyl]cyclopropan-1-ol | 403.43 | 404.21 | 0.7 | 5 |
| 1-({4-[(4-{imidazo[1,2-a]pyridin-6-yl}phenyl)carbonyl]piperazin-1-yl}carbonyl)cyclopropan-1-ol | 390.44 | 391.21 | 0.55 | 5 |
| 1-({4-[(4-phenylphenyl)carbonyl]piperazin-1-yl}carbonyl)cyclobutan-1-ol | 364.44 | 365.17 | 1.29 | 1 |
| 1-{[4-({4-[4-fluoro-2-(trifluoromethyl)phenyl]phenyl}carbonyl)piperazin-1-yl]carbonyl}cyclopropan-1-ol | 436.40 | 437.20 | 1.38 | 5 |
| 1-[(4-{[4-(3-fluoro-4-methylphenyl)phenyl]carbonyl}piperazin-1-yl)carbonyl]cyclopropan-1-ol | 382.43 | 383.22 | 1.55 | 5 |
| 1-[(4-{[4-(2,1,3-benzoxadiazol-5-yl)phenyl]carbonyl}piperazin-1-yl)carbonyl]cyclopropan-1-ol | 392.41 | 393.16 | 1.17 | 3 |
| 1-[(4-{[2-methoxy-4-(quinolin-3-yl)phenyl]carbonyl}piperazin-1-yl)carbonyl]cyclopropan-1-ol | 431.48 | 432.20 | 1.01 | 5 |
| 1-[(4-{[5-(4-chloro-2-fluorophenyl)pyrimidin-2-yl]carbonyl}piperazin-1-yl)carbonyl]cyclopropan-1-ol | 404.82 | 405.16 | 1.12 | 1 |

TABLE 2-3

| IC50 (uM) ≥5.0 | Mol. Weight | Mass Ion Observed | HPLC retention time (min) | Method |
|---|---|---|---|---|
| 1-{[4-({4-[6-(trifluoromethyl)pyridin-3-yl]phenyl}carbonyl)piperazin-1-yl]carbonyl}cyclopropan-1-ol | 419.40 | 420.18 | 1.37 | 5 |
| 1-{[4-({4-[2-fluoro-3-(propan-2-yloxy)phenyl]phenyl}carbonyl)piperazin-1-yl]carbonyl}cyclopropan-1-ol | 426.48 | 427.21 | 1.58 | 5 |
| 1-({4-[(4-[6-fluoroimidazo[1,2-a]pyridin-2-yl]phenyl}carbonyl]piperazin-1-yl}carbonyl)cyclopropan-1-ol | 408.43 | 409.18 | 0.65 | 3 |
| 1-[(4-{[6-(4-fluorophenyl)imidazo[1,2-a]pyridin-2-yl]carbonyl}piperazin-1-yl)carbonyl]cyclopropan-1-ol | 408.43 | 409.11 | 1.08 | 5 |
| 1-[(4-{[4-(2-chloro-5-fluorophenyl)phenyl]carbonyl}piperazin-1-yl)carbonyl]cyclopropan-1-ol | 402.85 | 403.13 | 1.52 | 5 |
| 1-[(4-{{4-[2,3-difluorophenyl)phenyl]carbonyl}piperazin-1-yl)carbonyl]cyclopropan-1-ol | 386.39 | 387.18 | 1.45 | 5 |
| 1-[(4-{[4-(3-fluoro-2-methoxyphenyl)phenyl]carbonyl}piperazin-1-yl)carbonyl]cyclopropan-1-ol | 398.43 | 399.20 | 1.46 | 5 |
| 1-[(4-{[4-(1,5-naphthyridin-3-yl)phenyl]carbonyl}piperazin-1-yl)carbonyl]cyclopropan-1-ol | 402.45 | 403.19 | 0.8 | 2 |
| 1-[(4-{[4-(2-fluoro-5-methoxyphenyl)phenyl]carbonyl}piperazin-1-yl)carbonyl]cyclopropan-1-ol | 398.43 | 399.21 | 1.44 | 5 |
| 1-{[(2S,5R)-4-{[4-(isoquinolin-6-yl)pheny]carbonyl}-2,5-dimethylpiperazin-1-yl]carbonyl}cyclopropan-1-ol | 429.51 | 430.18 | 0.79 | 9 |
| 1-{[4-({6-phenylimidazo[1,2-a]pyridin-2-yl}carbonyl)piperazin-1-yl]carbonyl}cyclopropan-1-ol | 390.44 | 391.16 | 1.04 | 5 |
| 1-[(4-{[4-(4,5-difluoro-2-methoxyphenyl)phenyl]carbonyl}piperazin-1-yl)carbonyl]cyclopropan-1-ol | 416.42 | 417.18 | 1.49 | 5 |
| 1-{[(2S)-4-{[4-(4-chloro-2-fluorophenyl)phenyl]carbonyl}-2-(hydroxymethyl)piperazin-1-yl]carbonyl}cyclopropan-1-ol | 432.87 | 433.04 | 1.29 | 1 |
| 1-({4-[(4-phenoxyphenyl)carbonyl]piperazin-1-yl}carbonyl)cyclopropan-1-ol | 366.41 | 367.12 | 1.21 | 9 |
| 5-fluoro-2-[4-({4-[(1-hydroxycyclopropyl)carbonyl]piperazin-1-yl}carbonyl)phenyl]benzonitrile | 393.41 | 394.17 | 1.15 | 5 |
| 2-methoxy-2-methyl-1-{4-[(4-phenylphenyl)carbonyl]piperazin-1-yl}propan-1-one | 366.45 | 367.15 | 1.44 | 8 |
| 3,3,3-trifluoro-2-hydroxy-2-methyl-1-{4-[(4-phenylphenyl)carbonyl]piperazin-1-yl}propan-1-one | 406.40 | 407.13 | 1.43 | 1 |
| 1-[(4-{[4-(2-chloro-4-methoxyphenyl)phenyl]carbonyl}piperazin-1-yl)carbonyl]cyclopropan-1-ol | 414.88 | 415.17 | 1.52 | 5 |
| 2-hydroxy-2-methyl-1-{4-[(4-phenylphenyl)carbonyl]piperazin-1-yl}propan-1-one | 352.43 | 353.14 | 1.24 | 1 |
| 1-[(4-{[4-(4-methylphenyl)phenyl]carbonyl}piperazin-1-yl)carbonyl]cyclopropan-1-ol | 364.44 | 365.25 | 1.53 | 5 |
| 1-{[4-({4-[2-chloro-5-(hydroxymethyl)phenyl]phenyl}carbonyl)piperazin-1-yl]carbonyl}cyclopropan-1-ol | 414.88 | 415.17 | 1.22 | 5 |
| 1-[(4-{[2-(1,3-benzothiazol-5-yl)-4-methyl-1,3-thiazol-5-yl]carbonyl}piperazin-1-yl)carbonyl]cyclopropan-1-ol | 428.53 | 429.13 | 0.97 | 5 |
| 1-({4-[(3-phenoxyphenyl)carbonyl]piperazin-1-yl}carbonyl)cyclopropan-1-ol | 366.41 | 367.09 | 1.19 | 9 |
| 1-[(4-{[4-(3-methylphenyl)phenyl]carbonyl}piperazin-1-yl)carbonyl]cyclopropan-1-ol | 364.44 | 365.22 | 1.53 | 5 |
| 1-{(4-{[4-(3-methoxypyridin-4-yl)phenyl]carbonyl}piperazin-1-yl)carbonyl}cyclopropan-1-ol | 381.43 | 382.24 | 0.64 | 5 |
| 1-({4-[(4-phenylphenyl)carbonyl]piperazin-1-yl}carbonyl)cyclopentan-1-ol | 378.46 | 379.25 | 1.37 | 5 |
| 1-[(4-{[4-(1-methyl-1H-indazol-7-yl)phenyl]carbonyl}piperazin-1-yl)carbonyl]cyclopropan-1-ol | 404.46 | 405.21 | 1.3 | 5 |

TABLE 2-3-continued

| IC50 (uM) ≥5.0 | Mol. Weight | Mass Ion Observed | HPLC retention time (min) | Method |
|---|---|---|---|---|
| 1-[(4-{[4-(6-methylpyridin-3-yl)phenyl]carbonyl}piperazin-1-yl)carbonyl]cyclopropan-1-ol | 365.43 | 366.23 | 0.58 | 5 |
| (2S)-2-hydroxy-1-{4-[(4-phenylphenyl)carbonyl]piperazin-1-yl}propan-1-one | 338.40 | 339.14 | 1.17 | 1 |
| 1-{[4-([5-chioro-2-(propan-2-yloxy)phenyl]phenyl}carbonyl)piperazin-1-yl]carbonyl}cyclopropan-1-ol | 442.94 | 443.20 | 1.74 | 5 |
| 1-[(4-{[6-(4-chloro-2-fluorophenyl)pyridin-3-yl]carbonyl}piperazin-1-yl)carbonyl]cyclopropan-1-ol | 403.84 | 404.14 | 1.22 | 1 |
| 1-[(4-{[4-(5-fluoropyridin-3-yl)phenyl]carbonyl}piperazin-1-yl)carbonyl]cyclopropan-1-ol | 369.39 | 370.17 | 1.11 | 5 |
| 1-[(4-{[4-(2,5-difluorophenyl)phenyl]carbonyl}piperazin-1-yl)carbonyl]cyclopropan-1-ol | 386.39 | 387.18 | 1.46 | 5 |
| 2-hydroxy-1-{4-[(4-phenylphenyl)carbonyl]piperazin-1-yl}ethan-1-one | 324.37 | 325.16 | 1.1 | 5 |
| 1-[(4-{[4-(2-fluoro-4-methylphenyl)phenyl]carbonyl}piperazin-1-yl)carbonyl]cyclopropan-1-ol | 382.43 | 383.17 | 1.55 | 5 |
| 1-[(4-{[4-(2,6-dimethoxypyridin-3-yl)phenyl]carbonyl}piperazin-1-yl)carbonyl]cyclopropan-1-ol | 411.45 | 412.18 | 1.48 | 5 |
| 1-[(4-{[4-(2,4-dichloro-3-methoxyphenyl)phenyl]carbonyl}piperazin-1-yl)carbonyl]cyclopropan-1-ol | 449.33 | 449.15 | 1.62 | 5 |
| 1-[(4-{[4-(5-fluoro-2-methylphenyl)phenyl]carbonyl}piperazin-1-yl)carbonyl]cyclopropan-1-ol | 382.43 | 383.20 | 1.53 | 5 |

Cell Proliferation Assays for FASN Inhibitors

The effects of the FASN inhibitors on cultured cancer cell proliferation were studies with cell proliferation assays. PC3 cells were maintained at standard culture media (F12K media supplemented with 10% fetal bovine serum, 1×MEM nonessential amino acid and 1× penicillin/streptomycin). 2000-3000 cells/100 L/well was seeded in a 96-well clear culture plate. The cells were incubated overnight in 5% $CO_2$ at 37° C. for attachment. Cell media were removed and replaced with F12K media containing 10% lipid reduced serum and compound. The final DMSO concentration is 0.1%. The cells were maintained in 5% $CO_2$ at 37° C. for 4 days. The viability of cells was determined by MTT assays. The IC50 of a given compound was calculated by fitting the dose response curve with a four parameter logistic equation.

Results

Table 3-1 lists the compounds having an IC50≤0.5 μM.

Table 3-2 lists the compounds having an IC50≥0.5 μM.

In addition, the Molecular Weight, Mass Ion Spectrometry Results, HPLC retention time, and the Method used to synthesize the compound are also listed.

TABLE 3-1

| IC50 (uM) <0.5 | Mol. Weight | Mass Ion Observed | HPLC retention time (min) | Method |
|---|---|---|---|---|
| 1-[(4-{[2-fluoro-4-(1-methyl-1H-indol-5-yl)phenyl]carbonyl}piperazin-1-yl)carbonyl]cyclopropan-1-ol | 421.46 | 422.22 | 1.29 | 5 |
| 1-[(4-{[4-(isoquinolin-6-yl)phenyl]carbonyl}piperazin-1-yl)carbonyl]cyclopropan-1-ol | 401.17 | 402.02 | 1.48 | 1 |
| 1-[(4-{[3-chloro-4-(quinolin-3-yl)phenyl]carbonyl}piperazin-1-yl)carbonyl]cyclopropan-1-ol | 435.90 | 436.15 | 1.14 | 5 |
| 5-[2-chloro-4-({4-[(1-hydroxycyclopropyl)carbonyl]piperazin-1-yl}carbonyl)phenyl]-1H-indole-3-carbonitrile | 448.90 | 449.10 | 1.06 | 5 |
| 1-[(4-{[4-(quinolin-2-yl)phenyl]carbonyl}piperazin-1-yl)carbonyl]cyclopropan-1-ol | 401.46 | 402.16 | 1.14 | 7 |
| 1-[(4-{[3-chloro-4-(1-methyl-1H-indol-5-yl)phenyl]carbonyl}piperazin-1-yl)carbonyl]cyclopropan-1-ol | 437.92 | 438.18 | 1.33 | 5 |

TABLE 3-1-continued

| IC50 (uM) <0.5 | Mol. Weight | Mass Ion Observed | HPLC retention time (min) | Method |
|---|---|---|---|---|
| 1-[(4-{[2-chloro-4-(1-methyl-1H-indol-5-yl)phenyl]carbonyl}piperazin-1-yl)carbonyl]cyclopropan-1-ol | 437.92 | 438.15 | 1.32 | 5 |
| 1-[(4-{[4-(1H-indol-4-yl)phenyl]carbonyl}piperazin-1-yl)carbonyl]cyclopropan-1-ol | 389.45 | 390.18 | 1.06 | 7 |
| 1-[(4-{[3-methyl-4-(1-methyl-1H-indol-5-yl)phenyl]carbonyl}piperazin-1-yl)carbonyl]cyclopropan-1-ol | 417.50 | 418.25 | 1.3 | 5 |
| 1-[(4-{[4-(1-benzofuran-5-yl)phenyl]carbonyl}piperazin-1-yl)carbonyl]cyclopropan-1-ol | 390.16 | 391.01 | 2.43 | 2 |
| 5-[4-({4-[(1-hydroxycyclopropyl)carbonyl]piperazin-1-yl}carbonyl)phenyl]-1H-indole-2-carbonitrile | 414.46 | 415.15 | 1.09 | 3 |
| 1-({4-[(4-{imidazo[1,2-b]pyridazin-6-yl}phenyl)carbonyl]piperazin-1-yl}carbonyl)cyclopropan-1-ol | 391.42 | 392.10 | 0.69 | 7 |
| 1-[(4-{[4-(1H-indol-5-yl)phenyl]carbonyl}piperazin-1-yl)carbonyl]cyclopropan-1-ol | 389.17 | 390.06 | 2.11 | 2 |
| 1-[(4-{[4-(1-methyl-1H-1,3-benzodiazol-5-yl)phenyl]carbonyl}piperazin-1-yl)carbonyl]cyclopropan-1-ol | 404.46 | 405.08 | 0.68 | 7 |
| 5-[4-({4-[(1-hydroxycyclopropyl)carbonyl]piperazin-1-yl}carbonyl)phenyl]-1H-indole-3-carbonitrile | 414.46 | 415.17 | 0.97 | 7 |
| 1-[(4-{[4-(1,3-benzothiazol-5-yl)-3-chlorophenyl]carbonyl}piperazin-1-yl)carbonyl]cyclopropan-1-ol | 441.93 | 442.12 | 1.16 | 5 |
| 1-[(4-{[2-fluoro-4-(6-methoxyquinolin-2-yl)phenyl]carbonyl}piperazin-1-yl)carbonyl]cyclopropan-1-ol | 449.47 | 450.15 | 1.25 | 5 |
| 1-[(4-{[2-chloro-4-(quinolin-3-yl)phenyl]carbonyl}piperazin-1-yl)carbonyl]cyclopropan-1-ol | 435.90 | 436.16 | 1.11 | 5 |
| 1-[(4-{[3-methyl-4-(quinolin-3-yl)phenyl]carbonyl}piperazin-1-yl)carbonyl]cyclopropan-1-ol | 415.48 | 416.21 | 1.07 | 5 |
| 1-[(4-{[2-fluoro-4-(quinolin-3-yl)phenyl]carbonyl}piperazin-1-yl)carbonyl]cyclopropan-1-ol | 419.45 | 420.18 | 1.07 | 5 |
| 1-[(4-{[3-chloro-4-(quinolin-6-yl)phenyl]carbonyl}piperazin-1-yl)carbonyl]cyclopropan-1-ol | 435.90 | 436.16 | 0.99 | 5 |
| 1-[(4-{[4-(6-methoxynaphthalen-2-yl)phenyl}carbonyl}piperazin-1-yl)carbonyl]cyclopropan-1-ol | 430.50 | 431.12 | 1.36 | 5 |
| 1-[(4-{[2-fluoro-4-(7-fluoro-1H-indol-5-yl)phenyl]carbonyl}piperazin-1-yl)carbonyl]cyclopropan-1-ol | 425.43 | 426.04 | 1.16 | 5 |
| 1-({4-[(4-{pyrazolo[1,5-a]pyridin-2-yl}phenyl)carbonyl]piperazin-1-yl}carbonyl)cyclopropan-1-ol | 390.44 | 391.15 | 0.95 | 3 |
| 1-[(4-{[3-fluoro-4-(quinolin-3-yl)phenyl]carbonyl}piperazin-1-yl)carbonyl]cyclopropan-1-ol | 419.45 | 420.20 | 1.08 | 5 |
| 1-[(4-{[4-(1-methyl-1H-indazol-6-yl)phenyl]carbonyl}piperazin-1-yl)carbonyl]cyclopropan-1-ol | 404.46 | 405.09 | 1.05 | 5 |
| 1-[(4-{[2-fluoro-4-(quinolin-6-yl)phenyl]carbonyl}piperazin-1-yl)carbonyl]cyclopropan-1-ol | 419.45 | 420.19 | 0.91 | 5 |
| 1-[(4-{[4-(2-methyl-2H-indazol-6-yl)phenyl]carbonyl}piperazin-1-yl)carbonyl]cyclopropan-1-ol | 404.46 | 405.08 | 0.94 | 5 |
| 1-[(4-{[4-(quinolin-5-yl)phenyl]carbonyl}piperazin-1-yl)carbonyl]cyclopropan-1-ol | 401.46 | 402.17 | 0.84 | 7 |
| 2-[4-({4-[(1-hydroxycyclopropyl)carbonyl]piperazin-1-yl}carbonyl)phenyl]-1,3-benzoxazole-6-carbonitrile | 416.43 | 417.15 | 1.06 | 4 |

TABLE 3-1-continued

| IC50 (uM) <0.5 | Mol. Weight | Mass Ion Observed | HPLC retention time (min) | Method |
| --- | --- | --- | --- | --- |
| 1-[(4-{[4-(1,3-benzothiazol-6-yl)phenyl]carbonyl}piperazin-1-yl)carbonyl]cyclopropan-1-ol | 407.49 | 408.14 | 1 | 2 |
| 1-[(4-{[4-(1,3-benzothiazol-5-yl)phenyl]carbonyl}piperazin-1-yl)carbonyl]cyclopropan-1-ol | 407.49 | 408.13 | 1.04 | 2 |
| N-{3-[4-({4-[(1-hydroxycyclopropyl)carbonyl]piperazin-1-yl}carbonyl)phenyl]phenyl}cyclopropanesulfonamide | 469.55 | 470.08 | 1.04 | 11 |
| 1-({4-[(4-{1H-pyrrolo[3,2-b]pyridin-5-yl}phenyl)carbonyl]piperazin-1-yl}carbonyl)cyclopropan-1-ol | 390.44 | 391.14 | 0.58 | 2 |
| 1-[(4-{[4-(1H-indazol-3-yl)phenyl]carbonyl}piperazin-1-yl)carbonyl]cyclopropan-1-ol | 390.44 | 391.12 | 0.98 | 7 |
| 1-[(4-{[2-fluoro-4-(2-methoxyquinolin-3-yl)phenyl]carbonyl}piperazin-1-yl)carbonyl]cyclopropan-1-ol | 449.47 | 450.17 | 1.39 | 5 |
| 1-{[4-({3-chloro-4-[1-(trifluoromethyl)-1H-indol-5-yl]phenyl}carbonyl)piperazin-1-yl]carbonyl}cyclopropan-1-ol | 491.89 | 492.03 | 1.3 | 10 |
| 1-[(4-{[2,3-difluoro-4-(quinolin-2-yl)phenyl]yl)phenyl]carbonyl}piperazin-1-yl)carbonyl]cyclopropan-1-ol | 437.44 | 438.15 | 1.27 | 7 |
| 1-[(4-{[4-(1,3-dimethyl-1H-indazol-5-methylphenyl]carbonyl}piperazin-1-yl)carbonyl]cyclopropan-1-ol | 421.51 | 422.16 | 1.13 | 2 |
| 1-[(4-{[4-(1,3-dimethyl-1H-indazol-5-yl)phenyl]carbonyl}piperazin-1-yl)carbonyl]cyclopropan-1-ol | 418.49 | 419.09 | 1.07 | 7 |
| 1-[(4-{[3-methyl-4-(quinolin-6-yl)phenyl]carbonyl}piperazin-1-yl)carbonyl]cyclopropan-1-ol | 415.48 | 416.21 | 0.92 | 5 |
| 1-[(4-{[4-(1-methyl-1H-indol-2-yl)phenyl]carbonyl}piperazin-1-yl)carbonyl]cyclopropan-1-ol | 403.47 | 404.25 | 1.56 | 5 |
| 1-{[4-({4-[1-(trifluoromethyl)-1H-indol-5-yl]phenyl}carbonyl)piperazin-1-yl]carbonyl}cyclopropan-1-ol | 457.45 | 458.12 | 1.22 | 10 |
| 1-[(4-{[4-(6-chloro-1,3-benzoxazol-2-yl)phenyl]carbonyl}piperazin-1-yl)carbonyl]cyclopropan-1-ol | 425.87 | 426.11 | 1.33 | 4 |
| 1-[(4-{[4-(6-methoxyquinolin-2-yl)phenyl]carbonyl}piperazin-1-yl)carbonyl]cyclopropan-1-ol | 431.48 | 432.20 | 1.16 | 5 |
| N-{3-[4-(({4-[(1-hydroxycyclopropyl)carbonyl]piperazin-1-yl}carbonyl)phenyl]phenyl}benzenesulfonamide | 505.59 | 506.10 | 1.18 | 11 |
| 1-{{4-({4-[2-methoxy-5-(trifluoromethoxy)phenyl]phenyl}carbonyl)piperazin-1-yl]carbonyl}cyclopropan-1-ol | 464.43 | 465.17 | 1.43 | 5 |
| 1-[(4-{[4-(6-fluoro-1,3-benzoxazol-2-yl)phenyl]carbonyl}piperazin-1-yl)carbonyl]cyclopropan-1-ol | 409.41 | 410.14 | 1.2 | 4 |
| N-{3-[4-({4-[(1-hydroxycyclopropyl)carbonyl]piperazin-1-yl}carbonyl)phenyl]phenyl}propane-2-sulfonamide | 471.57 | 472.19 | 1.08 | 11 |
| 1-[(4-{[4-(isoquinolin-6-yl)phenyl]carbonyl}piperazin-1-yl)carbonyl]cyclobutan-1-ol | 415.19 | 416.04 | 1.61 | 1 |
| 1-[(4-{[4-(2,1,3-benzothiadiazol-5-yl)phenyl]carbonyl}piperazin-1-yl)carbonyl]cyclopropan-1-ol | 408.47 | 409.11 | 1.17 | 3 |
| 1-[(4-{[4-(1,3-benzoxazol-2-yl)phenyl]carbonyl}piperazin-1-yl)carbonyl]cyclopropan-1-ol | 391.42 | 392.16 | 1.14 | 4 |
| 1-[(4-{[4-(2-methyl-2H-indazol-5-yl)phenyl]carbonyl}piperazin-1-yl)carbonyl]cyclopropan-1-ol | 404.46 | 405.17 | 0.88 | 7 |
| 5-[3-chloro-4-({4-[(1-hydroxycyclopropyl)carbonyl]piperazin-1-yl}carbonyl)phenyl]-1H-indole-3-carbonitrile | 448.90 | 449.10 | 1.06 | 5 |

TABLE 3-1-continued

| IC50 (uM) <0.5 | Mol. Weight | Mass Ion Observed | HPLC retention time (min) | Method |
|---|---|---|---|---|
| 1-[(4-{[4-(1,3-benzothiazol-5-yl)-3-fluorophenyl]carbonyl}piperazin-1-yl)carbonyl]cyclopropan-1-ol | 425.48 | 426.12 | 1.1 | 5 |
| 1-[(4-{[4-(5-fluoro-1,3-benzoxazol-2-yl)phenyl]carbonyl}piperazin-1-yl)carbonyl]cyclopropan-1-ol | 409.41 | 410.14 | 1.18 | 4 |
| 1-[(4-{[4-(5-chloro-1,3-benzoxazol-2-yl)phenyl]carbonyl}piperazin-1-yl)carbonyl]cyclopropan-1-ol | 425.87 | 426.13 | 1.31 | 4 |
| 1-[(4-{[4-(1,3-benzothiazol-5-yl)-2-chlorophenyl]carbonyl}piperazin-1-yl)carbonyl]cyclopropan-1-ol | 441.93 | 442.11 | 1.14 | 5 |
| 1-[(4-{[4-(3-chloro-2-methoxyphenyl)phenyl]carbonyl}piperazin-1-yl)carbonyl]cyclopropan-1-ol | 414.88 | 415.15 | 1.34 | 5 |
| 1-[(4-{[4-(6-methoxy-4-methylquinolin-2-yl)phenyl]carbonyl}piperazin-1-yl)carbonyl]cyclopropan-1-ol | 445.51 | 446.16 | 1.16 | 7 |
| 1-[(4-{[4-(2-methoxyquinolin-6-yl)phenyl]carbonyl}piperazin-1-yl)carbonyl]cyclopropan-1-ol | 431.18 | 432.08 | 2.28 | 2 |
| 1-[(4-{[4-(1H-1,3-benzodiazol-5-yl)phenyl]carbonyl}piperazin-1-yl)carbonyl]cyclopropan-1-ol | 390.44 | 391.20 | 0.6 | 2 |
| 1-({4-[(2-chloro-4-{imidazo[1,2-a]pyridin-2-yl}phenyl)carbonyl]piperazin-1-yl}carbonyl)cyclopropan-1-ol | 424.88 | 425.11 | 0.71 | 3 |
| 1-[(4-{[5-(1-methyl-1H-indol-5-yl)pyridin-2-yl]carbonyl}piperazin-1-yl)carbonyl]cyclopropan-1-ol | 404.46 | 405.28 | 1.1 | 5 |
| 6-[4-({4-[(oxetan-2-yl)carbonyl]piperazin-1-yl}carbonyl)phenyl]isoquinoline | 401.17 | 402.02 | 1.46 | 2 |
| 1-({4-[(4-{imidazo[1,2-a]pyridin-2-yl}phenyl)carbonyl]piperazin-1-yl}carbonyl)cyclopropan-1-ol | 390.44 | 391.19 | 0.61 | 3 |
| 1-[(4-{[4-(quinolin-3-yl)phenyl]carbonyl}piperazin-1-yl)carbonyl]cyclobutan-1-ol | 415.19 | 416.04 | 2.13 | 1 |
| 1-[(4-{[4-(isoquinolin-1-yl)phenyl]carbonyl}piperazin-1-yl)carbonyl]cyclopropan-1-ol | 401.46 | 402.20 | 0.9 | 7 |
| 1-({4-[(4-{furo[3,2-b]pyridin-5-yl}phenyl)carbonyl]piperazin-1-yl}carbonyl)cyclopropan-1-ol | 391.42 | 392.08 | 0.97 | 7 |
| 1-[(4-{[4-(4-chloro-2-fluorophenyl)phenyl]carbonyl}piperazin-1-yl)carbonyl]cyclopropan-1-ol | 402.85 | 403.12 | 1.36 | 1 |
| 1-[(4-{[4-(5-chloro-2-fluorophenyl)phenyl]carbonyl}piperazin-1-yl)carbonyl]cyclopropan-1-ol | 402.85 | 403.10 | 1.33 | 1 |
| 1-[(4-{[4-(1,3-benzoxazol-5-yl)phenyl]carbonyl}piperazin-1-yl)carbonyl]cyclopropan-1-ol | 391.42 | 392.16 | 0.97 | 2 |
| 1-[(4-{[4-(1H-1,3-benzodiazol-4-yl)phenyl]carbonyl}piperazin-1-yl)carbonyl]cyclopropan-1-ol | 390.44 | 391.14 | 0.7 | 7 |
| 1-[(4-{[4-(2H-1,2,3-benzotriazol-5-yl)phenyl]carbonyl}piperazin-1-yl)carbonyl]cyclopropan-1-ol | 391.42 | 392.14 | 0.79 | 3 |
| 1-[(4-{[4-(4-chloroquinolin-3-yl)phenyl]carbonyl}piperazin-1-yl)carbonyl]cyclopropan-1-ol | 435.90 | 436.11 | 1.19 | 7 |
| 3-[3-fluoro-4-({4-[(1-hydroxycyclopropyl)carbonyl]piperazin-1-yl}carbonyl)phenyl]quinolin-2-ol | 435.45 | 436.13 | 0.96 | 5 |
| 3-[4-({4-[(1-hydroxycyclopropyl)carbonyl]piperazin-1-yl}carbonyl)phenyl]-1,2-dihydroquinolin-2-one | 417.46 | 418.15 | 0.93 | 1 |
| N-{3-[4-({4-[(1-hydroxycyclopropyl)carbonyl]piperazin-1-yl}carbonyl)phenyl]phenyl}methanesulfonamide | 443.52 | 444.17 | 0.93 | 11 |
| 6-[4-({4-[(1-hydroxycyclopropyl)carbonyl]piperazin-1-yl}carbonyl)phenyl]-1,2-dihydroquinolin-2-one | 417.46 | 418.13 | 0.76 | 3 |

TABLE 3-1-continued

| IC50 (uM) <0.5 | Mol. Weight | Mass Ion Observed | HPLC retention time (min) | Method |
|---|---|---|---|---|
| 1-[(4-{[4-(1-methyl-1H-indol-5-yl)-2-(trifluoromethyl)phenyl]carbonyl}piperazin-1-yl)carbonyl]cyclopropan-1-ol | 471.47 | 472.22 | 1.39 | 5 |
| 1-[(4-{[4-(1,3-benzothiazol-2-yl)phenyl carbonyl]piperazin-1-yl)carbonyl]cyclopropan-1-ol | 407.49 | 408.09 | 1.24 | 6 |
| 5-[4-({4-[(1-hydroxycyclopropyl)carbonyl]piperazin-1-yl}carbonyl)phenyl]-1-(propan-2-yl)-1H-indole-3-carbonitrile | 456.54 | 457.16 | 1.29 | 10 |
| 1-[(4-{[2-chloro-4-(quinolin-6-yl)phenyl]carbonyl}piperazin-1-yl)carbonyl]cyclopropan-1-ol | 435.90 | 436.14 | 0.96 | 5 |
| 1-({4-[(2-phenyl-1,3-benzothiazol-6-yl)carbonyl]piperazin-1-yl}carbonyl)cyclopropan-1-ol | 407.49 | 408.09 | 1.22 | 5 |
| 1-[(4-{[4-(1H-1,3-benzodiazol-2-yl)phenyl]carbonyl}piperazin-1-yl)carbonyl]cyclopropan-1-ol | 390.44 | 391.14 | 0.73 | 3 |

TABLE 3-2

| IC50 (uM) ≥0.5 | MOL. Weight | Mass Ion Observed | HPLC retention time (min) | Method |
|---|---|---|---|---|
| 1-{[4-({3-chloro-4-[1-(propan-2-yl)-1H-indol-5-yl]phenyl}carbonyl)piperazin-1-yl]carbonyl}cyclopropan-1-ol | 465.97 | 466.05 | 1.5 | 10 |
| 1-{[4-({4-[2-methoxy-4-(1H-pyrazol-1-yl)phenyl]phenyl}carbonyl)piperazin-1-yl]carbonyl}cyclopropan-1-ol | 446.50 | 447.23 | 1.19 | 5 |
| 5-[4-({4-[(oxetan-2-yl)carbonyl]piperazin-1-yl}carbonyl)phenyl]-1H-indole | 389.45 | 389.18 | 1.03 | 2 |
| 3-[4-({4-[(oxetan-2-yl)carbonyl]piperazin-1-yl}carbonyl)phenyl]quinoline | 401.46 | 402.14 | 0.95 | 2 |
| 1-({4-{[4-(2,4-dichlorophenyl)phenyl]carbonyl}piperazin-1-yl)carbonyl]cyclopropan-1-ol | 419.30 | 419.12 | 1.47, 1.68 | 5 |

ENUMERATED EMBODIMENTS

The present disclosure also relates to the following enumerated embodiments:
1. A fatty acid synthase inhibitor comprising the structure of formula I:

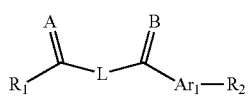

(I)

wherein:
$R_1$ is a $C_1$-$C_3$ hydroxyl-alkyl either unsubstituted or substituted with —$CH_3$ or —$CH_zF_{3-z}$, 5 membered cycloalkyl either unsubstituted or substituted with substituents selected from the group consisting of deuterium, —$R_p$, —$OR_p$, —$NHR_p$, and —$NR_pR_{p1}$,
or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —$R_a$, —$OR_a$, —$NHR_a$, and —$NR_aR_{a1}$;

L is a 5-10 membered monocyclic or bicyclic alkyl or heteroalkyl wherein (i) the heteroatom ring members of the 5-10 membered monocyclic or bicyclic heteroalkyl are independently selected from O, S, or N, and (ii) each of the 5-10 membered monocyclic or bicyclic alkyl or heteroalkyl is either unsubstituted or optionally substituted with substituents selected from the group consisting of deuterium and —$R_b$;

A and B are independently O or S;

$Ar_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —$CH_zF_{3-z}$, cyano, hydroxyl, hydroxylalkyl, amino, aminoalkyl-, (amino)alkoxy-, —$CONH_2$, —C(O)NH(alkyl), —C(O)N(alkyl)$_2$, —C(O)NH(aryl), —C(O)N(aryl)$_2$, —$OCH_zF_{3-z}$, -alkyl, -alkenyl, -alkynyl, -alkoxy (alkoxyalkyl)amino-, —N(Re)—C(O)-alkyl, —N($R_c$)—C(O)-aryl, -cycloalkyl, -heterocycloalkyl, -aryl, and -heteroaryl, with the proviso that no two adjacent ring heteroatoms are both S or both O;

$R_2$ is H or a 4-15 membered monocyclic, bicyclic or tricyclic aryl, heteroaryl, cycloalkyl, or heterocycloalkyl, (i) the 4-15 membered monocyclic, bicyclic or tricyclic heteroaryl or heterocycloalkyl has 1, 2, 3, 4, 5, 6, 7 or 8 heteroatoms that are independently selected from N, S or O, and (ii) wherein each of said aryl, heteroaryl, cycloalkyl, or heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycloalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycloalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_a$)(cycloalkyl), methylenedioxy, —CH$_z$F$_{3-z}$, —OCH$_z$F$_{3-z}$, and -alkoxy;

R$_p$ and R$_{p1}$ are independently H, halo, C$_1$-C$_4$ alkyl, or C$_3$-C$_4$ cycloalkyl;

R$_a$ and R$_{a1}$ are independently H, halo, C$_1$-C$_4$ alkyl, or C$_3$-C$_4$ cycloalkyl;

R$_b$ is H, halo, C$_1$-C$_4$ alkyl, C$_1$-C$_3$ hydroxyl-alkyl, or C$_3$-C$_4$ cycloalkyl;

R$_c$ is H, halo, C$_1$-C$_4$ alkyl, or C$_3$-C$_4$ cycloalkyl;

R$_d$ is H, halo, C$_1$-C$_4$ alkyl, or C$_3$-C$_4$ cycloalkyl;

and z is 0, 1 or 2;

and pharmaceutically acceptable salts thereof.

2. A Compound of formula I:

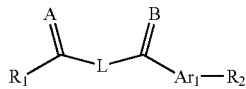

(I)

wherein:

R$_1$ is a C$_1$-C$_3$ hydroxyl-alkyl either unsubstituted or substituted with —CH$_3$ or —CH$_z$F$_{3-z}$, 5 membered cycloalkyl either unsubstituted or substituted with substituents selected from the group consisting of deuterium, —R$_p$, —OR$_p$, —NHR$_p$, and —NR$_p$R$_{p1}$, or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —R$_a$, —OR$_a$, —NHR$_a$, and —NR$_a$R$_{a1}$;

L is a 5-10 membered monocyclic or bicyclic alkyl or heteroalkyl wherein (i) the heteroatom ring members of the 5-10 membered monocyclic or bicyclic heteroalkyl are independently selected from O, S, or N, and (ii) each of the 5-10 membered monocyclic or bicyclic alkyl or heteroalkyl is either unsubstituted or optionally substituted with substituents selected from the group consisting of deuterium and —R$_b$;

A and B are independently O or S;

Ar$_1$ is a 4-10 membered monocyclic or bicyclic aryl, heteroaryl or heterocycloalkyl, wherein (i) said 4-10 membered monocyclic or bicyclic heteroaryl or heterocycloalkyl have 1, 2, 3, or 4 heteroatoms which are independently selected from N, S or O, and (ii) each of said 4-10 membered monocyclic or bicyclic aryl, heteroaryl, or heterocycloalkyl is either unsubstituted or optionally independently substituted with 1 or more substituents which can be the same or different and are independently selected from the group consisting of deuterium, halo, alkyl, —CH$_z$F$_{3-z}$, cyano, hydroxyl, hydroxylalkyl, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —OCH$_z$F$_{3-z}$, -alkyl, -alkenyl, -alkynyl, -alkoxy or (alkoxyalkyl)amino-, —N(R$_c$)—C(O)-alkyl, —N(Re)—C(O)-aryl, -cycloalkyl, -heterocycloalkyl, -aryl, and -heteroaryl, with the proviso that no two adjacent ring heteroatoms are both S or both O;

R$_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms that are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycloalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycloalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_a$)(cycloalkyl), methylenedioxy, —CH$_z$F$_{3-z}$, —OCH$_z$F$_{3-z}$, and -alkoxy;

R$_p$ and R$_{p1}$ are independently H, halo, C$_1$-C$_4$ alkyl, or C$_3$-C$_4$ cycloalkyl;

R$_a$ and R$_{a1}$ are independently H, halo, C$_1$-C$_4$ alkyl, or C$_3$-C$_4$ cycloalkyl;

R$_b$ is H, halo, C$_1$-C$_4$ alkyl, C$_1$-C$_3$ hydroxyl-alkyl, or C$_3$-C$_4$ cycloalkyl;

R$_c$ is H, halo, C$_1$-C$_4$ alkyl, or C$_3$-C$_4$ cycloalkyl;

R$_d$ is H, halo, C$_1$-C$_4$ alkyl, or C$_3$-C$_4$ cycloalkyl;

and z is 0, 1 or 2;

and pharmaceutically acceptable salts thereof.

further wherein:

R$_2$ is not a
a substituted or unsubstituted form of

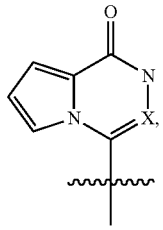

where X is N or CH;
when R$_1$ is

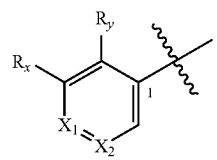

connected to

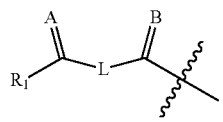

at position 1, and X$_1$ and X$_2$ are independently N or C—R$_z$, and R$_y$ and R$_z$ are any substituent, then Rx does not include alkynyl, alkenyl, aryl, 5-14 membered heterocyclic, 5-14 membered heteroaromatic, or 4-9 membered carbocyclic;

when R$_2$ is

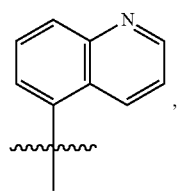 [SMILES: *c1cccc2ncccc12]

Ar$_1$ is not a substituted or unsubstituted form of

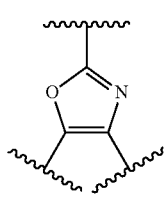 , 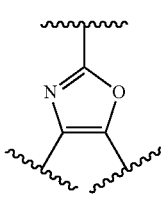 , 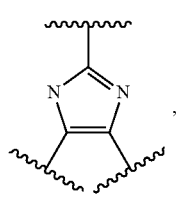 ,

-continued

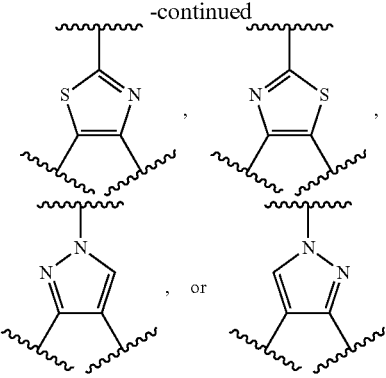

and when Ar$_1$ is a substituted or unsubstituted form of a 5 membered heteroaryl, Ar$_1$ is

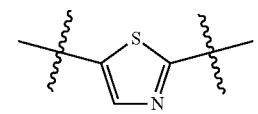

3. The compound of embodiment 1, wherein R$_1$ is selected from the group consisting of:

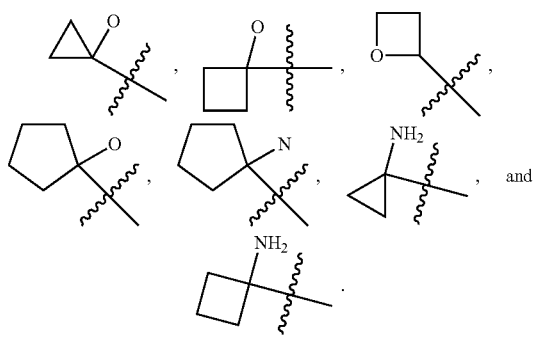

4. The compound of embodiment 2, wherein R$_1$ is

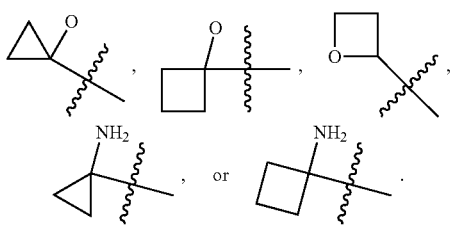

5. The compound of embodiment 2, wherein R$_1$ is selected from the group consisting of:

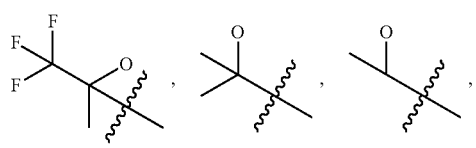

-continued

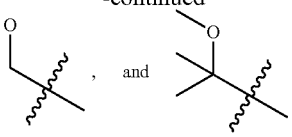, and

6. The compound of embodiment 2, wherein A and B are O.
7. The compound of embodiment 2, wherein L is:

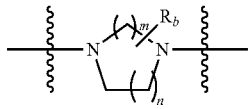

m is 1, 2, or 3 and
n is 0, 1, 2, or 3.

8. The compound of embodiment 7, wherein L is:

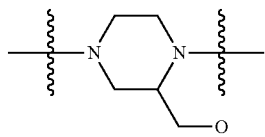

9. The compound of embodiment 7, wherein L is:

10. The compound of embodiment 2, wherein $Ar_1$ is a substituted or unsubstituted 5-6 membered monocyclic aryl or heteroaryl.
11. The compound of embodiment 10, wherein $Ar_1$ is a substituted or unsubstituted 5 membered monocyclic aryl or heteroaryl and said heteroaryl has 1 or 2 heteroatoms which are independently S or N.
12. The compound of embodiment 11, wherein $Ar_1$ is a substituted or unsubstituted form of:

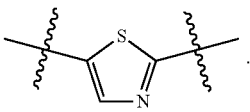 [SMILES: *c1cnc(*)s1]

13. The compound of embodiment 10, wherein $Ar_1$ is a substituted or unsubstituted 6 membered monocyclic aryl or heteroaryl and said heteroaryl has 1 or 2 heteroatoms which are N.
14. The compound of embodiment 13, wherein $Ar_1$ is

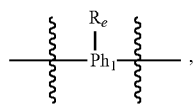

$Ph_1$ is phenyl, pyridinyl, pyrazinyl, or pyrimidinyl, and $R_c$ is H, halo, or $C_1$-$C_3$ alkyl.

15. The compound of embodiment 14, wherein $Ar_1$ is a substituted or unsubstituted form of:

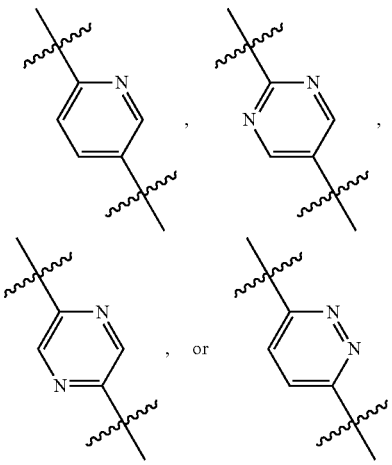

16. The compound of embodiment 14, wherein $Ar_1$ is

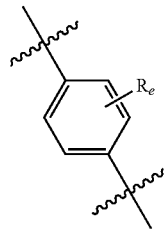

17. The compound of embodiment 16, wherein $Ar_1$ is

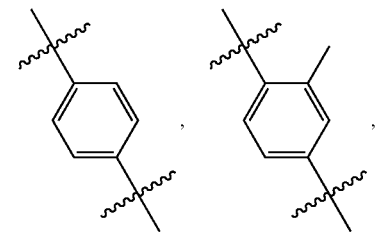

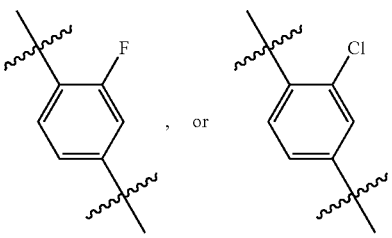

18. The compound of embodiment 2, wherein $Ar_1$ is a substituted or unsubstituted 9 membered 6,5-bicyclic heteroaryl and said heteroaryl has 1, 2, or 3 heteroatoms which are independently O, S or N.

19. The compound of embodiment 18, wherein Ar$_1$ is
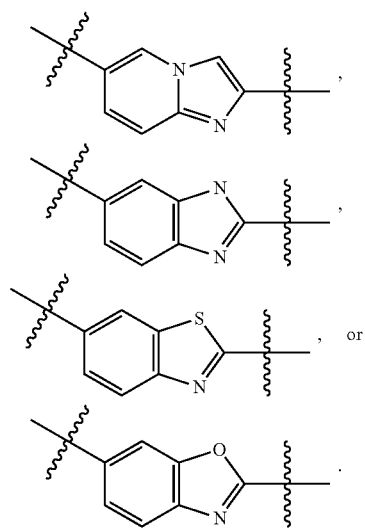
20. The compound of embodiment 2, wherein R$_2$ is a substituted or unsubstituted monocyclic or bicyclic 5-10 membered aryl or heteroaryl.
21. The compound of embodiment 20, wherein R$_2$ is a substituted or unsubstituted monocylic 6 membered aryl.
22. The compound of embodiment 21, wherein R$_2$ is:
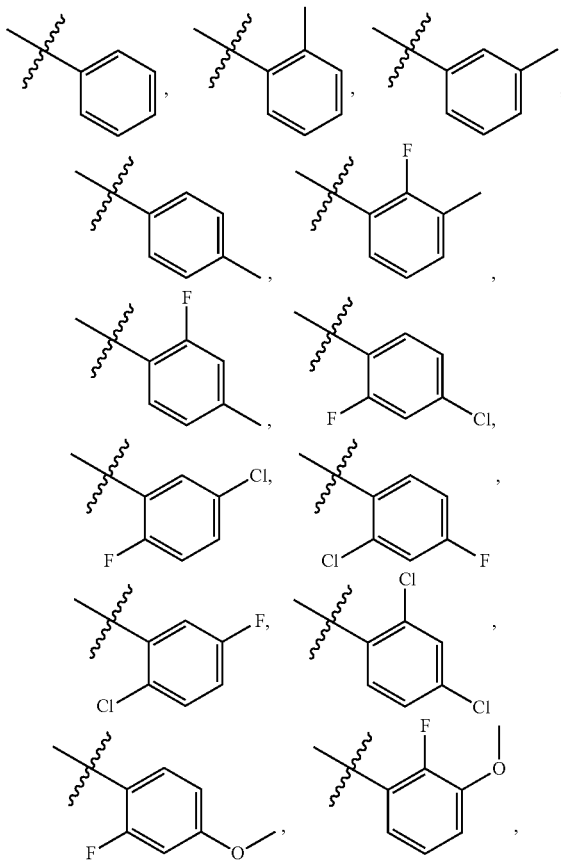
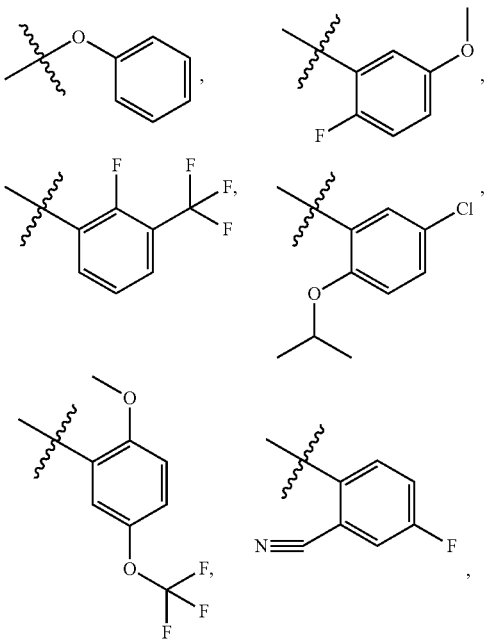
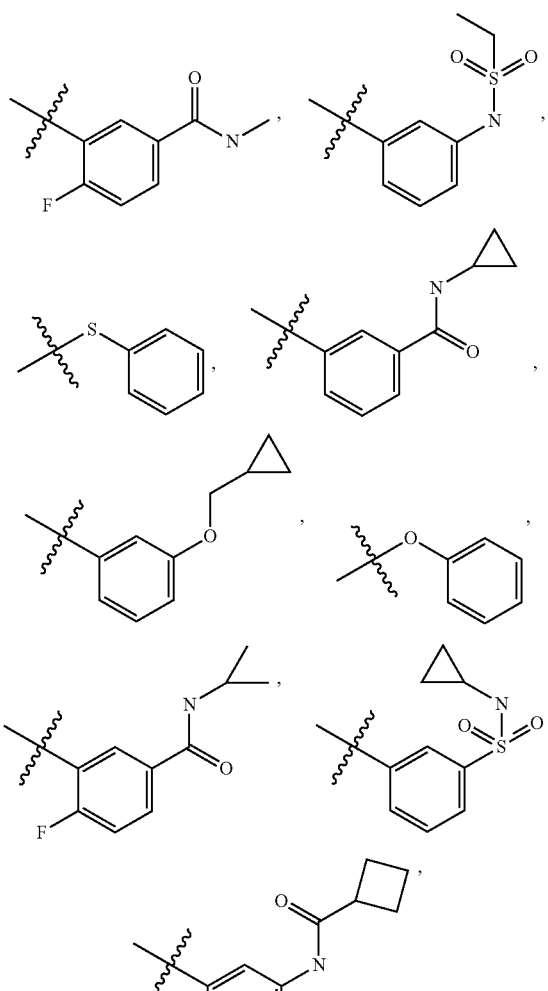

-continued

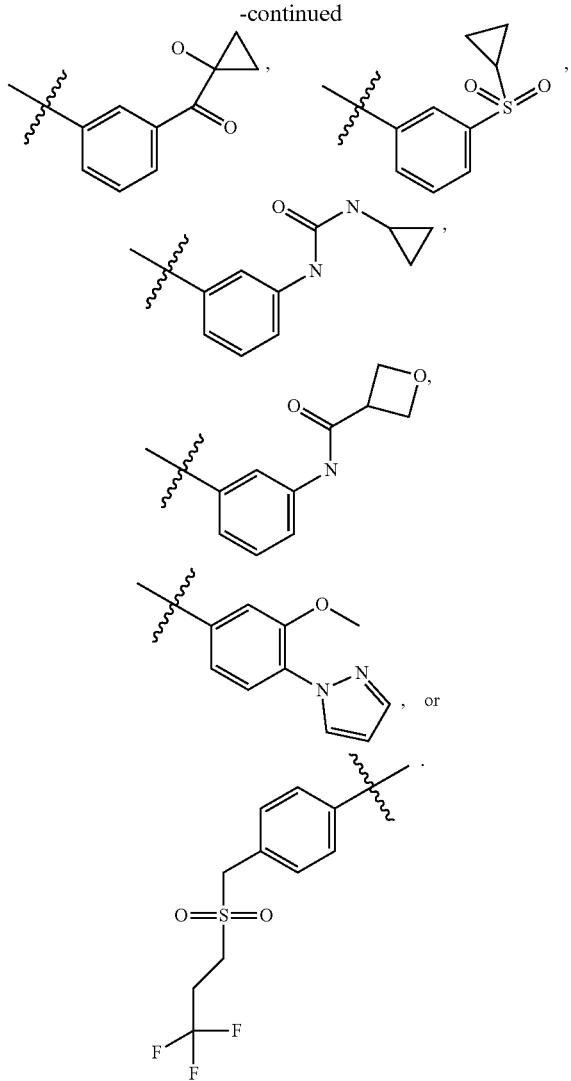

23. The compound of embodiment 20, wherein R₂ is a substituted or unsubstituted bicyclic 8-10 membered aryl or 8-10 membered heteroaryl.
24. The compound of embodiment 23, wherein R₂ is a substituted or unsubstituted 8 membered 5,5 bicyclic heteroaryl and said heteroaryl has 1, 2, 3, or 4 heteroatoms and said heteroatoms are independently O, S, or N.
25. The compound of embodiment 24, wherein R₂ is a substituted or unsubstituted form of:

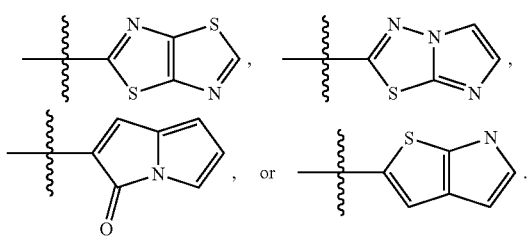

26. The compound of embodiment 20, wherein R₂ is a substituted or unsubstituted 9 membered 6,5 bicyclic heteroaryl and said heteroaryl has 1, 2, 3, or 4 heteroatoms and said heteroatoms are independently O, S, or N.
27. The compound of embodiment 26, wherein R₂ is a substituted or unsubstituted form of:

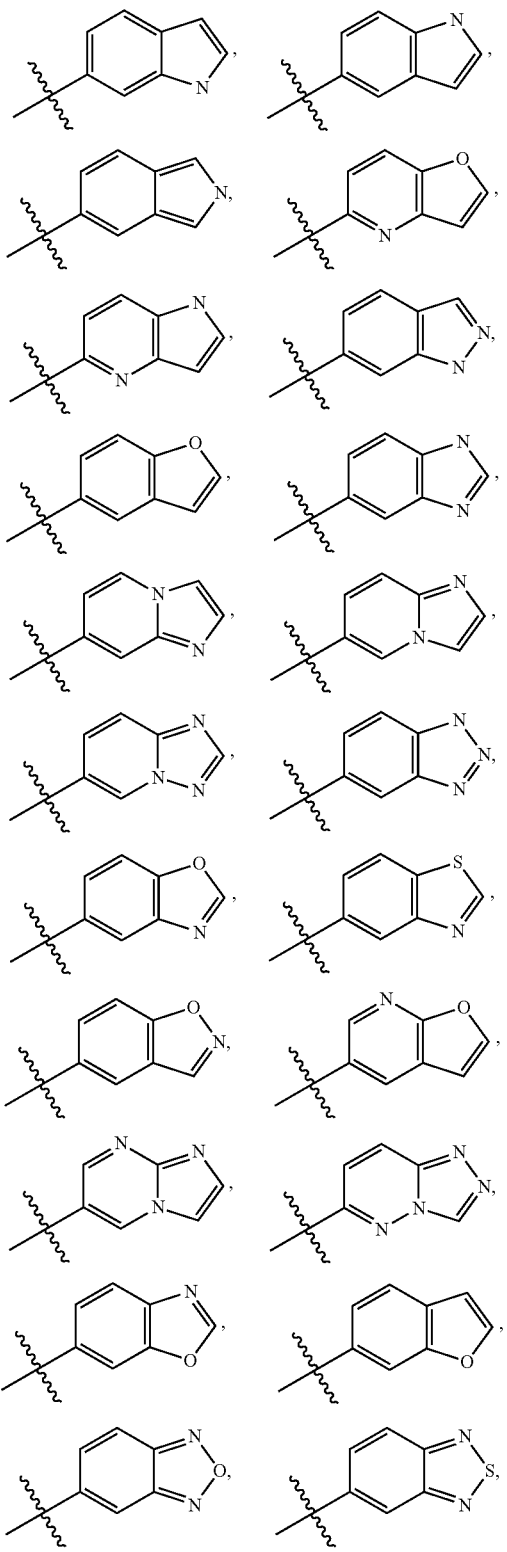

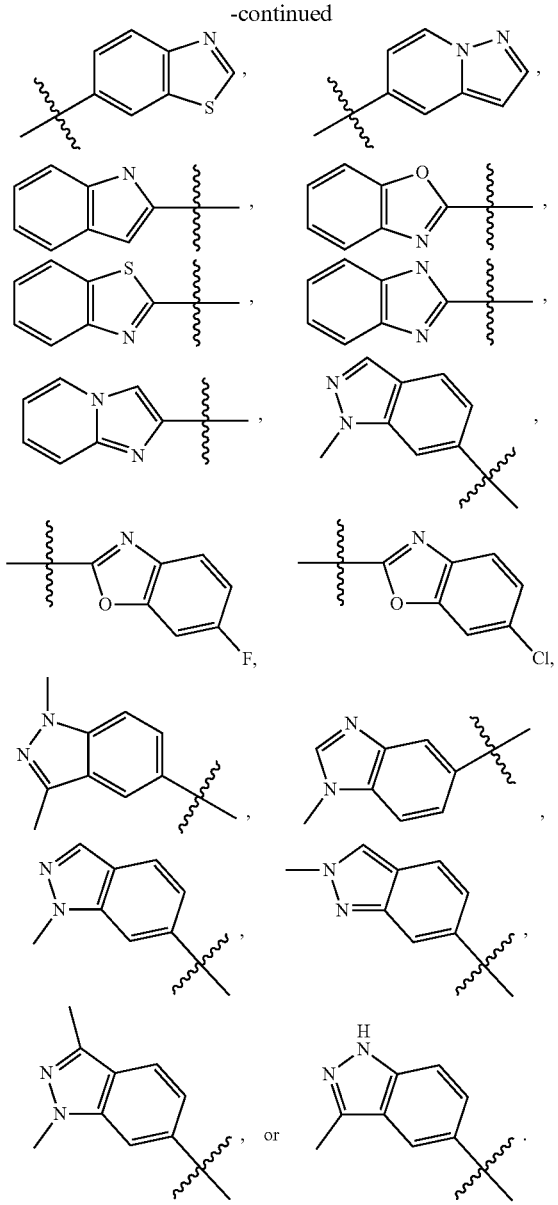

28. The compound of embodiment 20, wherein $R_2$ is a substituted or unsubstituted 10 membered 6,6 bicyclic aryl or heteroaryl and said heteroaryl has 1, 2, 3, or 4 heteroatoms and said heteroatoms are O, S, or N.

29. The compound of embodiment 28, wherein $R_2$ is a substituted or unsubstituted form of:

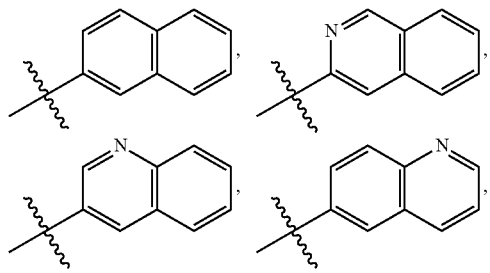

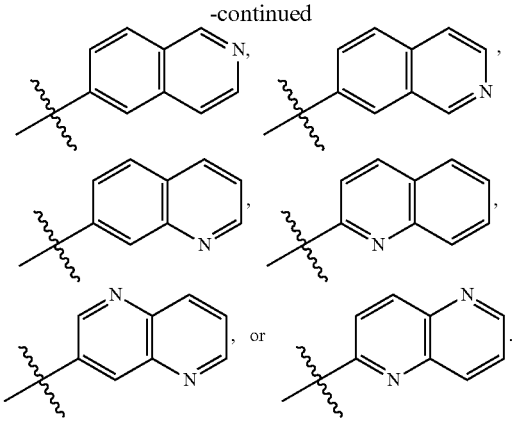

30. A Compound of formula I-A:

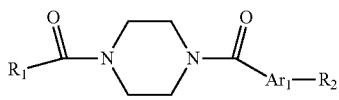

(I-A)

wherein:

$R_1$ is a $C_1$-$C_3$ hydroxyl-alkyl either unsubstituted or substituted with —$CH_3$ or —$CH_zF_{3-z}$, 5 membered cycloalkyl either unsubstituted or substituted with substituents selected from the group consisting of deuterium, —$R_p$, —$OR_p$, —$NHR_p$, and —$NR_pR_{p1}$, or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —$R_a$, —$OR_a$, —$NHR_a$, and —$NR_aR_{a1}$;

$Ar_1$ is a 4-10 membered monocyclic or bicyclic aryl, heteroaryl, or heterocycloalkyl, wherein (i) said 4-10 membered monocyclic, bicyclic heteroaryl, or heterocycloalkyl have 1, 2, 3, or 4 heteroatoms which are independently selected from N, S or O, and (ii) each of said 4-10 membered monocyclic or bicyclic aryl or heteroaryl is either unsubstituted or optionally independently substituted with 1 or more substituents which can be the same or different and are independently selected from the group consisting of deuterium, halo, alkyl, —$CH_zF_{3-z}$, cyano, hydroxyl, hydroxylalkyl, amino, aminoalkyl-, (amino) alkoxy-, —$CONH_2$, —C(O)NH(alkyl), —C(O)N(alkyl)$_2$, —C(O)NH(aryl), —C(O)N(aryl)$_2$, —$OCH_zF_{3-z}$, -alkyl, -alkenyl, -alkynyl, -alkoxy or (alkoxyalkyl)amino-, —N(R)—C(O)-alkyl, —N(R)—C(O)-aryl, -cycloalkyl, -heterocycloalkyl, -aryl, and -heteroaryl, with the proviso that no two adjacent ring heteroatoms are both S or both O;

$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycloalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycloalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_a$)(cycloalkyl), methylenedioxy, —CH$_z$F$_{3-z}$, —OCH$_z$F$_{3-z}$, and -alkoxy;

R$_p$ and R$_{p1}$ are independently H, halo, C$_1$-C$_4$ alkyl, or C$_3$-C$_4$ cycloalkyl;

R$_a$ and R$_{a1}$ are independently H, halo, C$_1$-C$_4$ alkyl, or C$_3$-C$_4$ cycloalkyl;

R$_c$ is H, halo, C$_1$-C$_4$ alkyl, or C$_3$-C$_4$ cycloalkyl;

R$_d$ is H, halo, C$_1$-C$_4$ alkyl, or C$_3$-C$_4$ cycloalkyl;

and z is 0, 1 or 2;

and pharmaceutically acceptable salts thereof.

31. The compound of embodiment 30, wherein R$_1$ is

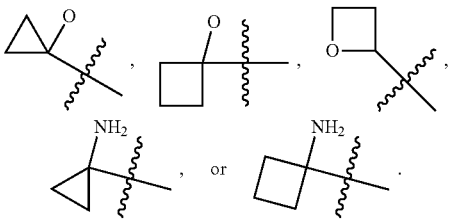

32. A Compound of formula I-B:

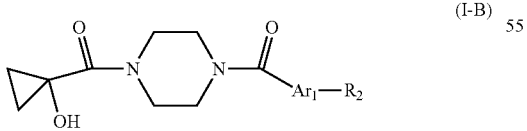

(I-B)

wherein:

Ar$_1$ is a 4-10 membered monocyclic or bicyclic aryl, heteroaryl, or heterocycloalkyl, wherein (i) said 4-10 membered monocyclic or bicyclic heteroaryl or heterocycloalkyl have 1, 2, 3, or 4 heteroatoms which are independently selected from N, S, or O, and (ii) each of said 4-10 membered monocyclic or bicyclic aryl or heteroaryl is either unsubstituted or optionally independently substituted with 1 or more substituents which can be the same or different and are independently selected from the group consisting of deuterium, halo, alkyl, —CH$_z$F$_{3-z}$, cyano, hydroxyl, hydroxylalkyl, amino, aminoalkyl-, (amino)alkoxy-, —CONH$_2$, —C(O)NH(alkyl), —C(O)N(alkyl)$_2$, —C(O)NH(aryl), —C(O)N(aryl)$_2$, —OCH$_z$F$_{3-z}$, -alkyl, -alkenyl, -alkynyl, -alkoxy or (alkoxyalkyl)amino-, —N(R$_c$)—C(O)-alkyl, —N(R)—C(O)-aryl, -cycloalkyl, -heterocycloalkyl, -aryl, and -heteroaryl, with the proviso that no two adjacent ring heteroatoms are both S or both 0;

R$_2$ is H or a 4-15 membered monocyclic, bicyclic, or tricyclic aryl, heteroaryl, cycloalkyl, or heterocycloalkyl, (i) the 4-15 membered monocyclic, bicyclic, tricyclic heteroaryl or heterocycloalkyl has 1, 2, 3, 4, 5, 6, 7, or 8 heteroatoms which are independently selected from N, S, or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycloalkyl-, hydroxyl-heterocycloalkyl-, hydroxyl-aryl-, hydroxyl-heteroaryl-, amino, aminoalkyl, (amino)alkoxy-, —CONH$_2$, —C(O)NH(alkyl), —C(O)N(alkyl)$_2$, —C(O)NH(aryl), —C(O)N(aryl)$_2$, —CH$_z$F$_{3-z}$, —OCH$_z$F$_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), ONH$_2$, —C(O)NH(alkyl), —C(O)N(aryl)$_2$, —C(O)NH(cycloalkyl), —NH(CO)cycloalkyl, —NH(SO$_2$), —NH(SO$_2$)alkyl, —NH(SO$_2$)aryl, —NH(SO$_2$)heteroaryl, —N(SO$_2$)cycloalkyl, —C(O)N(alkyl)$_2$, (aryl)alkyl-, -heteroaryl, (heteroaryl)alkyl-, —S(O)$_2$-alkyl, —S(O)$_2$-aryl, —S(O)$_2$-cycloalkyl, —C(O)N(alkyl)$_2$, —C(O)alkyl, —NH—C(O)-alkyl, —NH—C(O)-cycloalkyl, NH—C(O)-heterocycloalkyl, NH—C(O)-heterocloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), —C(O)N(R$_a$)(cycloalkyl), methylenedioxy, —CH$_z$F$_{3-z}$, —OCH$_z$F$_{3-z}$, and -alkoxy;

R$_c$ is H, halo, C$_1$-C$_4$ alkyl, or C$_3$-C$_4$ cycloalkyl;

R$_d$ is H, halo, C$_1$-C$_4$ alkyl, or C$_3$-C$_4$ cycloalkyl;

and z is 0, 1 or 2;

and pharmaceutically acceptable salts thereof.

33. A Compound of formula I-C:

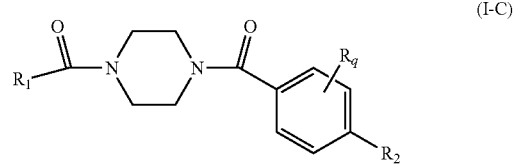

(I-C)

wherein:

R$_1$ is a C$_1$-C$_3$ hydroxyl-alkyl either unsubstituted or substituted with —CH$_3$ or —CH$_z$F$_{3-z}$, 5 membered cycloalkyl either unsubstituted or substituted with substituents selected from the group consisting of deuterium, —$R_p$, —$OR_p$, —$NHR_p$, and —$NR_pR_{p1}$, or 3 or 4 membered cycloalkyl or heterocycloalkyl wherein (i) the heteroatom ring member of the 3 or 4 membered heterocycloalkyl is independently selected from O, S, or N, and (ii) each of said 3 or 4 membered cycloalkyl or heterocycloalkyl is either unsubstituted or optionally substituted with substituents selected from the group consisting of deuterium, —$R_a$, —$OR_a$, —$NHR_a$, and —$NR_aR_{a1}$;

$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycloalkyl-, hydroxyl-heterocycloalkyl-, hydroxyl-aryl-, hydroxyl-heteroaryl-, amino, aminoalkyl, (amino)alkoxy-, —$CONH_2$, —C(O)NH(alkyl), —$C(O)N(alkyl)_2$, —C(O)NH(aryl), —$C(O)N(aryl)_2$, —$CH_zF_{3-z}$, —$OCH_zF_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), $ONH_2$, —C(O)NH(alkyl), —$C(O)N(aryl)_2$, —C(O)NH(cycloalkyl), $NH_2(CO)$cycloalkyl-, —NH(CO)cycloalkyl, —$NH(SO_2)$, —$NH(SO_2)$alkyl, —$NH(SO_2)$aryl, —$NH(SO_2)$heteroaryl, —$N(SO_2)$cycloalkyl, —$C(O)N(alkyl)_2$, (aryl)alkyl-, -heteroaryl, (heteroaryl)alkyl-, —$S(O)_2$-alkyl, —$S(O)_2$-aryl, —$S(O)_2$-cycloalkyl, —$C(O)N(alkyl)_2$, —C(O)alkyl, —NH—C(O)-alkyl, —NH—C(O)-cycloalkyl, NH—C(O)-heterocycloalkyl, NH—C(O)-heterocycloalkyl-$R_d$, —NH—C(O)—$R_d$—(O)alkyl, —NH—C(O)-aryl, —NH—C(O)—NH-alkyl, NH—C(O)—NH-cycloalkyl, NH—C(O)—NH-aryl, —NH—C(O)—O-alkyl, NH—C(O)—NH-cycloalkyl, —NH—C(O)—O— cycloalkyl, —NH($R_a$)—C(O)-alkyl, —NH($R_a$)—C(O)-aryl, —NH($R_a$)—$S(O_2)$cycloalkyl, —$S(O_2)NH_2$, —$S(O_2)$NH(alkyl), —$S(O_2)N(R_a)$cycloalkyl, —$S(O_2)N(alkyl)_2$, —C(O)N(H)(alkyl), —C(O)N($R_d$)(cycloalkyl), methylenedioxy, —$CH_zF_{3-z}$, —$OCH_zF_{3-z}$, and -alkoxy;

$R_p$ and $R_{p1}$ are independently H, halo, $C_1$-$C_4$ alkyl, or $C_3$-$C_4$ cycloalkyl;

$R_a$ and $R_{a1}$ are independently H, halo, $C_1$-$C_4$ alkyl, or $C_3$-$C_4$ cycloalkyl;

$R_d$ is H, halo, $C_1$-$C_4$ alkyl, or $C_3$-$C_4$ cycloalkyl;

$R_q$ is H, halo, $C_1$-$C_4$ alkyl, or $C_3$-$C_4$ cycloalkyl;

and z is 0, 1 or 2;

and pharmaceutically acceptable salts thereof.

34. The compound of embodiment 33, wherein $R_1$ is

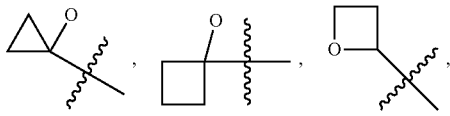

-continued

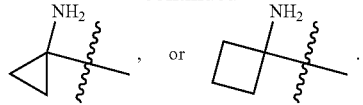

35. A compound of formula I-D:

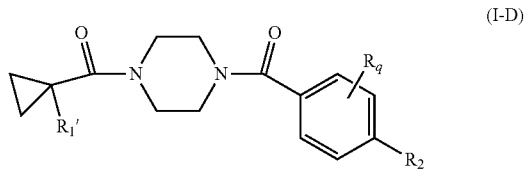

(I-D)

wherein:

$R_1'$ is OH or $NH_2$;

$R_2$ is H or a 4-15 membered monocyclic, bicyclic, or tricyclic aryl, heteroaryl, cycloalkyl, or heterocycloalkyl, (i) the 4-15 membered monocyclic, bicyclic, or tricyclic heteroaryl or heterocycloalkyl has 1, 2, 3, 4, 5, 6, 7, or 8 heteroatoms which are independently selected from N, S or O, and (ii) wherein each of said aryl, heteroaryl, cycloalkyl, and heterocycloalkyl is either unsubstituted or optionally substituted with 1 or more substituents which can be the same or different and are independently selected from the group consisting of deuterium, halo, cyano, hydroxyl, hydroxyl-alkyl-, hydroxylcycloalkyl-, hydroxyl-heterocycloalkyl-, hydroxyl-aryl-, hydroxyl-heteroaryl-, amino, aminoalkyl, (amino)alkoxy-, —$CONH_2$, —C(O)NH(alkyl), —$C(O)N(alkyl)_2$, —C(O)NH(aryl), —$C(O)N(aryl)_2$, —$CH_zF_{3-z}$, —$OCH_zF_{3-z}$, -alkyl, alkoxy-, -alkenyl, -alkynyl, aryloxy-, (alkoxyalkyl)amino-, -cycloalkyl, -heterocycloalkyl, (heterocycloalkyl)alkyl-, -aryl, -heteroaryl, —O(alkyl), —O(cycloalkyl), —O(heterocycloalkyl), —O(aryl), —O(heteroaryl), $ONH_2$, —C(O)NH(alkyl), —$C(O)N(aryl)_2$, —C(O)NH(cycloalkyl), $NH_2(CO)$cycloalkyl-, —NH(CO)cycloalkyl, —$NH(SO_2)$, —$NH(SO_2)$alkyl, —$NH(SO_2)$aryl, —$NH(SO_2)$heteroaryl, —$N(SO_2)$cycloalkyl, —$C(O)N(alkyl)_2$, (aryl)alkyl-, -heteroaryl, (heteroaryl)alkyl-, —$S(O)_2$-alkyl, —$S(O)_2$-aryl, —$S(O)_2$-cycloalkyl, —$C(O)N(alkyl)_2$, —C(O)alkyl, —NH—C(O)-alkyl, —NH—C(O)-cycloalkyl, NH—C(O)-heterocycloalkyl, NH—C(O)-heterocycloalkyl-$R_d$, —NH—C(O)—$R_d$—(O)alkyl, —NH—C(O)-aryl, —NH—C(O)—NH-alkyl, NH—C(O)—NH-cycloalkyl, NH—C(O)—NH-aryl, —NH—C(O)—O-alkyl, NH—C(O)—NH-cycloalkyl, —NH—C(O)—O— cycloalkyl, —NH($R_a$)—C(O)-alkyl, —NH($R_a$)—C(O)-aryl, —NH($R_a$)—$S(O_2)$cycloalkyl, —$S(O_2)NH_2$, —$S(O_2)$NH(alkyl), —$S(O_2)N(R_a)$cycloalkyl, —$S(O_2)N(alkyl)_2$, —C(O)N(H)(alkyl), —C(O)N($R_d$)(cycloalkyl), methylenedioxy, —$CH_zF_{3-z}$, —$OCH_zF_{3-z}$, and -alkoxy;

$R_d$ is H, halo, $C_1$-$C_4$ alkyl, or $C_3$-$C_4$ cycloalkyl;

$R_q$ is H, halo, $C_1$-$C_4$ alkyl, or $C_3$-$C_4$ cycloalkyl;

and z is 0, 1 or 2;

and pharmaceutically acceptable salts thereof.

36. The compounds of embodiment 35, wherein $R_2$ is a:

6 membered aryl either unsubstituted or optionally substituted with 1 or more substituents which can be the same or different and are independently selected from the group consisting of deuterium, halo, cyano, alkyl, aryl, —$S(O)_2$-alkyl, —$S(O)_2$-aryl, —$S(O)_2$-cycloalkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), and —C(O)N(R$_a$)(cycloalkyl); or 9 membered bicyclic heteroaryl having 1, 2, or 3 or 4 heteroatoms which are independently selected from N, S or O, and wherein each of said heteroaryl, is either unsubstituted or optionally substituted with 1 or more substituents which can be the same or different and are independently selected from the group consisting of deuterium, halo, cyano, alkyl, aryl, —S(O)$_2$-alkyl, —S(O)$_2$-aryl, —S(O)$_2$-cycloalkyl, —NH—C(O)-alkyl, —NH—C(O)-cycloalkyl, NH—C(O)-heterocycloalkyl, NH—C(O)-heterocycloalkyl-R$_d$, —NH—C(O)—R$_d$—(O)alkyl, —NH—C(O)-aryl, —NH—C(O)—NH-alkyl, NH—C(O)—NH-cycloalkyl, NH$_2$(CO)cycloalkyl-, NH—C(O)—NH-aryl, —NH—C(O)—O-alkyl, NH—C(O)—NH-cycloalkyl, —NH—C(O)—O-cycloalkyl, —NH(R$_a$)—C(O)-alkyl, —NH(R$_a$)—C(O)-aryl, —NH(R$_a$)—S(O$_2$)cycloalkyl, —S(O$_2$)NH$_2$, —S(O$_2$)NH(alkyl), —S(O$_2$)N(R$_a$)cycloalkyl, —S(O$_2$)N(alkyl)$_2$, —C(O)N(H)(alkyl), and —C(O)N(R$_a$)(cycloalkyl).

37. A compound selected from:

| IUPAC Name | Compound Structure |
|---|---|
| 1-({4-[(4-phenylphenyl)carbonyl]piperazin-1-yl}carbonyl)cyclopropan-1-ol | 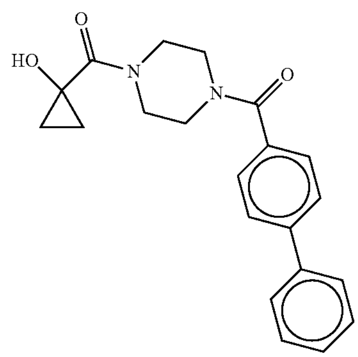 |
| 2-hydroxy-2-methyl-1-{4-[(4-phenylphenyl)carbonyl]piperazin-1-yl}propan-1-one | 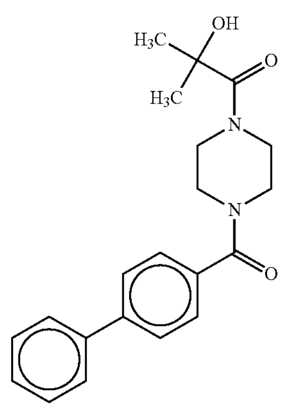 |
| 2-hydroxy-1-{4-[(4-phenylphenyl)carbonyl]piperazin-1-yl}ethan-1-one | 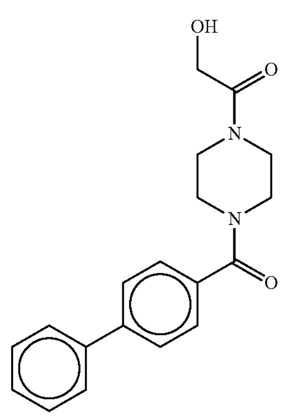 |

| IUPAC Name | Compound Structure |
|---|---|
| 1-({4-[(4-phenylphenyl)carbonyl]piperazin-1-yl}carbonyl)cyclopentan-1-one | 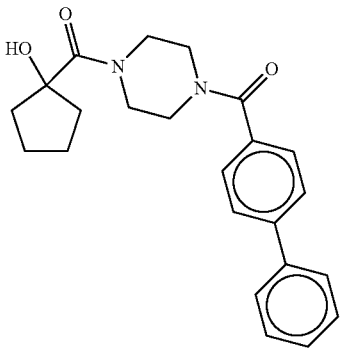 |
| 3,3,3-trifluoro-2-hydroxy-2-methyl-1-{4-[4-phenylphenyl)carbonyl]piperazin-1-yl}propan-1-one | 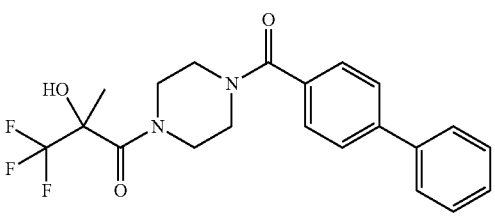 [SMILES: CC(O)(C(=O)N1CCN(C(=O)c2ccc(-c3ccccc3)cc2)CC1)C(F)(F)F] |
| 1-[(4-{[4-(3-methylphenyl)phenyl]carbonyl}piperazin-1-yl)carbonyl]cyclopropan-1-ol | 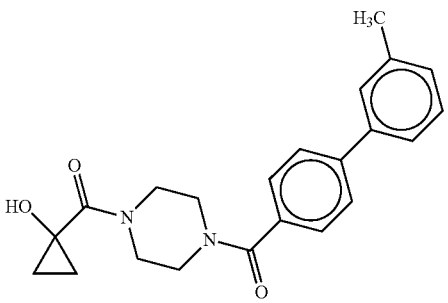 |
| 1-[(4-{[4-(4-methylphenyl)phenyl]carbonyl}piperazin-1-yl)carbonyl]cyclopropan-1-ol | 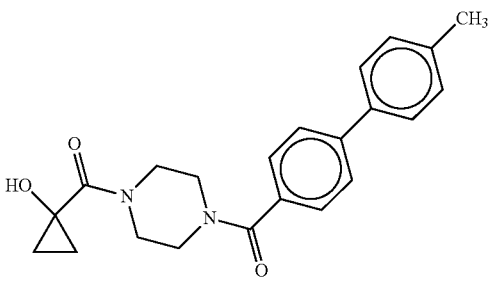 |
| 1-[(4-{[4-(2-fluoro-3-methoxyphenyl)phenyl]carbonyl}piperazin-1-yl)carbonyl]cyclopropan-1-ol | 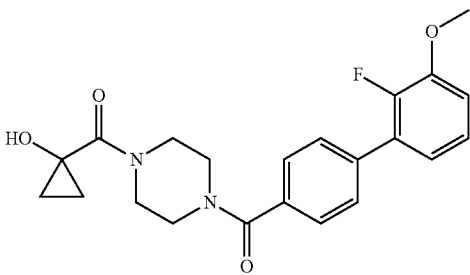 [SMILES: COc1cccc(-c2ccc(C(=O)N3CCN(C(=O)C4(O)CC4)CC3)cc2)c1F] |

| IUPAC Name | Compound Structure |
|---|---|
| 1-[(4-{[4-(2-fluoro-4-methylphenyl)phenyl]carbonyl}piperazin-1-yl)carbonyl]cyclopropan-1-ol | 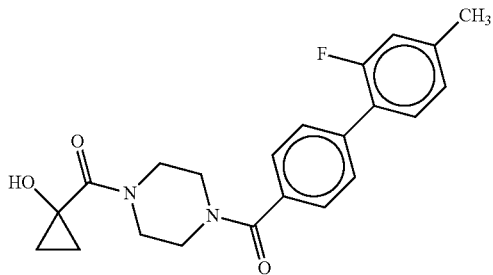 |
| 1-[(4-{[4-(2-fluoro-4-methoxyphenyl)phenyl]carbonyl}piperazin-1-yl)carbonyl]cyclopropan-1-ol | 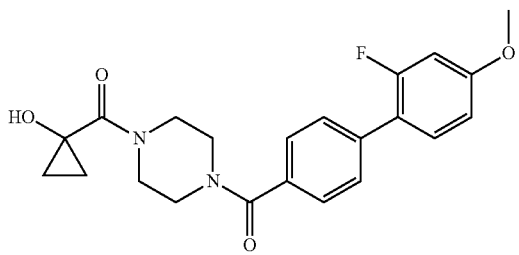 [SMILES: COc1ccc(-c2ccc(C(=O)N3CCN(C(=O)C4(O)CC4)CC3)cc2)c(F)c1] |
| 1-[(4-{[4-(2-chloro-4-fluorophenyl)phenyl]carbonyl}piperazin-1-yl)carbonyl]cyclopropan-1-ol | 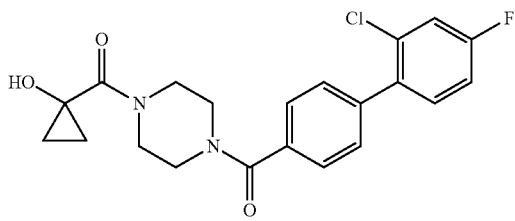 |
| 1-[(4-{[4-(3-chloro-4-fluorophenyl)phenyl]carbonyl}piperazin-1-yl)carbonyl]cyclopropan-1-ol | 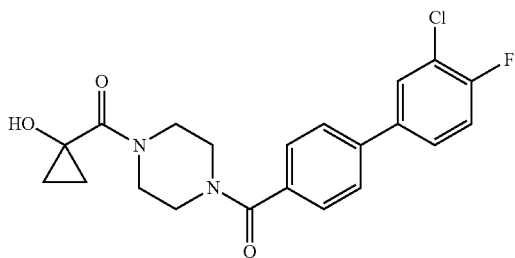 |
| 1-[(4-{[4-(4-chloro-2-fluorophenyl)phenyl]carbonyl}piperazin-1-yl)carbonyl]cyclopropan-1-ol | 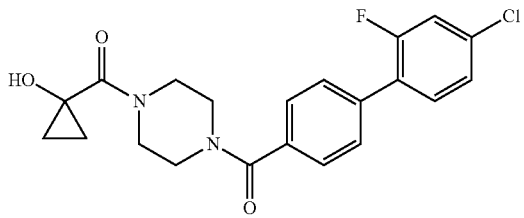 |
| 1-[(4-{[4-(2,4-dichlorophenyl)phenyl]carbonyl}piperazin-1-yl)carbonyl]cyclopropan-1-ol | 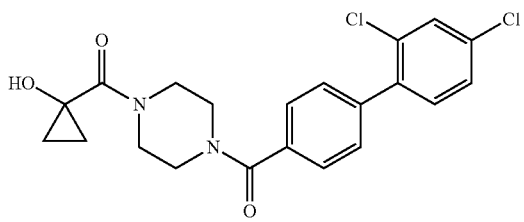 |

| IUPAC Name | Compound Structure |
| --- | --- |
| 1-[(4-{[4-(5-fluoro-2-methylphenyl)phenyl]carbonyl}piperazin-1-yl)carbonyl]cyclopropan-1-ol | 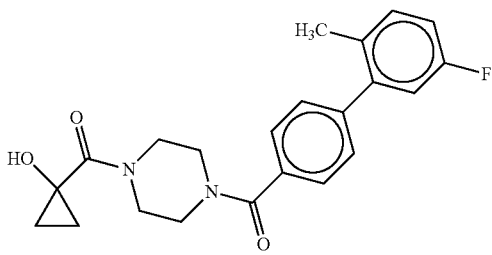 |
| 1-[(4-{[4-(3-fluoro-4-methylphenyl)phenyl]carbonyl}piperazin-1-yl)carbonyl]cyclopropan-1-ol | 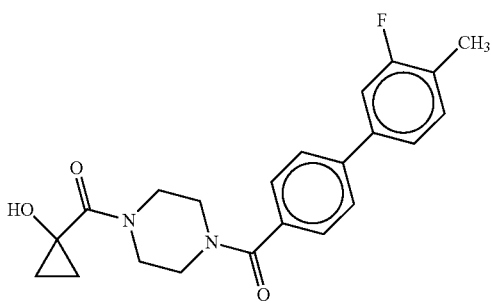 |
| 1-[(4-{[4-(2,3-dichlorophenyl)phenyl]carbonyl}piperazin-1-yl)carbonyl]cyclopropan-1-ol | 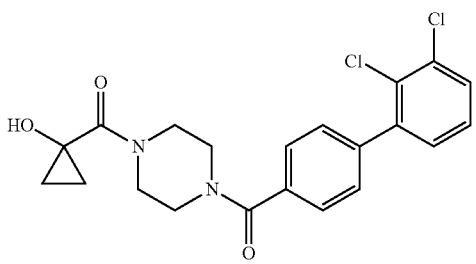 |
| 1-[(4-{[4-(2,5-dichlorophenyl)phenyl]carbonyl}piperazin-1-yl)carbonyl]cyclopropan-1-ol | 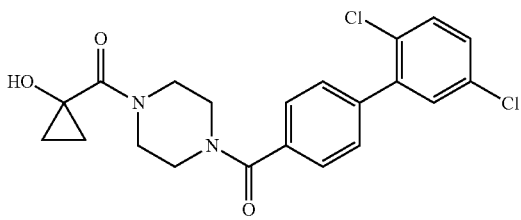 |
| 1-[(4-{[4-(4-chloro-3-fluorophenyl)phenyl]carbonyl}piperazin-1-yl)carbonyl]cylcopropan-1-ol | 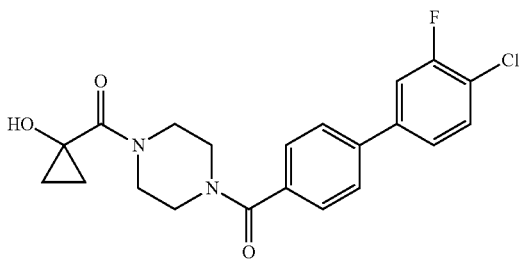 |
| 1-[(4-{[4-(2,5-difluorophenyl)phenyl]carbonyl}piperazin-1-yl)carbonyl]cyclopropan-1-ol | 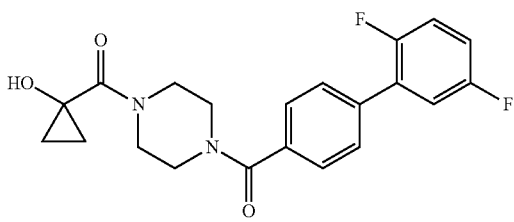 |

| IUPAC Name | Compound Structure |
|---|---|
| 1-[(4-{[4-(3,4-dichlorophenyl)phenyl]carbonyl}piperazin-1-yl)carbonyl]cyclopropan-1-ol | 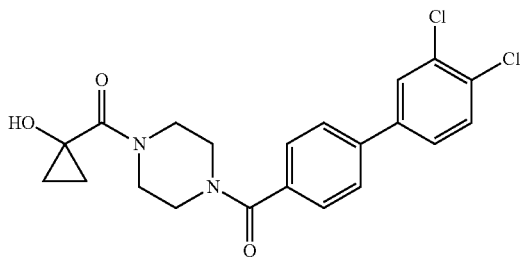 |
| 1-[(4-{[4-(2,3-difluorophenyl)phenyl]carbonyl}piperazin-1-yl)carbonyl]cyclopropan-1-ol | 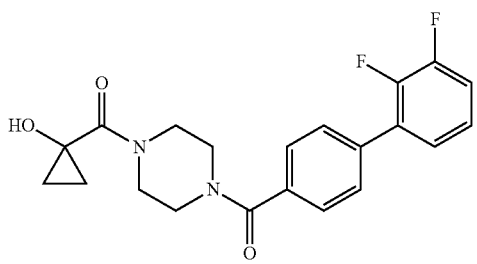 |
| 1-[(4-{[4-(1-methyl-1H-indol-5-yl)phenyl]carbonyl}piperazin-1-yl)carbonyl]cyclopropan-1-ol | 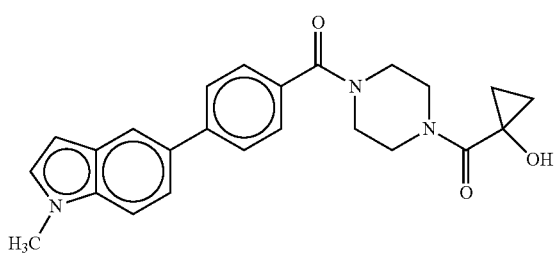 |
| 1-{[4-({4-[2-methoxy-4-(1H-pyrazol-1-yl)phenyl]phenyl}carbonyl)piperazin-1-yl]carbonyl}cyclopropan-1-ol | 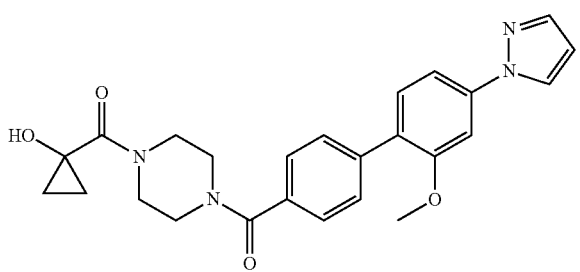 [SMILES: COc1cc(-n2cccn2)ccc1-c1ccc(C(=O)N2CCN(C(=O)C3(O)CC3)CC2)cc1] |
| 1-[(4-{[4-(2-fluoro-5-methylphenyl)phenyl]carbonyl}piperazin-1-yl)carbonyl]cyclopropan-1-ol | 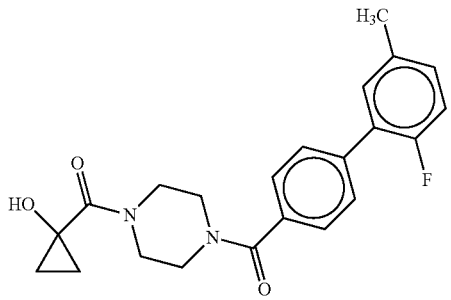 |

| IUPAC Name | Compound Structure |
|---|---|
| 1-{[4-{[4-[2-chloro-5-(trifluoromethyl)phenyl]phenyl}carbonyl)piperazin-1-yl]carbonyl}cyclopropan-1-ol | 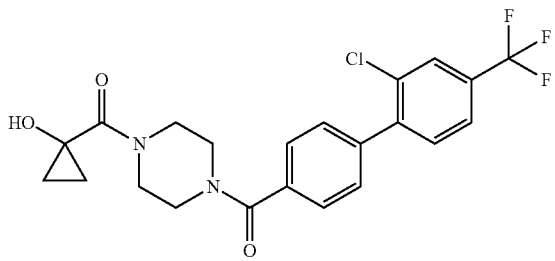 |
| 1-[(4-{[4-(4-chloro-2-methoxyphenyl)phenyl]carbonyl}piperazin-1-yl)carbonyl]cyclopropan-1-ol | 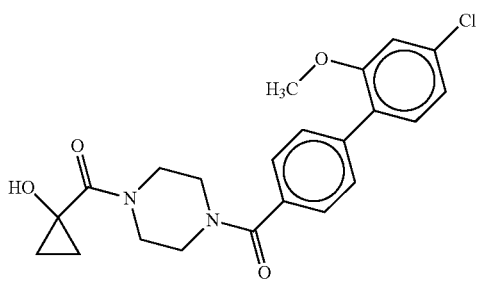 |
| 1-[(4-{[4-(3-chloro-2-methoxyphenyl)phenyl]carbonyl}piperazin-1-yl)carbonyl]cyclopropan-1-ol | 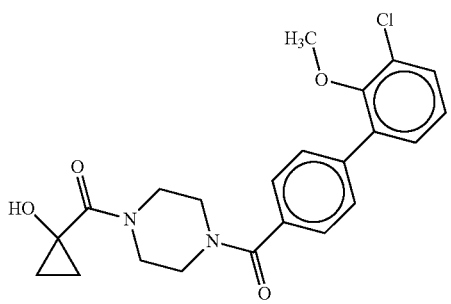 |
| 1-[(4-{[4-(4,5-difluoro-2-methoxyphenyl)phenyl]carbonyl}piperazin-1-yl)carbonyl]cyclopropan-1-ol | 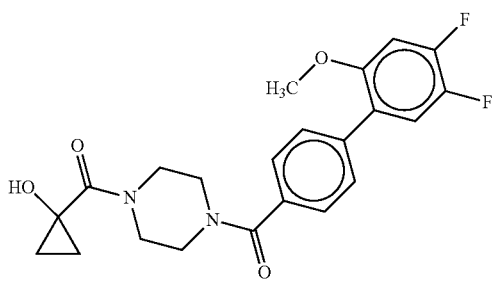 |
| 1-{[4-([4-[2-fluoro-3-(trifluoromethyl)phenyl]phenyl}carbonyl)piperazin-1-yl]carbonyl}cyclopropan-1-ol | 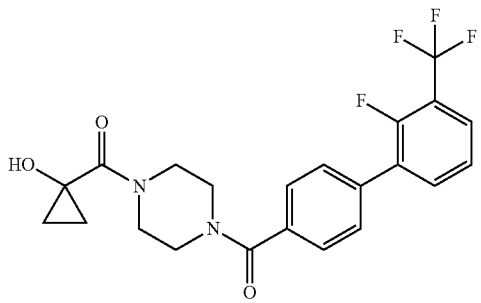 [SMILES: O=C(c1ccc(-c2cccc(C(F)(F)F)c2F)cc1)N1CCN(C(=O)C2(O)CC2)CC1] |

| IUPAC Name | Compound Structure |
|---|---|
| 1-{[4-({4-[4-chloro-2-(trifluoromethyl)phenyl]phenyl}carbonyl)piperazin-1-yl]carbonyl}cyclopropan-1-ol | 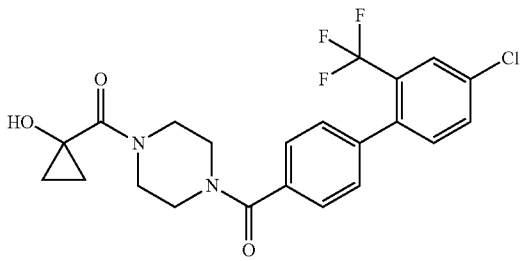 [SMILES: O=C(c1ccc(-c2ccc(Cl)cc2C(F)(F)F)cc1)N1CCN(C(=O)C2(O)CC2)CC1] |
| 1-[(4-{[4-(2-chloro-4-methoxyphenyl)phenyl]carbonyl}piperazin-1-yl)carbonyl]cyclopropan-1-ol | 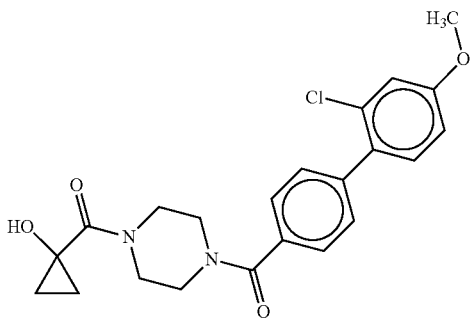 |
| 1-{[4-({4-[5-chloro-2-(propan-2-yloxy)phenyl]phenyl}carbonyl)piperazin-1-yl]carbonyl}cyclopropan-1-ol | 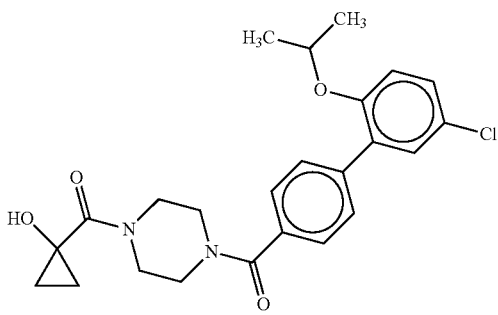 |
| 1-{[4-({4-[3-fluoro-5-(trifluoromethyl)phenyl]phenyl}carbonyl)piperazin-1-yl]carbonyl}cyclopropan-1-ol | 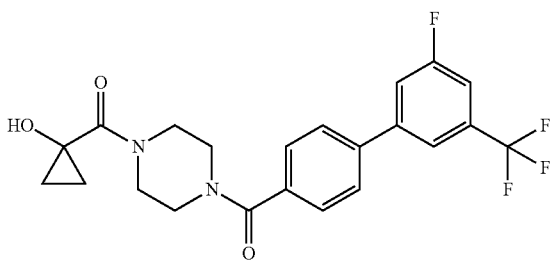 |
| 1-{[4-({4-[2-methoxy-5-(trifluoromethoxy)phenyl]phenyl}carbonyl)piperazin-1-yl]carbonyl}cyclopropan-1-ol | 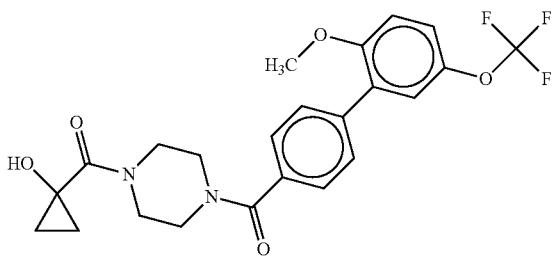 |

-continued

| IUPAC Name | Compound Structure |
|---|---|
| 1-[(4-{[4-(3-fluoro-2-methoxyphenyl)phenyl]carbonyl}piperazin-1-yl)carbonyl]cyclopropan-1-ol | 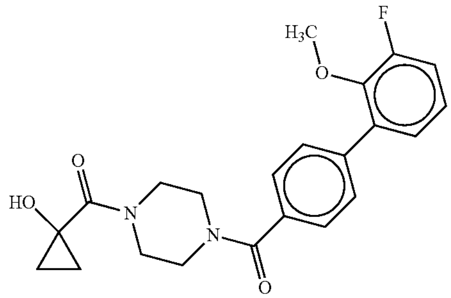 |
| 1-[(4-{[4-(3-methoxypyridin-4-yl)phenyl]carbonyl}piperazin-1-yl)carbonyl]cyclopropan-1-ol | 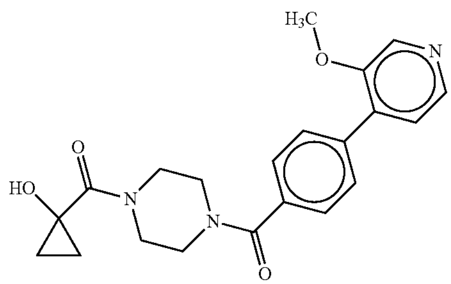 |
| 1-[(4-{[4-(quinolin-3-yl)phenyl]carbonyl}piperazin-1-yl)carbonyl]cyclopropan-1-ol | 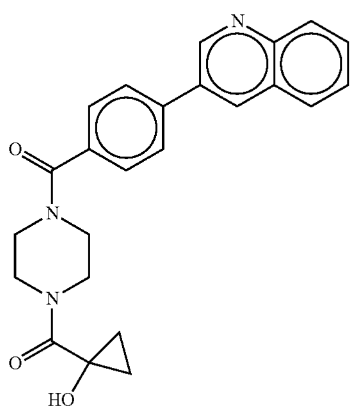 |
| 1-[(4-{[4-(isoquinolin-6-yl)phenyl]carbonyl}piperazin-1-yl)carbonyl]cyclopropan-1-ol | 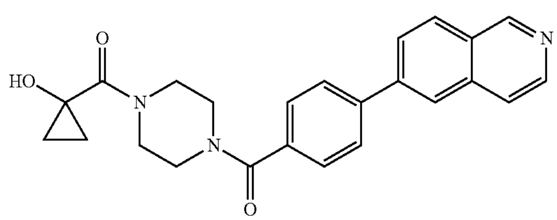 [SMILES: O=C(c1ccc(-c2ccc3cnccc3c2)cc1)N1CCN(C(=O)C2(O)CC2)CC1] |
| 1-({4-[(4-[imidazo[1,2-a]pyridin-6-yl)phenyl)carbonyl]piperazin-1-yl}carbonyl)cyclopropan-1-ol | 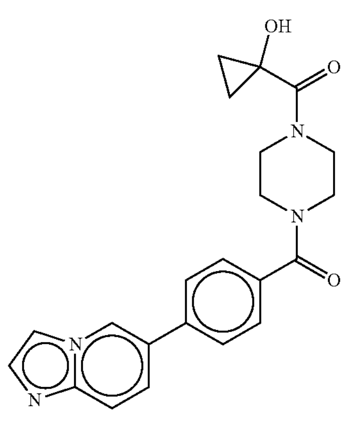 |

| IUPAC Name | Compound Structure |
|---|---|
| 1-[(4-{[4-(1,3-benzothiazol-5-yl)phenyl]carbonyl)piperazin-1-yl]carbonyl}cyclopropan-1-ol | 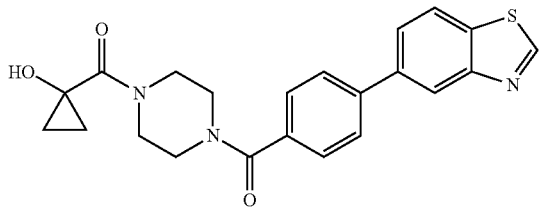 [SMILES: O=C(c1ccc(-c2ccc3scnc3c2)cc1)N1CCN(C(=O)C2(O)CC2)CC1] |
| 1-{[4-([4-[6-(trifluoromethyl)pyridin-3-yl]phenyl}carbonyl)piperazin-1-yl]carbonyl}cyclopropan-1-ol | 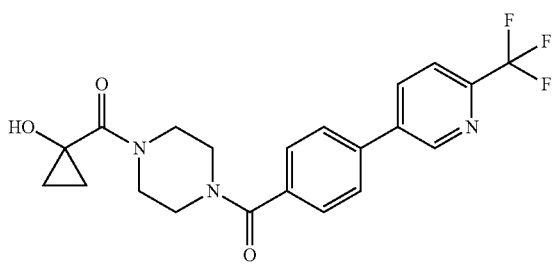 |
| 1-[(4-{[4-(5-chloro-2-fluorophenyl)phenyl]carbonyl}piperazin-1-yl)carbonyl]cyclopropan-1-ol | 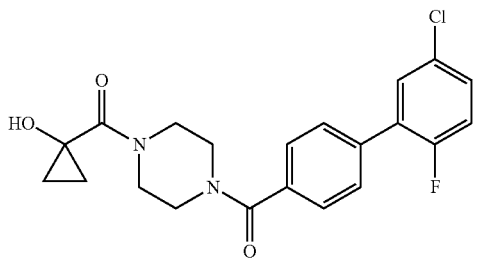 |
| 1-[(4-{[4-(6-methylpyridin-3-yl)phenyl]carbonyl}piperazin-1-yl)carbonyl]cyclopropan-1-ol | 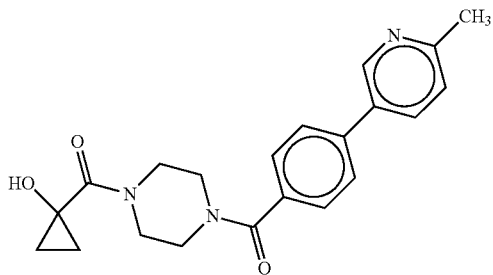 |
| 1-[(4-{[4-(2,6-dimethoxypyridin-3-yl)phenyl]carbonyl}piperazin-1-yl)carbonyl]cyclopropan-1-ol | 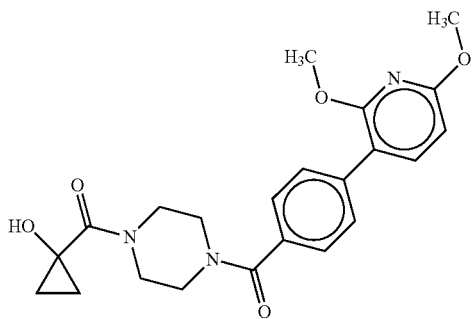 |

| IUPAC Name | Compound Structure |
|---|---|
| 1-[(4-{[4-(5-fluoropyridin-3-yl)phenyl]carbonyl}piperazin-1-yl)carbonyl]cyclopropan-1-ol | 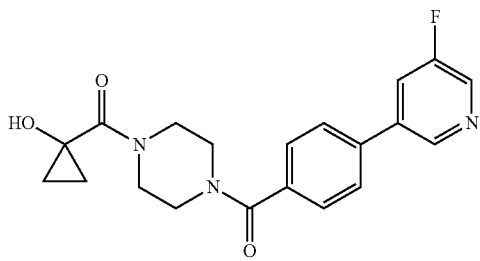 [SMILES: O=C(c1ccc(-c2cncc(F)c2)cc1)N1CCN(C(=O)C2(O)CC2)CC1] |
| 1-[(4-{[4-(1-methyl-1H-indol-2-yl)phenyl]carbonyl}piperazin-1-yl)carbonyl]cyclopropan-1-ol | 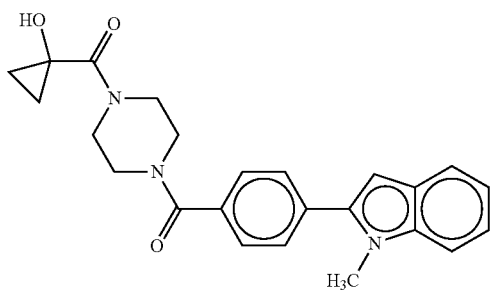 |
| 1-[(4-{[4-(2-chloro-5-fluorophenyl)phenyl]carbonyl}piperazin-1-yl)carbonyl]cyclopropan-1-ol | 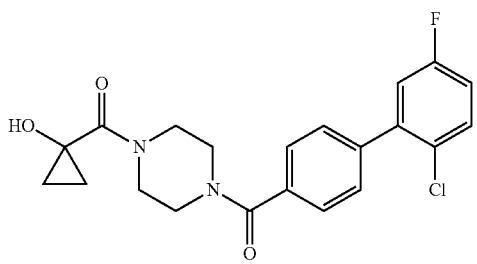 |
| 1-[(4-{[4-(2-fluoro-5-methoxyphenyl)phenyl]carbonyl}piperazin-1-yl)carbonyl]cyclopropan-1-ol | 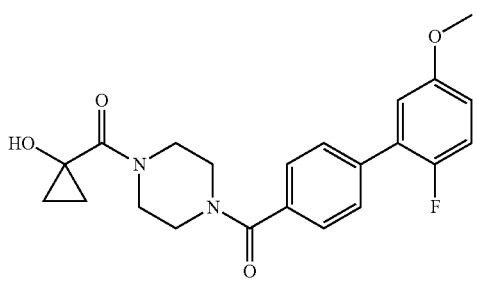 |
| 1-[(4-{[4-(2-fluoro-3-methylphenyl)phenyl]carbonyl}piperazin-1-yl)carbonyl]cyclopropan-1-ol | 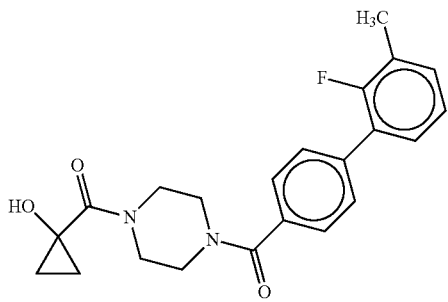 |

| IUPAC Name | Compound Structure |
|---|---|
| 1-{[4-({4-[4-fluoro-2-(trifluoromethyl)phenyl]phenyl}carbonyl)piperazin-1-yl]carbonyl}cyclopropan-1-ol | 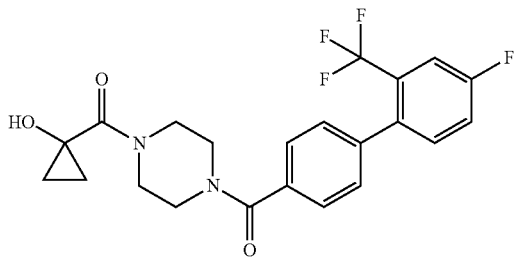 |
| 1-{[4-({4-[2-chloro-5-(hydroxymethyl)phenyl]phenyl}carbonyl)piperazin-1-yl]carbonyl}cyclopropan-1-ol | 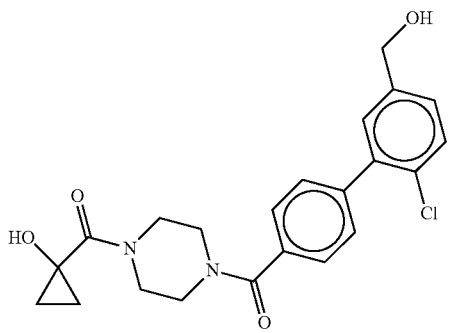 |
| 1-[(4-{[4-(2-methyl-2H-indazol-6-yl)phenyl]carbonyl}piperazin-1-yl)carbonyl]cyclopropan-1-ol | 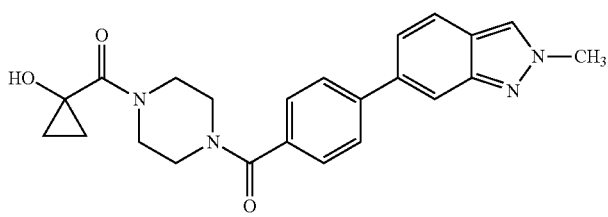 [SMILES: Cn1cc2ccc(-c3ccc(C(=O)N4CCN(C(=O)C5(O)CC5)CC4)cc3)cc2n1] |
| 1-[(4-{[4-(1-methyl-1H-indazol-7-yl)phenyl]carbonyl}piperazin-1-yl)carbonyl]cyclopropan-1-ol | 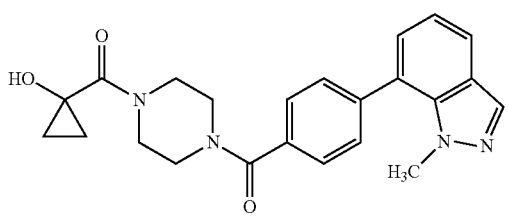 |
| 1-[(4-{[4-(1H-indol-4-yl)phenyl]carbonyl}piperazin-1-yl)carbonyl]cyclopropan-1-ol | 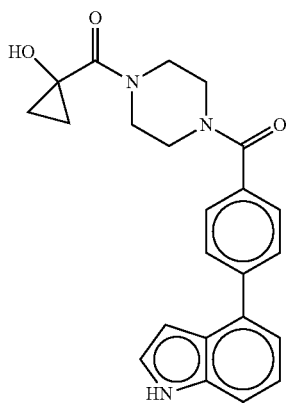 |

-continued

| IUPAC Name | Compound Structure |
|---|---|
| N-cyclopropyl-3-[4-({4-[(1-hydroxycyclopropyl)carbonyl]piperazin-1-yl}carbonyl)phenyl]benzamide | 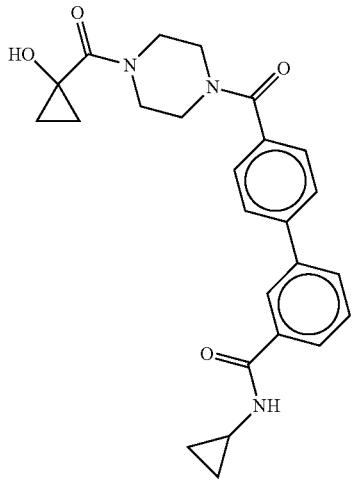 |
| N-{3-[4-({4-[(1-hydroxycyclopropyl)carbonyl]piperazin-1-yl}carbonyl)phenyl]phenyl}ethane-1-sulfonamide | 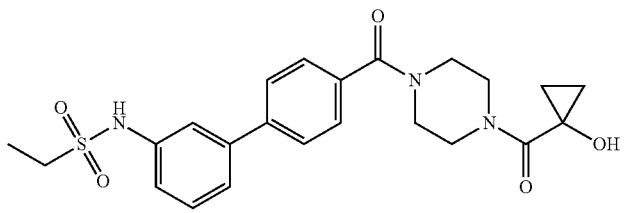 [SMILES: CCS(=O)(=O)Nc1cccc(-c2ccc(C(=O)N3CCN(C(=O)C4(O)CC4)CC3)cc2)c1] |
| 4-fluoro-3-[4-({4-[(1-hydroxycyclopropyl)carbonyl]piperazin-1-yl}carbonyl)phenyl]-N-methylbenzamide | 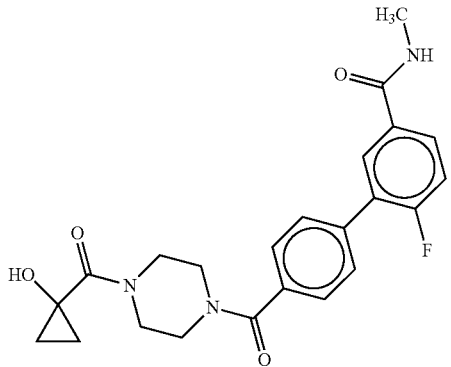 |
| 4-fluoro-3-[4-({4-[(1-hydroxycyclopropyl)carbonyl]piperazin-1-yl}carbonyl)phenyl]-N-(propan-2-yl)benzamide | 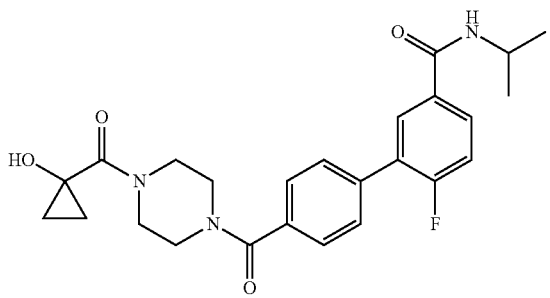 [SMILES: CC(C)NC(=O)c1ccc(F)c(-c2ccc(C(=O)N3CCN(C(=O)C4(O)CC4)CC3)cc2)c1] |

| IUPAC Name | Compound Structure |
|---|---|
| 1-[(4-{[4-(2,4-dichloro-3-methoxyphenyl)phenyl]carbonyl}piperazin-1-yl)carbonyl]cyclopropan-1-ol | 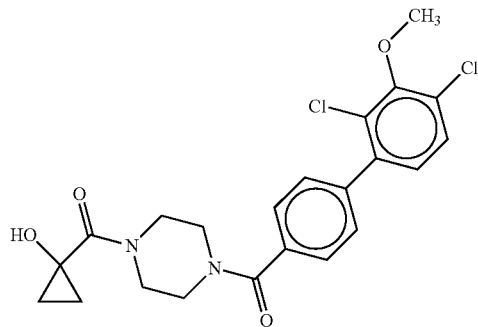 |
| 1-{[4-({4-[2-fluoro-3-(propan-2-yloxy)phenyl]phenyl}carbonyl)piperazin-1-yl]carbonyl}cyclopropan-1-ol | 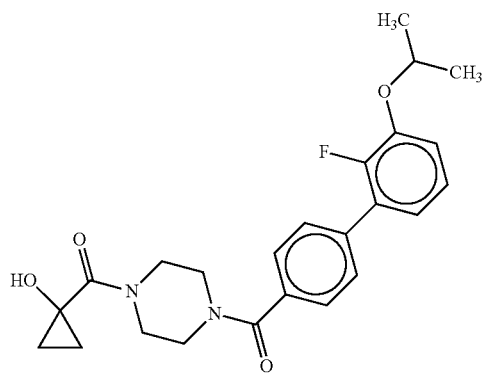 |
| 1-{[4-({4-[2-fluoro-3-(trifluoromethoxy)phenyl]phenyl}carbonyl)piperazin-1-yl]carbonyl}cyclopropan-1-ol | 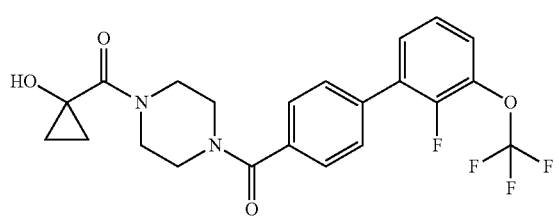 |
| 1-{4-([4-[3-(cyclopropylmethoxy)phenyl]phenyl}carbonyl)piperazin-1-yl]carbonyl}cyclopropan-1-ol | 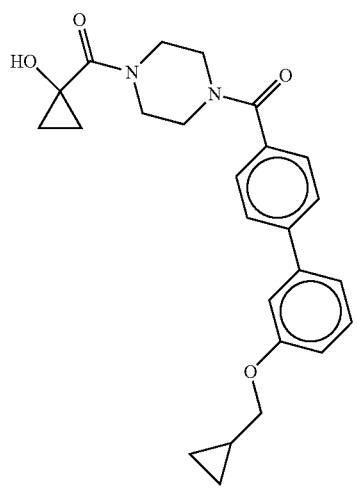 |

| IUPAC Name | Compound Structure |
|---|---|
| 5-fluoro-2-[4-({4-[(1-hydroxycyclopropyl)carbonyl]piperazin-1-yl}carbonyl)phenyl]benzonitrile | 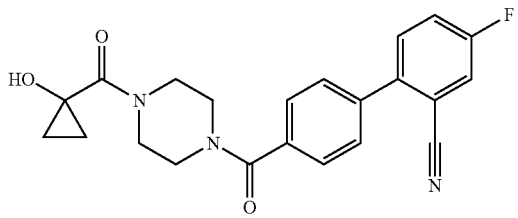 |
| 1-[(4-{[4-(1-methyl-1H-indazol-6-yl)phenyl]carbonyl}piperazin-1-yl)carbonyl]cyclopropan-1-ol | 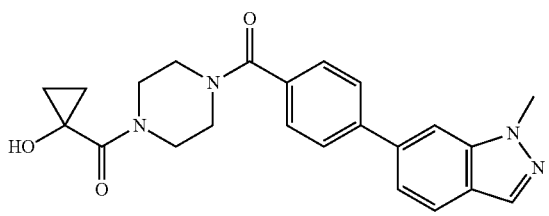 |
| 1-[(4-{[4-(1-methyl-1H-indazol-5-yl)phenyl]carbonyl}piperazin-1-yl)carbonyl]cyclopropan-1-ol | 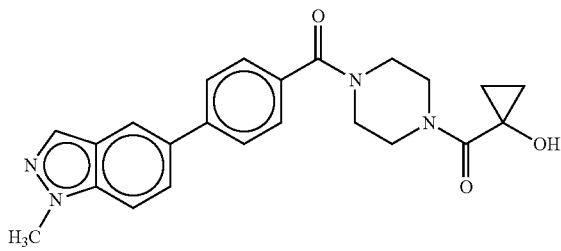 |
| 1-[(4-{[6-(1-methyl-1H-indol-5-yl)pyridin-3-yl]carbonyl}piperazin-1-yl)carbonyl]cyclopropan-1-ol | 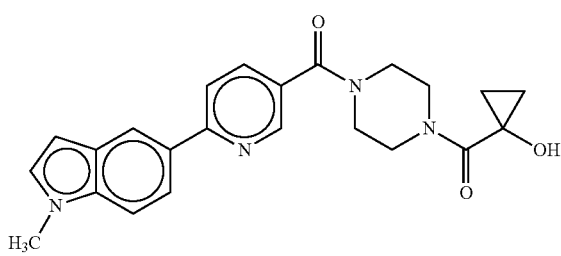 |
| 1-[(4-{[5-(1-methyl-1H-indol-5-yl)pyridin-2-yl]carbonyl}piperazin-1-yl)carbonyl]cyclopropan-1-ol | 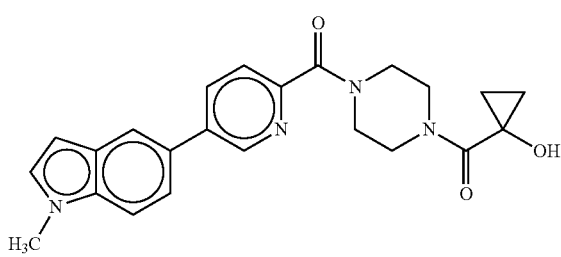 |
| 1-[(4-{[2-fluoro-4-(1-methyl-1H-indol-5-yl)phenyl]carbonyl}piperazin-1-yl)carbonyl]cyclopropan-1-ol | 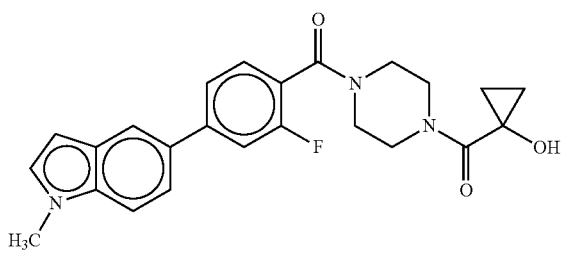 |

| IUPAC Name | Compound Structure |
|---|---|
| 1-[(4-{[2-fluoro-4-(quinolin-6-yl)phenyl]carbonyl}piperazin-1-yl)carbonyl]cyclopropan-1-ol | 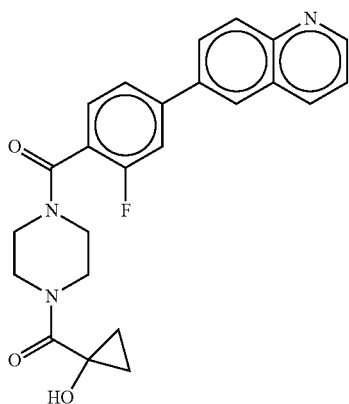 |
| 2-methoxy-2-methyl-1-{4-[(4-phenylphenyl)carbonyl]piperazin-1-yl}propan-1-one | 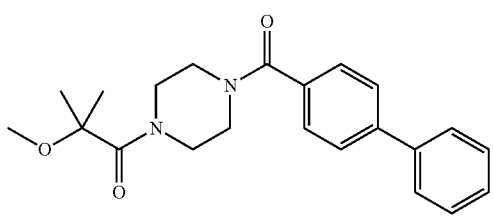 [SMILES: COC(C)(C)C(=O)N1CCN(C(=O)c2ccc(-c3ccccc3)cc2)CC1] |
| (2S)-2-hydroxy-1-{4-[(4-phenylphenyl)carbonyl]piperazin-1-yl}propan-1-one | 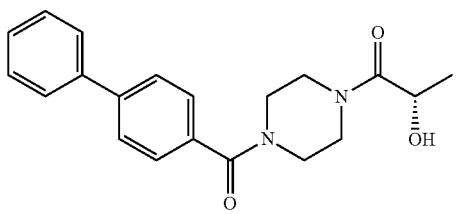 |
| 1-[(4-{[4-(quinolin-3-yl)phenyl]carbonyl}piperazin-1-yl)carbonyl]cyclobutan-1-ol | 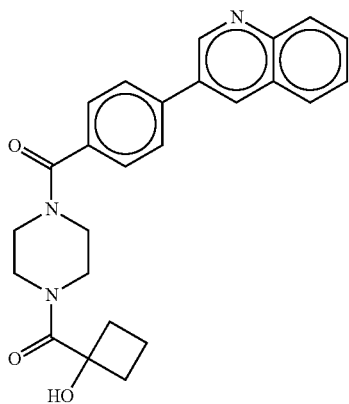 |

| IUPAC Name | Compound Structure |
|---|---|
| 1-[(4-{[2-chloro-4-(quinolin-6-yl)phenyl]carbonyl}piperazin-1-yl)carbonyl]cyclopropan-1-ol | 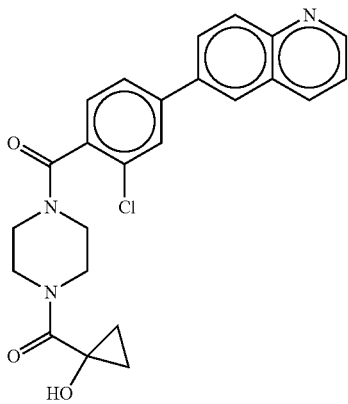 |
| 1-[(4-{[2-chloro-4-(1-methyl-1H-indol-5-yl)phenyl]carbonyl}piperazin-1-yl)carbonyl]cyclopropan-1-ol | 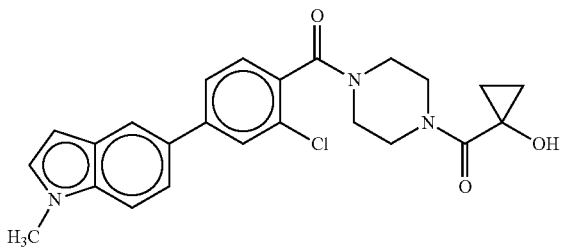 |
| 1-[(4-{[6-(quinolin-6-yl)pyridin-3-yl]carbonyl}piperazin-1-yl)carbonyl]cyclopropan-1-ol | 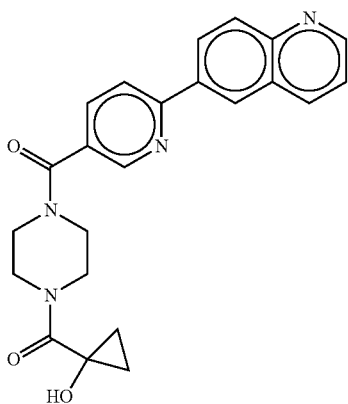 |
| 1-[(4-{[4-methyl-2-(1-methyl-1H-indol-5-yl)-1,3-thiazol-5-yl]carbonyl}piperazin-1-yl)carbonyl]cyclopropan-1-ol | 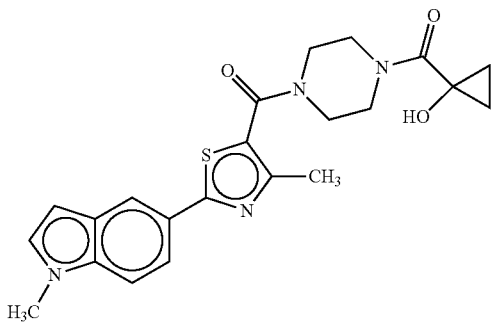 |

-continued
| IUPAC Name | Compound Structure |
|---|---|
| 1-[(4-{[4-methyl-2-(quinolin-3-yl)-1,3-thiazol-5-yl]carbonyl}piperazin-1-yl)carbonyl]cyclopropan-1-ol | 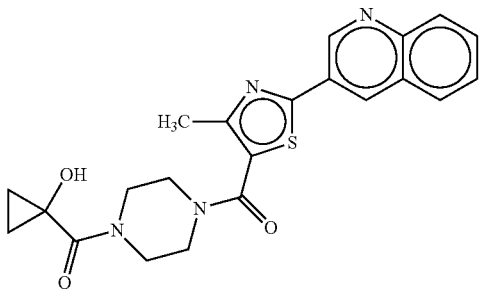 |
| 1-[(4-{[2-(1,3-benzothiazol-5-yl)-4-methyl-1,3-thiazol-5-yl]carbonyl}piperazin-1-yl)carbonyl]cyclopropan-1-ol | 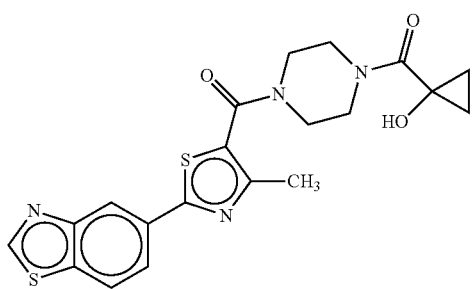 |
| 1-[(4-{[3-fluoro-4-(quinolin-3-yl)phenyl]carbonyl}piperazin-1-yl)carbonyl]cyclopropan-1-ol | 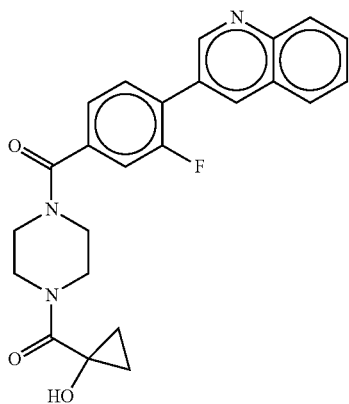 |
| 1-[(4-{[3-fluoro-4-(quinolin-6-yl)phenyl]carbonyl}piperazin-1-yl)carbonyl]cyclopropan-1-ol | 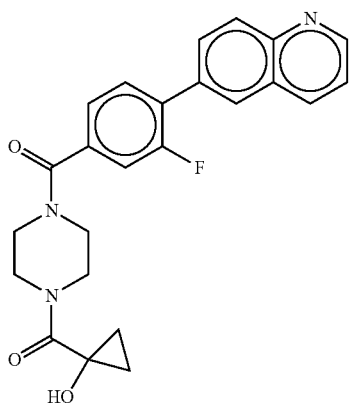 |

| IUPAC Name | Compound Structure |
|---|---|
| 1-[(4-{[4-(1,3-benzothiazol-5-yl)-3-fluorophenyl]carbonyl}piperazin-1-yl)carbonyl]cyclopropan-1-ol | 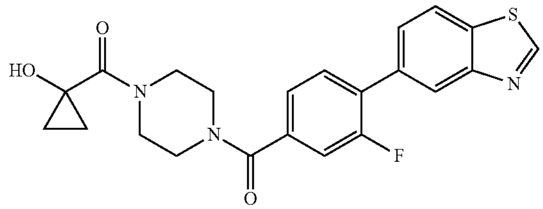 [SMILES: O=C(c1ccc(-c2ccc3scnc3c2)c(F)c1)N1CCN(C(=O)C2(O)CC2)CC1] |
| 1-[(4-{[3-methyl-4-(1-methyl-1H-indol-5-yl)phenyl]carbonyl}piperazin-1-yl)carbonyl]cyclopropan-1-ol | 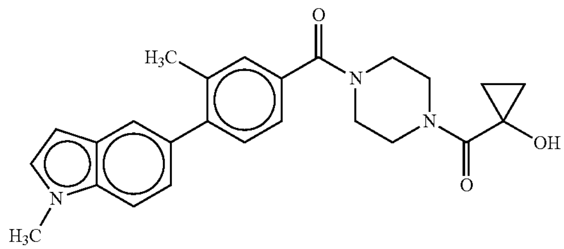 |
| 1-[(4-{[3-methyl-4-(quinolin-3-yl)phenyl]carbonyl}piperazin-1-yl)carbonyl]cyclopropan-1-ol | 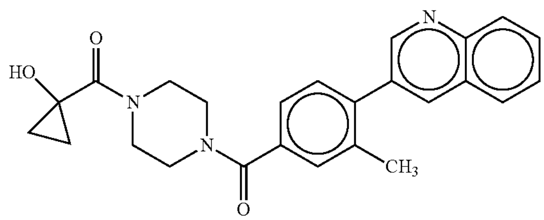 |
| 1-[(4-{[3-methyl-4-(quinolin-6-yl)phenyl]carbonyl}piperazin-1-yl)carbonyl]cyclopropan-1-ol | 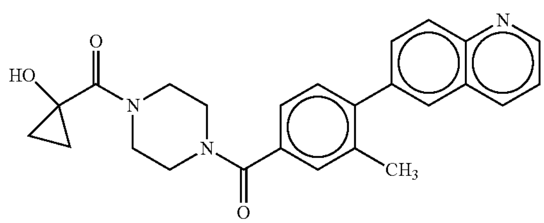 |
| 1-[(4-{[4-(1,3-benzothiazol-5-yl)-3-methylphenyl]carbonyl}piperazin-1-yl)carbonyl]cyclopropan-1-ol | 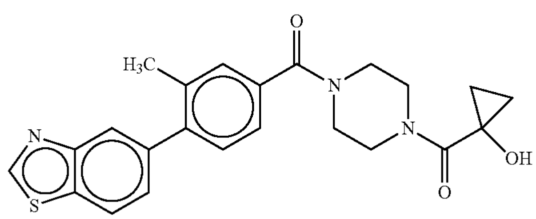 |
| 1-[(4-{[2-chloro-4-(quinolin-3-yl)phenyl]carbonyl}piperazin-1-yl)carbonyl]cyclopropan-1-ol | 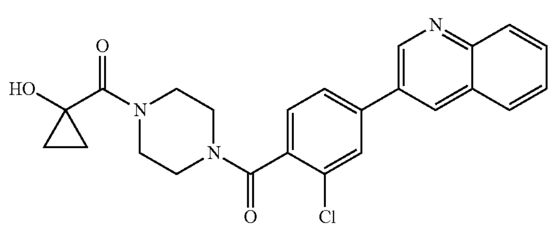 [SMILES: O=C(c1ccc(-c2cnc3ccccc3c2)cc1Cl)N1CCN(C(=O)C2(O)CC2)CC1] |
| 1-[(4-{[4-(1,3-benzothiazol-5-yl)-2-chlorophenyl]carbonyl}piperazin-1-yl)carbonyl]cyclopropan-1-ol | 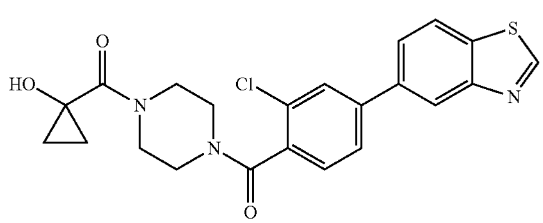 [SMILES: O=C(c1ccc(-c2ccc3scnc3c2)cc1Cl)N1CCN(C(=O)C2(O)CC2)CC1] |

| IUPAC Name | Compound Structure |
| --- | --- |
| 1-[(4-{[3-chloro-4-(1-methyl-1H-indol-5-yl)phenyl]carbonyl}piperazin-1-yl)carbonyl]cyclopropan-1-ol | 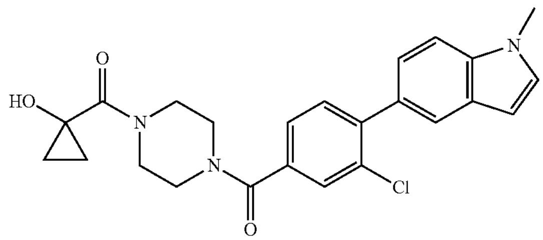 [SMILES: Cn1ccc2cc(-c3ccc(C(=O)N4CCN(C(=O)C5(O)CC5)CC4)cc3Cl)ccc21] |
| 1-[(4-{[3-chloro-4-(quinolin-3-yl)phenyl]carbonyl}piperazin-1-yl)carbonyl]cyclopropan-1-ol | 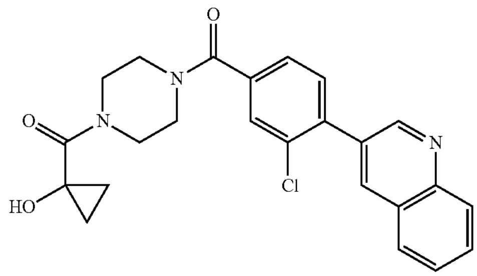 [SMILES: O=C(c1ccc(-c2cnc3ccccc3c2)c(Cl)c1)N1CCN(C(=O)C2(O)CC2)CC1] |
| 1-[(4-{[3-chloro-4-(quinolin-6-yl)phenyl]carbonyl}piperazin-1-yl)carbonyl]cyclopropan-1-ol | 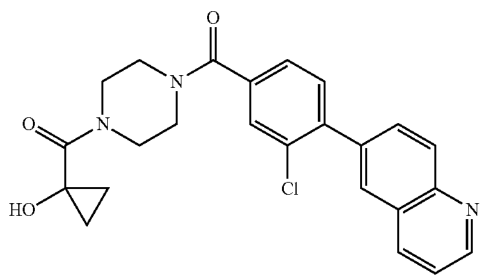 [SMILES: O=C(c1ccc(-c2ccc3ncccc3c2)c(Cl)c1)N1CCN(C(=O)C2(O)CC2)CC1] |
| 1-[(4-{[4-(1,3-benzothiazol-5-yl)-3-chlorophenyl]carbonyl}piperazin-1-yl)carbonyl]cyclopropan-1-ol | 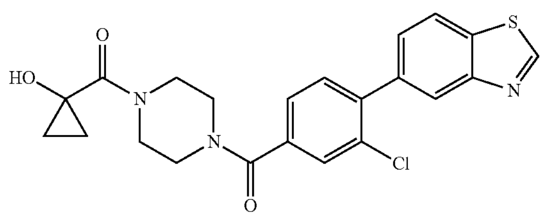 [SMILES: O=C(c1ccc(-c2ccc3scnc3c2)c(Cl)c1)N1CCN(C(=O)C2(O)CC2)CC1] |
| 1-[(4-{[4-(1-methyl-1H-indol-5-yl)-2-(trifluoromethyl)phenyl]carbonyl}piperazin-1-yl)carbonyl]cyclopropan-1-ol | |
| 1-[(4-{[4-(quinolin-6-yl)-2-(trifluoromethyl)phenyl]carbonyl}piperazin-1-yl)carbonyl]cyclopropan-1-ol | |

| IUPAC Name | Compound Structure |
|---|---|
| 1-[(4-{[3-methoxy-4-(quinolin-6-yl)phenyl]carbonyl}piperazin-1-yl)carbonyl]cyclopropan-1-ol | 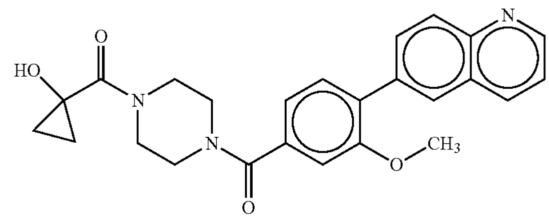 |
| 1-[(4-{[2-methoxy-4-(quinolin-3-yl)phenyl]carbonyl}piperazin-1-yl)carbonyl]cyclopropan-1-ol | 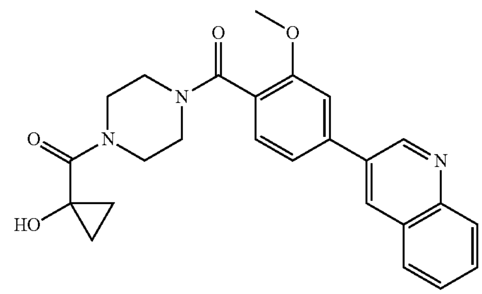 [SMILES: COc1cc(-c2cnc3ccccc3c2)ccc1C(=O)N1CCN(C(=O)C2(O)CC2)CC1] |
| 1-[(4-{[2-methoxy-4-(quinolin-6-yl)phenyl]carbonyl}piperazin-1-yl)carbonyl]cyclopropan-1-ol | 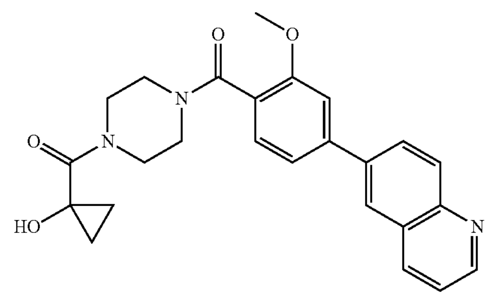 [SMILES: COc1cc(-c2ccc3ncccc3c2)ccc1C(=O)N1CCN(C(=O)C2(O)CC2)CC1] |
| 1-[(4-{[4-(1,3-benzothiazol-5-yl)-2-methoxyphenyl]carbonyl}piperazin-1-yl)carbonyl]cyclopropan-1-ol | 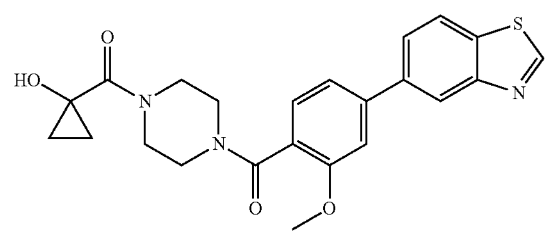 [SMILES: COc1cc(-c2ccc3scnc3c2)ccc1C(=O)N1CCN(C(=O)C2(O)CC2)CC1] |
| 1-[(4-{[5-(quinolin-6-yl)pyrimidin-2-yl]carbonyl}piperazin-1-yl)carbonyl]cyclopropan-1-ol | 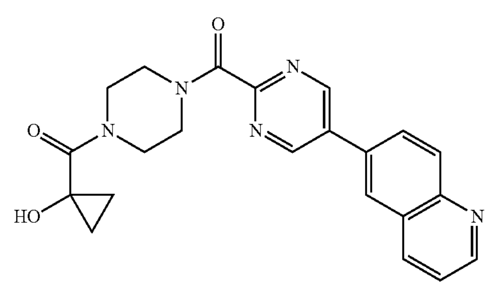 [SMILES: O=C(c1ncc(-c2ccc3ncccc3c2)cn1)N1CCN(C(=O)C2(O)CC2)CC1] |
| 1-[(4-{[5-(1-methyl-1H-indol-5-yl)pyrazin-2-yl]carbonyl}piperazin-1-yl)carbonyl]cyclopropan-1-ol | 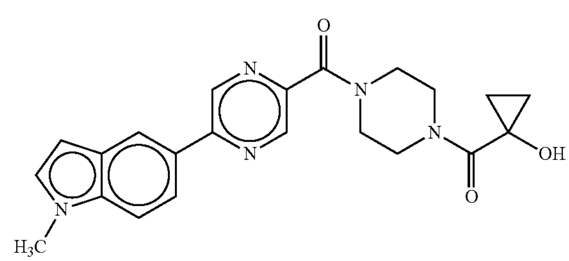 |

| IUPAC Name | Compound Structure |
|---|---|
| 1-[(4-{[5-(quinolin-3-yl)pyrazin-2-yl]carbonyl}piperazin-1-yl)carbonyl]cyclopropan-1-ol | 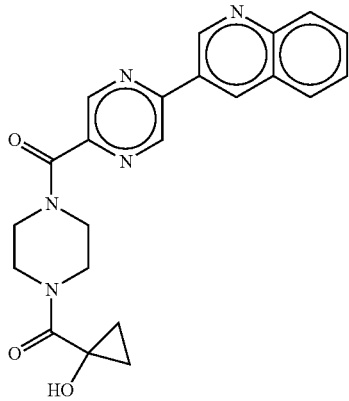 |
| 1-[(4-{[5-(quinolin-6-yl)pyrazin-2-yl]carbonyl}piperazin-1-yl)carbonyl]cyclopropan-1-ol | 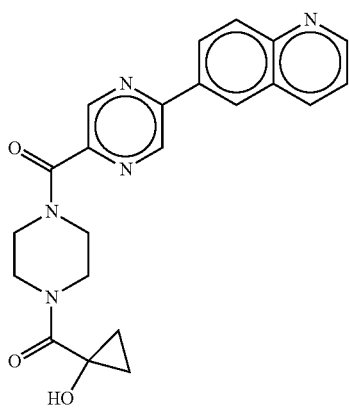 |
| 1-({4-[(4-phenylphenyl)carbonyl]piperazin-1-yl}carbonyl)cyclobutan-1-ol | 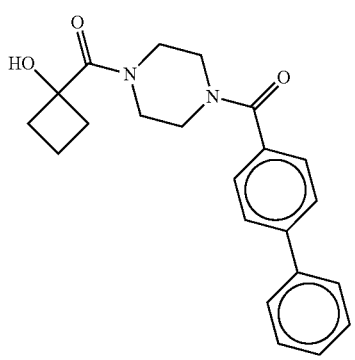 |
| 1-[(4-{[4-(isoquinolin-6-yl)phenyl]carbonyl}piperazin-1-yl)carbonyl]cyclobutan-1-ol | 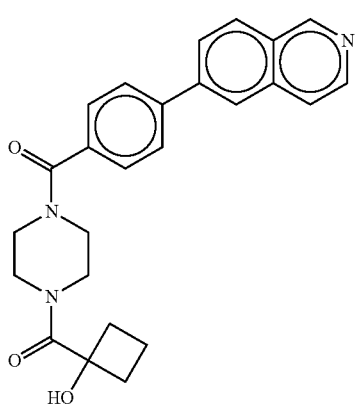 |

| IUPAC Name | Compound Structure |
|---|---|
| 1-{[(2S,5R)-4-{[4-(isoquinolin-6-yl)phenyl]carbonyl}-2,5-dimethylpiperazin-1-yl]carbonyl}cyclopropan-1-ol | 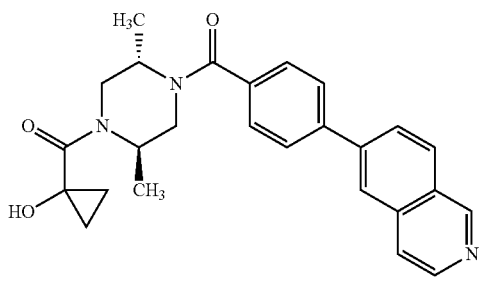 [SMILES: C[C@@H]1CN(C(=O)c2ccc(-c3ccc4cnccc4c3)cc2)[C@@H](C)CN1C(=O)C1(O)CC1] |
| 1-[(4-{[4-(1H-indol-5-yl)phenyl]carbonyl}piperazin-1-yl)carbonyl]cyclopropan-1-ol | 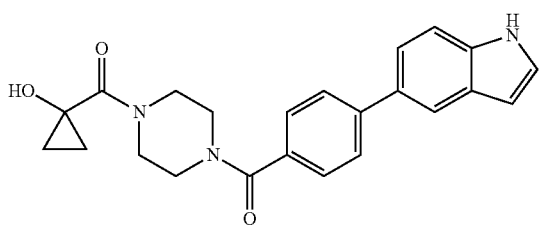 [SMILES: O=C(c1ccc(-c2ccc3[nH]ccc3c2)cc1)N1CCN(C(=O)C2(O)CC2)CC1] |
| 3-[4-({4-[(oxetan-2-yl)carbonyl]piperazin-1-yl}carbonyl)phenyl]quinoline | 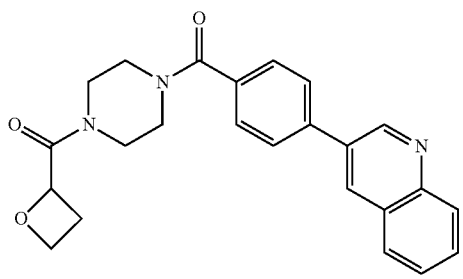 [SMILES: O=C(c1ccc(-c2cnc3ccccc3c2)cc1)N1CCN(C(=O)C2CCO2)CC1] |
| 5-[4-({4-[(oxetan-2-yl)carbonyl]piperazin-1-yl}carbonyl)phenyl]-1H-indole | 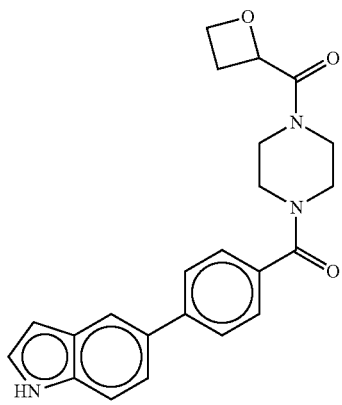 |
| 1-[(4-{[2-fluoro-4-(quinolin-3-yl)phenyl]carbonyl}piperazin-1-yl)carbonyl]cyclopropan-1-ol | 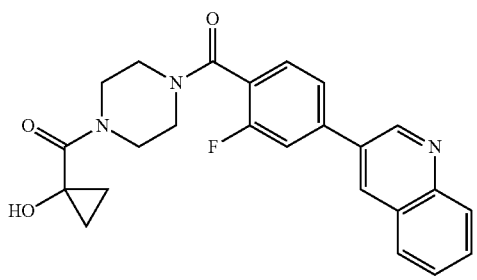 [SMILES: O=C(c1ccc(-c2cnc3ccccc3c2)cc1F)N1CCN(C(=O)C2(O)CC2)CC1] |

-continued

| IUPAC Name | Compound Structure |
|---|---|
| 6-[4-({4-[(oxetan-2-yl)carbonyl]piperazin-1-yl}carbonyl)phenyl]isoquinoline | 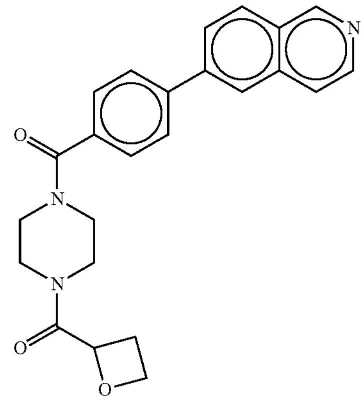 |
| 1-[(4-{[4-(1,5-naphthyridin-3-yl)phenyl]carbonyl}piperazin-1-yl)carbonyl]cyclopropan-1-ol | 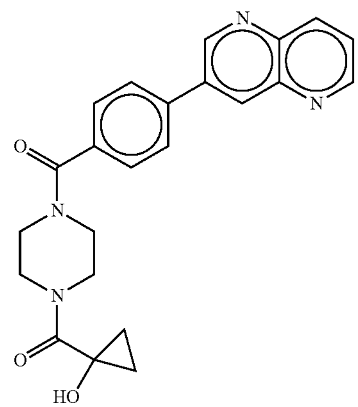 |
| 1-[(4-{[4-(1-benzofuran-5-yl)phenyl]carbonyl}piperazin-1-yl)carbonyl]cyclopropan-1-ol | 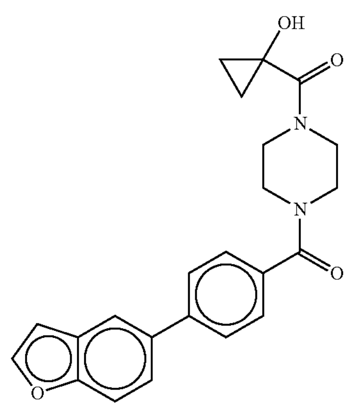 |
| 1-({4-[(4-phenoxyphenyl)carbonyl]piperazin-1-yl}carbonyl)cyclopropan-1-ol | 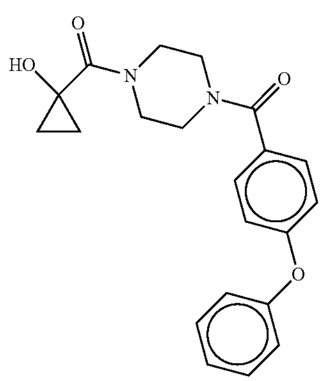 |

| IUPAC Name | Compound Structure |
|---|---|
| 1-[(4-{[2-fluoro-4-(7-fluoro-1H-indol-5-yl)phenyl]carbonyl}piperazin-1-yl)carbonyl]cyclopropan-1-ol | 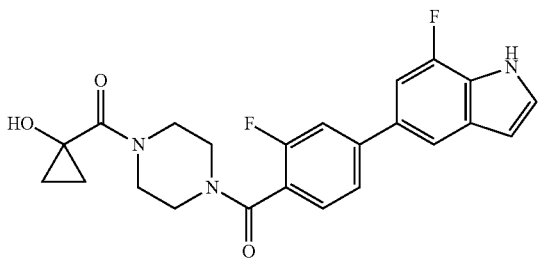 [SMILES: O=C(c1ccc(-c2cc(F)c3[nH]ccc3c2)cc1F)N1CCN(C(=O)C2(O)CC2)CC1] |
| 1-{[4-({3-chloro-4-[1-(trifluoromethyl)-1H-indol-5-yl]phenyl}carbonyl)piperazin-1-yl]carbonyl}cyclopropan-1-ol | 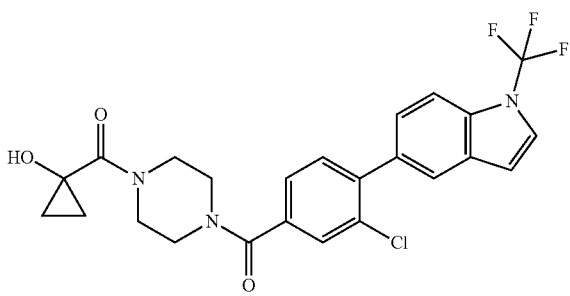 [SMILES: O=C(c1ccc(-c2ccc3c(ccn3C(F)(F)F)c2)c(Cl)c1)N1CCN(C(=O)C2(O)CC2)CC1] |
| 1-[(4-{[4-(1,3-benzoxazol-5-yl)phenyl]carbonyl}piperazin-1-yl)carbonyl]cyclopropan-1-ol | 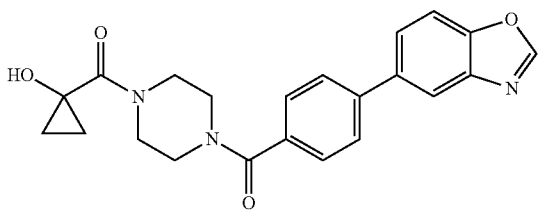 [SMILES: O=C(c1ccc(-c2ccc3ocnc3c2)cc1)N1CCN(C(=O)C2(O)CC2)CC1] |
| 1-[(4-{[4-(1,3-benzothiazol-6-yl)phenyl]carbonyl}piperazin-1-yl)carbonyl]cyclopropan-1-ol | 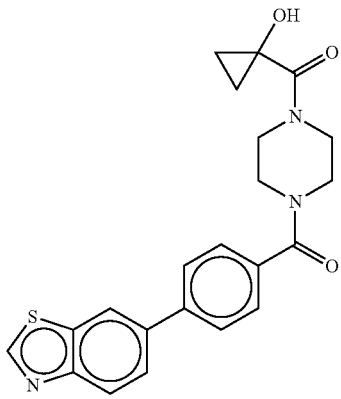 |
| 1-{[4-({3-chloro-4-[1-(propan-2-yl)-1H-indol-5-yl]phenyl}carbonyl)piperazin-1-yl]carbonyl}cyclopropan-1-ol | 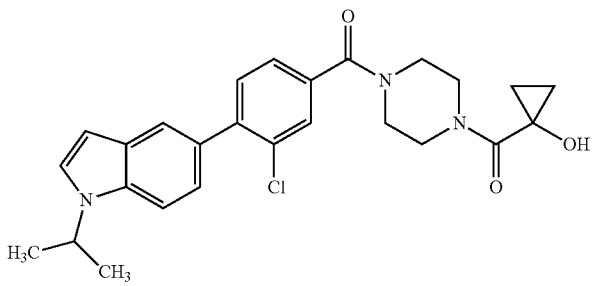 [SMILES: CC(C)n1ccc2cc(-c3ccc(C(=O)N4CCN(C(=O)C5(O)CC5)CC4)cc3Cl)ccc21] |

| IUPAC Name | Compound Structure |
|---|---|
| 1-[(4-{[4-(1H-1,3-benzodiazol-5-yl)phenyl]carbonyl}piperazin-1-yl)carbonyl]cyclopropan-1-ol | 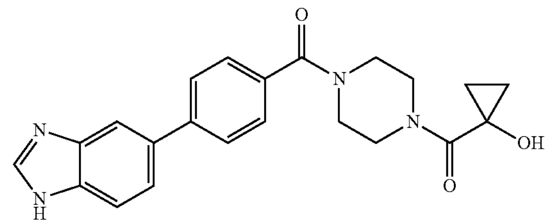 [SMILES: O=C(c1ccc(-c2ccc3[nH]cnc3c2)cc1)N1CCN(C(=O)C2(O)CC2)CC1] |
| 5-[4-({4-[(1-hydroxycyclopropyl)carbonyl]piperazin-1-yl}carbonyl)phenyl]-1H-indole-3-carbonitrile | 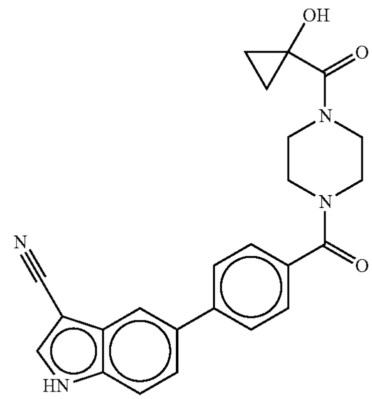 |
| 3-[3-fluoro-4-({4-[(1-hydroxycyclopropyl)carbonyl]piperazin-1-yl}carbonyl)phenyl]quinolin-2-ol | 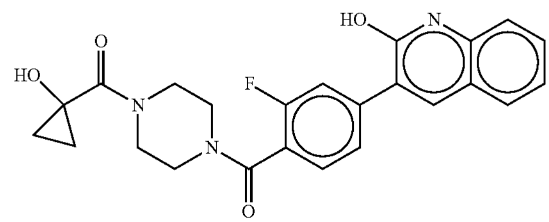 |
| 1-[(4-{[4-(1,3-benzoxazol-2-yl)phenyl]carbonyl}piperazin-1-yl)carbonyl]cyclopropan-1-ol | 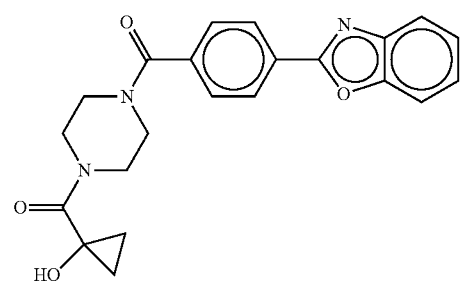 |
| 1-[(4-{[2-fluoro-4-(2-methoxyquinolin-3-yl)phenyl]carbonyl}piperazin-1-yl)carbonyl]cyclopropan-1-ol | 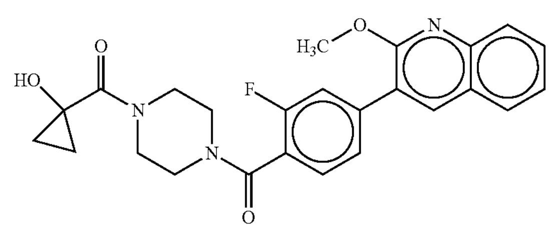 |
| 1-[(4-{[4-(4-chloroquinolin-3-yl)phenyl]carbonyl}piperazin-1-yl)carbonyl]cyclopropan-1-ol | 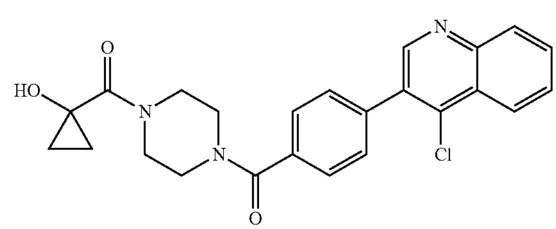 [SMILES: O=C(c1ccc(-c2cnc3ccccc3c2Cl)cc1)N1CCN(C(=O)C2(O)CC2)CC1] |

-continued

| IUPAC Name | Compound Structure |
|---|---|
| 1-[(4-{[4-(7-fluoro-1H-indol-5-yl)phenyl]carbonyl}piperazin-1-yl)carbonyl]cyclopropan-1-ol | 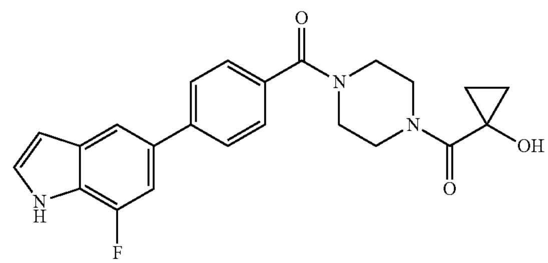 [SMILES: O=C(c1ccc(-c2cc(F)c3[nH]ccc3c2)cc1)N1CCN(C(=O)C2(O)CC2)CC1] |
| 1-[(4-{[4-(quinolin-2-yl)phenyl]carbonyl}piperazin-1-yl)carbonyl]cyclopropan-1-ol | 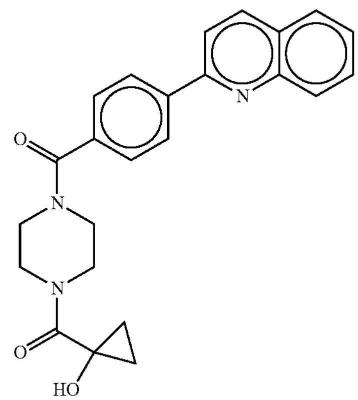 |
| 1-[(4-{[4-(1,3-benzothiazol-2-yl)phenyl]carbonyl}piperazin-1-yl)carbonyl]cyclopropan-1-ol | 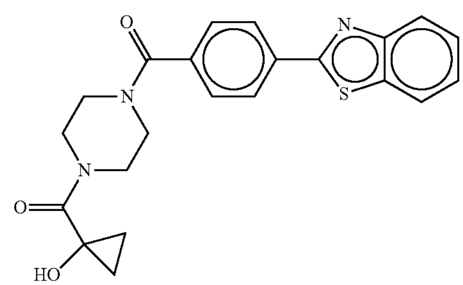 |
| 1-[(4-{[4-(2-methoxyquinolin-6-yl)phenyl]carbonyl}piperazin-1-yl)carbonyl]cyclopropan-1-ol | 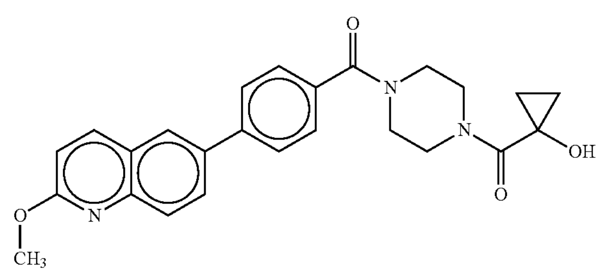 |
| 1-{[4-({4-[1-(trifluoromethyl)-1H-indol-5-yl]phenyl}carbonyl)piperazin-1-yl]carbonyl}cyclopropan-1-ol | |

| IUPAC Name | Compound Structure |
|---|---|
| 1-[(4-{[4-(6-methoxynaphthalen-2-yl)phenyl]carbonyl}piperazin-1-yl)carbonyl]cyclopropan-1-ol | 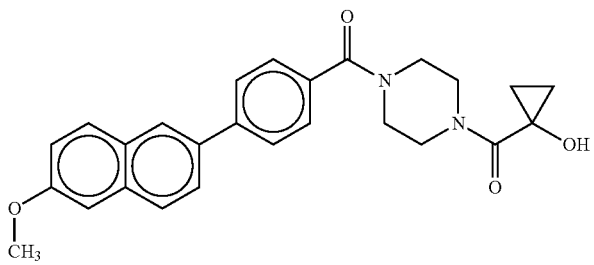 |
| 1-[(4-{[4-(5-chloro-1,3-benzoxazol-2-yl)phenyl]carbonyl}piperazin-1-yl)carbonyl]cyclopropan-1-ol | 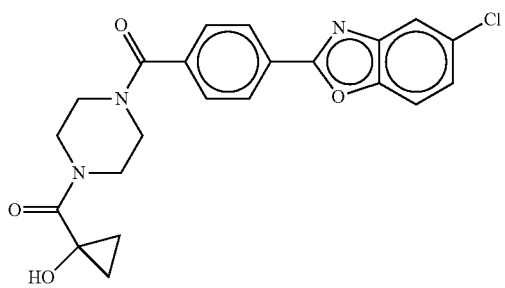 |
| 1-[(4-{[4-(6-chloro-1,3-benzoxazol-2-yl)phenyl]carbonyl}piperazin-1-yl)carbonyl]cyclopropan-1-ol | 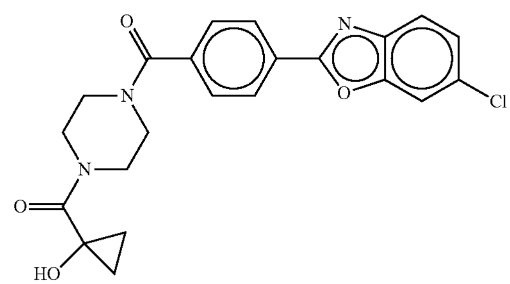 |
| 1-[(4-{[4-(5-fluoro-1,3-benzoxazol-2-yl)phenyl]carbonyl}piperazin-1-yl)carbonyl]cyclopropan-1-ol | 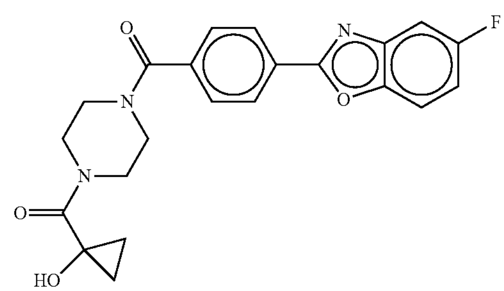 |
| 1-[(4-{[4-(6-fluoro-1,3-benzoxazol-2-yl)phenyl]carbonyl}piperazin-1-yl)carbonyl]cyclopropan-1-ol | 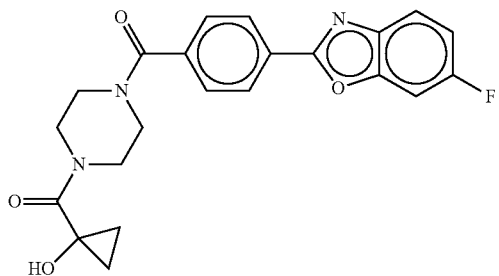 |

| IUPAC Name | Compound Structure |
|---|---|
| 1-[(4-{[4-(6-methoxynaphthalen-2-yl)phenyl]carbonyl}piperazin-1-yl)carbonyl]cyclopropan-1-ol | 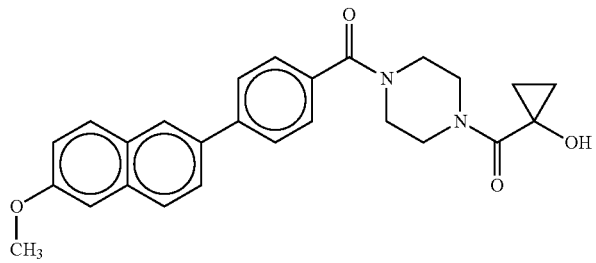 |
| 1-[(4-{[4-(5-chloro-1,3-benzoxazol-2-yl)phenyl]carbonyl}piperazin-1-yl)carbonyl]cyclopropan-1-ol | 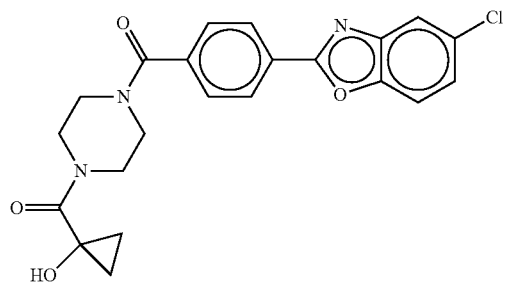 |
| 1-[(4-{[4-(6-chloro-1,3-benzoxazol-2-yl)phenyl]carbonyl}piperazin-1-yl)carbonyl]cyclopropan-1-ol | 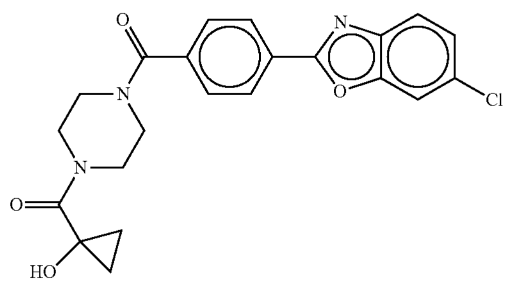 |
| 1-[(4-{[4-(5-fluoro-1,3-benzoxazol-2-yl)phenyl]carbonyl}piperazin-1-yl)carbonyl]cyclopropan-1-ol | 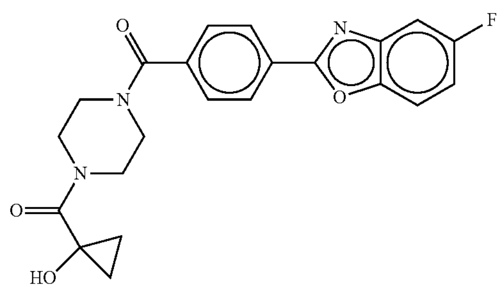 |
| 1-[(4-{[4-(6-fluoro-1,3-benzoxazol-2-yl)phenyl]carbonyl}piperazin-1-yl)carbonyl]cyclopropan-1-ol | 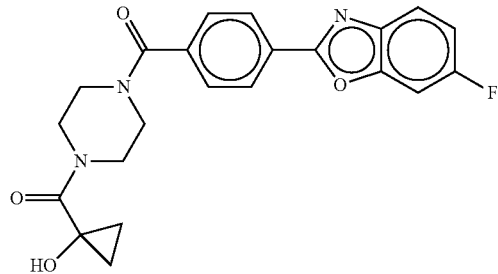 |

| IUPAC Name | Compound Structure |
|---|---|
| 1-({4-[(4-{pyrazolo[1,5-a]pyridin-2-yl}phenyl)carbonyl]piperazin-1-yl}carbonyl)cyclopropan-1-ol | 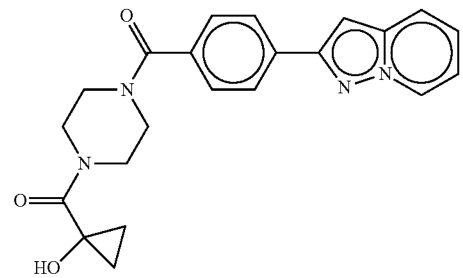 |
| 1-{[4-({4-[1-(propan-2-yl)-1H-indazol-5-yl]phenyl}carbonyl)piperazin-1-yl]carbonyl}cyclopropan-1-ol | 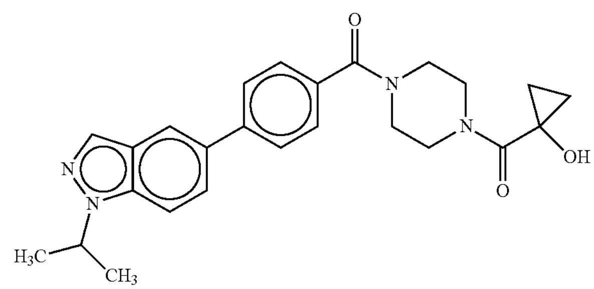 |
| 1-[(4-{[6-(2-methoxyquinolin-6-yl)pyridin-3-yl]carbonyl}piperazin-1-yl)carbonyl]cyclopropan-1-ol | 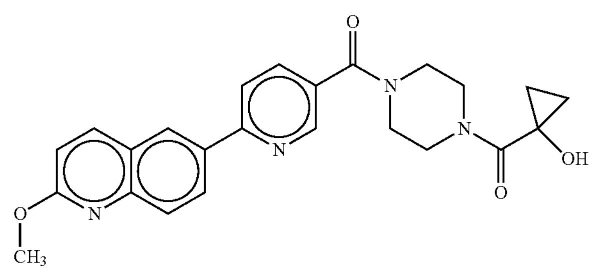 |
| 1-[(4-{[5-(2-methoxyquinolin-6-yl)pyridin-2-yl]carbonyl}piperazin-1-yl)carbonyl]cyclopropan-1-ol | 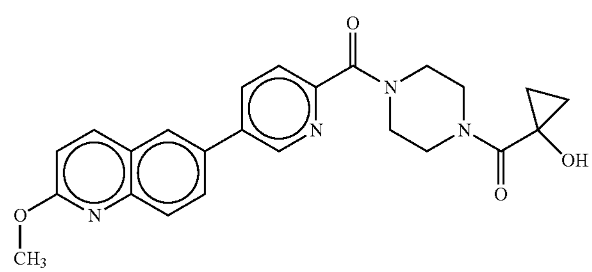 |
| 1-{[4-({6-phenylimidazo[1,2-a]pyridin-2-yl}carbonyl)piperazin-1-yl]carbonyl}cyclopropan-1-ol | 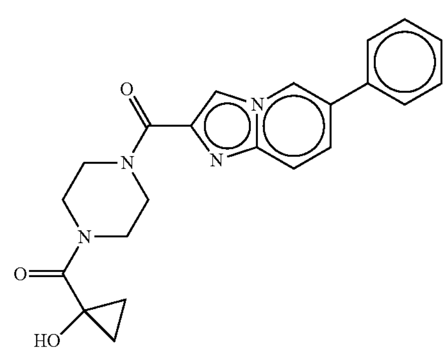 |

-continued

| IUPAC Name | Compound Structure |
|---|---|
| 1-[(4-{[6-(4-fluorophenyl)imidazo[1,2-a]pyridin-2-yl]carbonyl}piperazin-1-yl)carbonyl]cyclopropan-1-ol | 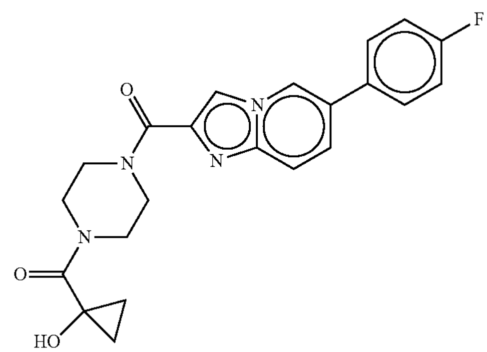 |
| 1-[(4-{[5-(4-chloro-2-fluorophenyl)pyridin-2-yl]carbonyl}piperazin-1-yl)carbonyl]cyclopropan-1-ol | 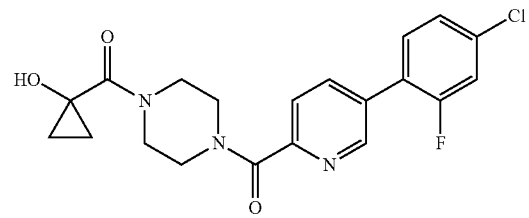 |
| 1-[(4-{[6-(4-chloro-2-fluorophenyl)pyridin-3-yl]carbonyl}piperazin-1-yl)carbonyl]cyclopropan-1-ol | 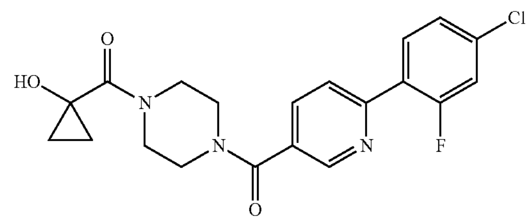 |
| 1-[(4-{[5-(4-chloro-2-fluorophenyl)pyrimidin-2-yl]carbonyl}piperazin-1-yl)carbonyl]cyclopropan-1-ol | 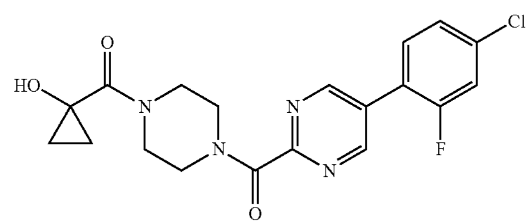 |
| 1-[(4-{[2-fluoro-4-(6-fluoroquinolin-2-yl)phenyl]carbonyl}piperazin-1-yl)carbonyl}cyclopropan-1-ol | 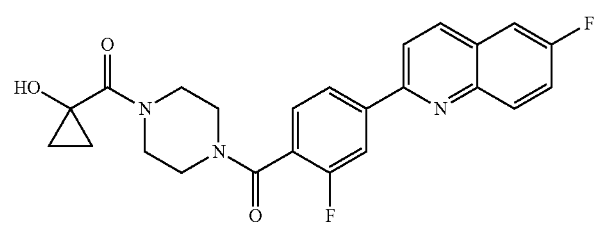 [SMILES: O=C(c1ccc(-c2ccc3cc(F)ccc3n2)cc1F)N1CCN(C(=O)C2(O)CC2)CC1] |
| 1-[(4-{[2-fluoro-4-(6-methoxyquinolin-2-yl)phenyl]carbonyl}piperazin-1-yl)carbonyl]cyclopropan-1-ol | 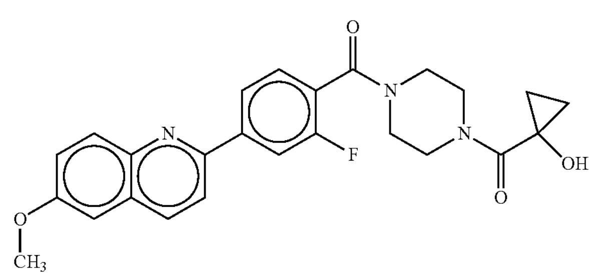 |

| IUPAC Name | Compound Structure |
|---|---|
| 1-[(4-{[2,3-difluoro-4-(quinolin-2-yl)phenyl]carbonyl}piperazin-1-yl)carbonyl]cyclopropan-1-ol | 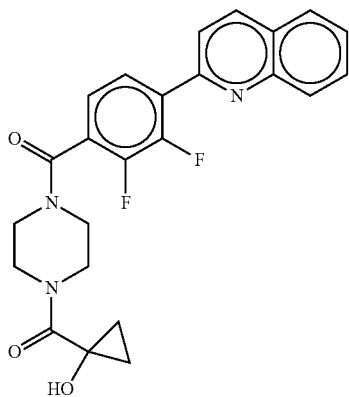 |
| 1-[(4-{[2,3-difluoro-4-(6-fluoroquinolin-2-yl)phenyl]carbonyl}piperazin-1-yl)carbonyl]cyclopropan-1-ol | 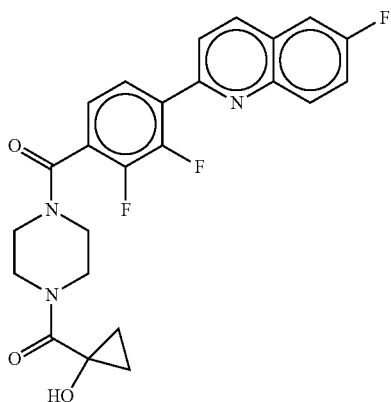 |
| 1-[(4-{[2,3-difluoro-4-(6-methoxyquinolin-2-yl)phenyl]carbonyl}piperazin-1-yl)carbonyl]cyclopropan-1-ol | 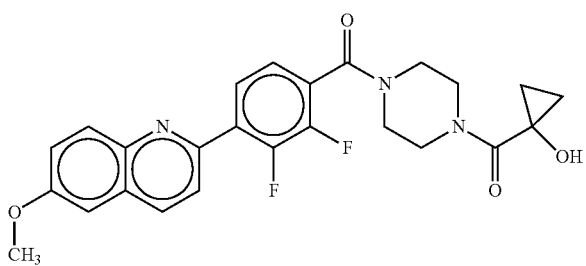 |
| 1-[(4-{[4-(6-fluoroquinolin-2-yl)phenyl]carbonyl}piperazin-1-yl)carbonyl]cyclopropan-1-ol | 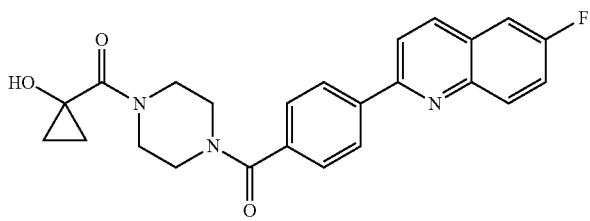 [SMILES: O=C(c1ccc(-c2ccc3cc(F)ccc3n2)cc1)N1CCN(C(=O)C2(O)CC2)CC1] |
| 1-[(4-{[4-(6-methoxyquinolin-2-yl)phenyl]carbonyl}piperazin-1-yl)carbonyl]cyclopropan-1-ol | 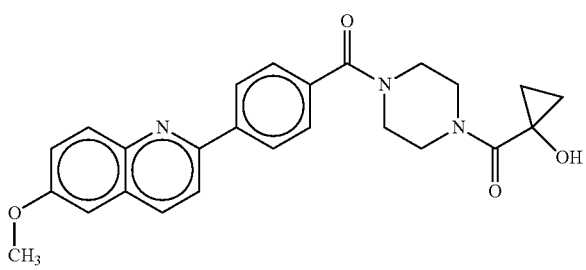 |

| IUPAC Name | Compound Structure |
|---|---|
| 1-({4-[(4-{imidazo[1,2-a]pyridin-2-yl)phenyl)carbonyl]piperazin-1-yl}carbonyl)cyclopropan-1-ol | 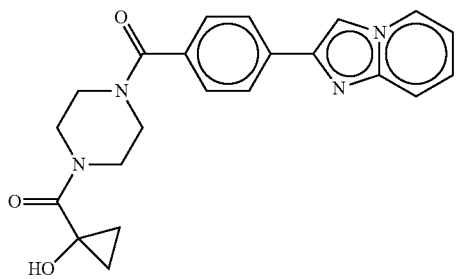 |
| 1-[(4-{[4-(2,1,3-benzoxadiazol-5-yl)phenyl]carbonyl}piperazin-1-yl)carbonyl]cyclopropan-1-ol | 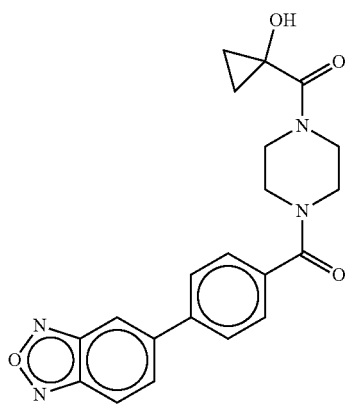 |
| N-{3-[4-({4-[(1-hydroxycyclopropyl)carbonyl]piperazin-1-yl}carbonyl)phenyl]phenyl}benzenesulfonamide | 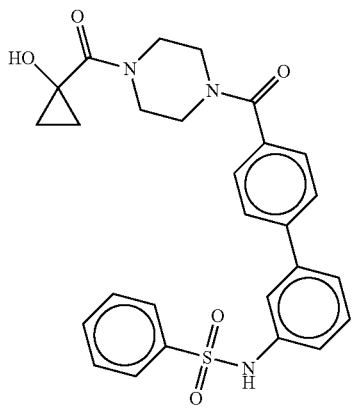 |
| N-{3-[4-({4-[(1-hydroxycyclopropyl)carbonyl]piperazin-1-yl}carbonyl)phenyl]phenyl}methanesulfonamide | 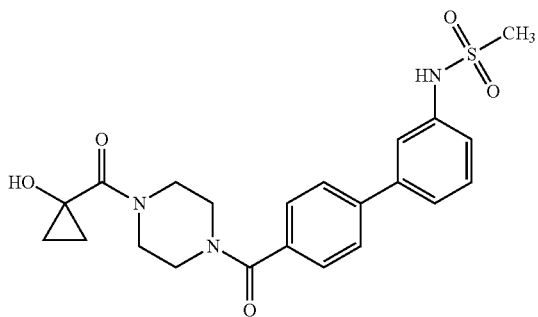 [SMILES: CS(=O)(=O)Nc1cccc(-c2ccc(C(=O)N3CCN(C(=O)C4(O)CC4)CC3)cc2)c1] |

| IUPAC Name | Compound Structure |
|---|---|
| N-{3-[4-({4-[(1-hydroxycyclopropyl)carbonyl]piperazin-1-yl}carbonyl)phenyl]phenyl}propane-2-sulfonamide | 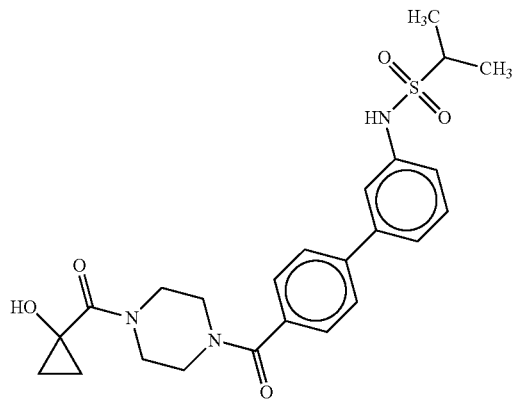 |
| N-{3-[4-({4-[(1-hydroxycyclopropyl)carbonyl]piperazin-1-yl}carbonyl)phenyl]phenyl}cyclopropanesulfonamide | 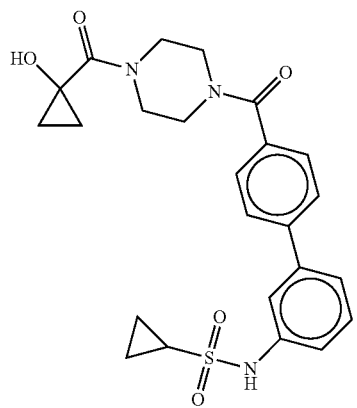 |
| 1-[(4-{[4-(isoquinolin-1-yl)phenyl]carbonyl}piperazin-1-yl)carbonyl]cyclopropan-1-ol | 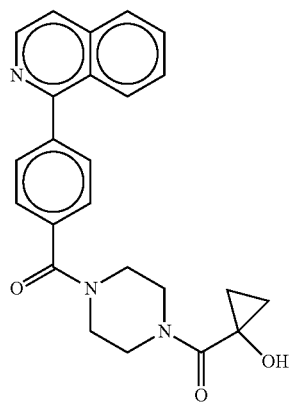 |

| IUPAC Name | Compound Structure |
|---|---|
| 1-{[4-({4-[7-(trifluoromethyl)quinolin-4-yl]phenyl}carbonyl)piperazin-1-yl]carbonyl}cyclopropan-1-ol | 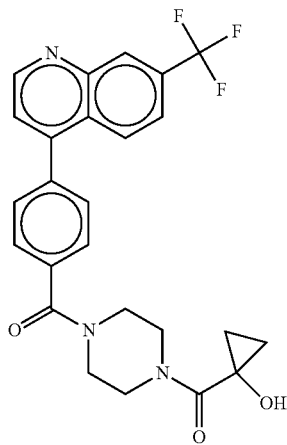 |
| 1-[(4-{[4-(6-methoxy-4-methylquinolin 2-yl)phenyl]carbonyl}piperazin-1-yl)carbonyl]cyclopropan-1-ol | 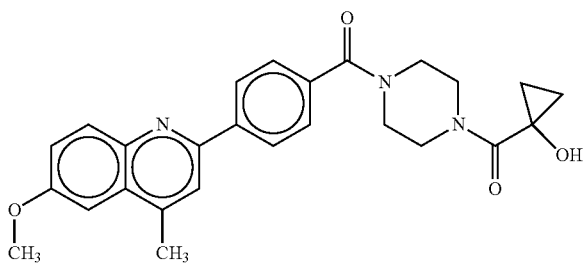 |
| 1-[(4-{[4-(5-chloro-1H-1,3-benzodiazol-2-yl)phenyl]carbonyl}piperazin-1-yl)carbonyl]cyclopropan-1-ol | 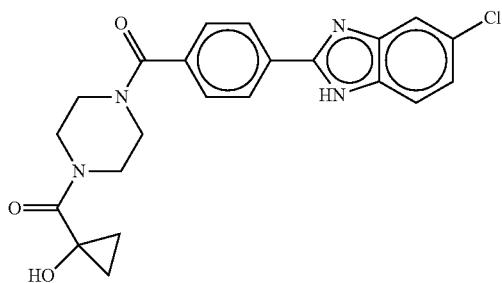 |
| 1-[(4-{[4-(4-chloro-1H-1,3-benzodiazol-2-yl)phenyl]carbonyl}piperazin-1-yl)carbonyl]cyclopropan-1-ol | 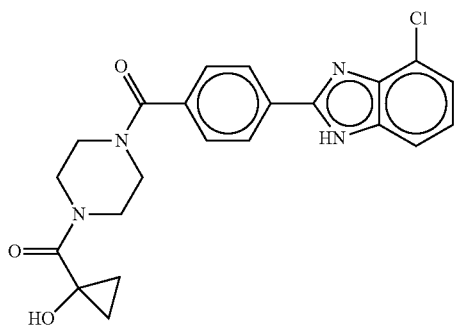 |

| IUPAC Name | Compound Structure |
|---|---|
| 1-[(4-{[4-(5,6-difluoro-1H-1,3-benzodiazol-2-yl)phenyl]carbonyl}piperazin-1-yl)carbonyl]cyclopropan-1-ol | 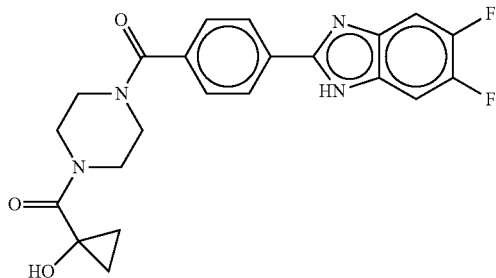 |
| 1-[(4-{[4-(5-methoxy-1H-1,3-benzodiazol-2-yl)phenyl]carbonyl}piperazin-1-yl)carbonyl]cyclopropan-1-ol | 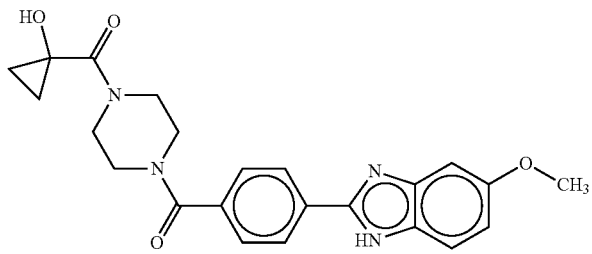 |
| 1-[(4-{[4-(5-fluoro-1H-1,3-benzodiazol-2-yl)phenyl]carbonyl}piperazin-1-yl)carbonyl]cyclopropan-1-ol | 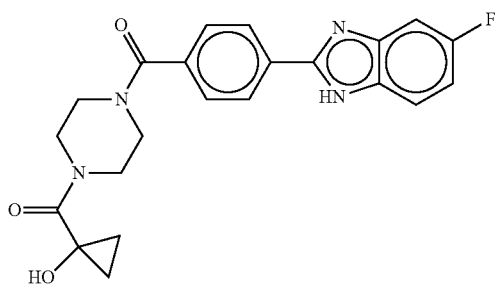 |
| 1-[(4-{[4-(1,3-dimethyl-1H-indazol-5-yl)phenyl]carbonyl}piperazin-1-yl)carbonyl]cyclopropan-1-ol | 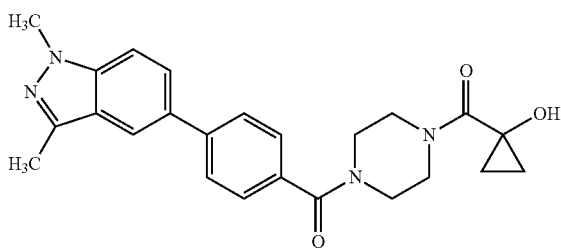 [SMILES: Cc1nn(C)c2ccc(-c3ccc(C(=O)N4CCN(C(=O)C5(O)CC5)CC4)cc3)cc12] |
| 6-[4-({4-[(1-hydroxycyclopropyl)carbonyl]piperazin-1-yl}carbonyl)phenyl]-2,3-dihydro-1,3-benzoxazol-2-one | 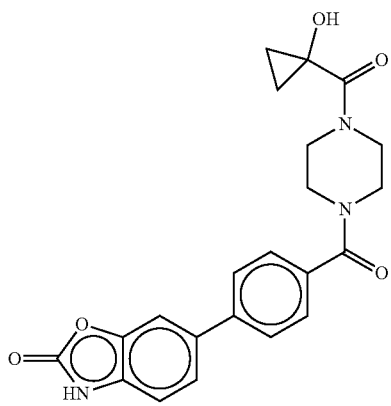 |

| IUPAC Name | Compound Structure |
|---|---|
| 5-[4-({4-[(1-hydroxycyclopropyl)carbonyl]piperazin-1-yl}carbonyl)phenyl]-2,3-dihydro-1,3-benzoxazol-2-one | 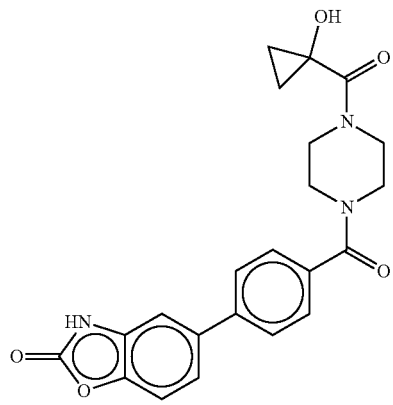 |
| 1-[(4-{[4-(3-methyl-1,2-benzoxazol-6-yl)phenyl]carbonyl}piperazin-1-yl)carbonyl]cyclopropan-1-ol | 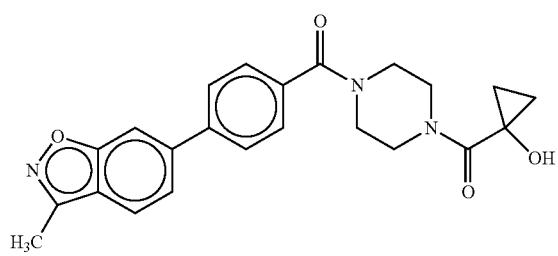 |
| 1-[(4-{[4-(1H-1,3-benzodiazol-4-yl)phenyl]carbonyl}piperazin-1-yl)carbonyl]cyclopropan-1-ol | 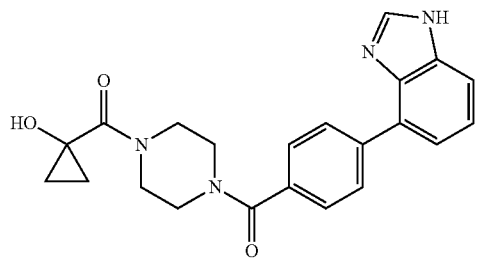 |
| 1-[(4-{[4-(1,3-benzoxazol-4-yl)phenyl]carbonyl}piperazin-1-yl)carbonyl]cyclopropan-1-ol | 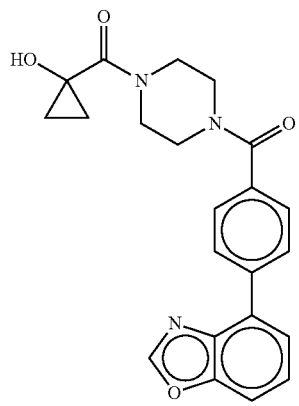 |

-continued
| IUPAC Name | Compound Structure |
|---|---|
| 1-[(4-{[4-(quinolin-5-yl)phenyl]carbonyl}piperazin-1-yl)carbonyl]cyclopropan-1-ol | 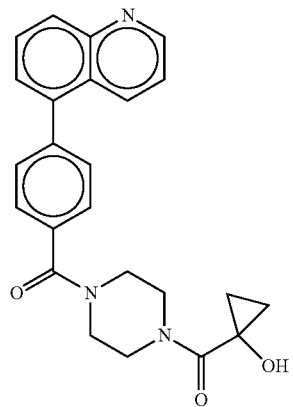 |
| 1-[(4-{[4-(1H-indazol-3-yl)phenyl]carbonyl}piperazin-1-yl)carbonyl]cyclopropan-1-ol | 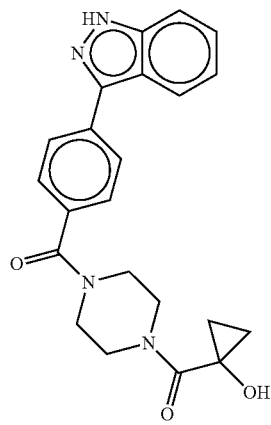 |
| 1-({4-[(4-{furo[3,2-b]pyridin-5-yl}phenyl)carbonyl]piperazin-1-yl}carbonyl)cyclopropan-1-ol | 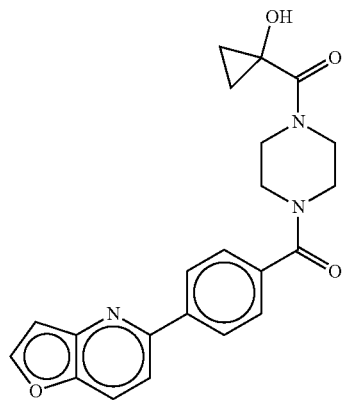 |

| IUPAC Name | Compound Structure |
|---|---|
| 1-({4-[(4-{furo[3,2-c]pyridin-4-yl}phenyl)carbonyl]piperazin-1-yl}carbonyl)cyclopropan-1-ol | 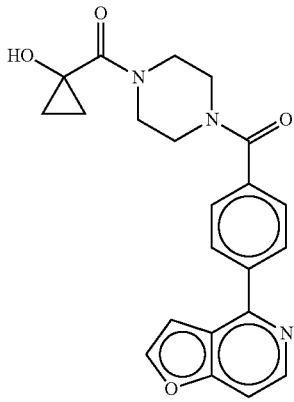 |
| 1-({4-[(4-{[1,2,4]triazolo[4,3-b]pyridazin-6-yl}phenyl)carbonyl]piperazin-1-yl}carbonyl)cyclopropan-1-ol | 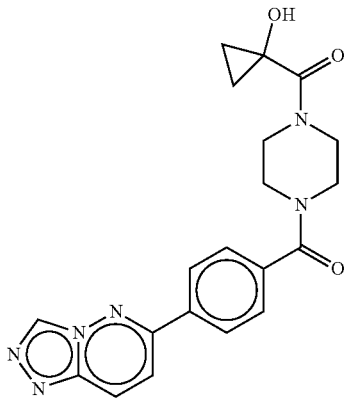 |
| 1-({4-[(4-{imidazo[1,2-a]pyrazin-6-yl}phenyl)carbonyl]piperazin-1-yl}carbonyl)cyclopropan-1-ol | 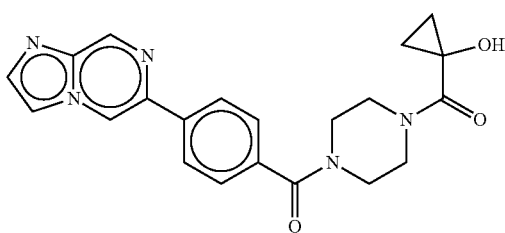 |
| 1-({4-[(4-{1H-pyrrolo[3,2-b]pyridin-5-yl}phenyl)carbonyl]piperazin-1-yl}carbonyl)cyclopropan-1-ol | 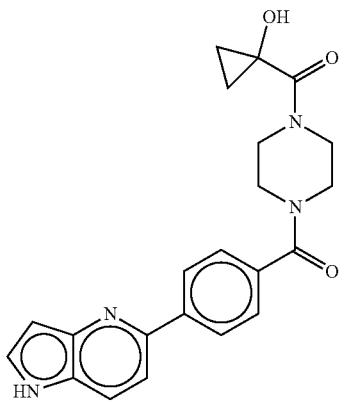 |

| IUPAC Name | Compound Structure |
|---|---|
| 1-({4-[(4-{imidazo[1,2-b]pyridazin-6-yl}phenyl)carbonyl]piperazin-1-yl}carbonyl)cyclopropan-1-ol | 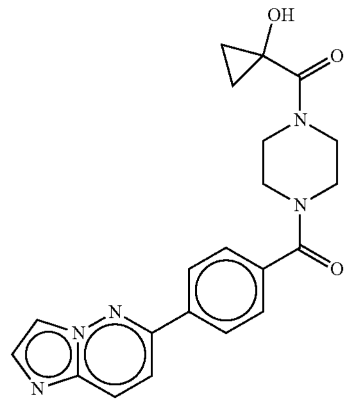 |
| 1-[(4-{[4-(1-methyl-1H-1,3-benzodiazol-5-yl)phenyl]carbonyl}piperazin-1-yl)carbonyl]cyclopropan-1-ol | 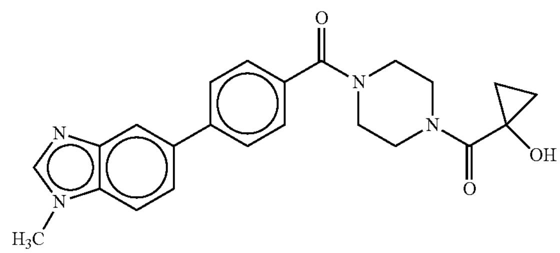 |
| 1-[(4-{[4-(2,1,3-benzothiadiazol-4-yl)phenyl]carbonyl}piperazin-1-yl)carbonyl]cyclopropan-1-ol | 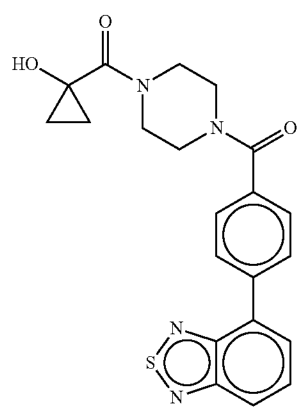 |
| 1-{[4-({4-[2-(trifluoromethyl)imidazo[1,2-a]pyridin-6-yl]phenyl}carbonyl)piperazin-1-yl]carbonyl}cyclopropan-1-ol | 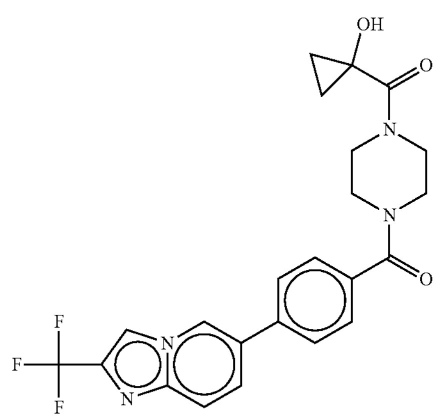 |

| IUPAC Name | Compound Structure |
|---|---|
| 1-({4-[(4-{6-chloroimidazo[1,2-a]pyridin-3-yl}phenyl)carbonyl]piperazin-1-yl]carbonyl)cyclopropan-1-ol | 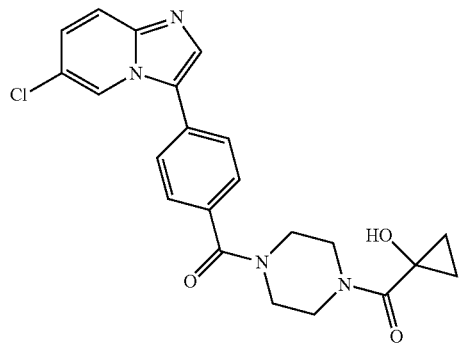 [SMILES: O=C(c1ccc(-c2cnc3ccc(Cl)cn23)cc1)N1CCN(C(=O)C2(O)CC2)CC1] |
| 1-[(4-{[4-(2-methyl-2H-indazol-5-yl)phenyl]carbonyl}piperazin-1-yl)carbonyl]cyclopropan-1-ol | 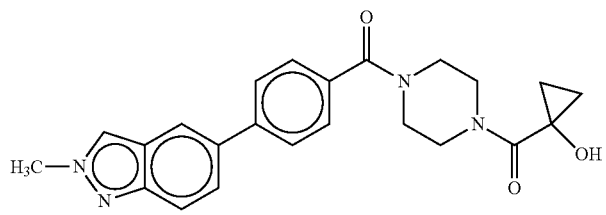 |
| 1-({4-[(4-{imidazo[1,2-a]pyrimidin-7-yl}phenyl)carbonyl]piperazin-1-yl}carbonyl)cyclopropan-1-ol | 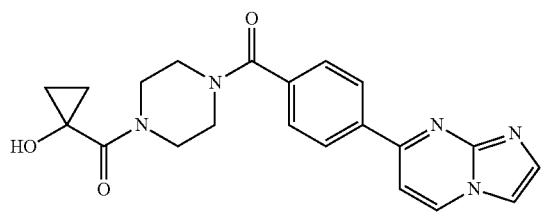 [SMILES: O=C(c1ccc(-c2ccn3ccnc3n2)cc1)N1CCN(C(=O)C2(O)CC2)CC1] |
| 5-[4-({4-[(1-hydroxycyclopropyl)carbonyl]piperazin-1-yl}carbonyl)phenyl]-1H-indole-2-carbonitrile | 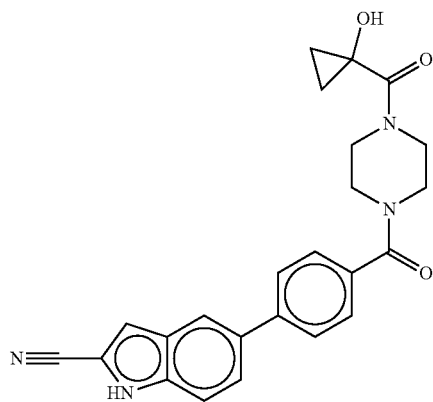 |
| 2-[4-({4-[(1-hydroxycyclopropyl)carbonyl]piperazin-1-yl}carbonyl)phenyl]-1,3-benzoxazole-6-carbonitrile | 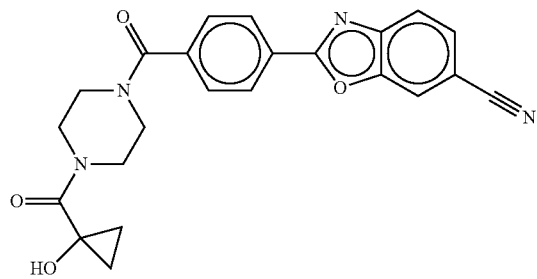 |

-continued

| IUPAC Name | Compound Structure |
|---|---|
| 1-[(4-{[4-(2,1,3-benzothiadiazol-5-yl)phenyl]carbonyl}piperazin-1-yl)carbonyl]cyclopropan-1-ol | 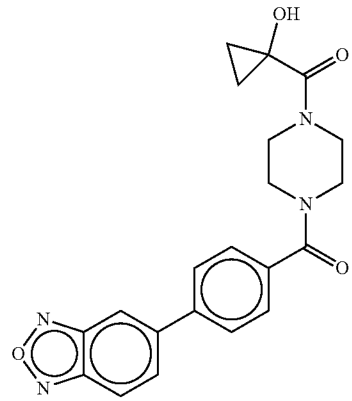 |
| 1-[(4-{[4-(2H-1,2,3-benzotriazol-5-yl)phenyl]carbonyl}piperazin-1-yl)carbonyl]cyclopropan-1-ol | 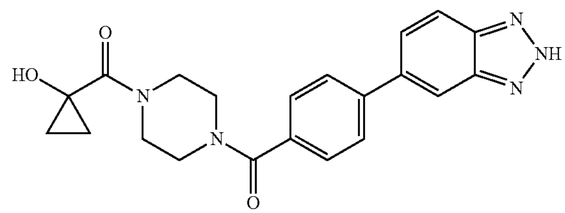 [SMILES: O=C(c1ccc(-c2ccc3n[nH]nc3c2)cc1)N1CCN(C(=O)C2(O)CC2)CC1] |
| 1-({4-[(2-phenyl-1,3-benzothiazol-6-yl)carbonyl]piperazin-1-yl}carbonyl)cylcopropan-1-ol | 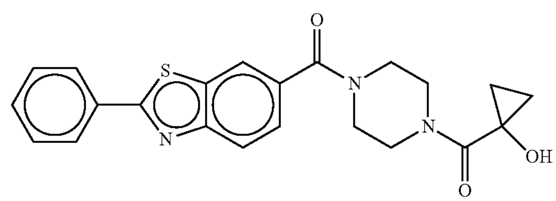 |
| 1-[(4-{[2-(4-fluorophenyl)-1,3-benzothiazol-6-yl]carbonyl}piperazin-1 yl)carbonyl]cyclopropan-1-ol | 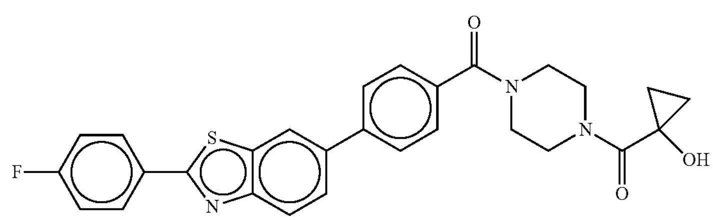 |
| 2-[4-({4-[(1-hydroxycyclopropyl)carbonyl]piperazin-1-yl}carbonyl)phenyl]-1,3-benzoxazole-5-carbonitrile | 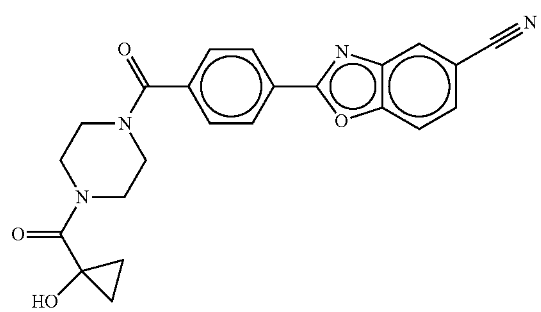 |
| 3-[4-({4-[(1-hydroxycyclopropyl)carbonyl)piperazin-1-yl}carbonyl)phenyl]-1,2-dihydroquinolin-2-one | |

| IUPAC Name | Compound Structure |
|---|---|
| 1-({4-[(2-chloro-4-{imidazo[1,2-a]pyridin-2-yl}phenyl)carbonyl]piperazin-1-yl}carbonyl)cyclopropan-1-ol | 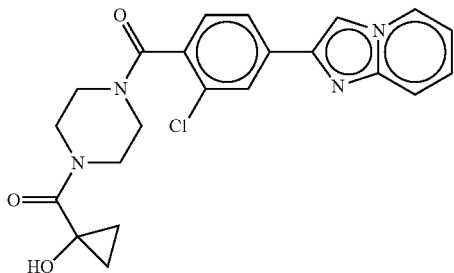 |
| 1-({4-[(3-phenoxyphenyl)carbonyl]piperazin-1-yl}carbonyl)cyclopropan-1-ol | 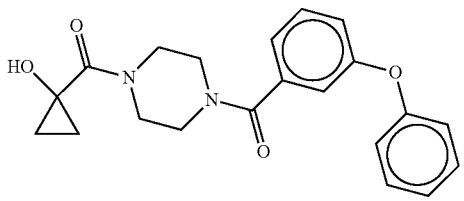 |
| 1-({4-[(4-{6-fluoroimidazo[1,2-a]pyridin-2-yl}phenyl)carbonyl]piperazin-1-yl}carbonyl)cyclopropan-1-ol | 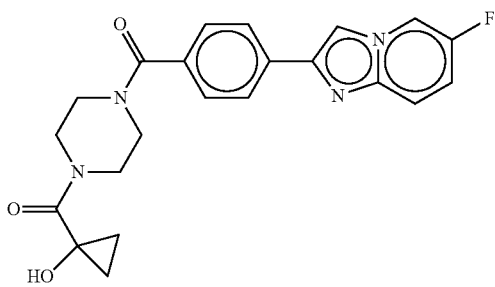 |
| 1-({4-[(4-{6-methoxyimidazo[1,2-a]pyridin-2-yl}phenyl)carbonyl]piperazin-1-yl}carbonyl)cyclopropan-1-ol | 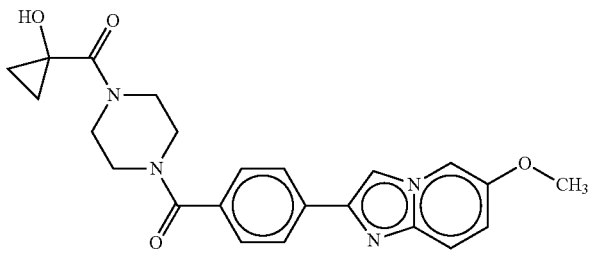 |
| N-{3-[4-({4-[(1-hydroxycyclopropyl)carbonyl]piperazin-1-yl}carbonyl)phenyl]phenyl}cyclopropanecarboxamide | 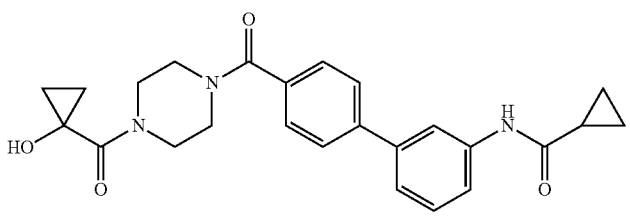 |
| 1-{[(2S)-4-{[4-(4-chloro-2-fluorophenyl)phenyl]carbonyl}-2-(hydroxymethyl)piperazin-1-yl]carbonyl}cyclopropan-1-ol | 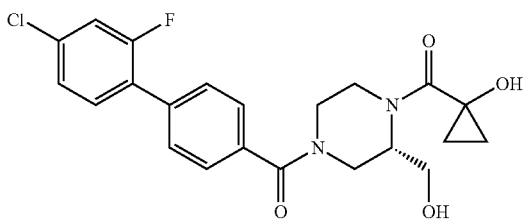 [SMILES: O=C(c1ccc(-c2ccc(Cl)cc2F)cc1)N1CCN(C(=O)C2(O)CC2)[C@H](CO)C1] |

| IUPAC Name | Compound Structure |
|---|---|
| 1-[(4-{[4-(3-cyclopropoxyphenyl)phenyl]carbonyl}piperazin-1-yl)carbonyl]cyclopropan-1-ol | 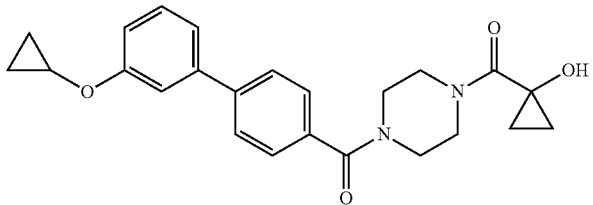 [SMILES: O=C(c1ccc(-c2cccc(OC3CC3)c2)cc1)N1CCN(C(=O)C2(O)CC2)CC1] |
| N-cyclopropyl-3-[4-({4-[(1-hydroxycyclopropyl)carbonyl]piperazin-1-yl}carbonyl)phenyl]benzene-1-sulfonamide | 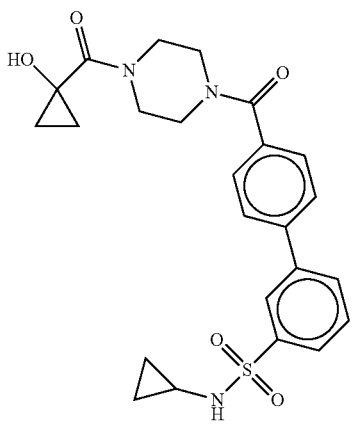 |
| 5-[4-({4-[(1-hydroxycyclopropyl)carbonyl]piperazin-1-yl}carbonyl)phenyl]-1H-indole-2-carboxamide | 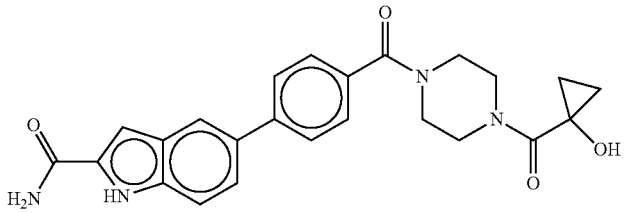 |
| 1-[(4-{[4-(3-chlorophenyl)phenyl]carbonyl}piperazin-1-yl)carbonyl]cyclopropan-1-ol | 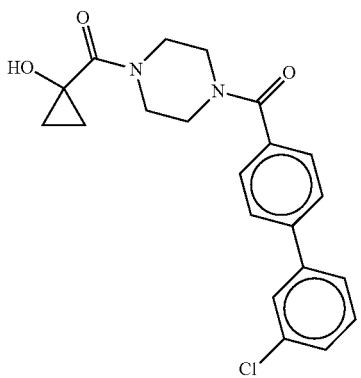 |
| 1-[(4-{[4-(4-chlorophenyl)phenyl]carbonyl}piperazin-1-yl)carbonyl]cyclopropan-1-ol | 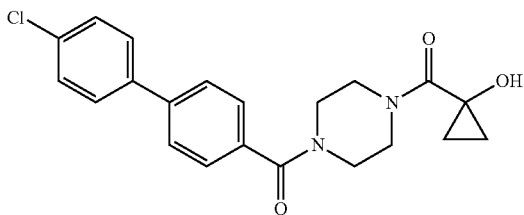 [SMILES: O=C(c1ccc(-c2ccc(Cl)cc2)cc1)N1CCN(C(=O)C2(O)CC2)CC1] |

-continued

| IUPAC Name | Compound Structure |
|---|---|
| 1-{[(3S)-4-{[4-(4-chloro-2-fluorophenyl)phenyl]carbonyl}-3-(hydroxymethyl)piperazin-1-yl]carbonyl}cyclopropan-1-ol | 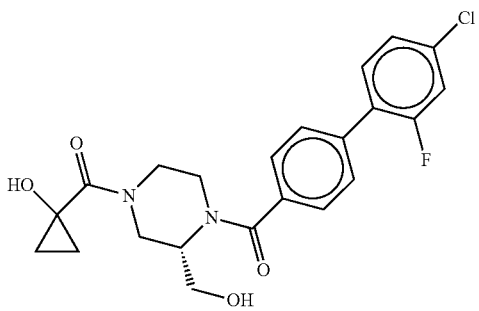 |
| 1-[(4-{[4-(1H-indol-2-yl)phenyl]carbonyl}piperazin-1-yl)carbonyl]cyclopropan-1-ol | 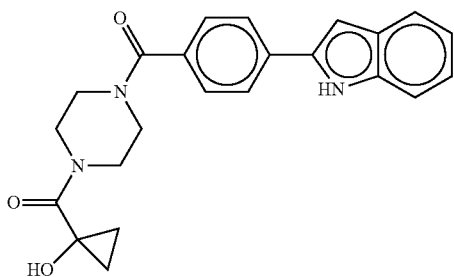 |
| 1-({4-[(4-{3-chloroimidazo[1,2-a]pyridin-2-yl}phenyl)carbonyl]piperazin-1-yl}carbonyl)cyclopropan-1-ol | 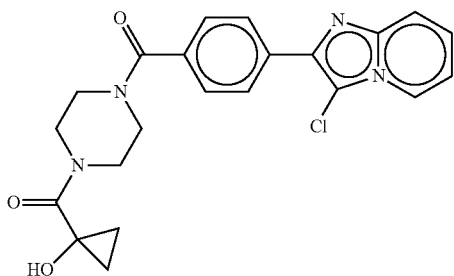 |
| 1-[(4-{[4-(1-methyl-1H-1,3-benzodiazol-2-yl)phenyl]carbonyl}piperazin-1-yl)carbonyl]cyclopropan-1-ol | 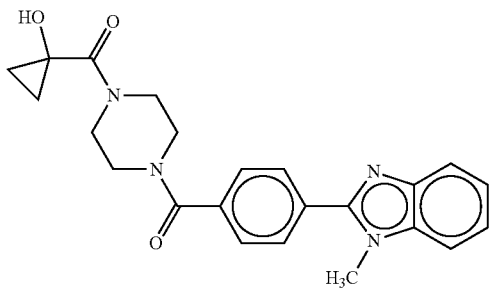 |
| 3-[3-chloro-4-({4-[(1-hydroxycyclopropyl)carbonyl]piperazin-1-yl}carbonyl)phenyl]-N-cyclopropylbenzene-1-sulfonamide | 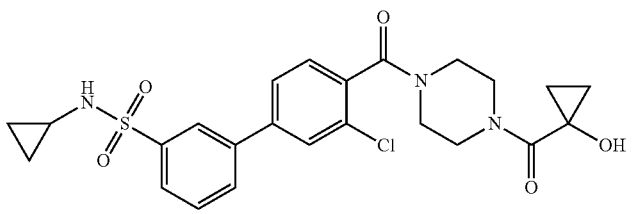 [SMILES: O=C(c1ccc(-c2cccc(S(=O)(=O)NC3CC3)c2)cc1Cl)N1CCN(C(=O)C2(O)CC2)CC1] |

-continued

| IUPAC Name | Compound Structure |
|---|---|
| 1-({4-[(2-chloro-4-{furo[3,2-b]pyridin-5-yl}phenyl)carbonyl]piperazin-1-yl}carbonyl)cyclopropan-1-ol | 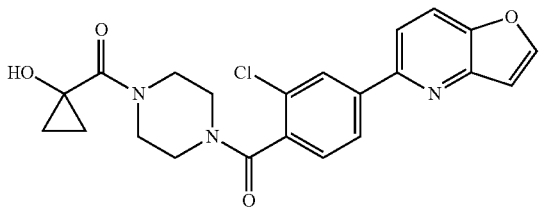 [SMILES: O=C(c1ccc(-c2ccc3occc3n2)cc1Cl)N1CCN(C(=O)C2(O)CC2)CC1] |
| 1-[(4-{[2-chloro-4-(1-methyl-1H-1,3-benzodiazol-5-yl)phenyl]carbonyl}piperazin-1-yl)carbonyl]cyclopropan-1-ol | 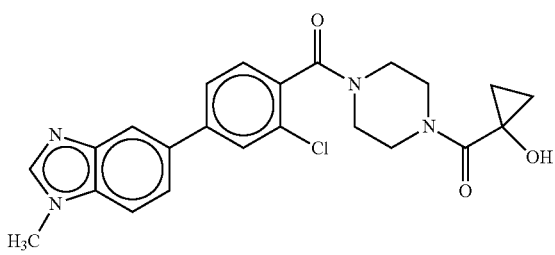 |
| N-{3-[3-chloro-4-([4-[(1-hydroxycyclopropyl)carbonyl]piperazin-1-yl}carbonyl)phenyl]phenyl}cyclopropanesulfonamide | 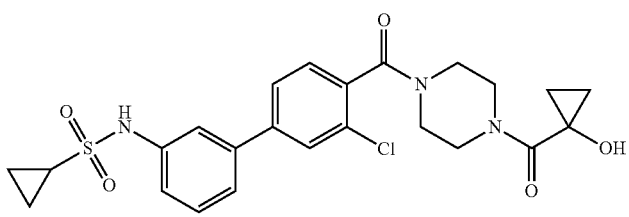 [SMILES: O=C(c1ccc(-c2cccc(NS(=O)(=O)C3CC3)c2)cc1Cl)N1CCN(C(=O)C2(O)CC2)CC1] |
| N-{3-[4-({4-[(1-hydroxycyclopropyl)carbonyl]piperazin-1-yl)carbonyl]phenyl]phenyl}cyclobutanecarboxamide | 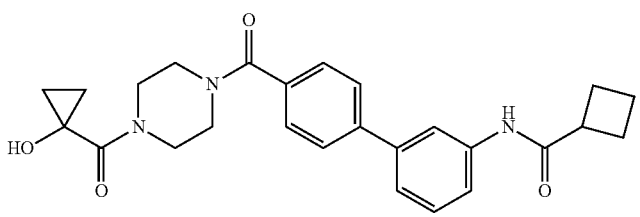 [SMILES: O=C(Nc1cccc(-c2ccc(C(=O)N3CCN(C(=O)C4(O)CC4)CC3)cc2)c1)C1CCC1] |
| 1-{[4-({4-[3-(cyclopropanesulfonyl)phenyl]phenyl}carbonyl)piperazin-1-yl]carbonyl}cyclopropan-1-ol | 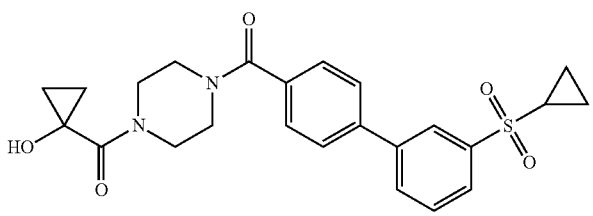 [SMILES: O=C(c1ccc(-c2cccc(S(=O)(=O)C3CC3)c2)cc1)N1CCN(C(=O)C2(O)CC2)CC1] |
| N-{5-[3-chloro-4-({4-[(1-hydroxycyclopropyl)carbonyl]piperazin-1-yl}carbonyl)phenyl]pyridin-3-yl}cyclopropanesulfonamide | 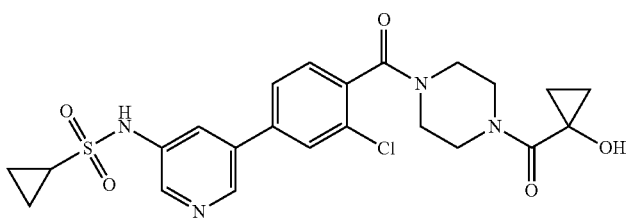 [SMILES: O=C(c1ccc(-c2cncc(NS(=O)(=O)C3CC3)c2)cc1Cl)N1CCN(C(=O)C2(O)CC2)CC1] |

-continued

| IUPAC Name | Compound Structure |
|---|---|
| N-{5-[3-chloro-4-([4-[(1-hydroxycyclopropyl)carbonyl]piperazin-1-yl}carbonyl]phenyl]pyridin-3-yl}cyclopropanecarboxamide | 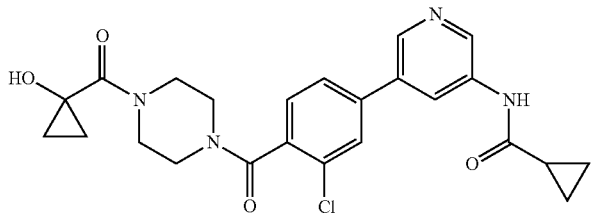 |
| N-{3-[4-({4-[(1-hydroxycyclopropyl)carbonyl]piperazin-1-yl}carbonyl)phenyl]phenyl}oxetane-3-carboxamide | 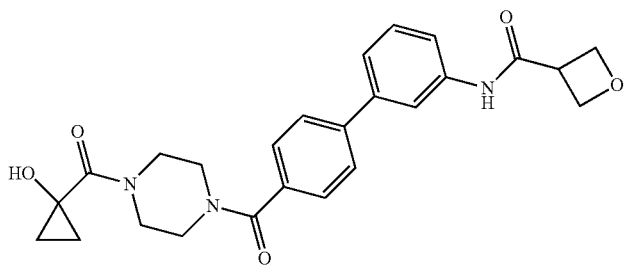 [SMILES: O=C(Nc1cccc(-c2ccc(C(=O)N3CCN(C(=O)C4(O)CC4)CC3)cc2)c1)C1COC1] |
| 1-{[4-({4-[3-(cyclopropanesulfonyl)phenyl]phenyl}carbonyl)piperazin-1-yl]carbonyl}cyclobutan-1-ol | 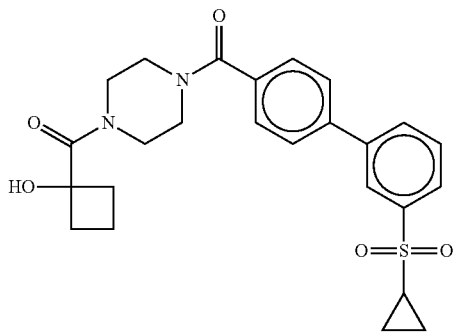 |
| 1-({4-[3-(cyclopropanesulfonyl)phenyl]phenyl}carbonyl)-4-[(oxetan-2-yl)carbonyl]piperazine | 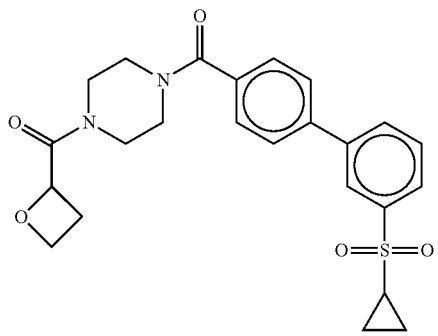 |
| 1-({4-[(4-{3-chloroimidazo[1,2-a]pyridin-2-yl}phenyl)carbonyl]piperazin-1-yl}carbonyl)cyclobutan-1-ol | 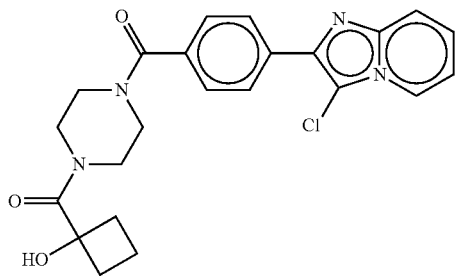 |

| IUPAC Name | Compound Structure |
|---|---|
| 1-[(4-{3-chloroimidazo[1,2-a]pyridin-2-yl}phenyl)carbonyl]-4-[(oxetan-2-yl)carbonyl]piperaizne | 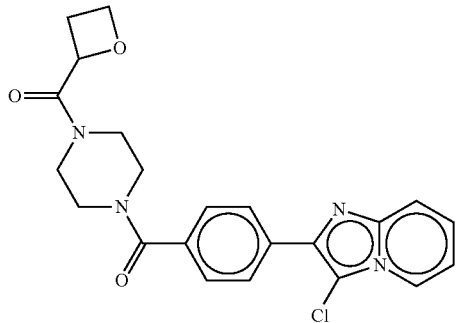 |
| 1-[(4-{[4-(3-cyclopropoxyphenyl)phenyl]carbonyl}piperazin-1-yl)carbonyl]cyclobutan-1-ol | 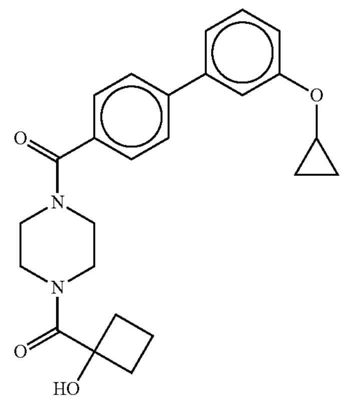 |
| 1-{[4-(3-cyclopropoxyphenyl)phenyl]carbonyl}-4-[(oxetan-2-yl)carbonyl]piperazine | 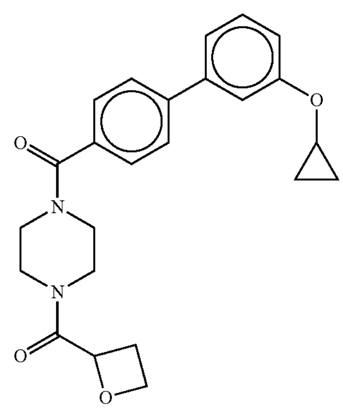 |
| N-{3-[4-({4-[(1-hydroxycyclobutyl)carbonyl]piperazin-1-yl}carbonyl)phenyl]phenyl}cyclopropanecarboxamide | 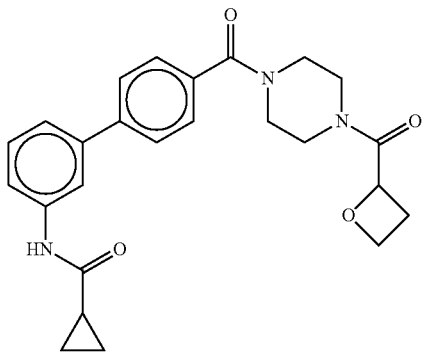 |

| IUPAC Name | Compound Structure |
|---|---|
| N-{3-[4-({4-[(oxetan-2-yl)carbonyl]piperazin-1-yl}carbonyl)phenyl]phenyl}cyclopropanecarboxamide | 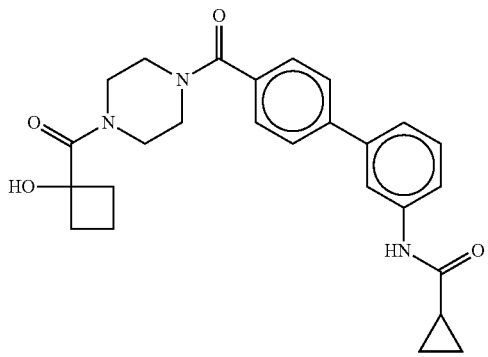 |
| lp;3p 3-[4-({4-[(1-hydroxycyclobutyl)carbonyl]piperazin-1-yl}carbonyl)phenyl]-1,2-dihydroquinolin-2-one | 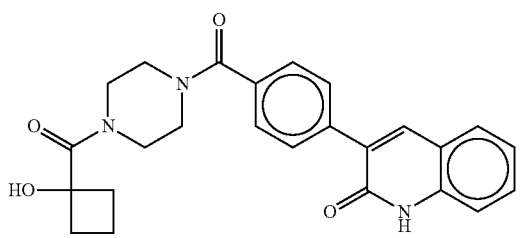 |
| 3-[4-({4-[(oxetan-2-yl)carbonyl]piperazin-1-yl}carbonyl)phenyl]-1,2-dihydroquinolin-2-one | 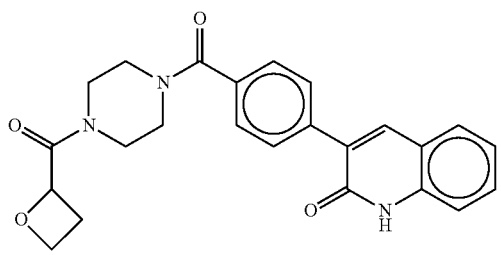 |
| 5-[4-({4-[(1-hydroxycyclobutyl)carbonyl]piperazin-1-yl}carbonyl)phenyl]-1H-indole-2-carbonitrile | 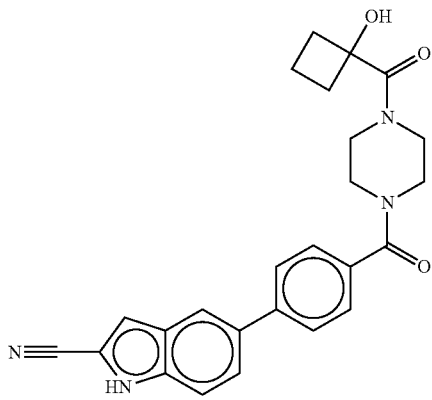 |

| IUPAC Name | Compound Structure |
|---|---|
| 5-[4-({4-[(oxetan-2-yl)carbonyl]piperazin-1-yl}carbonyl)phenyl]-1H-indole-2-carbonitrile | 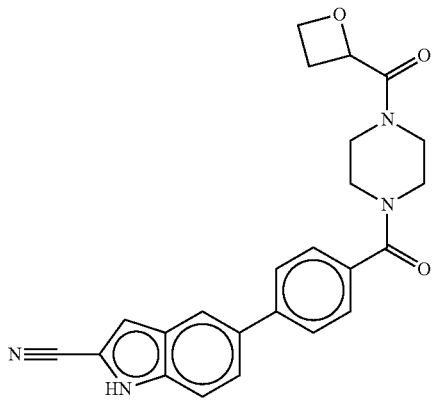 |
| 1-[(4-{[4-(1-methyl-1H-1,3-benzodiazol-5-yl)phenyl]carbonyl}piperazin-1-yl)carbonyl]cyclobutan-1-ol | 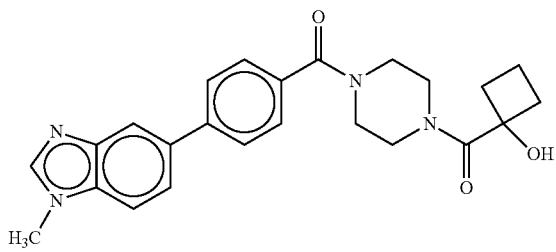 |
| 1-methyl-5-[4-({4-[(oxetan-2-yl)carbonyl]piperazin-1-yl}carbonyl)phenyl]-1H-1,3-benzodiazole | 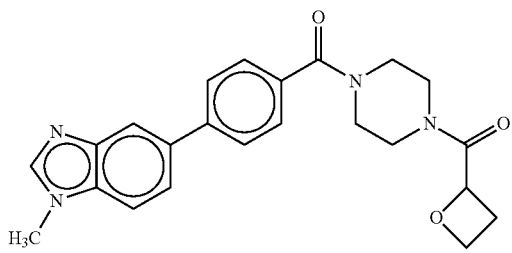 |
| 1-({4-[(4-{imidazo[1,2-b]pyridazin-6-yl]phenyl)carbonyl]piperazin-1-yl}carbonyl)cyclobutan-1-ol | 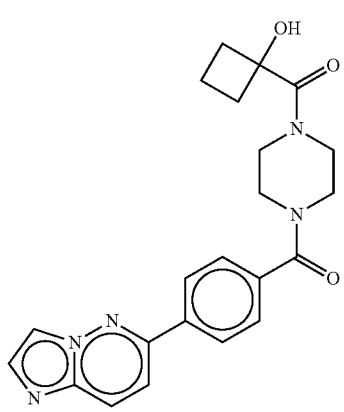 |

| IUPAC Name | Compound Structure |
|---|---|
| 1-[(4-{imidazo[1,2-b]pyridazin-6-yl}phenyl)carbonyl]-4-[(oxetan-2-yl)carbonyl]piperazine | 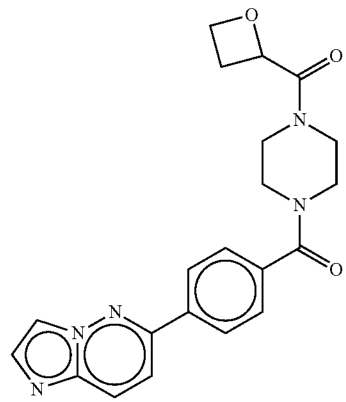 |
| 1-({4-[(4-{furo[3,2-b]pyridin-5-yl}phenyl)carbonyl]piperazin-1-yl}carbonyl)cyclobutan-1-ol | 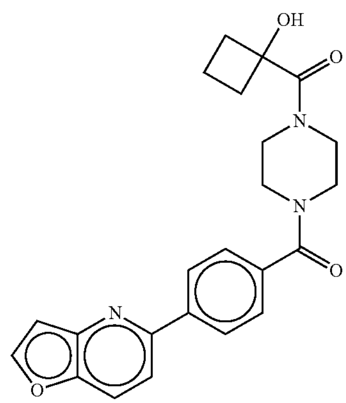 |
| 1-[(4-{furo[3,2-b]pyridin-5-yl}phenyl)carbonyl]-4-[(oxetan-2-yl)carbonyl]piperazine | 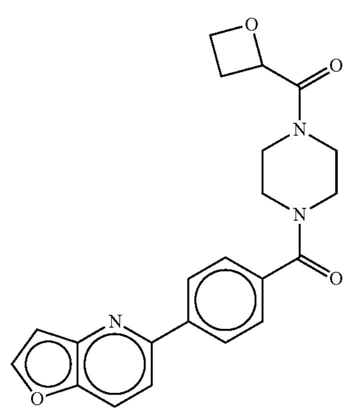 |

-continued
| IUPAC Name | Compound Structure |
|---|---|
| 1-[(4-{[4-(1H-indazol-3-yl)phenyl]carbonyl}piperazin-1-yl)carbonyl]cyclobutan-1-ol | 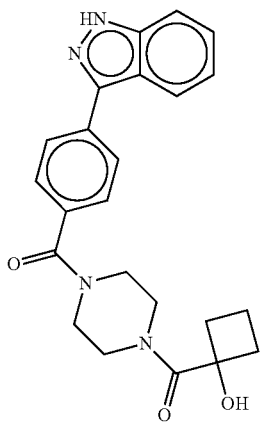 |
| 3-[4-({4-[(oxetan-2-yl)carbonyl]piperazin-1-yl}carbonyl)phenyl]-1H-indazole | 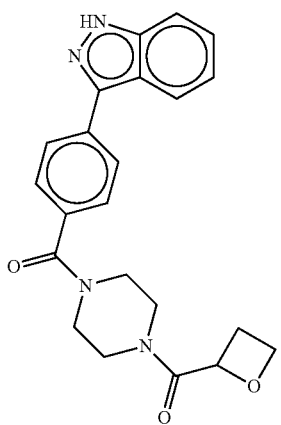 |
| 1-[(4-{[4-(1,3-dimethyl-1H-indazol-5-yl)phenyl]carbonyl}piperazin-1-yl)carbonyl]cyclobutan-1-ol | 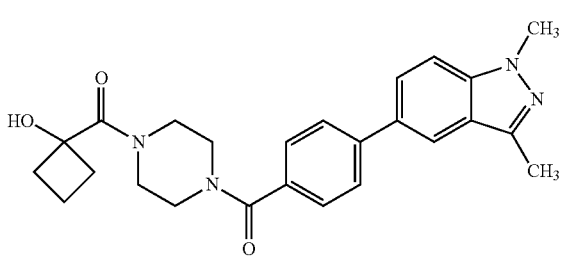 |
| 1,3-dimethyl-5-[4-({4-[(oxetan-2-yl)carbonyl]piperazin-1-yl}carbonyl)phenyl]-1H-indazole | 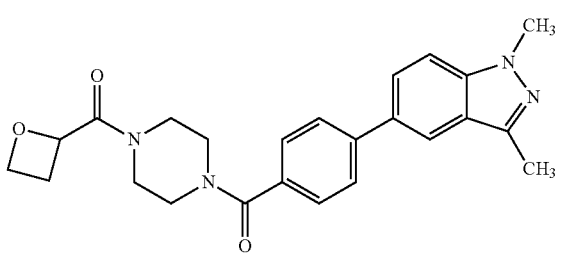 [SMILES: Cc1nn(C)c2ccc(-c3ccc(C(=O)N4CCN(C(=O)C5CCO5)CC4)cc3)cc12] |

| IUPAC Name | Compound Structure |
|---|---|
| N-{3-[4-({4-[(1-hydroxycyclobutyl)carbonyl]piperazin-1-yl}carbonyl)phenyl]phenyl}cyclopropanesulfonamide | 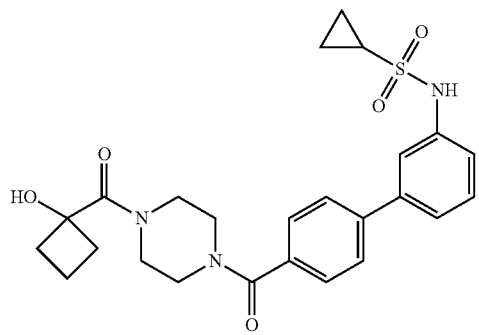 [SMILES: O=C(c1ccc(-c2cccc(NS(=O)(=O)C3CC3)c2)cc1)N1CCN(C(=O)C2(O)CCC2)CC1] |
| N-{3-[4-({4-[(oxetan-2-yl)carbonyl]piperazin-1-yl}carbonyl)phenyl]phenyl}cyclopropanesulfonamide | 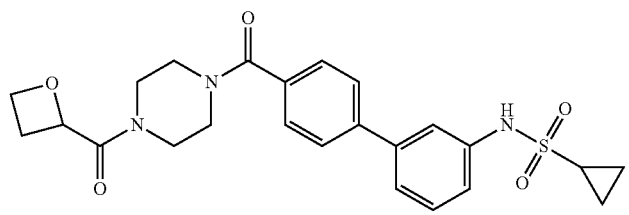 [SMILES: O=C(c1ccc(-c2cccc(NS(=O)(=O)C3CC3)c2)cc1)N1CCN(C(=O)C2CCO2)CC1] |
| 1-[(4-{[4-(6-fluoro-1,3-benzoxazol-2-yl)phenyl]carbonyl}piperazin-1-yl)carbonyl]cyclobutan-1-ol | 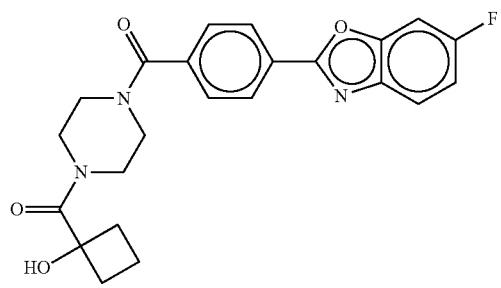 |
| 6-fluoro-2-[4-({4-[(oxetan-2-yl)carbonyl]piperazin-1-yl}carbonyl)phenyl]-1,3-benzoxazole | 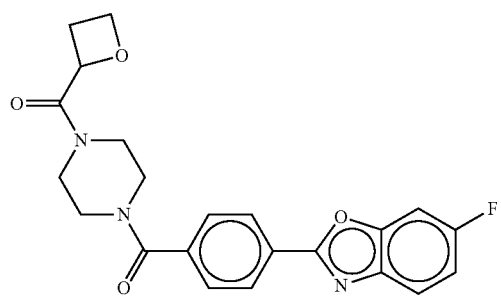 |
| 1-[(4-{[4-(6-chloro-1,3-benzoxazol-2-yl)phenyl]carbonyl}piperazin-1-yl)carbonyl]cyclobutan-1-ol | 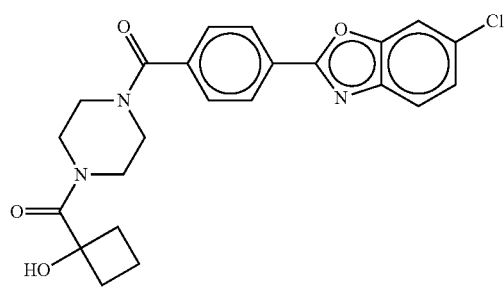 |

| IUPAC Name | Compound Structure |
|---|---|
| 6-chloro-2-[4-({4-[(oxetan-2-yl)carbonyl]piperazin-1-yl}carbonyl)phenyl]-1,3-benzoxazole | 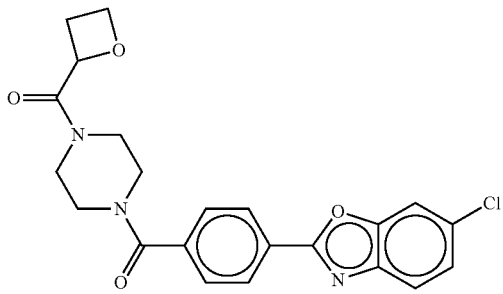 |
| 5-[4-({4-[(1-hydroxycyclobutyl)carbonyl]piperazin-1-yl}carbonyl)phenyl]-1H-indole-3-carbonitrile | 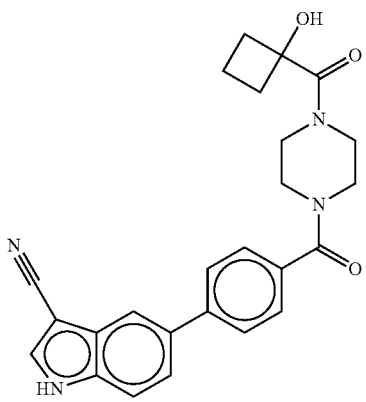 |
| 5-[4-({4-[(oxetan-2-yl)carbonyl]piperazin-1-yl}carbonyl)phenyl]-1H-indole-3-carbonitrile | 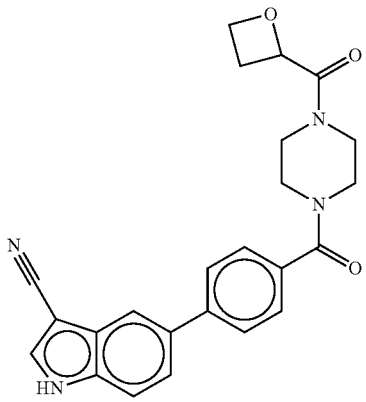 |
| 1-[(4-{[4-(1,3-benzothiazol-2-yl)phenyl]carbonyl}piperazin-1-yl)carbonyl]cyclobutan-1-ol | 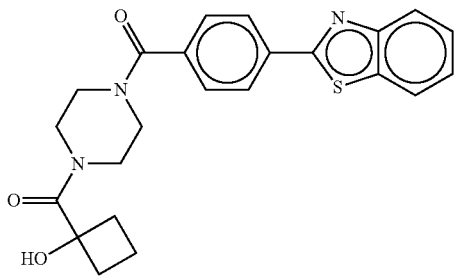 |

| IUPAC Name | Compound Structure |
|---|---|
| 2-[4-({4-[(oxetan-2-yl)carbonyl]piperazin-1-yl}carbonyl)phenyl]-1,3-benzothiazole | 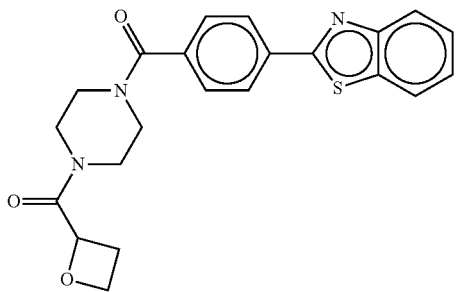 |
| 1-[(4-{[4-(quinolin-2-yl)phenyl]carbonyl}piperazin-1-yl)carbonyl]cyclobutan-1-ol | 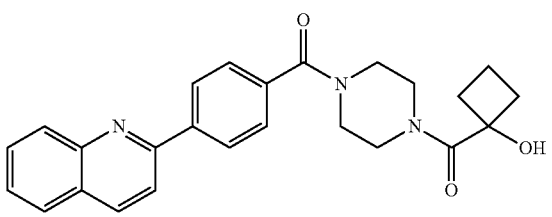 [SMILES: O=C(c1ccc(-c2ccc3ccccc3n2)cc1)N1CCN(C(=O)C2(O)CCC2)CC1] |
| 2-[4-({4-[(oxetan-2-yl)carbonyl]piperazin-1-yl}carbonyl)phenyl]quinoline | 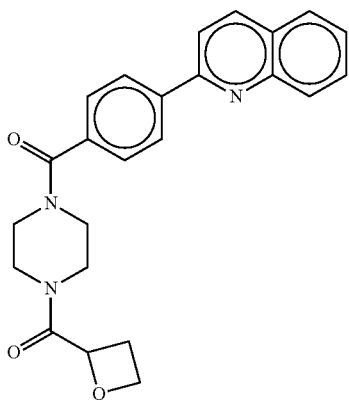 |
| 1-[(4-{[4-(1H-1,3-benzodiazol-5-yl)phenyl]carbonyl}piperazin-1-yl)carbonyl]cyclobutan-1-ol | 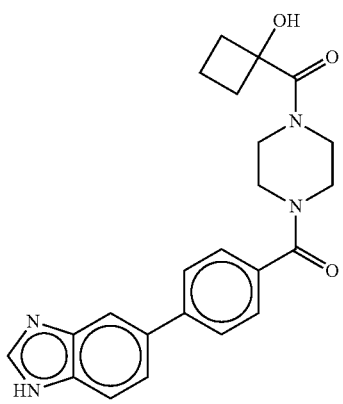 |

| IUPAC Name | Compound Structure |
|---|---|
| 5-[4-({4-[(oxetan-2-yl)carbonyl]piperazin-1-yl}carbonyl)phenyl]-1H-1,3-benzodiazole | 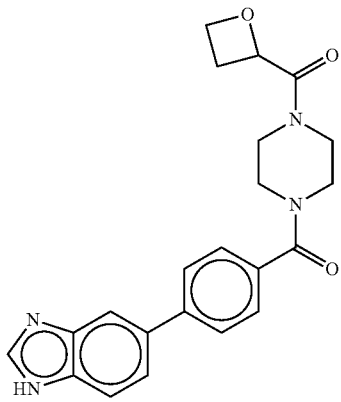 |
| 1-[(4-{[4-(1,3-benzothiazol-6-yl)phenyl]carbonyl}piperazin-1-yl)carbonyl]cyclobutan-1-ol | 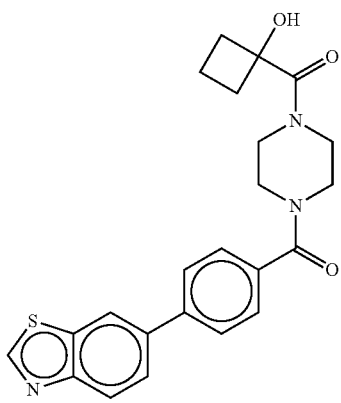 |
| 6-[4-({4-[(oxetan-2-yl)carbonyl]piperazin-1-yl}carbonyl)phenyl]-1,3-benzothiazole | 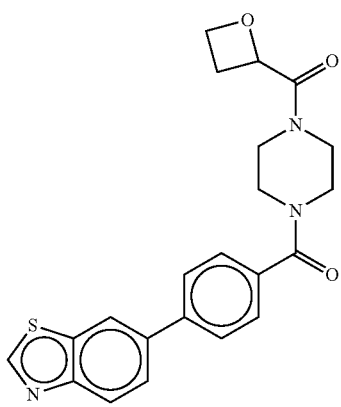 |
| 1-[(4-{[4-(1,3-benzoxazol-5-yl)phenyl]carbonyl}piperazin-1-yl)carbonyl]cyclobutan-1-ol | 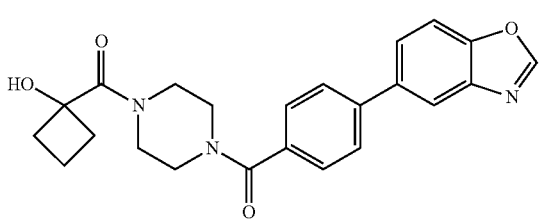 [SMILES: O=C(c1ccc(-c2ccc3ocnc3c2)cc1)N1CCN(C(=O)C2(O)CCC2)CC1] |

| IUPAC Name | Compound Structure |
|---|---|
| 5-[4-({4-[(oxetan-2-yl)carbonyl]piperazin-1-yl}carbonyl)phenyl]-1,3-benozoxazole | 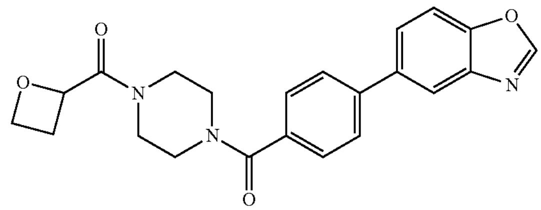 [SMILES: O=C(c1ccc(-c2ccc3ocnc3c2)cc1)N1CCN(C(=O)C2CCO2)CC1] |
| 1-[(4-{[4-(1,3-benzothiazol-5-yl)phenyl]carbonyl}piperazin-1-yl)carbonyl]cyclobutan-1-ol | 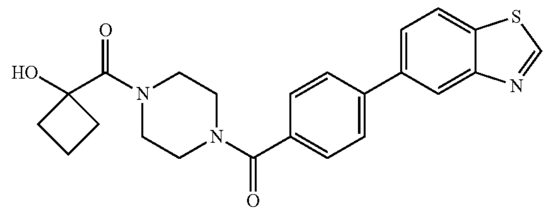 |
| 5-{4-({4-[(oxetan-2-yl)carbonyl]piperazin-1-yl}carbonyl)phenyl]-1,3-benzothiazole | 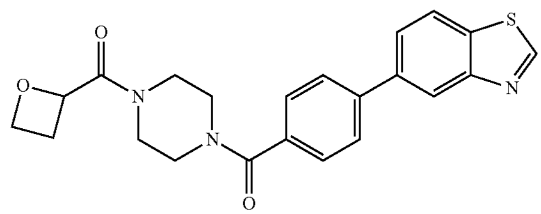 [SMILES: O=C(c1ccc(-c2ccc3scnc3c2)cc1)N1CCN(C(=O)C2CCO2)CC1] |
| 1-[(4-{[4-(1-methyl-1H-indazol-6-yl)phenyl]carbonyl}piperazin-1-yl)carbonyl]cyclobutan-1-ol | 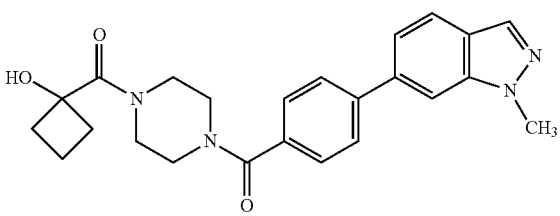 [SMILES: Cn1ncc2ccc(-c3ccc(C(=O)N4CCN(C(=O)C5(O)CCC5)CC4)cc3)cc21] |
| 1-methyl-6-[4-({4-[(oxetan-2-yl)carbonyl]piperazin-1-yl}carbonyl)phenyl]-1H-indazole | 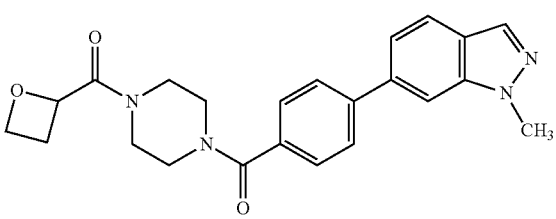 [SMILES: Cn1ncc2ccc(-c3ccc(C(=O)N4CCN(C(=O)C5CCO5)CC4)cc3)cc21] |
| N-cyclopropyl-3-[4-({4-[(1-hydroxycyclobutyl)carbonyl]piperazin-1-yl}carbonyl)phenyl]benzamide | 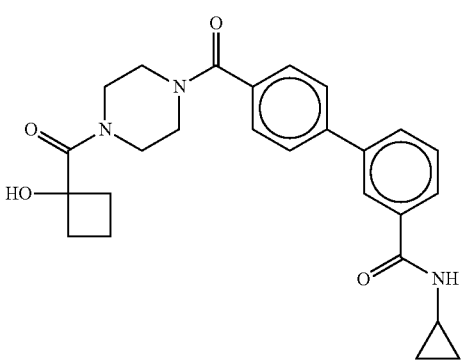 |

-continued

| IUPAC Name | Compound Structure |
|---|---|
| N-cyclopropyl-3-[4-({4-[(oxetan-2-yl)carbonyl]piperazin-1-yl}carbonyl)phenyl]benzamide | 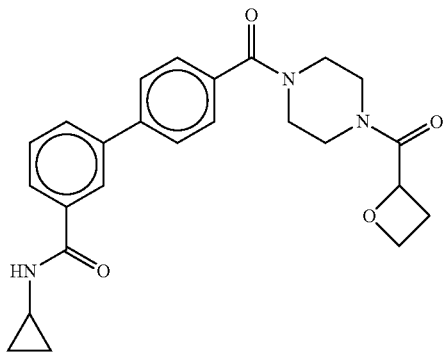 |
| 1-[(4-{[4-(2-methyl-2H-indazol-6-yl)phenyl]carbonyl}piperazin-1-yl)carbonyl]cyclobutan-1-ol | 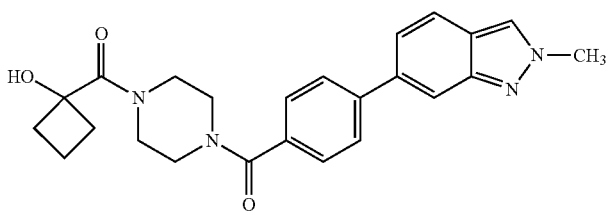 |
| 2-methyl-6-[4-({4-[(oxetan-2-yl)carbonyl]piperazin-1-yl}carbonyl)phenyl]-2H-indazole | 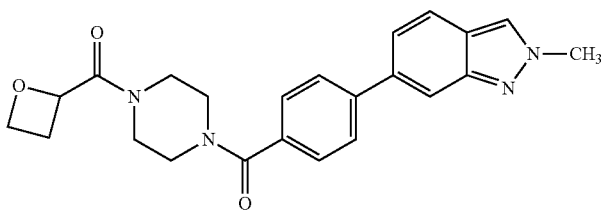 [SMILES: Cn1cc2ccc(-c3ccc(C(=O)N4CCN(C(=O)C5CCO5)CC4)cc3)cc2n1] |
| 1-[(4-{[4-(4-chloro-2-fluorophenyl)phenyl]carbonyl}piperazin-1-yl)carbonyl]cyclobutan-1-ol | 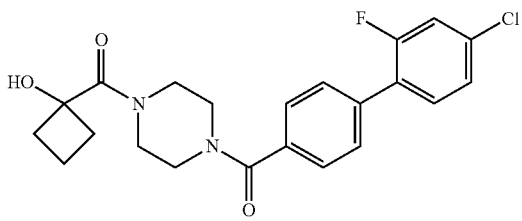 |
| 1-{[4-(4-chloro-2-fluorophenyl)phenyl]carbonyl}-4-[(oxetan-2-yl)carbonyl]piperazine | 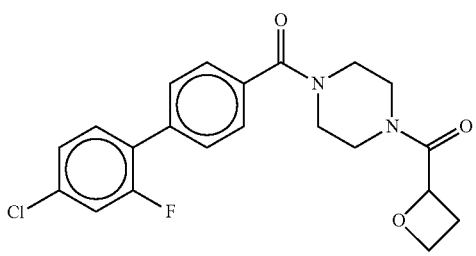 |
| 1-[(4-{[4-(5-chloro-2-fluorophenyl)phenyl]carbonyl}piperazin-1-yl)carbonyl]cyclobutan-1-ol | 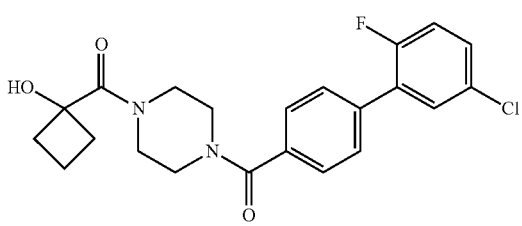 |

| IUPAC Name | Compound Structure |
|---|---|
| 1-{[4-(5-chloro-2-fluorophenyl)phenyl]carbonyl}-4-[(oxetan-2-yl)carbonyl]piperazine | 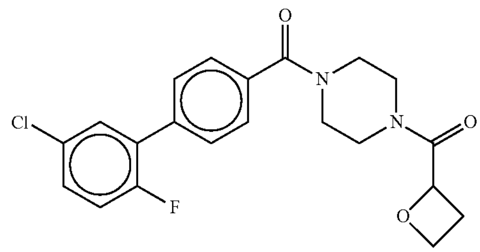 |
| 1-{[4-({4-[3-(cyclopropanesulfonyl)phenyl]phenyl}carbonyl)piperazin-1-yl]carbonyl}cyclobutan-1-amine | 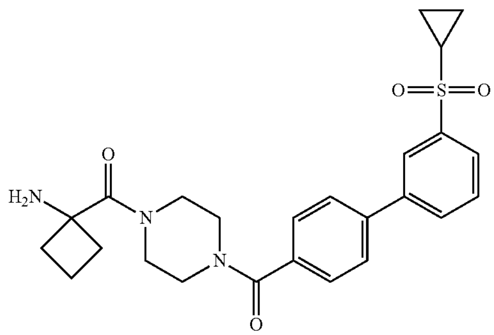 [SMILES: NC1(C(=O)N2CCN(C(=O)c3ccc(-c4cccc(S(=O)(=O)C5CC5)c4)cc3)CC2)CCC1] |
| 1-{[4-({4-[3-(cyclopropanesulfonyl)phenyl]phenyl}carbonyl)piperazin-1-yl]carbonyl}cyclopropan-1-amine | 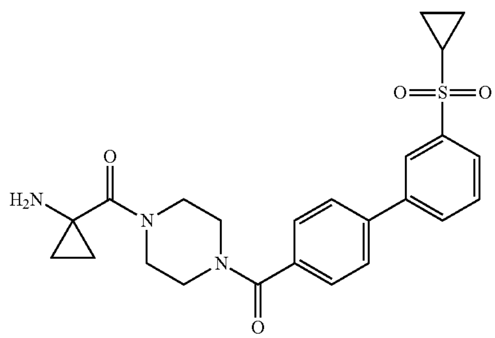 [SMILES: NC1(C(=O)N2CCN(C(=O)c3ccc(-c4cccc(S(=O)(=O)C5CC5)c4)cc3)CC2)CC1] |
| 1-({4-[(4-{3-chloroimidazo[1,2-a]pyridin-2-yl}phenyl)carbonyl]piperazin-1-yl}carbonyl)cyclobutan-1-amine | 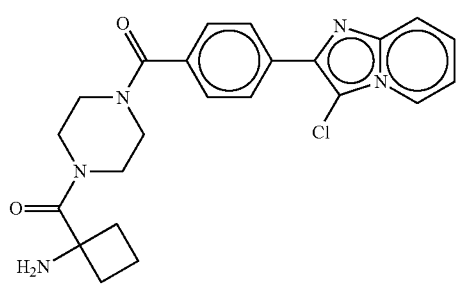 |
| 1-({4-[(4-{3-chloroimidazo[1,2-a]pyridin-2-yl}phenyl)carbonyl]piperazin-1-yl}carbonyl)cyclopropan-1-amine | 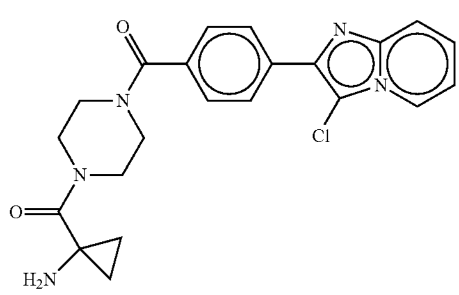 |

| IUPAC Name | Compound Structure |
|---|---|
| 1-[(4-{[4-(3-cyclopropoxyphenyl)phenyl]carbonyl}piperazin-1-yl)carbonyl]cyclobutan-1-amine | 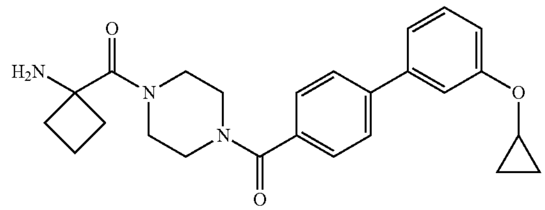 [SMILES: NC1(C(=O)N2CCN(C(=O)c3ccc(-c4cccc(OC5CC5)c4)cc3)CC2)CCC1] |
| 1-[(4-{[4-(3-cyclopropoxyphenyl)phenyl]carbonyl}piperazin-1-yl)carbonyl]cyclopropan-1-amine | 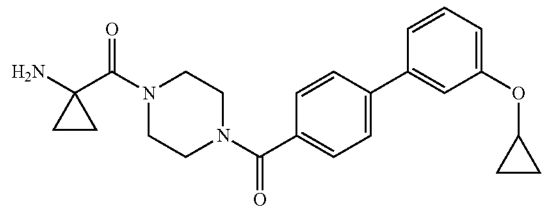 [SMILES: NC1(C(=O)N2CCN(C(=O)c3ccc(-c4cccc(OC5CC5)c4)cc3)CC2)CC1] |
| N-{3-[4-({4-[(1-aminocyclobutyl)carbonyl]piperazin-1-yl}carbonyl)phenyl]phenyl}cyclopropanecarboxamide | |
| N-{3-[4-({4-[(1-aminocyclopropyl)carbonyl]piperazin-1-yl}carbonyl)phenyl]phenyl}cyclopropanecarboxamide | |
| 3-[4-({4-[(1-aminocyclobutyl)carbonyl]piperazin-1-yl}carbonyl)phenyl]-1,2-dihydroquinolin-2-one | 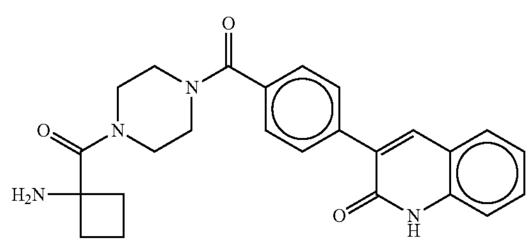 |
| 3-[4-({4-[(1-aminocyclopropyl)carbonyl]piperazin-1-yl}carbonyl)phenyl]-1,2-dihydroquinolin-2-one | 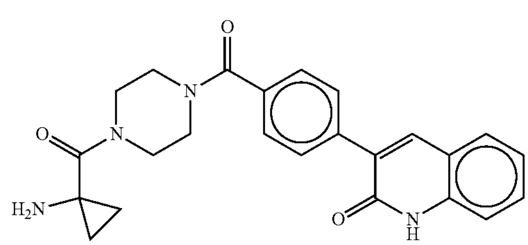 |

| IUPAC Name | Compound Structure |
|---|---|
| 5-[4-({4-[(1-aminocyclobutyl)carbonyl]piperazin-1-yl}carbonyl)phenyl]-1H-indole-2-carbonitrile | 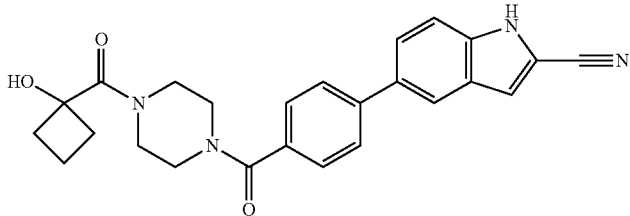 [SMILES: N#Cc1cc2cc(-c3ccc(C(=O)N4CCN(C(=O)C5(O)CCC5)CC4)cc3)ccc2[nH]1] |
| 5-[4-({4-[(1-aminocyclopropyl)carbonyl]piperazin-1-yl}carbonyl)phenyl]-1H-indole-2-carbonitrile | 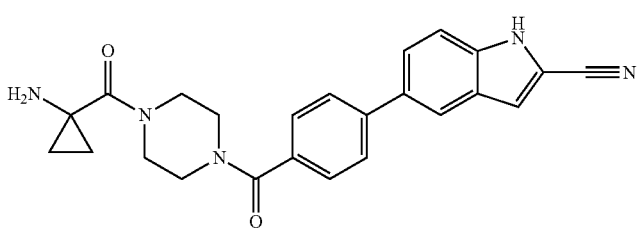 [SMILES: N#Cc1cc2cc(-c3ccc(C(=O)N4CCN(C(=O)C5(N)CC5)CC4)cc3)ccc2[nH]1] |
| 1-[(4-{[4-(1-methyl-1H-1,3-benzodiazol-5-yl)phenyl]carbonyl}piperazin-1-yl)carbonyl]cyclobutan-1-amine | 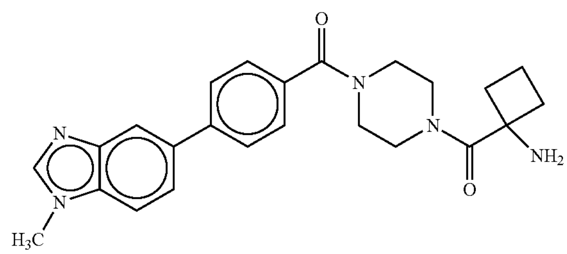 |
| 1-[(4-{[4-(1-methyl-1H-1,3-benzodiazol-5-yl)phenyl]carbonyl}piperazin-1-yl)carbonyl]cyclopropan-1-amine | 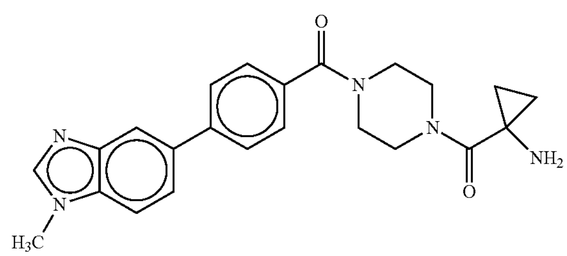 |
| 1-({4-[(4-{imidazo[1,2-b]pyridazin-6-yl}phenyl)carbonyl]piperazin-1-yl}carbonyl)cyclobutan-1-amine | 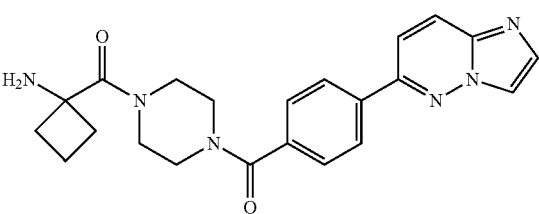 [SMILES: NC1(C(=O)N2CCN(C(=O)c3ccc(-c4ccc5nccn5n4)cc3)CC2)CCC1] |
| 1-({4-[(4-{imidazo[1,2-b]pyridazin-6-yl}phenyl)carbonyl]piperazin-1-yl}carbonyl)cyclopropan-1-amine | 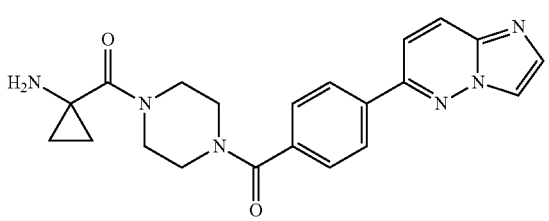 [SMILES: NC1(C(=O)N2CCN(C(=O)c3ccc(-c4ccc5nccn5n4)cc3)CC2)CC1] |

| IUPAC Name | Compound Structure |
|---|---|
| 1-({4-[(4-{furo[3,2-b]pyridin-5-yl}phenyl)carbonyl]piperazin-1-yl}carbonyl)cyclobutan-1-amine | 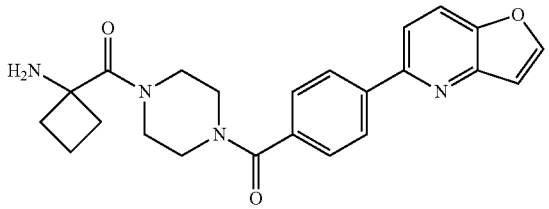 [SMILES: NC1(C(=O)N2CCN(C(=O)c3ccc(-c4ccc5occc5n4)cc3)CC2)CCC1] |
| 1-({4-[(4-{furo[3,2-b]pyridin-5-yl}phenyl)carbonyl]piperazin-1-yl}carbonyl)cyclopropan-1-amine | 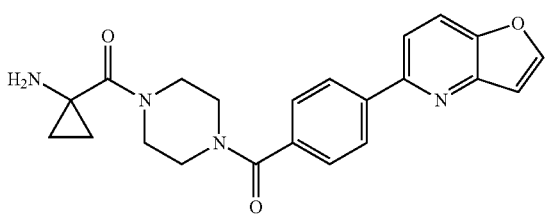 [SMILES: NC1(C(=O)N2CCN(C(=O)c3ccc(-c4ccc5occc5n4)cc3)CC2)CC1] |
| 1-[(4-{[4-(1H-indazol-3-yl)phenyl]carbonyl}piperazin-1-yl)carbonyl]cyclobutan-1-amine | 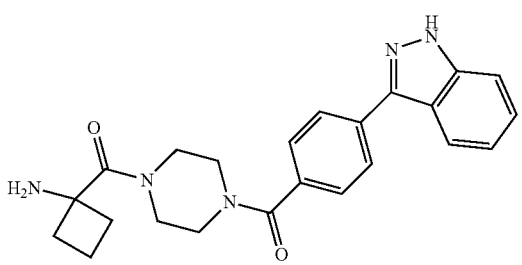 [SMILES: NC1(C(=O)N2CCN(C(=O)c3ccc(-c4n[nH]c5ccccc45)cc3)CC2)CCC1] |
| 1-[(4-{[4-(1H-indazol-3-yl)phenyl]carbonyl}piperazin-1-yl)carbonyl]cyclopropan-1-amine | 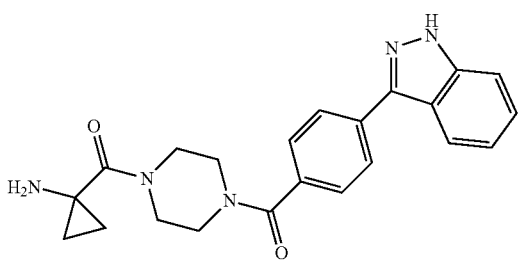 [SMILES: NC1(C(=O)N2CCN(C(=O)c3ccc(-c4n[nH]c5ccccc45)cc3)CC2)CC1] |
| 1-[(4-{[4-(1,3-dimethyl-1H-indazol-5-yl)phenyl]carbonyl}piperazin-1-yl)carbonyl]cyclobutan-1-amine | 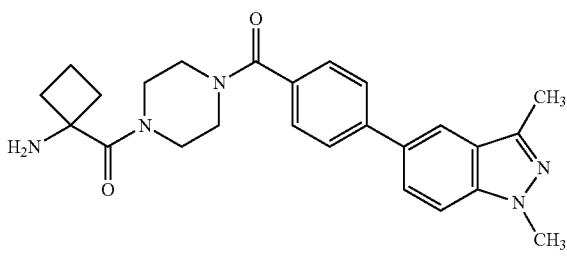 [SMILES: Cc1nn(C)c2ccc(-c3ccc(C(=O)N4CCN(C(=O)C5(N)CCC5)CC4)cc3)cc12] |
| 1-[(4-{[4-(1,3-dimethyl-1H-indazol-5-yl)phenyl]carbonyl}piperazin-1-yl)carbonyl]cyclopropan-1-amine | 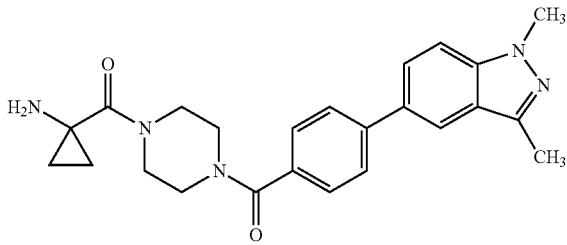 [SMILES: Cc1nn(C)c2ccc(-c3ccc(C(=O)N4CCN(C(=O)C5(N)CC5)CC4)cc3)cc12] |

| IUPAC Name | Compound Structure |
|---|---|
| N-{3-[4-({4-[(1-aminocyclobutyl)carbonyl]piperazin-1-yl}carbonyl)phenyl]phenyl}cyclopropanesulfonamide | |
| N-{3-[4-({4-[(1-aminocyclopropyl)carbonyl]piperazin-1-yl}carbonyl)phenyl]phenyl}cyclopropanesulfonamide | |
| 1-[(4-{[4-(6-fluoro-1,3-benzoxazol-2-yl)phenyl]carbonyl}piperazin-1-yl)carbonyl]cyclobutan-1-amine | 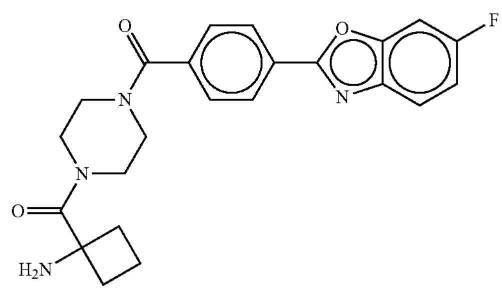 |
| 1-[(4-{[4-(6-fluoro-1,3-benzoxazol-2-yl)phenyl]carbonyl}piperazin-1-yl)carbonyl]cyclopropan-1-amine | 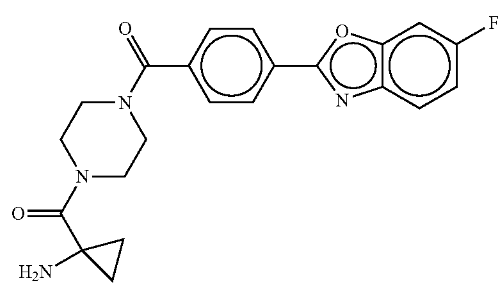 |
| 1-[(4-{[4-(6-chloro-1,3-benzoxazol-2-yl)phenyl]carbonyl}piperazin-1-yl)carbonyl]cyclobutan-1-amine | 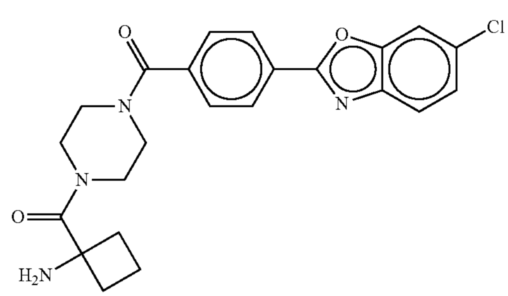 |

-continued
| IUPAC Name | Compound Structure |
|---|---|
| 1-[(4-{[4-(6-chloro-1,3-benzoxazol-2-yl)phenyl]carbonyl}piperazin-1-yl)carbonyl]cyclopropan-1-amine | 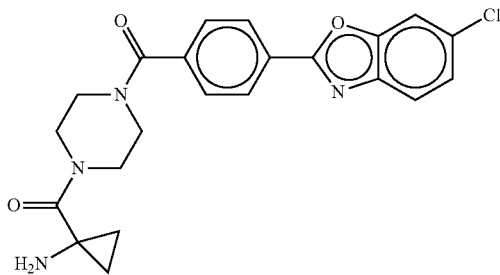 |
| 5-[4-({4-[(1-aminocyclobutyl)carbonyl]piperazin-1-yl}carbonyl)phenyl]-1H-indole-3-carbonitrile | 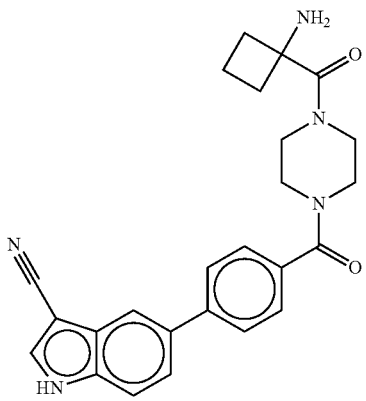 |
| 5-[4-({4-[(1-aminocyclopropyl)carbonyl]piperazin-1-yl}carbonyl)phenyl]-1H-indole-3-carbonitrile | 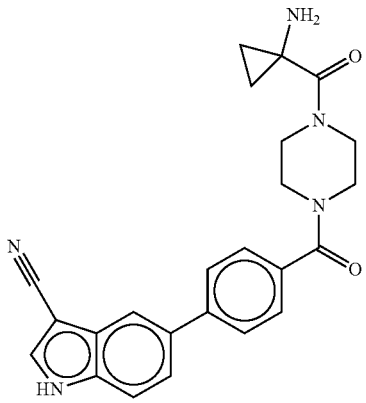 |
| 1-[(4-{[4-(1,3-benzothiazol-2-yl)phenyl]carbonyl}piperazin-1-yl)carbonyl]cyclobutan-1-amine | 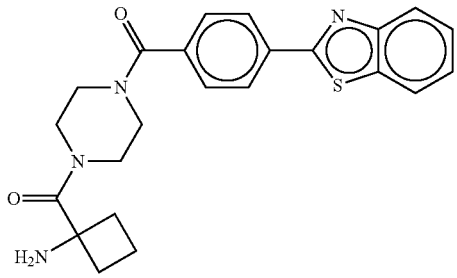 |

-continued

| IUPAC Name | Compound Structure |
|---|---|
| 1-[(4-{[4-(1,3-benzothiazol-2-yl)phenyl]carbonyl}piperazin-1-yl)carbonyl]cyclopropan-1-amine | 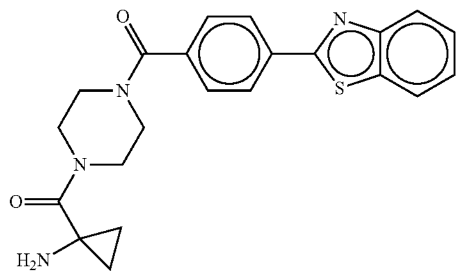 |
| 1-[(4-{[4-(quinolin-2-yl)phenyl]carbonyl}piperazin-1-yl)carbonyl]cyclobutan-1-amine | 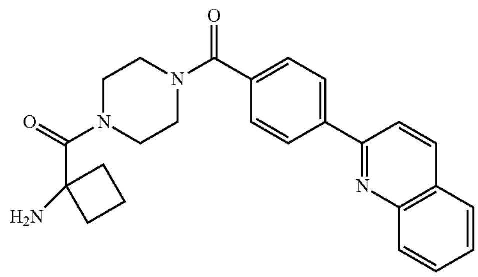 [SMILES: NC1(C(=O)N2CCN(C(=O)c3ccc(-c4ccc5ccccc5n4)cc3)CC2)CCC1] |
| 1-[(4-{[4-(quinolin-2-yl)phenyl]carbonyl}piperazin-1-yl)carbonyl]cyclopropan-1-amine | 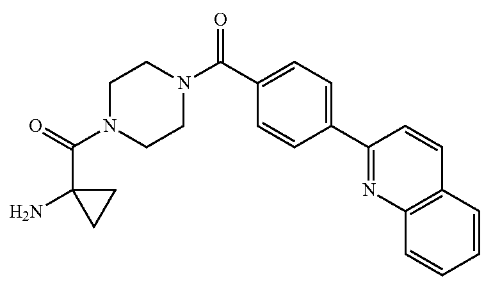 [SMILES: NC1(C(=O)N2CCN(C(=O)c3ccc(-c4ccc5ccccc5n4)cc3)CC2)CC1] |
| 1-[(4-{[4-(1H-1,3-benzodiazol-5-yl)phenyl]carbonyl}piperazin-1-yl)carbonyl]cyclobutan-1-amine | 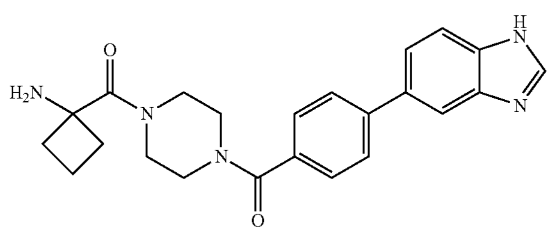 [SMILES: NC1(C(=O)N2CCN(C(=O)c3ccc(-c4ccc5[nH]cnc5c4)cc3)CC2)CCC1] |
| 1-[(4-{[4-(1H-1,3-benzodiazol-5-yl)phenyl]carbonyl}piperazin-1-yl)carbonyl]cyclopropan-1-amine | 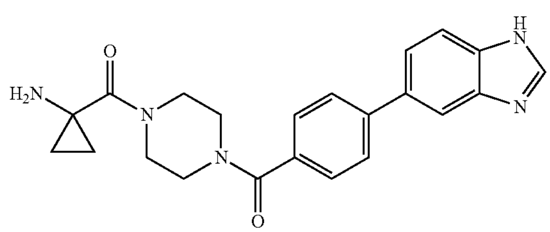 [SMILES: NC1(C(=O)N2CCN(C(=O)c3ccc(-c4ccc5[nH]cnc5c4)cc3)CC2)CC1] |
| 1-[(4-{[4-(1,3-benzothiazol-6-yl)phenyl]carbonyl}piperazin-1-yl)carbonyl]cyclobutan-1-amine | 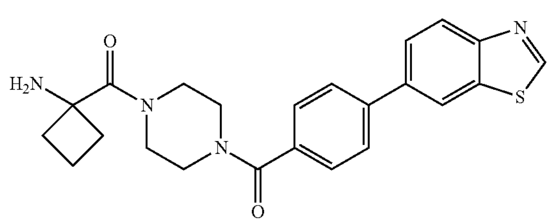 [SMILES: NC1(C(=O)N2CCN(C(=O)c3ccc(-c4ccc5ncsc5c4)cc3)CC2)CCC1] |

| IUPAC Name | Compound Structure |
|---|---|
| 1-[(4-{[4-(1,3-benzothiazol-6-yl)phenyl]carbonyl}piperazin-1-yl)carbonyl]cyclopropan-1-amine | 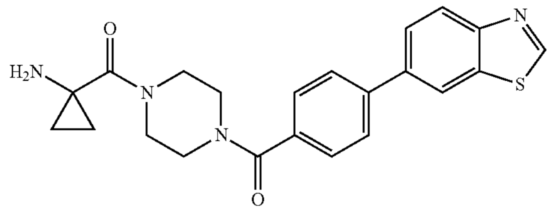 [SMILES: NC1(C(=O)N2CCN(C(=O)c3ccc(-c4ccc5ncsc5c4)cc3)CC2)CC1] |
| 1-[(4-{[4-(1,3-benzoxazol-5-yl)phenyl]carbonyl}piperazin-1-yl)carbonyl]cyclobutan-1-amine | 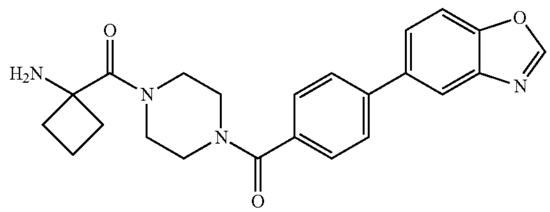 [SMILES: NC1(C(=O)N2CCN(C(=O)c3ccc(-c4ccc5ocnc5c4)cc3)CC2)CCC1] |
| 1-[(4-{[4-(1,3-benzoxazol-5-yl)phenyl]carbonyl}piperazin-1-yl)carbonyl]cyclopropan-1-amine | 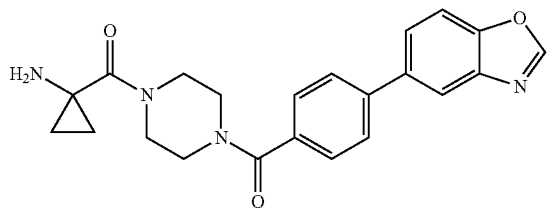 |
| 1-[(4-{[4-(1,3-benzothiazol-5-yl)phenyl]carbonyl}piperazin-1-yl)carbonyl]cyclobutan-1-amine | 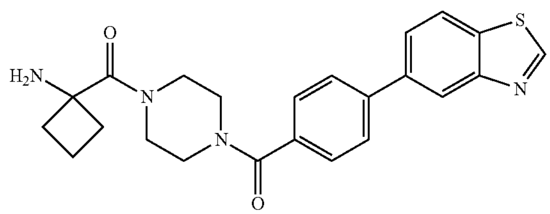 [SMILES: NC1(C(=O)N2CCN(C(=O)c3ccc(-c4ccc5scnc5c4)cc3)CC2)CCC1] |
| 1-[(4-{[4-(1,3-benzothiazol-5-yl)phenyl]carbonyl}piperazin-1-yl)carbonyl]cyclopropan-1-amine | 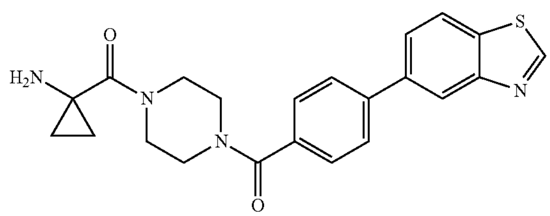 |
| 1-[(4-{[4-(1-methyl-1H-indazol-6-yl)phenyl]carbonyl}piperazin-1-yl)carbonyl]cyclobutan-1-amine | 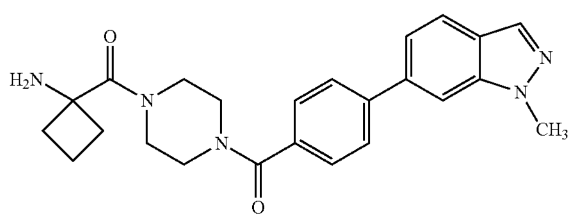 [SMILES: Cn1ncc2ccc(-c3ccc(C(=O)N4CCN(C(=O)C5(N)CCC5)CC4)cc3)cc21] |
| 1-[(4-{[4-(1-methyl-1H-indazol-6-yl)phenyl]carbonyl}piperazin-1-yl)carbonyl]cyclopropan-1-amine | 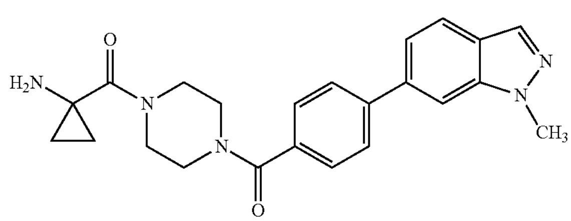 [SMILES: Cn1ncc2ccc(-c3ccc(C(=O)N4CCN(C(=O)C5(N)CC5)CC4)cc3)cc21] |

| IUPAC Name | Compound Structure |
|---|---|
| 3-[4-({4-[(1-aminocyclobutyl)carbonyl]piperazin-1-yl}carbonyl)phenyl]-N-cyclopropylbenzamide | 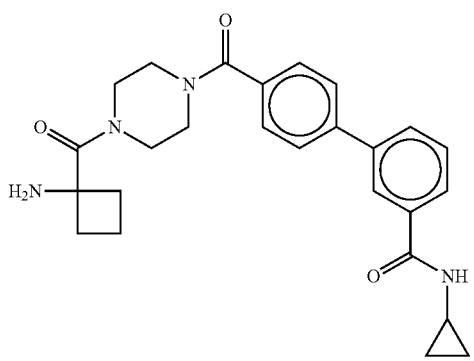 |
| 3-[4-({4-[(1-aminocyclopropyl)carbonyl]piperazin-1-yl}carbonyl)phenyl]-N-cyclopropylbenzamide | 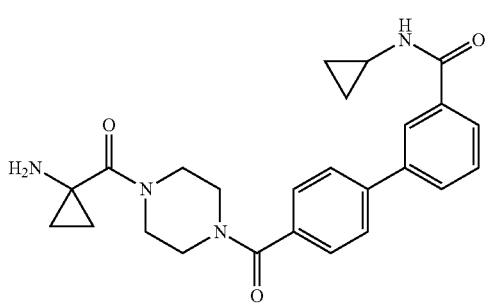 [SMILES: NC1(C(=O)N2CCN(C(=O)c3ccc(-c4cccc(C(=O)NC5CC5)c4)cc3)CC2)CC1] |
| 1-[(4-{[4-(1-methyl-2H-indazol-6-yl)phenyl]carbonyl}piperazin-1-yl)carbonyl]cyclobutan-1-amine | 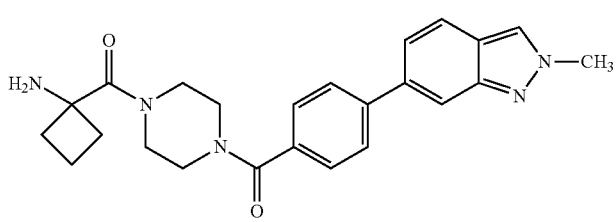 [SMILES: Cn1cc2ccc(-c3ccc(C(=O)N4CCN(C(=O)C5(N)CCC5)CC4)cc3)cc2n1] |
| 1-[(4-{[4-(2-methyl-2H-indazol-6-yl)phenyl]carbonyl}piperazin-1-yl)carbonyl]cyclopropan-1-amine | 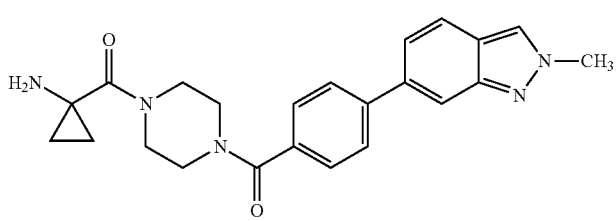 [SMILES: Cn1cc2ccc(-c3ccc(C(=O)N4CCN(C(=O)C5(N)CC5)CC4)cc3)cc2n1] |
| 1-[(4-{[4-(4-chloro-2-fluorophenyl)phenyl]carbonyl}piperazin-1-yl)carbonyl]cyclobutan-1-amine | 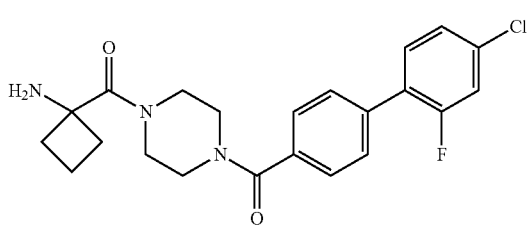 [SMILES: NC1(C(=O)N2CCN(C(=O)c3ccc(-c4ccc(Cl)cc4F)cc3)CC2)CCC1] |

| IUPAC Name | Compound Structure |
|---|---|
| 1-[(4-{[4-(4-chloro-2-fluorophenyl)phenyl]carbonyl}piperazin-1-yl)carbonyl]cyclopropan-1-amine | 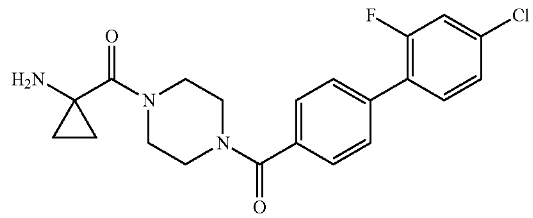 [SMILES: NC1(C(=O)N2CCN(C(=O)c3ccc(-c4ccc(Cl)cc4F)cc3)CC2)CC1] |
| 1-[(4-{[4-(5-chloro-2-fluorophenyl)phenyl]carbonyl}piperazin-1-yl)carbonyl]cyclobutan-1-amine | 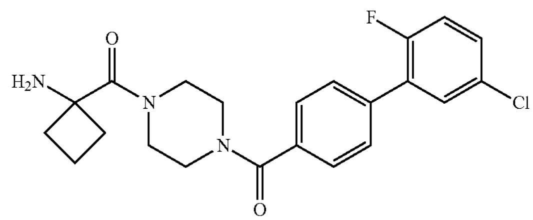 [SMILES: NC1(C(=O)N2CCN(C(=O)c3ccc(-c4cc(Cl)ccc4F)cc3)CC2)CCC1] |
| 1-[(4-{[4-(5-chloro-2-fluorophenyl)phenyl]carbonyl}piperazin-1-yl)carbonyl]cyclopropan-1-amine | 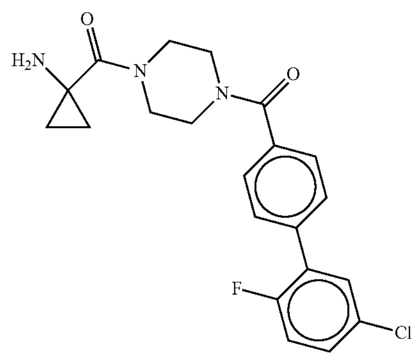 |
| 3-{[4-({4-[3-(cyclopropanesulfonyl)phenyl]phenyl}carbonyl)piperazin-1-yl]carbonyl}oxetan-3-ol | 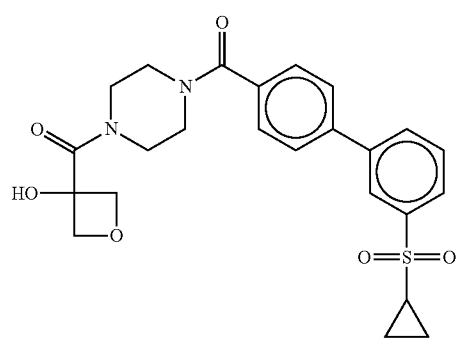 |
| 3-{[4-({4-[3-(cyclopropanesulfonyl)phenyl]phenyl}carbonyl)piperazin-1-yl]carbonyl}-oxetan-3-amine | 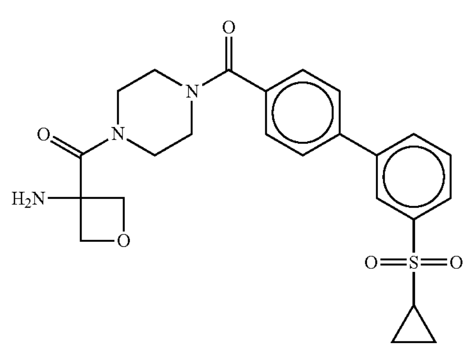 |

| IUPAC Name | Compound Structure |
|---|---|
| 3-({4-[(4-{3-chloroimidazo[1,2-a]pyridin-2-yl}phenyl)carbonyl]piperazin-1-yl}carbonyl)oxetan-3-ol | 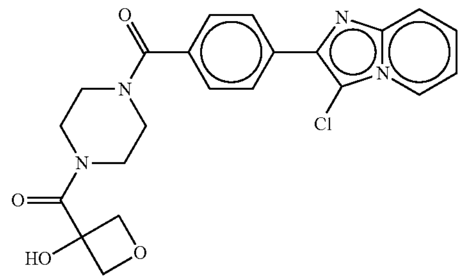 |
| 3-({4-[(4-[3-chloroimidazo[1,2-a]pyridin-2-yl}phenyl)carbonyl]piperazin-1-yl}carbonyl)oxetan-3-amine | 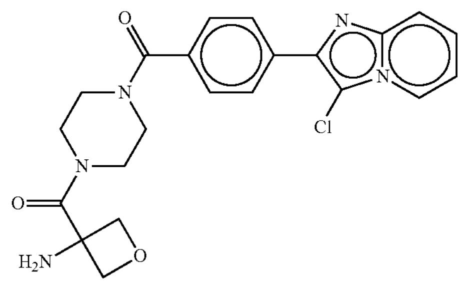 |
| 3-[(4-{[4-(3-cyclopropoxyphenyl)phenyl]carbonyl}piperazin-1-yl)carbonyl]oxetan-3-ol | 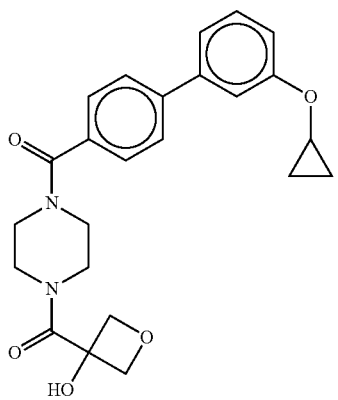 |
| 3-[(4-{[4-(3-cyclopropoxyphenyl)phenyl]carbonyl}piperazin-1-yl)carbonyl]oxetan-3-amine | 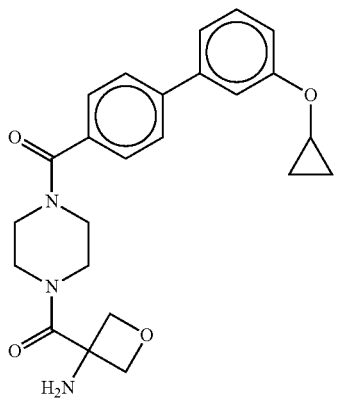 |

-continued

| IUPAC Name | Compound Structure |
|---|---|
| N-{3-[4-({4-[(3-hydroxyoxetan-3-yl)carbonyl]piperazin-1-yl}carbonyl)phenyl]phenyl}cyclo-propanecarboxamide | 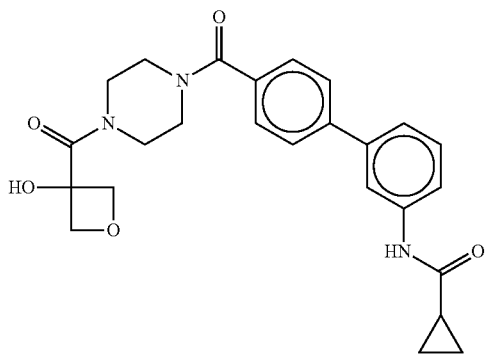 |
| N-{3-[4-({4-[(3-aminooxetan-3-yl)carbonyl]piperazin-1-yl}carbonyl)phenyl]phenyl}cyclo-propanecarboxamide | 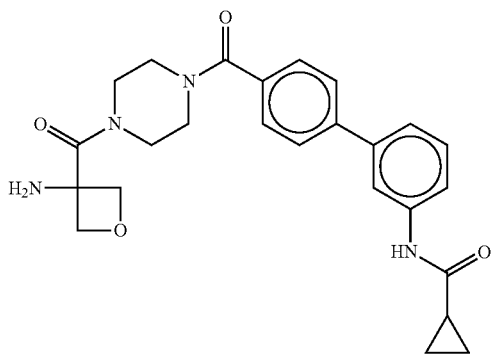 |
| 3-[4-({4-[(3-hydroxyoxetan-3-yl)carbonyl]piperazin-1-yl}carbonyl)phenyl]-1,2-dihydroquinolin-2-one | 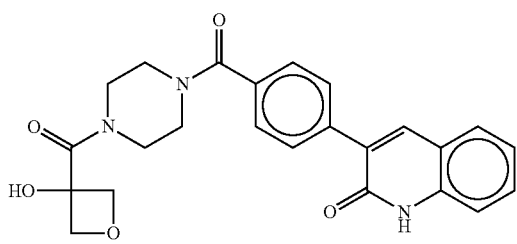 |
| 3-[4-({4-[(3-aminooxetan-3-yl)carbonyl]piperazin-1-yl}carbonyl)phenyl]-1,2-dihydroquinolin-2-one | 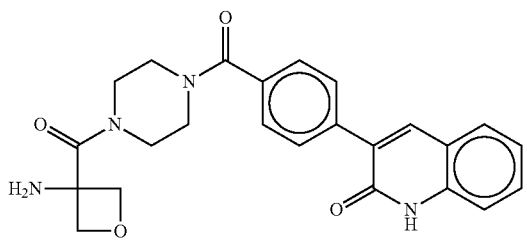 |

-continued
| IUPAC Name | Compound Structure |
|---|---|
| 5-[4-({4-[(3-hydroxyoxetan-3-yl)carbonyl]piperazin-1-yl}carbonyl)phenyl]-1H-indole-2-carbonitrile | 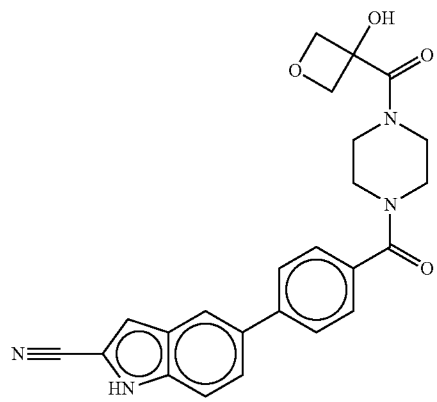 |
| 5-[4-({4-[(3-aminooxetan-3-yl)carbonyl]piperazin-1-yl}carbonyl)phenyl]-1H-indole-2-carbonitrile | 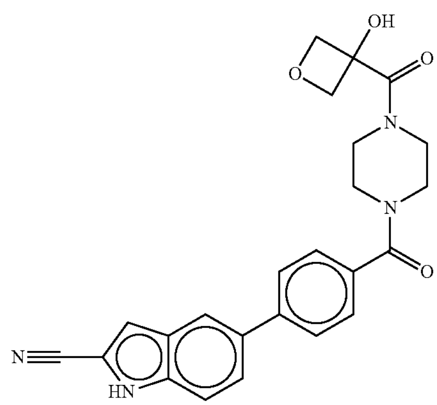 |
| 3-[(4-{[4-(1-methyl-1H-1,3-benzodiazol-5-yl)phenyl]carbonyl}piperazin-1-yl)carbonyl]oxetan-3-ol | 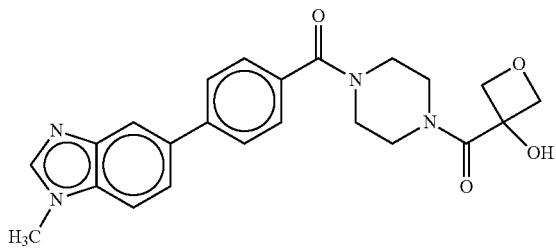 |
| 3-[(4-{[4-(1-methyl-1H-1,3-benzodiazol-5-yl)phenyl]carbonyl}piperazin-1-yl)carbonyl]oxetan-3-amine | 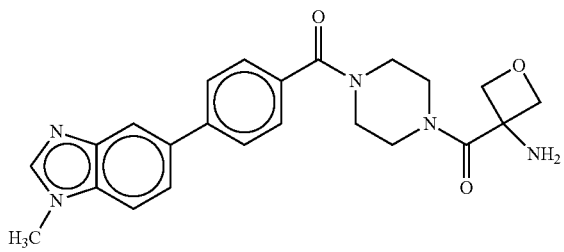 |

-continued
| IUPAC Name | Compound Structure |
|---|---|
| 3-({4-[(4-{imidazo[1,2-b]pyridazin-6-yl}phenyl)carbonyl)piperazin-1-yl}carbonyl)oxetan-3-ol | 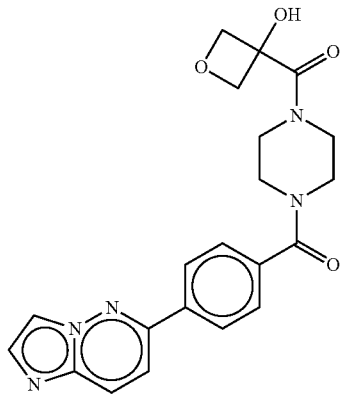 |
| 3-({4-[(4-{imidazo[1,2-b]pyridazin-6-yl}phenyl)carbonyl]piperazin-1-yl}carbonyl)oxetan-3-amine | 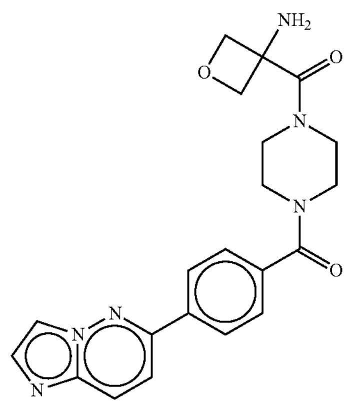 |
| 3-({4-[(4-{furo[3,2-b]pyridin-5-yl}phenyl)carbonyl]piperazin-1-yl}carbonyl)oxetan-3-ol | 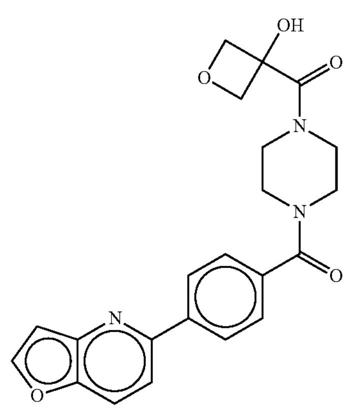 |

-continued
| IUPAC Name | Compound Structure |
|---|---|
| 3-({4-[(4-{furo[3,2-b]pyridin-5-yl}phenyl)carbonyl]piperazin-1-yl}carbonyl)oxetan-3-amine | 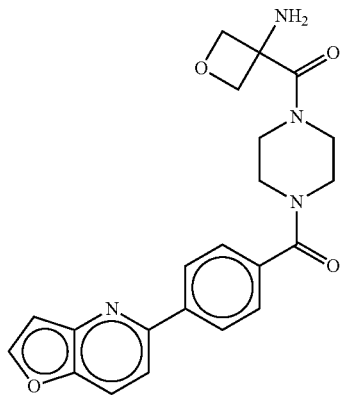 |
| 3-[(4-{[4-(1H-indazol-3-yl)phenyl]carbonyl}piperazin-1-yl)carbonyl]oxetan-3-ol | 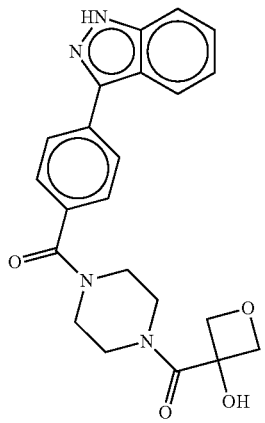 |
| 3-[(4-{[4-(1H-indazol-3-yl)phenyl]carbonyl}piperazin-1-yl)carbonyl]oxetan-3-amine | 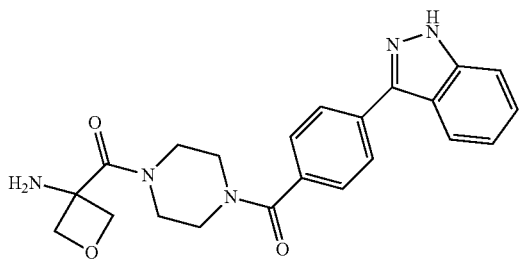 [SMILES: NC1(C(=O)N2CCN(C(=O)c3ccc(-c4n[nH]c5ccccc45)cc3)CC2)COC1] |
| 3-[(4-{[4-(1,3-dimethyl-1H-indazol-5-yl)phenyl]carbonyl}piperazin-1-yl)carbonyl]oxetan-3-ol | 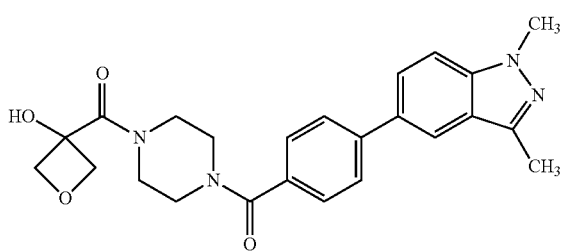 [SMILES: Cc1nn(C)c2ccc(-c3ccc(C(=O)N4CCN(C(=O)C5(O)COC5)CC4)cc3)cc12] |

-continued

| IUPAC Name | Compound Structure |
|---|---|
| 3-[(4-{[4-(1,3-dimethyl-1H-indazol-5-yl)phenyl]carbonyl}piperazin-1-yl)carbonyl]oxetan-3-amine | 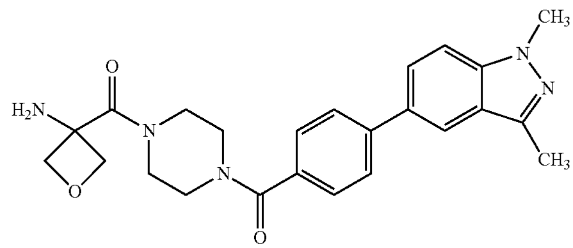 [SMILES: Cc1nn(C)c2ccc(-c3ccc(C(=O)N4CCN(C(=O)C5(N)COC5)CC4)cc3)cc12] |
| N-{3-[4-({4-[(3-hydroxyoxetan-3-yl)carbonyl]piperazin-1-yl}carbonyl)phenyl]phenyl}cyclopropanesulfonamide | 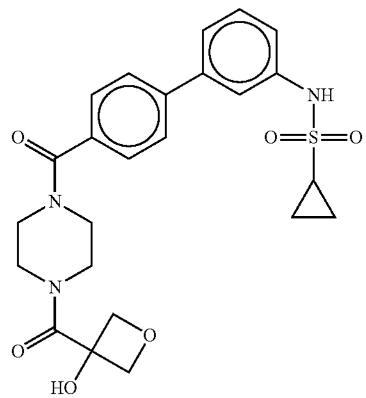 |
| N-{3-[4-({4-[(3-aminooxetan-3-yl)carbonyl]piperazin-1-yl}carbonyl)phenyl]phenyl}cyclopropanesulfonamide | 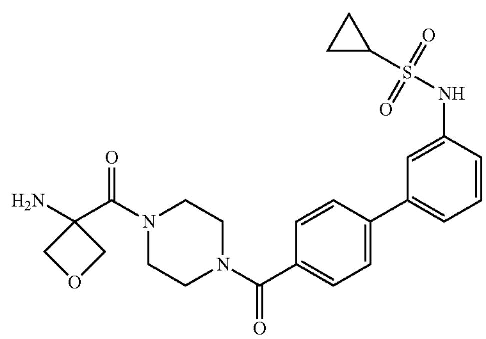 [SMILES: NC1(C(=O)N2CCN(C(=O)c3ccc(-c4cccc(NS(=O)(=O)C5CC5)c4)cc3)CC2)COC1] |
| 3-[(4-{[4-(6-fluoro-1,3-benzoxazol-2-yl)phenyl]carbonyl}piperazin-1-yl)carbonyl]oxetan-3-ol | 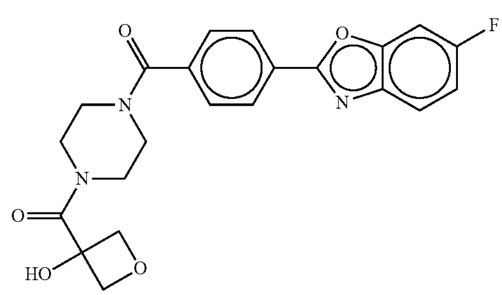 |
| 3-[(4-{[4-(6-fluoro-1,3-benzoxazol-2-yl)phenyl]carbonyl}piperazin-1-yl)carbonyl]oxetan-3-amine | 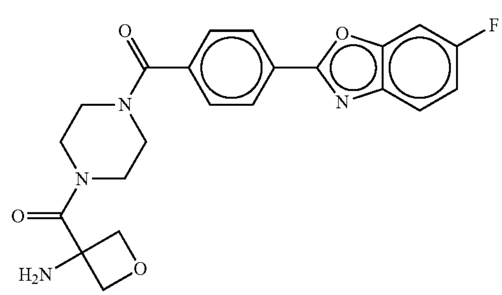 |

| IUPAC Name | Compound Structure |
|---|---|
| 3-[(4-{[4-(6-chloro-1,3-benzoxazol-2-yl)phenyl]carbonyl}piperazin-1-yl)carbonyl]oxetan-3-ol | 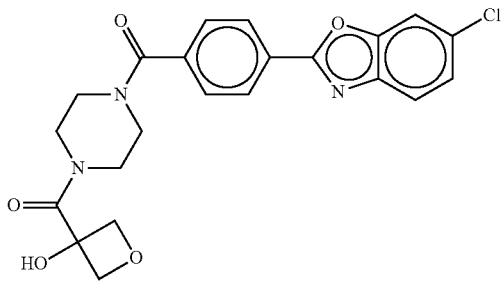 |
| 3-[(4-{[4-(6-chloro-1,3-benzoxazol-2-yl)phenyl]carbonyl}piperazin-1-yl)carbonyl]oxetan-3-amine | 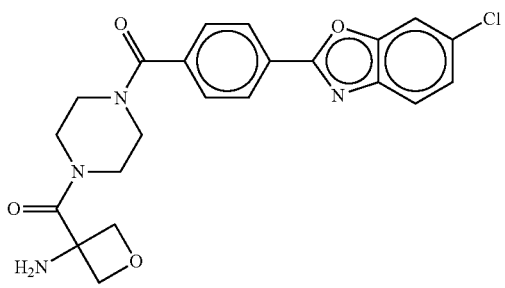 |
| 5-[4-({4-[(3-hydroxyoxetan-3-yl)carbonyl]piperazin-1-yl}carbonyl)phenyl]-1H-indole-3-carbonitrile | 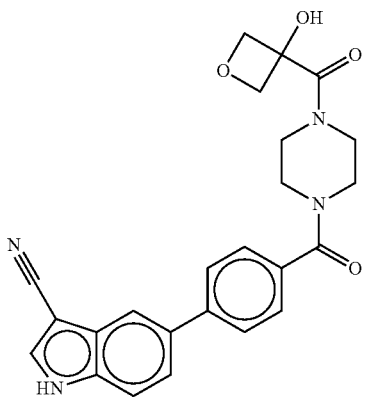 |
| 5-[4-({4-[(3-aminooxetan-3-yl)carbonyl]piperazin-1-yl}carbonyl)phenyl]-1H-indole-3-carbonitrile | 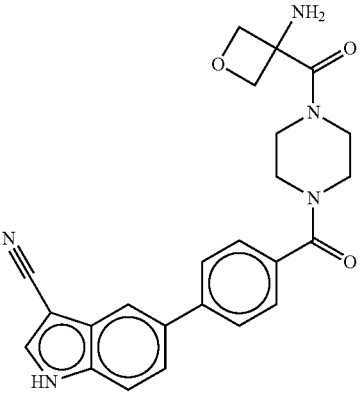 |

| IUPAC Name | Compound Structure |
|---|---|
| 3-[(4-{[4-(1,3-benzothiazol-2-yl)phenyl]carbonyl}piperazin-1-yl)carbonyl]oxetan-3-ol | 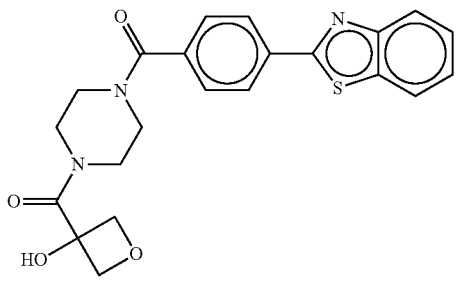 |
| 3-[(4-{[4-(1,3-benzothiazol-2-yl)phenyl]carbonyl}piperazin-1-yl)carbonyl]oxetan-3-amine | 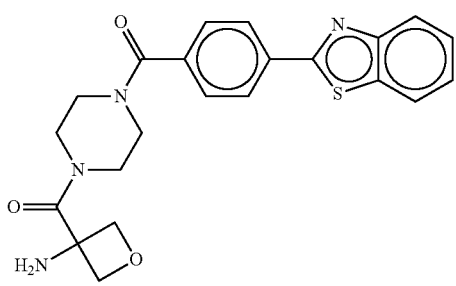 |
| 3-[(4-{[4-(quinolin-2-yl)phenyl]carbonyl}piperazin-1-yl)carbonyl]oxetan-3-ol | 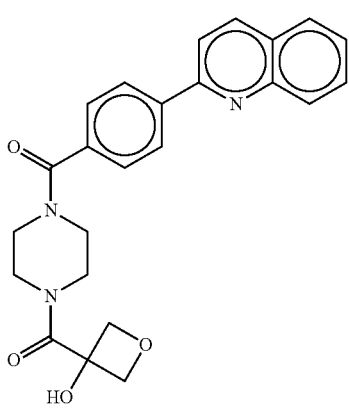 |
| 3-[(4-{[4-(quinolin-2-yl)phenyl]carbonyl}piperazin-1-yl)carbonyl]oxetan-3-amine | 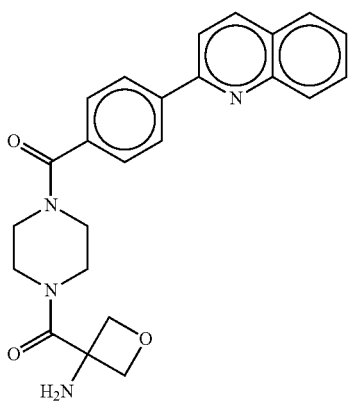 |

| IUPAC Name | Compound Structure |
|---|---|
| 3-[(4-{[4-(1H-1,3-benzodiazol-5-yl)phenyl]carbonyl}piperazin-1-yl)carbonyl]oxetan-3-ol | 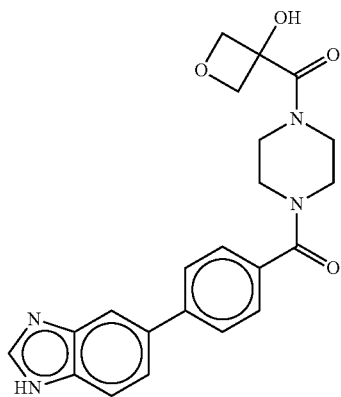 |
| 3-[(4-{[4-(1H-1,3-benzodiazol-5-yl)phenyl]carbonyl}piperazin-1-yl)carbonyl]oxetan-3-amine | 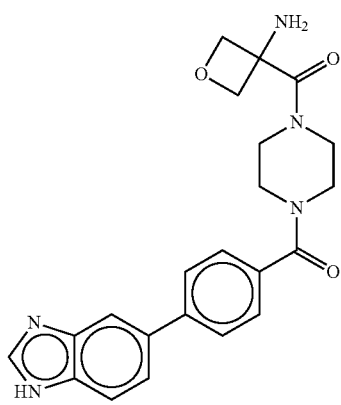 |
| 3-[(4-{[4-(1,3-benzothiazol-6-yl)phenyl]carbonyl}piperazin-1-yl)carbonyl]oxetan-3-ol | 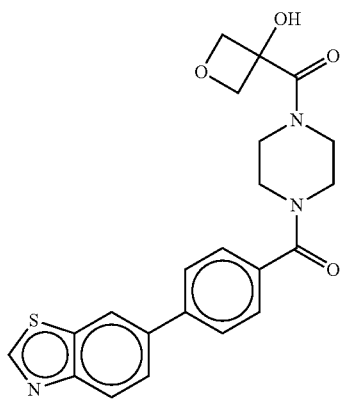 |

| IUPAC Name | Compound Structure |
|---|---|
| 3-[(4-{[4-(1,3-benzothiazol-6-yl)phenyl]carbonyl}piperazin-1-yl)carbonyl]oxetan-3-amine | 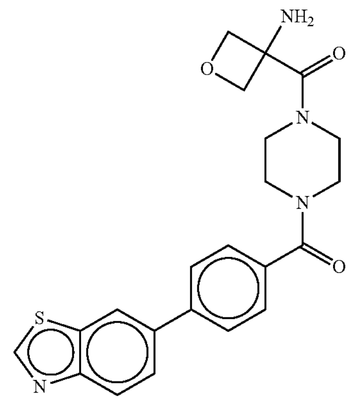 |
| 3-[(4-{[4-(1,3-benzoxazol-5-yl)phenyl]carbonyl}piperazin-1-yl)carbonyl]oxetan-3-ol | 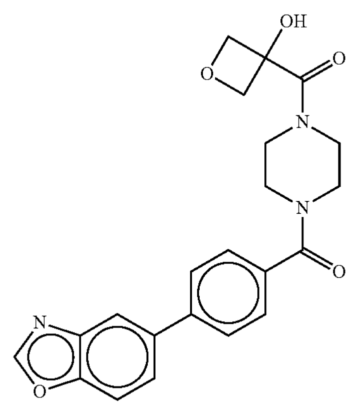 |
| 3-[(4-{[4-(1,3-benzoxazol-5-yl)phenyl]carbonyl}piperazin-1-yl)carbonyl]oxetan-3-amine | 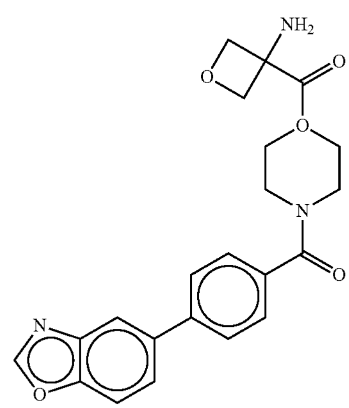 |

-continued

| IUPAC Name | Compound Structure |
|---|---|
| 3-[(4-{[4-(1,3-benzothiazol-5-yl)phenyl]carbonyl}piperazin-1-yl)carbonyl]oxetan-3-ol | 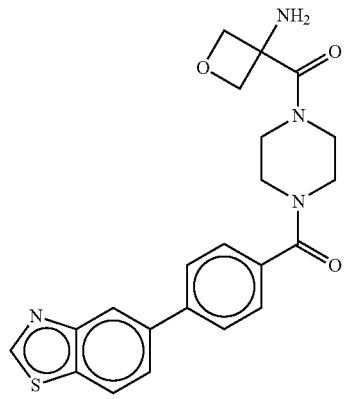 |
| 3-[(4-{[4-(1,3-benzothiazol-5-yl)phenyl]carbonyl}piperazin-1-yl)carbonyl]oxetan-3-amine | 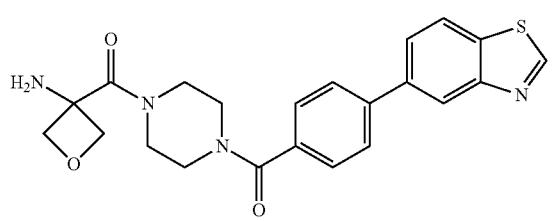 [SMILES: NC1(C(=O)N2CCN(C(=O)c3ccc(-c4ccc5scnc5c4)cc3)CC2)COC1] |
| 3-[(4-{[4-(1-methyl-1H-indazol-6-yl)phenyl]carbonyl}piperazin-1-yl)carbonyl]oxetan-3-ol | 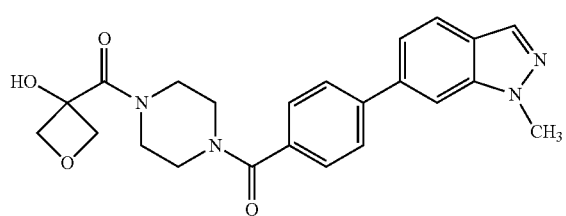 [SMILES: Cn1ncc2ccc(-c3ccc(C(=O)N4CCN(C(=O)C5(O)COC5)CC4)cc3)cc21] |
| 3-[(4-{[4-(1-methyl-1H-indazol-6-yl)phenyl]carbonyl}piperazin-1-yl)carbonyl]oxetan-3-amine | 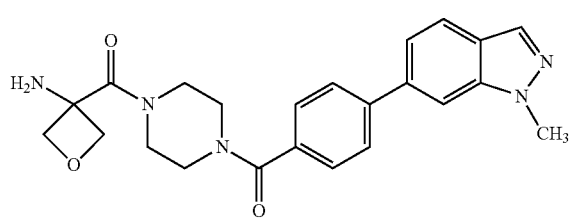 [SMILES: Cn1ncc2ccc(-c3ccc(C(=O)N4CCN(C(=O)C5(N)COC5)CC4)cc3)cc21] |
| N-cyclopropyl-3-[4-({4-[(3-hydroxyoxetan-3-yl)carbonyl]piperazin-1-yl}carbonyl)phenyl]benzamide | 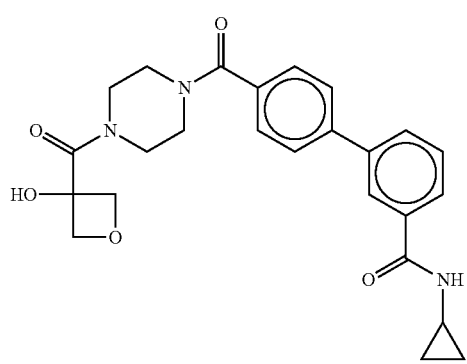 |

| IUPAC Name | Compound Structure |
|---|---|
| 3-[4-({4-[(3-aminooxetan-3-yl)carbonyl]piperazin-1-yl}carbonyl)phenyl]-N-cyclopropylbenzamide | 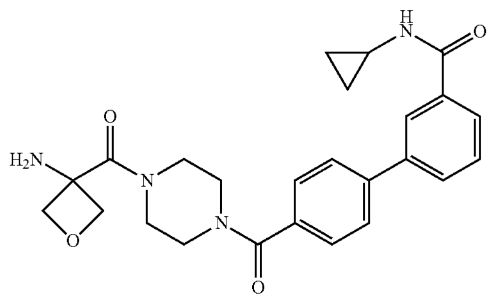 [SMILES: NC1(C(=O)N2CCN(C(=O)c3ccc(-c4cccc(C(=O)NC5CC5)c4)cc3)CC2)COC1] |
| 3-[(4-{[4-(1-methyl-2H-indazol-6-yl)phenyl]carbonyl}piperazin-1-yl)carbonyl]oxetan-3-ol | 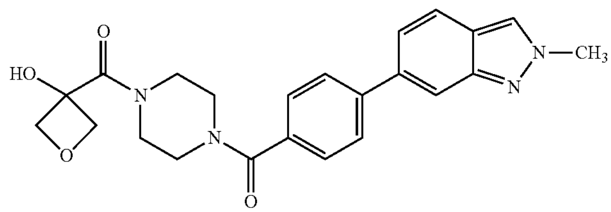 [SMILES: Cn1cc2ccc(-c3ccc(C(=O)N4CCN(C(=O)C5(O)COC5)CC4)cc3)cc2n1] |
| 3-[(4-{[4-(2-methyl-2H-indazol-6-yl)phenyl]carbonyl}piperazin-1-yl)carbonyl]oxetan-3-amine | 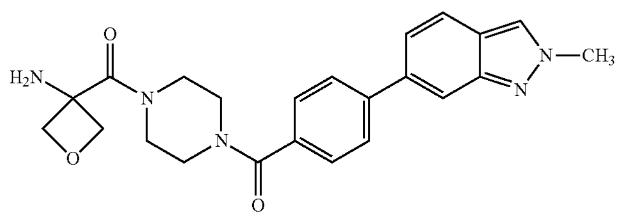 |
| 3-[(4-{[4-(4-chloro-2-fluorophenyl)phenyl]carbonyl}piperazin-1-yl)carbonyl]oxetan-3-ol | 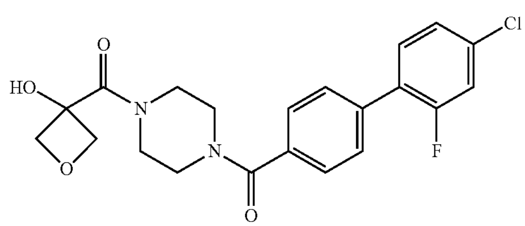 [SMILES: O=C(c1ccc(-c2ccc(Cl)cc2F)cc1)N1CCN(C(=O)C2(O)COC2)CC1] |
| 3-[(4-{[4-(4-chloro-2-fluorophenyl)phenyl]carbonyl}piperazin-1-yl)carbonyl]oxetan-3-amine | 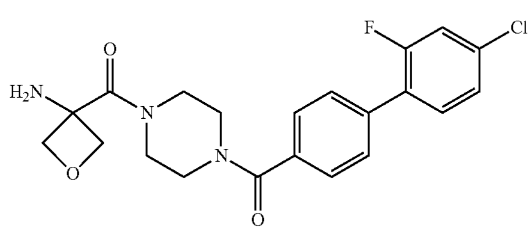 [SMILES: NC1(C(=O)N2CCN(C(=O)c3ccc(-c4ccc(Cl)cc4F)cc3)CC2)COC1] |
| 3-[(4-{[4-(5-chloro-2-fluorophenyl)phenyl]carbonyl}piperazin-1-yl)carbonyl]oxetan-3-ol | 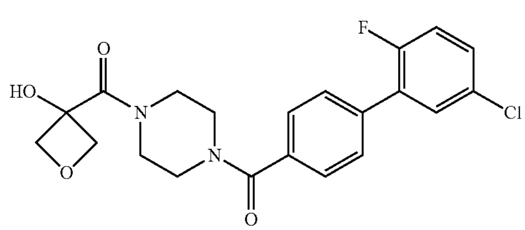 [SMILES: O=C(c1ccc(-c2cc(Cl)ccc2F)cc1)N1CCN(C(=O)C2(O)COC2)CC1] |

| IUPAC Name | Compound Structure |
|---|---|
| 3-[(4-{[4-(5-chloro-2-fluorophenyl)phenyl]carbonyl}piperazin-1-yl)carbonyl]oxetan-3-amine | 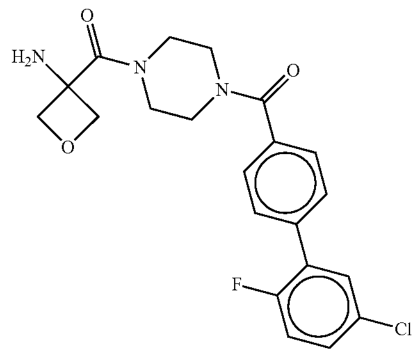 |
| 1-({4-[(4-{5-chloro-[1,3]thiazolo[5,4-d][1,3]thiazol-2-yl}phenyl)carbonyl]piperazin-1-yl}carbonyl)cyclopropan-1-ol | 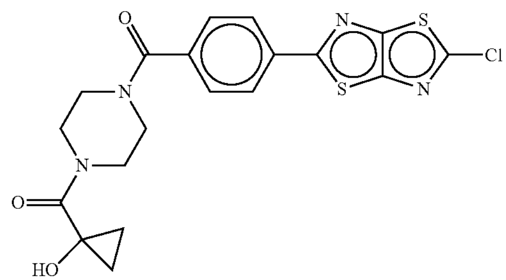 |
| 1-{[4-({4-[4-(2H-1,2,3,4-tetrazol-5-yl)phenyl]phenyl}carbonyl)piperazin-1-yl]carbonyl}cyclopropan-1-ol | 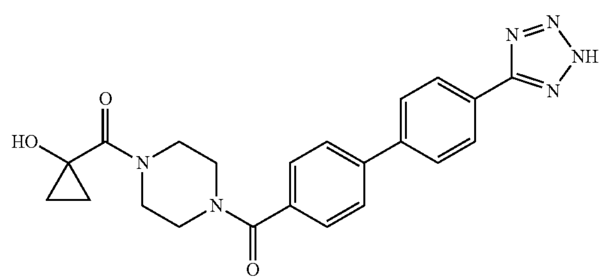 [SMILES: O=C(c1ccc(-c2ccc(-c3nn[nH]n3)cc2)cc1)N1CCN(C(=O)C2(O)CC2)CC1] |
| 1-({4-[(4-{imidazo[2,1-b][1,3,4]thiadiazol-2-yl}phenyl)carbonyl]piperazin-1-yl}carbonyl)cylcopropan-1-ol | 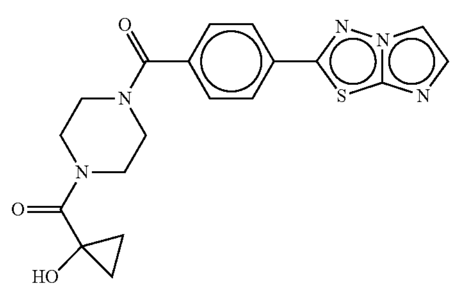 |
| 1-({4-[(4-{6H-thieno[2,3-b]pyrrol-2-yl}phenyl)carbonyl]piperazin-1-yl}carbonyl)cyclopropan-1-ol | 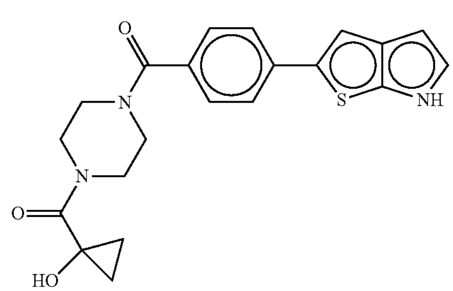 |

| IUPAC Name | Compound Structure |
|---|---|
| 1-({4-[(4-{4H-thieno[3,2-b]pyrrol-3-yl}phenyl)carbonyl]piperazin-1-yl}carbonyl)cyclopropan-1-ol | 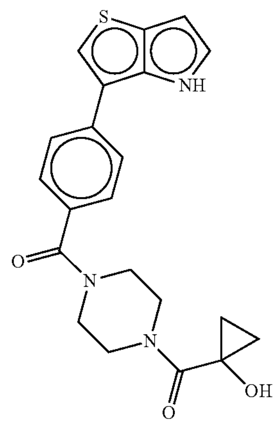 |
| 2-[4-({4-[(1-hydroxycyclopropyl)carbonyl]piperazin-1-yl}carbonyl)phenyl]-3H-pyrrolizin-3-one | 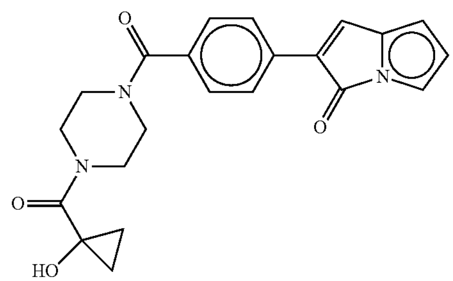 |
| 6-[4-({4-[(1-hydroxycyclopropyl)carbonyl]piperazin-1-yl}carbonyl)phenyl]-3H-pyrrolizin-3-one | 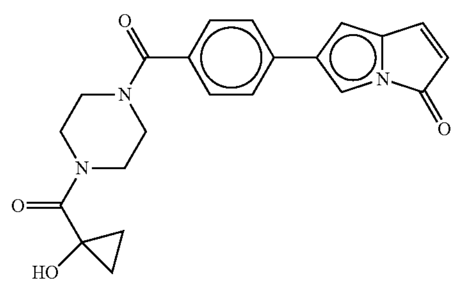 |
| 1-[4-{[4-(1-methanesulfonyl-1H-indol-6-yl)phenyl]carbonyl}piperazin-1-yl)carbonyl]cyclopropan-1-ol | 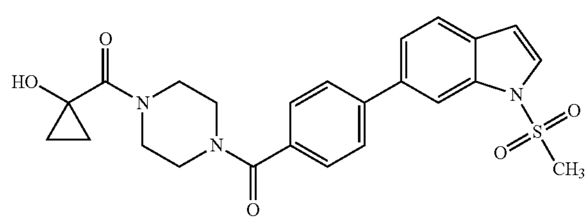 [SMILES: CS(=O)(=O)n1ccc2ccc(-c3ccc(C(=O)N4CCN(C(=O)C5(O)CC5)CC4)cc3)cc21] |
| 1-{[4-({4-[4-(1-methyl-1H-pyrazol-5-yl)phenyl]phenyl}carbonyl)piperazin-1-yl]carbonyl}cyclopropan-1-ol | 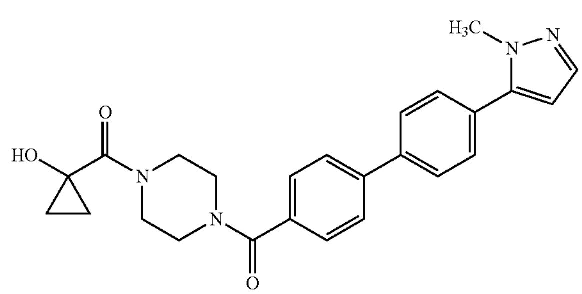 [SMILES: Cn1nccc1-c1ccc(-c2ccc(C(=O)N3CCN(C(=O)C4(O)CC4)CC3)cc2)cc1] |

| IUPAC Name | Compound Structure |
|---|---|
| 1-{[4-({4-[4-(1-methyl-1H-pyrazol-3-yl)phenyl]phenyl}carbonyl)piperazin-1-yl]carbonyl}cyclopropan-1-ol | 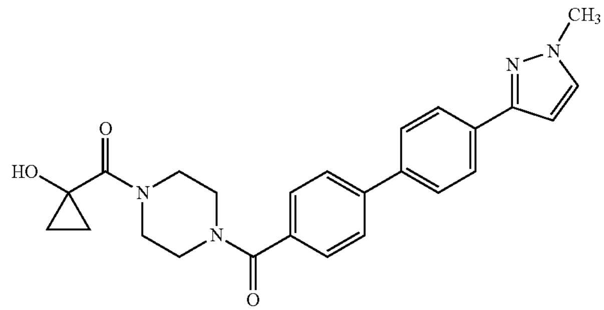 [SMILES: Cn1ccc(-c2ccc(-c3ccc(C(=O)N4CCN(C(=O)C5(O)CC5)CC4)cc3)cc2)n1] |
| 1-{[4-({4-[4-(1-methyl-1H-pyrazol-4-yl)phenyl]phenyl}carbonyl)piperazin-1-yl]carbonyl}cyclopropan-1-ol | 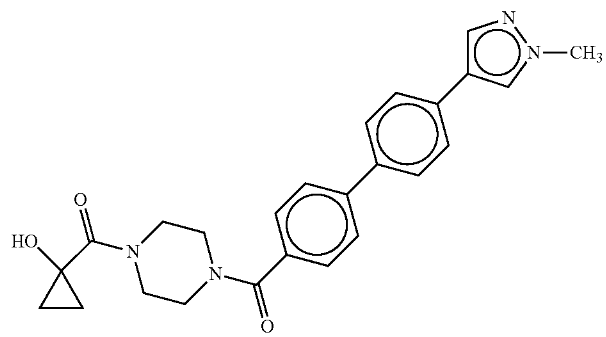 |
| 1-[(4-{[4-(1-ethyl-1H-indazol-5-yl)phenyl]carbonyl}piperazin-1-yl)carbonyl]cyclopropan-1-ol | 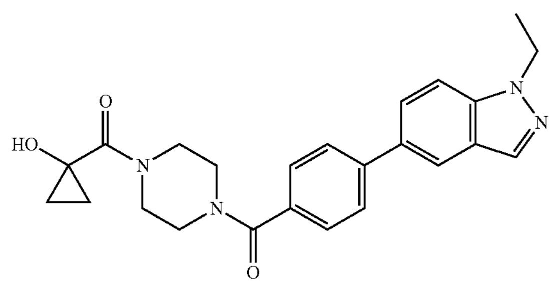 [SMILES: CCn1ncc2cc(-c3ccc(C(=O)N4CCN(C(=O)C5(O)CC5)CC4)cc3)ccc21] |
| 1-[(4-{[4-(1-cyclobutyl-1H-indazol-5-yl)phenyl]carbonyl}piperazin-1-yl)carbonyl]cyclopropan-1-ol | 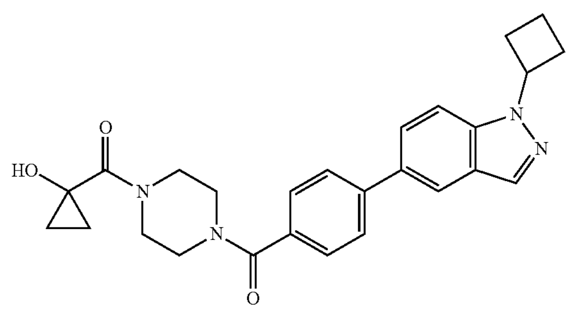 [SMILES: O=C(c1ccc(-c2ccc3c(cnn3C3CCC3)c2)cc1)N1CCN(C(=O)C2(O)CC2)CC1] |
| 1-{[4-({4-[1-(oxetan-3-yl)-1H-indazol-5-yl]phenyl}carbonyl)piperazin-1-yl]carbonyl}cyclopropan-1-ol | 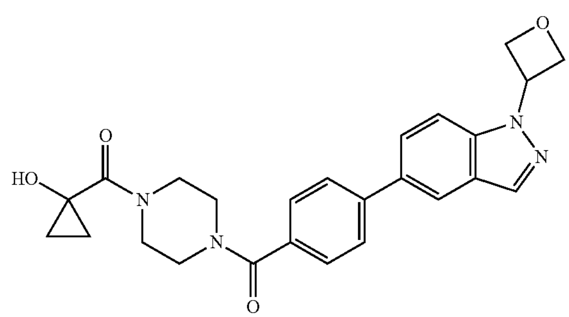 [SMILES: O=C(c1ccc(-c2ccc3c(cnn3C3COC3)c2)cc1)N1CCN(C(=O)C2(O)CC2)CC1] |

| IUPAC Name | Compound Structure |
|---|---|
| 1-{[4-({4-[1-(propan-2-yl)-1H-indazol-5-yl]phenyl}carbonyl)piperazin-1-yl]carbonyl}cyclopropan-1-ol | 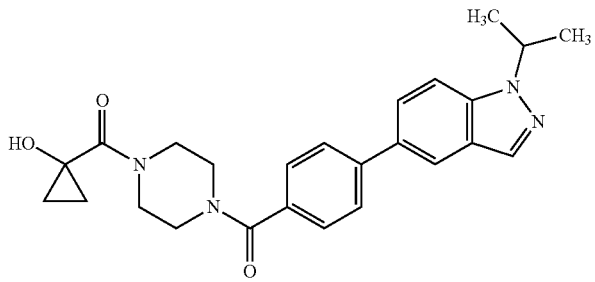 [SMILES: CC(C)n1ncc2cc(-c3ccc(C(=O)N4CCN(C(=O)C5(O)CC5)CC4)cc3)ccc21] |
| 1-{[4-({4-[1-(2-methoxyethyl)-1H-indazol-5-yl]phenyl}carbonyl)piperazin-1-yl]carbonyl}cyclopropan-1-ol | 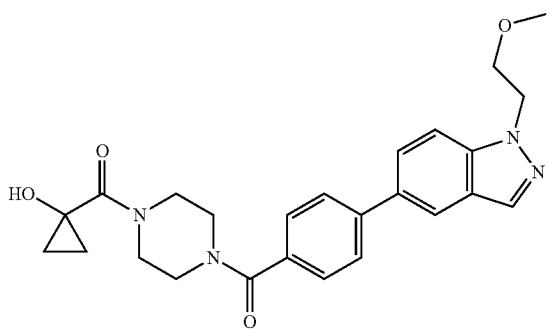 [SMILES: COCCn1ncc2cc(-c3ccc(C(=O)N4CCN(C(=O)C5(O)CC5)CC4)cc3)ccc21] |
| 1-{[4-({4-[1-(cyclopropylmethyl)-1H-indazol-5-yl]phenyl}carbonyl)piperazin-1-yl]carbonyl}cyclopropan-1-ol | 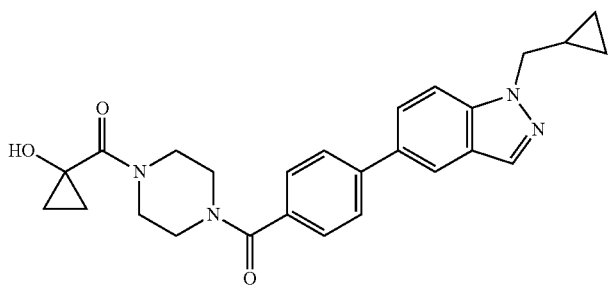 [SMILES: O=C(c1ccc(-c2ccc3c(cnn3CC3CC3)c2)cc1)N1CCN(C(=O)C2(O)CC2)CC1] |
| 1-[(4-{[4-(1-propyl-1H-indazol-5-yl)phenyl]carbonyl}piperazin-1-yl)carbonyl]cyclopropan-1-ol | 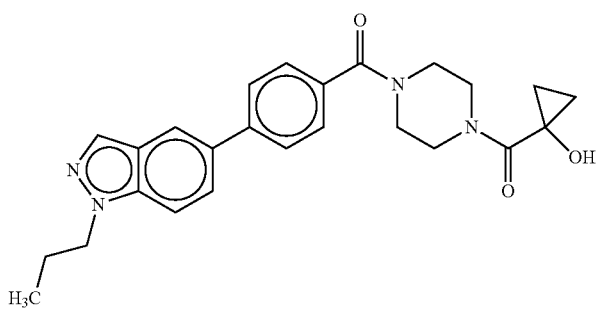 |
| 1-{[4-({4-[1-(cyclobutylmethyl)-1H-indazol-5-yl]phenyl}carbonyl)piperazin-1-yl]carbonyl}cyclopropan-1-ol | 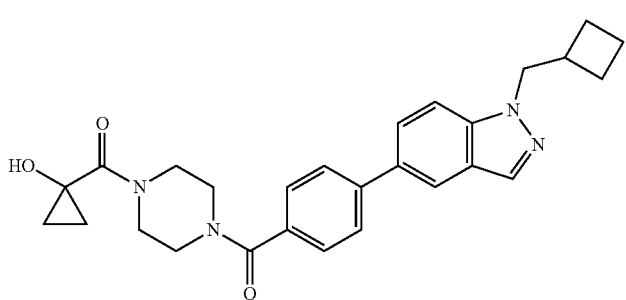 [SMILES: O=C(c1ccc(-c2ccc3c(cnn3CC3CCC3)c2)cc1)N1CCN(C(=O)C2(O)CC2)CC1] |

| IUPAC Name | Compound Structure |
|---|---|
| 1-{[4-({4-[1-(oxetan-3-ylmethyl)-1H-indazol-5-yl]phenyl}carbonyl)piperazin-1-yl]carbonyl}cyclopropan-1-ol | 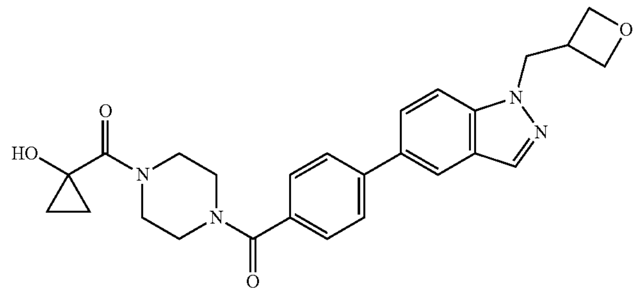 [SMILES: O=C(c1ccc(-c2ccc3c(cnn3CC3COC3)c2)cc1)N1CCN(C(=O)C2(O)CC2)CC1] |
| 1-{[4-({4-[1-(2-hydroxyethyl)-1H-indazol-5-yl]phenyl}carbonyl)piperazin-1-yl]carbonyl}cyclopropan-1-ol | 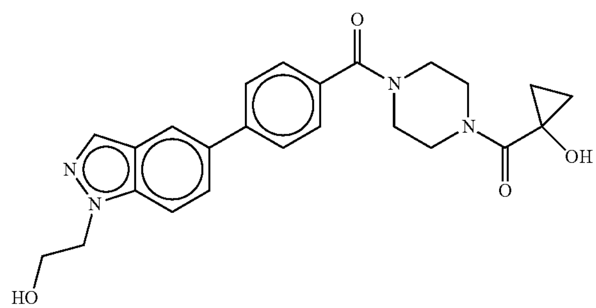 |
| 1-{[4-({4-[4-(1H-pyrazol-5-yl)phenyl]phenyl}carbonyl)piperazin-1-yl]carbonyl}cyclopropan-1-ol | 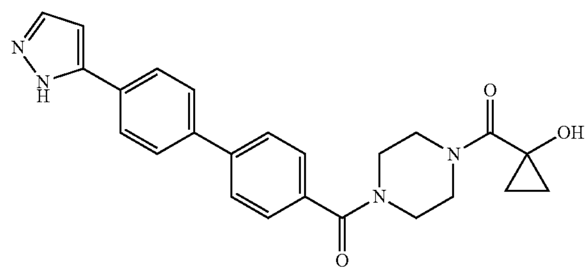 [SMILES: O=C(c1ccc(-c2ccc(-c3ccn[nH]3)cc2)cc1)N1CCN(C(=O)C2(O)CC2)CC1] |
| 1-{[4-({4-[4-(1H-pyrazol-4-yl)phenyl]phenyl}carbonyl)piperazin-1-yl]carbonyl}cyclopropan-1-ol | 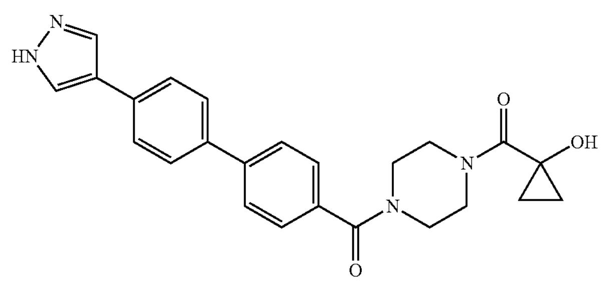 [SMILES: O=C(c1ccc(-c2ccc(-c3cn[nH]c3)cc2)cc1)N1CCN(C(=O)C2(O)CC2)CC1] |
| 1-{[4-({4-[4-(2-methyl-2H-1,2,3-triazol-4-yl)phenyl]phenyl}carbonyl)piperazin-1-yl]carbonyl}cyclopropan-1-ol | 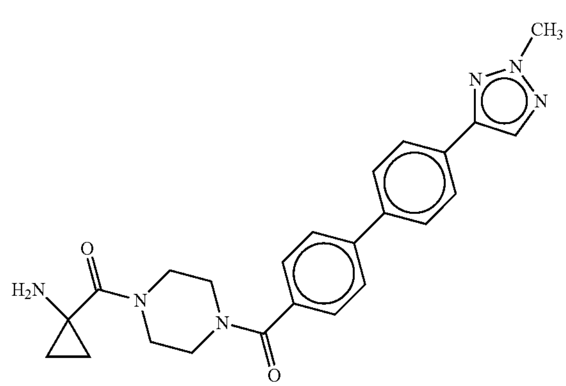 |

| IUPAC Name | Compound Structure |
|---|---|
| 1-{[4-({4-[4-(1-methyl-1H-1,2,3-triazol-4-yl)phenyl]phenyl}carbonyl)piperazin-1-yl]carbonyl}cyclopropan-1-ol | 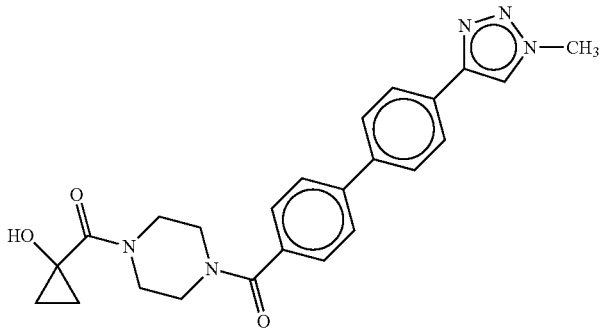 |
| 1-[(4-{[4-(1-methanesulfonyl-1H-indol-5-yl)phenyl]carbonyl}piperazin-1-yl)carbonyl]cyclopropan-1-ol | 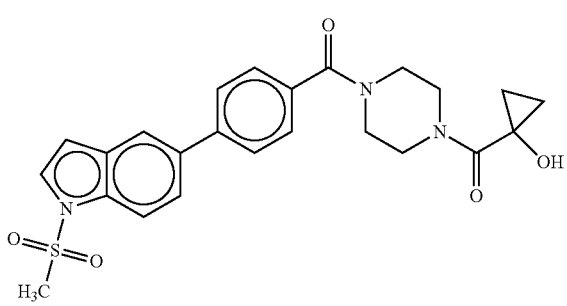 |
| 1-{[4-({4-[1-(cyclopropanesulfonyl)-1H-indol-5-yl]phenyl}carbonyl)piperazin-1-yl]carbonyl}cyclopropan-1-ol | 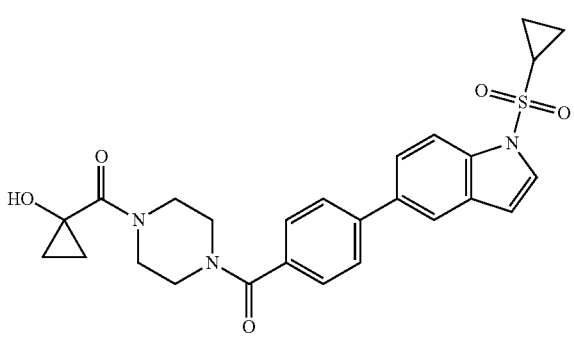 [SMILES: O=C(c1ccc(-c2ccc3c(ccn3S(=O)(=O)C3CC3)c2)cc1)N1CCN(C(=O)C2(O)CC2)CC1] |
| 1-{[4-({4-[1-(cyclopropanesulfonyl)-1H-indol-6-yl]phenyl}carbonyl)piperazin-1-yl]carbonyl}cyclopropan-1-ol | 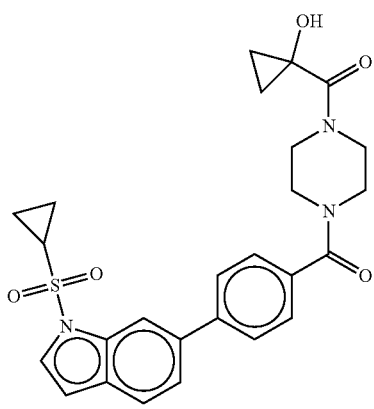 |

-continued

| IUPAC Name | Compound Structure |
|---|---|
| 1-{[4-({4-[2-(hydroxymethyl)-1H-indol-5-yl]phenyl}carbonyl)piperazin-1-yl]carbonyl}cyclopropan-ol | 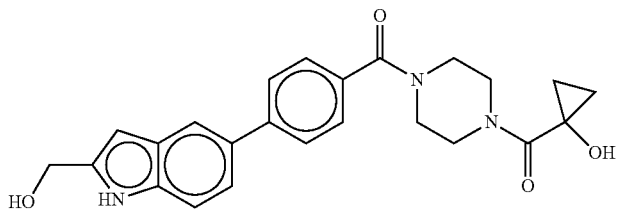 |
| 2-{5-[4-({4-[(1-hydroxycyclopropyl)carbonyl]piperazin-1-yl}carbonyl)phenyl]-1H-indol-3-yl}acetonitrile | 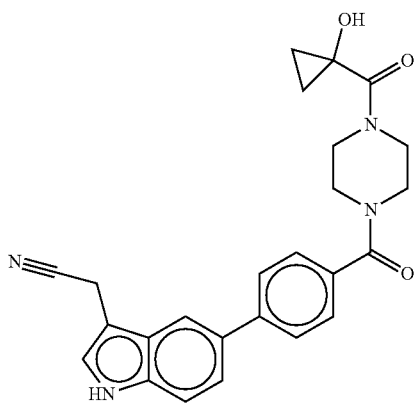 |
| 1-{[4-({4-[3-(2-hydroxyethyl)-1H-indol-5-yl]phenyl}carbonyl)piperazin-1-yl]carbonyl}cyclopropan-1-ol | 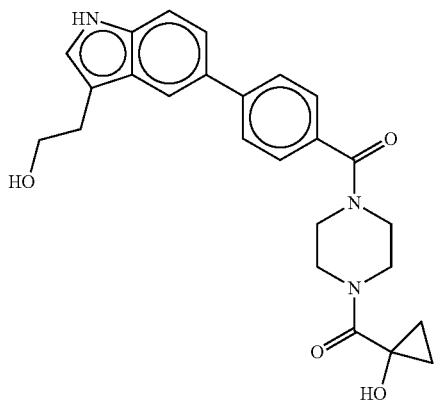 |
| 5-[4-({4-[(1-hydroxycyclopropyl)carbonyl]piperazin-1-yl}carbonyl)phenyl]-1-benzofuran-2-carbonitrile | 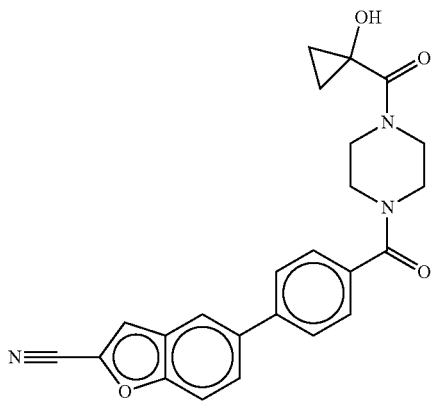 |

| IUPAC Name | Compound Structure |
|---|---|
| 1-[(4-{[4-(3-amino-1-methyl-1H-indazol-6-yl)phenyl]carbonyl}piperazin-1-yl)carbonyl]cyclopropan-1-ol | 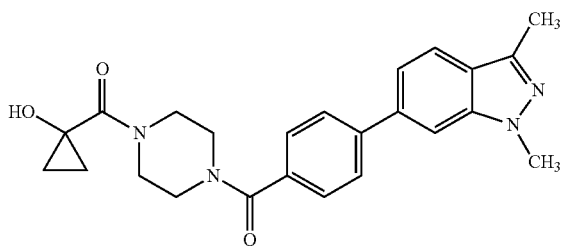 [SMILES: Cc1nn(C)c2cc(-c3ccc(C(=O)N4CCN(C(=O)C5(O)CC5)CC4)cc3)ccc12] |
| 1-[(4-{[4-(1-aminoisoquinolin-6-yl)phenyl]carbonyl}piperazin-1-yl)carbonyl]cyclopropan-1-ol | 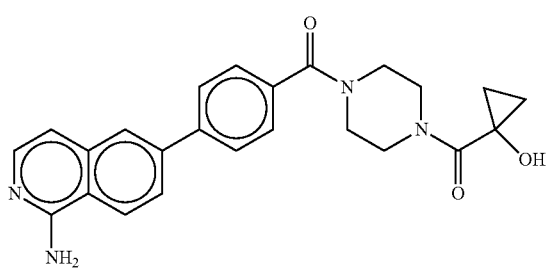 |
| 1-[(4-{[4-(3-aminoisoquinolin-6-yl)phenyl]carbonyl}piperazin-1-yl)carbonyl]cyclopropan-1-ol | 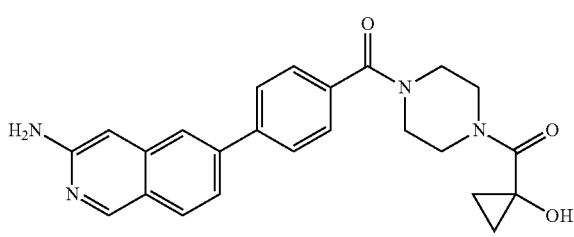 [SMILES: Nc1cc2cc(-c3ccc(C(=O)N4CCN(C(=O)C5(O)CC5)CC4)cc3)ccc2cn1] |
| 1-[(4-{[4-(1,3-dimethylisoquinolin-6-yl)phenyl]carbonyl}piperazin-1-yl)carbonyl]cyclopropan-1-ol | 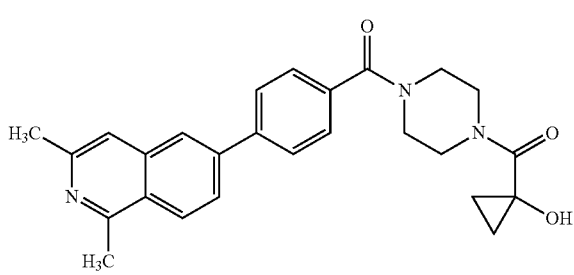 [SMILES: Cc1cc2cc(-c3ccc(C(=O)N4CCN(C(=O)C5(O)CC5)CC4)cc3)ccc2c(C)n1] |
| 1-{[4-([4-{3-(methoxymethyl)-1-methyl-1H-indazol-6-yl]phenyl}carbonyl)piperazin-1-yl]carbonyl}cyclopropan-1-ol | 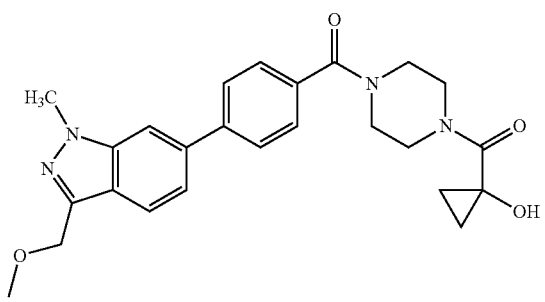 [SMILES: COCc1nn(C)c2cc(-c3ccc(C(=O)N4CCN(C(=O)C5(O)CC5)CC4)cc3)ccc12] |

| IUPAC Name | Compound Structure |
| --- | --- |
| 1-{[4-({4-[3-(hydroxymethyl)-1-methyl-1H-indazol-6-yl]phenyl}carbonyl)piperazin-1-yl]carbonyl}cyclopropan-1-ol | 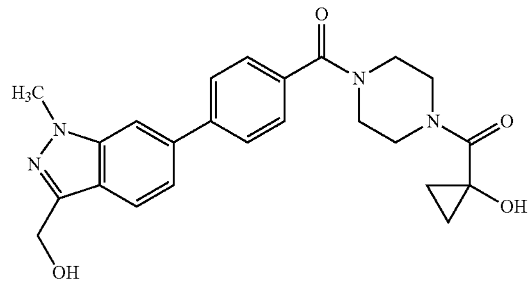 [SMILES: Cn1nc(CO)c2ccc(-c3ccc(C(=O)N4CCN(C(=O)C5(O)CC5)CC4)cc3)cc21] |
| 1-[(4-{[4-(2-methylquinolin-6-yl)phenyl]carbonyl}piperazin-1-yl)carbonyl]cyclopropan-1-ol | 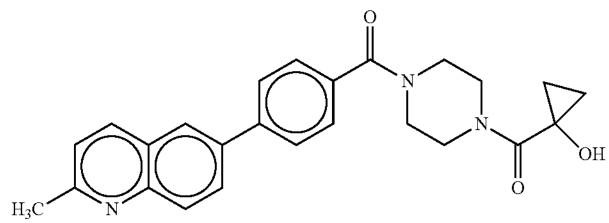 |
| 1-[(4-{[4-(2-aminoquinolin-6-yl)phenyl]carbonyl}piperazin-1-yl)carbonyl]cyclopropan-1-ol | 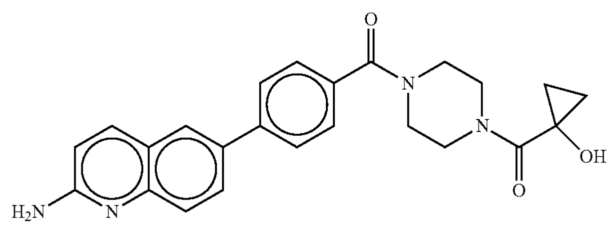 |
| 1-[(4-{[4-(1-ethyl-1H-indazol-6-yl)phenyl]carbonyl}piperazin-1-yl)carbonyl]cyclopropan-1-ol | 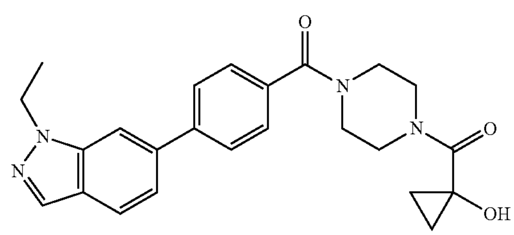 [SMILES: CCn1ncc2ccc(-c3ccc(C(=O)N4CCN(C(=O)C5(O)CC5)CC4)cc3)cc21] |
| 1-[(4-{[4-(1-cyclobutyl-1H-indazol-6-yl)phenyl]carbonyl}piperazin-1-yl)carbonyl]cyclopropan-1-ol | 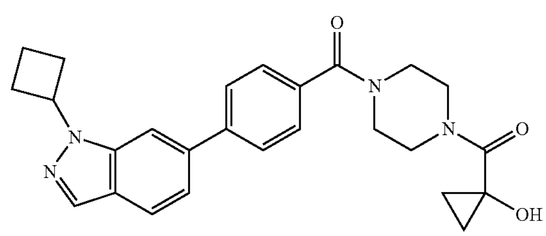 [SMILES: O=C(c1ccc(-c2ccc3cnn(C4CCC4)c3c2)cc1)N1CCN(C(=O)C2(O)CC2)CC1] |
| 1-{[4-({4-[1-(oxetan-3-yl)-1H-indazol-6-yl]phenyl}carbonyl)piperazin-1-yl]carbonyl}cyclopropan-1-ol | 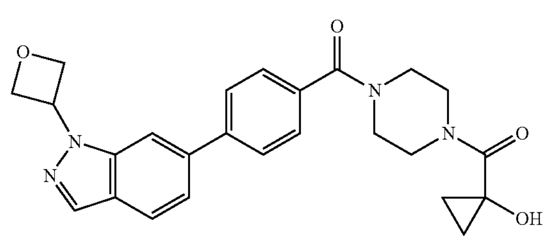 [SMILES: O=C(c1ccc(-c2ccc3cnn(C4COC4)c3c2)cc1)N1CCN(C(=O)C2(O)CC2)CC1] |

| IUPAC Name | Compound Structure |
|---|---|
| 1-{[4-({4-[1-(propan-2-yl)-1H-indazol-6-yl]phenyl}carbonyl)piperazin-1-yl]carbonyl}cyclopropan-1-ol | 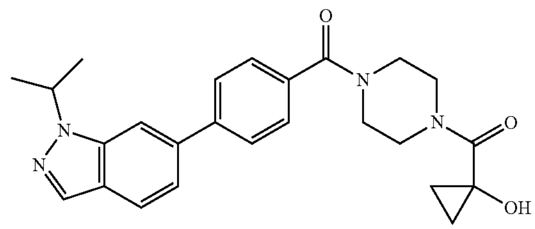 [SMILES: CC(C)n1ncc2ccc(-c3ccc(C(=O)N4CCN(C(=O)C5(O)CC5)CC4)cc3)cc21] |
| 1-{[4-({4-[1-(2-methoxyethyl)-1H-indazol-6-yl]phenyl}carbonyl)piperazin-1-yl]carbonyl}cyclopropan-1-ol | 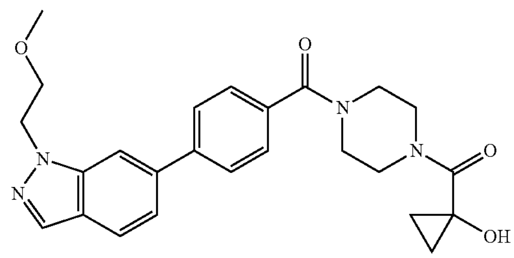 [SMILES: COCCn1ncc2ccc(-c3ccc(C(=O)N4CCN(C(=O)C5(O)CC5)CC4)cc3)cc21] |
| 1-{[4-({4-[1-(cyclopropylmethyl)-1H-indazol-6-yl]phenyl}carbonyl)piperazin-1-yl]carbonyl}cyclopropan-1-ol | 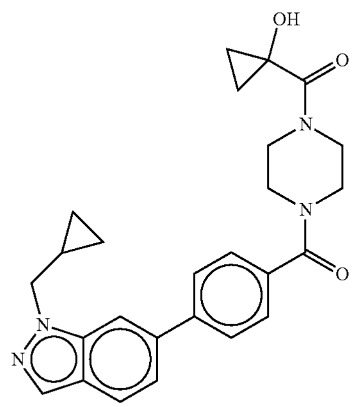 |
| 1-[(4-{[4-(1-propyl-1H-indazol-6-yl)phenyl]carbonyl}piperazin-1-yl)carbonyl]cyclopropan-1-ol | 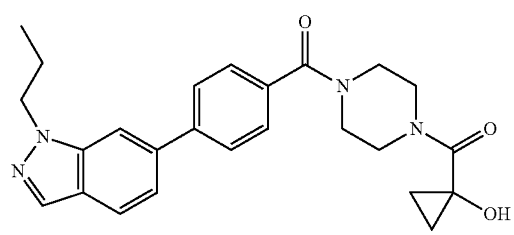 [SMILES: CCCn1ncc2ccc(-c3ccc(C(=O)N4CCN(C(=O)C5(O)CC5)CC4)cc3)cc21] |
| 1-{[4-({4-[1-(cyclobutylmethyl)-1H-indazol-6-yl]phenyl}carbonyl)piperazin-1-yl]carbonyl}cyclopropan-1-ol | 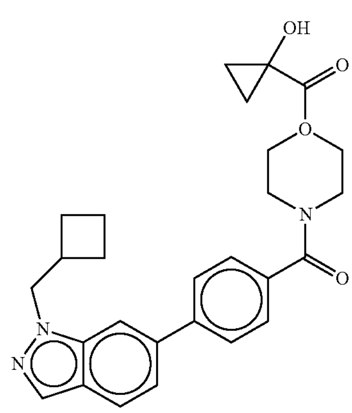 |

-continued

| IUPAC Name | Compound Structure |
|---|---|
| 1-{[4-({4-[1-(oxetan-3-ylmethyl)-1H-indazol-6-yl]phenyl}carbonyl)piperazin-1-yl]carbonyl}cyclopropan-1-ol | 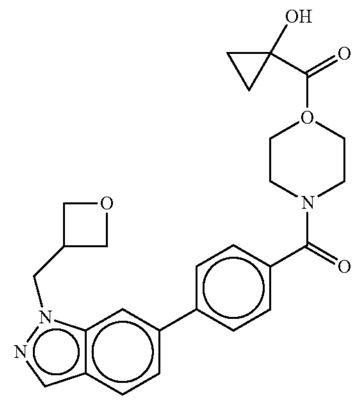 |
| 1-{[4-({4-[1-(2-hydroxyethyl)-1H-indazol-6-yl]phenyl}carbonyl)piperazin-1-yl]carbonyl}cyclopropan-1-ol | 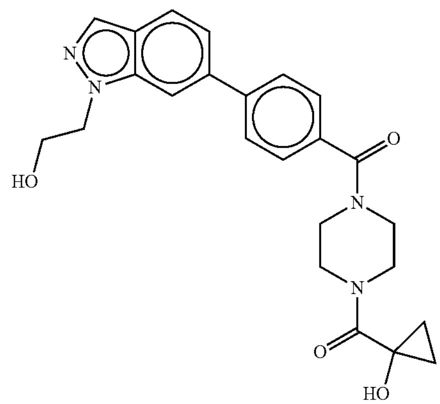 |
| 1-[(4-{[4-(1-cyclopropyl-1H-indazol-6-yl)phenyl]carbonyl}piperazin-1-yl)carbonyl]cyclopropan-1-ol | 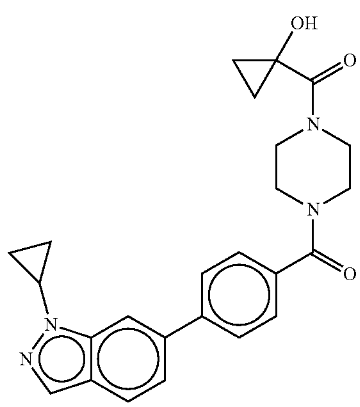 |
| N-{3-[4-({4-[(1-hydroxycyclopropyl)carbonyl]piperazin-1-yl}carbonyl)phenyl]phenyl}-N-methylcyclopropanecarboxamide | 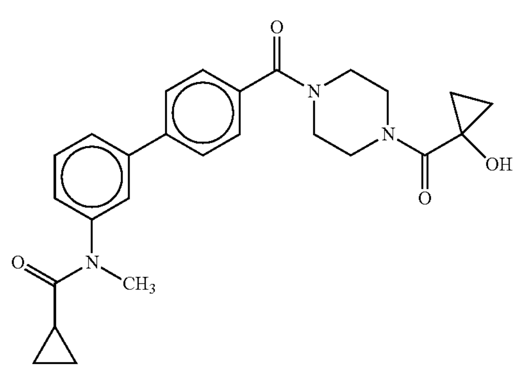 |

| IUPAC Name | Compound Structure |
|---|---|
| N-{3-[4-({4-[(1-hydroxycyclopropyl)carbonyl]piperazin-1-yl}carbonyl)phenyl]phenyl}-N-methylcyclobutanecarboxamide | 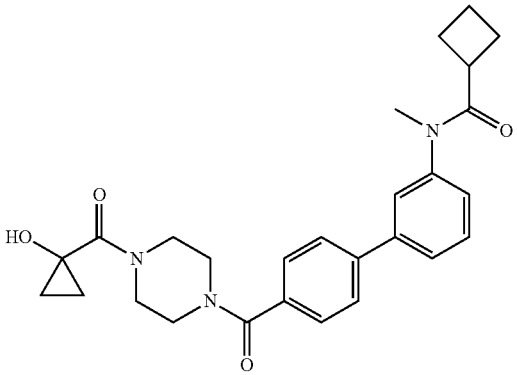 |
| N-{3-[4-({4-[(1-hydroxycyclopropyl)carbonyl]piperazin-1-yl}carbonyl)phenyl]phenyl}-N-methylcyclobutanesulfonamide | 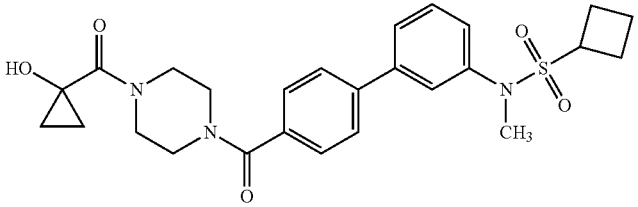 |
| N-cyclopropyl-3-[4-({4-[(1-hydroxycyclopropyl)carbonyl]piperazin-1-yl}carbonyl)phenyl]-N-methylbenzene-1-sulfonamide | 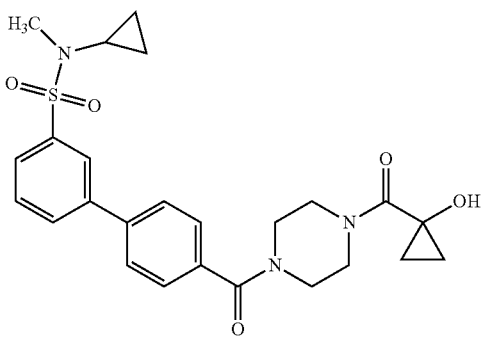 [SMILES: CN(C1CC1)S(=O)(=O)c1cccc(-c2ccc(C(=O)N3CCN(C(=O)C4(O)CC4)CC3)cc2)c1] |
| N-cyclopropyl-3-[4-({4-[(1-hydroxycyclopropyl)carbonyl]piperazin-1-yl}carbonyl)phenyl]-N-methylbenzamide | 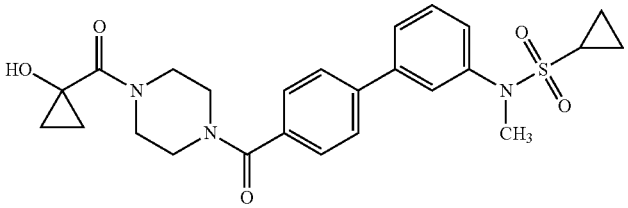 [SMILES: CN(c1cccc(-c2ccc(C(=O)N3CCN(C(=O)C4(O)CC4)CC3)cc2)c1)S(=O)(=O)C1CC1] |
| 2-cyclobutyl-N-{3-[4-({4-[(1-hydroxycyclopropyl)carbonyl]piperazin-1-yl}carbonyl)phenyl]phenyl}acetamide | 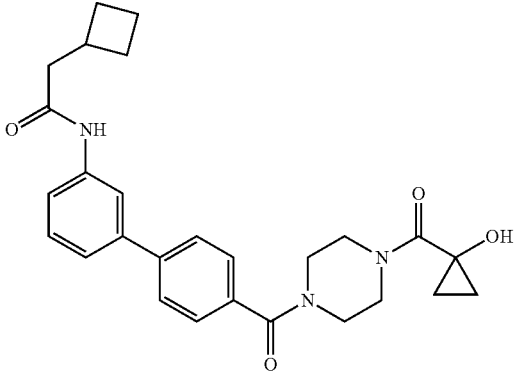 [SMILES: O=C(CC1CCC1)Nc1cccc(-c2ccc(C(=O)N3CCN(C(=O)C4(O)CC4)CC3)cc2)c1] |

| IUPAC Name | Compound Structure |
|---|---|
| N-{3-[4-({4-[(1-hydroxycyclopropyl)carbonyl]piperazin-1-yl}carbonyl)phenyl]phenyl}-1-methylazetidine-3-carboxamide | 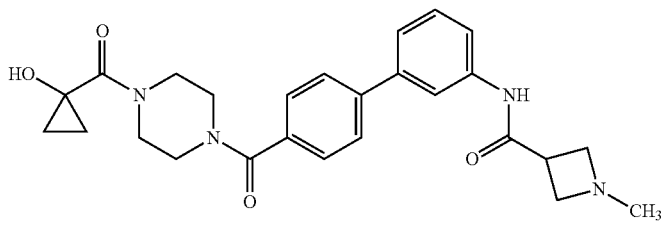 [SMILES: CN1CC(C(=O)Nc2cccc(-c3ccc(C(=O)N4CCN(C(=O)C5(O)CC5)CC4)cc3)c2)C1] |
| N-{3-[4-({4-[(1-hydroxycyclopropyl)carbonyl]piperazin-1-yl}carbonyl)phenyl]phenyl}-3-methyloxetane-3-carboxamide | 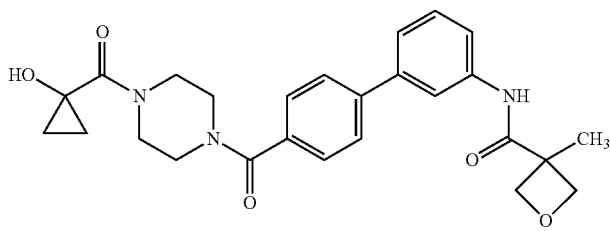 |
| N-{3-[4-({4-[(1-hydroxycyclopropyl)carbonyl]piperazin-1-yl}carbonyl)phenyl]phenyl}-2-(oxetan-3-yl)acetamide | 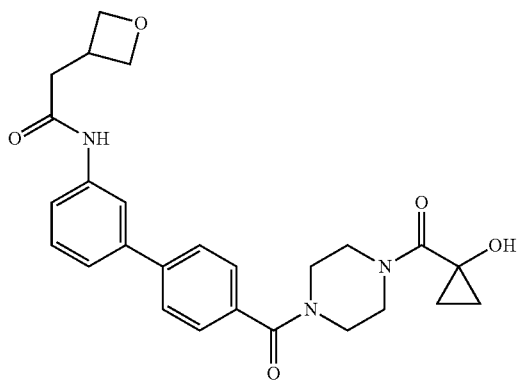 [SMILES: O=C(CC1COC1)Nc1cccc(-c2ccc(C(=O)N3CCN(C(=O)C4(O)CC4)CC3)cc2)c1] |
| 3-fluoro-N-{3-[4-({4-[(1-hydroxycyclopropyl)carbonyl]piperazin-1-yl}carbonyl)phenyl]phenyl}cyclobutane-1-carboxamide | 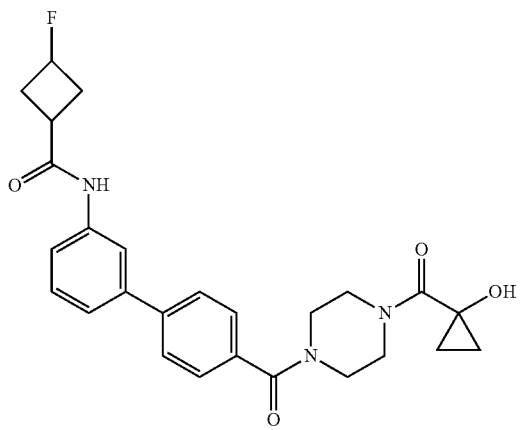 [SMILES: O=C(Nc1cccc(-c2ccc(C(=O)N3CCN(C(=O)C4(O)CC4)CC3)cc2)c1)C1CC(F)C1] |

| IUPAC Name | Compound Structure |
|---|---|
| 3-ethyl-N-{3-[4-({4-[(1-hydroxycyclopropyl)carbonyl]piperazin-1-yl}carbonyl)phenyl]phenyl}oxetane-3-carboxamide | 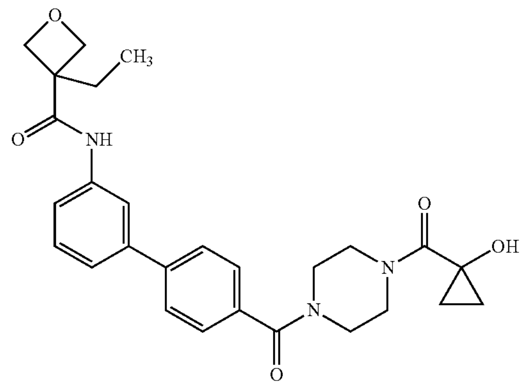 [SMILES: CCC1(C(=O)Nc2cccc(-c3ccc(C(=O)N4CCN(C(=O)C5(O)CC5)CC4)cc3)c2)COC1] |
| N-{3-[4-({4-[(1-hydroxycyclopropyl)carbonyl]piperazin-1-yl}carbonyl)phenyl]phenyl}propanamide | 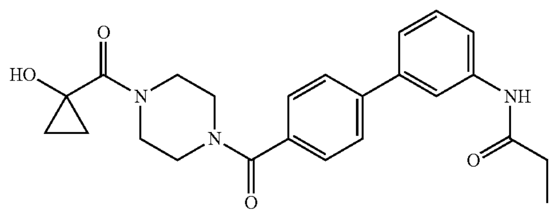 [SMILES: CCC(=O)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}-2-methylpropanamide | 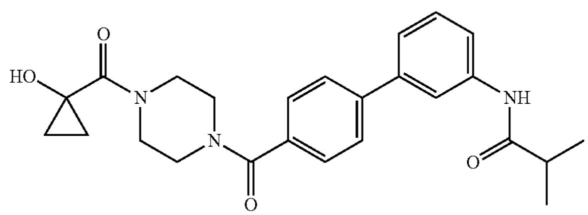 [SMILES: CC(C)C(=O)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}butanamide | 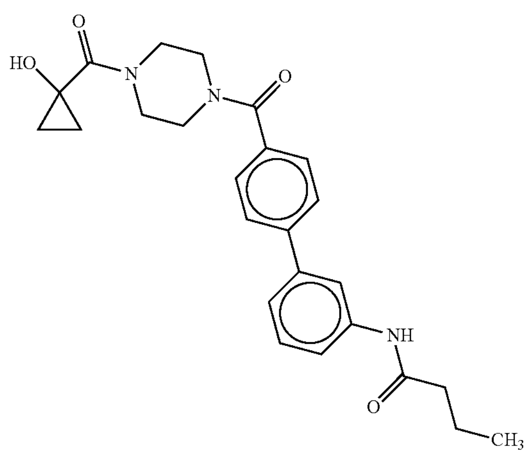 |
| N-{3-[4-({4-[(1-hydroxycyclopropyl)carbonyl]piperazin-1-yl}carbonyl)phenyl]phenyl}-2-methoxyacetamide | 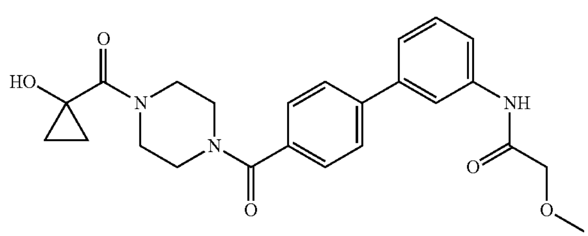 [SMILES: COCC(=O)Nc1cccc(-c2ccc(C(=O)N3CCN(C(=O)C4(O)CC4)CC3)cc2)c1] |

| IUPAC Name | Compound Structure |
|---|---|
| 2-cyclopropyl-N-{3-[4-({4-[(1-hydroxycyclopropyl)carbonyl]piperazin-1-yl}carbonyl)phenyl]phenyl}acetamide | 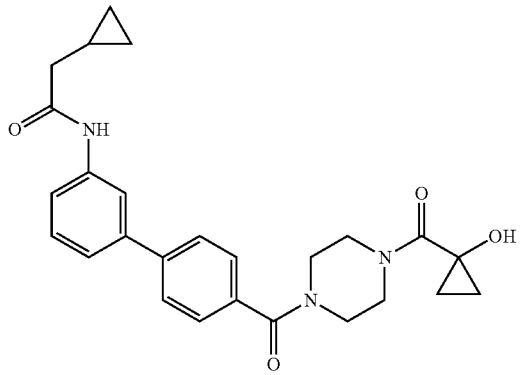 [SMILES: O=C(CC1CC1)Nc1cccc(-c2ccc(C(=O)N3CCN(C(=O)C4(O)CC4)CC3)cc2)c1] |
| 2,2-difluoro-N-{3-[4-({4-[(1-hydroxycyclopropyl)carbonyl]piperazin-1-yl}carbonyl)phenyl]phenyl}acetamide | 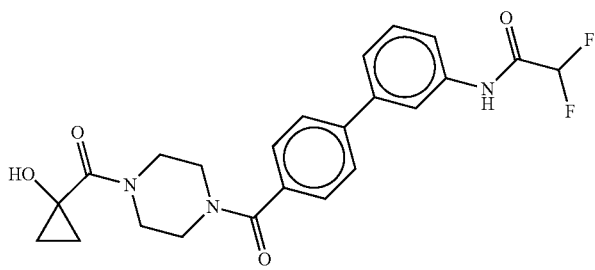 |
| N-{3-[4-({4-[(1-hydroxycyclopropyl)carbonyl]piperazin-1-yl}carbonyl)phenyl]phenyl}-1-methylcyclopropane-1-carboxamide | 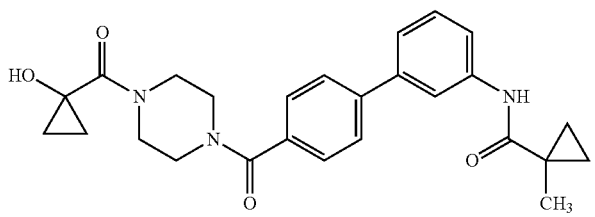 [SMILES: CC1(C(=O)Nc2cccc(-c3ccc(C(=O)N4CCN(C(=O)C5(O)CC5)CC4)cc3)c2)CC1] |
| N-{3-[4-({4-[(1-hydroxycyclopropyl)carbonyl]piperazin-1-yl}carbonyl)phenyl]phenyl}cyclopentanecarboxamide | 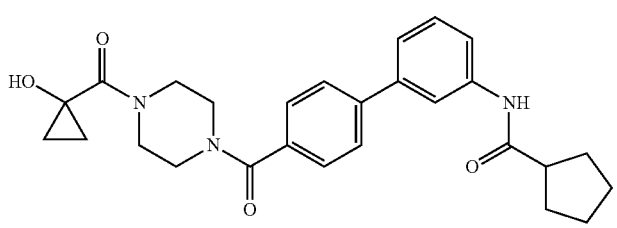 [SMILES: O=C(Nc1cccc(-c2ccc(C(=O)N3CCN(C(=O)C4(O)CC4)CC3)cc2)c1)C1CCCC1] |
| N-{3-[4-({4-[(1-hydroxycyclopropyl)carbonyl]piperazin-1-yl}carbonyl)phenyl]phenyl}cyclohexanecarboxamide | 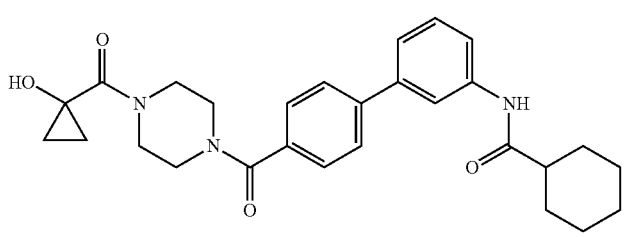 [SMILES: O=C(Nc1cccc(-c2ccc(C(=O)N3CCN(C(=O)C4(O)CC4)CC3)cc2)c1)C1CCCCC1] |

| IUPAC Name | Compound Structure |
|---|---|
| N-{3-[4-({4-[(1-hydroxycyclopropyl)carbonyl]piperazin-1-yl}carbonyl)phenyl]phenyl}oxane-4-carboxamide | 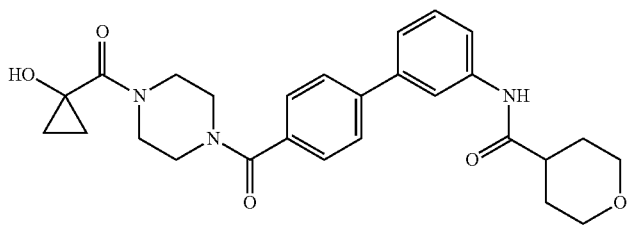 [SMILES: O=C(Nc1cccc(-c2ccc(C(=O)N3CCN(C(=O)C4(O)CC4)CC3)cc2)c1)C1CCOCC1] |
| 1-cyclopropyl-N-{3-[4-({4-[(1-hydroxycyclopropyl)carbonyl]piperazin-1-yl}carbonyl)phenyl]phenyl}methanesulfonamide | 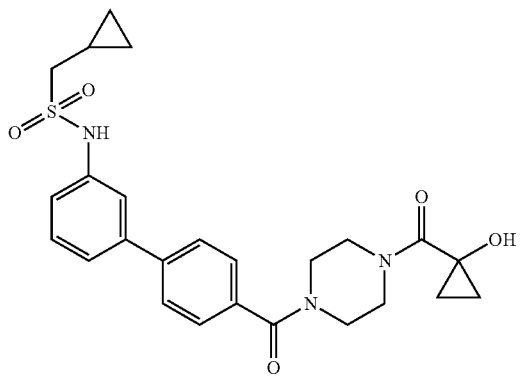 [SMILES: O=C(c1ccc(-c2cccc(NS(=O)(=O)CC3CC3)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}-2-methylpropane-1-sulfonamide | 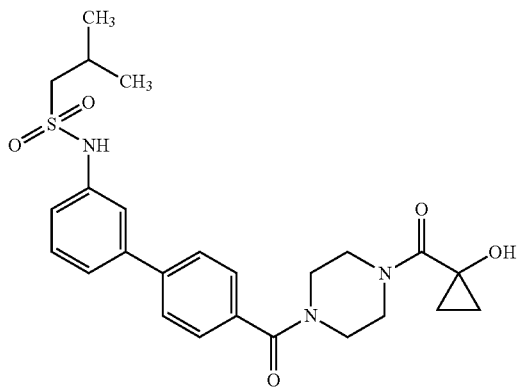 |
| 1,1-difluoro-N-{3-[4-({4-[(1-hydroxycyclopropyl)carbonyl]piperazin-1-yl}carbonyl)phenyl]phenyl}methanesulfonamide | 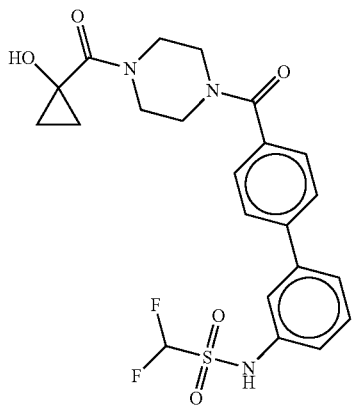 |

| IUPAC Name | Compound Structure |
|---|---|
| 3,3,3-trifluoro-N-{3-[4-({4-[(1-hydroxycyclopropyl)carbonyl]piperazin-1-yl}carbonyl)phenyl]phenyl}propane-1-sulfonamide | 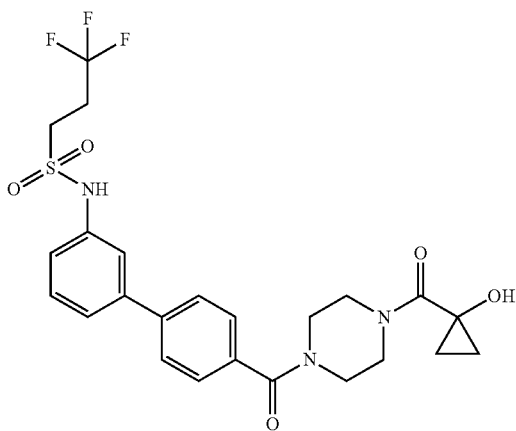 [SMILES: O=C(c1ccc(-c2cccc(NS(=O)(=O)CCC(F)(F)F)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}-1-methylcyclopropane-1-sulfonamide | 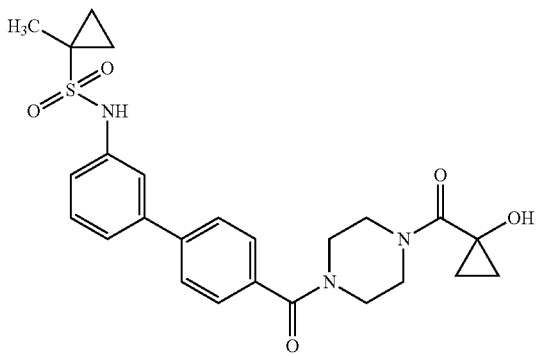 [SMILES: CC1(S(=O)(=O)Nc2cccc(-c3ccc(C(=O)N4CCN(C(=O)C5(O)CC5)CC4)cc3)c2)CC1] |
| N-{3-[4-({4-[(1-hydroxycyclopropyl)carbonyl]piperazin-1-yl}carbonyl)phenyl]phenyl}cyclobutanesulfonamide | 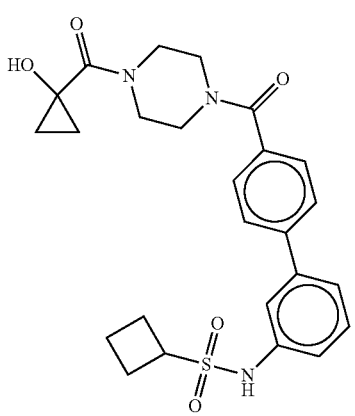 |

| IUPAC Name | Compound Structure |
|---|---|
| N-{3-[4-({4-[(1-hydroxycyclopropyl)carbonyl]piperazin-1-yl}carbonyl)phenyl]phenyl}oxolane-3-sulfonamide | 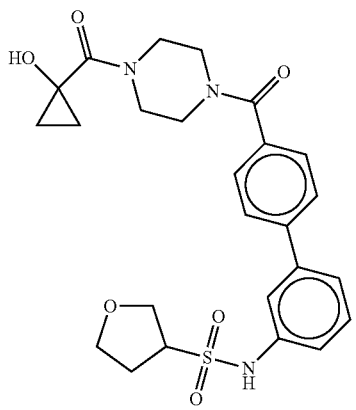 |
| N-{3-[4-({4-[(1-hydroxycyclopropyl)carbonyl]piperazin-1-yl}carbonyl)phenyl]phenyl}cyclopentanesulfonamide | 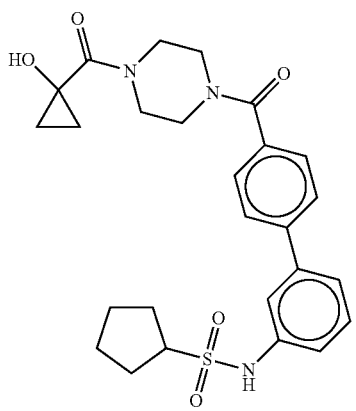 |
| 2,2-difluoro-N-{3-[4-({4-[(1-hydroxycyclopropyl)carbonyl]piperazin-1-yl}carbonyl)phenyl]phenyl}ethane-1-sulfonamide | 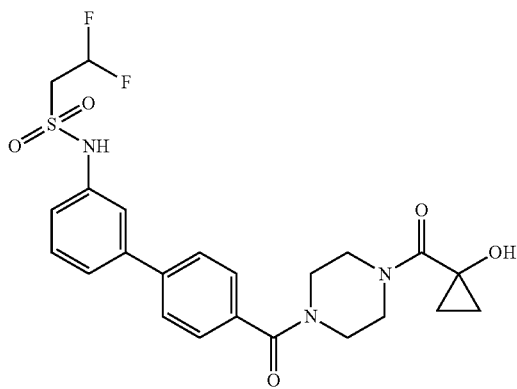 [SMILES: O=C(c1ccc(-c2cccc(NS(=O)(=O)CC(F)F)c2)cc1)N1CCN(C(=O)C2(O)CC2)CC1] |

| IUPAC Name | Compound Structure |
|---|---|
| N-{3-[4-({4-[(1-hydroxycyclopropyl)carbonyl]piperazin-1-yl}carbonyl)phenyl]phenyl}-2-methoxyethane-1-sulfonamide | 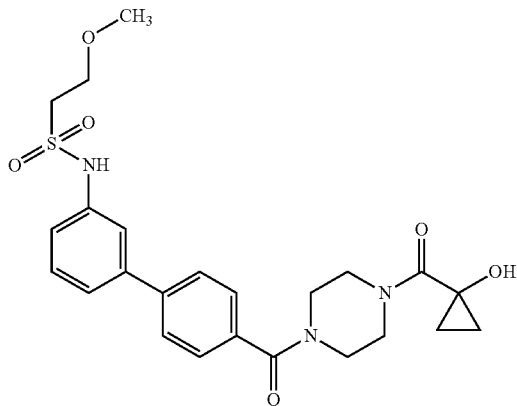 [SMILES: COCCS(=O)(=O)Nc1cccc(-c2ccc(C(=O)N3CCN(C(=O)C4(O)CC4)CC3)cc2)c1] |
| 1-cyclobutyl-N-{3-[4-({4-[(1-hydroxycyclopropyl)carbonyl]piperazin-1-yl}carbonyl)phenyl]phenyl}methanesulfonamide | 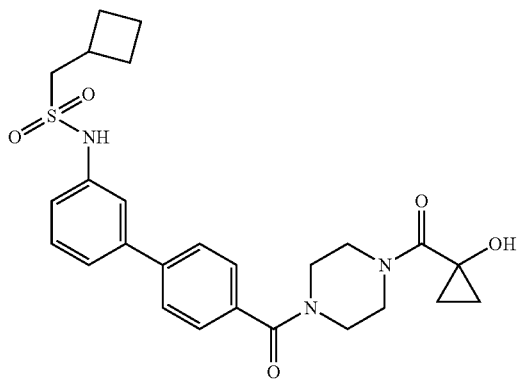 [SMILES: O=C(c1ccc(-c2cccc(NS(=O)(=O)CC3CCC3)c2)cc1)N1CCN(C(=O)C2(O)CC2)CC1] |
| 2-hydroxy-N-{3-[4-({4-[(1-hydroxycyclopropyl)carbonyl]piperazin-1-yl}carbonyl)phenyl]phenyl}ethane-1-sulfonamide | 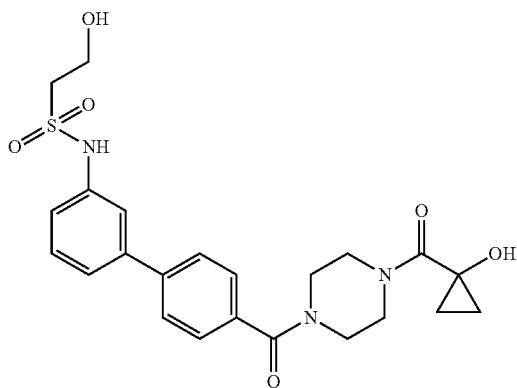 [SMILES: O=C(c1ccc(-c2cccc(NS(=O)(=O)CCO)c2)cc1)N1CCN(C(=O)C2(O)CC2)CC1] |

| IUPAC Name | Compound Structure |
|---|---|
| N-{3-[4-({4-[(1-hydroxycyclopropyl)carbonyl]piperazin-1-yl}carbonyl)phenyl]phenyl}oxane-4-sulfonamide | 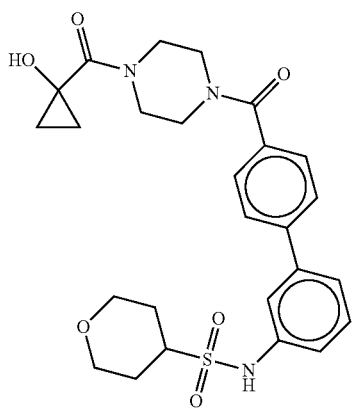 |
| 2-cyclopropyl-N-{3-[4-({4-[(1-hydroxycyclopropyl)carbonyl]piperazin-1-yl}carbonyl)phenyl]phenyl}ethane-1-sulfonamide | 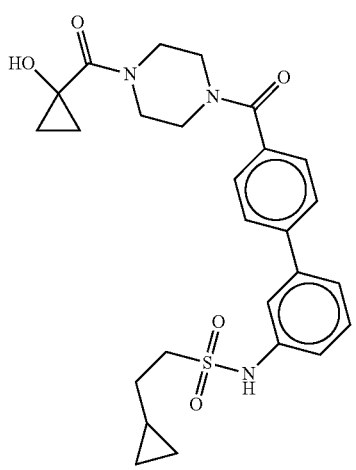 |
| 3,3-difluoro-N-{3-[4-({4-[(1-hydroxycyclopropyl)carbonyl]piperazin-1-yl}carbonyl)phenyl]phenyl}cyclobutane-1-carboxamide | 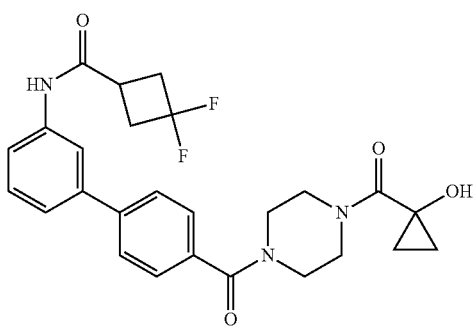 [SMILES: O=C(Nc1cccc(-c2ccc(C(=O)N3CCN(C(=O)C4(O)CC4)CC3)cc2)c1)C1CC(F)(F)C1] |

| IUPAC Name | Compound Structure |
|---|---|
| 1-[(4-{[4-(1H-1,3-benzodiazol-4-yl)-2-chlorophenyl]carbonyl}piperazin-1-yl)carbonyl]cyclopropan-1-ol | 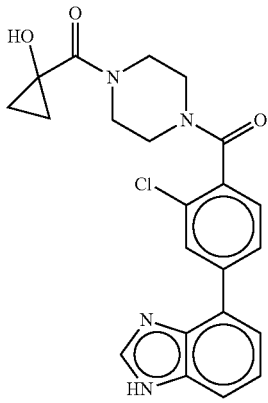 |
| 1-[(4-{[4-(2-cyclopropyl-2H-indazol-5-yl)phenyl]carbonyl}piperazin-1-yl)carobnyl]cyclopropan-1-ol | 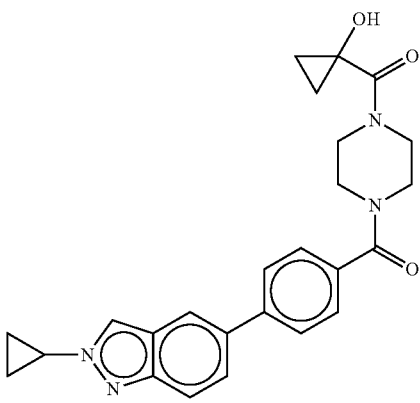 |
| 1-[(4-{[4-(1-cyclopropyl-1H-indazol-5-yl)phenyl]carbonyl}piperazin-1-yl)carbonyl]cyclopropan-1-ol | 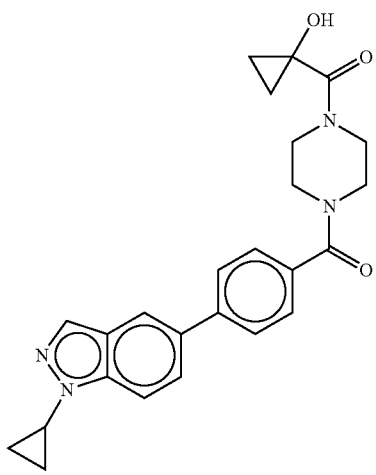 |

| IUPAC Name | Compound Structure |
|---|---|
| N-{4-[4-({4-[(1-hydroxycyclopropyl)carbonyl]piperazin-1-yl}carbonyl)phenyl]phenyl}cyclopropanecarboxamide | 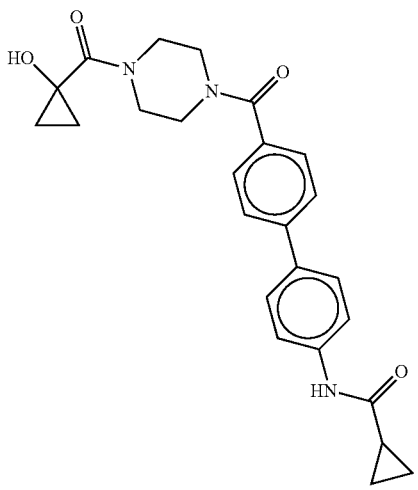 |
| N-{3-[4-({4-[(1-hydroxycyclopropyl)carbonyl]piperazin-1-yl}carbonyl)phenyl]phenyl}-N-methylcyclopropanesulfonamide | 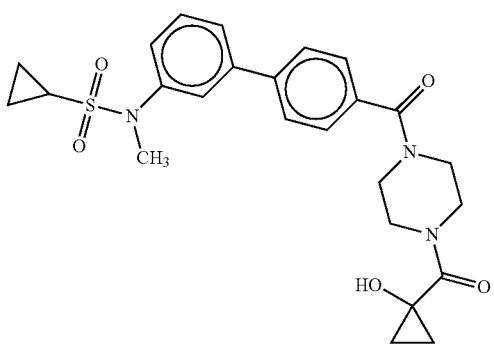 |
| N-{3-[4-({4-[(1-methoxycyclopropyl)carbonyl]piperazin-1-yl}carbonyl)phenyl]phenyl}-N-methylcyclopropanesulfonamide | 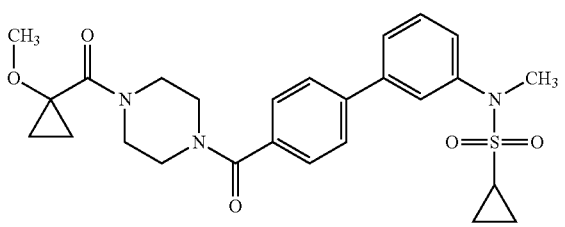 [SMILES: COC1(C(=O)N2CCN(C(=O)c3ccc(-c4cccc(N(C)S(=O)(=O)C5CC5)c4)cc3)CC2)CC1] |
| 3-cyclopropyl-1-{3-[4-({4-[(1-hydroxycyclopropyl)carbonyl]piperazin-1-yl}carbonyl)phenyl]phenyl}urea | 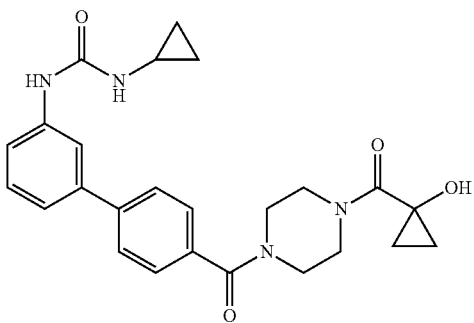 |

-continued

| IUPAC Name | Compound Structure |
|---|---|
| 3-[4-({4-[(1-hydroxycyclopropyl)carbonyl]piperazin-1-yl}carbonyl)phenyl]phenyl N-cyclopropylcarbamate | 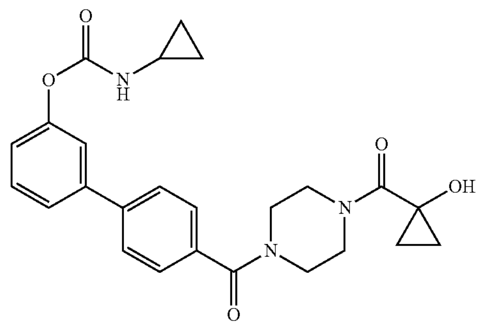 [SMILES: O=C(NC1CC1)Oc1cccc(-c2ccc(C(=O)N3CCN(C(=O)C4(O)CC4)CC3)cc2)c1] |
| N-{4-[4-({4-[(1-hydroxycyclopropyl)carbonyl]piperazin-1-yl}carbonyl)phenyl]phenyl}cyclopropanesulfonamide | 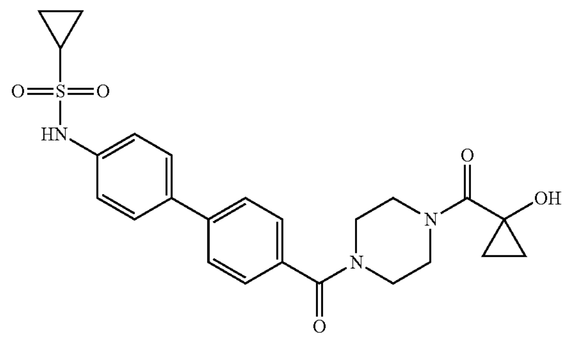 [SMILES: O=C(c1ccc(-c2ccc(NS(=O)(=O)C3CC3)cc2)cc1)N1CCN(C(=O)C2(O)CC2)CC1] |
| N-{3-[3-chloro-4-({4-[(1-hydroxycyclopropyl)carbonyl]piperazin-1-yl}carbonyl)phenyl]phenyl}cyclopropanecarboxamide | 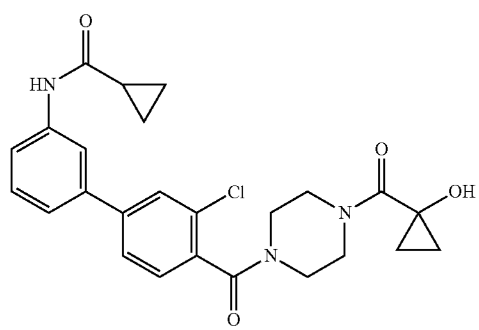 [SMILES: O=C(Nc1cccc(-c2ccc(C(=O)N3CCN(C(=O)C4(O)CC4)CC3)c(Cl)c2)c1)C1CC1] |
| N-(3-{4-[4-(1-hydroxycyclopropanecarbonyl)piperazine-1-carbonyl]phenyl}phenyl)cyclopentanecarboxamide | 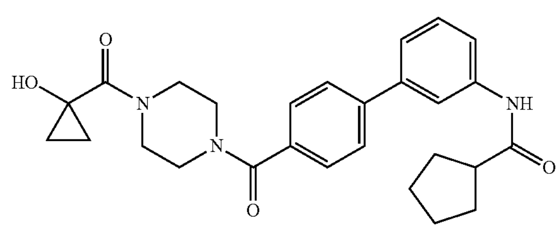 [SMILES: O=C(Nc1cccc(-c2ccc(C(=O)N3CCN(C(=O)C4(O)CC4)CC3)cc2)c1)C1CCCC1] |
| 1-(4-{4-[4-(1H-pyrazol-4-yl)phenyl]benzoyl}piperazine-1-carbonyl)cyclopropan-1-ol | 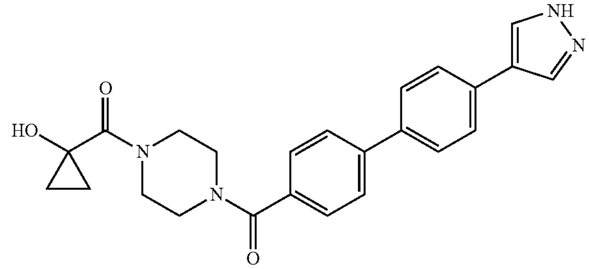 [SMILES: O=C(c1ccc(-c2ccc(-c3cn[nH]c3)cc2)cc1)N1CCN(C(=O)C2(O)CC2)CC1] |

| IUPAC Name | Compound Structure |
| --- | --- |
| 1-{4-[4-(1,2,3,4-tetrahydroisoquinolin-2-yl)benzoyl]piperazine-1-carbonyl}cyclopropan-1-ol | 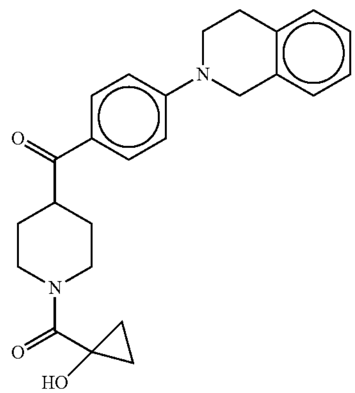 |
| 1-{4-[4-(1,3-dimethyl-1H-indazol-5-yl)-2-fluorobenzoyl]piperazine-1-carbonyl}cyclopropan-1-amine | 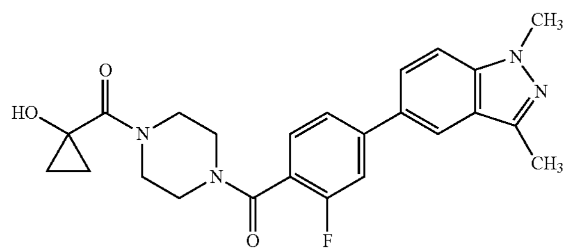 [SMILES: Cc1nn(C)c2ccc(-c3ccc(C(=O)N4CCN(C(=O)C5(O)CC5)CC4)c(F)c3)cc12] |
| 1-(4-{4-[4-(1-methyl-1H-pyrazol-4-yl)phenyl]benzoyl}piperazine-1-carbonyl)cyclopropan-1-ol | 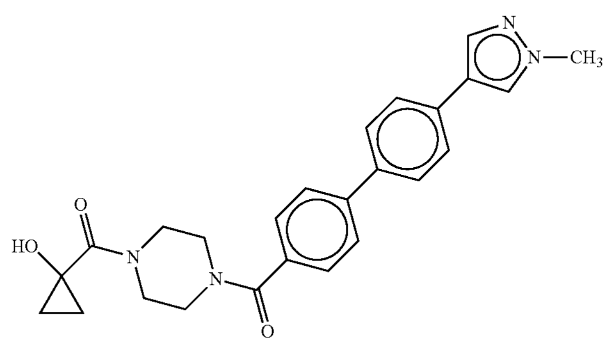 |
| 1-[(2S)-4-[2-fluoro-4-(1-methyl-1H-1,3-benzodiazol-5-yl)benzoyl]-2-methylpiperazine-1-carbonyl]cyclopropan-1-ol | 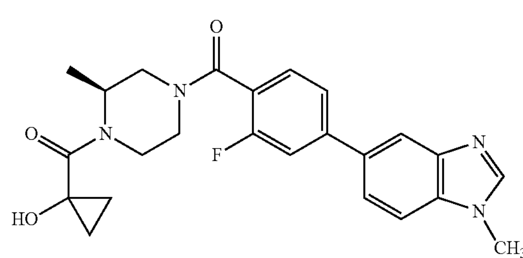 [SMILES: C[C@H]1CN(C(=O)c2ccc(-c3ccc4c(c3)ncn4C)cc2F)CCN1C(=O)C1(O)CC1] |
| 1-{4-[3-chloro-4-(1-methyl-1H-indazol-6-yl)benzoyl]piperazine-1-carbonyl}cyclopropan-1-ol | 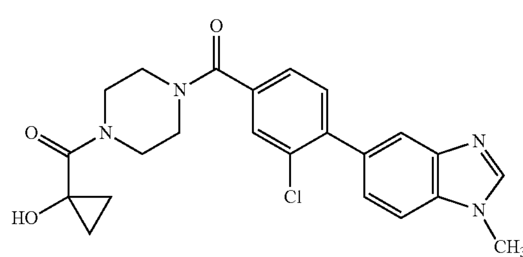 [SMILES: Cn1cnc2cc(-c3ccc(C(=O)N4CCN(C(=O)C5(O)CC5)CC4)cc3Cl)ccc21] |

-continued

| IUPAC Name | Compound Structure |
|---|---|
| 1-{4-[2-fluoro-4-(1-methyl-1H-1,3-benzodiazol-5-yl)benzoyl]piperazine-1-carbonyl}cyclopropan-1-ol | 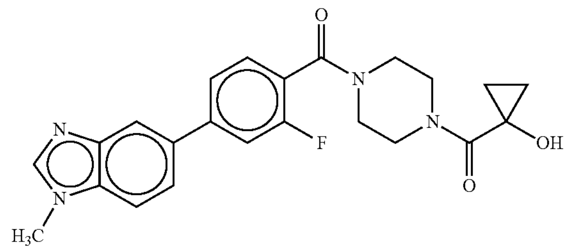 |
| 1-{4-[3-chloro-4-(1-methyl-1H-1,3-benzodiazol-5-yl)benzoyl]piperazine-1-carbonyl}cyclopropan-1-ol | 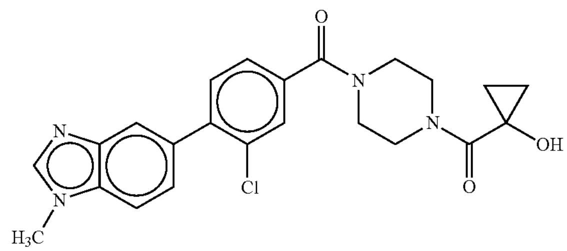 |
| 1-[4-(4-{pyrazolo[1,5-a]pyridin-6-yl}benzoyl)piperazine-1-carbonyl]cyclopropan-1-ol | 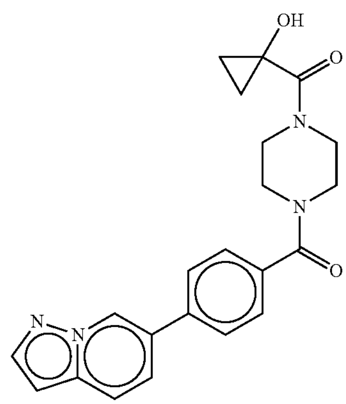 |
| 1-{4-[4-(4-fluoro-2,3-dihydro-1H-indol-1-yl)benzoyl]piperazine-1-carbonyl}cyclopropan-1-ol | 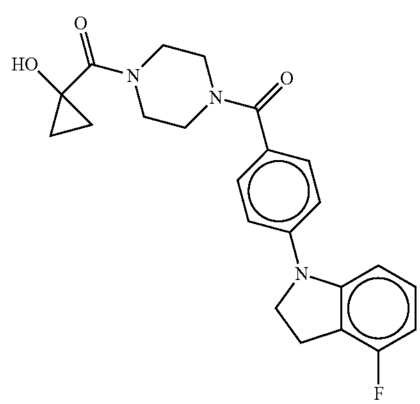 |
| 1-{4-[4-(3-methyl-1H-indazol-6-yl)benzoyl]piperazine-1-carbonyl}cyclopropan-1-ol | 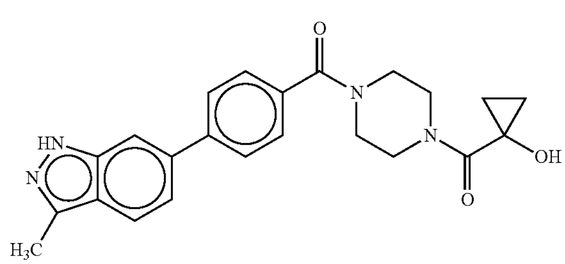 |

| IUPAC Name | Compound Structure |
| --- | --- |
| 1-{4-[2-fluoro-4-(3-methyl-1H-indazol-7-yl)benzoyl]piperazine-1-carbonyl}cyclopropan-1-ol | 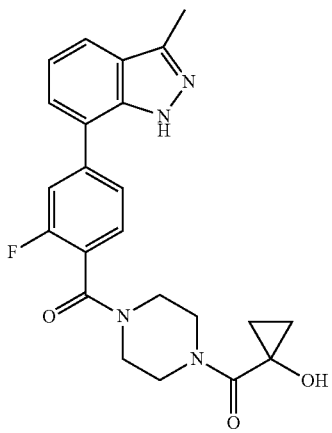 [SMILES: Cc1n[nH]c2c(-c3ccc(C(=O)N4CCN(C(=O)C5(O)CC5)CC4)c(F)c3)cccc12] |
| 1-[(2S)-2-methyl-4-[4-(1-methyl-1H-indazol-6-yl)benzoyl]piperazine-1-carbonyl]cyclopropan-1-ol | 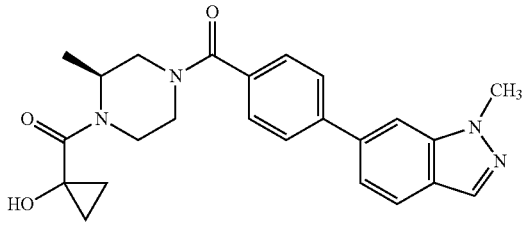 [SMILES: C[C@H]1CN(C(=O)c2ccc(-c3ccc4cnn(C)c4c3)cc2)CCN1C(=O)C1(O)CC1] |
| 1-{4-[3-chloro-4-(2-methyl-2H-indazol-6-yl)benzoyl]piperazine-1-carbonyl}cyclopropan-1-ol | 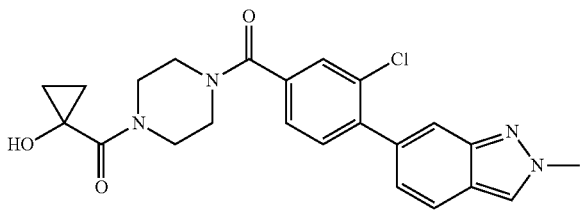 |
| 3,3,3-trifluoro-N-(3-{4-[4-(1-hydroxycyclopropanecarbonyl)piperazine-1-carbonyl]phenyl}phenyl)propane-1-sulfonamide | 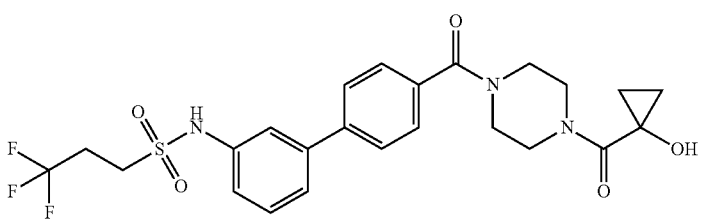 [SMILES: O=C(c1ccc(-c2cccc(NS(=O)(=O)CCC(F)(F)F)c2)cc1)N1CCN(C(=O)C2(O)CC2)CC1] |
| 1-{4-[2-fluoro-4-(1-methyl-1H-indazol-6-yl)benzoyl]piperazine-1-carbonyl}cyclopropan-1-ol | 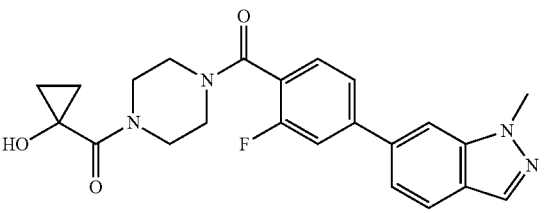 |

-continued

| IUPAC Name | Compound Structure |
|---|---|
| 1-{3,3-dimethyl-4-[4-(1-methyl-1H-1,3-benzodiazol-5-yl)benzoyl]piperazine-1-carbonyl}cyclopropan-1-ol | 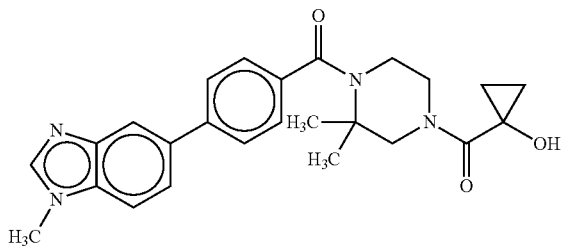 |
| 1-{4-[2,6-difluoro-4-(1-methyl-1H-1,3-benzodiazol-5-yl)benzoyl]piperazine-1-carbonyl}cyclopropan-1-ol | 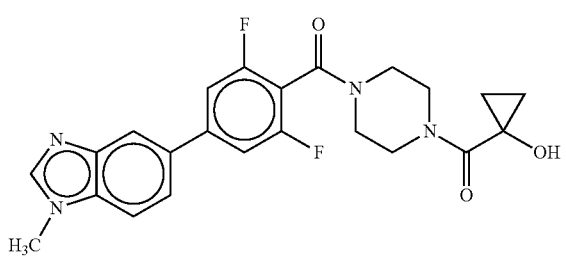 |
| 1-{4-[2-fluoro-4-(1-methyl-1H-indazol-6-yl)benzoyl]piperazine-1-carbonyl}cyclobutan-1-amine | 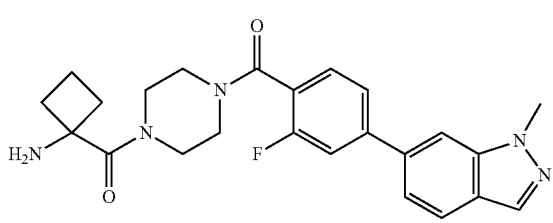 [SMILES: Cn1ncc2ccc(-c3ccc(C(=O)N4CCN(C(=O)C5(N)CCC5)CC4)c(F)c3)cc21] |
| 1-{4-[3-chloro-4-(6-chloro-1,3-benzoxazol-2-yl)benzoyl]piperazine-1-carbonyl}cyclopropan-1-ol | 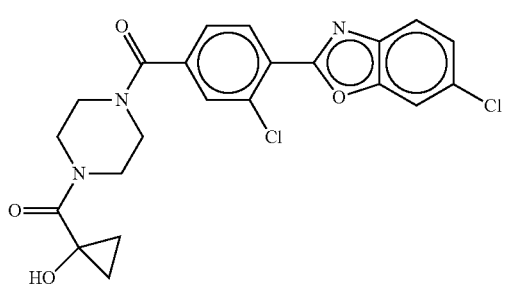 |
| 1-{4-[4-(1,3-dimethyl-1H-indazol-5-yl)-2-fluorobenzoyl]piperazine-1-carbonyl}cyclopropan-1-ol | 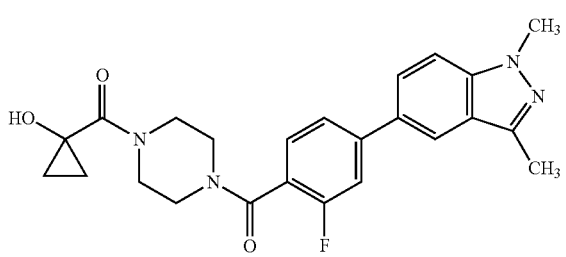 [SMILES: Cc1nn(C)c2ccc(-c3ccc(C(=O)N4CCN(C(=O)C5(O)CC5)CC4)c(F)c3)cc12] |

| IUPAC Name | Compound Structure |
|---|---|
| N-(3-{4-[4-(1-hydroxycyclopropanecarbonyl)piperazine-1-carbonyl]phenyl}phenyl)cyclobutane-sulfonamide | 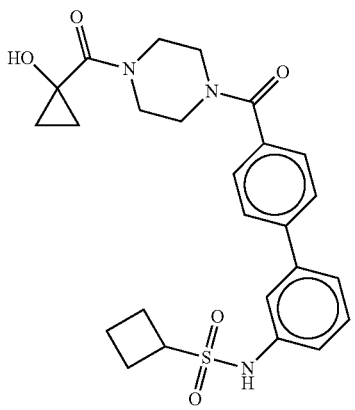 |
| 1-{4-[4-(2,3-dihydro-1H-indol-1-yl)benzoyl]piperazine-1-carbonyl}cyclopropan-1-ol | 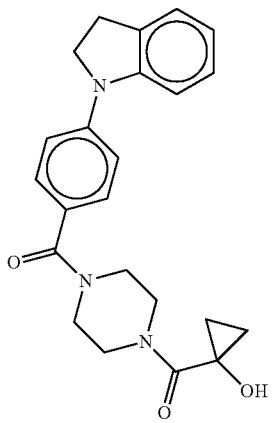 |
| 1-{4-[3-chloro-4-(1,3-dimethyl-1H-indazol-5-yl)benzoyl]piperazine-1-carbonyl}cyclopropan-1-ol | 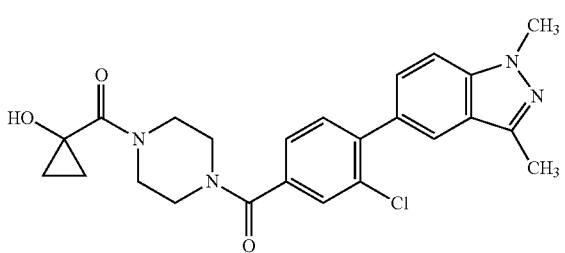 [SMILES: Cc1nn(C)c2ccc(-c3ccc(C(=O)N4CCN(C(=O)C5(O)CC5)CC4)cc3Cl)cc12] |
| 1-[(2S)-2-methyl-4-[4-(1-methyl-1H-1,3-benzodiazol-5-yl)benzoyl]piperazine-1-carbonyl]cyclopropan-1-ol | 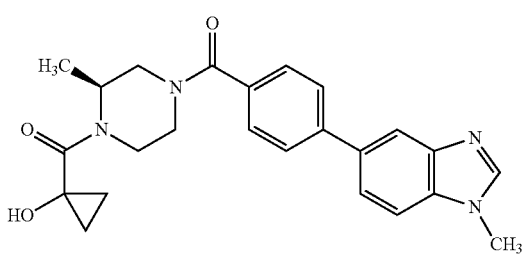 [SMILES: C[C@H]1CN(C(=O)c2ccc(-c3ccc4c(c3)ncn4C)cc2)CCN1C(=O)C1(O)CC1] |

| IUPAC Name | Compound Structure |
|---|---|
| 1-{4-[2,6-difluoro-4-(2-methyl-2H-indazol-6-yl)benzoyl]piperazine-1-carbonyl}cyclopropan-1-ol | 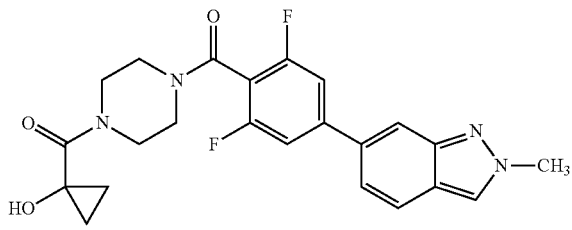 [SMILES: Cn1cc2ccc(-c3cc(F)c(C(=O)N4CCN(C(=O)C5(O)CC5)CC4)c(F)c3)cc2n1] |
| 1-(4-{4-[3-(5-amino-1,2-oxazol-3-yl)phenyl]-2-fluorobenzoyl}piperazine-1-carbonyl)cyclopropan-1-ol | 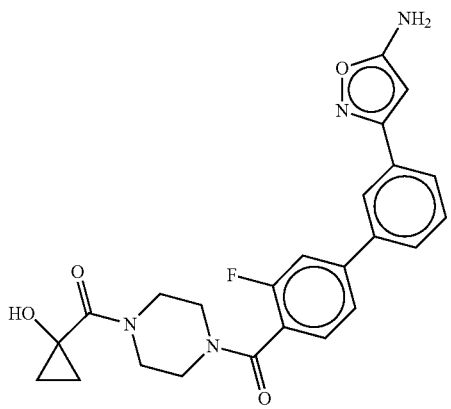 |
| 1-[(2S)-2-methyl-4-[4-(2-methyl-2H-indazol-6-yl)benzoyl]piperazine-1-carbonyl]cyclopropan-1-ol | 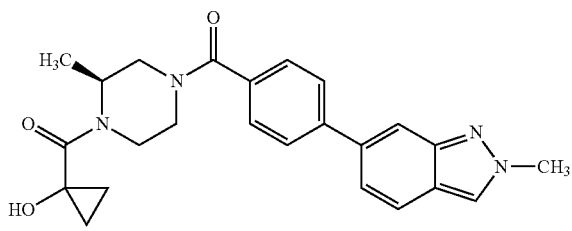 [SMILES: C[C@H]1CN(C(=O)c2ccc(-c3ccc4cn(C)nc4c3)cc2)CCN1C(=O)C1(O)CC1] |
| 1-cyclobutyl-N-(3-{4-[4-(1-hydroxycyclopropanecarbonyl)piperazine-1-carbonyl]phenyl}phenyl)methanesulfonamide | 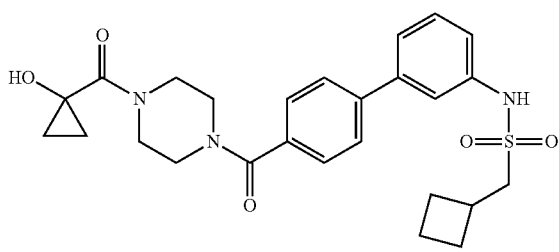 [SMILES: O=C(c1ccc(-c2cccc(NS(=O)(=O)CC3CCC3)c2)cc1)N1CCN(C(=O)C2(O)CC2)CC1] |

-continued
| IUPAC Name | Compound Structure |
|---|---|
| 1-{4-[2-fluoro-4-(7-fluoro-1H-indazol-3-yl)benzoyl]piperazine-1-carbonyl}cyclopropan-1-ol | 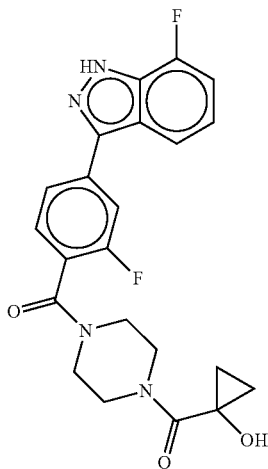 |
| 1-[(2S)-4-[4-(6-chloro-1,3-benzoxazol-2-yl)benzoyl]-2-methylpiperazine-1-carbonyl]cylcopropan-1-ol | 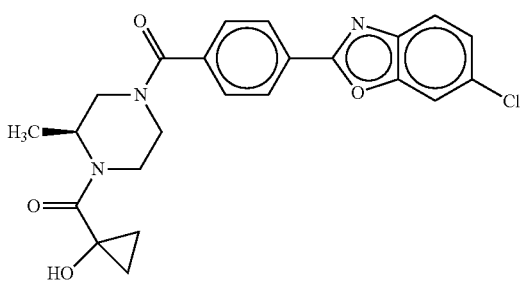 |
| 1-{4-[4-(1H-indol-1-yl)benzoyl]piperazine-1-carbonyl}cyclopropan-1-ol | 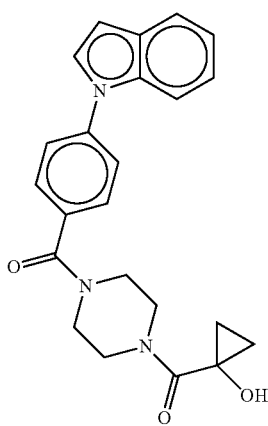 |

| IUPAC Name | Compound Structure |
|---|---|
| 1-{4-[4-(7-fluoro-1H-indazol-3-yl)benzoyl]piperazine-1-carbonyl}cyclopropan-1-ol | 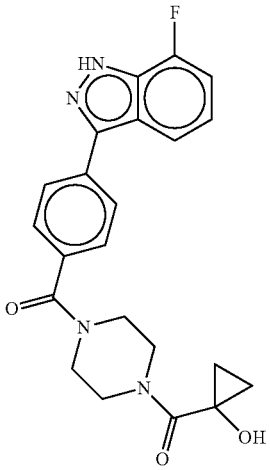 |
| 1-{4-[4-(7-fluoro-1,2,3,4-tetrahydroisoquinolin-2-yl)benzoyl]piperazine-1-carbonyl}cyclopropan-1-ol | 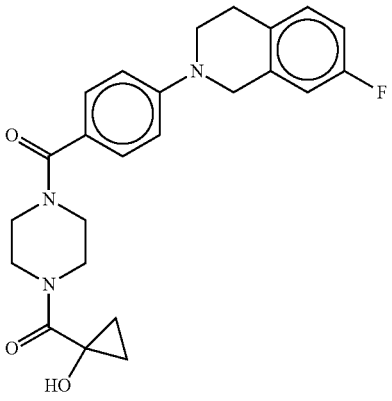 |
| 1-{4-[2-fluoro-4-(2-methyl-2H-indazol-6-yl)benzoyl]piperazine-1-carbonyl}cyclopropan-1-ol | 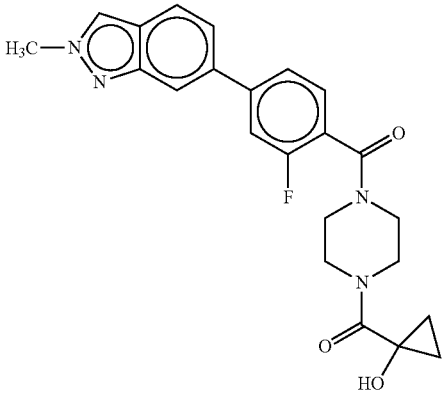 |
| 1-{4-[4-(3-amino-1H-indazol-6-yl)benzoyl]piperazine-1-carbonyl}cyclopropan-1-ol | 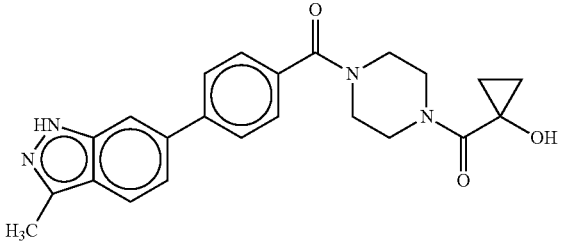 |

| IUPAC Name | Compound Structure |
|---|---|
| 1-{4-[4-(3-amino-1,2-benzoxazol-5-yl)benzoyl]piperazine-1-carbonyl}cyclopropan-1-ol | 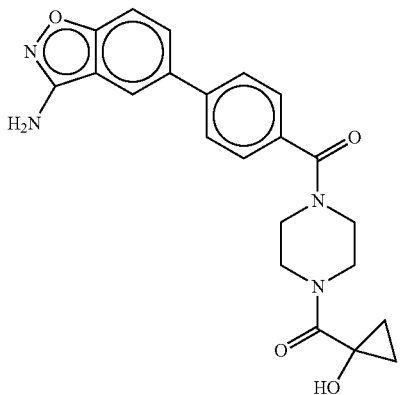 |
| 1-{4-[4-(1,3-dimethyl-1H-indazol-5-yl)-2-fluorobenzoyl]piperazine-1-carbonyl}cyclobutan-1-amine | 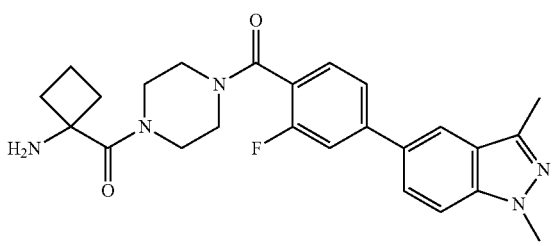 [SMILES: Cc1nn(C)c2ccc(-c3ccc(C(=O)N4CCN(C(=O)C5(N)CCC5)CC4)c(F)c3)cc12] |
| 1-{4-[2-fluoro-4-(3-methyl-1H-indazol-6-yl)benzoyl]piperazine-1-carbonyl}cyclopropan-1-ol | 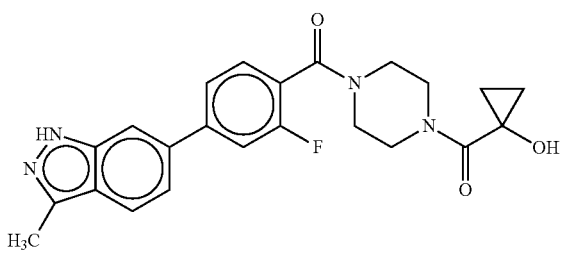 |
| ethyl N-(3-{4-[4-(1-hydroxycyclopropanecarbonyl)piperazine-1-carbonyl]phenyl}phenyl)carbamate | 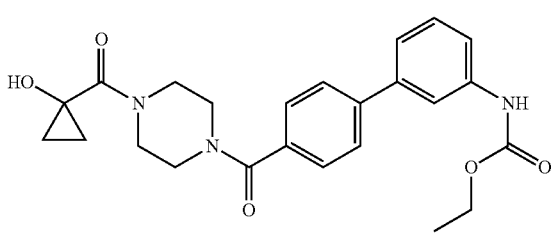 [SMILES: CCOC(=O)Nc1cccc(-c2ccc(C(=O)N3CCN(C(=O)C4(O)CC4)CC3)cc2)c1] |
| 1-{4-[4-(5-chloro-2-methyl-1H-1,3-benzodiazol-7-yl)benzoyl]piperazine-1-carbonyl}cyclopropan-1-ol | 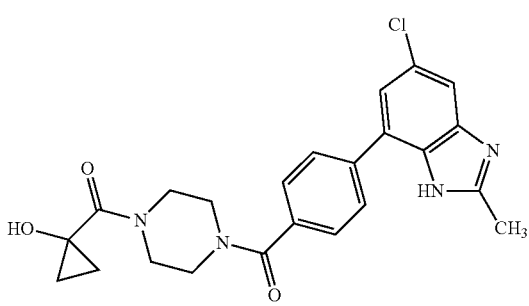 [SMILES: Cc1nc2cc(Cl)cc(-c3ccc(C(=O)N4CCN(C(=O)C5(O)CC5)CC4)cc3)c2[nH]1] |

| IUPAC Name | Compound Structure |
|---|---|
| 1-[4-(4-{1H,2H,3H,4H,9H-pyrido[3,4-b]indol-2-yl}benzoyl)piperazine-1-carbonyl]cyclopropan-1-ol | 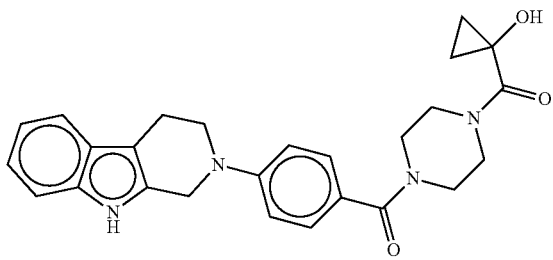 |
| 1-[(2R,6S)-2,6-dimethyl-4-[4-(1-methyl-1H-1,3-benzodiazol-5-yl)benzoyl]piperazine-1-carbonyl]cyclopropan-1-ol | 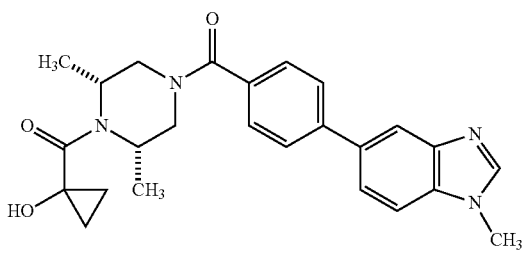 [SMILES: C[C@@H]1CN(C(=O)c2ccc(-c3ccc4c(c3)ncn4C)cc2)C[C@H](C)N1C(=O)C1(O)CC1] |
| 1-[4-(2-chloro-4-{3-chloroimidazo[1,2-a]pyridin-2-yl}benzoyl)piperazine-1-carbonyl]cyclopropan-1-ol | 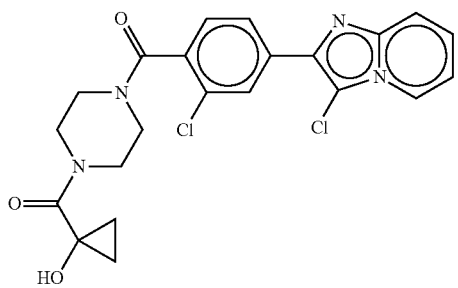 |
| 1-{4-[4-(4-chloro-2-fluorophenyl)benzoyl]-3,3-dimethylpiperazine-1-carbonyl}cyclopropan-1-ol | 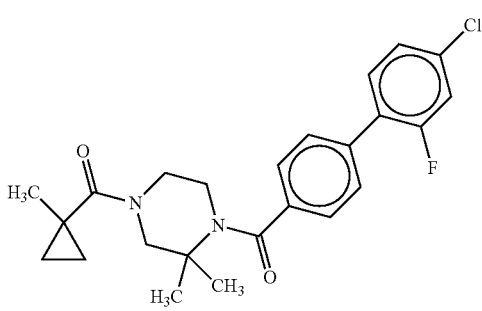 |
| 1-{4-[2-chloro-4-(1-methyl-1H-indazol-6-yl)benzoyl]piperazine-1-carbonyl}cyclopropan-1-ol | 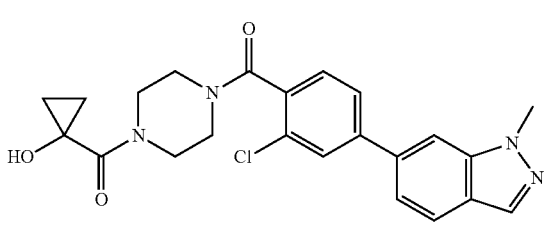 |

| IUPAC Name | Compound Structure |
|---|---|
| 1-[(2S)-4-[4-(4-chloro-2-fluorophenyl)benzoyl]-2-methylpiperazine-1-carbonyl]cyclopropan-1-ol | 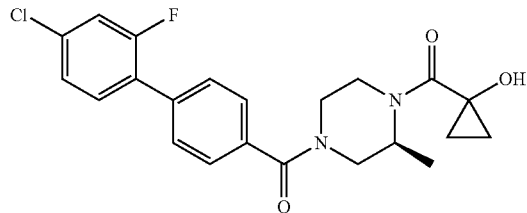 [SMILES: C[C@H]1CN(C(=O)c2ccc(-c3ccc(Cl)cc3F)cc2)CCN1C(=O)C1(O)CC1] |
| 1-[(2S)-4-[4-(1,3-dimethyl-1H-indazol-5-yl)benzoyl]-2-methylpiperazine-1-carbonyl]cyclopropan-1-ol | 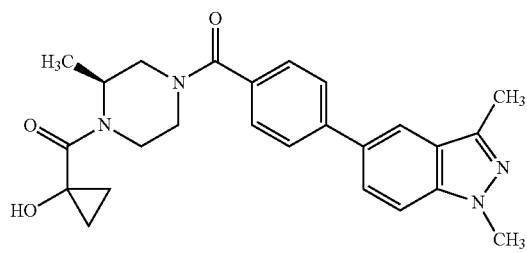 [SMILES: Cc1nn(C)c2ccc(-c3ccc(C(=O)N4CCN(C(=O)C5(O)CC5)[C@@H](C)C4)cc3)cc12] |
| 1-(4-{4-[3-(5-amino-1,2-oxazol-3-yl)phenyl]benzoyl}piperazine-1-carbonyl)cyclopropan-1-ol | 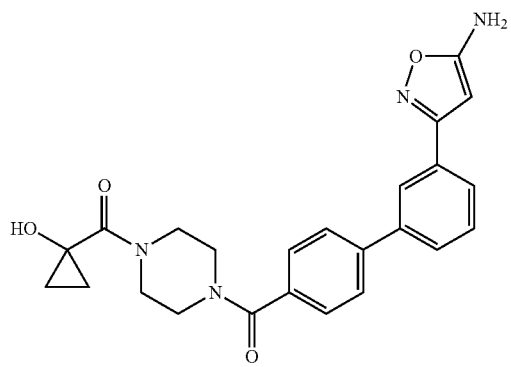 [SMILES: Nc1cc(-c2cccc(-c3ccc(C(=O)N4CCN(C(=O)C5(O)CC5)CC4)cc3)c2)no1] |
| 2-(3-{4-[4-(1-hydroxycyclopropanecarbonyl)piperazine-1-carbonyl]phenyl}phenyl)acetonitrile | 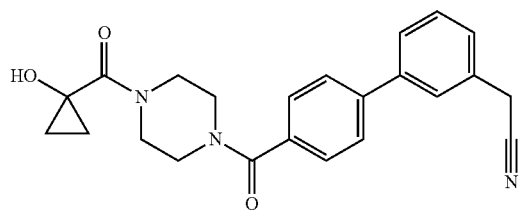 [SMILES: N#CCc1cccc(-c2ccc(C(=O)N3CCN(C(=O)C4(O)CC4)CC3)cc2)c1] |
| N-(3-{[4-(1-hydroxycyclopropanecarbonyl)piperazine-1-carbonyl]phenyl}phenyl)cyclopentanesulfonamide | 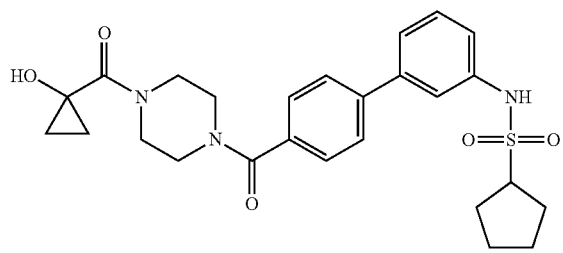 [SMILES: O=C(c1ccc(-c2cccc(NS(=O)(=O)C3CCCC3)c2)cc1)N1CCN(C(=O)C2(O)CC2)CC1] |

-continued

| IUPAC Name | Compound Structure |
|---|---|
| 1-[(3S)-3-methyl-4-[4-(1-methyl-1H-1,3-benzodiazol-5-yl)benzoyl]piperazine-1-carbonyl]cyclopropan-1-ol | 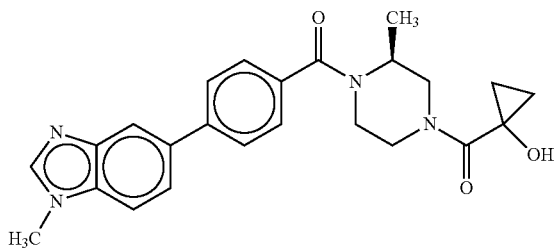 |
| 1-cyclopropyl-N-(3-{4-[4-(1-hydroxycyclopropanecarbonyl)piperazine-1-carbonyl]phenyl}phenyl)methanesulfonamide | 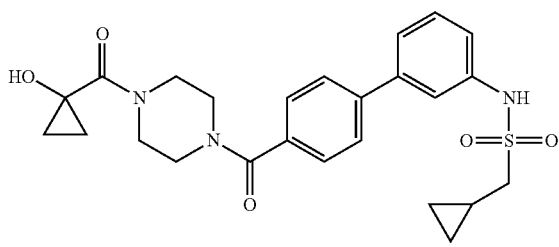 [SMILES: O=C(c1ccc(-c2cccc(NS(=O)(=O)CC3CC3)c2)cc1)N1CCN(C(=O)C2(O)CC2)CC1] |
| 1-{4-[3-chloro-4-(6-fluoro-1,3-benzoxazol-2-yl)benzoyl]piperazine-1-carbonyl}cyclopropan-1-ol | 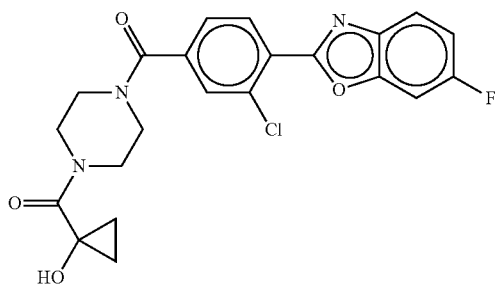 |
| 1-{4-[2-chloro-4-(2-methyl-2H-indazol-6-yl)benzoyl]piperazine-1-carbonyl}cyclopropan-1-ol | 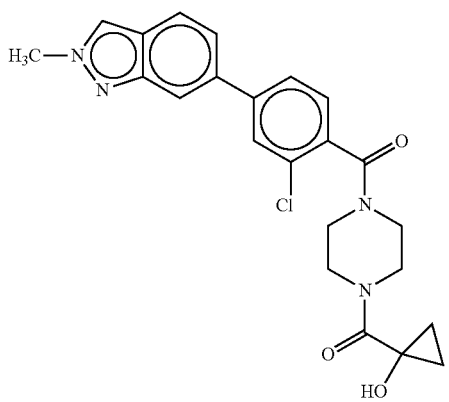 |
| 1-{4-[2,6-difluoro-4-(1-methyl-1H-indazol-6-yl)benzoyl]piperazine-1-carbonyl}cyclopropan-1-ol | 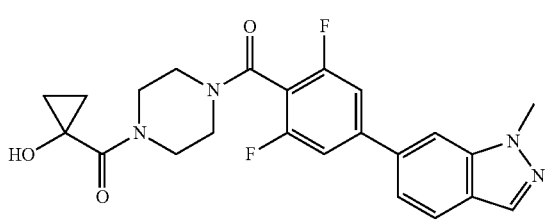 [SMILES: Cn1ncc2ccc(-c3cc(F)c(C(=O)N4CCN(C(=O)C5(O)CC5)CC4)c(F)c3)cc21] |

| IUPAC Name | Compound Structure |
|---|---|
| 1-[(3R)-3-methyl-4-[4-(1-methyl-1H-1,3-benzodiazol-5-yl)benzoyl]piperazine-1-carbonyl]cyclopropan-1-ol | 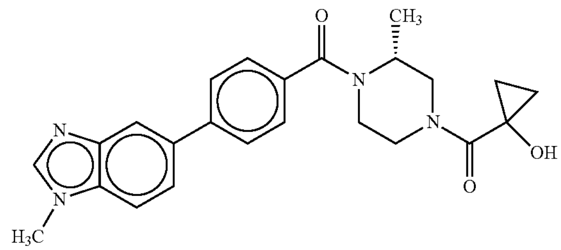 |
| N-(6-{4-[4-(1-hydroxycyclopropanecarbonyl)piperazine-1-carbonyl]phenyl}-1,2-benzoxazol-3-yl)cyclopropanecarboxamide | 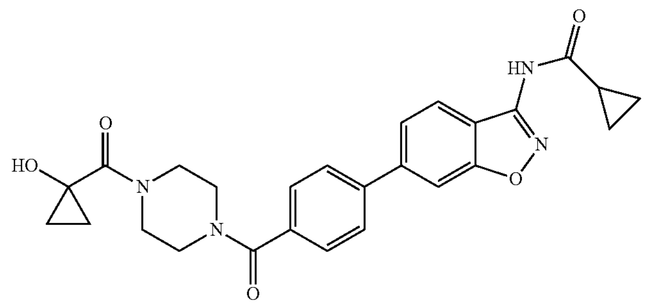 [SMILES: O=C(Nc1noc2cc(-c3ccc(C(=O)N4CCN(C(=O)C5(O)CC5)CC4)cc3)ccc12)C1CC1] |
| 1-[(3R,5S)-3,5-dimethyl-4-[4-(1-methyl-1H-1,3-benzodiazol-5-yl)benzoyl]piperazine-1-carbonyl]cyclopropan-1-ol | 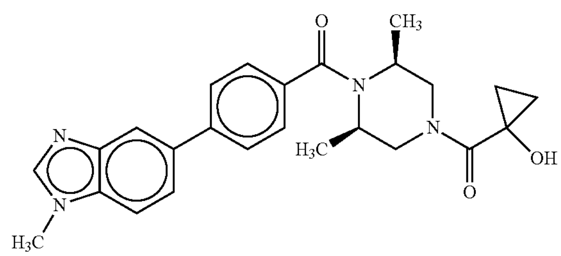 |
| propan-2-yl N-(3-{4-[4-(1-hydroxycyclopropanecarbonyl)piperazine-1-carbonyl]phenyl}phenyl)carbamate | 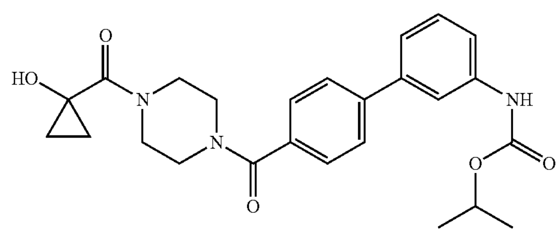 [SMILES: CC(C)OC(=O)Nc1cccc(-c2ccc(C(=O)N3CCN(C(=O)C4(O)CC4)CC3)cc2)c1] |
| 1-{4-[4-(3-amino-1H-indazol-5-yl)benzoyl]piperazine-1-carbonyl}cyclopropan-1-ol | 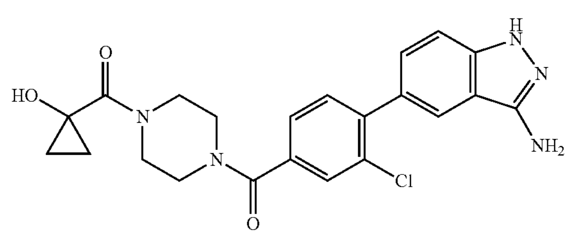 [SMILES: Nc1n[nH]c2ccc(-c3ccc(C(=O)N4CCN(C(=O)C5(O)CC5)CC4)cc3Cl)cc12] |
| 1-[(2R)-2-methyl-4-[4-(1-methyl-1H-1,3-benzodiazol-5-yl)benzoyl]piperazine-1-carbonyl]cyclopropan-1-ol | 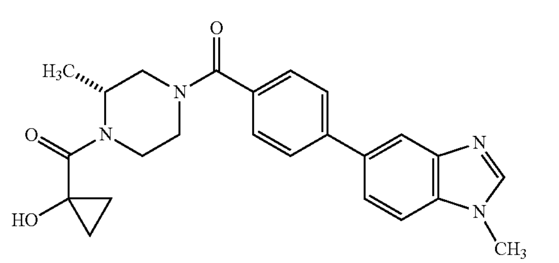 [SMILES: C[C@@H]1CN(C(=O)c2ccc(-c3ccc4c(c3)ncn4C)cc2)CCN1C(=O)C1(O)CC1] |

| IUPAC Name | Compound Structure |
|---|---|
| 3,3-difluoro-N-(3-{4-[4-(1-hydroxycyclopropanecarbonyl)piperazine-1-carbonyl]phenyl}phenyl)cyclobutane-1-carboxamide | 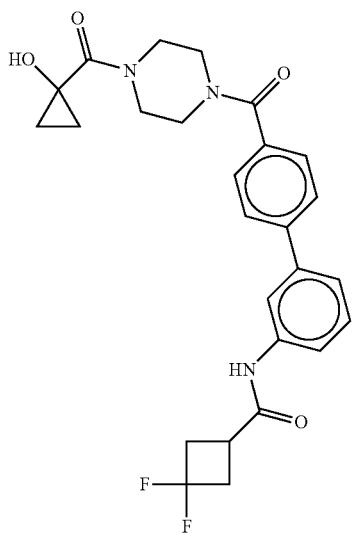 |
| 1-[(2S,6R)-4-[4-(6-fluoro-1,3-benzoxazol-2-yl)benzoyl]-2,6-dimethylpiperazine-1-carbonyl]cyclopropan-1-ol | 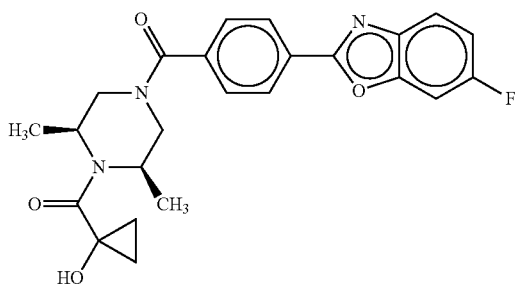 |
| 1-(4-{4-[1-(2-hydroxyethyl)-1H-1,3-benzodiazol-6-yl]benzoyl}piperazine-1-carbonyl)cyclopropan-1-ol | 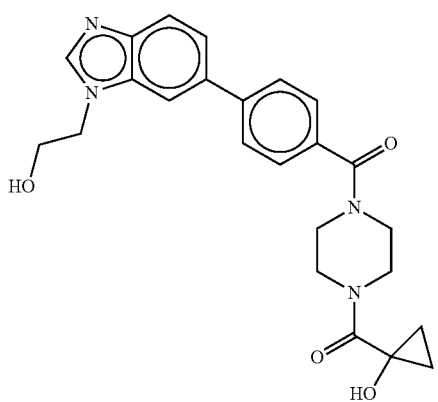 |
| 1-{4-[4-(1H-1,3-benzodiazol-4-yl)-2-chlorobenzoyl]piperazine-1-carbonyl}cyclopropan-1-ol | 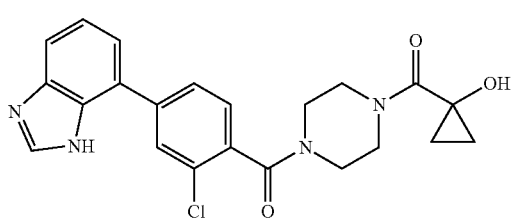 [SMILES: O=C(c1ccc(-c2cccc3nc[nH]c23)cc1Cl)N1CCN(C(=O)C2(O)CC2)CC1] |

| IUPAC Name | Compound Structure |
|---|---|
| 1-{4-[4-(5-fluoro-2,3-dihydro-1H-indol-1-yl)benzoyl]piperazine-1-carbonyl}cyclopropan-1-ol | 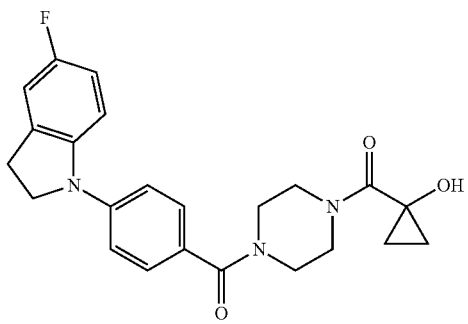 [SMILES: O=C(c1ccc(N2CCc3cc(F)ccc32)cc1)N1CCN(C(=O)C2(O)CC2)CC1] |
| 1-[4-(4-{3-chloroimidazo[1,2-a]pyridin-2-yl}-2-fluorobenzoyl)piperazine-1-carbonyl]cyclopropan-1-ol | 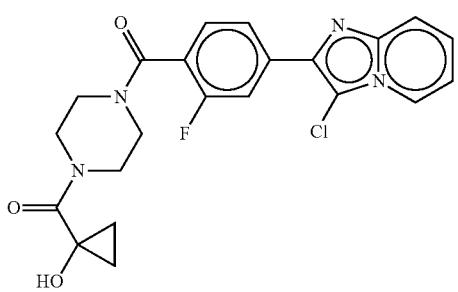 |
| 1-{4-[4-(4-chloro-2-fluorophenyl)-2-fluorobenzoyl]piperazine-1-carbonyl}cyclopropan-1-ol | 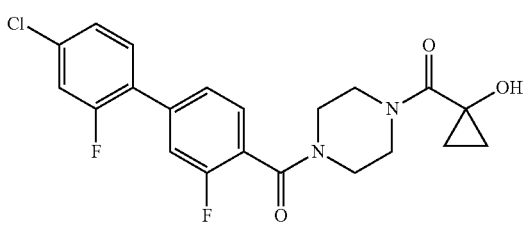 [SMILES: O=C(c1ccc(-c2ccc(Cl)cc2F)cc1F)N1CCN(C(=O)C2(O)CC2)CC1] |
| 1-{4-[3-chloro-4-(4-chloro-2-fluorophenyl)benzoyl]piperazine-1-carbonyl}cyclopropan-1-ol | 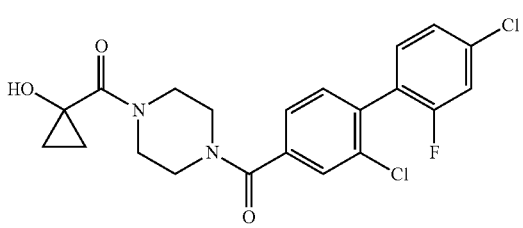 [SMILES: O=C(c1ccc(-c2ccc(Cl)cc2F)c(Cl)c1)N1CCN(C(=O)C2(O)CC2)CC1] |
| 1-{4-[2-chloro-4-(6-chloro-1,3-benzoxazol-2-yl)benzoyl]piperazine-1-carbonyl}cyclopropan-1-ol | 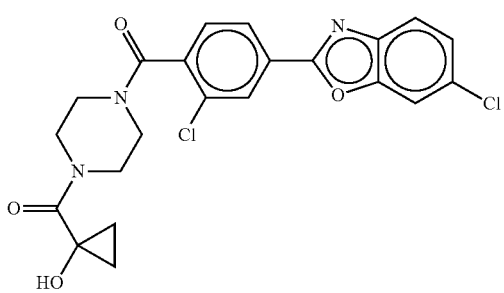 |

| IUPAC Name | Compound Structure |
|---|---|
| 1-{4-[4-(5-fluoro-2,3-dihydro-1H-isoindol-2-yl)benzoyl]piperazine-1-carbonyl}cyclopropan-1-ol | 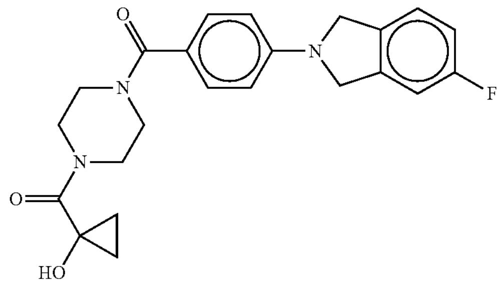 |
| 1-{4-[4-(3-methyl-1H-indazol-4-yl)benzoyl]piperazine-1-carbonyl}cyclopropan-1-ol | 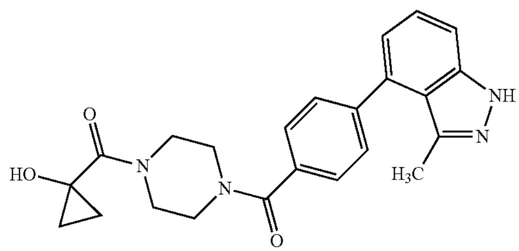 [SMILES: Cc1n[nH]c2cccc(-c3ccc(C(=O)N4CCN(C(=O)C5(O)CC5)CC4)cc3)c12] |
| 1-{4-[4-(6-methoxy-1,3-benzoxazol-2-yl)benzoyl]piperazine-1-carbonyl}cyclopropan-1-ol | 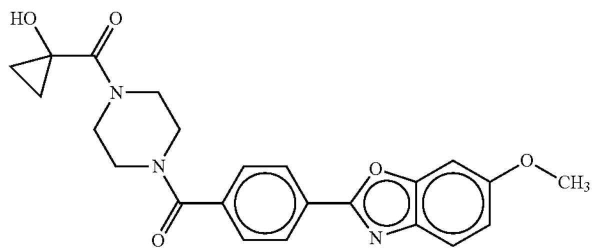 |
| 1-{4-[4-(3-methyl-1H-indazol-7-yl)benzoyl]piperazine-1-carbonyl}cyclopropan-1-ol | 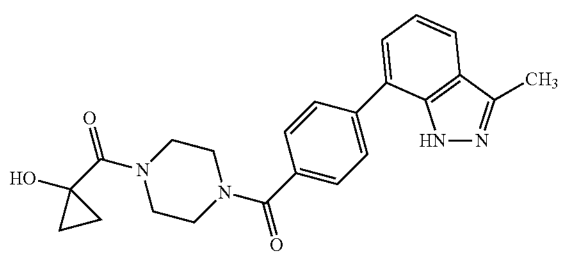 [SMILES: Cc1n[nH]c2c(-c3ccc(C(=O)N4CCN(C(=O)C5(O)CC5)CC4)cc3)cccc12] |
| 1-[(2R)-4-[4-(4-chloro-2-fluorophenyl)benzoyl]-2-methylpiperazine-1-carbonyl]cyclopropan-1-ol | 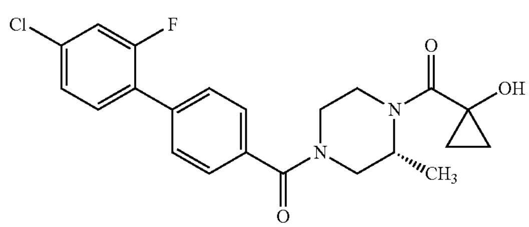 [SMILES: C[C@@H]1CN(C(=O)c2ccc(-c3ccc(Cl)cc3F)cc2)CCN1C(=O)C1(O)CC1] |
| 1-(3-{4-[4-(1-hydroxycyclopropanecarbonyl)piperazine-1-carbonyl]phenyl}phenyl)cyclobutan-1-carbonitrile | 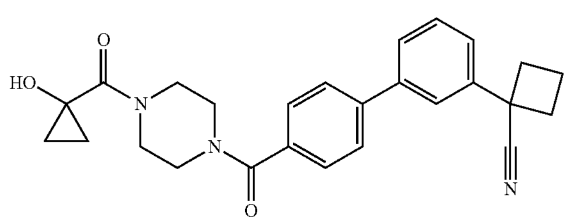 [SMILES: N#CC1(c2cccc(-c3ccc(C(=O)N4CCN(C(=O)C5(O)CC5)CC4)cc3)c2)CCC1] |

-continued

| IUPAC Name | Compound Structure |
|---|---|
| 1-{4-[2-fluoro-4-(6-fluoro-1,3-benzoxazol-2-yl)benzoyl]piperazine-1-carbonyl}cyclopropan-1-ol | 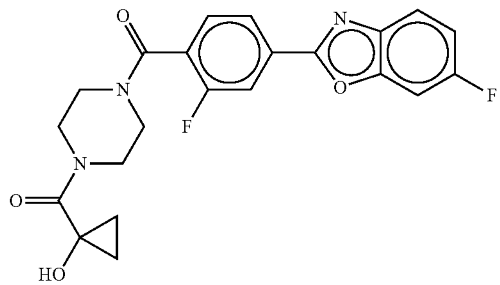 |
| 1-[4-(4-{1H,2H,3H,4H,5H-pyrido[4,3-b]pindol-2-yl}benzoyl)piperazine-1-carbonyl]cyclopropan-1-ol | 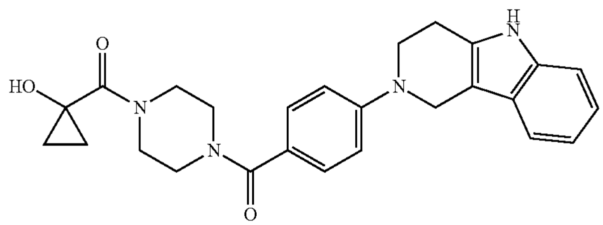 [SMILES: O=C(c1ccc(N2CCc3[nH]c4ccccc4c3C2)cc1)N1CCN(C(=O)C2(O)CC2)CC1] |
| 1-{4-[4-(2-methyl-1H-indol-1-yl)benzoyl]piperazine-1-carbonyl}cyclopropan-1-ol | 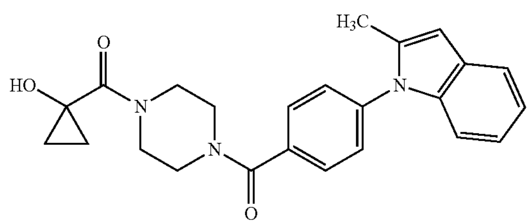 [SMILES: Cc1cc2ccccc2n1-c1ccc(C(=O)N2CCN(C(=O)C3(O)CC3)CC2)cc1] |
| 1-[(2S)-2-methyl-4-[4-(1-methyl-1H-1,3-benzodiazol-5-yl)benzoyl]piperazine-1-carbonyl]cyclopropan-1-amine | 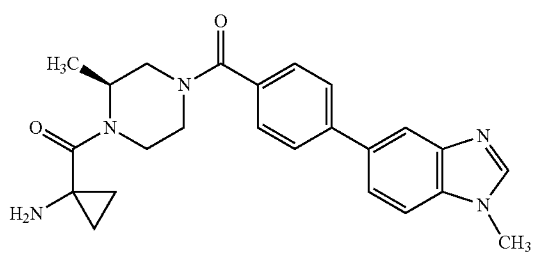 [SMILES: C[C@H]1CN(C(=O)c2ccc(-c3ccc4c(c3)ncn4C)cc2)CCN1C(=O)C1(N)CC1] |
| 1-{4-[3-fluoro-4-(1-methyl-1H-1,3-benzodiazol-5-yl)benzoyl]piperazine-1-carbonyl}cyclopropan-1-ol | 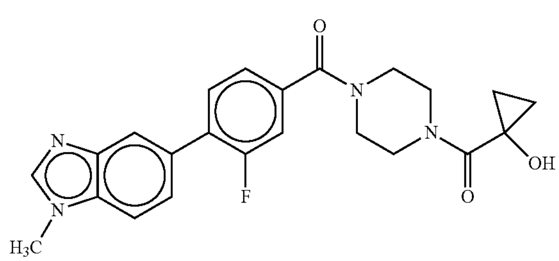 |
| 1-{4-[2-fluoro-4-(1-methyl-1H-1,3-benzodiazol-5-yl)benzoyl]piperazine-1-carbonyl}cylcobutan-1-amine | 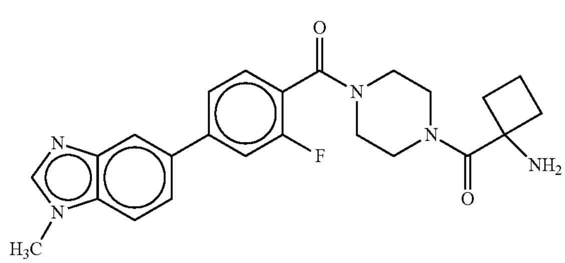 |

-continued

| IUPAC Name | Compound Structure |
|---|---|
| 1-{4-[3-fluoro-4-(1-methyl-1H-indazol-6-yl)benzoyl]piperazine-1-carbonyl}cyclopropan-1-ol | 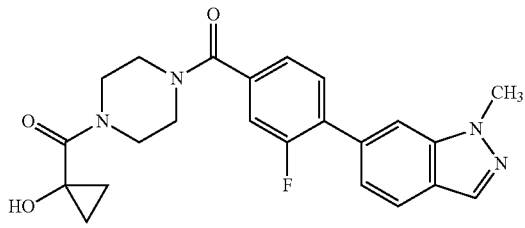 [SMILES: Cn1ncc2ccc(-c3ccc(C(=O)N4CCN(C(=O)C5(O)CC5)CC4)cc3F)cc21] |
| 1-[(2S)-4-[4-(6-fluoro-1,3-benzoxazol-2-yl)benzoyl]-2-methylpiperazine-1-carbonyl]cyclopropan-1-ol | 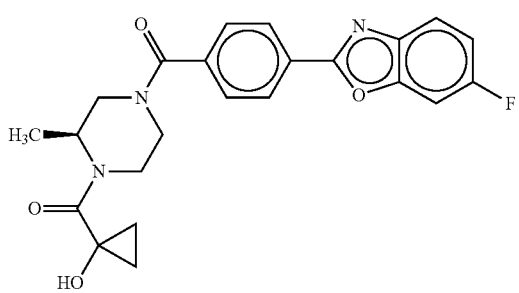 |
| 1-{4-[4-(4-fluoro-2,3-dihydro-1H-isoindol-2-yl)benzoyl]piperazine-1-carbonyl}cyclopropan-1-ol | 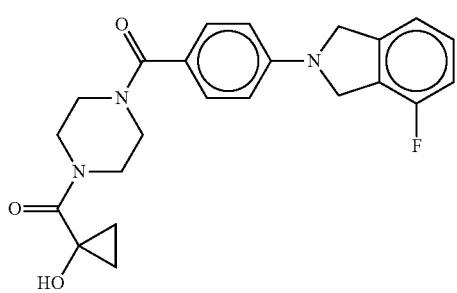 |
| 1-(4-{3-chloro-4-[3-(cyclopropanesulfonyl)phenyl]benzoyl}piperazine-1-carbonyl)cylcopropan-1-ol | 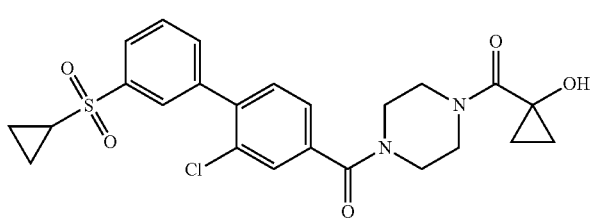 [SMILES: O=C(c1ccc(-c2cccc(S(=O)(=O)C3CC3)c2)c(Cl)c1)N1CCN(C(=O)C2(O)CC2)CC1] |
| 1-{4-[4-(7-fluoro-2,3-dihydro-1H-indol-1-yl)benzoyl]piperazine-1-carbonyl}cyclopropan-1-ol | 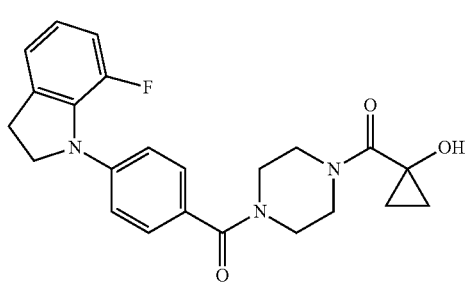 [SMILES: O=C(c1ccc(N2CCc3cccc(F)c32)cc1)N1CCN(C(=O)C2(O)CC2)CC1] |

-continued
| IUPAC Name | Compound Structure |
|---|---|
| 1-{4-[4-(3-cyclopropyl-1H-indazol-6-yl)benzoyl]piperazine-1-carbonyl}cyclopropan-1-ol | 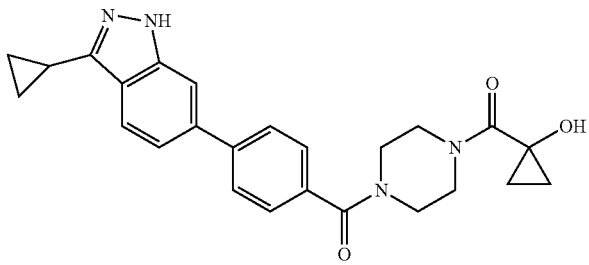 [SMILES: O=C(c1ccc(-c2ccc3c(C4CC4)n[nH]c3c2)cc1)N1CCN(C(=O)C2(O)CC2)CC1] |
| 1-{4-[4-(6-fluoro-1,3-benzoxazol-2-yl)benzoyl]-3,3-dimethylpiperazine-1-carbonyl}cyclopropan-1-ol | 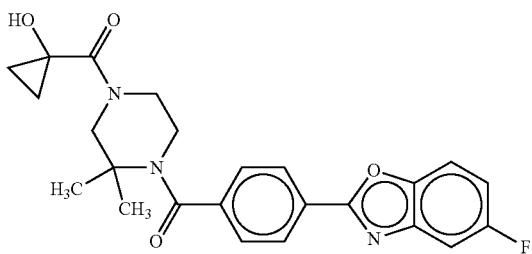 |
| 1-{4-[4-(3-methyl-1H-indazol-1-yl)benzyl]piperazine-1-carbonyl}cyclopropan-1-ol | 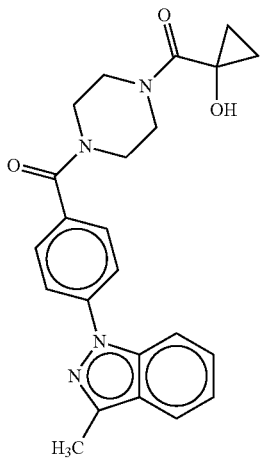 |
| 1-{4-[2-fluoro-4-(3-methyl-1H-indazol-7-yl)benzoyl]piperazine-1-carbonyl}cyclopropan-1-amine | 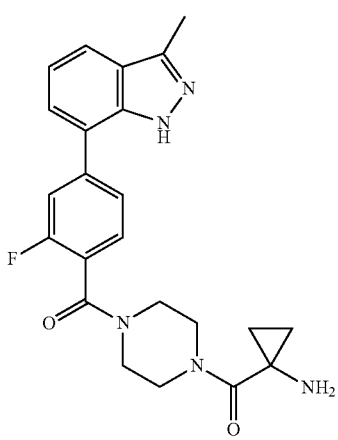 [SMILES: Cc1n[nH]c2c(-c3ccc(C(=O)N4CCN(C(=O)C5(N)CC5)CC4)c(F)c3)cccc12] |

| IUPAC Name | Compound Structure |
| --- | --- |
| 1-{4-[4-(1-methanesulfonyl-1H-indol-6-yl)benzyl]piperazine-1-carbonyl}cyclopropan-1-ol | 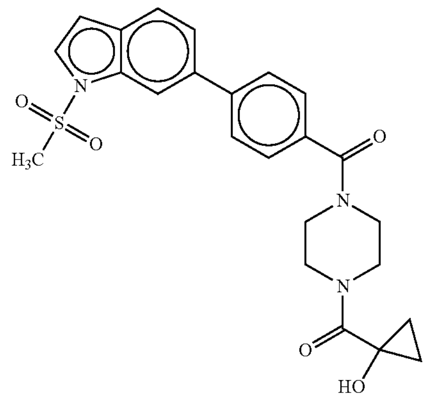 |
| 1-{4-[4-(1-methyl-1H-1,3-benzodiazol-5-yl)benzoyl]piperazine-1-carbonyl}cyclopropan-1-amine | 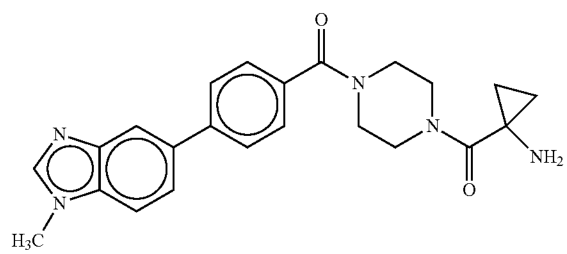 |
| 1-{4-[4-(2-methyl-2,3-dihydro-1H-indol-1-yl)benzoyl]piperazine-1-carbonyl}cyclopropan-1-ol | 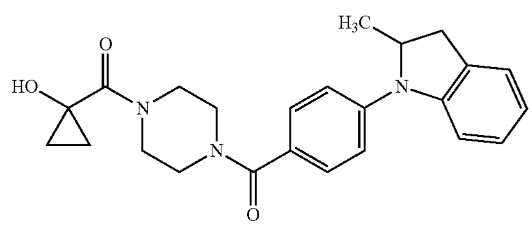 [SMILES: CC1Cc2ccccc2N1c1ccc(C(=O)N2CCN(C(=O)C3(O)CC3)CC2)cc1] |
| 1-{4-[4-(5-fluoro-1H-1,2,3-benzotriazol-6-yl)benzoyl]piperazine-1-carbonyl}cycloproapn-1-ol | 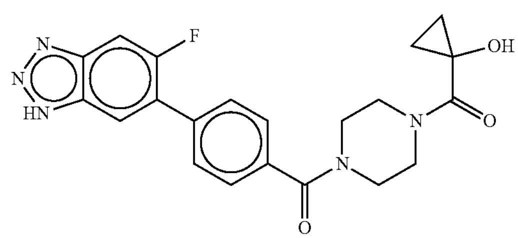 |
| 1-{4-[3-chloro-4-(5-chloro-2-fluorophenyl)benzoyl]piperazine-1-carbonyl}cyclopropan-1-ol | 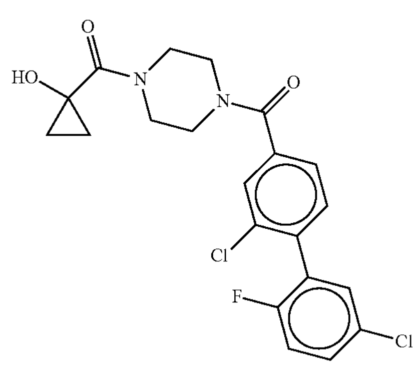 |

| IUPAC Name | Compound Structure |
|---|---|
| 1-[(2S,6R)-4-[4-(4-chloro-2-fluorophenyl)benzoyl]-2,6-dimethylpiperazine-1-carbonyl]cyclopropan-1-ol | 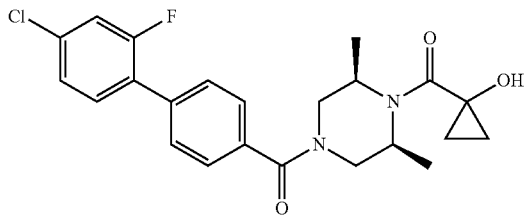 [SMILES: C[C@@H]1CN(C(=O)c2ccc(-c3ccc(Cl)cc3F)cc2)C[C@H](C)N1C(=O)C1(O)CC1] |
| N-(3-{4-[4-(1-hydroxycyclopropanecarbonyl)piperazine-1-carbonyl]phenyl}phenyl)oxane-4-sulfonamide | 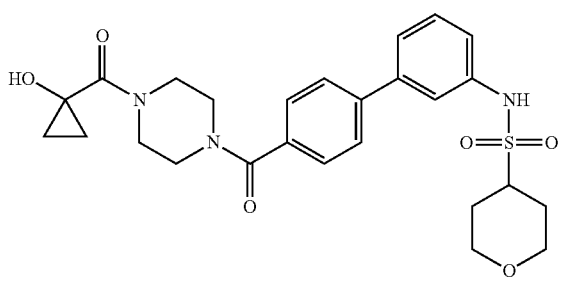 [SMILES: O=C(c1ccc(-c2cccc(NS(=O)(=O)C3CCOCC3)c2)cc1)N1CCN(C(=O)C2(O)CC2)CC1] |
| 1-{4-[4-(1-methyl-1H-indazol-6-yl)benzoyl]piperazine-1-carbonyl}cyclopropan-1-amine | 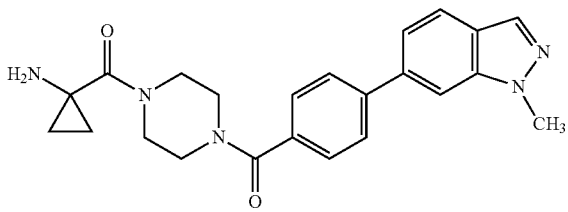 [SMILES: Cn1ncc2ccc(-c3ccc(C(=O)N4CCN(C(=O)C5(N)CC5)CC4)cc3)cc21] |
| 1-{4-[4-(7-methoxy-1,2,3,4-tetrahydroisoquinolin-2-yl)benzoyl]piperazine-1-carbonyl}cyclopropan-1-ol | 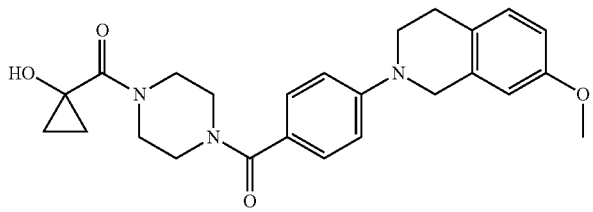 |
| 1-(3-{3-fluoro-4-[4-(1-hydroxycyclopropanecarbonyl)piperazine-1-carbonyl]phenyl}phenyl)cyclopropane-1-carbonitrile | 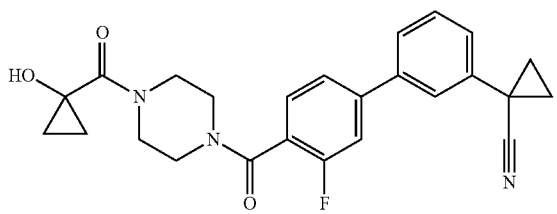 [SMILES: N#CC1(c2cccc(-c3ccc(C(=O)N4CCN(C(=O)C5(O)CC5)CC4)c(F)c3)c2)CC1] |
| 1-{4-[2-fluoro-4-(2-methyl-1H-indol-1-yl)benzoyl]piperazine-1-carobnyl}cyclopropan-1-ol | 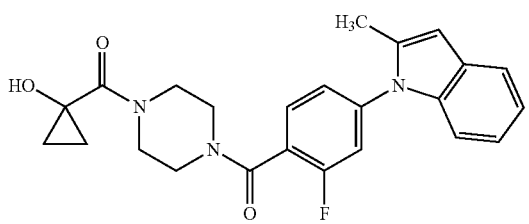 [SMILES: Cc1cc2ccccc2n1-c1ccc(C(=O)N2CCN(C(=O)C3(O)CC3)CC2)c(F)c1] |

| IUPAC Name | Compound Structure |
|---|---|
| 1-{4-[4-(1H-1,3-benzodiazol-1-yl)benzoyl]piperazine-1-carbonyl}cyclopropan-1-ol | 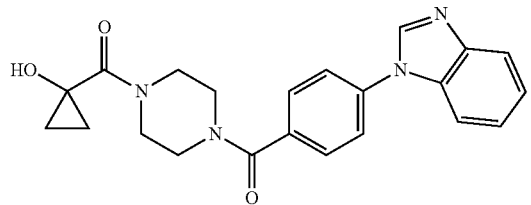 [SMILES: O=C(c1ccc(-n2cnc3ccccc32)cc1)N1CCN(C(=O)C2(O)CC2)CC1] |
| 1-(3-{4-[4-(1-hydroxycyclopropanecarbonyl)piperazine-1-carbonyl]phenyl}phenyl)cyclopropane-1-carbonitrile | 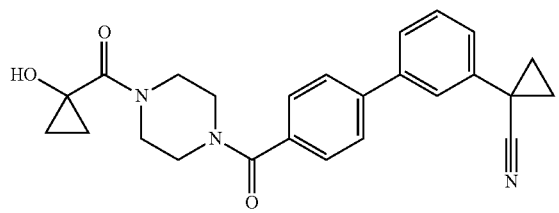 [SMILES: N#CC1(c2cccc(-c3ccc(C(=O)N4CCN(C(=O)C5(O)CC5)CC4)cc3)c2)CC1] |
| 1-{4-[2-fluoro-4-(3-methyl-1H-indazol-1-yl)benzoyl]piperazine-1-carbonyl}cycloproapn-1-ol | 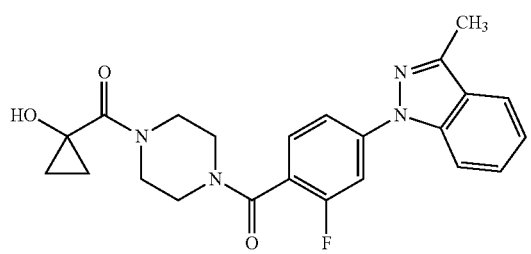 [SMILES: Cc1nn(-c2ccc(C(=O)N3CCN(C(=O)C4(O)CC4)CC3)c(F)c2)c2ccccc12] |
| 1-{4-[2-fluoro-4-(1-methyl-1H-indazol-6-yl)benzoyl]piperazine-1-carbonyl}cyclopropan-1-amine | 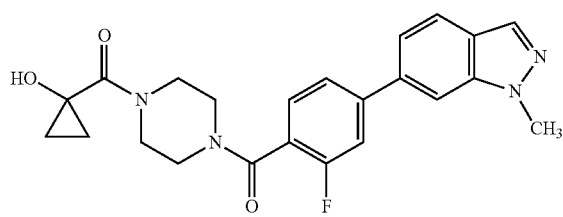 [SMILES: Cn1ncc2ccc(-c3ccc(C(=O)N4CCN(C(=O)C5(O)CC5)CC4)c(F)c3)cc21] |
| 2-{4-[4-(1-hydroxycyclopropanecarbonyl)piperazine-1-carbonyl]phenyl}-1,2,3,4-tetrahydroisoquinoline-7-carbonitrile | 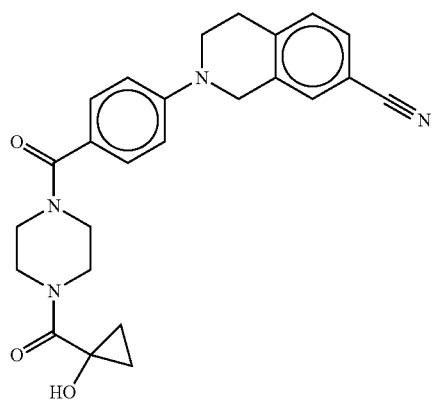 |

| IUPAC Name | Compound Structure |
|---|---|
| 1-(4-{4-[1-(2-hydroxyethyl)-1H-1,3-benzodiazol-5-yl]benzoyl}piperazine-1-carbonyl)cyclopropan-1-ol | 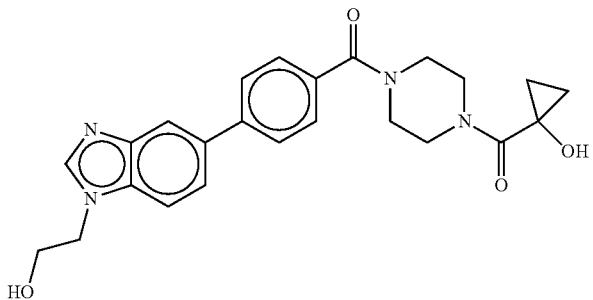 |
| 1-[(2R)-4-[4-(6-fluoro-1,3-benzoxazol-2-yl)benzoyl]-2-methylpiperazine-1-carbonyl]cyclopropan-1-ol | 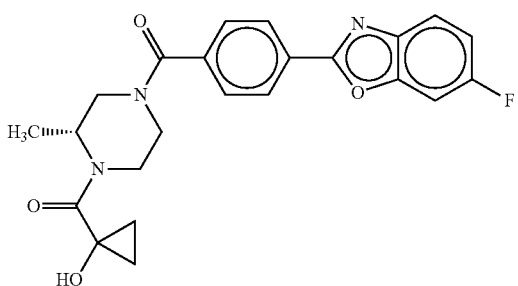 |
| 1-{4-[4-(1H-indazol-1-yl)benzoyl]piperazine-1-carbonyl}cyclopropan-1-ol | 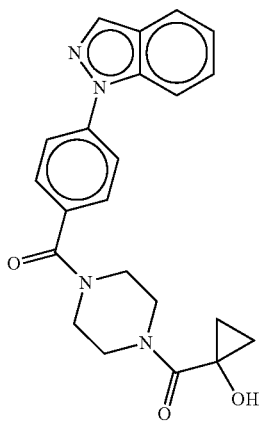 |
| 1-{4-[2-chloro-4-(5-chloro-2-fluorophenyl)benzoyl]piperazine-1-carbonyl}cyclopropan-1-ol | 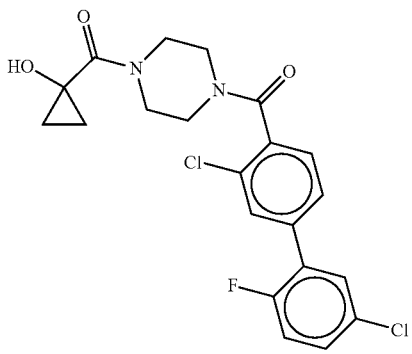 |

| IUPAC Name | Compound Structure |
|---|---|
| 1-{4-[4-(1,3-dimethyl-1H-indazol-5-yl)-3-fluorobenzoyl]piperazine-1-carbonyl}cyclopropan-1-ol | 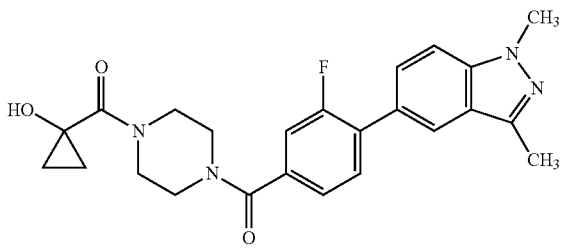 [SMILES: Cc1nn(C)c2ccc(-c3ccc(C(=O)N4CCN(C(=O)C5(O)CC5)CC4)cc3F)cc12] |
| 1-{4-[4-(4-chloro-2-fluorophenyl)benzoyl]-4,7-diazaspiro[2,5]octane-7-carbonyl}cyclopropan-1-ol | 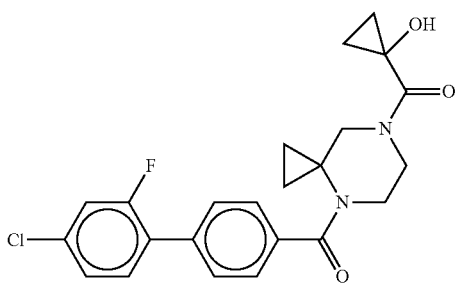 |
| 1-{4-[2-fluoro-4-(7-fluoro-1H-indazol-3-yl)benzoyl]piperazine-1-carbonyl}cycloproapn-1-amine | 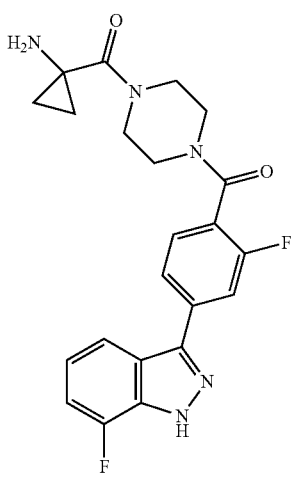 [SMILES: NC1(C(=O)N2CCN(C(=O)c3ccc(-c4n[nH]c5c(F)cccc45)cc3F)CC2)CC1] |
| 6-{1-[4-(1-hydroxycyclopropanecarbonyl)piperazine-1-carbonyl]piperidin-4-yl}naphthalene-2-carbonitrile | 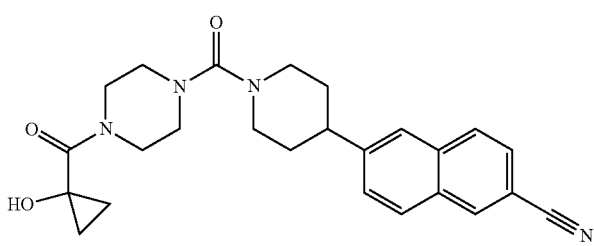 [SMILES: N#Cc1ccc2cc(C3CCN(C(=O)N4CCN(C(=O)C5(O)CC5)CC4)CC3)ccc2c1] |
| 1-(3-{4-[4-(1-hydroxycyclopropanecarbonyl)piperazine-1-carbonyl]phenyl}phenyl)imidazolidin-2-one | 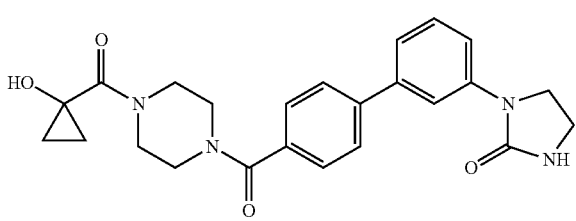 [SMILES: O=C(c1ccc(-c2cccc(N3CCNC3=O)c2)cc1)N1CCN(C(=O)C2(O)CC2)CC1] |

| IUPAC Name | Compound Structure |
|---|---|
| 1-{4-[2,6-difluoro-4-(2-methyl-2H-indazol-6-yl)benzoyl]piperazine-1-carbonyl}cyclopropan-1-amine | 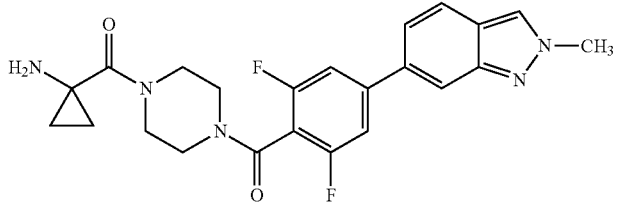 [SMILES: Cn1cc2ccc(-c3cc(F)c(C(=O)N4CCN(C(=O)C5(N)CC5)CC4)c(F)c3)cc2n1] |
| 1,3-dimethyl-5-{4-[4-(oxetane-2-carbonyl)piperazine-1-carbonyl]phenyl}-1H-indazole | 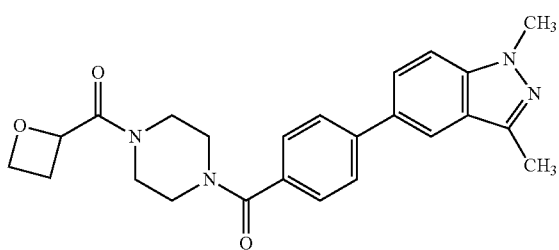 [SMILES: Cc1nn(C)c2ccc(-c3ccc(C(=O)N4CCN(C(=O)C5CCO5)CC4)cc3)cc12] |
| 1-{4-[2-fluoro-4-(2-methyl-2H-indazol-6-yl)benzoyl]piperazine-1-carbonyl}cyclopropan-1-amine | 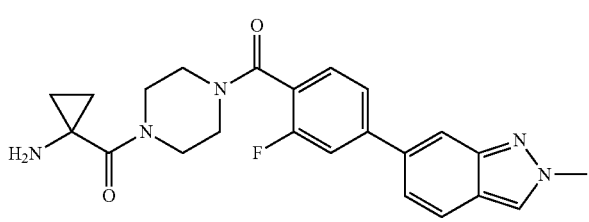 [SMILES: Cn1cc2ccc(-c3ccc(C(=O)N4CCN(C(=O)C5(N)CC5)CC4)c(F)c3)cc2n1] |
| 1-(4-{4-[3-(5-amino-1H-1,2,4-triazol-3-yl)phenyl]benzoyl}piperazine-1-carbonyl)cyclopropan-1-ol | 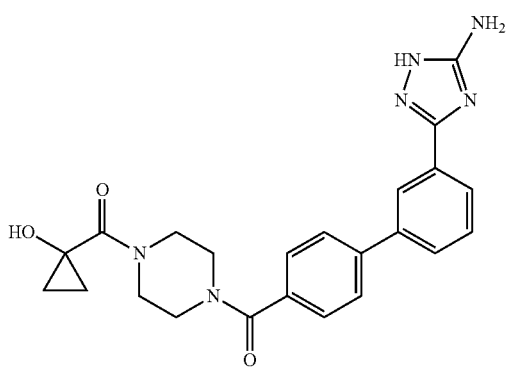 [SMILES: Nc1nc(-c2cccc(-c3ccc(C(=O)N4CCN(C(=O)C5(O)CC5)CC4)cc3)c2)n[nH]1] |
| 1-{4-[4-(1-methyl-1H-1,3-benzodiazol-5-yl)benzoyl]-4,7-diazaspiro[2.5]octane-7-carbonyl}cyclopropan-1-ol | 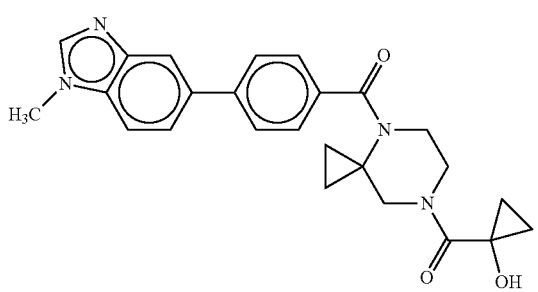 |

-continued

| IUPAC Name | Compound Structure |
|---|---|
| 1-{4-[4-(2-methyl-1H-indol-3-yl)benzoyl]piperazine-1-carbonyl}cyclopropan-1-ol | 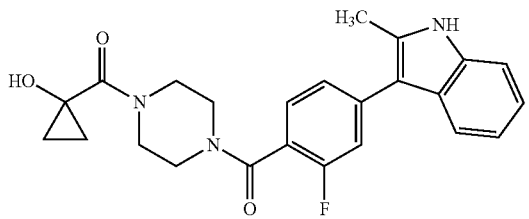 [SMILES: Cc1[nH]c2ccccc2c1-c1ccc(C(=O)N2CCN(C(=O)C3(O)CC3)CC2)c(F)c1] |
| 1-{4-[4-(2-methyl-1H-1,3-benzodiazol-5-yl)benzoyl]piperazine-1-carbonyl}cyclopropan-1-ol | 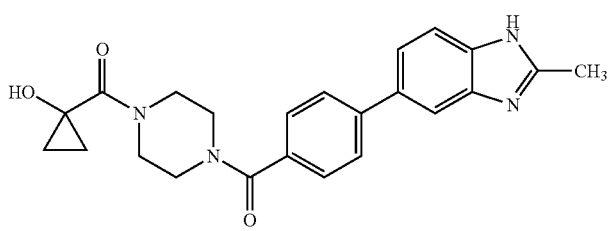 |
| 1-{4-[4-(6-fluoro-1,3-benzoxazol-2-yl)benzoyl]-4,7-diazaspiro[2.5]octane-7-carbonyl}cyclopropan-1-ol | 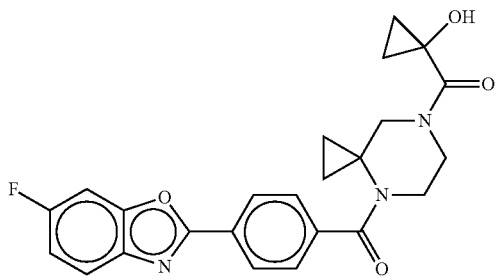 |
| 1-{4-[4-(6-fluoro-1-methyl-1H-1,2,3-benzotriazol-5-yl)benzoyl]piperazine-1-carbonyl}cyclopropan-1-ol | 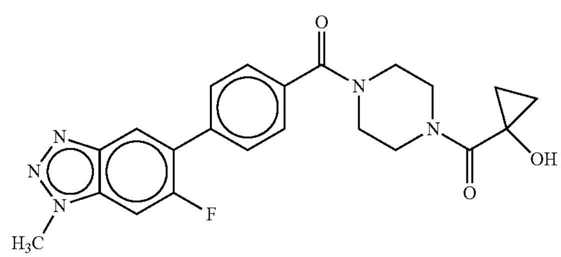 |
| 1-{4-[4-(1-methyl-1H-1,3-benzodiazol-5-yl)benzoyl]piperazine-1-carbonyl}cyclobutan-1-ol | 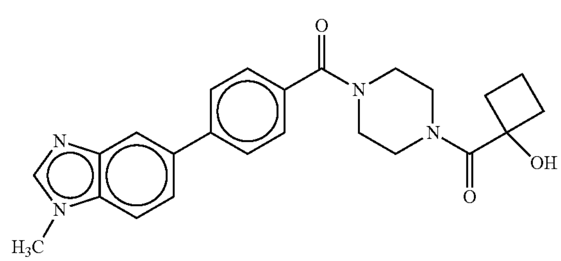 |

| IUPAC Name | Compound Structure |
|---|---|
| 6-chloro-4-{4-[4-(1-hydroxycyclopropanecarbonyl)piperazine-1-carbonyl]phenyl}-2,3-dihydro-1H,13-benzodiazol-2-one | 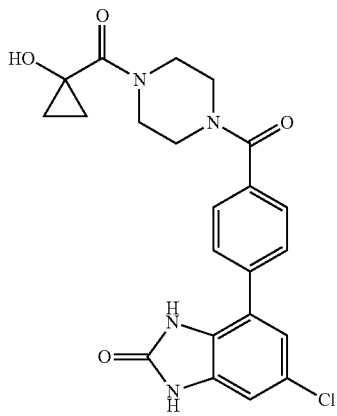 [SMILES: O=C(c1ccc(-c2cc(Cl)cc3[nH]c(=O)[nH]c23)cc1)N1CCN(C(=O)C2(O)CC2)CC1] |
| 1-(4-{4-[2-(hydroxymethyl)-1H-1,3-benzodiazol-5-yl]benzoyl}piperazine-1-carbonyl)cyclopropan-1-ol | 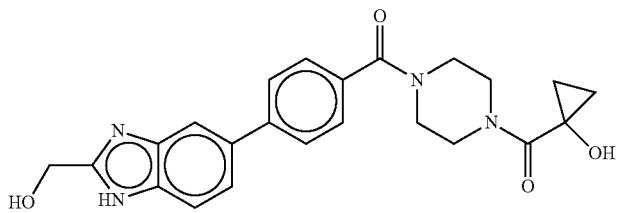 |
| 5-{4-[4-(1-aminocyclopropanecarbonyl)piperazine-1-carbonyl]phenyl}-1,2-benzoxazol-3-amine | 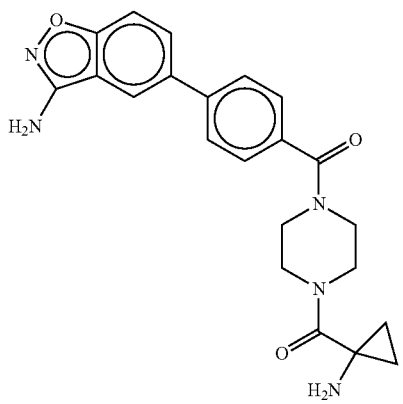 |
| 1-{4-[4-(2-cyclopropyl-2H-indazol-5-yl)benzoyl]piperazine-1-carbonyl}cyclopropan-1-ol | 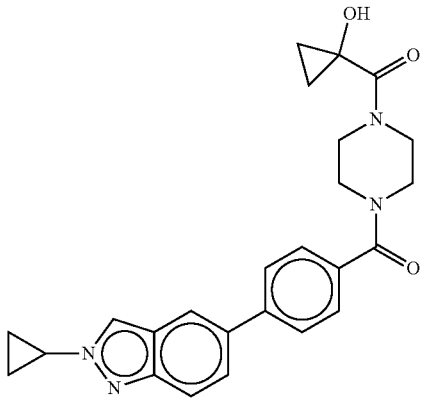 |

| IUPAC Name | Compound Structure |
|---|---|
| 1-{4-[2-fluoro-4-(5,6,7,8-tetrahydro-1,7-naphthyridin-7-yl)benzoyl]piperazine-1-carbonyl}cyclopropan-1-ol | 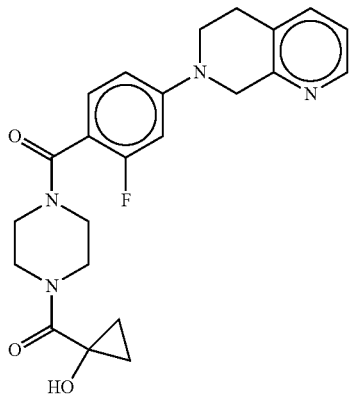 |
| 1-{4-[4-(3-methyl-1,2,3,4-tetrahydroisoquinolin-2-yl)benzoyl]piperazine-1-carbonyl}cyclopropan-1-ol | 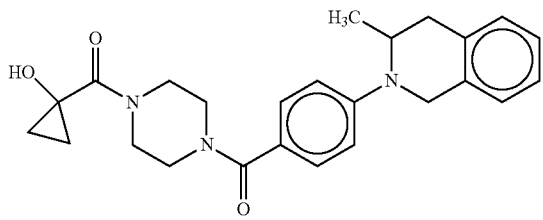 |
| 1-{4-[4-(2,3-dihydro-1H-isoindol-2-yl)benzoyl]piperazine-1-carbonyl}cyclopropan-1-ol | 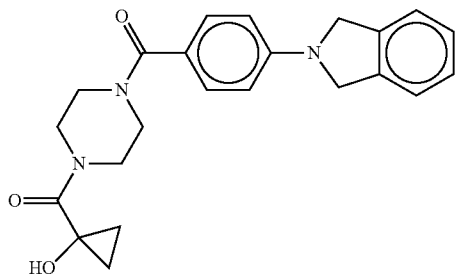 |
| 1-[(3R)-4-[4-(4-chloro-2-fluorophenyl)benzoyl]-3-methylpiperazine-1-carbonyl]cyclopropan-1-ol | 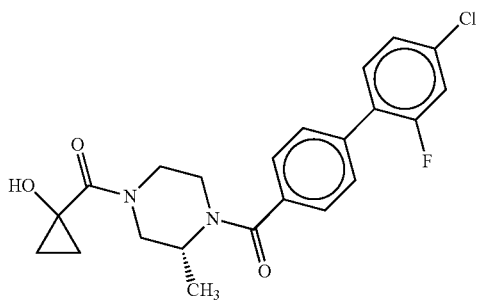 |
| 1-[4-(4-{3-methyl-1H-pyrazolo[3,4-b]pyridin-5-yl}benzoyl)piperazine-1-carbonyl]cyclopropan-1-ol | 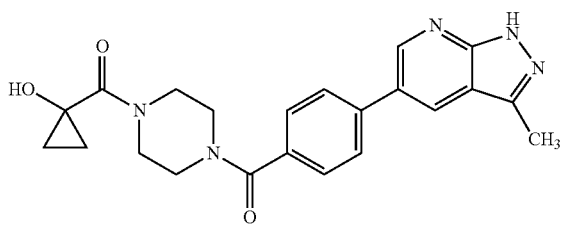 [SMILES: Cc1n[nH]c2ncc(-c3ccc(C(=O)N4CCN(C(=O)C5(O)CC5)CC4)cc3)cc12] |

| IUPAC Name | Compound Structure |
|---|---|
| 1-{4-[4-(3-methyl-1H-indazol-6-yl)benzoyl]piperazine-1-carbonyl}cyclopropan-1-amine | 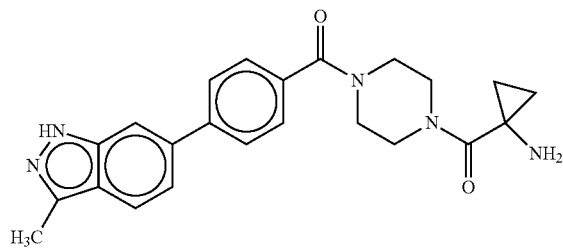 |
| 1-{4-[2-fluoro-4-(1-methyl-1H-1,3-benzodiazol-5-yl)benzoyl]piperazine-1-carbonyl}cyclopropan-1-amine | 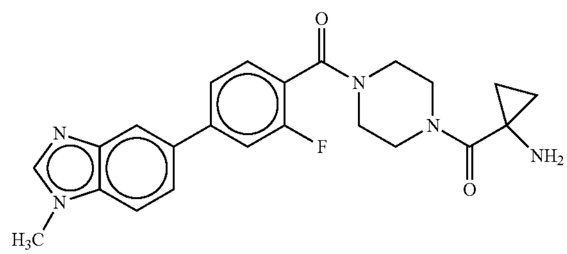 |
| 6-{4-[4-(1-hydroxycyclopropanecarbonyl)piperazine-1-carbonyl]phenyl}-1-methyl-1H-indazol-3-ol | 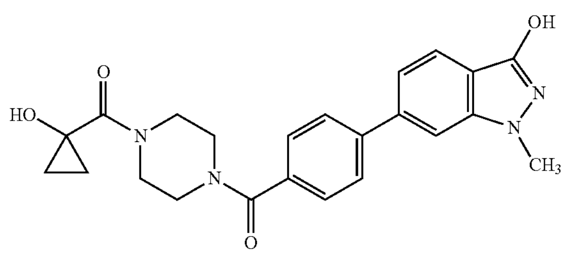 [SMILES: Cn1nc(O)c2ccc(-c3ccc(C(=O)N4CCN(C(=O)C5(O)CC5)CC4)cc3)cc21] |
| 1-{4-[4-(1,2,3,4-tetrahydroquinolin-1-yl)benzoyl]piperazine-1-carbonyl}cyclopropan-1-ol | 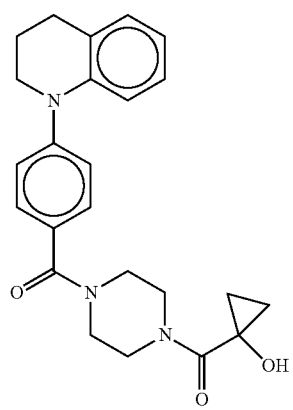 |

-continued
| IUPAC Name | Compound Structure |
|---|---|
| 1-{4-[4-(3-methyl-1H-indazol-7-yl)benzoyl]piperazine-1-carbonyl}cyclopropan-1-amine | 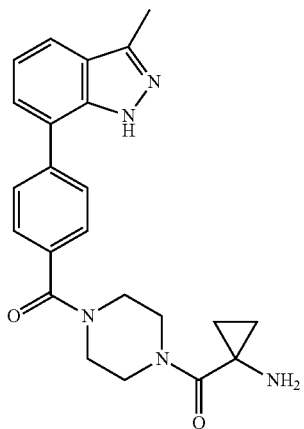 [SMILES: Cc1n[nH]c2c(-c3ccc(C(=O)N4CCN(C(=O)C5(N)CC5)CC4)cc3)cccc12] |
| 1-[4-(4-{4H,5H,6H,7H-thieno[3,2-c]pyridin-5-yl}benzoyl)piperazine-1-carbonyl]cyclopropan-1-ol | 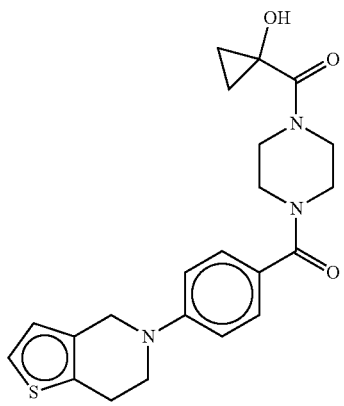 |
| 1-{4-[4-(1-methyl-1H-indazol-6-yl)benzoyl]piperazine-1-carbonyl}cyclobutan-1-amine | 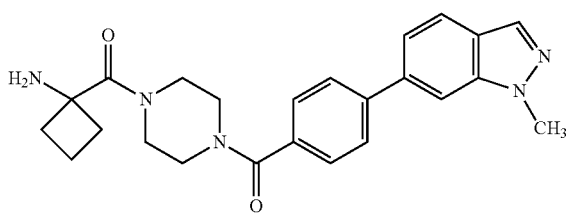 [SMILES: Cn1ncc2ccc(-c3ccc(C(=O)N4CCN(C(=O)C5(N)CCC5)CC4)cc3)cc21] |
| 1-(4-{4-[3-(2-amino-1,3-thiazol-4-yl)phenyl]benzoyl}piperazine-1-carbonyl)cyclopropan-1-ol | 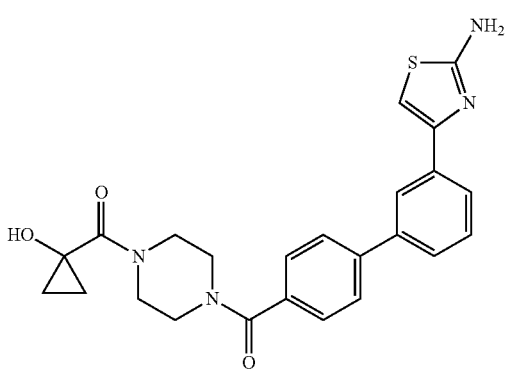 [SMILES: Nc1nc(-c2cccc(-c3ccc(C(=O)N4CCN(C(=O)C5(O)CC5)CC4)cc3)c2)cs1] |

-continued

| IUPAC Name | Compound Structure |
|---|---|
| 1-{4-[4-(1,3-dimethyl-1H-indazol-5-yl)benzoyl]piperazine-1-carbonyl}cyclobutan-1-amine | 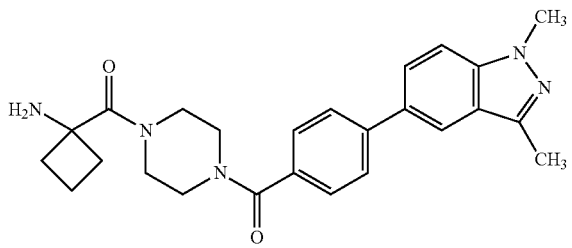 [SMILES: Cc1nn(C)c2ccc(-c3ccc(C(=O)N4CCN(C(=O)C5(N)CCC5)CC4)cc3)cc12] |
| 1-(4-{4-[3-(cyclopropanesulfonyl)phenyl]-2-fluorobenzoyl}piperazine-1-carbonyl)cyclopropan-1-ol | 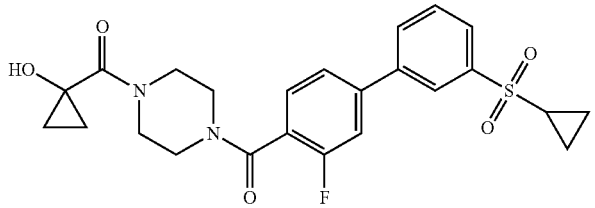 [SMILES: O=C(c1ccc(-c2cccc(S(=O)(=O)C3CC3)c2)cc1F)N1CCN(C(=O)C2(O)CC2)CC1] |
| 1-{4-[4-(6-fluoroquinazolin-2-yl)benzoyl]piperazine-1-carbonyl}cyclopropan-1-ol | 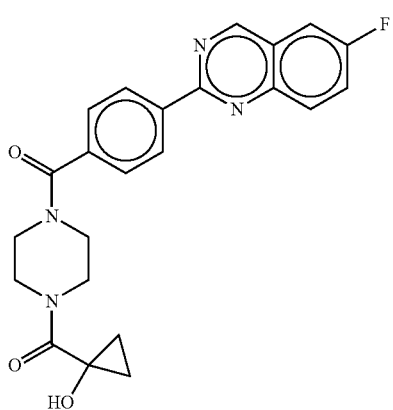 |
| N-(5-{4-[4-(1-hydroxycyclopropanecarbonyl)piperazine-1-carbonyl]phenyl}-1,2-benzoxazol-3-yl)cyclopropanecarboxamide | 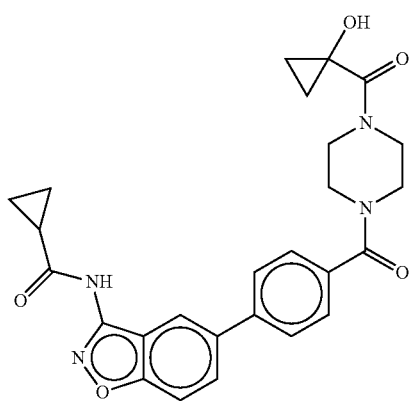 |

-continued
| IUPAC Name | Compound Structure |
|---|---|
| 4-{4-[4-(1-hydroxycyclopropanecarbonyl)piperazine-1-carbonyl]phenyl}-1-methyl-2,3-dihydro-1H-indol-2-one | 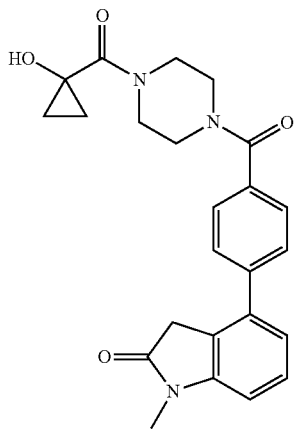 [SMILES: CN1C(=O)Cc2c(-c3ccc(C(=O)N4CCN(C(=O)C5(O)CC5)CC4)cc3)cccc21] |
| 1-[(3R)-4-[4-(6-fluoro-1,3-benzoxazol-2-yl)benzoyl]-3-methylpiperazine-1-carbonyl]cyclopropan-1-ol | 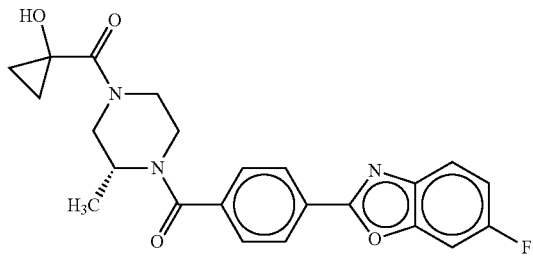 |
| 1-{4-[4-(2-methyl-1H-1,3-benzodiazol-1-yl)benzoyl]piperazine-1-carbonyl}cyclopropan-1-ol | 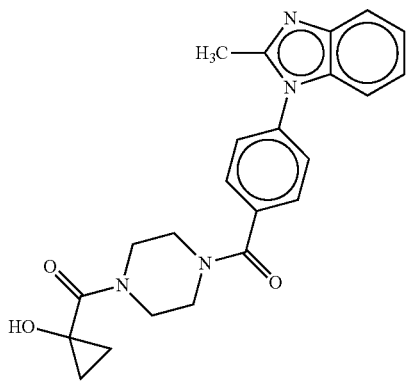 |
| 1-{4-[4-(5-chloro-2-fluorophenyl)benzoyl]piperazine-1-carbonyl}cyclopropan-1-amine | 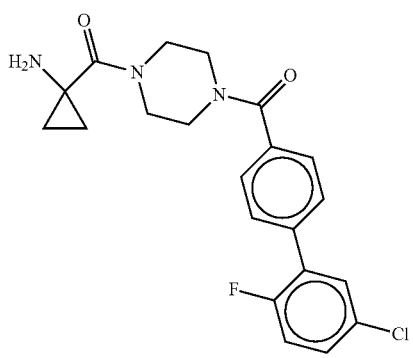 |

| IUPAC Name | Compound Structure |
| --- | --- |
| 1-{4-[3-fluoro-4-(2-methyl-2H-indazol-6-yl)benzoyl]piperazine-1-carbonyl}cyclopropan-1-ol | 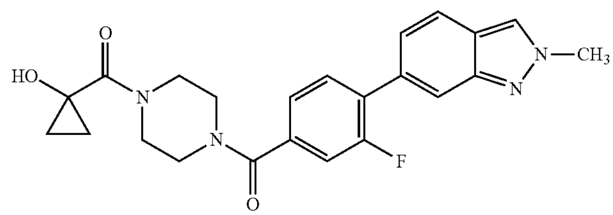 [SMILES: Cn1cc2ccc(-c3ccc(C(=O)N4CCN(C(=O)C5(O)CC5)CC4)cc3F)cc2n1] |
| 3-{4-[4-(1-hydroxycyclopropanecarbonyl)piperazine-1-carbonyl]phenyl}-N-methylbenzamide | 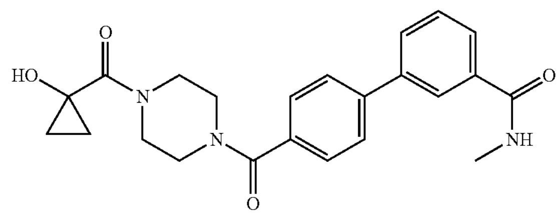 [SMILES: CNC(=O)c1cccc(-c2ccc(C(=O)N3CCN(C(=O)C4(O)CC4)CC3)cc2)c1] |
| 1-(4-{4-[3-(5-amino-1H-pyrazol-3-yl)phenyl]benzoyl}piperazine-1-carbonyl)cyclopropan-1-ol | 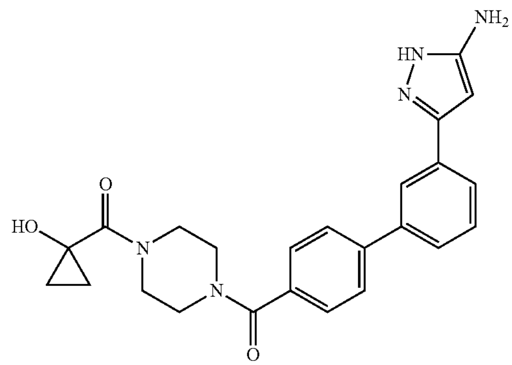 [SMILES: Nc1cc(-c2cccc(-c3ccc(C(=O)N4CCN(C(=O)C5(O)CC5)CC4)cc3)c2)n[nH]1] |
| 1-[(2S)-2-methyl-4-[4-(5,6,7,8-tetrahydro-1,7-naphthyridin-7-yl)benzoyl]piperazine-1-carbonyl]cyclopropan-1-ol | 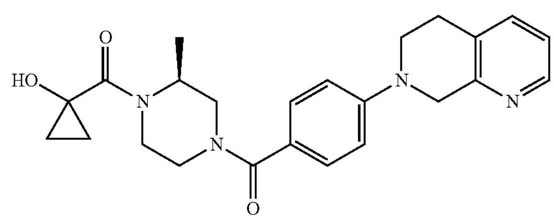 [SMILES: C[C@H]1CN(C(=O)c2ccc(N3CCc4cccnc4C3)cc2)CCN1C(=O)C1(O)CC1] |
| 1-[(3S)-4-[4-(4-chloro-2-fluorophenyl)benzoyl]-3-methylpiperazine-1-carbonyl]cyclopropan-1-ol | 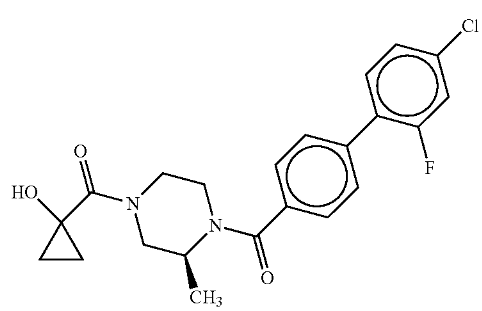 |
| 2-(3-{4-[4-(1-hydroxycyclopropanecarbonyl)piperazine-1-carbonyl]phenyl}phenoxy)-N-methylacetamide | 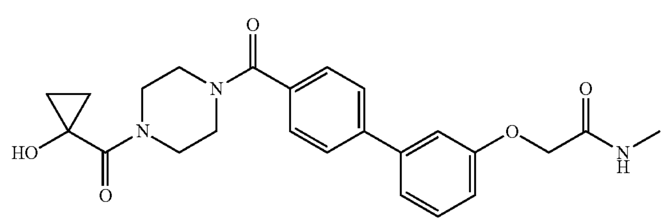 [SMILES: CNC(=O)COc1cccc(-c2ccc(C(=O)N3CCN(C(=O)C4(O)CC4)CC3)cc2)c1] |

| IUPAC Name | Compound Structure |
|---|---|
| 1-{4-[4-(1-cyclopropyl-1H-indazol-5-yl)benzoyl]piperazine-1-carbonyl}cyclopropan-1-ol | 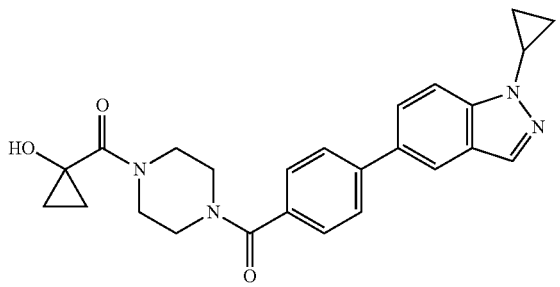 [SMILES: O=C(c1ccc(-c2ccc3c(cnn3C3CC3)c2)cc1)N1CCN(C(=O)C2(O)CC2)CC1] |
| 1-methyl-5-{4-[4-(oxetane-2-carbonyl)piperazine-1-carbonyl]phenyl}-1H-1,3-benzodiazole | 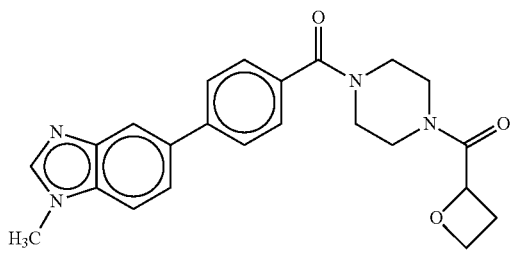 |
| (1-{4-[4-(1-methyl-1H-1,3-benzodiazol-5-yl)benzoyl]piperazine-1-carbonyl}cyclopropyl)methanol | 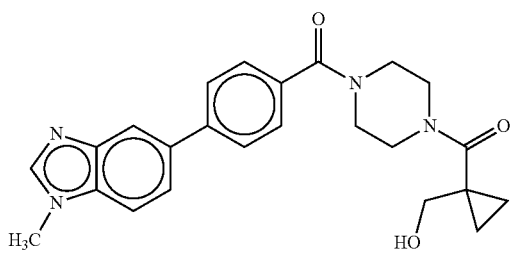 |
| 1-{4-[4-(1-methyl-1H-1,3-benzodiazol-5-yl)benzoyl]piperazine-1-carbonyl}cyclobutan-1-amine | 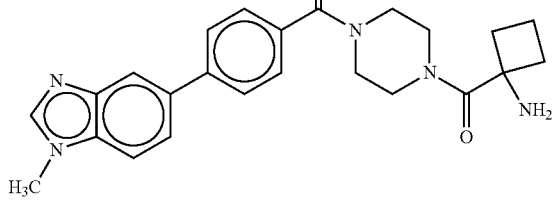 |
| 1-[4-(3-chloro-4-{3-chloroimidazo[1,2-a]pyridin-2-yl}benzoyl)piperazine-1-carbonyl]cyclopropan-1-ol | 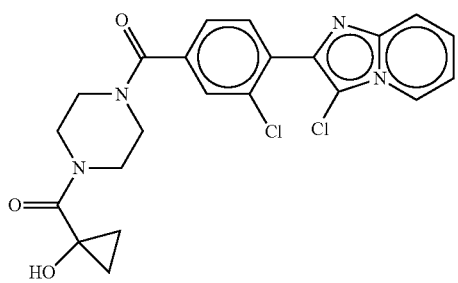 |

| IUPAC Name | Compound Structure |
|---|---|
| 1-[(2R)-2-(hydroxymethyl)-4-[4-(1-methyl-1H-1,3-benzodiazol-5-yl)benzoyl]piperazine-1-carbonyl]cyclopropan-1-ol | 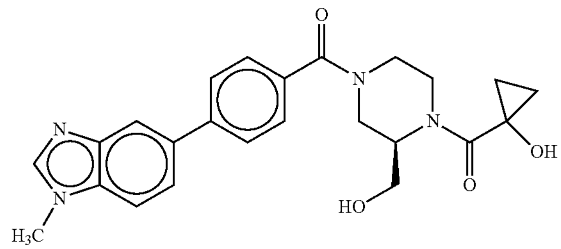 |
| 1-{4-[4-(2,3,4,5-tetrahydro-1H-3-benzazepin-3-yl)benzoyl]piperazine-1-carbonyl}cyclopropan-1-ol | 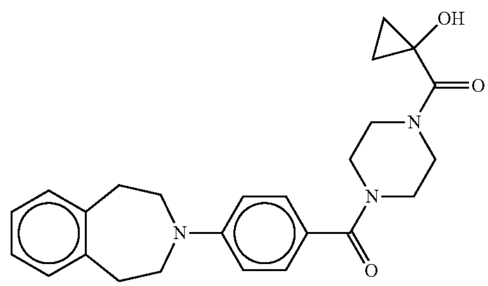 |
| 1-[(2S,6R)-4-[4-(6-fluoro-1,3-benzoxazol-2-yl)benzoyl]-2,6-dimethylpiperazine-1-carbonyl]cyclopropan-1-amine | 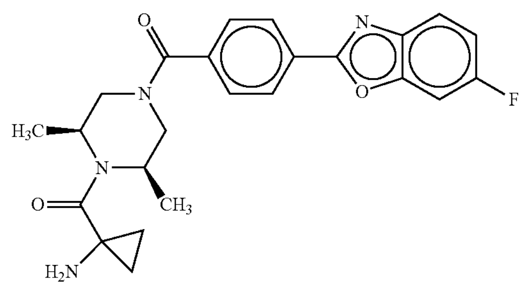 |
| 1-[(2S)-4-[4-(6-fluoro-1,3-benzoxazol-2-yl)benzoyl]-2-methylpiperazine-1-carbonyl]cyclopropan-1-amine | 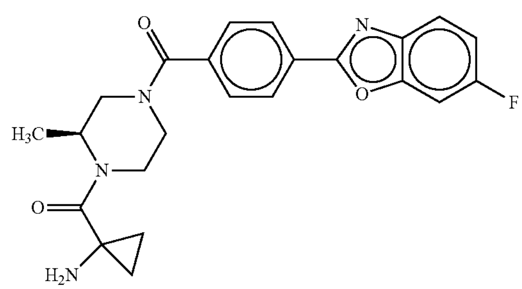 |
| 1-(4-{4-[3-(5-methyl-1,3,4-thiadiazol-2-yl)phenyl]benzoyl}piperazine-1-carbonyl)cyclopropan-1-ol | 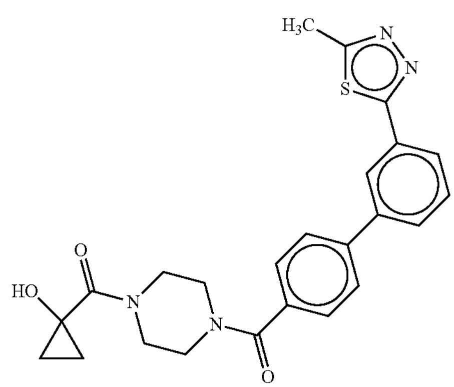 |

| IUPAC Name | Compound Structure |
|---|---|
| 1-{4-[4-(3-methyl-2H-indazol-2-yl)benzoyl]piperazine-1-carbonyl}cyclopropan-1-ol | 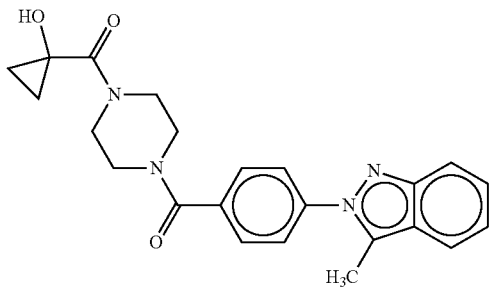 |
| 2-(3-{4-[4-(1-hydroxycyclopropanecarbonyl)piperazine-1-carbonyl]phenyl}phenyl)-2-methylpropanenitrile | 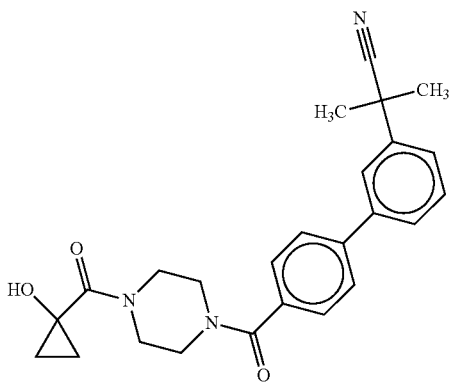 |
| 1-[(2S)-4-{4-[3-(cyclopropanesulfonyl)phenyl]benzoyl}-2-methylpiperazine-1-carbonyl]cyclopropan-1-ol | 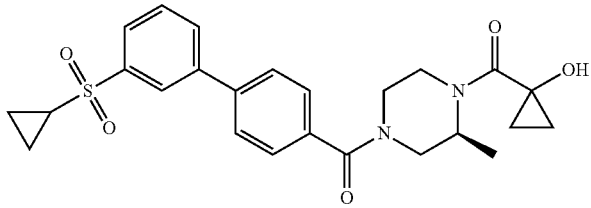 [SMILES: C[C@H]1CN(C(=O)c2ccc(-c3cccc(S(=O)(=O)C4CC4)c3)cc2)CCN1C(=O)C1(O)CC1] |
| 1-(3-{4-[4-(1-hydroxycyclopropanecarbonyl)piperazine-1-carbonyl]phenyl}phenyl)pyrrolidin-2-one | 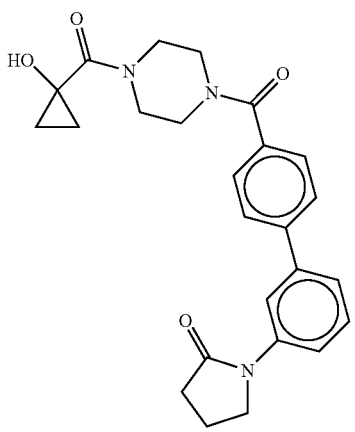 |

-continued

| IUPAC Name | Compound Structure |
|---|---|
| 3-(3-{4-[4-(1-aminocyclopropanecarbonyl)piperazine-1-carbonyl]-3-fluorophenyl}phenyl)-1,2-oxazol-5-amine | 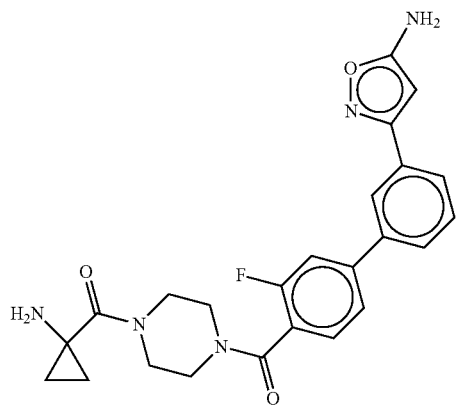 |
| 6-{4-[4-(1-hydroxycyclopropanecarbonyl)piperazine-1-carbonyl]phenyl}-N-methylpyridine-2-carboxamide | 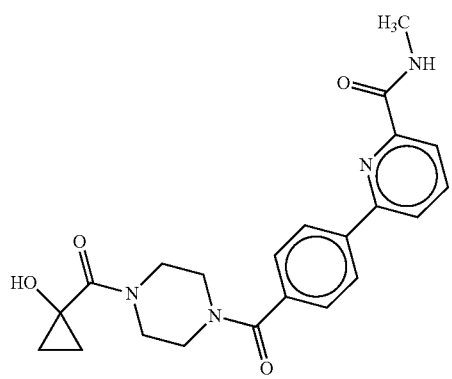 |
| 1-[(3S)-4-[4-(6-fluoro-1,3-benzoxazol-2-yl)benzoyl]-3-methylpiperazine-1-carobnyl]cyclopropan-1-ol | 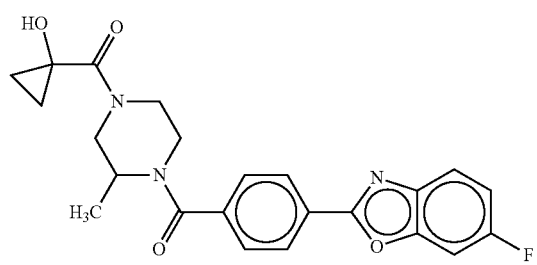 |
| 4-(3-{4-[4-(1-hydroxycyclopropanecarbonyl)piperazine-1-carbonyl]phenyl}phenyl)oxane-4-carbonitrile | 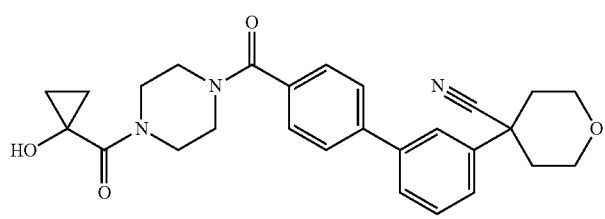 |

-continued
| IUPAC Name | Compound Structure |
|---|---|
| 1-(4-{4-[3-(5-methyl-1,2,4-oxadiazol-3-yl)phenyl]benzoyl}piperazine-1-carbonyl)cyclopropan-1-ol | 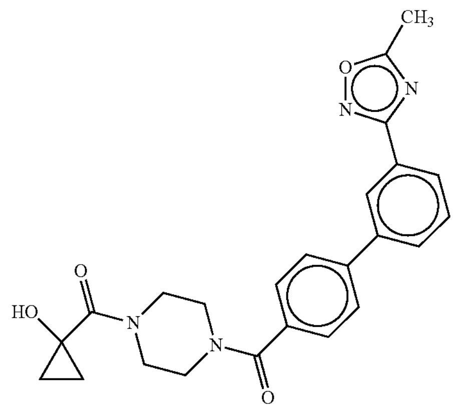 |
| 5-(3-{4-[4-(1-hydroxycyclopropanecarbonyl)piperazine-1-carbonyl]phenyl}phenyl)-5-methylimidazolidine-2,4-dione | 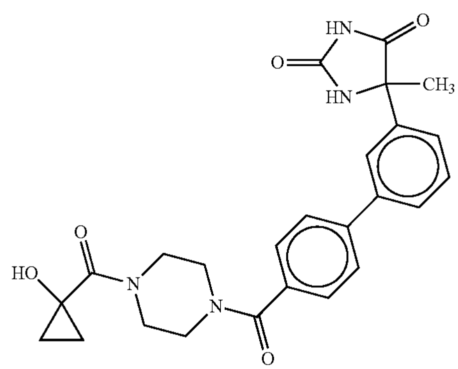 |
| 1-{4-[2-fluoro-4-(2-methyl-1H-indol-1-yl)benzoyl]piperazine-1-carobnyl}cyclopropan-1-amine | 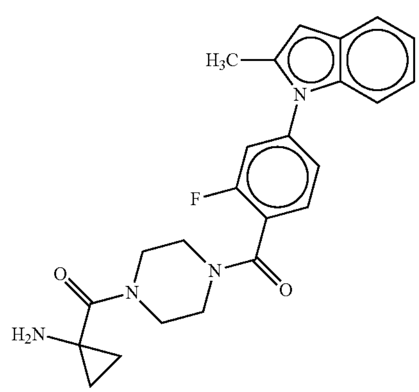 |
| 1-{4-[4-(3-amino-1,2-benzoxazol-6-yl)benzoyl]piperazine-1-carbonyl}cyclopropan-1-ol | 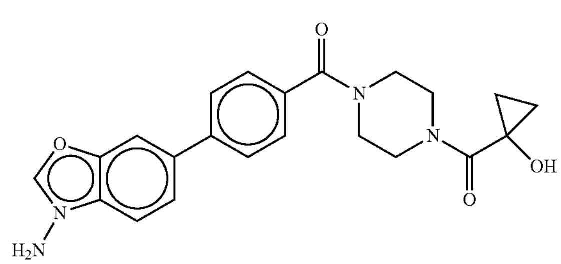 |
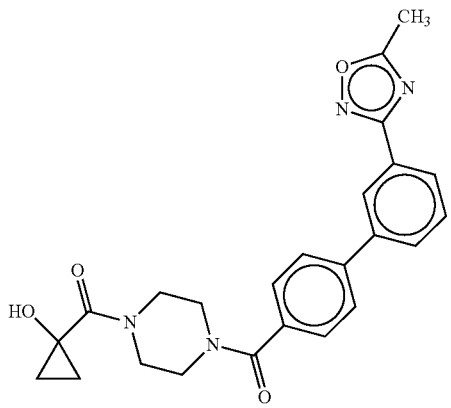

| IUPAC Name | Compound Structure |
|---|---|
| 1-{4-[2-fluoro-4-(2-methyl-2H-indazol-6-yl)benzoyl]piperazine-1-carbonyl}cyclobutan-1-amine | 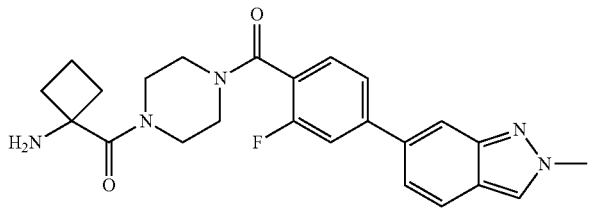 [SMILES: Cn1cc2ccc(-c3ccc(C(=O)N4CCN(C(=O)C5(N)CCC5)CC4)c(F)c3)cc2n1] |
| 2-(3-{4-[4-(1-hydroxycyclopropanecarbonyl)piperazine-1-carbonyl]phenyl}phenyl)-1λ⁶,2-thiazolidine-1,1-dione | 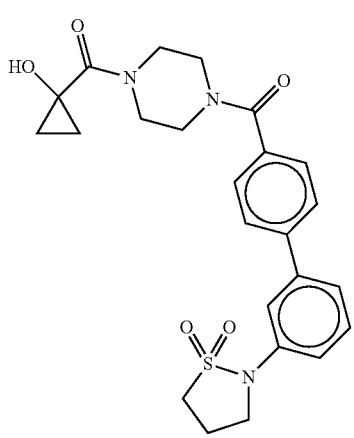 |
| 1-{4-[4-(6-chloro-1,3-benzoxazol-2-yl)-3-fluorobenozyl]piperazine-1-carbonyl}cyclopropan-1-ol | 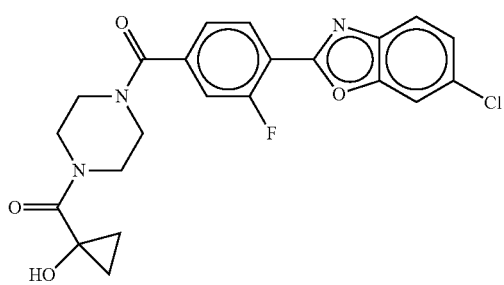 |
| 1-{4-[4-(2,3,4,5-tetrahydro-1H-2-benzazepin-2-yl)benzoyl]piperazine-1-carbonyl}cyclopropan-1-ol | 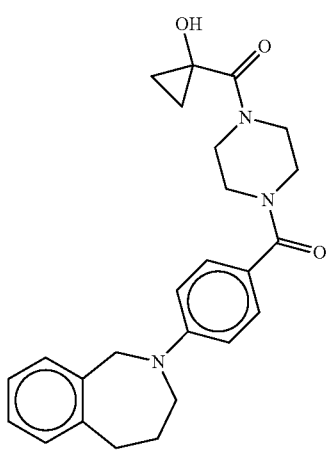 |

| IUPAC Name | Compound Structure |
|---|---|
| 1-[4-(4-{3-chloroimidazo[1,2-a]pyridin-2-yl}-3-fluorobenzyl)piperazine-1-carbonyl]cyclopropan-1-ol | 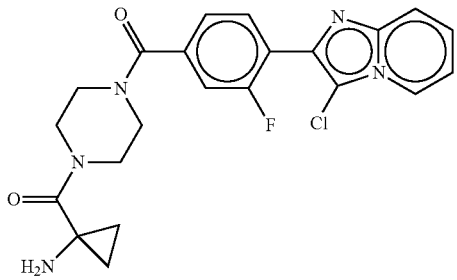 |
| 1-(3-{4-[4-(1-aminocyclopropanecarbonyl)piperazine-1-carbonyl]phenyl}phenyl)cyclopropane-1-carbonitrile | 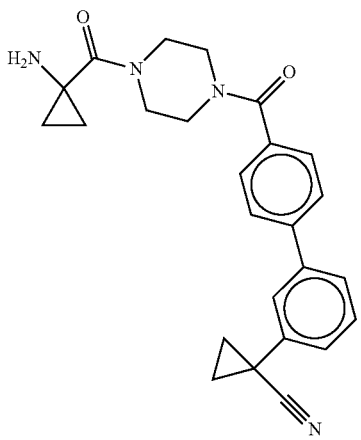 |
| 1-{4-[3-fluoro-4-(6-fluoro-1,3-benzoxazol-2-yl)benzoyl]piperazine-1-carbonyl}cyclopropan-1-ol | 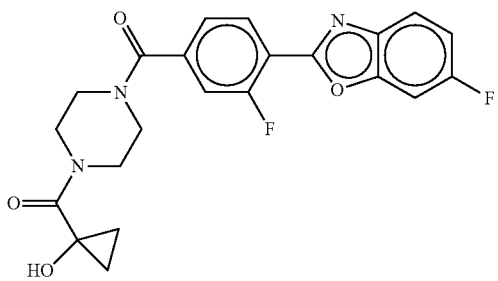 |
| 1-{4-[4-(2-methyl-2H-1,2,3-benzotriazol-5-yl)benzoyl]piperazine-1-carbonyl}cyclopropan-1-ol | 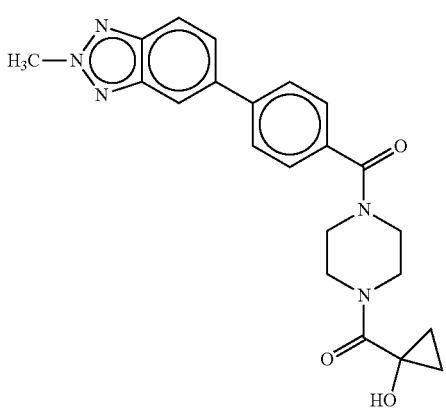 |

| IUPAC Name | Compound Structure |
| --- | --- |
| 1-[(3S)-3-methyl-4-[4-(1-methyl-1H-1,3-benzodiazol-5-yl)benzoyl]piperazine-1-carbonyl]cyclopropan-1-amine | 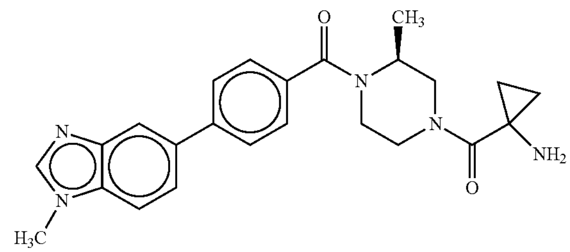 |

38. A pharmaceutical composition comprising therapeutically effective amounts of at least one compound of embodiment 2, or a pharmaceutically acceptable salt thereof, and at least one pharmaceutically acceptable carrier.
39. A method of inhibiting Fatty Acid Synthase ("FASN") in a patient by administering therapeutically effective amounts of at least one compound of embodiment 2, or a pharmaceutically acceptable salt thereof.
40. A method of inhibiting FASN in a patient by administering therapeutically effective amounts of the pharmaceutical composition of embodiment 38.
41. A method of treating, preventing, inhibiting or eliminating a disease or condition in a patient by inhibiting FASN in said patient by administering therapeutically effectives amount of at least one compound of embodiment 2, or a pharmaceutically acceptable salt thereof, wherein said disease or condition is selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, cerebrovascular accident, atherosclerosis, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system, obesity, viral infections, and diabetes.
42. A method of treating a disease or condition in a patient by inhibiting FASN in said patient by administering therapeutically effectives amounts of the composition of embodiment 38, wherein said disease or condition is selected from the group consisting of cancer, ovarian cancer, breast cancer, uterine cancer, colon cancer, cervical cancer, lung cancer, prostate cancer, skin cancer, bladder cancer, pancreatic cancer, leukemia, lymphoma, Hodgkin's disease, viral infections, Human Immunodeficiency Virus, hepatitis virus, herpes virus, herpes simplex, inflammatory disorders, irritable bowel syndrome, inflammatory bowel disease, rheumatoid arthritis, asthma, chronic obstructive pulmonary disease, osteoarthritis, osteoporosis, dermatitis, atoptic dermatitis, psoriasis, systemic lupus erythematosis, multiple sclerosis, psoriatic arthritis, ankylosing spodylitis, graft-versus-host disease, Alzheimer's disease, cerebrovascular accident, atherosclerosis, glomerulonephiritis, metabolic syndrome, non-small cell lung cancer, small cell lung cancer, multiple myeloma, leukemias, lymphomas, squamous cell cancers, kidney cancer, uretral and bladder cancers, cancers of head and neck, cancers of the brain and central nervous system, obesity, viral infections, and diabetes.
43. The method of embodiment 42, wherein said disease is a cancer.
44. The method of embodiment 43, wherein said cancer is selected from the group consisting of leukemia, lymphoma, ovarian cancer, breast cancer, uterine cancer, colon cancer, cervical cancer, lung cancer, prostate cancer, skin cancer, CNS cancer, bladder cancer, pancreatic cancer and Hodgkin's disease.
45. The method of embodiment 42, wherein said disease is a viral infection.
46. The method of embodiment 42, wherein said disease is obesity.
47. The method of embodiment 42, wherein said disease is diabetes.
48. The pharmaceutical composition of embodiment 38, further comprising therapeutically effective amounts of one or more additional therapeutic agents.
49. The pharmaceutical composition of embodiment 48, wherein said one or more additional therapeutic agents are selected from the group consisting of cytotoxic agent, cisplatin, doxorubicin, taxotere, taxol, etoposide, irinotecan, camptostar, topotecan, paclitaxel, docetaxel, the epothilones, tamoxifen, 5-fluorouracil, methoxtrexate, temozolomide, cyclophosphamide, SCH 66336, tipifarnib (Zarnestra®), R115777, L778,123, BMS 214662, Iressa®, Tarceva®, C225, GLEEVEC®, intron*, Peg-Intron*, aromatase combinations, ara-C, adriamycin, cytoxan, gemcitabine, Uracil mustard, Chlormethine, Ifosfamide, Melphalan, Chlorambucil, Pipobroman, Triethylenemelamine, Triethylenethiophosphoramine, Busulfan, Carmustine, Lomustine, Streptozocin, Dacarbazine, Floxuridine, Cytarabine, 6-Mercaptopurine, 6-Thioguanine, Fludarabine phosphate, leucovirin, oxaliplatin (ELOXATIN®), Pentostatine, Vinblastine, Vincristine, Vindesine, Bleomycin, Dactinomycin, Daunorubicin, Epirubicin, Idarubicin, Mithramycin™, Deoxycoformycin, Mitomycin-C, L-Asparaginase, Teniposide 17α-Ethinylestradiol, Diethylstilbestrol, Testosterone, Prednisone, Fluoxymesterone, Dromostanolone propionate, Testolactone, Megestrol acetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Carboplatin, Hydroxyurea, Amsacrine, Procarbazine, Mitotane, Mitoxantrone, Levamisole, Navelbene, Anastrazole, Letrazole, Capecitabine, Reloxafine, Droloxafine, Hexamethylmelamine, Avastin, herceptin, Bexxar, Velcade, Zevalin, Trisenox, Xeloda, Vinorelbine, Porfimer, Erbitux, Liposomal, Thiotepa, Altretamine, Melphalan, Trastuzumab, Lerozole, Fulvestrant, Exemestane, Rituximab, C225, Campath, leucovorin, dexamethasone, bicalutamide, carboplatin, chlorambucil, cisplatin, letrozole, and megestrol, valrubicin, 50. A pharmaceutical composition comprising therapeutically effective amounts of at least one compound of embodiment 37, or a pharmaceutically acceptable salt thereof, and at least one pharmaceutically acceptable carrier.

51. A method of inhibiting Fatty Acid Synthase ("FASN") in a patient by administering therapeutically effective amounts of at least one compound of embodiment 37, or a pharmaceutically acceptable salt thereof.

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound selected from the group consisting of:

| NAME | Structure |
| --- | --- |
| 1-({4-[(4-phenylphenyl)carbonyl]piperazin-1-yl}carbonyl)cyclopropan-1-ol | 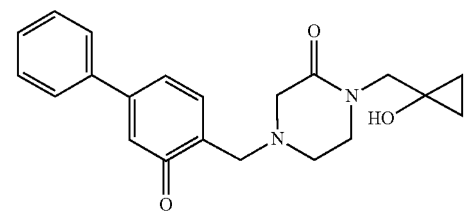 |
| 2-hydroxy-2-methyl-1-{4-[(4-phenylphenyl)carbonyl]piperazin-1-yl}propan-1-one | 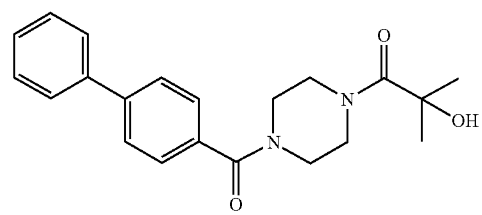 [SMILES: CC(C)(O)C(=O)N1CCN(C(=O)c2ccc(-c3ccccc3)cc2)CC1] |
| 2-hydroxy-1-{4-[(4-phenylphenyl)carbonyl]piperazin-1-yl}ethan-1-one | 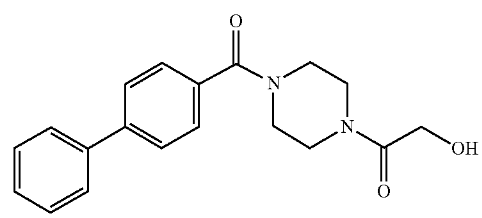 [SMILES: O=C(CO)N1CCN(C(=O)c2ccc(-c3ccccc3)cc2)CC1] |
| 1-({4-[(4-phenylphenyl)carbonyl]piperazin-1-yl}carbonyl)cyclopentan-1-ol | 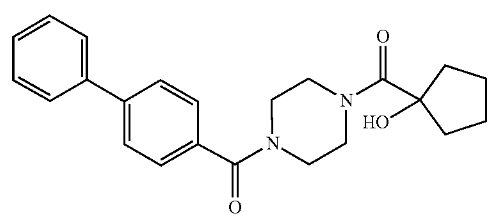 [SMILES: O=C(c1ccc(-c2ccccc2)cc1)N1CCN(C(=O)C2(O)CCCC2)CC1] |
| 3,3,3-trifluoro-2-hydroxy-2-methyl-1-{4[(4-phenylphenyl)carbonyl]piperazin-1-yl}propan-1-one | 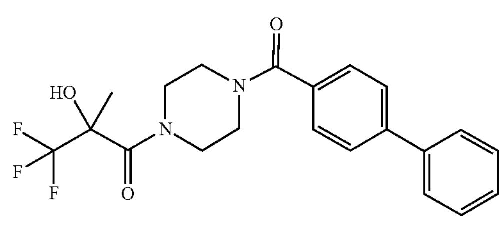 [SMILES: CC(O)(C(=O)N1CCN(C(=O)c2ccc(-c3ccccc3)cc2)CC1)C(F)(F)F] |

-continued

| NAME | Structure |
|---|---|
| 1-[(4-{[4-(3-methylphenyl)phenyl]carbonyl}piperazin-1-yl)carbonyl]cyclopropan-1-ol | 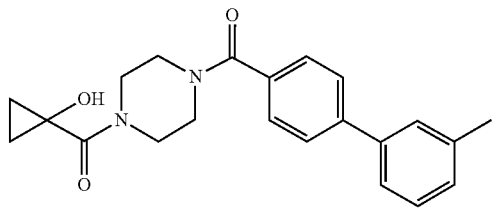 [SMILES: Cc1cccc(-c2ccc(C(=O)N3CCN(C(=O)C4(O)CC4)CC3)cc2)c1] |
| 1-[(4-{[4-(4-methylphenyl)phenyl]carbonyl}piperazin-1-yl)carbonyl]cyclopropan-1-ol | 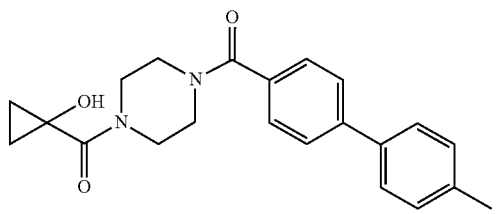 [SMILES: Cc1ccc(-c2ccc(C(=O)N3CCN(C(=O)C4(O)CC4)CC3)cc2)cc1] |
| 1-[(4-{[4-(2-fluoro-3-methoxyphenyl)phenyl]carbonyl}piperazin-1-yl)carbonyl]cyclopropan-1-ol | 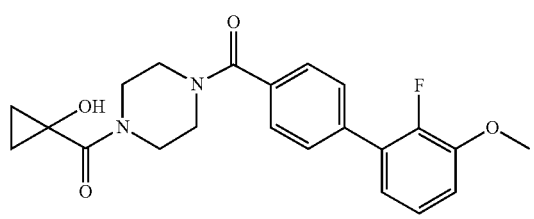 [SMILES: COc1cccc(-c2ccc(C(=O)N3CCN(C(=O)C4(O)CC4)CC3)cc2)c1F] |
| 1-[(4-{[4-(2-fluoro-4-methylphenyl)phenyl]carbonyl}piperazin-1-yl)carbonyl]cyclopropan-1-ol | 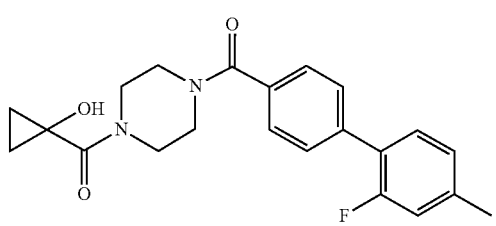 [SMILES: Cc1ccc(-c2ccc(C(=O)N3CCN(C(=O)C4(O)CC4)CC3)cc2)c(F)c1] |
| 1-[(4-{[4-(2-fluoro-4-methoxyphenyl)phenyl]carbonyl}piperazin-1-yl)carbonyl]cyclopropan-1-ol | 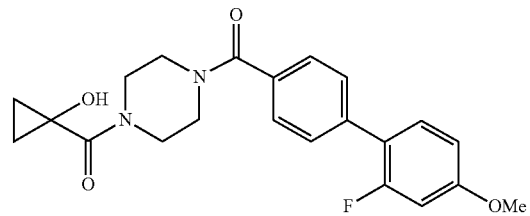 [SMILES: COc1ccc(-c2ccc(C(=O)N3CCN(C(=O)C4(O)CC4)CC3)cc2)c(F)c1] |
| 1-[(4-{[4-(2-chloro-4-fluorophenyl)phenyl]carbonyl}piperazin-1-yl)carbonyl]cyclopropan-1-ol | 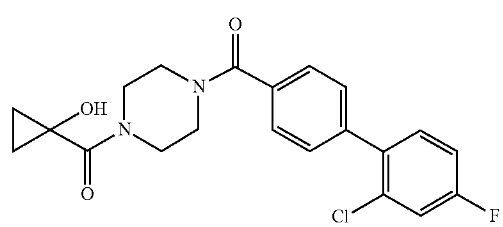 [SMILES: O=C(c1ccc(-c2ccc(F)cc2Cl)cc1)N1CCN(C(=O)C2(O)CC2)CC1] |
| 1-[(4-{[4-(3-chloro-4-fluorophenyl)phenyl]carbonyl}piperazin-1-yl)carbonyl]cyclopropan-1-ol | 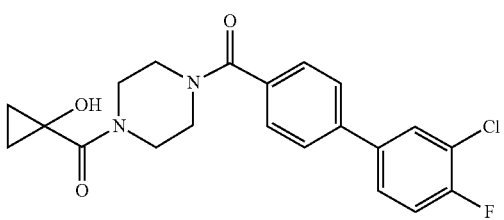 [SMILES: O=C(c1ccc(-c2ccc(F)c(Cl)c2)cc1)N1CCN(C(=O)C2(O)CC2)CC1] |

-continued

| NAME | Structure |
|---|---|
| 1-[(4-{[4-(4-chloro-2-fluorophenyl)phenyl]carbonyl}piperazin-1-yl)carbonyl]cyclopropan-1-ol | 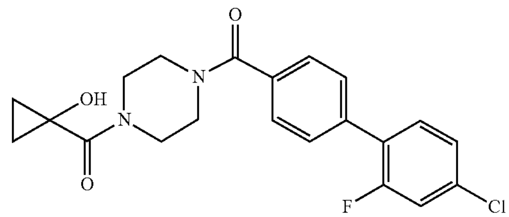 |
| 1-[(4-{[4-(2,4-dichlorophenyl)phenyl]carbonyl}piperazin-1-yl)carbonyl]cyclopropan-1-ol | 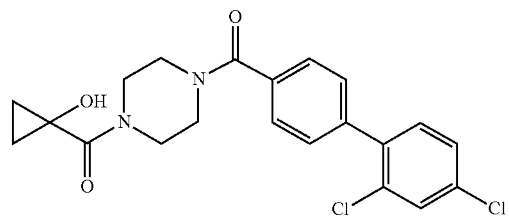 [SMILES: O=C(c1ccc(-c2ccc(Cl)cc2Cl)cc1)N1CCN(C(=O)C2(O)CC2)CC1] |
| 1-[(4-{[4-(5-fluoro-2-methylphenyl)phenyl]carbonyl}piperazin-1-yl)carbonyl]cyclopropan-1-ol | 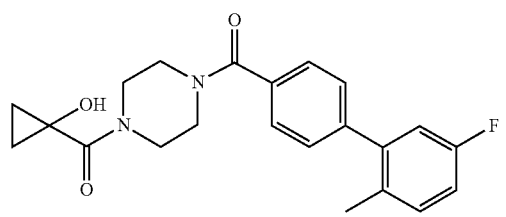 [SMILES: Cc1ccc(F)cc1-c1ccc(C(=O)N2CCN(C(=O)C3(O)CC3)CC2)cc1] |
| 1-[(4-{[4-(3-fluoro-5-methylphenyl)phenyl]carbonyl}piperazin-1-yl)carbonyl]cyclopropan-1-ol | 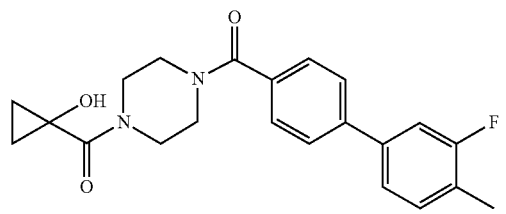 [SMILES: Cc1ccc(-c2ccc(C(=O)N3CCN(C(=O)C4(O)CC4)CC3)cc2)cc1F] |
| 1-[(4-{[4-(2,3-dichlorophenyl)phenyl]carbonyl}piperazin-1-yl)carbonyl]cyclopropan-1-ol | 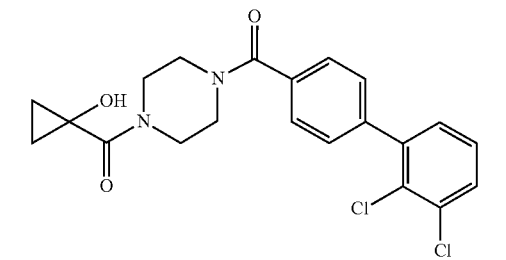 [SMILES: O=C(c1ccc(-c2cccc(Cl)c2Cl)cc1)N1CCN(C(=O)C2(O)CC2)CC1] |
| 1-[(4-{[4-(2,5-dichlorophenyl)phenyl]carbonyl}piperazin-1-yl)carbonyl]cyclopropan-1-ol | 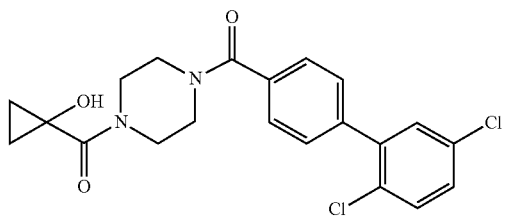 [SMILES: O=C(c1ccc(-c2cc(Cl)ccc2Cl)cc1)N1CCN(C(=O)C2(O)CC2)CC1] |
| 1-[(4-{[4-(4-chloro-3-fluorophenyl)phenyl]carbonyl}piperazin-1-yl)carbonyl]cyclopropan-1-ol | 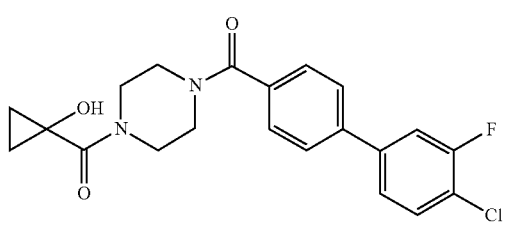 [SMILES: O=C(c1ccc(-c2ccc(Cl)c(F)c2)cc1)N1CCN(C(=O)C2(O)CC2)CC1] |

| NAME | Structure |
|---|---|
| 1-[(4-{[4-(2,5-difluorophenyl)phenyl]carbonyl}piperazin-1-yl)carbonyl]cyclopropan-1-ol | 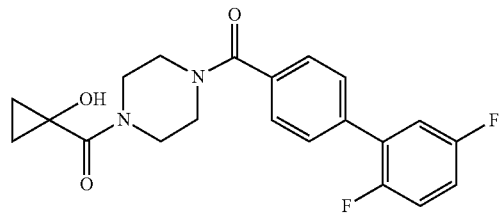 [SMILES: O=C(c1ccc(-c2cc(F)ccc2F)cc1)N1CCN(C(=O)C2(O)CC2)CC1] |
| 1-[(4-{[4-(3,4-difluorophenyl)phenyl]carbonyl}piperazin-1-yl)carbonyl]cyclopropan-1-ol | 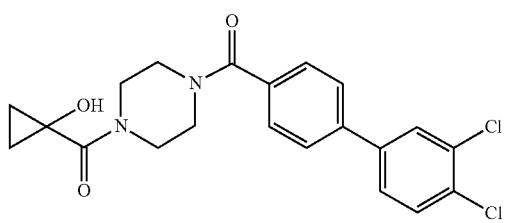 |
| 1-[(4-{[4-(2,3-difluorophenyl)phenyl]carbonyl}piperazin-1-yl)carbonyl]cyclopropan-1-ol | 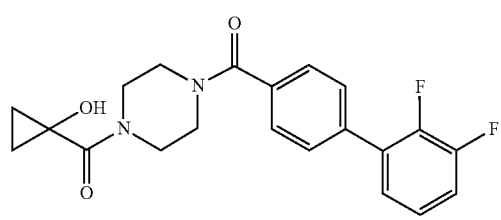 [SMILES: O=C(c1ccc(-c2cccc(F)c2F)cc1)N1CCN(C(=O)C2(O)CC2)CC1] |
| 1-[(4-{[4-(1-methyl-1H-indol-5-yl)phenyl]carbonyl}piperazin-1-yl)carbonyl]cyclopropan-1-ol | 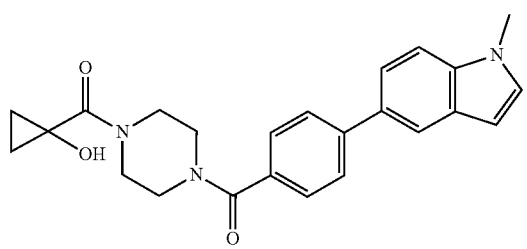 [SMILES: Cn1ccc2cc(-c3ccc(C(=O)N4CCN(C(=O)C5(O)CC5)CC4)cc3)ccc21] |
| 1-{[4-({4-[2-methoxy-4-(1H-pyrazol-1-yl)phenyl]phenyl}carbonyl)piperazin-1-yl]carbonyl}cyclopropan-1-ol | 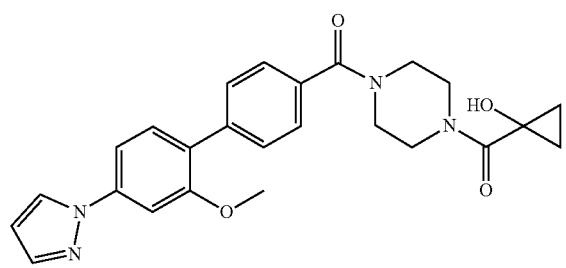 [SMILES: COc1cc(-n2cccn2)ccc1-c1ccc(C(=O)N2CCN(C(=O)C3(O)CC3)CC2)cc1] |
| 1-[(4-{[4-(2-fluoro-5-methylphenyl)phenyl]carbonyl}piperazin-1-yl)carbonyl]cyclopropan-1-ol | 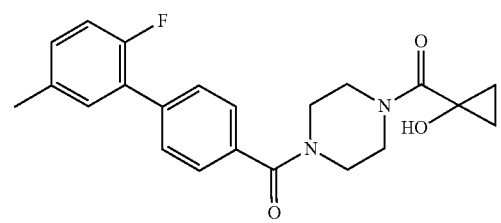 [SMILES: Cc1ccc(F)c(-c2ccc(C(=O)N3CCN(C(=O)C4(O)CC4)CC3)cc2)c1] |

| NAME | Structure |
|---|---|
| 1-{[4-({4-[2-chloro-5-(trifluoromethyl)phenyl]phenyl}carbonyl)piperazin-1-yl]carbonyl}cyclopropan-1-ol | 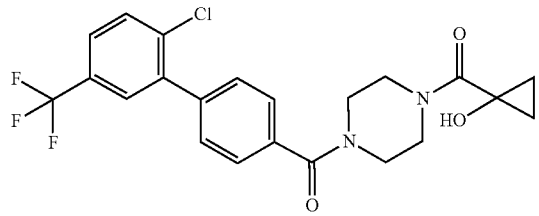 [SMILES: O=C(c1ccc(-c2cc(C(F)(F)F)ccc2Cl)cc1)N1CCN(C(=O)C2(O)CC2)CC1] |
| 1-[(4-{[4-(4-chloro-2-methoxyphenyl)phenyl]carbonyl}piperazin-1-yl)carbonyl]cyclopropan-1-ol | 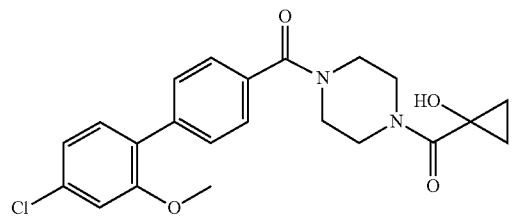 [SMILES: COc1cc(Cl)ccc1-c1ccc(C(=O)N2CCN(C(=O)C3(O)CC3)CC2)cc1] |
| 1-[(4-{[4-(3-chloro-2-methoxyphenyl)phenyl]carbonyl}piperazin-1-yl)carbonyl]cyclopropan-1-ol | 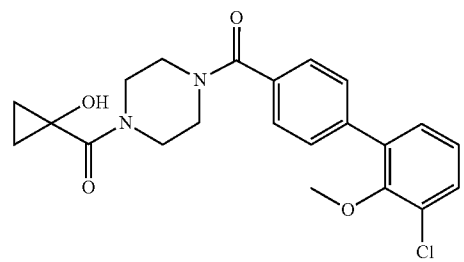 [SMILES: COc1c(Cl)cccc1-c1ccc(C(=O)N2CCN(C(=O)C3(O)CC3)CC2)cc1] |
| 1-[(4-{[4-(4,5-difluoro-2-methoxyphenyl)phenyl]carbonyl}piperazin-1-yl)carbonyl]cyclopropan-1-ol | 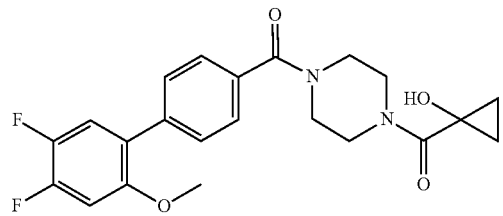 [SMILES: COc1cc(F)c(F)cc1-c1ccc(C(=O)N2CCN(C(=O)C3(O)CC3)CC2)cc1] |
| 1-{[4-({4-[2-fluoro-3-(trifluoromethyl)phenyl]phenyl}carbonyl)piperazin-1-yl]carbonyl}cyclopropan-1-ol | 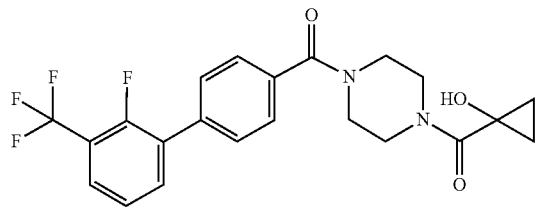 [SMILES: O=C(c1ccc(-c2cccc(C(F)(F)F)c2F)cc1)N1CCN(C(=O)C2(O)CC2)CC1] |
| 1-{[4-({4-[4-chloro-2-(trifluoromethyl)phenyl]phenyl}carbonyl)piperazin-1-yl]carbonyl}cyclopropan-1-ol | 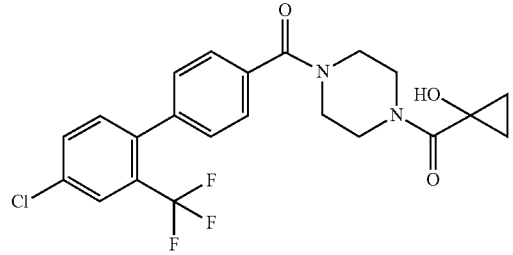 [SMILES: O=C(c1ccc(-c2ccc(Cl)cc2C(F)(F)F)cc1)N1CCN(C(=O)C2(O)CC2)CC1] |

| NAME | Structure |
|---|---|
| 1-[(4-{[4-(2-chloro-4-methoxyphenyl)phenyl]carbonyl}piperazin-1-yl)carbonyl]cyclopropan-1-ol | 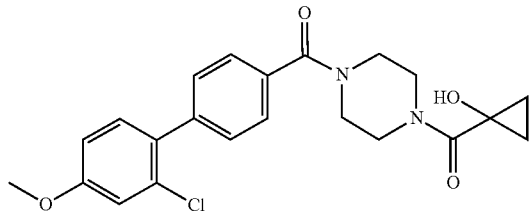 [SMILES: COc1ccc(-c2ccc(C(=O)N3CCN(C(=O)C4(O)CC4)CC3)cc2)c(Cl)c1] |
| 1-{[4-({4-[5-chloro-2-(propan-2-yloxy)phenyl]phenyl}carbonyl)piperazin-1-yl]carbonyl}cyclopropan-1-ol | 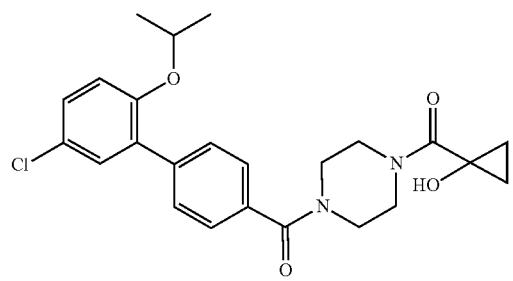 [SMILES: CC(C)Oc1ccc(Cl)cc1-c1ccc(C(=O)N2CCN(C(=O)C3(O)CC3)CC2)cc1] |
| 1-{[4-({4-[3-fluoro-5-(trifluoromethyl)phenyl]phenyl}carbonyl)piperazin-1-yl]carbonyl}cyclopropan-1-ol | 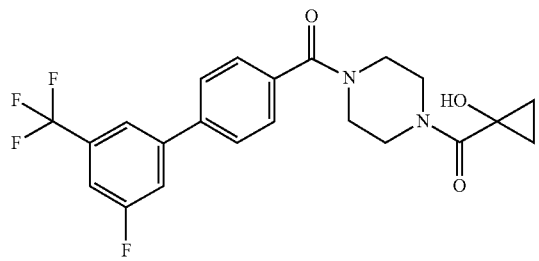 [SMILES: O=C(c1ccc(-c2cc(F)cc(C(F)(F)F)c2)cc1)N1CCN(C(=O)C2(O)CC2)CC1] |
| 1-{[4-({4-[2-methoxy-5-(trifluoromethyl)phenyl]phenyl}carbonyl)piperazin-1-yl]carbonyl}cyclopropan-1-ol | 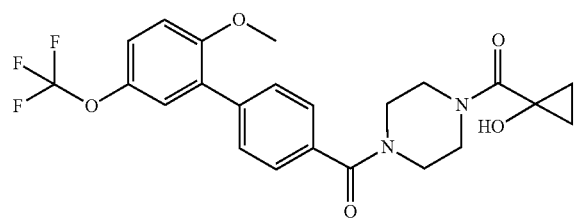 [SMILES: COc1ccc(OC(F)(F)F)cc1-c1ccc(C(=O)N2CCN(C(=O)C3(O)CC3)CC2)cc1] |
| 1-[(4-{[4-(3-fluoro-2-methoxyphenyl)phenyl]carbonyl}piperazin-1-yl)carbonyl]cyclopropan-1-ol | 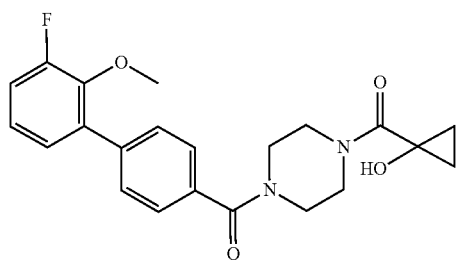 [SMILES: COc1c(F)cccc1-c1ccc(C(=O)N2CCN(C(=O)C3(O)CC3)CC2)cc1] |
| 1-[(4-{[4-(3-methoxypyridin-4-yl)phenyl]carbonyl}piperazin-1-yl)carbonyl]cyclopropan-1-ol | 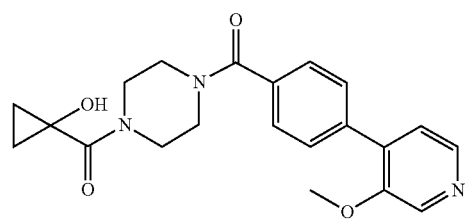 [SMILES: COc1cnccc1-c1ccc(C(=O)N2CCN(C(=O)C3(O)CC3)CC2)cc1] |

-continued

| NAME | Structure |
|---|---|
| 1-[(4-{[4-(quinolin-3-yl)phenyl]carbonyl}piperazin-1-yl)carbonyl]cyclopropan-1-ol | 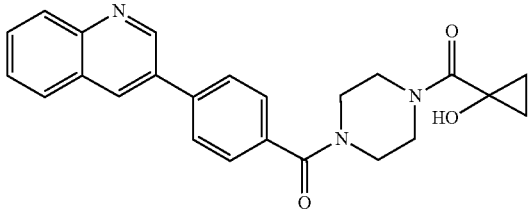 [SMILES: O=C(c1ccc(-c2cnc3ccccc3c2)cc1)N1CCN(C(=O)C2(O)CC2)CC1] |
| 1-[(4-{[4-(isoquinolin-6-yl)phenyl]carbonyl}piperazin-1-yl)carbonyl]cyclopropan-1-ol | 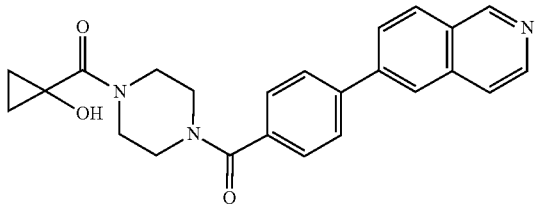 [SMILES: O=C(c1ccc(-c2ccc3cnccc3c2)cc1)N1CCN(C(=O)C2(O)CC2)CC1] |
| 1-({4-[(4-{imidazo[1,2-a]pyridin-6-yl}phenyl)carbonyl]piperazin-1-yl}carbonyl)cyclopropan-1-ol | 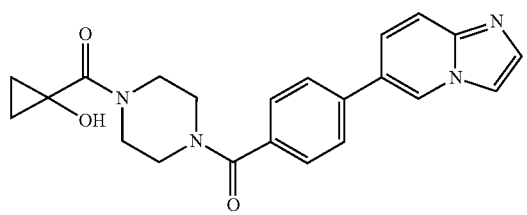 [SMILES: O=C(c1ccc(-c2ccc3nccn3c2)cc1)N1CCN(C(=O)C2(O)CC2)CC1] |
| 1-[(4-{[4-(1,3-benzothiazol-5-yl)phenyl]carbonyl}piperazin-1-yl)carbonyl]cyclopropan-1-ol | 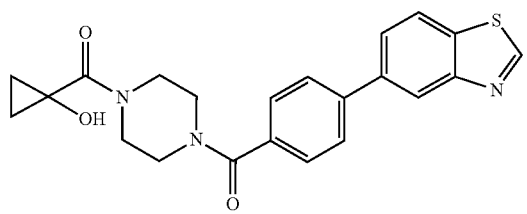 [SMILES: O=C(c1ccc(-c2ccc3scnc3c2)cc1)N1CCN(C(=O)C2(O)CC2)CC1] |
| 1-{[4-({4-[6-(trifluoromethyl)pyridin-3yl]phenyl}carbonyl)piperazin-1-yl]carbonyl}cyclopropan-1-ol | 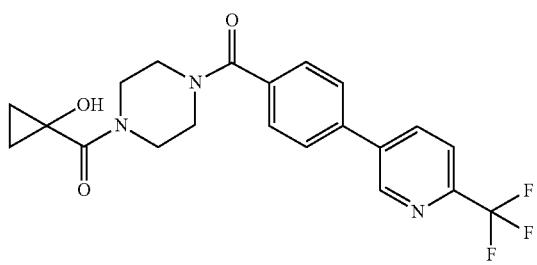 [SMILES: O=C(c1ccc(-c2ccc(C(F)(F)F)nc2)cc1)N1CCN(C(=O)C2(O)CC2)CC1] |
| 1-[(4-{[4-(5-chloro-2-fluorophenyl)phenyl]carbonyl}piperazin-1-yl)carbonyl]cyclopropan-1-ol | 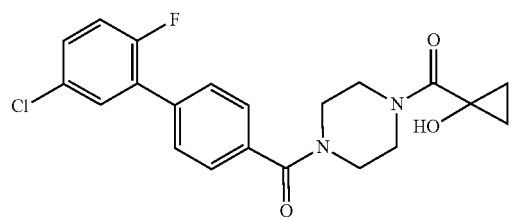 [SMILES: O=C(c1ccc(-c2cc(Cl)ccc2F)cc1)N1CCN(C(=O)C2(O)CC2)CC1] |
| 1-[(4-{[4-(6-methylpyridin-3-yl)phenyl]carbonyl}piperazin-1-yl)carbonyl]cyclopropan-1-ol | 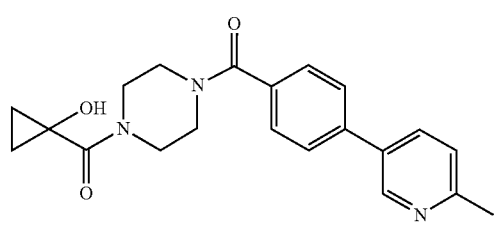 [SMILES: Cc1ccc(-c2ccc(C(=O)N3CCN(C(=O)C4(O)CC4)CC3)cc2)cn1] |

| NAME | Structure |
|---|---|
| 1-[(4-{[4-(2,6-dimethoxypyridin-3-yl)phenyl]carbonyl}piperazin-1-yl)carbonyl]cyclopropan-1-ol | 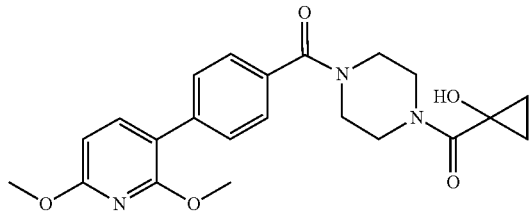 [SMILES: COc1ccc(-c2ccc(C(=O)N3CCN(C(=O)C4(O)CC4)CC3)cc2)c(OC)n1] |
| 1-[(4-{[4-(5-fluoropyridin-3-yl)phenyl]carbonyl}piperazin-1-yl)carbonyl]cyclopropan-1-ol | 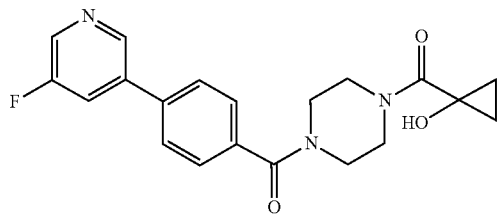 [SMILES: O=C(c1ccc(-c2cncc(F)c2)cc1)N1CCN(C(=O)C2(O)CC2)CC1] |
| 1-[(4-{[4-(1-methyl-1H-indol-2-yl)phenyl]carbonyl}piperazin-1-yl)carbonyl]cyclopropan-1-ol | 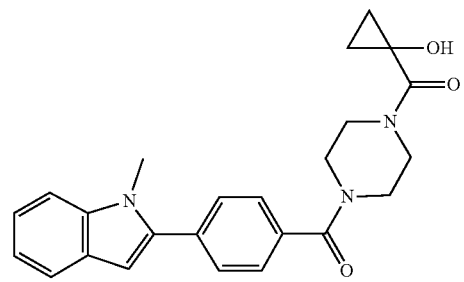 [SMILES: Cn1c(-c2ccc(C(=O)N3CCN(C(=O)C4(O)CC4)CC3)cc2)cc2ccccc21] |
| 1-[(4-{[4-(2-chloro-5-fluorophenyl)phenyl]carbonyl}piperazin-1-yl)carbonyl]cyclopropan-1-ol | 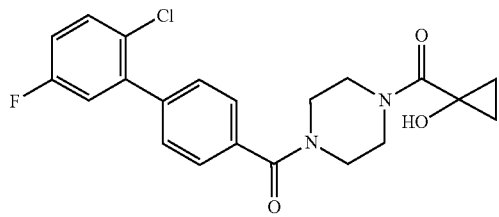 [SMILES: O=C(c1ccc(-c2cc(F)ccc2Cl)cc1)N1CCN(C(=O)C2(O)CC2)CC1] |
| 1-[(4-{[4-(2-fluoro-5-methoxyphenyl)phenyl]carbonyl}piperazin-1-yl)carbonyl]cyclopropan-1-ol | 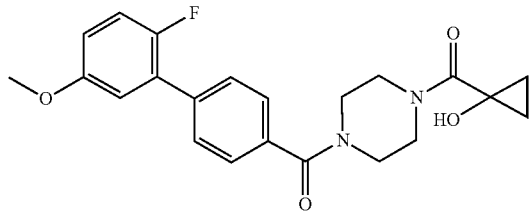 [SMILES: COc1ccc(F)c(-c2ccc(C(=O)N3CCN(C(=O)C4(O)CC4)CC3)cc2)c1] |
| 1-[(4-{[4-(2-fluoro-3-methoxyphenyl)phenyl]carbonyl}piperazin-1-yl)carbonyl]cyclopropan-1-ol | 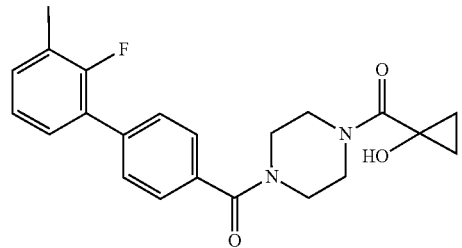 [SMILES: Cc1cccc(-c2ccc(C(=O)N3CCN(C(=O)C4(O)CC4)CC3)cc2)c1F] |

-continued

| NAME | Structure |
|---|---|
| 1-{[4-({4-[4-fluoro-2-(trifluoromethyl)phenyl]phenyl}carbonyl)piperazin-1-yl]carbonyl}cyclopropan-1-ol | 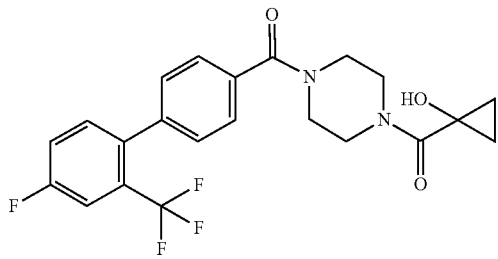 [SMILES: O=C(c1ccc(-c2ccc(F)cc2C(F)(F)F)cc1)N1CCN(C(=O)C2(O)CC2)CC1] |
| 1-{[4-({4-[2-chloro-5-(hydroxymethyl)phenyl]phenyl}carbonyl)piperazin-1-yl]carbonyl}cyclopropan-1-ol | 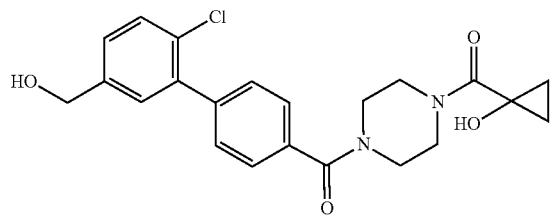 [SMILES: O=C(c1ccc(-c2cc(CO)ccc2Cl)cc1)N1CCN(C(=O)C2(O)CC2)CC1] |
| 1-[(4-{[4-(2-methyl-2H-indazol-6-yl)phenyl]carbonyl}piperazin-1-yl)carbonyl]cyclopropan-1-ol | 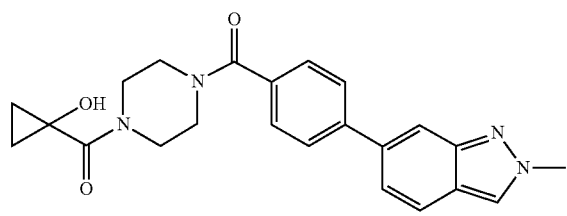 [SMILES: Cn1cc2ccc(-c3ccc(C(=O)N4CCN(C(=O)C5(O)CC5)CC4)cc3)cc2n1] |
| 1-[(4-{[4-(1-methyl-1H-indazol-7-yl)phenyl]carbonyl}piperazin-1-yl)carbonyl]cyclopropan-1-ol | 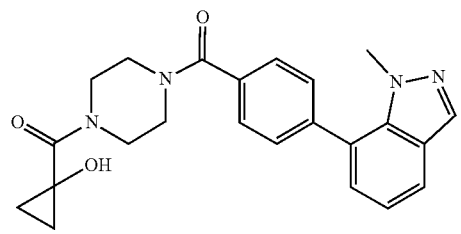 [SMILES: Cn1ncc2cccc(-c3ccc(C(=O)N4CCN(C(=O)C5(O)CC5)CC4)cc3)c21] |
| 1-[(4-{[4-(1H-indol-4-yl)phenyl]carbonyl}piperazin-1-yl)carbonyl]cyclopropan-1-ol | 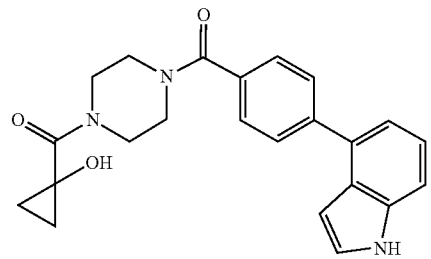 [SMILES: O=C(c1ccc(-c2cccc3[nH]ccc23)cc1)N1CCN(C(=O)C2(O)CC2)CC1] |
| N-cyclopropyl-3-[4-({4-[(1-hydroxycyclopropyl)carbonyl]piperazin-1-yl}carbonyl)phenyl]benzamide | 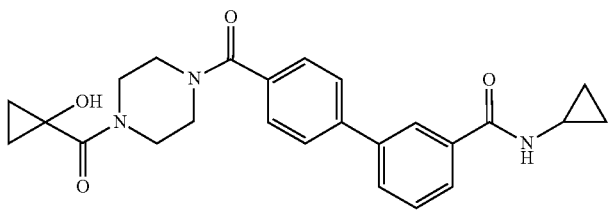 [SMILES: O=C(NC1CC1)c1cccc(-c2ccc(C(=O)N3CCN(C(=O)C4(O)CC4)CC3)cc2)c1] |

| NAME | Structure |
|---|---|
| N-{3-[4-({4-[(1-hydroxycyclopropyl)carbonyl]piperazin-1-yl}carbonyl)phenyl]phenyl}ethane-1-sulfonamide | 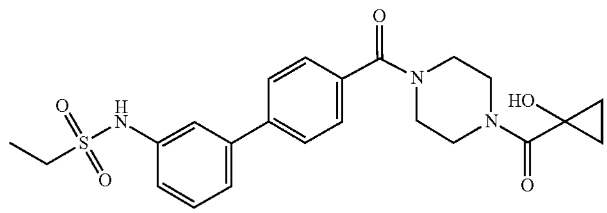 [SMILES: CCS(=O)(=O)Nc1cccc(-c2ccc(C(=O)N3CCN(C(=O)C4(O)CC4)CC3)cc2)c1] |
| 4-fluoro-3-[4-({4-[(1-hydroxycyclopropyl)carbonyl]piperazin-1-yl}carbonyl)phenyl]-N-methylbenzamide | 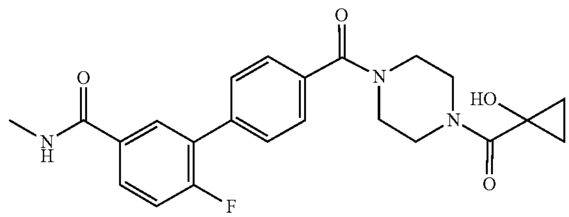 [SMILES: CNC(=O)c1ccc(F)c(-c2ccc(C(=O)N3CCN(C(=O)C4(O)CC4)CC3)cc2)c1] |
| 4-fluoro-3-[4-({4-[(1-hydroxycyclopropyl)carbonyl]piperazin-1-yl}carbonyl)phenyl]-N-(propan-2-yl)benzamide | 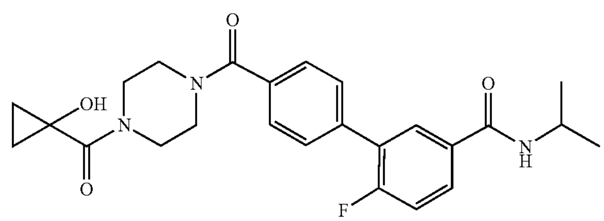 [SMILES: CC(C)NC(=O)c1ccc(F)c(-c2ccc(C(=O)N3CCN(C(=O)C4(O)CC4)CC3)cc2)c1] |
| 1-[(4-{[4-(2,4-dichloro-3-methoxyphenyl)phenyl]carbonyl}piperazin-1-yl)carbonyl]cyclopropan-1-ol | 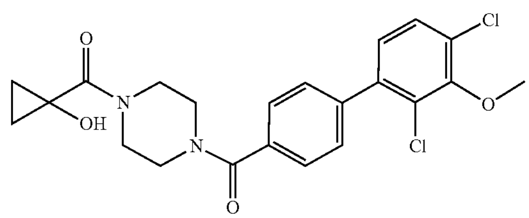 [SMILES: COc1c(Cl)ccc(-c2ccc(C(=O)N3CCN(C(=O)C4(O)CC4)CC3)cc2)c1Cl] |
| 1-{[4-({4-[2-fluoro-3-(propan-2-yloxy)phenyl]phenyl}carbonyl)piperazin-1-yl]carbonyl}cyclopropan-1-ol | 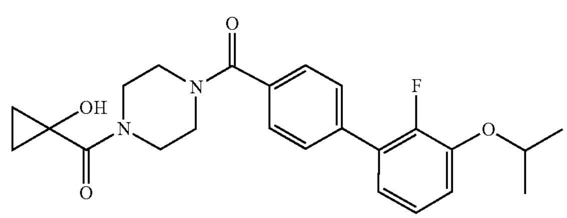 [SMILES: CC(C)Oc1cccc(-c2ccc(C(=O)N3CCN(C(=O)C4(O)CC4)CC3)cc2)c1F] |
| 1-{[4-({4-[2-fluoro-3-(trifluoromethyl)phenyl]phenyl}carbonyl)piperazin-1-yl]carbonyl}cyclopropan-1-ol | 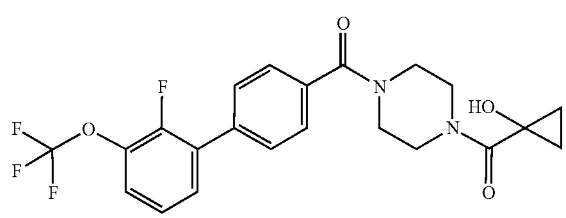 [SMILES: O=C(c1ccc(-c2cccc(OC(F)(F)F)c2F)cc1)N1CCN(C(=O)C2(O)CC2)CC1] |
| 1-{[4-({4-[3-(cyclopropylmethoxy)phenyl]phenyl}carbonyl)piperazin-1-yl]carbonyl}cyclopropan-1-ol | 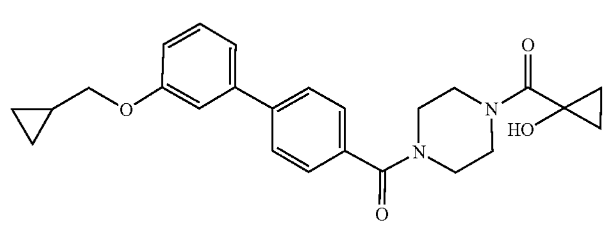 [SMILES: O=C(c1ccc(-c2cccc(OCC3CC3)c2)cc1)N1CCN(C(=O)C2(O)CC2)CC1] |

| NAME | Structure |
|---|---|
| 5-fluoro-2-[4-({4-[(1-hydroxycyclopropyl)carbonyl]piperazin-1-yl}carbonyl)phenyl]benzonitrile | 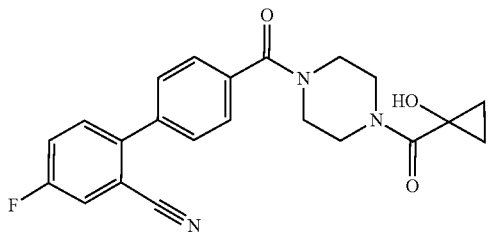 [SMILES: N#Cc1cc(F)ccc1-c1ccc(C(=O)N2CCN(C(=O)C3(O)CC3)CC2)cc1] |
| 1-[(4-{[4-(1-methyl-1H-indazol-6-yl)phenyl]carbonyl}piperazin-1-yl)carbonyl]cyclopropan-1-ol | 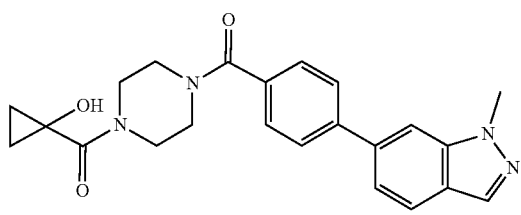 [SMILES: Cn1ncc2ccc(-c3ccc(C(=O)N4CCN(C(=O)C5(O)CC5)CC4)cc3)cc21] |
| 1-[(4-{[4-(1-methyl-1H-indazol-5-yl)phenyl]carbonyl}piperazin-1-yl)carbonyl]cyclopropan-1-ol | 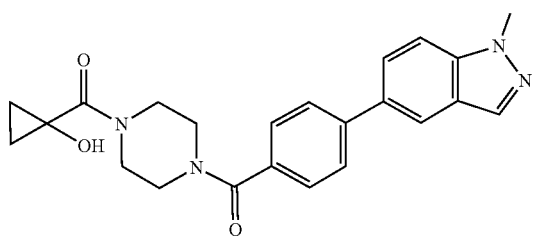 [SMILES: Cn1ncc2cc(-c3ccc(C(=O)N4CCN(C(=O)C5(O)CC5)CC4)cc3)ccc21] |
| 1-[(4-{[6-(1-methyl-1H-indol-5-yl)pyridin-3-yl]carbonyl}piperazin-1-yl)carbonyl]cyclopropan-1-ol | 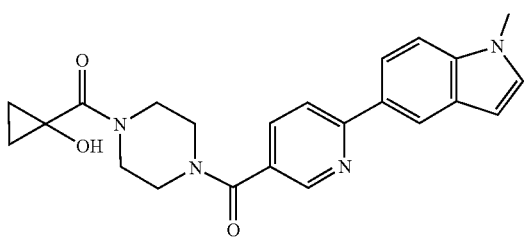 [SMILES: Cn1ccc2cc(-c3ccc(C(=O)N4CCN(C(=O)C5(O)CC5)CC4)cn3)ccc21] |
| 1-[(4-{[5-(1-methyl-1H-indol-5-yl)pyridin-2-yl]carbonyl}piperazin-1-yl)carbonyl]cyclopropan-1-ol | 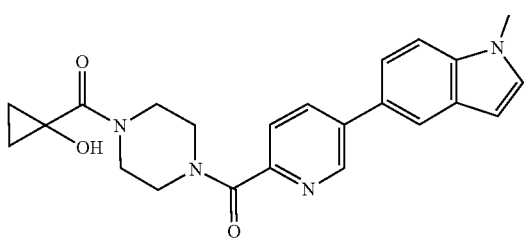 [SMILES: Cn1ccc2cc(-c3ccc(C(=O)N4CCN(C(=O)C5(O)CC5)CC4)nc3)ccc21] |
| 1-[(4-{[2-fluoro-4-(1-methyl-1H-indol-5-yl)phenyl]carbonyl}piperazin-1-yl)carbonyl]cyclopropan-1-ol | 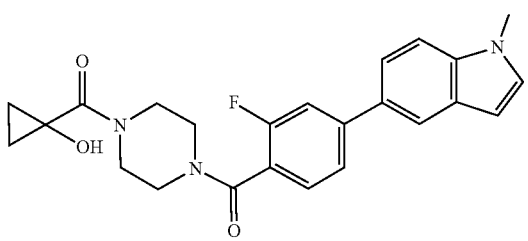 [SMILES: Cn1ccc2cc(-c3ccc(C(=O)N4CCN(C(=O)C5(O)CC5)CC4)c(F)c3)ccc21] |

-continued

| NAME | Structure |
|---|---|
| 1-[(4-{[2-fluoro-4-(quinolin-6-yl)phenyl]carbonyl}piperazin-1-yl)carbonyl]cyclopropan-1-ol | 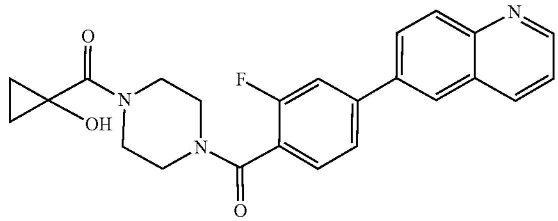 [SMILES: O=C(c1ccc(-c2ccc3ncccc3c2)cc1F)N1CCN(C(=O)C2(O)CC2)CC1] |
| 2-methoxy-2-methyl-1-{4-[(4-phenylphenyl)carbonyl]piperazin-1-yl}propan-1-one | 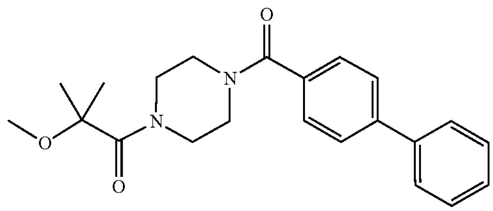 [SMILES: COC(C)(C)C(=O)N1CCN(C(=O)c2ccc(-c3ccccc3)cc2)CC1] |
| (2S)-2-hydroxy-1-{4-[(4-phenylphenyl)carbonyl]}piperazin-1-yl}propan-1-one | 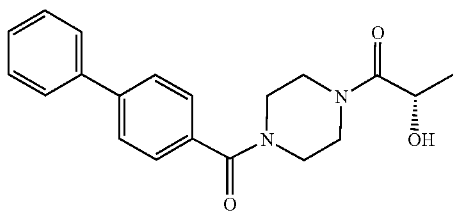 [SMILES: C[C@H](O)C(=O)N1CCN(C(=O)c2ccc(-c3ccccc3)cc2)CC1] |
| 1-[(4-{(4-(quinolin-3-yl)phenyl]carbonyl}piperazin-1-yl)carbonyl]cyclobutan-1-ol | 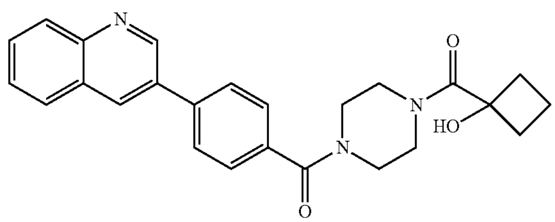 [SMILES: O=C(c1ccc(-c2cnc3ccccc3c2)cc1)N1CCN(C(=O)C2(O)CCC2)CC1] |
| 1-[(4-{[2-chloro-4-(quinolin-6-yl)phenyl]carbonyl}piperazin-1-yl)carbonyl]cyclopropan-1-ol | 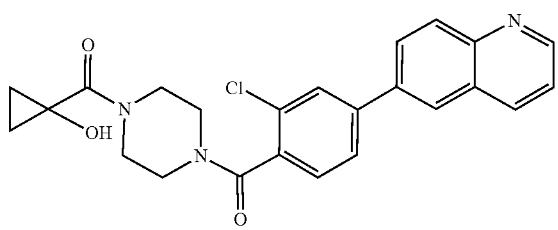 [SMILES: O=C(c1ccc(-c2ccc3ncccc3c2)cc1Cl)N1CCN(C(=O)C2(O)CC2)CC1] |
| 1-[(4-{[2-chloro-4-(1-methyl-1H-indol-5-yl)phenyl]carbonyl}piperazin-1-yl)carbonyl]cyclopropan-1-ol | 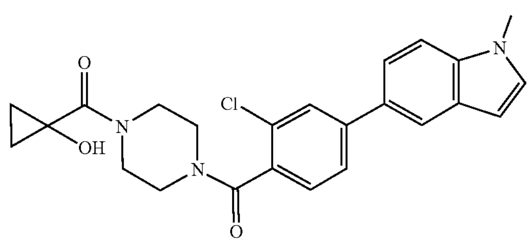 [SMILES: Cn1ccc2cc(-c3ccc(C(=O)N4CCN(C(=O)C5(O)CC5)CC4)c(Cl)c3)ccc21] |
| 1-[(4-{[6-(quinolin-6-yl)pyridin-3-yl]carbonyl}piperazin-1-yl)carbonyl]cyclopropan-1-ol | 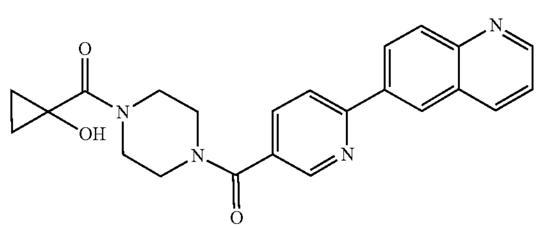 [SMILES: O=C(c1ccc(-c2ccc3ncccc3c2)nc1)N1CCN(C(=O)C2(O)CC2)CC1] |

| NAME | Structure |
|------|-----------|
| 1-[(4-{[4-methyl-2-(1-methyl-1H-indol-5-yl)-1,3-thiazol-5-yl]carbonyl}piperazin-1-yl)carbonyl]cyclopropan-1-ol | 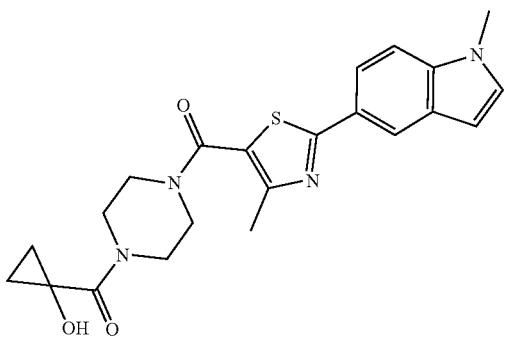 [SMILES: Cc1nc(-c2ccc3c(ccn3C)c2)sc1C(=O)N1CCN(C(=O)C2(O)CC2)CC1] |
| 1-[(4-{[4-methyl-2-(quinolin-3-yl)-1,3-thiazol-5-yl]carbonyl}piperazin-1-yl)carbonyl]cyclopropan-1-ol | 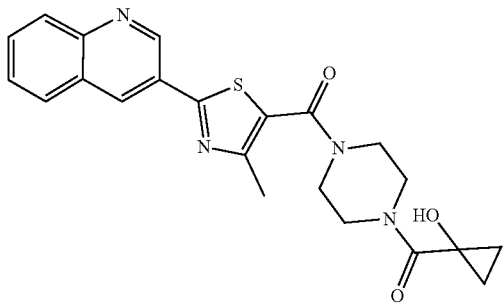 [SMILES: Cc1nc(-c2cnc3ccccc3c2)sc1C(=O)N1CCN(C(=O)C2(O)CC2)CC1] |
| 1-[(4-{[2-(1,3-benzothiazol-5-yl)-4-methyl-1,3-thiazol-5-yl]carbonyl}piperazin-1-yl)carbonyl]cyclopropan-1-ol | 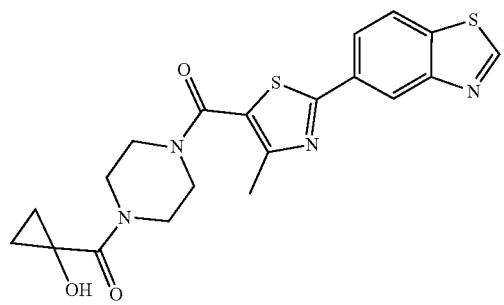 [SMILES: Cc1nc(-c2ccc3scnc3c2)sc1C(=O)N1CCN(C(=O)C2(O)CC2)CC1] |
| 1-[(4-{[3-fluoro-4-(quinolin-3-yl)phenyl]carbonyl}piperazin-1-yl)carbonyl]cyclopropan-1-ol | 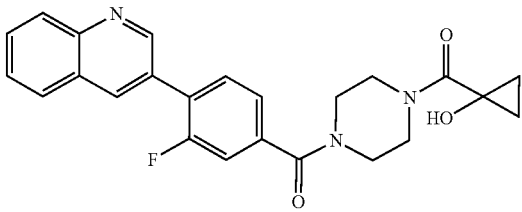 [SMILES: O=C(c1ccc(-c2cnc3ccccc3c2)c(F)c1)N1CCN(C(=O)C2(O)CC2)CC1] |
| 1-[(4-{[3-fluoro-4-(quinolin-6-yl)phenyl]carbonyl}piperazin-1-yl)carbonyl]cyclopropan-1-ol | 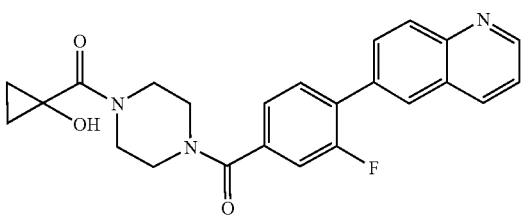 [SMILES: O=C(c1ccc(-c2ccc3ncccc3c2)c(F)c1)N1CCN(C(=O)C2(O)CC2)CC1] |

| NAME | Structure |
|---|---|
| 1-[(4-{[4-(1,3-benzothiazol-5-yl)-3-fluorophenyl]carbonyl}piperazin-1-yl)carbonyl]cyclopropan-1-ol | 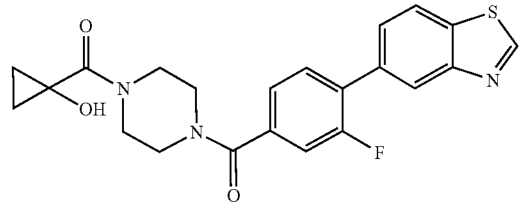 [SMILES: O=C(c1ccc(-c2ccc3scnc3c2)c(F)c1)N1CCN(C(=O)C2(O)CC2)CC1] |
| 1-[(4-{[3-methyl-4-(1-methyl-1H-indol-5-yl)phenyl]carbonyl}piperazin-1-yl)carbonyl]cyclopropan-1-ol | 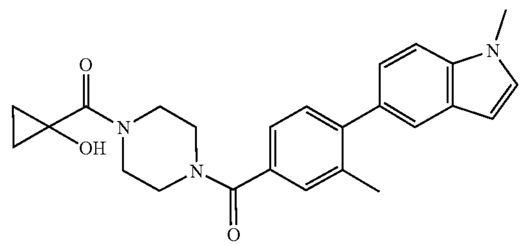 [SMILES: Cc1cc(C(=O)N2CCN(C(=O)C3(O)CC3)CC2)ccc1-c1ccc2c(ccn2C)c1] |
| 1-[(4-{[3-methyl-4-(quinolin-3-yl)phenyl]carbonyl}piperazin-1-yl)carbonyl]cyclopropan-1-ol | 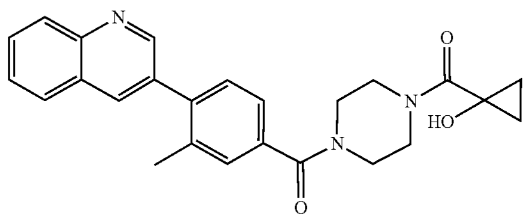 [SMILES: Cc1cc(C(=O)N2CCN(C(=O)C3(O)CC3)CC2)ccc1-c1cnc2ccccc2c1] |
| 1-[(4-{[3-methyl-4-(quinolin-6-yl)phenyl]carbonyl}piperazin-1-yl)carbonyl]cyclopropan-1-ol | 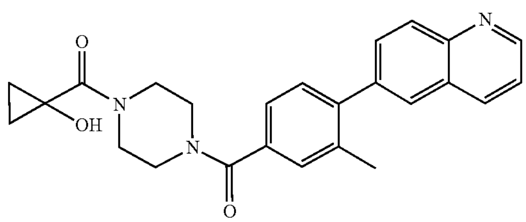 [SMILES: Cc1cc(C(=O)N2CCN(C(=O)C3(O)CC3)CC2)ccc1-c1ccc2ncccc2c1] |
| 1-[(4-{[4-(1,3-benzothiazol-5-yl)-3-methylphenyl]carbonyl}piperazin-1-yl)carbonyl]cyclopropan-1-ol | 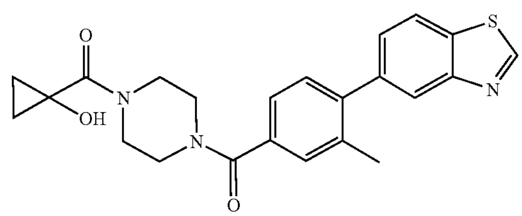 [SMILES: Cc1cc(C(=O)N2CCN(C(=O)C3(O)CC3)CC2)ccc1-c1ccc2scnc2c1] |
| 1-[(4-{[2-chloro-4-(quinolin-3-yl)phenyl]carbonyl}piperazin-1-yl)carbonyl]cyclopropan-1-ol | 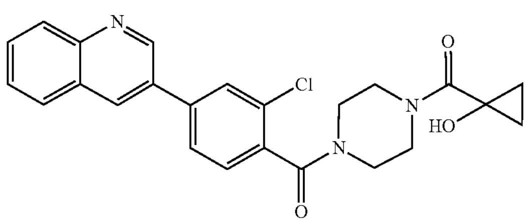 [SMILES: O=C(c1ccc(-c2cnc3ccccc3c2)cc1Cl)N1CCN(C(=O)C2(O)CC2)CC1] |
| 1-[(4-{[4-(1,3-benzothiazol-5-yl)-2-chlorophenyl]carbonyl}piperazin-1-yl)carbonyl]cyclopropan-1-ol | 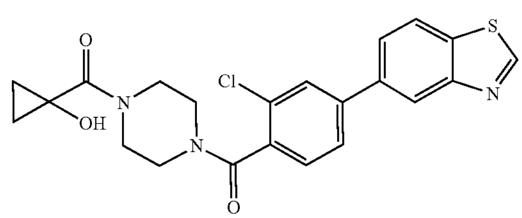 [SMILES: O=C(c1ccc(-c2ccc3scnc3c2)cc1Cl)N1CCN(C(=O)C2(O)CC2)CC1] |

-continued

| NAME | Structure |
|---|---|
| 1-[(4-{[3-chloro-4-(1-methyl-1H-indol-5-yl)phenyl]carbonyl}piperazin-1-yl)carbonyl]cyclopropan-1-ol | 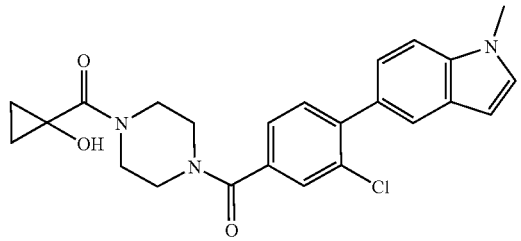 [SMILES: Cn1ccc2cc(-c3ccc(C(=O)N4CCN(C(=O)C5(O)CC5)CC4)cc3Cl)ccc21] |
| 1-[(4-{[3-chloro-4-(quinolin-3-yl)phenyl]carbonyl}piperazin-1-yl)carbonyl]cyclopropan-1-ol | 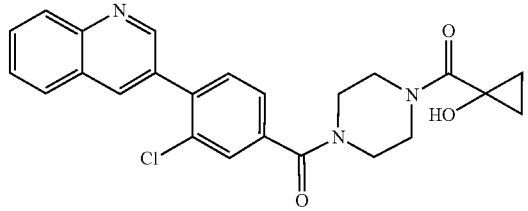 [SMILES: O=C(c1ccc(-c2cnc3ccccc3c2)c(Cl)c1)N1CCN(C(=O)C2(O)CC2)CC1] |
| 1-[(4-{[3-chloro-4-(quinolin-6-yl)phenyl]carbonyl}piperazin-1-yl)carbonyl]cyclopropan-1-ol | 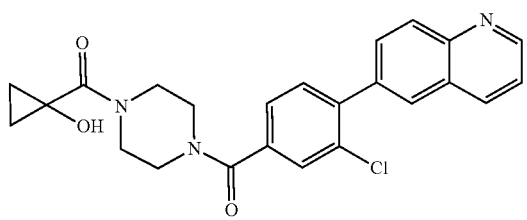 [SMILES: O=C(c1ccc(-c2ccc3ncccc3c2)c(Cl)c1)N1CCN(C(=O)C2(O)CC2)CC1] |
| 1-[(4-{[4-(1,3-benzothiazol-5-yl)-3-chlorophenyl]carbonyl)piperazin-1-yl}carbonyl]cyclopropan-1-ol | 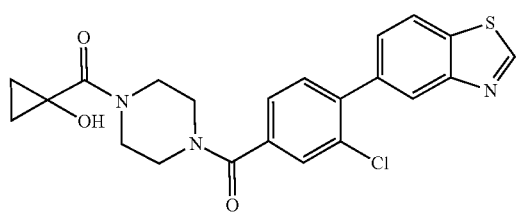 [SMILES: O=C(c1ccc(-c2ccc3scnc3c2)c(Cl)c1)N1CCN(C(=O)C2(O)CC2)CC1] |
| 1-[(4-{[4-(1-methyl-1H-indol-5-yl)-2-(trifluoromethyl)phenyl]carbonyl}piperazin-1-yl)carbonyl]cyclopropan-1-ol | 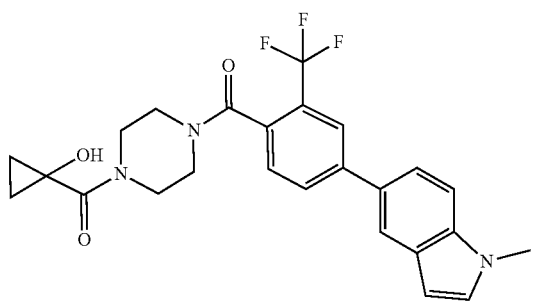 [SMILES: Cn1ccc2cc(-c3ccc(C(=O)N4CCN(C(=O)C5(O)CC5)CC4)c(C(F)(F)F)c3)ccc21] |
| 1-[(4-{[4-(quinolin-6-yl)-2-(trifluoromethyl)phenyl]carbonyl}piperazin-1-yl)carbonyl]cyclopropan-1-ol | 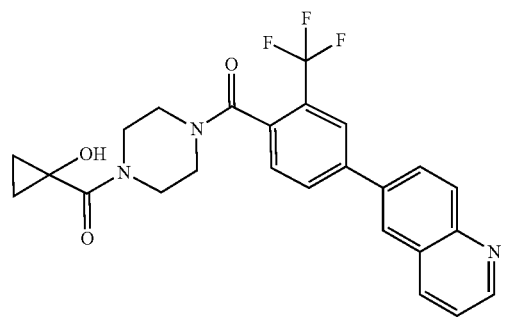 [SMILES: O=C(c1ccc(-c2ccc3ncccc3c2)cc1C(F)(F)F)N1CCN(C(=O)C2(O)CC2)CC1] |

-continued

| NAME | Structure |
|---|---|
| 1-[(4-{[3-methoxy-4-(quinolin-6-yl)phenyl]carbonyl}piperazin-1-yl)carbonyl]cyclopropan-1-ol | 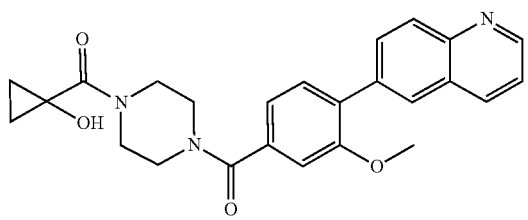 [SMILES: COc1cc(C(=O)N2CCN(C(=O)C3(O)CC3)CC2)ccc1-c1ccc2ncccc2c1] |
| 1-[(4-{[2-methoxy-4-(quinolin-3-yl)phenyl]carbonyl}piperazin-1-yl)carbonyl]cyclopropan-1-ol | 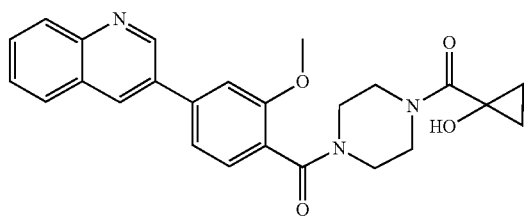 [SMILES: COc1cc(-c2cnc3ccccc3c2)ccc1C(=O)N1CCN(C(=O)C2(O)CC2)CC1] |
| 1-[(4-{[2-methoxy-4-(quinolin-6-yl)phenyl]carbonyl}piperazin-1-yl)carbonyl]cyclopropan-1-ol | 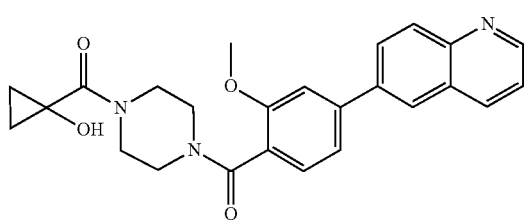 [SMILES: COc1cc(-c2ccc3ncccc3c2)ccc1C(=O)N1CCN(C(=O)C2(O)CC2)CC1] |
| 1-[(4-{[4-(1,3-benzothiazol-5-yl)-2-methoxyphenyl]carbonyl}piperazin-1-yl)carbonyl]cyclopropan-1-ol | 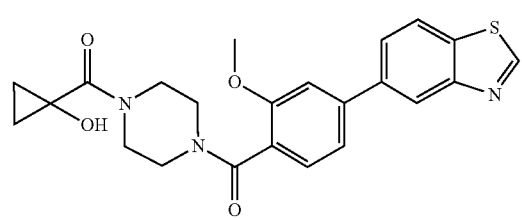 [SMILES: COc1cc(-c2ccc3scnc3c2)ccc1C(=O)N1CCN(C(=O)C2(O)CC2)CC1] |
| 1-[(4-{[5-(quinolin-6-yl)pyrimidin-2-yl]carbonyl}piperazin-1-yl)carbonyl]cyclopropan-1-ol | 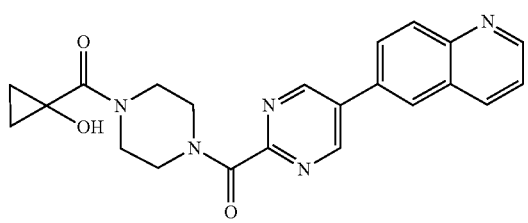 [SMILES: O=C(c1ncc(-c2ccc3ncccc3c2)cn1)N1CCN(C(=O)C2(O)CC2)CC1] |
| 1-[(4-{[5-(1-methyl-1H-indol-5-yl)pyrazin-2-yl]carbonyl}piperazin-1-yl)carbonyl]cyclopropan-1-ol | 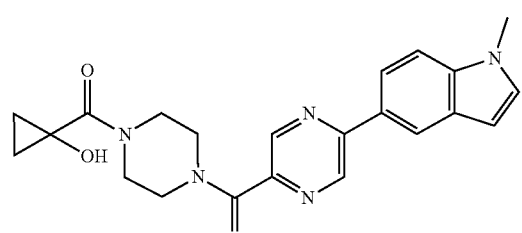 |
| 1-[(4-{[5-(quinolin-3-yl)pyrazin-2-yl]carbonyl}piperazin-1-yl)carbonyl]cyclopropan-1-ol | 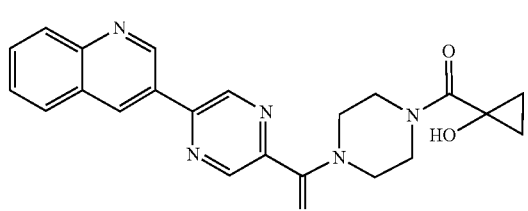 |

-continued

| NAME | Structure |
|---|---|
| 1-[(4-{[5-(quinolin-6-yl)pyrazin-2-yl]carbonyl}piperazin-1-yl)carbonyl]cyclopropan-1-ol | 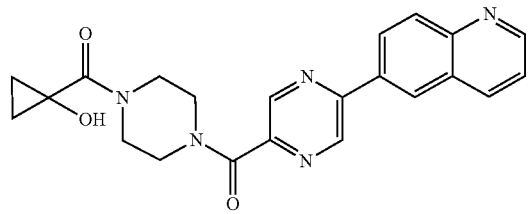 [SMILES: O=C(c1cnc(-c2ccc3ncccc3c2)cn1)N1CCN(C(=O)C2(O)CC2)CC1] |
| 1-({4-[(4-phenylphenyl)carbonyl]piperazin-1-yl}carbonyl)cyclobutan-1-ol | 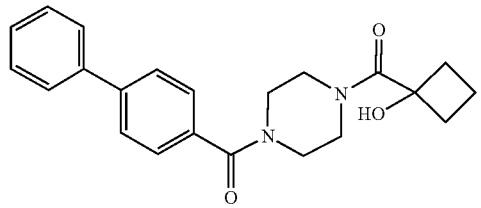 [SMILES: O=C(c1ccc(-c2ccccc2)cc1)N1CCN(C(=O)C2(O)CCC2)CC1] |
| 1-[(4-{[4-(isoquinolin-6-yl)phenyl]carbonyl}piperazin-1-yl)carbonyl]cyclobutan-1-ol | 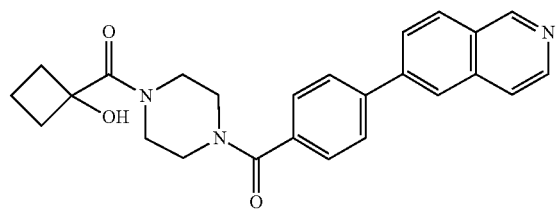 [SMILES: O=C(c1ccc(-c2ccc3cnccc3c2)cc1)N1CCN(C(=O)C2(O)CCC2)CC1] |
| 1-{[(2S,5R)-4-{[4-(isoquinolin-6-yl)phenyl]carbonyl}-2,5-dimethylpiperazin-1-yl]carbonyl}cyclopropan-1-ol | 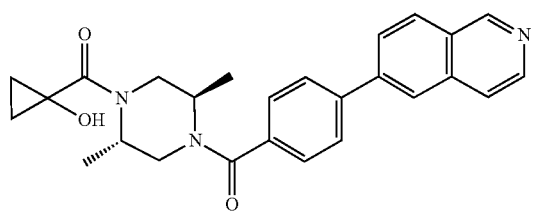 [SMILES: C[C@@H]1CN(C(=O)C2(O)CC2)[C@@H](C)CN1C(=O)c1ccc(-c2ccc3cnccc3c2)cc1] |
| 1-[(4-{[4-(1H-indol-5-yl)phenyl]carbonyl}piperazin-1-yl)carbonyl]cyclopropan-1-ol | 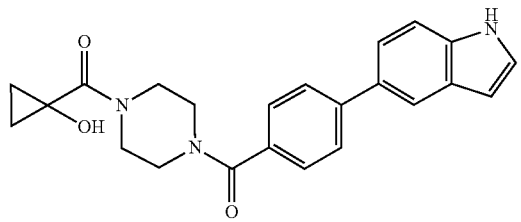 [SMILES: O=C(c1ccc(-c2ccc3[nH]ccc3c2)cc1)N1CCN(C(=O)C2(O)CC2)CC1] |
| 3-[4-({4-[(oxetan-2-yl)carbonyl]piperazin-1-yl}carbonyl)phenyl]quinoline | 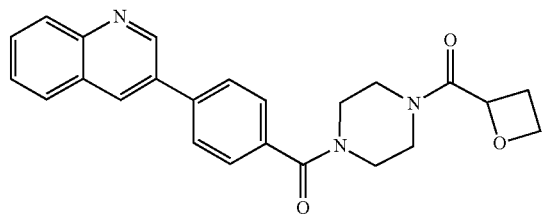 [SMILES: O=C(c1ccc(-c2cnc3ccccc3c2)cc1)N1CCN(C(=O)C2CCO2)CC1] |
| 5-[4-({4-[(oxetan-2-yl)carbonyl]piperazin-1-yl}carbonyl)phenyl]-1H-indole | 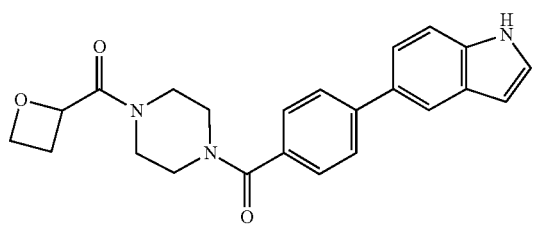 [SMILES: O=C(c1ccc(-c2ccc3[nH]ccc3c2)cc1)N1CCN(C(=O)C2CCO2)CC1] |

| NAME | Structure |
|---|---|
| 1-[(4-{[2-fluoro-4-(quinolin-3-yl)phenyl]carbonyl}piperazin-1-yl)carbonyl]cyclopropan-1-ol | 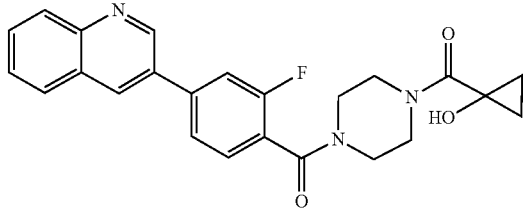 [SMILES: O=C(c1ccc(-c2cnc3ccccc3c2)cc1F)N1CCN(C(=O)C2(O)CC2)CC1] |
| 6-[4-({4-[(oxetan-2-yl)carbonyl]piperazin-1-yl}carbonyl)phenyl]isoquinoline | 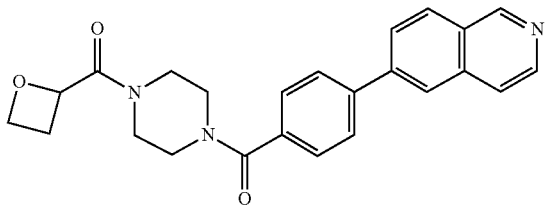 [SMILES: O=C(c1ccc(-c2ccc3cnccc3c2)cc1)N1CCN(C(=O)C2CCO2)CC1] |
| 1-[(4-{[4-(1,5-naphthyridin-3-yl)phenyl]carbonyl}piperazin-1-yl)carbonyl]cyclopropan-1-ol | 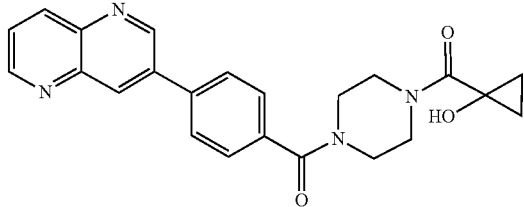 [SMILES: O=C(c1ccc(-c2cnc3cccnc3c2)cc1)N1CCN(C(=O)C2(O)CC2)CC1] |
| 1-[(4-{[4-(1-benzofuran-5-yl)phenyl]carbonyl}piperazin-1-yl)carbonyl]cyclopropan-1-ol | 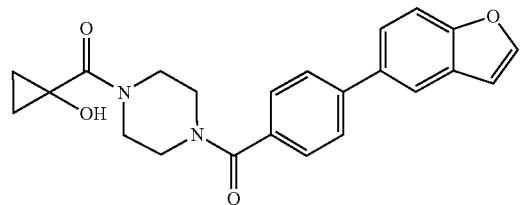 [SMILES: O=C(c1ccc(-c2ccc3occc3c2)cc1)N1CCN(C(=O)C2(O)CC2)CC1] |
| 1-({4-[(4-phenoxyphenyl)carbonyl]piperazin-1-yl}carbonyl)cyclopropan-1-ol | 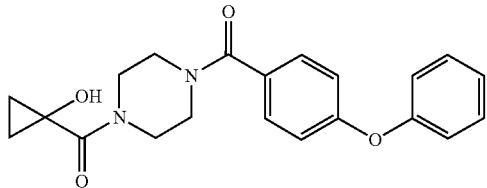 [SMILES: O=C(c1ccc(Oc2ccccc2)cc1)N1CCN(C(=O)C2(O)CC2)CC1] |
| 1-[(4-{[2-fluoro-4-(7-fluoro-1H-indol-5-yl)phenyl]carbonyl}piperazin-1-yl)carbonyl]cyclopropan-1-ol | 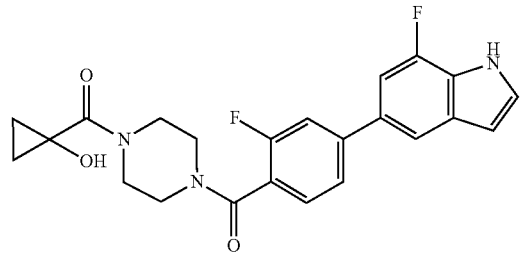 [SMILES: O=C(c1ccc(-c2cc(F)c3[nH]ccc3c2)cc1F)N1CCN(C(=O)C2(O)CC2)CC1] |

-continued

| NAME | Structure |
|---|---|
| 1-{[4-({3-chloro-4-[1-(trifluoromethyl)-1H-indol-5-yl]phenyl}carbonyl)piperazin-1-yl]carbonyl}cyclopropan-1-ol | 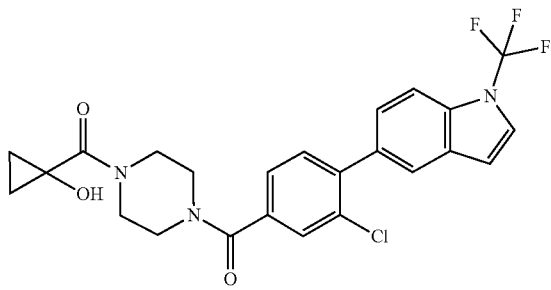 [SMILES: O=C(c1ccc(-c2ccc3c(ccn3C(F)(F)F)c2)c(Cl)c1)N1CCN(C(=O)C2(O)CC2)CC1] |
| 1-[(4-{[4-(1,3-benzoxazol-5-yl)phenyl]carbonyl}piperazin-1-yl)carbonyl]cyclopropan-1-ol | 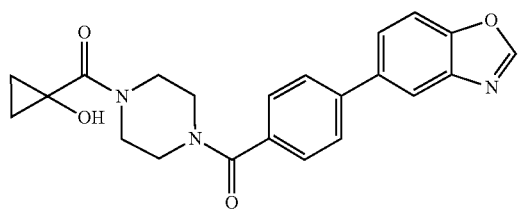 [SMILES: O=C(c1ccc(-c2ccc3ocnc3c2)cc1)N1CCN(C(=O)C2(O)CC2)CC1] |
| 1-[(4-{[4-(1,3-benzothiazol-6-yl)phenyl]carbonyl}piperazin-1-yl)carbonyl]cyclopropan-1-ol | 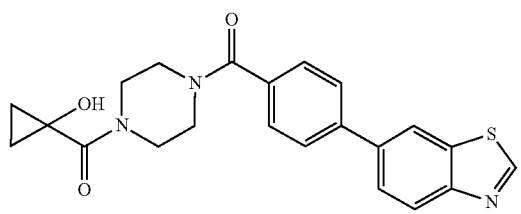 [SMILES: O=C(c1ccc(-c2ccc3ncsc3c2)cc1)N1CCN(C(=O)C2(O)CC2)CC1] |
| 1-{[4-({3-chloro-4-[1-(propan-2-yl)-1H-indol-5-yl]phenyl}carbonyl)piperazin-1-yl]carbonyl}cyclopropan-1-ol | 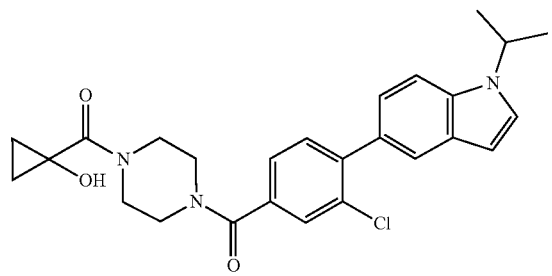 [SMILES: CC(C)n1ccc2cc(-c3ccc(C(=O)N4CCN(C(=O)C5(O)CC5)CC4)cc3Cl)ccc21] |
| 1-[(4-{[4-(1H-1,3-benzodiazol-5-yl)phenyl]carbonyl}piperazin-1-yl)carbonyl]cyclopropan-1-ol | 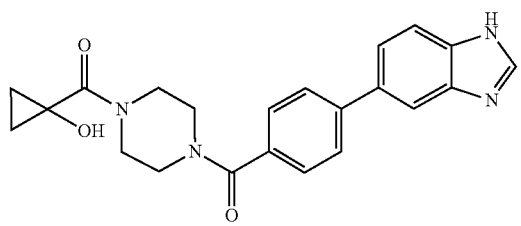 [SMILES: O=C(c1ccc(-c2ccc3[nH]cnc3c2)cc1)N1CCN(C(=O)C2(O)CC2)CC1] |
| 5-[4-({4-[(1-hydroxycyclopropyl)carbonyl]piperazin-1-yl}carbonyl)phenyl]-1H-indole-3-carbonitrile | 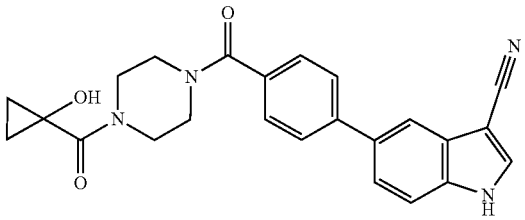 [SMILES: N#Cc1c[nH]c2ccc(-c3ccc(C(=O)N4CCN(C(=O)C5(O)CC5)CC4)cc3)cc12] |

-continued

| NAME | Structure |
|---|---|
| 3-[3-fluoro-4-({4-[(1-hydroxycyclopropyl)carbonyl]piperazin-1-yl}carbonyl)phenyl]quinolin-2-ol | 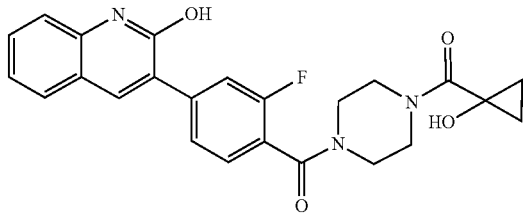 [SMILES: O=C(c1ccc(-c2cc3ccccc3nc2O)cc1F)N1CCN(C(=O)C2(O)CC2)CC1] |
| 1-[(4-{[4-(1,3-benzoxazol-2-yl)phenyl]carbonyl}piperazin-1-yl)carbonyl]cyclopropan-1-ol | 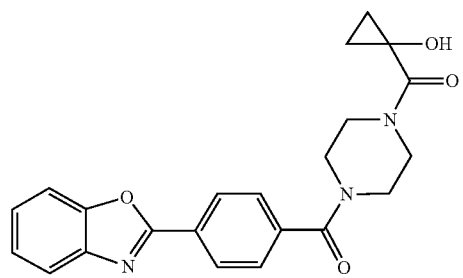 [SMILES: O=C(c1ccc(-c2nc3ccccc3o2)cc1)N1CCN(C(=O)C2(O)CC2)CC1] |
| 1-[(4-{[2-fluoro-4-(2-methoxyquinolin-3-yl)phenyl]carbonyl}piperazin-1-yl)carbonyl]cyclopropan-1-ol | 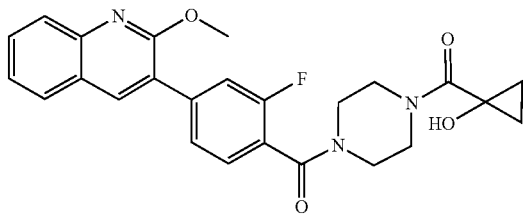 [SMILES: COc1nc2ccccc2cc1-c1ccc(C(=O)N2CCN(C(=O)C3(O)CC3)CC2)c(F)c1] |
| 1-[(4-{[4-(4-chloroquinolin-3-yl)phenyl]carbonyl}piperazin-1-yl)carbonyl]cyclopropan-1-ol | 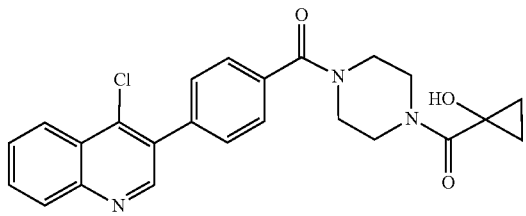 [SMILES: O=C(c1ccc(-c2cnc3ccccc3c2Cl)cc1)N1CCN(C(=O)C2(O)CC2)CC1] |
| 1-[(4-{[4-(7-fluoro-1H-indol-5-yl)phenyl]carbonyl}piperazin-1-yl)carbonyl]cyclopropan-1-ol | 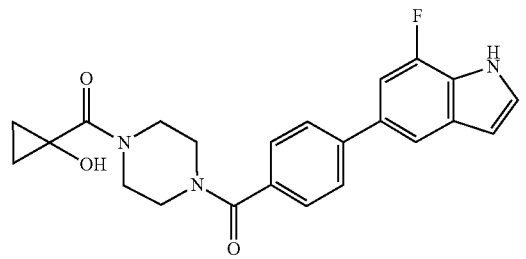 [SMILES: O=C(c1ccc(-c2cc(F)c3[nH]ccc3c2)cc1)N1CCN(C(=O)C2(O)CC2)CC1] |
| 1-[(4-{[4-(quinolin-2-yl)phenyl]carbonyl}piperazin-1-yl)carbonyl]cyclopropan-1-ol | 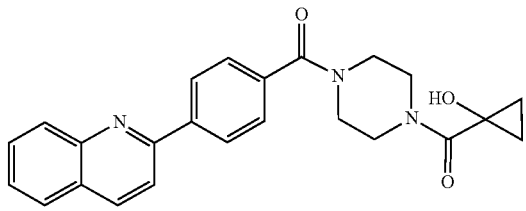 [SMILES: O=C(c1ccc(-c2ccc3ccccc3n2)cc1)N1CCN(C(=O)C2(O)CC2)CC1] |

-continued

| NAME | Structure |
|---|---|
| 1-[(4-{[4-(1,3-benzothiazol-2-yl)phenyl]carbonyl}piperazin-1-yl)carbonyl]cyclopropan-1-ol | 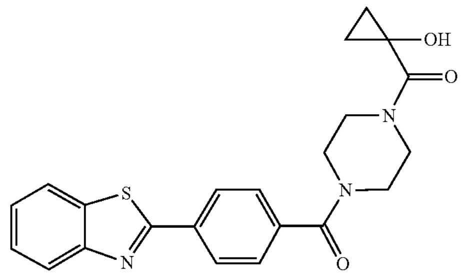 [SMILES: O=C(c1ccc(-c2nc3ccccc3s2)cc1)N1CCN(C(=O)C2(O)CC2)CC1] |
| 1-[(4-{[4-(2-methoxyquinolin-6-yl)phenyl]carbonyl}piperazin-1-yl)carbonyl]cyclopropan-1-ol | 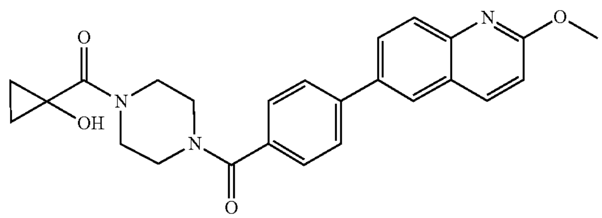 [SMILES: COc1ccc2cc(-c3ccc(C(=O)N4CCN(C(=O)C5(O)CC5)CC4)cc3)ccc2n1] |
| 1-{[4-({4[1-(trifluoromethyl)-1H-indol-5-yl]phenyl}carbonyl)piperazin-1-1yl]carbonyl}cyclopropan-1-ol | 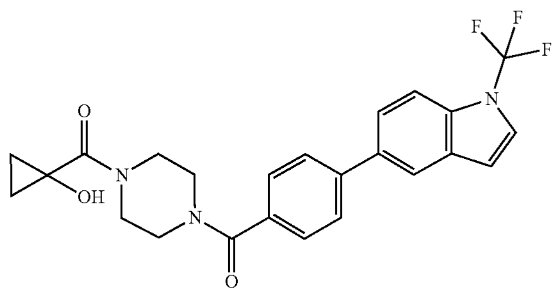 [SMILES: O=C(c1ccc(-c2ccc3c(ccn3C(F)(F)F)c2)cc1)N1CCN(C(=O)C2(O)CC2)CC1] |
| 1-[(4-{[4-(6-methoxynaphthalen-2-yl)phenyl]carbonyl}piperazin-1-yl)carbonyl]cyclopropan-1-ol | 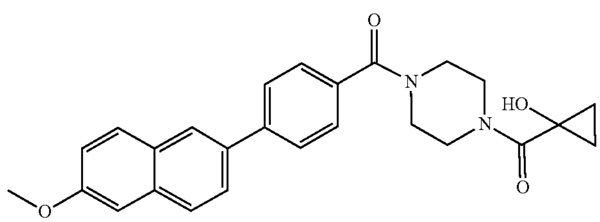 [SMILES: COc1ccc2cc(-c3ccc(C(=O)N4CCN(C(=O)C5(O)CC5)CC4)cc3)ccc2c1] |
| 1-[(4-{[4-(5-chloro-1,3-benzoxazol-2-yl)phenyl]carbonyl}piperazin-1-yl)carbonyl]cyclopropan-1-ol | 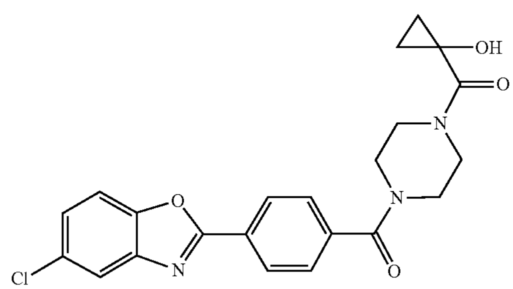 [SMILES: O=C(c1ccc(-c2nc3cc(Cl)ccc3o2)cc1)N1CCN(C(=O)C2(O)CC2)CC1] |
| 1-[(4-{[4-(6-chloro-1,3-benzoxazol-2-yl)phenyl]carbonyl}piperazin-1-yl)carbonyl]cyclopropan-1-ol | 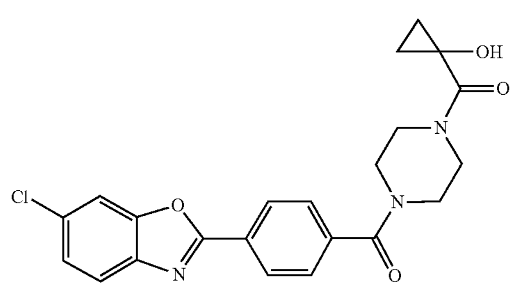 [SMILES: O=C(c1ccc(-c2nc3ccc(Cl)cc3o2)cc1)N1CCN(C(=O)C2(O)CC2)CC1] |

-continued

| NAME | Structure |
|---|---|
| 1-[(4-{[4-(5-fluoro-1,3-benzoxazol-2-yl)phenyl]carbonyl}piperazin-1-yl)carbonyl]cyclopropan-1-ol | 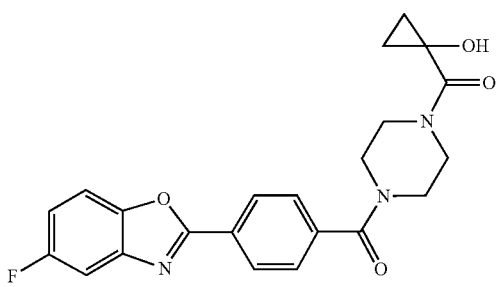 [SMILES: O=C(c1ccc(-c2nc3cc(F)ccc3o2)cc1)N1CCN(C(=O)C2(O)CC2)CC1] |
| 1-[(4-{[4-(6-fluoro-1,3-benzoxazol-2-yl)phenyl]carbonyl}piperazin-1-yl)carbonyl]cyclopropan-1-ol | 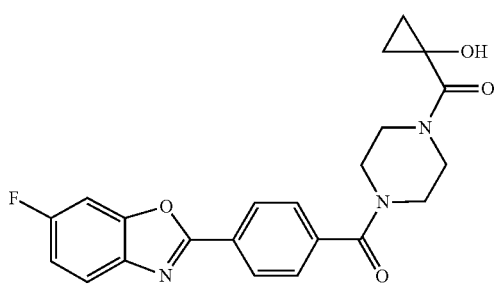 [SMILES: O=C(c1ccc(-c2nc3ccc(F)cc3o2)cc1)N1CCN(C(=O)C2(O)CC2)CC1] |
| 1-({4-[(4-{pyrazolo[1,5-a]pyridin-2-yl}phenyl)carbonyl]piperazin-1-yl}carbonyl)cyclopropan-1-ol | 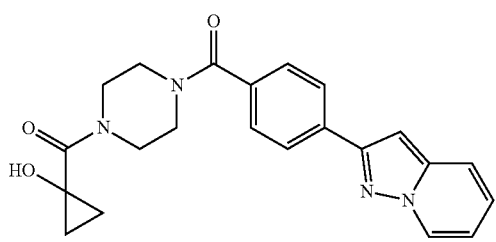 [SMILES: O=C(c1ccc(-c2cc3ccccn3n2)cc1)N1CCN(C(=O)C2(O)CC2)CC1] |
| 1-{[4-({4-[1-(propan-2-yl)-1H-indazol-5-yl]phenyl}carbonyl)piperazin-1-yl]carbonyl}cyclopropan-1-ol | 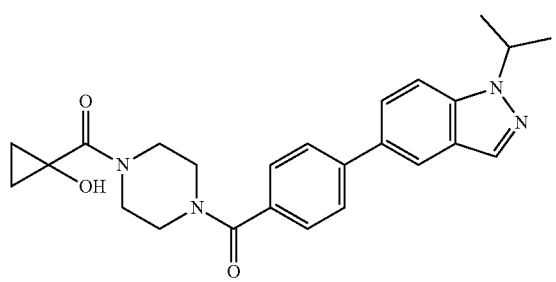 [SMILES: CC(C)n1ncc2cc(-c3ccc(C(=O)N4CCN(C(=O)C5(O)CC5)CC4)cc3)ccc21] |
| 1-[(4-{[6-(2-methoxyquinolin-6-yl)phenyl-3-yl]carbonyl}piperazin-1-yl)carbonyl]cyclopropan-1-ol | 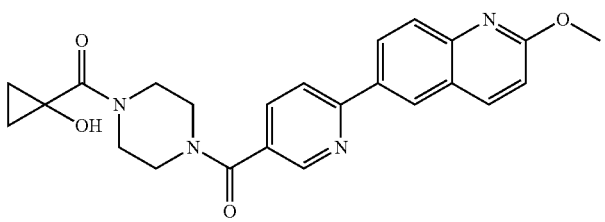 [SMILES: COc1ccc2cc(-c3ccc(C(=O)N4CCN(C(=O)C5(O)CC5)CC4)cn3)ccc2n1] |
| 1-[(4-{[5-(2-methoxyquinolin-6-yl)phenyl-2-yl]carbonyl}piperazin-1-yl)carbonyl]cyclopropan-1-ol | 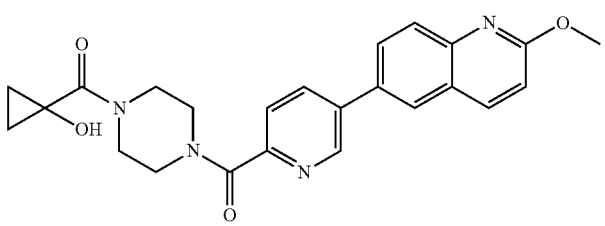 [SMILES: COc1ccc2cc(-c3ccc(C(=O)N4CCN(C(=O)C5(O)CC5)CC4)nc3)ccc2n1] |

-continued

| NAME | Structure |
|---|---|
| 1-{[4-({6-phenylimidazo[1,2-a]pyridine-2-yl}carbonyl)piperazin-1-yl]carbonyl}cyclopropan-1-ol | 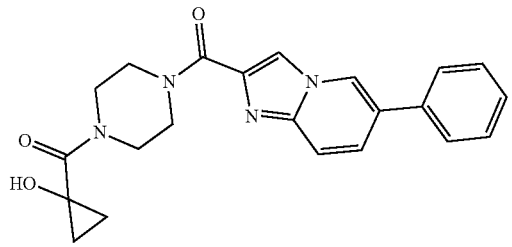 [SMILES: O=C(c1cn2cc(-c3ccccc3)ccc2n1)N1CCN(C(=O)C2(O)CC2)CC1] |
| 1-[(4-{[6-(4-fluorophenyl)imidazo[1,2-a]pyridine-2-yl]carbonyl}piperazin-1-yl)carbonyl]cyclopropan-1-ol | 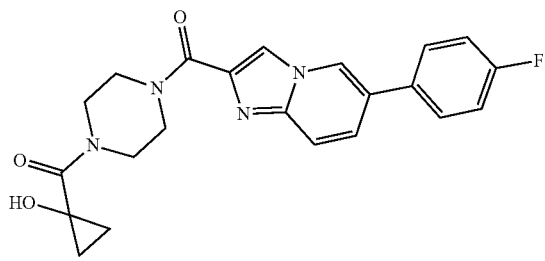 [SMILES: O=C(c1cn2cc(-c3ccc(F)cc3)ccc2n1)N1CCN(C(=O)C2(O)CC2)CC1] |
| 1-[(4-{[5-(4-chloro-2-fluorophenyl)pyridin-2-yl]carbonyl}piperazin-1-yl)carbonyl]cyclopropan-1-ol | 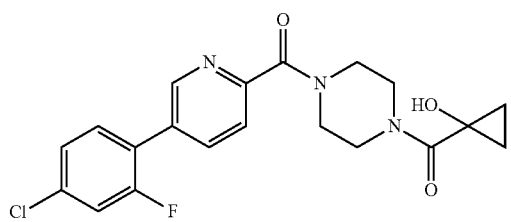 [SMILES: O=C(c1ccc(-c2ccc(Cl)cc2F)cn1)N1CCN(C(=O)C2(O)CC2)CC1] |
| 1-[(4-{[6-(4-chloro-2-fluorophenyl)pyridin-3-yl]carbonyl}piperazin-1-yl)carbonyl]cyclopropan-1-ol | 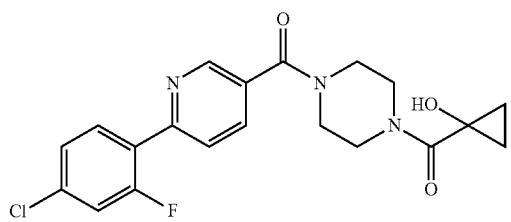 [SMILES: O=C(c1ccc(-c2ccc(Cl)cc2F)nc1)N1CCN(C(=O)C2(O)CC2)CC1] |
| 1-[(4-{[5-(4-chloro-2-fluorophenyl)pyridin-2-yl]carbonyl}piperazin-1-yl)carbonyl]cyclopropan-1-ol | 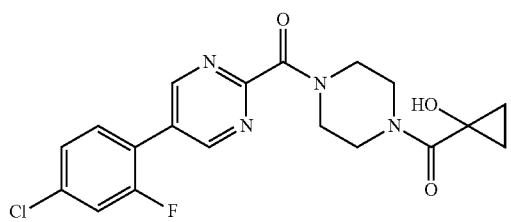 [SMILES: O=C(c1ncc(-c2ccc(Cl)cc2F)cn1)N1CCN(C(=O)C2(O)CC2)CC1] |
| 1-[(4-{[2-fluoro-4-(6-fluoroquinolin-2-yl)phenyl]carbonyl}piperazin-1-yl)carbonyl]cyclopropan-1-ol | 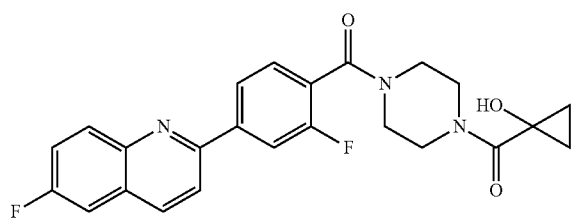 [SMILES: O=C(c1ccc(-c2ccc3cc(F)ccc3n2)cc1F)N1CCN(C(=O)C2(O)CC2)CC1] |

| NAME | Structure |
|---|---|
| 1-[(4-{[2-fluoro-4-(6-methoxyquinolin-2-yl)phenyl]carbonyl}piperazin-1-yl)carbonyl]cyclopropan-1-ol | 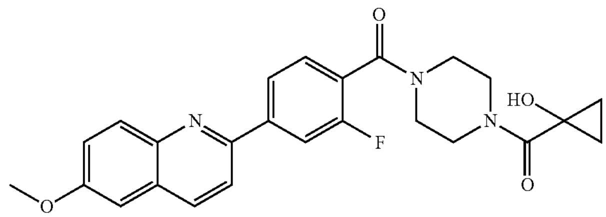 [SMILES: COc1ccc2nc(-c3ccc(C(=O)N4CCN(C(=O)C5(O)CC5)CC4)c(F)c3)ccc2c1] |
| 1-[(4-{[2,3-difluoro-4-(quinolin-2-yl)phenyl]carbonyl}piperazin-1-yl)carbonyl]cyclopropan-1-ol | 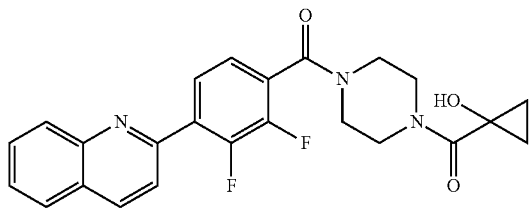 [SMILES: O=C(c1ccc(-c2ccc3ccccc3n2)c(F)c1F)N1CCN(C(=O)C2(O)CC2)CC1] |
| 1-[(4-{[2,3-difluoro-4-(6-fluoroquinolin-2-yl)phenyl]carbonyl}piperazin-1-yl)carbonyl]cyclopropan-1-ol | 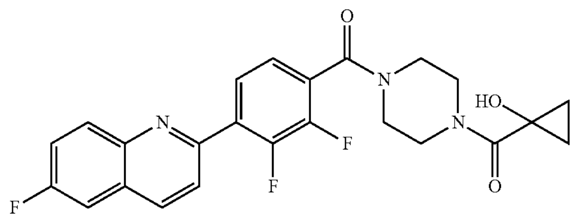 [SMILES: O=C(c1ccc(-c2ccc3cc(F)ccc3n2)c(F)c1F)N1CCN(C(=O)C2(O)CC2)CC1] |
| 1-[(4-{[2,3-difluoro-4-(6-methoxyquinolin-2-yl)phenyl]carbonyl}piperazin-1-yl)carbonyl]cyclopropan-1-ol | 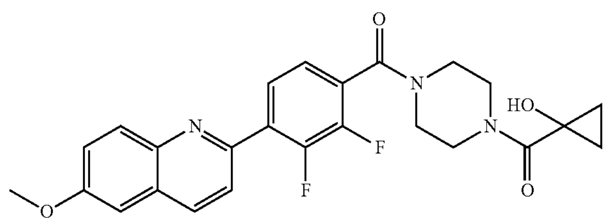 [SMILES: COc1ccc2nc(-c3ccc(C(=O)N4CCN(C(=O)C5(O)CC5)CC4)c(F)c3F)ccc2c1] |
| 1-[(4-{[4-(6-fluoroquinolin-2-yl)phenyl]carbonyl}piperazin-1-yl)carbonyl]cyclopropan-1-ol | 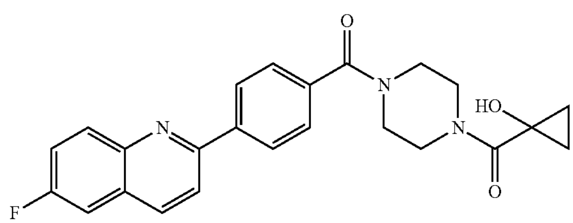 [SMILES: O=C(c1ccc(-c2ccc3cc(F)ccc3n2)cc1)N1CCN(C(=O)C2(O)CC2)CC1] |
| 1-[(4-{[4-(6-methoxyquinolin-2-yl)phenyl]carbonyl}piperazin-1-yl)carbonyl]cyclopropan-1-ol | 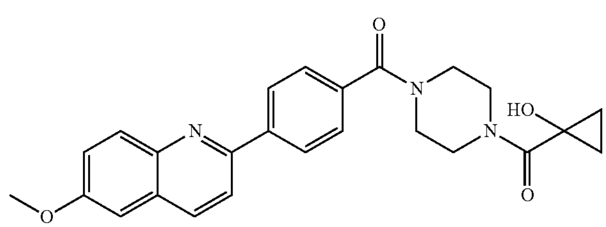 [SMILES: COc1ccc2nc(-c3ccc(C(=O)N4CCN(C(=O)C5(O)CC5)CC4)cc3)ccc2c1] |
| 1-({4-[(4-{imidazo[1,2-a]pyridin-2-yl}phenyl)carbonyl]piperazin-1-yl}carbonyl)cyclopropan-1-ol | 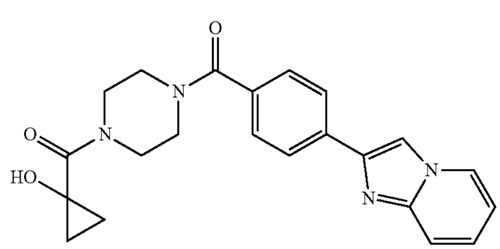 [SMILES: O=C(c1ccc(-c2cn3ccccc3n2)cc1)N1CCN(C(=O)C2(O)CC2)CC1] |

| NAME | Structure |
|---|---|
| 1-[(4-{[4-(2,1,3-benzoxadiazol-5-yl)phenyl]carbonyl}piperazin-1-yl)carbonyl]cyclopropan-1-ol | 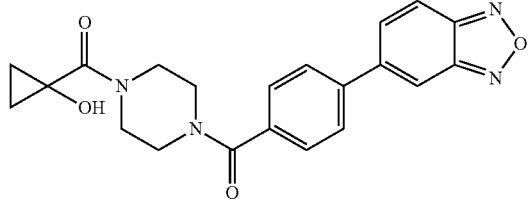 [SMILES: O=C(c1ccc(-c2ccc3nonc3c2)cc1)N1CCN(C(=O)C2(O)CC2)CC1] |
| N-{3[4-({4-[(1-hydroxycyclopropyl)carbonyl]piperazin-1-yl}carbonyl)phenyl]phenyl}benzenesulfonamide | 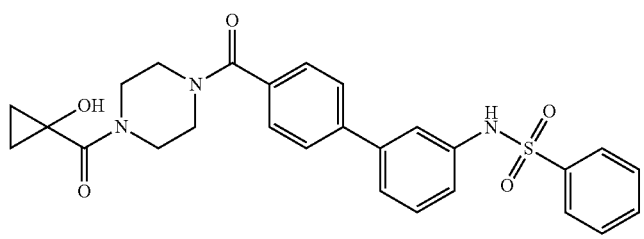 [SMILES: O=C(c1ccc(-c2cccc(NS(=O)(=O)c3ccccc3)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}methanesulfonamide | 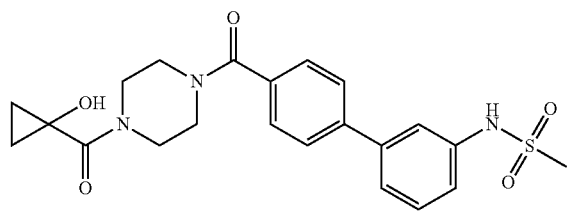 [SMILES: CS(=O)(=O)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}propane-2-sulfonamide | 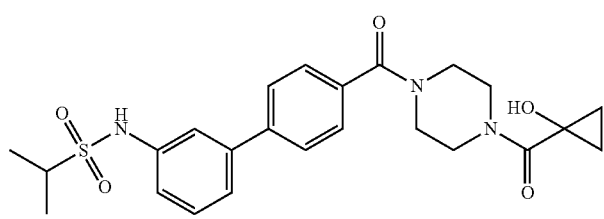 [SMILES: CC(C)S(=O)(=O)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}cyclopropanesulfonamide | 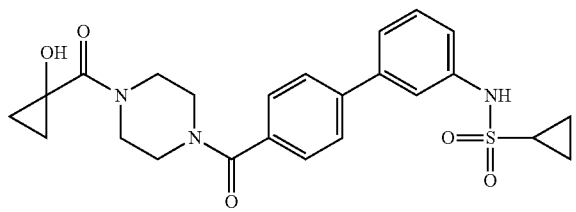 [SMILES: O=C(c1ccc(-c2cccc(NS(=O)(=O)C3CC3)c2)cc1)N1CCN(C(=O)C2(O)CC2)CC1] |
| 1-[(4-{[4-(isoquinolin-1-yl)phenyl]carbonyl}piperazin-1-yl)carbonyl]cyclopropan-1-ol | 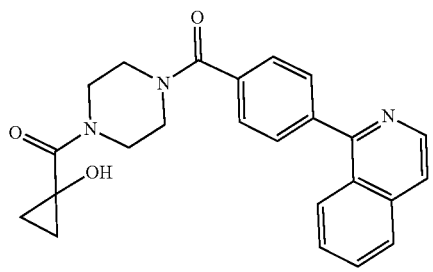 [SMILES: O=C(c1ccc(-c2nccc3ccccc23)cc1)N1CCN(C(=O)C2(O)CC2)CC1] |

-continued

| NAME | Structure |
|---|---|
| 1-{[4-({4-[7-(trifluoromethyl)quinolin-4-yl]phenyl}carbonyl)piperazin-1-yl]carbonyl}cyclopropan-1-ol | 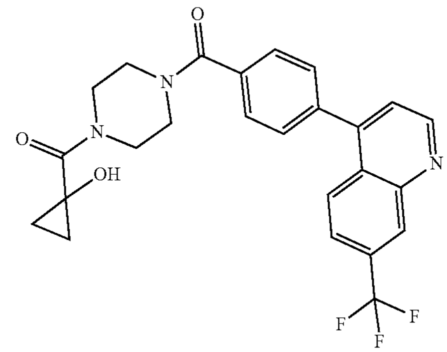 [SMILES: O=C(c1ccc(-c2ccnc3cc(C(F)(F)F)ccc23)cc1)N1CCN(C(=O)C2(O)CC2)CC1] |
| 1-[(4-{[4-(6-methoxy-4-methylquinolin-2-yl)phenyl]carbonyl}piperazin-1-yl)carbonyl]cyclopropan-1-ol | 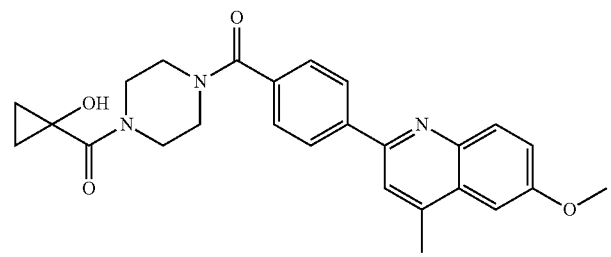 [SMILES: COc1ccc2nc(-c3ccc(C(=O)N4CCN(C(=O)C5(O)CC5)CC4)cc3)cc(C)c2c1] |
| 1-[(4-{[4-(5-chloro-1H-1,3-benzodiazol-2-yl)phenyl]carbonyl}piperazin-1-yl)carbonyl]cyclopropan-1-ol | 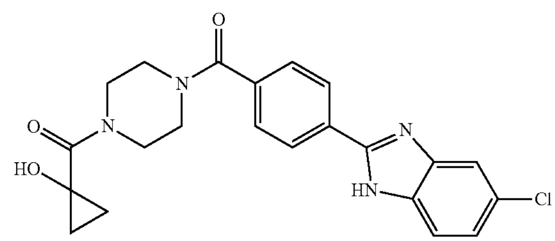 [SMILES: O=C(c1ccc(-c2nc3cc(Cl)ccc3[nH]2)cc1)N1CCN(C(=O)C2(O)CC2)CC1] |
| 1-[(4-{[4-(4-chloro-1H-1,3-benzodiazol-2-yl)phenyl]carbonyl}piperazin-1-yl)carbonyl]cyclopropan-1-ol | 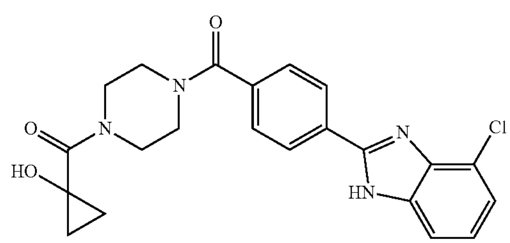 [SMILES: O=C(c1ccc(-c2nc3c(Cl)cccc3[nH]2)cc1)N1CCN(C(=O)C2(O)CC2)CC1] |
| 1-[(4-{[4-(5,6-difluoro-1H-1,3-benzodiazol-2-yl)phenyl]carbonyl}piperazin-1-yl)carbonyl]cyclopropan-1-ol | 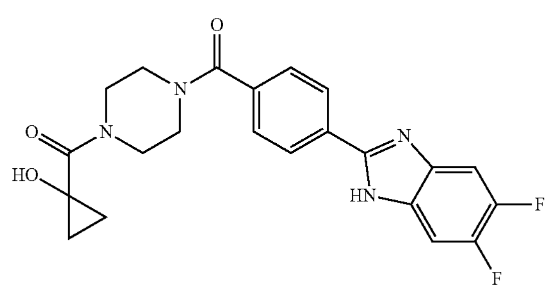 [SMILES: O=C(c1ccc(-c2nc3cc(F)c(F)cc3[nH]2)cc1)N1CCN(C(=O)C2(O)CC2)CC1] |
| 1-[(4-{[4-(5-methoxy-1H-1,3-benzodiazol-2-yl)phenyl]carbonyl}piperazin-1-yl)carbonyl]cyclopropan-1-ol | 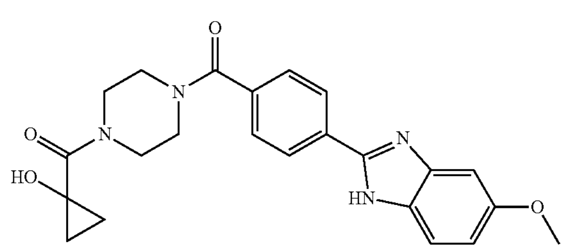 [SMILES: COc1ccc2[nH]c(-c3ccc(C(=O)N4CCN(C(=O)C5(O)CC5)CC4)cc3)nc2c1] |

| NAME | Structure |
|---|---|
| 1-[(4-{[4-(5-fluoro-1H-1,3-benzodiazol-2-yl)phenyl]carbonyl}piperazin-1-yl)carbonyl]cyclopropan-1-ol | 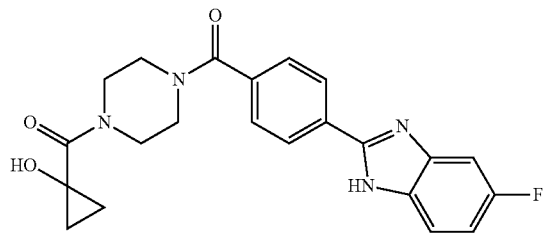 [SMILES: O=C(c1ccc(-c2nc3cc(F)ccc3[nH]2)cc1)N1CCN(C(=O)C2(O)CC2)CC1] |
| 1-[(4-{[4-(1,3-dimethyl-1H-indazol-5-yl)phenyl]carbonyl}piperazin-1-yl)carbonyl]cyclopropan-1-ol | 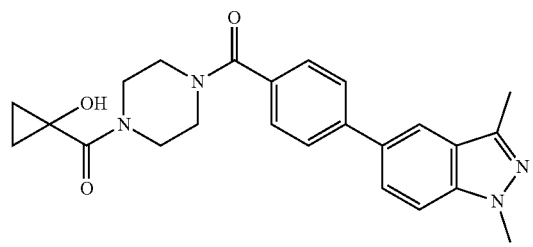 [SMILES: Cc1nn(C)c2ccc(-c3ccc(C(=O)N4CCN(C(=O)C5(O)CC5)CC4)cc3)cc12] |
| 6-[4-({4-[(1-hydroxycyclopropyl)carbonyl]piperazin-1-yl}carbonyl)phenyl]-2,3-dihydro-1,3-benzoxazol-2-one | 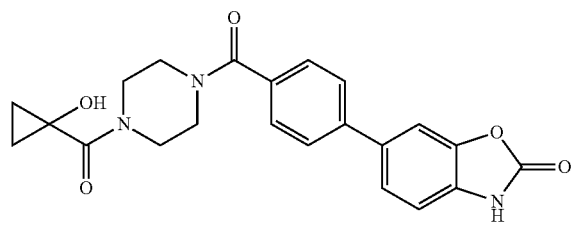 [SMILES: O=C(c1ccc(-c2ccc3[nH]c(=O)oc3c2)cc1)N1CCN(C(=O)C2(O)CC2)CC1] |
| 5-[4-({4-[(1-hydroxycyclopropyl)carbonyl]piperazin-1-yl}carbonyl)phenyl]-2,3-dihydro-1,3-benzoxazol-2-one | 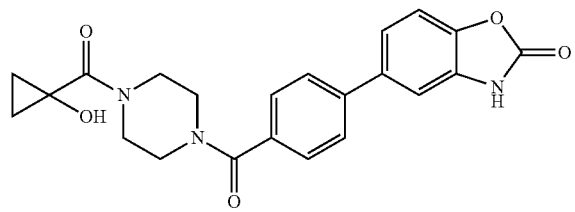 [SMILES: O=C(c1ccc(-c2ccc3oc(=O)[nH]c3c2)cc1)N1CCN(C(=O)C2(O)CC2)CC1] |
| 1-[(4-{[4-(3-methyl-1,2-benzoxazol-6-yl)phenyl]carbonyl}piperazin-1-yl)carbonyl]cyclopropan-1-ol | 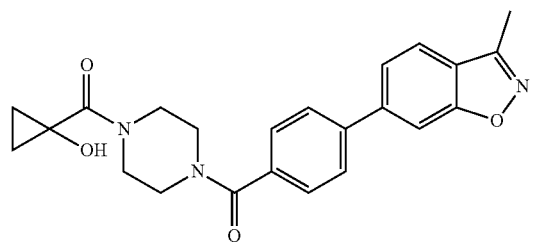 [SMILES: Cc1noc2cc(-c3ccc(C(=O)N4CCN(C(=O)C5(O)CC5)CC4)cc3)ccc12] |
| 1-[(4-{[4-(1H-1,3-benzodiazol-4-yl)phenyl]carbonyl}piperazin-1-yl)carbonyl]cyclopropan-1-ol | 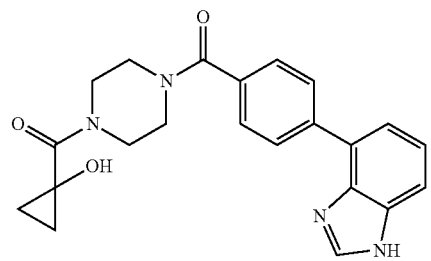 |

| NAME | Structure |
|---|---|
| 1-[(4-{[4-(1,3-benzoxazol-4-yl)phenyl]carbonyl}piperazin-1-yl)carbonyl]cyclopropan-1-ol | 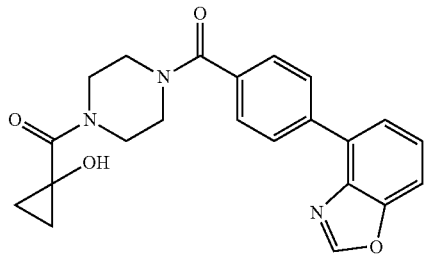 [SMILES: O=C(c1ccc(-c2cccc3ocnc23)cc1)N1CCN(C(=O)C2(O)CC2)CC1] |
| 1-[(4-{[4-(quinolin-5-yl)phenyl]carbonyl}piperazin-1-yl)carbonyl]cyclopropan-1-ol | 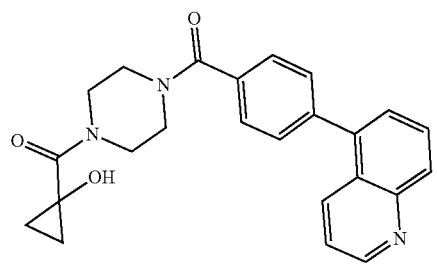 [SMILES: O=C(c1ccc(-c2cccc3ncccc23)cc1)N1CCN(C(=O)C2(O)CC2)CC1] |
| 1-[(4-{[4-(1H-indazol-3-yl)phenyl]carbonyl}piperazin-1-yl)carbonyl]cyclopropan-1-ol | 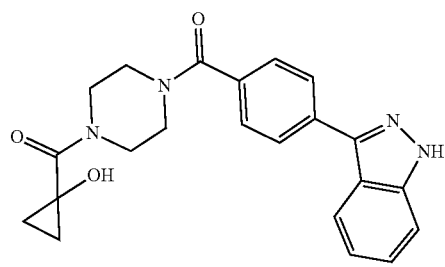 [SMILES: O=C(c1ccc(-c2n[nH]c3ccccc23)cc1)N1CCN(C(=O)C2(O)CC2)CC1] |
| 1-({4-[(4-{furo[3,2-b]pyridin-5-yl}phenyl)carbonyl]piperazin-1-yl}carbonyl)cyclopropan-1-ol | 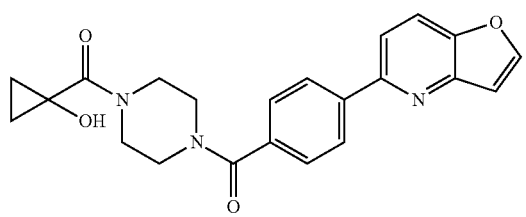 [SMILES: O=C(c1ccc(-c2ccc3occc3n2)cc1)N1CCN(C(=O)C2(O)CC2)CC1] |
| 1-({4-[(4-{furo[3,2-c]pyridin-4-yl}phenyl)carbonyl]piperazin-1-yl}carbonyl)cyclopropan-1-ol | 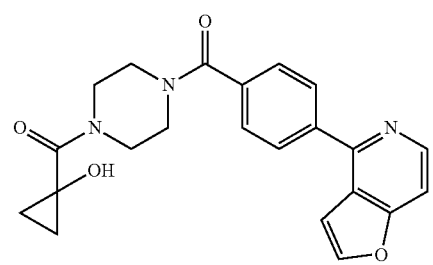 [SMILES: O=C(c1ccc(-c2nccc3occc23)cc1)N1CCN(C(=O)C2(O)CC2)CC1] |
| 1-({4-[(4-{[1,2,4]triazolo[4,3-b]pyridazin-6-yl}phenyl)carbonyl]piperazin-1-yl}carbonyl)cyclopropan-1-ol | 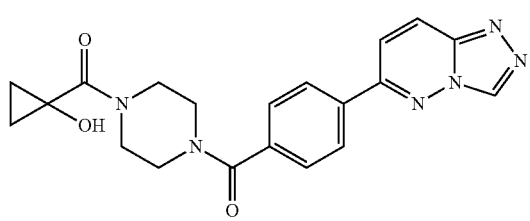 [SMILES: O=C(c1ccc(-c2ccc3nncn3n2)cc1)N1CCN(C(=O)C2(O)CC2)CC1] |

| NAME | Structure |
|------|-----------|
| 1-({4-[(4-{imidazo[1,2-a]pyrazin-6-yl}phenyl)carbonyl]piperazin-1-yl}carbonyl)cyclopropan-1-ol | 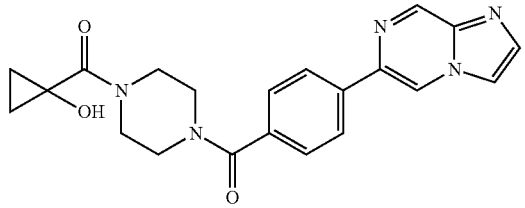 [SMILES: O=C(c1ccc(-c2cn3ccnc3cn2)cc1)N1CCN(C(=O)C2(O)CC2)CC1] |
| 1-({4-[(4-{1H-pyrrolo[3,2-b]pyridin-5-yl}phenyl)carbonyl]piperazin-1-yl}carbonyl)cyclopropan-1-ol | 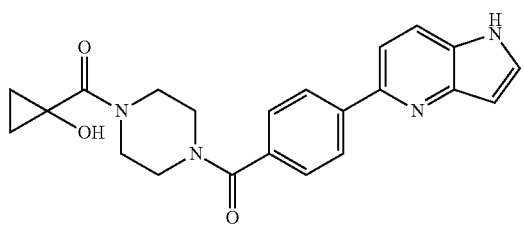 [SMILES: O=C(c1ccc(-c2ccc3[nH]ccc3n2)cc1)N1CCN(C(=O)C2(O)CC2)CC1] |
| 1-({4-[(4-{imidazo[1,2-b]pyridazin-6-yl}phenyl)carbonyl]piperazin-1-yl}carbonyl)cyclopropan-1-ol | 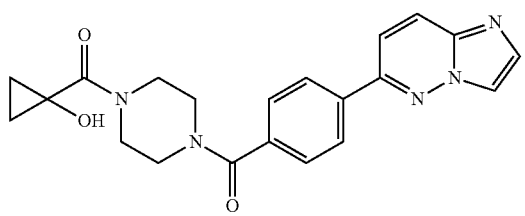 [SMILES: O=C(c1ccc(-c2ccc3nccn3n2)cc1)N1CCN(C(=O)C2(O)CC2)CC1] |
| 1-[(4-{[4-(1-methyl-1H-1,3-benzodiazol-5-yl)phenyl]carbonyl}piperazin-1-yl)carbonyl]cyclopropan-1-ol | 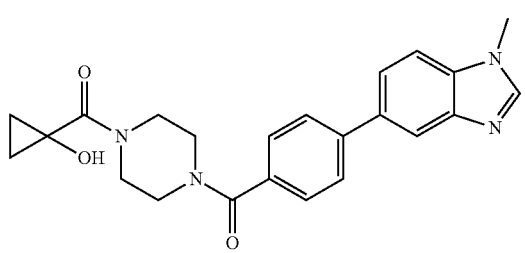 [SMILES: Cn1cnc2cc(-c3ccc(C(=O)N4CCN(C(=O)C5(O)CC5)CC4)cc3)ccc21] |
| 1-[(4-{[4-(2,1,3-benzothiadiazol-4-yl)phenyl]carbonyl}piperazin-1-yl)carbonyl]cyclopropan-1-ol | 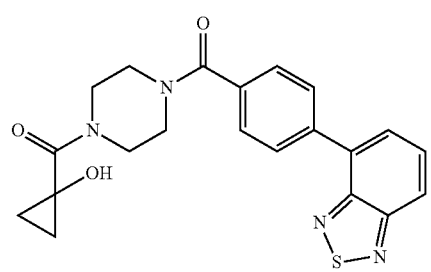 [SMILES: O=C(c1ccc(-c2cccc3nsnc23)cc1)N1CCN(C(=O)C2(O)CC2)CC1] |
| 1-{[4-({4-[2-(trifluoromethyl)imidazo[1,2-a]pyridin-6-yl]phenyl}carbonyl)piperazin-1-yl]carbonyl}cyclopropan-1-ol | 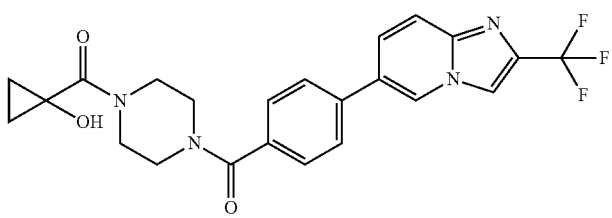 [SMILES: O=C(c1ccc(-c2ccc3nc(C(F)(F)F)cn3c2)cc1)N1CCN(C(=O)C2(O)CC2)CC1] |

| NAME | Structure |
|---|---|
| 1-({4-[(4-{6-chloroimidazo[1,2-a]pyridin-3-yl}phenyl)carbonyl]piperazin-1-yl}carbonyl)cyclopropan-1-ol | 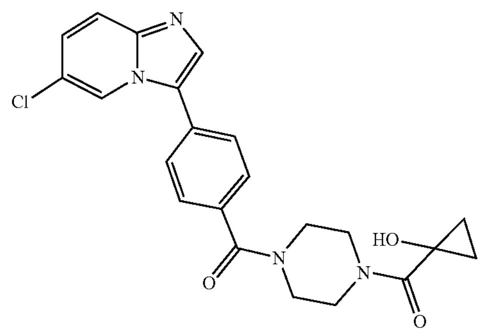 [SMILES: O=C(c1ccc(-c2cnc3ccc(Cl)cn23)cc1)N1CCN(C(=O)C2(O)CC2)CC1] |
| 1-[(4-{[4-(2-methyl-2H-indazol-5-yl)phenyl]carbonyl}piperazin-1-yl)carbonyl]cyclopropan-1-ol | 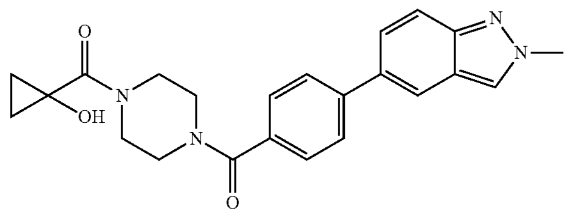 [SMILES: Cn1cc2cc(-c3ccc(C(=O)N4CCN(C(=O)C5(O)CC5)CC4)cc3)ccc2n1] |
| 1-({4-[(4-{imidazo[1,2-a]pyrimidin-7-yl}phenyl)carbonyl]piperazin-1-yl}carbonyl)cyclopropan-1-ol | 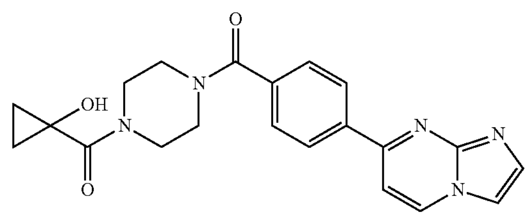 [SMILES: O=C(c1ccc(-c2ccn3ccnc3n2)cc1)N1CCN(C(=O)C2(O)CC2)CC1] |
| 5-[4({4-[(1-hydroxycyclopropyl)carbonyl]piperazin-1-yl}carbonyl)phenyl]-1H-indole-2-carbonitrile | 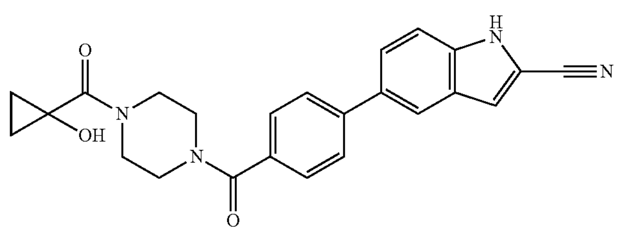 |
| 2-[4-({4-[(1-hydroxycyclopropyl)carbonyl]piperazin-1-yl}carbonyl)phenyl]-1,3-benzoxazole-6-carbonitrile | 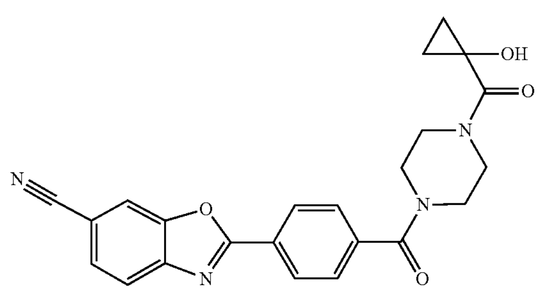 [SMILES: N#Cc1ccc2nc(-c3ccc(C(=O)N4CCN(C(=O)C5(O)CC5)CC4)cc3)oc2c1] |
| 1-[(4-{[4-(2,1,3-benzothiadiazol-5-yl)phenyl]carbonyl}piperazin-1-yl)carbonyl]cyclopropan-1-ol | 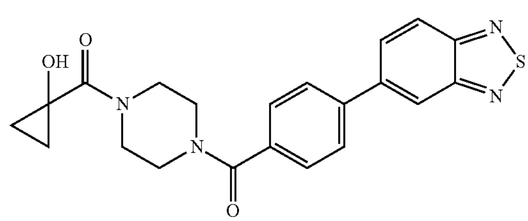 [SMILES: O=C(c1ccc(-c2ccc3nsnc3c2)cc1)N1CCN(C(=O)C2(O)CC2)CC1] |

-continued

| NAME | Structure |
|---|---|
| 1-[(4-{[4-(2H-1,2,3-benzotriazol-5-yl)phenyl]carbonyl}piperazin-1-yl)carbonyl]cyclopropan-1-ol | 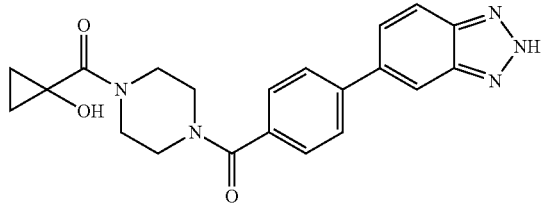 [SMILES: O=C(c1ccc(-c2ccc3n[nH]nc3c2)cc1)N1CCN(C(=O)C2(O)CC2)CC1] |
| 1-({4-[(2-phenyl-1,3-benzothiazol-6-yl)phenyl]piperazin-1-yl}carbonyl)cyclopropan-1-ol | 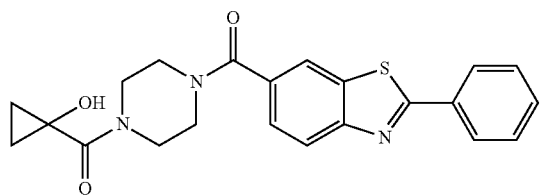 [SMILES: O=C(c1ccc2nc(-c3ccccc3)sc2c1)N1CCN(C(=O)C2(O)CC2)CC1] |
| 1-[(4-{[2-(4-fluorophenyl)-1,3-benzothiazol-6-yl]carbonyl}piperazin-1-yl)carbonyl]cyclopropan-1-ol | 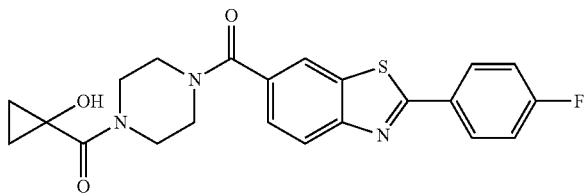 [SMILES: O=C(c1ccc2nc(-c3ccc(F)cc3)sc2c1)N1CCN(C(=O)C2(O)CC2)CC1] |
| 2-[4-({4-[(1-hydroxycyclopropyl)carbonyl]piperazin-1-yl}carbonyl)phenyl]-1,3-benzoxazole-5-carbonitrile | 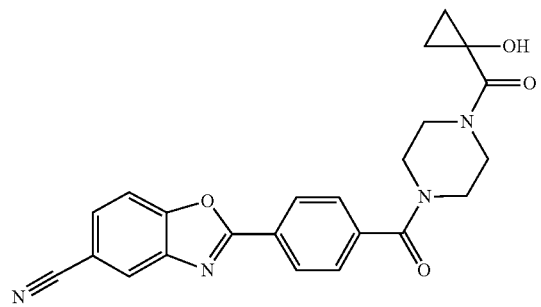 [SMILES: N#Cc1ccc2oc(-c3ccc(C(=O)N4CCN(C(=O)C5(O)CC5)CC4)cc3)nc2c1] |
| 3-[4-({4-[(1-hydroxycyclopropyl)carbonyl]piperazin-1-yl}carbonyl)phenyl]-1,3-dihydroquinolin-2-one | 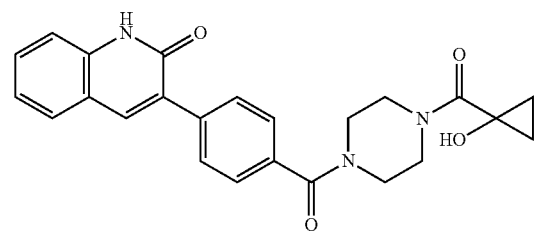 [SMILES: O=C(c1ccc(-c2cc3ccccc3[nH]c2=O)cc1)N1CCN(C(=O)C2(O)CC2)CC1] |
| 1-({4-[(2-chloro-4-{imidazo[1,2-a]pyridin-2-yl}phenyl)carbonyl]piperazin-1-yl}carbonyl)cyclopropan-1-ol | 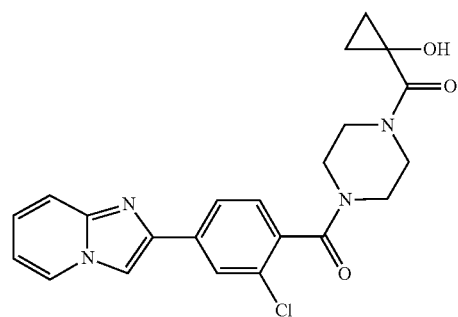 [SMILES: O=C(c1ccc(-c2cn3ccccc3n2)cc1Cl)N1CCN(C(=O)C2(O)CC2)CC1] |

-continued

| NAME | Structure |
|---|---|
| 1-({4-[(3-phenoxyphenyl)carbonyl]piperazin-1-yl}carbonyl)cyclopropan-1-ol | 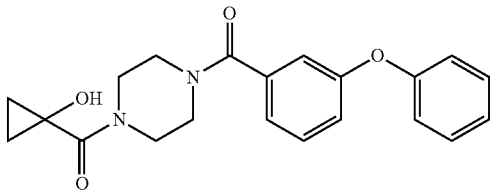 [SMILES: O=C(c1cccc(Oc2ccccc2)c1)N1CCN(C(=O)C2(O)CC2)CC1] |
| 1-({4-[(4-{6-fluoroimidazo[1,2-a]pyridin-2-yl}phenyl)carbonyl]piperazin-1-yl}carbonyl)cyclopropan-1-ol | 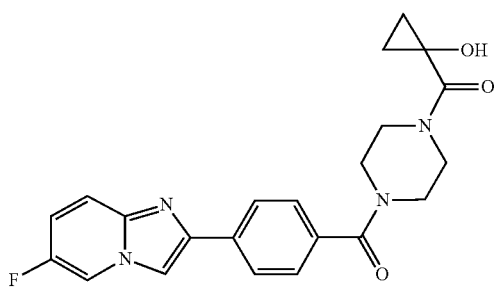 [SMILES: O=C(c1ccc(-c2cn3cc(F)ccc3n2)cc1)N1CCN(C(=O)C2(O)CC2)CC1] |
| 1-({4-[(4-{6-methoxyimidazo[1,2-a]pyridin-2-yl}phenyl)carbonyl]piperazin-1-yl}carbonyl)cyclopropan-1-ol | 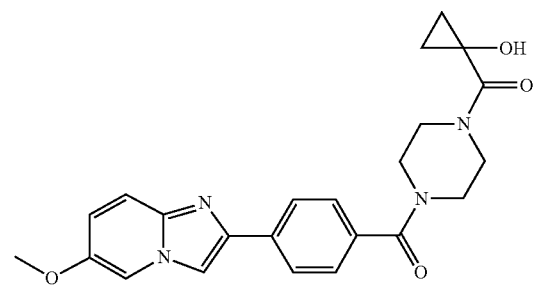 [SMILES: COc1ccc2nc(-c3ccc(C(=O)N4CCN(C(=O)C5(O)CC5)CC4)cc3)cn2c1] |
| N-{3-[4-({4-[(1-hydroxycyclopropyl)carbonyl]piperazin-1-yl}carbonyl)phenyl]phenyl}cyclopropanecarboxamide | 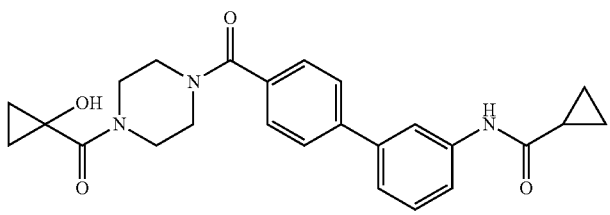 |
| 1-{[(2S)-4-{[4-(4-chloro-2-fluorophenyl)phenyl]carbonyl}-2-(hydroxymethyl)piperazin-1-yl]carbonyl}cyclopropan-1-ol | 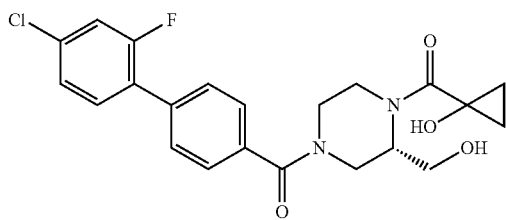 [SMILES: O=C(c1ccc(-c2ccc(Cl)cc2F)cc1)N1CCN(C(=O)C2(O)CC2)[C@H](CO)C1] |
| 1-[(4-{[4-(3-cyclopropoxyphenyl)phenyl]carbonyl}piperazin-1-yl)carbonyl]cyclopropan-1-ol | 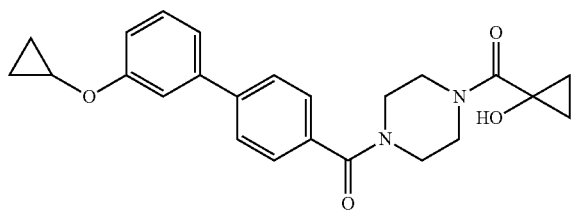 [SMILES: O=C(c1ccc(-c2cccc(OC3CC3)c2)cc1)N1CCN(C(=O)C2(O)CC2)CC1] |

| NAME | Structure |
|---|---|
| N-cyclopropyl-3-[4-({4-[(1-hydroxycyclopropyl)carbonyl]piperazin-1-yl}carbonyl)phenyl]benzene-1-sulfonamide | 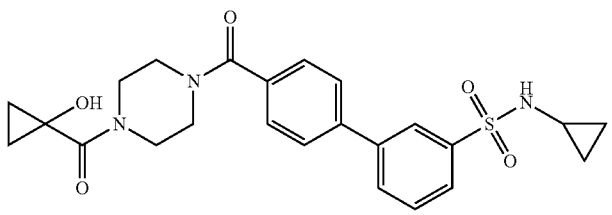 [SMILES: O=C(c1ccc(-c2cccc(S(=O)(=O)NC3CC3)c2)cc1)N1CCN(C(=O)C2(O)CC2)CC1] |
| 5-[4-({4-[(1-hydroxycyclopropyl)carbonyl]piperazin-1-yl}carbonyl)phenyl]-1H-indole-2-carboxamide | 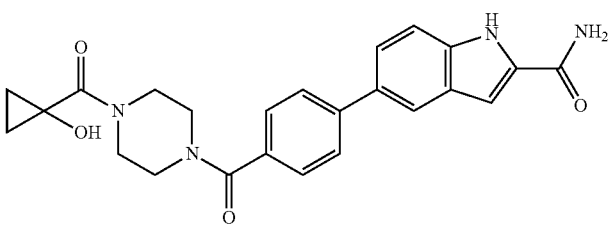 [SMILES: NC(=O)c1cc2cc(-c3ccc(C(=O)N4CCN(C(=O)C5(O)CC5)CC4)cc3)ccc2[nH]1] |
| 1-[(4-{[4-(3-chlorophenyl)phenyl]carbonyl}piperazin-1-yl)carbonyl]cyclopropan-1-ol | 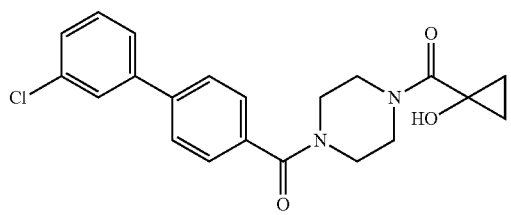 [SMILES: O=C(c1ccc(-c2cccc(Cl)c2)cc1)N1CCN(C(=O)C2(O)CC2)CC1] |
| 1-[(4-{[4-(4-chlorophenyl)phenyl]carbonyl}piperazin-1-yl)carbonyl]cyclopropan-1-ol | 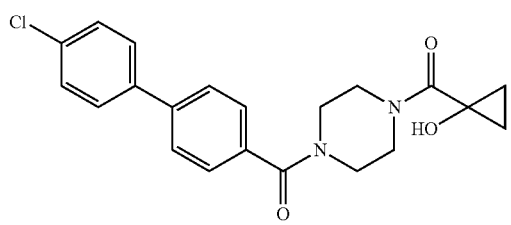 [SMILES: O=C(c1ccc(-c2ccc(Cl)cc2)cc1)N1CCN(C(=O)C2(O)CC2)CC1] |
| 1-{[(3S)-4-{[4-(4-chloro-2-fluorophenyl)phenyl]carbonyl}-3-(hydroxymethyl)piperazin-1-yl]carbonyl}cyclopropan-1-ol | 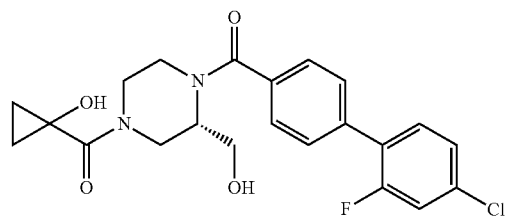 [SMILES: O=C(c1ccc(-c2ccc(Cl)cc2F)cc1)N1CCN(C(=O)C2(O)CC2)C[C@H]1CO] |
| 1-[(4-{[4-(1H-indol-2-yl)phenyl]carbonyl}piperazin-1-yl)carbonyl]cyclopropan-1-ol | 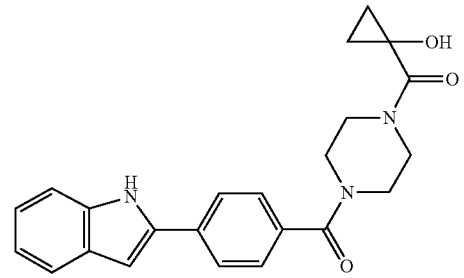 [SMILES: O=C(c1ccc(-c2cc3ccccc3[nH]2)cc1)N1CCN(C(=O)C2(O)CC2)CC1] |

-continued

| NAME | Structure |
|---|---|
| 1-({4-[(4-{3-chloroimidazo[1,2-a]pyridin-2-yl}phenyl)carbonyl]piperazin-1-yl}carbonyl)cyclopropan-1-ol | 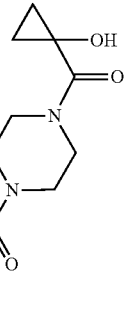 |
| 1-[(4-{[4-(1-methyl-1H-1,3-benzodiazol-2-yl)phenyl]carbonyl}piperazin-1-yl)carbonyl]cyclopropan-1-ol | 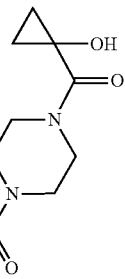 |
| 3-[3-chloro-4-({4-[(1-hydroxycyclopropyl)carbonyl]piperazin-1-yl}carbonyl)phenyl]-N-cyclopropylbenzene-1-sulfonamide | 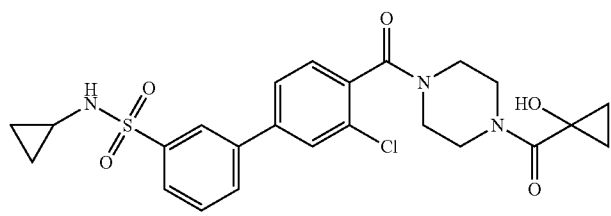 [SMILES: O=C(c1ccc(-c2cccc(S(=O)(=O)NC3CC3)c2)cc1Cl)N1CCN(C(=O)C2(O)CC2)CC1] |
| 1-({4-[(2-chloro-4-{furo[3,2-b]pyridin-5-yl}phenyl)carbonyl]piperazin-1-yl}carbonyl)cyclopropan-1-ol | 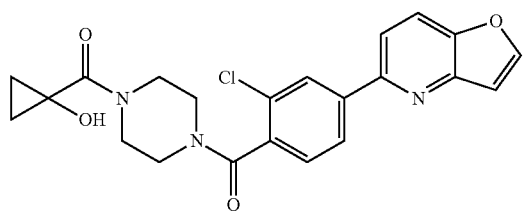 [SMILES: O=C(c1ccc(-c2ccc3occc3n2)cc1Cl)N1CCN(C(=O)C2(O)CC2)CC1] |
| 1-[(4-{[2-chloro-4-(1-melhyl-1H-1,3-benzodiazol-5-yl)phenyl]carbonyl}piperazin-1-yl)carbonyl]cyclopropan-1-ol | 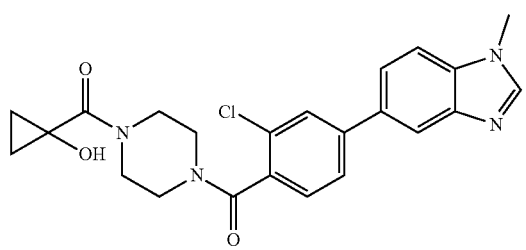 [SMILES: Cn1cnc2cc(-c3ccc(C(=O)N4CCN(C(=O)C5(O)CC5)CC4)c(Cl)c3)ccc21] |
| N-{3-[3-chloro-4-({4-[(1-hydroxycyclopropyl)carbonyl]piperazin-1-yl}carbonyl)phenyl]phenyl}cyclopropanecarboxamide | 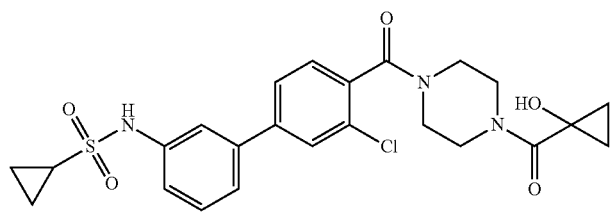 [SMILES: O=C(c1ccc(-c2cccc(NS(=O)(=O)C3CC3)c2)cc1Cl)N1CCN(C(=O)C2(O)CC2)CC1] |

-continued

| NAME | Structure |
|---|---|
| N-{3-[4-({4-[(1-hydroxycyclobropyl)carbonyl]piperazin-1-yl}carbonyl)phenyl]phenyl}cyclobutane-carboxamide | 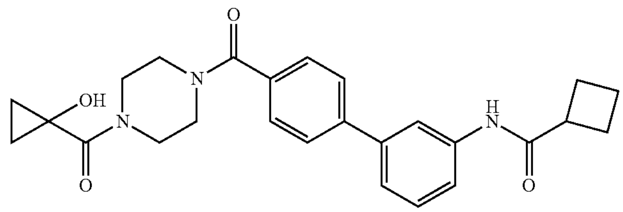 [SMILES: O=C(Nc1cccc(-c2ccc(C(=O)N3CCN(C(=O)C4(O)CC4)CC3)cc2)c1)C1CCC1] |
| 1-{[4-({4-[3-(cyclopropanesulfonyl)phenyl]phenyl}carbonyl)piperazin-1-yl]carbonyl}cyclopropan-1-ol | 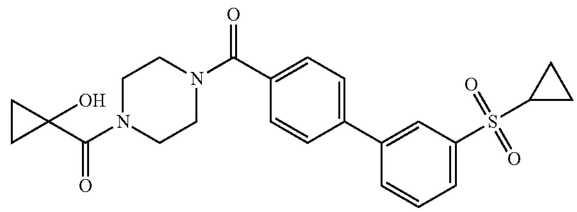 [SMILES: O=C(c1ccc(-c2cccc(S(=O)(=O)C3CC3)c2)cc1)N1CCN(C(=O)C2(O)CC2)CC1] |
| N-{5-[3-chloro-4-({4-[(1-hydroxycyclopropyl)carbonyl]piperazin-1-yl}carbonyl)phenyl]pyridin-3-yl}cyclopropanesulfonamide | |
| N-{5-[3-chloro-4-({4-[(1-hydroxycyclopropyl)carbonyl]piperazin-1-yl}carbonyl)phenyl]pyridin-3-yl}cyclopropanesulfonamide | |
| N-{3-[4-({4-[(1-hydroxycyclopropyl)carbonyl]piperazin-1-yl}carbonyl)phenyl]phenyl}oxetane-3-carboxamide | 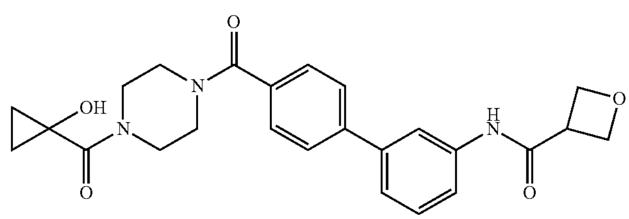 [SMILES: O=C(Nc1cccc(-c2ccc(C(=O)N3CCN(C(=O)C4(O)CC4)CC3)cc2)c1)C1COC1] |
| 1-{[4-({4-[3-(cyclopropanesulfonyl)phenyl]phenyl}carbonyl)piperazin-1-yl]carbonyl}cyclobutan-1-ol | 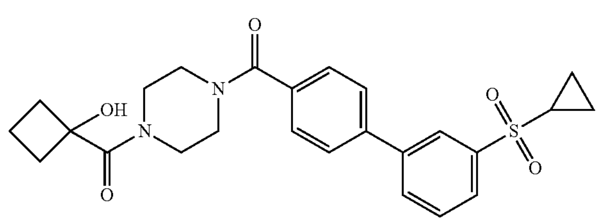 [SMILES: O=C(c1ccc(-c2cccc(S(=O)(=O)C3CC3)c2)cc1)N1CCN(C(=O)C2(O)CCC2)CC1] |
| 1-{[4-[3-(cyclopropanesulfonyl)phenyl]phenyl}carbonyl)-4-[(oxetan-2-yl)carbonyl]piperazine | 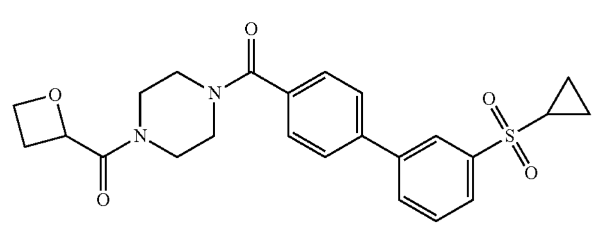 [SMILES: O=C(c1ccc(-c2cccc(S(=O)(=O)C3CC3)c2)cc1)N1CCN(C(=O)C2CCO2)CC1] |

-continued

| NAME | Structure |
|---|---|
| 1-({4-[(4-{3-chloroimidazo[1,2-a]pyridin-2-yl}phenyl)carbonyl]piperazin-1-yl}carbonyl)cyclopropan-1-ol | 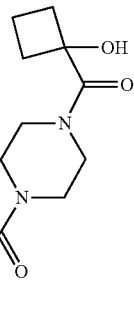 |
| 1-[(4-{3-chloroimidazo[1,2-a]pyridin-2-yl}phenyl)carbonyl]-4-[(oxetan-2-yl)carbonyl]piperazine | 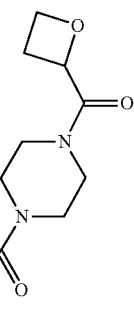 |
| 1-[(4-{[4-(3-cyclopropoxyphenyl)phenyl]carbonyl}piperazin-1-yl)carbonyl]cyclobutan-1-ol | 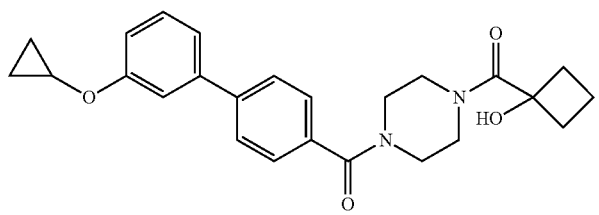 [SMILES: O=C(c1ccc(-c2cccc(OC3CC3)c2)cc1)N1CCN(C(=O)C2(O)CCC2)CC1] |
| 1-{[4-(3-cyclopropoxyphenyl)phenyl]carbonyl}-4-[(oxetan-2-yl)carbonyl]piperazine | 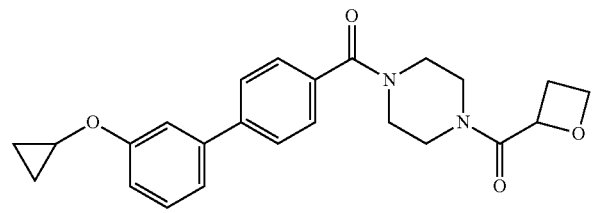 [SMILES: O=C(c1ccc(-c2cccc(OC3CC3)c2)cc1)N1CCN(C(=O)C2CCO2)CC1] |
| N-{3-[4-({4-[(1-hydroxycyclobutyl)carbonyl]piperazin-1-yl}carbonyl)phenyl]phenyl}cyclopropanecarboxamide | 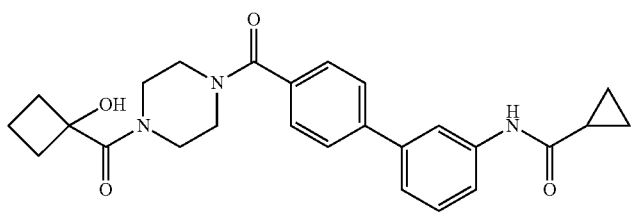 [SMILES: O=C(Nc1cccc(-c2ccc(C(=O)N3CCN(C(=O)C4(O)CCC4)CC3)cc2)c1)C1CC1] |
| N-{3-[4-({4-[(oxetan-2-yl)carbonyl]piperazin-1-yl}carbonyl)phenyl]phenyl}cyclopropanecarboxamide | 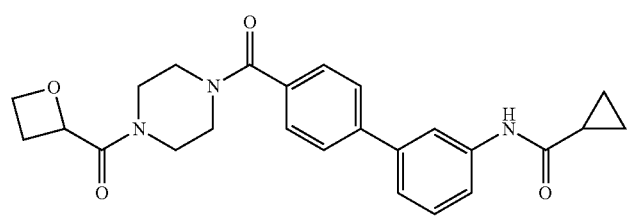 [SMILES: O=C(Nc1cccc(-c2ccc(C(=O)N3CCN(C(=O)C4CCO4)CC3)cc2)c1)C1CC1] |

| NAME | Structure |
|---|---|
| 3-[4-({4-[(1-hydroxycyclobutyl)carbonyl]piperazin-1-yl}carbonyl)phenyl]-1,2-dihydroquinolin-2-one | 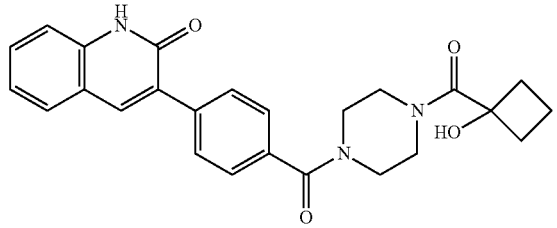 [SMILES: O=C(c1ccc(-c2cc3ccccc3[nH]c2=O)cc1)N1CCN(C(=O)C2(O)CCC2)CC1] |
| 3-[4-({4-[(oxetan-2-yl)carbonyl]piperazin-1-yl}carbonyl)phenyl]-1,2-dihydroquinolin-2-one | 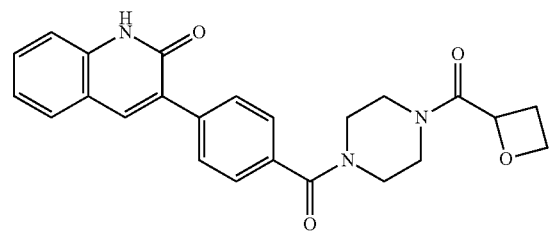 [SMILES: O=C(c1ccc(-c2cc3ccccc3[nH]c2=O)cc1)N1CCN(C(=O)C2CCO2)CC1] |
| 5-[4-({4-[(1-hydroxycyclobutyl)carbonyl]perazin-1-yl}carbonyl)phenyl]-1H-indole-2-carbonitrile | 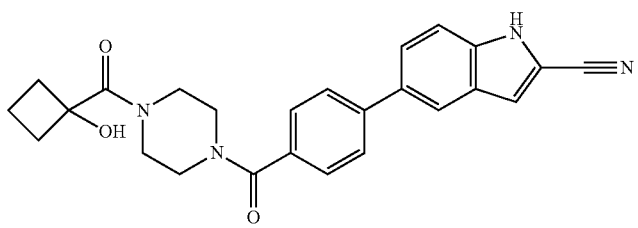 [SMILES: N#Cc1cc2cc(-c3ccc(C(=O)N4CCN(C(=O)C5(O)CCC5)CC4)cc3)ccc2[nH]1] |
| 5-[4-({4-[(oxetan-2-yl)carbonyl]piperazin-1-yl}carbonyl)phenyl]-1H-indole-2-carbonitrile | 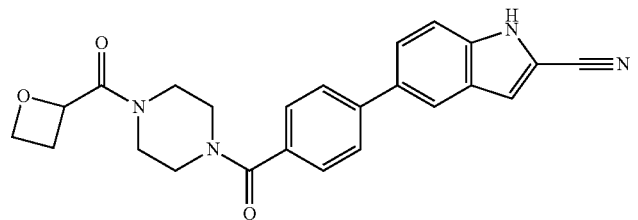 [SMILES: N#Cc1cc2cc(-c3ccc(C(=O)N4CCN(C(=O)C5CCO5)CC4)cc3)ccc2[nH]1] |
| 1-[(4-{[4-(1-melhyl-1H-1,3-benzodiazol-5-yl)phenyl]carbonyl}piperazin-1-yl)carbonyl]cyclobutan-1-ol | 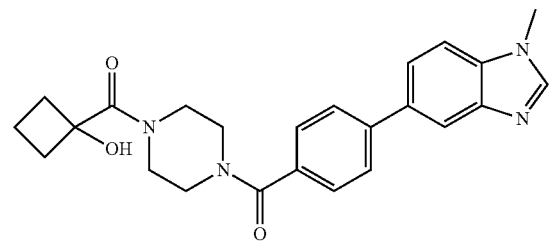 [SMILES: Cn1cnc2cc(-c3ccc(C(=O)N4CCN(C(=O)C5(O)CCC5)CC4)cc3)ccc21] |
| 1-methyl-5-[4-({4-[(oxetan-2-yl)carbonyl]piperazin-1-yl}carbonyl)phenyl]-1H-1,3-benzodiazole | 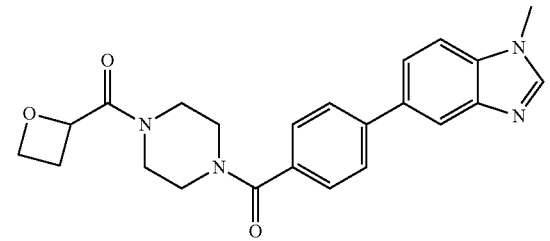 [SMILES: Cn1cnc2cc(-c3ccc(C(=O)N4CCN(C(=O)C5CCO5)CC4)cc3)ccc21] |

| NAME | Structure |
|---|---|
| 1-({4-[(4-{imidazo[1,2-b]pyridazin-6-yl}phenyl)carbonyl]piperazin-1-yl}carbonyl)cyclobutan-1-ol | 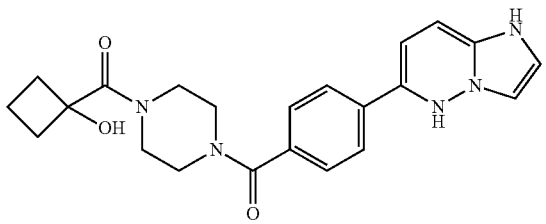 [SMILES: O=C(c1ccc(C2=CC=C3NC=CN3N2)cc1)N1CCN(C(=O)C2(O)CCC2)CC1] |
| 1-[(4-{imidazo[1,2-b]pyridazin-6-yl}phenyl)carbonyl]-4-[(oxetan-2-yl)carbonyl]piperazine | 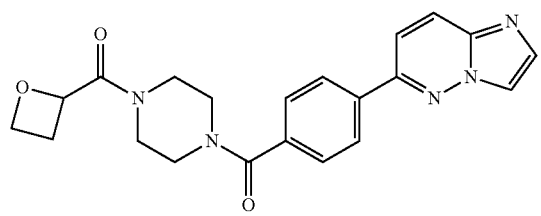 [SMILES: O=C(c1ccc(-c2ccc3nccn3n2)cc1)N1CCN(C(=O)C2CCO2)CC1] |
| 1-({4-[(4-{furo[3,2-b]pyridin-5-yl}phenyl)carbonyl]piperazin-1-yl}carbonyl)cyclobutan-1-ol | 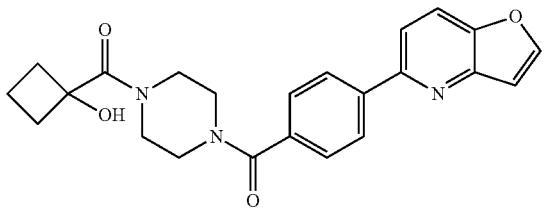 [SMILES: O=C(c1ccc(-c2ccc3occc3n2)cc1)N1CCN(C(=O)C2(O)CCC2)CC1] |
| 1-[(4-{furo[3,2-b]pyridin-5-yl}phenyl)carbonyl]-4-[(oxetan-2-yl)carbonyl]piperazine | 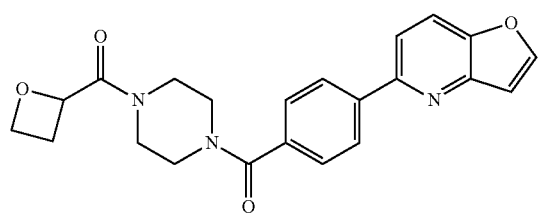 [SMILES: O=C(c1ccc(-c2ccc3occc3n2)cc1)N1CCN(C(=O)C2CCO2)CC1] |
| 1-[(4-{[4-(1H-indazol-3-yl)phenyl]carbonyl}piperazin-1-yl)carbonyl]cyclobutan-1-ol | 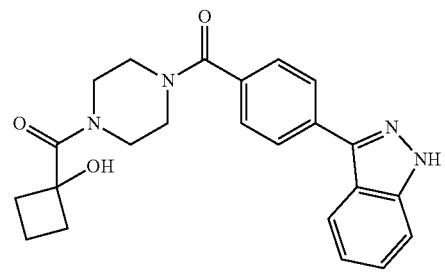 |
| 3-[4-({4-[(oxetan-2-yl)carbonyl]piperazin-1-yl}carbonyl)phenyl]-1H-indazole | 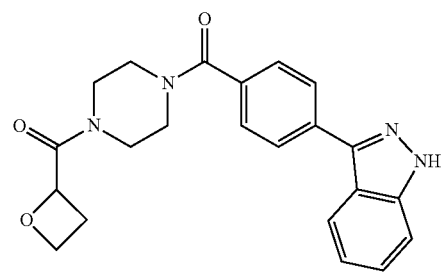 [SMILES: O=C(c1ccc(-c2n[nH]c3ccccc23)cc1)N1CCN(C(=O)C2CCO2)CC1] |

| NAME | Structure |
|---|---|
| 1-[(4-{[4-(1,3-dimethyl-1H-indazol-5-yl)phenyl]carbonyl}piperazin-1-yl)carbonyl]cyclobutan-1-ol | 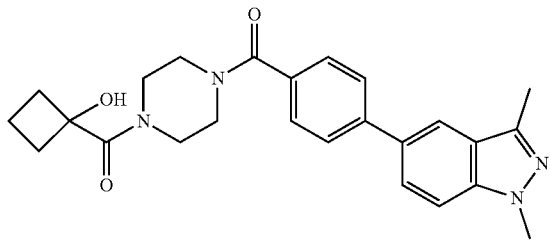 [SMILES: Cc1nn(C)c2ccc(-c3ccc(C(=O)N4CCN(C(=O)C5(O)CCC5)CC4)cc3)cc12] |
| 1,3-dimethyl-5-[4-({4-[(oxetan-2-yl)carbonyl]piperazin-1-yl}carbonyl)phenyl]-1H-indazole | 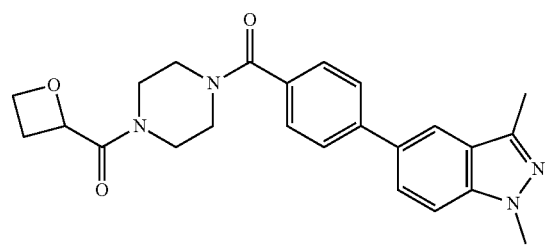 [SMILES: Cc1nn(C)c2ccc(-c3ccc(C(=O)N4CCN(C(=O)C5CCO5)CC4)cc3)cc12] |
| N-{3-[4-({4-[(1-hydroxycyclobutyl)carbonyl]piperazin-1-yl}carbonyl)phenyl]phenyl}cyclopropanesulfonamide | 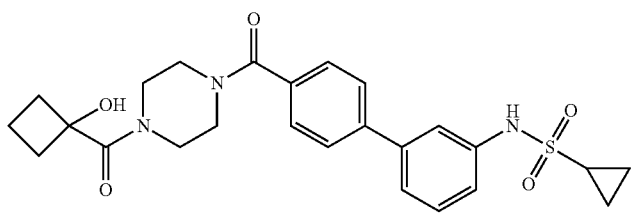 [SMILES: O=C(c1ccc(-c2cccc(NS(=O)(=O)C3CC3)c2)cc1)N1CCN(C(=O)C2(O)CCC2)CC1] |
| N-{3-[4-({4-[(oxetan-2-yl)carbonyl]piperazin-1-yl}carbonyl)phenyl]phenyl}cyclopropanesulfonamide | 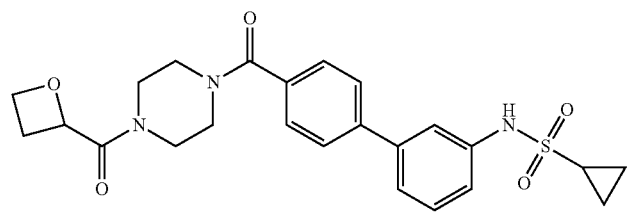 [SMILES: O=C(c1ccc(-c2cccc(NS(=O)(=O)C3CC3)c2)cc1)N1CCN(C(=O)C2CCO2)CC1] |
| 1-[(4-{[4-(6-fluoro-1,3-benzoxazol-2-yl)phenyl]carbonyl}piperazin-1-yl)carbonyl]cyclobutan-1-ol | 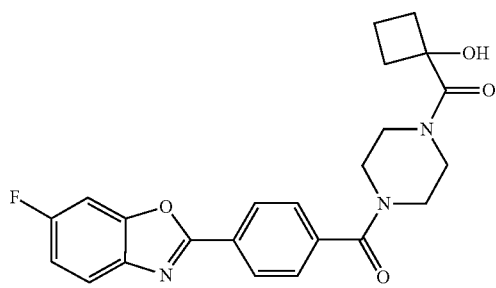 [SMILES: O=C(c1ccc(-c2nc3ccc(F)cc3o2)cc1)N1CCN(C(=O)C2(O)CCC2)CC1] |
| 6-fluoro-2-[4-({4-[(oxetan-2-yl)carbonyl]piperazin-1-yl}carbonyl)phenyl]-1,3-benzoxazole | 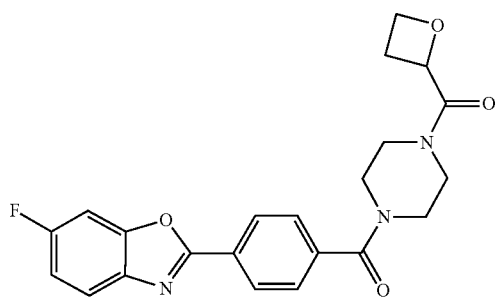 [SMILES: O=C(c1ccc(-c2nc3ccc(F)cc3o2)cc1)N1CCN(C(=O)C2CCO2)CC1] |

| NAME | Structure |
|---|---|
| 1-[(4-{[4-(6-chloro-1,3-benzoxazol-2-yl)phenyl]carbonyl}piperazin-1-yl)carbonyl]cyclobutan-1-ol | 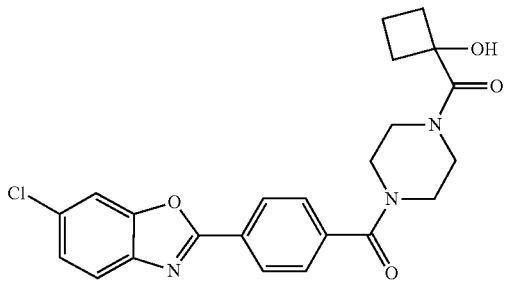 [SMILES: O=C(c1ccc(-c2nc3ccc(Cl)cc3o2)cc1)N1CCN(C(=O)C2(O)CCC2)CC1] |
| 6-chloro-2-[4-({4-[(oxetan-2-yl)carbonyl]piperazin-1-yl}carbonyl)phenyl]-1,3-benzoxazole | 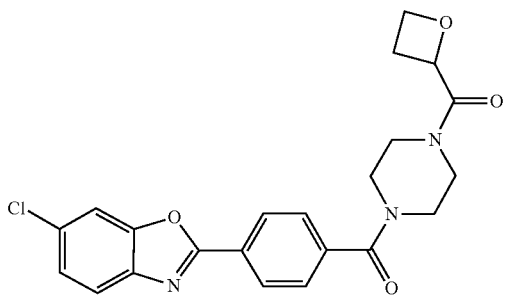 [SMILES: O=C(c1ccc(-c2nc3ccc(Cl)cc3o2)cc1)N1CCN(C(=O)C2CCO2)CC1] |
| 5-[4-({4-[(1-hydroxycyclobutyl)carbonyl]piperazin-1-yl}carbonyl)phenyl]-1H-indole-3-carbonitrile | 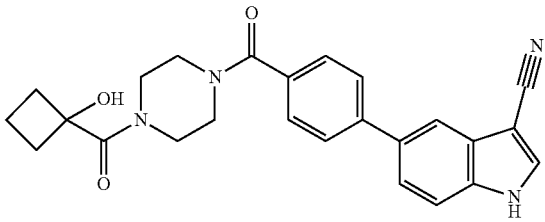 [SMILES: NCc1c[nH]c2ccc(-c3ccc(C(=O)N4CCN(C(=O)C5(O)CCC5)CC4)cc3)cc12] |
| 5-[4-({4-[(oxetan-2-yl)carbonyl]piperazin-1-yl}carbonyl)phenyl]-1H-indole-3-carbonitrile | 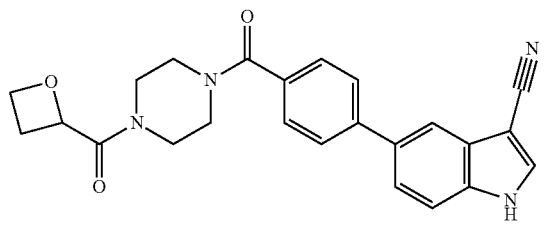 [SMILES: NCc1c[nH]c2ccc(-c3ccc(C(=O)N4CCN(C(=O)C5CCO5)CC4)cc3)cc12] |
| 1-[(4-{[4-(1,3-benzothiazol-2-yl)phenyl]carbonyl}piperazin-1-yl)carbonyl]cyclobutan-1-ol | 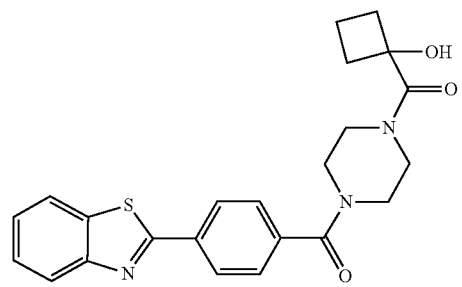 [SMILES: O=C(c1ccc(-c2nc3ccccc3s2)cc1)N1CCN(C(=O)C2(O)CCC2)CC1] |

| NAME | Structure |
|---|---|
| 2-[4-({4-[(oxetan-2-yl)carbonyl]piperazin-1-yl}carbonyl)phenyl]-1,3-benzothiazole | 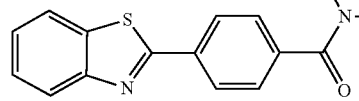 |
| 1-[(4-{[4-(quinolin-2-yl)phenyl]carbonyl}piperazin-1-yl)carbonyl]cyclobutan-1-ol | 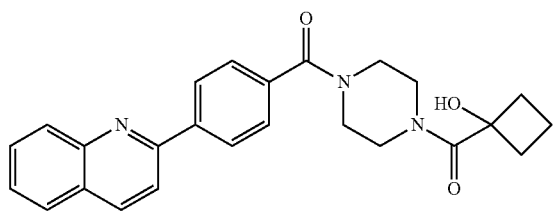 [SMILES: O=C(c1ccc(-c2ccc3ccccc3n2)cc1)N1CCN(C(=O)C2(O)CCC2)CC1] |
| 2-[4-({4-[(oxetan-2-yl)carbonyl]piperazin-1-yl}carbonyl)phenyl]quinoline | 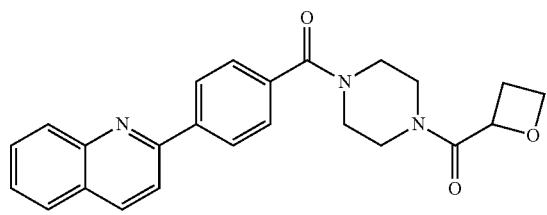 [SMILES: O=C(c1ccc(-c2ccc3ccccc3n2)cc1)N1CCN(C(=O)C2CCO2)CC1] |
| 1-[(4-{[4-(1H-1,3-benzodiazol-5-yl)phenyl]carbonyl}piperazin-1-yl)carbonyl]cyclobutan-1-ol | 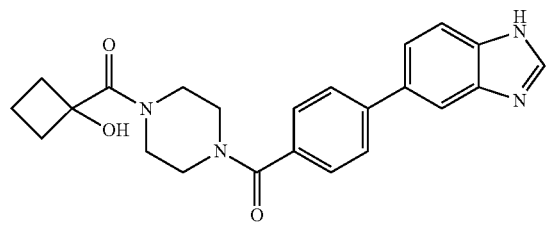 [SMILES: O=C(c1ccc(-c2ccc3[nH]cnc3c2)cc1)N1CCN(C(=O)C2(O)CCC2)CC1] |
| 5-[4-({4-[(oxetan-2-yl)carbonyl]piperazin-1-yl}carbonyl)phenyl]-1H-1,3-benzodiazole | 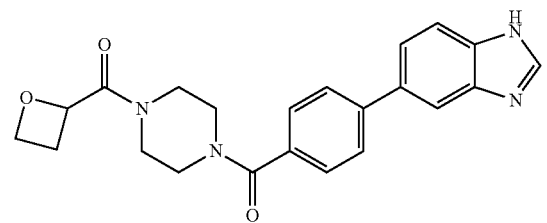 [SMILES: O=C(c1ccc(-c2ccc3[nH]cnc3c2)cc1)N1CCN(C(=O)C2CCO2)CC1] |
| 1-[(4-{[4-(1,3-benzothiazol-6-yl)phenyl]carbonyl}piperazin-1-yl)carbonyl]cyclobutan-1-ol | 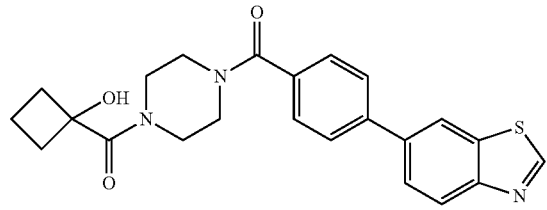 [SMILES: O=C(c1ccc(-c2ccc3ncsc3c2)cc1)N1CCN(C(=O)C2(O)CCC2)CC1] |

-continued

| NAME | Structure |
|---|---|
| 6-[4-({4-[(oxetan-2-yl)carbonyl]piperazin-1-yl}carbonyl)phenyl]-1,3-benzothiazole | 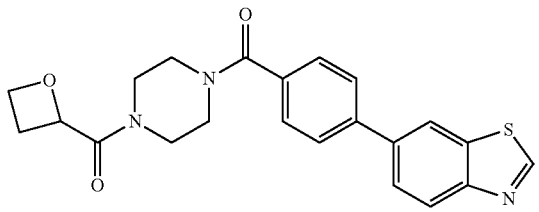 [SMILES: O=C(c1ccc(-c2ccc3ncsc3c2)cc1)N1CCN(C(=O)C2CCO2)CC1] |
| 1-[(4-{[4-(1,3-benzoxazol-5-yl)phenyl]carbonyl}piperazin-1-yl)carbonyl]cyclobutan-1-ol | 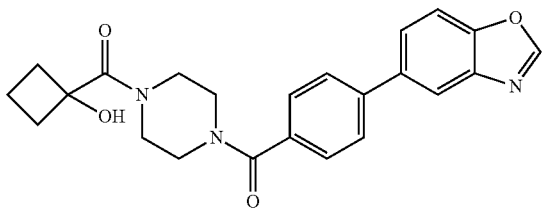 [SMILES: O=C(c1ccc(-c2ccc3ocnc3c2)cc1)N1CCN(C(=O)C2(O)CCC2)CC1] |
| 5-[4-({4-[(oxetan-2-yl)carbonyl]piperazin-1-yl}carbonyl)phenyl]-1,3-benzothiazole | 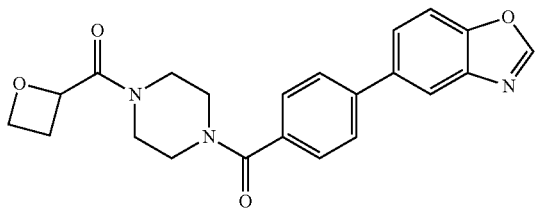 |
| 1-[(4-{[4-(1,3-benzothiazol-5-yl)phenyl]carbonyl}piperazin-1-yl)carbonyl]cyclobutan-1-ol | 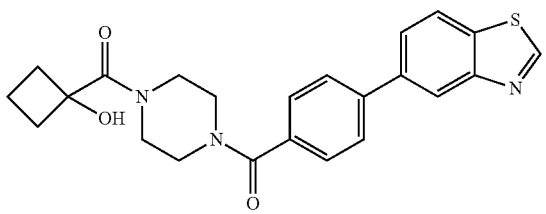 [SMILES: O=C(c1ccc(-c2ccc3scnc3c2)cc1)N1CCN(C(=O)C2(O)CCC2)CC1] |
| 5-[4-({4-[(oxetan-2-yl)carbonyl]piperazin-1-yl}carbonyl)phenyl]-1,3-benzothiazole | 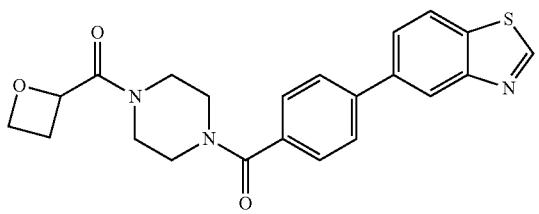 |
| 1-[(4-{[4-(1-methyl-1H-indazol-6-yl)phenyl]carbonyl}piperazin-1-yl)carbonyl]cyclobutan-1-ol | 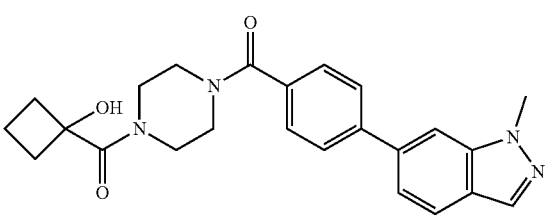 [SMILES: Cn1ncc2ccc(-c3ccc(C(=O)N4CCN(C(=O)C5(O)CCC5)CC4)cc3)cc21] |
| 1-methyl-6-[4-({4-[(oxetan-2-yl)carbonyl]piperazin-1-yl}carbonyl)phenyl]-1H-indazole | 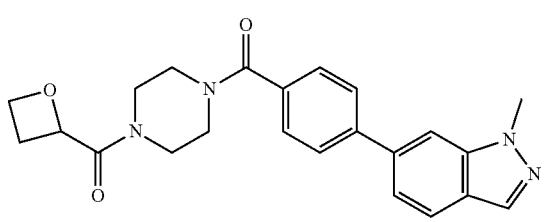 [SMILES: Cn1ncc2ccc(-c3ccc(C(=O)N4CCN(C(=O)C5CCO5)CC4)cc3)cc21] |

-continued

| NAME | Structure |
|---|---|
| N-cyclopropyl-3-[4-({4-[(1-hydroxycyclobutyl)carbonyl]piperazin-1-yl}carbonyl)phenyl]benzamide | 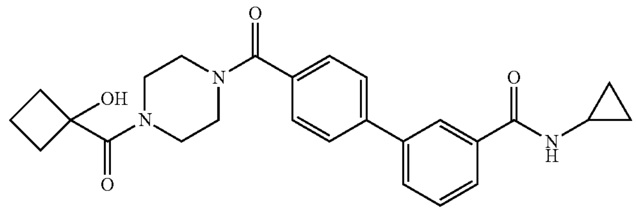 [SMILES: O=C(NC1CC1)c1cccc(-c2ccc(C(=O)N3CCN(C(=O)C4(O)CCC4)CC3)cc2)c1] |
| N-cyclopropyl-3-[4-({4-[(oxetan-2-yl)carbonyl]piperazin-1-yl}carbonyl)phenyl]benzamide | 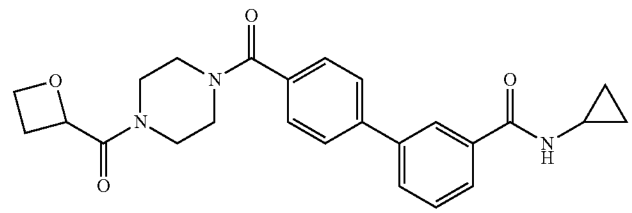 [SMILES: O=C(NC1CC1)c1cccc(-c2ccc(C(=O)N3CCN(C(=O)C4CCO4)CC3)cc2)c1] |
| 1-[(4-{[4-(2-methyl-2H-indazol-6-yl)phenyl]carbonyl}piperazin-1-yl)carbonyl]cyclobutan-1-ol | 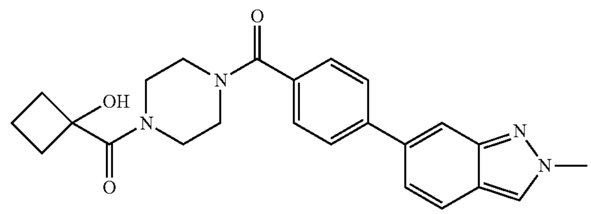 [SMILES: Cn1cc2ccc(-c3ccc(C(=O)N4CCN(C(=O)C5(O)CCC5)CC4)cc3)cc2n1] |
| 2-methyl-6-[4-({4-[(oxetan-2-yl)carbonyl]piperazin-1-yl}carbonyl)phenyl]-2H-indazole | 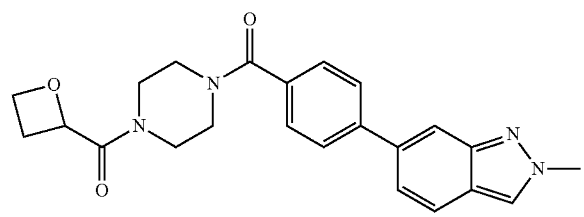 [SMILES: Cn1cc2ccc(-c3ccc(C(=O)N4CCN(C(=O)C5CCO5)CC4)cc3)cc2n1] |
| 1-[(4-{[4-(4-chloro-2-fluorophenyl)phenyl]carbonyl}piperazin-1-yl)carbonyl]cyclobutan-1-ol | 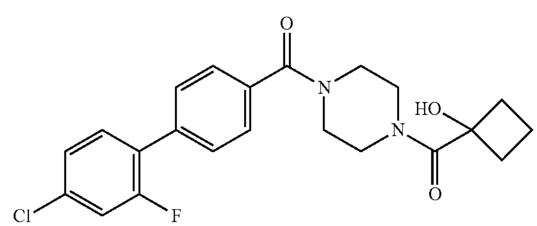 [SMILES: O=C(c1ccc(-c2ccc(Cl)cc2F)cc1)N1CCN(C(=O)C2(O)CCC2)CC1] |
| 1-{[4-(4-chloro-2-fluorophenyl)phenyl]carbonyl}-4-[(oxetan-2-yl)carbonyl]piperazine | 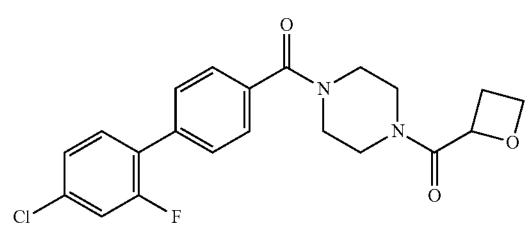 [SMILES: O=C(c1ccc(-c2ccc(Cl)cc2F)cc1)N1CCN(C(=O)C2CCO2)CC1] |
| 1-[(4-{[4-(5-chloro-2-fluorophenyl)phenyl]carbonyl}piperazin-1-yl)carbonyl]cyclobutan-1-ol | 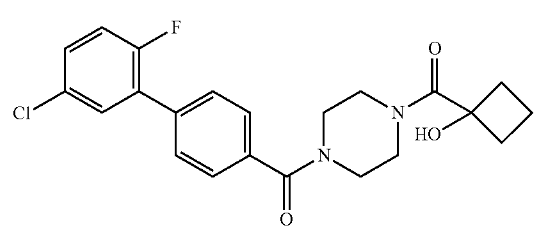 [SMILES: O=C(c1ccc(-c2cc(Cl)ccc2F)cc1)N1CCN(C(=O)C2(O)CCC2)CC1] |

| NAME | Structure |
|---|---|
| 1-{[4-(5-chloro-2-fluorophenyl)phenyl]carbonyl}-4-[(oxetan-2-yl)carbonyl]piperazine | 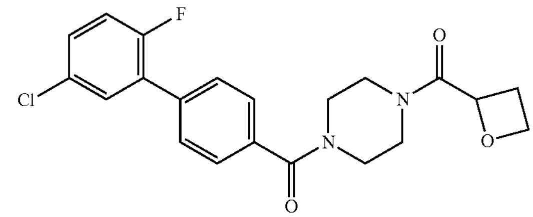 [SMILES: O=C(c1ccc(-c2cc(Cl)ccc2F)cc1)N1CCN(C(=O)C2CCO2)CC1] |
| 1-{[4-({4-[3-(cyclopropanesulfonyl)phenyl]phenyl}carbonyl)piperazin-1-yl]carbonyl}cyclobutan-1-amine | 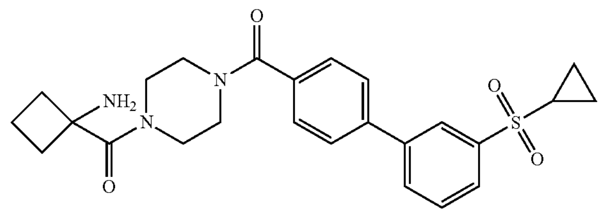 [SMILES: NC1(C(=O)N2CCN(C(=O)c3ccc(-c4cccc(S(=O)(=O)C5CC5)c4)cc3)CC2)CCC1] |
| 1-{[4-({4-[3-(cyclopropanesulfonyl)phenyl]phenyl}carbonyl)piperazin-1-yl]carbonyl}cyclopropane-1-amine | 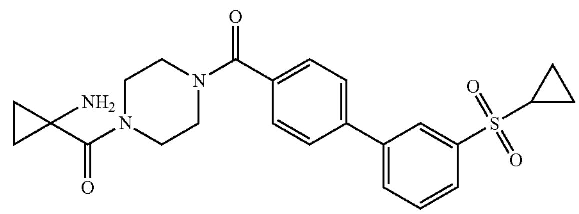 [SMILES: NC1(C(=O)N2CCN(C(=O)c3ccc(-c4cccc(S(=O)(=O)C5CC5)c4)cc3)CC2)CC1] |
| 1-({4-[(4-{3-chloroimidazo[1,2-a]pyridin-2-yl}phenyl)carbonyl]piperazin-1-yl}carbonyl)cyclobutan-1-amine | |
| 1-({4-[(4-{3-chloroimidazo[1,2-a]pyridin-2-yl}phenyl)carbonyl]piperazin-1-yl}carbonyl)cyclobutan-1-amine | |
| 1-[(4-{[4-(3-cyclopropoxyphenyl)phenyl]carbonyl}piperazin-1-yl)carbonyl]cyclobutan-1-amine | 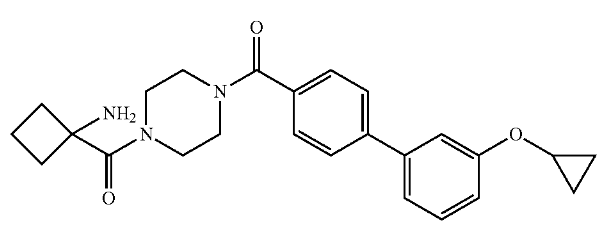 [SMILES: NC1(C(=O)N2CCN(C(=O)c3ccc(-c4cccc(OC5CC5)c4)cc3)CC2)CCC1] |

-continued

| NAME | Structure |
|---|---|
| 1-[(4-{[4-(3-cyclopropoxyphenyl)phenyl]carbonyl}piperazin-1-yl)carbonyl]cyclopropan-1-amine | 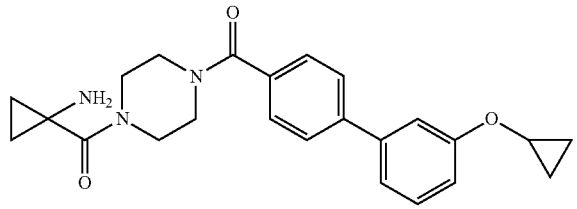 [SMILES: NC1(C(=O)N2CCN(C(=O)c3ccc(-c4cccc(OC5CC5)c4)cc3)CC2)CC1] |
| N-{3-[4-({4-[(1-aminocyclobutyl)carbonyl]piperazin-1-yl}carbonyl)phenyl]phenyl}cyclopropanecarboxamide | 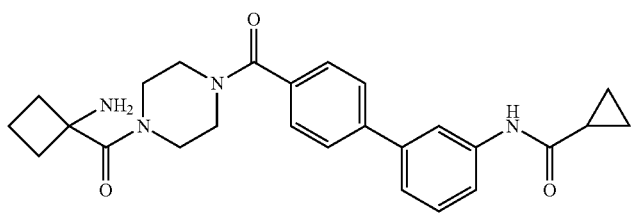 |
| N-{3-[4-({4-[(1-aminocyclopropyl)carbonyl]piperazin-1-yl}carbonyl)phenyl]phenyl}cyclopropanecarboxamide | 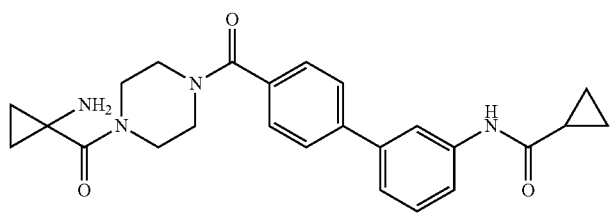 [SMILES: NC1(C(=O)N2CCN(C(=O)c3ccc(-c4cccc(NC(=O)C5CC5)c4)cc3)CC2)CC1] |
| 3-[4-({4-[(1-aminocyclobutyl)carbonyl]piperazin-1-yl}carbonyl)phenyl]-1,2-dihydroquinolin-2-one | 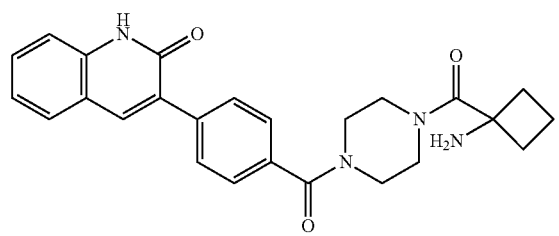 [SMILES: NC1(C(=O)N2CCN(C(=O)c3ccc(-c4cc5ccccc5[nH]c4=O)cc3)CC2)CCC1] |
| 3-[4-({4-[(1-aminocyclopropyl)carbonyl]piperazin-1-yl}carbonyl)phenyl]-1,2-dihydroquinolin-2-one | 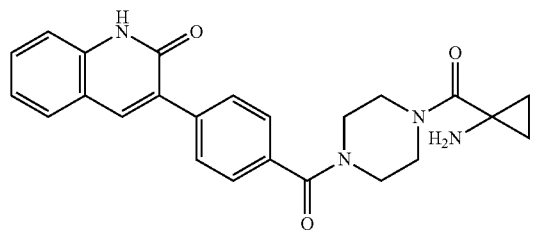 |
| 5-[4-({4-[(1-aminocyclobutyl)carbonyl]piperazin-1-yl}carbonyl)phenyl]-1H-indole-2-carbonitrile | 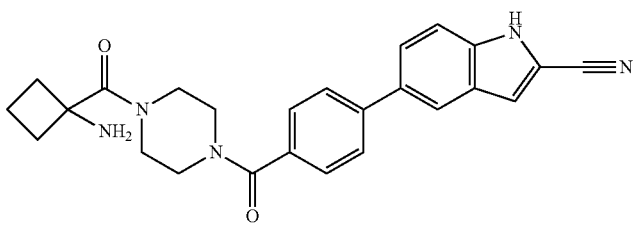 [SMILES: N#Cc1cc2cc(-c3ccc(C(=O)N4CCN(C(=O)C5(N)CCC5)CC4)cc3)ccc2[nH]1] |
| 5-[4-({4-[(1-aminocyclopropyl)carbonyl]piperazin-1-yl}carbonyl)phenyl]-1H-indole-2-carbonitrile | 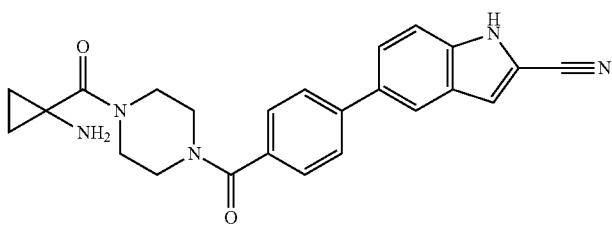 |

| NAME | Structure |
|---|---|
| 1-[(4-{[4-(1-methyl-1H-1,3-benzodiazol-5-yl)phenyl]carbonyl}piperazin-1-yl)carbonyl]cyclobutan-1-amine | 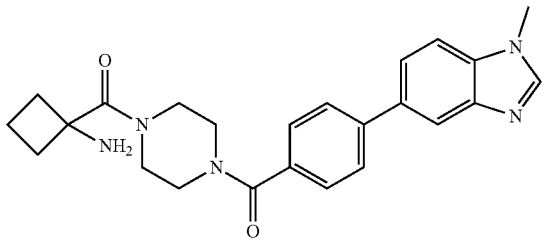 |
| 1-[(4-{[4-(1-methyl-1H-1,3-benzodiazol-5-yl)phenyl]carbonyl}piperazin-1-yl)carbonyl]cyclopropan-1-amine | 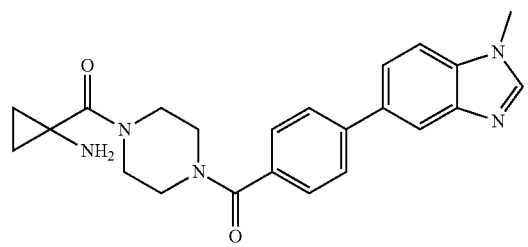 |
| 1-({4-[(4-{imidazo[1,2-b]pyridazin-6-yl}phenyl)carbonyl]piperazin-1-yl}carbonyl)cyclobutan-1-amine | 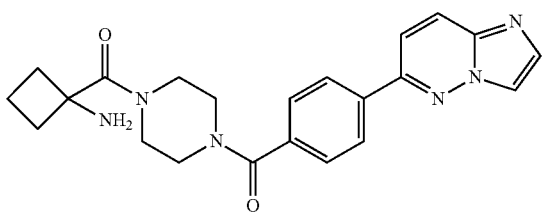 [SMILES: NC1(C(=O)N2CCN(C(=O)c3ccc(-c4ccc5nccn5n4)cc3)CC2)CCC1] |
| 1-({4-[(4-{imidazo[1,2-b]pyridazin-6-yl}phenyl)carbonyl]piperazin-1-yl}carbonyl)cyclopropan-1-amine | 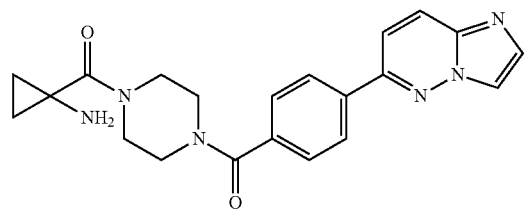 [SMILES: NC1(C(=O)N2CCN(C(=O)c3ccc(-c4ccc5nccn5n4)cc3)CC2)CC1] |
| 1-({4-[(4-{furo[3,2-b]pyridin-5-yl}phenyl)carbonyl]piperazin-1-yl}carbonyl)cyclopropan-1-amine | 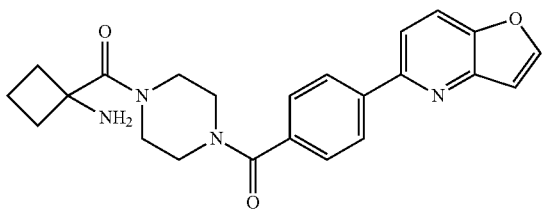 |
| 1-({4-[(4-{furo[3,2-b]pyridin-5-yl}phenyl)carbonyl]piperazin-1-yl}carbonyl)cyclopropan-1-amine | 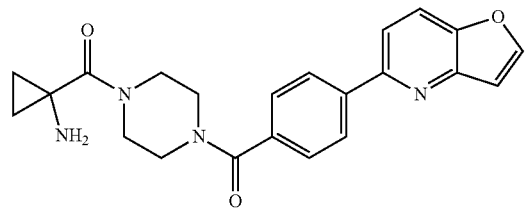 [SMILES: NC1(C(=O)N2CCN(C(=O)c3ccc(-c4ccc5occc5n4)cc3)CC2)CC1] |

-continued

| NAME | Structure |
|---|---|
| 1-[(4-{[4-(1H-indazol-3-yl)phenyl]carbonyl}piperazin-1-yl)carbonyl]cyclobutan-1-amine | 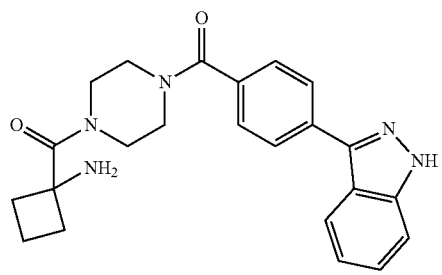 [SMILES: NC1(C(=O)N2CCN(C(=O)c3ccc(-c4n[nH]c5ccccc45)cc3)CC2)CCC1] |
| 1-[(4-{[4-(1H-indazol-3-yl)phenyl]carbonyl}piperazin-1-yl)carbonyl]cyclopropan-1-amine | 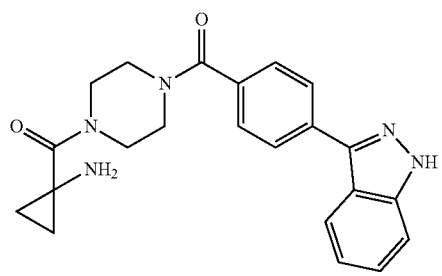 [SMILES: NC1(C(=O)N2CCN(C(=O)c3ccc(-c4n[nH]c5ccccc45)cc3)CC2)CC1] |
| 1-[(4-{[4-(1,3-dimethyl-1H-indazol-5-yl)phenyl]carbonyl}piperazin-1-yl)carbonyl]cyclobutan-1-amine | 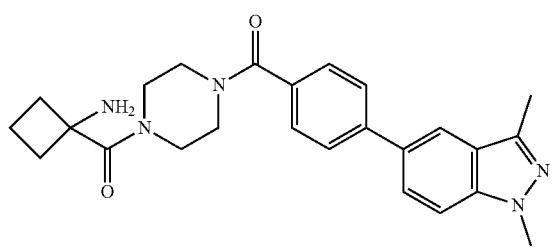 |
| 1-[(4-{[4-(1,3-dimethyl-1H-indazol-5-yl)phenyl]carbonyl}piperazin-1-yl)carbonyl]cyclopropan-1-amine | 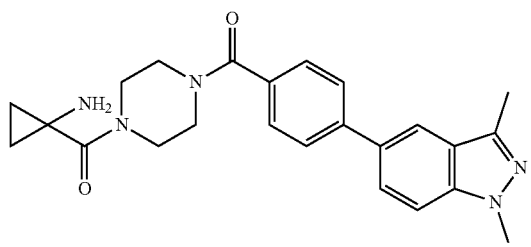 [SMILES: Cc1nn(C)c2ccc(-c3ccc(C(=O)N4CCN(C(=O)C5(N)CC5)CC4)cc3)cc12] |
| N-{3-[4-({4-[(1-aminocyclobutyl)carbonyl]piperazin-1-yl}carbonyl)phenyl]phenyl}cyclopropanesulfonamide | 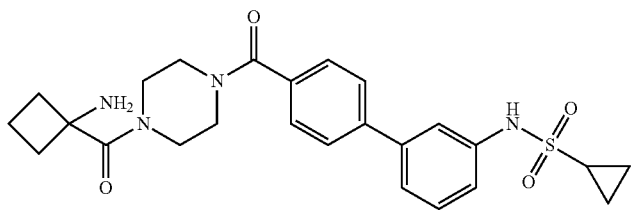 |
| N-{3-[4-({4-[(1-aminocyclopropyl)carbonyl]piperazin-1-yl}carbonyl)phenyl]phenyl}cyclopropanesulfonamide | 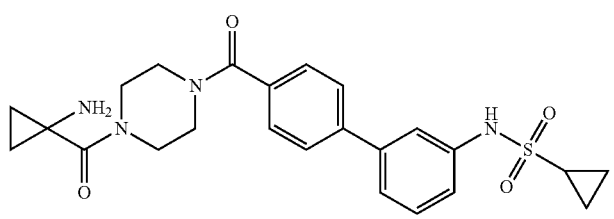 [SMILES: NC1(C(=O)N2CCN(C(=O)c3ccc(-c4cccc(NS(=O)(=O)C5CC5)c4)cc3)CC2)CC1] |

-continued

| NAME | Structure |
|---|---|
| 1-[(4-{[4-(6-fluoro-1,3-benzoxazol-2-yl)phenyl]carbonyl}piperazin-1-yl)carbonyl]cyclobutan-1-amine | 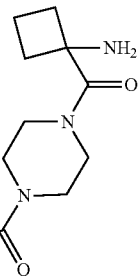 |
| 1-[(4-{[4-(6-fluoro-1,3-benzoxazol-2-yl)phenyl]carbonyl}piperazin-1-yl)carbonyl]cyclopropan-1-amine | 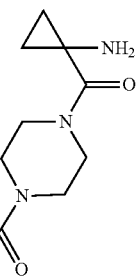 |
| 1-[(4-{[4-(6-chloro-1,3-benzoxazol-2-yl)phenyl]carbonyl}piperazin-1-yl)carbonyl]cyclobutan-1-amine | 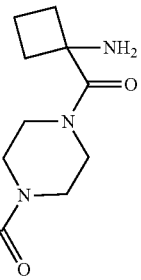 |
| 1-[(4-{[4-(6-chloro-1,3-benzoxazol-2-yl)phenyl]carbonyl}piperazin-1-yl)carbonyl]cyclopropan-1-amine | 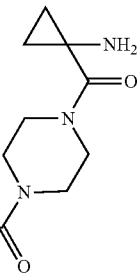 |
| 5-[4-({4-[(1-aminocyclobutyl)carbonyl]piperazin-1-yl}carbonyl)phenyl]-1H-indole-3-carbonitrile | 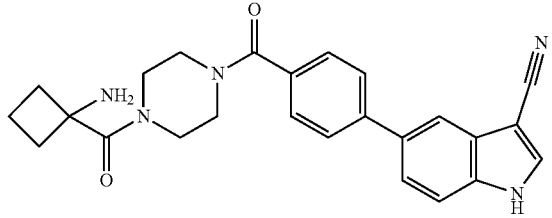 [SMILES: N#Cc1c[nH]c2ccc(-c3ccc(C(=O)N4CCN(C(=O)C5(N)CCC5)CC4)cc3)cc12] |
| 5-[4-({4-[(1-aminocyclobutyl)carbonyl]piperazin-1-yl}carbonyl)phenyl]-1H-indole-3-carbonitrile | 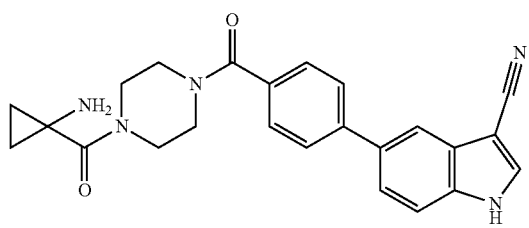 [SMILES: N#Cc1c[nH]c2ccc(-c3ccc(C(=O)N4CCN(C(=O)C5(N)CC5)CC4)cc3)cc12] |

| NAME | Structure |
|---|---|
| 1-[(4-{[4-(1,3-benzothiazol-2-yl)phenyl]carbonyl}piperazin-1-yl)carbonyl]cyclobutan-1-amine | 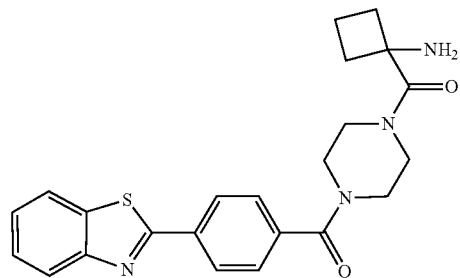 |
| 1-[(4-{[4-(1,3-benzothiazol-2-yl)phenyl]carbonyl}piperazin-1-yl)carbonyl]cyclopropan-1-amine | 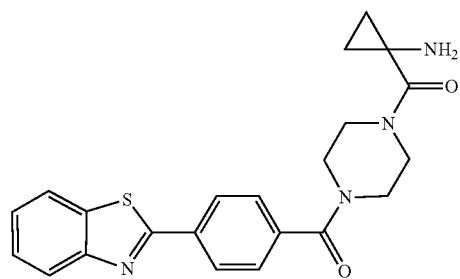 [SMILES: NC1(C(=O)N2CCN(C(=O)c3ccc(-c4nc5ccccc5s4)cc3)CC2)CC1] |
| 1-[(4-{[4-(quinolin-2-yl)phenyl]carbonyl}piperazin-1-yl)carbonyl]cyclobutan-1-amine | 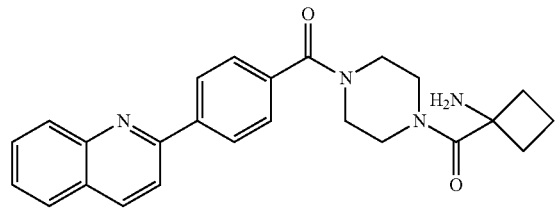 [SMILES: NC1(C(=O)N2CCN(C(=O)c3ccc(-c4ccc5ccccc5n4)cc3)CC2)CCC1] |
| 1-[(4-{[4-(quinolin-2-yl)phenyl]carbonyl}piperazin-1-yl)carbonyl]cyclopropan-1-amine | 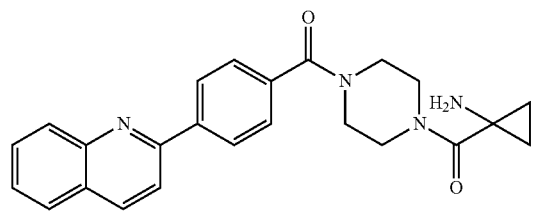 [SMILES: NC1(C(=O)N2CCN(C(=O)c3ccc(-c4ccc5ccccc5n4)cc3)CC2)CC1] |
| 1-[(4-{[4-(1H-1,3-benzodiazol-5-yl)phenyl]carbonyl}piperazin-1-yl)carbonyl]cyclobutan-1-amine | 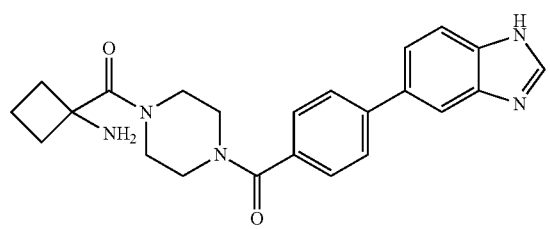 |
| 1-[(4-{[4-(1H-1,3-benzodiazol-5-yl)phenyl]carbonyl}piperazin-1-yl)carbonyl]cyclopropan-1-amine | 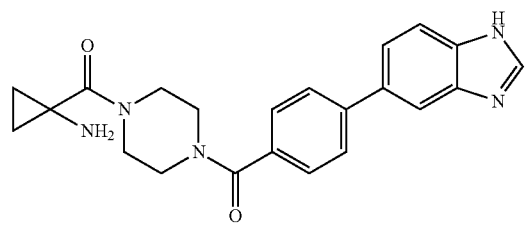 [SMILES: NC1(C(=O)N2CCN(C(=O)c3ccc(-c4ccc5[nH]cnc5c4)cc3)CC2)CC1] |

| NAME | Structure |
|---|---|
| 1-[(4-{[4-(1,3-benzothiazol-6-yl)phenyl]carbonyl}piperazin-1-yl)carbonyl]cyclobutan-1-amine | 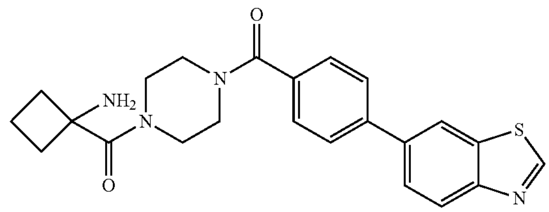 |
| 1-[(4-{[4-(1,3-benzothiazol-6-yl)phenyl]carbonyl}piperazin-1-yl)carbonyl]cyclopropan-1-amine | 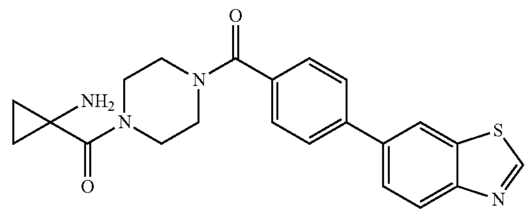 [SMILES: NC1(C(=O)N2CCN(C(=O)c3ccc(-c4ccc5ncsc5c4)cc3)CC2)CC1] |
| 1-[(4-{[4-(1,3-benzoxazol-5-yl)phenyl]carbonyl}piperazin-1-yl)carbonyl]cyclobutan-1-amine | 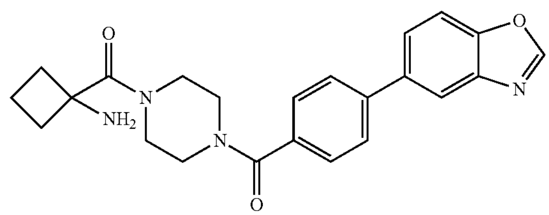 [SMILES: NC1(C(=O)N2CCN(C(=O)c3ccc(-c4ccc5ocnc5c4)cc3)CC2)CCC1] |
| 1-[(4-{[4-(1,3-benzoxazol-5-yl)phenyl]carbonyl}piperazin-1-yl)carbonyl]cyclopropan-1-amine | 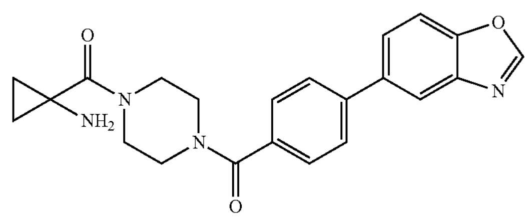 [SMILES: NC1(C(=O)N2CCN(C(=O)c3ccc(-c4ccc5ocnc5c4)cc3)CC2)CC1] |
| 1-[(4-{[4-(1,3-benzothiazol-5-yl)phenyl]carbonyl}piperazin-1-yl)carbonyl]cyclobutan-1-amine | 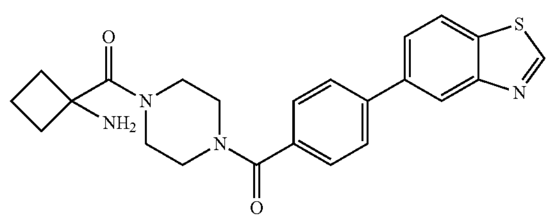 [SMILES: NC1(C(=O)N2CCN(C(=O)c3ccc(-c4ccc5scnc5c4)cc3)CC2)CCC1] |
| 1-[(4-{[4-(1,3-benzothiazol-5-yl)phenyl]carbonyl}piperazin-1-yl)carbonyl]cyclopropan-1-amine | 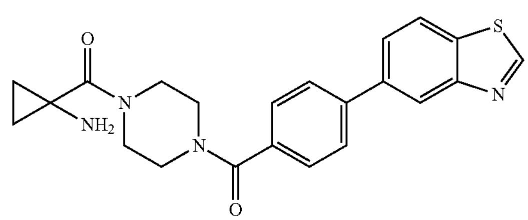 [SMILES: NC1(C(=O)N2CCN(C(=O)c3ccc(-c4ccc5scnc5c4)cc3)CC2)CC1] |
| 1-[(4-{[4-(1-methyl-1H-indazol-6-yl)phenyl]carbonyl}piperazin-1-yl)carbonyl]cyclobutan-1-amine | 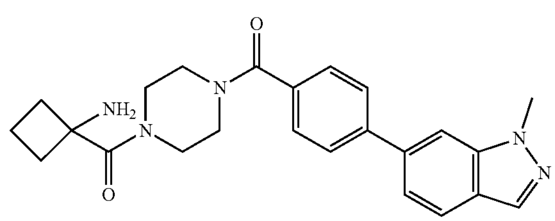 |

| NAME | Structure |
|------|-----------|
| 1-[(4-{[4-(1-methyl-1H-indazol-6-yl)phenyl]carbonyl}piperazin-1-yl)carbonyl]cyclopropan-1-amine | 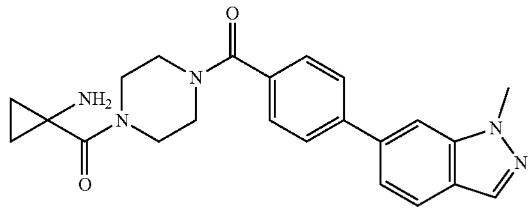 [SMILES: Cn1ncc2ccc(-c3ccc(C(=O)N4CCN(C(=O)C5(N)CC5)CC4)cc3)cc21] |
| 3-[4-({4-[(1-aminocyclobutyl)carbonyl]piperazin-1-yl}carbonyl)phenyl]-N-cyclopropylbenzamide | 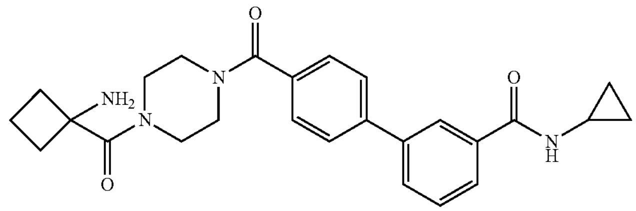 [SMILES: NC1(C(=O)N2CCN(C(=O)c3ccc(-c4cccc(C(=O)NC5CC5)c4)cc3)CC2)CCC1] |
| 3-[4-({4-[(1-aminocyclopropyl)carbonyl]piperazin-1-yl}carbonyl)phenyl]-N-cyclopropylbenzamide | 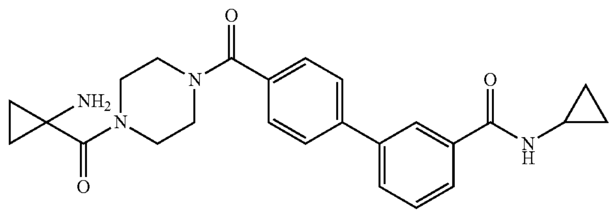 [SMILES: NC1(C(=O)N2CCN(C(=O)c3ccc(-c4cccc(C(=O)NC5CC5)c4)cc3)CC2)CC1] |
| 1-[(4-{[4-(2-methyl-2H-indazol-6-yl)phenyl]carbonyl}piperazin-1-yl)carbonyl]cyclobutan-1-amine | 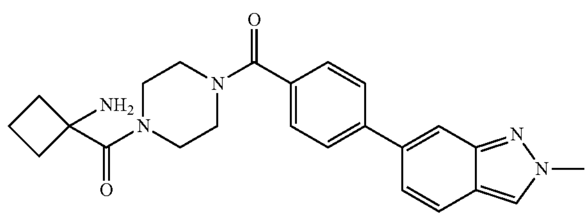 |
| 1-[(4-{[4-(2-methyl-2H-indazol-6-yl)phenyl]carbonyl}piperazin-1-yl)carbonyl]cyclopropan-1-amine | 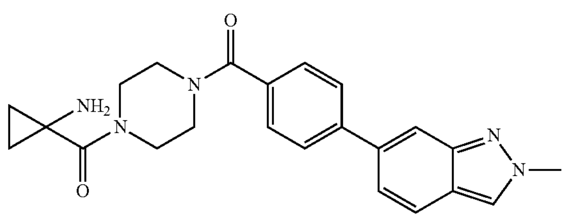 [SMILES: Cn1cc2ccc(-c3ccc(C(=O)N4CCN(C(=O)C5(N)CC5)CC4)cc3)cc2n1] |
| 1-[(4-{[4-(4-chloro-2-fluorophenyl)phenyl]carbonyl}piperazin-1-yl)carbonyl]cyclobutan-1-amine | 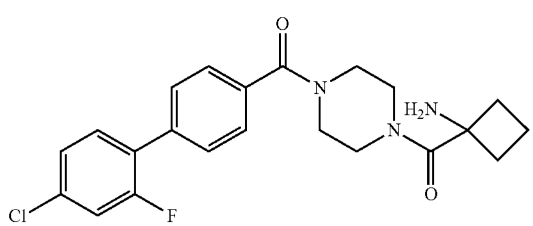 [SMILES: NC1(C(=O)N2CCN(C(=O)c3ccc(-c4ccc(Cl)cc4F)cc3)CC2)CCC1] |
| 1-[(4-{[4-(4-chloro-2-fluorophenyl)phenyl]carbonyl}piperazin-1-yl)carbonyl]cyclopropan-1-amine | 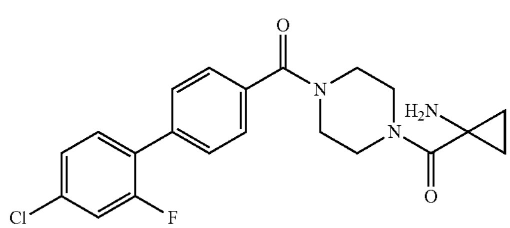 [SMILES: NC1(C(=O)N2CCN(C(=O)c3ccc(-c4ccc(Cl)cc4F)cc3)CC2)CC1] |

-continued

| NAME | Structure |
|---|---|
| 1-[(4-{[4-(5-chloro-2-fluorophenyl)phenyl]carbonyl}piperazin-1-yl)carbonyl]cyclobutan-1-amine | 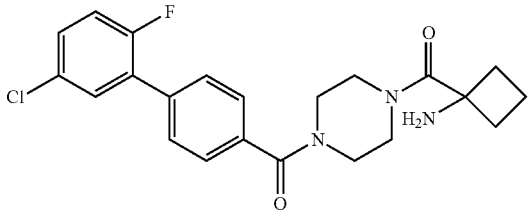 [SMILES: NC1(C(=O)N2CCN(C(=O)c3ccc(-c4cc(Cl)ccc4F)cc3)CC2)CCC1] |
| 1-[(4-{[4-(5-chloro-2-fluorophenyl)phenyl]carbonyl}piperazin-1-yl)carbonyl]cyclopropan-1-amine | 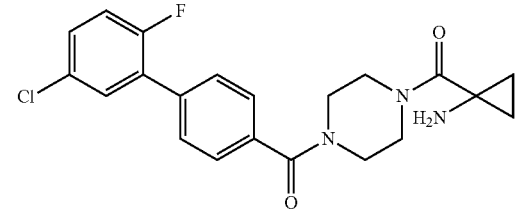 [SMILES: NC1(C(=O)N2CCN(C(=O)c3ccc(-c4cc(Cl)ccc4F)cc3)CC2)CC1] |
| 3-{[4-({4-[3-(cyclopropanesulfonyl)phenyl]phenyl}carbonyl)piperazin-1-yl]carbonyl}oxetan-3-ol | 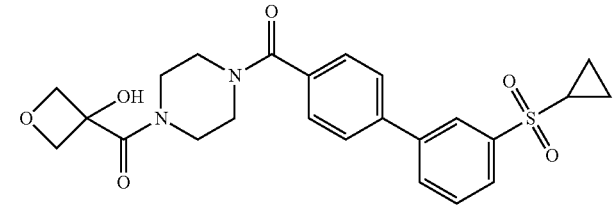 [SMILES: O=C(c1ccc(-c2cccc(S(=O)(=O)C3CC3)c2)cc1)N1CCN(C(=O)C2(O)COC2)CC1] |
| 3-{[4-({4-[3-(cyclopropanesulfonyl)phenyl]phenyl}carbonyl)piperazin-1-yl]carbonyl}oxetan-3-amine | 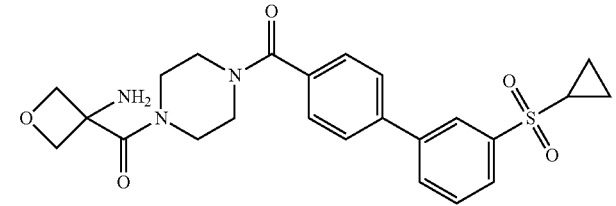 [SMILES: NC1(C(=O)N2CCN(C(=O)c3ccc(-c4cccc(S(=O)(=O)C5CC5)c4)cc3)CC2)COC1] |
| 3-({4-[(4-{3-chloroimidazo[1,2-a]pyridin-2-yl}phenyl)carbonyl]piperazin-1-yl}carbonyl)oxetan-3-ol | 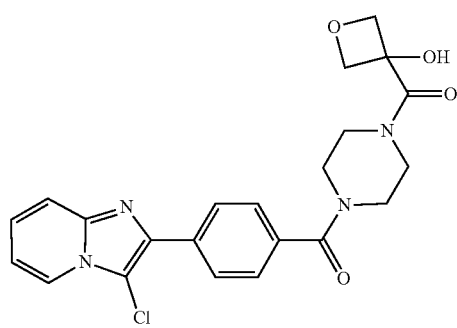 [SMILES: O=C(c1ccc(-c2nc3ccccn3c2Cl)cc1)N1CCN(C(=O)C2(O)COC2)CC1] |
| 3-({4-[(4-{3-chloroimidazo[1,2-a]pyridin-2-yl}phenyl)carbonyl]piperazin-1-yl}carbonyl)oxetan-3-amine | 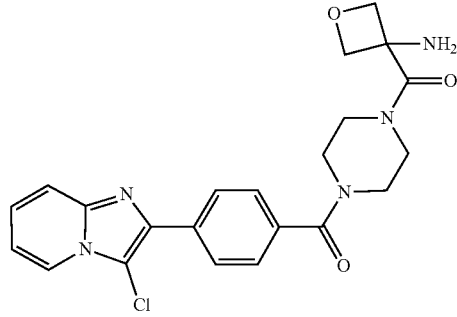 [SMILES: NC1(C(=O)N2CCN(C(=O)c3ccc(-c4nc5ccccn5c4Cl)cc3)CC2)COC1] |

-continued

| NAME | Structure |
|---|---|
| 3-[(4-{[4-(3-(cyclopropoxyphenyl)phenyl]carbonyl}piperazin-1-yl)carbonyl}oxetan-3-ol | |
| 3-[(4-{[4-(3-(cyclopropoxyphenyl)phenyl]carbonyl}piperazin-1-yl)carbonyl}oxetan-3-ol | |
| N-{3-[4-({4-[(3-hydroxyoxetan-3-yl)carbonyl]piperazin-1-yl}carbonyl)phenyl]phenyl}cyclopropanecarboxamide | 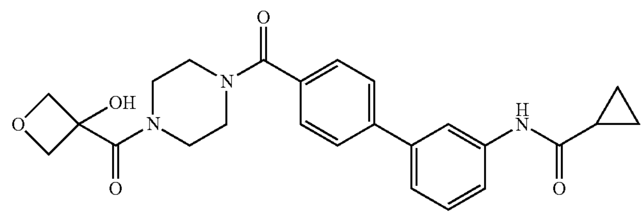 [SMILES: O=C(Nc1cccc(-c2ccc(C(=O)N3CCN(C(=O)C4(O)COC4)CC3)cc2)c1)C1CC1] |
| N-{3-[4-({4-[(3-aminooxetan-3-yl)carbonyl]piperazin-1-yl}carbonyl)phenyl]phenyl}cyclopropanecarboxamide | 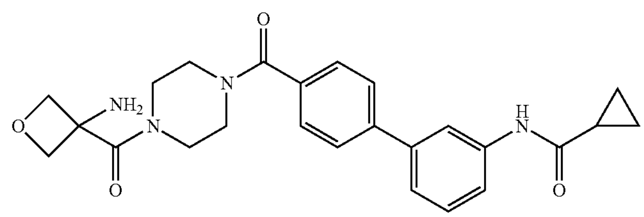 |
| 3-[4-({4-[(3-hydroxyoxetan-3-yl)carbonyl]piperazin-1-yl}carbonyl)phenyl]-1,2-dihydroquinolin-2-one | 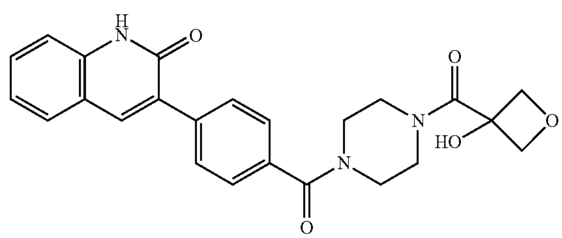 [SMILES: O=C(c1ccc(-c2cc3ccccc3[nH]c2=O)cc1)N1CCN(C(=O)C2(O)COC2)CC1] |
| 3-[4-({4-[(3-aminooxetan-3-yl)carbonyl]piperazin-1-yl}carbonyl)phenyl]-1,2-dihydroquinolin-2-one | 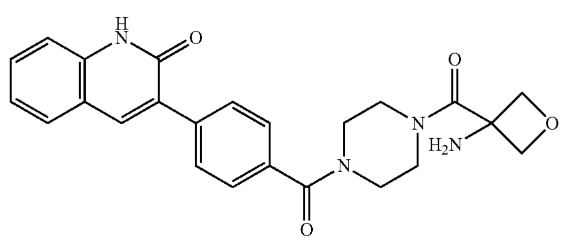 [SMILES: NC1(C(=O)N2CCN(C(=O)c3ccc(-c4cc5ccccc5[nH]c4=O)cc3)CC2)COC1] |
| 5-[4-({4-[(3-hydroxyoxetan-3-yl)carbonyl]piperazin-1-yl}carbonyl)phenyl]-1H-indole-2-carbonitrile | 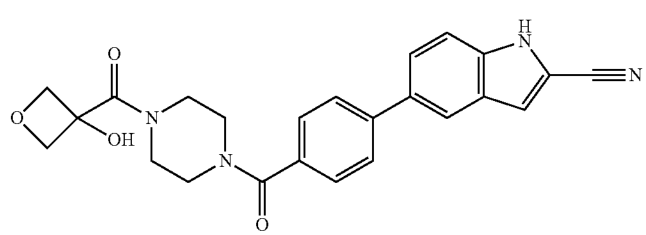 [SMILES: N#Cc1cc2cc(-c3ccc(C(=O)N4CCN(C(=O)C5(O)COC5)CC4)cc3)ccc2[nH]1] |

| NAME | Structure |
|---|---|
| 5-[4-({4-[(3-aminooxetan-3-yl)carbonyl]piperazin-1-yl}carbonyl)phenyl]-1H-indole-2-carbonitrile | 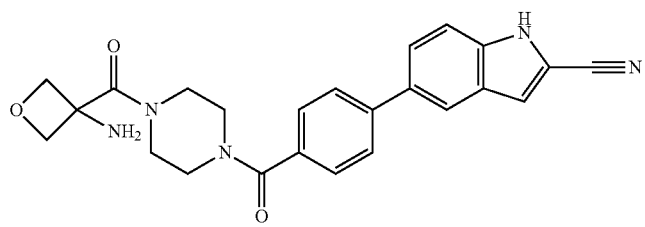 [SMILES: N#Cc1cc2cc(-c3ccc(C(=O)N4CCN(C(=O)C5(N)COC5)CC4)cc3)ccc2[nH]1] |
| 3-[(4-{[4-(1-methyl-1H-1,3-benzodiazol-5-yl)phenyl]carbonyl}piperazin-1-yl)carbonyl]oxetan-3-ol | 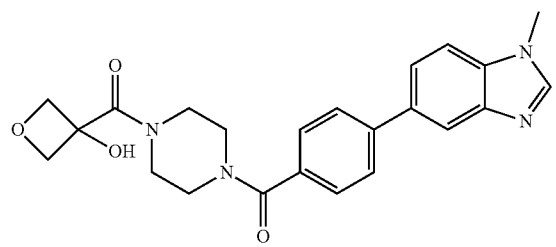 [SMILES: Cn1cnc2cc(-c3ccc(C(=O)N4CCN(C(=O)C5(O)COC5)CC4)cc3)ccc21] |
| 3-[(4-{[4-(1-methyl-1H-1,3-benzodiazol-5-yl)phenyl]carbonyl}piperazin-1-yl)carbonyl]oxetan-3-amine | 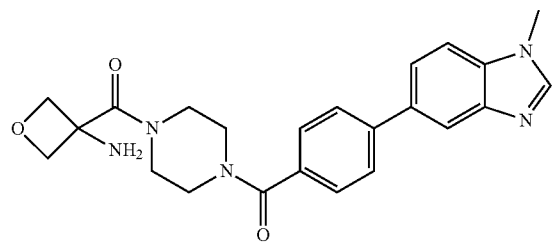 [SMILES: Cn1cnc2cc(-c3ccc(C(=O)N4CCN(C(=O)C5(N)COC5)CC4)cc3)ccc21] |
| 3-({4-[(4-{imidazo[1,2-b]pyridazin-6-yl}phenyl)carbonyl]piperazin-1-yl}carbonyl)oxetan-3-ol | 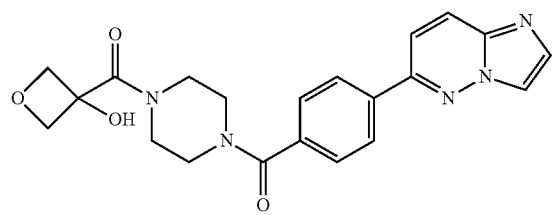 [SMILES: O=C(c1ccc(-c2ccc3nccn3n2)cc1)N1CCN(C(=O)C2(O)COC2)CC1] |
| 3-({4-[(4-{imidazo[1,2-b]pyridazin-6-yl}phenyl)carbonyl]piperazin-1-yl}carbonyl)oxetan-3-amine | 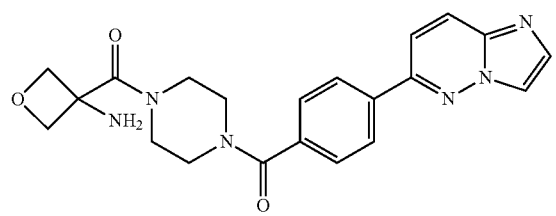 [SMILES: NC1(C(=O)N2CCN(C(=O)c3ccc(-c4ccc5nccn5n4)cc3)CC2)COC1] |
| 3-({4-[(4-{furo[3,2-b]pyridin-5-yl}phenyl)carbonyl]piperazin-1-yl}carbonyl)oxetan-3-amine | 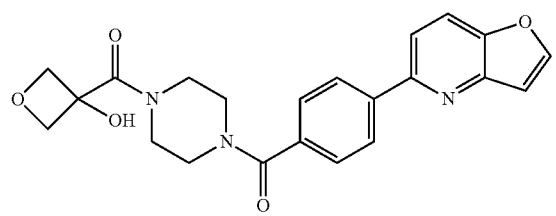 [SMILES: O=C(c1ccc(-c2ccc3occc3n2)cc1)N1CCN(C(=O)C2(O)COC2)CC1] |
| 3-({4-[(4-{furo[3,2-b]pyridin-5-yl}phenyl)carbonyl]piperazin-1-yl}carbonyl)oxetan-3-amine | 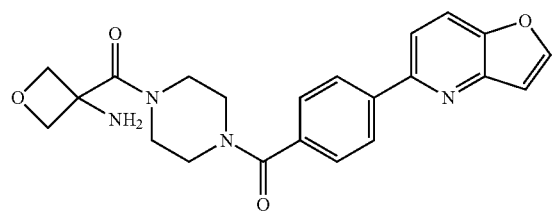 [SMILES: NC1(C(=O)N2CCN(C(=O)c3ccc(-c4ccc5occc5n4)cc3)CC2)COC1] |

-continued

| NAME | Structure |
|---|---|
| 3-[(4-{[4-(1H-indazol-3-yl)phenyl]carbonyl}piperazin-1-yl)carbonyl]oxetan-3-ol | 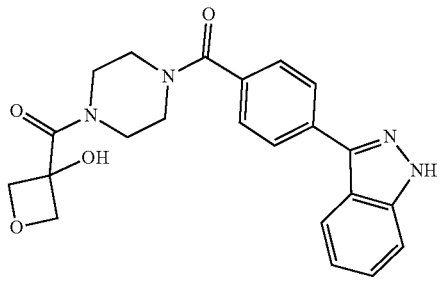 [SMILES: O=C(c1ccc(-c2n[nH]c3ccccc23)cc1)N1CCN(C(=O)C2(O)COC2)CC1] |
| 3-[(4-{[4-(1H-indazol-3-yl)phenyl]carbonyl}piperazin-1-yl)carbonyl]oxetan-3-amine | 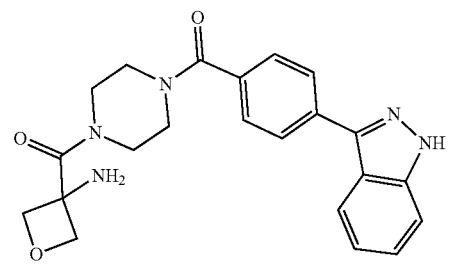 [SMILES: NC1(C(=O)N2CCN(C(=O)c3ccc(-c4n[nH]c5ccccc45)cc3)CC2)COC1] |
| 3-[(4-{[4-(1,3-dimethyl-1H-indazol-5-yl)phenyl]carbonyl}piperazin-1-yl)carbonyl]oxetan-3-ol | 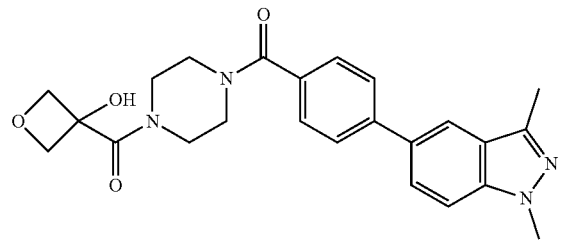 |
| 3-[(4-{[4-(1,3-dimethyl-1H-indazol-5-yl)phenyl]carbonyl}piperazin-1-yl)carbonyl]oxetan-3-amine | 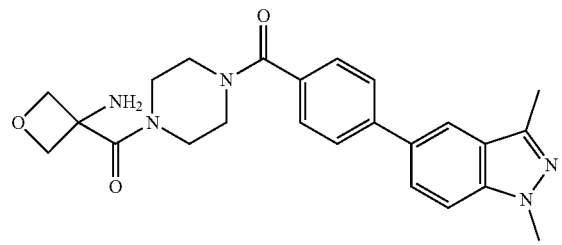 [SMILES: Cc1nn(C)c2ccc(-c3ccc(C(=O)N4CCN(C(=O)C5(O)COC5)CC4)cc3)cc12] |
| N-{3-[4-({4-[(3-hydroxyoxetan-3-yl)carbonyl]piperazin-1-yl}carbonyl)phenyl]phenyl}cyclopropanesulfonamide | 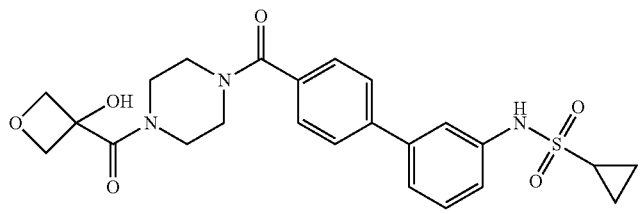 [SMILES: O=C(c1ccc(-c2cccc(NS(=O)(=O)C3CC3)c2)cc1)N1CCN(C(=O)C2(O)COC2)CC1] |
| N-{3-[4-({4-[(3-aminooxetan-3-yl)carbonyl]piperazin-1-yl}carbonyl)phenyl]phenyl}cyclopropanesulfonamide | 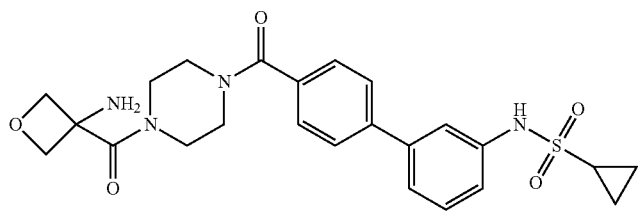 |

| NAME | Structure |
|---|---|
| 3-[(4-{[4-(6-fluoro-1,3-benzoxazol-2-yl)phenyl]carbonyl}piperazin-1-yl)carbonyl]oxetan-3-ol | 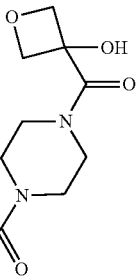 |
| 3-[(4-{[4-(6-fluoro-1,3-benzoxazol-2-yl)phenyl]carbonyl}piperazin-1-yl)carbonyl]oxetan-3-amine | 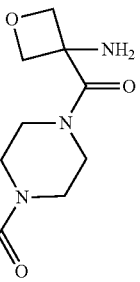 |
| 3-[(4-{[4-(6-chloro-1,3-benzoxazol-2-yl)phenyl]carbonyl}piperazin-1-yl)carbonyl]oxetan-3-ol | 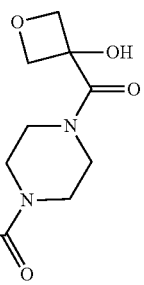 |
| 3-[(4-{[4-(6-chloro-1,3-benzoxazol-2-yl)phenyl]carbonyl}piperazin-1-yl)carbonyl]oxetan-3-amine | 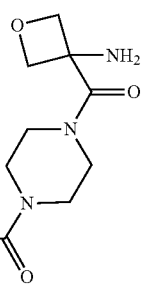 |
| 5-[4-({4-[(3-hydroxyoxetan-3-yl)carbonyl]piperazin-1-yl}carbonyl)phenyl]-1H-indole-3-carbonitrile | 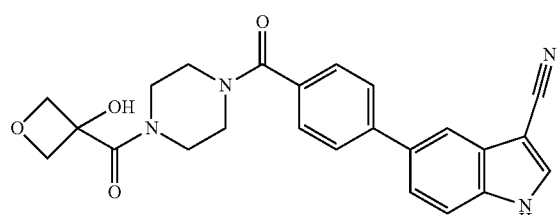 |
| 5-[4-({4-[(3-aminooxetan-3-yl)carbonyl]piperazin-1-yl}carbonyl)phenyl]-1H-indole-3-carbonitrile | 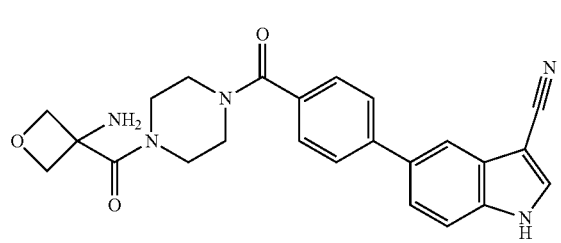 [SMILES: N#Cc1c[nH]c2ccc(-c3ccc(C(=O)N4CCN(C(=O)C5(N)COC5)CC4)cc3)cc12] |

| NAME | Structure |
|---|---|
| 3-[(4-{[4-(1,3-benzothiazol-2-yl)phenyl]carbonyl}piperazin-1-yl)carbonyl]oxetan-3-ol | 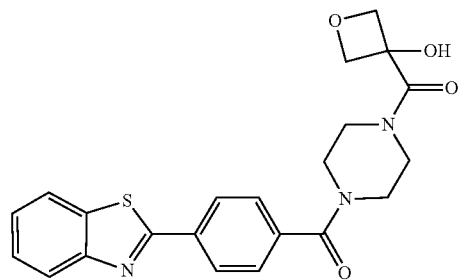 [SMILES: O=C(c1ccc(-c2nc3ccccc3s2)cc1)N1CCN(C(=O)C2(O)COC2)CC1] |
| 3-[(4-{[4-(1,3-benzothiazol-2-yl)phenyl]carbonyl}piperazin-1-yl)carbonyl]oxetan-3-amine | 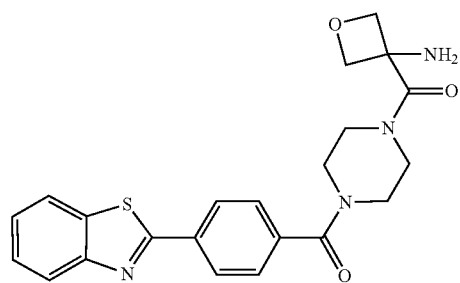 [SMILES: NC1(C(=O)N2CCN(C(=O)c3ccc(-c4nc5ccccc5s4)cc3)CC2)COC1] |
| 3-[(4-{[4-(quinolin-2-yl)phenyl]carbonyl}piperazin-1-yl)carbonyl]oxetan-3-ol | 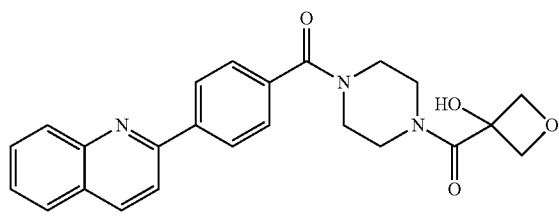 [SMILES: O=C(c1ccc(-c2ccc3ccccc3n2)cc1)N1CCN(C(=O)C2(O)COC2)CC1] |
| 3-[(4-{[4-(quinolin-2-yl)phenyl]carbonyl}piperazin-1-yl)carbonyl]oxetan-3-amine | 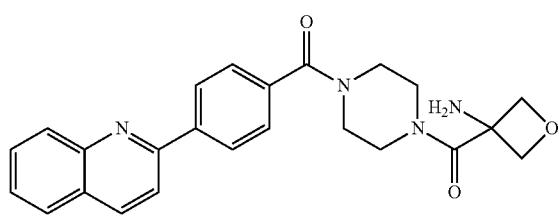 [SMILES: NC1(C(=O)N2CCN(C(=O)c3ccc(-c4ccc5ccccc5n4)cc3)CC2)COC1] |
| 3-[(4-{[4-(1H-1,3-benzodiazol-5-yl)phenyl]carbonyl}piperazin-1-yl)carbonyl]oxetan-3-ol | 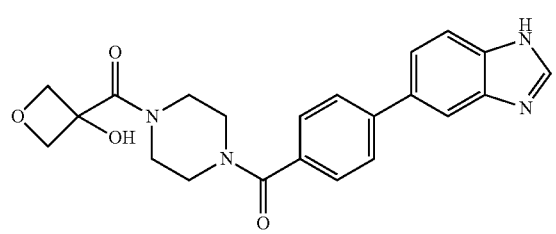 [SMILES: O=C(c1ccc(-c2ccc3[nH]cnc3c2)cc1)N1CCN(C(=O)C2(O)COC2)CC1] |
| 3-[(4-{[4-(1H-1,3-benzodiazol-5-yl)phenyl]carbonyl}piperazin-1-yl)carbonyl]oxetan-3-amine | 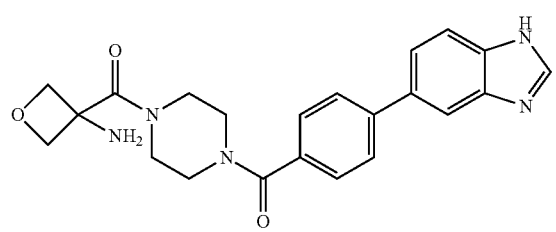 [SMILES: NC1(C(=O)N2CCN(C(=O)c3ccc(-c4ccc5[nH]cnc5c4)cc3)CC2)COC1] |

| NAME | Structure |
|---|---|
| 3-[(4-{[4-(1,3-benzothiazol-6-yl)phenyl]carbonyl}piperazin-1-yl)carbonyl]oxetan-3-ol | 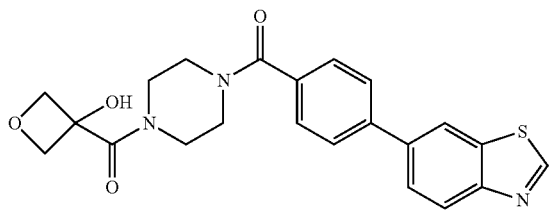 [SMILES: O=C(c1ccc(-c2ccc3ncsc3c2)cc1)N1CCN(C(=O)C2(O)COC2)CC1] |
| 3-[(4-{[4-(1,3-benzothiazol-6-yl)phenyl]carbonyl}piperazin-1-yl)carbonyl]oxetan-3-amine | 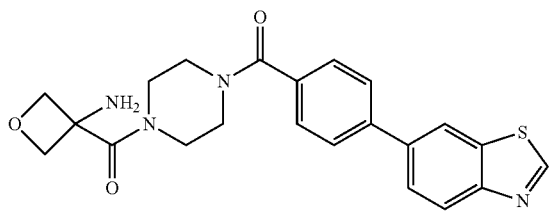 |
| 3-[(4-{[4-(1,3-benzoxazol-5-yl)phenyl]carbonyl}piperazin-1-yl)carbonyl]oxetan-3-ol | 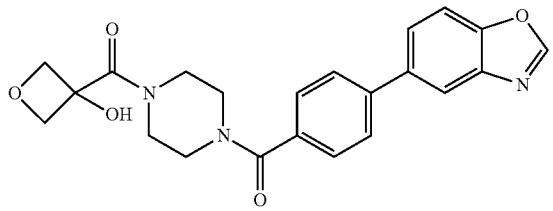 [SMILES: O=C(c1ccc(-c2ccc3ocnc3c2)cc1)N1CCN(C(=O)C2(O)COC2)CC1] |
| 3-[(4-{[4-(1,3-benzoxazol-5-yl)phenyl]carbonyl}piperazin-1-yl)carbonyl]oxetan-3-amine | 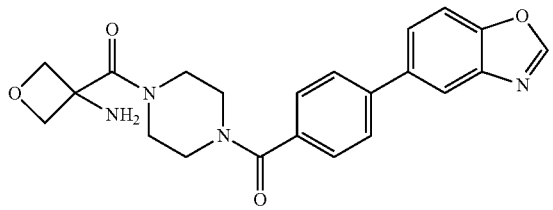 [SMILES: NC1(C(=O)N2CCN(C(=O)c3ccc(-c4ccc5ocnc5c4)cc3)CC2)COC1] |
| 3-[(4-{[4-(1,3-benzothiazol-5-yl)phenyl]carbonyl}piperazin-1-yl)carbonyl]oxetan-3-ol | 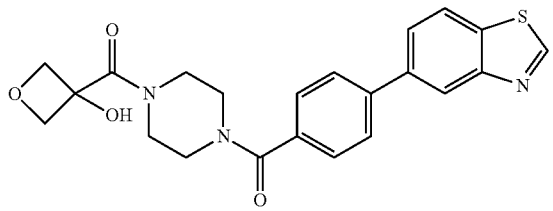 [SMILES: O=C(c1ccc(-c2ccc3scnc3c2)cc1)N1CCN(C(=O)C2(O)COC2)CC1] |
| 3-[(4-{[4-(1,3-benzothiazol-5-yl)phenyl]carbonyl}piperazin-1-yl)carbonyl]oxetan-3-amine | 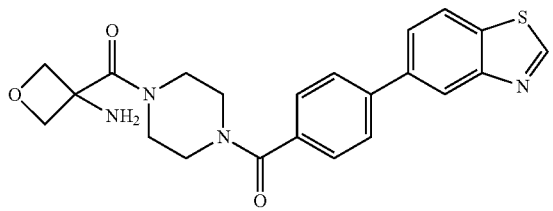 |
| 3-[(4-{[4-(1-methyl-1H-indazol-6-yl)phenyl]carbonyl}piperazin-1-yl)carbonyl]oxetan-3-ol | 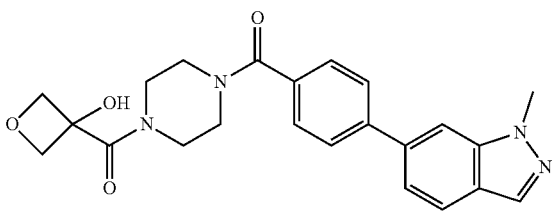 |

-continued

| NAME | Structure |
|---|---|
| 3-[(4-{[4-(1-methyl-1H-indazol-6-yl)phenyl]carbonyl}piperazin-1-yl)carbonyl]oxetan-3-amine | 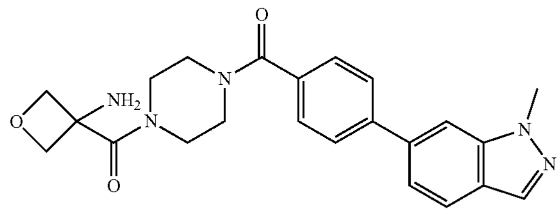 [SMILES: Cn1ncc2ccc(-c3ccc(C(=O)N4CCN(C(=O)C5(O)COC5)CC4)cc3)cc21] |
| N-cyclopropyl-3-[4-({4-[(3-hydroxyoxetan-3-yl)carbonyl]piperazin-1-yl}carbonyl)phenyl]benzamide | 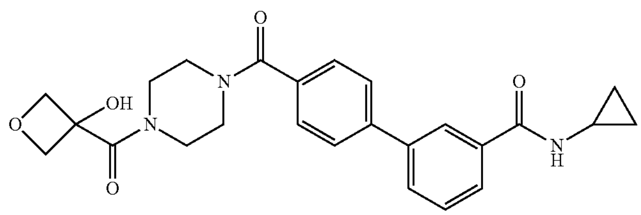 [SMILES: O=C(NC1CC1)c1cccc(-c2ccc(C(=O)N3CCN(C(=O)C4(O)COC4)CC3)cc2)c1] |
| 3-[4-({4-[(3-aminooxetan-3-yl)carbonyl]piperazin-1-yl}carbonyl)phenyl]-N-cyclopropylbenzamide | 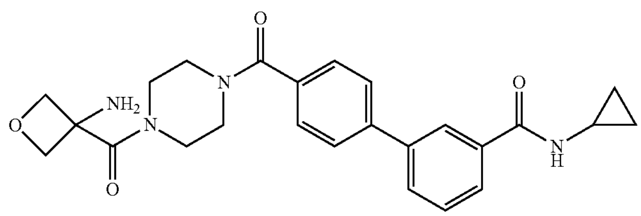 [SMILES: NC1(C(=O)N2CCN(C(=O)c3ccc(-c4cccc(C(=O)NC5CC5)c4)cc3)CC2)COC1] |
| 3-[(4-{[4-(2-methyl-2H-indazol-6-yl)phenyl]carbonyl}piperazin-1-yl)carbonyl]oxetan-3-ol | 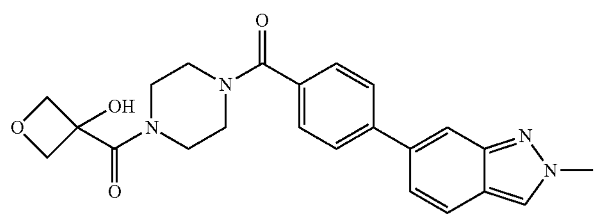 [SMILES: Cn1cc2ccc(-c3ccc(C(=O)N4CCN(C(=O)C5(O)COC5)CC4)cc3)cc2n1] |
| 3-[(4-{[4-(2-methyl-2H-indazol-6-yl)phenyl]carbonyl}piperazin-1-yl)carbonyl]oxetan-3-amine | 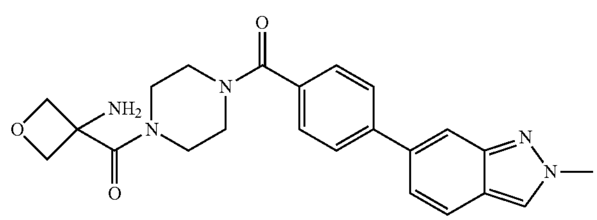 [SMILES: Cn1cc2ccc(-c3ccc(C(=O)N4CCN(C(=O)C5(N)COC5)CC4)cc3)cc2n1] |
| 3-[(4-{[4-(4-chloro-2-fluorophenyl)phenyl]carbonyl}piperazin-1-yl)carbonyl]oxetan-3-ol | 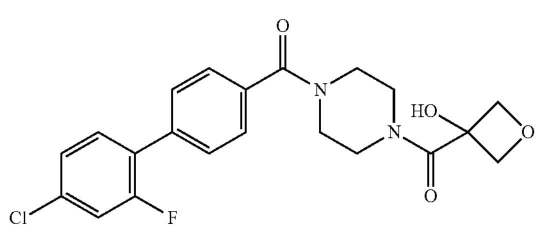 [SMILES: O=C(c1ccc(-c2ccc(Cl)cc2F)cc1)N1CCN(C(=O)C2(O)COC2)CC1] |
| 3-[(4-{[4-(4-chloro-2-fluorophenyl)phenyl]carbonyl}piperazin-1-yl)carbonyl]oxetan-3-amine | 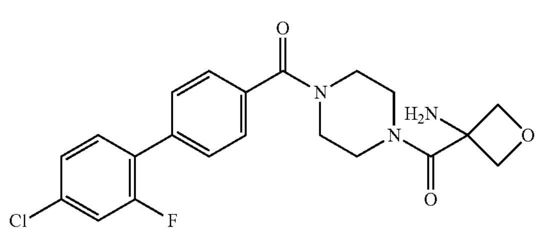 [SMILES: NC1(C(=O)N2CCN(C(=O)c3ccc(-c4ccc(Cl)cc4F)cc3)CC2)COC1] |

-continued

| NAME | Structure |
|---|---|
| 3-[(4-{[4-(5-chloro-2-fluorophenyl)phenyl]carbonyl}piperazin-1-yl)carbonyl]oxetan-3-ol | 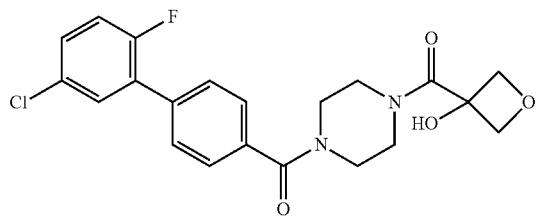 [SMILES: O=C(c1ccc(-c2cc(Cl)ccc2F)cc1)N1CCN(C(=O)C2(O)COC2)CC1] |
| 3-[(4-{[4-(5-chloro-2-fluorophenyl)phenyl]carbonyl}piperazin-1-yl)carbonyl]oxetan-3-amine | 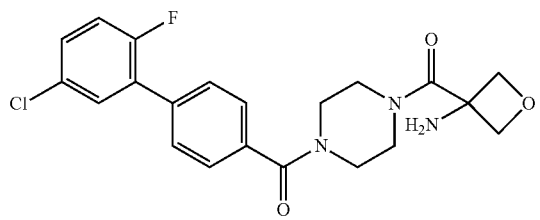 [SMILES: NC1(C(=O)N2CCN(C(=O)c3ccc(-c4cc(Cl)ccc4F)cc3)CC2)COC1] |
| 1-({4-[(4-{5-chloro-[1,3]thiazolo[5,4-d][1,3]thiazol-2-yl}phenyl)carbonyl]piperazin-1-yl}carbonyl)cyclopropan-1-ol | 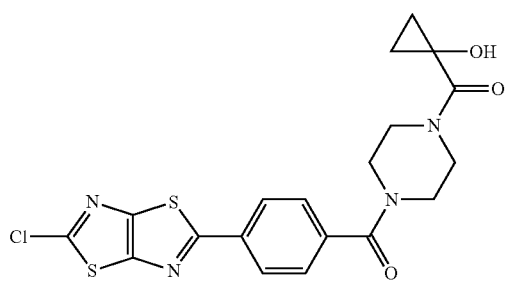 [SMILES: O=C(c1ccc(-c2nc3sc(Cl)nc3s2)cc1)N1CCN(C(=O)C2(O)CC2)CC1] |
| 1-{[4-({4-[4-(2H-1,2,3,4-tetrazol-5-yl)phenyl]phenyl}carbonyl)piperazin-1-yl]carbonyl}cyclopropan-1-ol | 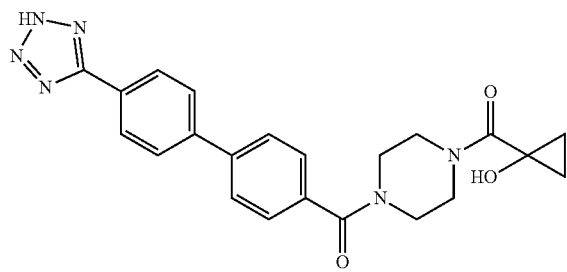 [SMILES: O=C(c1ccc(-c2ccc(-c3nn[nH]n3)cc2)cc1)N1CCN(C(=O)C2(O)CC2)CC1] |
| 1-({4-[(4-{imidazo[2,1-b][1,3,4]thiadiazol-2-yl}phenyl)carbonyl]piperazin-1-yl}carbonyl)cyclopropan-1-ol | 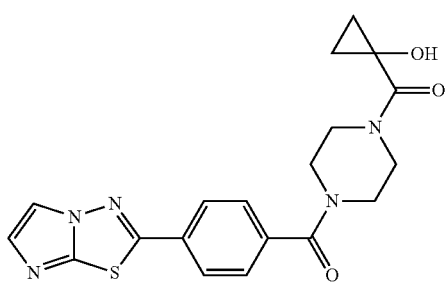 [SMILES: O=C(c1ccc(-c2nn3ccnc3s2)cc1)N1CCN(C(=O)C2(O)CC2)CC1] |
| 1-({4-[(4-{6H-thieno[2,3-b]pyrrol-2-yl}phenyl)carbonyl]piperazin-1-yl}carbonyl)cyclopropan-1-ol | 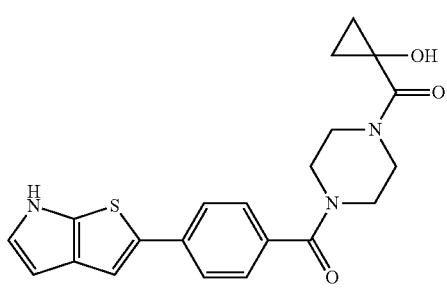 [SMILES: O=C(c1ccc(-c2cc3cc[nH]c3s2)cc1)N1CCN(C(=O)C2(O)CC2)CC1] |

-continued

| NAME | Structure |
|---|---|
| 1-({4-[(4-{4H-thieno[3,2-b]pyrrol-3-yl}phenyl)carbonyl]piperazin-1-yl}carbonyl)cyclopropan-1-ol | 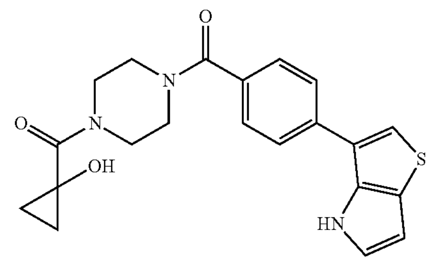 [SMILES: O=C(c1ccc(-c2csc3cc[nH]c23)cc1)N1CCN(C(=O)C2(O)CC2)CC1] |
| 2-[4-({4-[(1-hydroxycyclopropyl)carbonyl]piperazin-1-yl}carbonyl)phenyl]-3H-pyrrolizin-3-one | 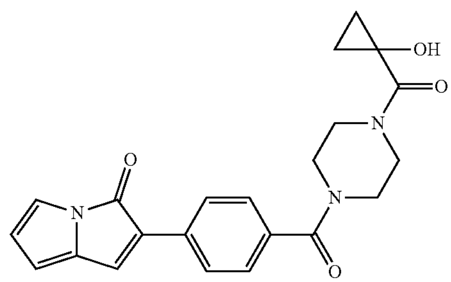 [SMILES: O=C(c1ccc(C2=Cc3cccn3C2=O)cc1)N1CCN(C(=O)C2(O)CC2)CC1] |
| 6-[4-({4-[(1-hydroxycyclopropyl)carbonyl]piperazin-1-yl}carbonyl)phenyl]-3H-pyrrolizin-3-one | 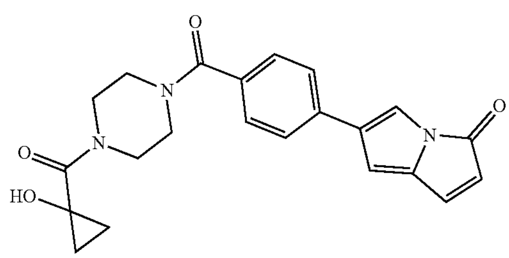 [SMILES: O=C(c1ccc(-c2cc3n(c2)C(=O)C=C3)cc1)N1CCN(C(=O)C2(O)CC2)CC1] |
| 1-[(4-{[4-(1-methanesulfonyl-1H-indol-6-yl)phenyl]carbonyl}piperazin-1-yl)carbonyl]cyclopropan-1-ol | 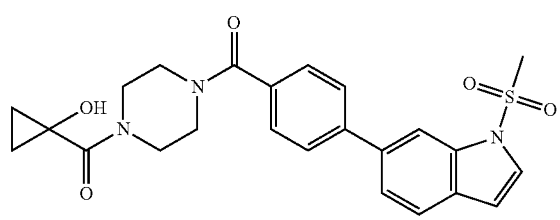 [SMILES: CS(=O)(=O)n1ccc2ccc(-c3ccc(C(=O)N4CCN(C(=O)C5(O)CC5)CC4)cc3)cc21] |
| 1-{[4-({4-[4-(1-methyl-1H-pyrazol-5-yl)phenyl]phenyl}carbonyl)piperazin-1-yl]carbonyl}cyclopropan-1-ol | 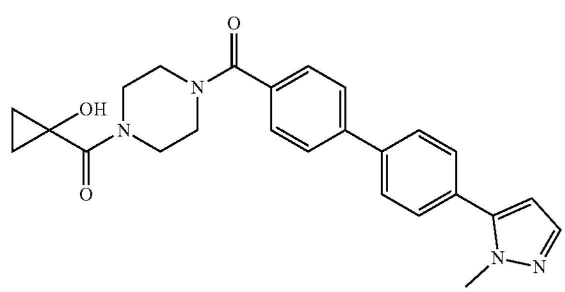 [SMILES: Cn1nccc1-c1ccc(-c2ccc(C(=O)N3CCN(C(=O)C4(O)CC4)CC3)cc2)cc1] |
| 1-{[4-({4-[4-(1-methyl-1H-pyrazol-3-yl)phenyl]phenyl}carbonyl)piperazin-1-yl]carbonyl}cyclopropan-1-ol | 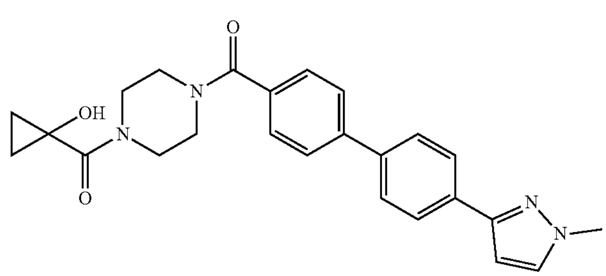 [SMILES: Cn1ccc(-c2ccc(-c3ccc(C(=O)N4CCN(C(=O)C5(O)CC5)CC4)cc3)cc2)n1] |

-continued

| NAME | Structure |
|---|---|
| 1-{[4-({4-[4-(1-methyl-1H-pyrazol-4-yl)phenyl]phenyl}carbonyl)piperazin-1-yl]carbonyl}cyclopropan-1-ol | 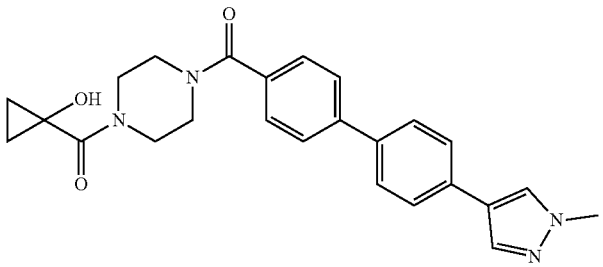 [SMILES: Cn1cc(-c2ccc(-c3ccc(C(=O)N4CCN(C(=O)C5(O)CC5)CC4)cc3)cc2)cn1] |
| 1-[(4-{[4-(1-ethyl-1H-indazol-5-yl)phenyl]carbonyl}piperazin-1-yl)carbonyl]cyclopropan-1-ol | 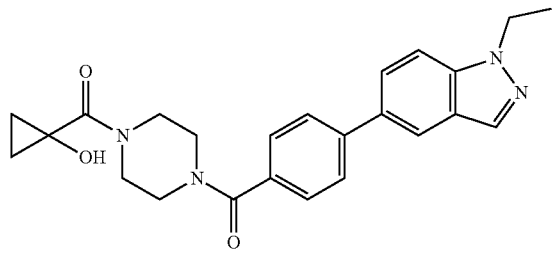 [SMILES: CCn1ncc2cc(-c3ccc(C(=O)N4CCN(C(=O)C5(O)CC5)CC4)cc3)ccc21] |
| 1-[(4-{[4-(1-cyclobutyl-1H-indazol-5-yl)phenyl]carbonyl}piperazin-1-yl)carbonyl]cyclopropan-1-ol | 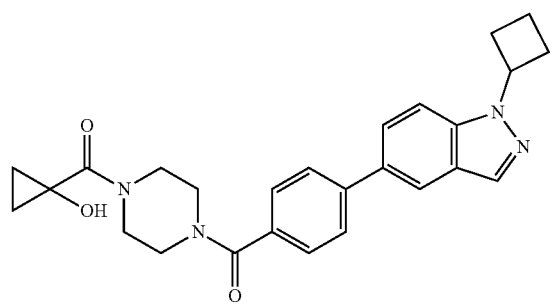 [SMILES: O=C(c1ccc(-c2ccc3c(cnn3C3CCC3)c2)cc1)N1CCN(C(=O)C2(O)CC2)CC1] |
| 1-{[4-({4-[1-(oxetan-3-yl)-1H-indazol-5-yl]phenyl}carbonyl)piperazin-1-yl]carbonyl}cyclopropan-1-ol | 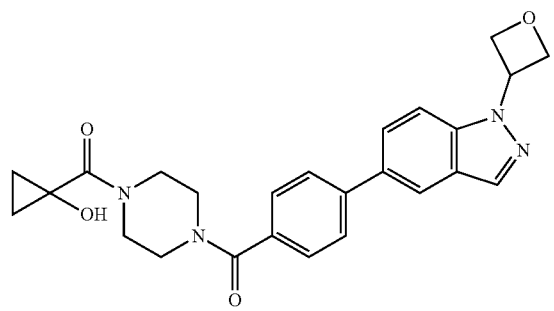 [SMILES: O=C(c1ccc(-c2ccc3c(cnn3C3COC3)c2)cc1)N1CCN(C(=O)C2(O)CC2)CC1] |
| 1-{[4-({4-[1-(propan-2-yl)-1H-indazol-5-yl]phenyl}carbonyl)piperazin-1-yl]carbonyl}cyclopropan-1-ol | 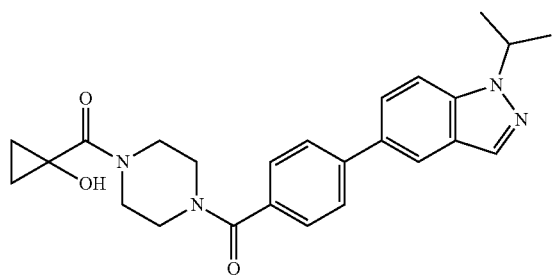 [SMILES: CC(C)n1ncc2cc(-c3ccc(C(=O)N4CCN(C(=O)C5(O)CC5)CC4)cc3)ccc21] |

| NAME | Structure |
|---|---|
| 1-{[4-({4-[1-(2-methoxyethyl)-1H-indazol-5-yl]phenyl}carbonyl)piperazin-1-yl]carbonyl}cyclopropan-1-ol | 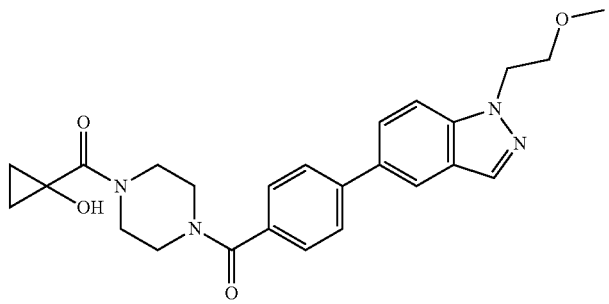 [SMILES: COCCn1ncc2cc(-c3ccc(C(=O)N4CCN(C(=O)C5(O)CC5)CC4)cc3)ccc21] |
| 1-{[4-({4-[1-(cyclopropylmethyl)-1H-1H-indazol-5-yl]phenyl}carbonyl)piperazin-1-yl]carbonyl}cyclopropan-1-ol | 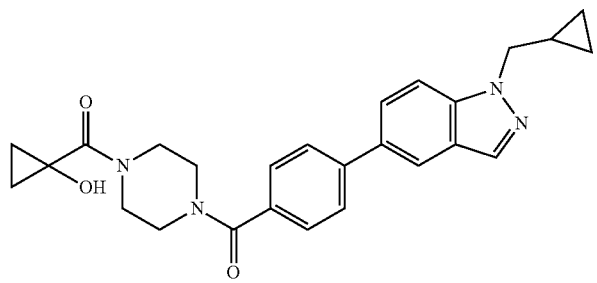 [SMILES: O=C(c1ccc(-c2ccc3c(cnn3CC3CC3)c2)cc1)N1CCN(C(=O)C2(O)CC2)CC1] |
| 1-[(4-{[4-(1-propyl-1H-indazol-5-yl)phenyl]carbonyl}piperazin-1-yl)carbonyl]cyclopropan-1-ol | 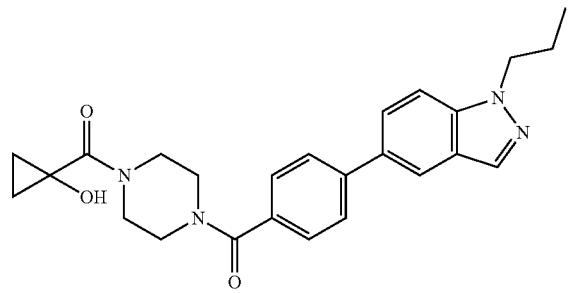 [SMILES: CCCn1ncc2cc(-c3ccc(C(=O)N4CCN(C(=O)C5(O)CC5)CC4)cc3)ccc21] |
| 1-{[4-({4-[1-(cyclobutylmethyl)-1H-indazol-5-yl]phenyl}carbonyl)piperazin-1-yl]carbonyl}cyclopropan-1-ol | 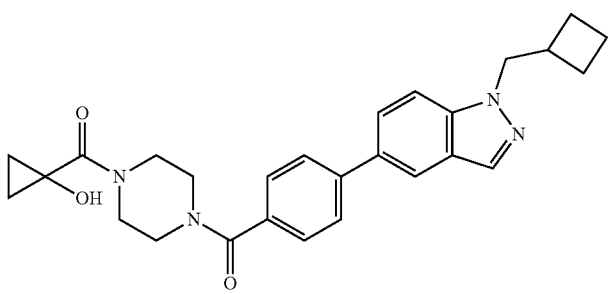 [SMILES: O=C(c1ccc(-c2ccc3c(cnn3CC3CCC3)c2)cc1)N1CCN(C(=O)C2(O)CC2)CC1] |
| 1-{[4-({4-[1-(oxetan-3-ylmethyl)-1H-indazol-5-yl]phenyl}carbonyl)piperazin-1-yl]carbonyl}cyclopropan-1-ol | 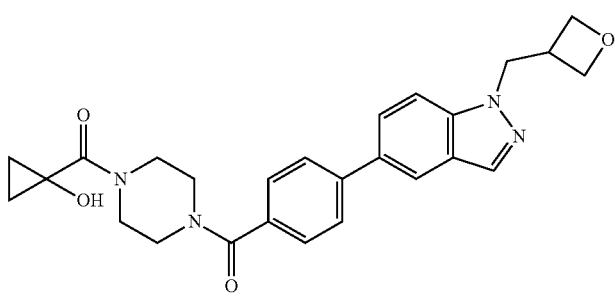 [SMILES: O=C(c1ccc(-c2ccc3c(cnn3CC3COC3)c2)cc1)N1CCN(C(=O)C2(O)CC2)CC1] |

| NAME | Structure |
|---|---|
| 1-{[4-({4-[1-(2-hydroxyethyl)-1H-indazol-5-yl]phenyl}carbonyl)piperazin-1-yl]carbonyl}cyclopropan-1-ol | 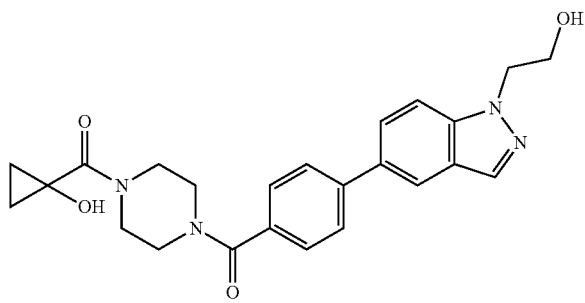 [SMILES: O=C(c1ccc(-c2ccc3c(cnn3CCO)c2)cc1)N1CCN(C(=O)C2(O)CC2)CC1] |
| 1-{[4-({4-[4-(1H-pyrazol-5-yl)phenyl]phenyl}carbonyl)piperazin-1-yl]carbonyl}cyclopropan-1-ol | 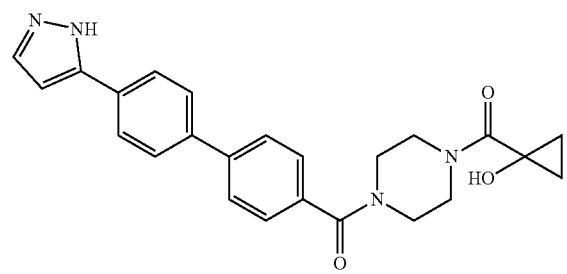 [SMILES: O=C(c1ccc(-c2ccc(-c3ccn[nH]3)cc2)cc1)N1CCN(C(=O)C2(O)CC2)CC1] |
| 1-{[4-({4-[4-(1H-pyrazol-4-yl)phenyl]phenyl}carbonyl)piperazin-1-yl]carbonyl}cyclopropan-1-ol | 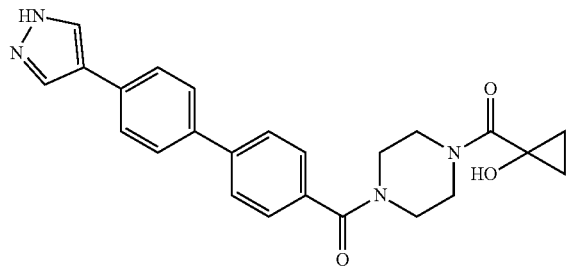 [SMILES: O=C(c1ccc(-c2ccc(-c3cn[nH]c3)cc2)cc1)N1CCN(C(=O)C2(O)CC2)CC1] |
| 1-{[4-({4-[4-(2-methyl-2H-1,2,3-triazol-4-yl)phenyl]phenyl}carbonyl)piperazin-1-yl]carbonyl}cyclopropan-1-ol | 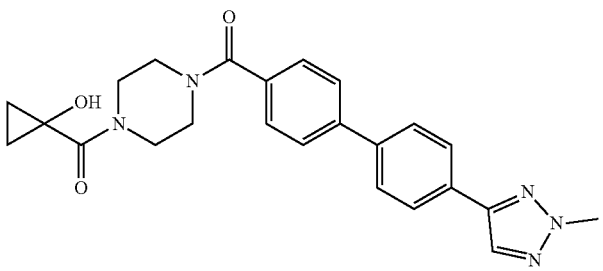 [SMILES: Cn1ncc(-c2ccc(-c3ccc(C(=O)N4CCN(C(=O)C5(O)CC5)CC4)cc3)cc2)n1] |
| 1-{[4-({4-[4-(1-methyl-1H-1,2,3-triazol-4-yl)phenyl]phenyl}carbonyl)piperazin-1-yl]carbonyl}cyclopropan-1-ol | 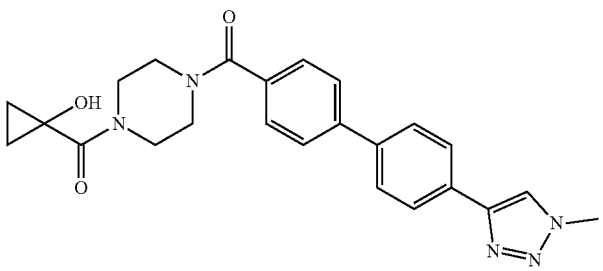 |

-continued

| NAME | Structure |
|---|---|
| 1-[(4-{[4-(1-methanesulfonyl-1H-indol-5-yl)phenyl]carbonyl}piperazin-1-yl)carbonyl]cyclopropan-1-ol | 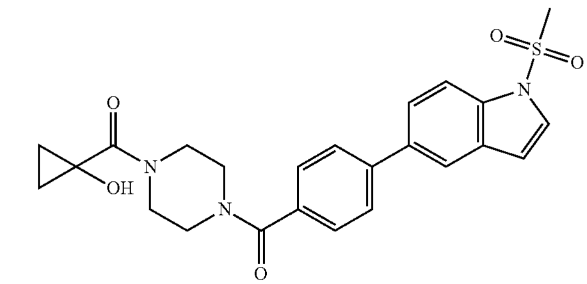 [SMILES: CS(=O)(=O)n1ccc2cc(-c3ccc(C(=O)N4CCN(C(=O)C5(O)CC5)CC4)cc3)ccc21] |
| 1-{[4-({4-[1-(cyclopropanesulfonyl)-1H-indol-5-yl]phenyl}carbonyl)piperazin-1-yl]carbonyl}cyclopropan-1-ol | 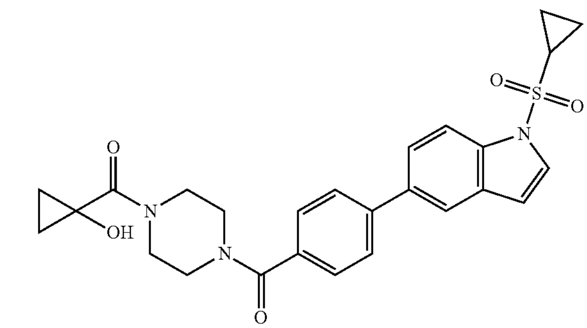 [SMILES: O=C(c1ccc(-c2ccc3c(ccn3S(=O)(=O)C3CC3)c2)cc1)N1CCN(C(=O)C2(O)CC2)CC1] |
| 1-{[4-({4-[1-(cyclopropanesulfonyl)-1H-indol-6-yl]phenyl}carbonyl)piperazin-1-yl]carbonyl}cyclopropan-1-ol | 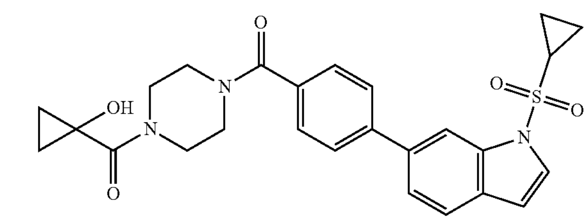 [SMILES: O=C(c1ccc(-c2ccc3ccn(S(=O)(=O)C4CC4)c3c2)cc1)N1CCN(C(=O)C2(O)CC2)CC1] |
| 1-{[4-({4-[2-(hydroxymethyl)-1H-indol-5-yl]phenyl}carbonyl)piperazin-1-yl]carbonyl}cyclopropan-1-ol | 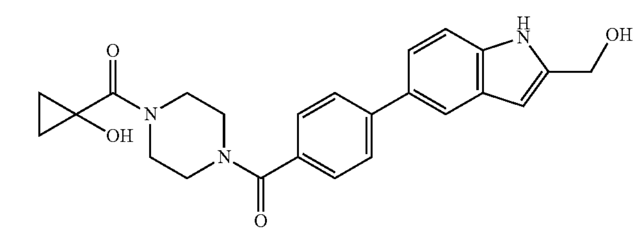 [SMILES: O=C(c1ccc(-c2ccc3[nH]c(CO)cc3c2)cc1)N1CCN(C(=O)C2(O)CC2)CC1] |
| 2-{5-[4-({4-[(1-hydroxycyclopropyl)carbonyl]piperazin-1-yl}carbonyl)phenyl]-1H-indol-3-yl}acetonitrile | 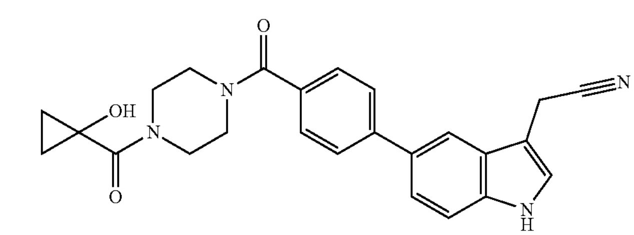 [SMILES: N#CCc1c[nH]c2ccc(-c3ccc(C(=O)N4CCN(C(=O)C5(O)CC5)CC4)cc3)cc12] |
| 1-{[4-({4-[3-(2-hydroxyethyl)-1H-indol-5-yl]phenyl}carbonyl)piperazin-1-yl]carbonyl}cyclopropan-1-ol | 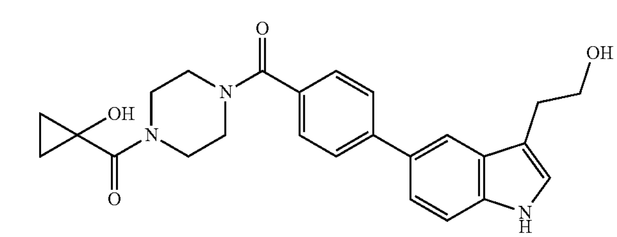 [SMILES: O=C(c1ccc(-c2ccc3[nH]cc(CCO)c3c2)cc1)N1CCN(C(=O)C2(O)CC2)CC1] |

| NAME | Structure |
|---|---|
| 5-[4-({4-[(1-hydroxycyclopropyl)carbonyl]piperazin-1-yl}carbonyl)phenyl]-1-benzofuran-2-carbonitrile | 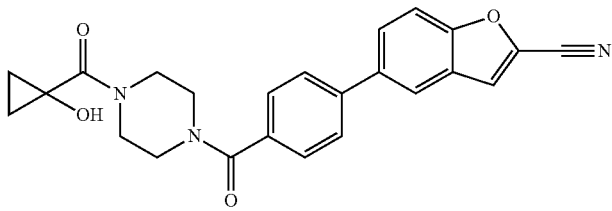 [SMILES: N#Cc1cc2cc(-c3ccc(C(=O)N4CCN(C(=O)C5(O)CC5)CC4)cc3)ccc2o1] |
| 1-[(4-{[4-(3-amino-1-methyl-1H-indazol-6-yl)phenyl]carbonyl}piperazin-1-yl)carbonyl]cyclopropan-1-ol | 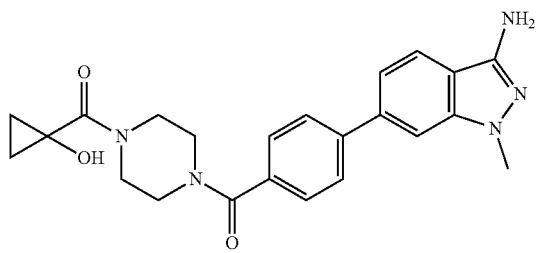 [SMILES: Cn1nc(N)c2ccc(-c3ccc(C(=O)N4CCN(C(=O)C5(O)CC5)CC4)cc3)cc21] |
| 1-[(4-{[4-(1-aminoisoquinolin-6-yl)phenyl]carbonyl}piperazin-1-yl)carbonyl]cyclopropan-1-ol | 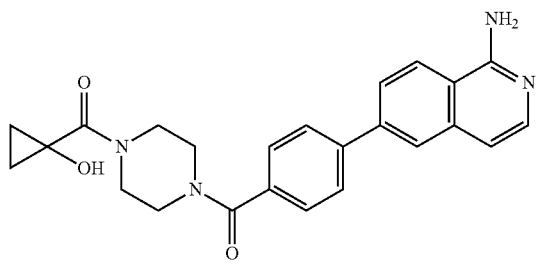 [SMILES: Nc1nccc2cc(-c3ccc(C(=O)N4CCN(C(=O)C5(O)CC5)CC4)cc3)ccc12] |
| 1-[(4-{[4-(3-aminoisoquinolin-6-yl)phenyl]carbonyl}piperazin-1-yl)carbonyl]cyclopropan-1-ol | 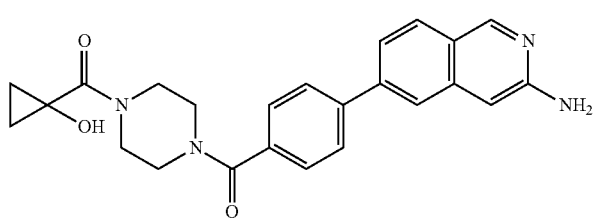 [SMILES: Nc1cc2cc(-c3ccc(C(=O)N4CCN(C(=O)C5(O)CC5)CC4)cc3)ccc2cn1] |
| 1-[(4-{[4-(1,3-dimethylisoquinolin-6-yl)phenyl]carbonyl}piperazin-1-yl)carbonyl]cyclopropan-1-ol | 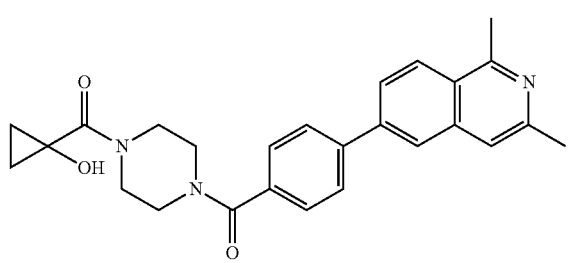 [SMILES: Cc1cc2cc(-c3ccc(C(=O)N4CCN(C(=O)C5(O)CC5)CC4)cc3)ccc2c(C)n1] |
| 1-{[4-{4-[3-(methoxymethyl)-1-methyl-1H-indazol-6-yl]phenyl}carbonyl)piperazin-1-yl]carbonyl}cyclopropan-1-ol | 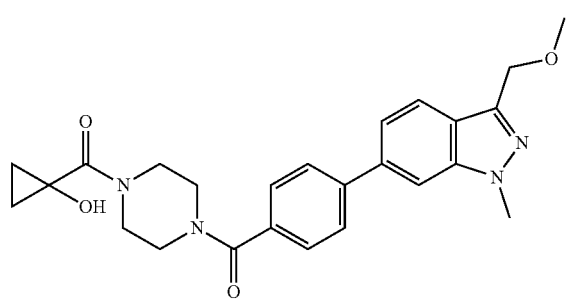 [SMILES: COCc1nn(C)c2cc(-c3ccc(C(=O)N4CCN(C(=O)C5(O)CC5)CC4)cc3)ccc12] |

-continued

| NAME | Structure |
|---|---|
| 1-{[4-({4-[3-(hydroxymethyl)-1-methyl-1H-indazol-6-yl]phenyl}carbonyl)piperazin-1-yl]carbonyl}cyclopropan-1-ol | 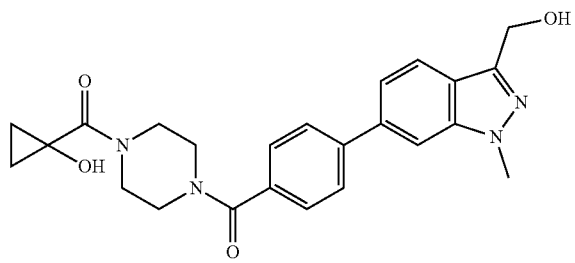 [SMILES: Cn1nc(CO)c2ccc(-c3ccc(C(=O)N4CCN(C(=O)C5(O)CC5)CC4)cc3)cc21] |
| 1-[(4-{[4-(2-methylquinolin-6-yl)phenyl]carbonyl}piperazin-1-yl)carbonyl]cyclopropan-1-ol | 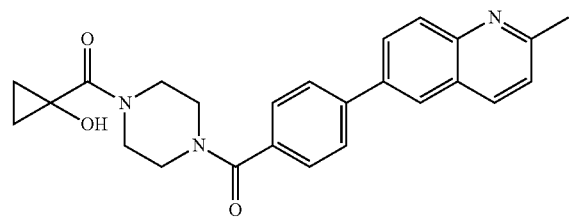 [SMILES: Cc1ccc2cc(-c3ccc(C(=O)N4CCN(C(=O)C5(O)CC5)CC4)cc3)ccc2n1] |
| 1-[(4-{[4-(2-aminoquinolin-6-yl)phenyl]carbonyl}piperazin-1-yl)carbonyl]cyclopropan-1-ol | 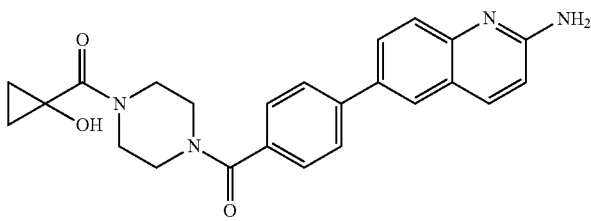 [SMILES: Nc1ccc2cc(-c3ccc(C(=O)N4CCN(C(=O)C5(O)CC5)CC4)cc3)ccc2n1] |
| 1-[(4-{[4-(1-ethyl-1H-indazol-6-yl)phenyl]carbonyl}piperazin-1-yl)carbonyl]cyclopropan-1-ol | 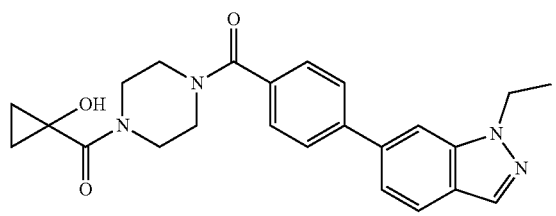 [SMILES: CCn1ncc2ccc(-c3ccc(C(=O)N4CCN(C(=O)C5(O)CC5)CC4)cc3)cc21] |
| 1-[(4-{[4-(1-cyclobutyl-1H-indazol-6-yl)phenyl]carbonyl}piperazin-1-yl)carbonyl]cyclopropan-1-ol | 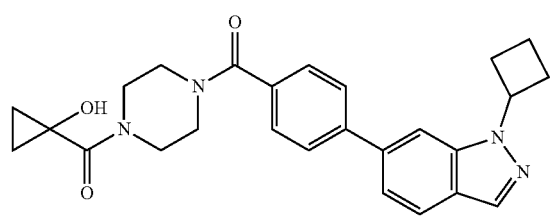 [SMILES: O=C(c1ccc(-c2ccc3cnn(C4CCC4)c3c2)cc1)N1CCN(C(=O)C2(O)CC2)CC1] |
| 1-{[4-({4-[1-(oxetan-3-yl)-1H-indazol-6-yl]phenyl}carbonyl)piperazin-1-yl]carbonyl}cyclopropan-1-ol | 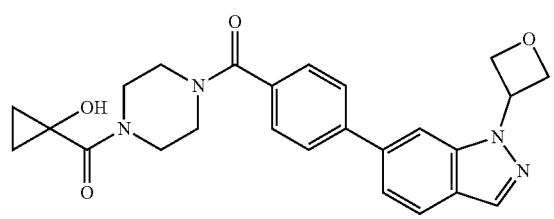 [SMILES: O=C(c1ccc(-c2ccc3cnn(C4COC4)c3c2)cc1)N1CCN(C(=O)C2(O)CC2)CC1] |
| 1-{[4-({4-[1-(propan-2-yl)-1H-indazol-6-yl]phenyl}carbonyl)piperazin-1-yl]carbonyl}cyclopropan-1-ol | 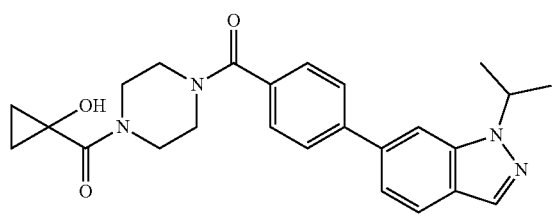 [SMILES: CC(C)n1ncc2ccc(-c3ccc(C(=O)N4CCN(C(=O)C5(O)CC5)CC4)cc3)cc21] |

-continued

| NAME | Structure |
|---|---|
| 1-{[4-({4-[1-(2-methoxyethyl)-1H-indazol-6-yl]phenyl}carbonyl)piperazin-1-yl]carbonyl}cyclopropan-1-ol | 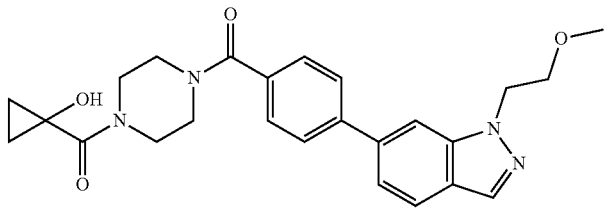 [SMILES: COCCn1ncc2ccc(-c3ccc(C(=O)N4CCN(C(=O)C5(O)CC5)CC4)cc3)cc21] |
| 1-{[4-({4-[1-(cyclopropylmethyl)-1H-indazol-6-yl]phenyl}carbonyl)piperazin-1-yl]carbonyl}cyclopropan-1-ol | 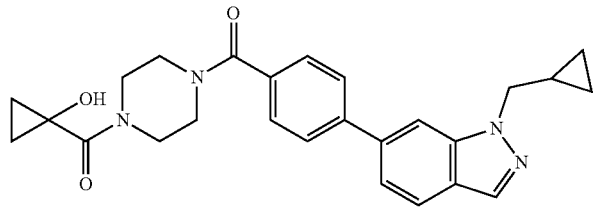 [SMILES: O=C(c1ccc(-c2ccc3cnn(CC4CC4)c3c2)cc1)N1CCN(C(=O)C2(O)CC2)CC1] |
| 1-[(4-{[4-(1-propyl-1H-indazol-6-yl)phenyl]carbonyl}piperazin-1-yl)carbonyl]cyclopropan-1-ol | 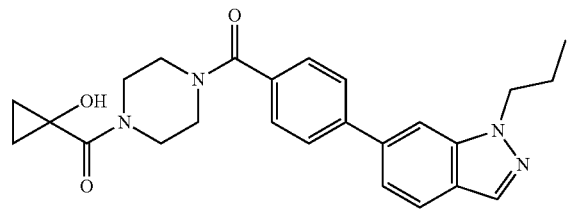 [SMILES: CCCn1ncc2ccc(-c3ccc(C(=O)N4CCN(C(=O)C5(O)CC5)CC4)cc3)cc21] |
| 1-{[4-({4-[1-(cyclobutylmethyl)-indazol-6-yl]phenyl}carbonyl)piperazin-1-yl]carbonyl}cyclopropan-1-ol | 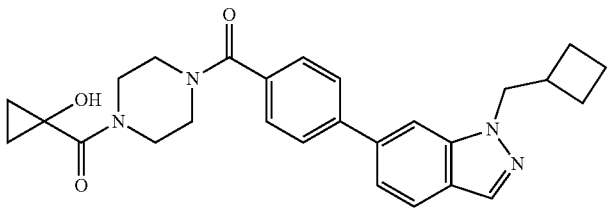 [SMILES: O=C(c1ccc(-c2ccc3cnn(CC4CCC4)c3c2)cc1)N1CCN(C(=O)C2(O)CC2)CC1] |
| 1-{[4-({4-[1-(oxetan-3-ylmethyl)-1H-indazol-6-yl]phenyl}carbonyl)piperazin-1-yl]carbonyl}cyclopropan-1-ol | 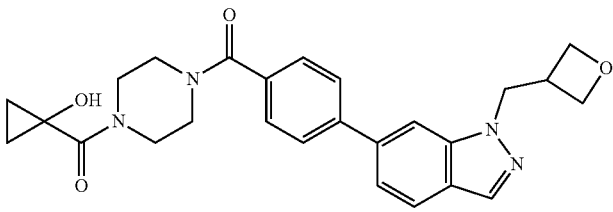 [SMILES: O=C(c1ccc(-c2ccc3cnn(CC4COC4)c3c2)cc1)N1CCN(C(=O)C2(O)CC2)CC1] |
| 1-{[4-({4-[1-(2-hydroxyethyl)-1H-indazol-6-yl]phenyl}carbonyl)piperazin-1-yl]carbonyl}cyclopropan-1-ol | 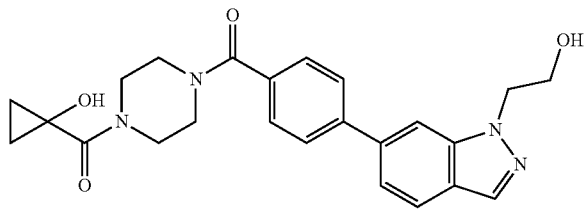 [SMILES: O=C(c1ccc(-c2ccc3cnn(CCO)c3c2)cc1)N1CCN(C(=O)C2(O)CC2)CC1] |
| 1-[(4-{[4-(1-cyclopropyl-1H-indazol-6-yl]phenyl}carbonyl)piperazin-1-yl)carbonyl]cyclopropan-1-ol | 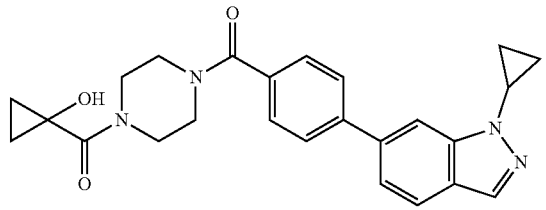 [SMILES: O=C(c1ccc(-c2ccc3cnn(C4CC4)c3c2)cc1)N1CCN(C(=O)C2(O)CC2)CC1] |

-continued

| NAME | Structure |
|---|---|
| N-{3-[4-({4-[(1-hydroxycyclopropyl)carbonyl]piperazin-1-yl}carbonyl)phenyl]phenyl}-N-methylcyclopropanecarboxamide | |
| N-{3-[4-({4-[(1-hydroxycyclopropyl)carbonyl]piperazin-1-yl}carbonyl)phenyl]phenyl}-N-methylcyclopropanecarboxamide | |
| N-{3-[4-({4-[(1-hydroxycyclopropyl)carbonyl]piperazin-1-yl}carbonyl)phenyl]phenyl}-N-methylcyclopropanecarboxamide | |
| N-cyclopropyl-3-[4-({4-[(1-hydroxycyclopropyl)carbonyl]piperazin-1-yl}carbonyl)phenyl]-N-methylbenzene-1-sulfonamide | 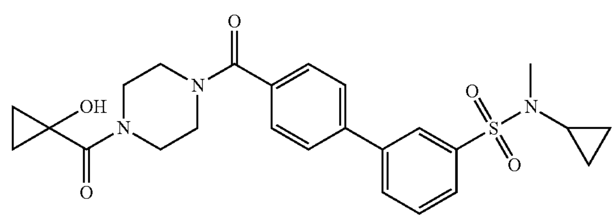 [SMILES: CN(C1CC1)S(=O)(=O)c1cccc(-c2ccc(C(=O)N3CCN(C(=O)C4(O)CC4)CC3)cc2)c1] |
| N-cyclopropyl-3-[4-({4-[(1-hydroxycyclopropyl)carbonyl]piperazin-1-yl}carbonyl)phenyl]-N-methylbenzamide | 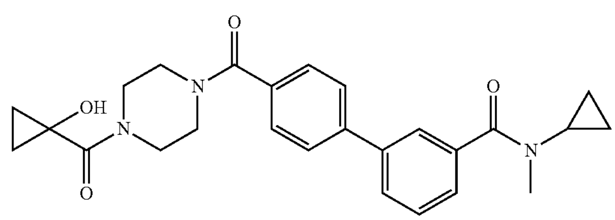 [SMILES: CN(C(=O)c1cccc(-c2ccc(C(=O)N3CCN(C(=O)C4(O)CC4)CC3)cc2)c1)C1CC1] |
| 2-cyclobutyl-N-{3-[4-({4-[(1-hydroxycyclopropyl)carbonyl]piperazin-1-yl}carbonyl)phenyl]phenyl}acetamide | 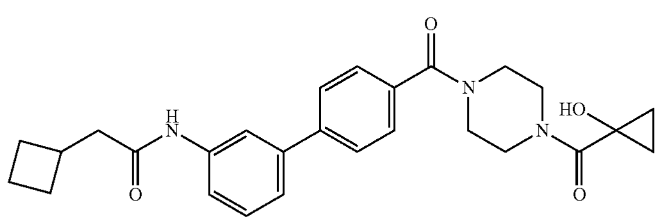 [SMILES: O=C(CC1CCC1)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}-1-methylazetidine-3-carboxamide | 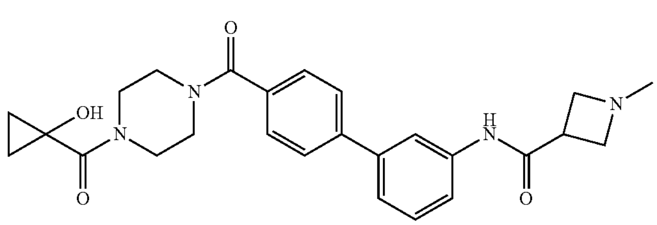 [SMILES: CN1CC(C(=O)Nc2cccc(-c3ccc(C(=O)N4CCN(C(=O)C5(O)CC5)CC4)cc3)c2)C1] |

| NAME | Structure |
|---|---|
| N-{3-[4-({4-[(1-hydroxycyclopropyl)carbonyl]piperazin-1-yl}carbonyl)phenyl]phenyl}-3-methylazetidine-3-carboxamide | 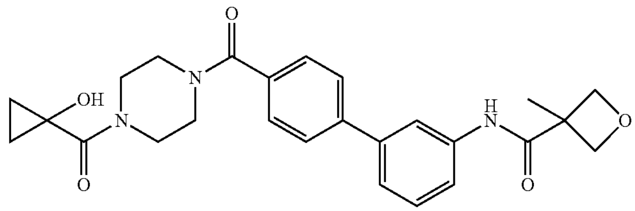 [SMILES: CC1(C(=O)Nc2cccc(-c3ccc(C(=O)N4CCN(C(=O)C5(O)CC5)CC4)cc3)c2)COC1] |
| N-{3-[4-({4-[(1-hydroxycyclopropyl)carbonyl]piperazin-1-yl}carbonyl)phenyl]phenyl}-2-(oxetan-3-yl)acetamide | 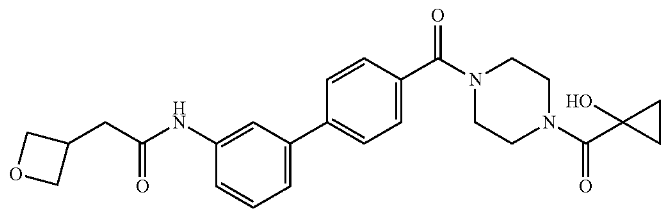 [SMILES: O=C(CC1COC1)Nc1cccc(-c2ccc(C(=O)N3CCN(C(=O)C4(O)CC4)CC3)cc2)c1] |
| 3-fluoro-N-{3-[4-({4-[(1-hydroxycyclopropyl)carbonyl]piperazin-1-yl}carbonyl)phenyl]phenyl}cyclobutane-1-carboxamide | 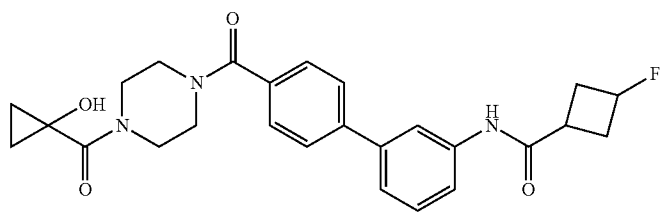 [SMILES: O=C(Nc1cccc(-c2ccc(C(=O)N3CCN(C(=O)C4(O)CC4)CC3)cc2)c1)C1CC(F)C1] |
| 3-ethyl-N-{3-[4-({4-[(1-hydroxycyclopropyl)carbonyl]piperazin-1-yl}carbonyl)phenyl]phenyl}oxetane-3-carboxamide | 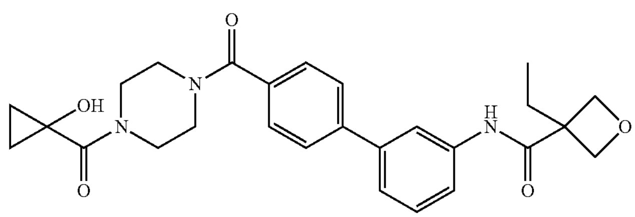 [SMILES: CCC1(C(=O)Nc2cccc(-c3ccc(C(=O)N4CCN(C(=O)C5(O)CC5)CC4)cc3)c2)COC1] |
| N-{3-[4-({4-[(1-hydroxycyclopropyl)carbonyl]piperazin-1-yl}carbonyl)phenyl]phenyl}propanamide | 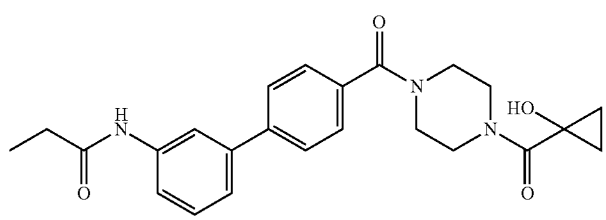 [SMILES: CCC(=O)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}-2-methylpropanamide | 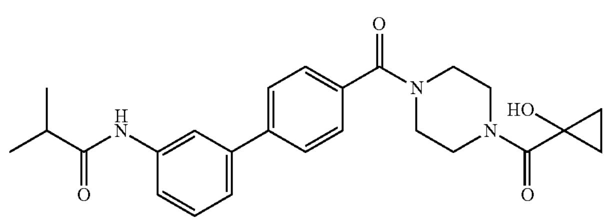 [SMILES: CC(C)C(=O)Nc1cccc(-c2ccc(C(=O)N3CCN(C(=O)C4(O)CC4)CC3)cc2)c1] |
| N-{3-[4-({4-[(1-hydroxycyclopropyl)carbonyl]piperazin-1-yl}carbonyl)phenyl]phenyl}butanamide | 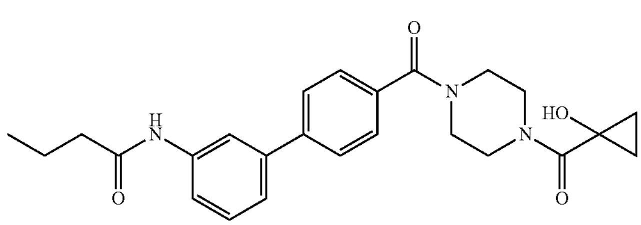 [SMILES: CCCC(=O)Nc1cccc(-c2ccc(C(=O)N3CCN(C(=O)C4(O)CC4)CC3)cc2)c1] |

-continued

| NAME | Structure |
| --- | --- |
| N-{3-[4-({4-[(1-hydroxycyclopropyl)carbonyl]piperazin-1-yl}carbonyl)phenyl]phenyl}-2-methoxy-acetamide | 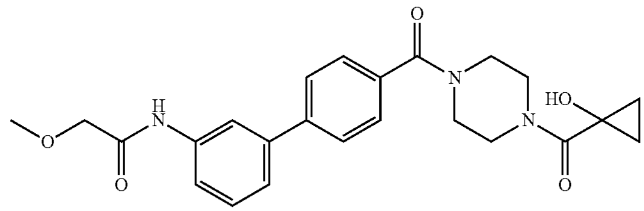 [SMILES: COCC(=O)Nc1cccc(-c2ccc(C(=O)N3CCN(C(=O)C4(O)CC4)CC3)cc2)c1] |
| 2-cyclopropyl-N-{3-[4-({4-[(1-hydroxycyclopropyl)carbonyl]piperazin-1-yl}carbonyl)phenyl]phenyl}acetamide | 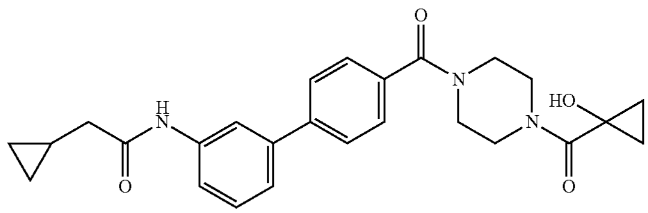 [SMILES: O=C(CC1CC1)Nc1cccc(-c2ccc(C(=O)N3CCN(C(=O)C4(O)CC4)CC3)cc2)c1] |
| 2,2-difluoro-N-{3-[4-({4-[(1-hydroxycyclopropyl)carbonyl]piperazin-1-yl}carbonyl)phenyl]phenyl}acetamide | 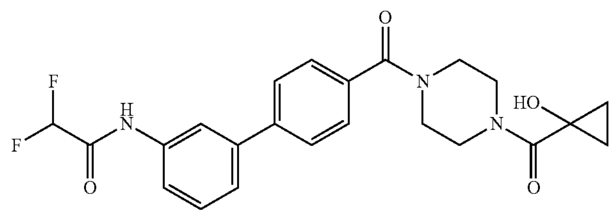 [SMILES: O=C(Nc1cccc(-c2ccc(C(=O)N3CCN(C(=O)C4(O)CC4)CC3)cc2)c1)C(F)F] |
| N-{3-[4-({4-[(1-hydroxycyclopropyl)carbonyl]piperazin-1-yl}carbonyl)phenyl]phenyl}-1-methylcyclopropane-1-carboxamide | 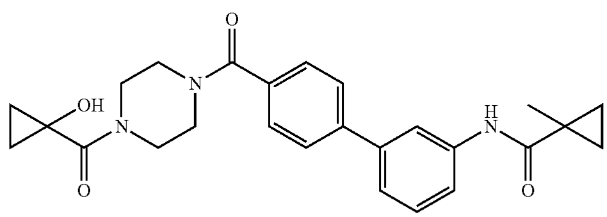 [SMILES: CC1(C(=O)Nc2cccc(-c3ccc(C(=O)N4CCN(C(=O)C5(O)CC5)CC4)cc3)c2)CC1] |
| N-{3-[4-({4-[(1-hydroxycyclopropyl)carbonyl]piperazin-1-yl}carbonyl)phenyl]phenyl}cyclopentane-carboxamide | 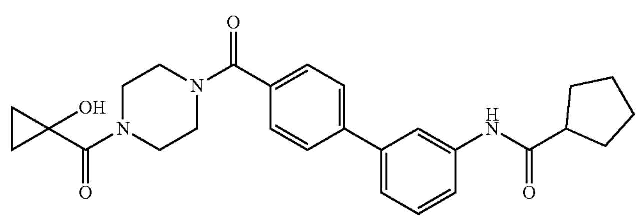 [SMILES: O=C(Nc1cccc(-c2ccc(C(=O)N3CCN(C(=O)C4(O)CC4)CC3)cc2)c1)C1CCCC1] |
| N-{3-[4-({4-[(1-hydroxycyclopropyl)carbonyl]piperazin-1-yl}carbonyl)phenyl]phenyl}cyclohexane-carboxamide | 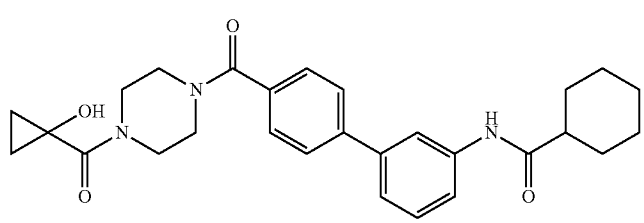 [SMILES: O=C(Nc1cccc(-c2ccc(C(=O)N3CCN(C(=O)C4(O)CC4)CC3)cc2)c1)C1CCCCC1] |
| N-{3-[4-({4-[(1-hydroxycyclopropyl)carbonyl]piperazin-1-yl}carbonyl)phenyl]phenyl}oxane-4-carboxamide | 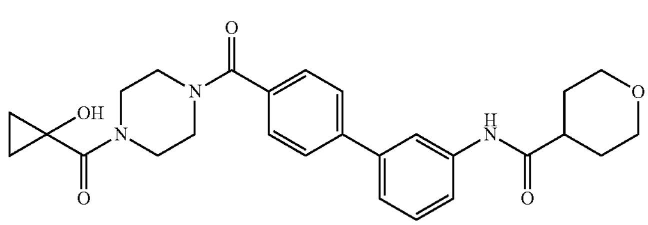 [SMILES: O=C(Nc1cccc(-c2ccc(C(=O)N3CCN(C(=O)C4(O)CC4)CC3)cc2)c1)C1CCOCC1] |

| NAME | Structure |
|---|---|
| 1-cyclopropyl-N-{3-[4-({4-[(1-hydroxycyclopropyl)carbonyl]piperazin-1-yl}carbonyl)phenyl]phenyl}methanesulfonamide | |
| N-{3-[4-({4-[(1-hydroxycyclopropyl)carbonyl]piperazin-1-yl}carbonyl)phenyl]phenyl}-2-methyl-propane-1-sulfonamide | 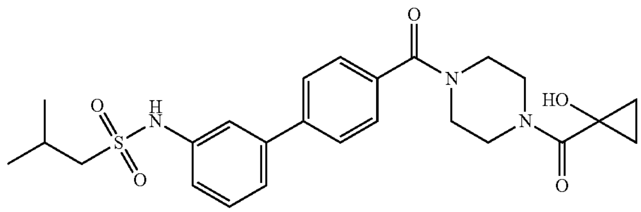 [SMILES: CC(C)CS(=O)(=O)Nc1cccc(-c2ccc(C(=O)N3CCN(C(=O)C4(O)CC4)CC3)cc2)c1] |
| 1,1-difluoro-N-{3-[4-({4-[(1-hydroxycyclopropyl)carbonyl]piperazin-1-yl}carbonyl)phenyl]phenyl}methanesulfonamide | |
| 3,3,3-trifluoro-N-{3-[4-({4-[(1-hydroxycyclopropyl)carbonyl]piperazin-1-yl}carbonyl)phenyl]phenyl}propane-1-sulfonamide | 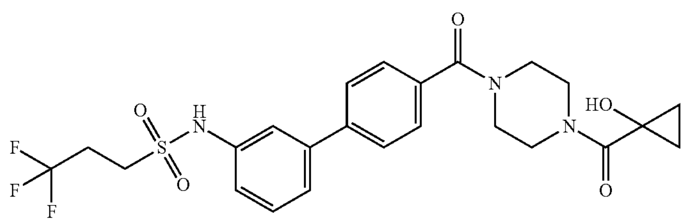 [SMILES: O=C(c1ccc(-c2cccc(NS(=O)(=O)CCC(F)(F)F)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}-1-methyl-cyclopropane-1-sulfonamide | 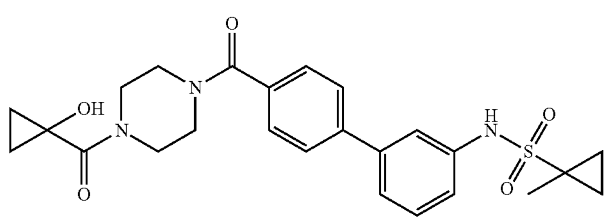 [SMILES: CC1(S(=O)(=O)Nc2cccc(-c3ccc(C(=O)N4CCN(C(=O)C5(O)CC5)CC4)cc3)c2)CC1] |
| N-{3-[4-({4-[(1-hydroxycyclopropyl)carbonyl]piperazin-1-yl}carbonyl)phenyl]phenyl}cyclobutane-sulfonamide | 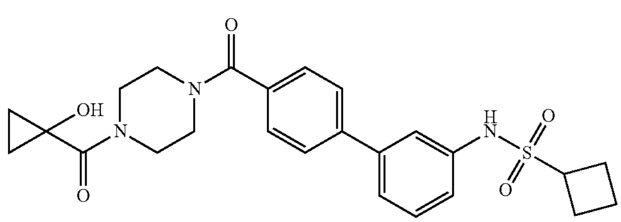 [SMILES: O=C(c1ccc(-c2cccc(NS(=O)(=O)C3CCC3)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}oxolane-3-sulfonamide | 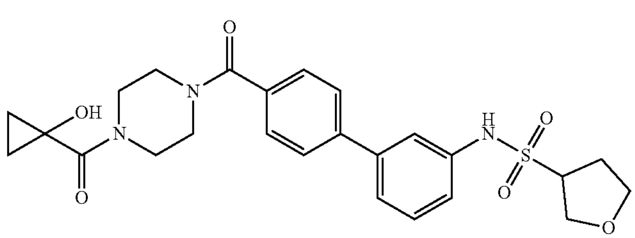 [SMILES: O=C(c1ccc(-c2cccc(NS(=O)(=O)C3CCOC3)c2)cc1)N1CCN(C(=O)C2(O)CC2)CC1] |

-continued

| NAME | Structure |
|---|---|
| N-{3-[4-({4-[(1-hydroxycyclopropyl)carbonyl]piperazin-1-yl}carbonyl)phenyl]phenyl}cyclopentane-sulfonamide | 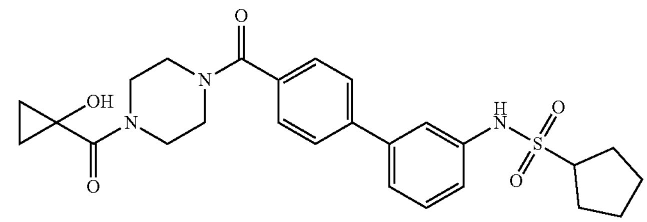 [SMILES: O=C(c1ccc(-c2cccc(NS(=O)(=O)C3CCCC3)c2)cc1)N1CCN(C(=O)C2(O)CC2)CC1] |
| 2,2-difluoro-N-{3-[4-({4-[(1-hydroxycyclopropyl)carbonyl]piperazin-1-yl}carbonyl)phenyl]phenyl}ethane-1-sulfonamide | 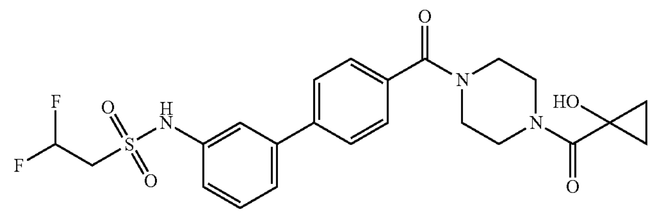 [SMILES: O=C(c1ccc(-c2cccc(NS(=O)(=O)CC(F)F)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}-2-methyoxyethane-1-sulfonamide | 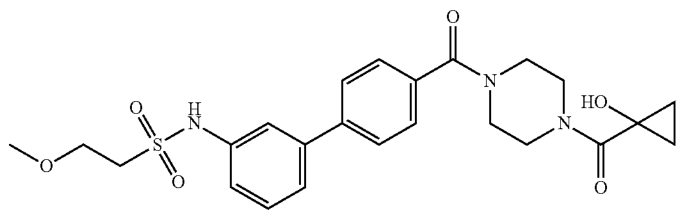 [SMILES: COCCS(=O)(=O)Nc1cccc(-c2ccc(C(=O)N3CCN(C(=O)C4(O)CC4)CC3)cc2)c1] |
| 1-cyclobutyl-N-{3-[4-({4-[(1-hydroxycyclopropyl)carbonyl]piperazin-1-yl}carbonyl)phenyl]phenyl}methane-sulfonamide | 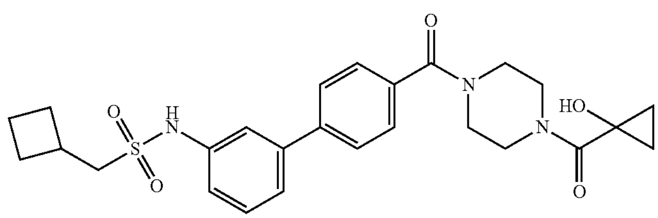 [SMILES: O=C(c1ccc(-c2cccc(NS(=O)(=O)CC3CCC3)c2)cc1)N1CCN(C(=O)C2(O)CC2)CC1] |
| 2-hydroxy-N-{3-[4-({4-[(1-hydroxycyclopropyl)carbonyl]piperazin-1-yl}carbonyl)phenyl]phenyl}ethane-1-sulfonamide | 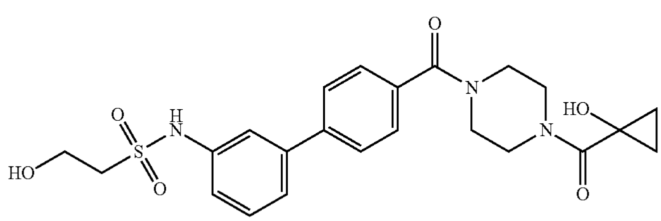 [SMILES: O=C(c1ccc(-c2cccc(NS(=O)(=O)CCO)c2)cc1)N1CCN(C(=O)C2(O)CC2)CC1] |
| N-{3-[4-({4-[(1-hydroxycyclopropyl)carbonyl]piperazin-1-yl}carbonyl)phenyl]phenyl}oxane-4-sulfonamide | 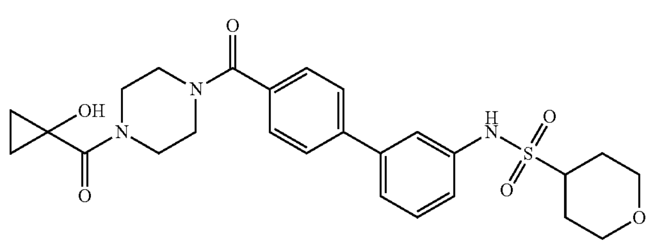 [SMILES: O=C(c1ccc(-c2cccc(NS(=O)(=O)C3CCOCC3)c2)cc1)N1CCN(C(=O)C2(O)CC2)CC1] |
| 2-cyclopropyl-N-{3-[4-({4-[(1-hydroxycyclopropyl)carbonyl]piperazin-1-yl}carbonyl)phenyl]phenyl}ethane-1-sulfonamide | 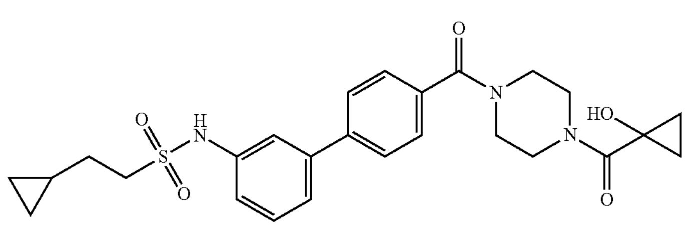 [SMILES: O=C(c1ccc(-c2cccc(NS(=O)(=O)CCC3CC3)c2)cc1)N1CCN(C(=O)C2(O)CC2)CC1] |

| NAME | Structure |
|---|---|
| 3,3-difluoro-N-{3-[4-({4-[(1-hydroxycyclopropyl)carbonyl]piperazin-1-yl}carbonyl)phenyl]phenyl}cyclobutane-1-carboxamide | 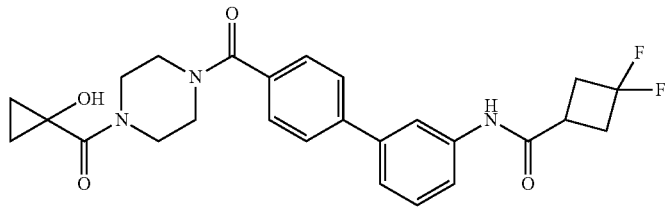 [SMILES: O=C(Nc1cccc(-c2ccc(C(=O)N3CCN(C(=O)C4(O)CC4)CC3)cc2)c1)C1CC(F)(F)C1] |
| 1-[(4-{[4-(1H-1,3-benzodiazol-4-yl)-2-chlorophenyl]carbonyl}piperazin-1-yl)carbonyl]cyclopropan-1-ol | 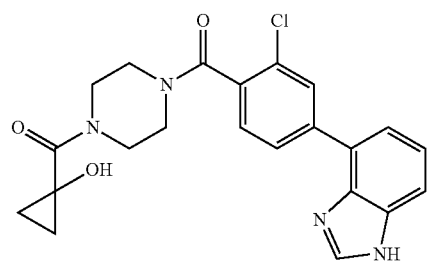 [SMILES: O=C(c1ccc(-c2cccc3[nH]cnc23)cc1Cl)N1CCN(C(=O)C2(O)CC2)CC1] |
| 1-[(4-{[4-(2-cyclopropyl-2H-indazol-5-yl)phenyl]carbonyl}piperazin-1-yl)carbonyl]cyclopropan-1-ol | 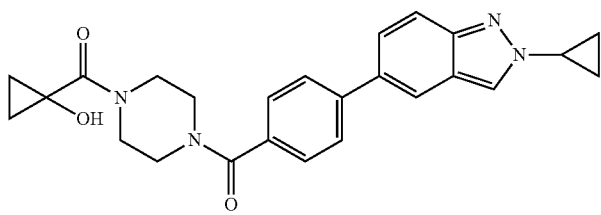 [SMILES: O=C(c1ccc(-c2ccc3nn(C4CC4)cc3c2)cc1)N1CCN(C(=O)C2(O)CC2)CC1] |
| 1-[(4-{[4-(1-cyclopropyl-1H-indazol-5-yl)phenyl]carbonyl}piperazin-1-yl)carbonyl]cyclopropan-1-ol | 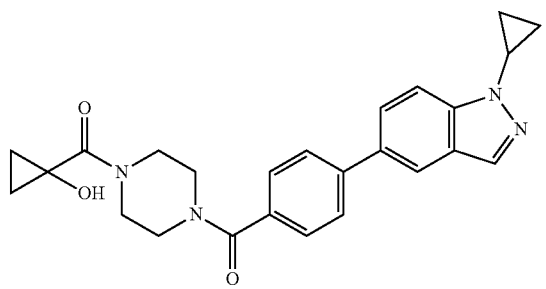 [SMILES: O=C(c1ccc(-c2ccc3c(cnn3C3CC3)c2)cc1)N1CCN(C(=O)C2(O)CC2)CC1] |
| N-{4-[4-({4-[(1-hydroxycyclopropyl)carbonyl]piperazin-1-yl}carbonyl)phenyl]phenyl}cyclopropanecarboxamide | 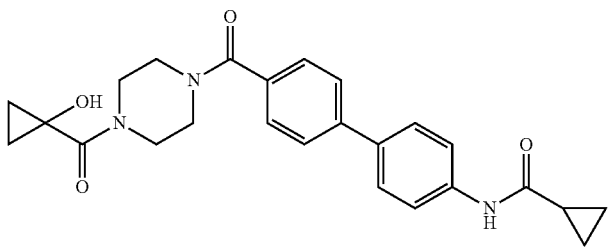 [SMILES: O=C(Nc1ccc(-c2ccc(C(=O)N3CCN(C(=O)C4(O)CC4)CC3)cc2)cc1)C1CC1] |
| N-{3-[4-({4-[(1-hydroxycyclopropyl)carbonyl]piperazin-1-yl}carbonyl)phenyl]phenyl}-N-methylcyclopropanesulfonamide | 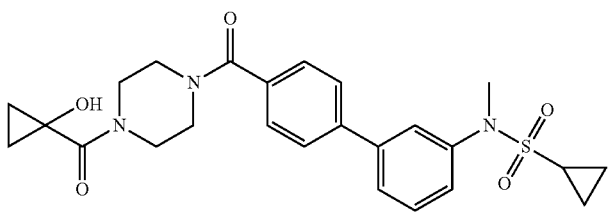 [SMILES: CN(c1cccc(-c2ccc(C(=O)N3CCN(C(=O)C4(O)CC4)CC3)cc2)c1)S(=O)(=O)C1CC1] |

-continued

| NAME | Structure |
|---|---|
| N-{3-[4-({4-[(1-methoxycyclopropyl)carbonyl]piperazin-1-yl}carbonyl)phenyl]phenyl}-N-methylcyclopropanesulfonamide | 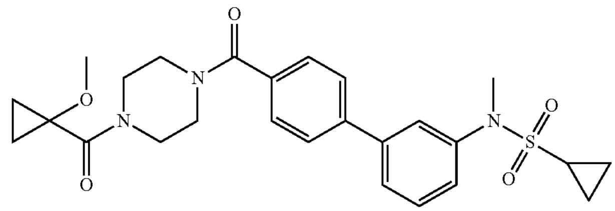 [SMILES: COC1(C(=O)N2CCN(C(=O)c3ccc(-c4cccc(N(C)S(=O)(=O)C5CC5)c4)cc3)CC2)CC1] |
| 3-cyclopropyl-1-{3-[4-({4-[(1-hydroxycyclopropyl)carbonyl]piperazin-1-yl}carbonyl)phenyl]phenyl}urea | 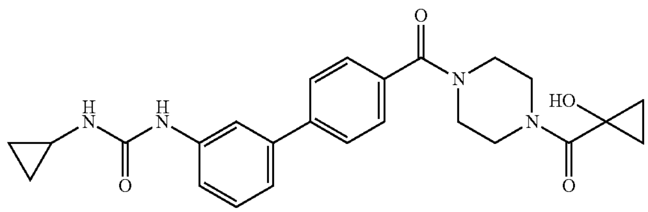 [SMILES: O=C(Nc1cccc(-c2ccc(C(=O)N3CCN(C(=O)C4(O)CC4)CC3)cc2)c1)NC1CC1] |
| 3-[4-({4-[(1-hydroxycyclopropyl)carbonyl]piperazin-1-yl}carbonyl)phenyl]phenyl N-cyclopropylcarbamate | 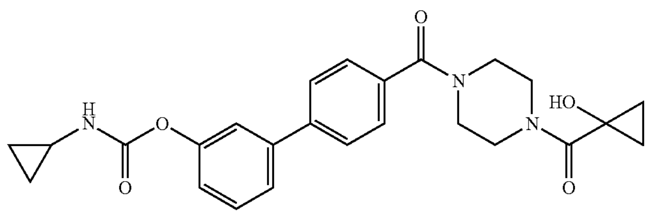 [SMILES: O=C(NC1CC1)Oc1cccc(-c2ccc(C(=O)N3CCN(C(=O)C4(O)CC4)CC3)cc2)c1] |
| N-{4-[4-({4-[(1-hydroxycyclopropyl)carbonyl]piperazin-1-yl}carbonyl)phenyl]phenyl}cyclopropanesulfonamide | 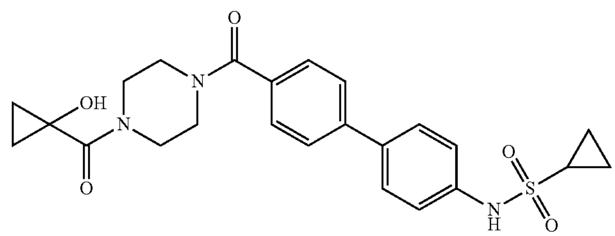 [SMILES: O=C(c1ccc(-c2ccc(NS(=O)(=O)C3CC3)cc2)cc1)N1CCN(C(=O)C2(O)CC2)CC1] |
| N-{3-[3-chloro-4-({4-[(1-hydroxycyclopropyl)carbonyl]piperazin-1-yl}carbonyl)phenyl]phenyl}cyclopropanesulfonamide | 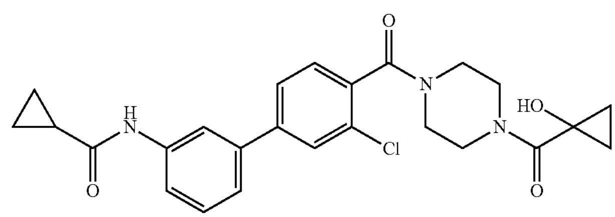 [SMILES: O=C(Nc1cccc(-c2ccc(C(=O)N3CCN(C(=O)C4(O)CC4)CC3)c(Cl)c2)c1)C1CC1] |
| N-(3-{4-[4-(1-hydroxycyclopropanecarbonyl)piperazin-1-carbonyl]phenyl}phenyl)cyclopentanecarboxamide | 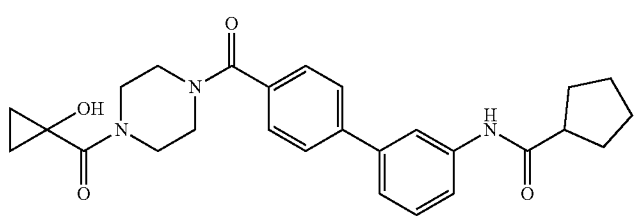 [SMILES: O=C(Nc1cccc(-c2ccc(C(=O)N3CCN(C(=O)C4(O)CC4)CC3)cc2)c1)C1CCCC1] |
| 1-(4-{4-[4-(1H-pyrazol-4-yl)phenyl]benzoyl}piperazin-1-carbonyl)cyclopropan-1-ol | 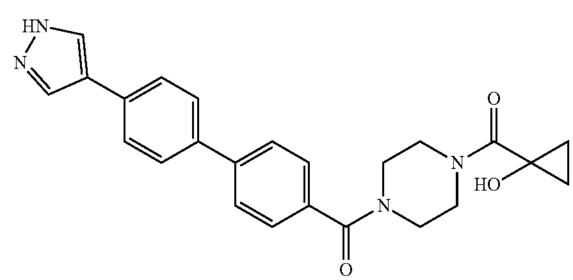 [SMILES: O=C(c1ccc(-c2ccc(-c3cn[nH]c3)cc2)cc1)N1CCN(C(=O)C2(O)CC2)CC1] |

-continued

| NAME | Structure |
|---|---|
| 1-{4-{4-(1,2,3,4-tetrahydroisoquinolin-2-yl)benzoyl}piperazine-1-carbonyl}cyclopropan-1-ol | 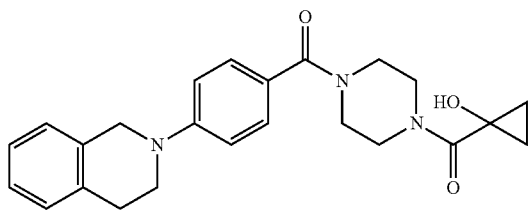 [SMILES: O=C(c1ccc(N2CCc3ccccc3C2)cc1)N1CCN(C(=O)C2(O)CC2)CC1] |
| 1-{4-[4-(L3-dimethyl-1H-indazol-5-yl)-2-fluorobenzoyl]piperazine-1-carbonyl}cyclopropan-1-amine | 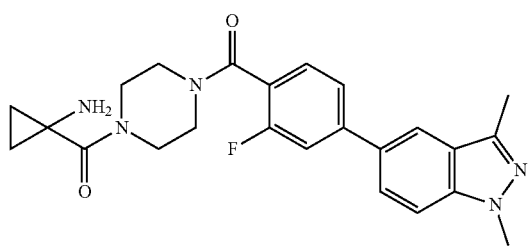 [SMILES: Cc1nn(C)c2ccc(-c3ccc(C(=O)N4CCN(C(=O)C5(N)CC5)CC4)c(F)c3)cc12] |
| 1-(4-{4-[4-(1-methyl-1H-pyrazol-4-yl)phenyl]benzoyl}piperazin-1-carbonyl)cyclopropan-1-ol | 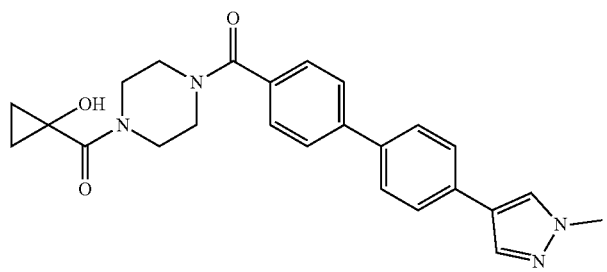 [SMILES: Cn1cc(-c2ccc(-c3ccc(C(=O)N4CCN(C(=O)C5(O)CC5)CC4)cc3)cc2)cn1] |
| 1-[(2S)-4-[2-fluoro-4-(1-methyl-1H-1,3-benzodiazol-5-yl)benzoyl]-2-methylpiperazine-1-carbonyl]cyclopropan-1-ol | 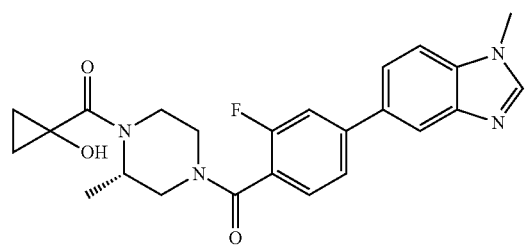 [SMILES: C[C@H]1CN(C(=O)c2ccc(-c3ccc4c(c3)ncn4C)cc2F)CCN1C(=O)C1(O)CC1] |
| 1-{4-[3-chloro-4-(1-methyl-1H-indazol-6-yl)benzoyl]piperazin-1-carbonyl}cyclopropan-1-ol | 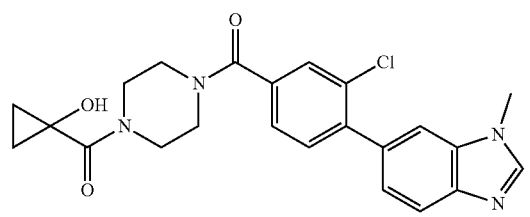 [SMILES: Cn1cnc2ccc(-c3ccc(C(=O)N4CCN(C(=O)C5(O)CC5)CC4)cc3Cl)cc21] |
| 1-{4-[2-fluoro-4-(1-methyl-1H-1,3-benzodiazol-5-yl)benzoyl]piperazin-1-carbonyl}cyclopropan-1-ol | 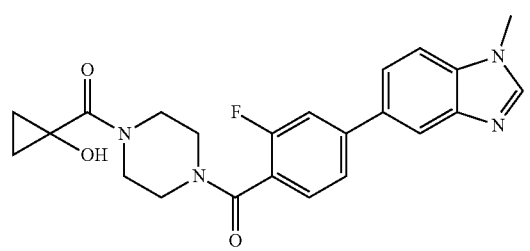 [SMILES: Cn1cnc2cc(-c3ccc(C(=O)N4CCN(C(=O)C5(O)CC5)CC4)c(F)c3)ccc21] |

-continued

| NAME | Structure |
|---|---|
| 1-{4-[3-chloro-4-(1-methyl-1H-1,3-benzodiazol-5-yl)benzoyl]piperazin-1-carbonyl}cyclopropan-1-ol | 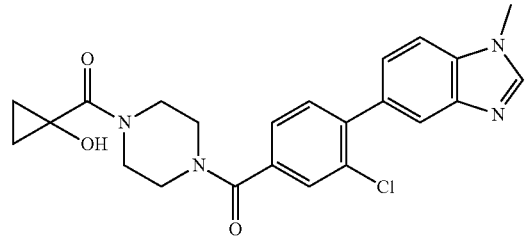 [SMILES: Cn1cnc2cc(-c3ccc(C(=O)N4CCN(C(=O)C5(O)CC5)CC4)cc3Cl)ccc21] |
| 1-[4-(4-{pyrazolo[1,5-a]pyridin-6-yl}benzoyl)piperazin-1-carbonyl]cyclopropan-1-ol | 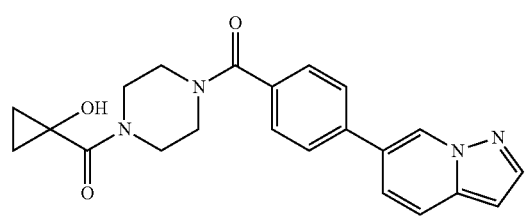 [SMILES: O=C(c1ccc(-c2ccc3ccnn3c2)cc1)N1CCN(C(=O)C2(O)CC2)CC1] |
| 1-{4-[4-(4-fluoro-23-dihydro-1H-indol-1-yl)benzoyl]piperazin-1-carbonyl}cyclopropan-1-ol | 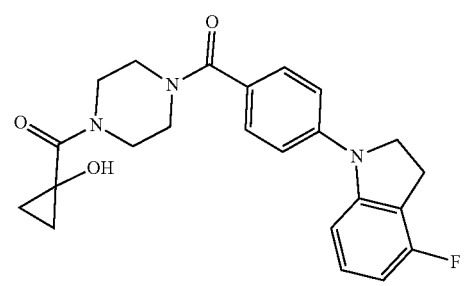 [SMILES: O=C(c1ccc(N2CCc3c(F)cccc32)cc1)N1CCN(C(=O)C2(O)CC2)CC1] |
| 1-{4-[4-(3-methyl-1H-indazol-6-yl)benzoyl]piperazin-1-carbonyl}cyclopropan-1-ol | 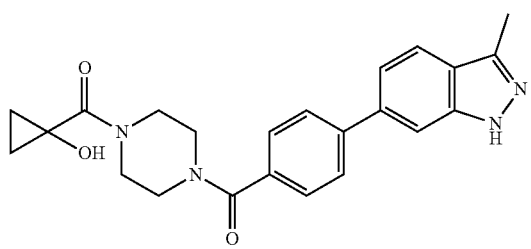 [SMILES: Cc1n[nH]c2cc(-c3ccc(C(=O)N4CCN(C(=O)C5(O)CC5)CC4)cc3)ccc12] |
| 1-{4-[2-fluoro-4-(3-methyl-1H-indazol-7-yl)benzoyl]piperazin-1-carbonyl}cyclopropan-1-ol | 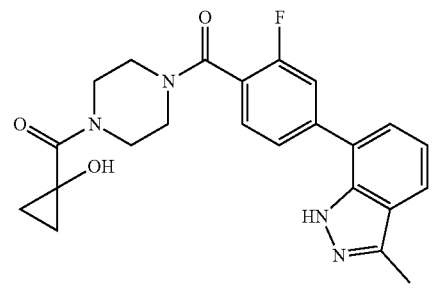 [SMILES: Cc1n[nH]c2c(-c3ccc(C(=O)N4CCN(C(=O)C5(O)CC5)CC4)c(F)c3)cccc12] |
| 1-[(2S)-2-methyl-4-[4-(1-methyl-1H-indazol-6-yl)benzoyl]piperazin-1-carbonyl]cyclopropan-1-ol | 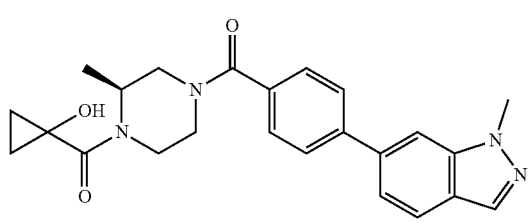 [SMILES: C[C@H]1CN(C(=O)c2ccc(-c3ccc4cnn(C)c4c3)cc2)CCN1C(=O)C1(O)CC1] |

| NAME | Structure |
|---|---|
| 1-{4-[3-chloro-4-(2-methyl-2H-indazol-6-yl)benzoyl]piperazin-1-carbonyl}cyclopropan-1-ol | 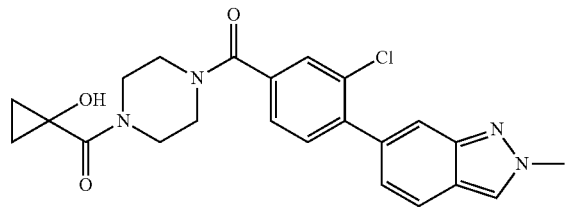 |
| 3,3,3-trifluoro-N-(3-{4-[4-(1-hydroxycyclopropanecarbonyl)piperazine-1-carbonyl]phenyl}phenyl)propane-1-sulfonamide | 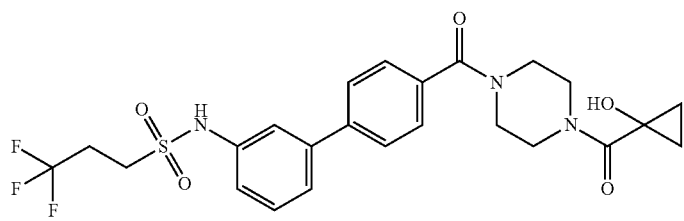 [SMILES: O=C(c1ccc(-c2cccc(NS(=O)(=O)CCC(F)(F)F)c2)cc1)N1CCN(C(=O)C2(O)CC2)CC1] |
| 1-{4-[2-fluoro-4-(1-methyl-1H-indazol-6-yl)benzoyl]piperazin-1-carbonyl}cyclopropan-1-ol | 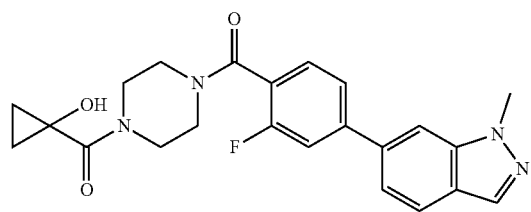 [SMILES: Cn1ncc2ccc(-c3ccc(C(=O)N4CCN(C(=O)C5(O)CC5)CC4)c(F)c3)cc21] |
| 1-{3,3-dimethyl-4-[4-(1-methyl-1H-1,3-benzodiazol-5-yl)benzoyl]piperazin-1-carbonyl}cyclopropan-1-ol | 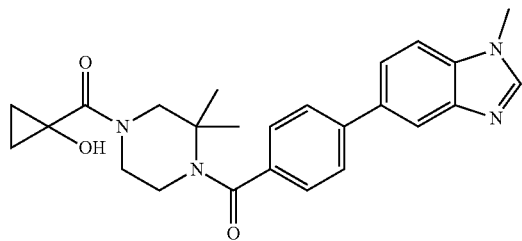 [SMILES: Cn1cnc2cc(-c3ccc(C(=O)N4CCN(C(=O)C5(O)CC5)CC4(C)C)cc3)ccc21] |
| 1-{4-[2,6-difluoro-4-(1-methyl-1H-1,3-benzodiazol-5-yl)benzoyl]piperazin-1-carbonyl}cyclopropan-1-ol | 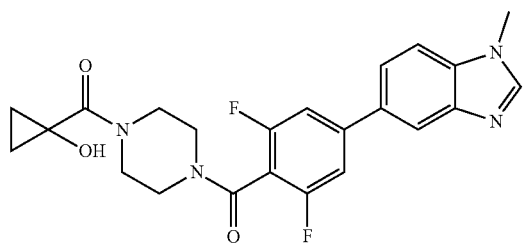 [SMILES: Cn1cnc2cc(-c3cc(F)c(C(=O)N4CCN(C(=O)C5(O)CC5)CC4)c(F)c3)ccc21] |
| 1-{4-[2-fluoro-4-(1-methyl-1H-indazol-6-yl)benzoyl]piperazin-1-carbonyl}cyclobutan-1-amine | 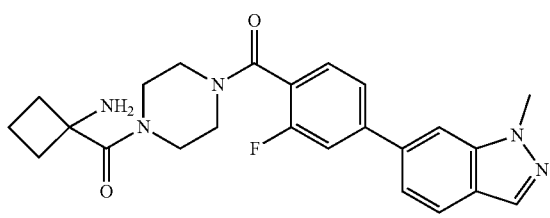 [SMILES: Cn1ncc2ccc(-c3ccc(C(=O)N4CCN(C(=O)C5(N)CCC5)CC4)c(F)c3)cc21] |

-continued

| NAME | Structure |
|---|---|
| 1-{4-[3-chloro-4-(6-chloro-1,3-benzoxazol-2-yl)benzoyl]piperazin-1-carbonyl}cyclopropan-1-ol | |
| 1-{4-[4-(1,3-dimethyl-1H-indazol-5-yl)-2-fluorobenzoyl]piperazine-1-carbonyl}cyclopropan-1-ol | |
| N-(3-{4-[4-(1-hydroxycyclopropanecarbonyl)piperazine-1-carbonyl}phenyl}phenyl)cyclobutanesulfonamide | |
| 1-{4-[4-(2,3-dihydro-1H-indol-1-yl)benzoyl]piperazine-1-carbonyl}cyclopropan-1-ol | |
| 1-{4-[3-chloro-4-(1,3-dimethyl-1H-indazol-5-yl)benzoyl]piperazin-1-carbonyl}cyclopropan-1-ol | |
| 1-[(2S)-2-methyl-4-[4-(1-methyl-1H-1,3-benzodiazol-5-yl)benzoyl]piperazin-1-carbonyl]cyclopropan-1-ol | |

| NAME | Structure |
|---|---|
| 1-{4-[2,6-difluoro-4-(2-methyl-2H-indazol-6-yl)benzoyl]piperazin-1-carbonyl}cyclopropan-1-ol | 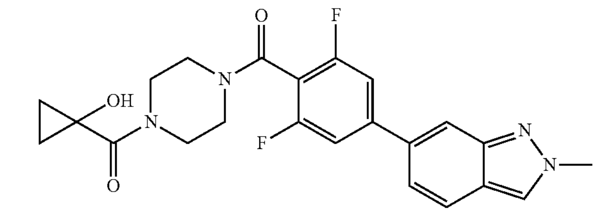 [SMILES: Cn1cc2ccc(-c3cc(F)c(C(=O)N4CCN(C(=O)C5(O)CC5)CC4)c(F)c3)cc2n1] |
| 1-(4-{4-[3-(5-amino-1,2-oxazol-3-yl)phenyl]-2-fluorobenzoyl}piperazine-1-carbonyl)cyclopropan-1-ol | 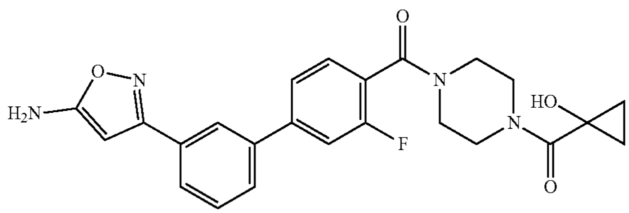 [SMILES: Nc1cc(-c2cccc(-c3ccc(C(=O)N4CCN(C(=O)C5(O)CC5)CC4)c(F)c3)c2)no1] |
| 1-[(2S)-2-methyl-4-[4-(2-methyl-2H-indazol-6-yl)benzoyl]piperazin-1-carbonyl]cyclopropan-1-ol | 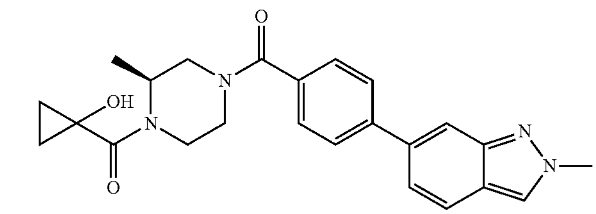 [SMILES: C[C@H]1CN(C(=O)c2ccc(-c3ccc4cn(C)nc4c3)cc2)CCN1C(=O)C1(O)CC1] |
| 1-cyclobutyl-N-(3-{4-[4-(1-hydroxycyclopropanecarbonyl)piperazine-1-carbonyl]phenyl}phenyl)methanesulfonamide | |
| 1-{4-[2-fluoro-4-(7-fluoro-1H-indazol-3-yl)benzoyl]piperazin-1-carbonyl}cyclopropan-1-ol | 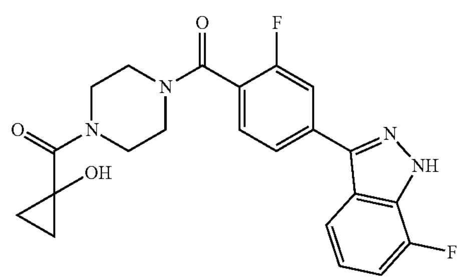 [SMILES: O=C(c1ccc(-c2n[nH]c3c(F)cccc23)cc1F)N1CCN(C(=O)C2(O)CC2)CC1] |
| 1-[(2S)-4-[4-(6-chloro-1,3-benzoxazol-2-yl)benzoyl]-2-methylpiperazine-1-carbonyl]cyclopropan-1-ol | 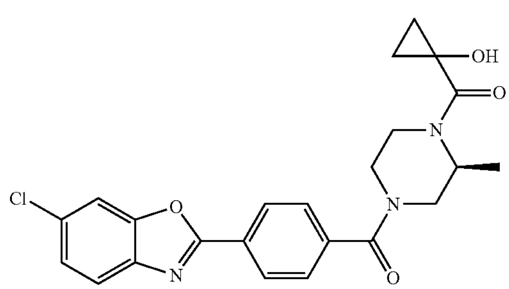 [SMILES: C[C@H]1CN(C(=O)c2ccc(-c3nc4ccc(Cl)cc4o3)cc2)CCN1C(=O)C1(O)CC1] |

| NAME | Structure |
|---|---|
| 1-{4-[4-(1H-indol-1-yl)benzoyl]piperazin-1-carbonyl}cyclopropan-1-ol | 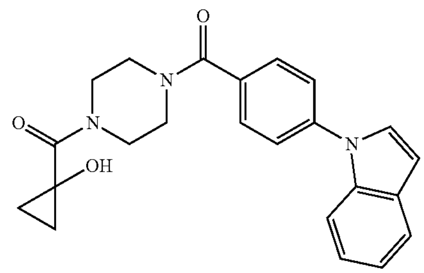 [SMILES: O=C(c1ccc(-n2ccc3ccccc32)cc1)N1CCN(C(=O)C2(O)CC2)CC1] |
| 1-{4-[4-(7-fluoro-1H-indazol-3-yl)benzoyl]piperazin-1-carbonyl}cyclopropan-1-ol | 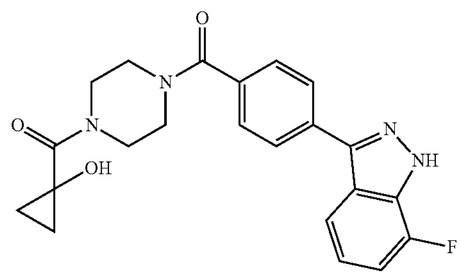 [SMILES: O=C(c1ccc(-c2n[nH]c3c(F)cccc23)cc1)N1CCN(C(=O)C2(O)CC2)CC1] |
| 1-{4-[4-(7-fluoro-1,2,3,4-tetrahydroisoquinolin-2-yl)benzoyl]piperazine-1-carbonyl}cyclopropan-1-ol | 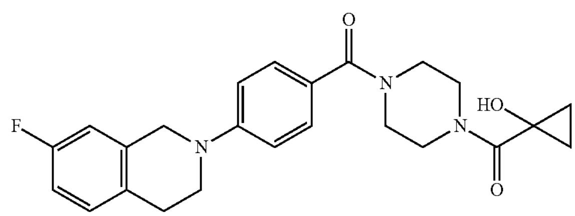 [SMILES: O=C(c1ccc(N2CCc3ccc(F)cc3C2)cc1)N1CCN(C(=O)C2(O)CC2)CC1] |
| 1-{4-[2-fluoro-4-(2-methyl-2H-indazol-6-yl)benzoyl]piperazin-1-carbonyl}cyclopropan-1-ol | 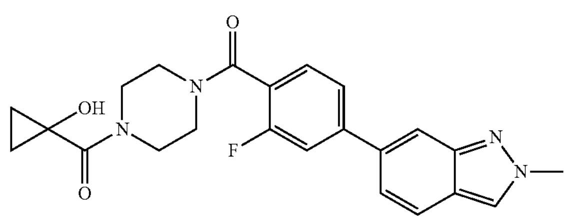 [SMILES: Cn1cc2ccc(-c3ccc(C(=O)N4CCN(C(=O)C5(O)CC5)CC4)c(F)c3)cc2n1] |
| 1-{4-[4-(3-amino-1H-indazol-6-yl)benzoyl]piperazin-1-carbonyl}cyclopropan-1-ol | 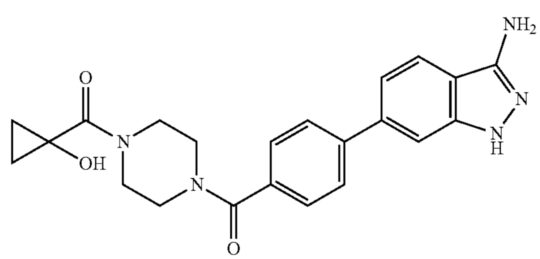 [SMILES: Nc1n[nH]c2cc(-c3ccc(C(=O)N4CCN(C(=O)C5(O)CC5)CC4)cc3)ccc12] |
| 1-{4-[4-(3-amino-1,2-benzoxazol-5-yl)benzoyl]piperazin-1-carbonyl}cyclopropan-1-ol | 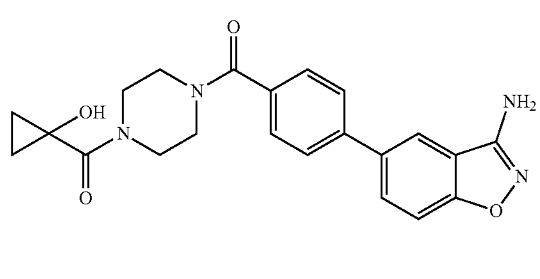 [SMILES: Nc1noc2ccc(-c3ccc(C(=O)N4CCN(C(=O)C5(O)CC5)CC4)cc3)cc12] |

-continued

| NAME | Structure |
|---|---|
| 1-{4-[4-(1,3-dimethyl-1H-indazol-5-yl)-2-fluorobenzoyl]piperazine-1-carbonyl}cyclobutan-1-amine | 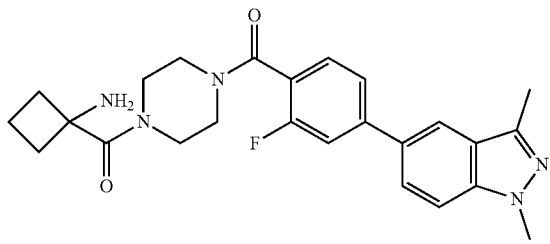 [SMILES: Cc1nn(C)c2ccc(-c3ccc(C(=O)N4CCN(C(=O)C5(N)CCC5)CC4)c(F)c3)cc12] |
| 1-{4-[2-fluoro-4-(3-methyl-1H-indazol-6-yl)benzoyl]piperazin-1-carbonyl}cyclopropan-1-ol | 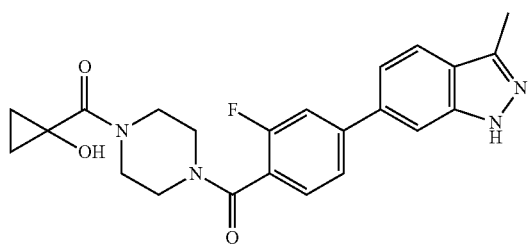 [SMILES: Cc1n[nH]c2cc(-c3ccc(C(=O)N4CCN(C(=O)C5(O)CC5)CC4)c(F)c3)ccc12] |
| ethyl N-(3-{4-[4-(1-hydroxycyclopropanecarbonyl)piperazine-1-carbonyl]phenyl}phenyl)carbamate | 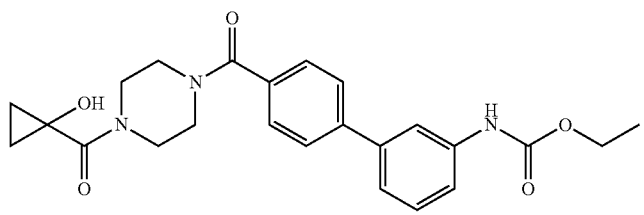 [SMILES: CCOC(=O)Nc1cccc(-c2ccc(C(=O)N3CCN(C(=O)C4(O)CC4)CC3)cc2)c1] |
| 1-{4-[4-(5-chloro-2-methyl-1H-1,3-benzodiazol-7-yl)benzoyl]piperazin-1-carbonyl}cyclopropan-1-ol | 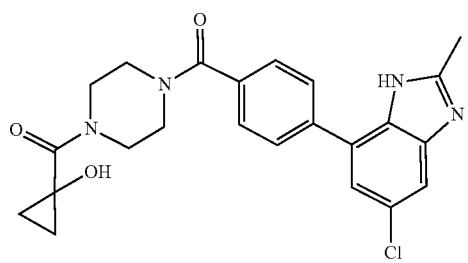 [SMILES: Cc1nc2cc(Cl)cc(-c3ccc(C(=O)N4CCN(C(=O)C5(O)CC5)CC4)cc3)c2[nH]1] |
| 1-[4-(4-{1H,2H,3H,4H,9H-pyrido[3,4-b]indol-2-yl}benzoyl)piperazine-1-carbonyl]cyclopropan-1-ol | 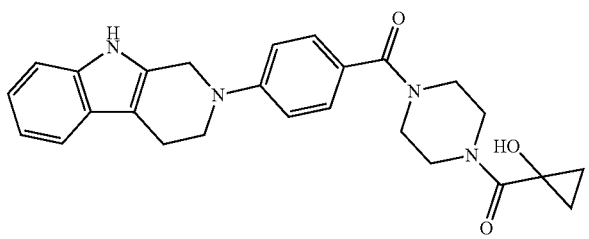 [SMILES: O=C(c1ccc(N2CCc3c([nH]c4ccccc34)C2)cc1)N1CCN(C(=O)C2(O)CC2)CC1] |
| 1-[(2R,6S)-2,6-dimethyl-4-[4-(1-methyl-1H-1,3-benzodiazol-5-yl)benzoyl]piperazine-1-carbonyl]cyclopropan-1-ol | 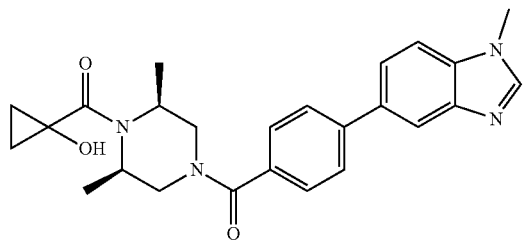 [SMILES: C[C@@H]1CN(C(=O)c2ccc(-c3ccc4c(c3)ncn4C)cc2)C[C@H](C)N1C(=O)C1(O)CC1] |

-continued

| NAME | Structure |
| --- | --- |
| 1-[4-(2-chloro-4-{3-chloroimidazo[1,2-a]pyridin-2-yl}benzoyl)piperazine-1-carbonyl]cyclopropan-1-ol | 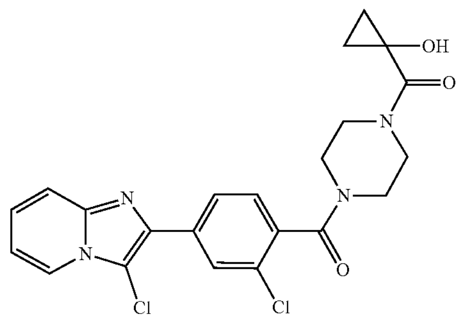 [SMILES: O=C(c1ccc(-c2nc3ccccn3c2Cl)cc1Cl)N1CCN(C(=O)C2(O)CC2)CC1] |
| 1-{4-[4-(4-chloro-2-fluorophenyl)benzoyl]-3,3-dimethylpiperazine-1-carbonyl}cyclopropan-1-ol | 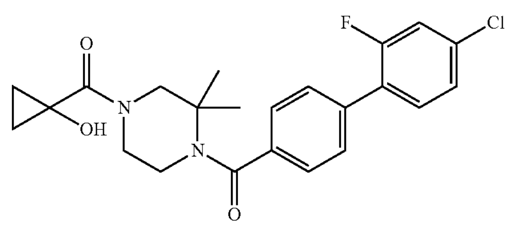 [SMILES: CC1(C)CN(C(=O)C2(O)CC2)CCN1C(=O)c1ccc(-c2ccc(Cl)cc2F)cc1] |
| 1-{4-[2-chloro-4-(1-methyl-1H-indazol-6-yl)benzoyl]piperazin-1-carbonyl}cyclopropan-1-ol | 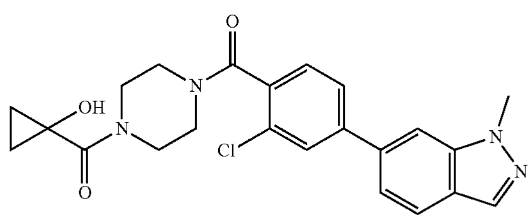 [SMILES: Cn1ncc2ccc(-c3ccc(C(=O)N4CCN(C(=O)C5(O)CC5)CC4)c(Cl)c3)cc21] |
| 1-[(2S)-4-[4-(4-chloro-2-fluorophenyl)benzoyl]-2-methylpiperazine-1-carbonyl]cyclopropan-1-ol | 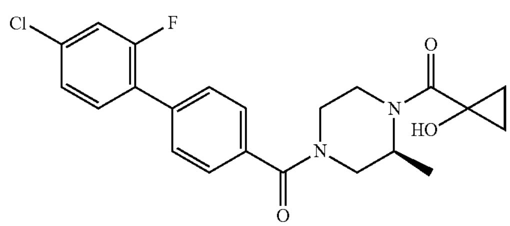 [SMILES: C[C@H]1CN(C(=O)c2ccc(-c3ccc(Cl)cc3F)cc2)CCN1C(=O)C1(O)CC1] |
| 1-[(2S)-4-[4-(1,3-dimethyl-1H-indazol-5-yl)benzoyl]-2-methylpiperazine-1-carbonyl]cyclopropan-1-ol | 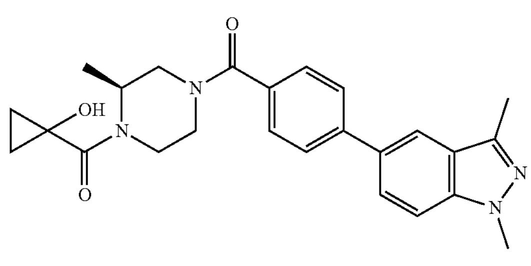 [SMILES: Cc1nn(C)c2ccc(-c3ccc(C(=O)N4CCN(C(=O)C5(O)CC5)[C@@H](C)C4)cc3)cc12] |
| 1-(4-{4-[3-(5-amino-1,2-oxazol-3-yl)phenyl]benzoyl}piperazine-1-carbonyl)cyclopropan-1-ol | 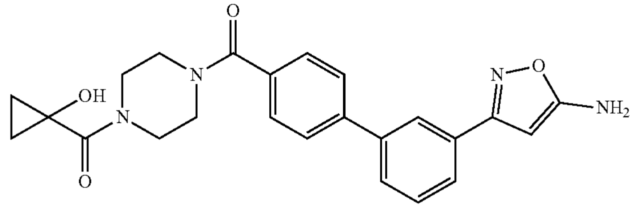 [SMILES: Nc1cc(-c2cccc(-c3ccc(C(=O)N4CCN(C(=O)C5(O)CC5)CC4)cc3)c2)no1] |

| NAME | Structure |
|---|---|
| 2-(3-{4-[4-(1-hydroxycyclopropanecarbonyl)piperazine-1-carbonyl]phenyl}phenyl)acetonitrile | 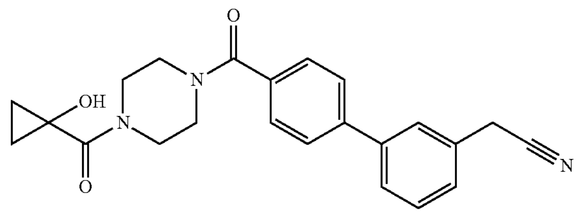 [SMILES: N#CCc1cccc(-c2ccc(C(=O)N3CCN(C(=O)C4(O)CC4)CC3)cc2)c1] |
| N-(3-{4-[4-(1-hydroxycyclopropanecarbonyl)piperazine-1-carbonyl]phenyl}phenyl)cyclopentanesulfonamide | |
| 1-[(3S)-3-methyl-4-[4-(1-methyl-1H-1,3-benzodiazol-5-yl)benzoyl]piperazin-1-carbonyl]cyclopropan-1-ol | 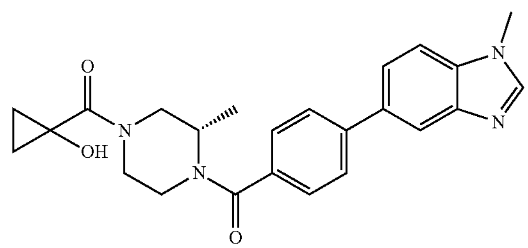 [SMILES: C[C@H]1CN(C(=O)C2(O)CC2)CCN1C(=O)c1ccc(-c2ccc3c(c2)ncn3C)cc1] |
| 1-cyclopropyl-N-(3-{4-[4-(1-hydroxycyclopropanecarbonyl)piperazine-1-carbonyl]phenyl}phenyl)methanesulfonamide | |
| 1-{4-[3-chloro-4-(6-fluoro-1,3-benzoxazol-2-yl)benzoyl]piperazin-1-carbonyl}cyclopropan-1-ol | 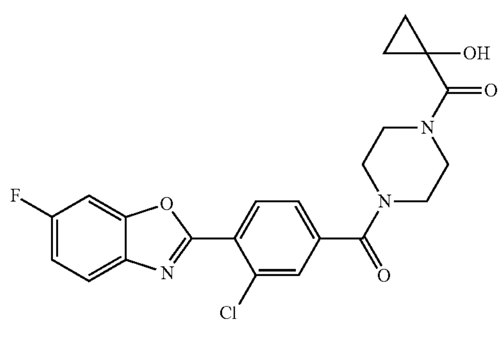 [SMILES: O=C(c1ccc(-c2nc3ccc(F)cc3o2)c(Cl)c1)N1CCN(C(=O)C2(O)CC2)CC1] |
| 1-{4-[2-chloro-4-(2-methyl-2H-indazol-6-yl)benzoyl]piperazin-1-carbonyl}cyclopropan-1-ol | 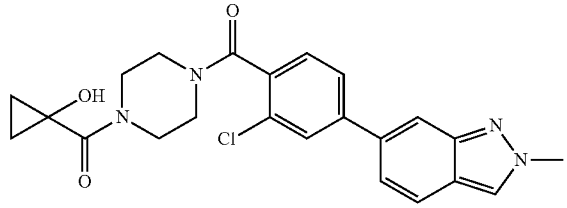 [SMILES: Cn1cc2ccc(-c3ccc(C(=O)N4CCN(C(=O)C5(O)CC5)CC4)c(Cl)c3)cc2n1] |

-continued

| NAME | Structure |
|---|---|
| 1-{4-[2,6-difluoro-4-(1-methyl-1H-indazol-6-yl)benzoyl]piperazin-1-carbonyl}cyclopropan-1-ol | 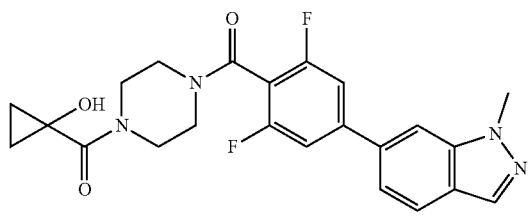 [SMILES: Cn1ncc2ccc(-c3cc(F)c(C(=O)N4CCN(C(=O)C5(O)CC5)CC4)c(F)c3)cc21] |
| 1-[(3R)-3-methyl-4-[4-(1-methyl-1H-1,3-benzodiazol-5-yl)benzoyl]piperazine-1-carbonyl]cyclopropan-1-ol | 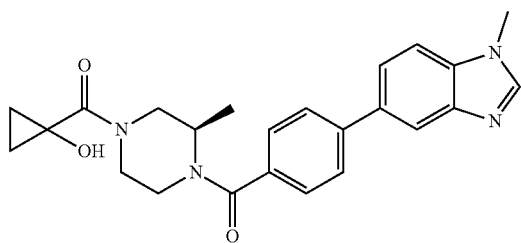 [SMILES: C[C@@H]1CN(C(=O)C2(O)CC2)CCN1C(=O)c1ccc(-c2ccc3c(c2)ncn3C)cc1] |
| N-(6-{4-[4-(1-hydroxycyclopropanecarbonyl)piperazine-1-carbonyl]phenyl}-1,2-benzoxazol-3-yl)cyclopropanecarboxamide | 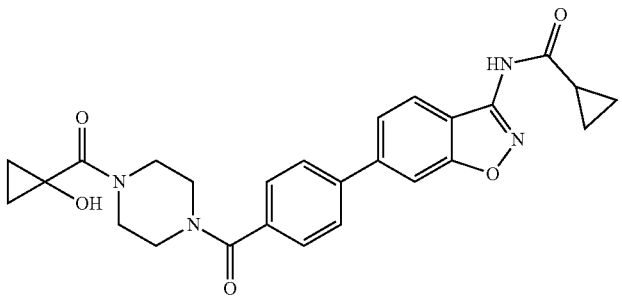 [SMILES: O=C(Nc1noc2cc(-c3ccc(C(=O)N4CCN(C(=O)C5(O)CC5)CC4)cc3)ccc12)C1CC1] |
| 1-[(3R,5S)-3,5-dimethyl-4-[4-(1-methyl-1H-1,3-benzodiazol-5-yl)benzoyl]piperazine-1-carbonyl]cyclopropan-1-ol | 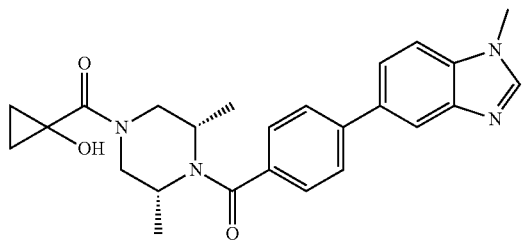 [SMILES: C[C@@H]1CN(C(=O)C2(O)CC2)C[C@H](C)N1C(=O)c1ccc(-c2ccc3c(c2)ncn3C)cc1] |
| propan-2-yl N-(3-{4-[4-(1-hydroxycyclopropanecarbonyl)piperazine-1-carbonyl]phenyl}phenyl)carbamate | 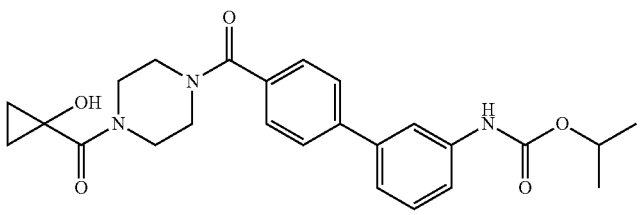 [SMILES: CC(C)OC(=O)Nc1cccc(-c2ccc(C(=O)N3CCN(C(=O)C4(O)CC4)CC3)cc2)c1] |
| 1-{4-[4-(3-amino-1H-indazol-5-yl)benzoyl]piperazine-1-carbonyl}cyclopropan-1-ol | 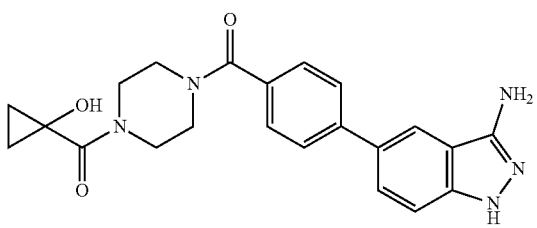 [SMILES: Nc1n[nH]c2ccc(-c3ccc(C(=O)N4CCN(C(=O)C5(O)CC5)CC4)cc3)cc12] |

-continued

| NAME | Structure |
|---|---|
| 1-[(2R)-2-methyl-4-[4-(1-methyl-1H-1,3-benzodiazol-5-yl)benzoyl]piperazine-1-carbonyl]cyclopropan-1-ol | 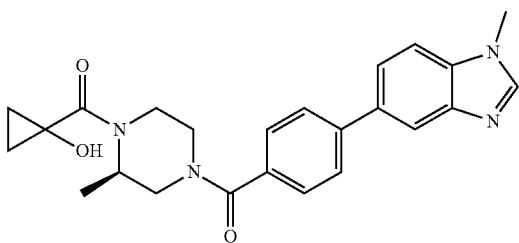 [SMILES: C[C@@H]1CN(C(=O)c2ccc(-c3ccc4c(c3)ncn4C)cc2)CCN1C(=O)C1(O)CC1] |
| 3,3-difluoro-N-(3-{4-[4-(1-hydroxycyclopropanecarbonyl)piperazine-1-carbonyl]phenyl}phenyl)cyclobutane-1-carboxamide | 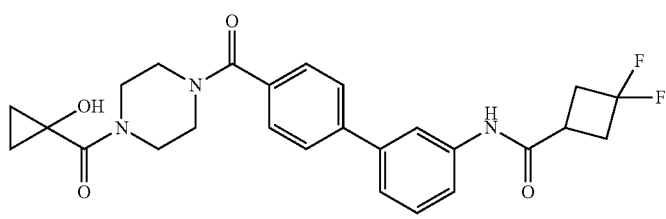 [SMILES: O=C(Nc1cccc(-c2ccc(C(=O)N3CCN(C(=O)C4(O)CC4)CC3)cc2)c1)C1CC(F)(F)C1] |
| 1-[(2S,6R)-4-[4-(6-fluoro-1,3-benzoxazol-2-yl)benzoyl]-2,6-dimethylpiperazine-1-carbonyl]cyclopropan-1-ol | 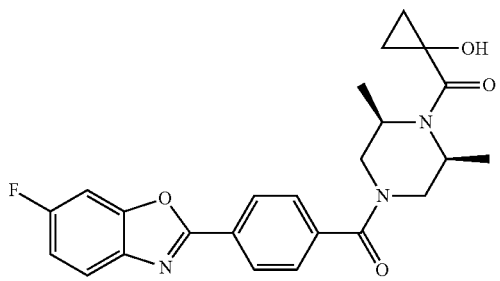 [SMILES: C[C@@H]1CN(C(=O)c2ccc(-c3nc4ccc(F)cc4o3)cc2)C[C@H](C)N1C(=O)C1(O)CC1] |
| 1-(4-{4-[1-(2-hydroxyethyl)-1H-1,3-benzodiazol-6-yl]benzoyl}piperazine-1-carbonyl)cyclopropan-1-ol | 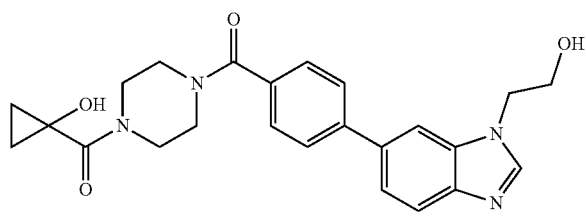 [SMILES: O=C(c1ccc(-c2ccc3ncn(CCO)c3c2)cc1)N1CCN(C(=O)C2(O)CC2)CC1] |
| 1-{4-[4-(1H-1,3-benzodiazol-4-yl)-2-chlorobenzoyl]piperazine-1-carbonyl}cyclopropan-1-ol | 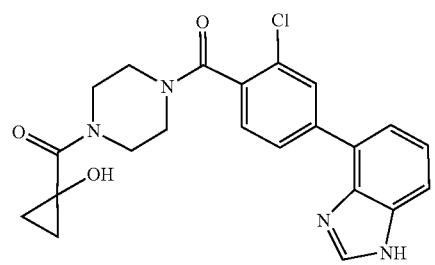 [SMILES: O=C(c1ccc(-c2cccc3[nH]cnc23)cc1Cl)N1CCN(C(=O)C2(O)CC2)CC1] |
| 1-{4-[4-(5-fluoro-2,3-dihydro-1H-indol-1-yl)benzoyl]piperazine-1-carbonyl}cyclopropan-1-ol | 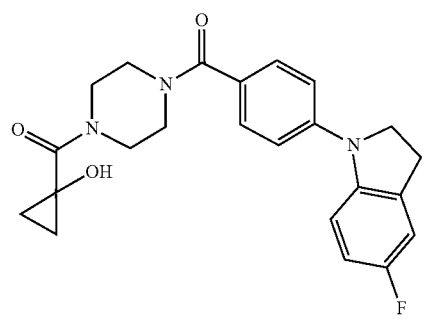 [SMILES: O=C(c1ccc(N2CCc3cc(F)ccc32)cc1)N1CCN(C(=O)C2(O)CC2)CC1] |

| NAME | Structure |
|---|---|
| 1-[4-(4-{3-chloroimidazo[1,2-a]pyridin-2-yl}-2-fluorobenzoyl)piperazine-1-carbonyl]cyclopropan-1-ol | 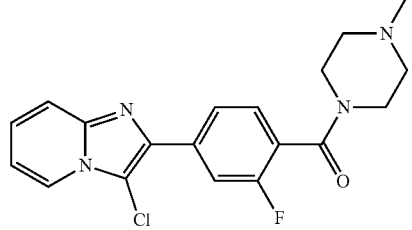 |
| 1-{4-[4-(4-chloro-2-fluorophenyl)-2-fluorobenzoyl]piperazine-1-carbonyl}cyclopropan-1-ol | 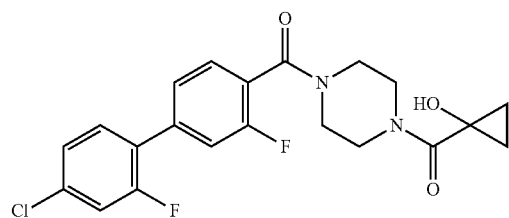 [SMILES: O=C(c1ccc(-c2ccc(Cl)cc2F)cc1F)N1CCN(C(=O)C2(O)CC2)CC1] |
| 1-{4-[3-chloro-4-(4-chloro-2-fluorophenyl)benzoyl]piperazine-1-carbonyl}cyclopropan-1-ol | 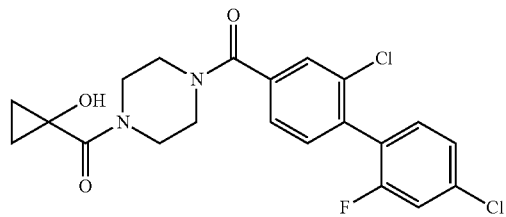 [SMILES: O=C(c1ccc(-c2ccc(Cl)cc2F)c(Cl)c1)N1CCN(C(=O)C2(O)CC2)CC1] |
| 1-{4-[2-chloro-4-(6-chloro-1,3-benzoxazol-2-yl)benzoyl]piperazine-1-carbonyl}cyclopropan-1-ol | 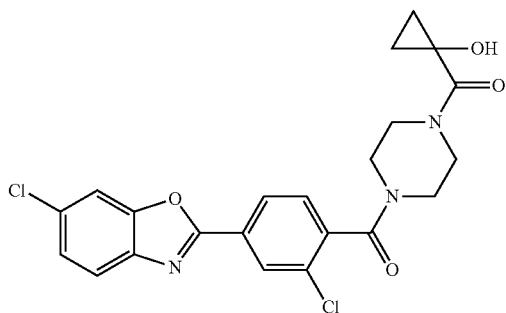 [SMILES: O=C(c1ccc(-c2nc3ccc(Cl)cc3o2)cc1Cl)N1CCN(C(=O)C2(O)CC2)CC1] |
| 1-{4-[4-(5-fluoro-2,3-dihydro-1H-isoindol-2-yl)benzoyl]piperazine-1-carbonyl}cyclopropan-1-ol | 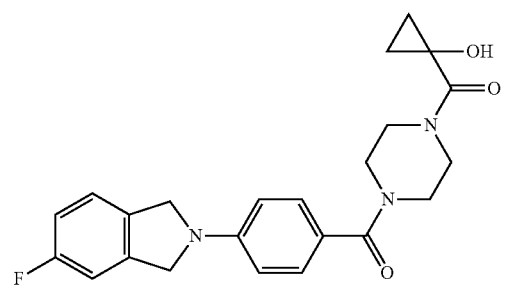 [SMILES: O=C(c1ccc(N2Cc3ccc(F)cc3C2)cc1)N1CCN(C(=O)C2(O)CC2)CC1] |

-continued

| NAME | Structure |
|---|---|
| 1-{4-[4-(3-methyl-1H-indazol-4-yl)benzoyl]piperazine-1-carbonyl}cyclopropan-1-ol | 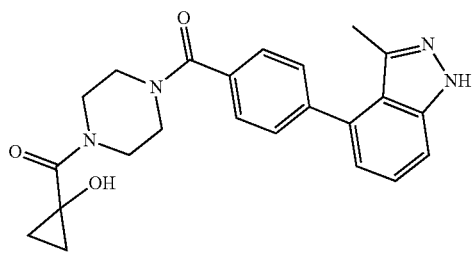 [SMILES: Cc1n[nH]c2cccc(-c3ccc(C(=O)N4CCN(C(=O)C5(O)CC5)CC4)cc3)c12] |
| 1-{4-[4-(6-methoxy-1,3-benzoxazol-2-yl)benzoyl]piperazine-1-carbonyl}cyclopropan-1-ol | 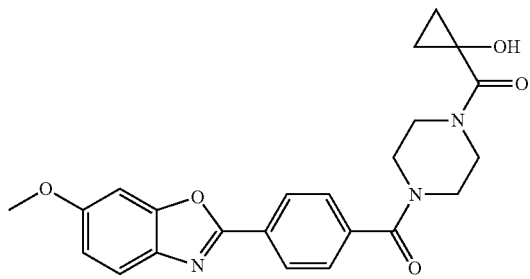 [SMILES: COc1ccc2nc(-c3ccc(C(=O)N4CCN(C(=O)C5(O)CC5)CC4)cc3)oc2c1] |
| 1-{4-[4-(3-methyl-1H-indazol-7-yl)benzoyl]piperazine-1-carbonyl}cyclopropan-1-ol | 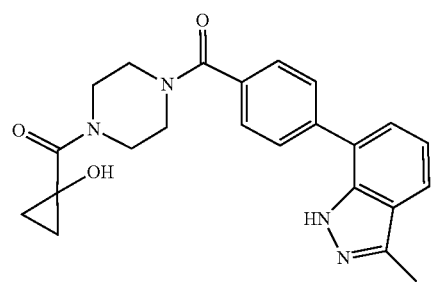 [SMILES: Cc1n[nH]c2c(-c3ccc(C(=O)N4CCN(C(=O)C5(O)CC5)CC4)cc3)cccc12] |
| 1-[(2R)-4-[4-(4-chloro-2-fluorophenyl)benzoyl]2-methylpiperazine-1-carbonyl]cyclopropan-1-ol | 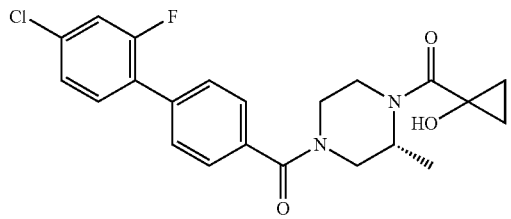 [SMILES: C[C@@H]1CN(C(=O)c2ccc(-c3ccc(Cl)cc3F)cc2)CCN1C(=O)C1(O)CC1] |
| 1-(3-{4-[4-(1-hydroxycyclopropanecarbonyl)piperazine-1-carbonyl]phenyl}phenyl)cyclo-butane-1-carbonitrile | 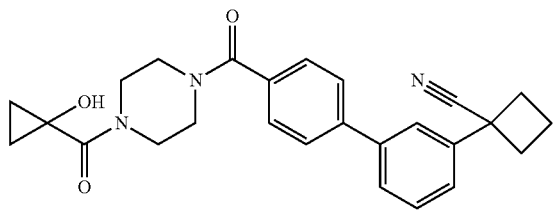 [SMILES: N#CC1(c2cccc(-c3ccc(C(=O)N4CCN(C(=O)C5(O)CC5)CC4)cc3)c2)CCC1] |
| 1-{4-[2-fluoro-4-(6-fluoro-1,3-benzoxazol-2-yl)benzoyl]piperazine-1-carbonyl}cyclopropan-1-ol | 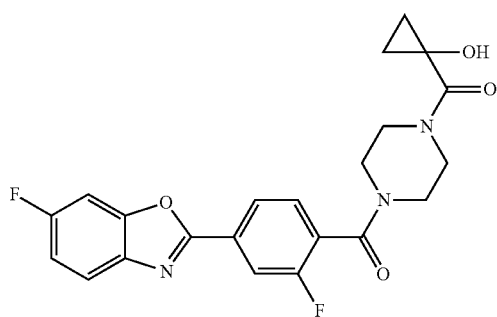 [SMILES: O=C(c1ccc(-c2nc3ccc(F)cc3o2)cc1F)N1CCN(C(=O)C2(O)CC2)CC1] |

-continued

| NAME | Structure |
|---|---|
| 1-[4-(4-{1H,2H,3H,4H,5H-pyrido[4,3-b]indol-2-yl}benzoyl)piperazine-1-carbonyl]cyclopropan-1-ol | 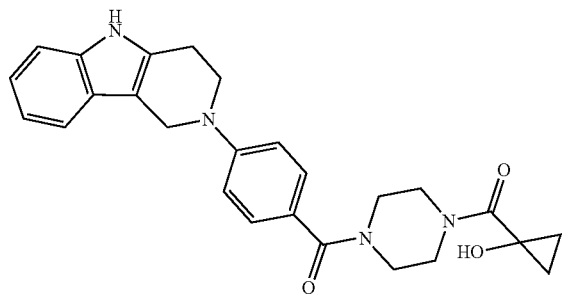 [SMILES: O=C(c1ccc(N2CCc3[nH]c4ccccc4c3C2)cc1)N1CCN(C(=O)C2(O)CC2)CC1] |
| 1-{4-[4-(2-methyl-1H-indol-1-yl)benzoyl]piperazine-1-carbonyl}cyclopropan-1-ol | 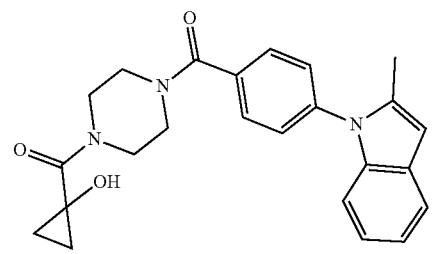 [SMILES: Cc1cc2ccccc2n1-c1ccc(C(=O)N2CCN(C(=O)C3(O)CC3)CC2)cc1] |
| 1-[(2S)-2-methyl-4-[4-(1-methyl-1H-1,3-benzodiazol-5-yl)benzoyl}piperazine-1-carbonyl]cyclopropan-1-amine | 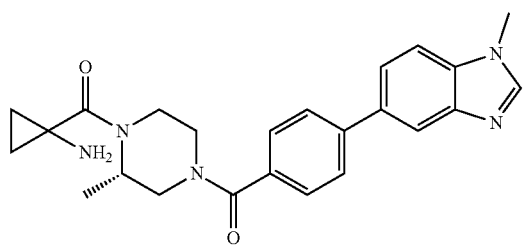 |
| 1-{4-[3-fluoro-4-(1-methyl-1H-1,3-benzodiazol-5-yl)benzoyl]piperazine-1-carbonyl}cyclopropan-1-ol | 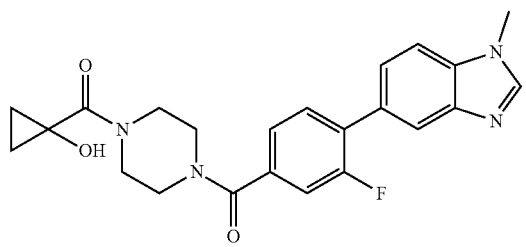 [SMILES: Cn1cnc2cc(-c3ccc(C(=O)N4CCN(C(=O)C5(O)CC5)CC4)cc3F)ccc21] |
| 1-{4-[2-fluoro-4-(1-methyl-1H-1,3-benzodiazol-5-yl)benzoyl]piperazine-1-carbonyl}cyclobutan-1-amine | 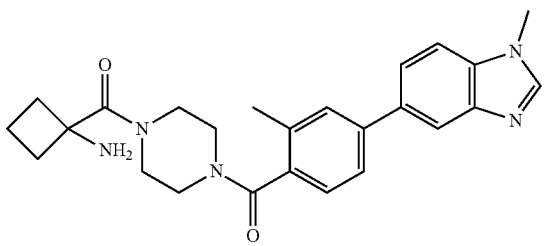 [SMILES: Cc1cc(-c2ccc3c(c2)ncn3C)ccc1C(=O)N1CCN(C(=O)C2(N)CCC2)CC1] |
| 1-{4-[3-fluoro-4-(1-methyl-1H-indazol-6-yl)benzoyl]piperazin-1-carbonyl}cyclopropan-1-ol | 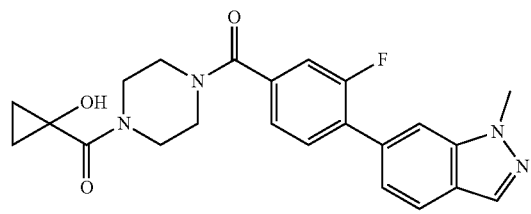 [SMILES: Cn1ncc2ccc(-c3ccc(C(=O)N4CCN(C(=O)C5(O)CC5)CC4)cc3F)cc21] |

-continued

| NAME | Structure |
|---|---|
| 1-[(2S)-4-[4-(6-fluoro-1,3-benzoxazol-2-yl)benzoyl]-2-methylpiperazine-1-carbonyl]cyclopropan-1-ol | 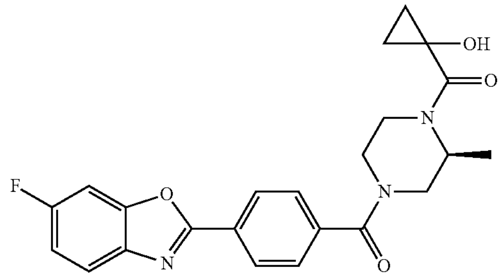 [SMILES: C[C@H]1CN(C(=O)c2ccc(-c3nc4ccc(F)cc4o3)cc2)CCN1C(=O)C1(O)CC1] |
| 1-{4-[4-(4-fluoro-2,3-dihydro-1H-isoindol-2-yl)-benzoyl]piperazine-1-carbonyl}cyclopropan-1-ol | 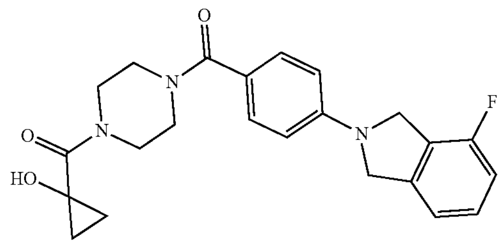 [SMILES: O=C(c1ccc(N2Cc3cccc(F)c3C2)cc1)N1CCN(C(=O)C2(O)CC2)CC1] |
| 1-(4-{3-chloro-4-[3-(cyclopropanesulfonyl)phenyl]benzoyl}piperazine-1-carbonyl)cyclopropan-1-ol | 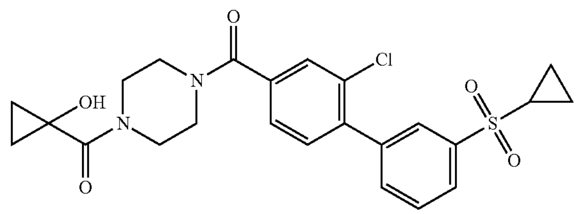 [SMILES: O=C(c1ccc(-c2cccc(S(=O)(=O)C3CC3)c2)c(Cl)c1)N1CCN(C(=O)C2(O)CC2)CC1] |
| 1-{4-[4-(7-fluoro-2,3-dihydro-1H-indol-1-yl)benzoyl]piperazine-1-carbonyl}cyclopropan-1-ol | 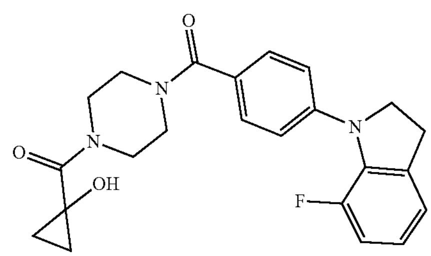 [SMILES: O=C(c1ccc(N2CCc3cccc(F)c32)cc1)N1CCN(C(=O)C2(O)CC2)CC1] |
| 1-{4-[4-(3-cyclopropyl-1H-indazol-6-yl)benzoyl]piperazine-1-carbonyl}cyclopropan-1-ol | 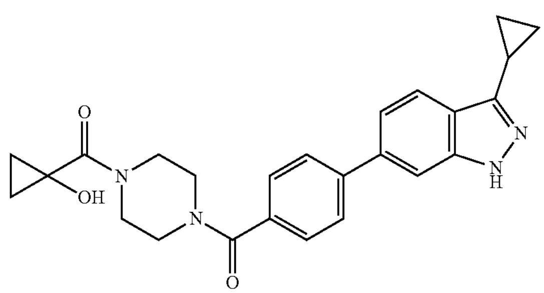 [SMILES: O=C(c1ccc(-c2ccc3c(C4CC4)n[nH]c3c2)cc1)N1CCN(C(=O)C2(O)CC2)CC1] |
| 1-{4-[4-(6-fluoro-1,3-benzoxazol-2-yl)benzoyl]-3,3-dimethylpiperazine-1-carbonyl}cyclopropan-1-ol | 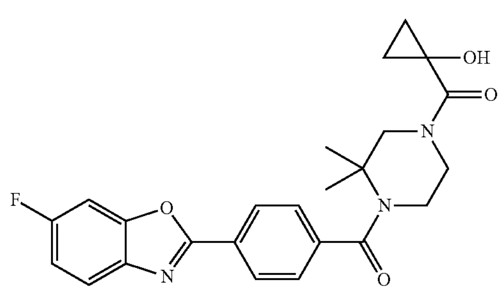 [SMILES: CC1(C)CN(C(=O)C2(O)CC2)CCN1C(=O)c1ccc(-c2nc3ccc(F)cc3o2)cc1] |

-continued

| NAME | Structure |
|---|---|
| 1-{4-[4-(3-methyl-1H-indazol-1-yl)benzoyl]piperazine-1-carbonyl}cyclopropan-1-ol | 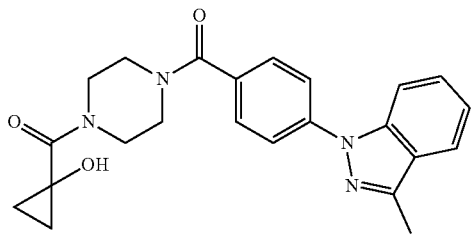 [SMILES: Cc1nn(-c2ccc(C(=O)N3CCN(C(=O)C4(O)CC4)CC3)cc2)c2ccccc12] |
| 1-{4-[2-fluoro-4-(3-methyl-1H-indazol-7-yl)benzoyl]piperazine-1-carbonyl}cyclopropan-1-amine | 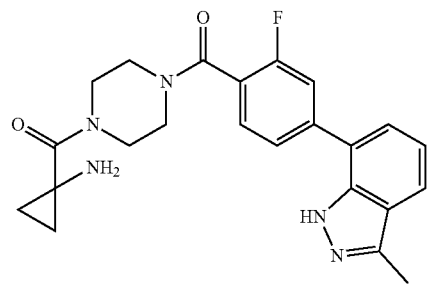 [SMILES: Cc1n[nH]c2c(-c3ccc(C(=O)N4CCN(C(=O)C5(N)CC5)CC4)c(F)c3)cccc12] |
| 1-{4-[4-(1-methanesulfonyl-1H-indol-6-yl)benzoyl]piperazine-1-carbonyl}cyclopropan-1-ol | 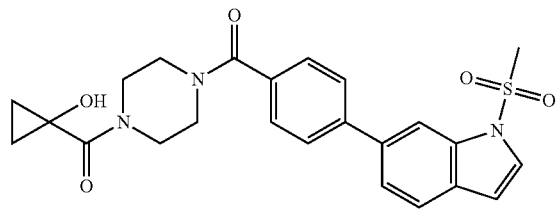 [SMILES: CS(=O)(=O)n1ccc2ccc(-c3ccc(C(=O)N4CCN(C(=O)C5(O)CC5)CC4)cc3)cc21] |
| 1-{4-[4-(1-methyl-1H-1,3-benzodiazol-5-yl)benzoyl]piperazine-1-carbonyl}cyclopropan-1-amine | 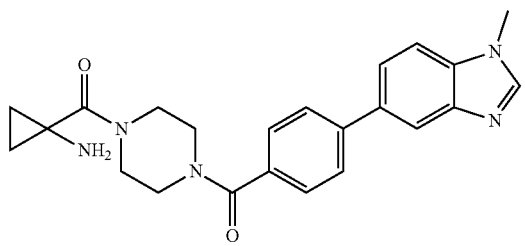 [SMILES: Cn1cnc2cc(-c3ccc(C(=O)N4CCN(C(=O)C5(N)CC5)CC4)cc3)ccc21] |
| 1-{4-[4-(2-methyl-2,3-dihydro-1H-indol-1-yl)benzoyl]piperazine-1-carbonyl}cyclopropan-1-ol | 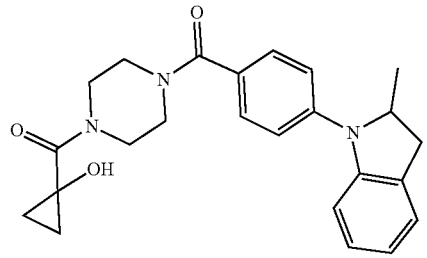 [SMILES: CC1Cc2ccccc2N1c1ccc(C(=O)N2CCN(C(=O)C3(O)CC3)CC2)cc1] |
| 1-{4-[4-(5-fluoro-1H-1,2,3-benzotriazol-6-yl)benzoyl]piperazine-1-carbonyl}cyclopropan-1-ol | 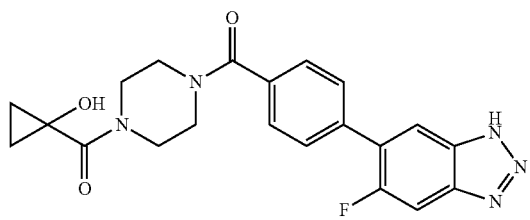 [SMILES: O=C(c1ccc(-c2cc3[nH]nnc3cc2F)cc1)N1CCN(C(=O)C2(O)CC2)CC1] |

| NAME | Structure |
|---|---|
| 1-{4-[3-chloro-4-(5-chloro-2-fluorophenyl)benzoyl]piperazine-1-carbonyl}cyclopropan-1-ol | 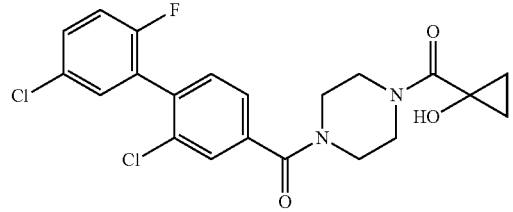 [SMILES: O=C(c1ccc(-c2cc(Cl)ccc2F)c(Cl)c1)N1CCN(C(=O)C2(O)CC2)CC1] |
| 1-[(2S,6R)-4-[4-(4-chloro-2-fluorophenyl)benzoyl]-2,6-dimethylpiperazine-1-carbonyl]cyclopropan-1-ol | 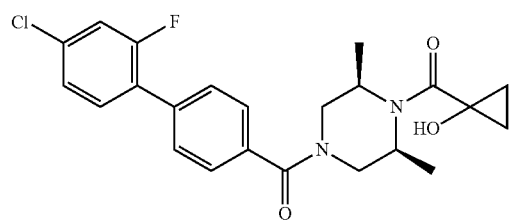 [SMILES: C[C@@H]1CN(C(=O)c2ccc(-c3ccc(Cl)cc3F)cc2)C[C@H](C)N1C(=O)C1(O)CC1] |
| N-(3-{4-[4-(1-hydroxycyclopropanecarbonyl)piperazine-1-carbonyl]phenyl}phenyl)oxane-4-sulfonamide | 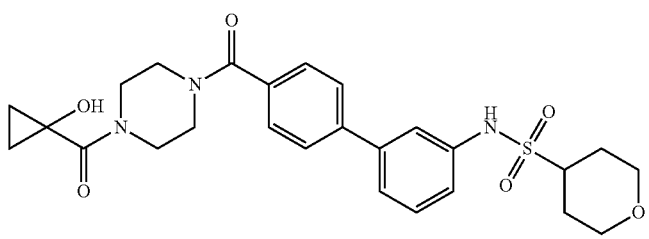 [SMILES: O=C(c1ccc(-c2cccc(NS(=O)(=O)C3CCOCC3)c2)cc1)N1CCN(C(=O)C2(O)CC2)CC1] |
| 1-{4-[4-(1-methyl-1H-indazol-6-yl)benzoyl]piperazine-1-carbonyl}cyclopropan-1-amine | 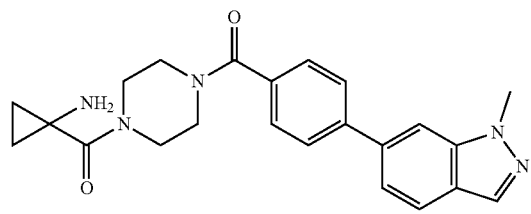 [SMILES: Cn1ncc2ccc(-c3ccc(C(=O)N4CCN(C(=O)C5(N)CC5)CC4)cc3)cc21] |
| 1-{4-[4-(7-methoxy-1,2,3,4-tetrahydroisoquinolin-2-yl)benzoyl]piperazine-1-carbonyl}cyclopropan-1-ol | 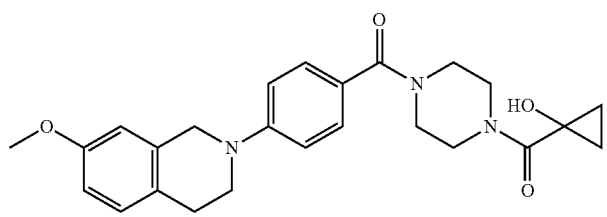 [SMILES: COc1ccc2c(c1)CN(c1ccc(C(=O)N3CCN(C(=O)C4(O)CC4)CC3)cc1)CC2] |
| 1-(3-{3-fluoro-4-[4-(1-hydroxycyclopropanecarbonyl)piperazine-1-carbonyl]phenyl}phenyl)cyclopropane-1-carbonitrile | 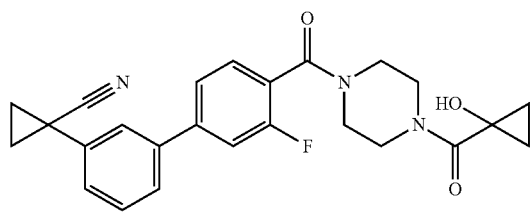 [SMILES: N#CC1(c2cccc(-c3ccc(C(=O)N4CCN(C(=O)C5(O)CC5)CC4)c(F)c3)c2)CC1] |

-continued

| NAME | Structure |
|---|---|
| 1-{4-[2-fluoro-4-(2-methyl-1H-indol-1-yl)benzoyl]piperazine-1-carbonyl}cyclopropan-1-ol | 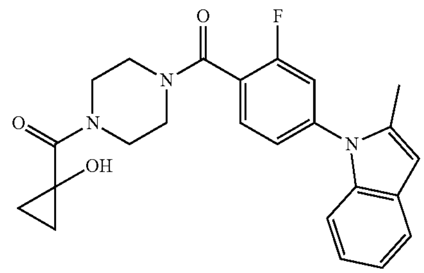 [SMILES: Cc1cc2ccccc2n1-c1ccc(C(=O)N2CCN(C(=O)C3(O)CC3)CC2)c(F)c1] |
| 1-{4-[4-(1H-1,3-benzodiazol-1-yl)benzoyl]piperazine-1-carbonyl}cyclopropan-1-ol | 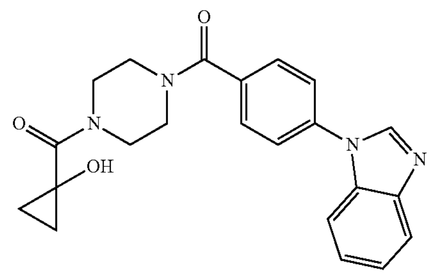 [SMILES: O=C(c1ccc(-n2cnc3ccccc32)cc1)N1CCN(C(=O)C2(O)CC2)CC1] |
| 1-(3-{4-[4-(1-hydroxycyclopropanecarbonyl)piperazine-1-carbonyl]phenyl}phenyl)cyclopropane-1-carbonitrile | 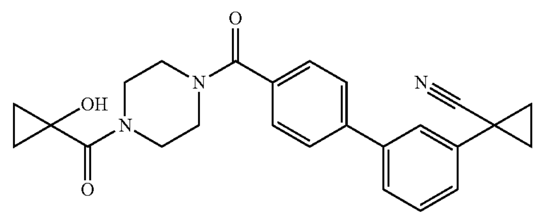 [SMILES: N#CC1(c2cccc(-c3ccc(C(=O)N4CCN(C(=O)C5(O)CC5)CC4)cc3)c2)CC1] |
| 1-{4-[2-fluoro-4-(3-methyl-1H-indazol-1-yl)benzoyl]piperazine-1-carbonyl}cyclopropan-1-ol | 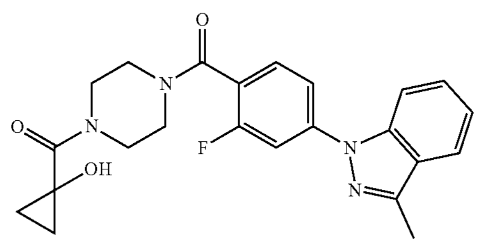 [SMILES: Cc1nn(-c2ccc(C(=O)N3CCN(C(=O)C4(O)CC4)CC3)c(F)c2)c2ccccc12] |
| 1-{4-[2-fluoro-4-(1-methyl-1H-indazol-6-yl)benzoyl]piperazine-1-carbonyl}cyclopropan-1-amine | 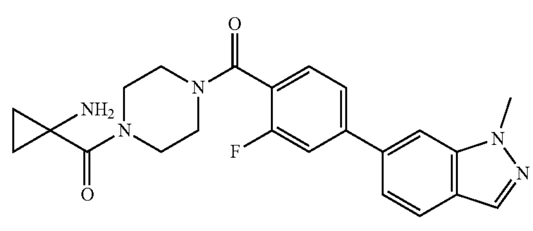 [SMILES: Cn1ncc2ccc(-c3ccc(C(=O)N4CCN(C(=O)C5(N)CC5)CC4)c(F)c3)cc21] |
| 2-{4-[4-(1-hydroxycyclopropanecarbonyl)piperazine-1-carbonyl]phenyl}-1,2,3,4-tetrahydroisoquinoline-7-carbonitrile | 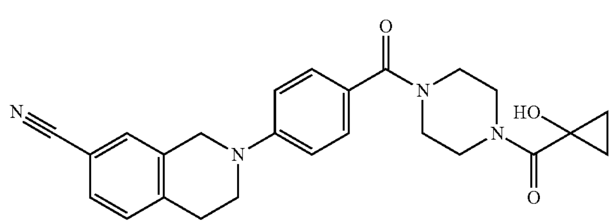 [SMILES: N#Cc1ccc2c(c1)CN(c1ccc(C(=O)N3CCN(C(=O)C4(O)CC4)CC3)cc1)CC2] |

| NAME | Structure |
|---|---|
| 1-(4-{4-[1-(2-hydroxyethyl)-1H-1,3-benzodiazol-5-yl]benzoyl}piperazine-1-carbonyl)cyclopropan-1-ol | |
| 1-[(2R)-4-[4-(6-fluoro-1,3-benzoxazol-2-yl)benzoyl]-2-methylpiperazine-1-carbonyl]cyclopropan-1-ol | 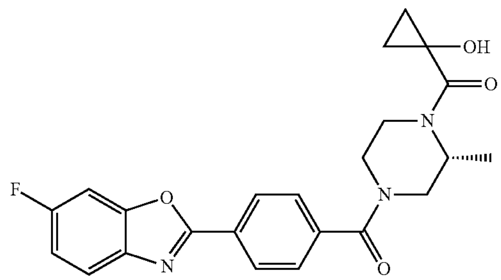 [SMILES: C[C@@H]1CN(C(=O)c2ccc(-c3nc4ccc(F)cc4o3)cc2)CCN1C(=O)C1(O)CC1] |
| 1-{4-[4-(1H-indazol-1-yl)benzoyl]piperazine-1-carbonyl}cyclopropan-1-ol | 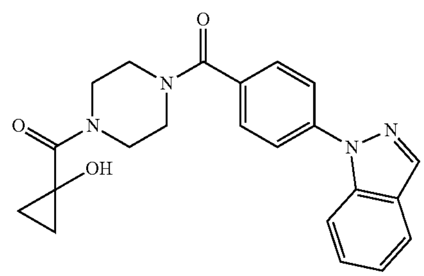 |
| 1-{4-[2-chloro-4-(5-chloro-2-fluorophenyl)benzoyl]piperazine-1-carbonyl}cyclopropan-1-ol | 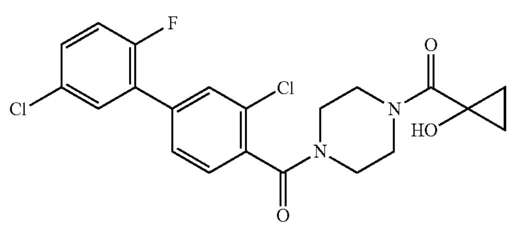 [SMILES: O=C(c1ccc(-c2cc(Cl)ccc2F)cc1Cl)N1CCN(C(=O)C2(O)CC2)CC1] |
| 1-{4-[4-(1,3-dimethyl-1H-indazol-5-yl)-3-fluorobenzoyl]piperazine-1-carbonyl}cyclopropan-1-ol | 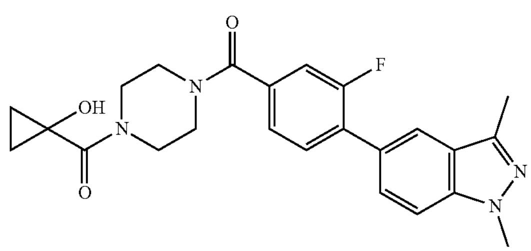 [SMILES: Cc1nn(C)c2ccc(-c3ccc(C(=O)N4CCN(C(=O)C5(O)CC5)CC4)cc3F)cc12] |
| 1-{4-[4-(4-chloro-2-fluorophenyl)benzoyl]-4,7-diazaspiro[2.5]octane-7-carbonyl}cyclopropan-1-ol | 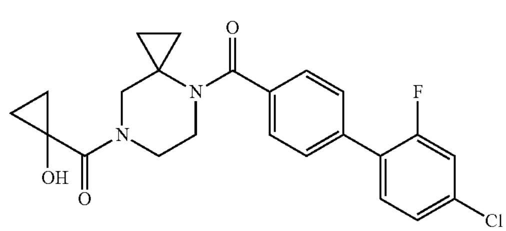 [SMILES: O=C(c1ccc(-c2ccc(Cl)cc2F)cc1)N1CCN(C(=O)C2(O)CC2)CC12CC2] |

-continued

| NAME | Structure |
|---|---|
| 1-{4-[2-fluoro-4-(7-fluoro-1H-indazol-3-yl)benzoyl]piperazine-1-carbonyl}cyclopropan-1-amine | 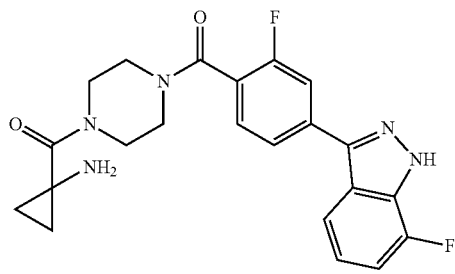 |
| 6-{1-[4-(1-hydroxycyclopropanecarbonyl)piperazine-1-carbonyl]piperidin-4-yl}naphthalene-2-carbonitrile | 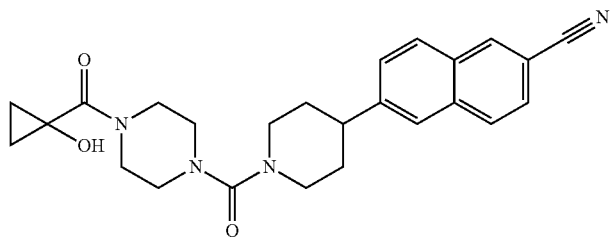 [SMILES: N#Cc1ccc2cc(C3CCN(C(=O)N4CCN(C(=O)C5(O)CC5)CC4)CC3)ccc2c1] |
| 1-(3-{4-[4-(1-hydroxycyclopropanecarbonyl)piperazine-1-carbonyl]phenyl}phenyl)imidazolidin-2-one | 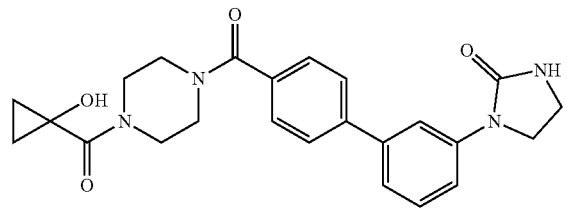 |
| 1-{4-[2,6-difluoro-4-(2-methyl-2H-indazol-6-yl)benzoyl]piperazine-1-carbonyl}cyclopropan-1-amine | 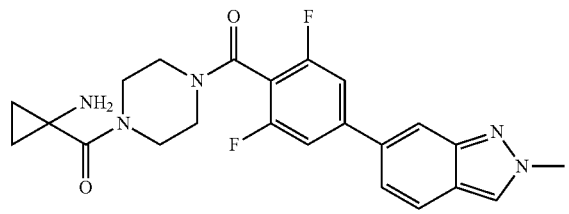 [SMILES: Cn1cc2ccc(-c3cc(F)c(C(=O)N4CCN(C(=O)C5(N)CC5)CC4)c(F)c3)cc2n1] |
| 1,3-dimethyl-5-{4-[4-(oxetane-2-carbonyl)piperazine-1-carbonyl]phenyl}-1H-indazole | 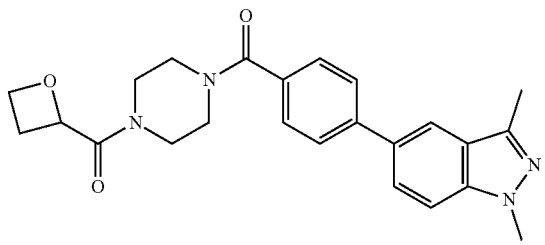 [SMILES: Cc1nn(C)c2ccc(-c3ccc(C(=O)N4CCN(C(=O)C5CCO5)CC4)cc3)cc12] |
| 1-{4-[2-fluoro-4-(2-methyl-2H-indazol-6-yl)benzoyl]piperazine-1-carbonyl}cyclopropan-1-amine | 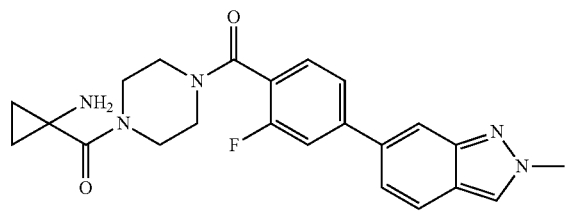 [SMILES: Cn1cc2ccc(-c3ccc(C(=O)N4CCN(C(=O)C5(N)CC5)CC4)c(F)c3)cc2n1] |

-continued

| NAME | Structure |
|---|---|
| 1-(4-{4-[3-(5-amino-1H-1,2,4-triazol-3-yl)phenyl]benzoyl}piperazine-1-carbonyl)}cyclopropan-1-ol | 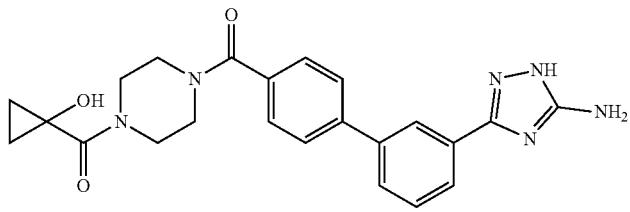 [SMILES: Nc1nc(-c2cccc(-c3ccc(C(=O)N4CCN(C(=O)C5(O)CC5)CC4)cc3)c2)n[nH]1] |
| 1-{4-[4-(1-methyl-1H-1,3-benzodiazol-5-yl)benzoyl]-4,7-diazaspiro[2.5]octane-7-carbonyl}cyclopropan-1-ol | 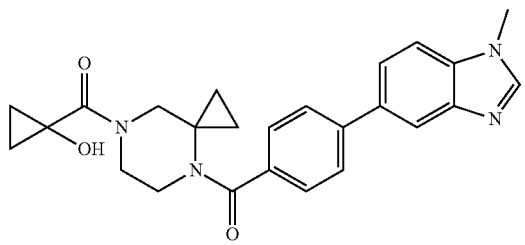 |
| 1-{4-[4-(2-methyl-1H-indol-3-yl)benzoyl]piperazine-1-carbonyl}cyclopropan-1-ol | 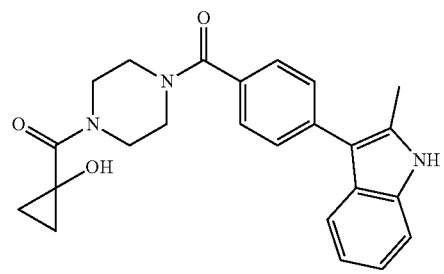 [SMILES: Cc1[nH]c2ccccc2c1-c1ccc(C(=O)N2CCN(C(=O)C3(O)CC3)CC2)cc1] |
| 1-{4-[4-(2-methyl-1H-1,3-benzodiazol-5-yl)benzoyl]piperazine-1-carbonyl}cyclopropan-1-ol | 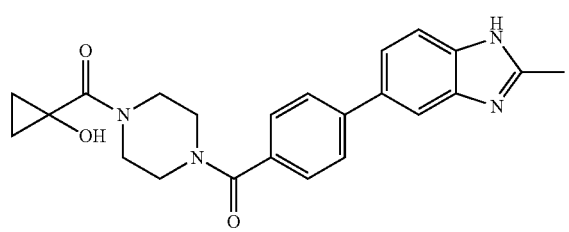 [SMILES: Cc1nc2cc(-c3ccc(C(=O)N4CCN(C(=O)C5(O)CC5)CC4)cc3)ccc2[nH]1] |
| 1-{4-[4-(6-fluoro-1,3-benzoxazol-2-yl)benzoyl]-4,7-diazaspiro[2.5]octane-7-carbonyl}cyclopropan-1-ol | 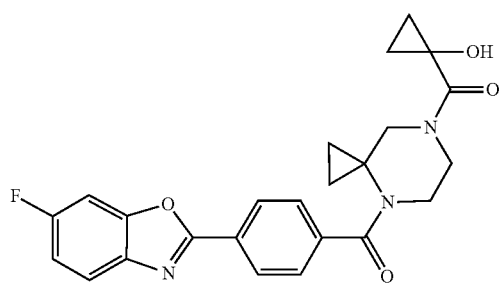 [SMILES: O=C(c1ccc(-c2nc3ccc(F)cc3o2)cc1)N1CCN(C(=O)C2(O)CC2)CC12CC2] |
| 1-{4-[4-(6-fluoro-1-methyl-1H-1,2,3-benzotriazol-5-yl)benzoyl]piperazine-1-carbonyl}cyclopropan-1-ol | 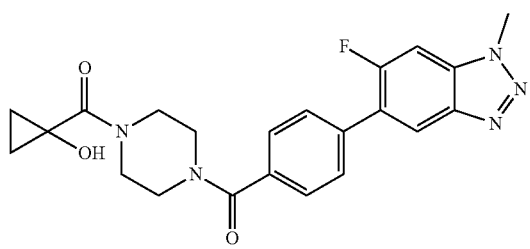 [SMILES: Cn1nnc2cc(-c3ccc(C(=O)N4CCN(C(=O)C5(O)CC5)CC4)cc3)c(F)cc21] |

-continued

| NAME | Structure |
|---|---|
| 1-{4-[4-(1-methyl-1H-1,3-benzodiazol-5-yl)benzoyl]piperazine-1-carbonyl}cyclobutan-1-ol | 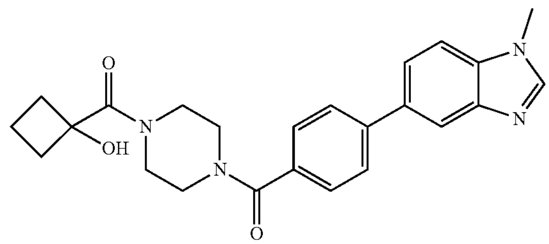 |
| 6-chloro-4-{4-[4-(1-hydroxycyclopropanecarbonyl)piperazine-1-carbonyl]phenyl}-2,3-dihydro-1H-1,3-benzodiazol-2-one | 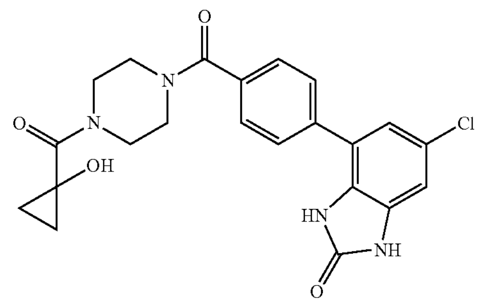 [SMILES: O=C(c1ccc(-c2cc(Cl)cc3[nH]c(=O)[nH]c23)cc1)N1CCN(C(=O)C2(O)CC2)CC1] |
| 1-(4-{4-[2-(hydroxymethyl)-1H-1,3-benzodiazol-5-yl]benzoyl}piperazine-1-carbonyl)cyclopropan-1-ol | 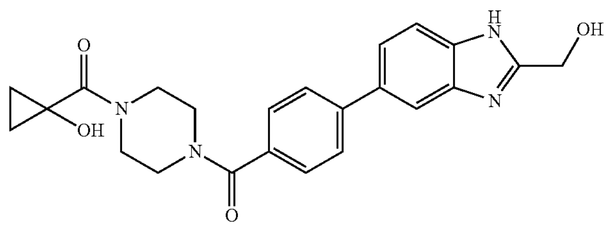 [SMILES: O=C(c1ccc(-c2ccc3[nH]c(CO)nc3c2)cc1)N1CCN(C(=O)C2(O)CC2)CC1] |
| 5-{4-[4-(1-aminocyclopropanecarbonyl)piperazine-1-carbonyl]phenyl}-1,2-benzoxazol-3-amine | 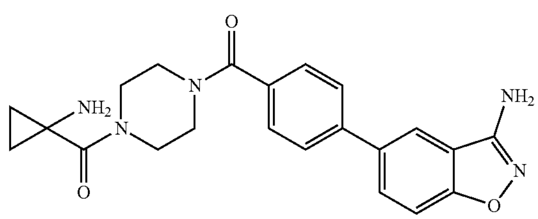 [SMILES: Nc1noc2ccc(-c3ccc(C(=O)N4CCN(C(=O)C5(N)CC5)CC4)cc3)cc12] |
| 1-{4-[4-(2-cyclopropyl-2H-indazol-5-yl)benzoyl]piperazine-1-carbonyl}cyclopropan-1-ol | 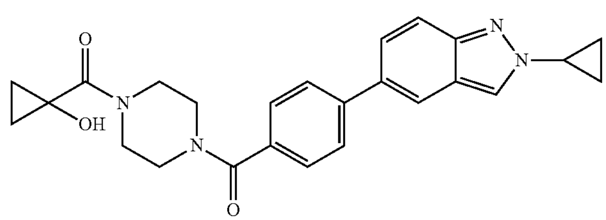 [SMILES: O=C(c1ccc(-c2ccc3nn(C4CC4)cc3c2)cc1)N1CCN(C(=O)C2(O)CC2)CC1] |
| 1-{4-[2-fluoro-4-(5,6,7,8-tetrahydro-1,7-naphthyridin-7-yl)benzoyl]piperazine-1-carbonyl}cyclopropan-1-ol | 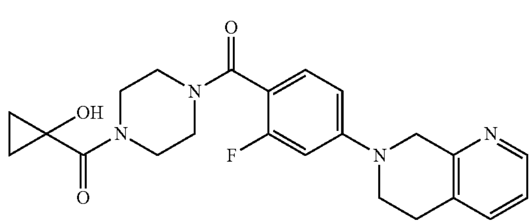 [SMILES: O=C(c1ccc(N2CCc3cccnc3C2)cc1F)N1CCN(C(=O)C2(O)CC2)CC1] |

| NAME | Structure |
|---|---|
| 1-{4-[4-(3-methyl-1,2,3,4-tetrahydroisoquinolin-2-yl)benzoyl]piperazine-1-carbonyl}cyclopropan-1-ol | 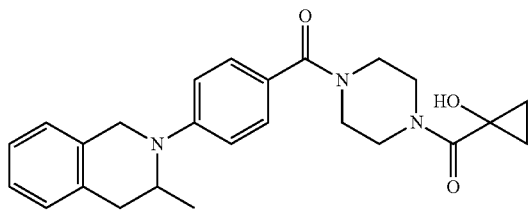 [SMILES: CC1Cc2ccccc2CN1c1ccc(C(=O)N2CCN(C(=O)C3(O)CC3)CC2)cc1] |
| 1-{4-[4-(2,3-dihydro-1H-isoindol-2-yl)benzoyl]piperazine-1-carbonyl}cyclopropan-1-ol | 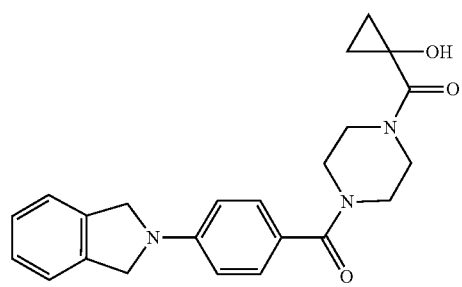 [SMILES: O=C(c1ccc(N2Cc3ccccc3C2)cc1)N1CCN(C(=O)C2(O)CC2)CC1] |
| 1-[(3R)-4-[4-(4-chloro-2-fluorophenyl)benzoyl]-3-methylpiperazine-1-carbonyl]cyclopropan-1-ol | 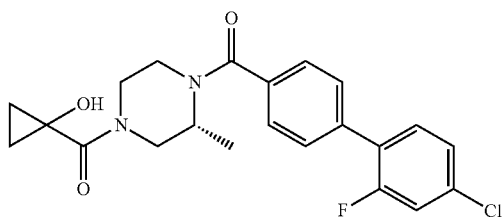 [SMILES: C[C@@H]1CN(C(=O)C2(O)CC2)CCN1C(=O)c1ccc(-c2ccc(Cl)cc2F)cc1] |
| 1-[4-(4-{3-methyl-1H-pyrazolo[3,4-b]pyridin-5-yl}benzoyl)piperazine-1-carbonyl]cyclopropan-1-ol | 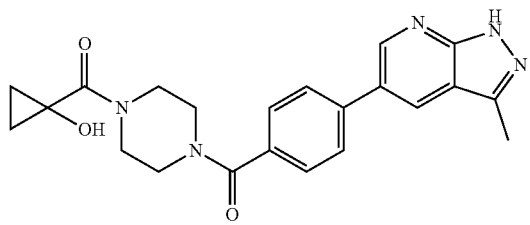 [SMILES: Cc1n[nH]c2ncc(-c3ccc(C(=O)N4CCN(C(=O)C5(O)CC5)CC4)cc3)cc12] |
| 1-{4-[4-(3-methyl-1H-indazol-6-yl)benzoyl]piperazine-1-carbonyl}cyclopropan-1-amine | 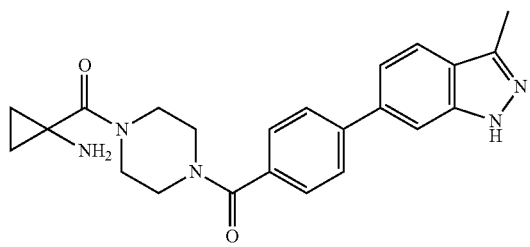 [SMILES: Cc1n[nH]c2cc(-c3ccc(C(=O)N4CCN(C(=O)C5(N)CC5)CC4)cc3)ccc12] |
| 1-{4-[2-fluoro-4-(1-methyl-1H-1,3-benzodiazol-5-yl)benzoyl]piperazine-1-carbonyl}cyclopropan-1-amine | 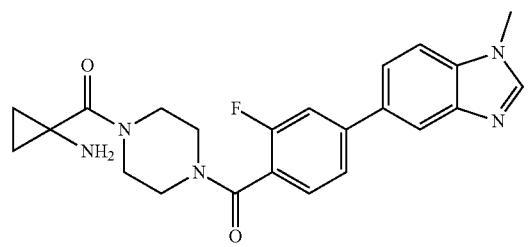 [SMILES: Cn1cnc2cc(-c3ccc(C(=O)N4CCN(C(=O)C5(N)CC5)CC4)c(F)c3)ccc21] |

| NAME | Structure |
|---|---|
| 6-{4-[4-(1-hydroxycyclopropanecarbonyl)piperazine-1-carbonyl]phenyl}-1-methyl-1H-indazol-3-ol | 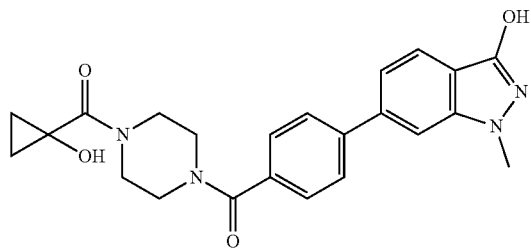 [SMILES: Cn1nc(O)c2ccc(-c3ccc(C(=O)N4CCN(C(=O)C5(O)CC5)CC4)cc3)cc21] |
| 1-{4-[4-(1,2,3,4-tetrahydroquinolin-1-yl)benzoyl]piperazine-1-carbonyl}cyclopropan-1-ol | 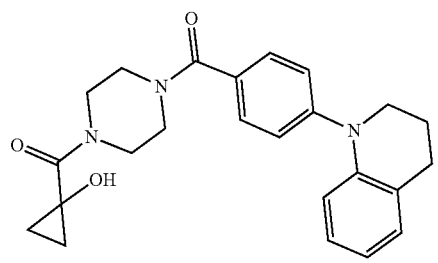 [SMILES: O=C(c1ccc(N2CCCc3ccccc32)cc1)N1CCN(C(=O)C2(O)CC2)CC1] |
| 1-{4-[4-(3-methyl-1H-indazol-7-yl)benzoyl]piperazine-1-carbonyl}cyclopropan-1-amine | 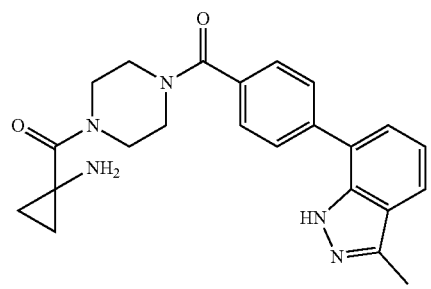 [SMILES: Cc1n[nH]c2c(-c3ccc(C(=O)N4CCN(C(=O)C5(N)CC5)CC4)cc3)cccc12] |
| 1-[4-(4-{4H,5H,6H,7H-thieno[3,2-c]pyridin-5-yl}benzoyl)piperazine-1-carbonyl]cyclopropan-1-ol | 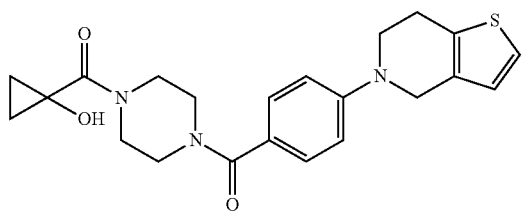 [SMILES: O=C(c1ccc(N2CCc3sccc3C2)cc1)N1CCN(C(=O)C2(O)CC2)CC1] |
| 1-{4-[4-(1-methyl-1H-indazol-6-yl)benzoyl]piperazine-1-carbonyl}cyclobutan-1-amine | 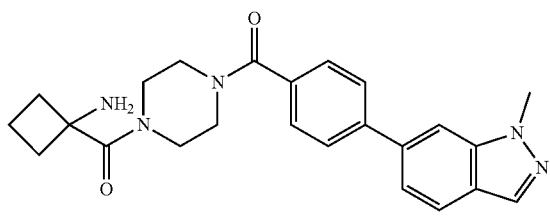 |
| 1-(4-{4-[3-(2-amino-1,3-thiazol-4-yl)phenyl]benzoyl}piperazine-1-carbonyl)cyclopropan-1-ol | 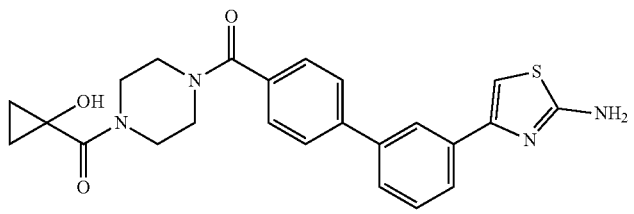 [SMILES: Nc1nc(-c2cccc(-c3ccc(C(=O)N4CCN(C(=O)C5(O)CC5)CC4)cc3)c2)cs1] |

-continued

| NAME | Structure |
|---|---|
| 1-{4-[4-(1,3-dimethyl-1H-indazol-5-yl)benzoyl]piperazine-1-carbonyl}cyclobutan-1-amine | 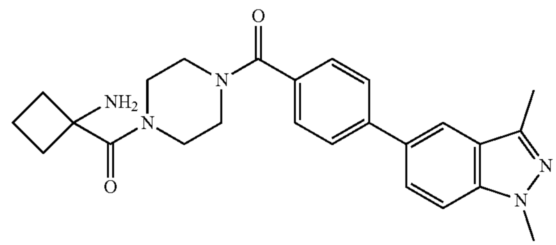 |
| 1-(4-{4-[3-(cyclopropanesulfonyl)phenyl]}-2-fluorobenzoyl}piperazine-1-carbonyl)cyclopropan-1-ol | 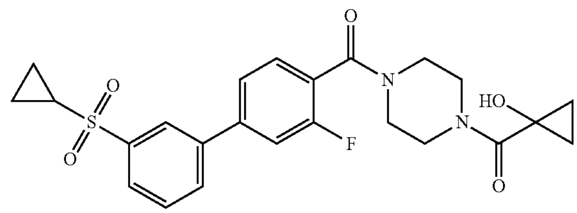 [SMILES: O=C(c1ccc(-c2cccc(S(=O)(=O)C3CC3)c2)cc1F)N1CCN(C(=O)C2(O)CC2)CC1] |
| 1-{4-[4-(6-fluoroquinazolin-2-yl)benzoyl}piperazine-1-carbonyl}cyclopropan-1-ol | 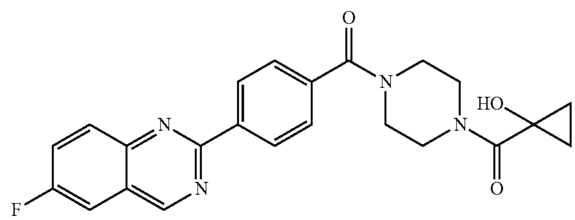 [SMILES: O=C(c1ccc(-c2ncc3cc(F)ccc3n2)cc1)N1CCN(C(=O)C2(O)CC2)CC1] |
| N-(5-{4-[4-(1-hydroxycyclopropanecarbonyl)piperazine-1-carbonyl]phenyl}-1,2-benzoxazol-3-yl)cyclopropanecarboxamide | 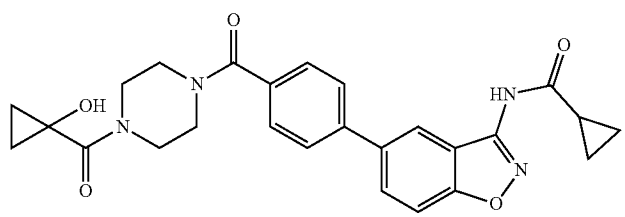 [SMILES: O=C(Nc1noc2ccc(-c3ccc(C(=O)N4CCN(C(=O)C5(O)CC5)CC4)cc3)cc12)C1CC1] |
| 4-{4-[4-(1-hydroxycyclopropanecarbonyl)piperazine-1-carbonyl}phenyl}-1-methyl-2,3-dihydro-1H-indol-2-one | 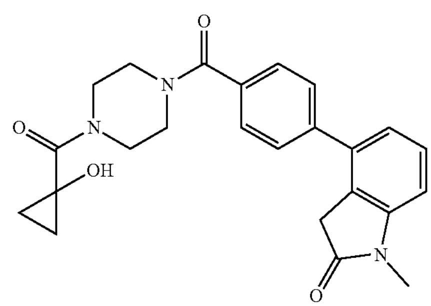 [SMILES: CN1C(=O)Cc2c(-c3ccc(C(=O)N4CCN(C(=O)C5(O)CC5)CC4)cc3)cccc21] |
| 1-[(3R)-4-[4-(6-fluoro-1,3-benzoxazol-2-yl)benzoyl]-3-methylpiperazine-1-carbonyl]cyclopropan-1-ol | 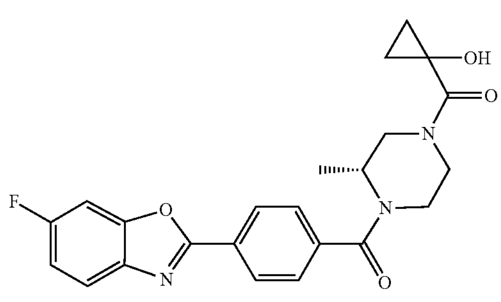 [SMILES: C[C@@H]1CN(C(=O)C2(O)CC2)CCN1C(=O)c1ccc(-c2nc3ccc(F)cc3o2)cc1] |

-continued

| NAME | Structure |
|---|---|
| 1-{4-[4-(2-methyl-1H-1,3-benzodiazol-1-yl)benzoyl]piperazine-1-carbonyl}cyclopropan-1-ol | 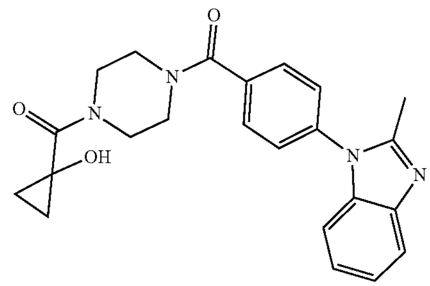 [SMILES: Cc1nc2ccccc2n1-c1ccc(C(=O)N2CCN(C(=O)C3(O)CC3)CC2)cc1] |
| 1-{4-[4-(5-chloro-2-fluorophenyl)benzoyl]piperazine-1-carbonyl}cyclopropan-1-amine | 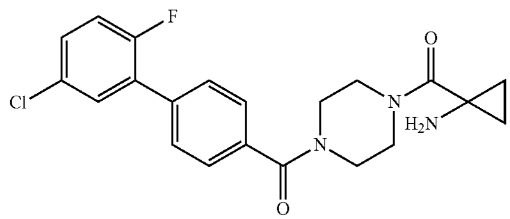 [SMILES: NC1(C(=O)N2CCN(C(=O)c3ccc(-c4cc(Cl)ccc4F)cc3)CC2)CC1] |
| 1-{4-[3-fluoro-4-(2-methyl-2H-indazol-6-yl)benzoyl]piperazine-1-carbonyl}cyclopropan-1-ol | 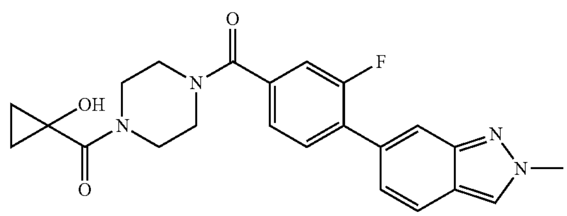 [SMILES: Cn1cc2ccc(-c3ccc(C(=O)N4CCN(C(=O)C5(O)CC5)CC4)cc3F)cc2n1] |
| 3-{4-[4-(1-hydroxycyclopropanecarbonyl)piperazine-1-carbonyl]phenyl}-N-methylbenzamide | 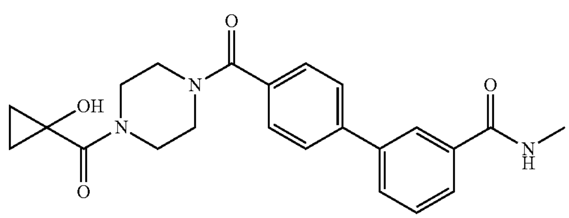 [SMILES: CNC(=O)c1cccc(-c2ccc(C(=O)N3CCN(C(=O)C4(O)CC4)CC3)cc2)c1] |
| 1-(4-{4-[3-(5-amino-1H-pyrazol-3-yl)phenyl]benzoyl}piperazine-1-carbonyl)cyclopropan-1-ol | 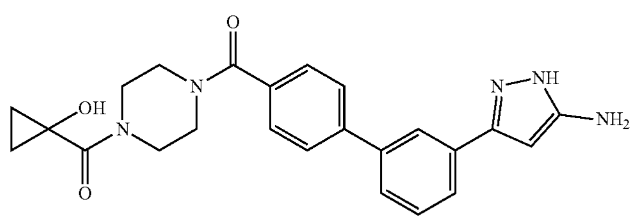 [SMILES: Nc1cc(-c2cccc(-c3ccc(C(=O)N4CCN(C(=O)C5(O)CC5)CC4)cc3)c2)n[nH]1] |
| 1-[(2S)-2-methyl-4-[4-(5,6,7,8-tetrahydro-1,7-naphthyridin-7-yl)benzoyl]piperazine-1-carbonyl]cyclopropan-1-ol | 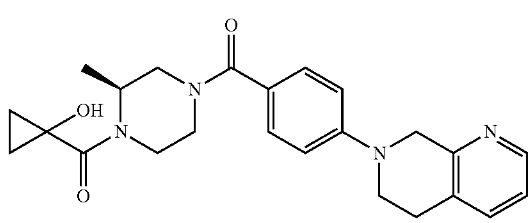 [SMILES: C[C@H]1CN(C(=O)c2ccc(N3CCc4cccnc4C3)cc2)CCN1C(=O)C1(O)CC1] |
| 1-[(3S)-4-[4-(4-chloro-2-fluorophenyl)benzoyl]-3-methylpiperazine-1-carbonyl]cyclopropan-1-ol | 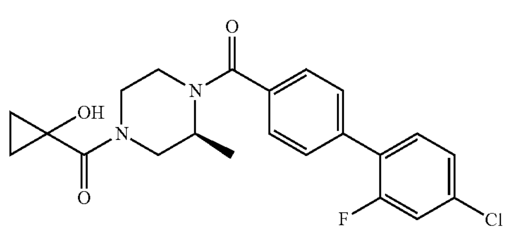 [SMILES: C[C@H]1CN(C(=O)C2(O)CC2)CCN1C(=O)c1ccc(-c2ccc(Cl)cc2F)cc1] |

-continued

| NAME | Structure |
|---|---|
| 2-(3-{4-[4-(1-hydroxycyclopropanecarbonyl)piperazine-1-carbonyl]phenyl}phenoxy)-N-methylacetamide | 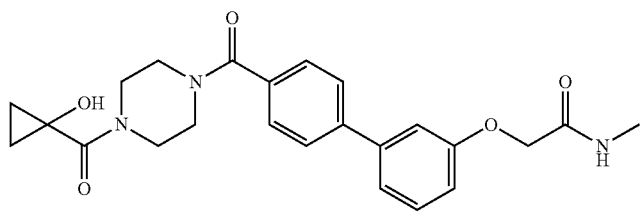 [SMILES: CNC(=O)COc1cccc(-c2ccc(C(=O)N3CCN(C(=O)C4(O)CC4)CC3)cc2)c1] |
| 1-{4-[4-(1-cyclopropyl-1H-indazol-5-yl)benzoyl]piperazine-1-carbonyl}cyclopropan-1-ol | 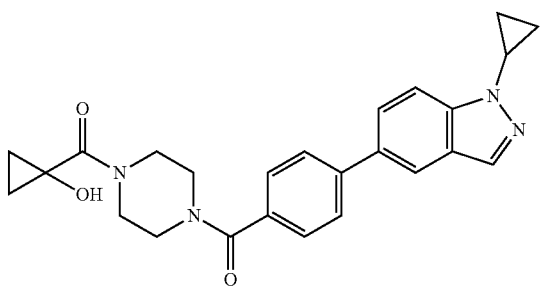 [SMILES: O=C(c1ccc(-c2ccc3c(cnn3C3CC3)c2)cc1)N1CCN(C(=O)C2(O)CC2)CC1] |
| 1-methyl-5-{4-[4-(oxetane-2-carbonyl)piperazine-1-carbonyl]phenyl}-1H-1,3-benzodiazole | 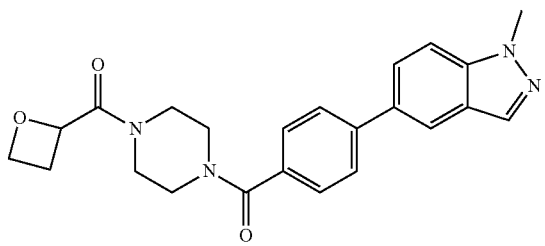 [SMILES: Cn1ncc2cc(-c3ccc(C(=O)N4CCN(C(=O)C5CCO5)CC4)cc3)ccc21] |
| (1-{4-[4-(1-methyl-1H-1,3-benzodiazol-5-yl)benzoyl]piperazine-1-carbonyl}cyclopropyl)methanol | 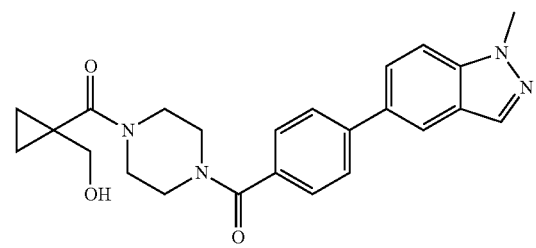 [SMILES: Cn1ncc2cc(-c3ccc(C(=O)N4CCN(C(=O)C5(CO)CC5)CC4)cc3)ccc21] |
| 1-{4-[4-(1-methyl-1H-1,3-benzodiazol-5-yl)benzoyl]piperazine-1-carbonyl}cyclobutan-1-amine | 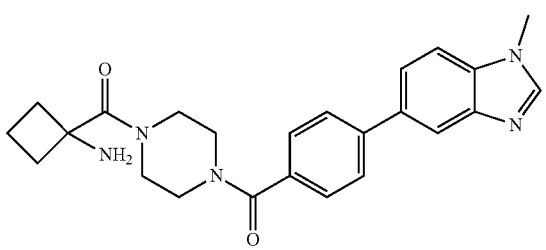 [SMILES: Cn1cnc2cc(-c3ccc(C(=O)N4CCN(C(=O)C5(N)CCC5)CC4)cc3)ccc21] |
| 1-[4-(3-chloro-4-{3-chloroimidazo[1,2-a]pyridin-2-yl}benzoyl)piperazine-1-carbonyl]cyclopropan-1-ol | 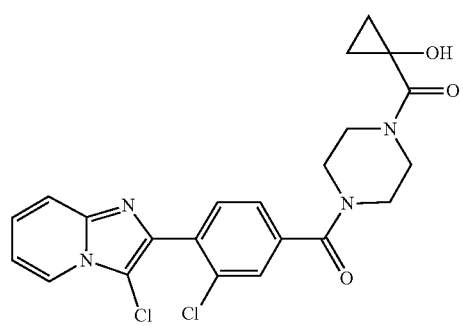 [SMILES: O=C(c1ccc(-c2nc3ccccn3c2Cl)c(Cl)c1)N1CCN(C(=O)C2(O)CC2)CC1] |

| NAME | Structure |
|---|---|
| 1-[(2R)-2-(hydroxymethyl)-4-[4-(1-methyl-1H-1,3-benzodiazol-5-yl)benzoyl]piperazine-1-carbonyl]cyclopropan-1-ol | 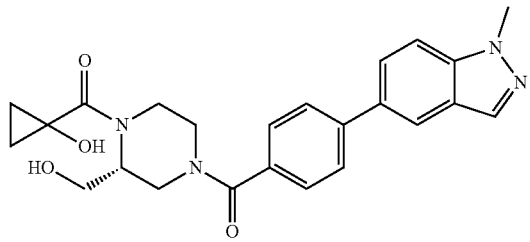 [SMILES: Cn1ncc2cc(-c3ccc(C(=O)N4CCN(C(=O)C5(O)CC5)[C@@H](CO)C4)cc3)ccc21] |
| 1-{4-[4-(2,3A,5-tetrahydro-1H-3-benzazepin-3-yl)benzoyl]piperazine-1-carbonyl}cyclopropan-1-ol | 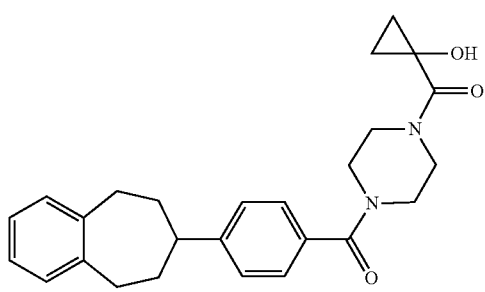 [SMILES: O=C(c1ccc(C2CCc3ccccc3CC2)cc1)N1CCN(C(=O)C2(O)CC2)CC1] |
| 1-[(2S,6R)-4-[4-(6-fluoro-1,3-benzoxazol-2-yl)benzoyl]-2,6-dimethylpiperazine-1-carbonyl]cyclopropan-1-amine | 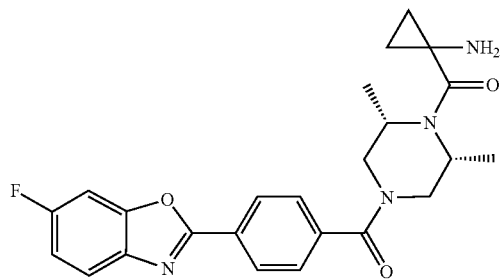 [SMILES: C[C@@H]1CN(C(=O)c2ccc(-c3nc4ccc(F)cc4o3)cc2)C[C@H](C)N1C(=O)C1(N)CC1] |
| 1-[(2S)-4-[4-(6-fluoro-1,3-benzoxazol-2-yl)benzoyl]-2-methylpiperazine-1-carbonyl]cyclopropan-1-amine | 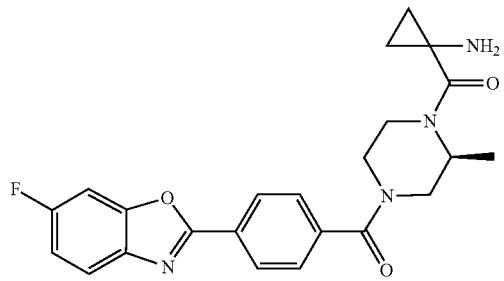 [SMILES: C[C@H]1CN(C(=O)c2ccc(-c3nc4ccc(F)cc4o3)cc2)CCN1C(=O)C1(N)CC1] |
| 1-(4-{4-[3-(5-methyl-1,3,4-thiadiazol-2-yl)phenyl]benzoyl}piperazine-1-carbonyl)cyclopropan-1-ol | 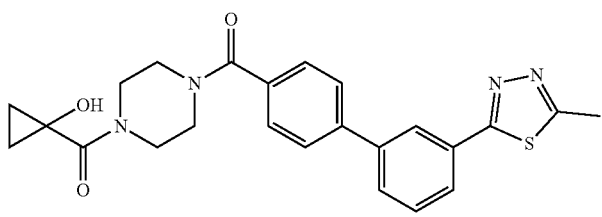 [SMILES: Cc1nnc(-c2cccc(-c3ccc(C(=O)N4CCN(C(=O)C5(O)CC5)CC4)cc3)c2)s1] |

| NAME | Structure |
|---|---|
| 1-{4-[4-(3-methyl-2H-indazol-2-yl)benzoyl]piperazine-1-carbonyl}cyclopropan-1-ol | 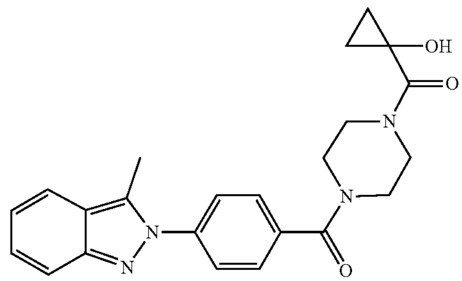 [SMILES: Cc1c2ccccc2nn1-c1ccc(C(=O)N2CCN(C(=O)C3(O)CC3)CC2)cc1] |
| 2-(3-{4-[4-(1-hydroxycyclopropanecarbonyl)piperazine-1-carbonyl]phenyl}phenyl)-2-methylpropanenitrile | 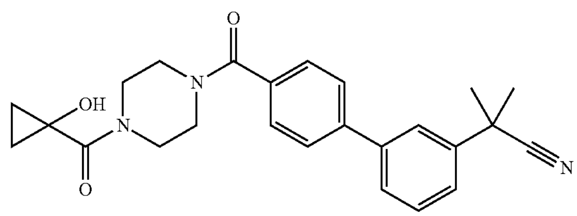 [SMILES: CC(C)(C#N)c1cccc(-c2ccc(C(=O)N3CCN(C(=O)C4(O)CC4)CC3)cc2)c1] |
| 1-[(2S)-4-{4-[3-(cyclopropanesulfonyl)phenyl]benzoyl}-2-methylpiperazine-1-carbonyl]cyclopropan-1-ol | |
| 1-(3-{4-[4-(1-hydroxycyclopropanecarbonyl)piperazine-1-carbonyl]phenyl}phenyl)pyrrolidin-2-one | 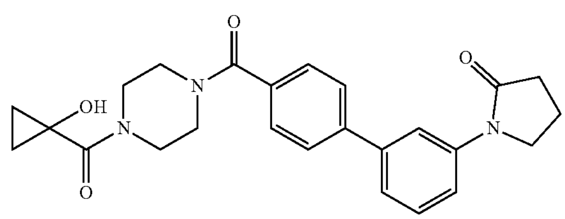 [SMILES: O=C(c1ccc(-c2cccc(N3CCCC3=O)c2)cc1)N1CCN(C(=O)C2(O)CC2)CC1] |
| 3-(3-{4-[4-(1-aminocyclopropanecarbonyl)piperazine-1-carbonyl]-3-fluorophenyl}phenyl)-1,2-oxazol-5-amine | 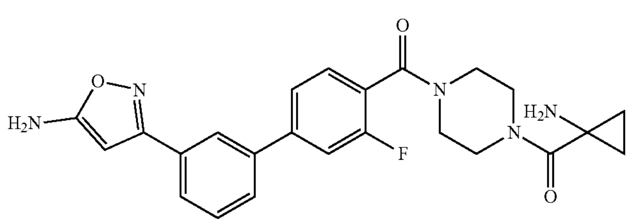 [SMILES: Nc1cc(-c2cccc(-c3ccc(C(=O)N4CCN(C(=O)C5(N)CC5)CC4)c(F)c3)c2)no1] |
| 6-{4-[4-(1-hydroxycyclopropanecarbonyl)piperazine-1-carbonyl]phenyl}-N-methylpyridine-2-carboxamide | 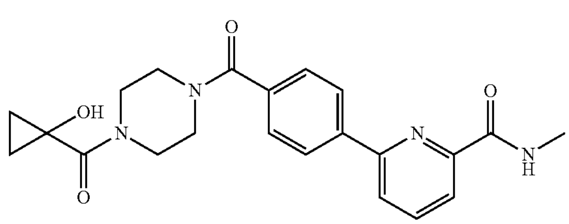 [SMILES: CNC(=O)c1cccc(-c2ccc(C(=O)N3CCN(C(=O)C4(O)CC4)CC3)cc2)n1] |

| NAME | Structure |
|---|---|
| 1-[(3S)-4-[4-(6-fluoro-1,3-benzoxazol-2-yl)benzoyl]-3-methylpiperazine-1-carbonyl]cyclopropan-1-ol | 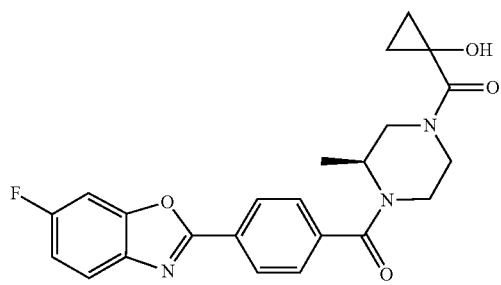 [SMILES: C[C@H]1CN(C(=O)C2(O)CC2)CCN1C(=O)c1ccc(-c2nc3ccc(F)cc3o2)cc1] |
| 4-(3-{4-[4-(1-hydroxycyclopropanecarbonyl)piperazine-1-carbonyl]phenyl}phenyl)oxane-4-carbonitrile | 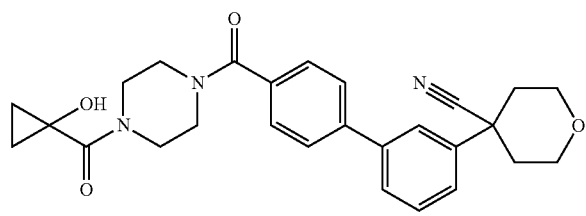 [SMILES: N#CC1(c2cccc(-c3ccc(C(=O)N4CCN(C(=O)C5(O)CC5)CC4)cc3)c2)CCOCC1] |
| 1-(4-{4-[3-(5-methyl-1,2,4-oxadiazol-3-yl)phenyl]benzoyl}piperazine-1-carbonyl)cyclopropan-1-ol | 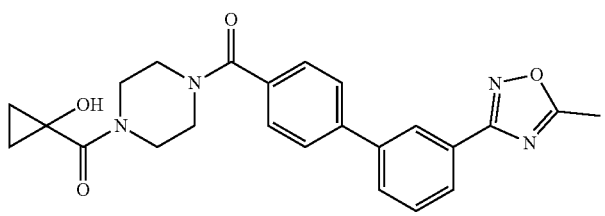 [SMILES: Cc1nc(-c2cccc(-c3ccc(C(=O)N4CCN(C(=O)C5(O)CC5)CC4)cc3)c2)no1] |
| 5-(3-{4-[4-(1-hydroxycyclopropanecarbonyl)piperazine-1-carbonyl]phenyl}phenyl)-5-methylimidazolidine-2,4-dione | 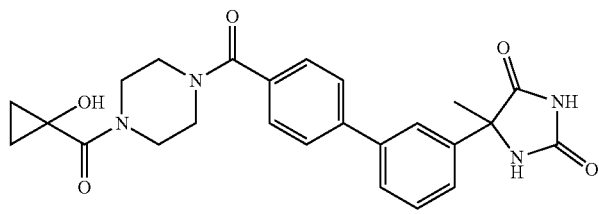 [SMILES: CC1(c2cccc(-c3ccc(C(=O)N4CCN(C(=O)C5(O)CC5)CC4)cc3)c2)NC(=O)NC1=O] |
| 1-{4-[2-fluoro-4-(2-methyl-1H-indol-1-yl)benzoyl]piperazine-1-carbonyl}cyclopropan-1-amine | 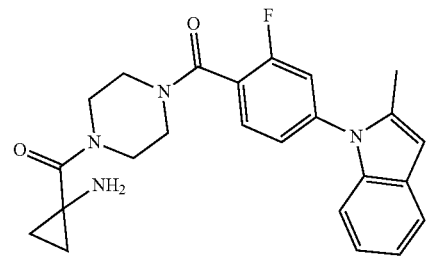 [SMILES: Cc1cc2ccccc2n1-c1ccc(C(=O)N2CCN(C(=O)C3(N)CC3)CC2)c(F)c1] |
| 1-{4-[4-(3-amino-1,2-benzoxazol-6-yl)benzoyl]piperazine-1-carbonyl}cyclopropan-1-ol | 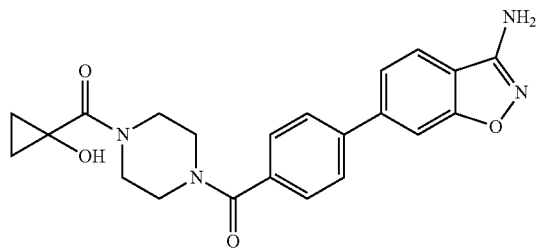 [SMILES: Nc1noc2cc(-c3ccc(C(=O)N4CCN(C(=O)C5(O)CC5)CC4)cc3)ccc12] |

-continued

| NAME | Structure |
|---|---|
| 1-{4-[2-fluoro-4-(2-methyl-2H-indazol-6-yl)benzoyl]piperazine-1-carbonyl}cyclobutan-1-amine | 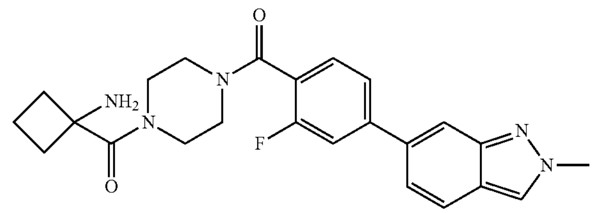 [SMILES: Cn1cc2ccc(-c3ccc(C(=O)N4CCN(C(=O)C5(N)CCC5)CC4)c(F)c3)cc2n1] |
| 2-(3-{4-[4-(1-hydroxycyclopropanecarbonyl)piperazine-1-carbonyl]phenyl}phenyl)-1$\lambda^6$,2-thiazolidine-1,1-dione | |
| 1-{4-[4-(6-chloro-1,3-benzoxazol-2-yl)-3-fluorobenzoyl]piperazine-1-carbonyl}cyclopropan-1-ol | 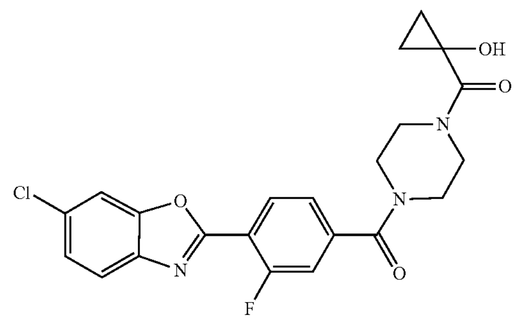 [SMILES: O=C(c1ccc(-c2nc3ccc(Cl)cc3o2)c(F)c1)N1CCN(C(=O)C2(O)CC2)CC1] |
| 1-{4-[4-(2,3,4,5-tetrahydro-1H-2-benzazepin-2-yl)benzoyl]piperazine-1-carbonyl}cyclopropan-1-ol | 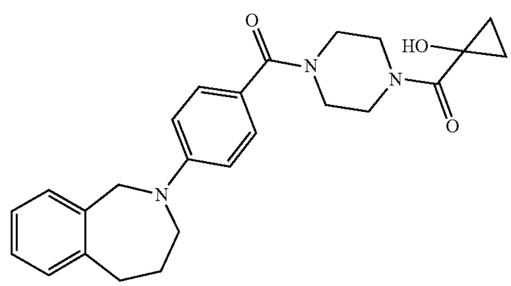 [SMILES: O=C(c1ccc(N2CCCc3ccccc3C2)cc1)N1CCN(C(=O)C2(O)CC2)CC1] |
| 1-[4-(4-{3-chloroimidazo[1,2-a]pyridin-2-yl}-3-fluorobenzoyl)piperazine-1-carbonyl]cyclopropan-1-ol | 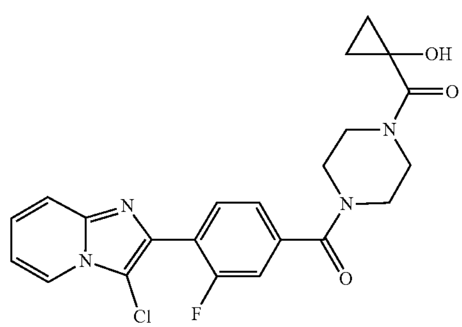 [SMILES: O=C(c1ccc(-c2nc3ccccn3c2Cl)c(F)c1)N1CCN(C(=O)C2(O)CC2)CC1] |
| 1-(3-{4-[4-(1-aminocyclopropanecarbonyl)piperazine-1-carbonyl]phenyl}phenyl)cyclopropane-1-carbonitrile | 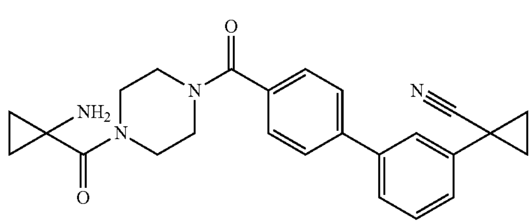 [SMILES: N#CC1(c2cccc(-c3ccc(C(=O)N4CCN(C(=O)C5(N)CC5)CC4)cc3)c2)CC1] |

-continued

| NAME | Structure |
|---|---|
| 1-{4-[3-fluoro-4-(6-fluoro-1,3-benzoxazol-2-yl)benzoyl]piperazine-1-carbonyl}cyclopropan-1-ol | 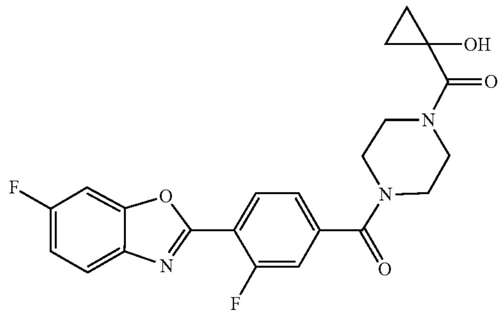 [SMILES: O=C(c1ccc(-c2nc3ccc(F)cc3o2)c(F)c1)N1CCN(C(=O)C2(O)CC2)CC1] |
| 1-{4-[4-(2-methyl-2H-1,2,3-benzotriazol-5-yl)benzoyl]piperazine-1-carbonyl}cyclopropan-1-ol | 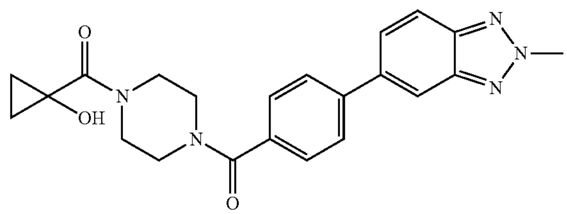 |
| 1-[(3S)-3-methyl-4-[4-(1-methyl-1H-1,3-benzodiazol-5-yl)benzoyl]piperazine-1-carbonyl]cyclopropan-1-amine | | or a pharmaceutically acceptable salt thereof.

2. A pharmaceutical composition comprising therapeutically effective amounts of at least one compound of claim 1, or a pharmaceutically acceptable salt thereof, and at least one pharmaceutically acceptable carrier.

* * * * *